United States Patent
Lee et al.

(10) Patent No.: US 12,171,143 B2
(45) Date of Patent: Dec. 17, 2024

(54) COMPOUND, ORGANIC OPTOELECTRONIC DIODE, AND DISPLAY DEVICE

(71) Applicant: LT MATERIALS CO., LTD., Yongin-Si (KR)

(72) Inventors: Yun-Ji Lee, Osan-si (KR); Min-Ji Park, Osan-si (KR); Won-Jang Jeong, Hwaseong-si (KR)

(73) Assignee: LT MATERIALS CO., LTD., Yongin (KR)

( * ) Notice: Subject to any disclaimer, the term of this patent is extended or adjusted under 35 U.S.C. 154(b) by 763 days.

(21) Appl. No.: 17/417,209

(22) PCT Filed: Jan. 22, 2020

(86) PCT No.: PCT/KR2020/001112
§ 371 (c)(1),
(2) Date: Jun. 22, 2021

(87) PCT Pub. No.: WO2020/153758
PCT Pub. Date: Jul. 30, 2020

(65) Prior Publication Data
US 2022/0085298 A1    Mar. 17, 2022

(30) Foreign Application Priority Data

Jan. 25, 2019 (KR) .................. 10-2019-0009760

(51) Int. Cl.
*C07D 491/04* (2006.01)
*C07D 491/048* (2006.01)
*C07D 495/04* (2006.01)
*H10K 85/60* (2023.01)
*H10K 50/16* (2023.01)
*H10K 50/18* (2023.01)

(52) U.S. Cl.
CPC ....... *H10K 85/657* (2023.02); *C07D 491/048* (2013.01); *C07D 495/04* (2013.01); *H10K 85/654* (2023.02); *H10K 85/6572* (2023.02); *H10K 85/6574* (2023.02); *H10K 85/6576* (2023.02); *H10K 50/16* (2023.02); *H10K 50/18* (2023.02)

(58) Field of Classification Search
None
See application file for complete search history.

(56) References Cited

U.S. PATENT DOCUMENTS

| | | | | |
|---|---|---|---|---|
| 4,356,429 A | * | 10/1982 | Tang | H10K 50/17 313/503 |
| 10,446,765 B2 | | 10/2019 | Lee et al. | |
| 10,644,244 B2 | | 5/2020 | Lee et al. | |
| 2016/0141515 A1 | * | 5/2016 | Hayama | C07D 491/048 544/215 |
| 2017/0033295 A1 | | 2/2017 | Xia et al. | |
| 2017/0141325 A1 | * | 5/2017 | Lee | H10K 85/654 |
| 2017/0338419 A1 | * | 11/2017 | Sim | H10K 50/818 |
| 2019/0140191 A1 | * | 5/2019 | Tsai | H10K 85/6572 |
| 2020/0388768 A1 | * | 12/2020 | Masuda | C07D 307/91 |
| 2021/0234102 A1 | * | 7/2021 | Ji | H10K 85/622 |

FOREIGN PATENT DOCUMENTS

| | | | | |
|---|---|---|---|---|
| KR | 20140079306 A | * | 6/2014 | ............. C09K 11/06 |
| KR | 10-1579289 B1 | | 12/2015 | |
| KR | 10-2016-0018458 A | | 2/2016 | |
| KR | 10-2017-0015216 A | | 2/2017 | |
| KR | 10-1763222 B1 | | 7/2017 | |
| KR | 10-2019-0033885 A | | 4/2019 | |
| KR | 10-2019-0033911 A | | 4/2019 | |

OTHER PUBLICATIONS

International Search Report (PCT/ISA/210) issued in PCT/KR2020/001112 mailed on May 1, 2020.
Kuwabara et al., "Thermally Stable Multilayered Organic Electroluminescent Devices Using Novel Starburst Molecules, 4,4',4"-Tri(N-carbazolyl)triphenylamine (TCTA) and 4,4',4" -Tris(3-methylphenylphenylamino)triphenylamine (m-MTDATA), as Hole-Transport Materials", Advanced Materials, 1994, vol. 6, No. 9, pp. 677-679.

* cited by examiner

*Primary Examiner* — Robert S Loewe
(74) *Attorney, Agent, or Firm* — Birch, Stewart, Kolasch & Birch, LLP

(57) ABSTRACT

The present application relates to a compound represented by Chemical Formula 1, an organic optoelectronic diode and a display device.

[Chemical Formula 1]

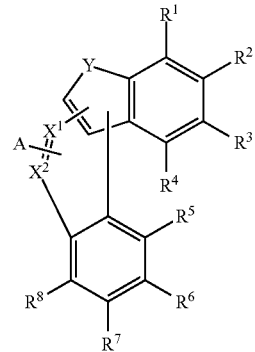

In Chemical Formula 1, each substituent has the same definition as in the specification.

13 Claims, 3 Drawing Sheets

【FIG. 1】
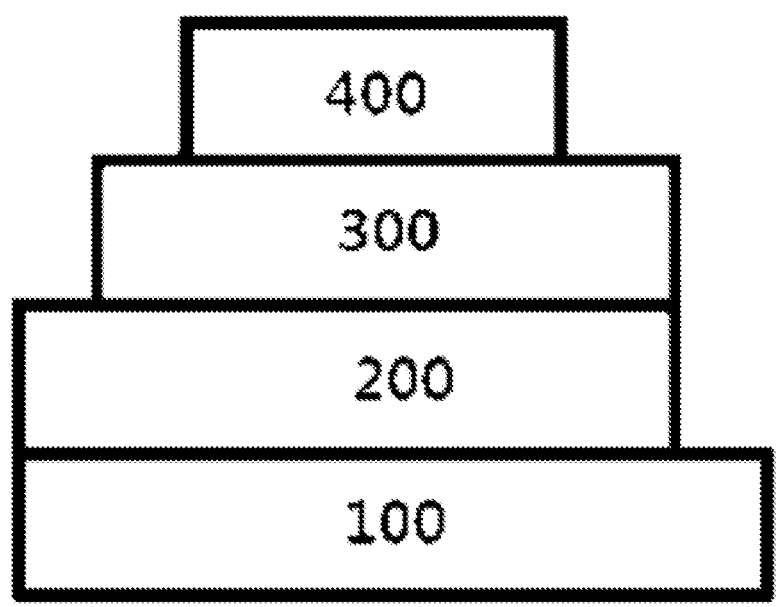

【FIG. 2】
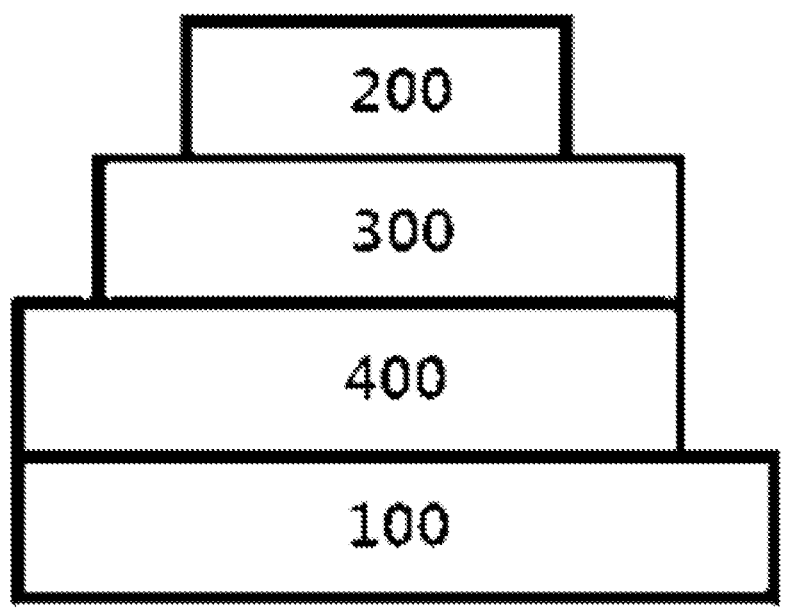

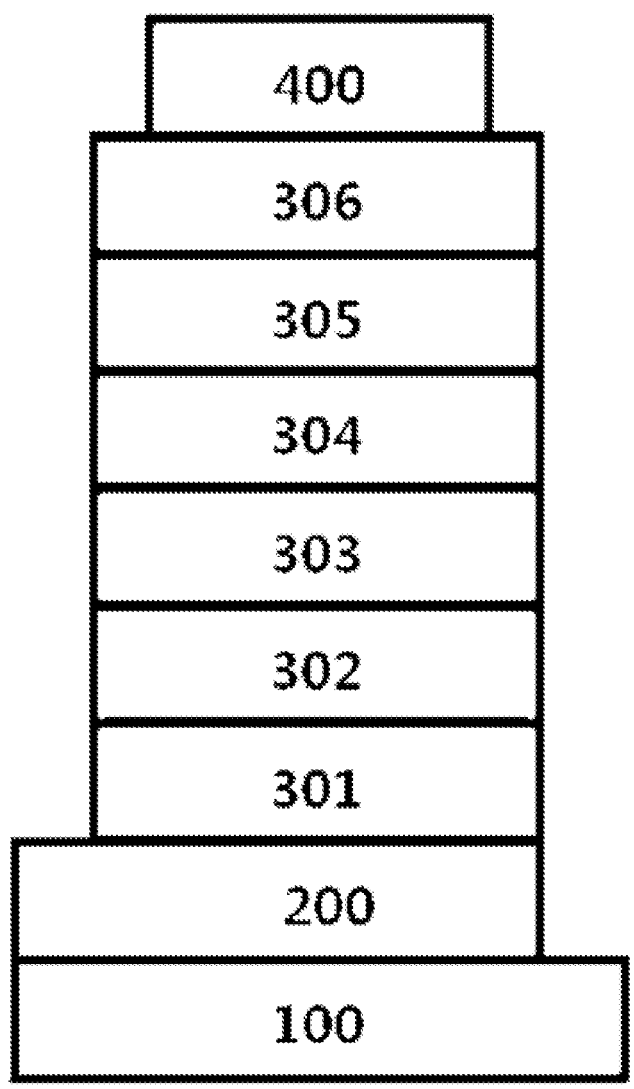

COMPOUND, ORGANIC OPTOELECTRONIC DIODE, AND DISPLAY DEVICE

TECHNICAL FIELD

This application claims priority to and the benefits of Korean Patent Application No. 10-2019-0009760, filed with the Korean Intellectual Property Office on Jan. 25, 2019, the entire contents of which are incorporated herein by reference.

The present application relates to a compound, an organic optoelectronic diode and a display device.

BACKGROUND ART

An organic optoelectronic diode is a device capable of interconverting electrical energy and light energy.

An organic optoelectronic diode may be divided into two types depending on the operating principle. One is an optoelectronic diode in which excitons formed by light energy are separated into electrons and holes and electrical energy is generated while the electrons and the holes are each transferred to different electrodes, and the other one is a light emitting diode generating light energy from electrical energy by supplying a voltage or a current to electrodes.

Examples of the organic optoelectronic diode may comprise an organic photoelectric diode, an organic light emitting diode, an organic solar cell, an organic photo conductor drum and the like.

Among these, an organic light emitting diode (OLED) has received much attention recently as demands for flat panel display devices have increased. An organic light emitting diode is a device converting electrical energy to light, and performance of an organic light emitting diode is greatly affected by organic materials disposed between electrodes.

An organic light emitting diode has a structure disposing an organic thin film between two electrodes. When a voltage is applied to an organic light emitting diode having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used.

In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting diode.

DISCLOSURE

Technical Problem

One embodiment of the present specification is directed to providing a compound capable of obtaining an organic optoelectronic diode with high efficiency and long lifetime.

Another embodiment of the present specification is directed to providing an organic optoelectronic diode comprising the compound.

Still another embodiment of the present specification is directed to providing a display device comprising the organic optoelectronic diode.

Technical Solution

One embodiment of the present specification provides a compound represented by the following Chemical Formula 1.

[Chemical Formula 1]

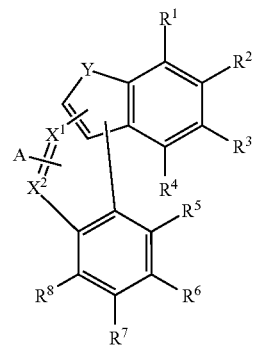

In Chemical Formula 1,
at least one of $X^1$ and $X^2$ is —N—, the other one is —CA-, Y is —S— or —O—, A and $R^1$ to $R^8$ are each independently hydrogen, deuterium, a cyano group, a substituted or unsubstituted C1 to C60 alkyl group or a substituted or unsubstituted C6 to C60 aryl group, and any one of A and $R^1$ to $R^4$ is represented by the following Chemical Formula 2,

[Chemical Formula 2]

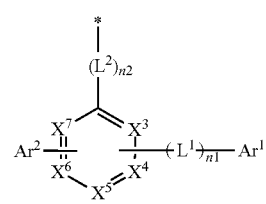

in Chemical Formula 2,
$Ar^1$ and $Ar^2$ are each independently a substituted or unsubstituted C6 to C60 aryl group or a substituted or unsubstituted C2 to C60 heteroaryl group, at least one of $X^3$ to $X^7$ is —N—, one of $X^3$ to $X^7$ is —C$((L^1)_{n1}$-$Ar^1)$—, one of $X^3$ to $X^7$ is —C($Ar^2$)—, and the rest are one of —N—, —CH— or —CR—, $L^1$ and $L^2$ are each independently a single bond, a substituted or unsubstituted C6 to C60 arylene group, or a substituted or unsubstituted C2 to C60 heteroarylene group, n1 and n2 are each independently one of integers of 0 to 2, R is deuterium, —CN, a substituted or unsubstituted C1 to C60 linear or branched alkyl group, a substituted or unsubstituted C6 to C60 monocyclic or polycyclic aryl group or a substituted or unsubstituted C2 to C60 monocyclic or polycyclic heteroaryl group, and when A of Chemical Formula 1 is represented by Chemical Formula 2, at least any one of $Ar^1$ and $Ar^2$ of Chemical Formula 2 is a substituted or unsubstituted C2 to C60 heteroaryl group or a substituted or unsubstituted C6 to C60 fused cyclic aryl group, and * is a bonding position.

More specifically, Chemical Formula 2 may be represented by the following Chemical Formula 3.

[Chemical Formula 3]

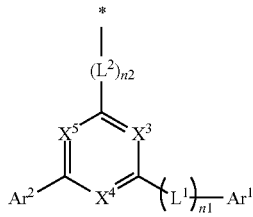

More specifically, the compound may be represented by any one of the following Chemical Formulae 4 and 5.

[Chemical Formula 4]

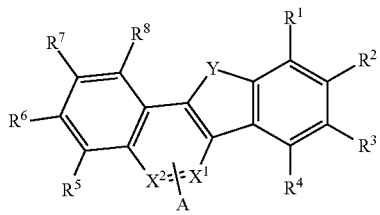

[Chemical Formula 5]

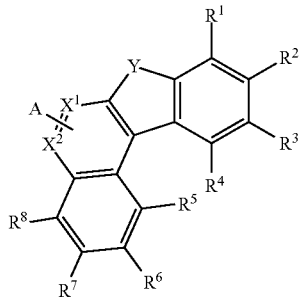

Another embodiment of the present specification provides an organic optoelectronic diode comprising an anode and a cathode facing each other, and at least one organic layer disposed between the anode and the cathode, wherein the organic layer comprises the compound.

Still another embodiment of the present specification provides a display device comprising the organic optoelectronic diode.

Advantageous Effects

An organic optoelectronic diode with high efficiency and long lifetime can be obtained.

DESCRIPTION OF DRAWINGS

FIG. 1 to FIG. 3 are sectional diagrams each illustrating an organic light emitting diode according to one embodiment of the present specification.
100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

MODE FOR DISCLOSURE

Hereinafter, embodiments of the present disclosure will be described in detail. However, these are for illustrative purposes only, and the present disclosure is not limited thereto, and is only defined by the category of claims to describe later.

In the present specification, "substituted or unsubstituted" means being substituted with one or more substituents selected from the group consisting of deuterium; a halogen group; —CN; a C1 to C60 linear or branched alkyl group; a C2 to C60 linear or branched alkenyl group; a C2 to C60 linear or branched alkynyl group; a C3 to C60 monocyclic or polycyclic cycloalkyl group; a C2 to C60 monocyclic or polycyclic heterocycloalkyl group; a C6 to C60 monocyclic or polycyclic aryl group; a C2 to C60 monocyclic or polycyclic heteroaryl group; —SiRR'R''; —P(=O)RR'; a C1 to C20 alkylamine group; a C6 to C60 monocyclic or polycyclic arylamine group; a C2 to C60 monocyclic or polycyclic heteroarylamine group, a substituted or unsubstituted alkoxy group, a substituted or unsubstituted aryloxy group, a substituted or unsubstituted heteroaryloxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted boron group, a substituted or unsubstituted silyl group, a substituted or unsubstituted arylphosphine group, a substituted or unsubstituted phosphine oxide group, a substituted or unsubstituted fluorenyl group and a substituted or unsubstituted aromatic or aliphatic heterocyclic group comprising one or more of N, O and S atoms, or being unsubstituted, or being substituted with a substituent bonding two or more of the substituents, or being unsubstituted, or being substituted with a substituent linking two or more substituents selected from among the above-mentioned substituents, or being unsubstituted. In addition, these may further form a ring with adjacent substituents.

For example, the "substituent linking two or more substituents" may comprise a biphenyl group. In other words, a biphenyl group may be an aryl group, or interpreted as a substituent linking two phenyl groups. The additional substituents may be further substituted. R, R' and R'' are the same as or different from each other, and each independently hydrogen; deuterium; —CN; a substituted or unsubstituted C1 to C60 linear or branched alkyl group; a substituted or unsubstituted C3 to C60 monocyclic or polycyclic cycloalkyl group; a substituted or unsubstituted C6 to C60 monocyclic or polycyclic aryl group; or a substituted or unsubstituted C2 to C60 monocyclic or polycyclic heteroaryl group.

According to one embodiment of the present application, the "substituted or unsubstituted" means being substituted with one or more substituents selected from the group consisting of deuterium, a halogen group, —CN, —SiRR'R'', —P(=O)RR', a C1 to C20 linear or branched alkyl group, a C6 to C60 monocyclic or polycyclic aryl group and a C2 to C60 monocyclic or polycyclic heteroaryl group, or being unsubstituted, and R, R' and R'' are the same as or different from each other and each independently hydrogen; deuterium; —CN; a C1 to C60 alkyl group unsubstituted or substituted with deuterium, a halogen group, —CN, a C1 to C20 alkyl group, a C6 to C60 aryl group and a C2 to C60 heteroaryl group; a C3 to C60 cycloalkyl group unsubstituted or substituted with deuterium, halogen, —CN, a C1 to C20 alkyl group, a C6 to C60 aryl group and a C2 to C60 heteroaryl group; a C6 to C60 aryl group unsubstituted or substituted with deuterium, halogen, —CN, a C1 to C20 alkyl group, a C6 to C60 aryl group and a C2 to C60 heteroaryl group; or a C2 to C60 heteroaryl group unsubstituted or substituted with deuterium, halogen, —CN, a C1 to C20 alkyl group, a C6 to C60 aryl group and a C2 to C60 heteroaryl group.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may comprise fluorine, chlorine, bromine or iodine.

In the present specification, the alkyl group comprises a C1 to C60 linear or branched, and may be further substituted with other substituents. The number of carbon atoms of the alkyl group may be from 1 to 60, specifically from 1 to 40, specifically from 1 to 20, and more specifically from 1 to 10. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises a C2 to C60 linear or branched, and may be further substituted with other substituents. The number of carbon atoms of the alkenyl group may be from 2 to 60, specifically from 2 to 40, and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises a C2 to C60 linear or branched, and may be further substituted with other substituents. The number of carbon atoms of the alkynyl group may be from 2 to 60, specifically from 2 to 40, and more specifically from 2 to 20.

In the present specification, the cycloalkyl group comprises a C3 to C60 monocyclic or polycyclic, and may be further substituted with other substituents. Herein, the polycyclic means a group in which the cycloalkyl group is directly linked to or fused with another cyclic group. Herein, the another cyclic group may be a cycloalkyl group, but may also comprise other types of cyclic groups such as a heterocycloalkyl group, an aryl group and a heteroaryl group. The number of carbon atoms of the cycloalkyl group may be from 3 to 60, specifically from 3 to 40, and more specifically from to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the alkoxy group may comprise a C1 to C10 alkoxy group, and more specifically, a methoxy group, an ethoxy group, a propoxy group, a butoxy group, a pentoxy group and the like.

In the present specification, the silyl group may be represented by —SiRR'R", and R, R' and R" have the same definitions as above. More specifically, a dimethylsilyl group, a diethylsilyl group, a methylethylsilyl group and the like may be included.

In the present specification, the phosphine oxide group may be represented by —P(=O)RR', and R and R' have the same definitions as above. More specifically, a dimethylphosphine group, a diethylphosphine group, a methylethylphosphine group and the like may be included.

In the present specification, the fluorenyl group means a substituent comprising various substituents at the number 9 position. Specifically, a concept comprising a fluorenyl group in which the number 9 position is substituted with two hydrogens, two alkyl groups, two aryl groups or two heteroaryl groups may be used. More specifically, a 9-di-H-fluorenyl group, a 9-di-methyl-fluorenyl group, a 9-di-phenyl-fluorenyl group or the like may be used.

In the present specification, the heterocycloalkyl group comprises O, S, Se, N or Si as a heteroatom, comprises a C2 to C60 monocyclic or polycyclic, and may be further substituted with other substituents. Herein, the polycyclic means a group in which the heterocycloalkyl group is directly linked to or fused with another cyclic group. Herein, the another cyclic group may be a heterocycloalkyl group, but may also comprise other types of cyclic groups such as a cycloalkyl group, an aryl group and a heteroaryl group. The number of carbon atoms of the heterocycloalkyl group may be from 2 to 60, specifically from 2 to 40, and more specifically from 3 to 20.

In the present specification, the aryl group comprises a C6 to C60 monocyclic or polycyclic, and may be further substituted with other substituents. Herein, the polycyclic means a group in which the aryl group is directly linked to or fused with another cyclic group. Herein, the another cyclic group may be an aryl group, but may also comprise other types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40, specifically from 6 to 30, and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused cyclic group thereof and the like, but are not limited thereto.

In the present specification, the spiro group is a group comprising a spiro structure, and may be from C15 to C60. For example, the spiro group may comprise a structure in which a 2,3-dihydro-1H-indene group or a cyclohexane group spiro-bonds to a fluorenyl group. Specifically, the spiro group may comprise any one of the groups of the following structural formulae.

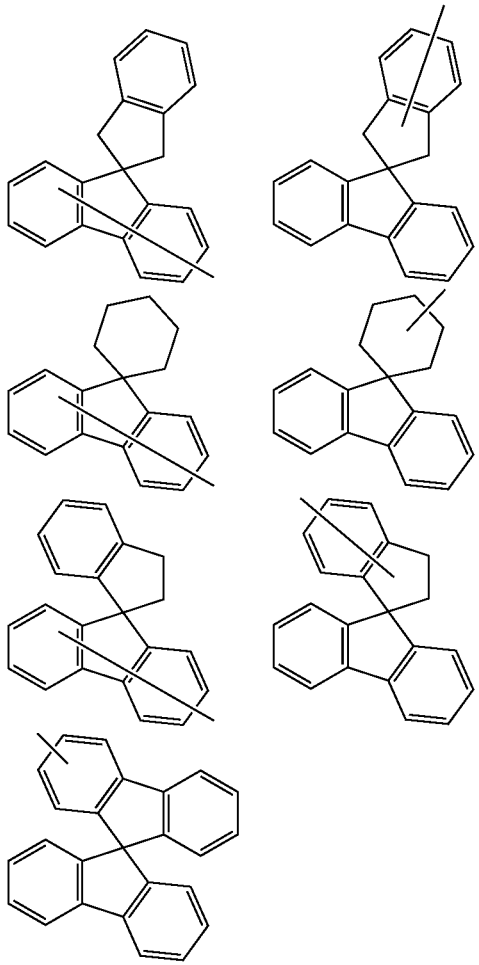

In the present specification, the heteroaryl group comprises S, O, Se, N or Si as a heteroatom, comprises a C2 to C60 monocyclic or polycyclic, and may be further substituted with other substituents. Herein, the polycyclic means a group in which the heteroaryl group is directly linked to or fused with another cyclic group. Herein, the another cyclic group may be a heteroaryl group, but may also comprise other types of cyclic groups such as a cycloalkyl group, a heterocycloalkyl group and an aryl group. The number of carbon atoms of the heteroaryl group may be from 2 to 60, specifically from 2 to 40, specifically from 2 to 30, and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a quinozolinyl group, a naphthyridyl group, an acridinyl group, a phenanthridinyl group, an imidazopyridinyl group, diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, 9,10-dihydroacridinyl group, a phenanthrazinyl group, a phenothiathiazinyl group, a phthalazinyl group, a naphthyridinyl group, a phenanthrolinyl group, a benzo[c][1,2,5]thiadiazolyl group, 5,10-dihydrodibenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means an aryl group having two bonding sites, that is, a divalent group. Descriptions on the aryl group provided above may be applied thereto except for each being a divalent group. In addition, the heteroarylene group means a heteroaryl group having two bonding sites, that is, a divalent group. Descriptions on the heteroaryl group provided above may be applied thereto except for each being a divalent group.

In the present specification, hole properties refer to properties capable of forming holes by donating electrons when applying an electric field, and means properties of, by having conducting properties along the HOMO level, facilitating injection of holes forming in an anode to a light emitting layer, migration of holes formed in a light emitting layer to an anode and migration in the light emitting layer.

Substituents having hole properties comprise a substituted or unsubstituted C6 to C60 aryl group having hole properties, a substituted or unsubstituted C2 to C60 heteroaryl group having hole properties, a substituted or unsubstituted arylamine group, a substituted or unsubstituted heteroarylamine group, or the like.

More specifically, the substituted or unsubstituted C6 to C60 aryl group having hole properties may be a substituted or unsubstituted phenyl group, a substituted or unsubstituted naphthyl group, a substituted or unsubstituted phenanthrenyl group, a substituted or unsubstituted anthracenyl group, a substituted or unsubstituted fluorenyl group, a substituted or unsubstituted triphenylenyl group, a substituted or unsubstituted spiro-fluorenyl group, a substituted or unsubstituted terphenyl group, a substituted or unsubstituted pyrenyl group, a substituted or unsubstituted perylenyl group, or a combination thereof.

More specifically, the substituted or unsubstituted C2 to C60 heteroaryl group having hole properties is a substituted or unsubstituted carbazolyl group, a substituted or unsubstituted dibenzofuranyl group, a substituted or unsubstituted dibenzothiophenyl group, a substituted or unsubstituted indolecarbazolyl group, or the like.

The aryl group or the heteroaryl group, a substituent bonding to the nitrogen of the substituted or unsubstituted arylamine group and the substituted or unsubstituted heteroarylamine group may be, more specifically, a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof.

In addition, electron properties refer to properties capable of receiving electrons when applying an electric field, and means properties of, by having conducting properties along the LUMO level, facilitating injection of electrons forming in a cathode to a light emitting layer, migration of electrons formed in a light emitting layer to a cathode and migration in the light emitting layer.

The substituted or unsubstituted C2 to C60 heteroaryl group having electron properties may be a substituted or unsubstituted imidazolyl group, a substituted or unsubstituted tetrazolyl group, a substituted or unsubstituted quinolinylene group, a substituted or unsubstituted isoquinolinylene group, a substituted or unsubstituted pyridinylene group, a substituted or unsubstituted pyrimidinylene group, a substituted or unsubstituted triazinylene group, a substituted or unsubstituted furanyl group, a substituted or unsubstituted benzofuranyl group, a substituted or unsubstituted isofuranyl group, a substituted or unsubstituted benzoisofuranyl group, a substituted or unsubstituted oxazoline group, a substituted or unsubstituted benzoxazoline group, a substituted or unsubstituted oxadiazoline group, a substituted or unsubstituted benzoxadiazoline group, a substituted or unsubstituted oxatriazolyl group, a substituted or unsubstituted thiophenyl group, a substituted or unsubstituted benzothiophenyl group, a substituted or unsubstituted isothiazoline group, a substituted or unsubstituted benzoisothiazoline group, a substituted or unsubstituted thiazoline group, a substituted or unsubstituted benzothiazoline group, a substituted or unsubstituted pyridazinyl group, a substituted or unsubstituted benzopyridazinyl group, a substituted or unsubstituted pyrazinyl group, a substituted or unsubstituted benzopyrazinyl group, a substituted or unsubstituted phthalazinyl group, a substituted or unsubstituted benzoquinolinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

More specifically, the substituted or unsubstituted C2 to C60 heteroaryl group having electron properties may be any one of the following Chemical Formulae X-1 to X-5.

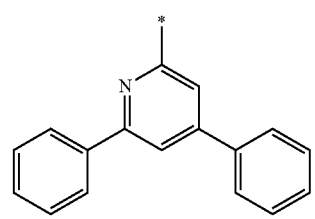

[Chemical Formula X-1]

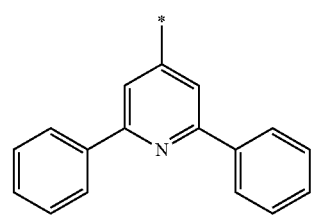

[Chemical Formula X-2]

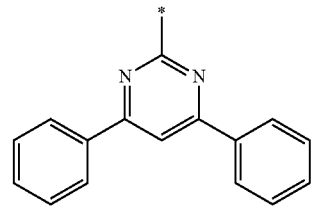

[Chemical Formula X-3]

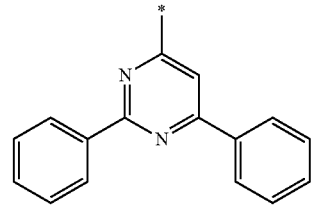

[Chemical Formula X-4]

-continued

[Chemical Formula X-5]

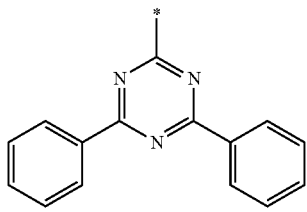

In one embodiment of the present application, L'' may be a direct bond (or a single bond); a substituted or unsubstituted arylene group; or a substituted or unsubstituted heteroarylene group.

In another embodiment, L'' may be a direct bond; a substituted or unsubstituted C6 to C60 arylene group; or a substituted or unsubstituted C2 to C60 heteroarylene group.

In another embodiment, L'' may be a direct bond; a substituted or unsubstituted C6 to C40 arylene group; or a substituted or unsubstituted C2 to C40 heteroarylene group.

In L'', n means a number for distinguishing substituents.

Hereinafter, a compound according to one embodiment will be described.

The compound according to one embodiment is represented by the following Chemical Formula 1.

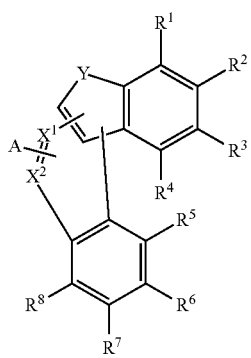

In Chemical Formula 1,
at least one of $X^1$ and $X^2$ is —N—, the other one is —CA-, Y is —S— or —O—, A and $R^1$ to $R^8$ are each independently hydrogen, deuterium, a cyano group, a substituted or unsubstituted C1 to C60 alkyl group or a substituted or unsubstituted C6 to C60 aryl group, and any one of A and $R^1$ to $R^4$ is represented by the following Chemical Formula 2,

[Chemical Formula 2]

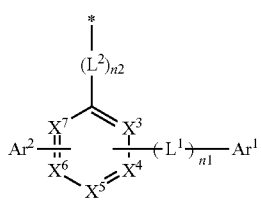

in Chemical Formula 2,
$Ar^1$ and $Ar^2$ are each independently a substituted or unsubstituted C6 to C60 aryl group or a substituted or unsubstituted C2 to C60 heteroaryl group, at least one of $X^3$ to $X^7$ is —N—, one of $X^3$ to $X^7$ is -($L^1$)$_{n1}$-$Ar^1$, one of $X^3$ to $X^7$ is —$Ar^2$— and the rest are one of —N—, —CH— or —CR—, $L^1$ and $L^2$ are each independently a single bond, a substituted or unsubstituted C6 to C60 arylene group, or a substituted or unsubstituted C2 to C60 heteroarylene group, n1 and n2 are each independently one of integers of 0 to 2, R is deuterium, —CN, a substituted or unsubstituted C1 to C60 linear or branched alkyl group, a substituted or unsubstituted C6 to C60 monocyclic or polycyclic aryl group or a substituted or unsubstituted C2 to C60 monocyclic or polycyclic heteroaryl group, and when A of Chemical Formula 1 is represented by Chemical Formula 2, at least any one of $Ar^1$ and $Ar^2$ of Chemical Formula 2 is a substituted or unsubstituted C2 to C60 heteroaryl group or a substituted or unsubstituted C6 to C60 fused cyclic aryl group, and * is a bonding position.

The compound according to one embodiment is represented by the following Chemical Formula 1-1.

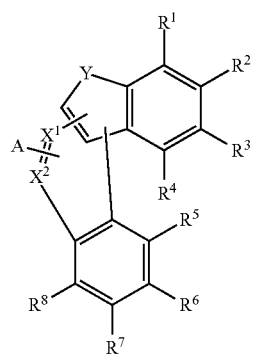

In Chemical Formula 1-1,
at least one of $X^1$ and $X^2$ is —N—, and the other one is —CA-,
Y is —S— or —O—,
A and $R^1$ to $R^8$ are each independently hydrogen, deuterium, a cyano group, a substituted or unsubstituted C1 to C60 alkyl group, or a substituted or unsubstituted C6 to C60 aryl group, and
any one of A and $R^1$ to $R^4$ is represented by the following Chemical Formula 2,

[Chemical Formula 2]

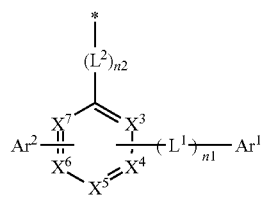

in Chemical Formula 2,
$Ar^1$ and $Ar^2$ are each independently a substituted or unsubstituted C6 to C60 aryl group, or a substituted or unsubstituted C2 to C60 heteroaryl group,
at least any one of $Ar^1$ and $Ar^2$ is a substituted or unsubstituted C2 to C60 heteroaryl group, or a substituted or unsubstituted C6 to C60 fused cyclic aryl group,
at least one of $X^3$ to $X^7$ is —N—, one of $X^3$ to $X^7$ is -($L^1$)$_1$-$Ar^1$, one of $X^3$ to $X^7$ is —$Ar^2$—, and the rest are one of —N—, —CH— or —CR—, L$^1$ and L$^2$ are each independently a single bond, a substituted or unsubstituted C6 to C60 arylene group, or a substituted or unsubstituted C2 to C60 heteroarylene group, n1 and n2 are each independently one of integers of 0 to 2, R is deuterium, —CN, a substituted or unsubstituted C1 to C60 linear or branched alkyl group, a substituted or unsubstituted C6 to C60 monocyclic or polycyclic aryl group, or a substituted or unsubstituted C2 to C60 monocyclic or polycyclic heteroaryl group, and

* is a bonding position.

Herein, the fused cyclic aryl group means a cyclic group in which carbon atoms share adjacent pairs.

Specifically, the C6 to C60 fused cyclic aryl group may be a substituted or unsubstituted naphthyl group, a substituted or unsubstituted triphenylenyl group, a substituted or unsubstituted fluorenyl group, a substituted or unsubstituted pyrenyl group, or a substituted or unsubstituted phenanthrenyl group.

The present application relates to the compound of Chemical Formula 1 or Chemical Formula 1-1.

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting diode to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and thereby has excellent thermal stability. Such an increase in the thermal stability becomes an important factor in providing driving stability to a device.

More specifically, Chemical Formula 2 may be represented by the following Chemical Formula 3.

[Chemical Formula 3]

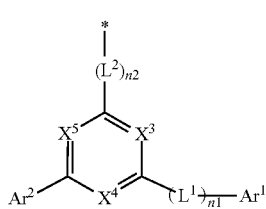

In Chemical Formula 3,

Ar$^1$ and Ar$^2$ are each independently a substituted or unsubstituted C6 to C60 aryl group or a substituted or unsubstituted C2 to C60 heteroaryl group, X$^3$ to X$^5$ are each independently —N—, —CH— or —CR—, at least one of X$^3$ to X$^5$ is —N—, L$^1$ and L$^2$ are each independently a single bond, a substituted or unsubstituted C6 to C60 arylene group or a substituted or unsubstituted C2 to C60 heteroarylene group, n1 and n2 are each independently one of integers of 0 to 2, and R is deuterium, —CN, a substituted or unsubstituted C1 to C60 linear or branched alkyl group, a substituted or unsubstituted C6 to C60 monocyclic or polycyclic aryl group or a substituted or unsubstituted C2 to C60 monocyclic or polycyclic heteroaryl group, when A of Chemical Formula 1 is represented by Chemical Formula 3, at least any one of Ar$^1$ and Ar$^2$ of Chemical Formula 3 is a substituted or unsubstituted C2 to C60 heteroaryl group or a substituted or unsubstituted C6 to C60 fused cyclic aryl group, and * is a bonding position.

More specifically, Chemical Formula 3 may be represented as follows.

[Chemical Formula 3]

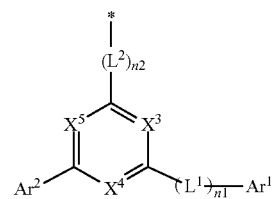

In Chemical Formula 3,

Ar$^1$ and Ar$^2$ are each independently a substituted or unsubstituted C6 to C60 aryl group or a substituted or unsubstituted C2 to C60 heteroaryl group, at least any one of Ar$^1$ and Ar$^2$ is a substituted or unsubstituted C2 to C60 heteroaryl group or a substituted or unsubstituted C6 to C60 fused cyclic aryl group, X$^3$ to X$^5$ are each independently —N—, —CH— or —CR—, at least one of X$^3$ to X$^5$ is —N—, L$^1$ and L$^2$ are each independently a single bond, a substituted or unsubstituted C6 to C60 arylene group or a substituted or unsubstituted C2 to C60 heteroarylene group, n1 and n2 are each independently one of integers of 0 to 2, and R is deuterium, —CN, a substituted or unsubstituted C1 to C60 linear or branched alkyl group, a substituted or unsubstituted C6 to C60 monocyclic or polycyclic aryl group or a substituted or unsubstituted C2 to C60 monocyclic or polycyclic heteroaryl group, and

* is a bonding position.

In the compound having the substituent represented by Chemical Formula 3, Ar$^1$ and Ar$^2$ are each independent, and the substituent having a substituted or unsubstituted C2 to C60 heteroaryl group or a substituted or unsubstituted C6 to C60 fused cyclic aryl group has relatively stronger hole transfer properties compared to other substituents. Having strong hole transfer properties affects overall electron migration, and more superior efficiency and lifetime may be obtained.

More specifically, the compound may be represented by the following Chemical Formula 4.

[Chemical Formula 4]

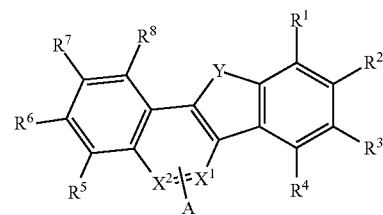

In Chemical Formula 4,
each substituent has the same definition as in Chemical Formula 1.

In addition, the compound may be represented by the following Chemical Formula 5.

[Chemical Formula 5]

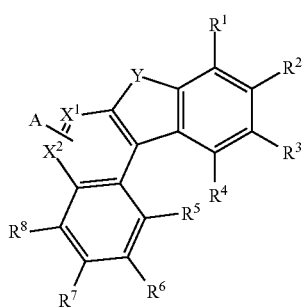

In Chemical Formula 5,
each substituent has the same definition as in Chemical Formula 1.

More specifically, in the compound of Chemical Formula 4, $X^1$ is —N—, $X^2$ is —CA-, and A may be represented by Chemical Formula 3.

More specifically, in the compound of Chemical Formula 4, $X^1$ is —CA-, $X^2$ is —N—, and A may be represented by Chemical Formula 3.

More specifically, in the compound of Chemical Formula 4, $X^1$ is —N—, $X^2$ is —CA-, and any one of $R^1$ to $R^4$ may be represented by Chemical Formula 3.

More specifically, in the compound of Chemical Formula 4, $X^1$ is —CA-, $X^2$ is —N—, and any one of $R^1$ to $R^4$ may be represented by Chemical Formula 3.

In addition, more specifically, in the compound of Chemical Formula 4, $X^1$ is —N—, $X^2$ is —CA-, any one of $R^1$ to $R^4$ is represented by Chemical Formula 3, and A may be a phenyl group or a naphthyl group.

In addition, more specifically, in the compound of Chemical Formula 4, $X^1$ is —CA-, $X^2$ is —N—, any one of $R^1$ to $R^4$ is represented by Chemical Formula 3, and A may be a phenyl group or a naphthyl group.

More specifically, in the compound of Chemical Formula 5, $X^1$ is —N—, $X^2$ is —CA-, and A may be represented by Chemical Formula 3.

More specifically, in the compound of Chemical Formula 5, $X^1$ is —CA-, $X^2$ is —N—, and A may be represented by Chemical Formula 3.

More specifically, in the compound of Chemical Formula 5, $X^1$ is —N—, $X^2$ is —CA-, and any one of $R^1$ to $R^4$ may be represented by Chemical Formula 3.

More specifically, in the compound of Chemical Formula 5, $X^1$ is —CA-, $X^2$ is —N—, and any one of $R^1$ to $R^4$ may be represented by Chemical Formula 3.

In addition, more specifically, in the compound of Chemical Formula 5, $X^1$ is —N—, $X^2$ is —CA-, any one of $R^1$ to $R^4$ is represented by Chemical Formula 3, and A may be a phenyl group or a naphthyl group.

In addition, more specifically, in the compound of Chemical Formula 5, $X^1$ is —CA-, $X^2$ is —N—, any one of $R^1$ to $R^4$ is represented by Chemical Formula 3, and A may be a phenyl group or a naphthyl group.

In addition, $Ar^1$ may be a substituent having hole properties.

In one embodiment of the present application, $L^1$ and $L^2$ may be each independently a single bond, a substituted or unsubstituted C6 to C60 arylene group, or a substituted or unsubstituted C2 to C60 heteroarylene group.

In another embodiment, $L^1$ and $L^2$ may be each independently a single bond, a substituted or unsubstituted C6 to C40 arylene group, or a substituted or unsubstituted C2 to C40 heteroarylene group.

In another embodiment, $L^1$ and $L^2$ may be each independently a single bond, a C6 to C40 arylene group or a C2 to C40 heteroarylene group.

In another embodiment, $L^1$ and $L^2$ may be each independently a single bond, or a monocyclic or polycyclic C6 to C40 arylene group.

In another embodiment, $L^1$ and $L^2$ may be each independently a single bond, a phenylene group, a biphenylene group or a naphthalene group.

In one embodiment of the present application, $Ar^1$ and $Ar^2$ may be each independently a substituted or unsubstituted C6 to C60 aryl group, or a substituted or unsubstituted C2 to C60 heteroaryl group.

In another embodiment, $Ar^1$ and $Ar^2$ may be each independently a substituted or unsubstituted C6 to C40 aryl group, or a substituted or unsubstituted C2 to C40 heteroaryl group.

In another embodiment, $Ar^1$ and $Ar^2$ may be each independently a C6 to C40 aryl group unsubstituted or substituted with a C1 to C10 alkyl group, or a C2 to C40 heteroaryl group unsubstituted or substituted with a C6 to C10 aryl group.

In another embodiment, $Ar^1$ and $Ar^2$ may be each independently a substituted or unsubstituted phenyl group, a substituted or unsubstituted naphthyl group, a substituted or unsubstituted biphenyl group, a substituted or unsubstituted triphenylenyl group, a substituted or unsubstituted fluorenyl group, a substituted or unsubstituted pyrenyl group, a substituted or unsubstituted phenanthrenyl group, a substituted or unsubstituted carbazole group, a substituted or unsubstituted dibenzothiophene group, or a substituted or unsubstituted dibenzofuran group.

In another embodiment, $Ar^1$ and $Ar^2$ may be each independently a phenyl group, a naphthyl group, a biphenyl group, a triphenylenyl group, a fluorenyl group unsubstituted or substituted with a methyl group, a benzene ring-fused 9,9-dimethylfluorenyl group, a pyrenyl group, a phenanthrenyl group, a carbazole group unsubstituted or substituted with a phenyl group, a dibenzothiophene group unsubstituted or substituted with a phenyl group, or a dibenzofuran group unsubstituted or substituted with a phenyl group.

In one embodiment of the present application, A and $R^1$ to $R^8$ are each independently hydrogen, deuterium, a cyano group, a substituted or unsubstituted C1 to C60 alkyl group or a substituted or unsubstituted C6 to C60 aryl group, and any one of A and $R^1$ to $R^4$ may be represented by Chemical Formula 2.

In another embodiment, A and R' to $R^8$ are each independently hydrogen or a substituted or unsubstituted C6 to C60 aryl group, and any one of A and $R^1$ to $R^4$ may be represented by Chemical Formula 2.

In another embodiment, A and $R^1$ to $R^8$ are each independently hydrogen or a substituted or unsubstituted C6 to C40 aryl group, and any one of A and $R^1$ to $R^4$ may be represented by Chemical Formula 2.

In another embodiment, A and $R^1$ to $R^8$ are each independently hydrogen or a C6 to C40 aryl group, and any one of A and $R^1$ to $R^4$ may be represented by Chemical Formula 2.

In another embodiment, A and $R^1$ to $R^8$ are each independently hydrogen, a phenyl group or a naphthyl group, and any one of A and $R^1$ to $R^4$ may be represented by Chemical Formula 2.

In one embodiment of the present application, when A is represented by Chemical Formula 2, at least any one of $Ar^1$ and $Ar^2$ of Chemical Formula 2 may be a substituted or unsubstituted C2 to C60 heteroaryl group or a substituted or unsubstituted C6 to C60 fused cyclic aryl group.

In another embodiment, when A is represented by Chemical Formula 2, at least any one of $Ar^1$ and $Ar^2$ of Chemical Formula 2 may be a substituted or unsubstituted C2 to C40 heteroaryl group or a substituted or unsubstituted C6 to C40 fused cyclic aryl group.

In another embodiment, when A is represented by Chemical Formula 2, at least any one of $Ar^1$ and $Ar^2$ of Chemical Formula 2 may be a C2 to C40 heteroaryl group unsubstituted or substituted with a C6 to C20 aryl group, or a C6 to C40 fused cyclic aryl group.

In another embodiment, when A is represented by Chemical Formula 2, at least any one of $Ar^1$ and $Ar^2$ of Chemical Formula 2 may be a carbazole group unsubstituted or substituted with a phenyl group, a dibenzothiophene group unsubstituted or substituted with a phenyl group, a dibenzofuran group unsubstituted or substituted with a phenyl group, a triphenylenyl group, a 9,9-dimethylfluorenyl group, a benzene ring-fused 9,9-dimethylfluorenyl group, a phenanthrenyl group or a pyrenyl group.

The benzene ring-fused 9,9-dimethylfluorenyl group may be any one of the following structures.

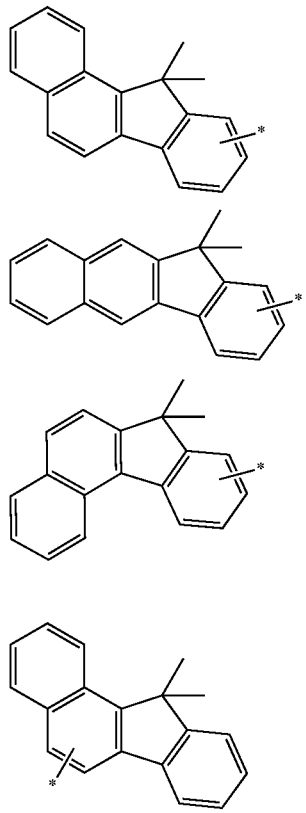

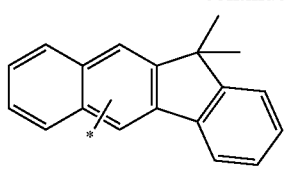

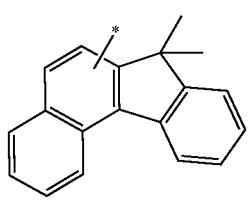

More specifically, $Ar^1$ is a substituted or unsubstituted carbazolyl group, a substituted or unsubstituted dibenzofuranyl group, a substituted or unsubstituted dibenzothiophenyl group, a substituted or unsubstituted 9,9-dialkylfluorenyl group or a 9,9-diarylfluorenyl group, and the alkyl group of the dialkyl may be a substituted or unsubstituted C1 to C60 alkyl group, and the aryl group of the diaryl group may be a substituted or unsubstituted C6 to C60 aryl group, or a substituted or unsubstituted 9,9-dimethylfluorenyl group.

When represented by such substituents, light emission efficiency and lifetime of an organic light emitting diode may be more superior compared to other cases.

More specifically, $Ar^1$ may be a substituted or unsubstituted anthracenyl group, a substituted or unsubstituted phenanthryl group, a substituted or unsubstituted pyrenyl group, a substituted or unsubstituted triphenylenyl group, a substituted or unsubstituted terphenyl group, or a substituted or unsubstituted quaterphenyl group.

When represented by such substituents, light emission efficiency and lifetime of an organic light emitting diode may be more superior compared to other cases.

More specifically, the compound represented by Chemical Formula 1 may be any one of compounds of the following Group I.

[Group I]

1

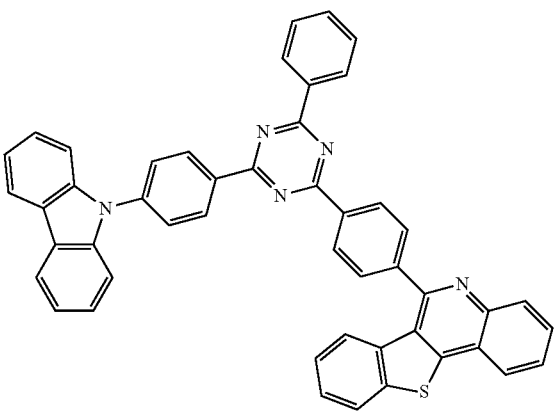

2
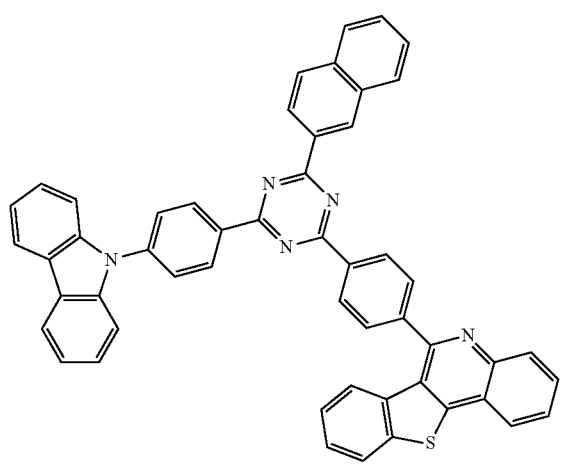
3
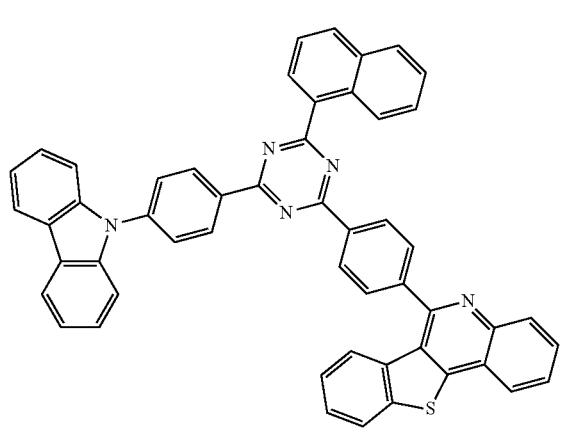
4
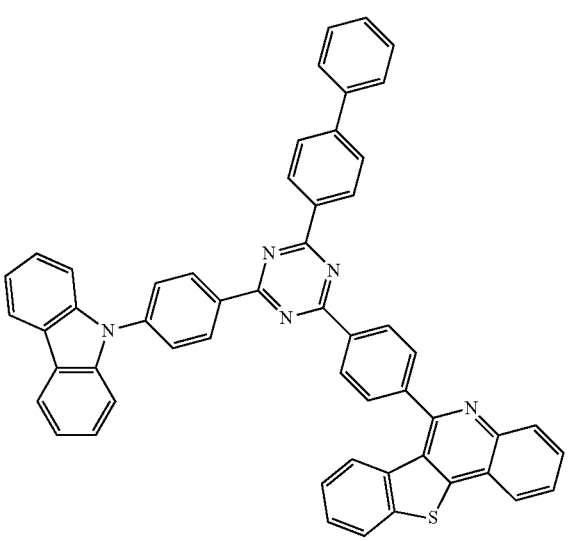
5
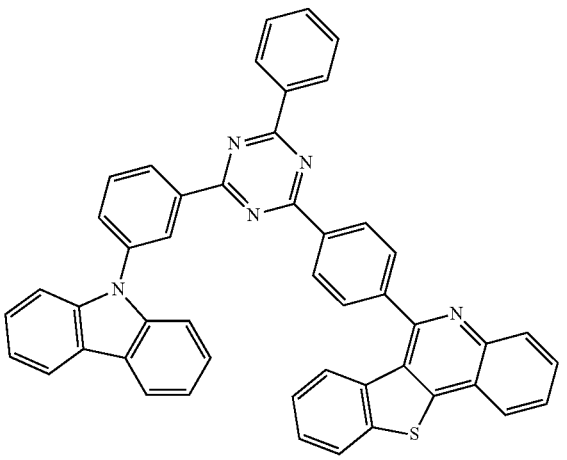
6
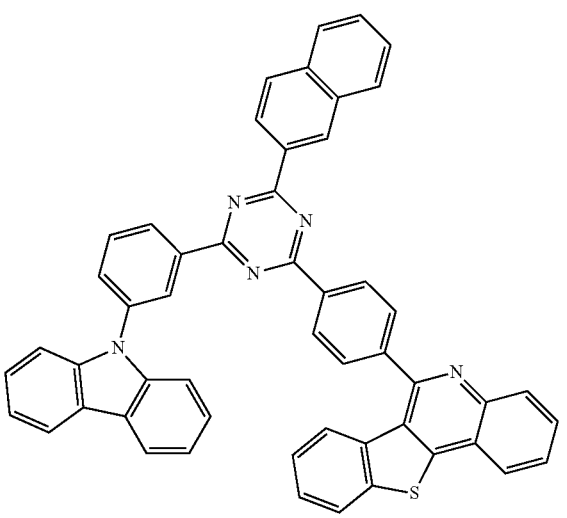
7
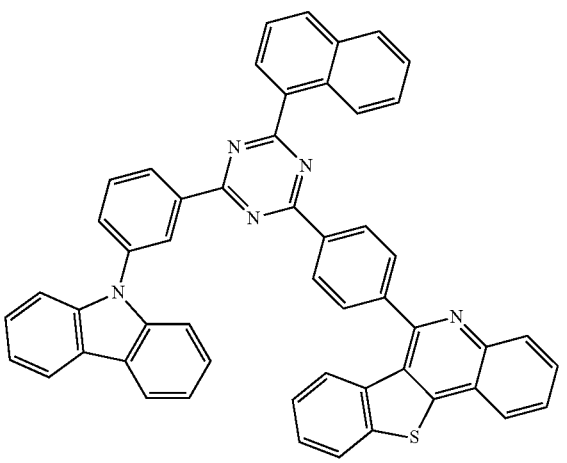

8
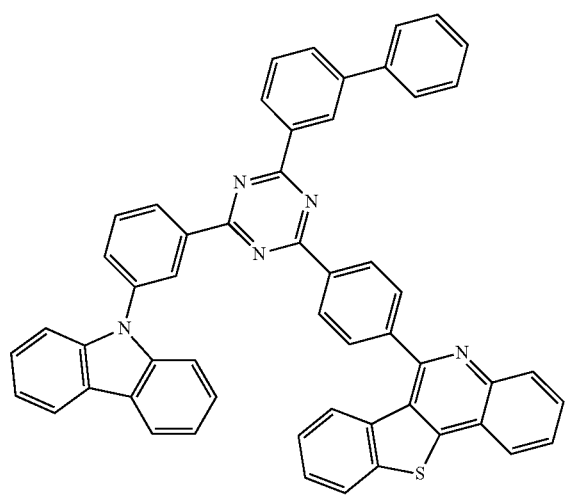
9
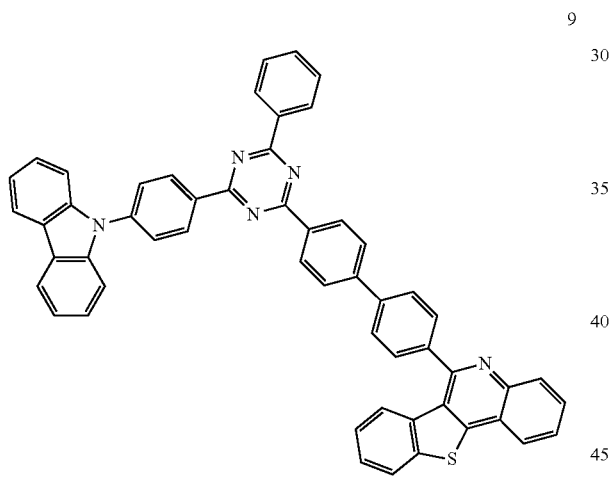
10
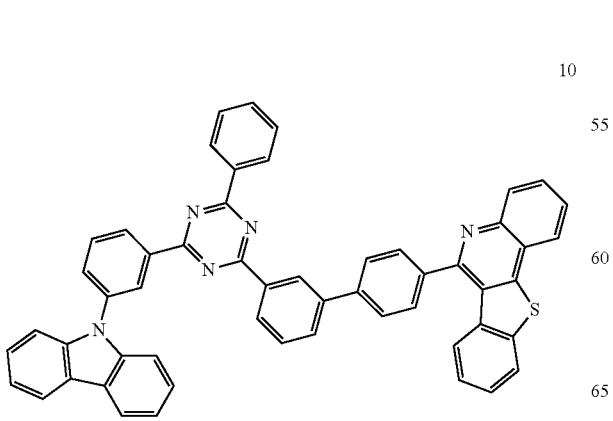
11
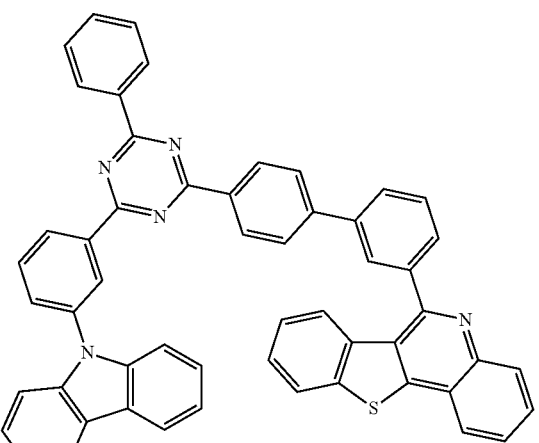
12
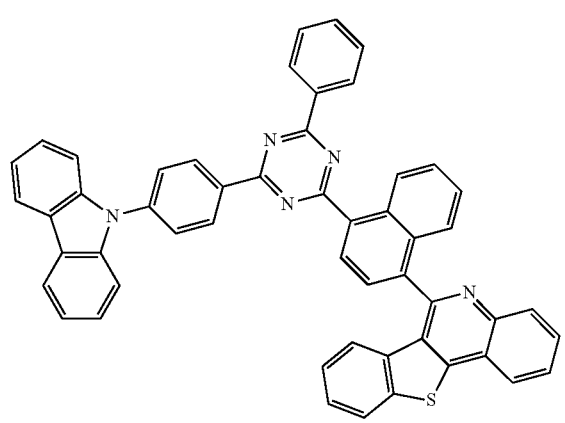
13

14
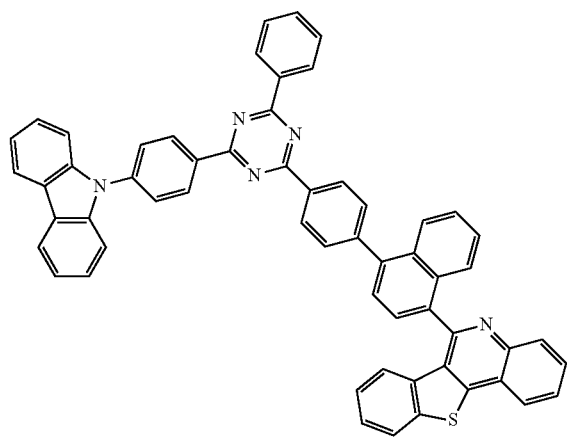
15
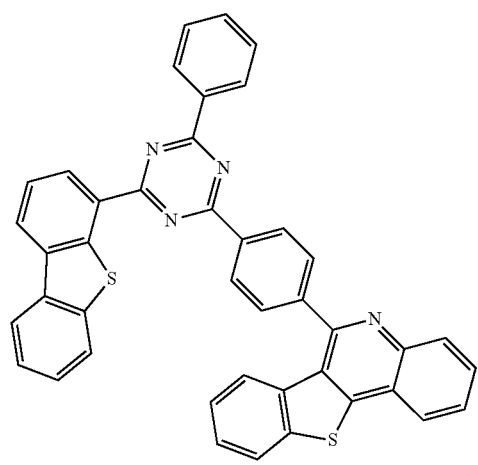
16
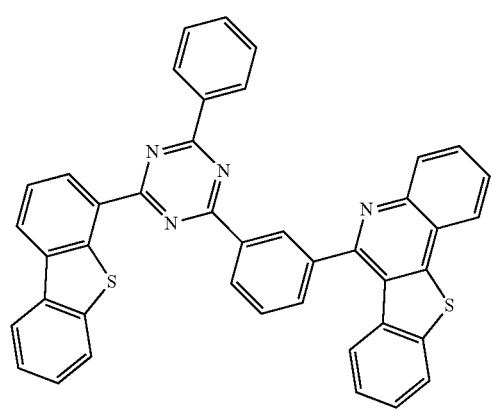
17
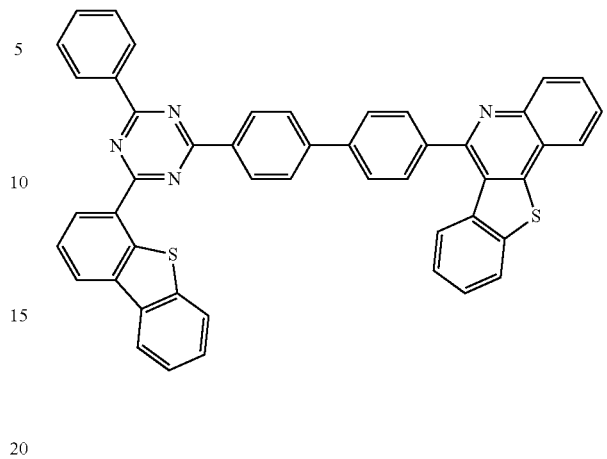
18
19

20
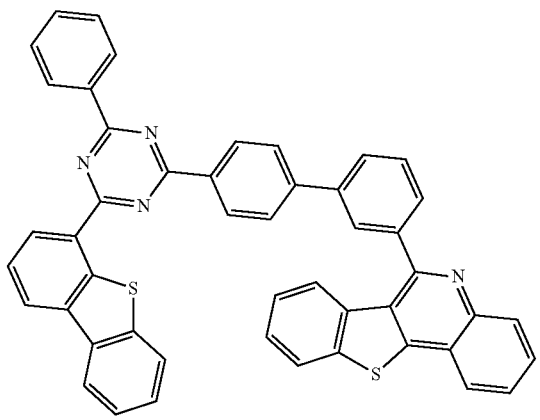
21
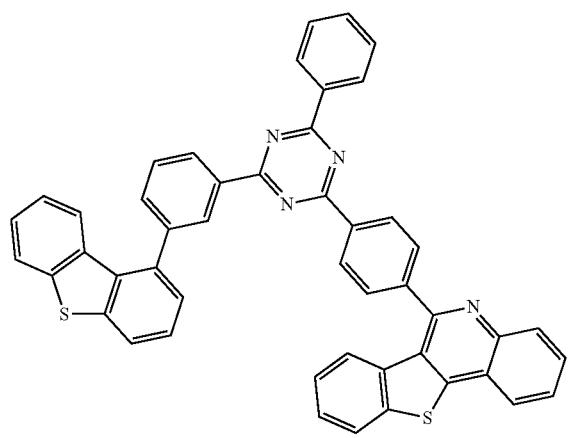
22
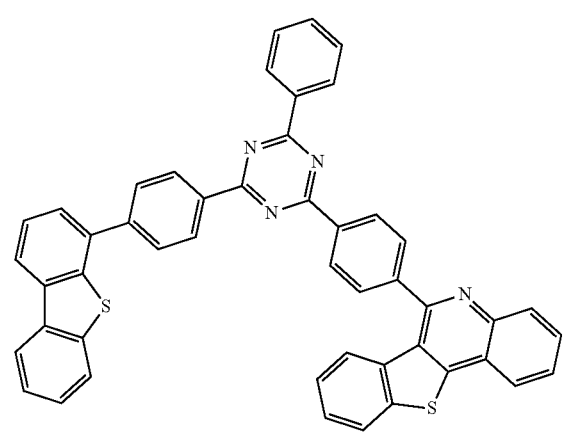
23
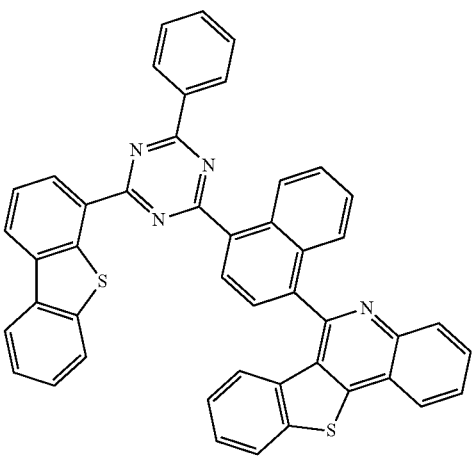
24
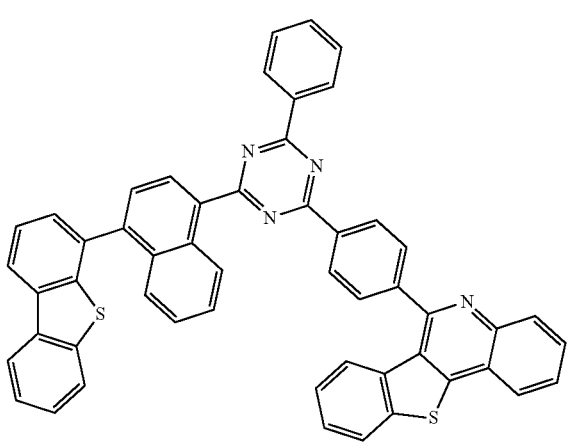
25

26
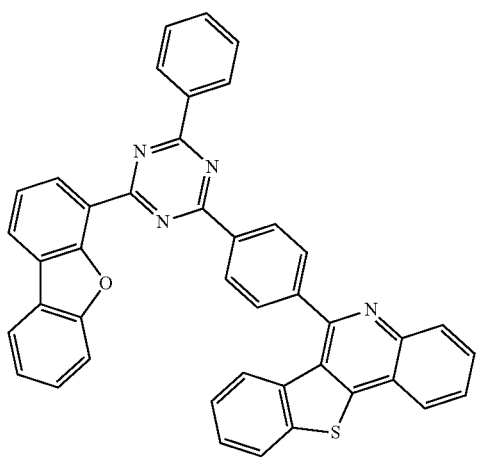
27
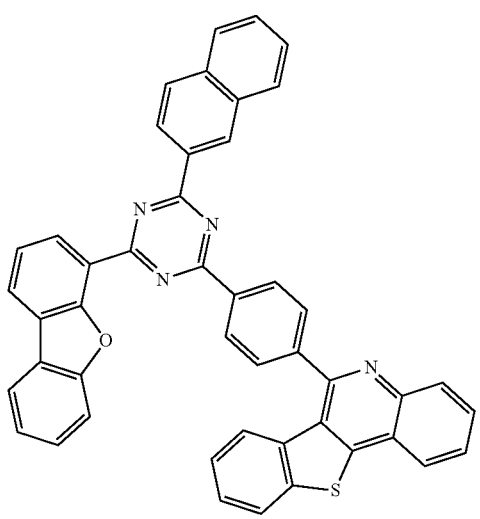
28
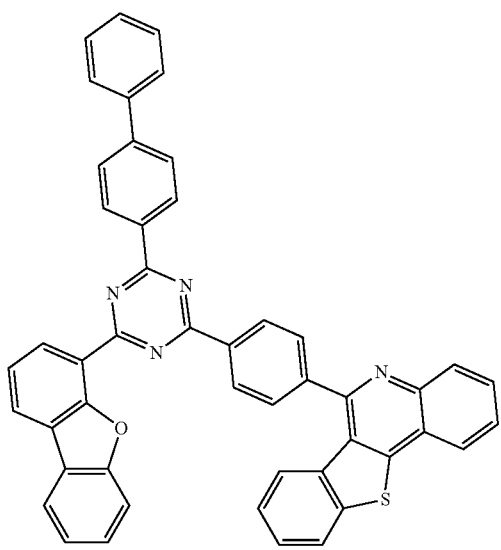
29
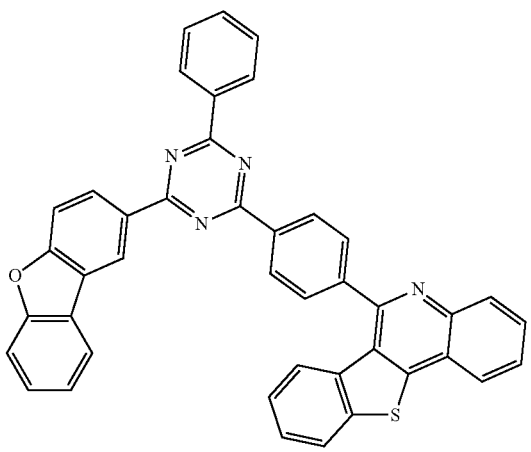
30
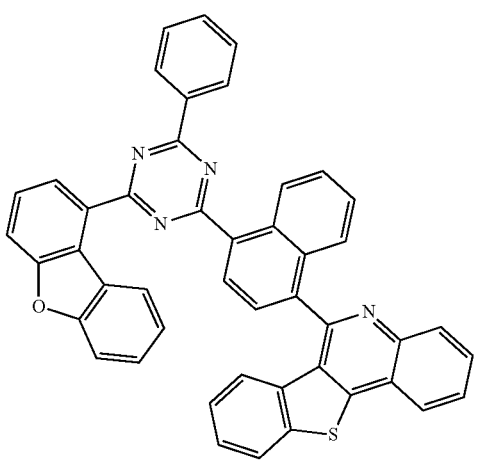
31
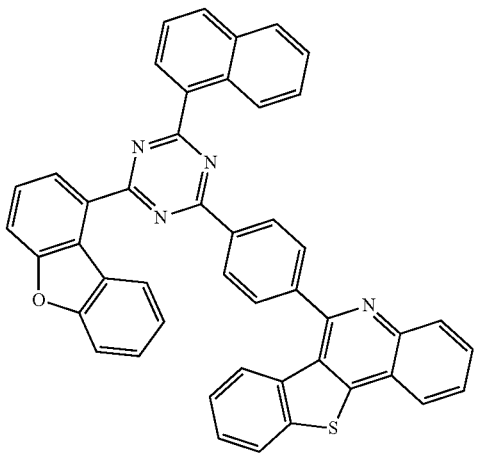

32
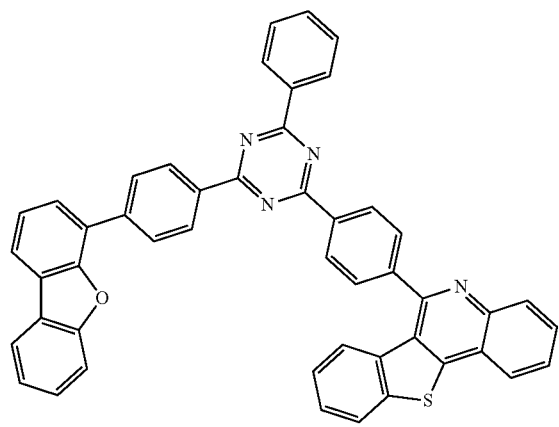
33
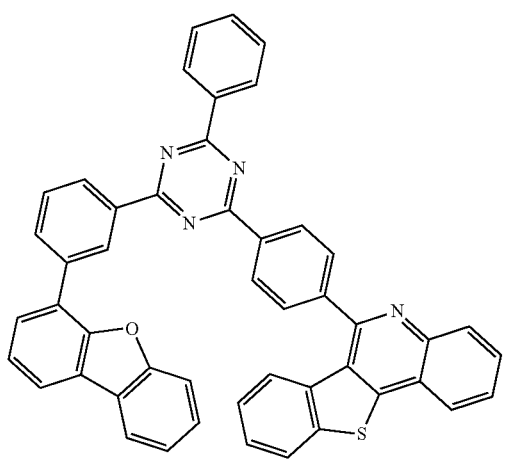
34
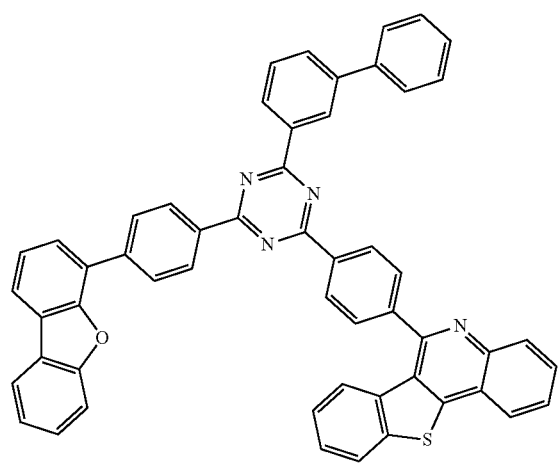
35
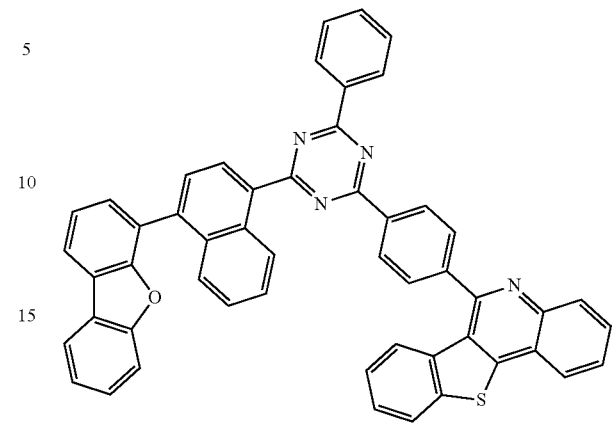
36
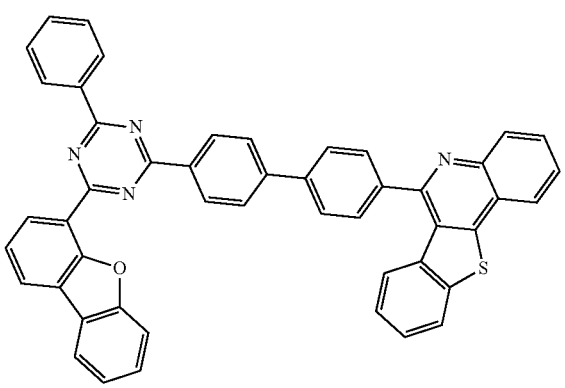
37
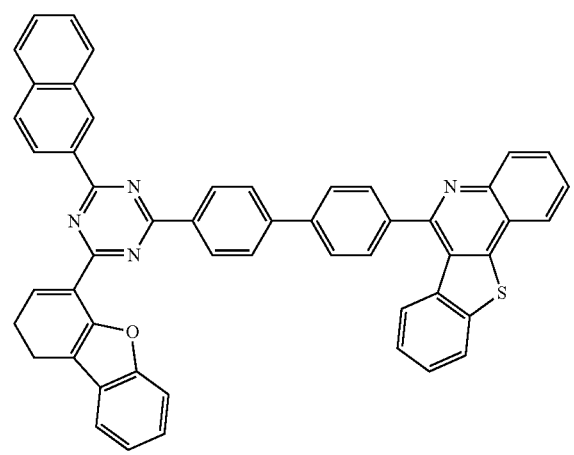

38
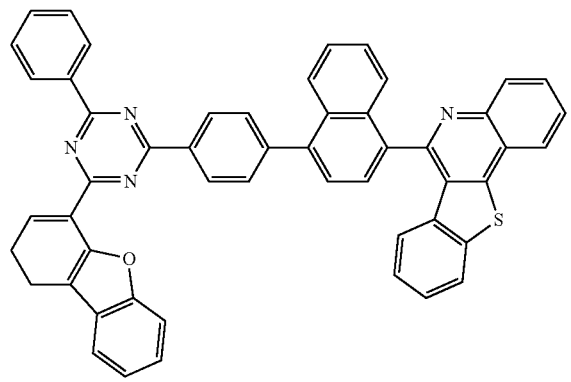
39
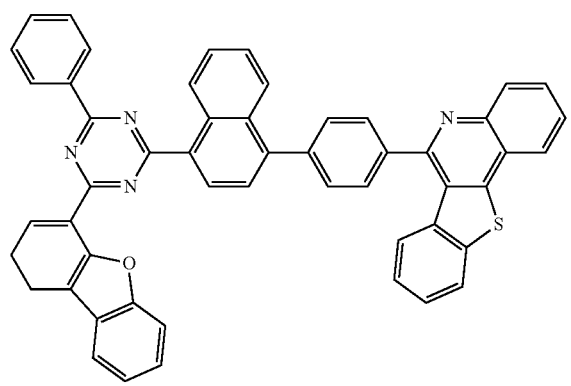
40
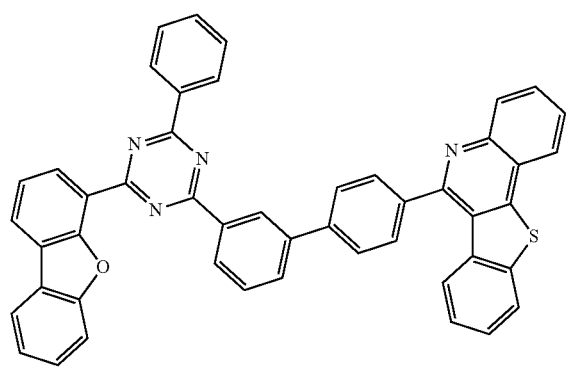
41
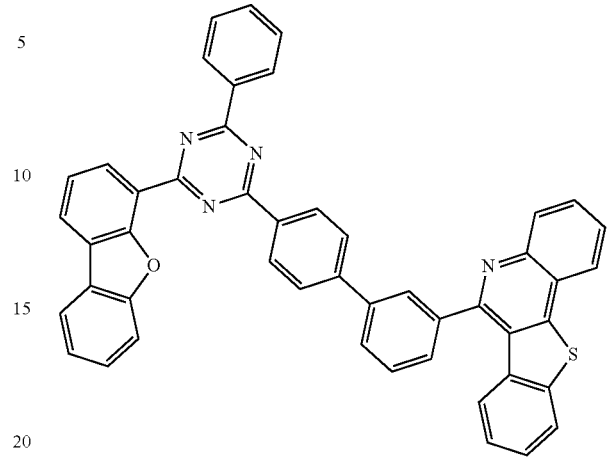
42
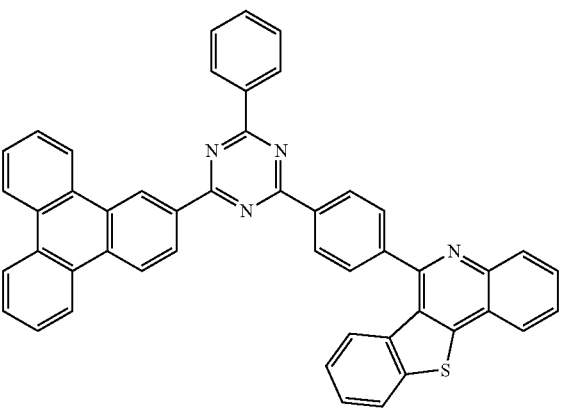
43
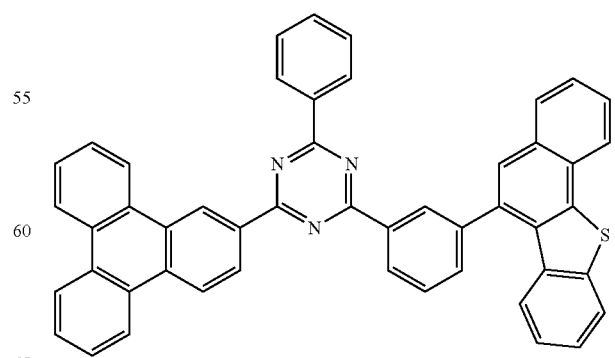

44
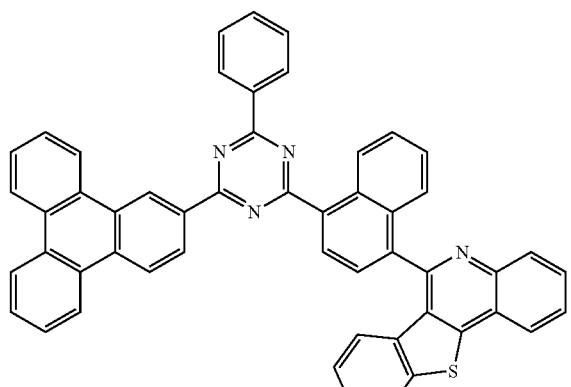
45
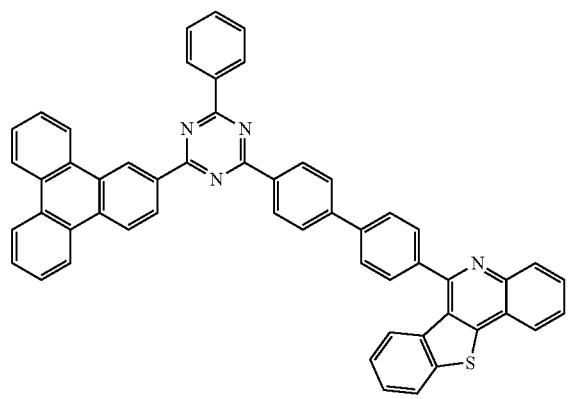
46
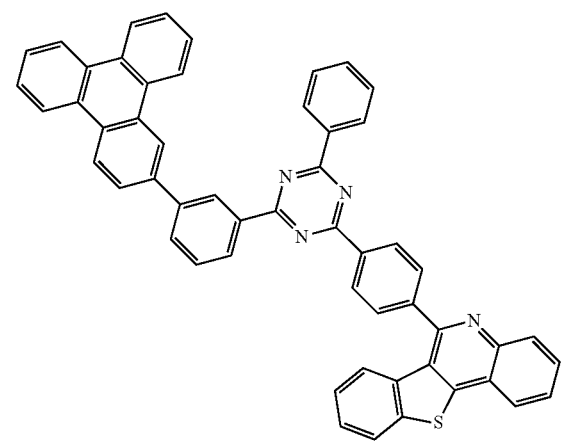
47
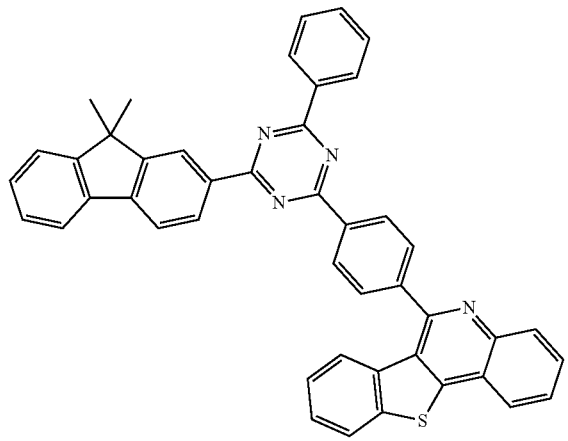
48
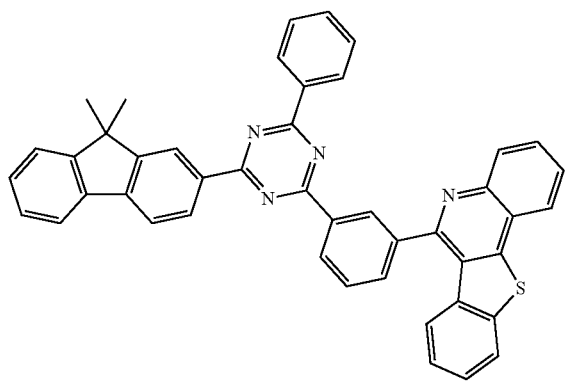
49
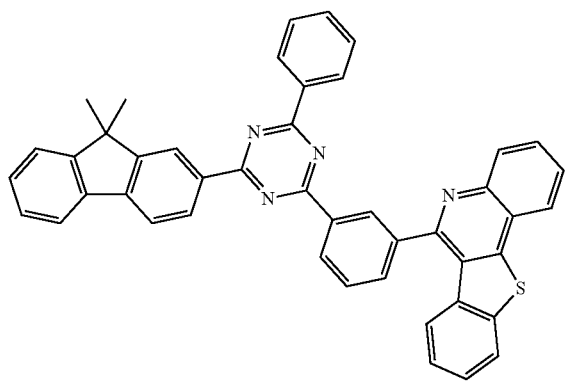

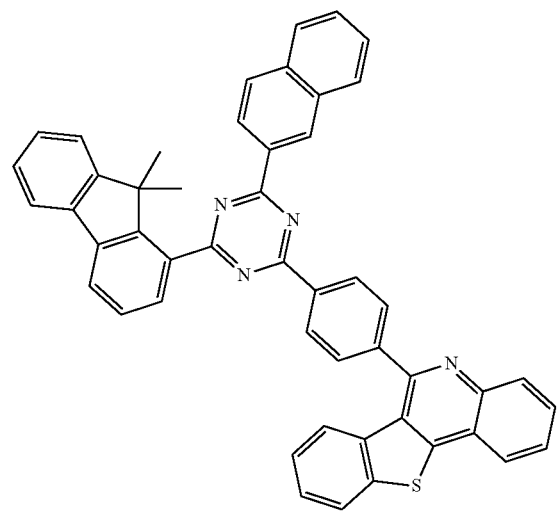
50
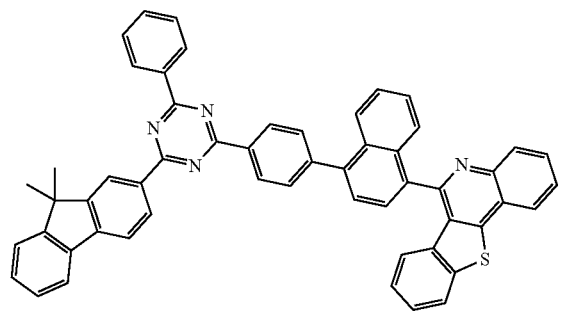
51
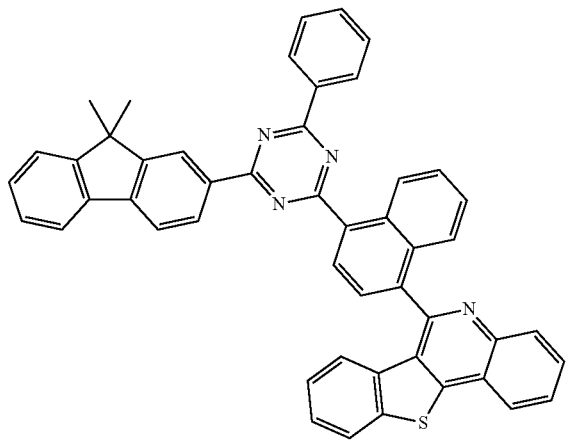
53
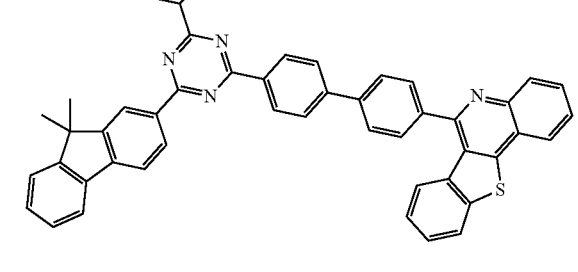
54
52
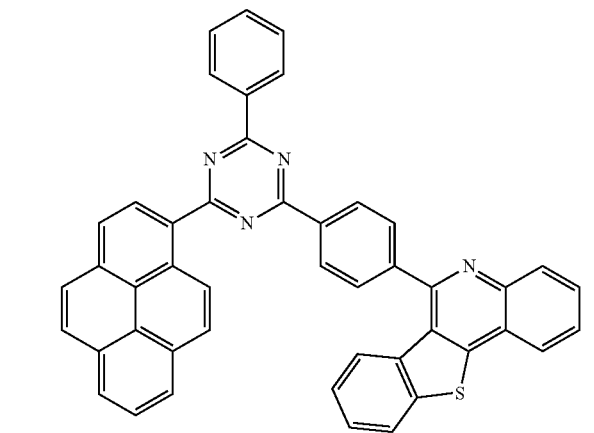
55

56
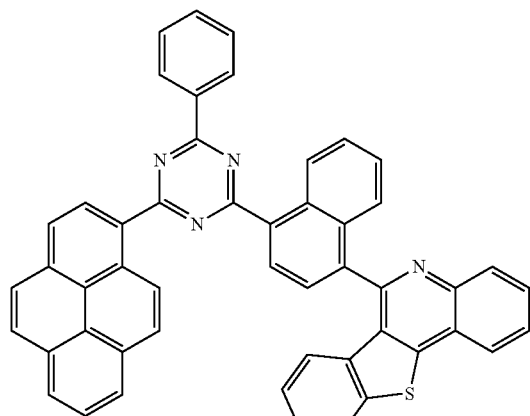
57
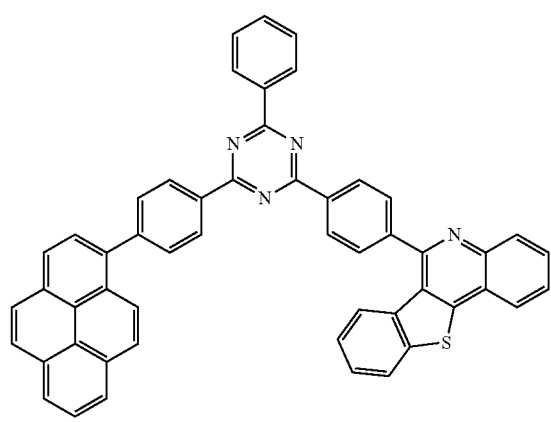
58
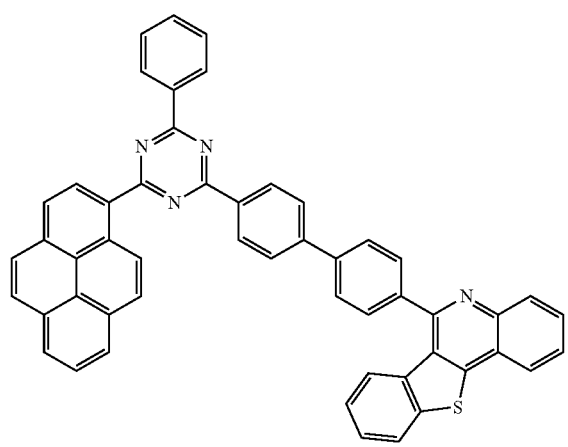
59
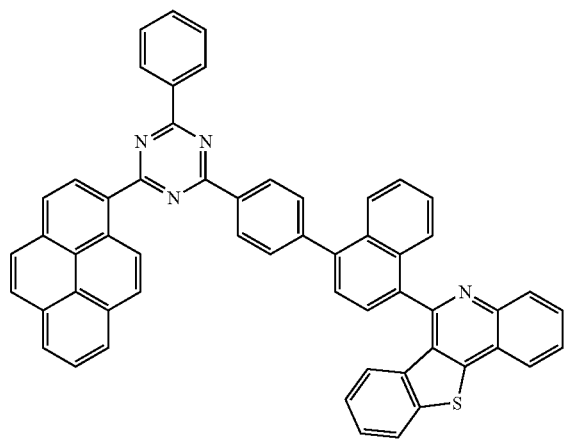
60
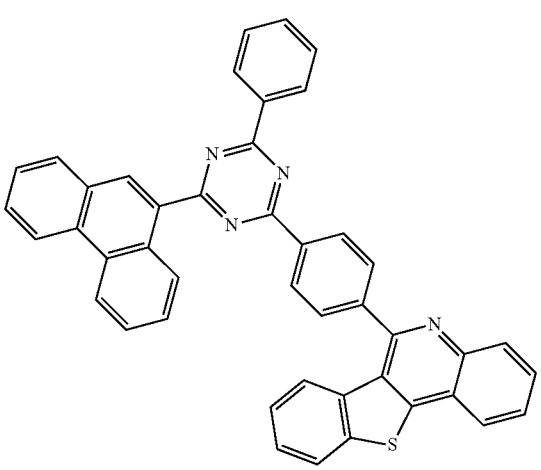
61
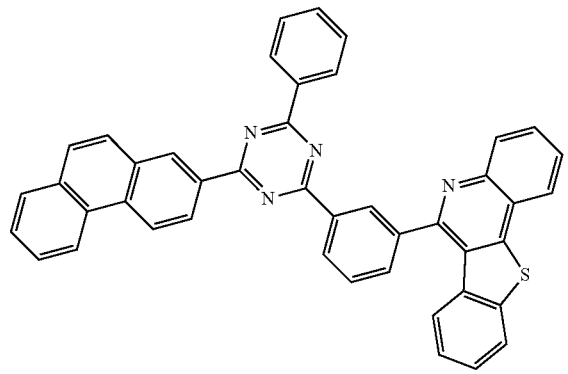

62
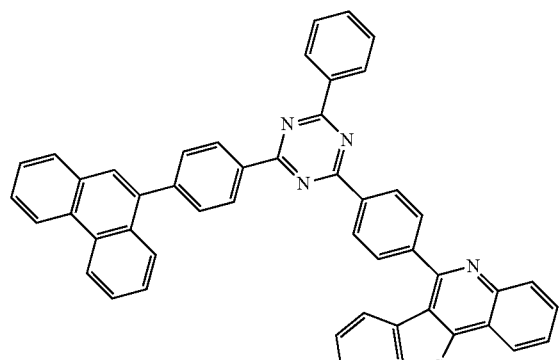
63
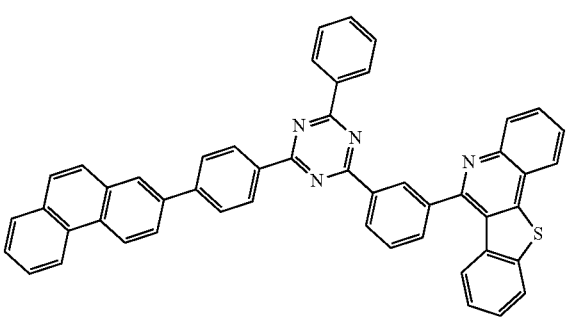
64
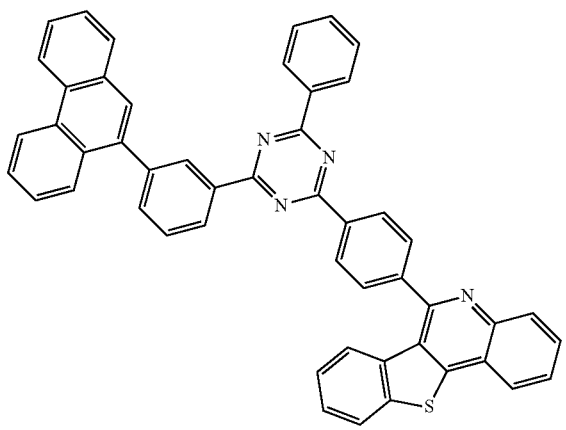
65
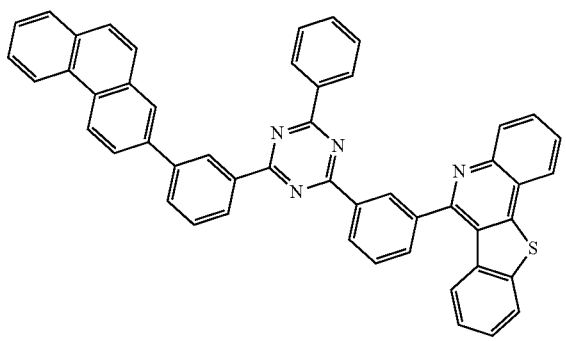
66
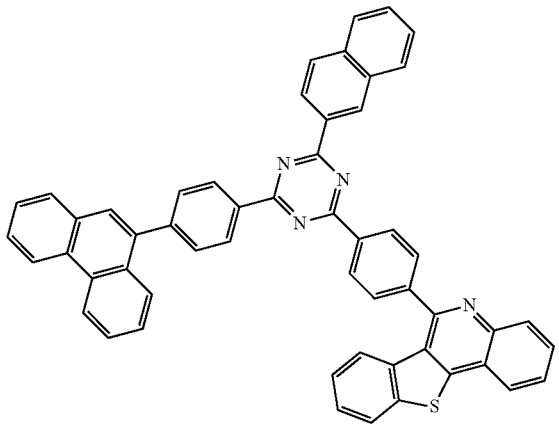
67
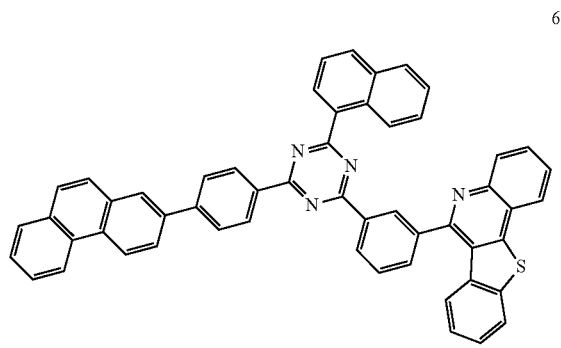
68
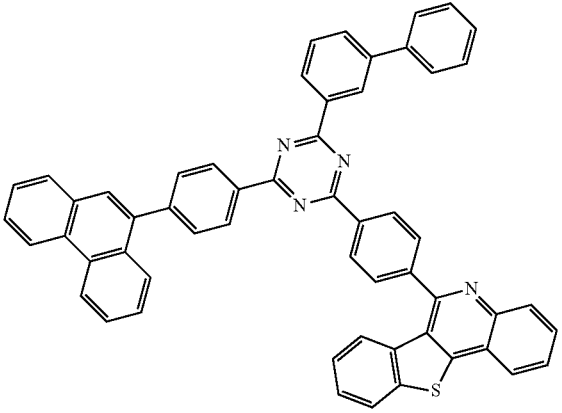
69
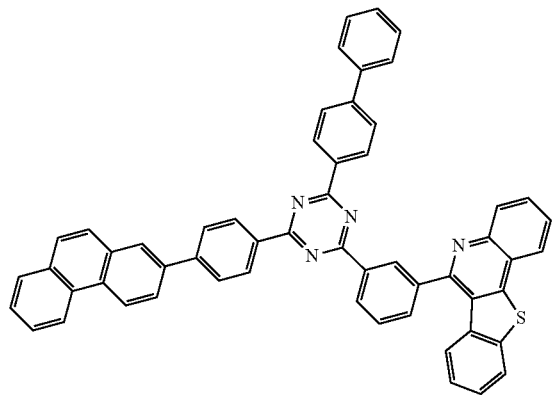

70
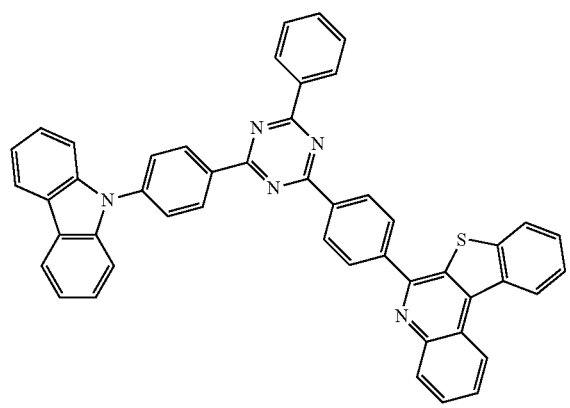
73
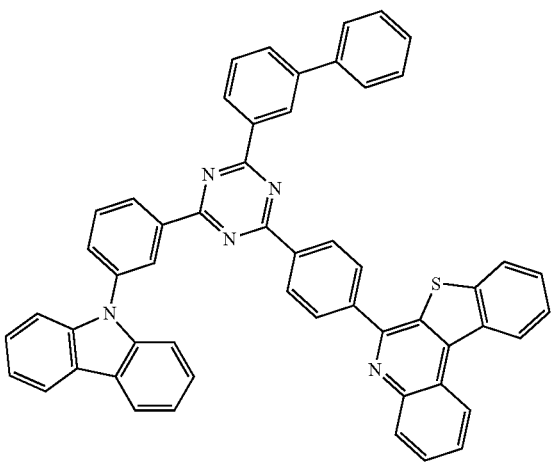
71
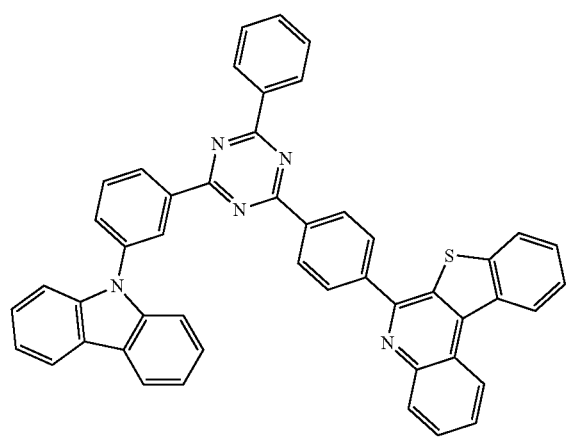
74
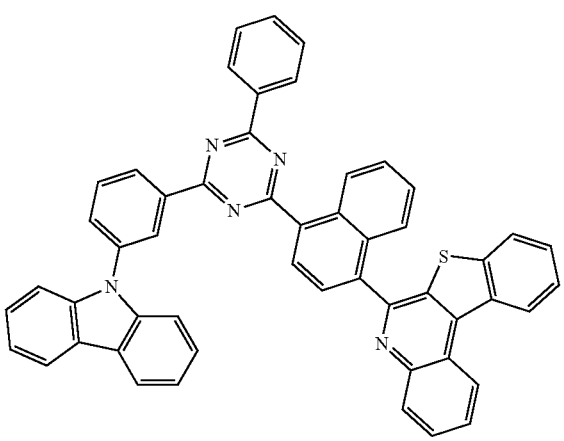
72
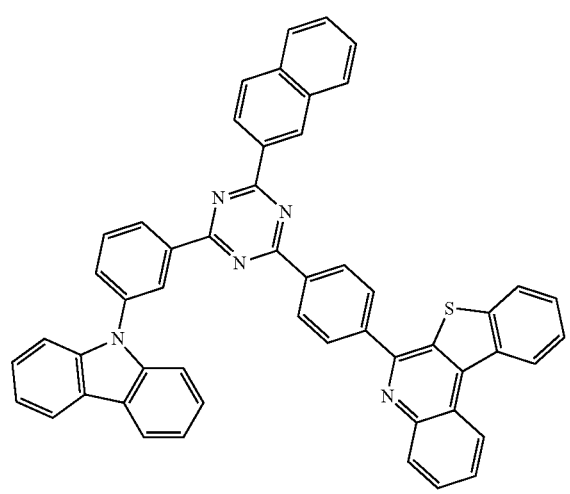
75
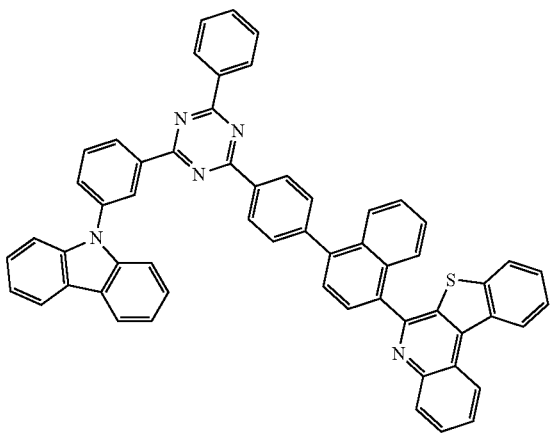

76
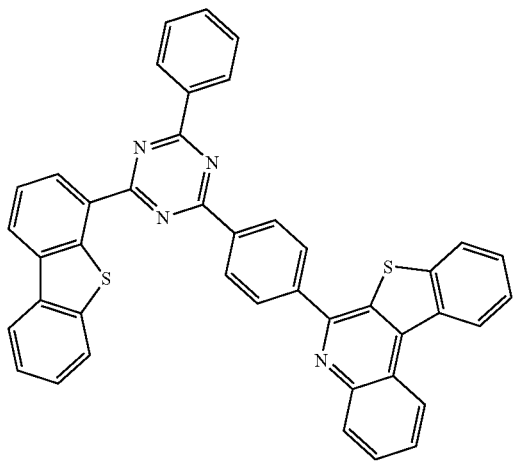
77
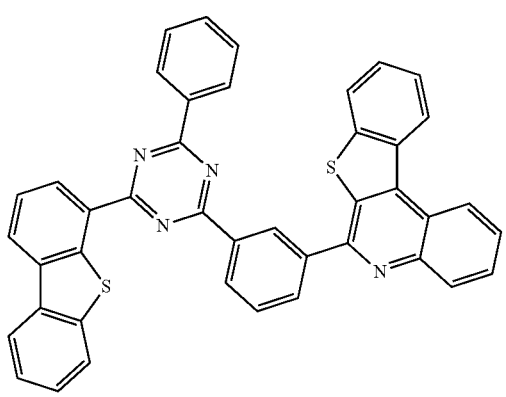
78
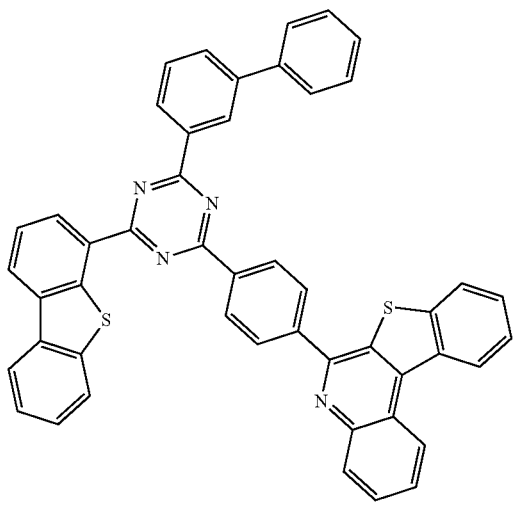
79
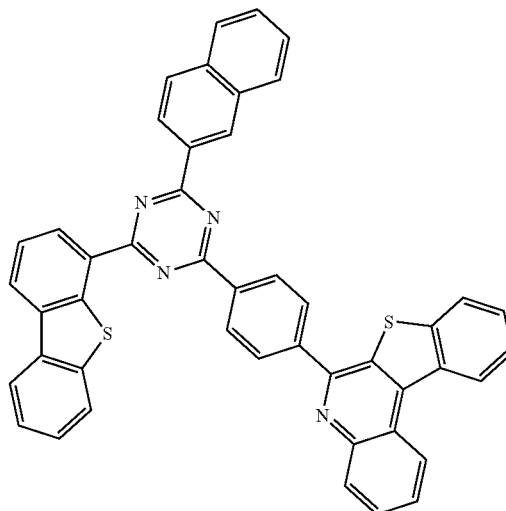
80
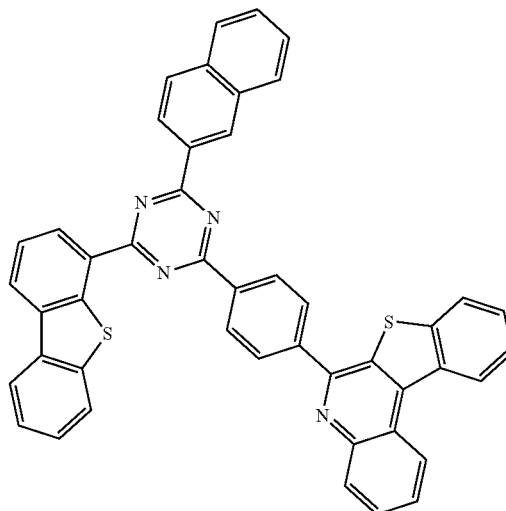
81
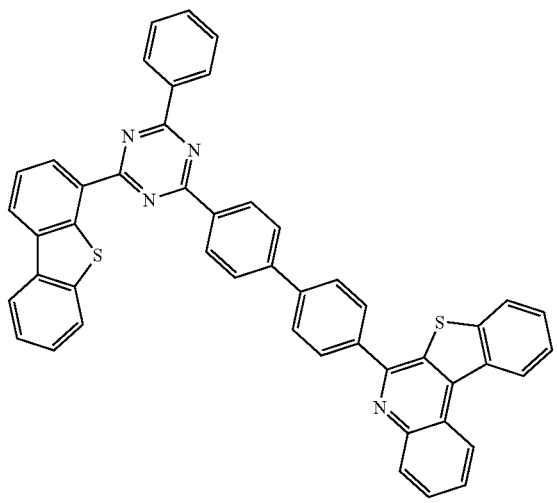

82
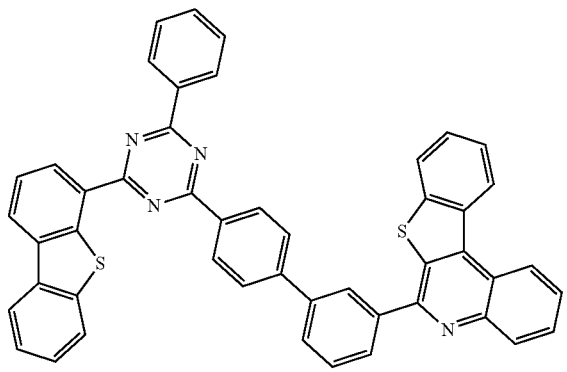
83
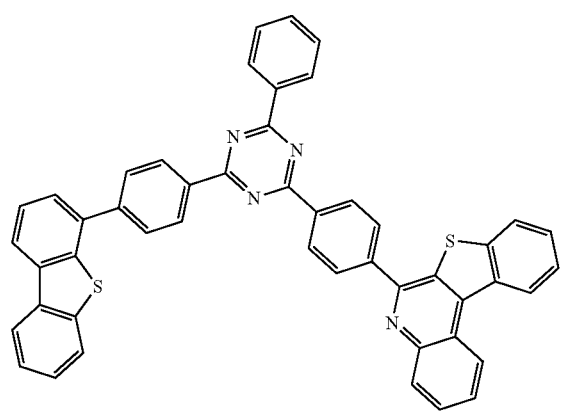
84
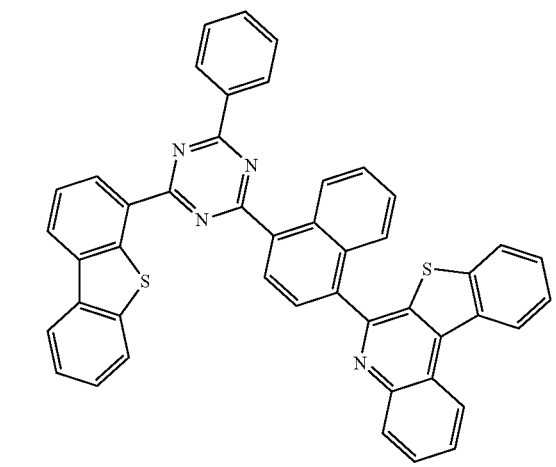
85
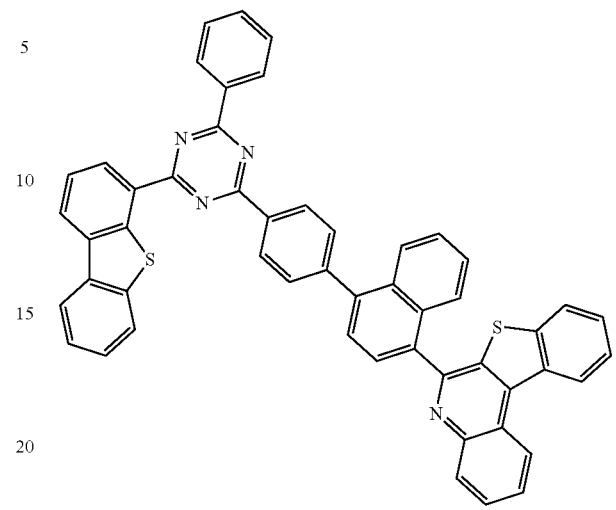
86
87
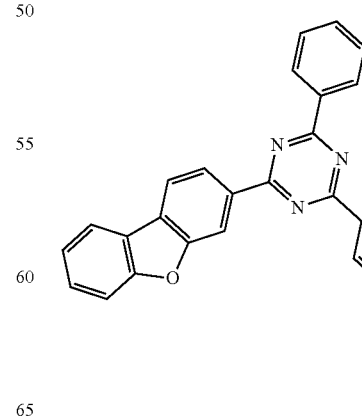

88
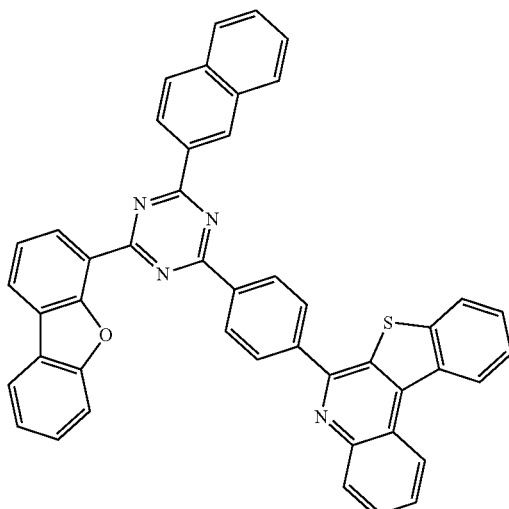
91
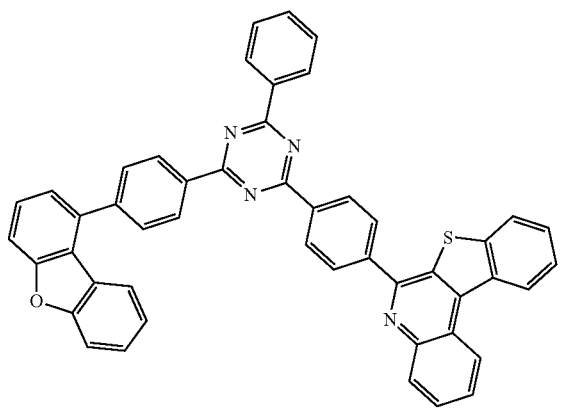
89
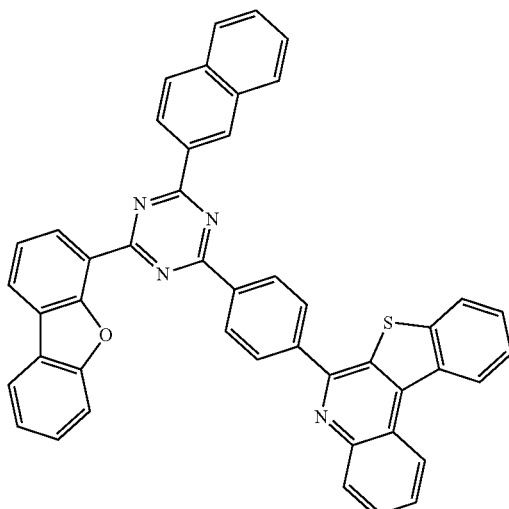
92
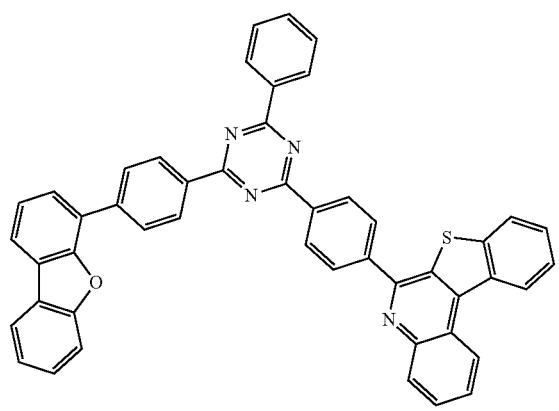
90
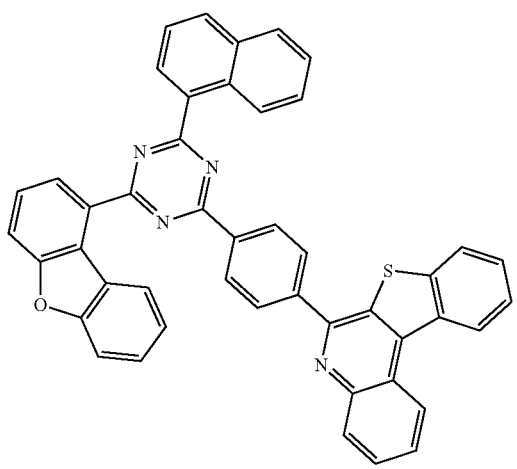
93
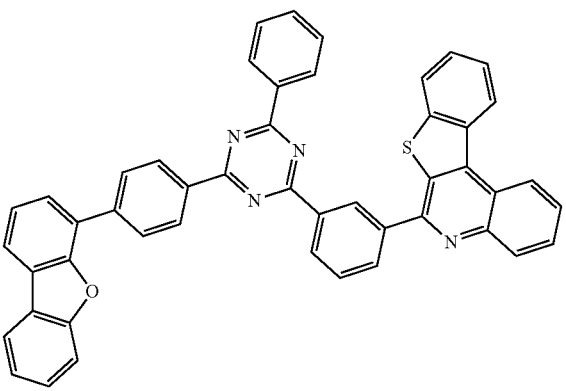

94
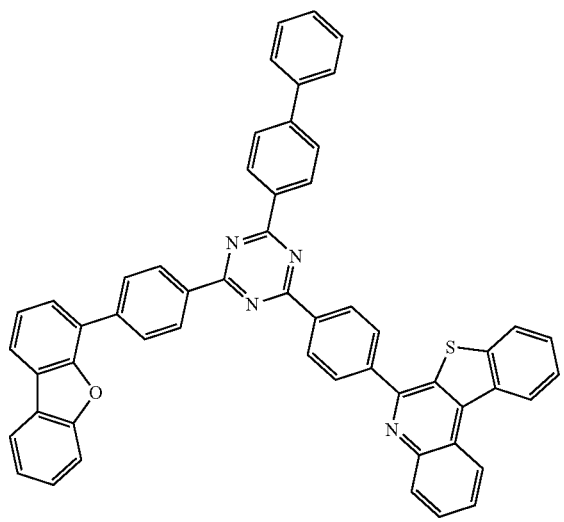
95
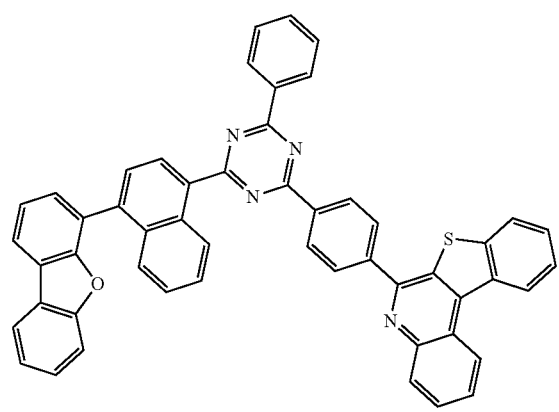
96
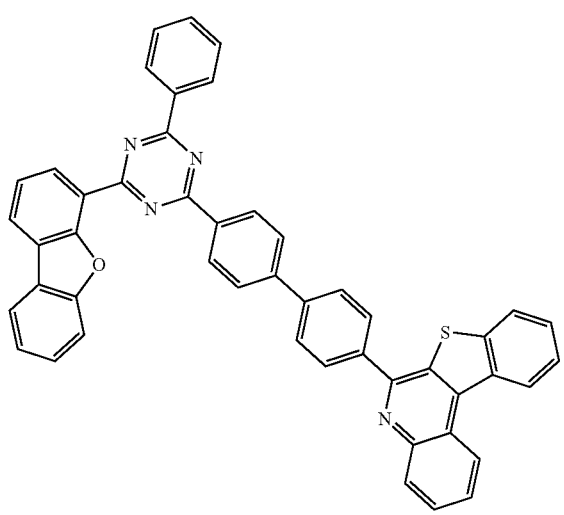
97
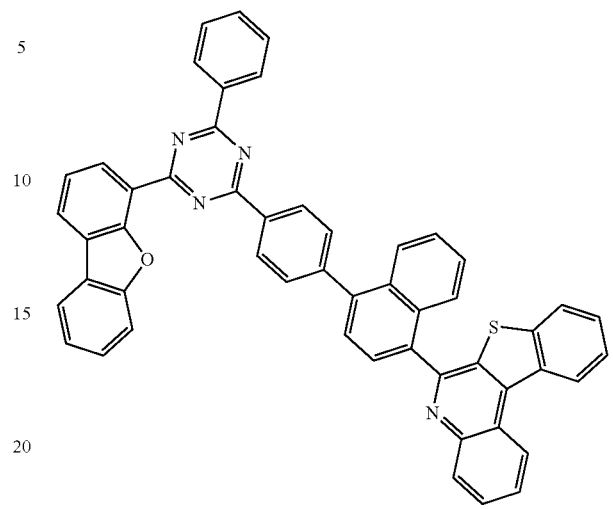
98
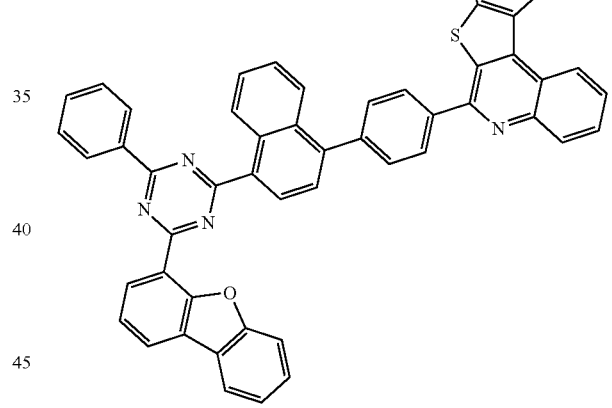
99
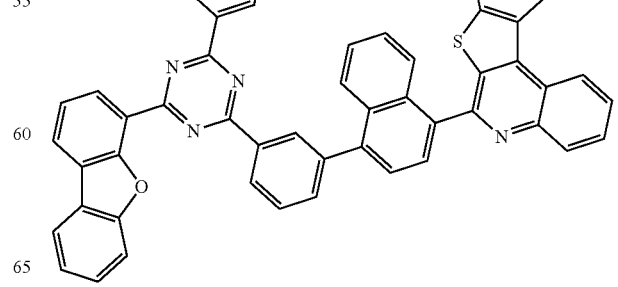

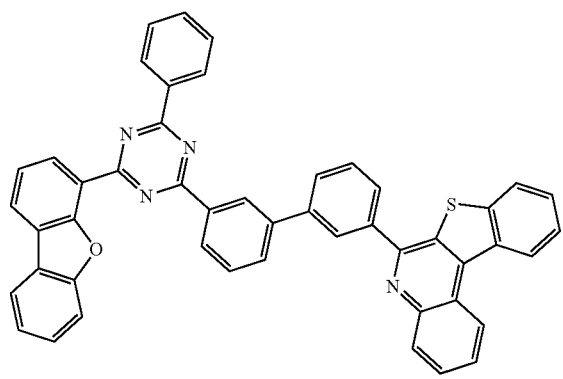
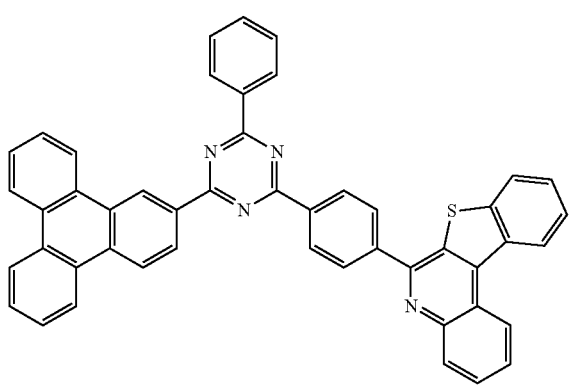
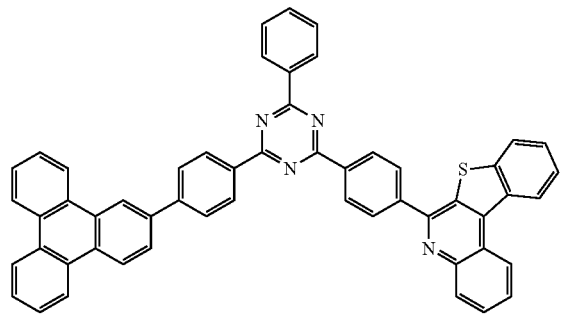
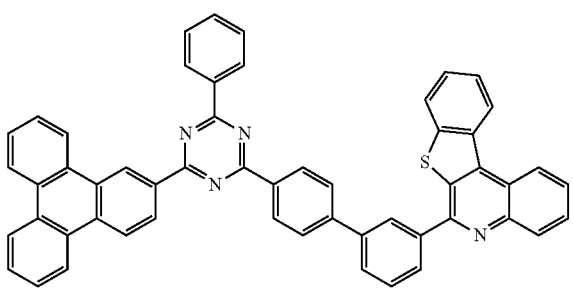
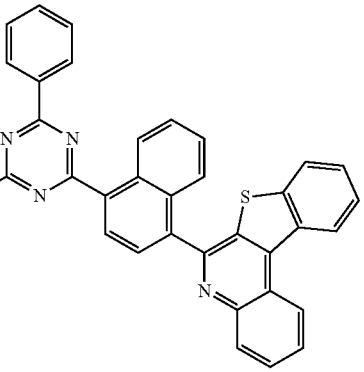

108
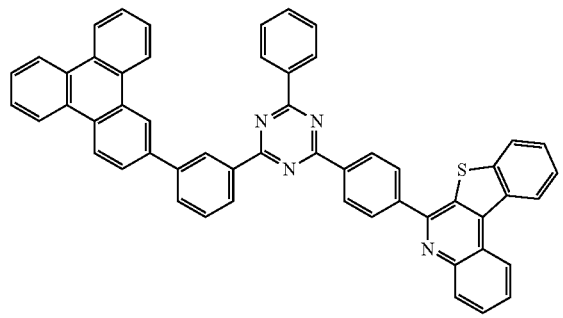
109
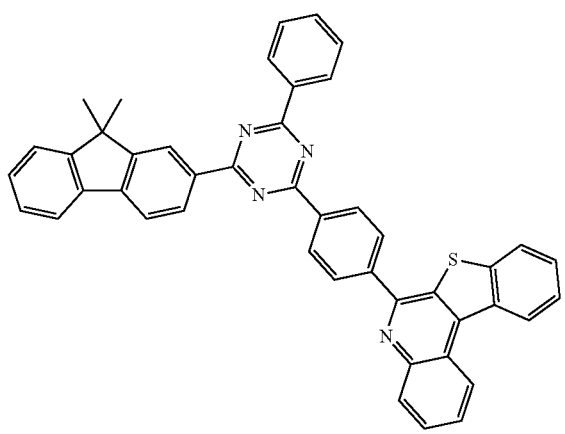
110
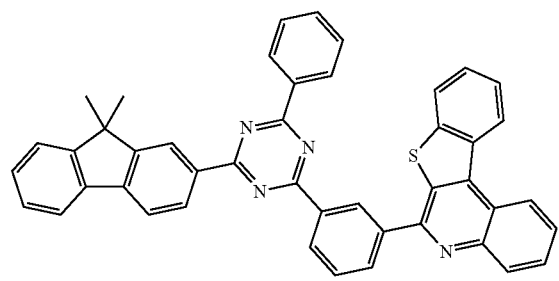
111
112
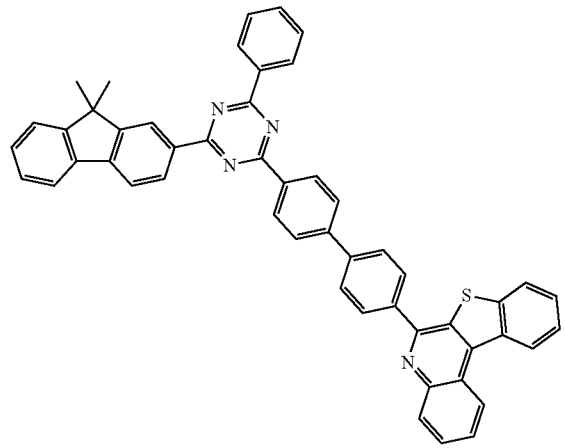
113
114
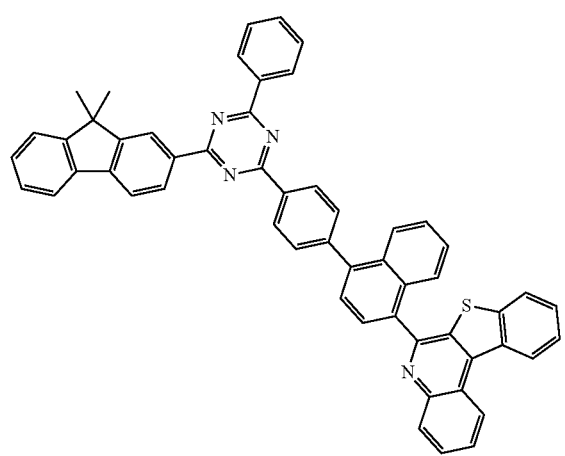

115
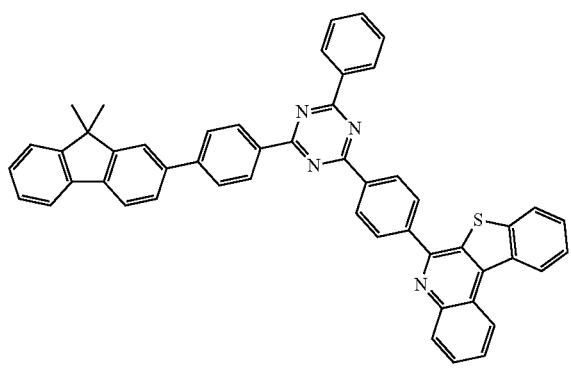
116
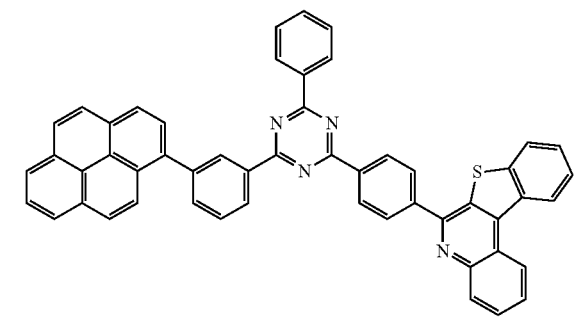
117
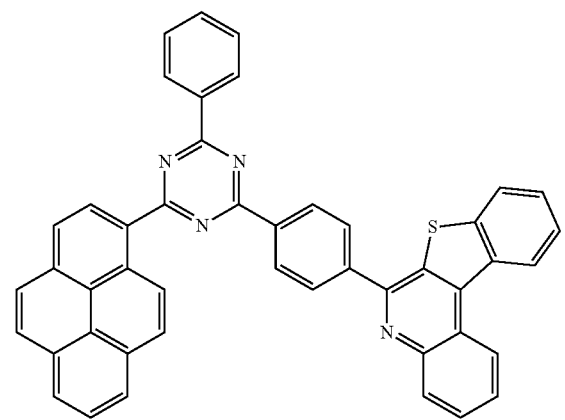
118
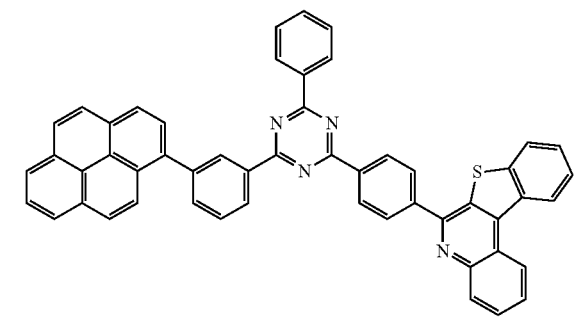
119
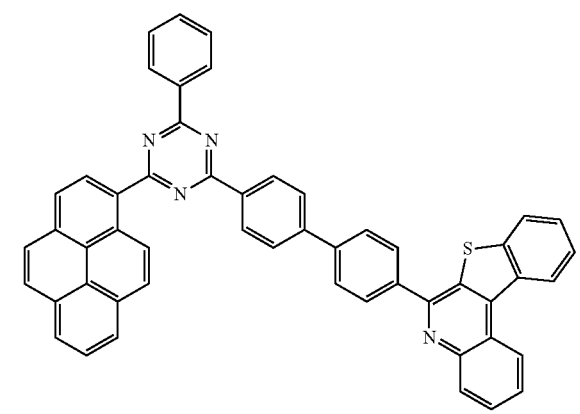
120
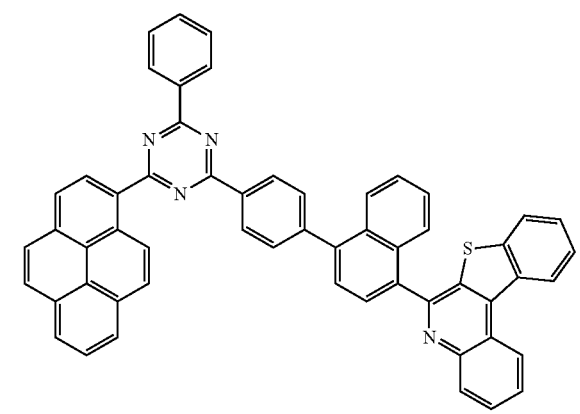
121
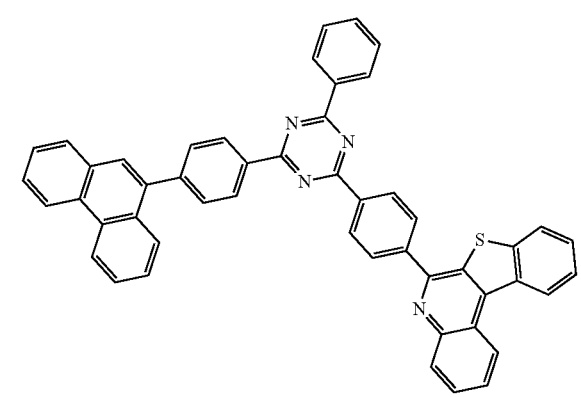

122
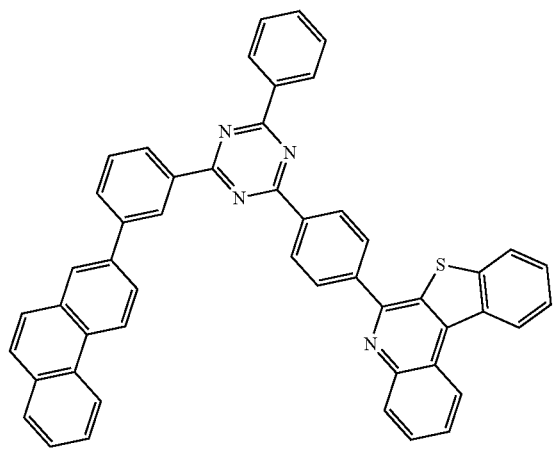
123
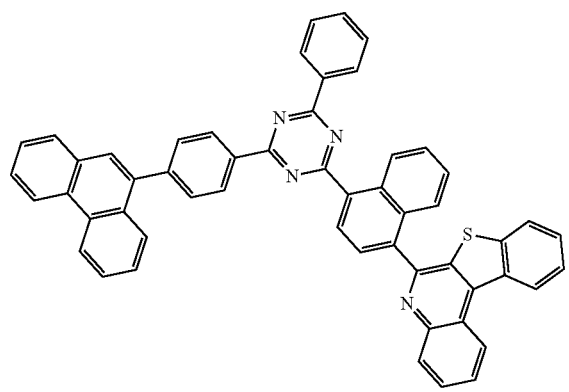
124
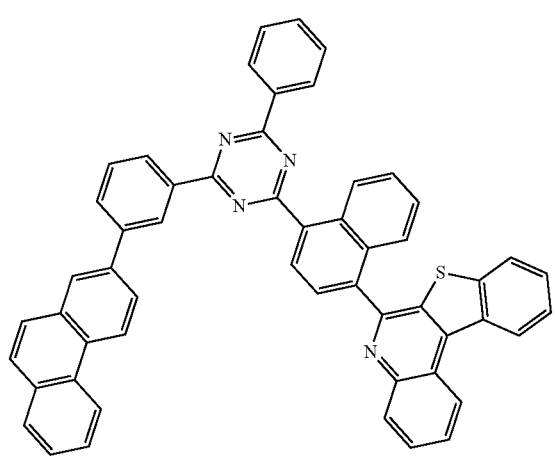
125
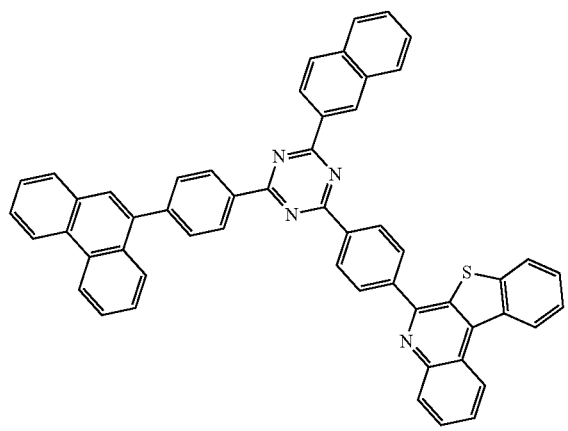
126
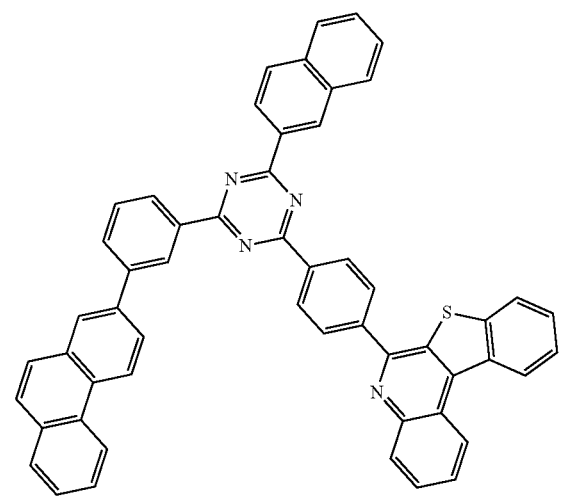
127
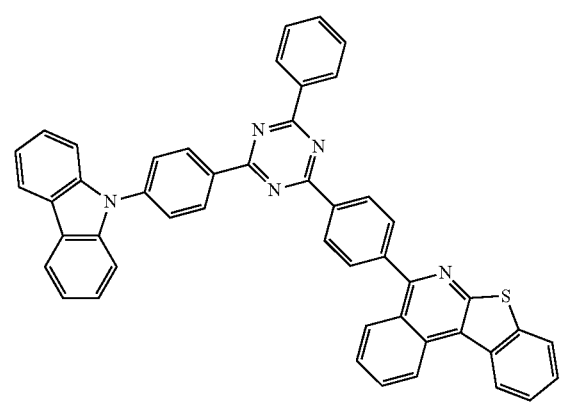

128
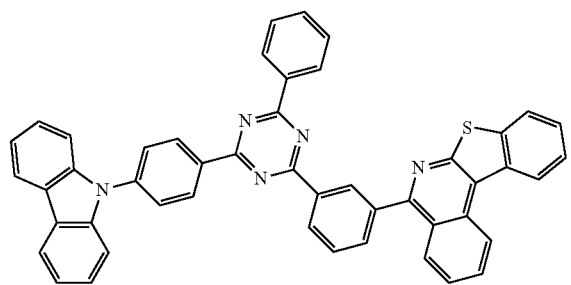
129
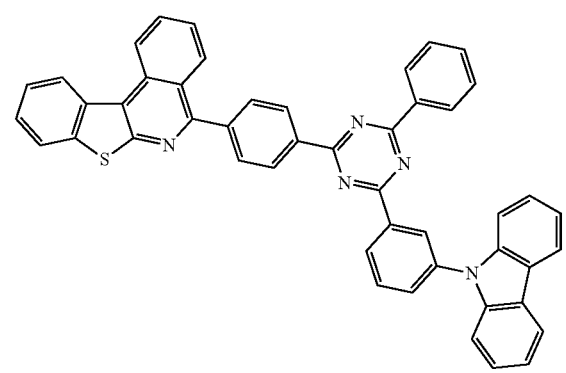
130
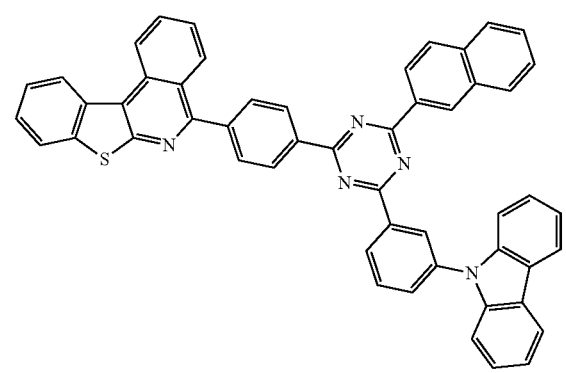
131
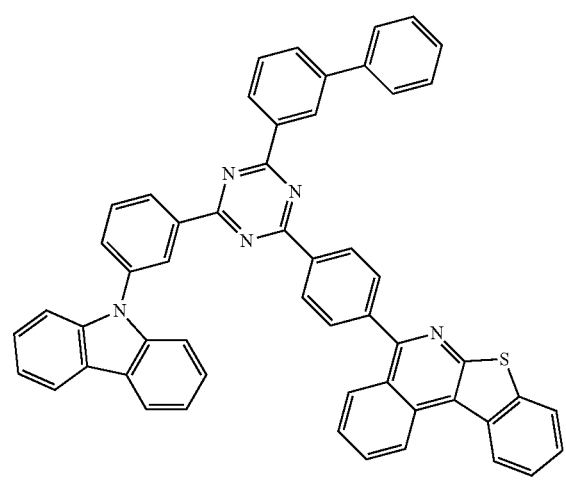
132
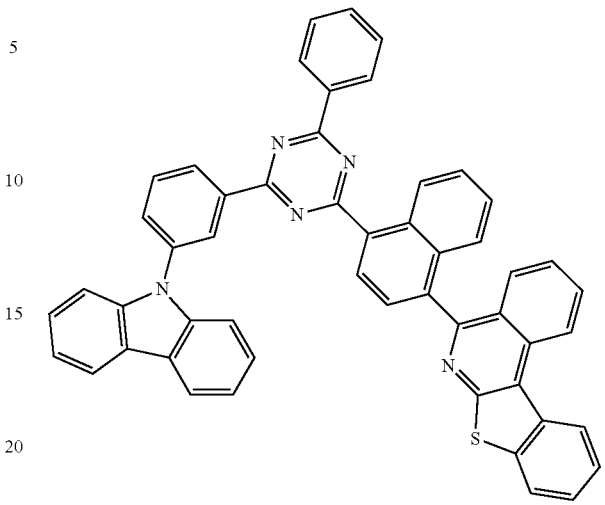
133
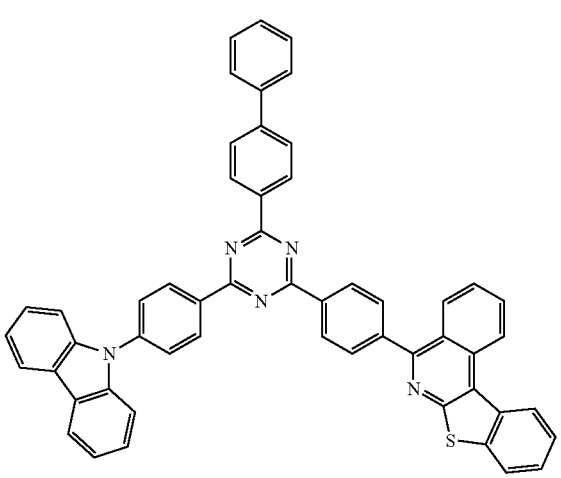
134
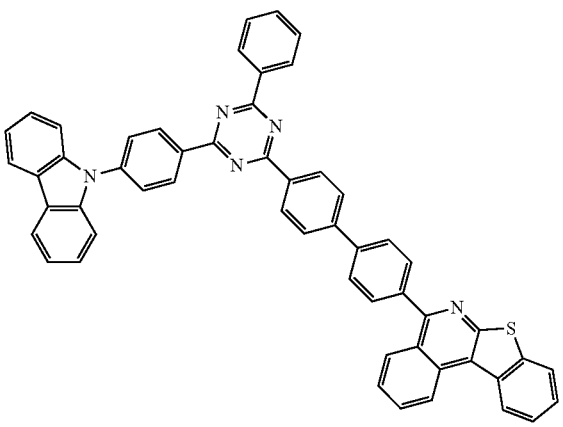

135
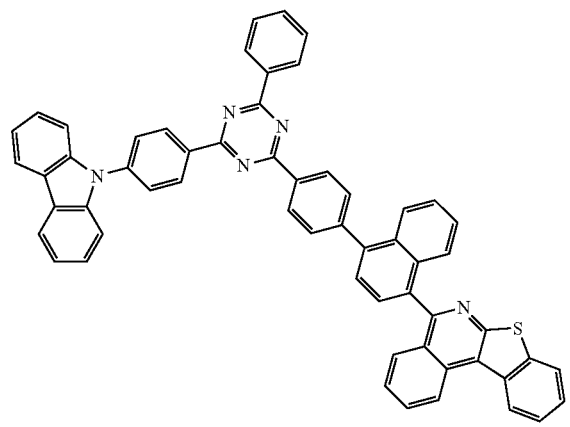
136
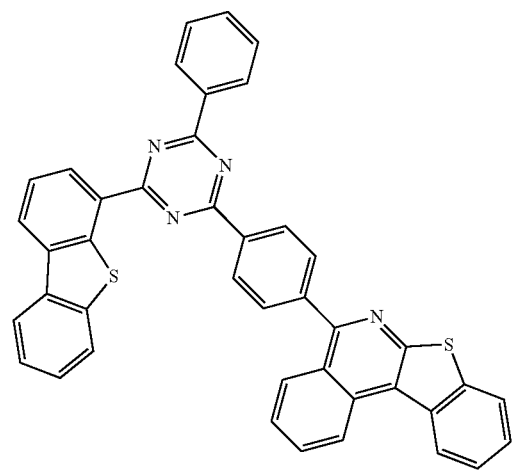
137
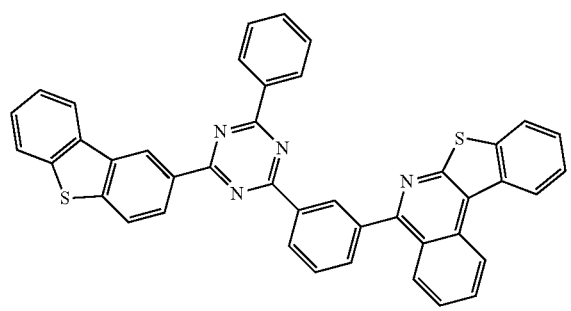
138
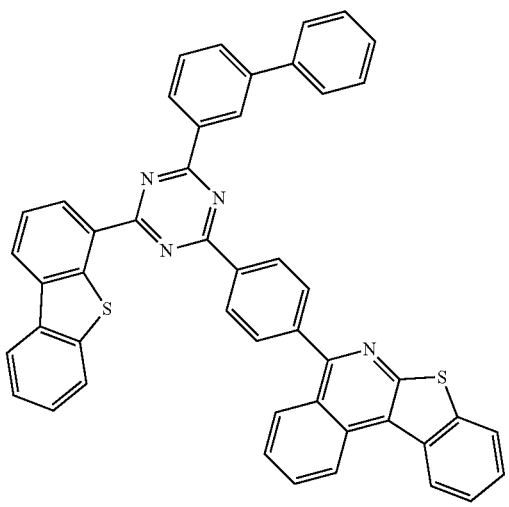
139
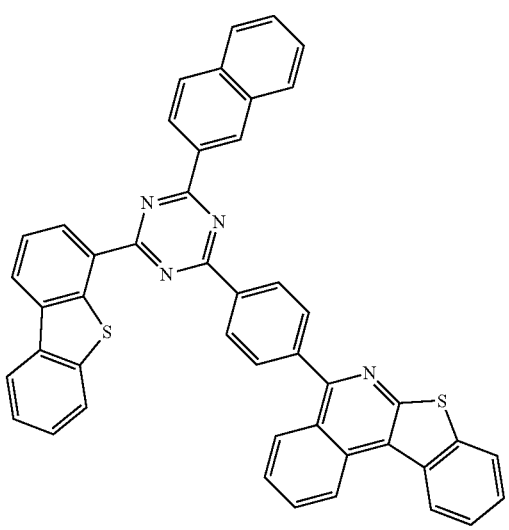
140
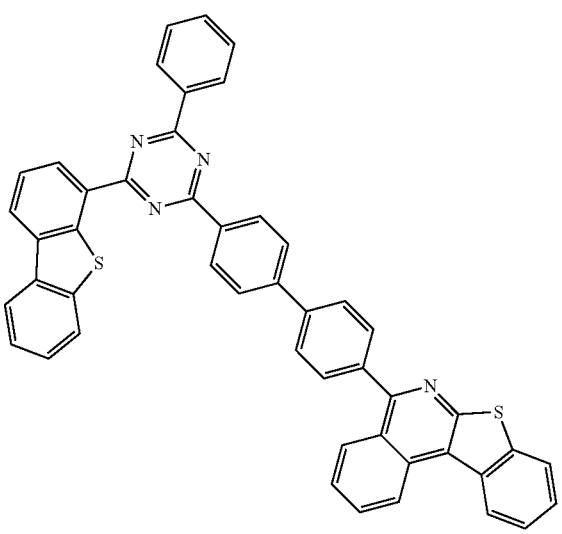

141
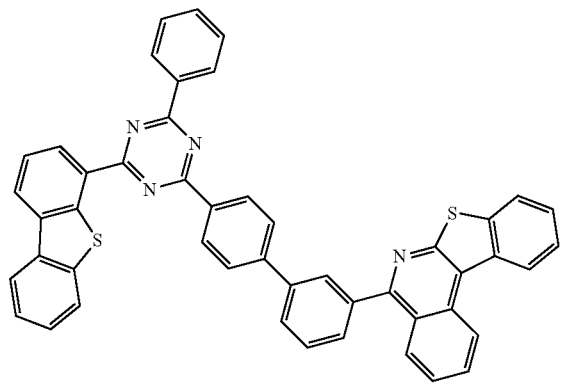
142
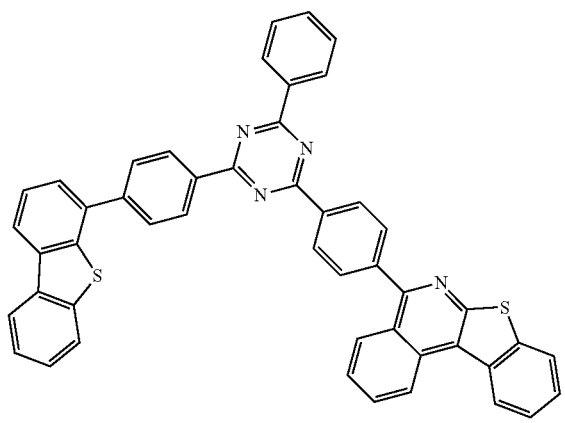
143
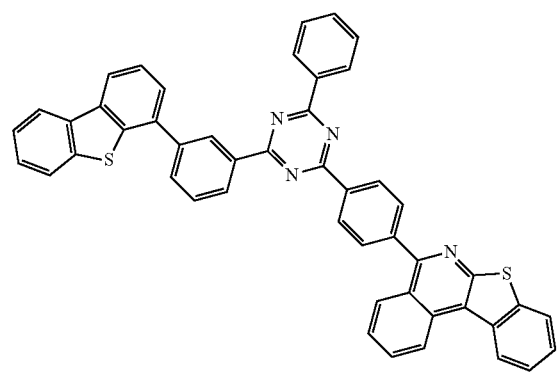
144
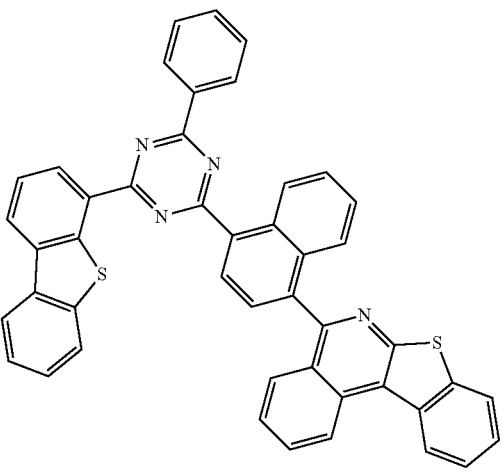
145
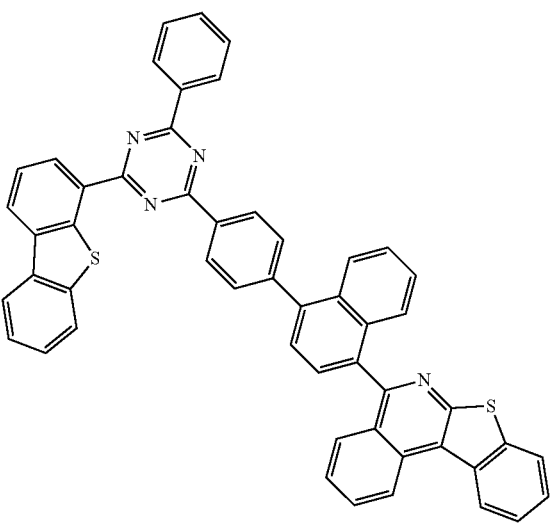
146
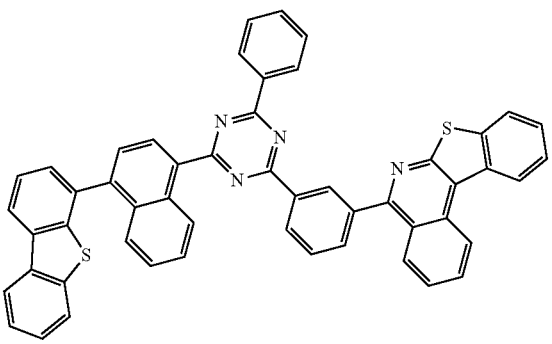

147
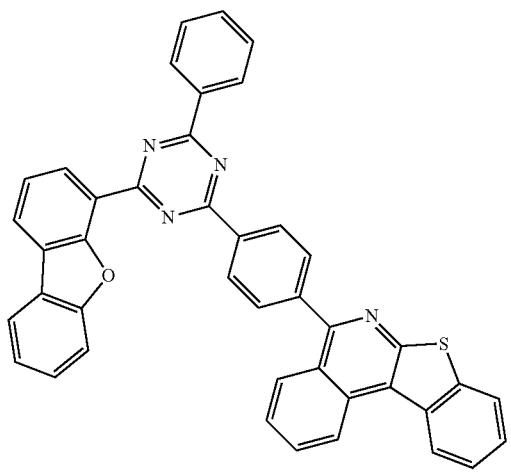
148
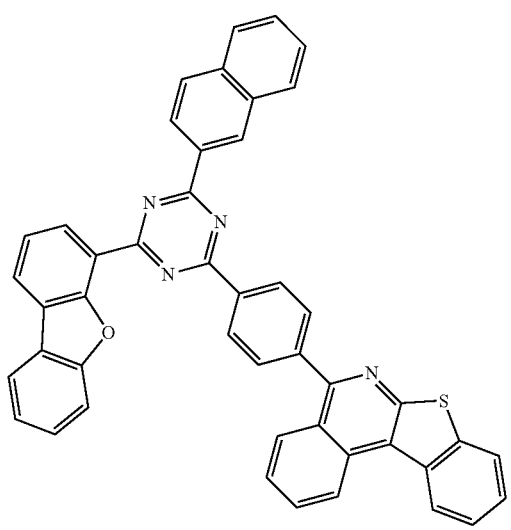
149
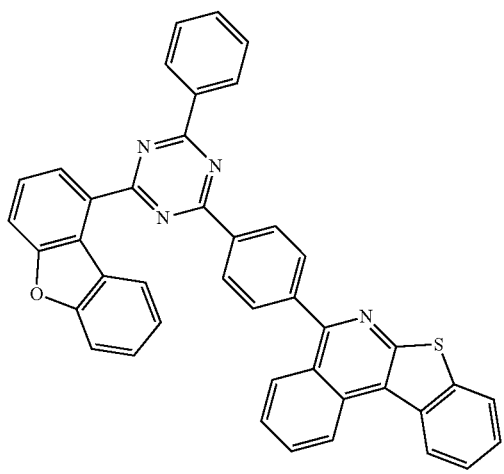
150
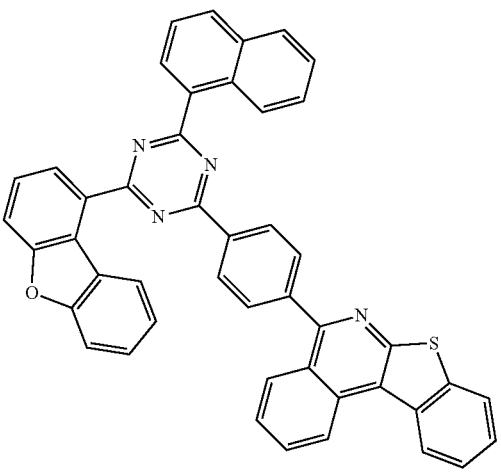
151
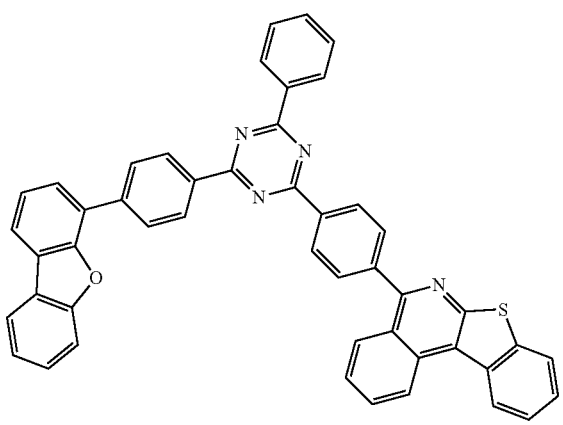
152
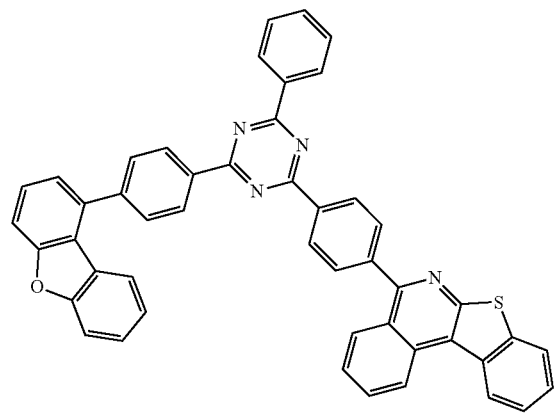

153
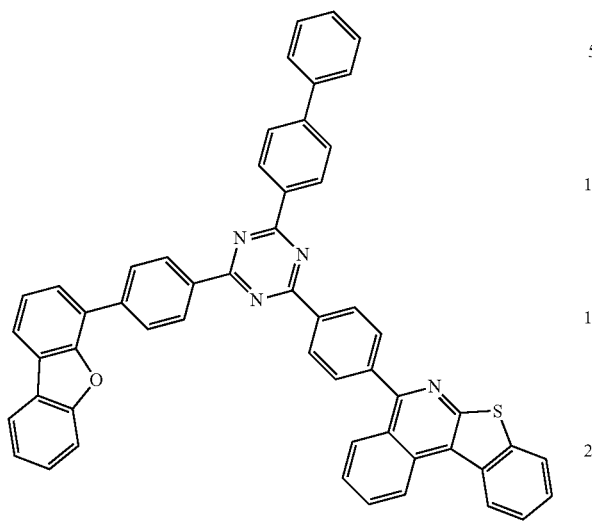
154
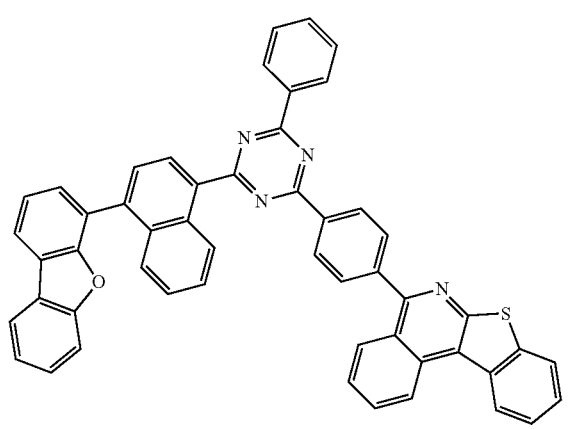
155
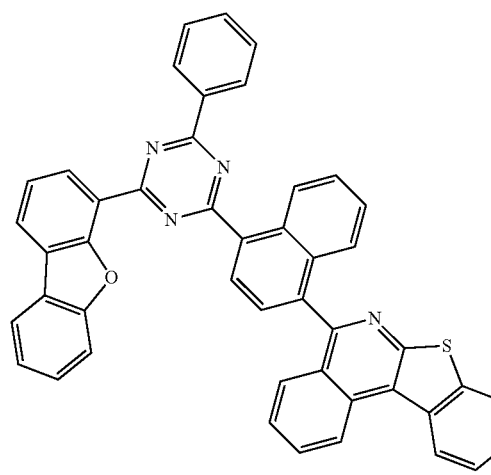
156
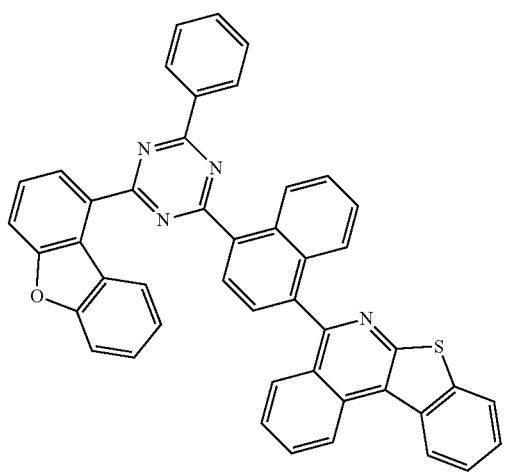
157
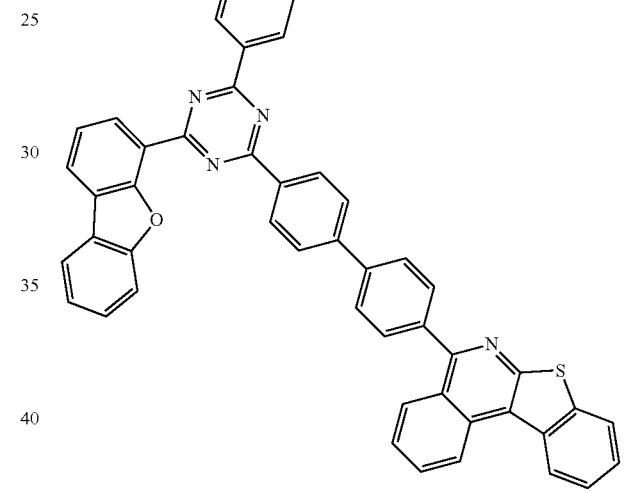
158
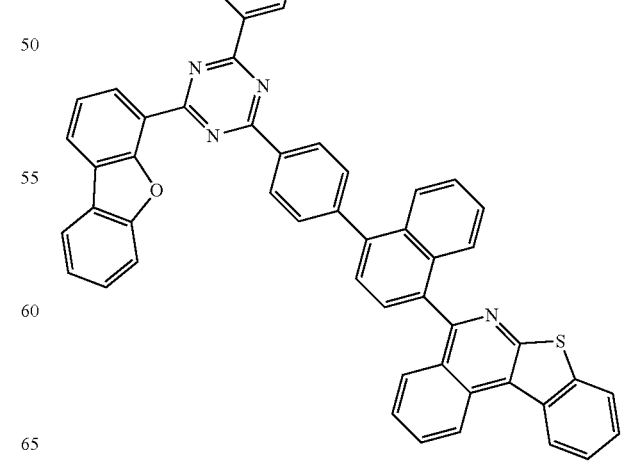

-continued
159
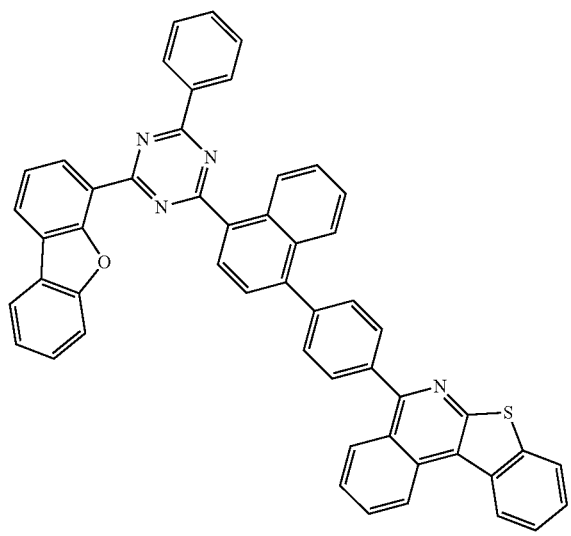
160
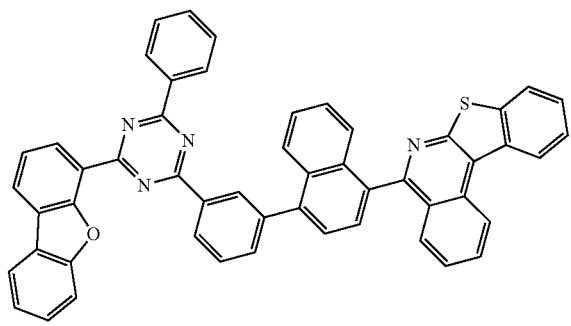
161
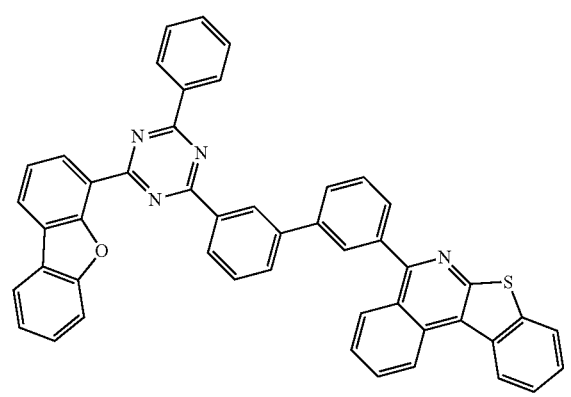
-continued
162
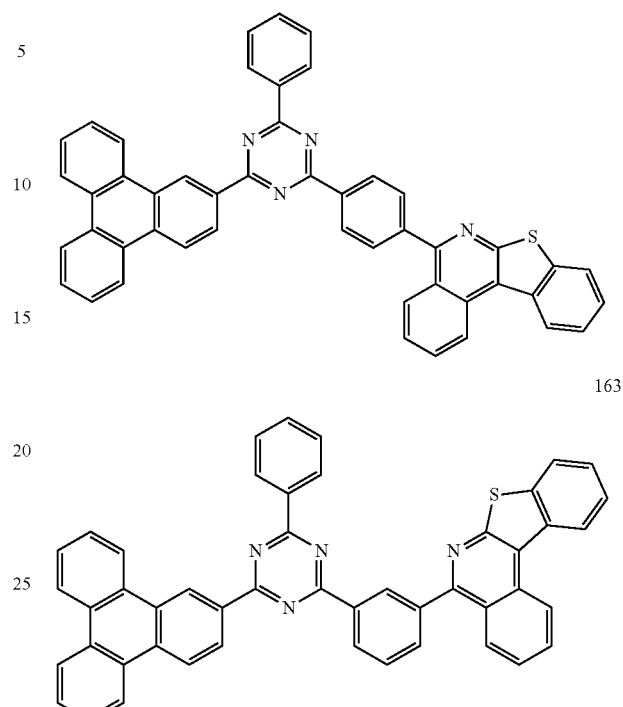
163
164
165
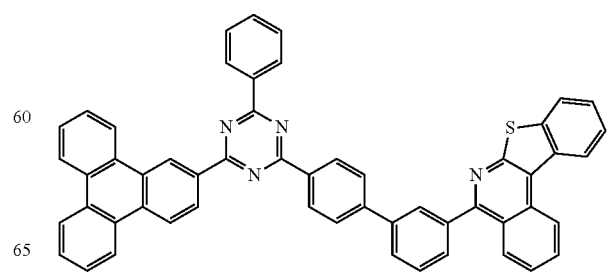

166
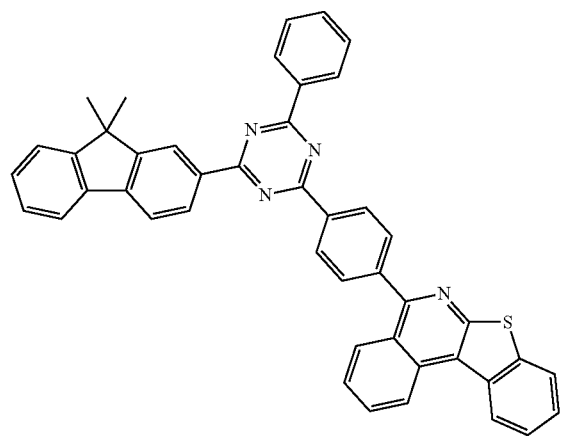
167
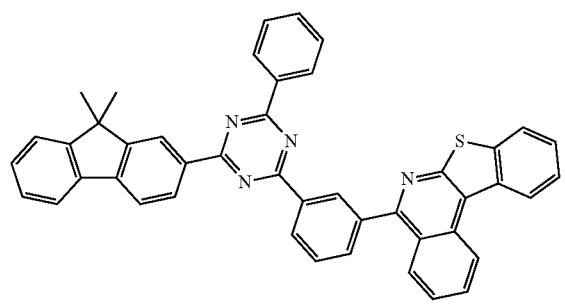
168
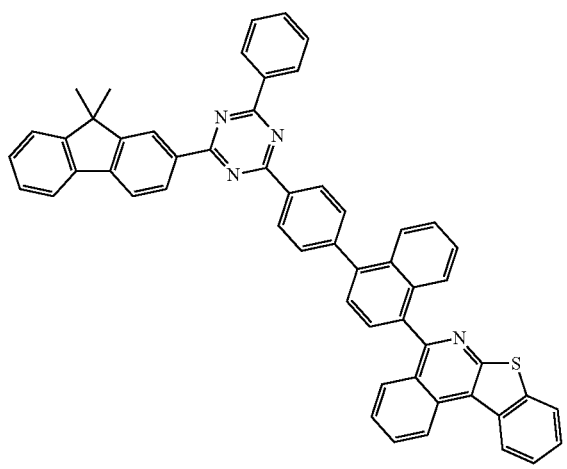
169
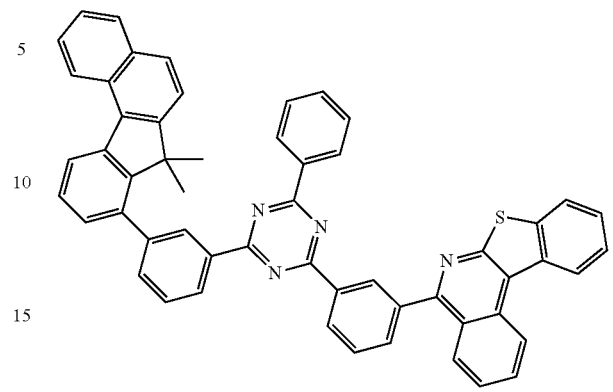
170
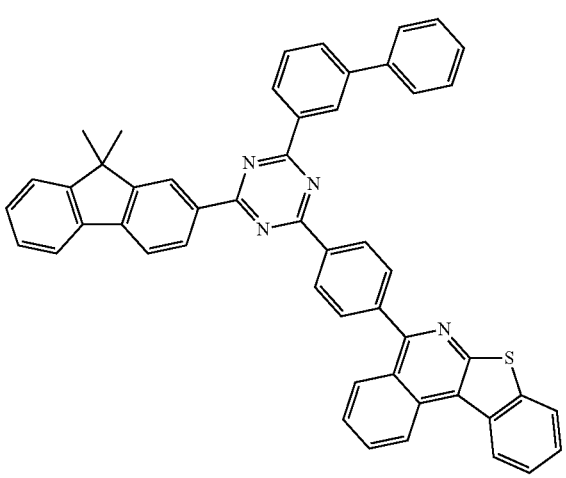
171
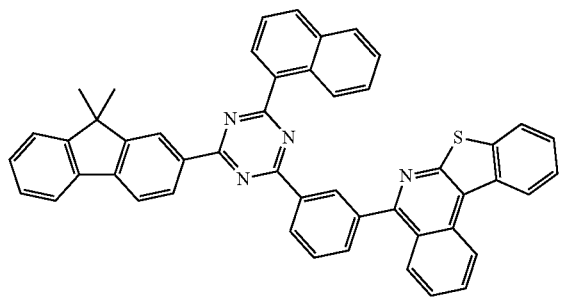

172 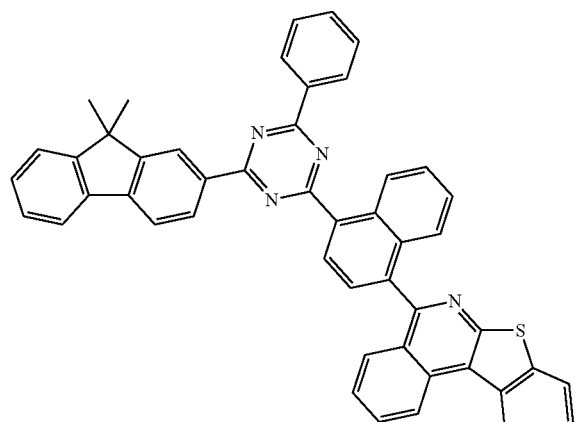
173 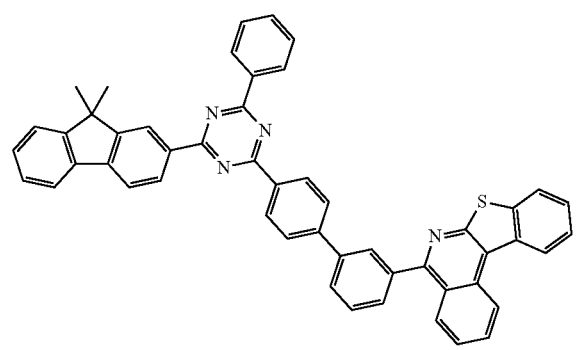
174 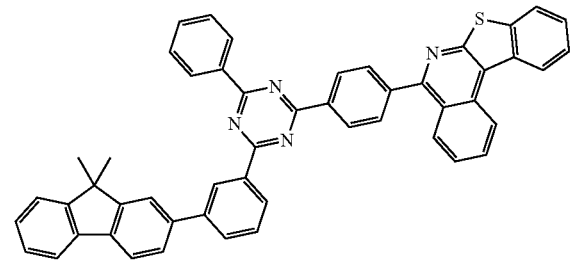
175 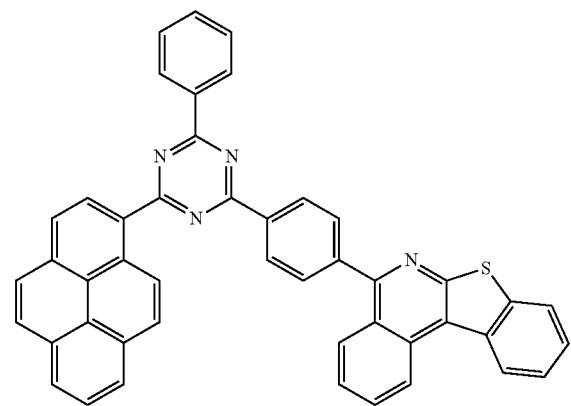
176 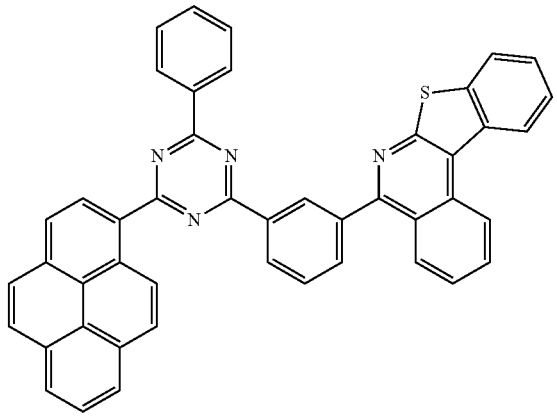
177 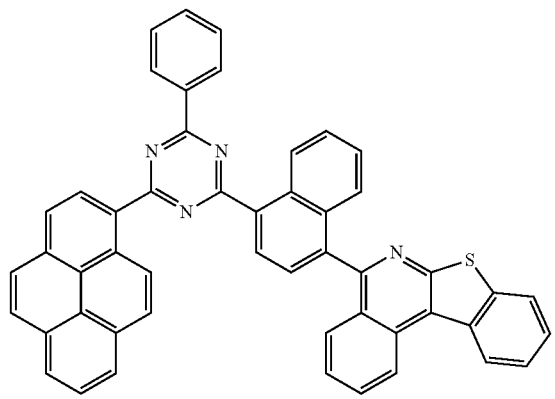
178 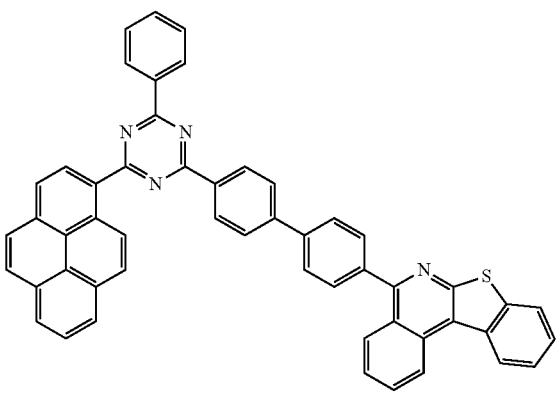
179 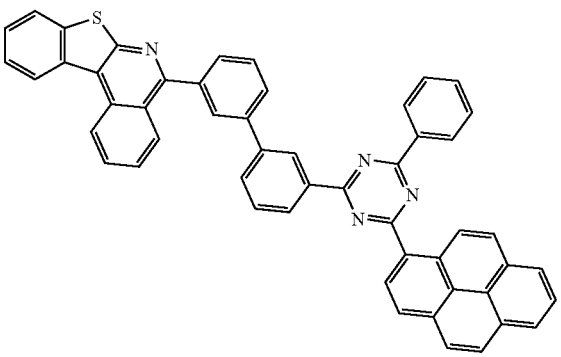

180
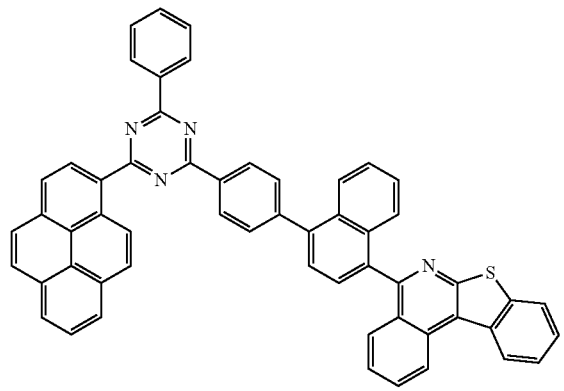
181
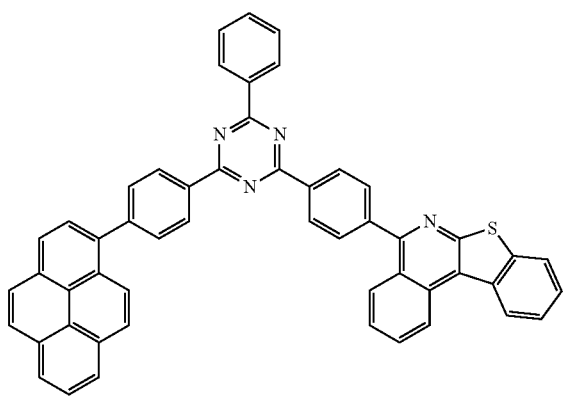
182
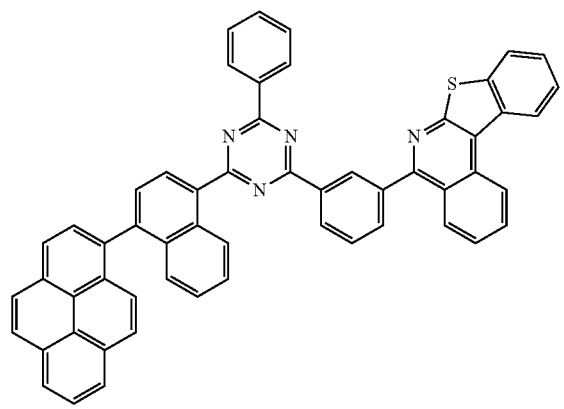
183
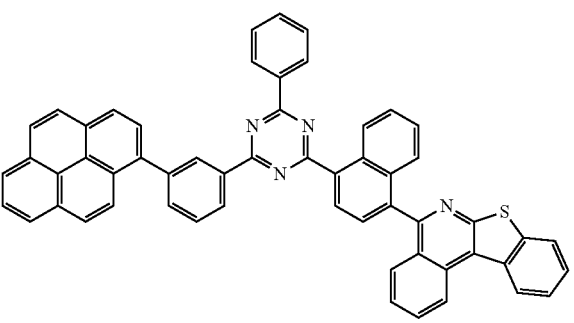
184
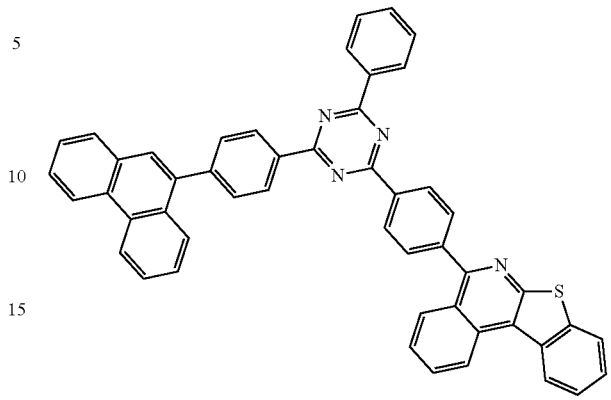
185
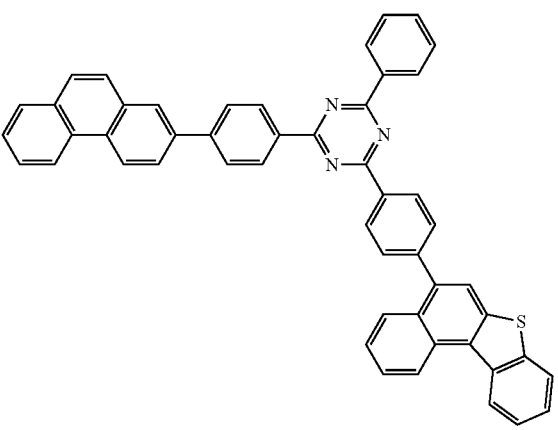
186
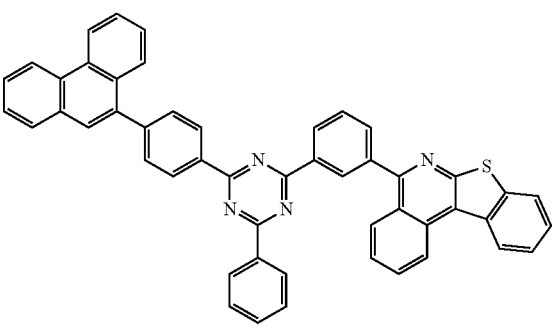

187
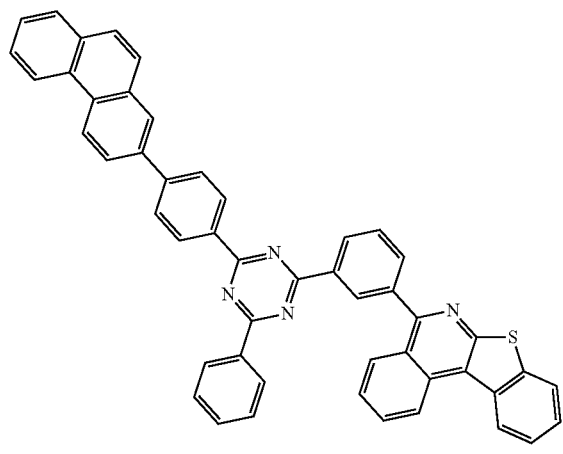
188
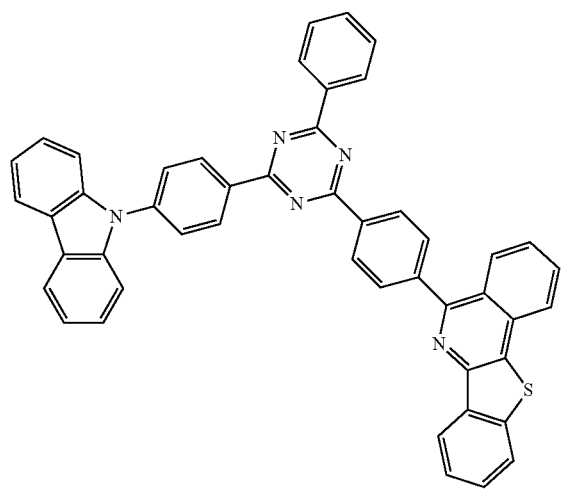
189
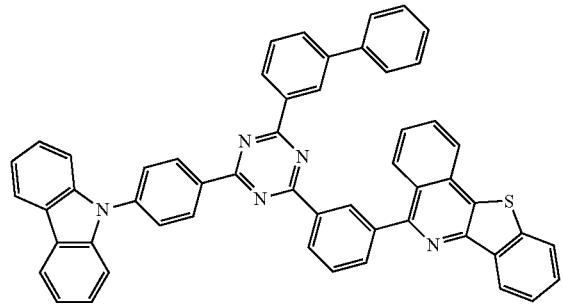
190
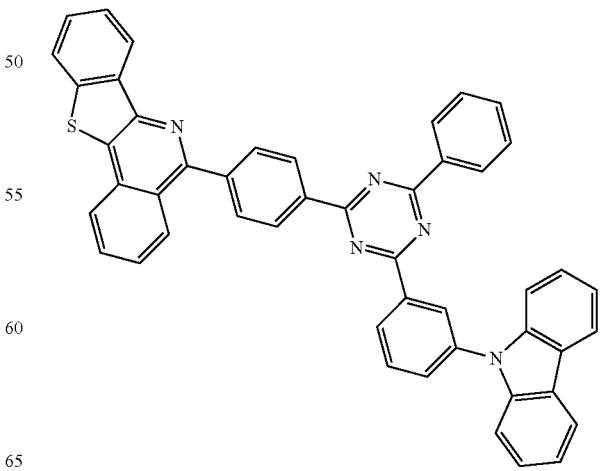
191
192

-continued
193
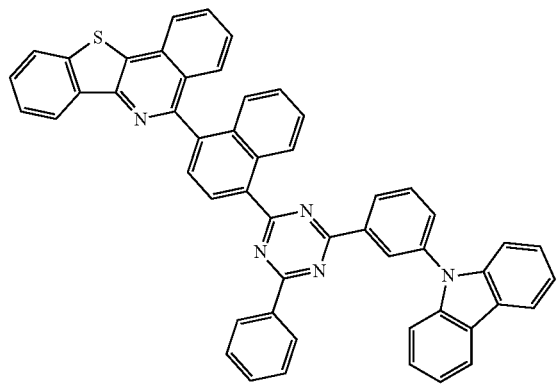
194
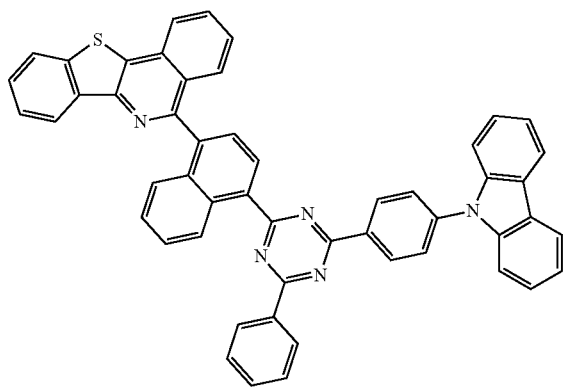
195
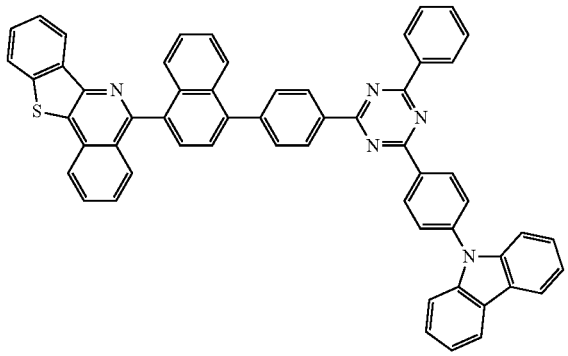
-continued
196
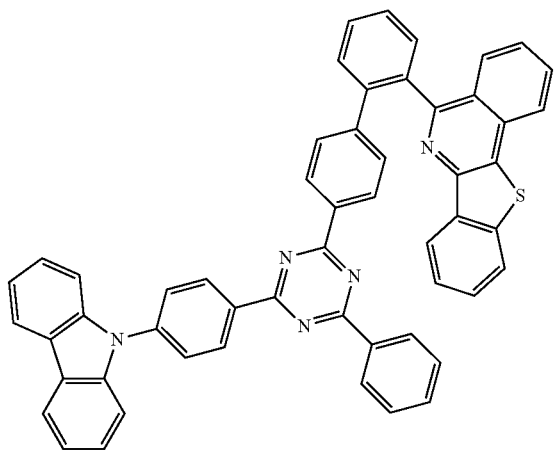
197
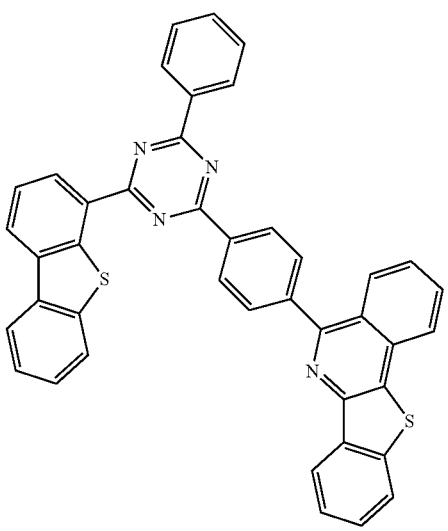
198
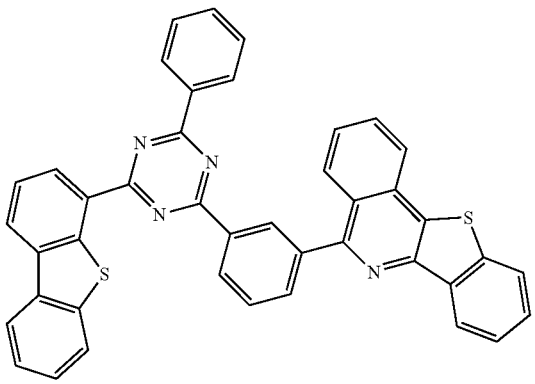

199
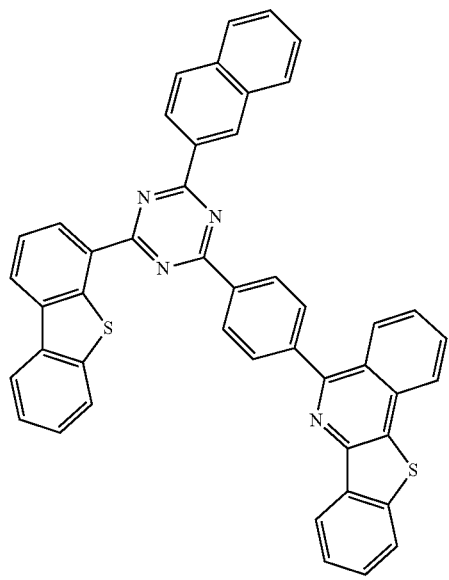
200
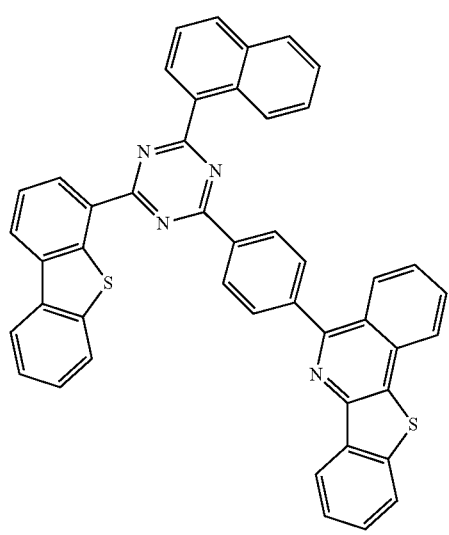
201
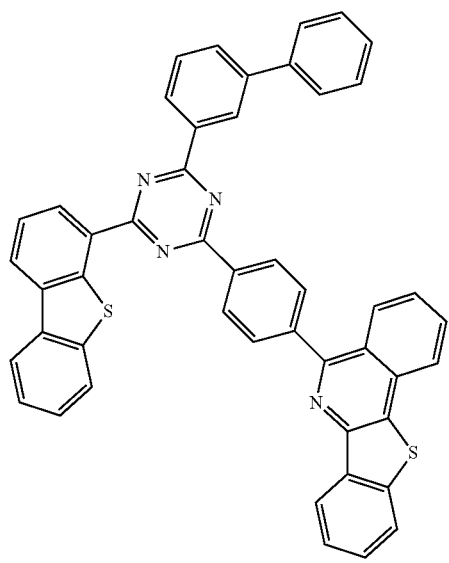
202
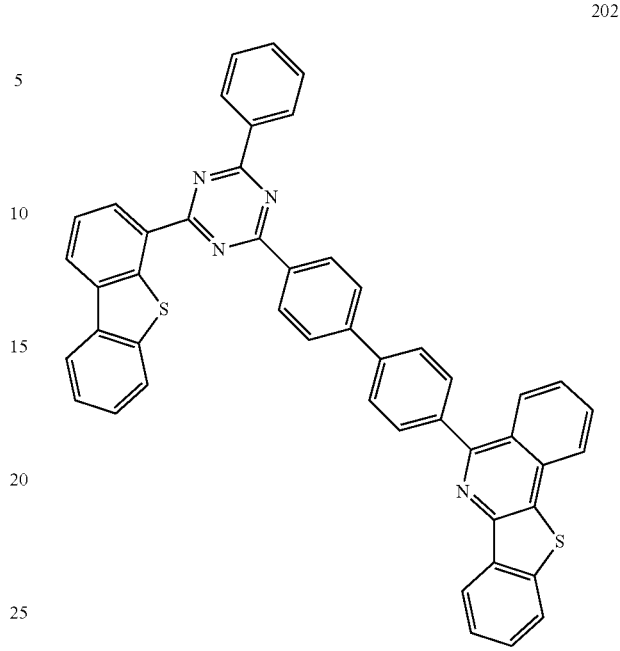
203
204

205
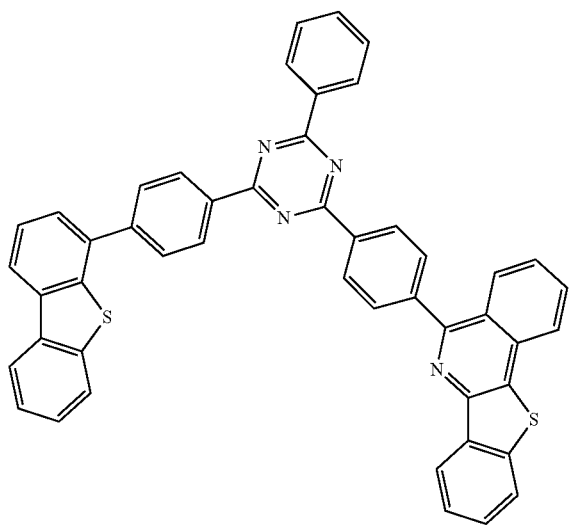
206
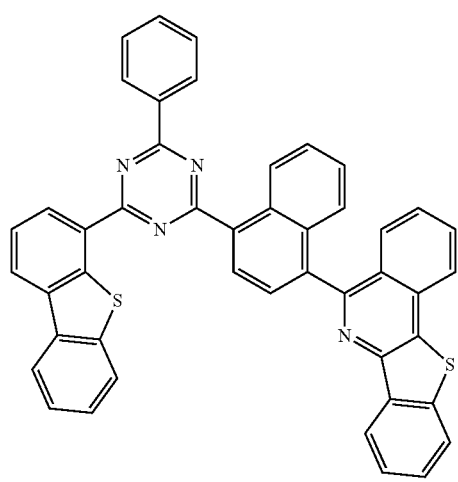
207
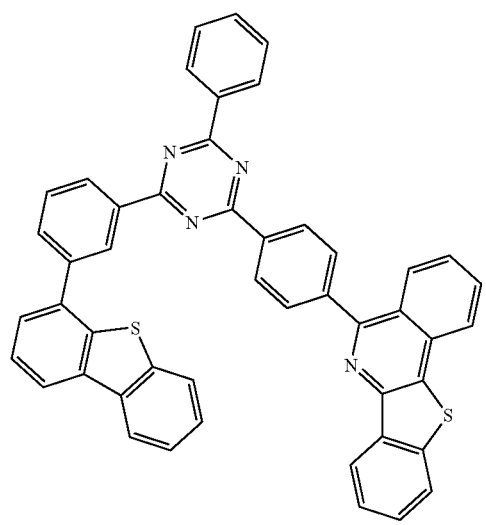
208
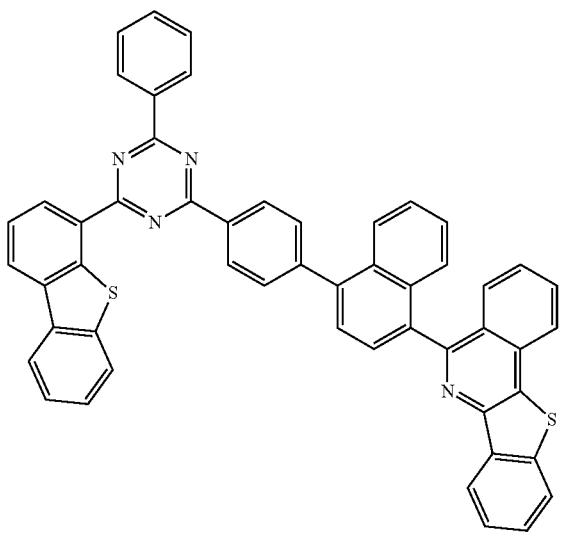
209
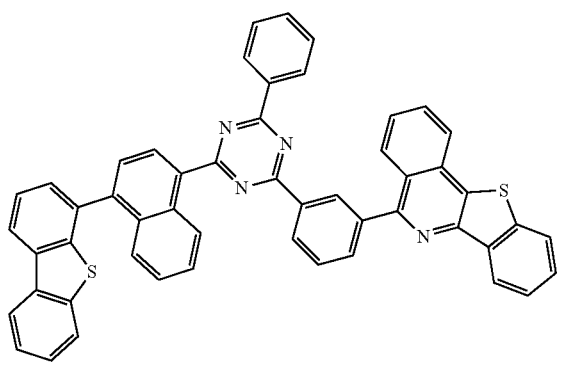
210
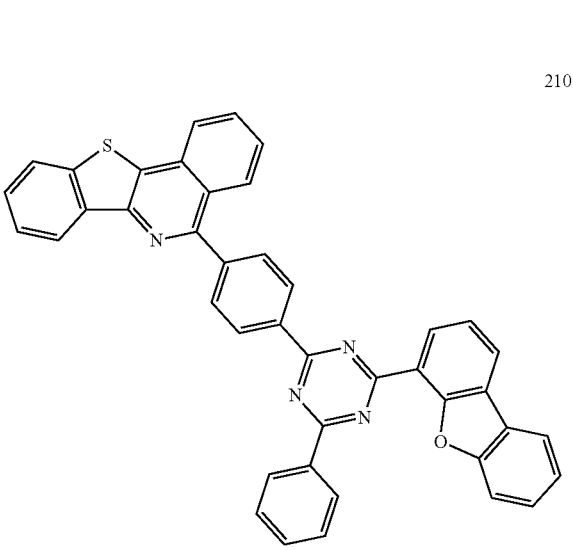 [SMILES: c1ccc(-c2cc(-c3cccc4c3oc3ccccc34)cc(-c3ccc(-c4nc5c6ccccc6oc5c5ccccc45)cc3)n2)cc1]

211
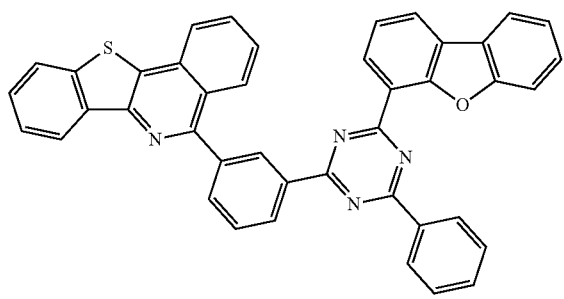
212
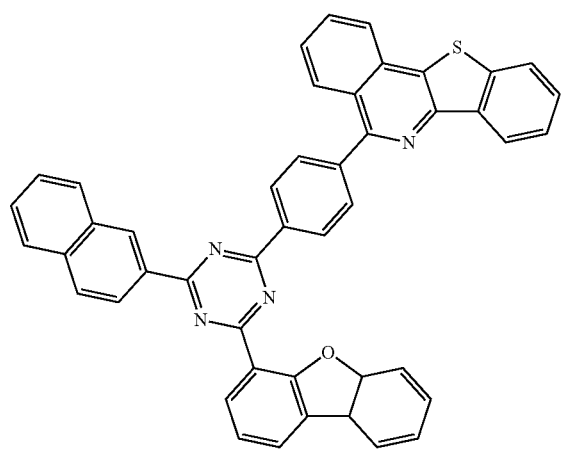
213
214
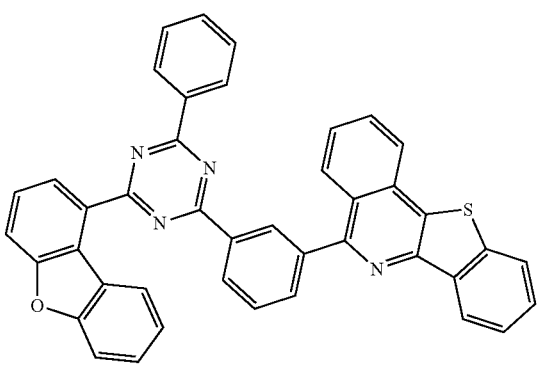
215
216
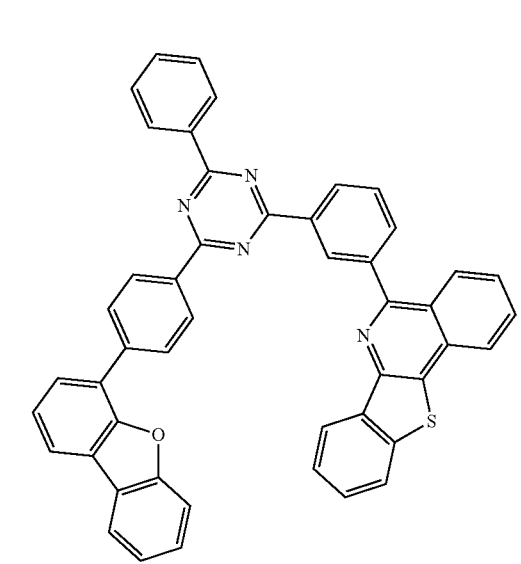

217
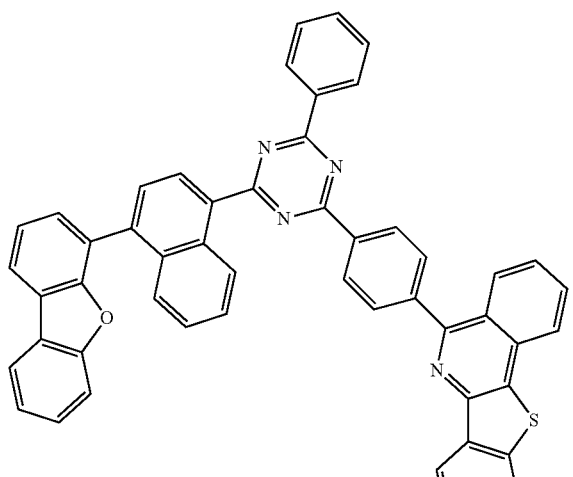
218
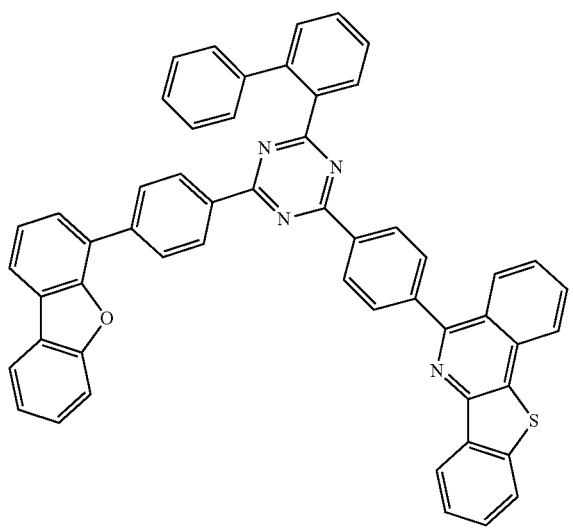
219
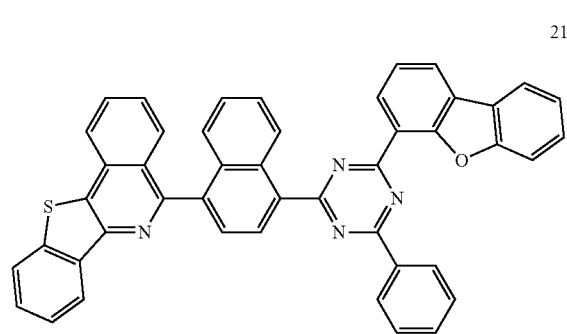
220
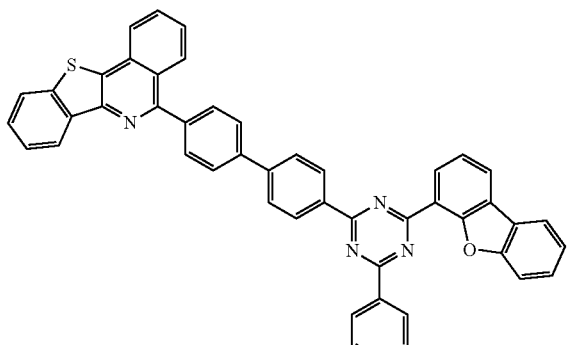
221
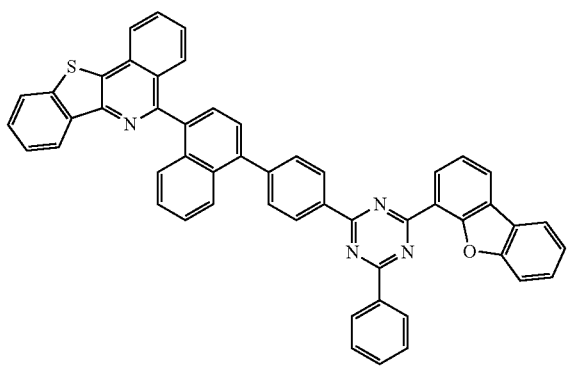
222
223
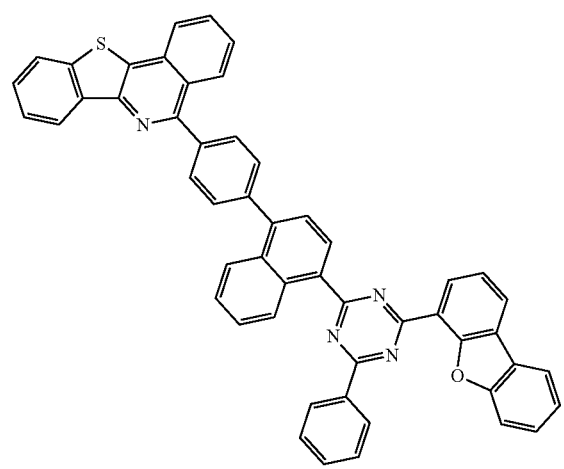

-continued
224
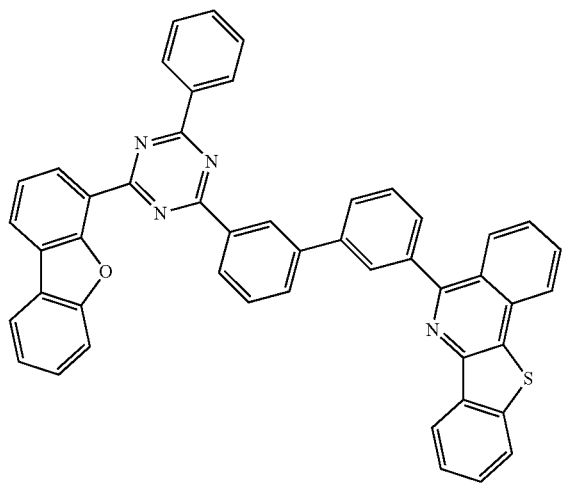
225
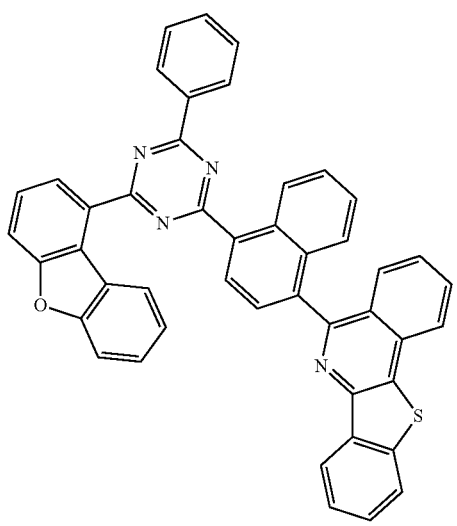
226
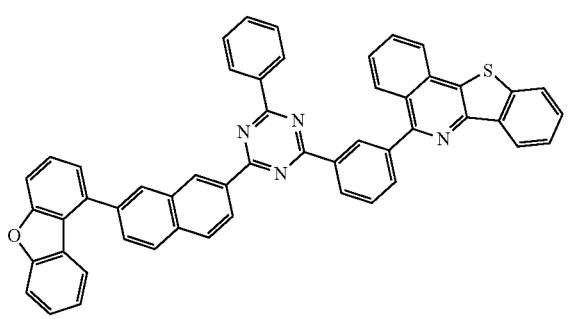
-continued
227
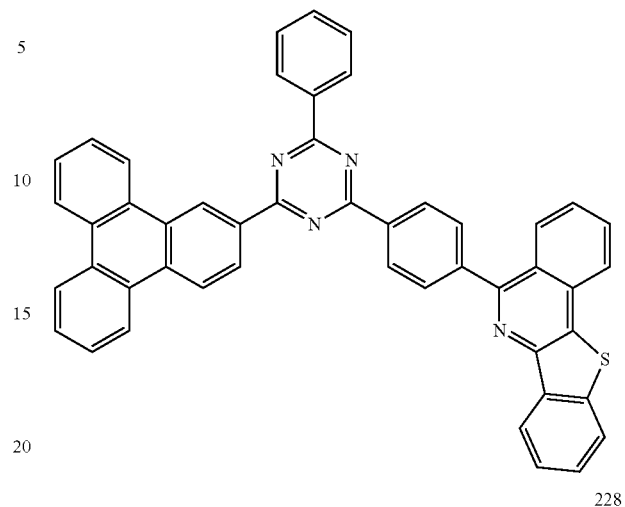
228
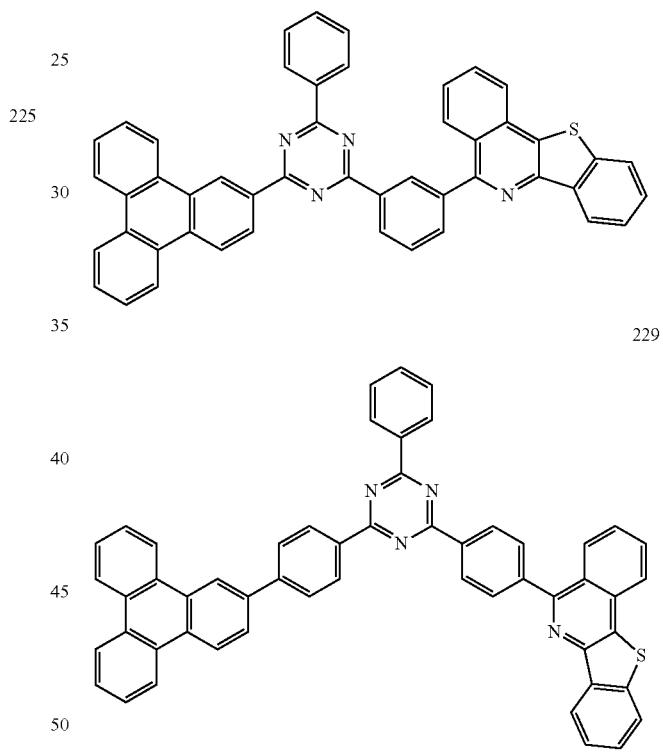
229
230
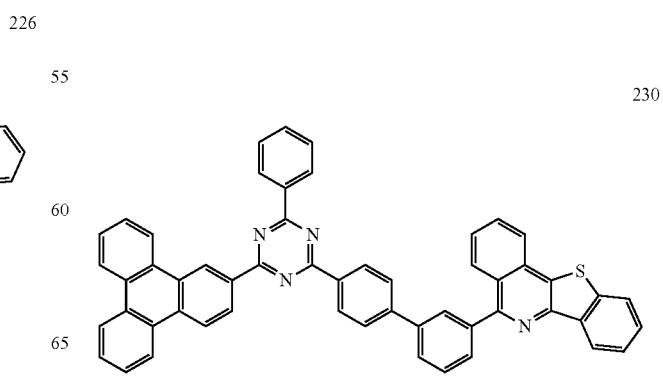

231
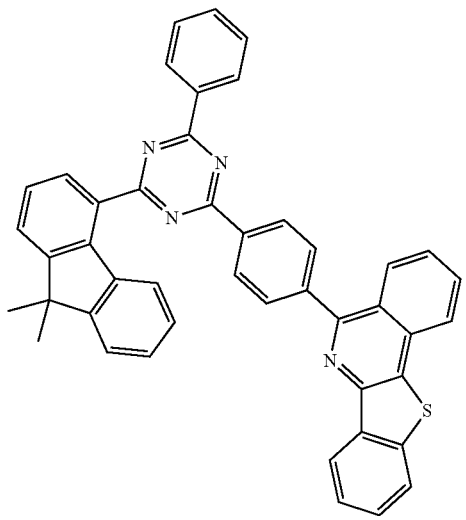
232
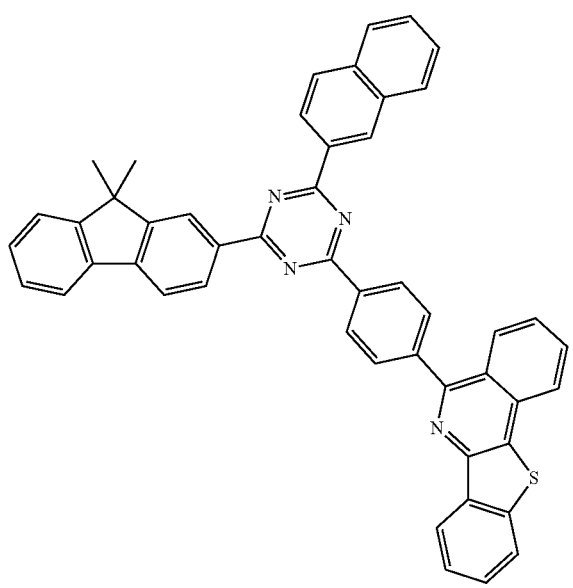
233
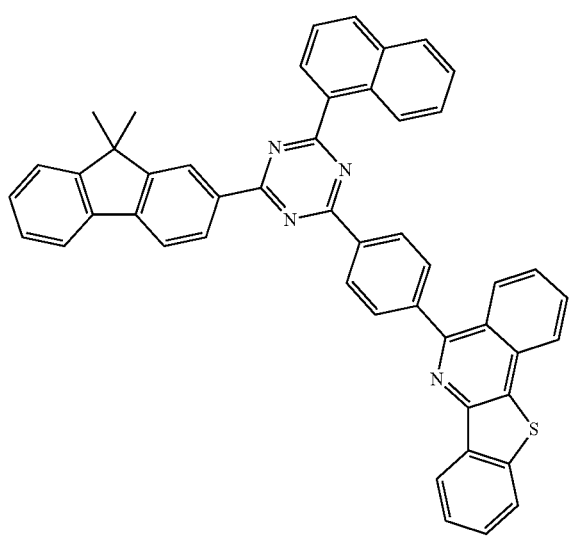
234
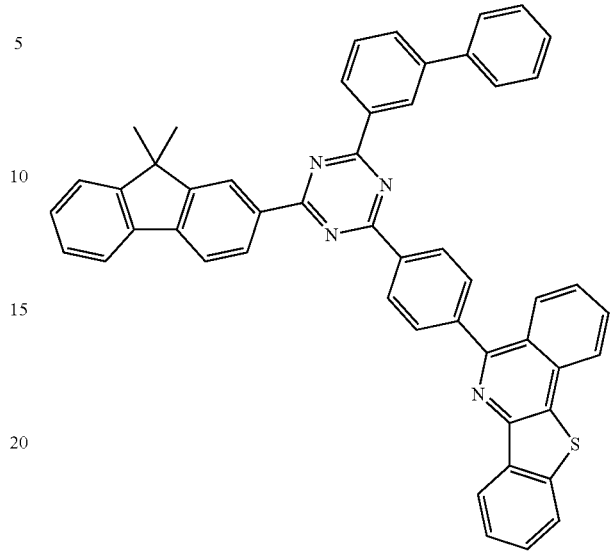
235
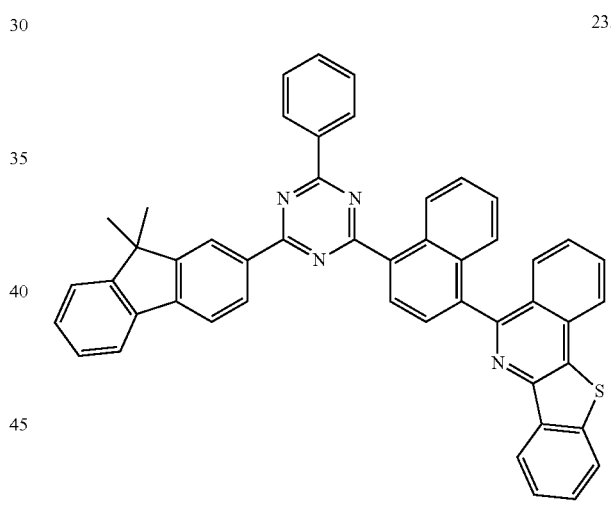
236
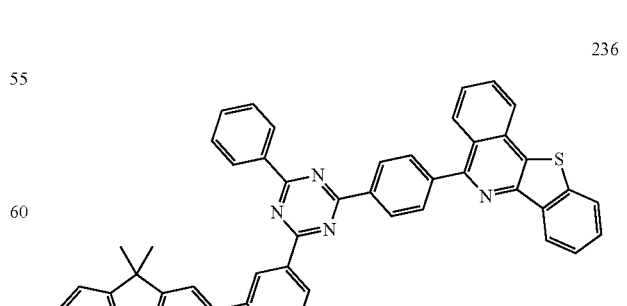

237
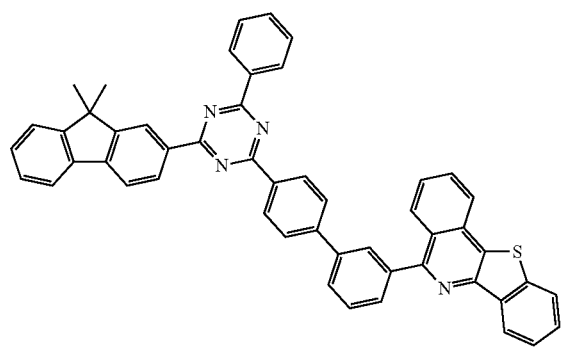
238
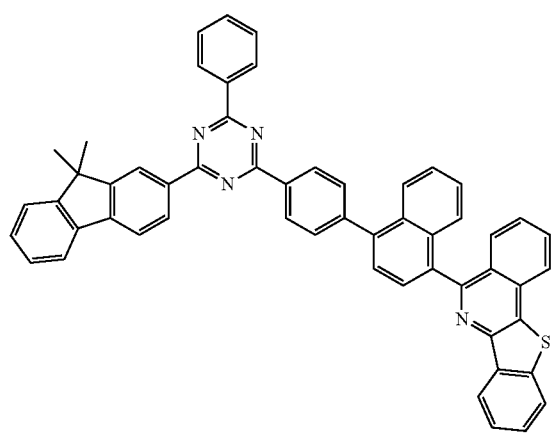
239
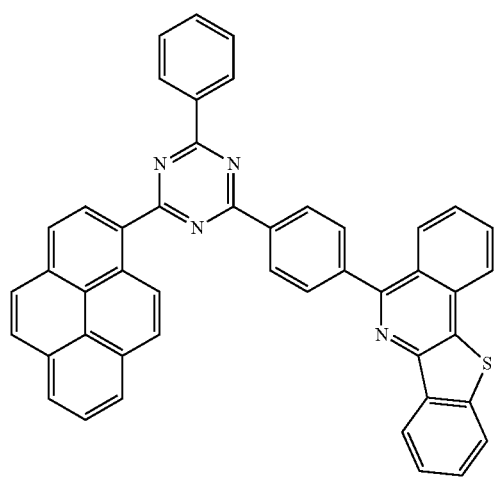
240
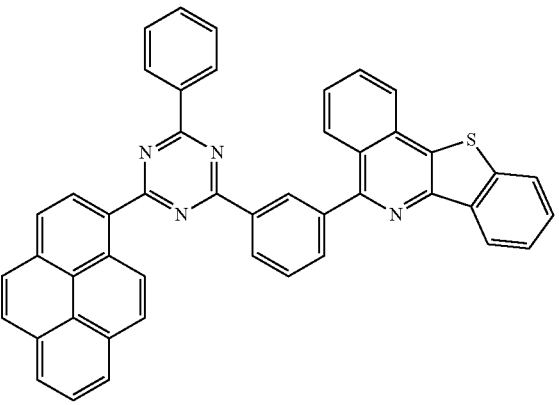
241
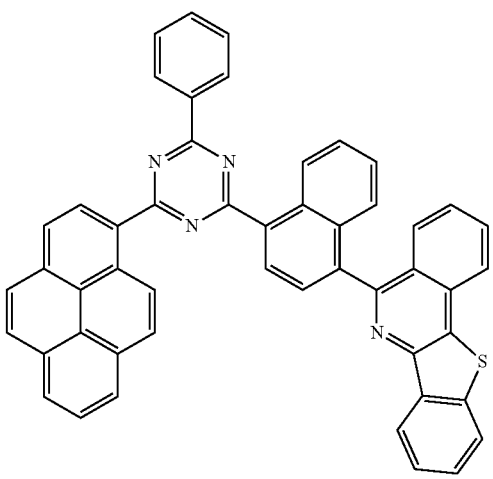
242
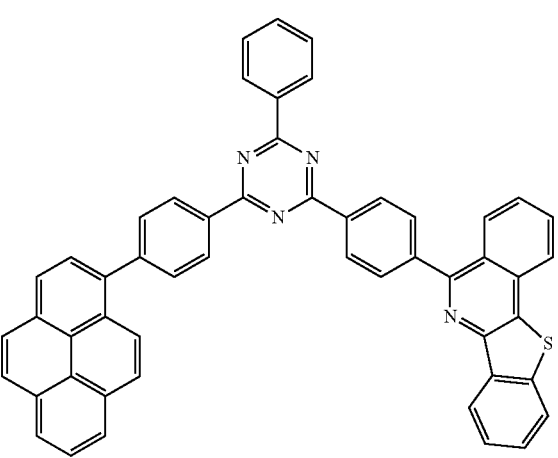

243
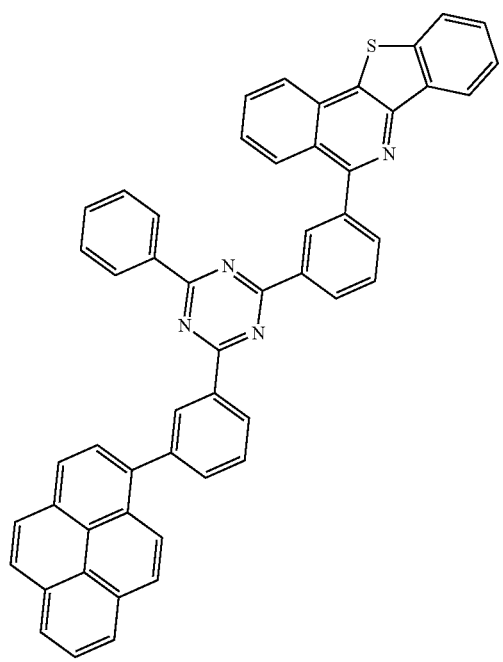
244
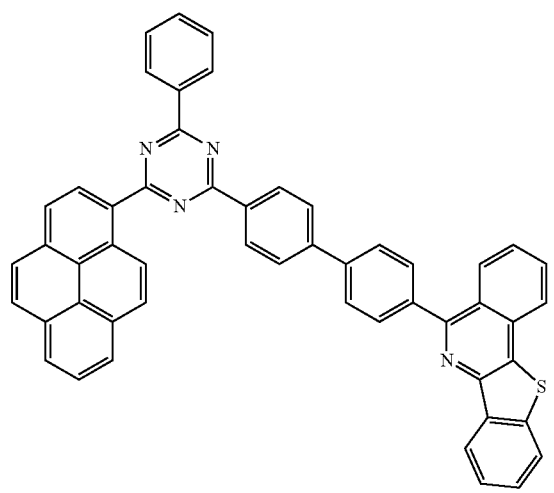
245
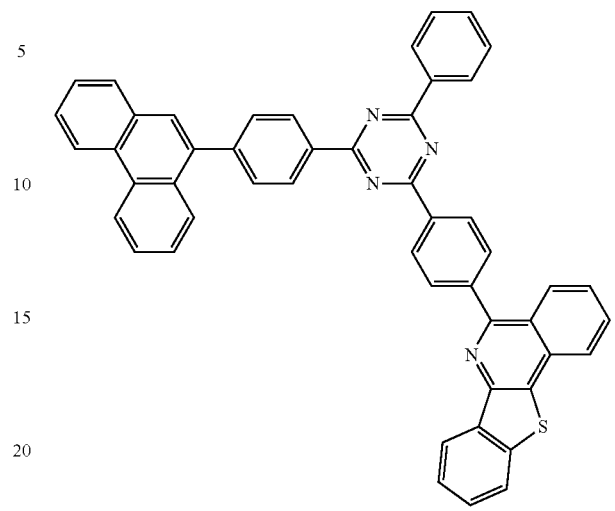
246
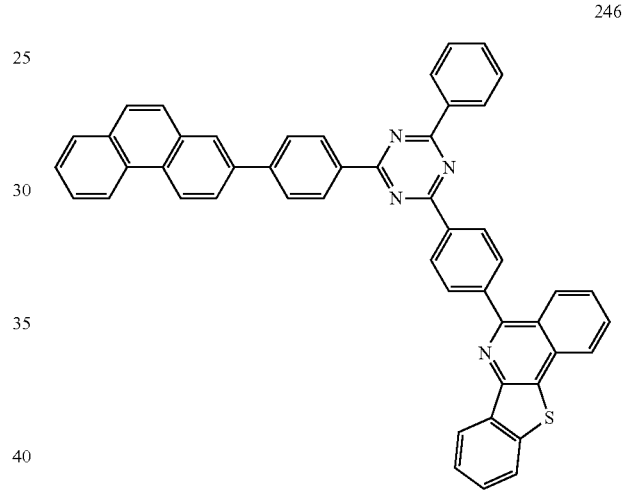
247
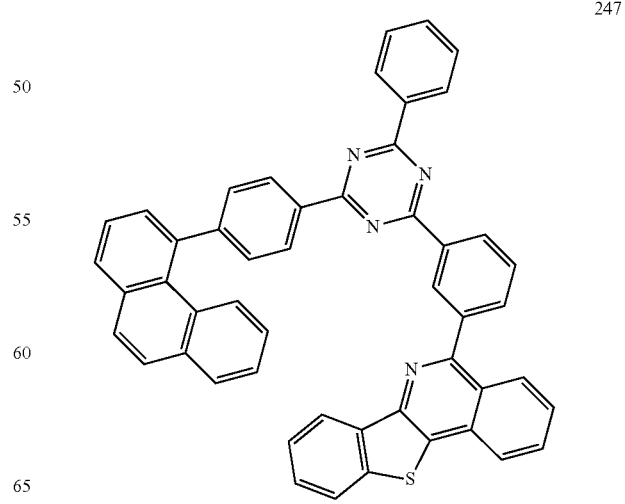

248
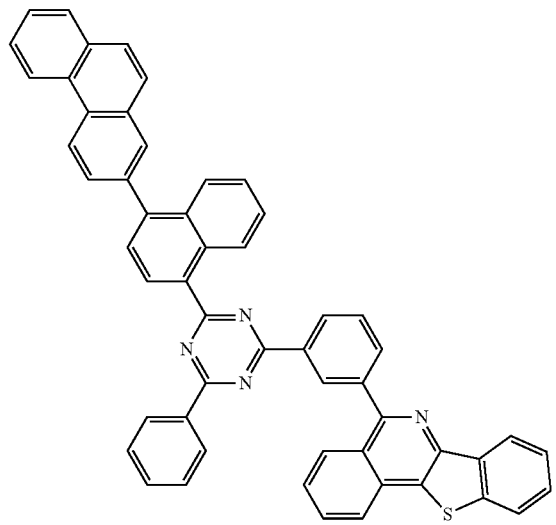
251
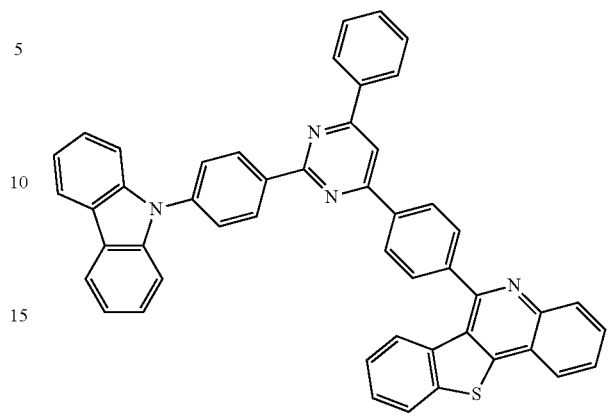
249
252
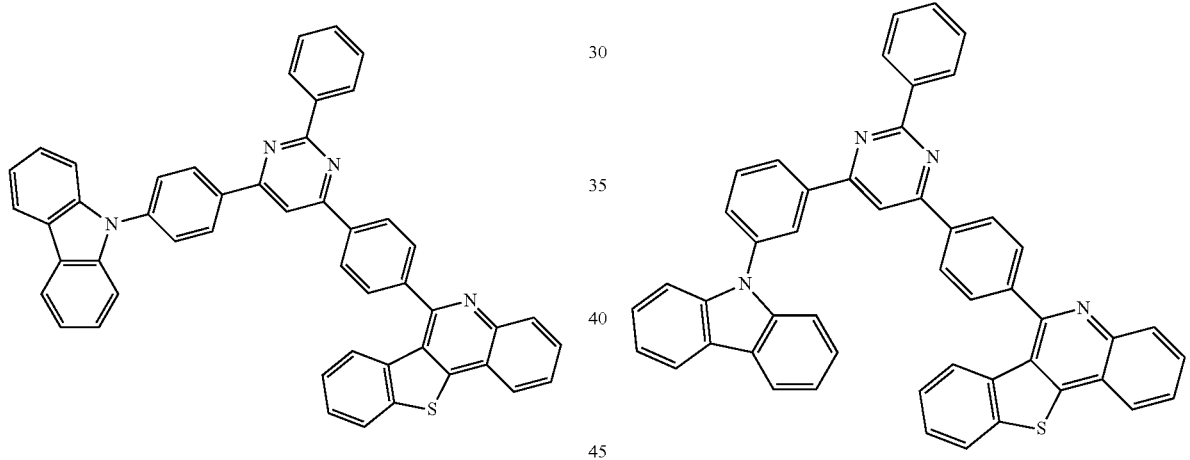
250
253
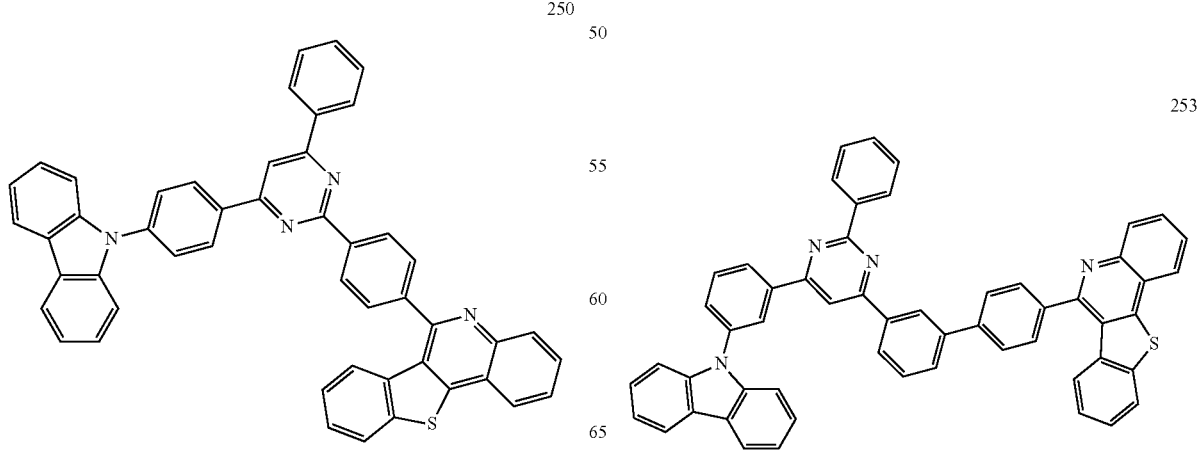

254
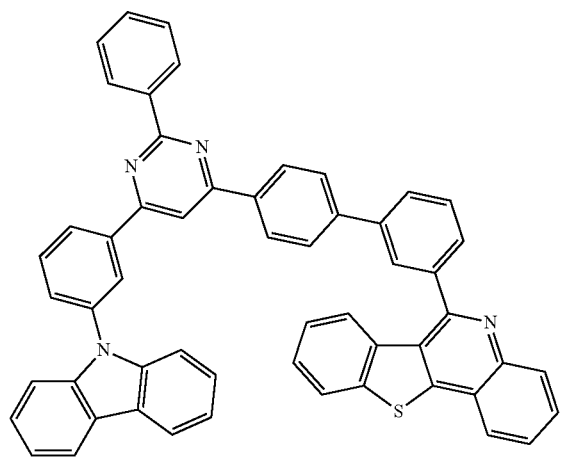
255
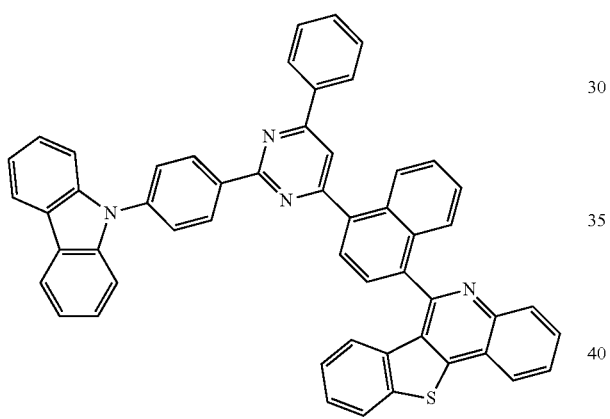
256
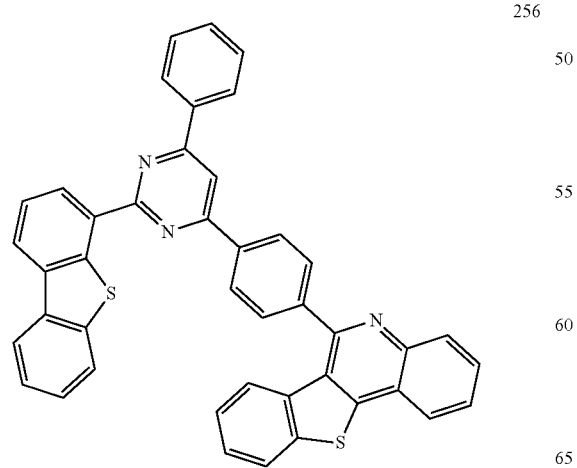
257
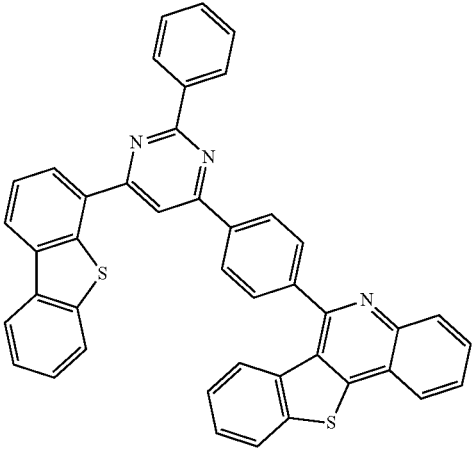
258
259

101
-continued
260
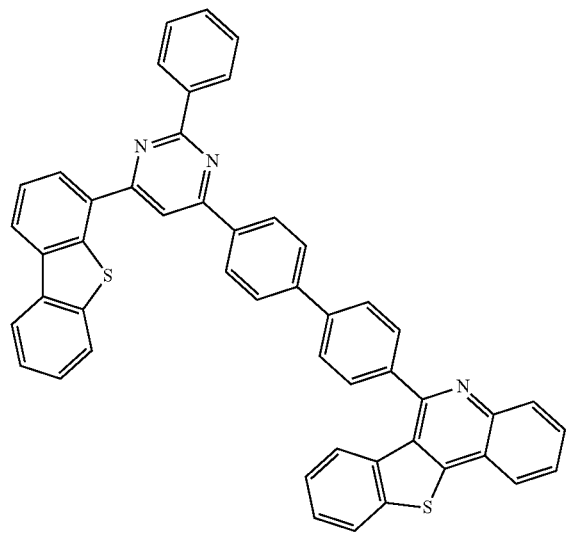
261
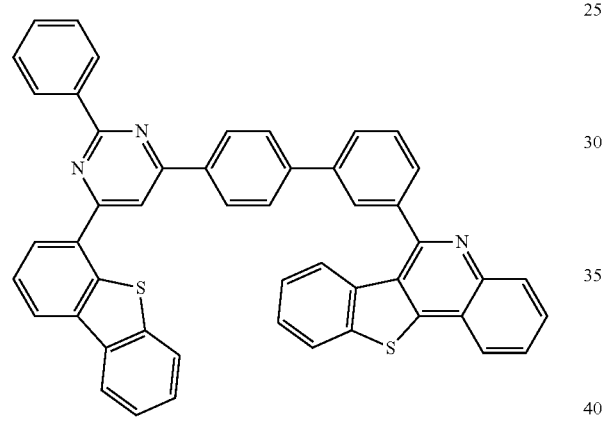
262
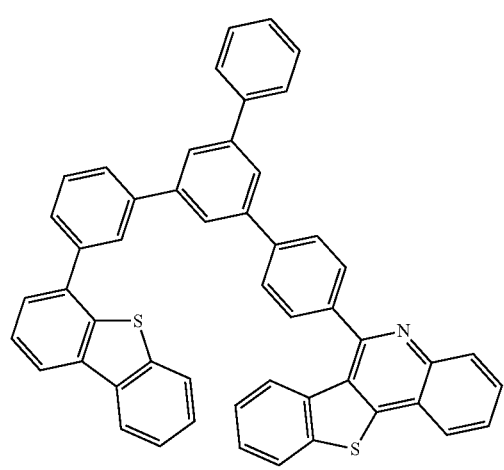
102
-continued
263
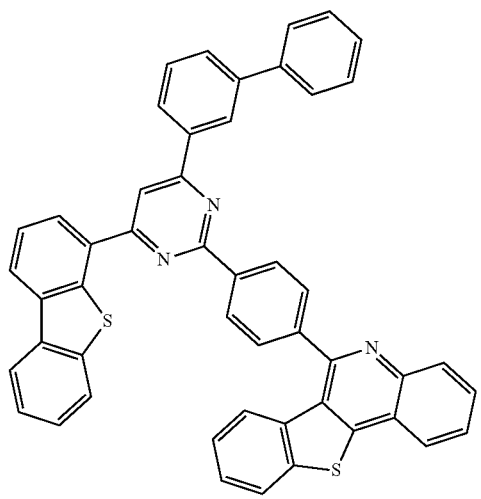
264
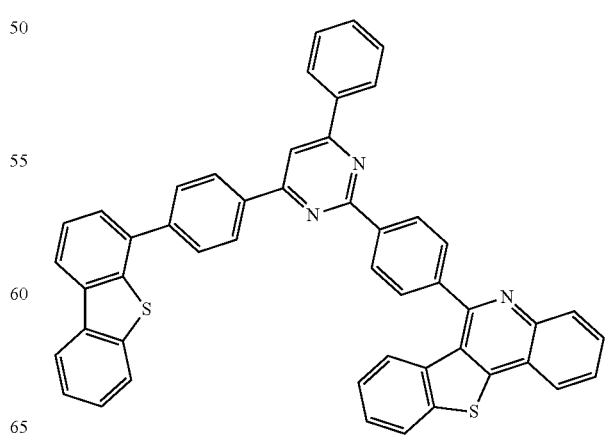

265
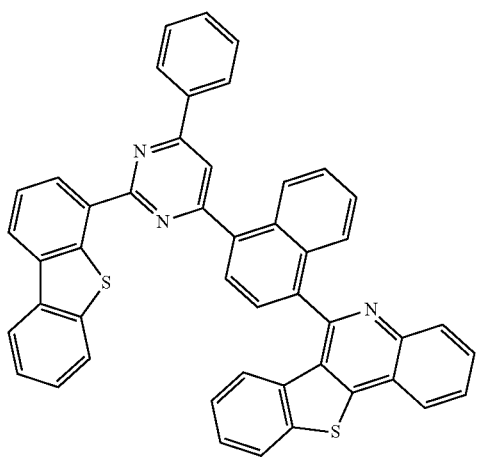
266
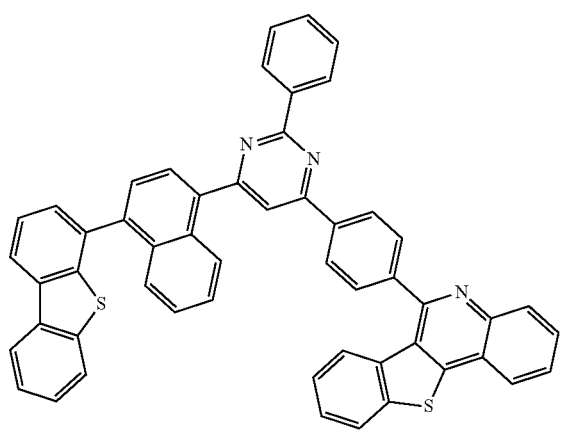
267
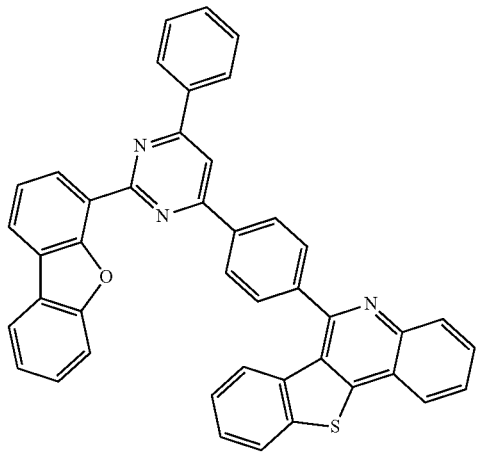
268
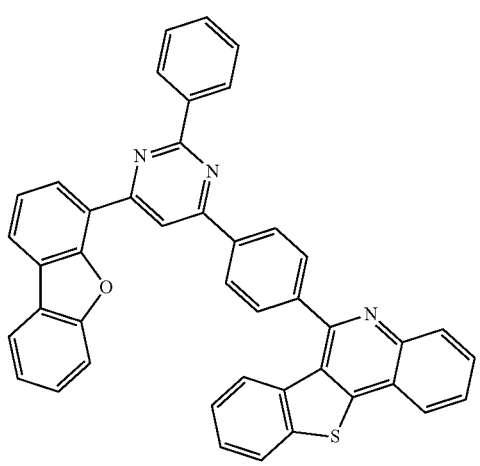
269
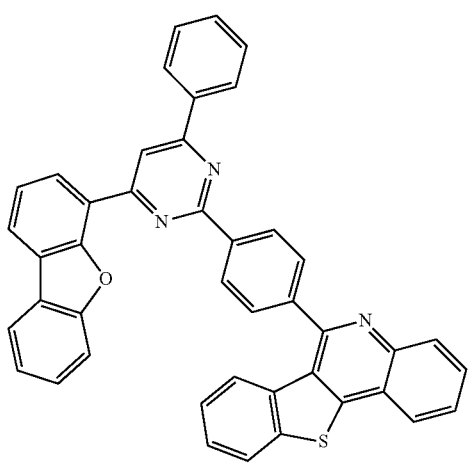
270
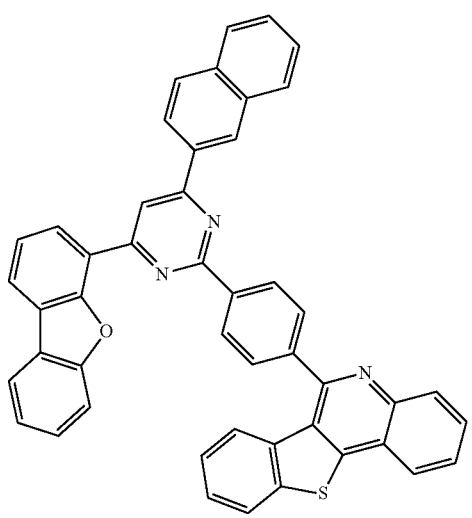

271
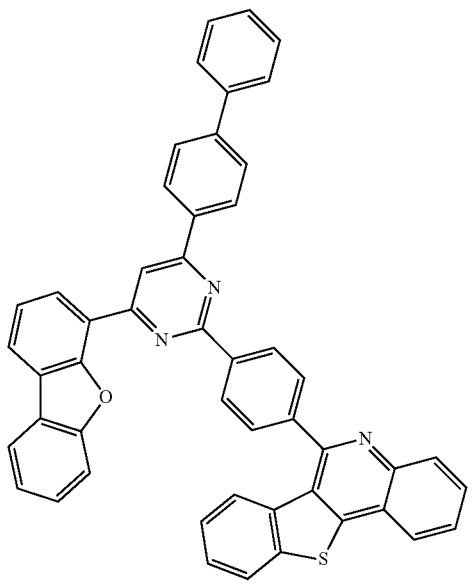
272
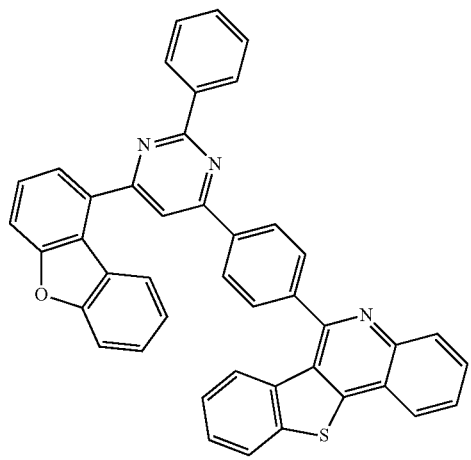
273
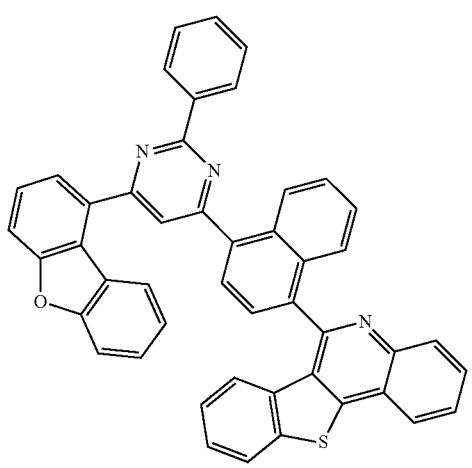
274
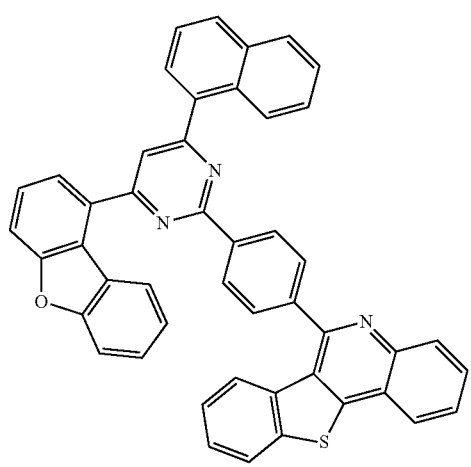
275
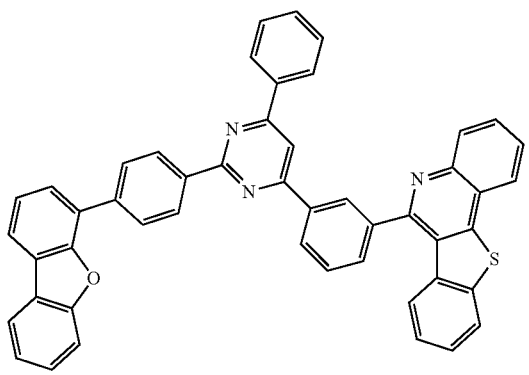
276
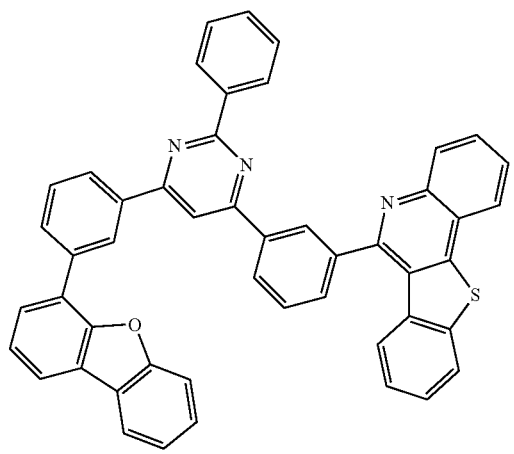

-continued
277
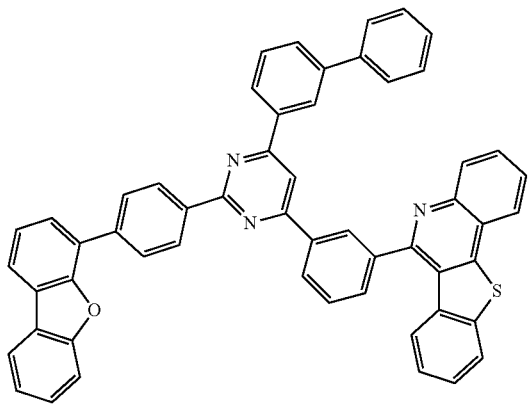
278
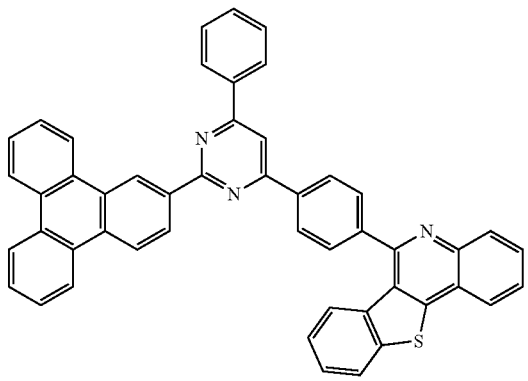
279
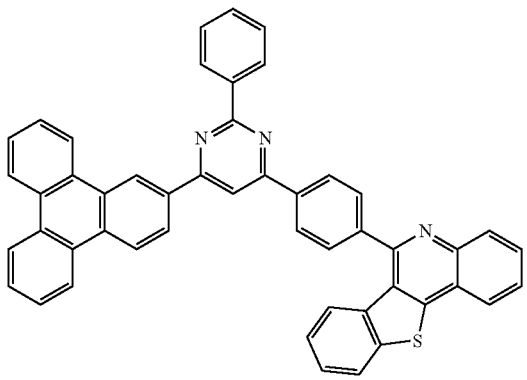
280
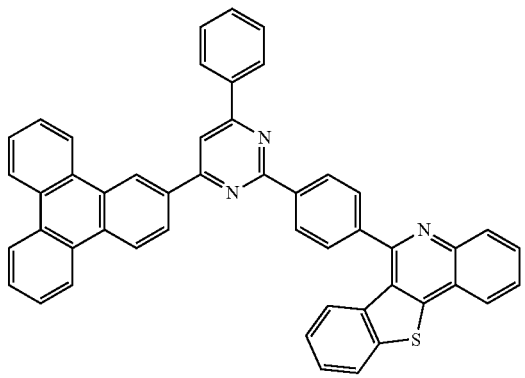
281
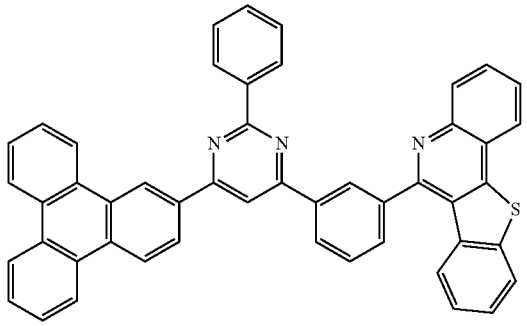
282
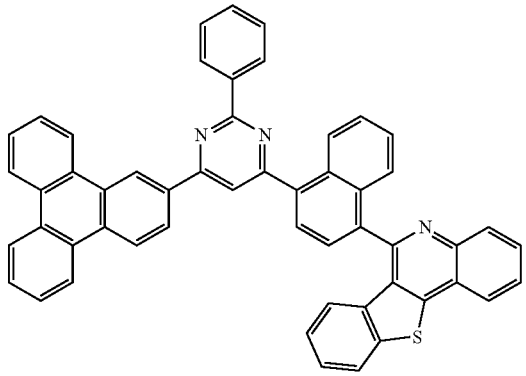
283
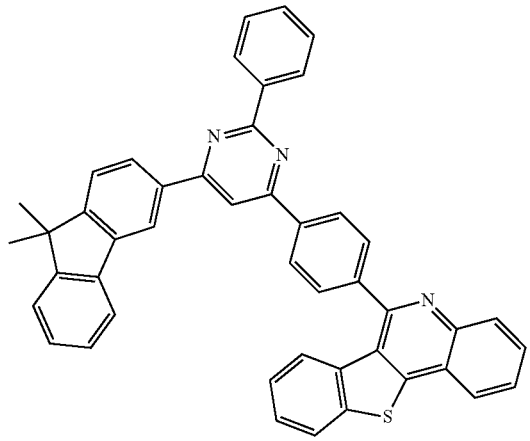
284
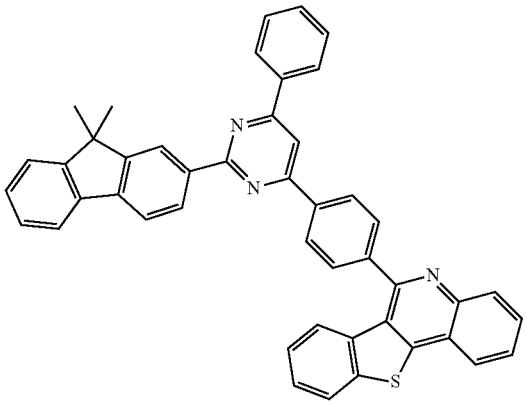

285
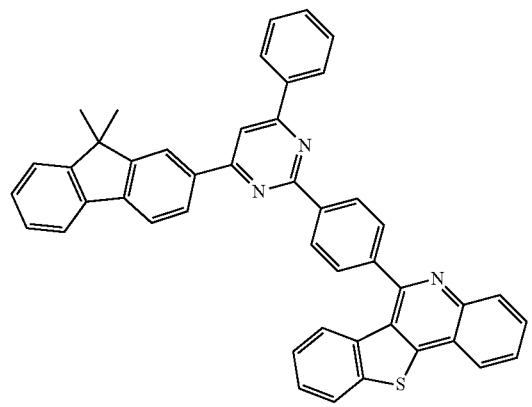
286
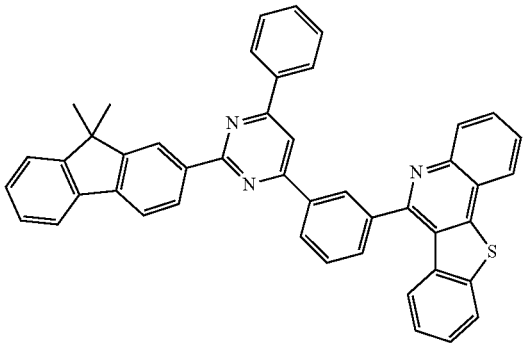
287
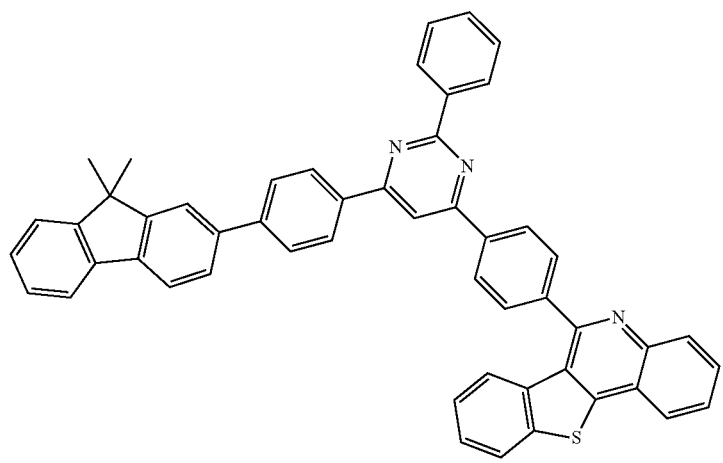
288
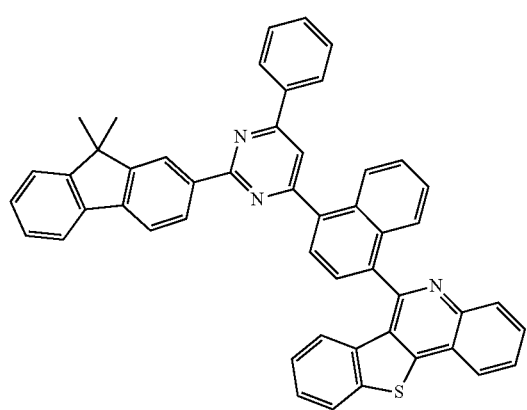

289
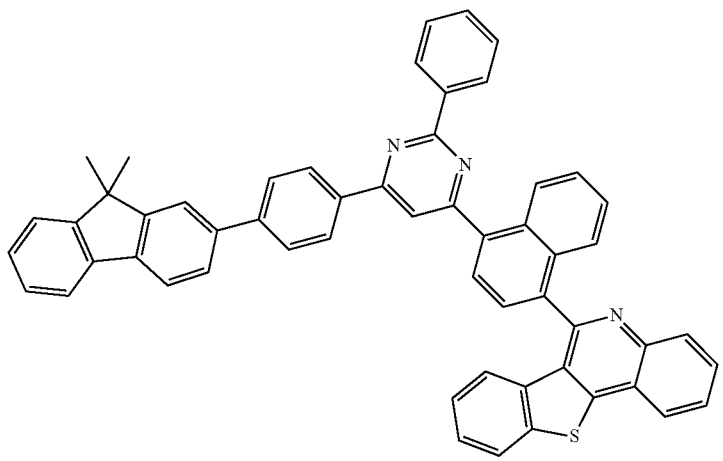
290
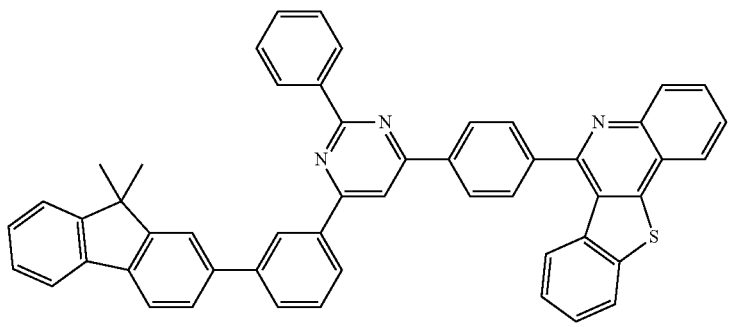
291
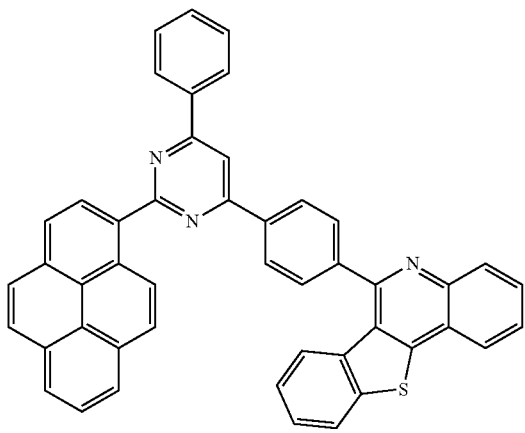 [SMILES: C1=CC2=CCc3ccc(-c4nc(-c5ccccc5)nc(-c5ccc(-c6nc7ccccc7c7sc8ccccc8c67)cc5)n4)c4c3C2C(=C1)C=C4]
292
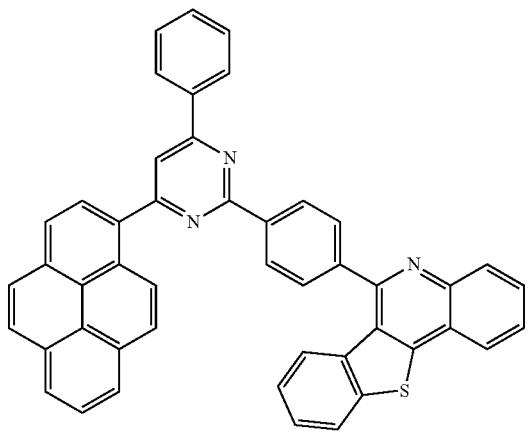

293
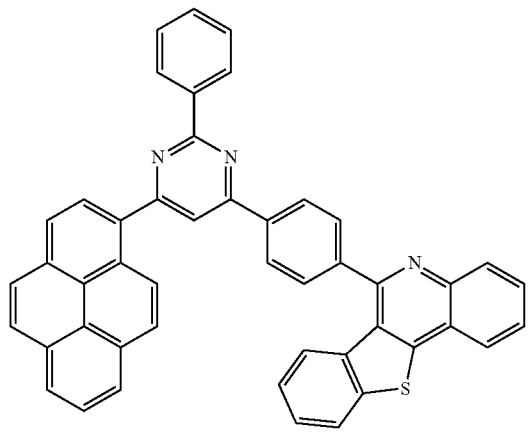
294
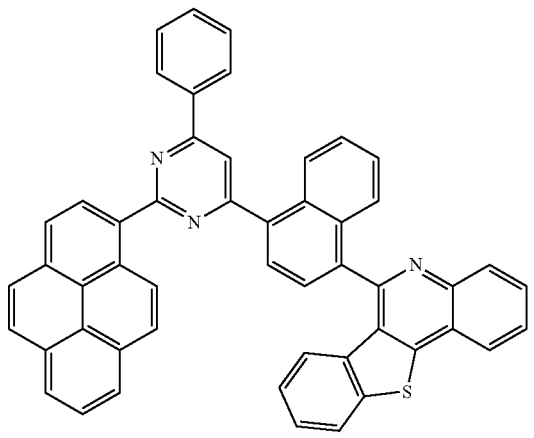
295
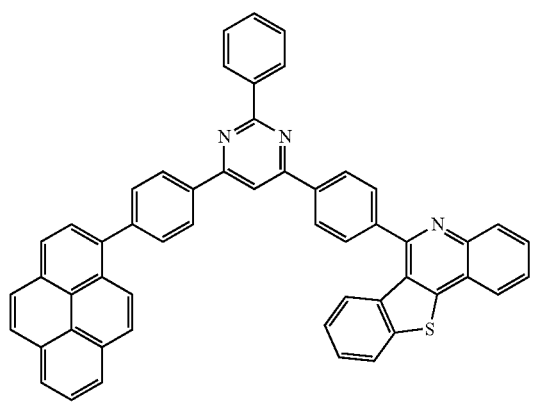
296
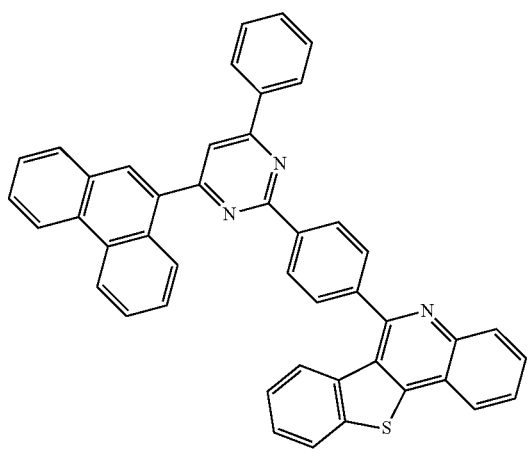
297
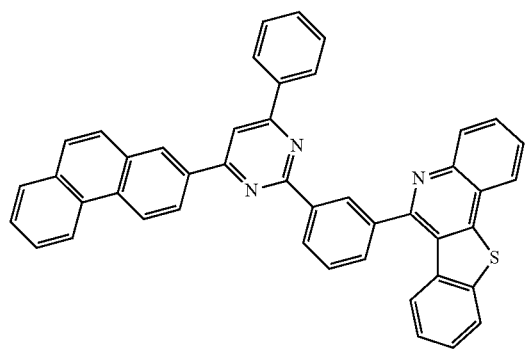
298
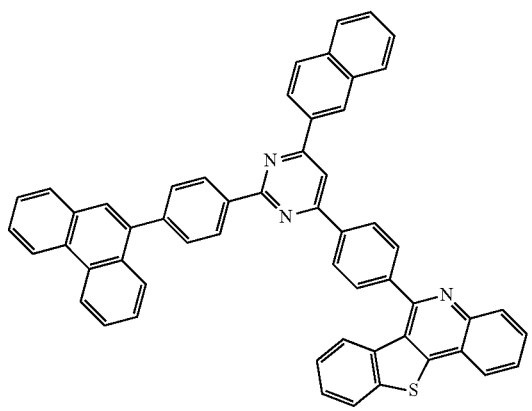

299
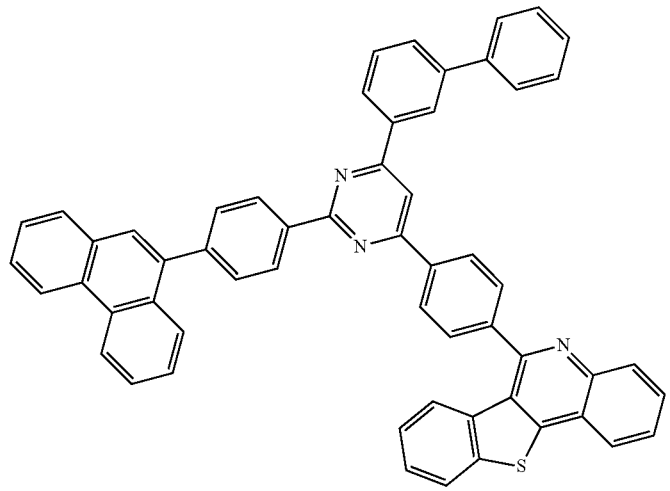
300
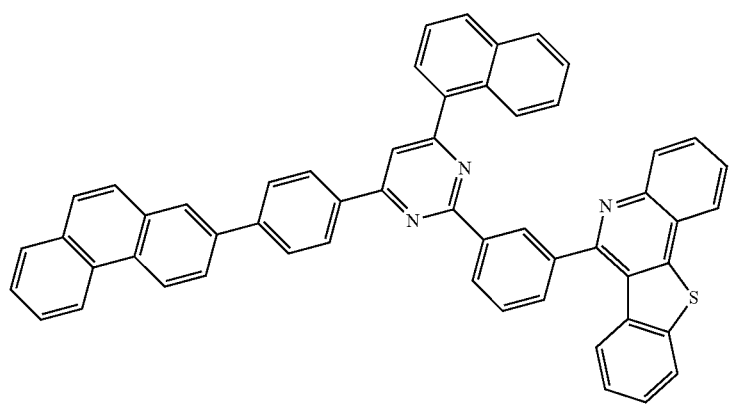
301
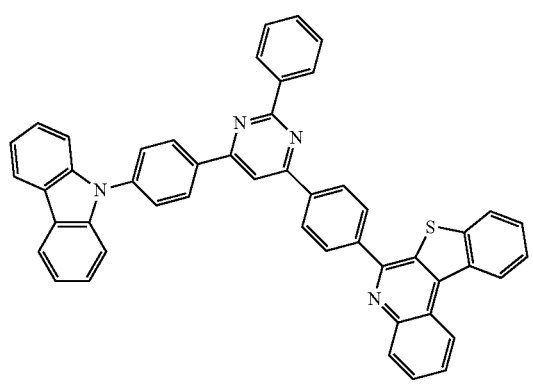
302
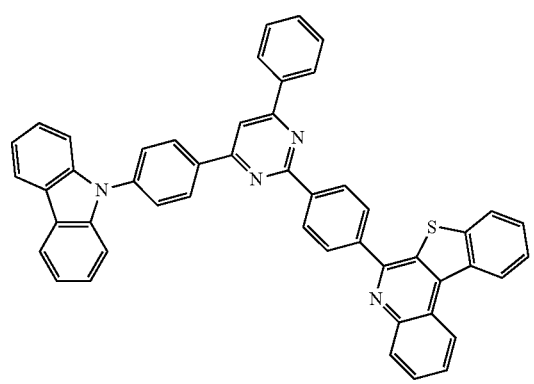

-continued
303
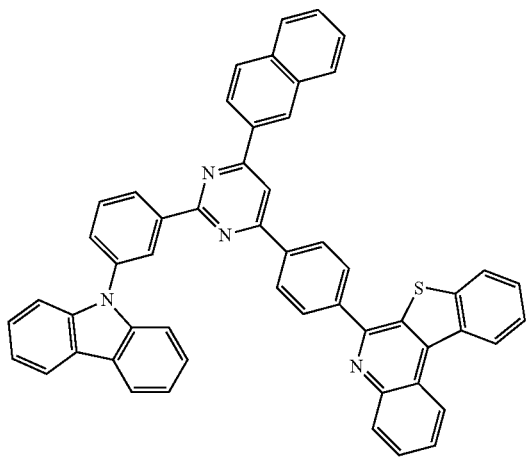
304
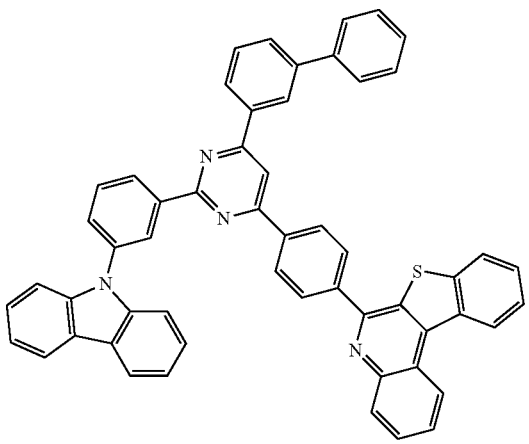
305
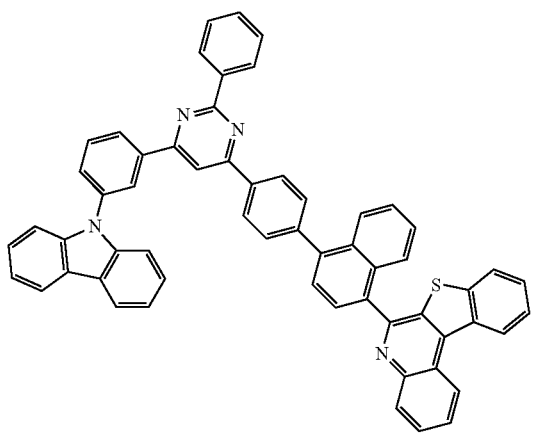
306
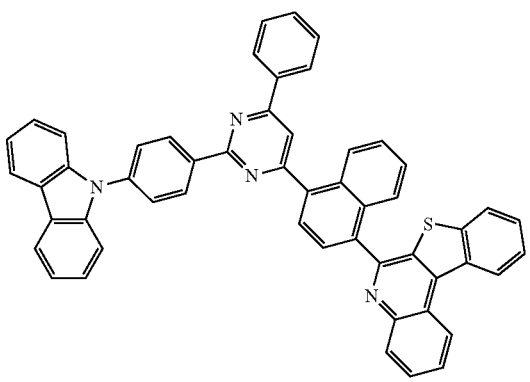
307
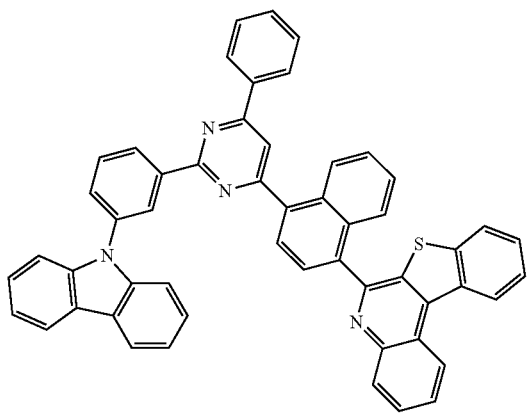
308
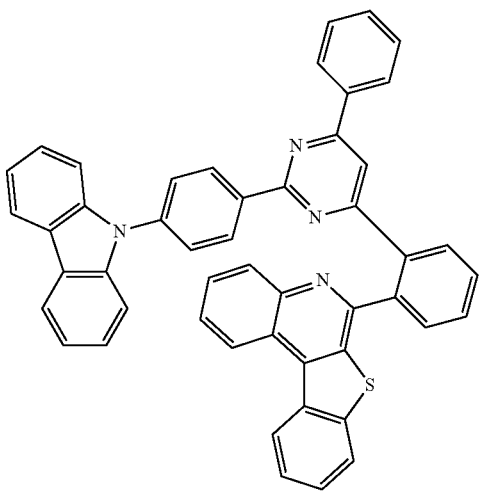

-continued
309
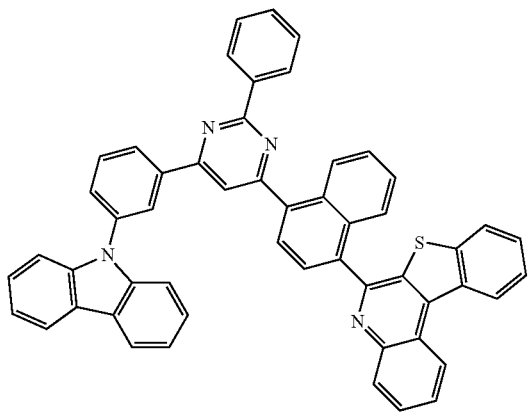
310
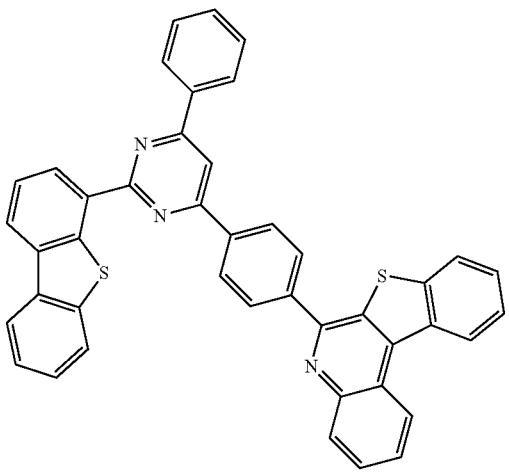
311
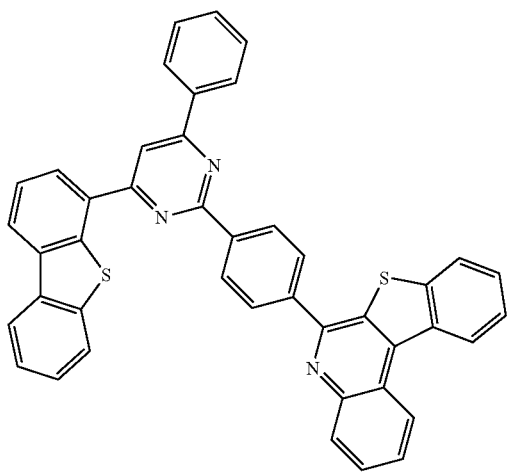
312
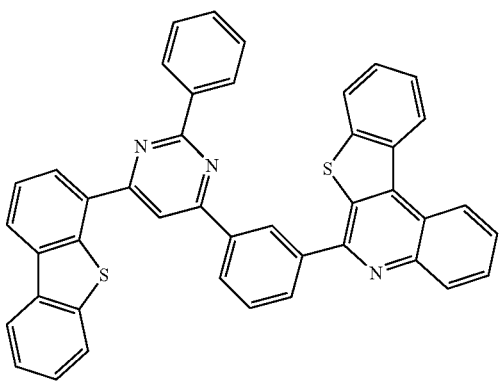
313
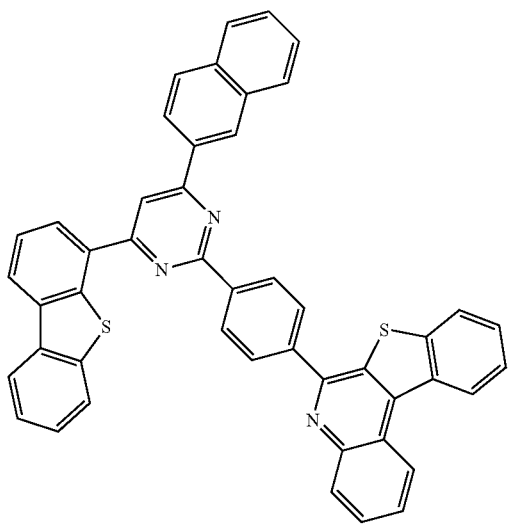
314
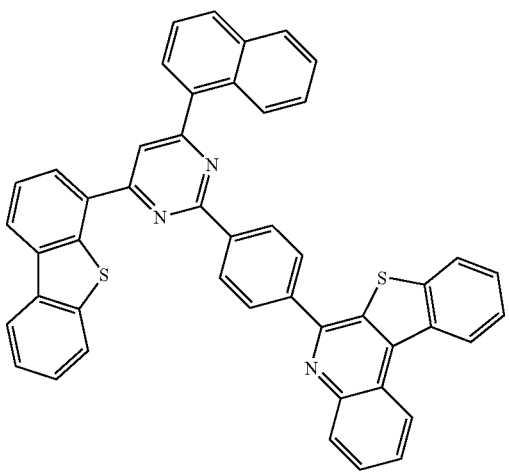

-continued
315
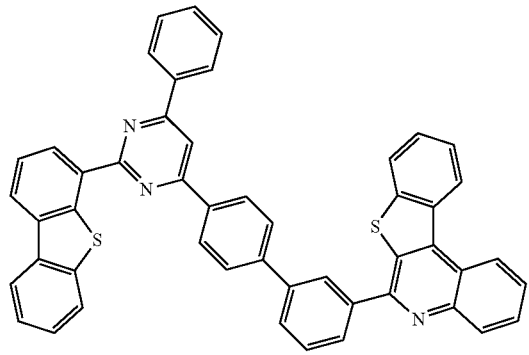
316
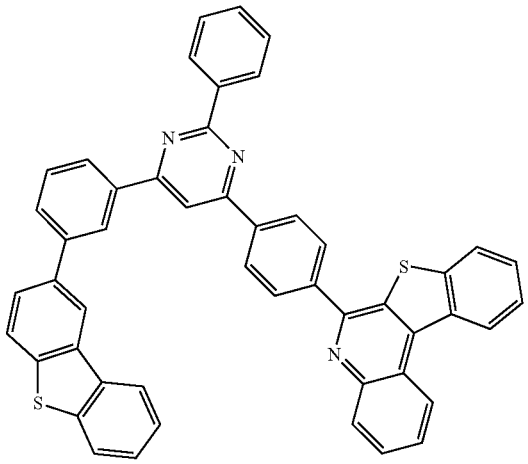
317
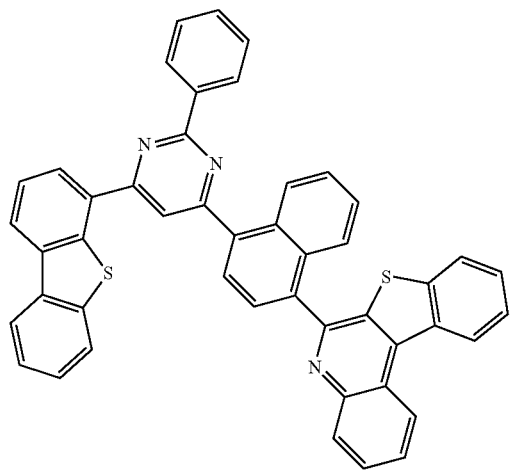
318
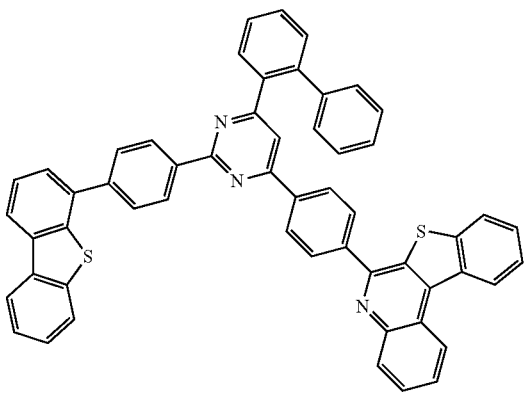
319
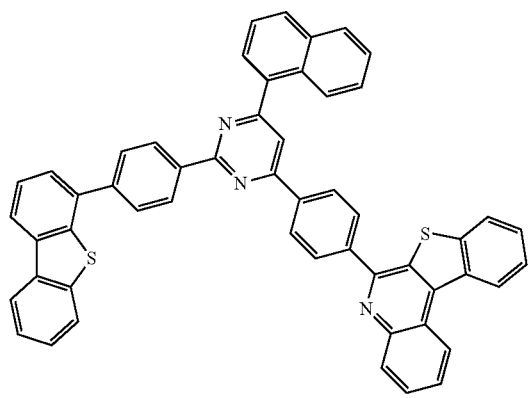
320
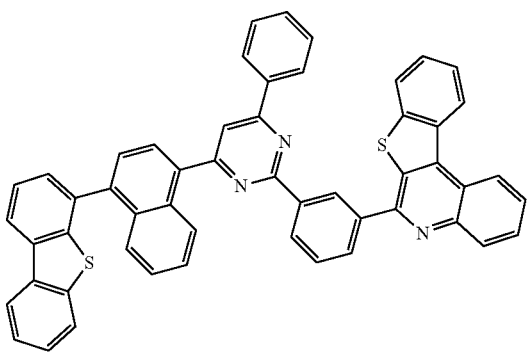

-continued
321
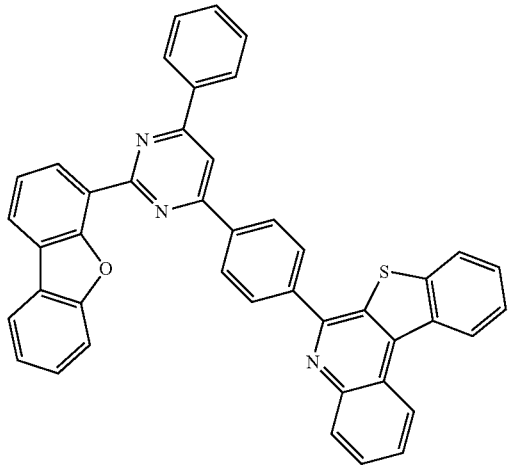
322
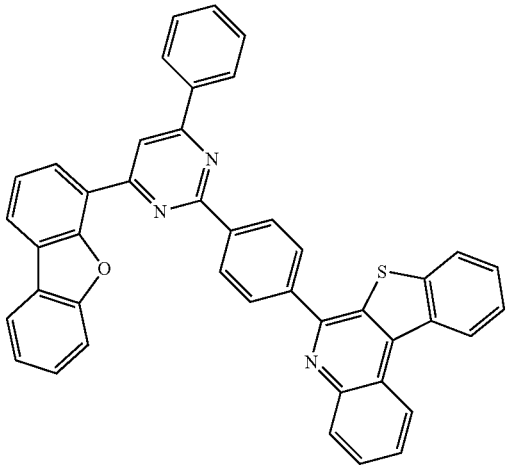
323
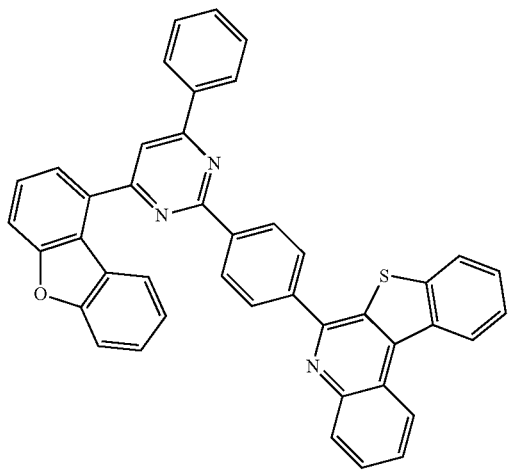
324
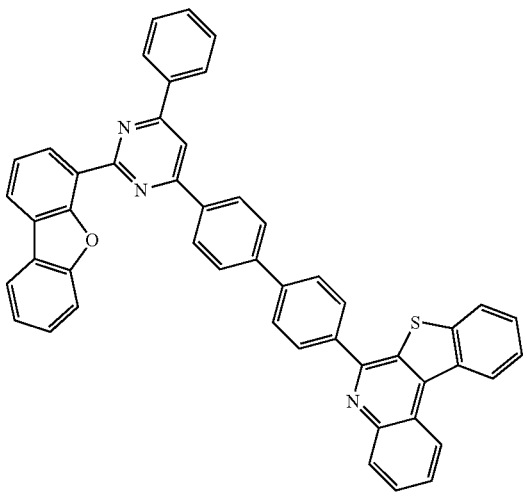
325
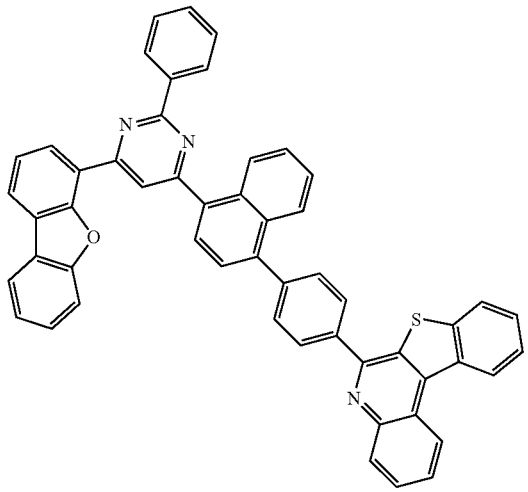
326
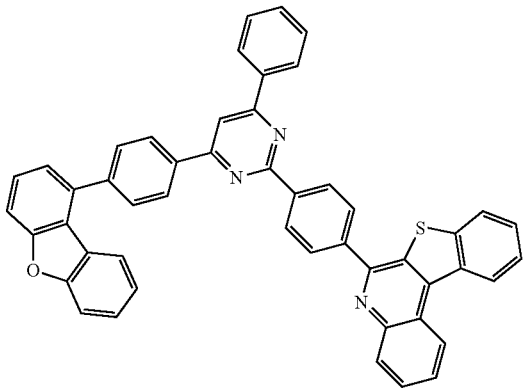

327
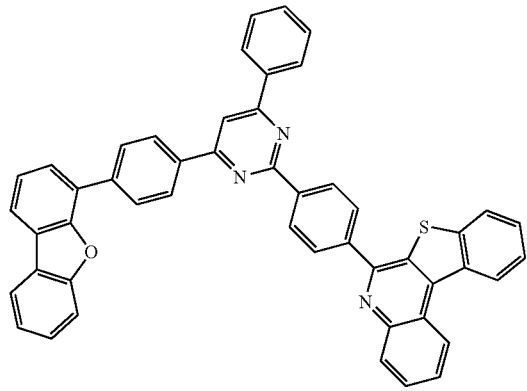
328
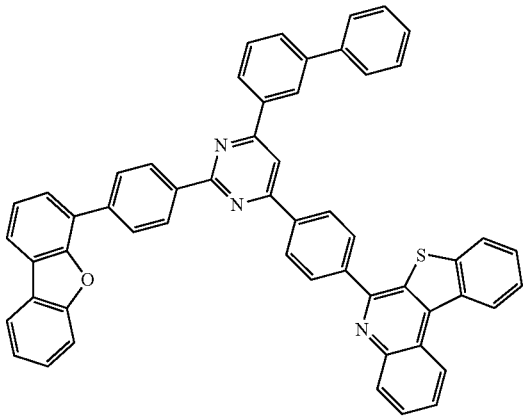
329
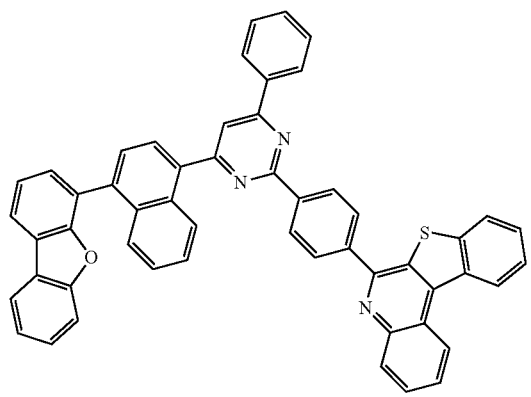
330
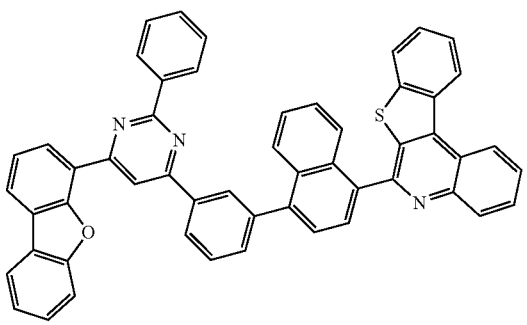
331
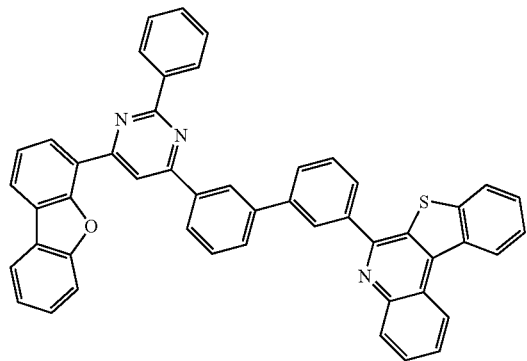
332
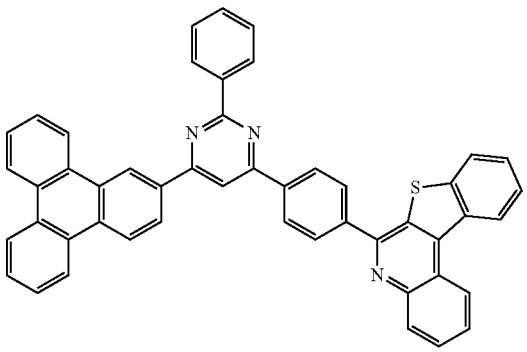
333
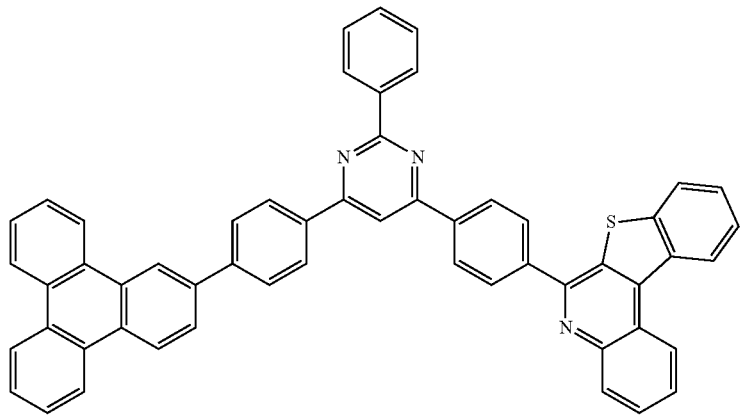

-continued
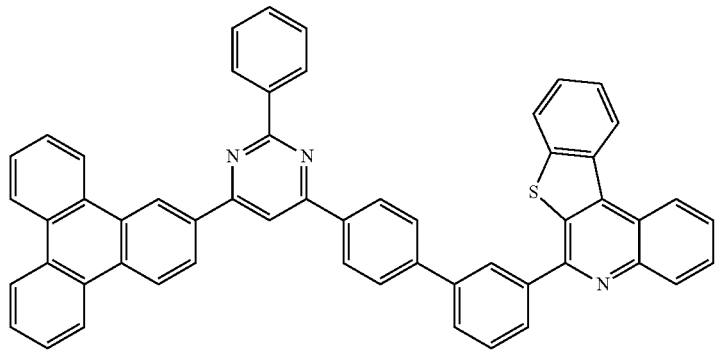
334
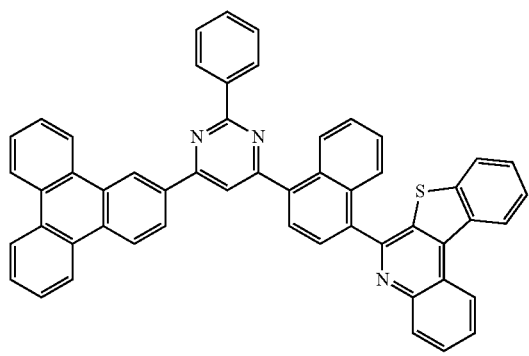
335
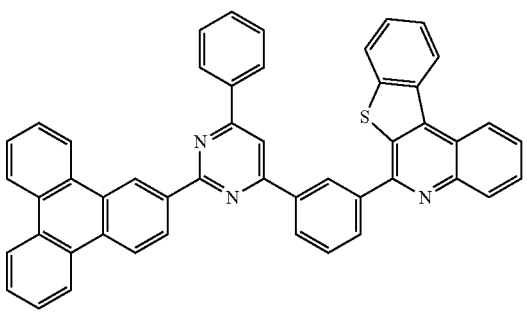
336
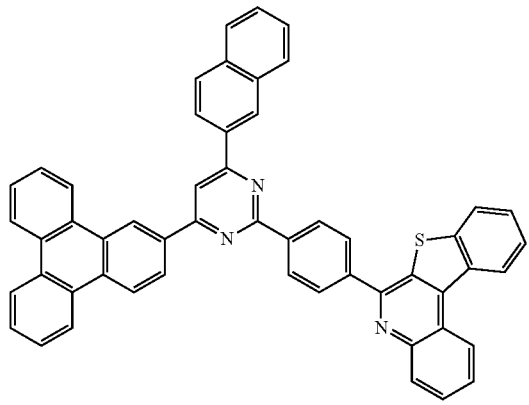
337
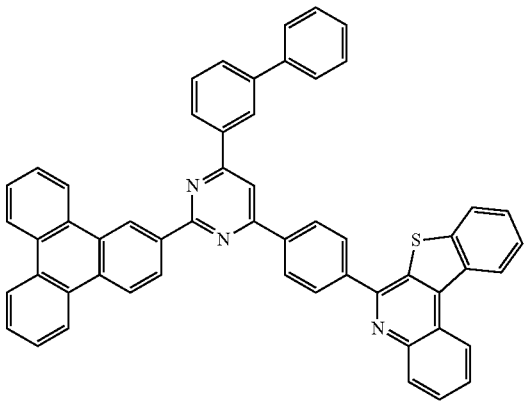
338
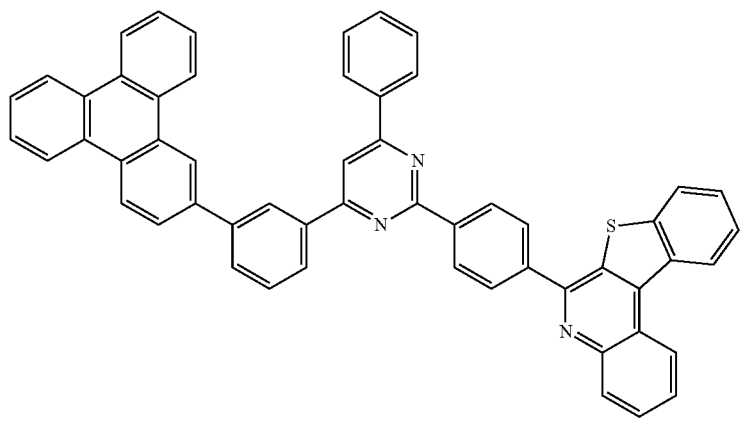
339

-continued
340
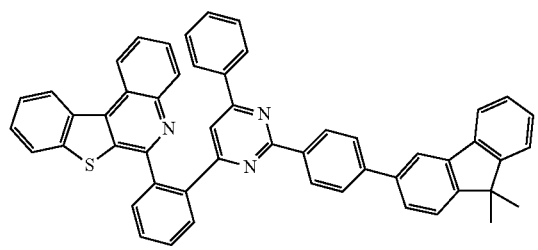
341
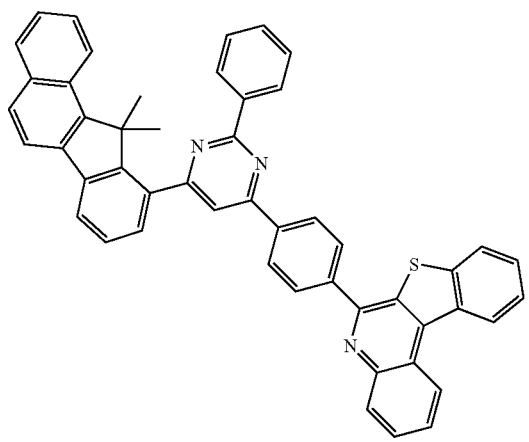
342
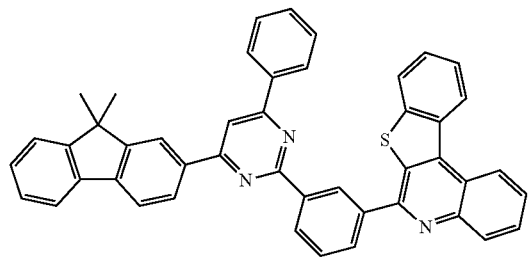
343
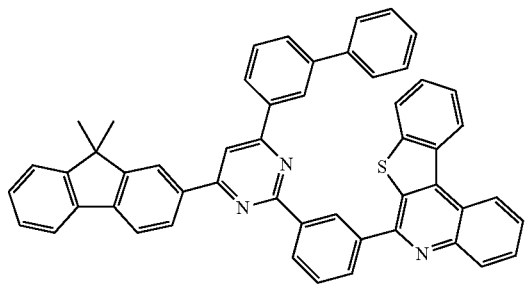
344
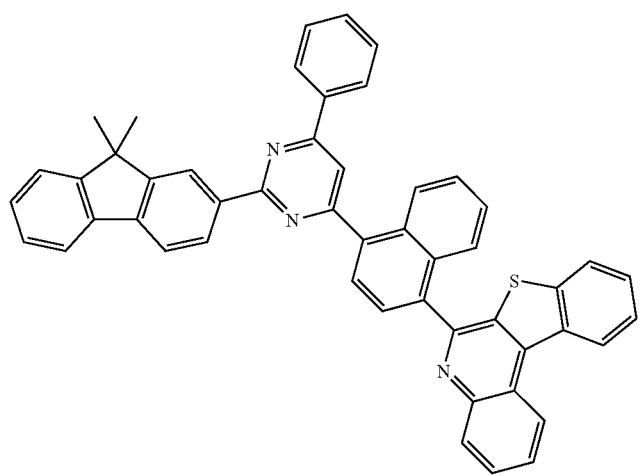

-continued
345
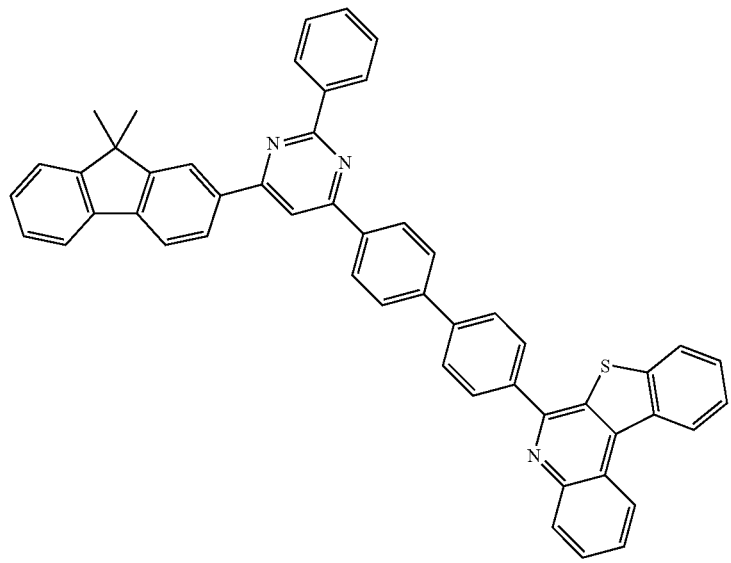
346
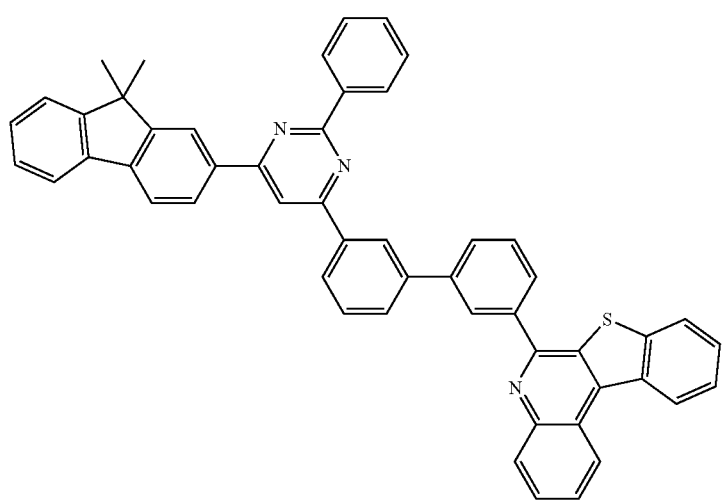
347
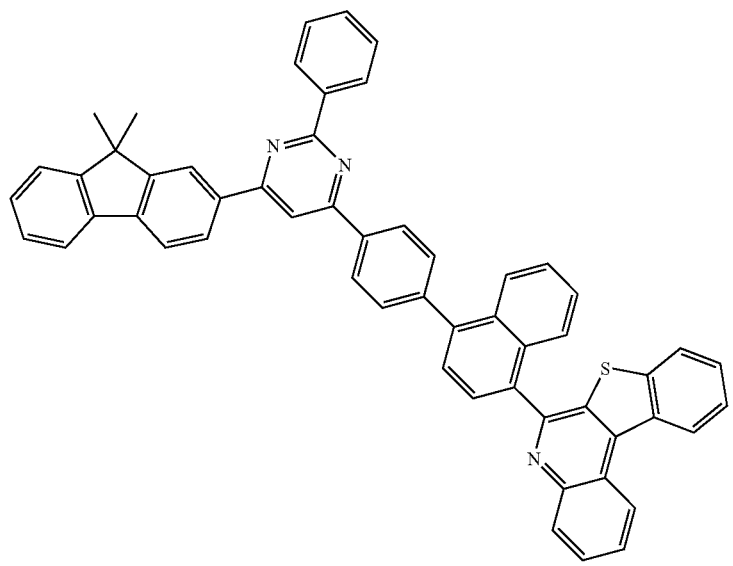

-continued
348
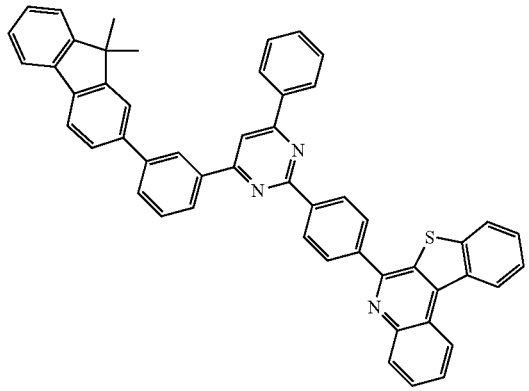
349
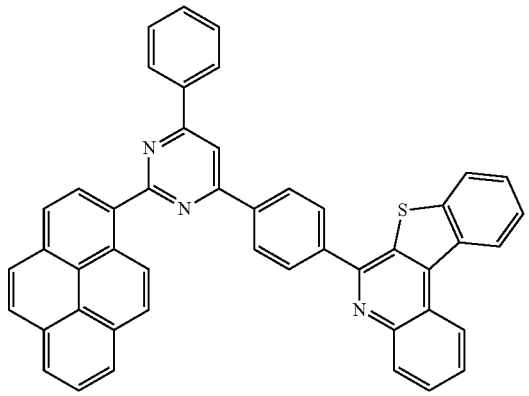
350
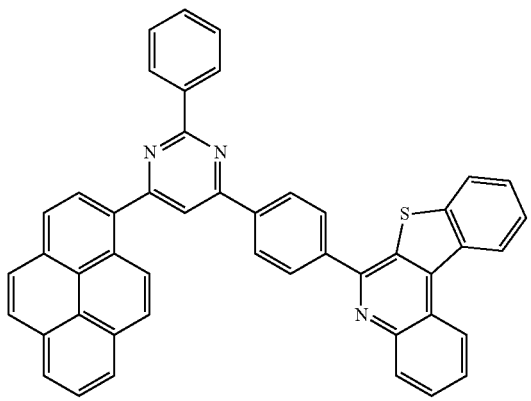
351
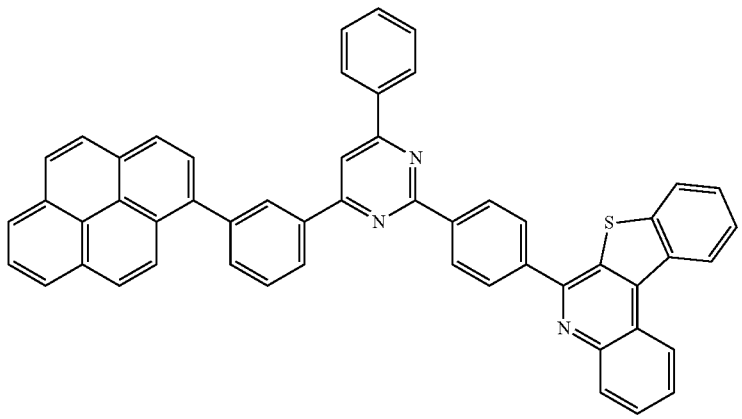
352
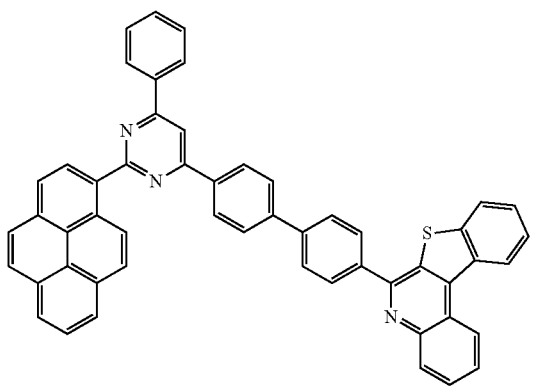
353
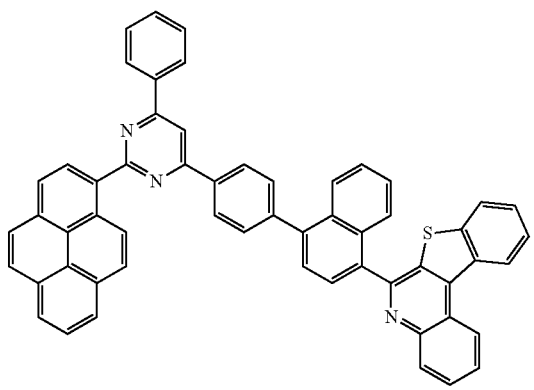

354
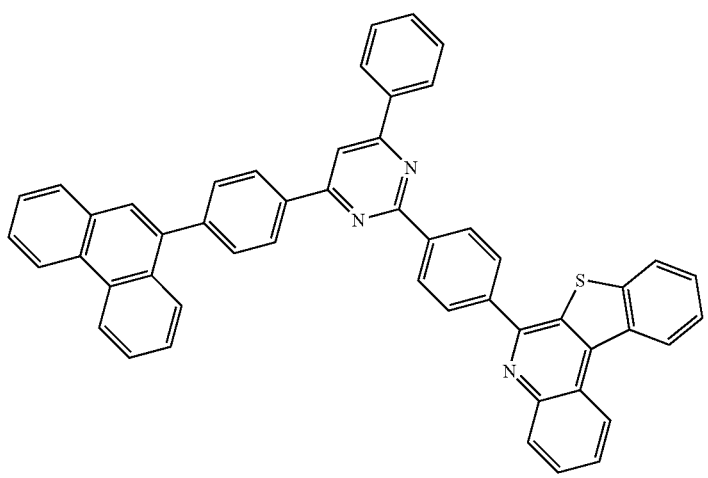
355
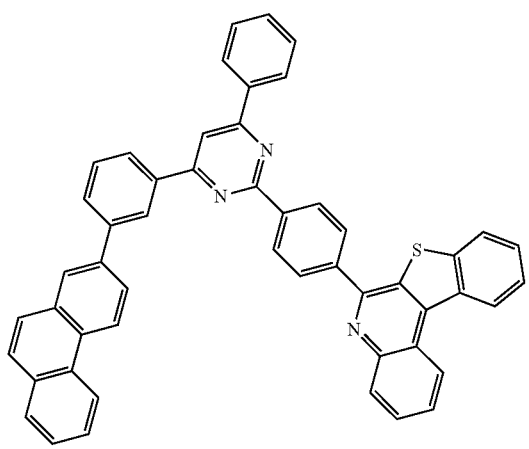
356
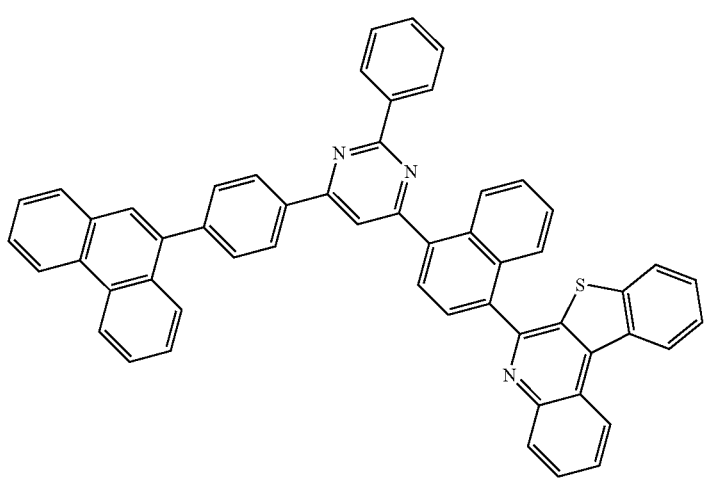

357
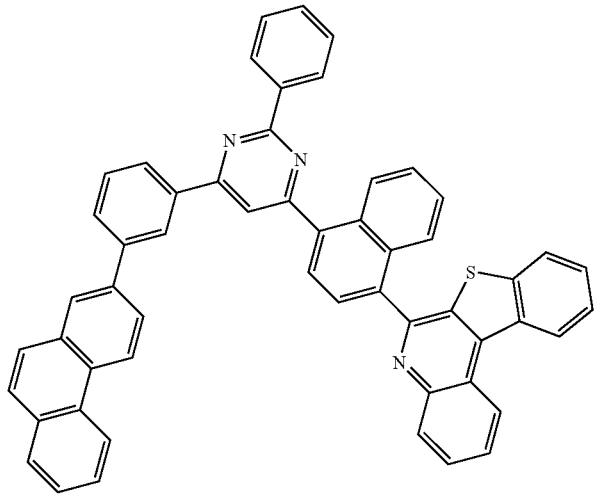
358
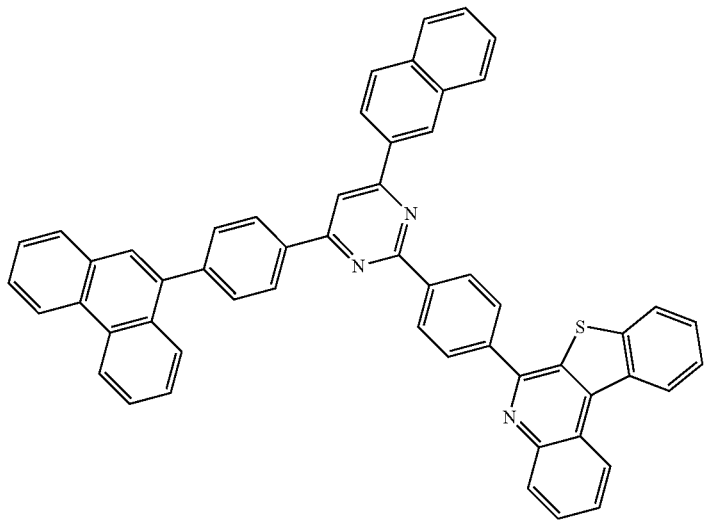
359
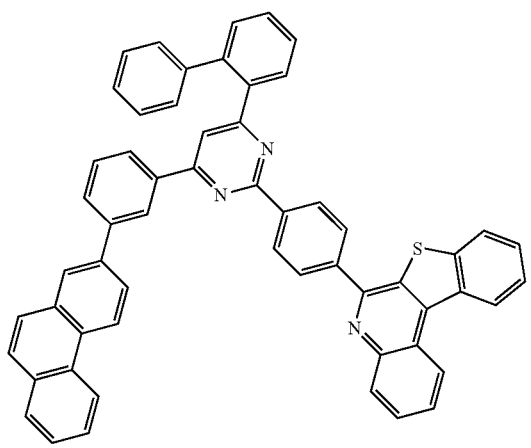
360
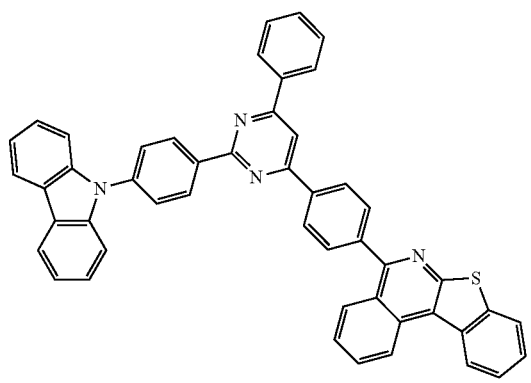

-continued
361
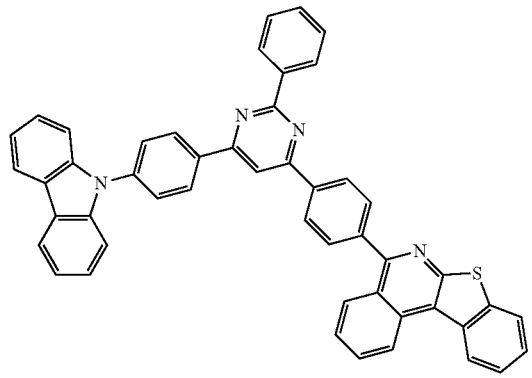
362
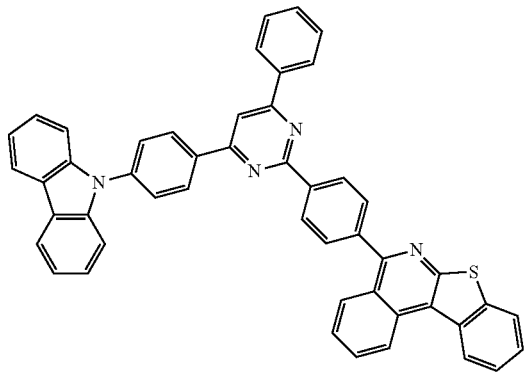
363
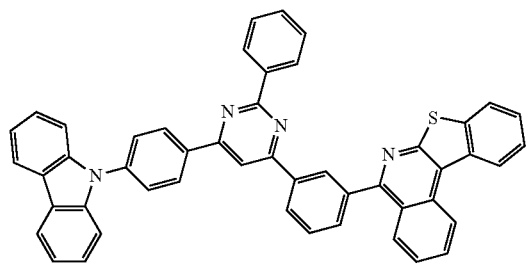
364
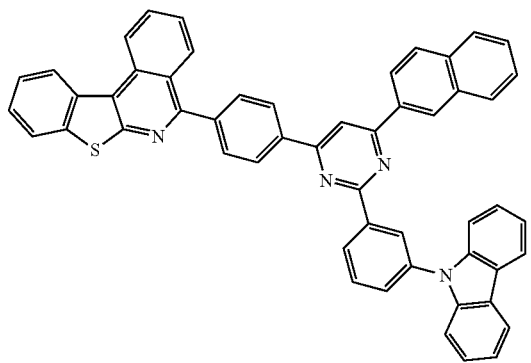
365
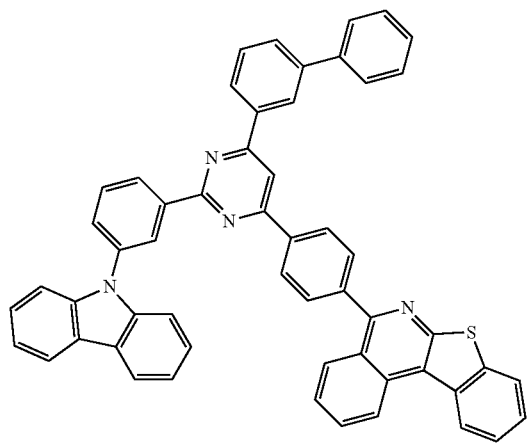
366
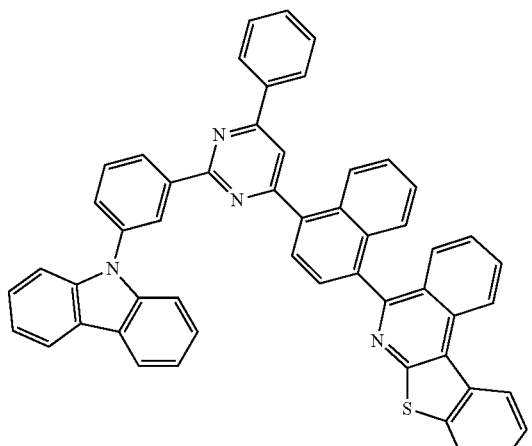

367
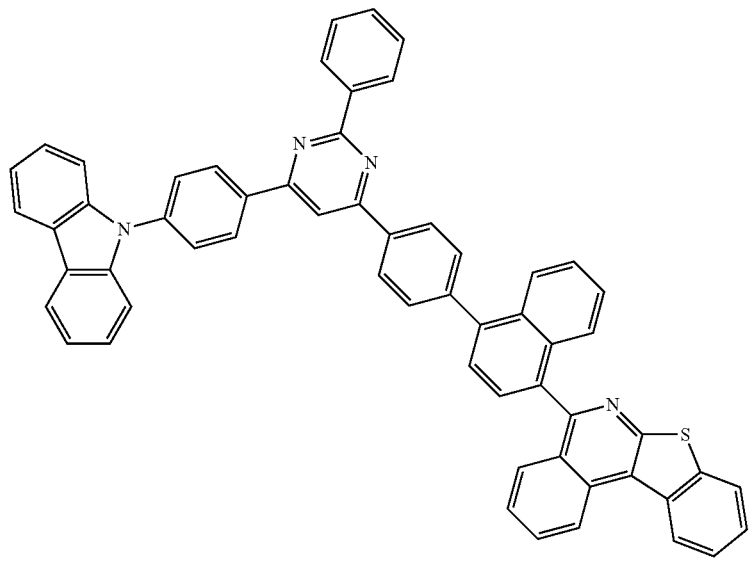
368
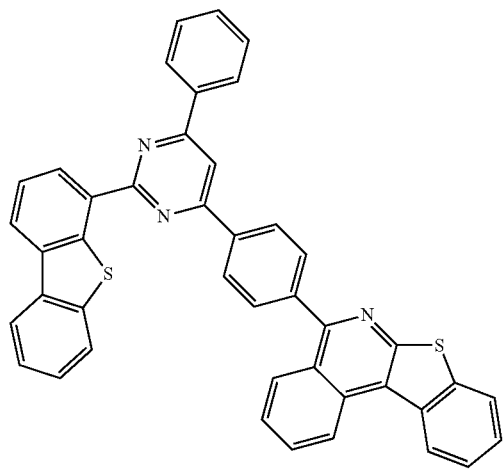
369
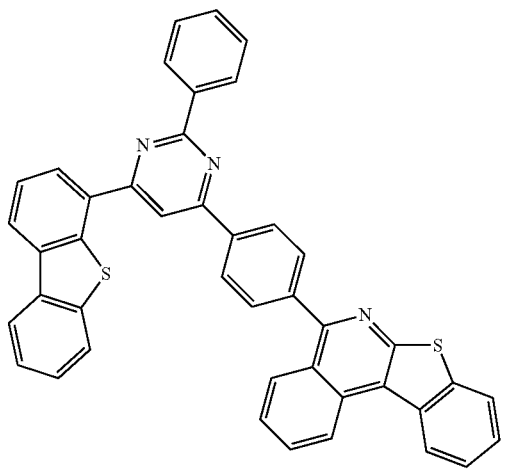
370
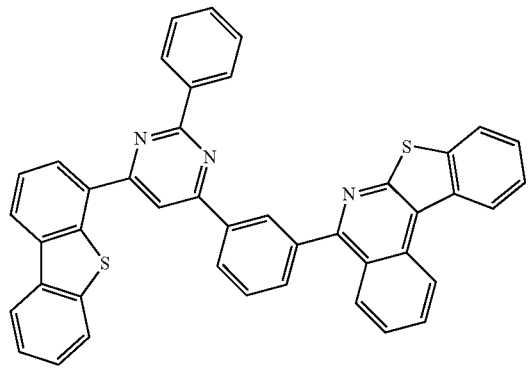
371
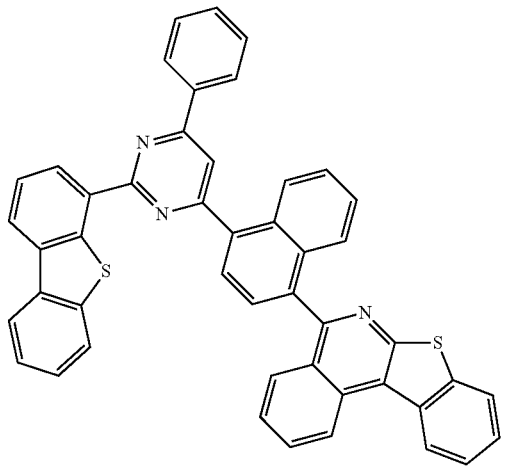

-continued
372
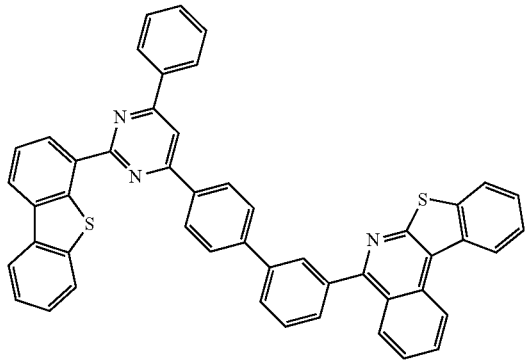
373
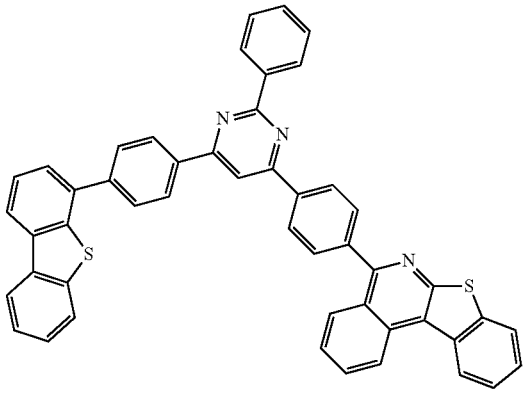
374
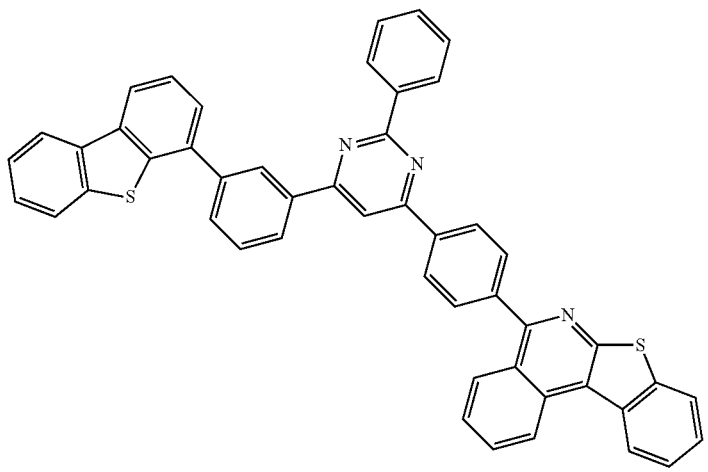
375
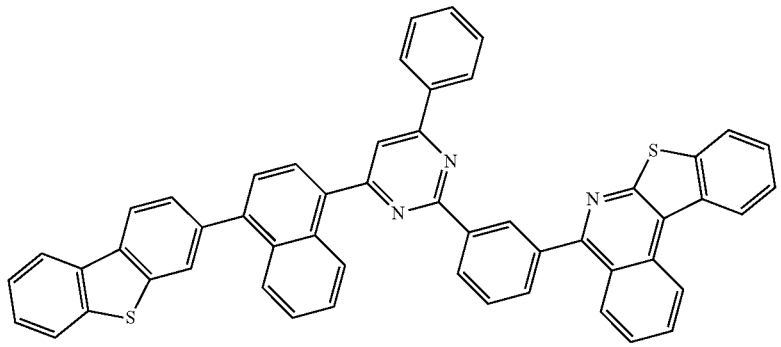

376
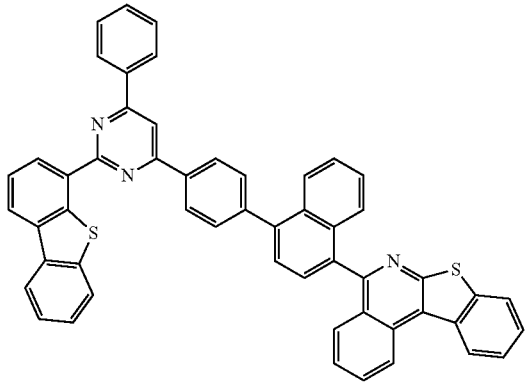
377
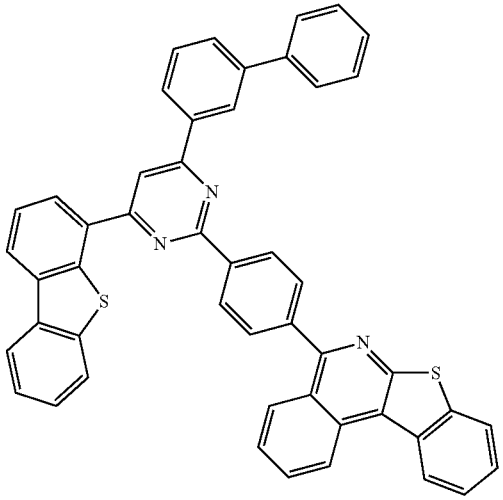
378
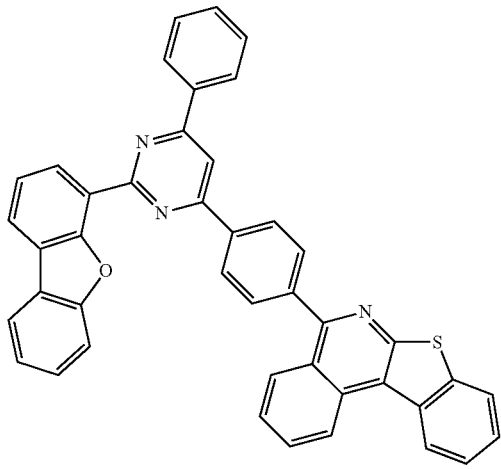
379
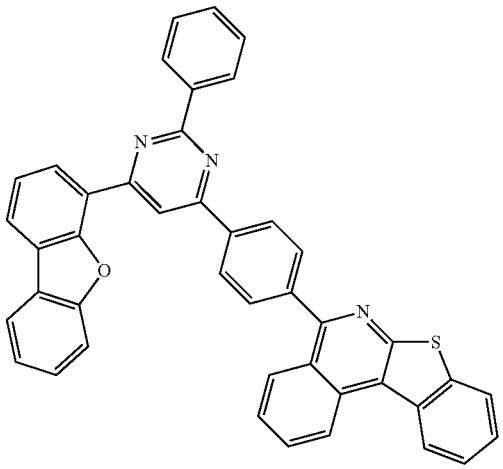
380
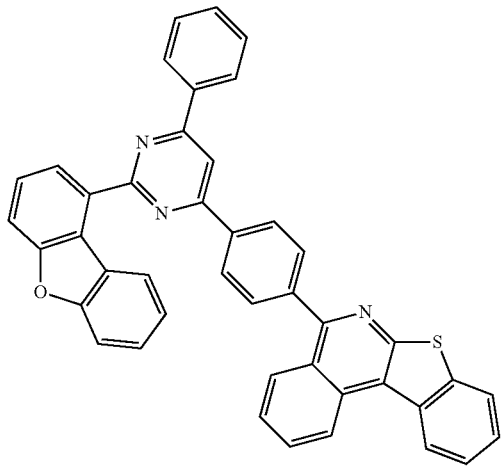
381
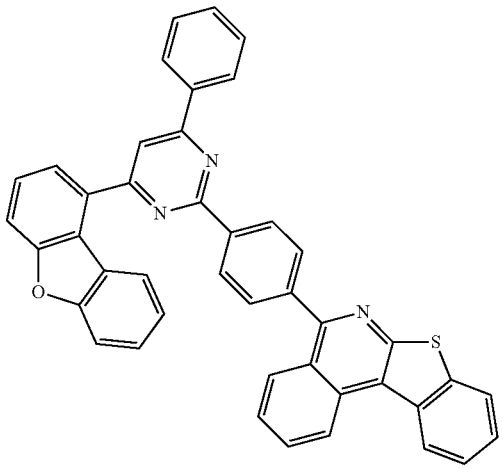

-continued
382
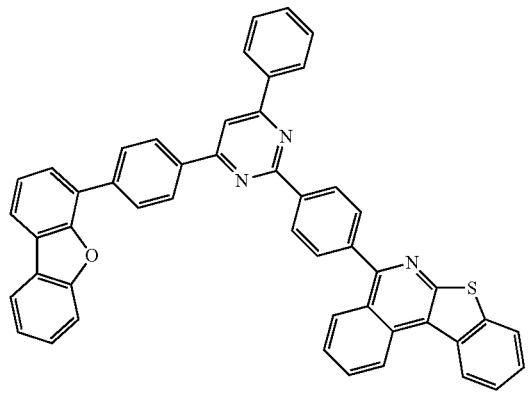
383
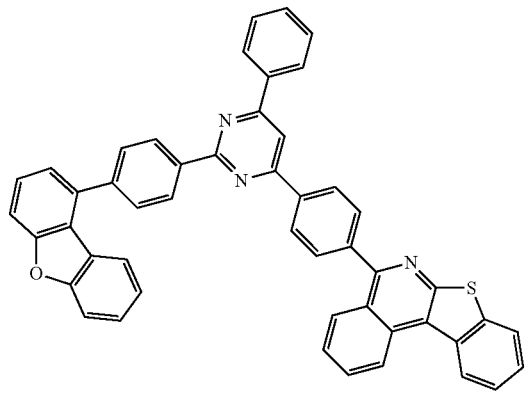
384
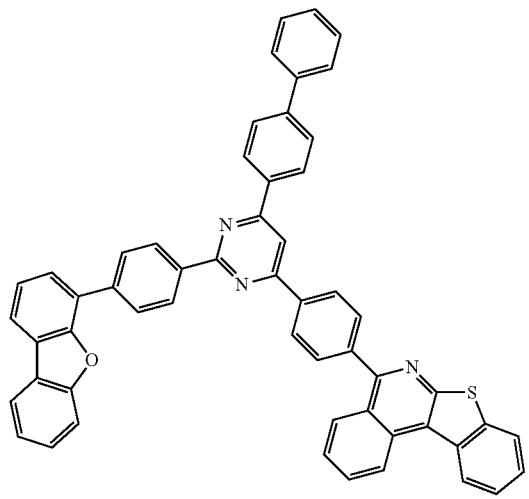
385
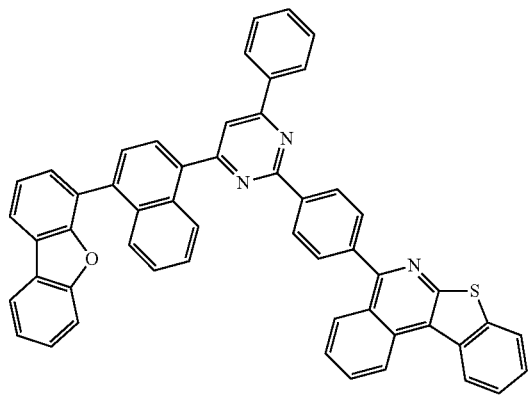
386
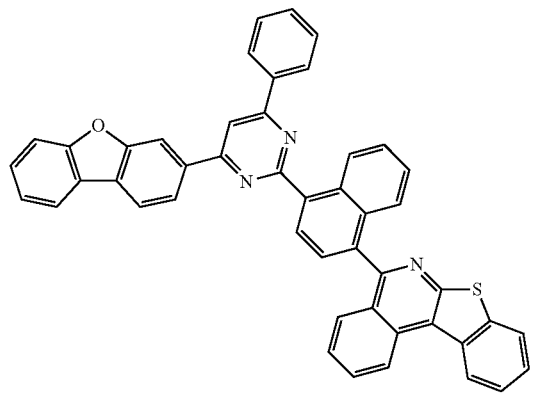
387
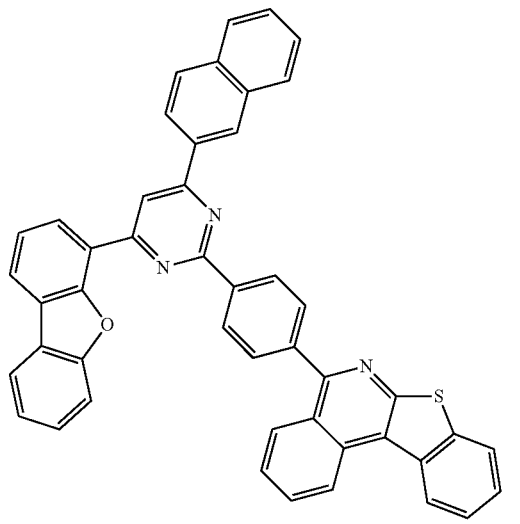

-continued
388
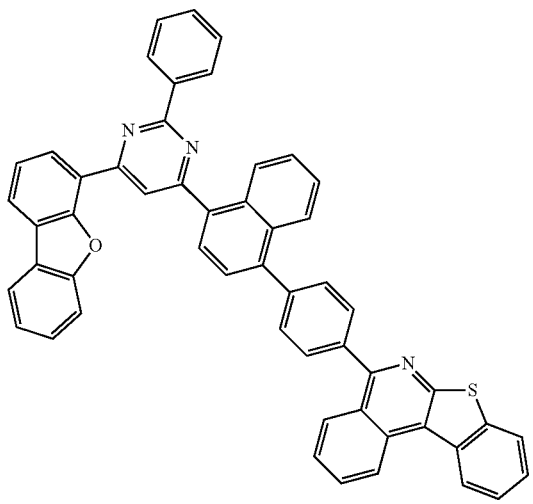
389
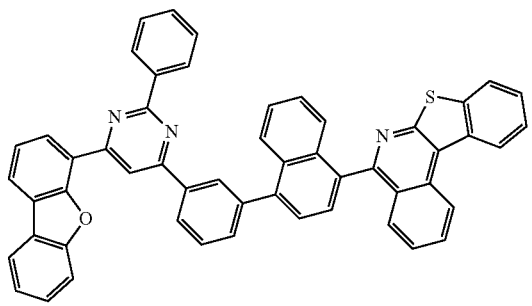
390
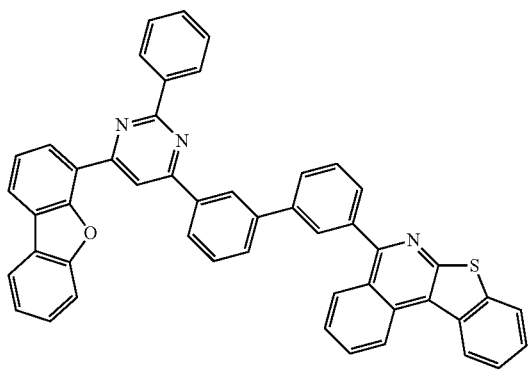
391
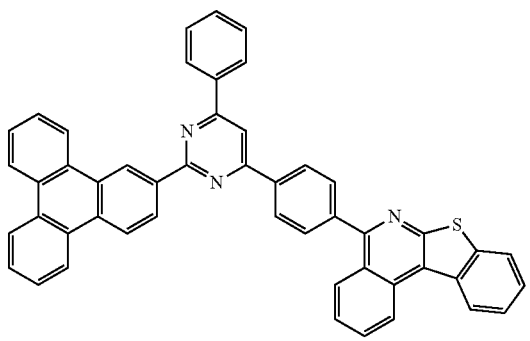
392
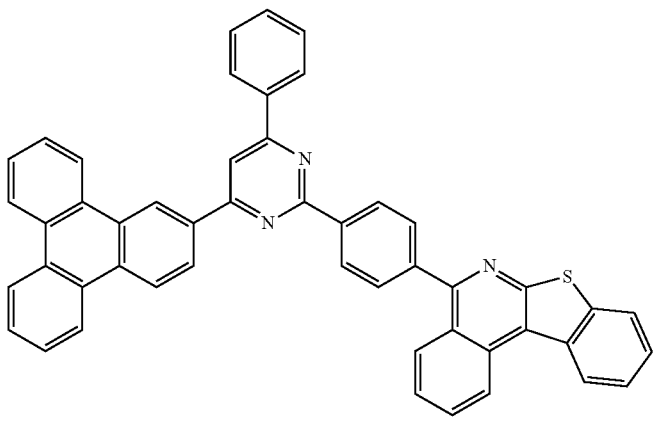

393
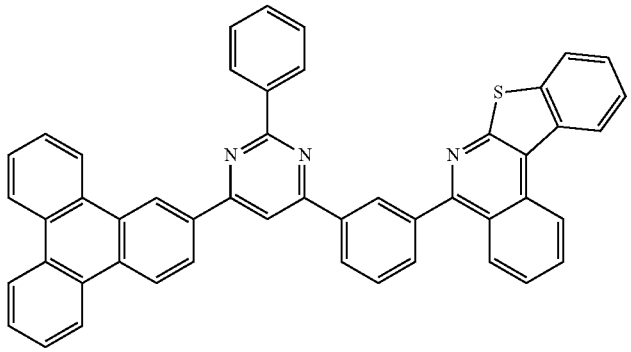
394
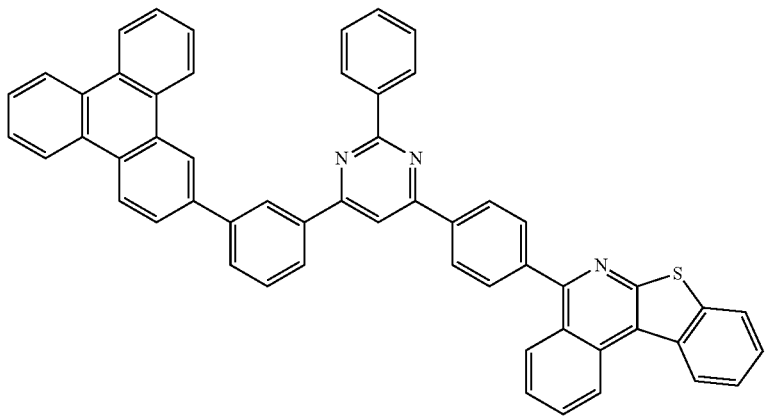
395
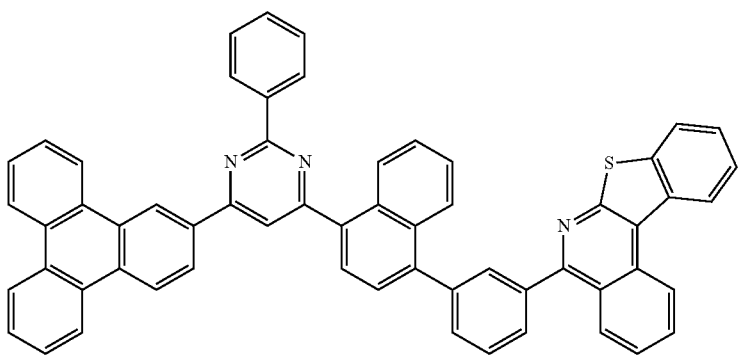
396
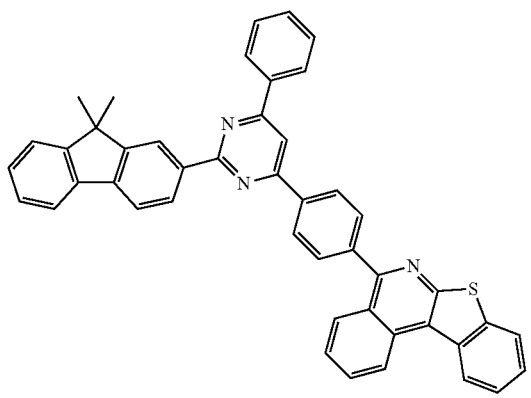
397
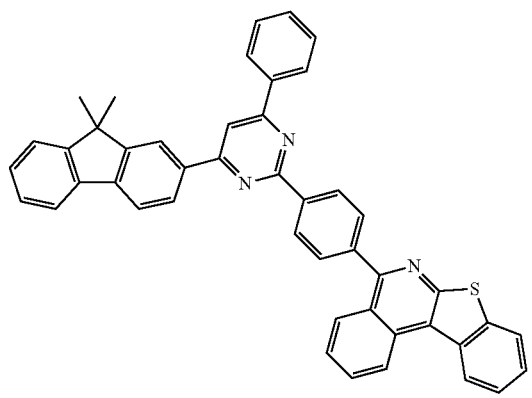

-continued
398
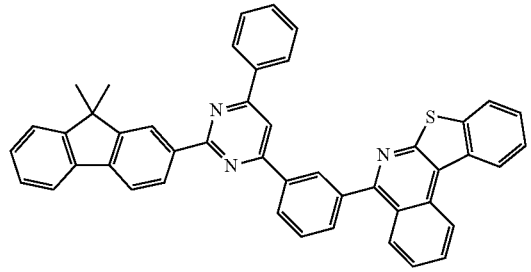
399
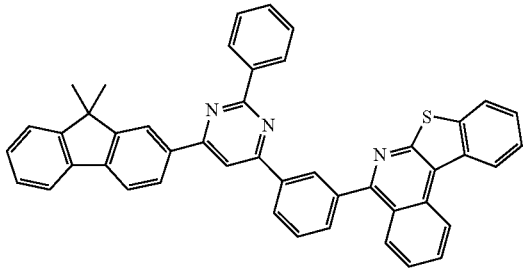
400
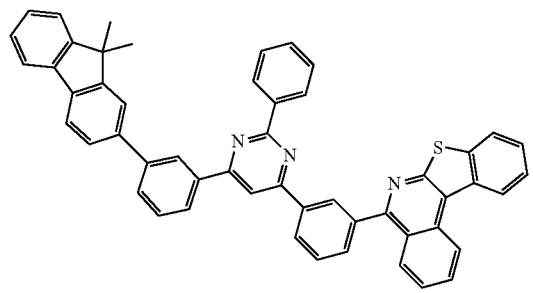
401
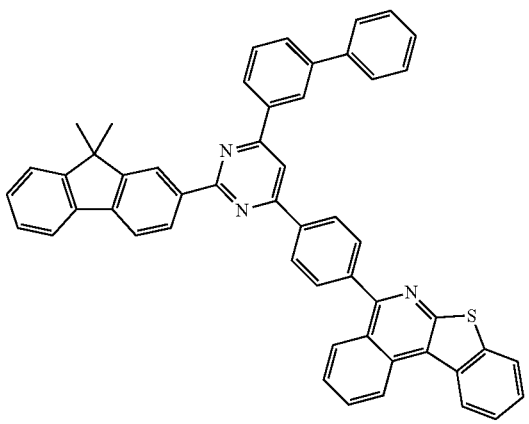
402
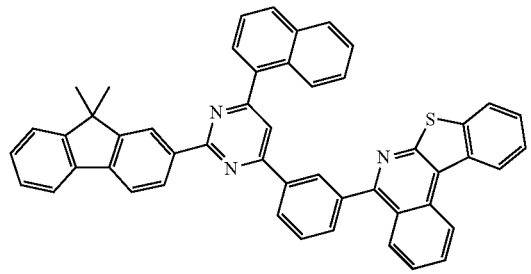
403
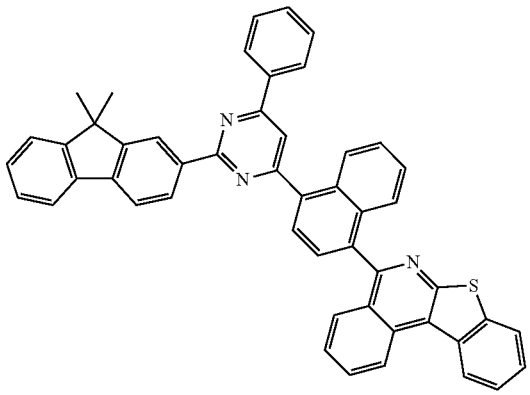
404
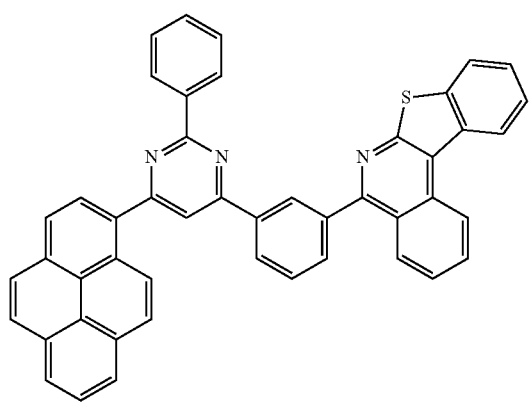
405
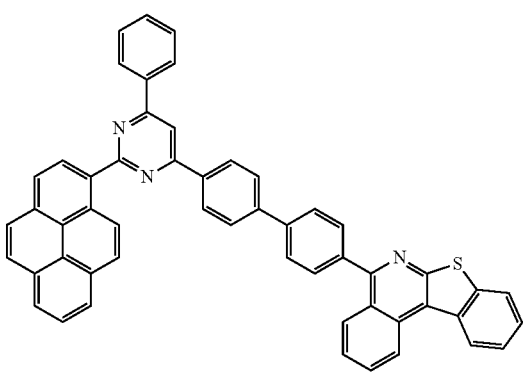

406
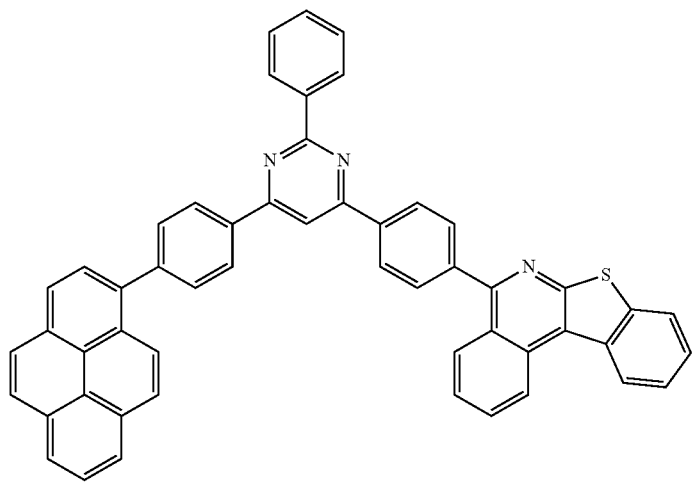
407
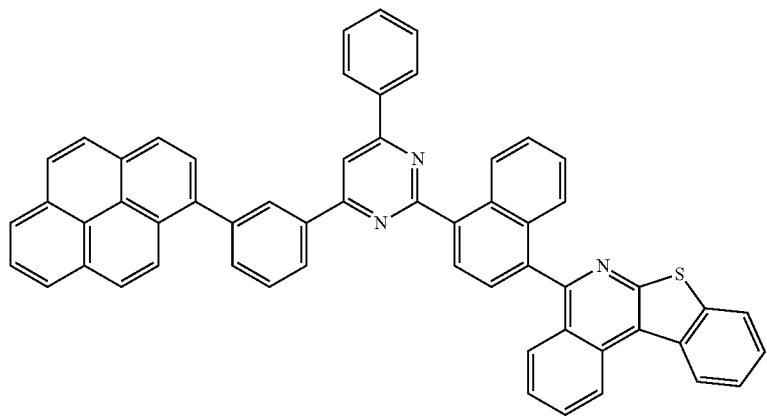
408
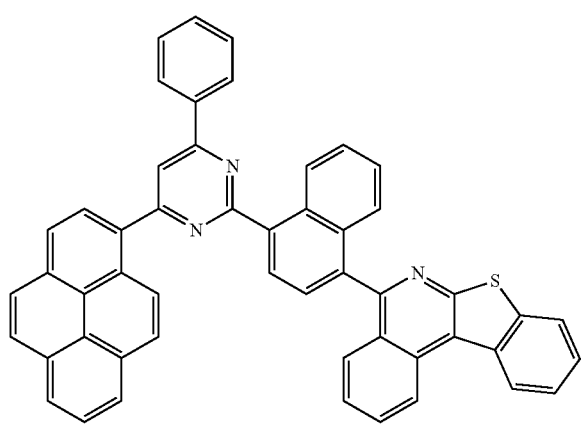

-continued
409
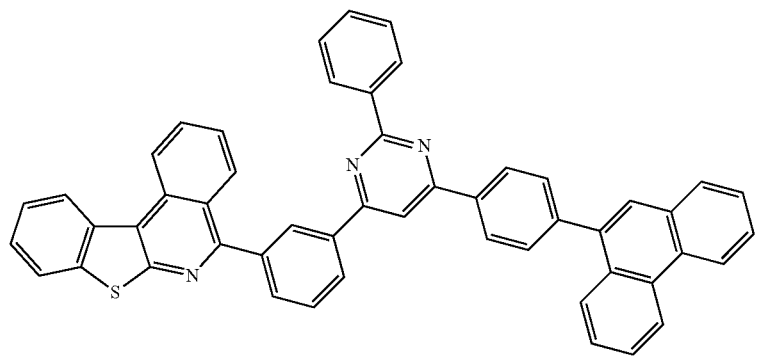
410
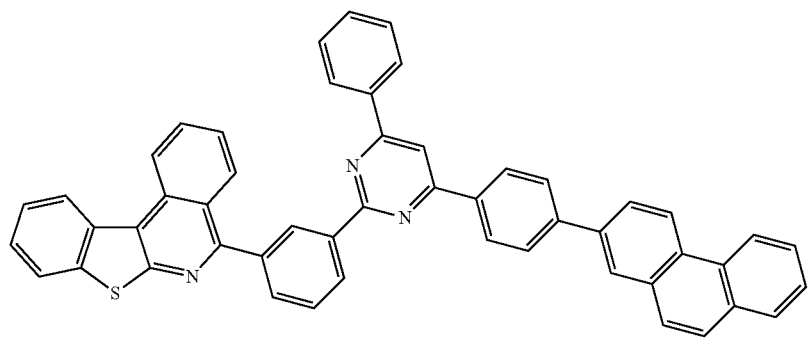
411
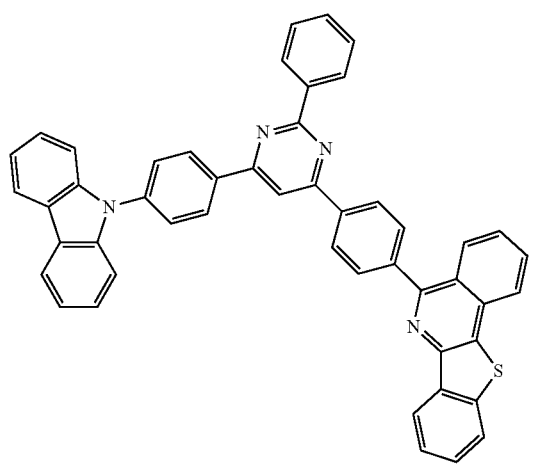
412
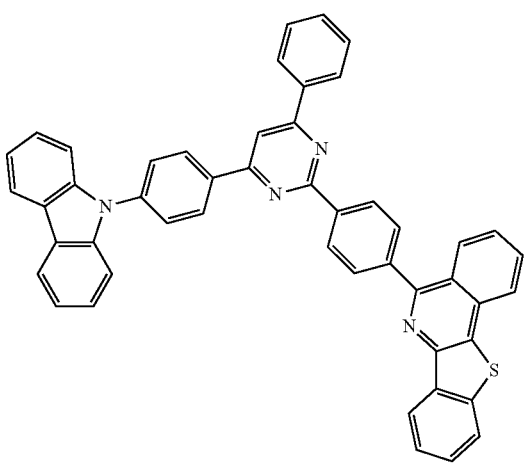
413
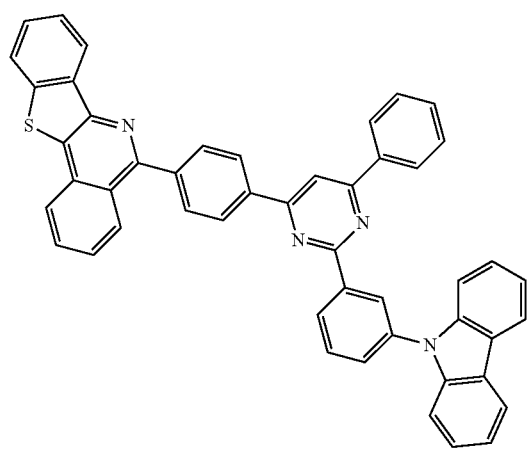
414
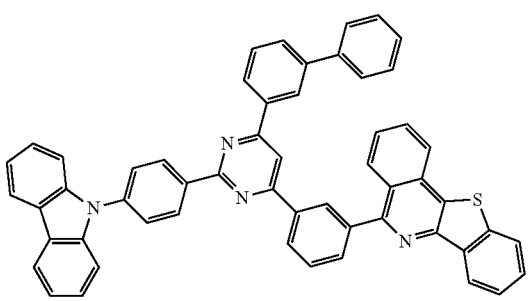

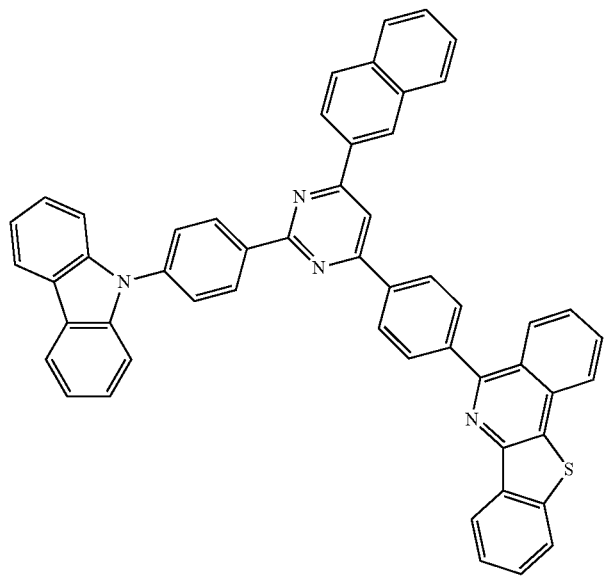
415
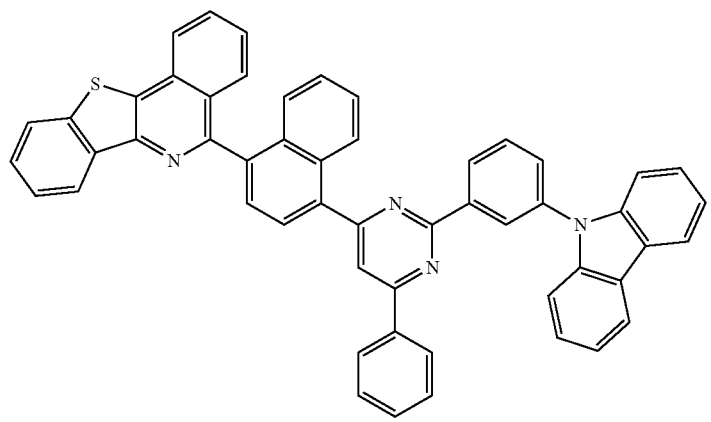
416
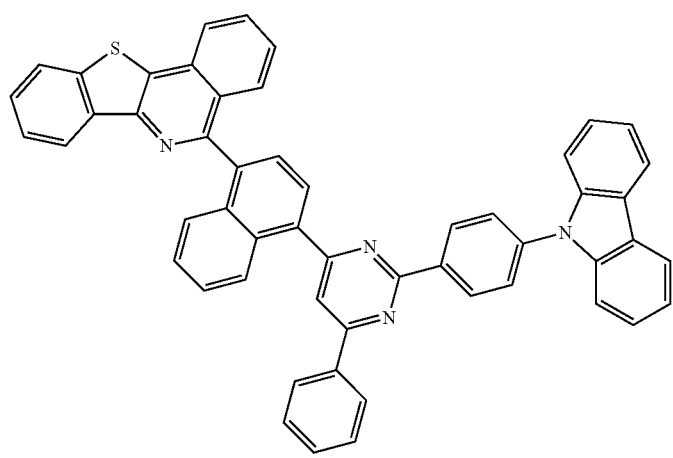
417

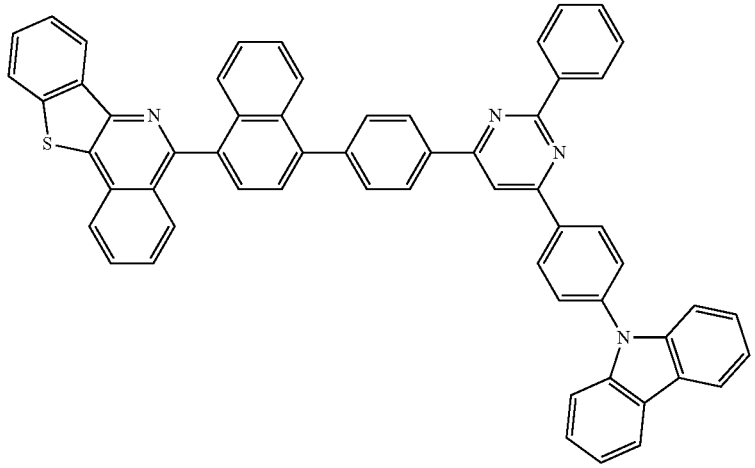
418
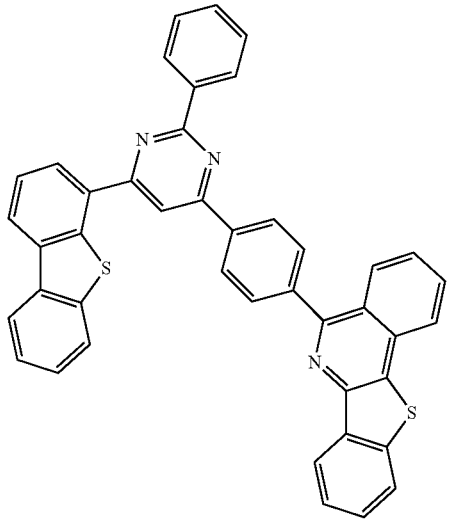
419
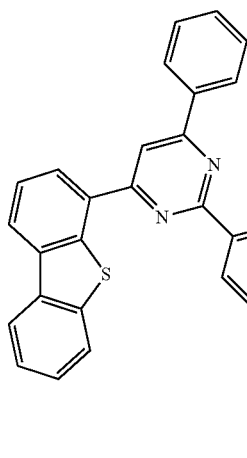
420
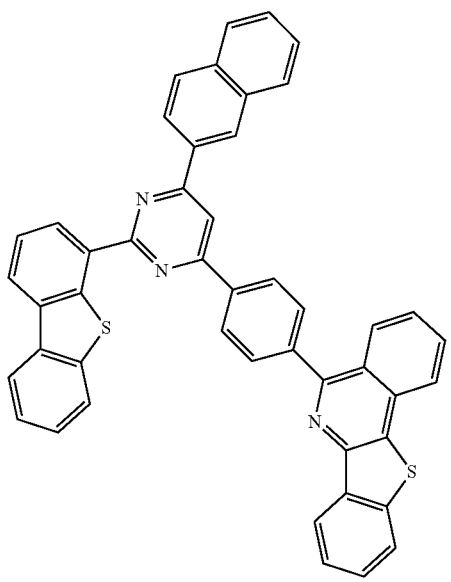
421
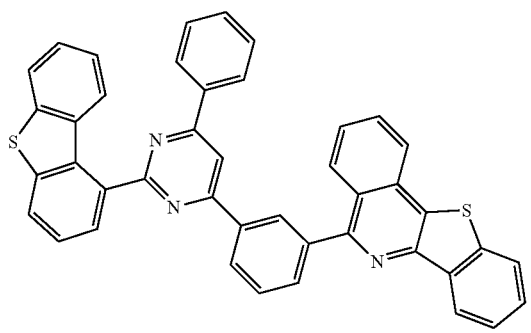
422

-continued
423
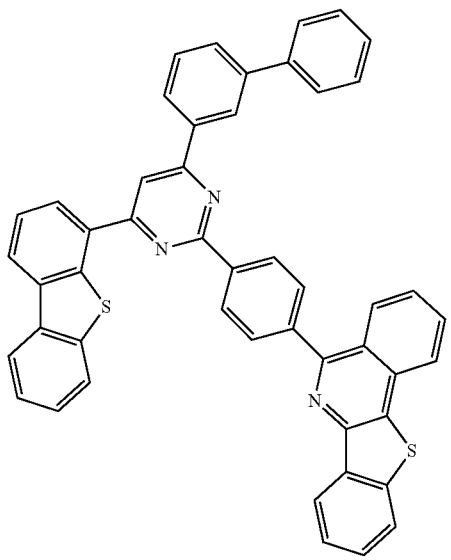
424
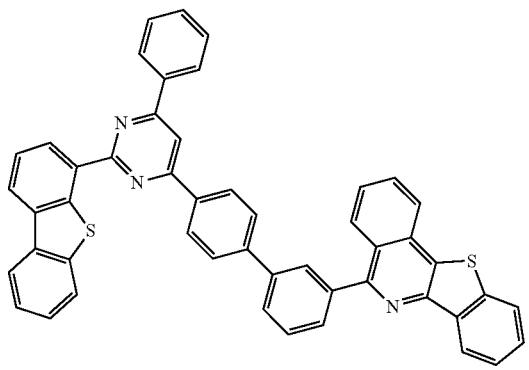
425
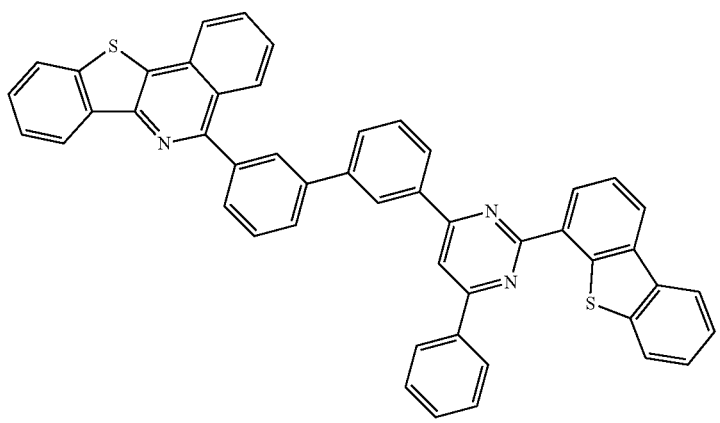
426
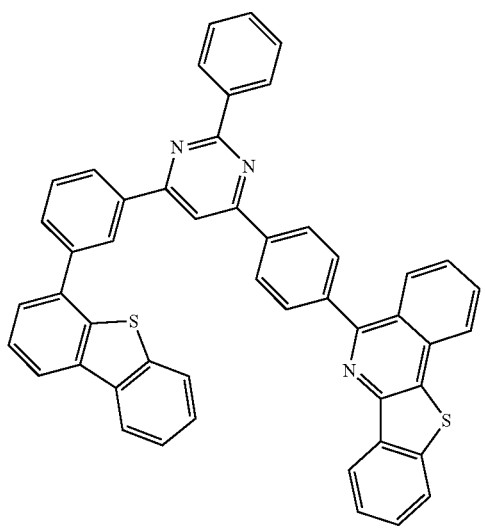
427
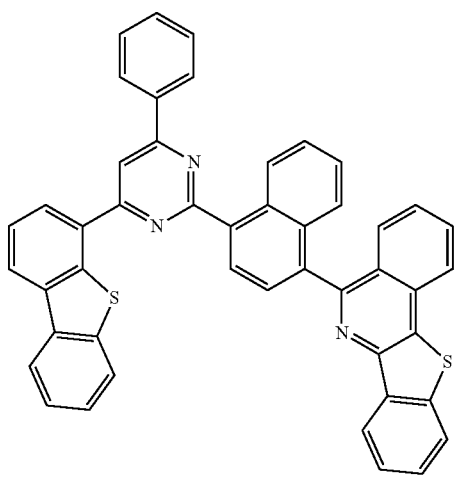

-continued
428
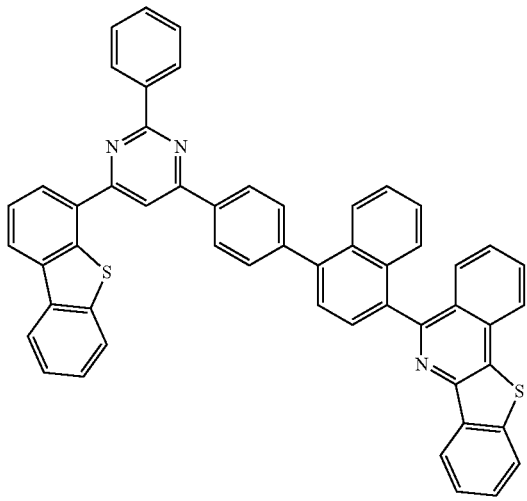
429
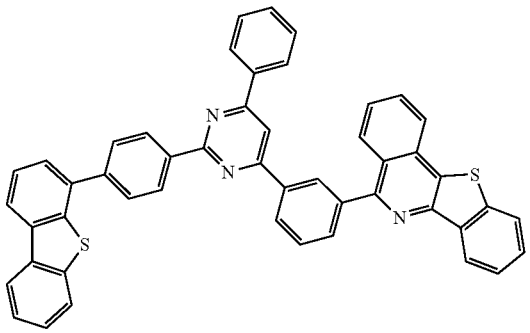
430
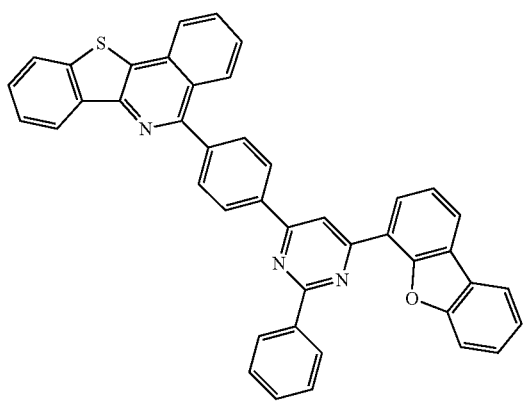
431
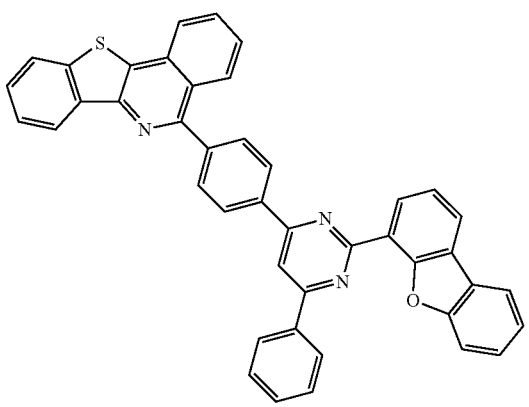
432
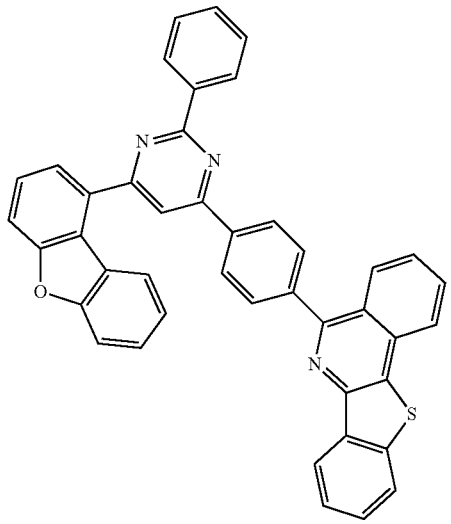
433
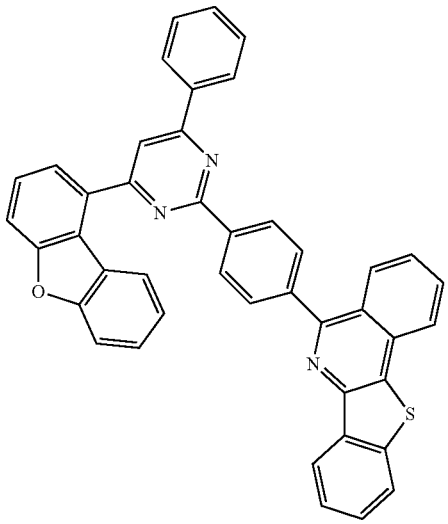

-continued
434
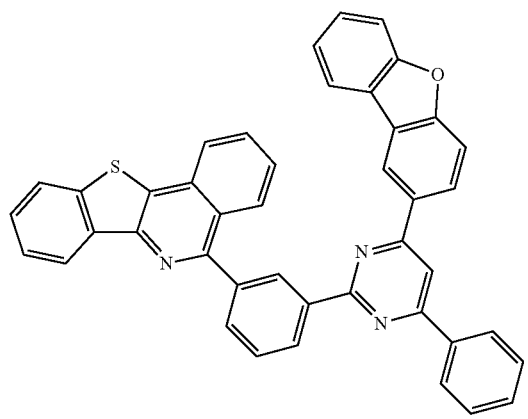
435
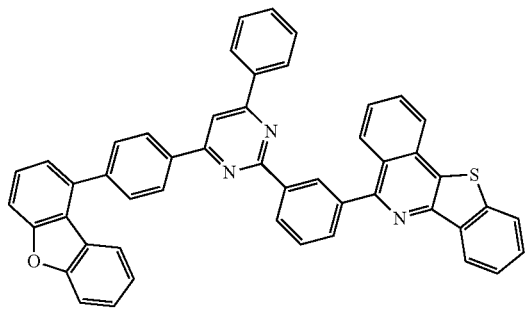
436
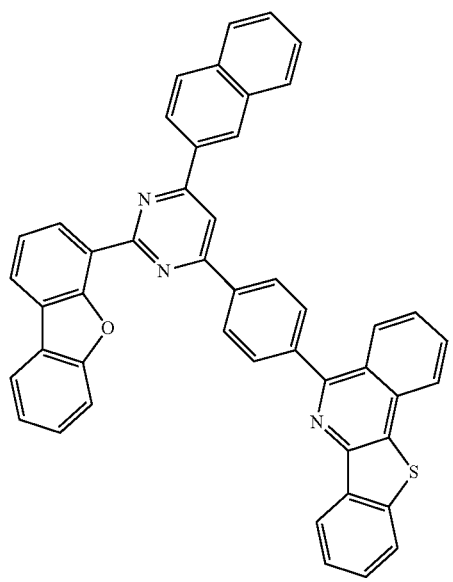
437
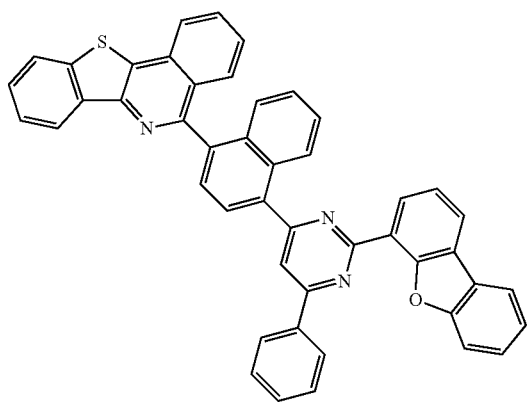
438
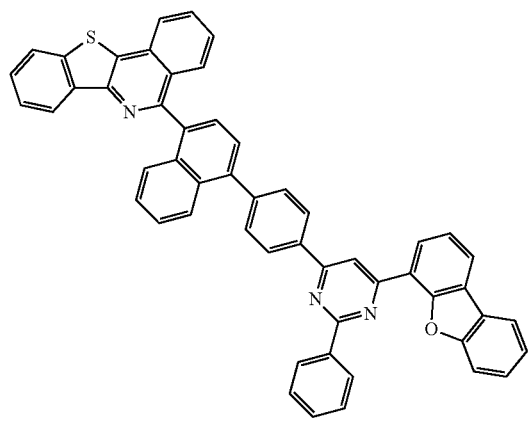
439
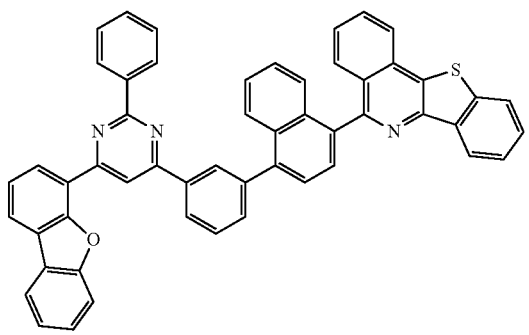

-continued
440
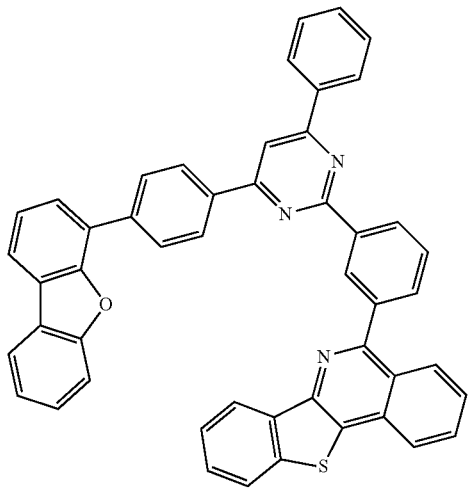
441
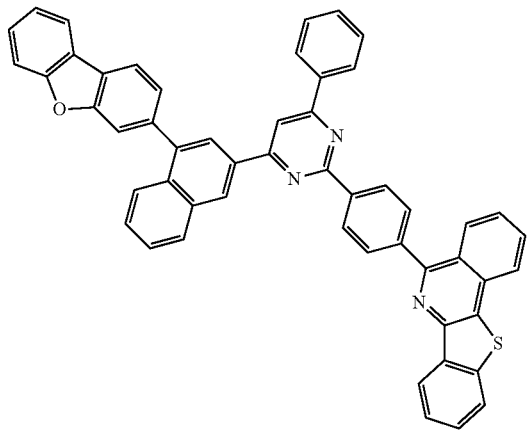
442
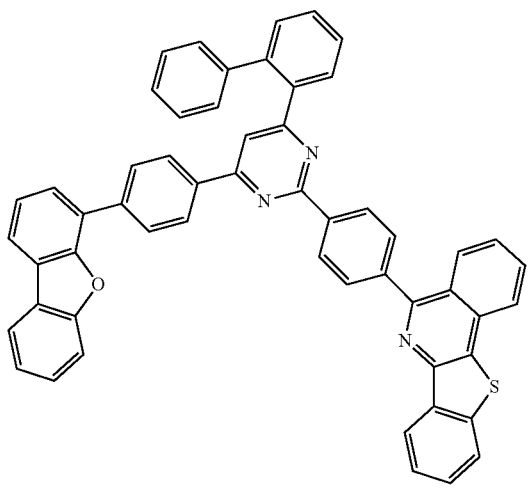
443
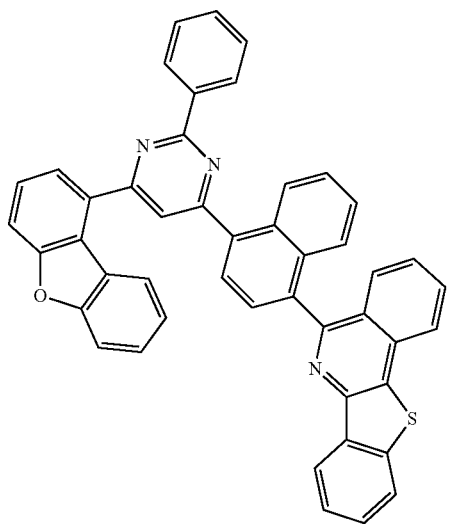
444
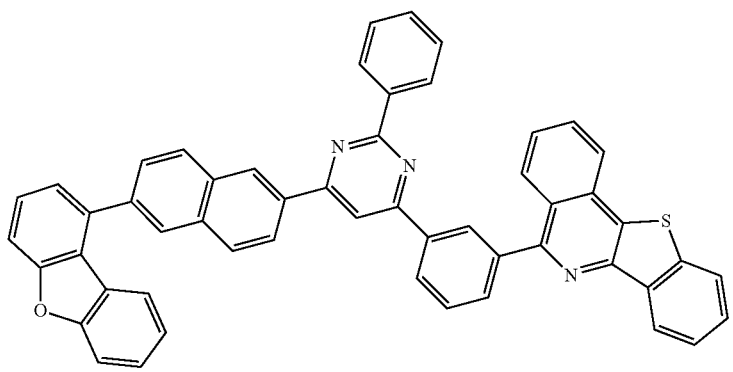

-continued
445
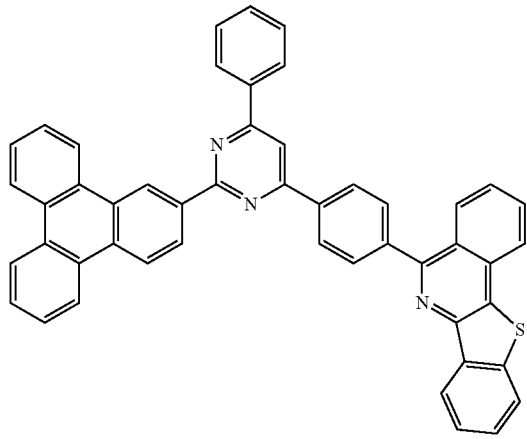
446
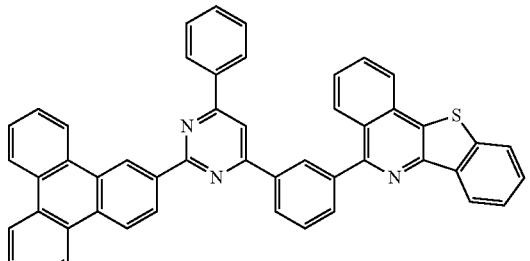
447
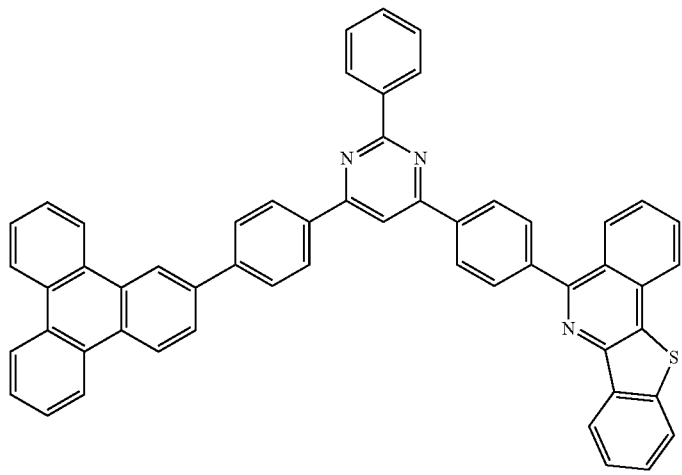
448
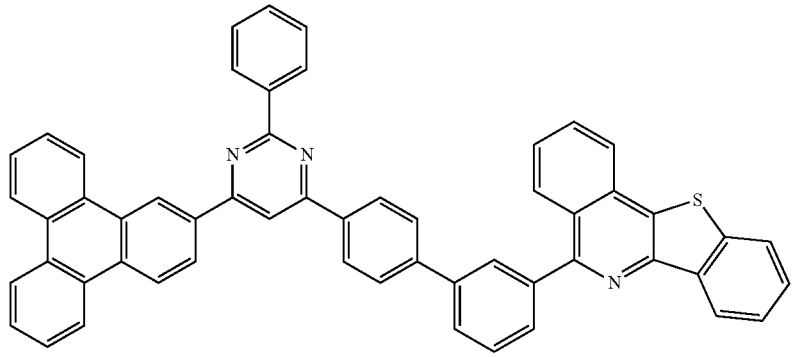
449
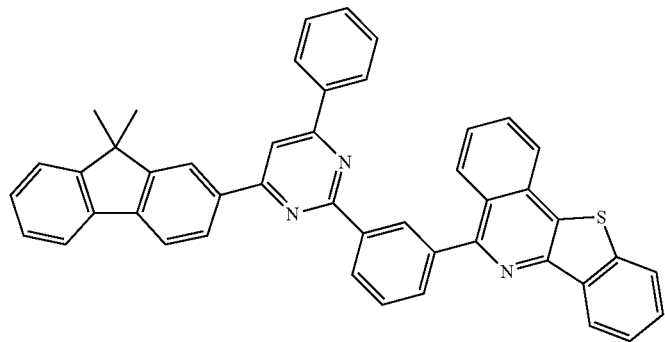

-continued
450
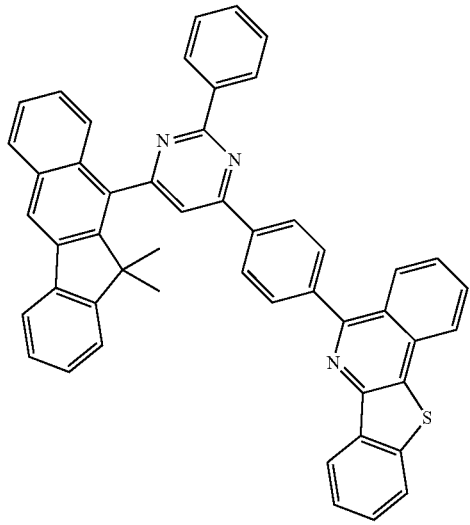
451
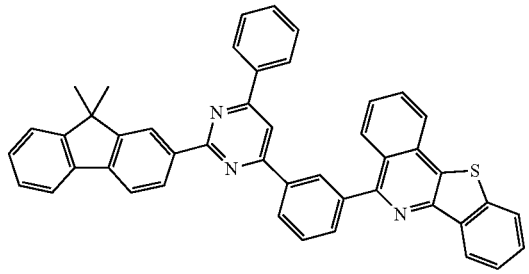
452
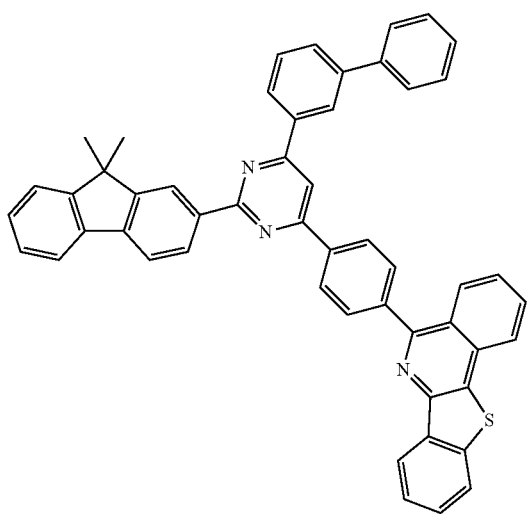
453
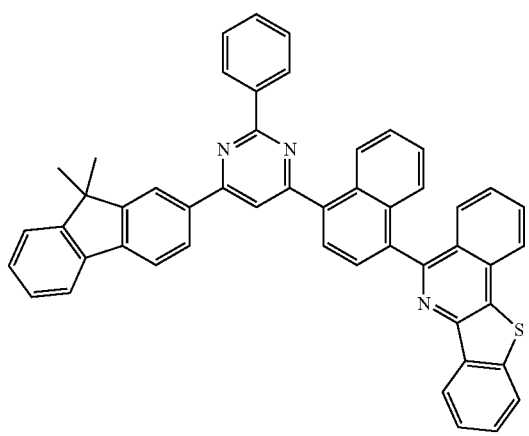
454
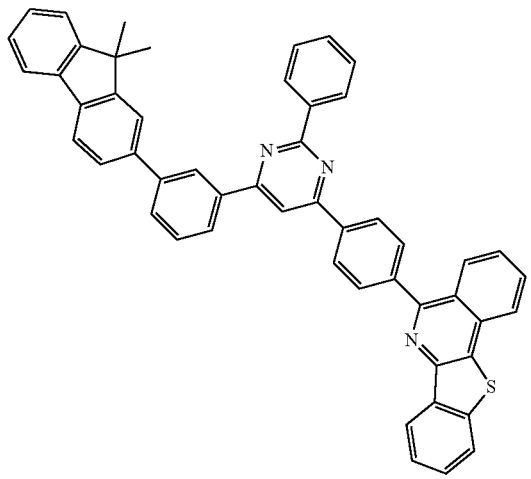
455
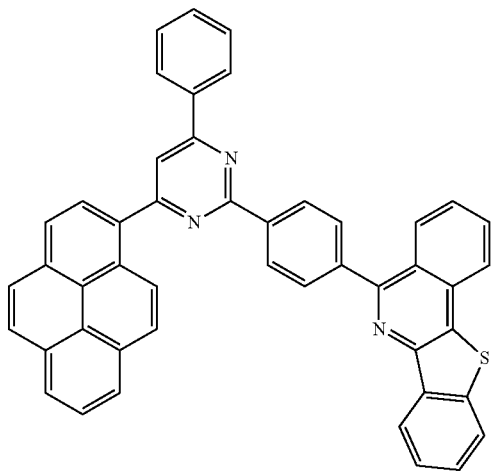

-continued
456
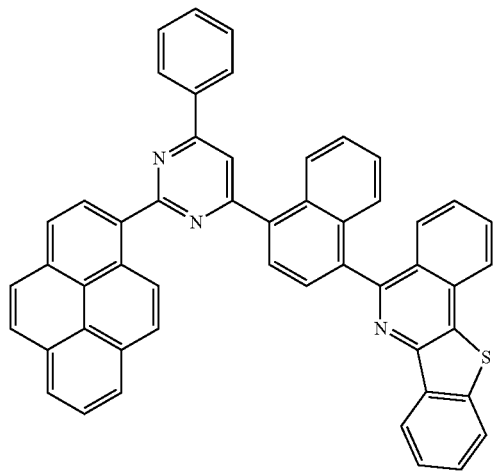
457
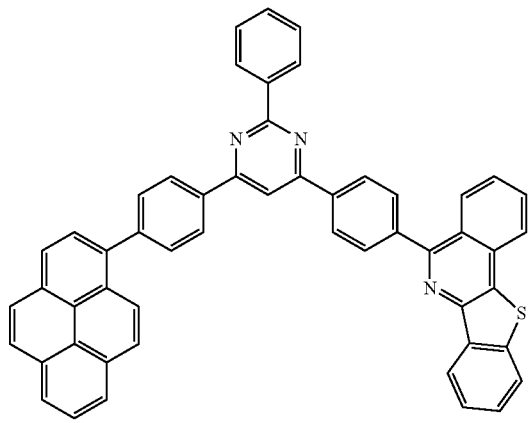
458
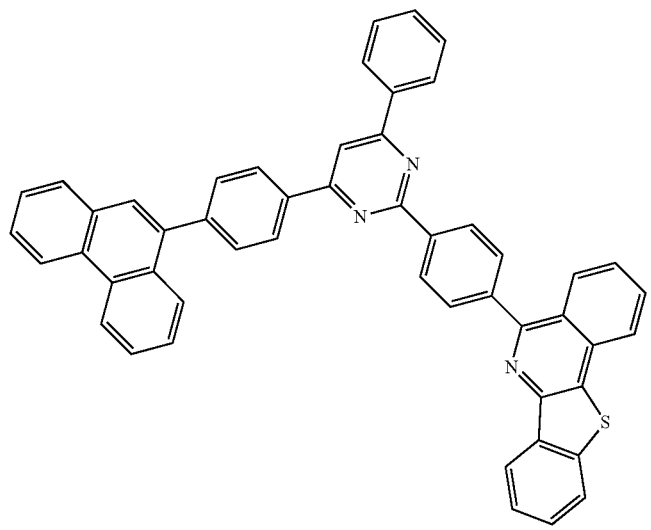
459
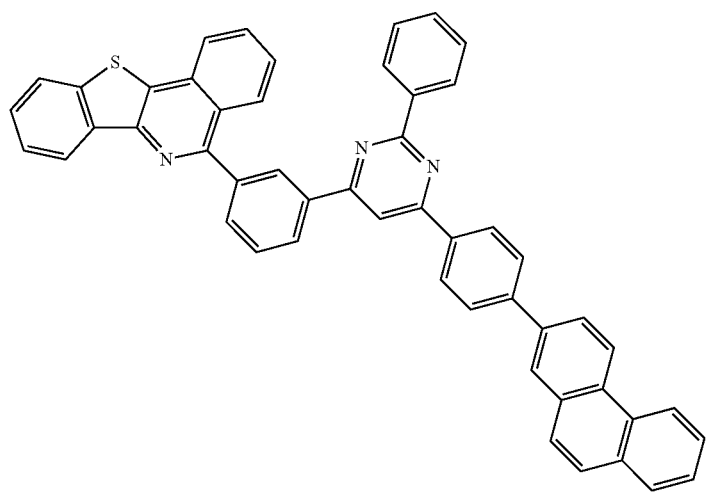

-continued
460
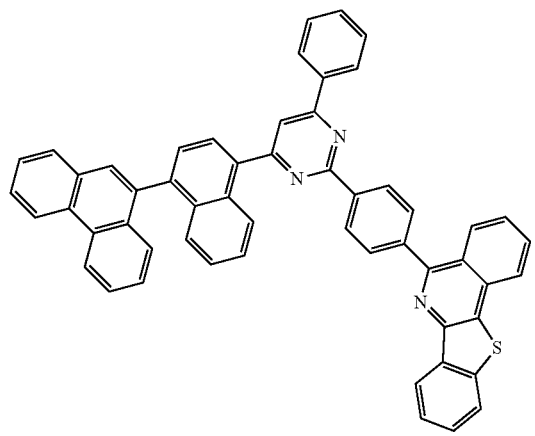
461
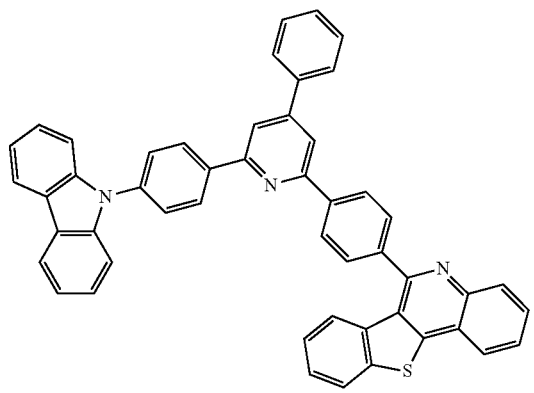
462
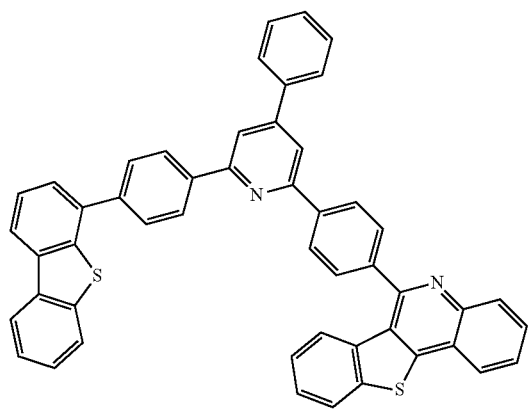
463
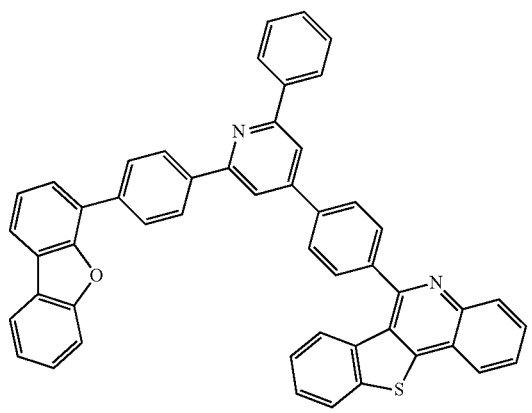
464
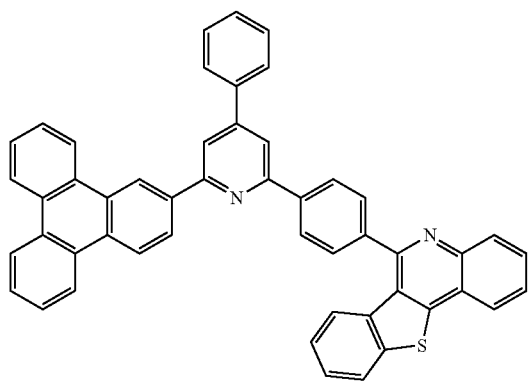
465
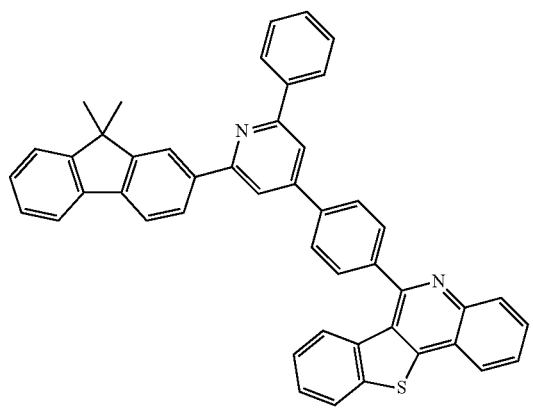

-continued
466
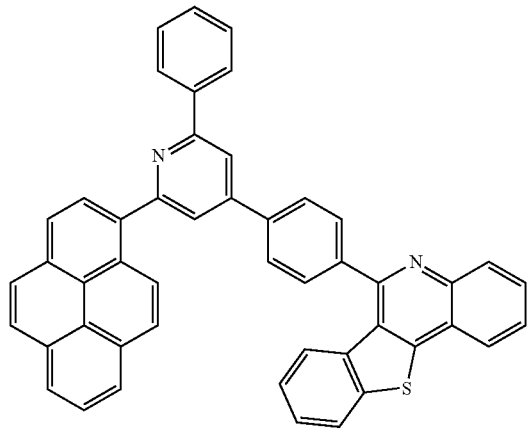
467
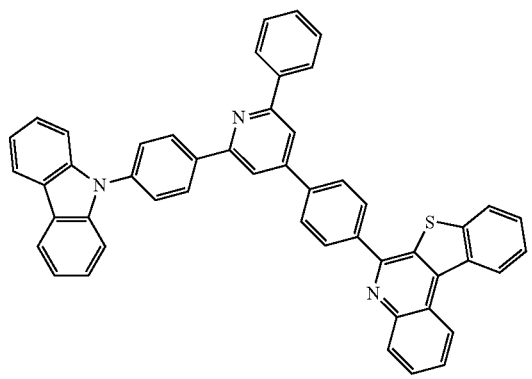
468
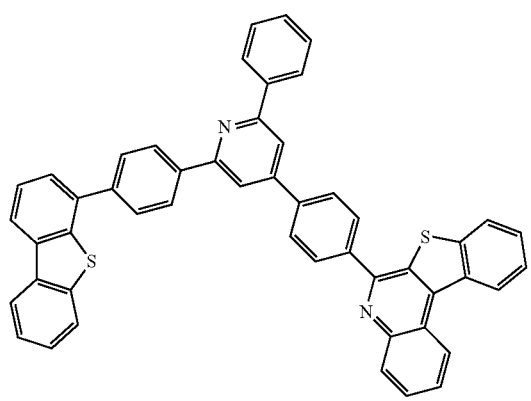
469
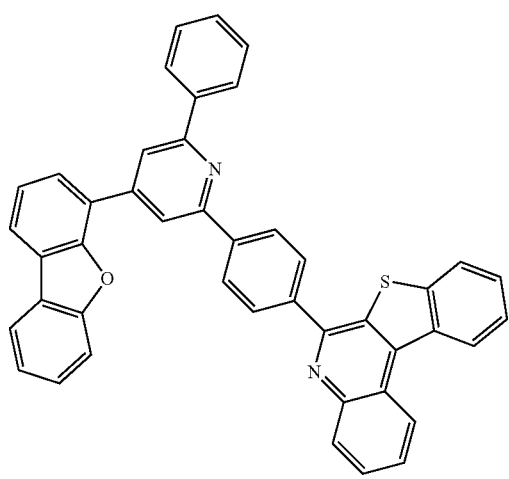
470
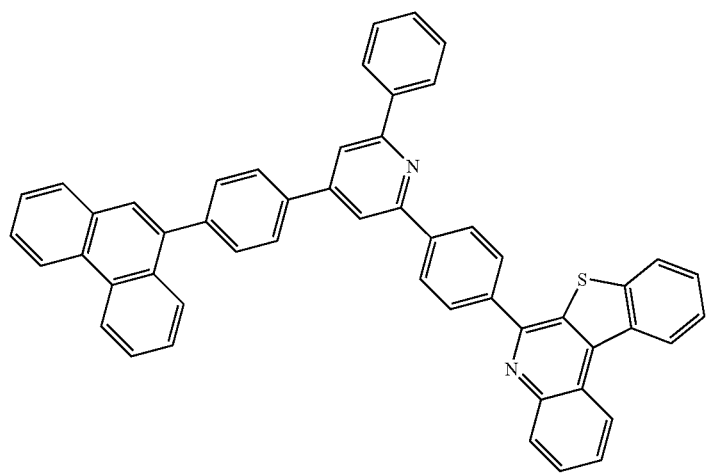

-continued
471
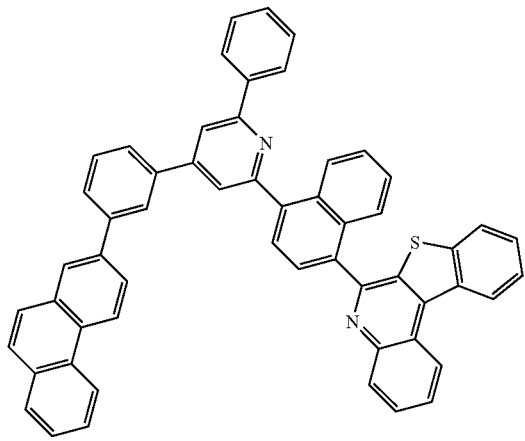
472
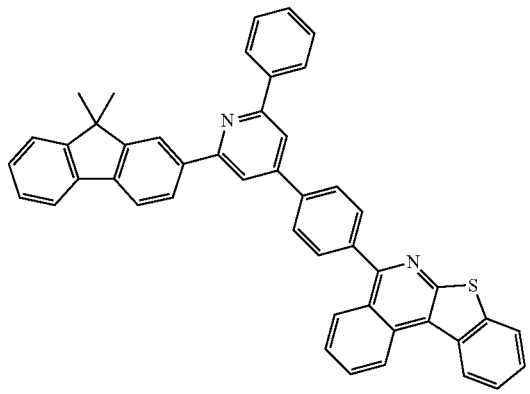
473
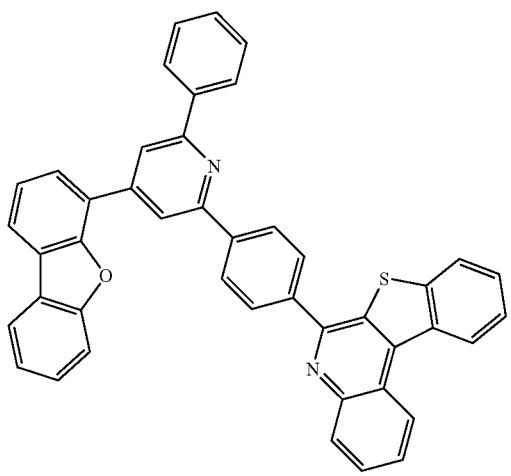
474
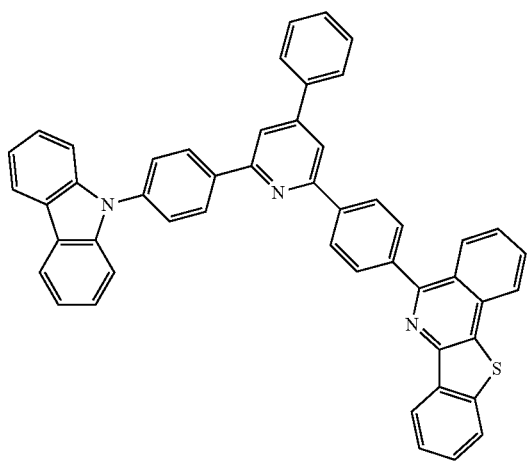
475
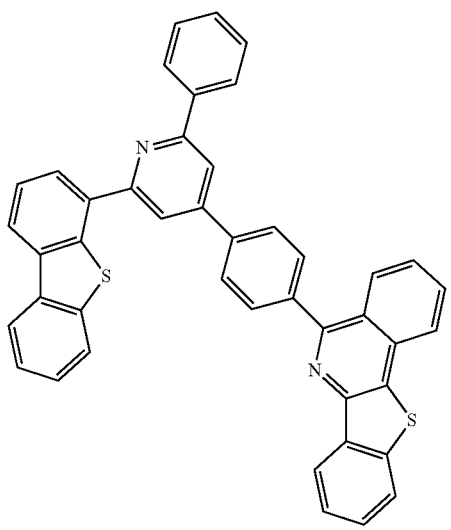

In addition, the compound represented by Chemical Formula 1 may be any one of compounds of the following Group II.
[Group II]
476
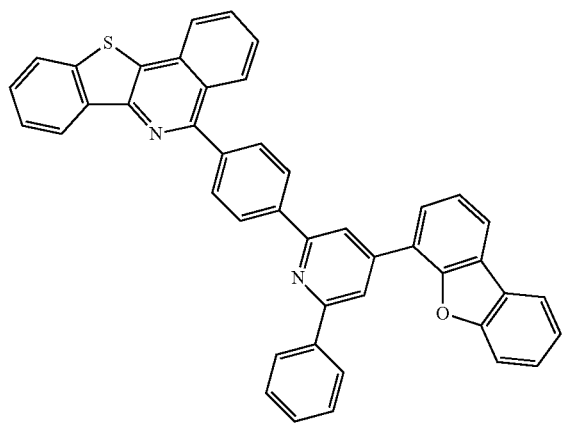
477
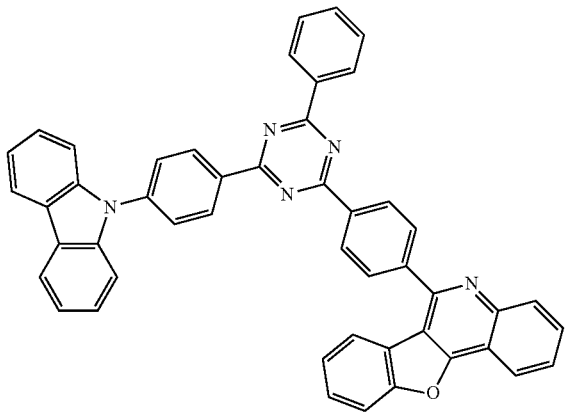
478
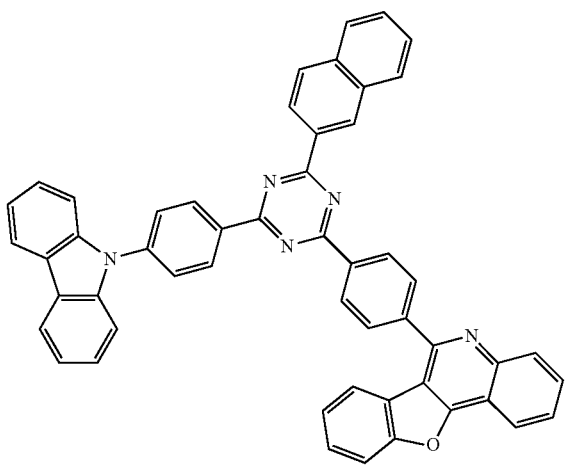
-continued
479
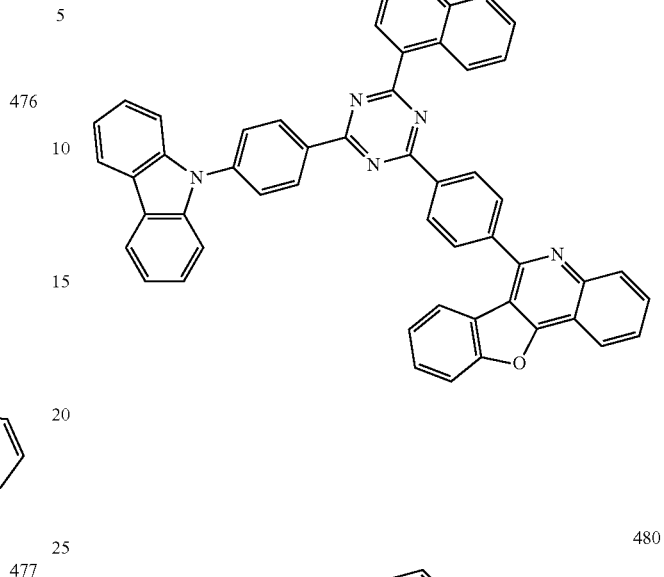
480
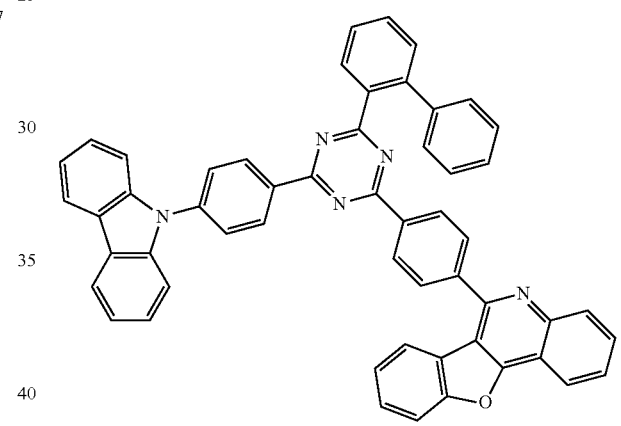
481
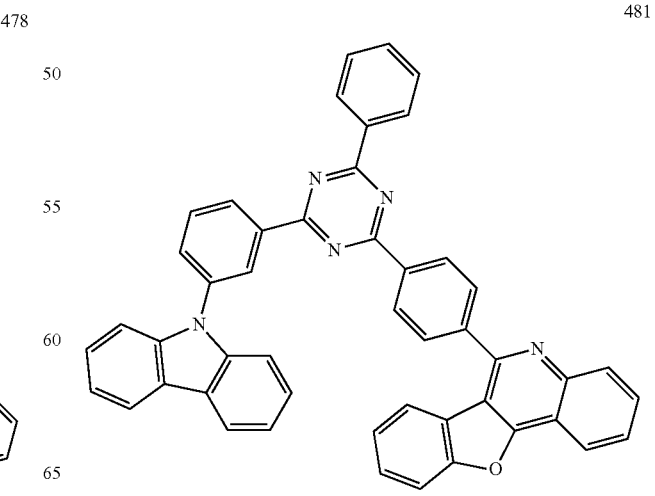

482
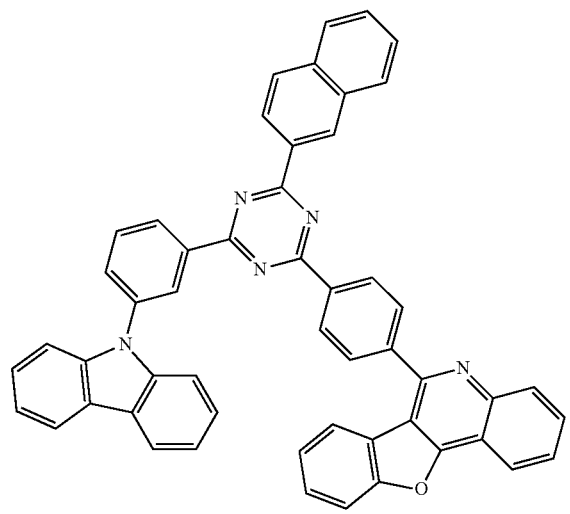
483
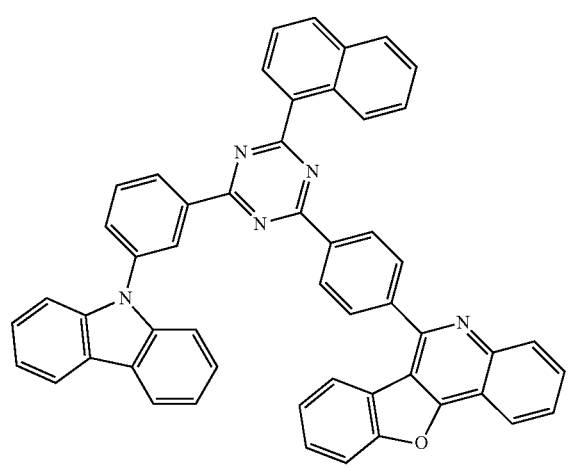
484
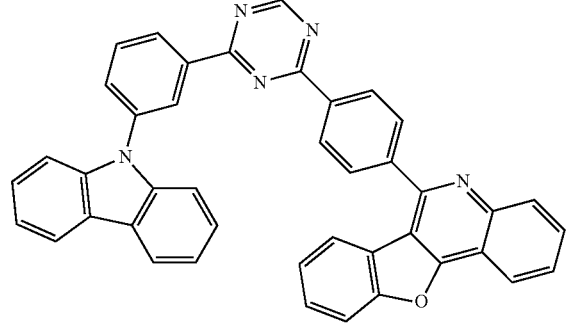
485
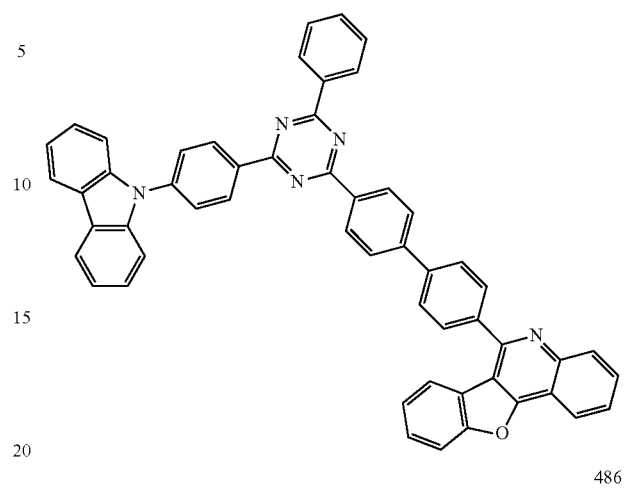
486
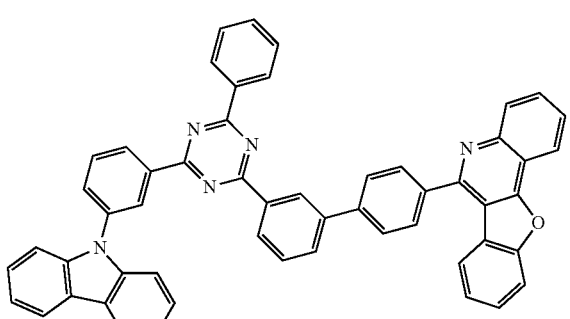
487
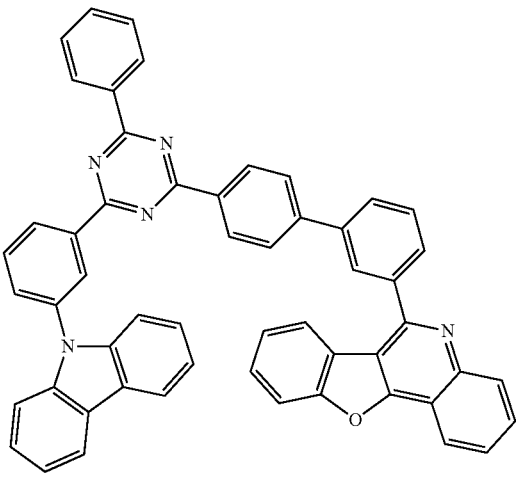
488
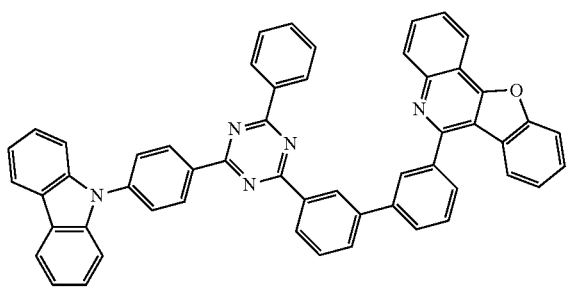

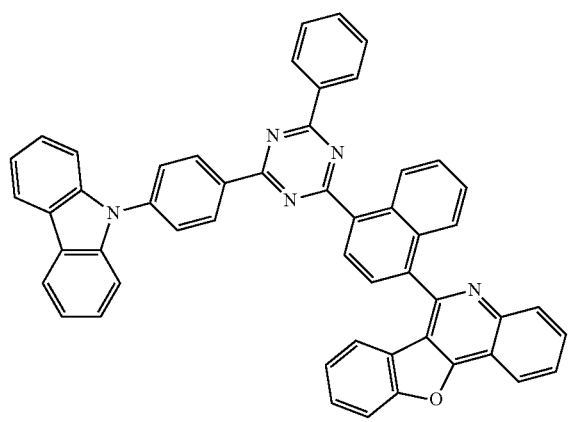
489
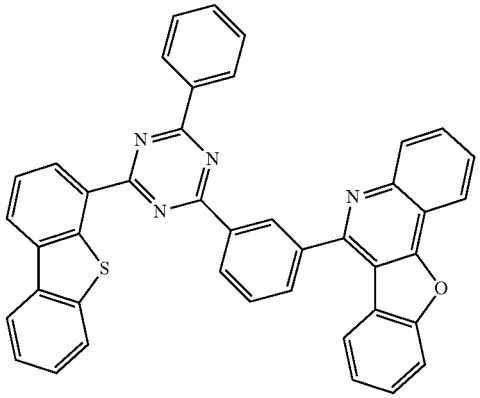
492
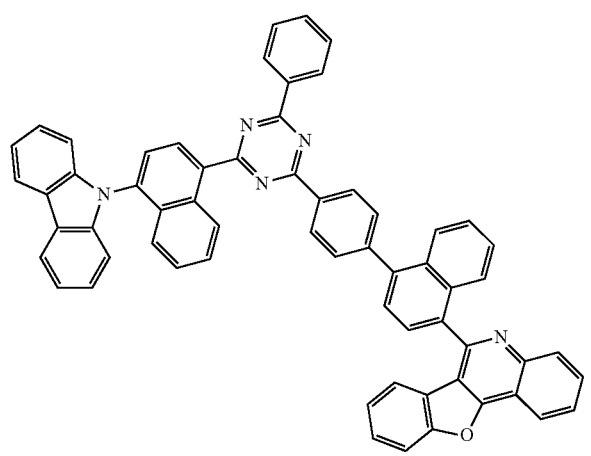
490
493
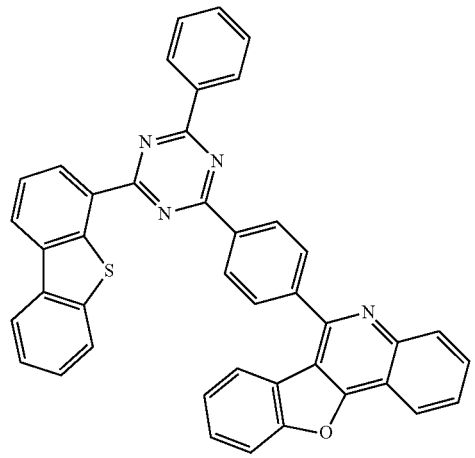
491
494

-continued
495
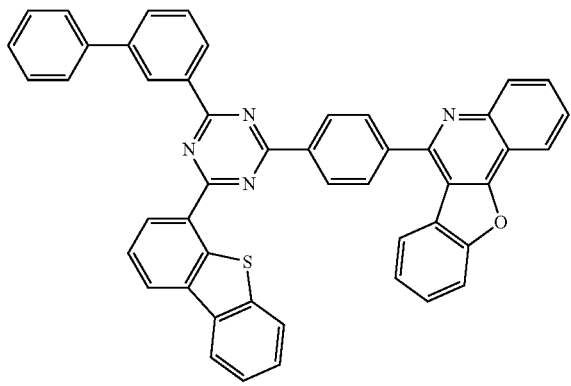
496
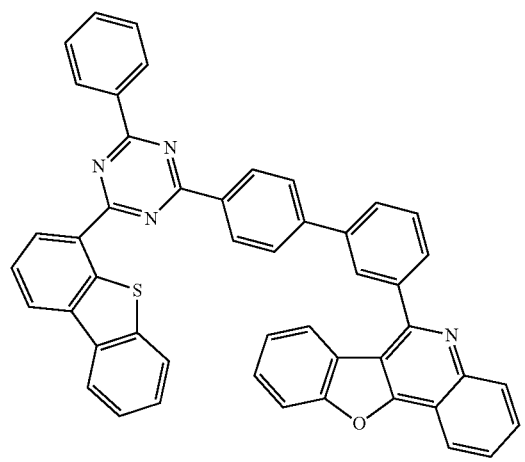
497
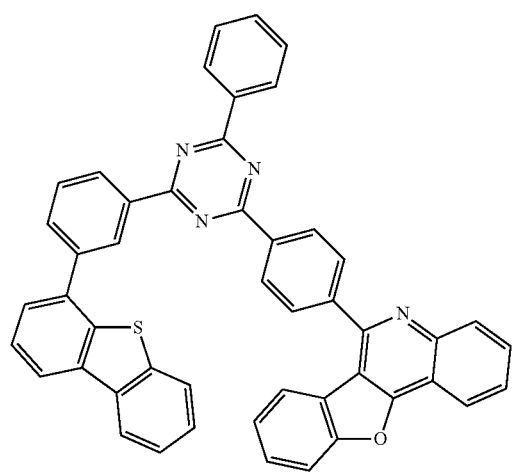
-continued
498
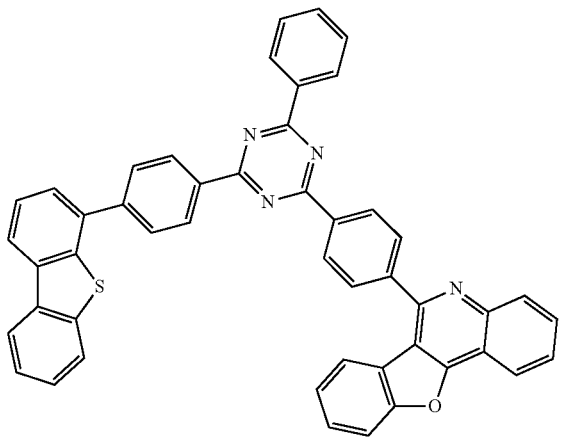
499
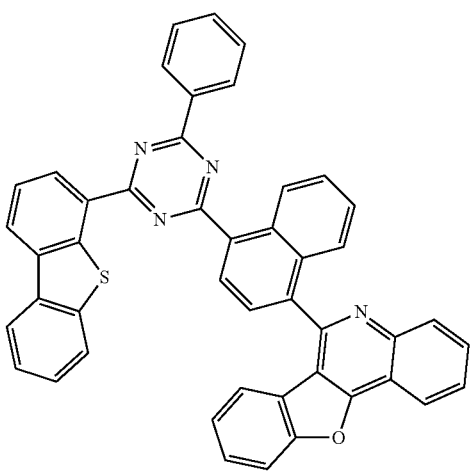
500
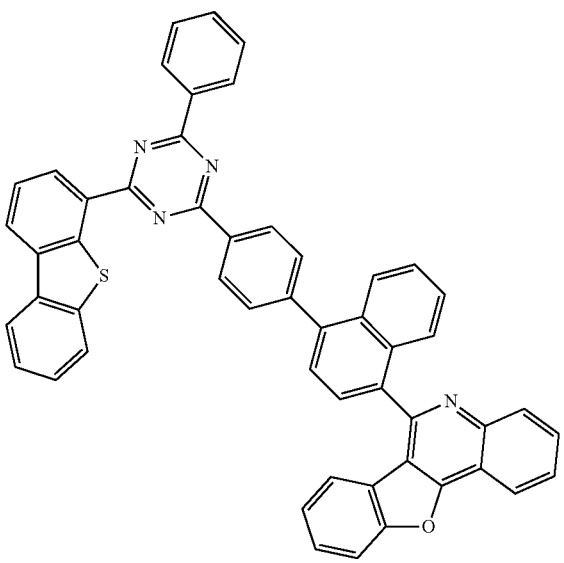

-continued
501
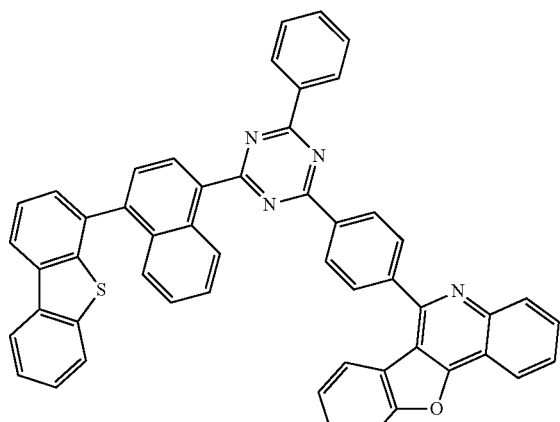
502
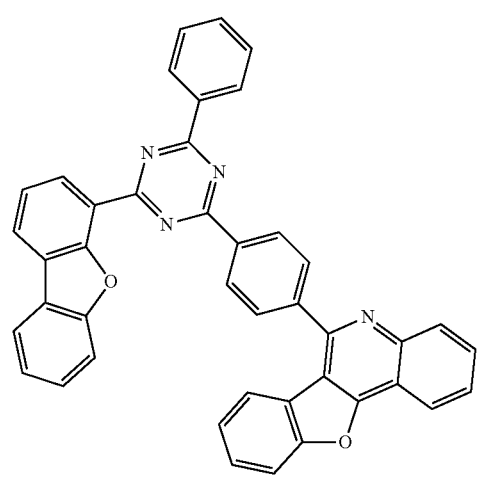
503
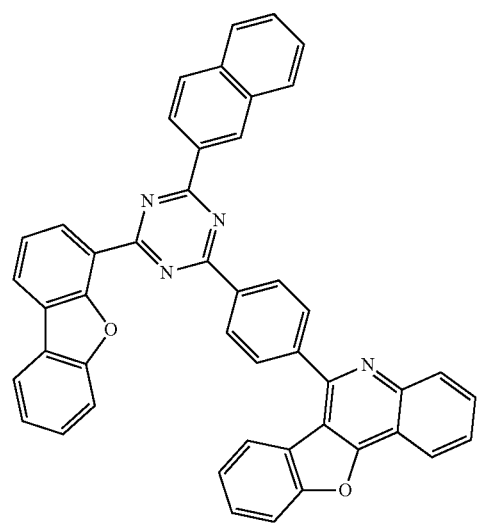
-continued
504
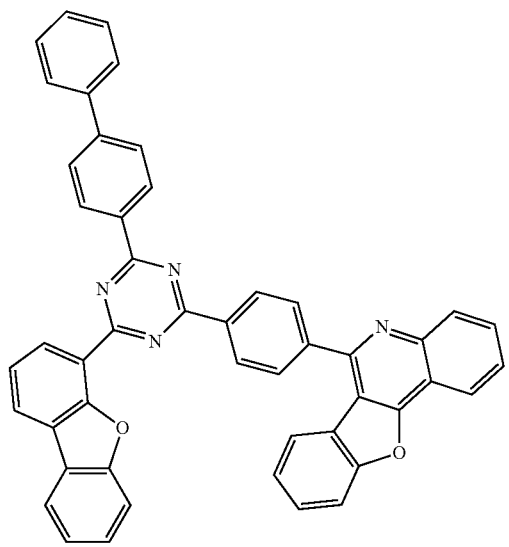
505
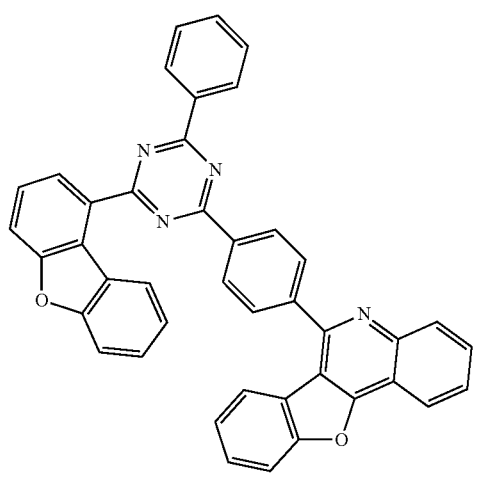
506
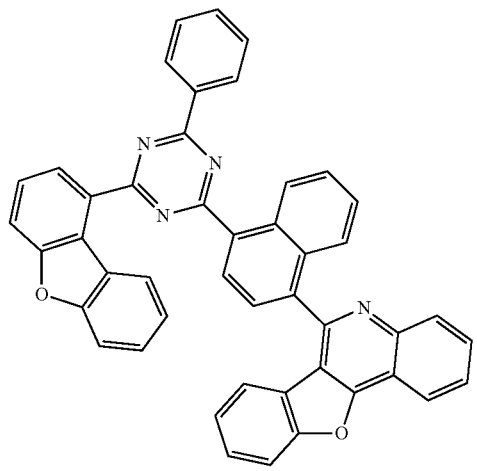

507
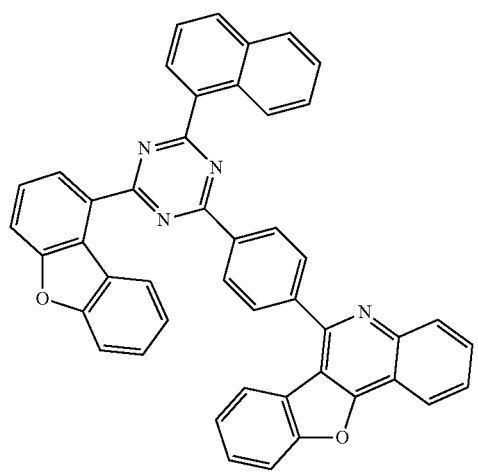
508
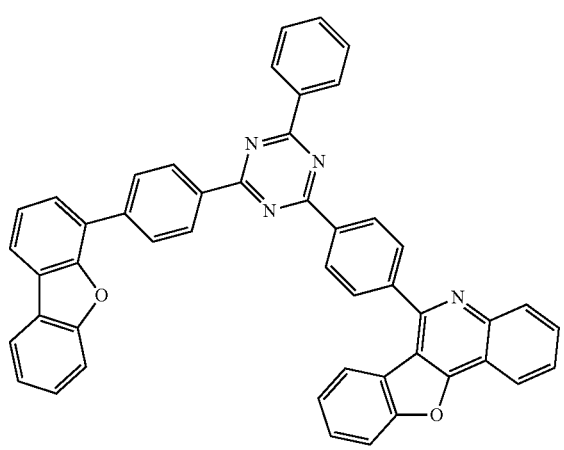
509
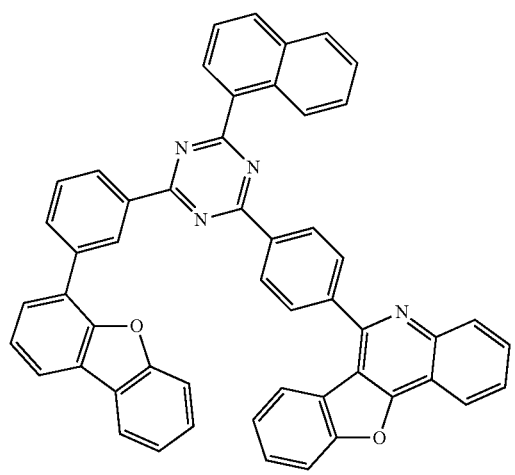
510
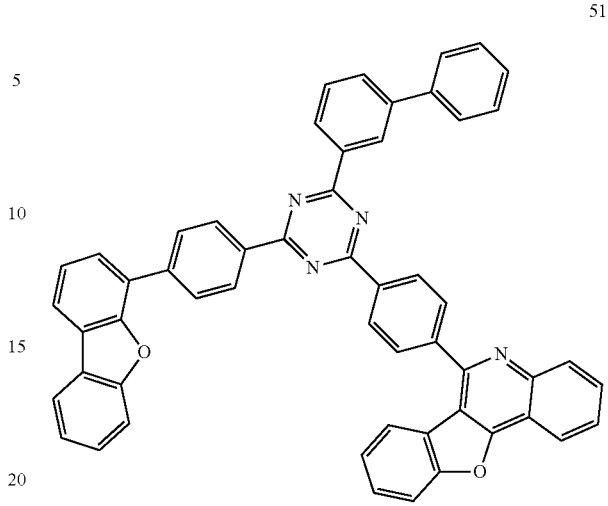
511
512
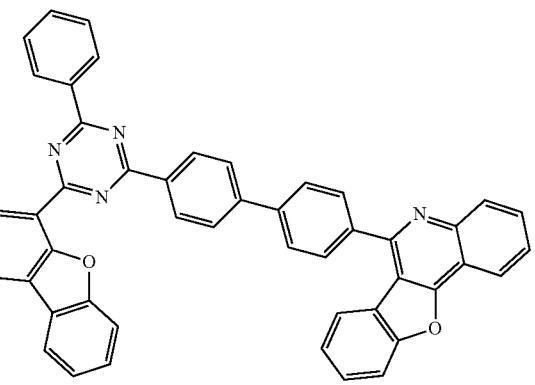

195
-continued
513
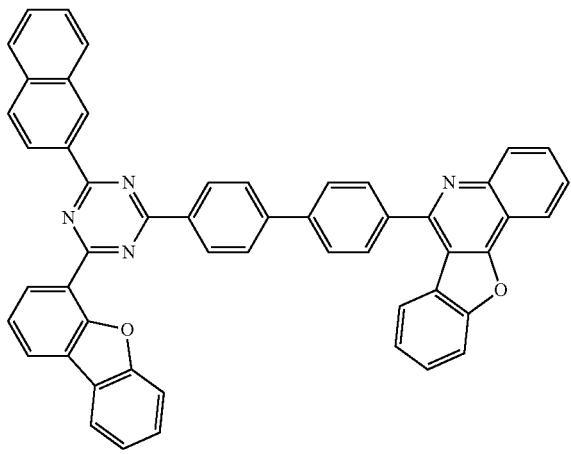
514
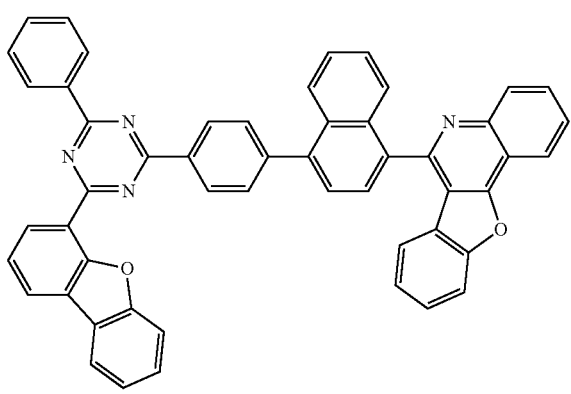 [SMILES: c1ccc(-c2nc(-c3ccc(-c4ccc(-c5nc6ccccc6c6sc7ccccc7c56)c5ccccc45)cc3)nc(-c3cccc4c3oc3ccccc34)n2)cc1]
515
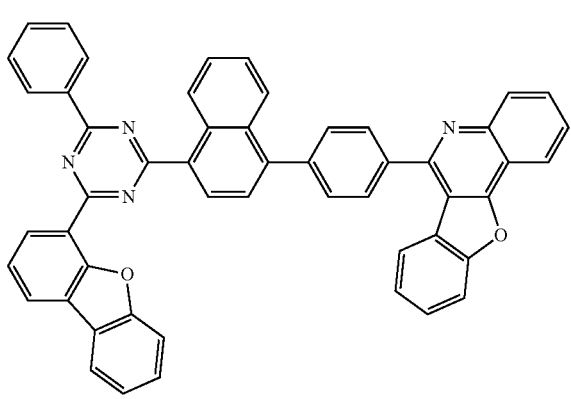
516
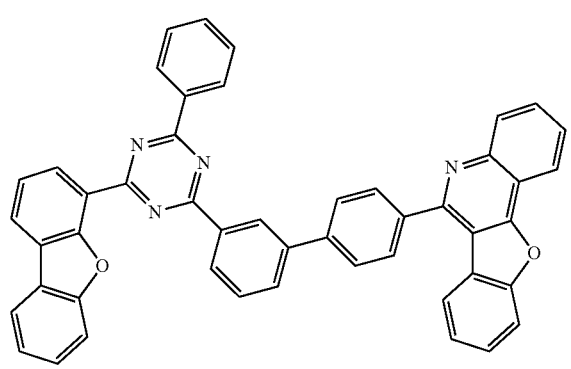
196
-continued
517
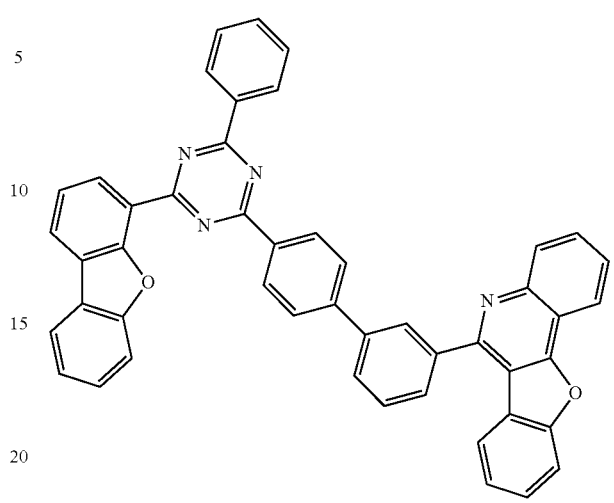
518
519

520
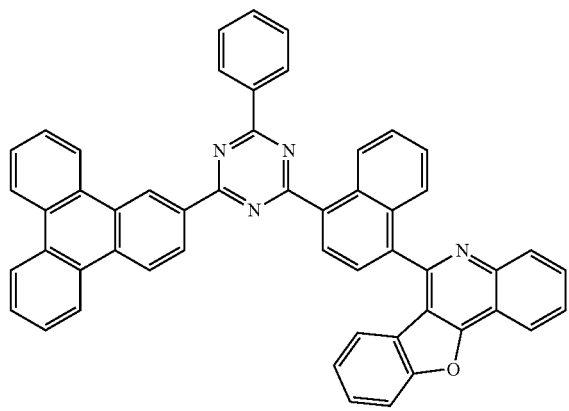 [SMILES: c1ccc(-c2nc(-c3ccc4c5ccccc5c5ccccc5c4c3)cc(-c3ccc(-c4nc5ccccc5c5sc6ccccc6c45)c4ccccc34)n2)cc1]
521
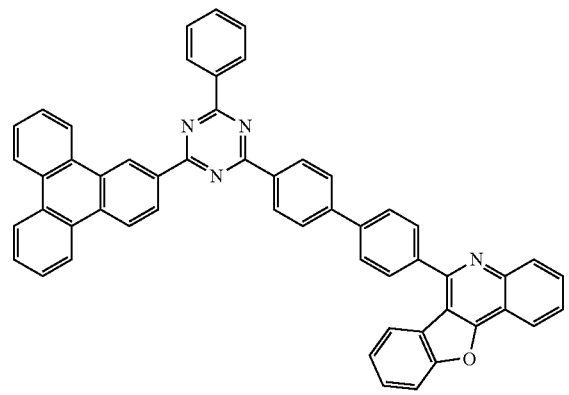
522
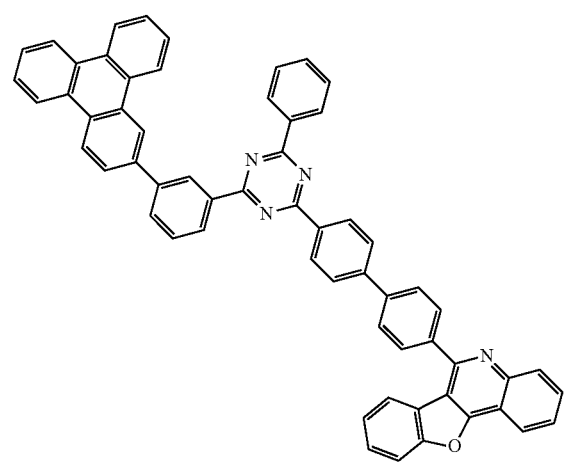
523
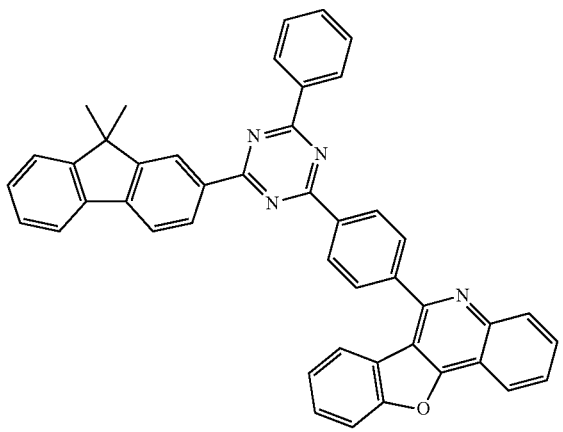
524
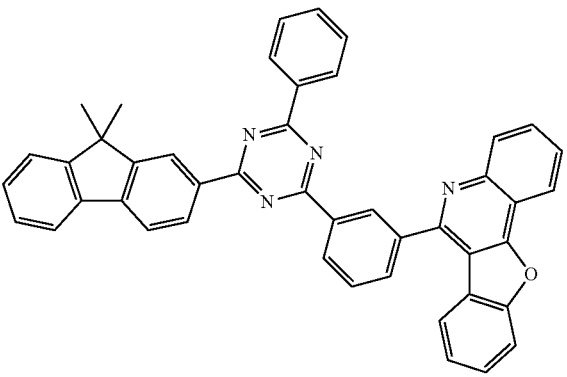
525
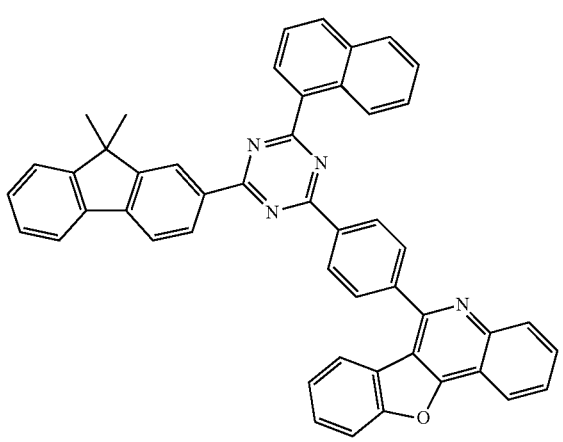

-continued
526
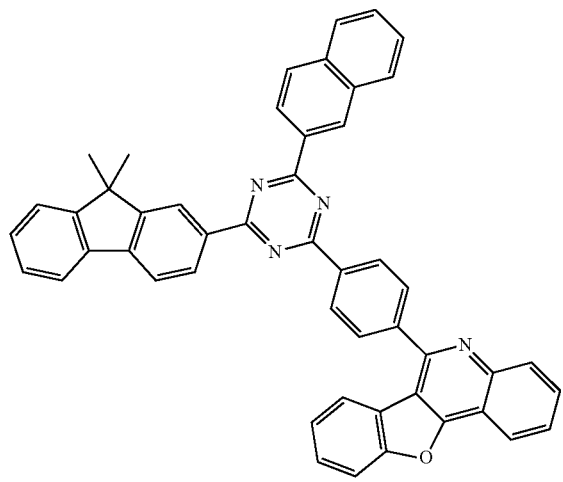
527
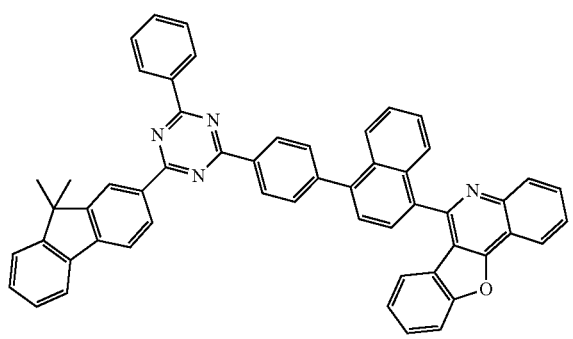
528
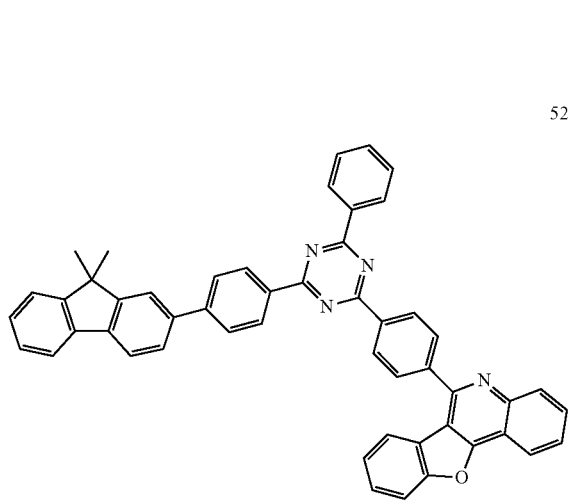
-continued
529
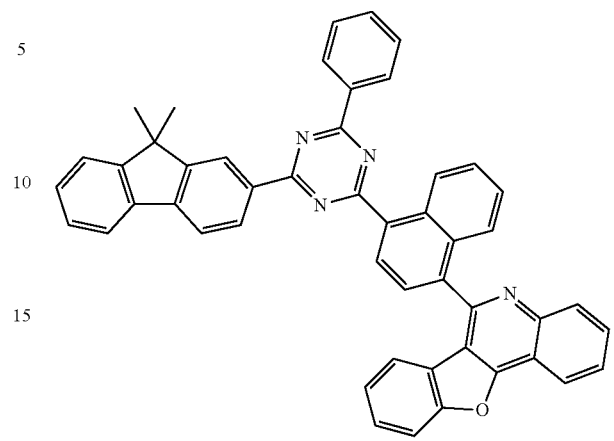
530
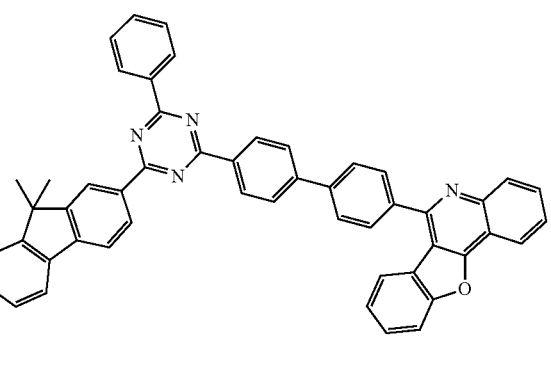
531
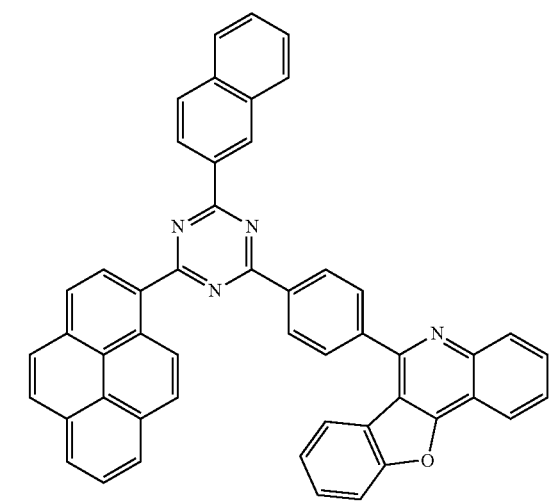

201
-continued
532
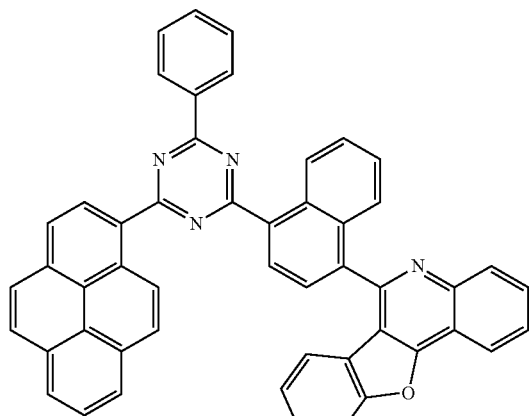
533
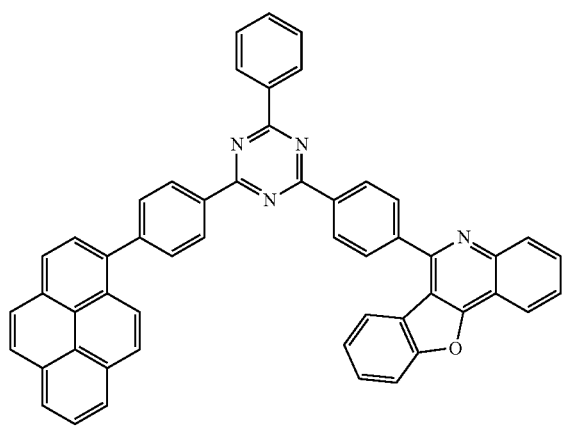
534
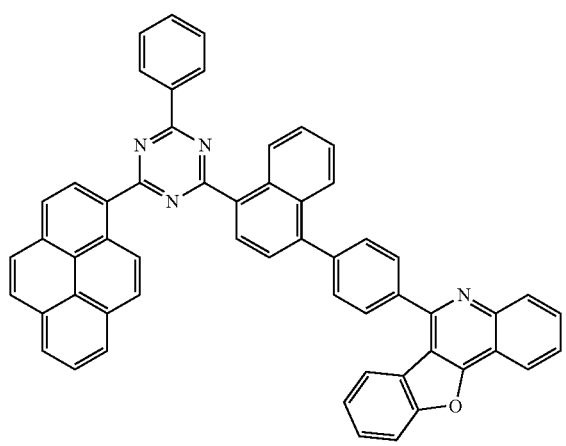
202
-continued
535
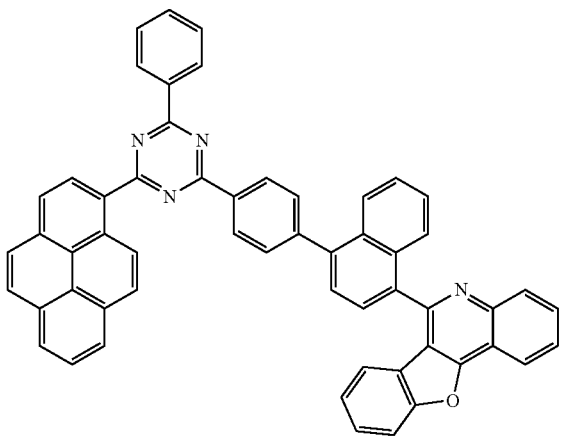
536
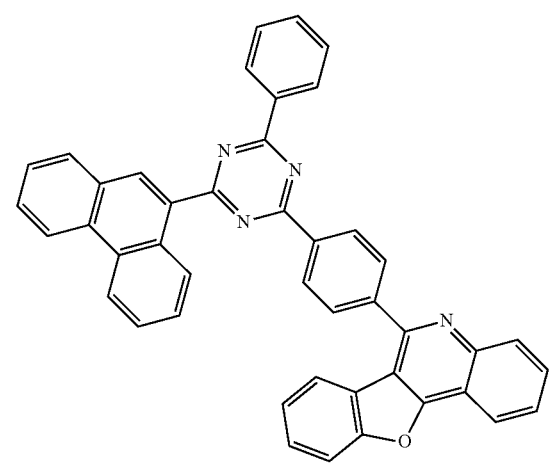
537
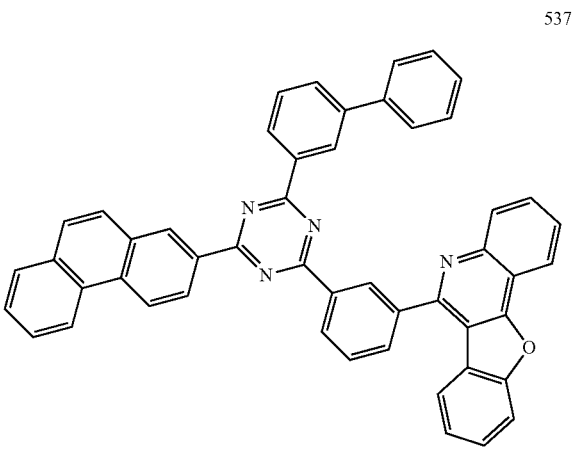

538
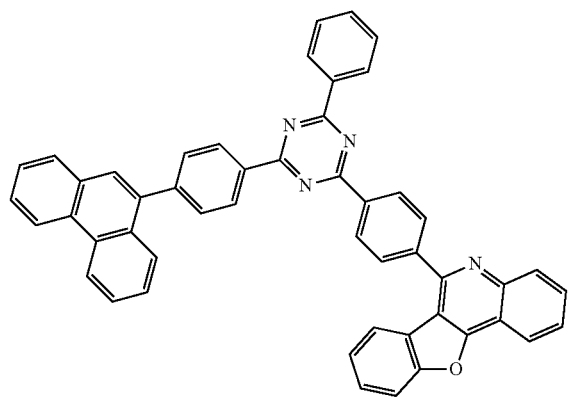
539
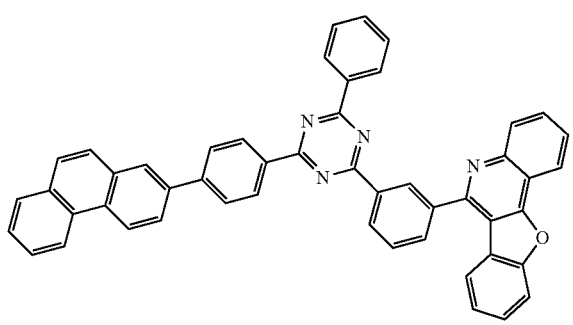
540
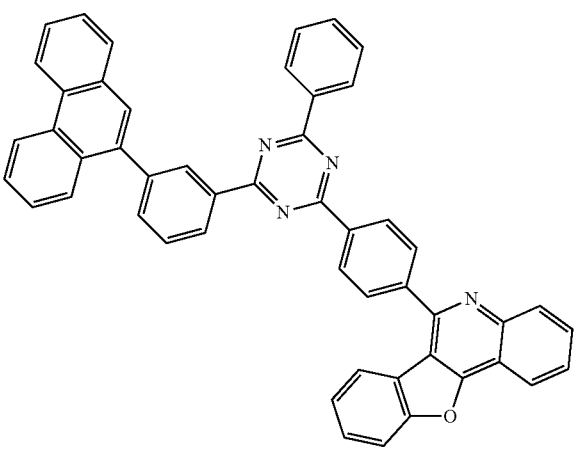
541
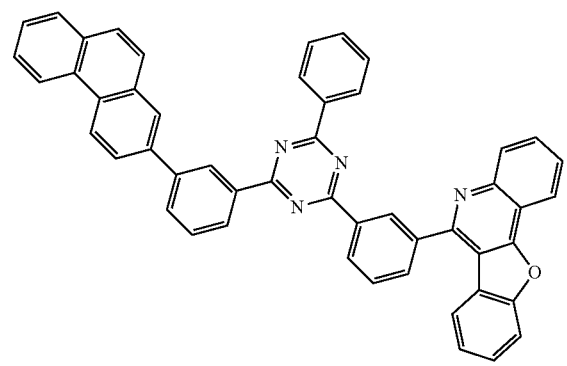
542
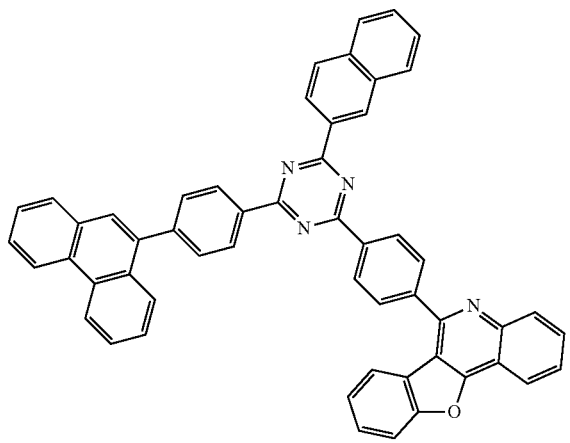
543
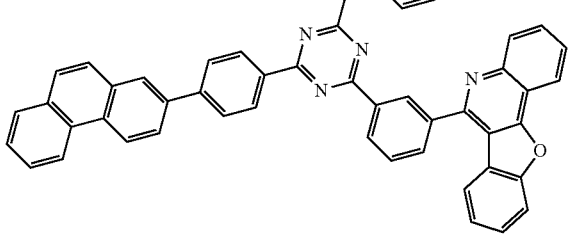
544
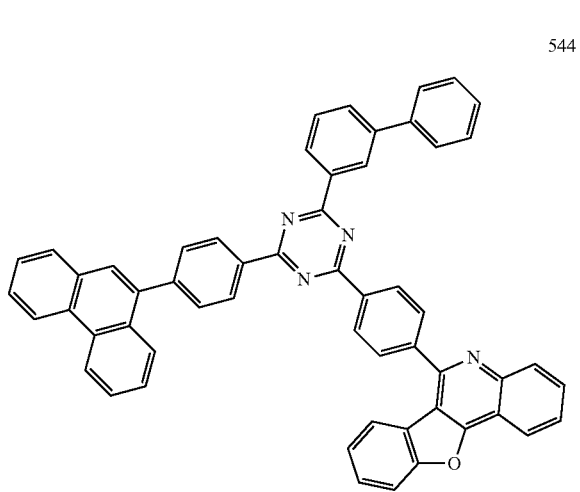

545
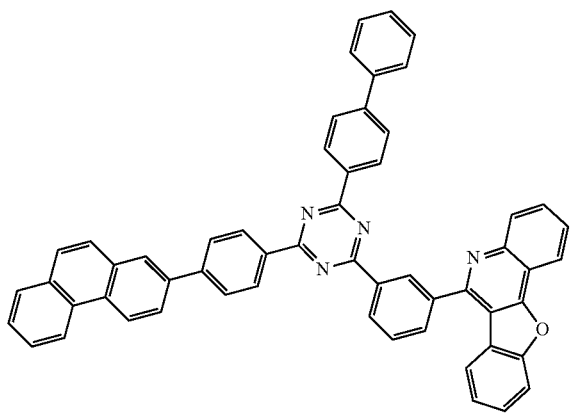
546
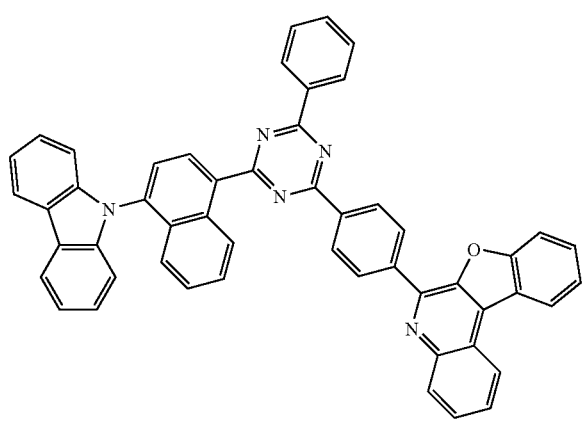
547
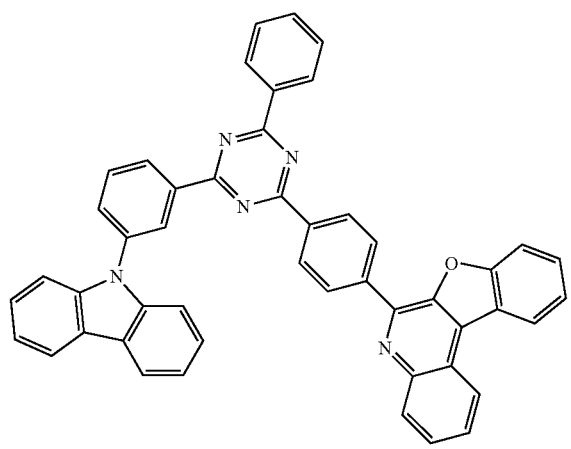
548
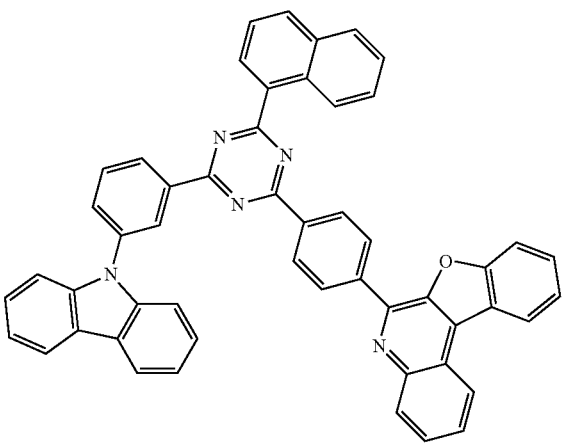
549
550
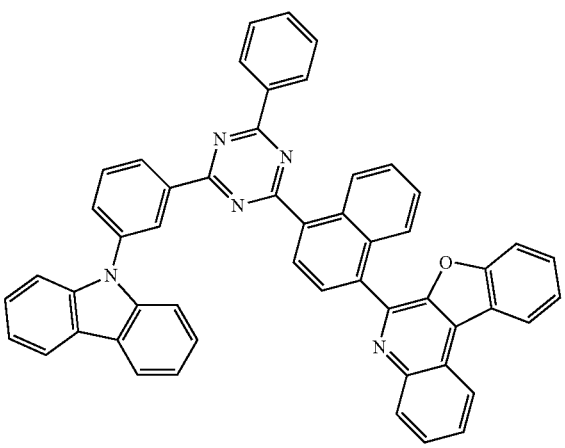

207
-continued
551
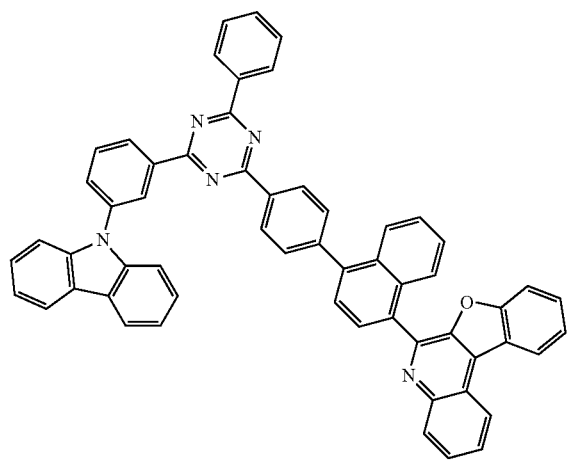
552
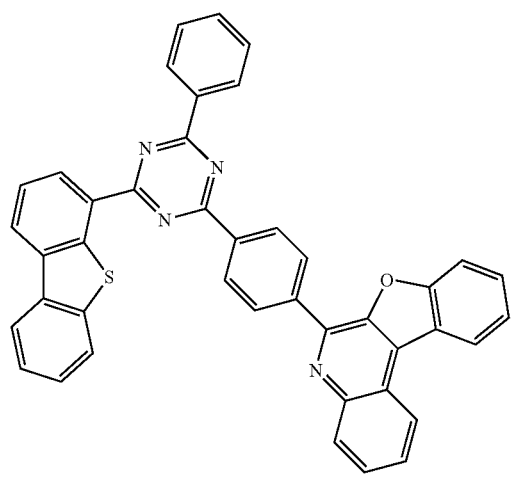
553
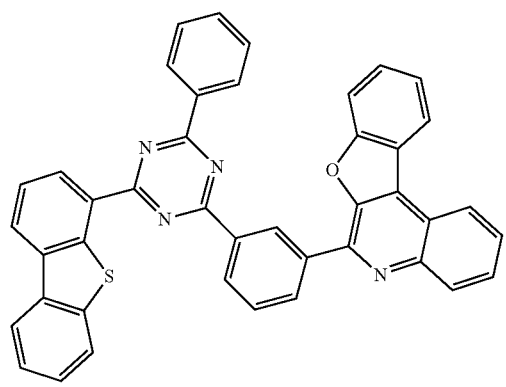
208
-continued
554
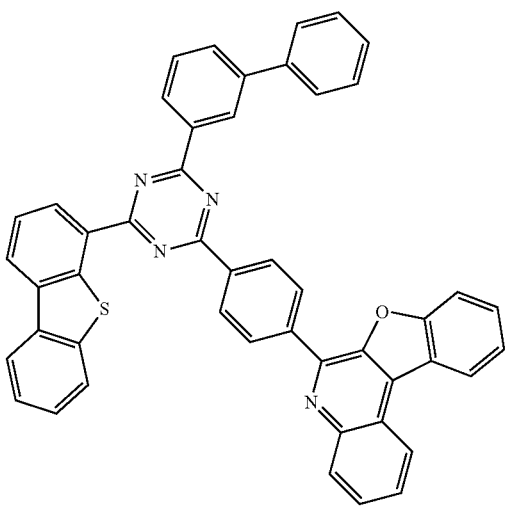
555
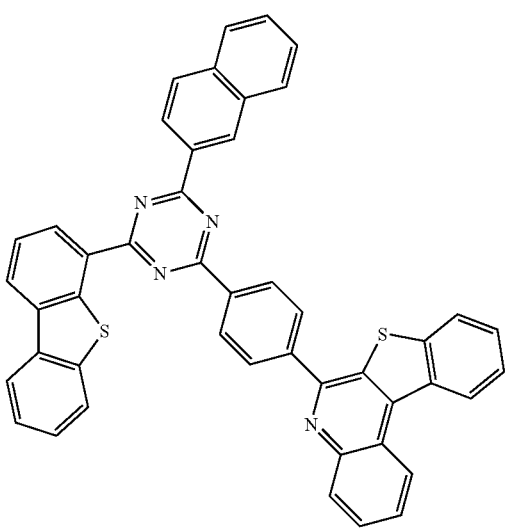
556
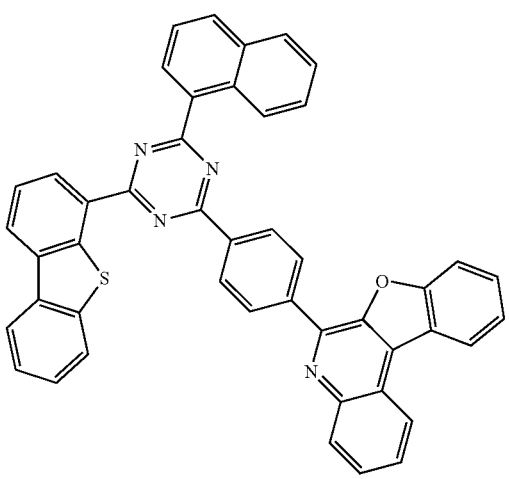

557
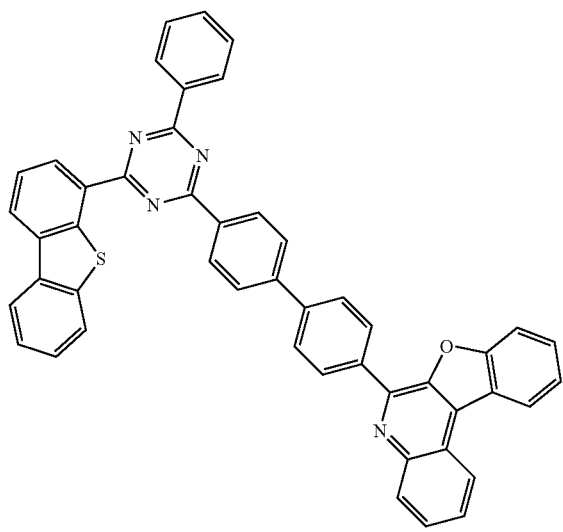
558
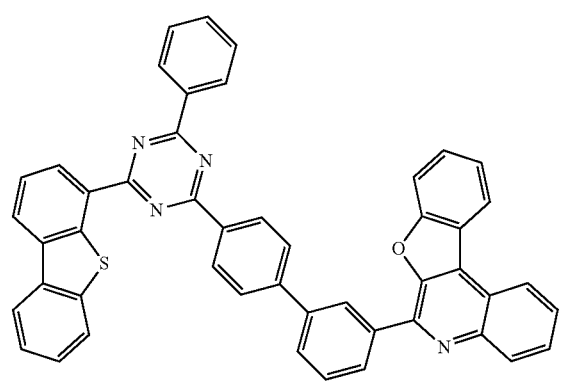
559
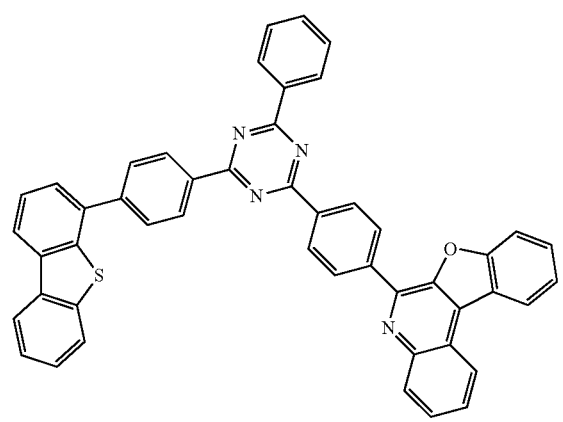
560
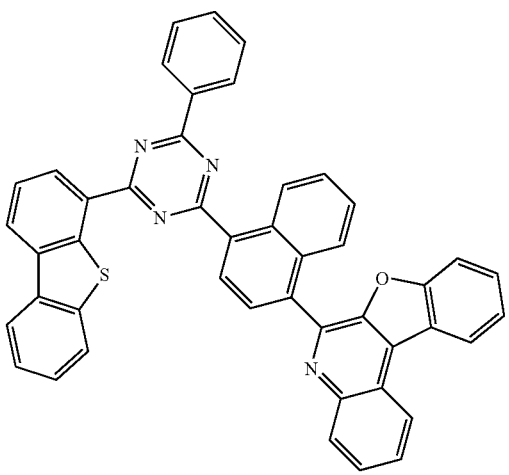
561
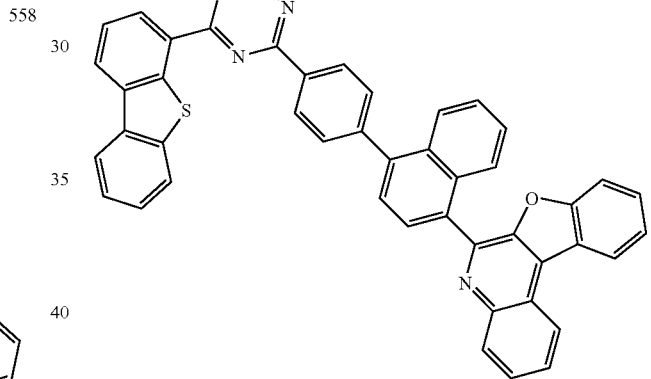
562
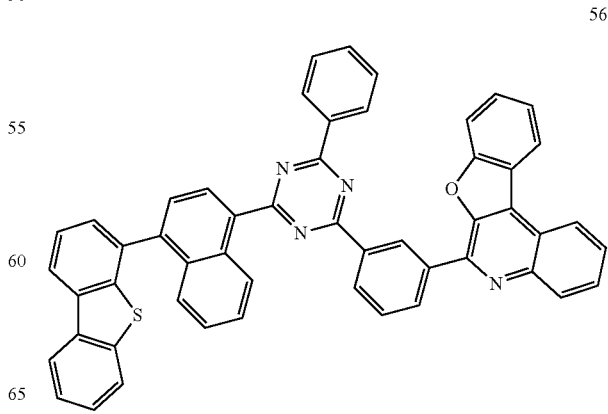

563
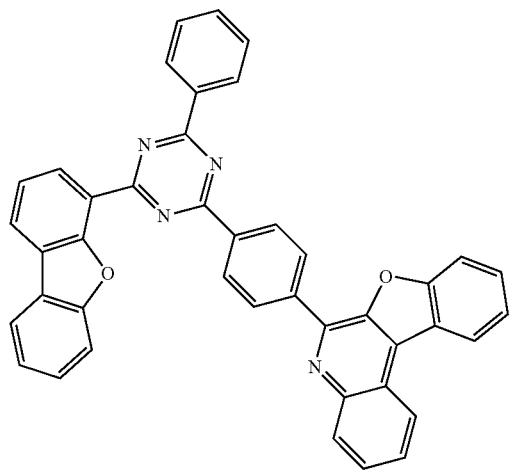
564
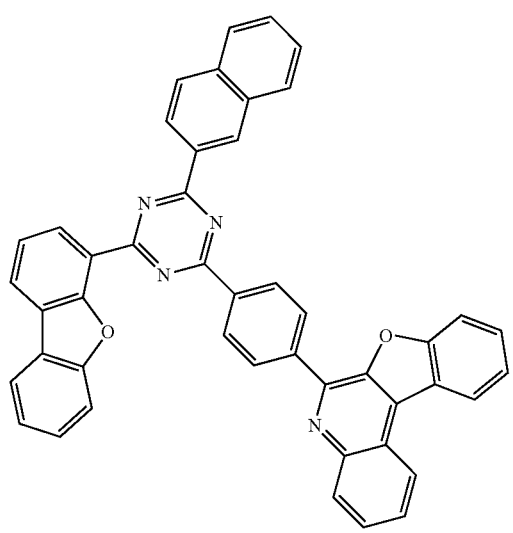
565
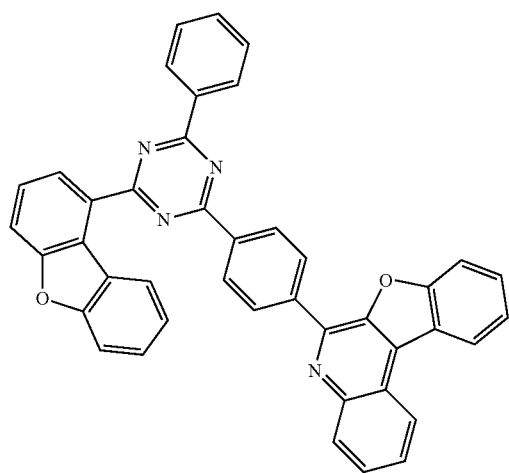
566
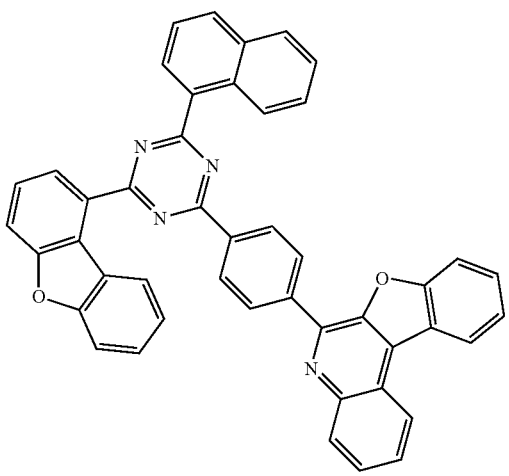
567
568
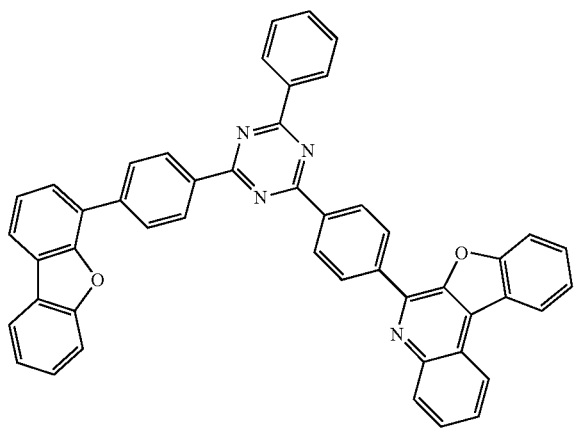

569
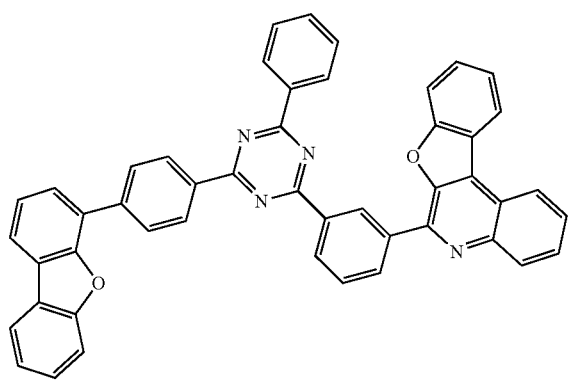
570
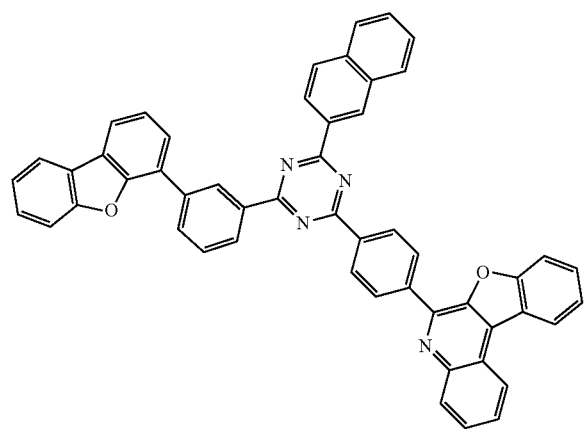
571
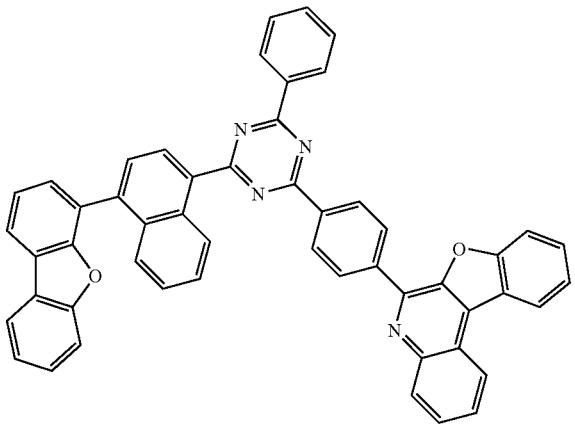
572
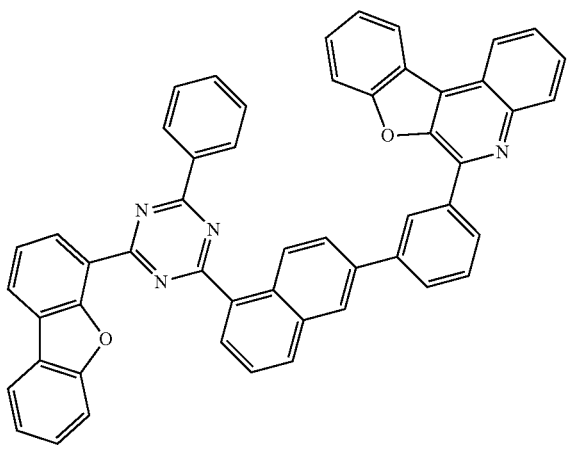
573
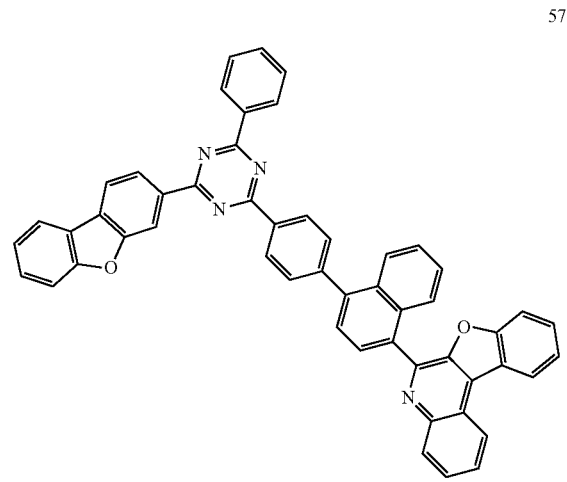
574
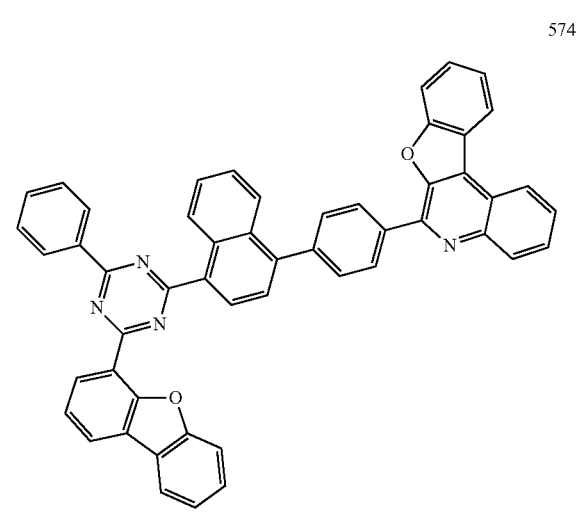

575
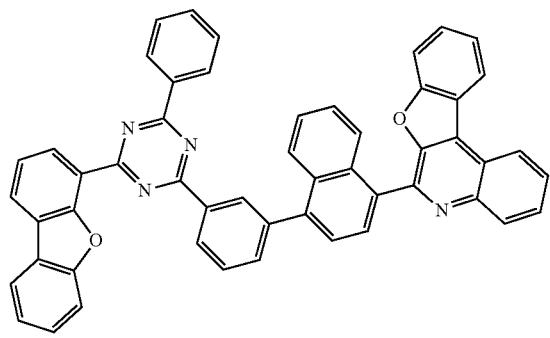
576
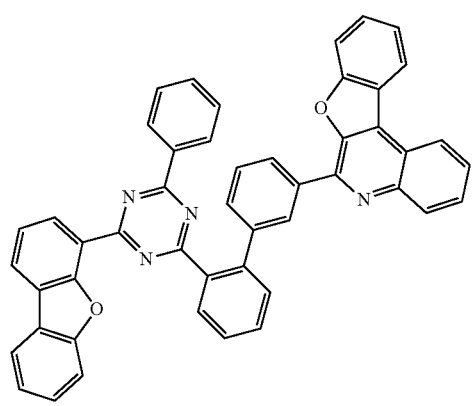
577
578
579
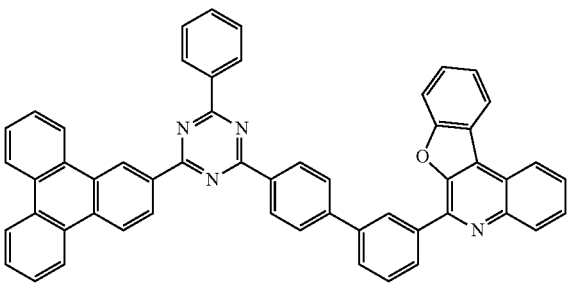
580
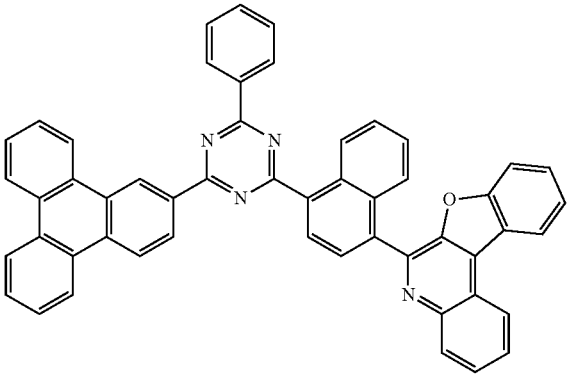
581
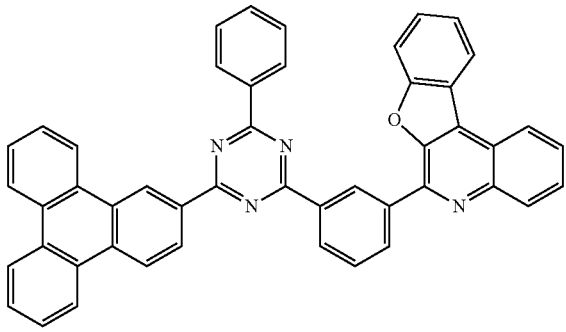
582
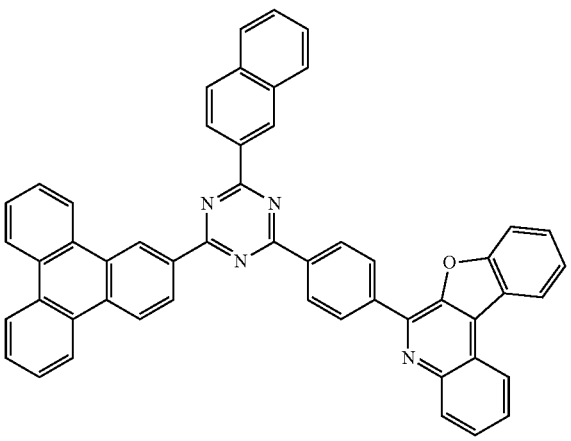 [SMILES: c1ccc2cc(-c3nc(-c4ccc(-c5nc6ccccc6c6c5sc5ccccc56)cc4)nc(-c4ccc5c6ccccc6c6ccccc6c5c4)n3)ccc2c1]

217
-continued
583
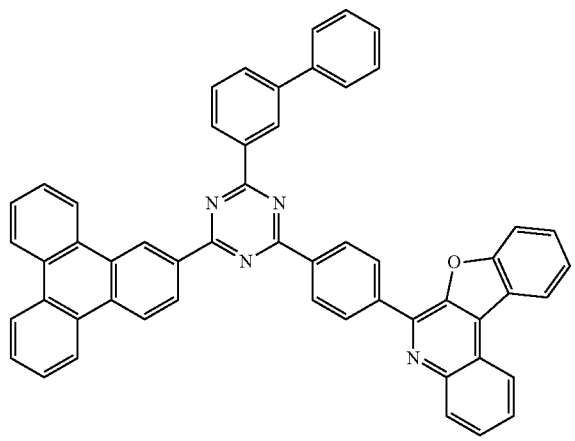
584
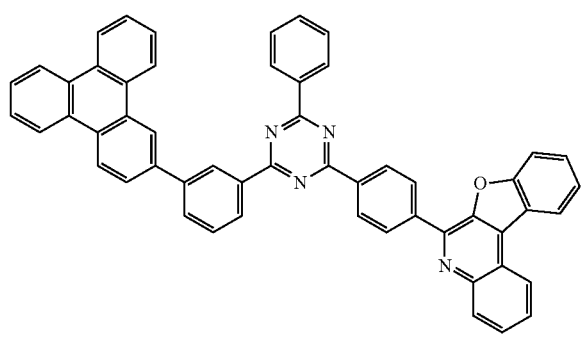
585
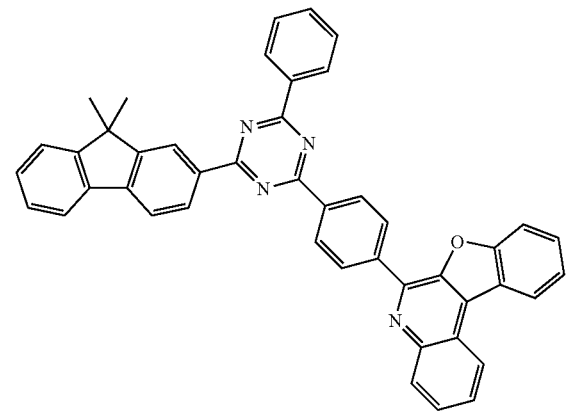
586
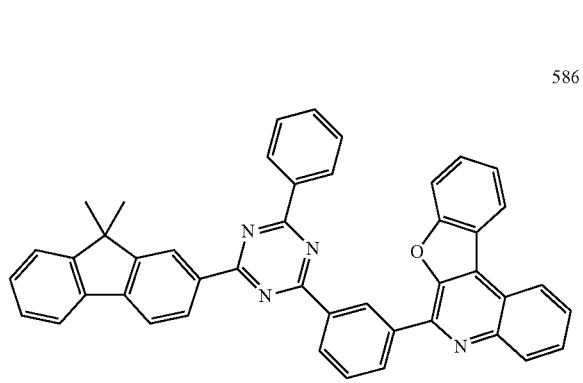
218
-continued
587
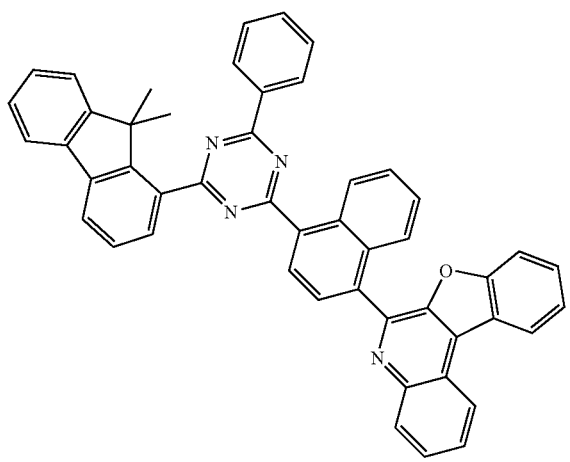
588
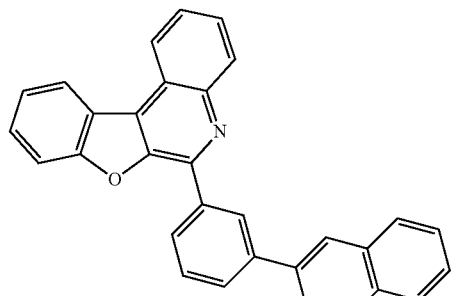
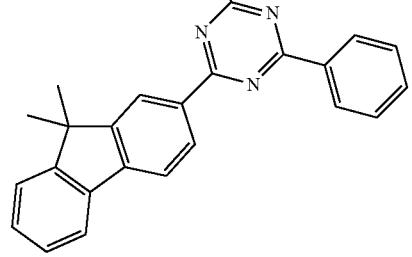
589
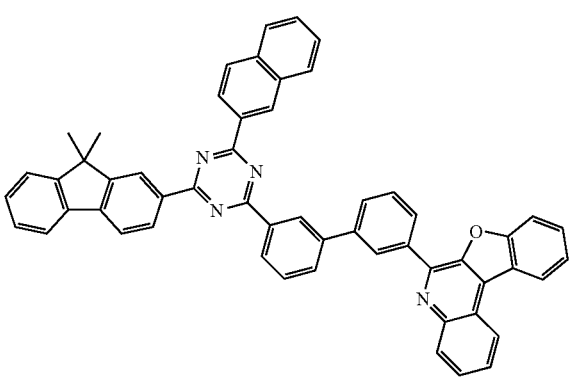

219
-continued
590
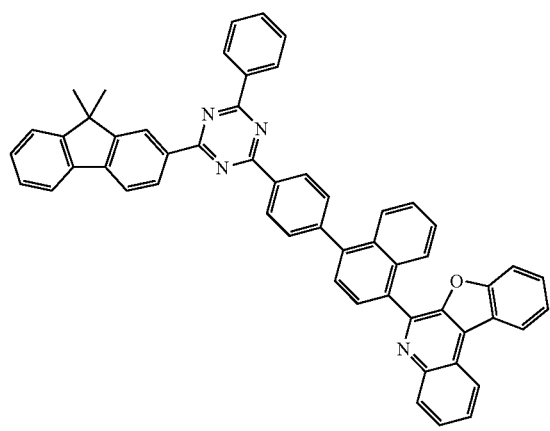
591
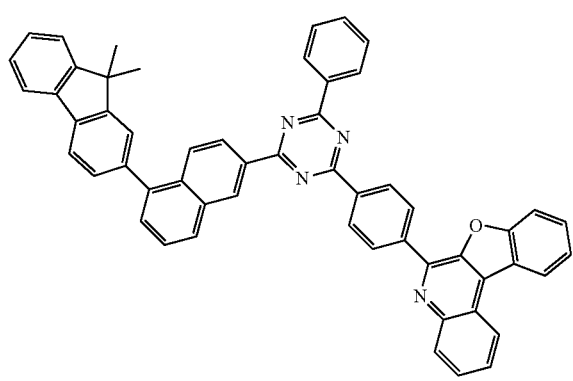
592
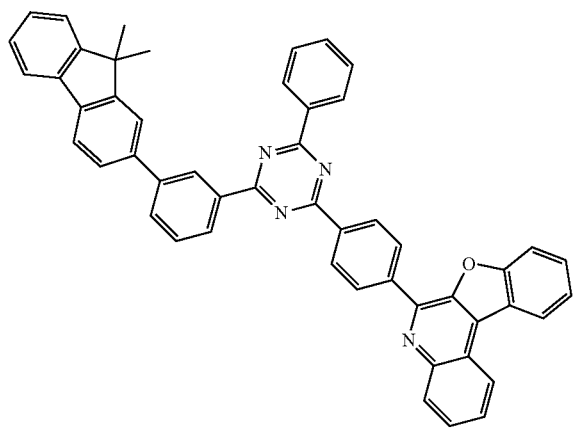
220
-continued
593
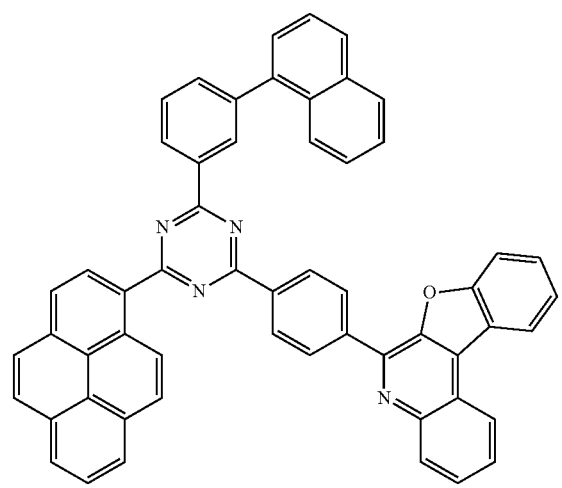
594
595
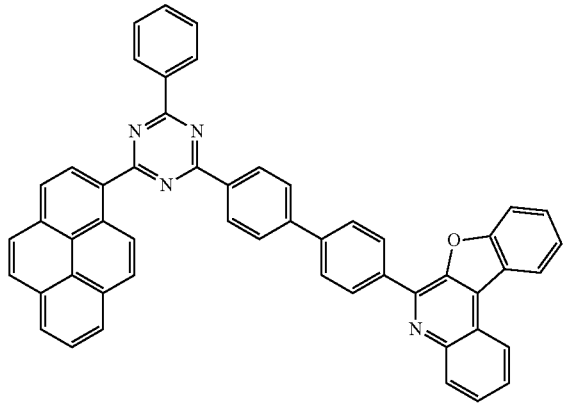

596
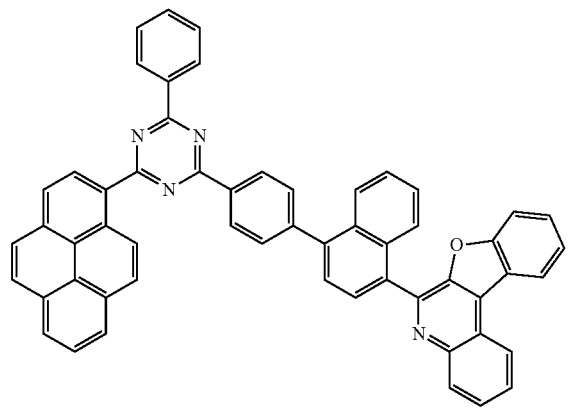
597
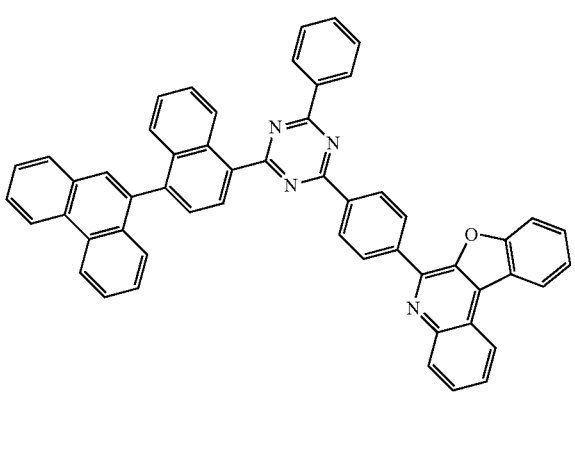
598
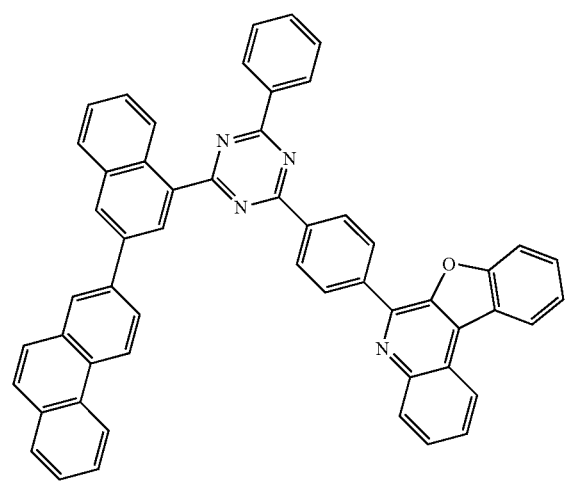
599
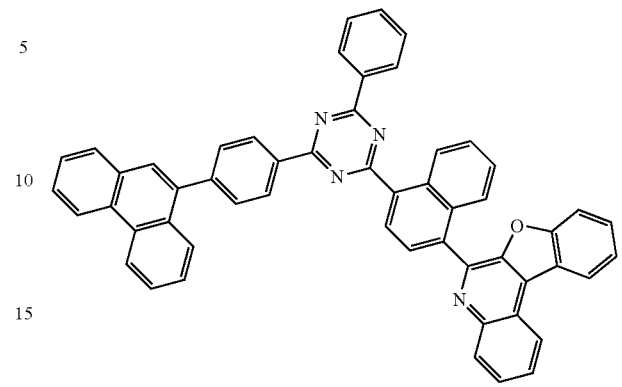
600
601

223
-continued
602
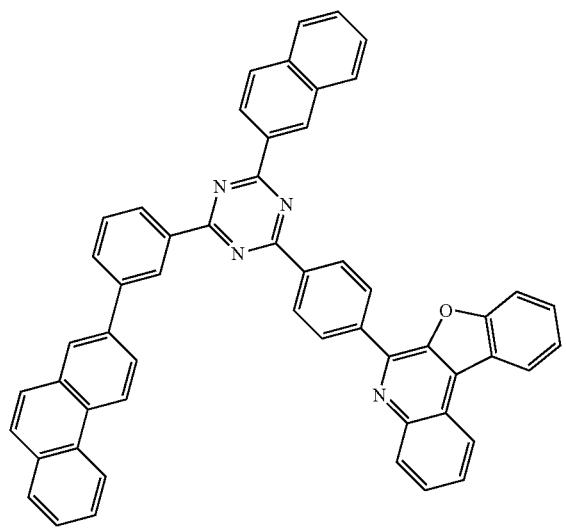
603
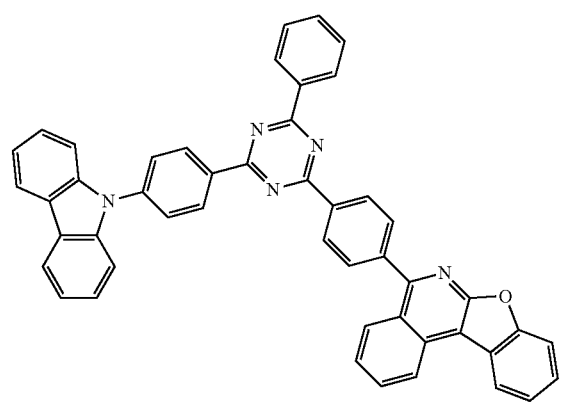
604
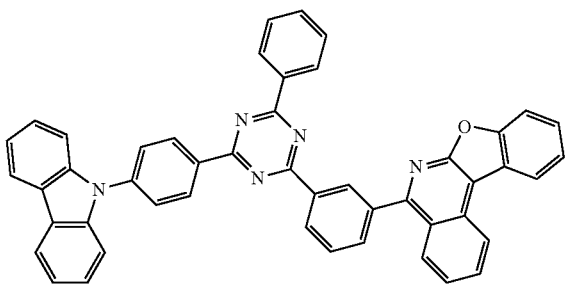
224
-continued
605
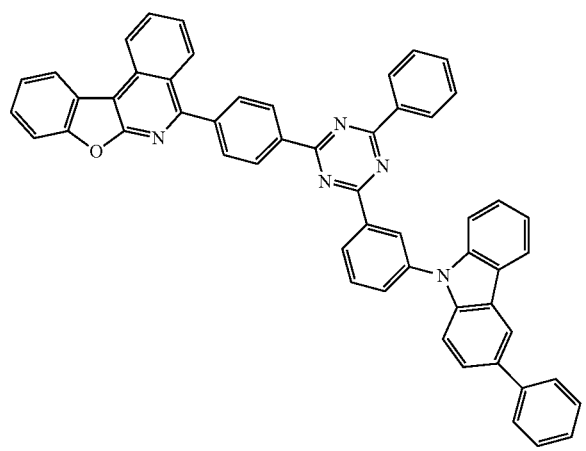
606
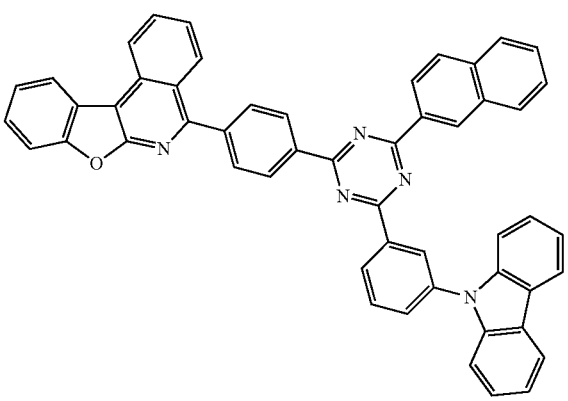
607
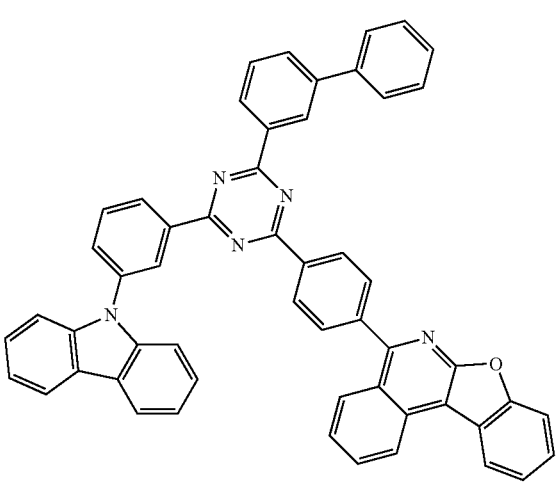

-continued
608
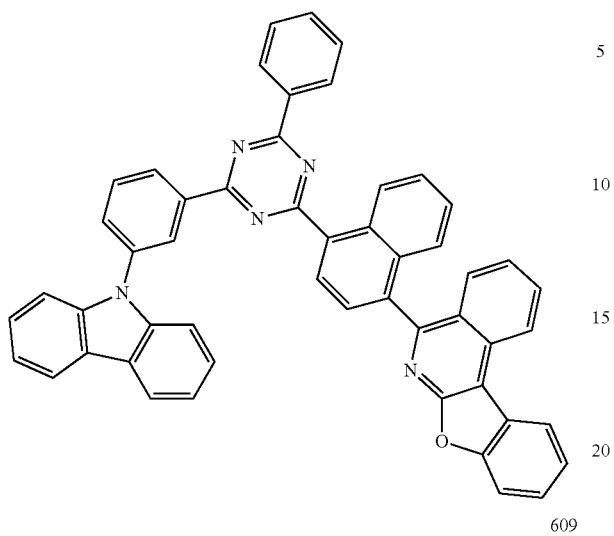
609
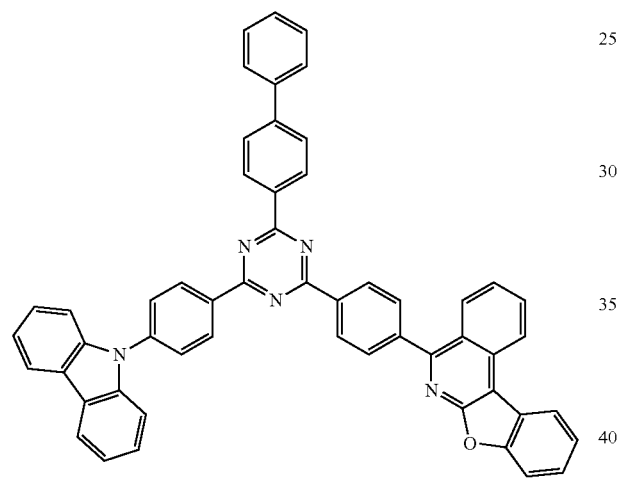
610
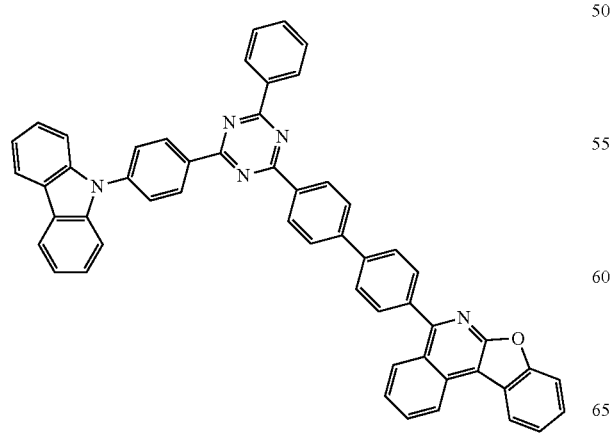
-continued
611
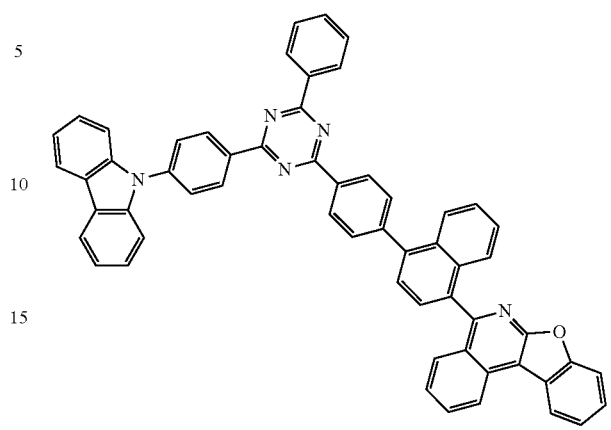
612
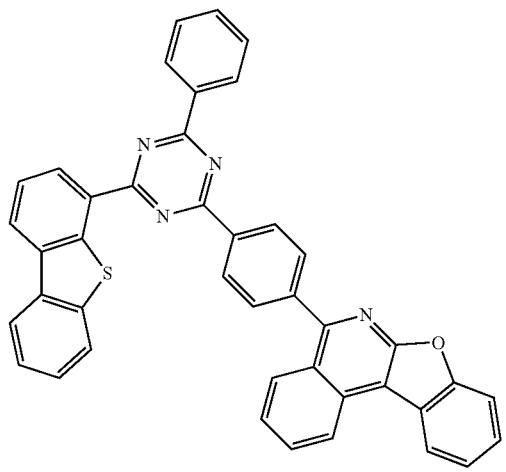
613
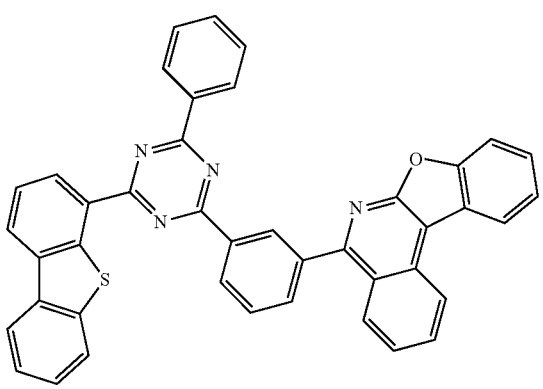

-continued
614
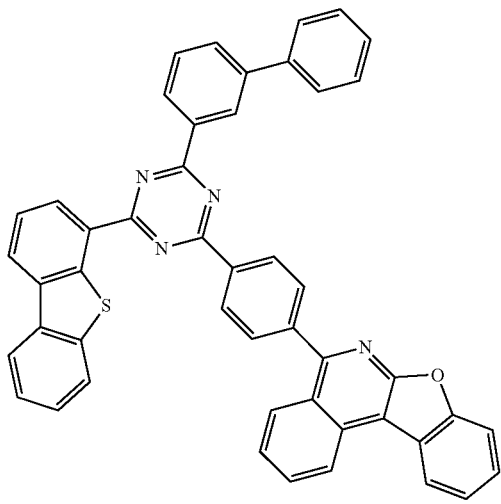
615
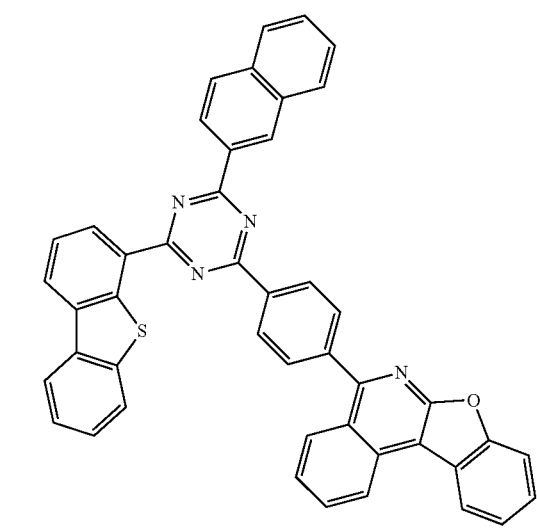
616
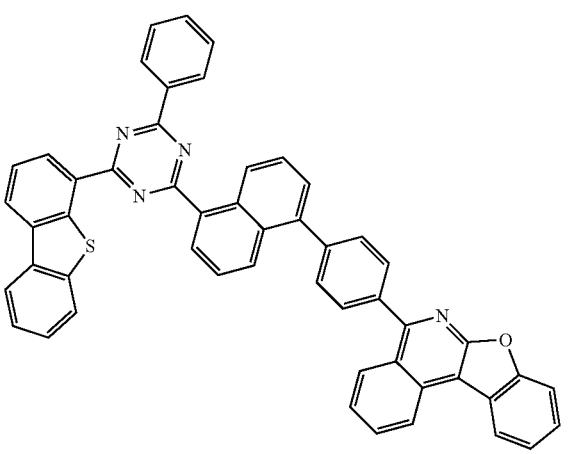
-continued
617
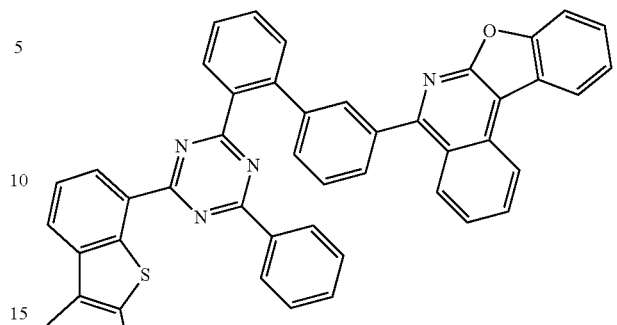
618
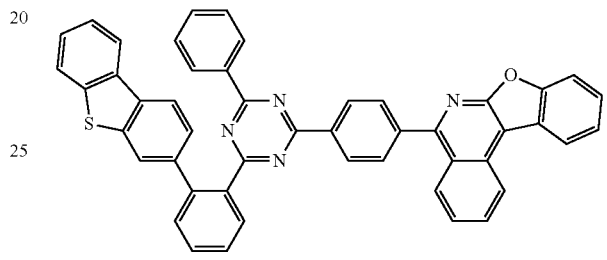
619
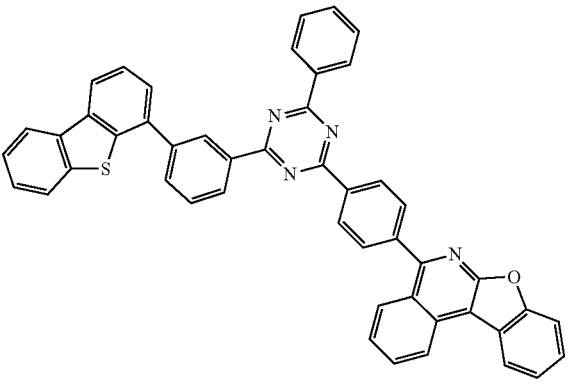
620
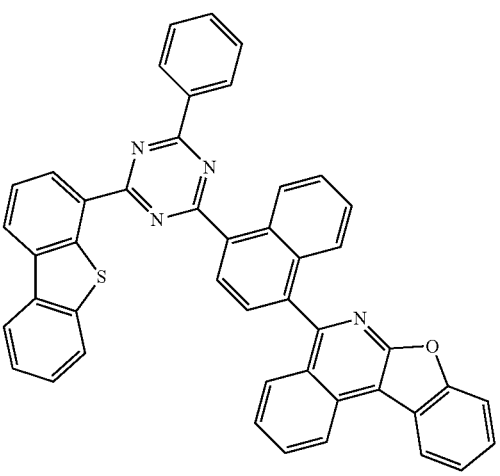

621
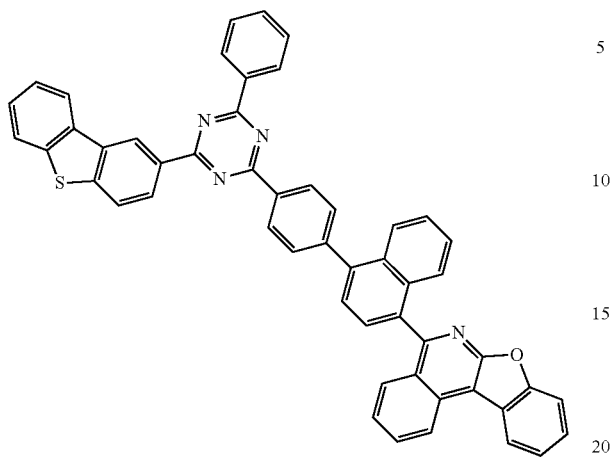
622
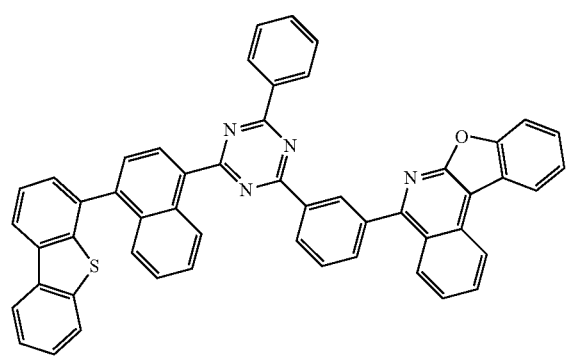
623
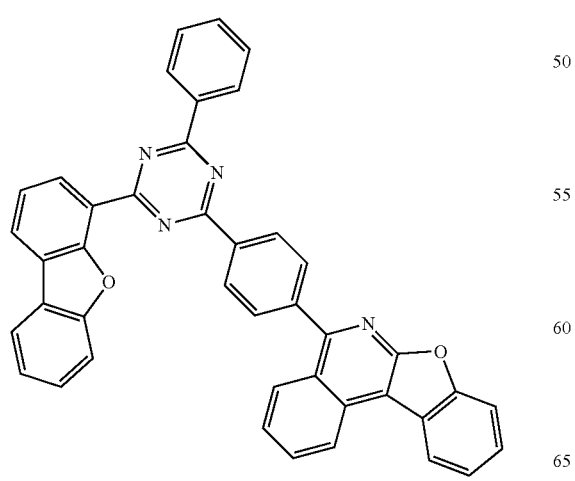
624
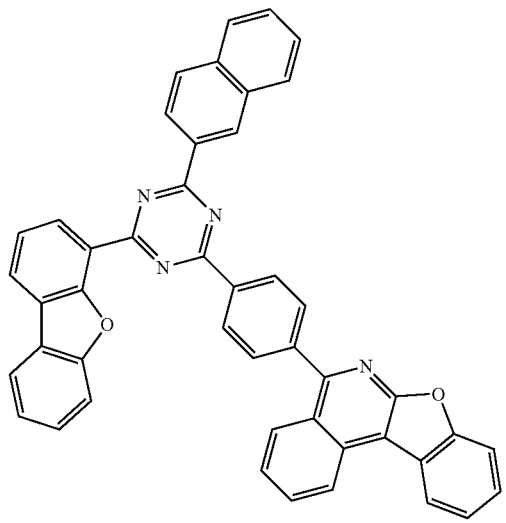
625
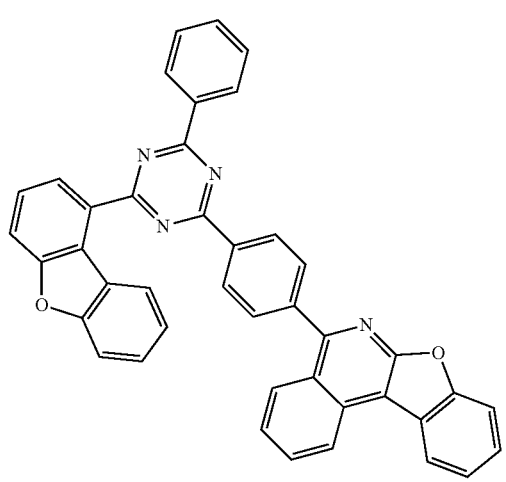
626
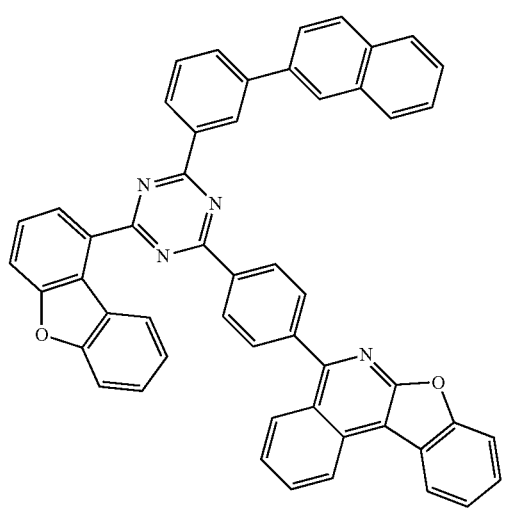

-continued
627
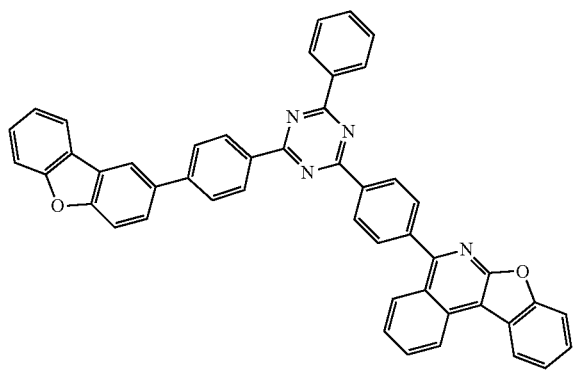
628
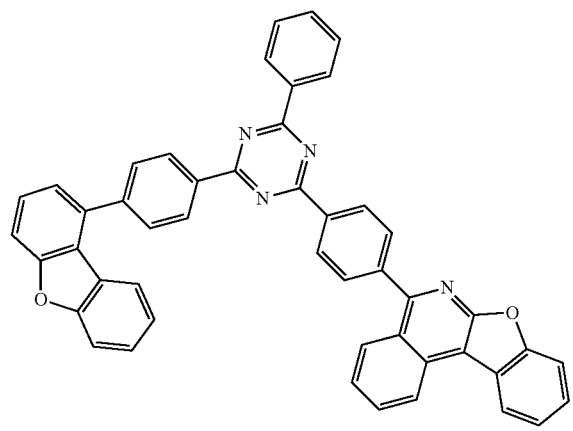
629
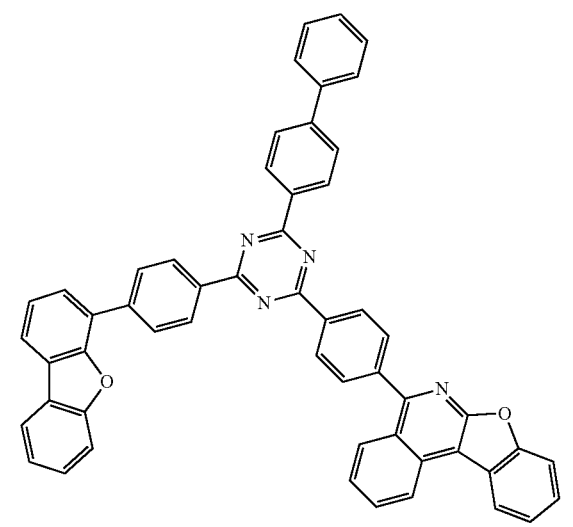
-continued
630
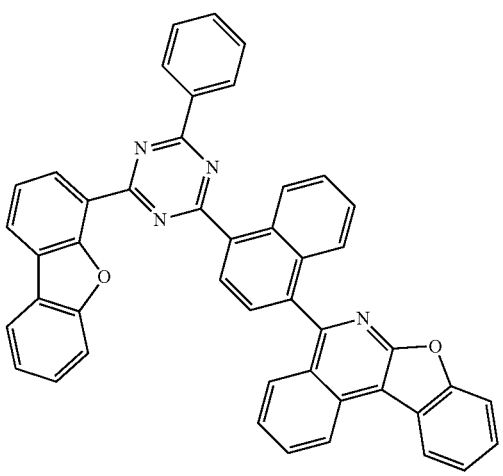
631
632
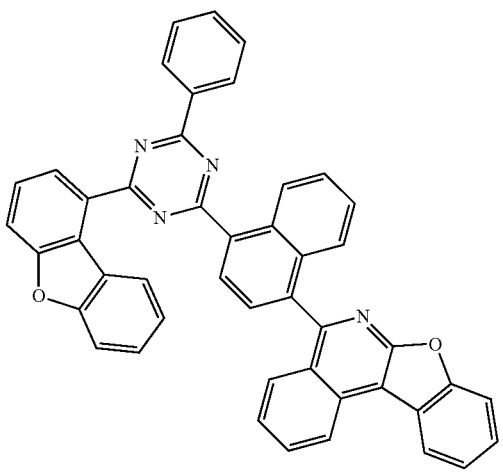

633
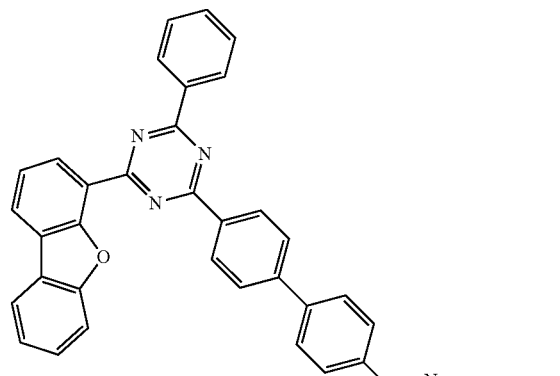
634
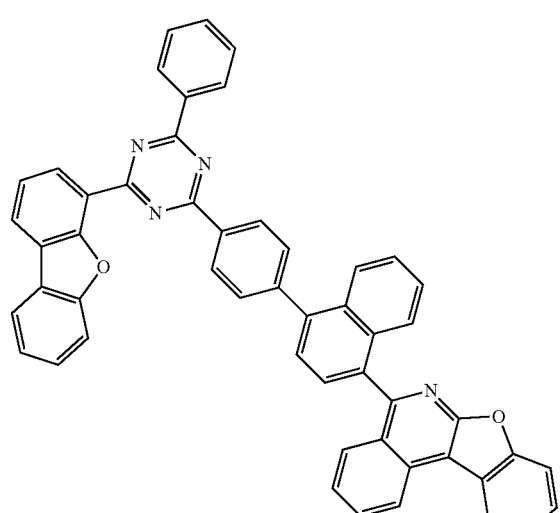
635
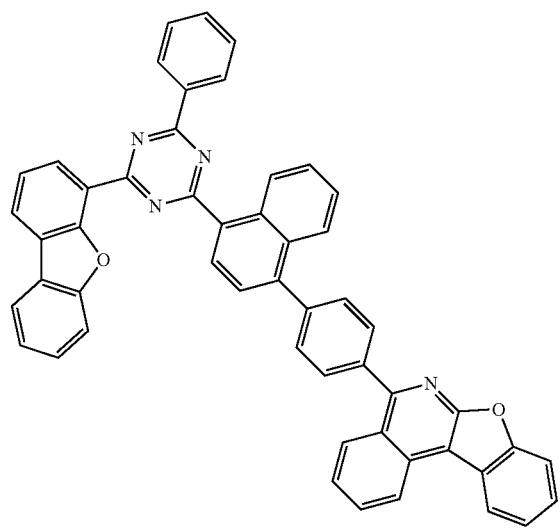
636
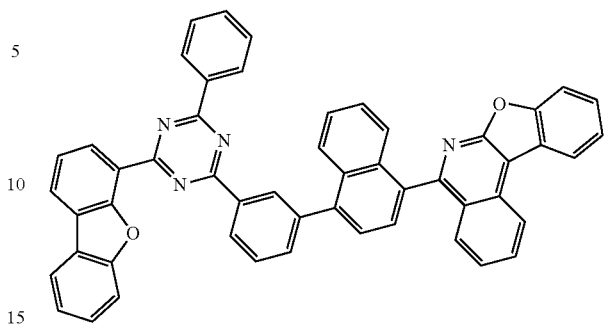
637
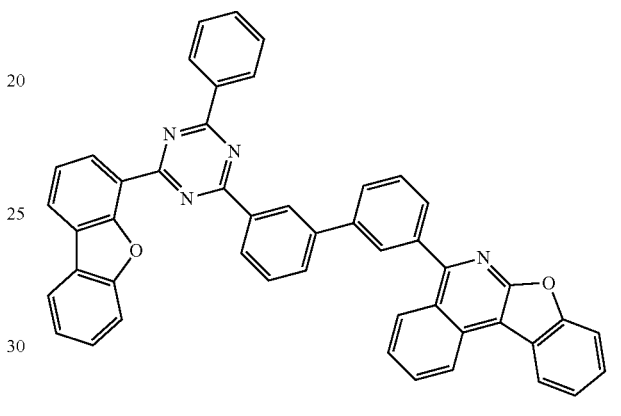
638
639
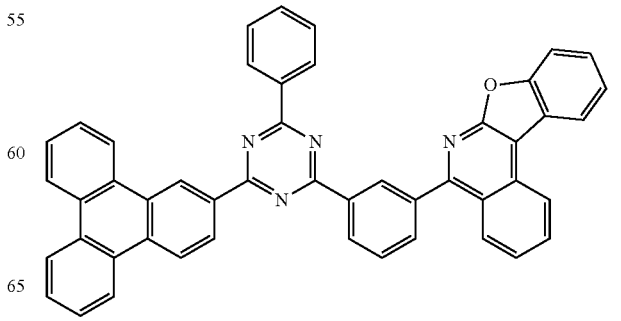

640
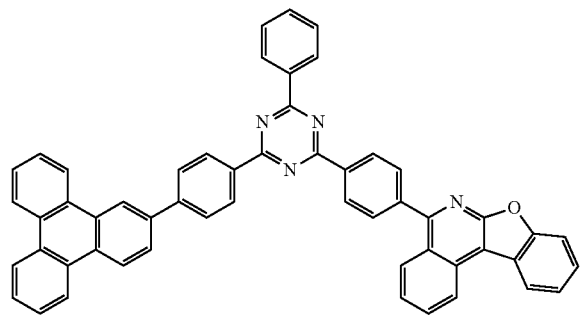
641
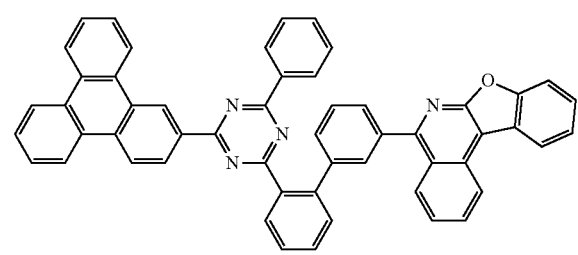
642
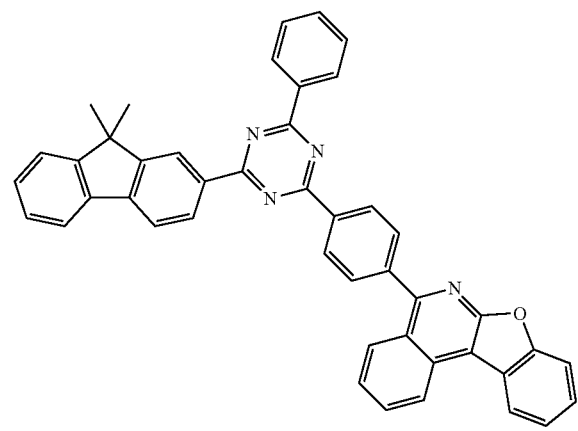
643
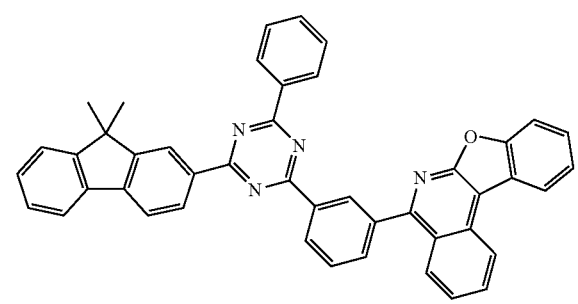
644
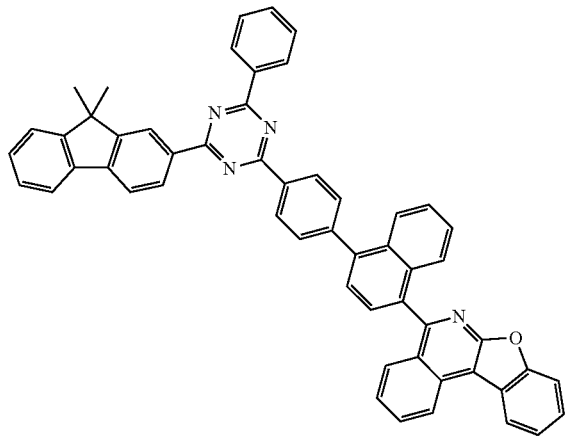
645
646
647
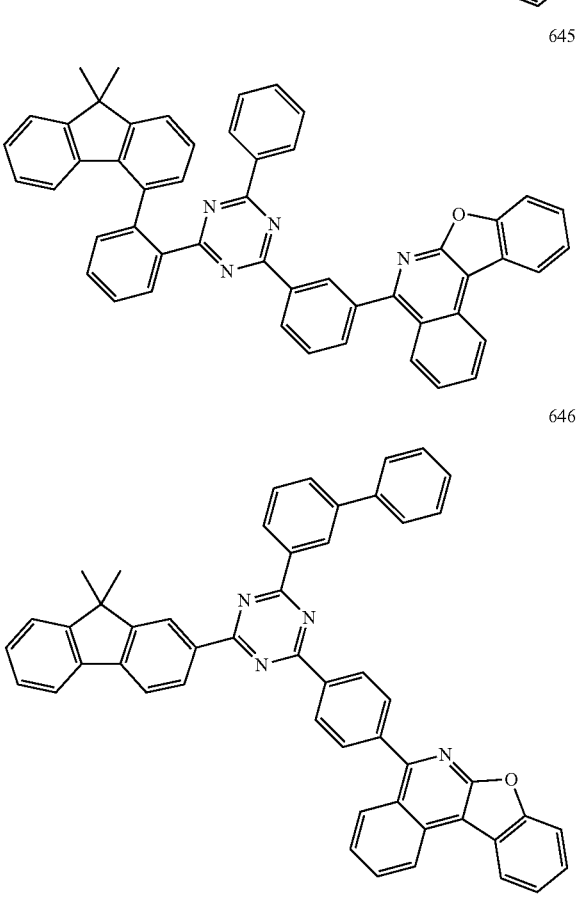

237
-continued
648
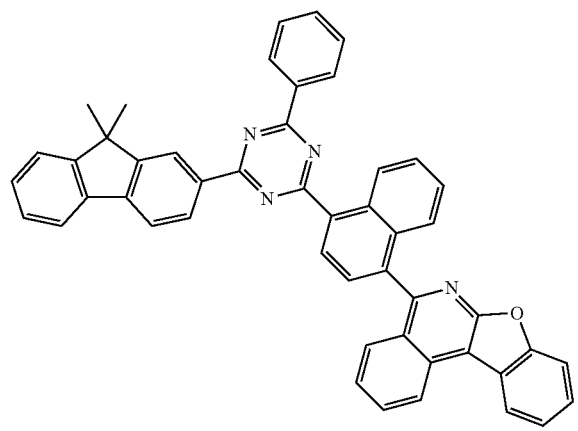
649
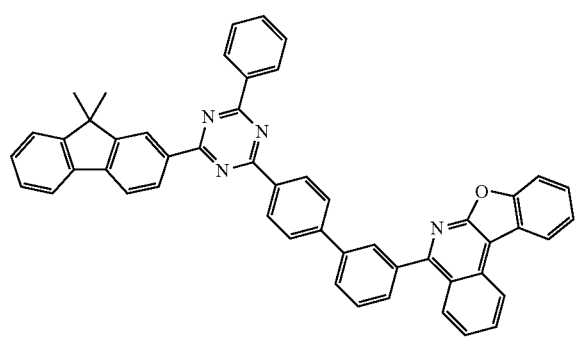
6500
238
-continued
651
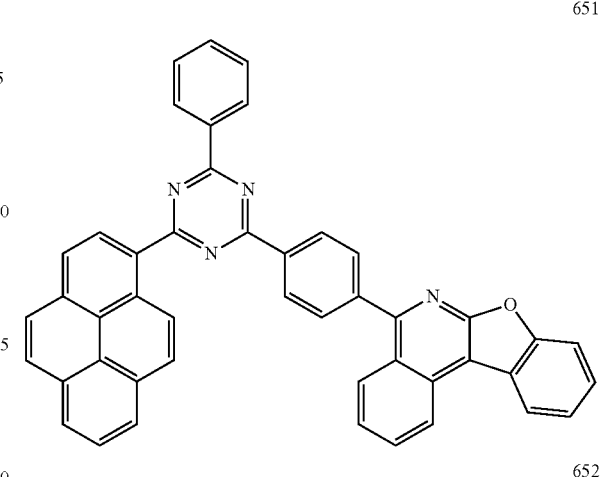
652
653
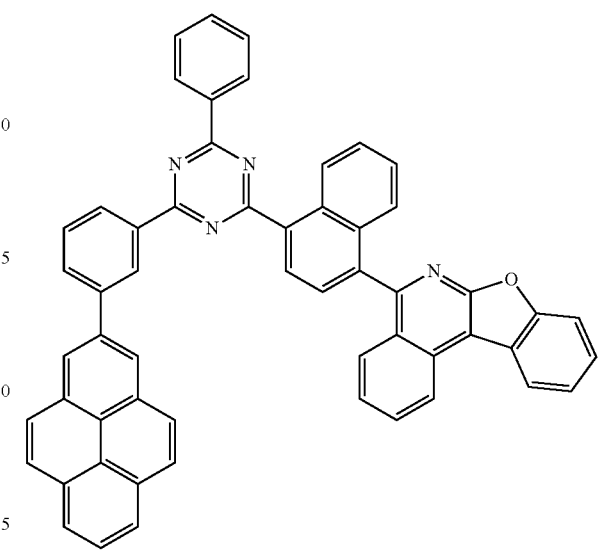

239
-continued
654
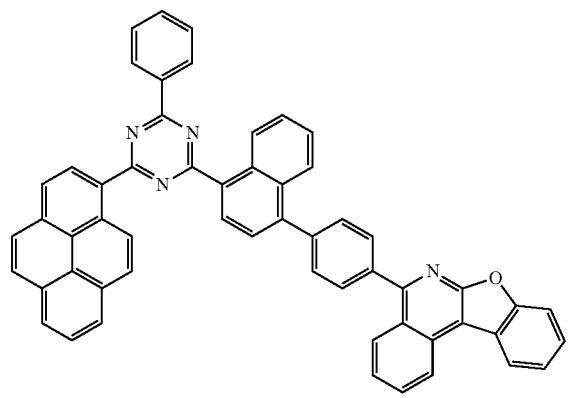
655
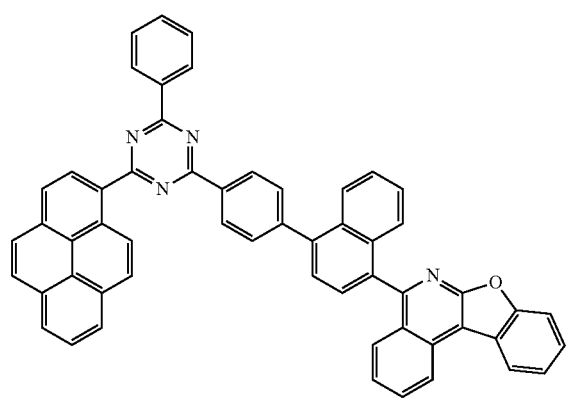
656
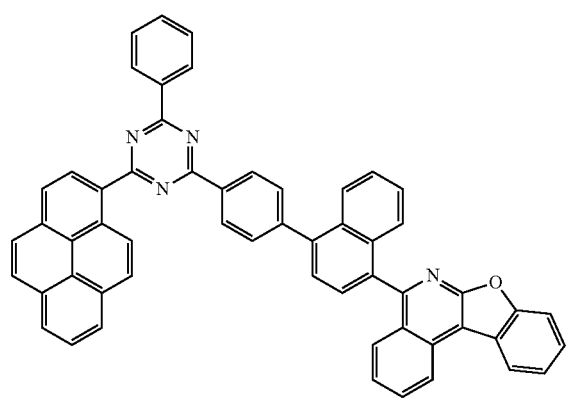
240
-continued
657
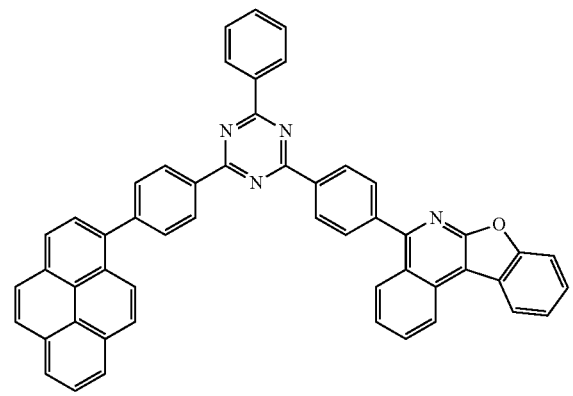
658
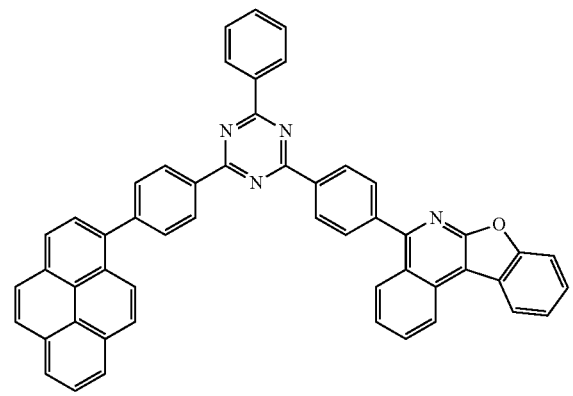
659
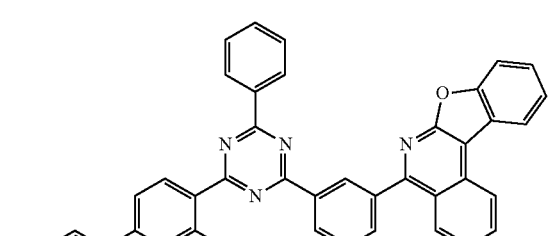
660
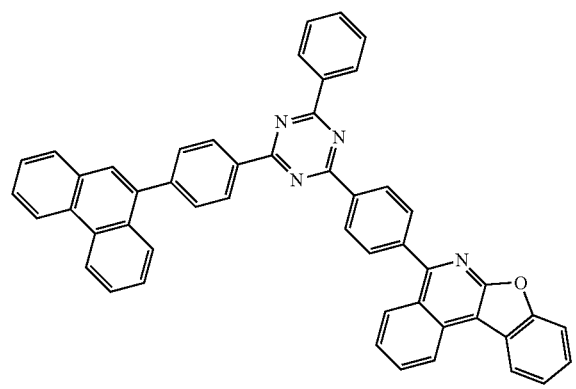

661
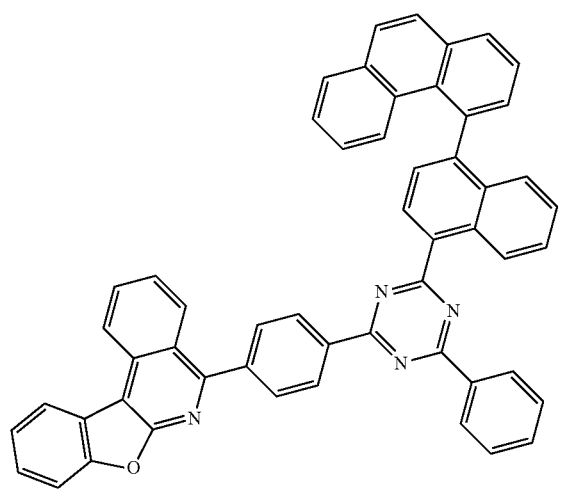
662
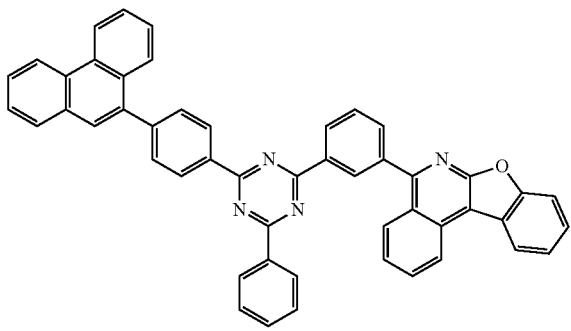
663
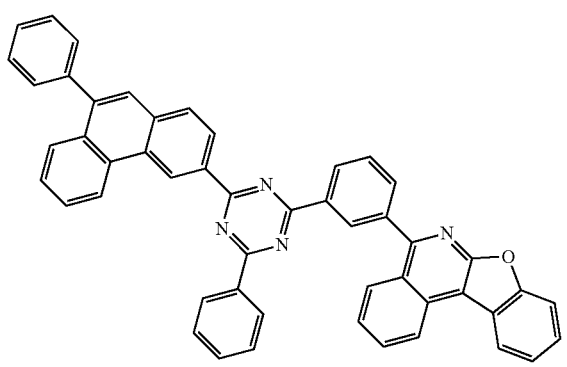
664
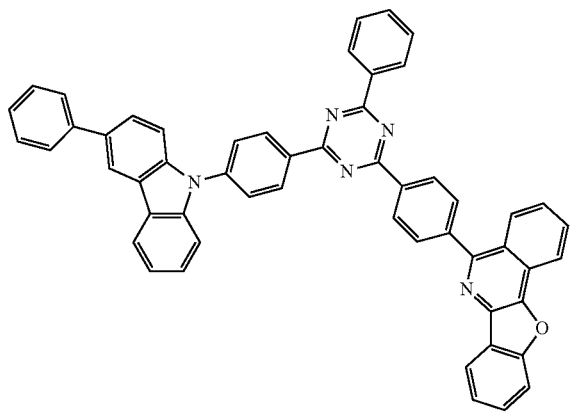
665
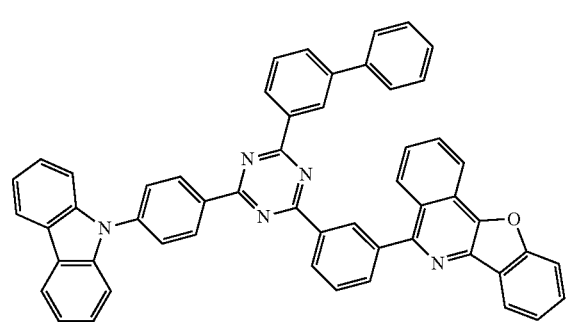
666
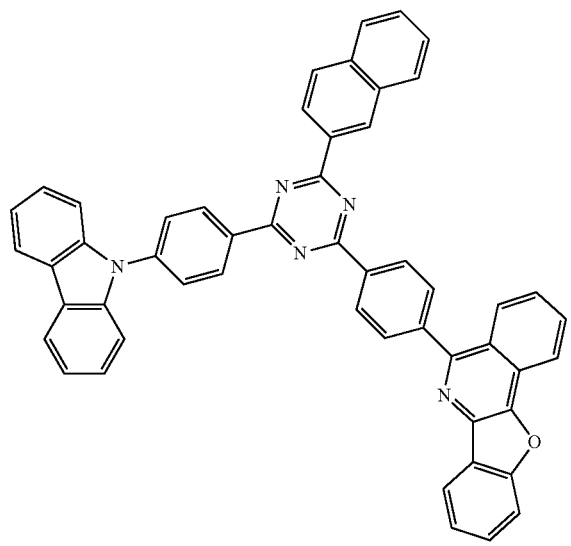
667
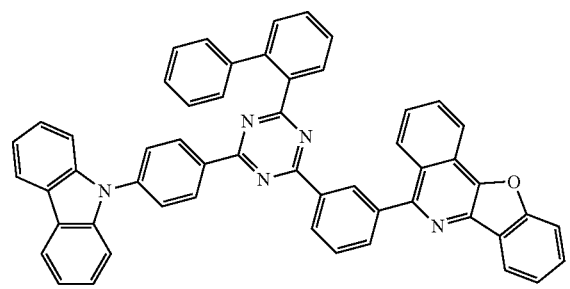

-continued
668
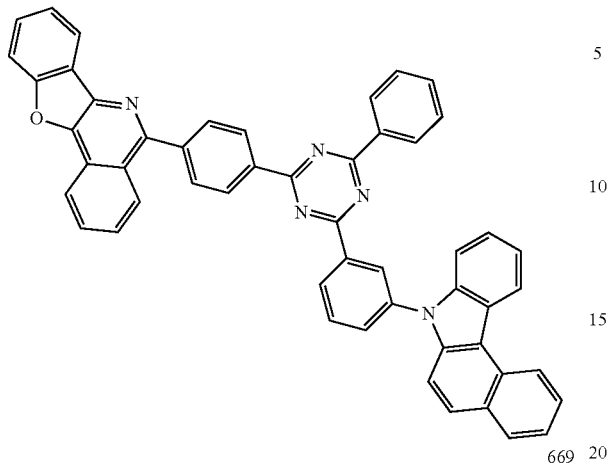
669
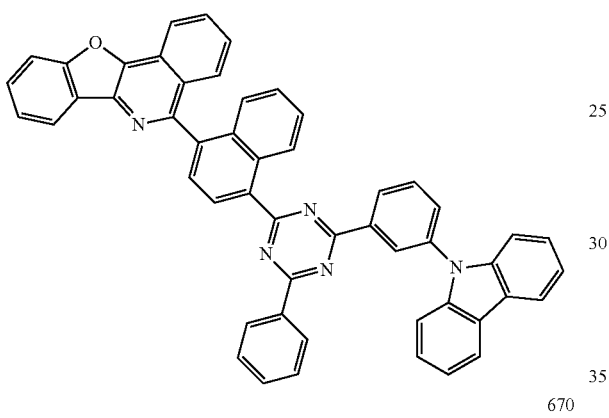
670
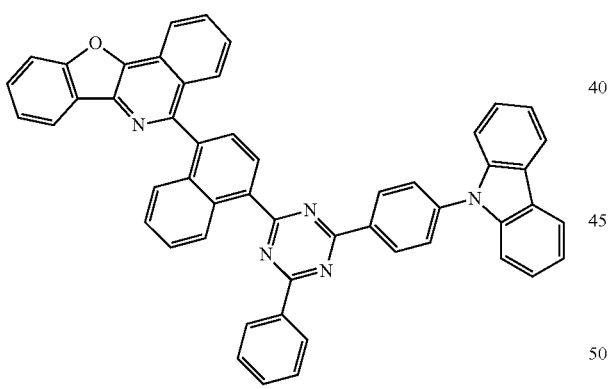
671
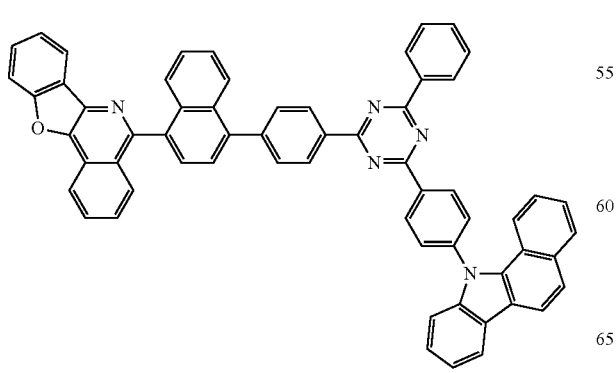
-continued
672
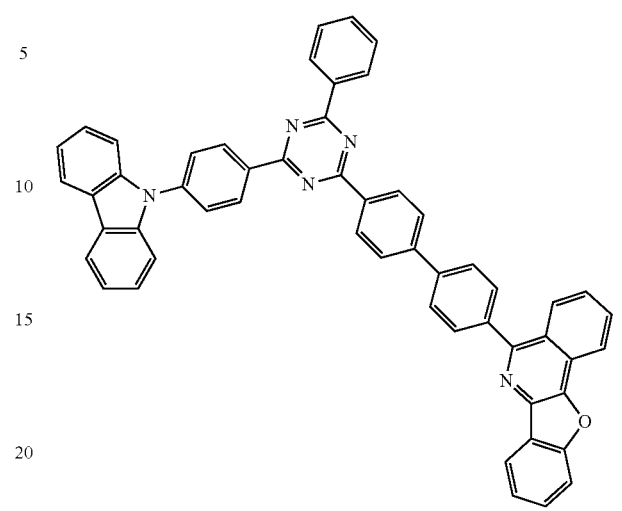
673
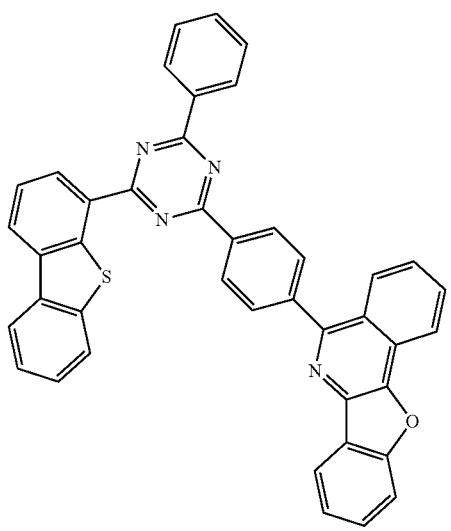
674
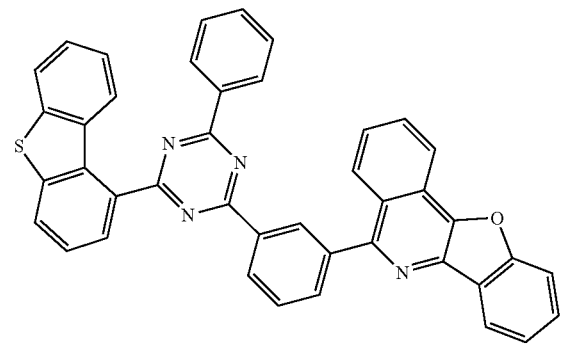

675
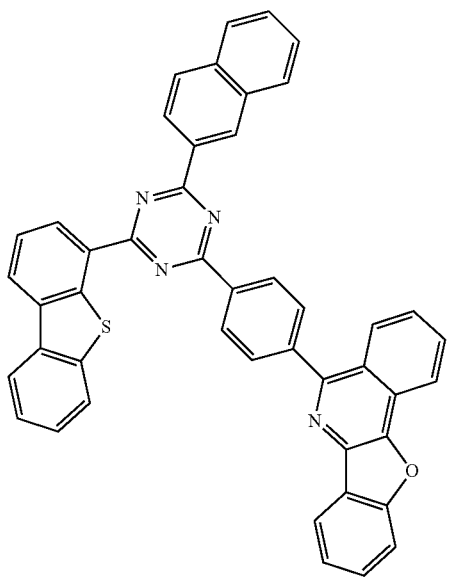
676
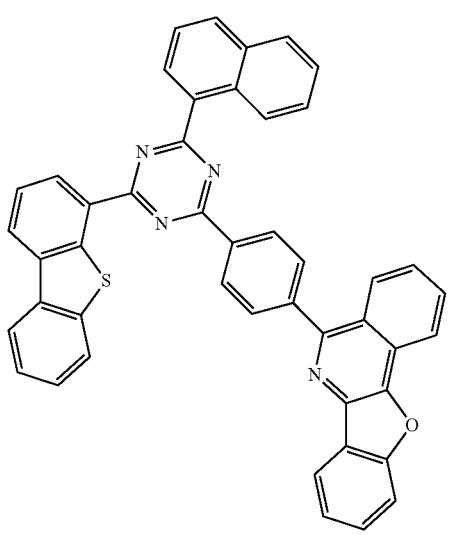
677
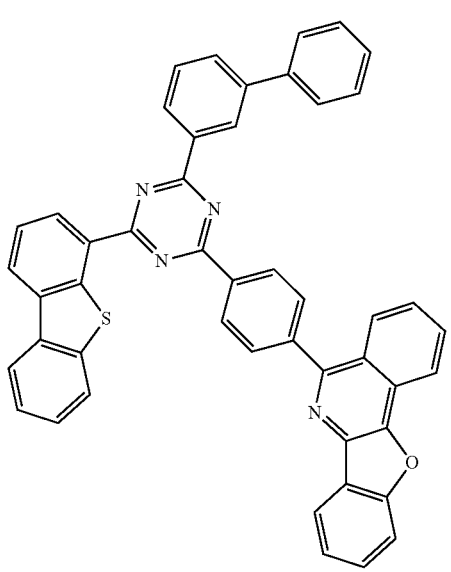
678
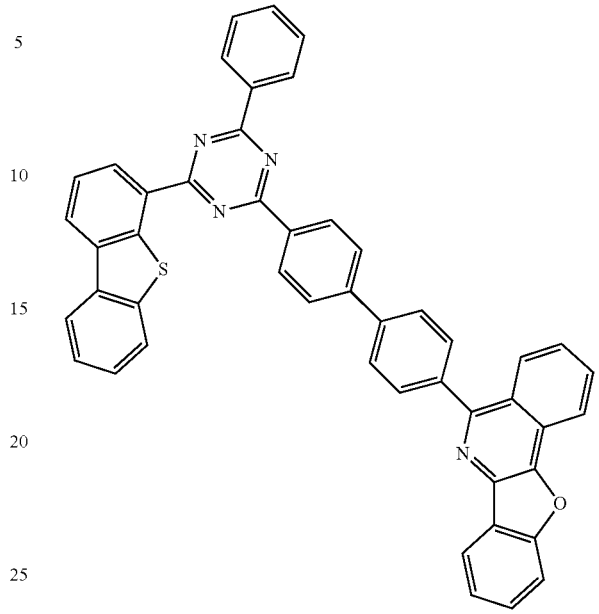
679
680
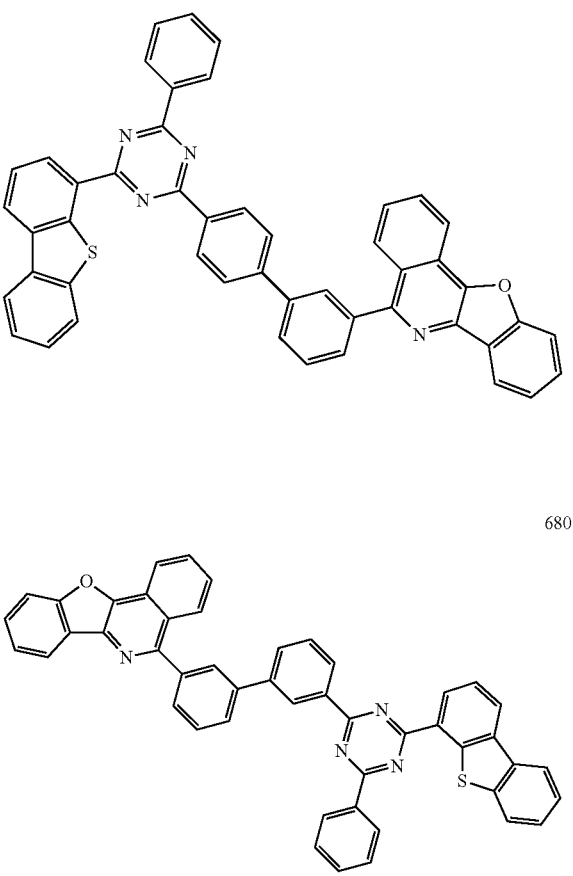

681
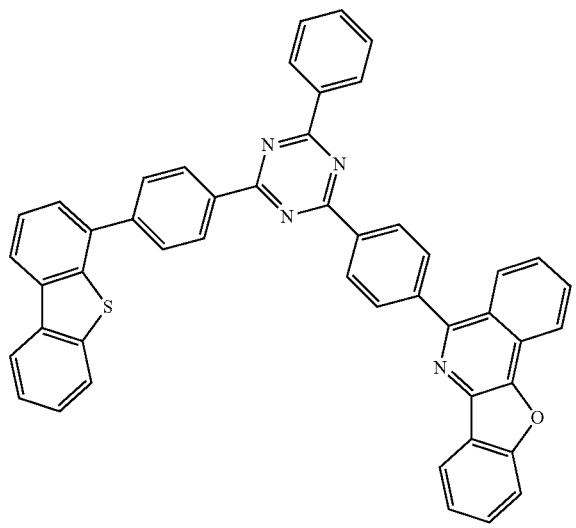
682
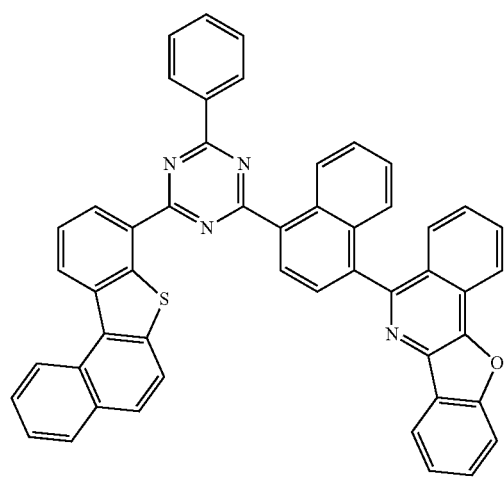
683
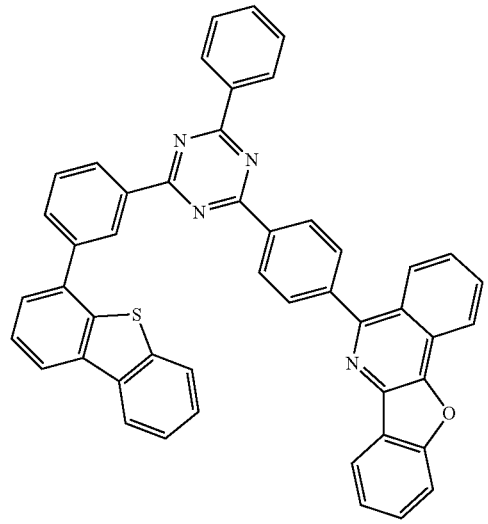
684
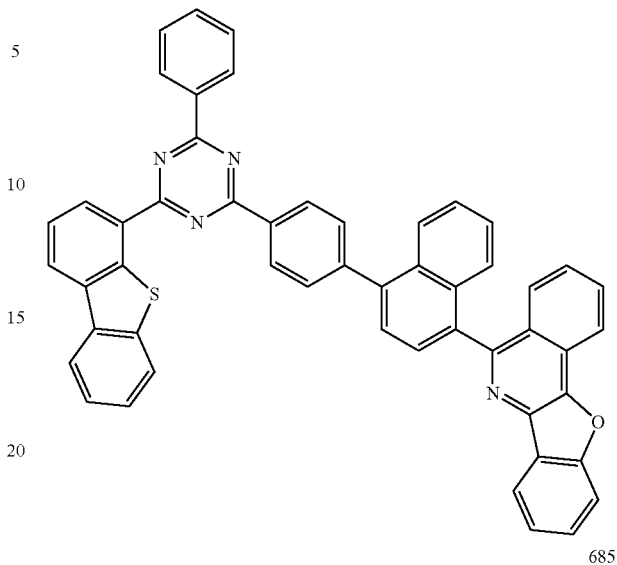
685
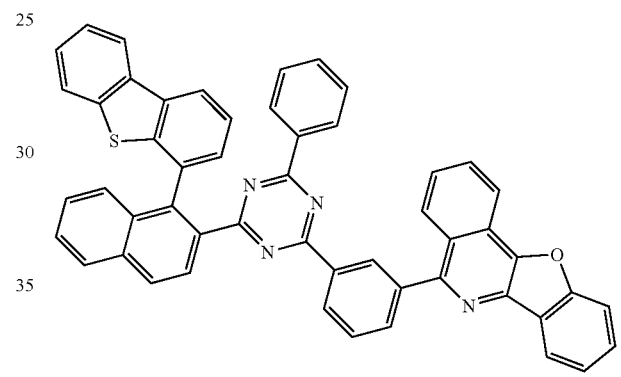
686
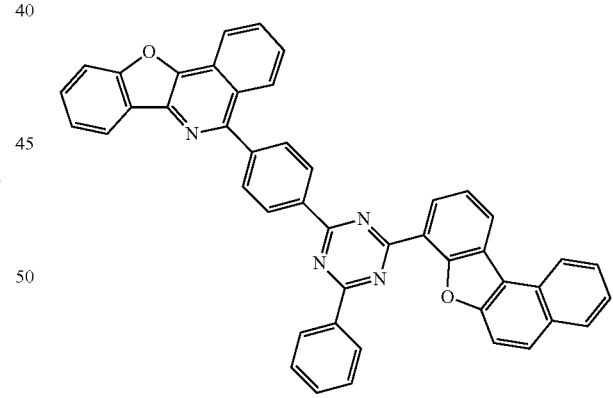
687
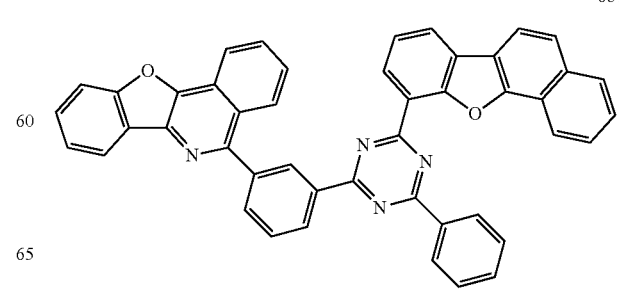

688
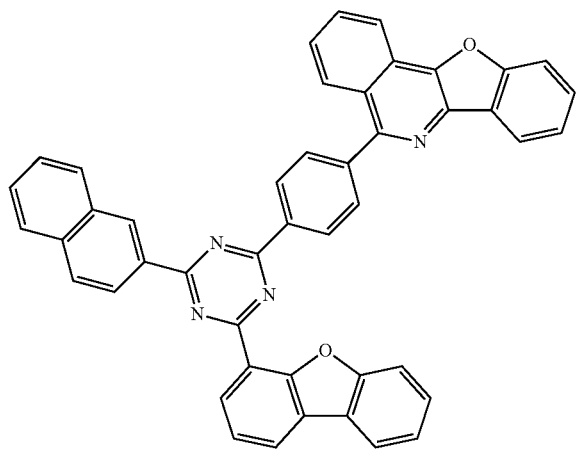
689
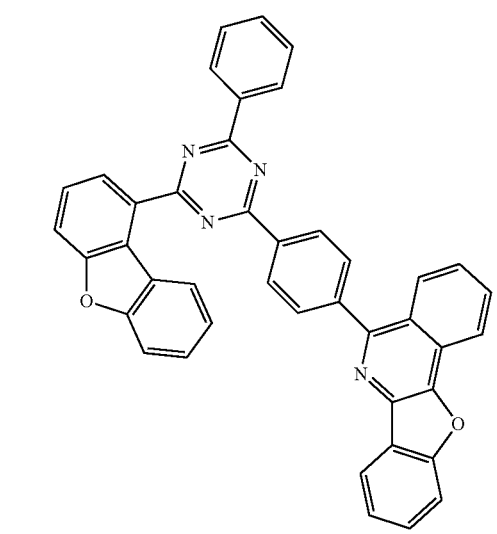
690
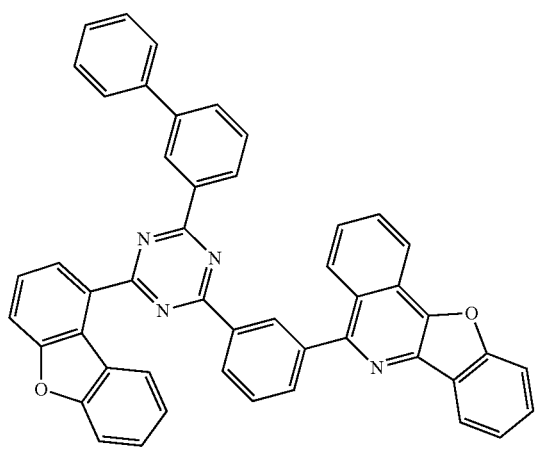
691
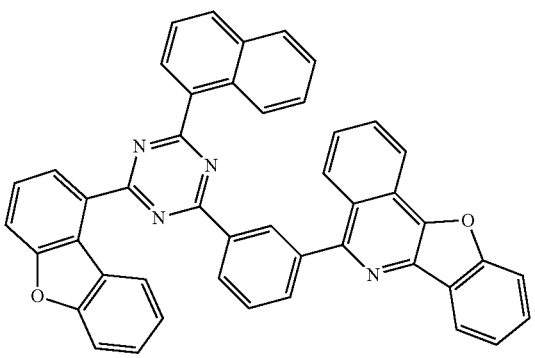
692
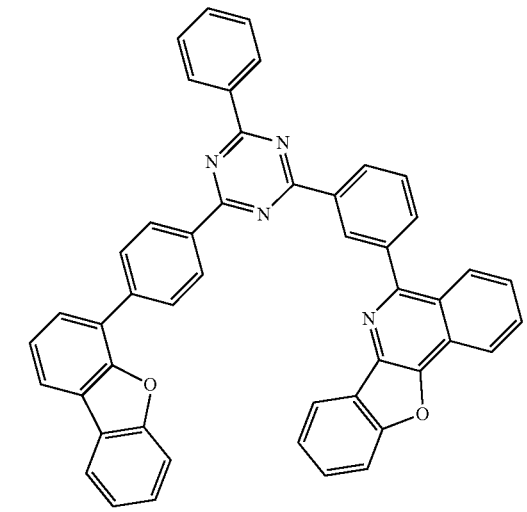
693
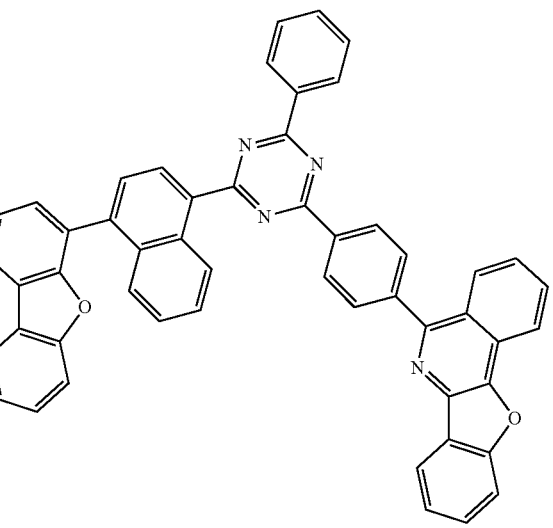

694
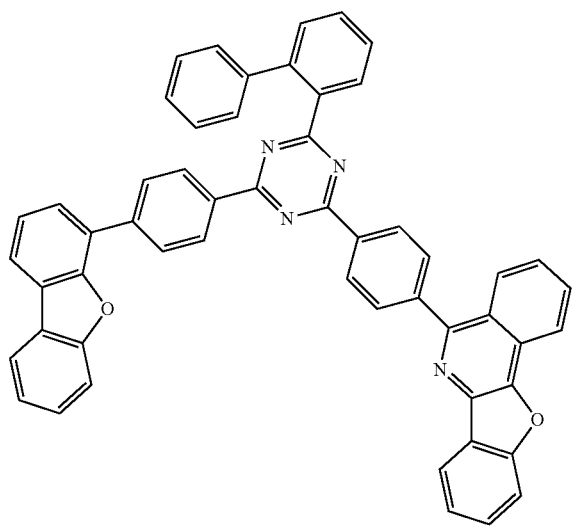
695
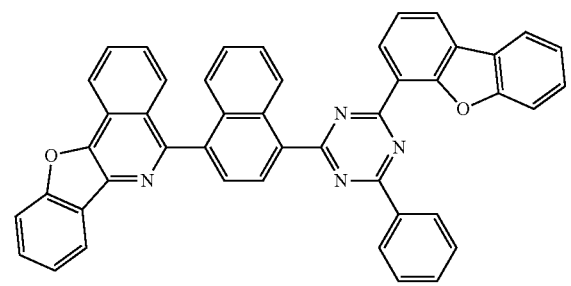
696
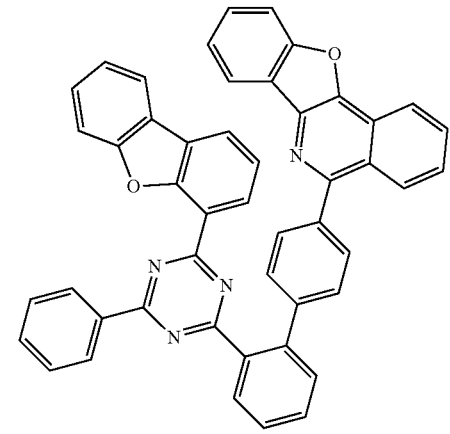
697
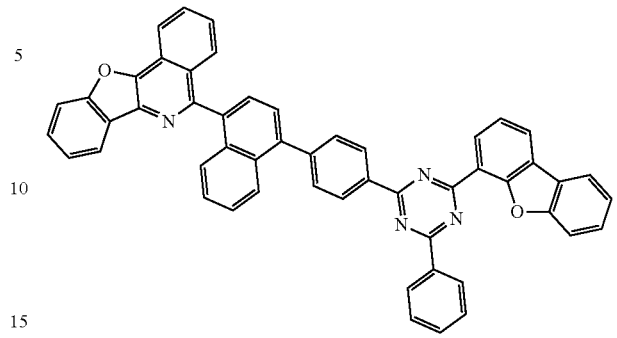
698
699
700

253
-continued
254
-continued
701
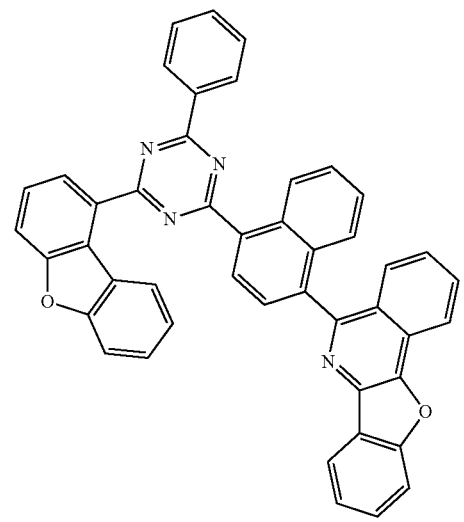
704
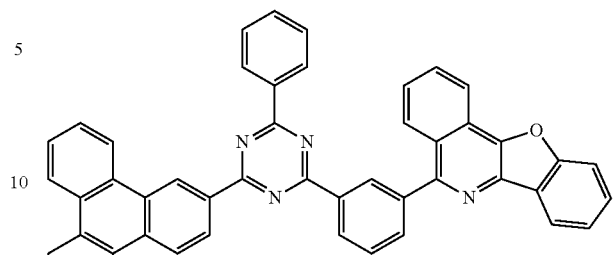
705
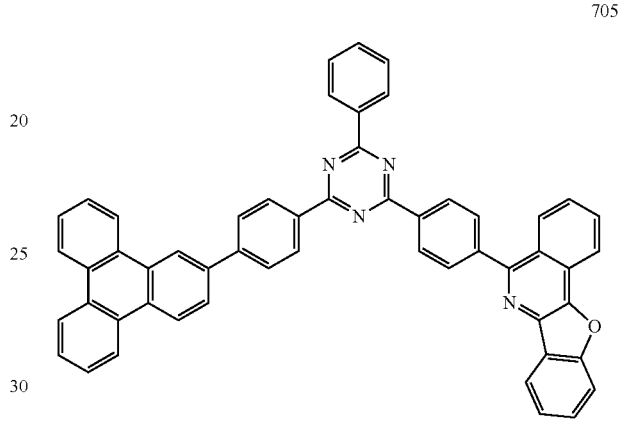
702
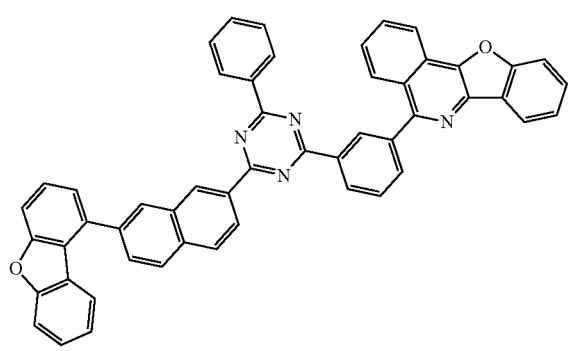
706
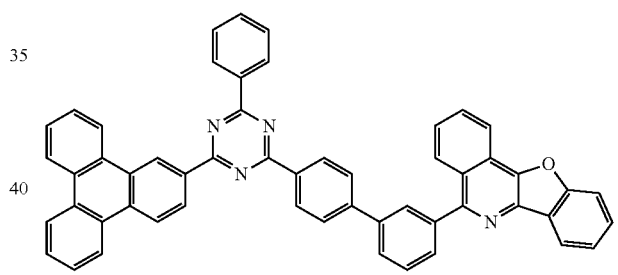
703
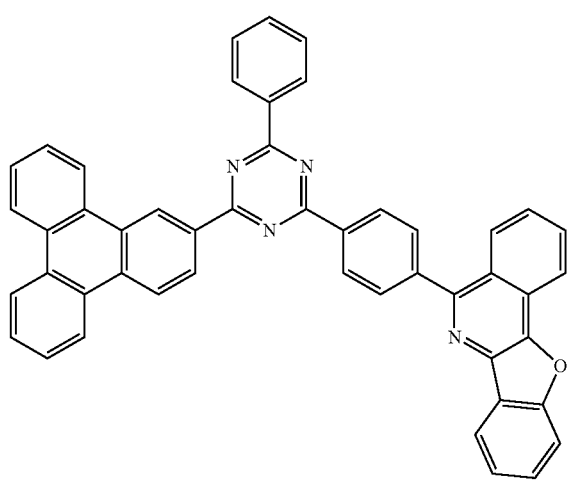
707
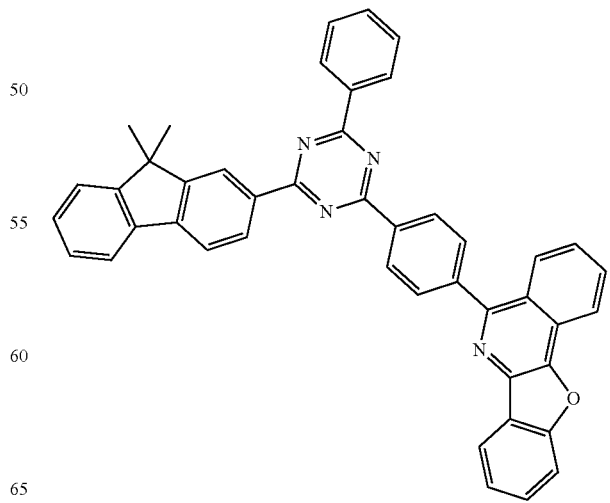

708
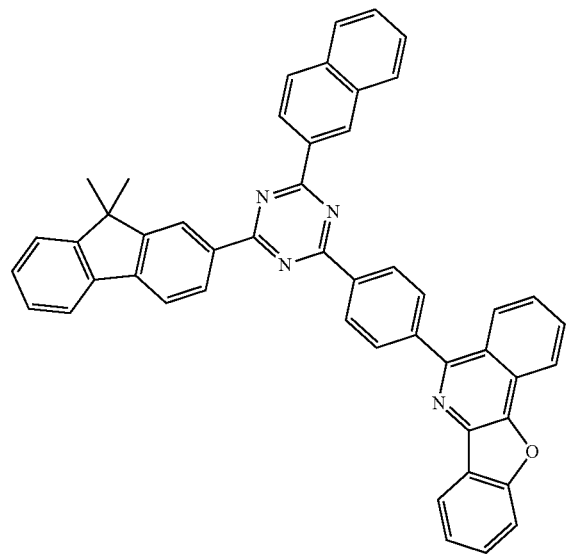
709
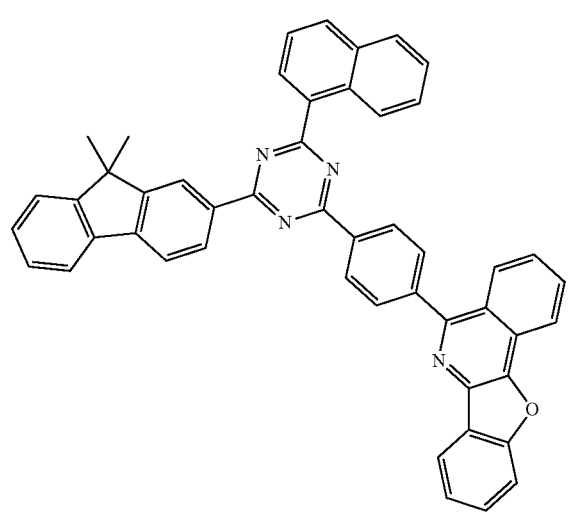
710
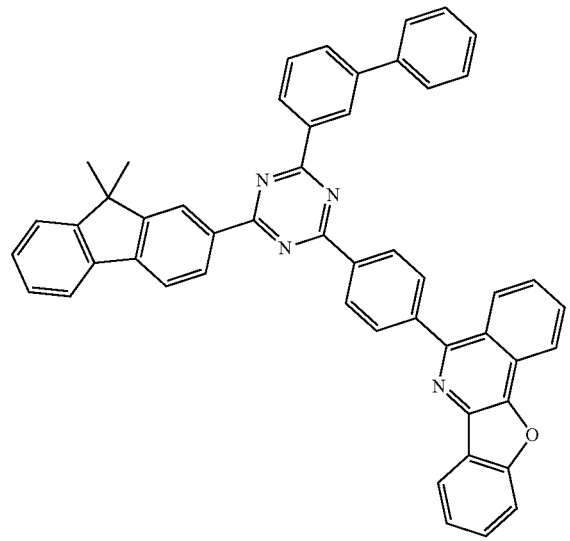
711
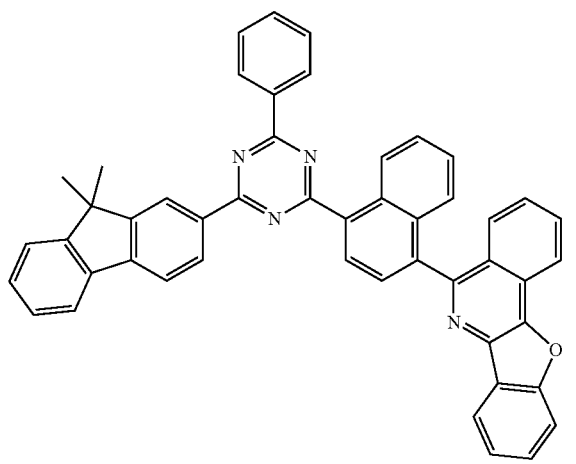
712
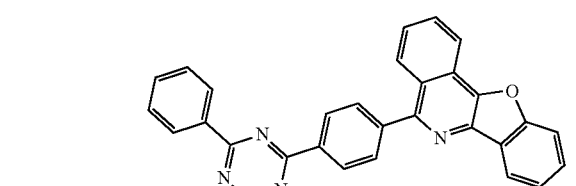
713
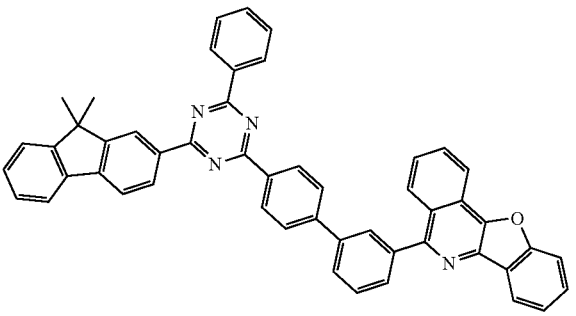
714
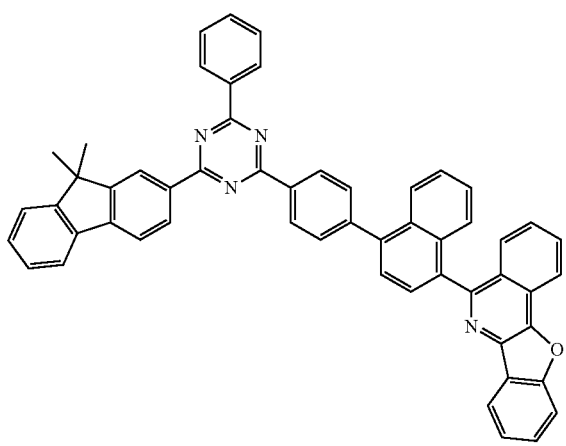

715
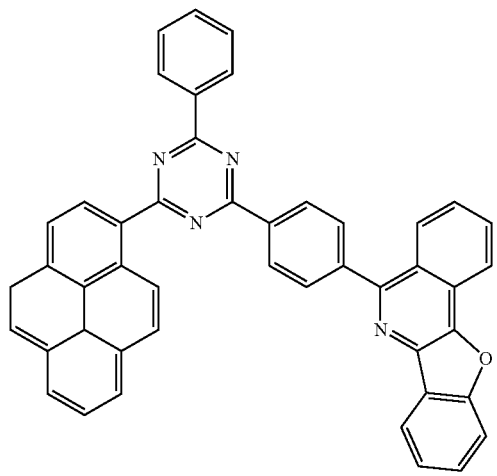
716
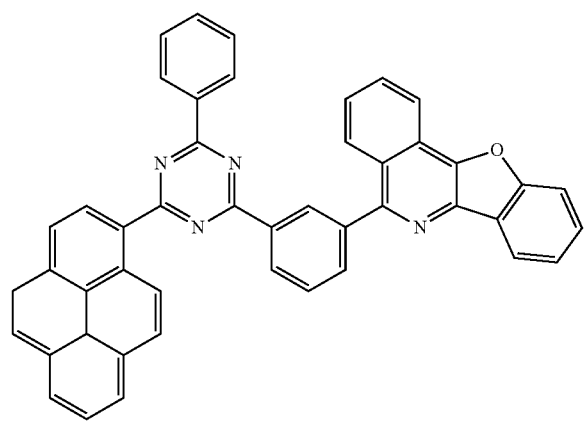
717
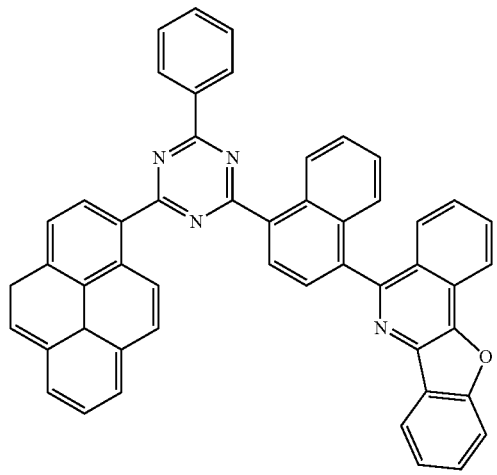
718
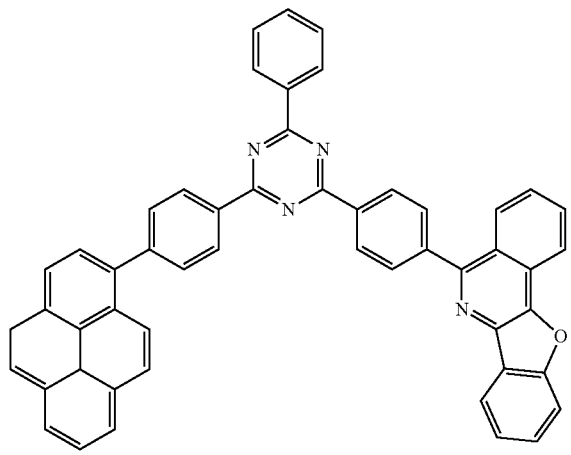
719
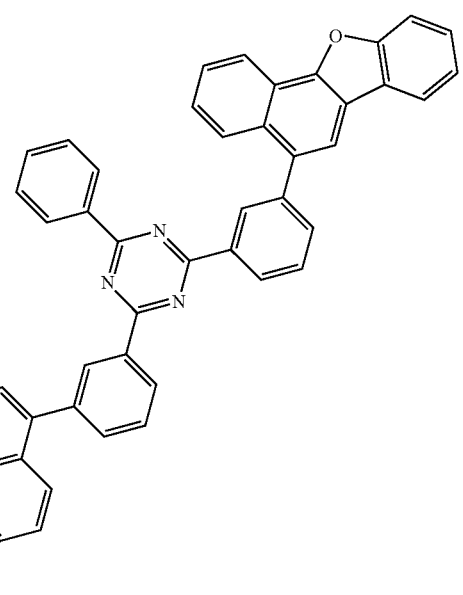
720
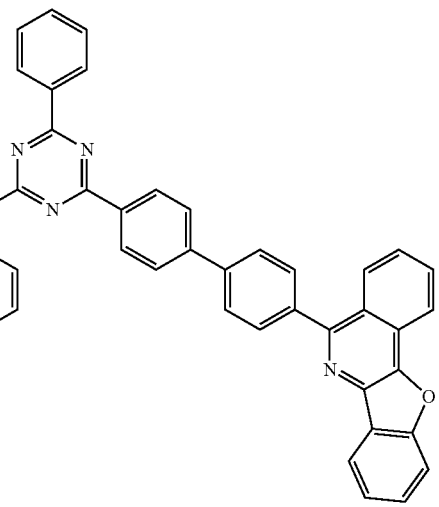

259
-continued
721
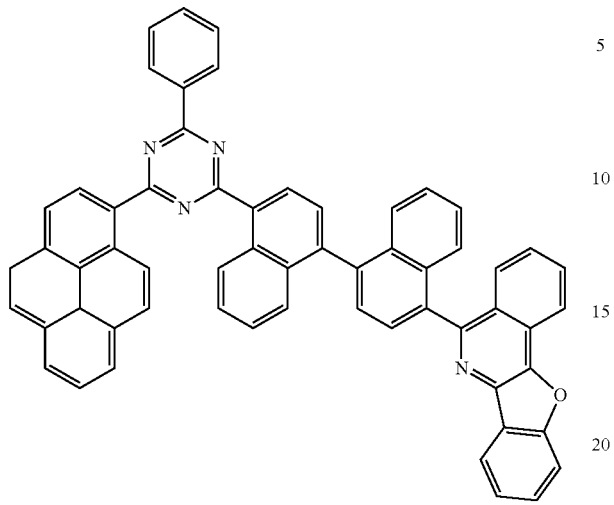
722
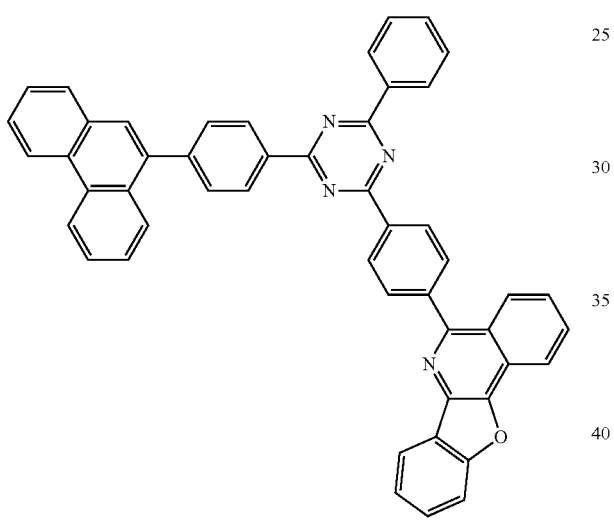
723
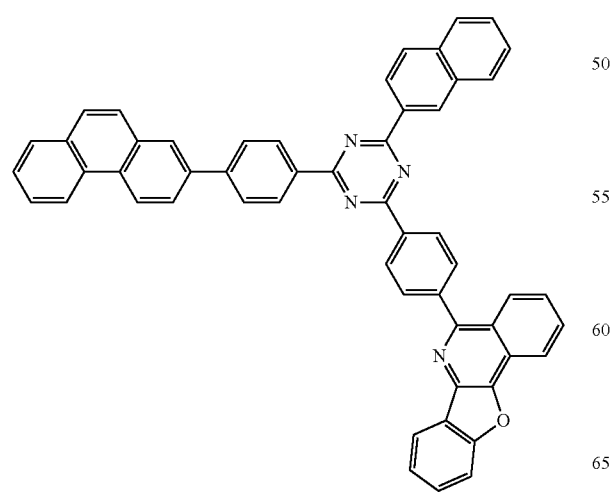
260
-continued
724
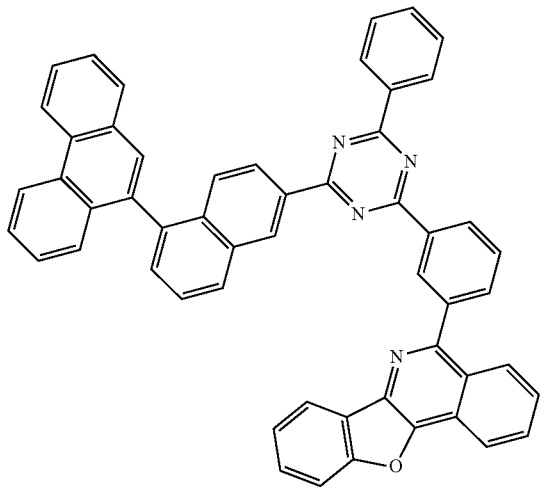
725
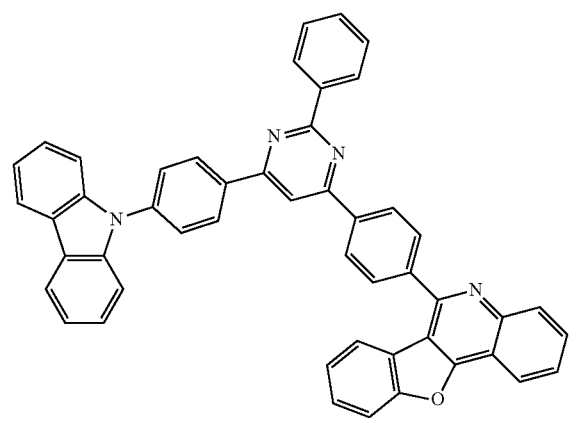
726
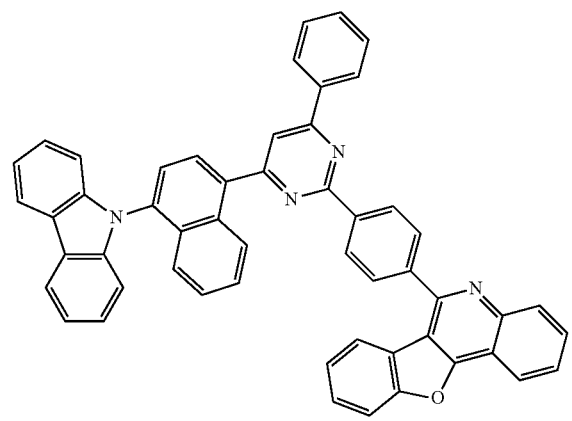

727
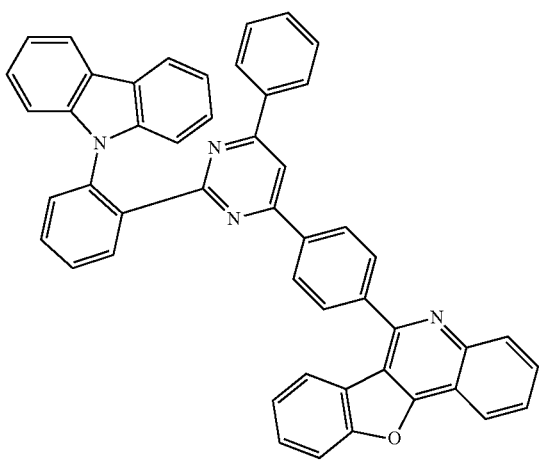
728
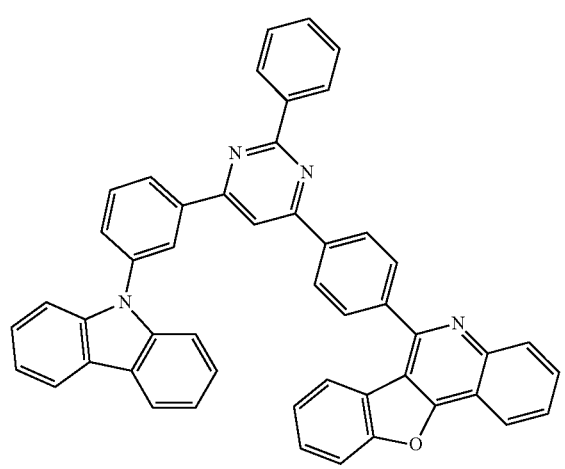
729
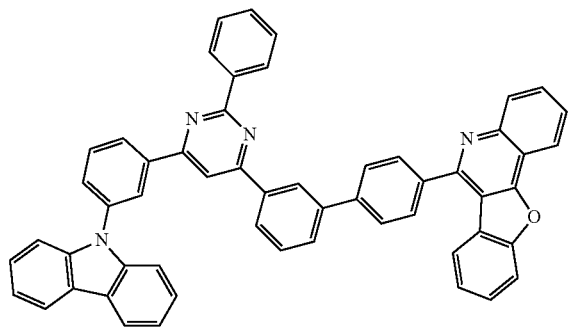
730
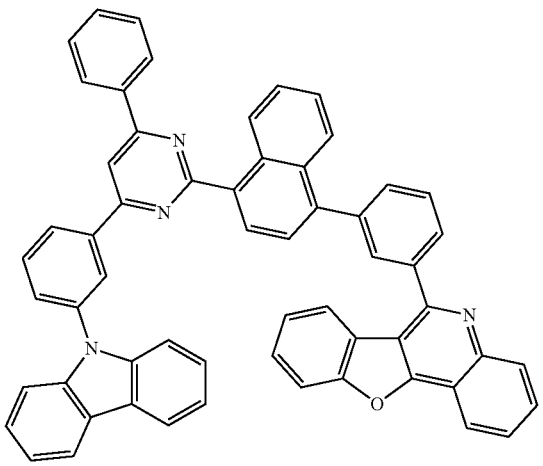
731
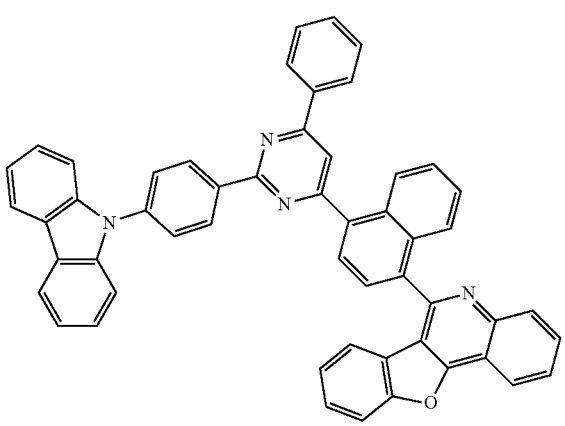
732
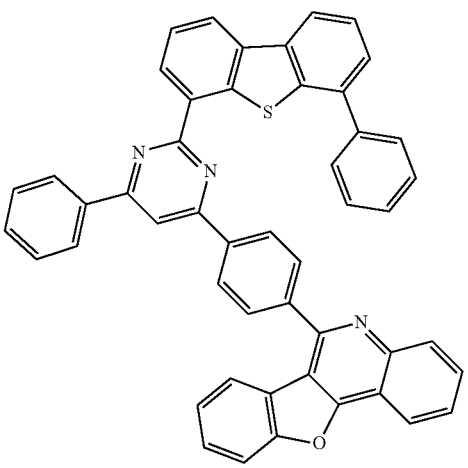

-continued
733
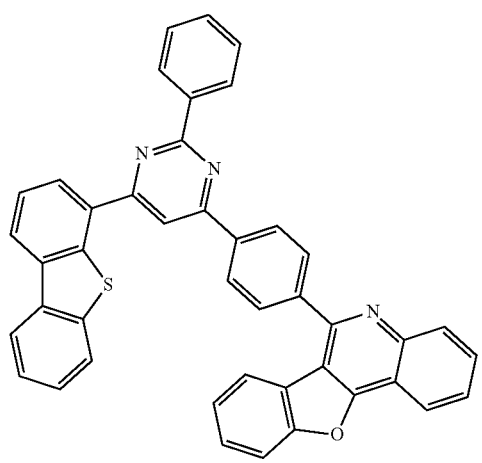
734
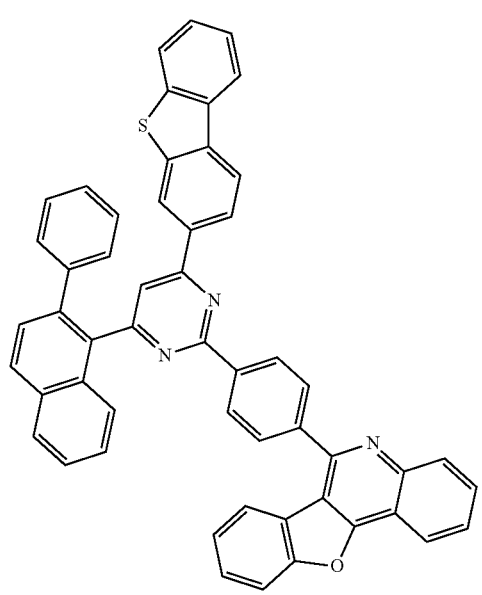
735
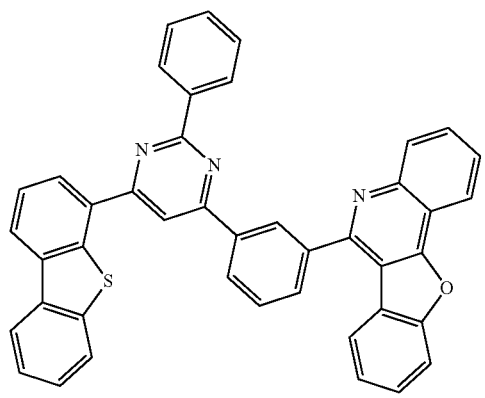
-continued
736
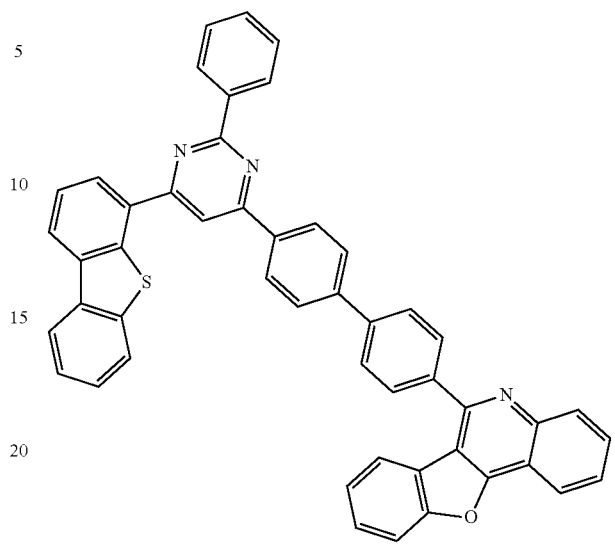
737
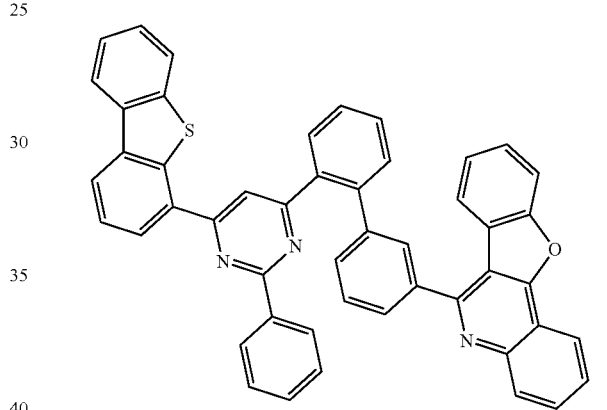
738
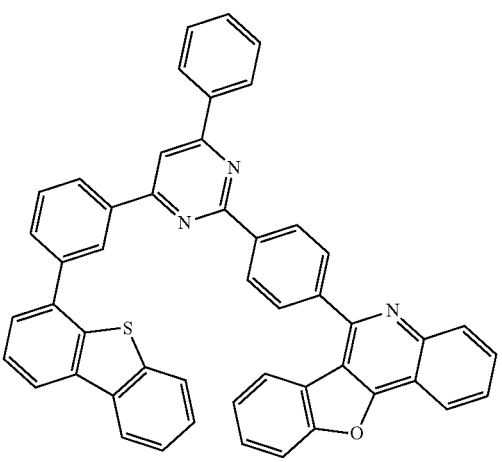

739
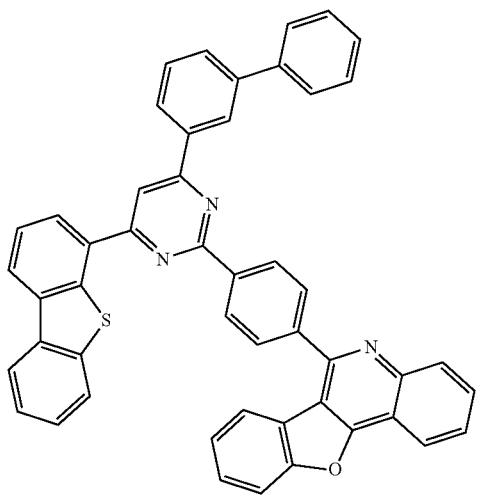
740
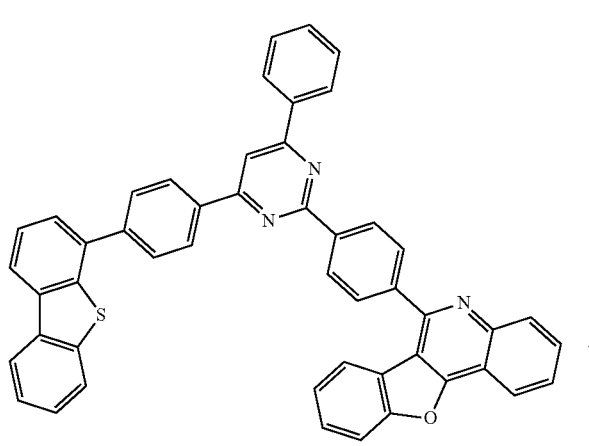
741
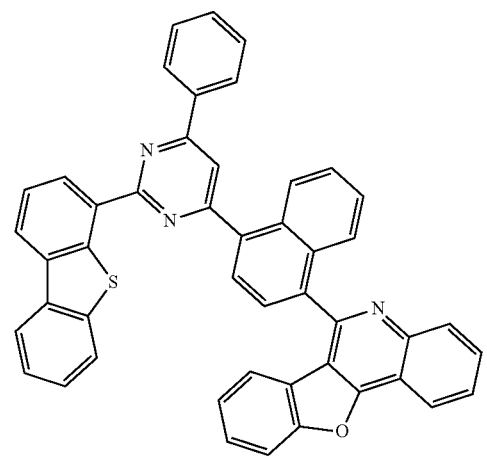
742
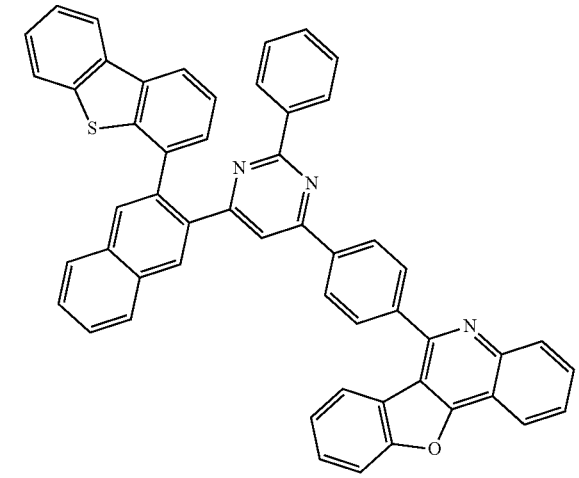
743
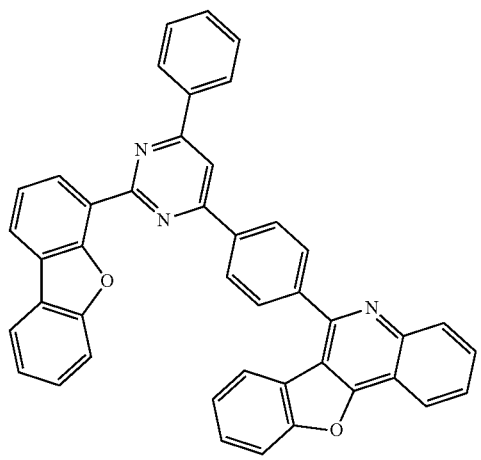
744
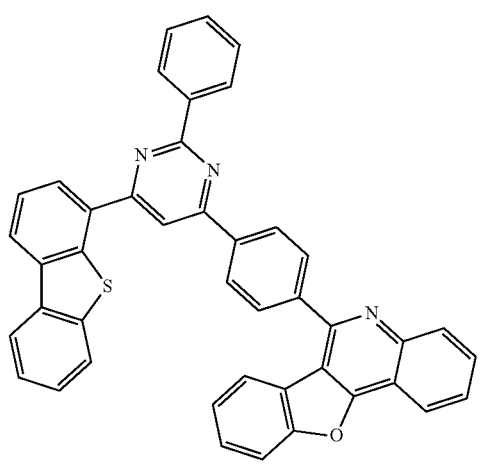

-continued
745
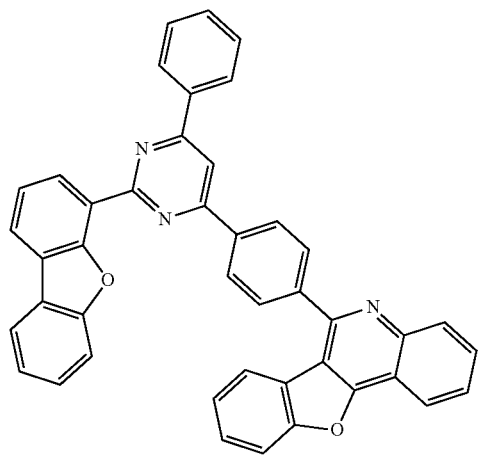
746
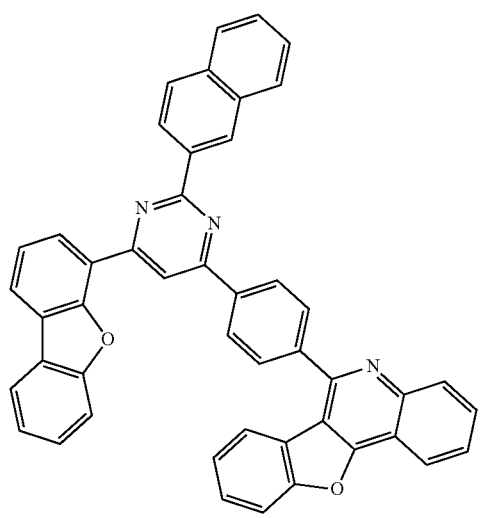
747
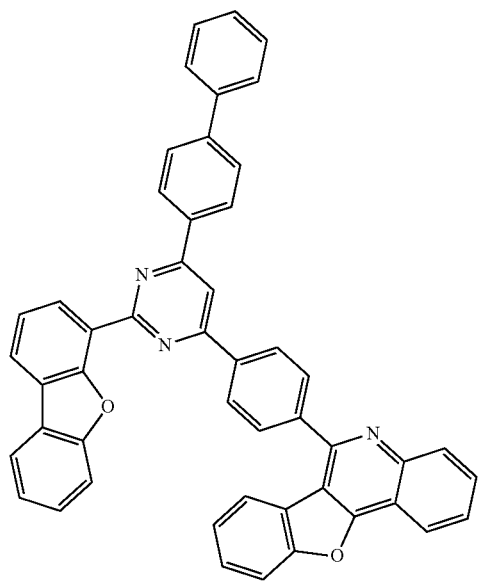
-continued
748
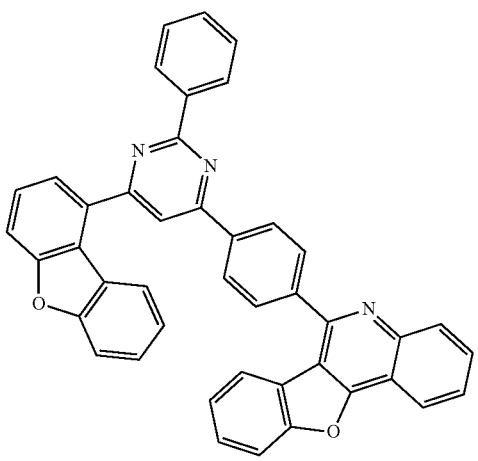
749
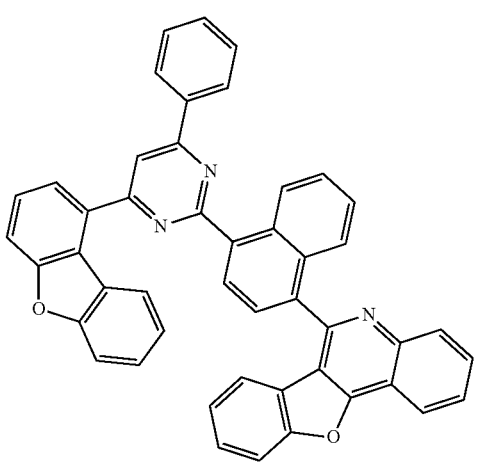
750
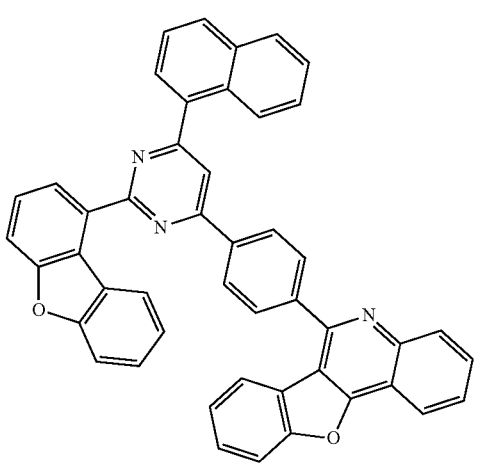

751
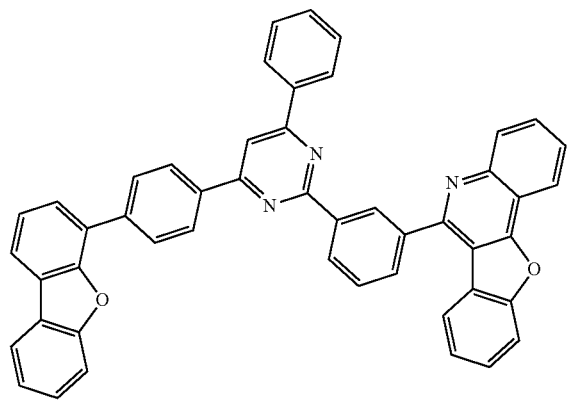
752
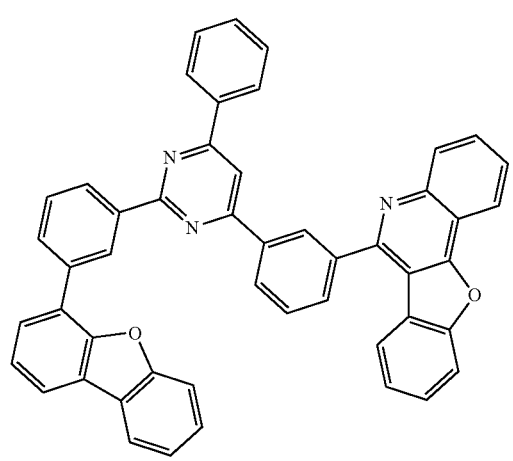
753
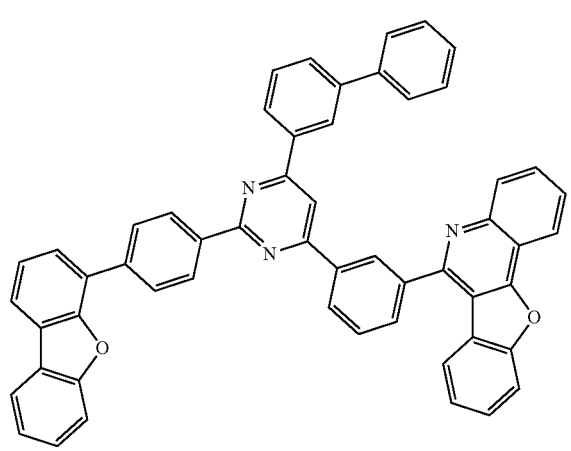
754
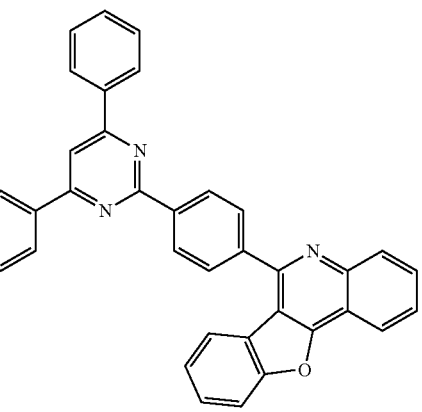
755
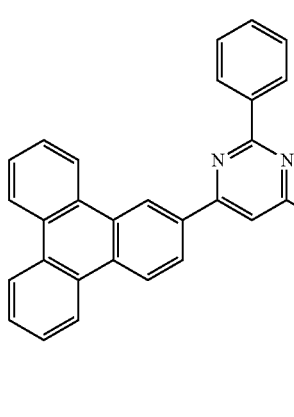
756
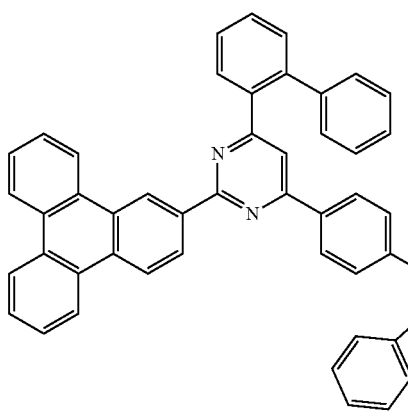

271
-continued
757
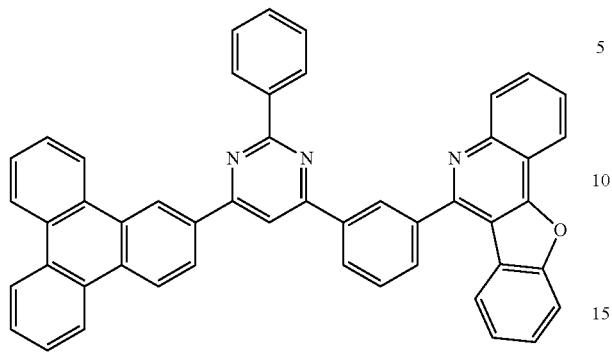
758
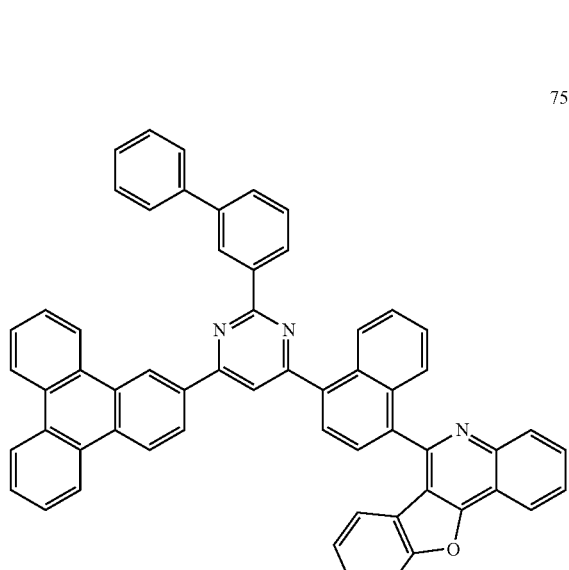
272
-continued
760
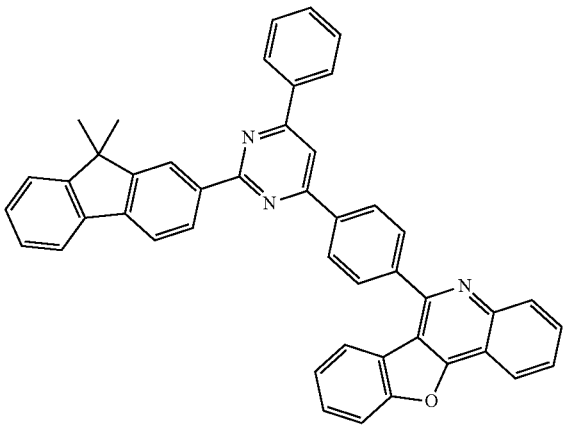
761
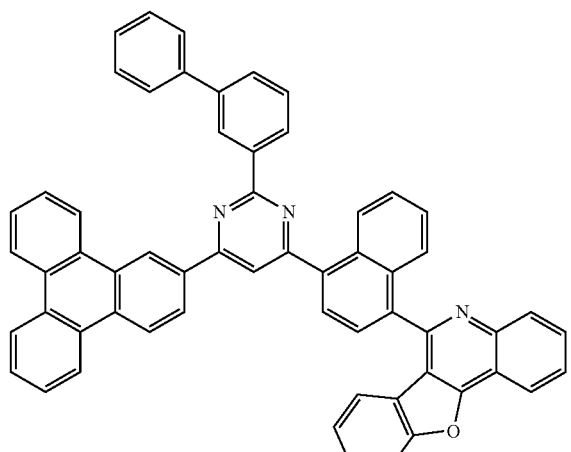
759
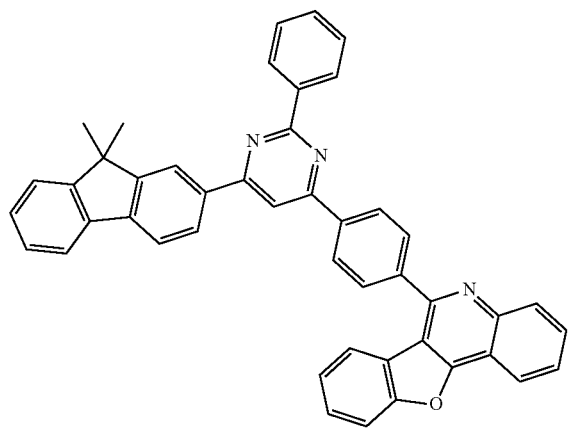
762
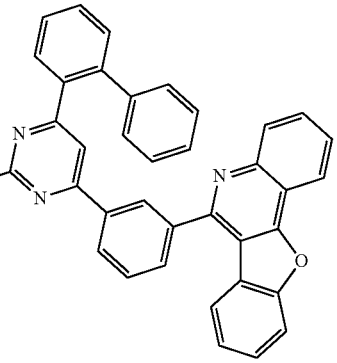

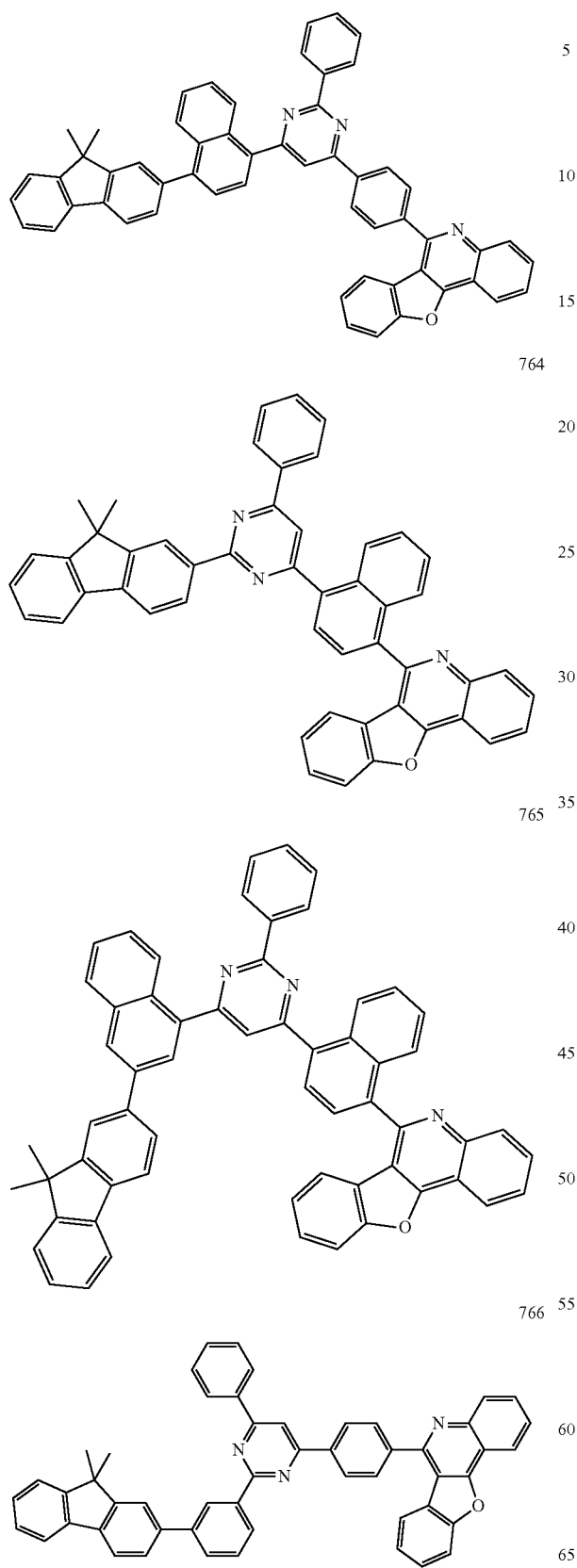
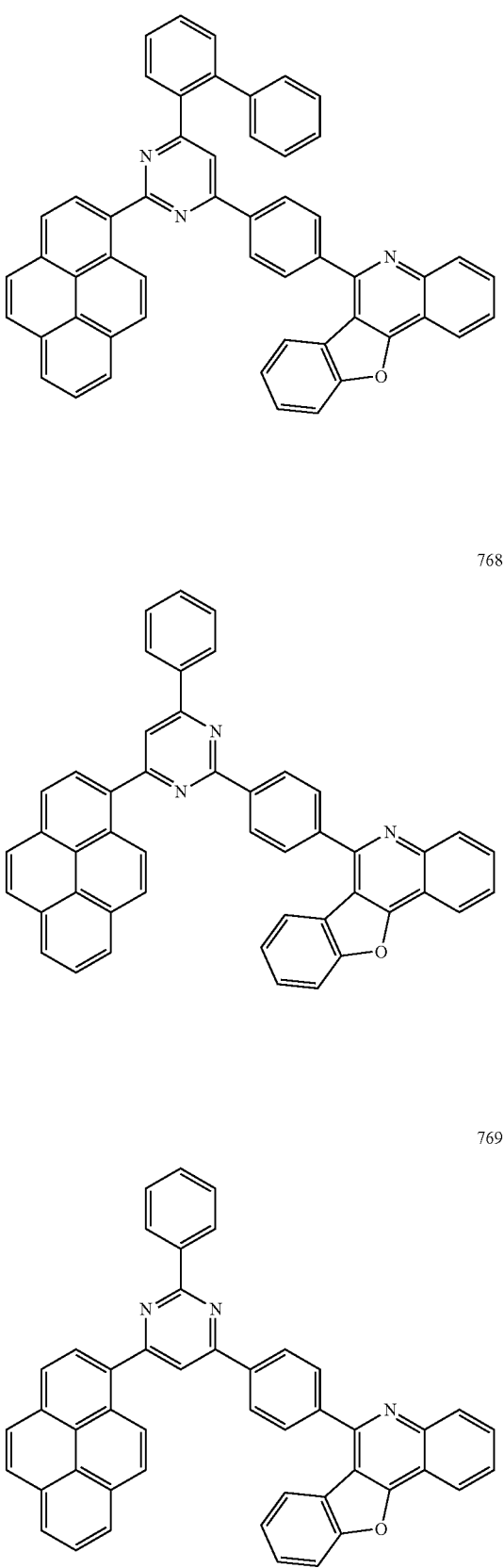

770
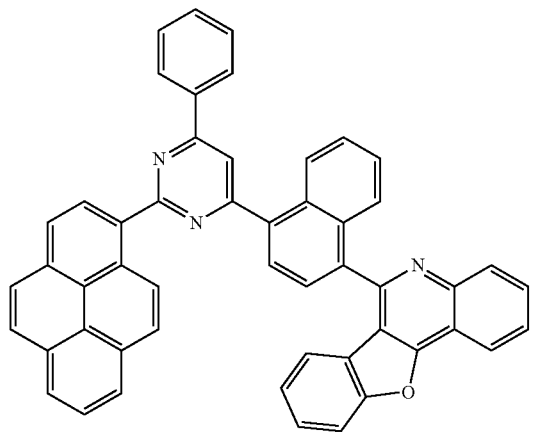
771
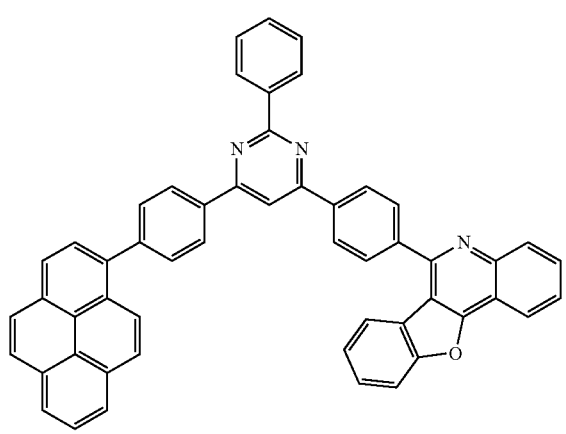
772
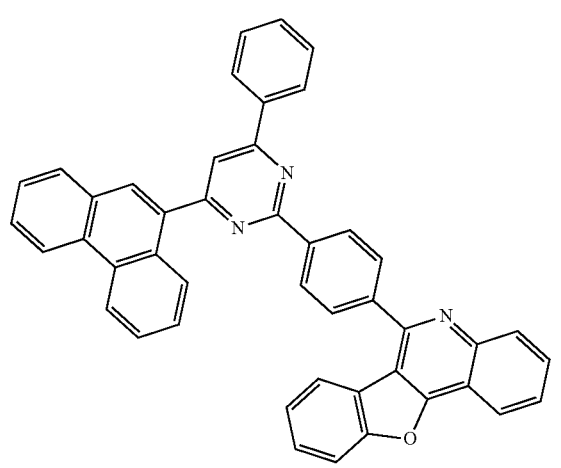
773
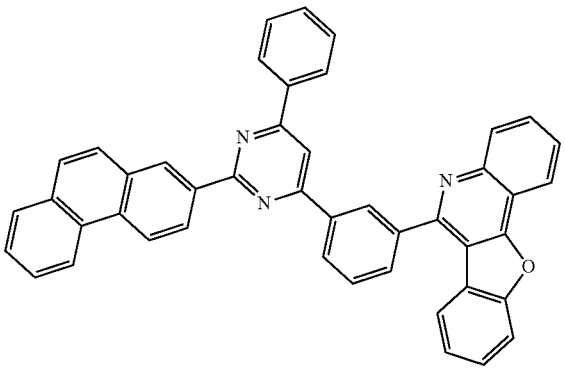
774
775
776
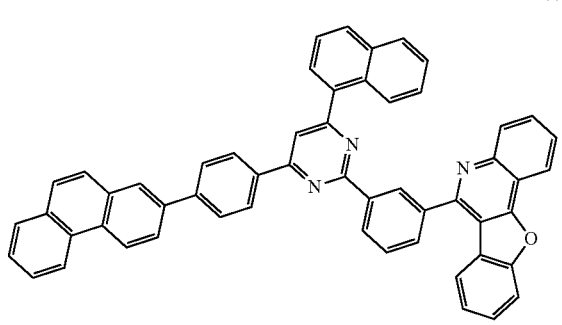

777
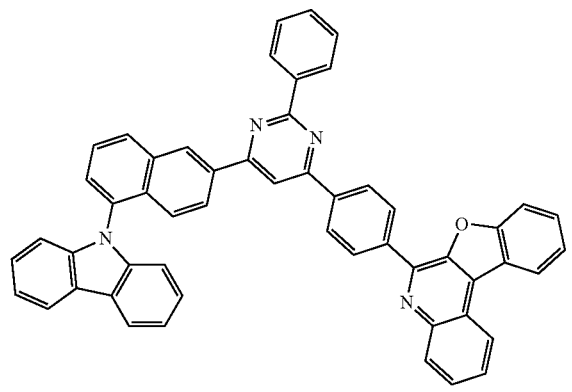
778
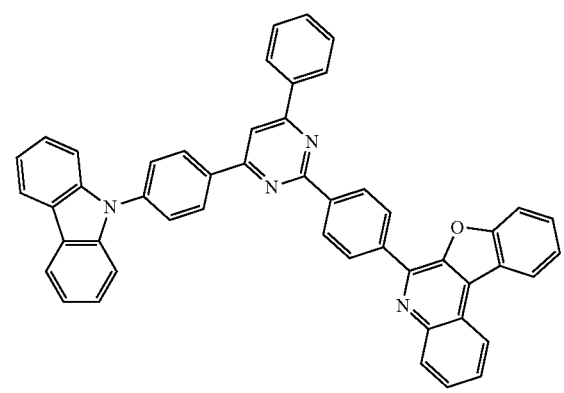
779
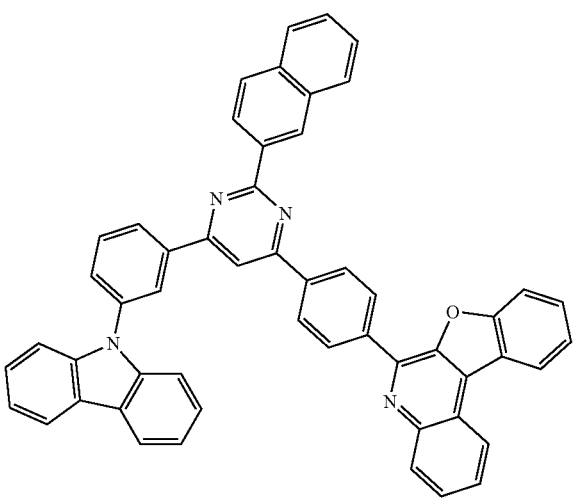
780
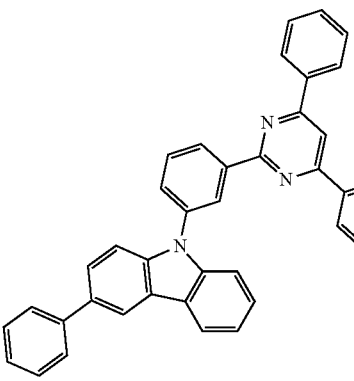
781
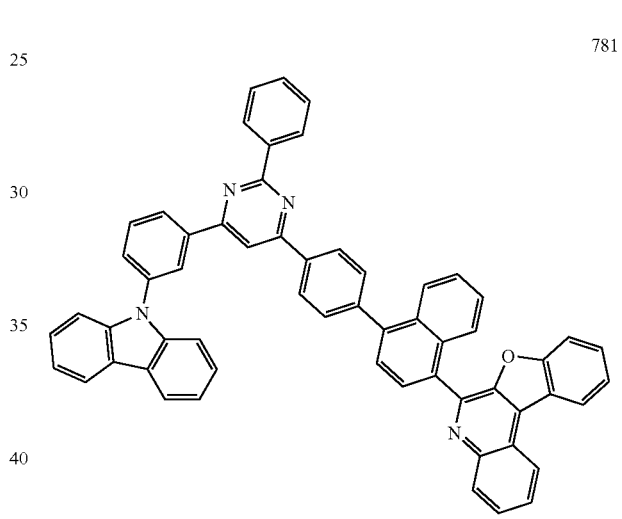
782
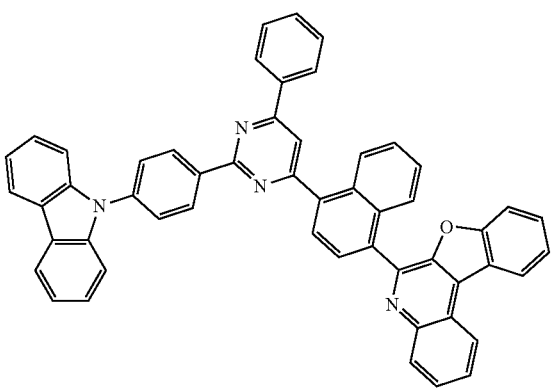

783
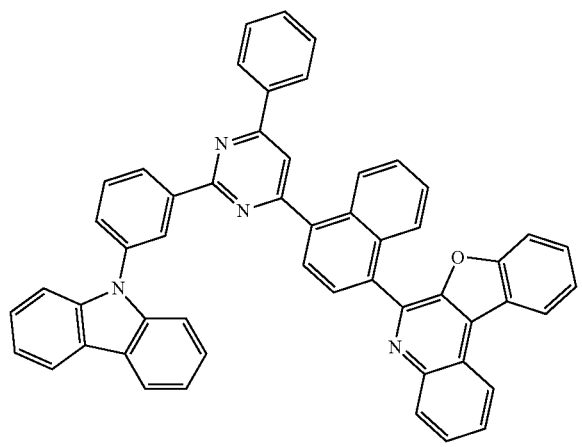
784
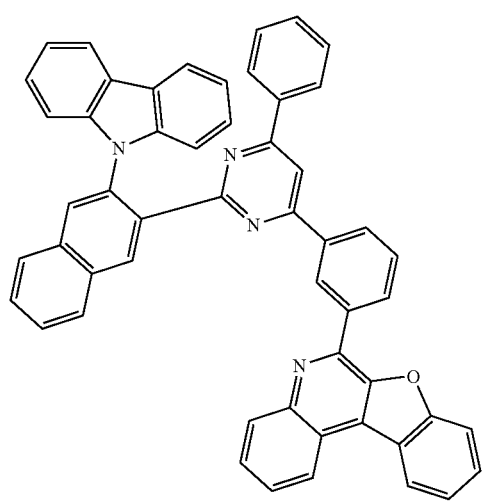
785
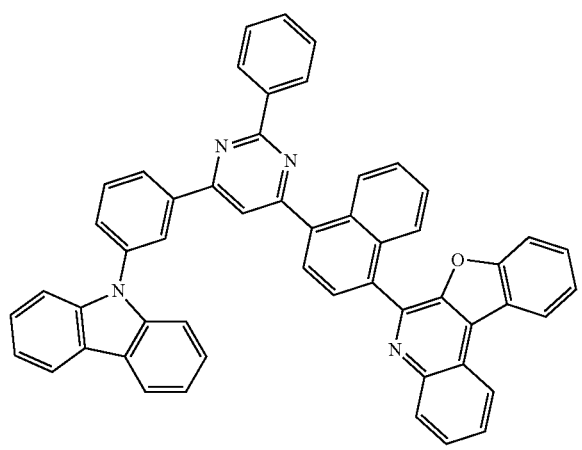
786
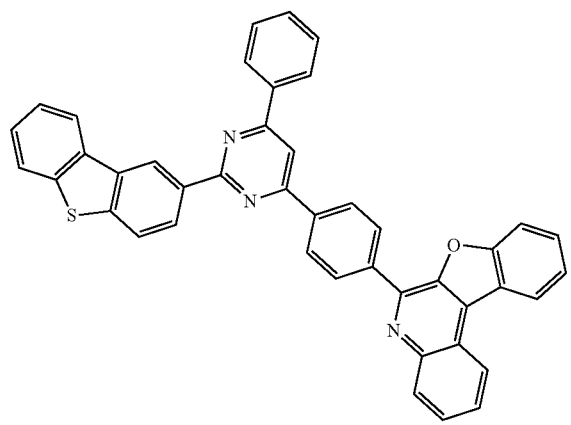
787
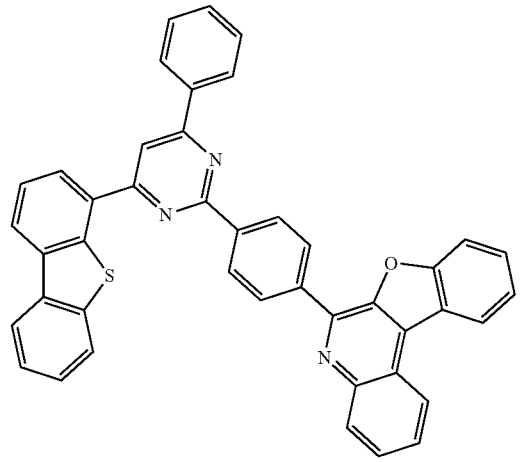
788
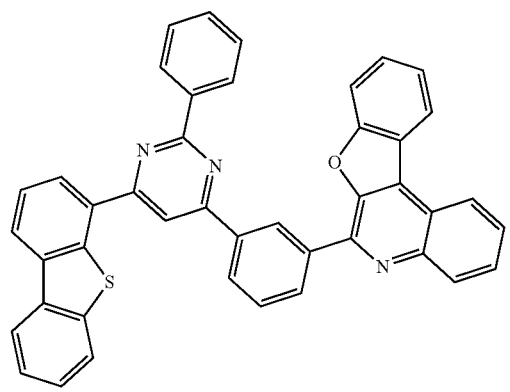

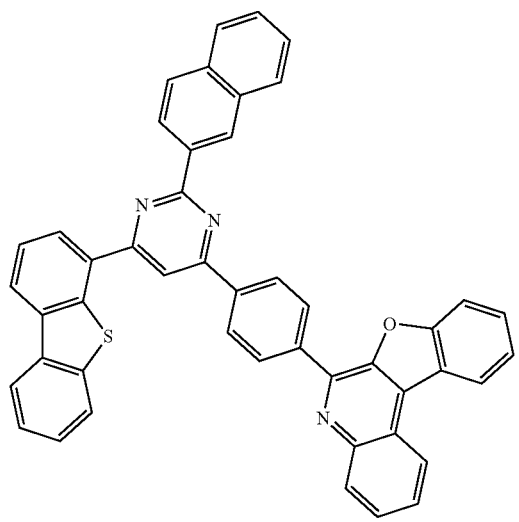
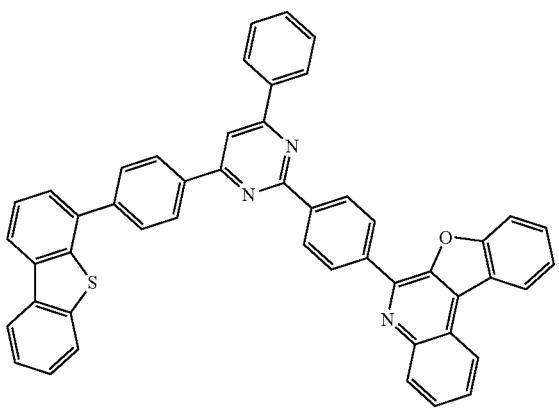
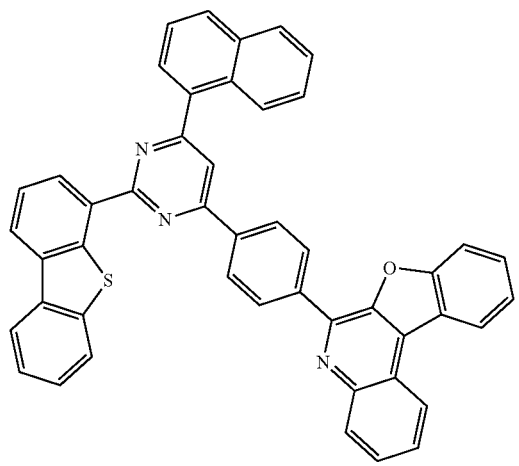
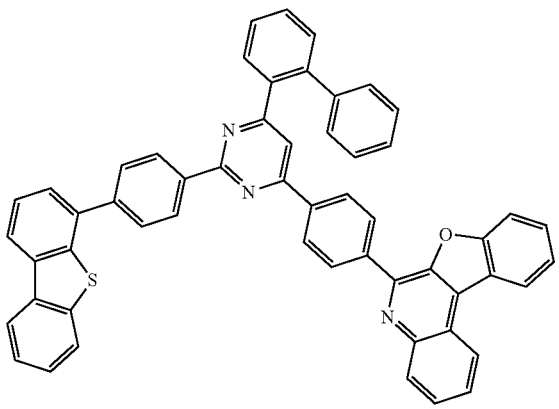

-continued
795
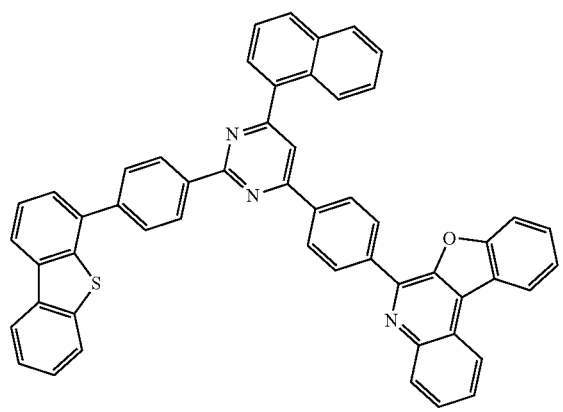
796
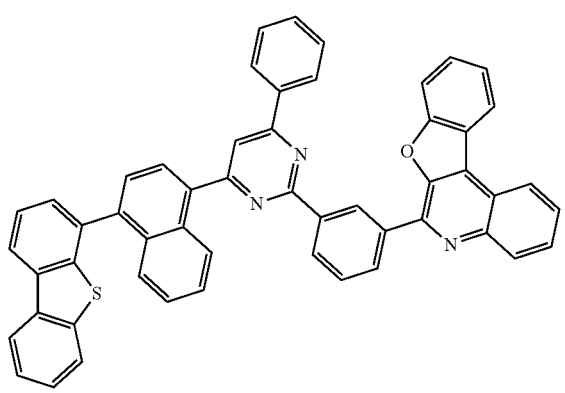
797
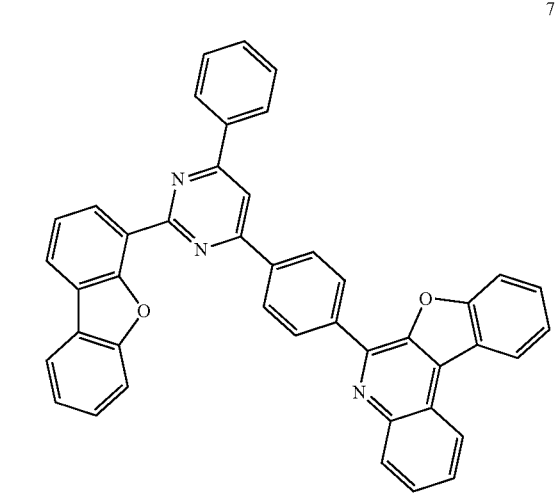
-continued
798
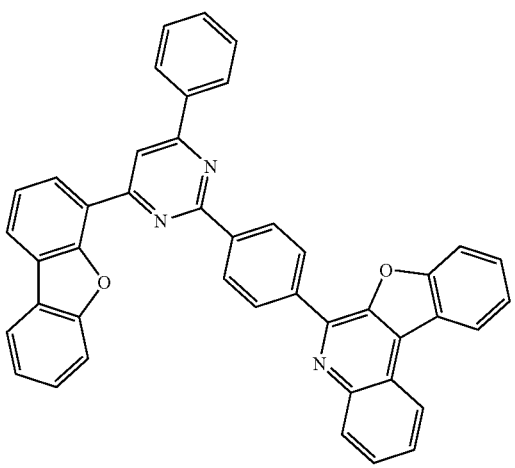
799
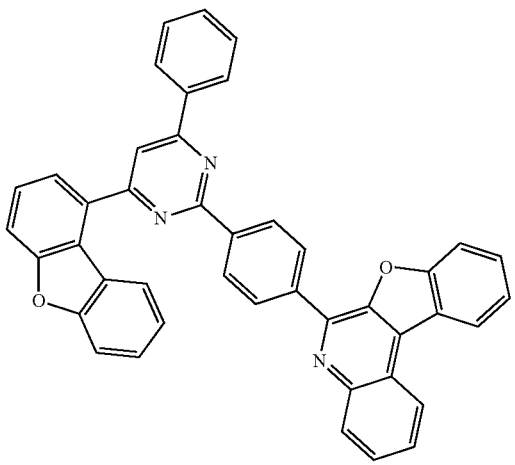
800
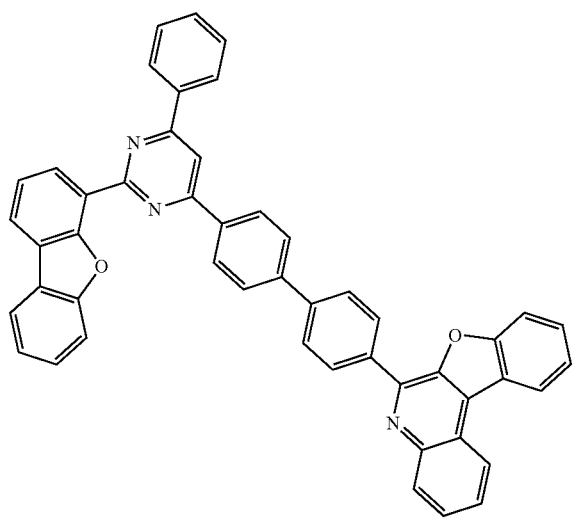

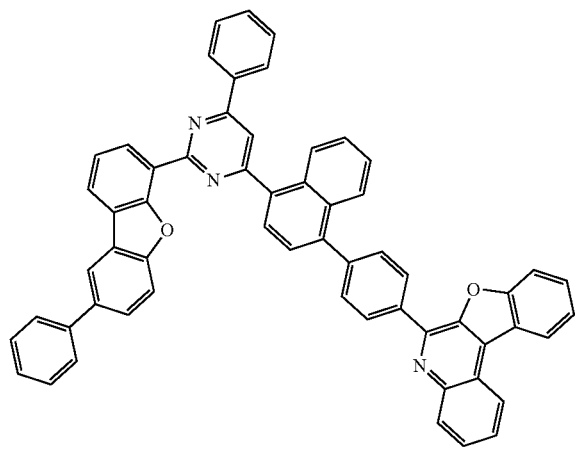
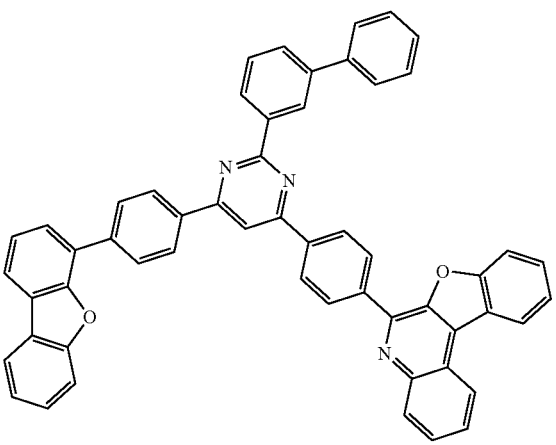
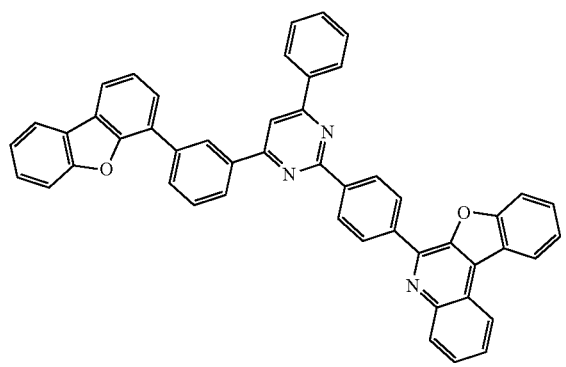

807
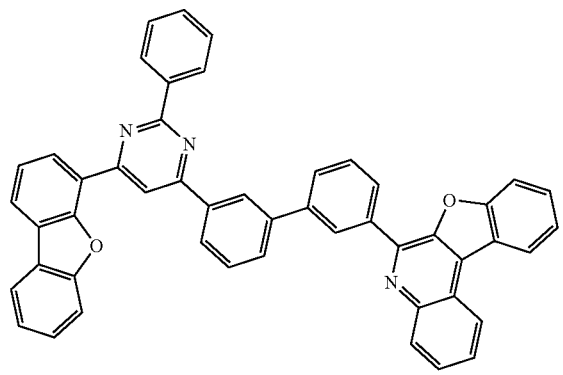
808
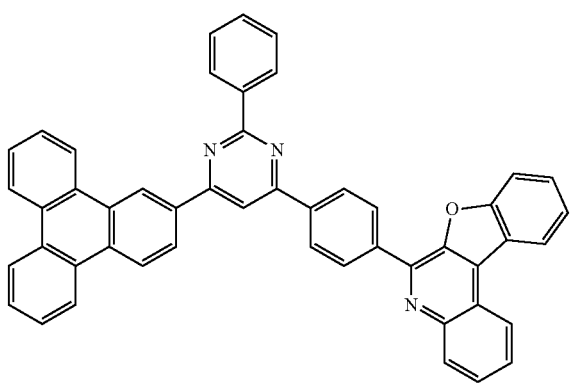 [SMILES: c1ccc(-c2nc(-c3ccc(-c4nc5ccccc5c5c4sc4ccccc45)cc3)cc(-c3ccc4c5ccccc5c5ccccc5c4c3)n2)cc1]
809
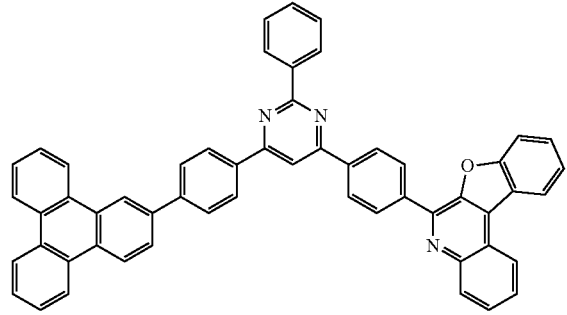
810
811
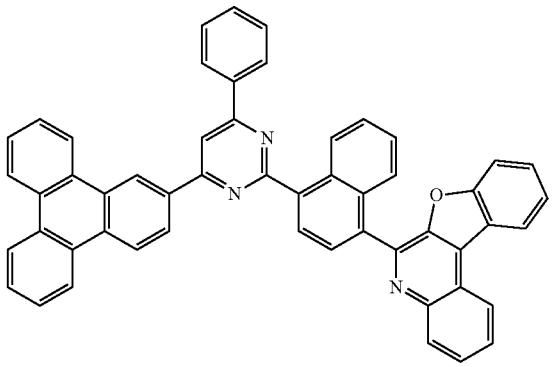
812
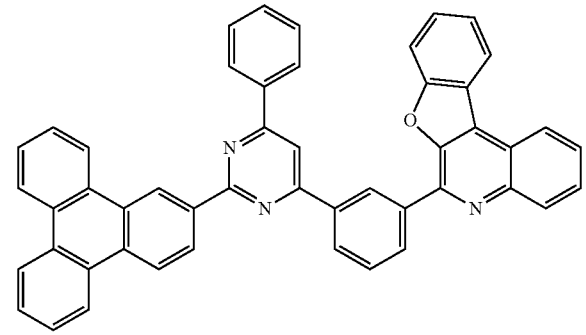
813
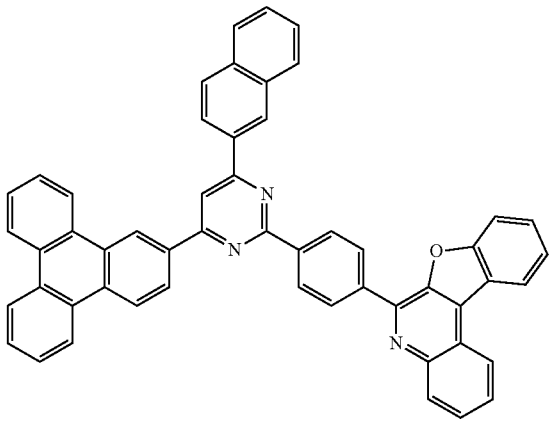
814
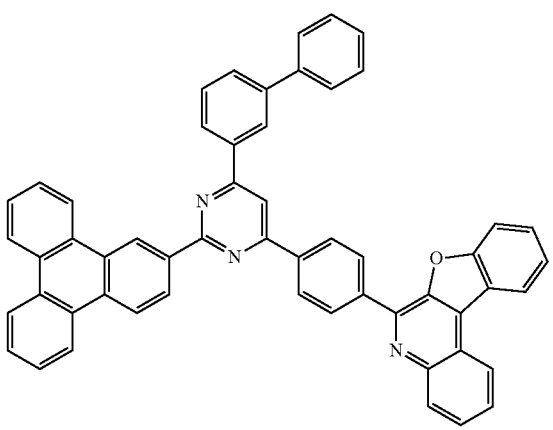

815
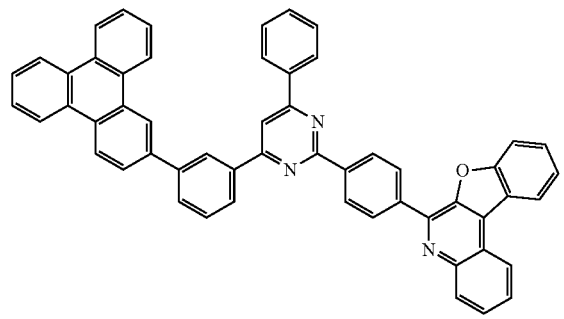
816
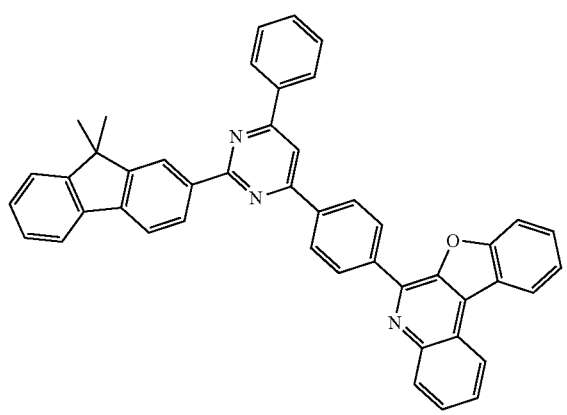
817
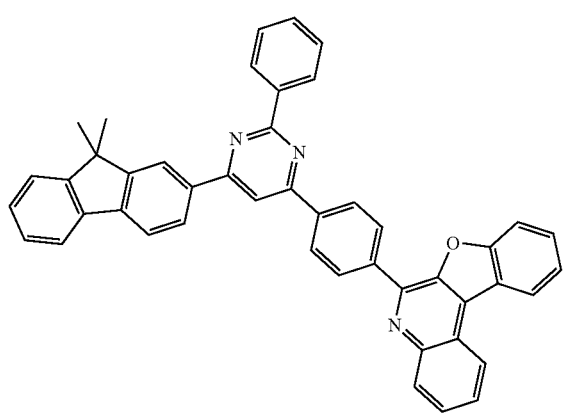
818
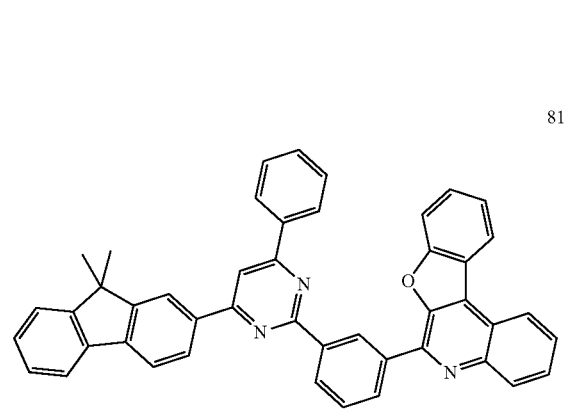
819
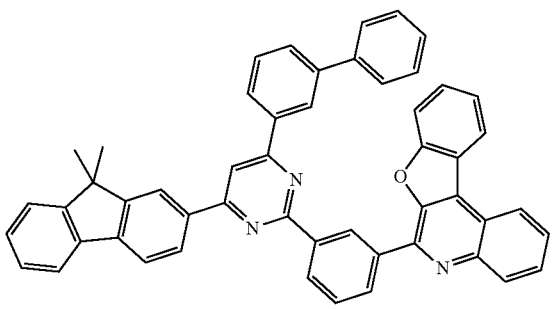
820
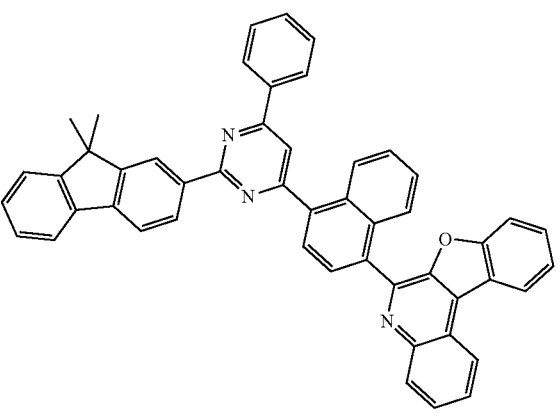
821
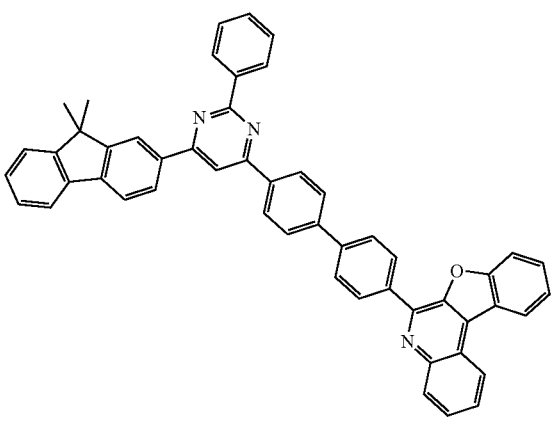
822
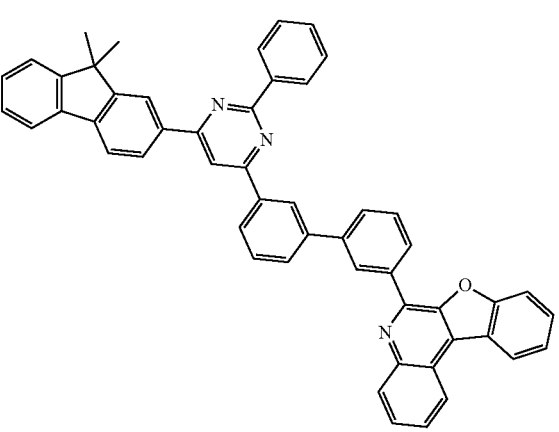

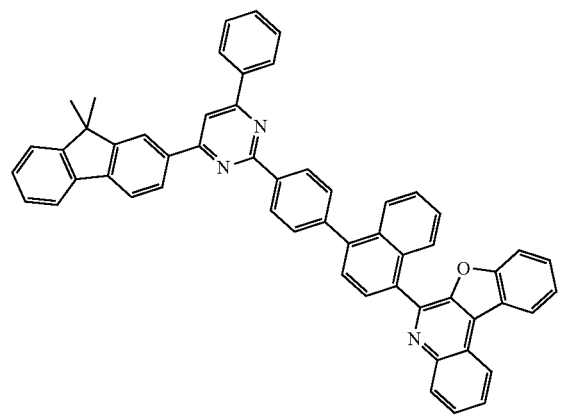
823
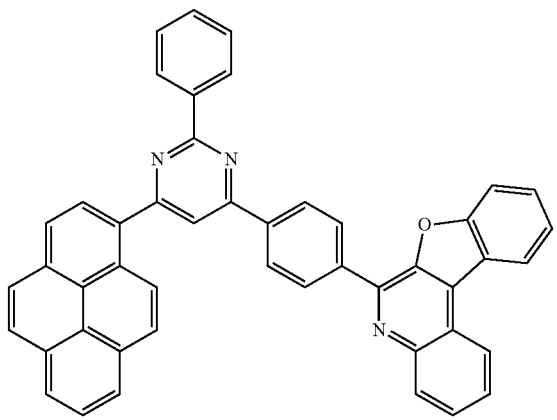
826
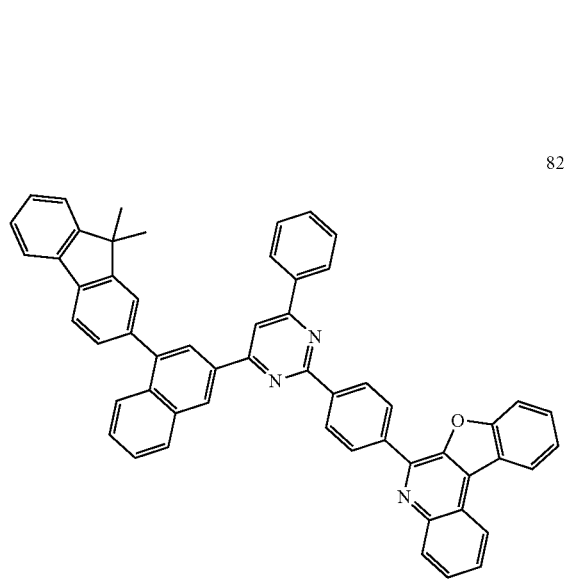
824
827
828
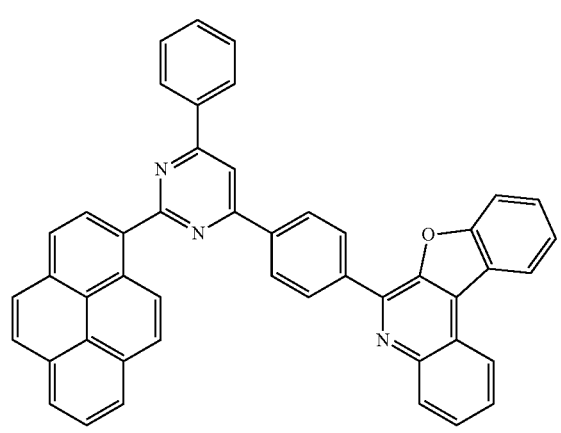
825
829

830
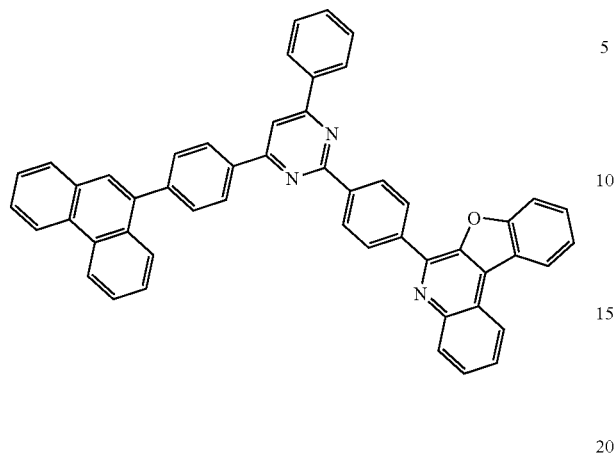
831
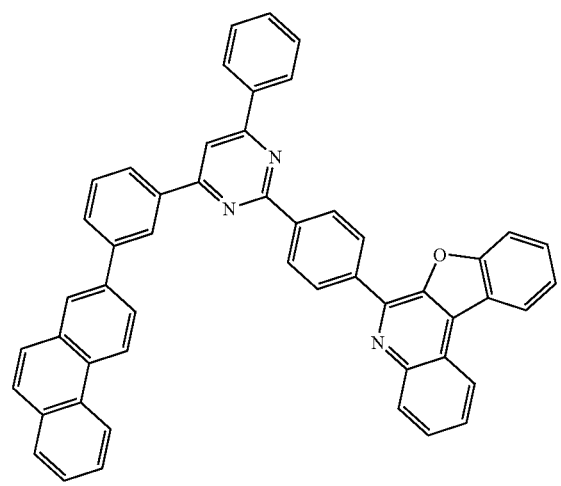
832
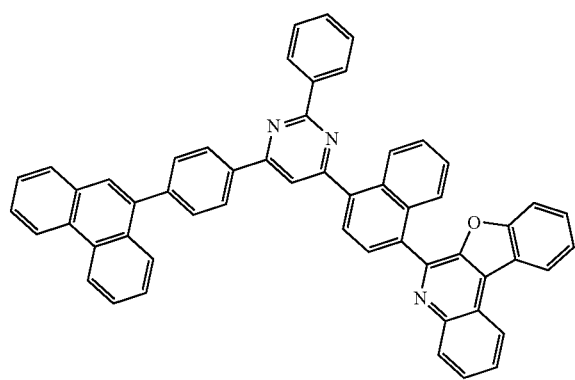
833
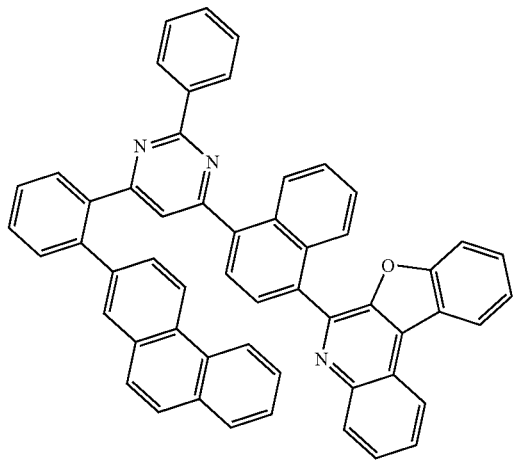
834
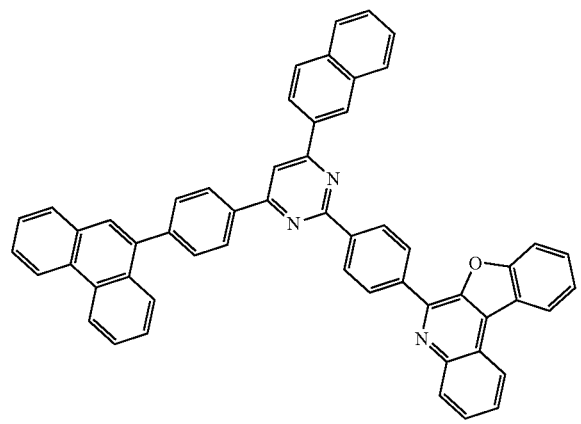
835
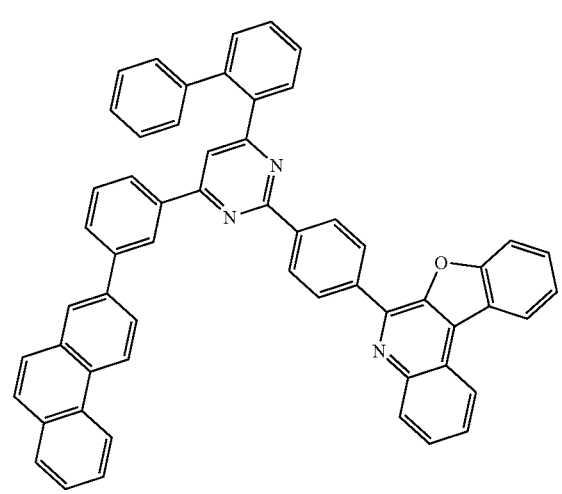

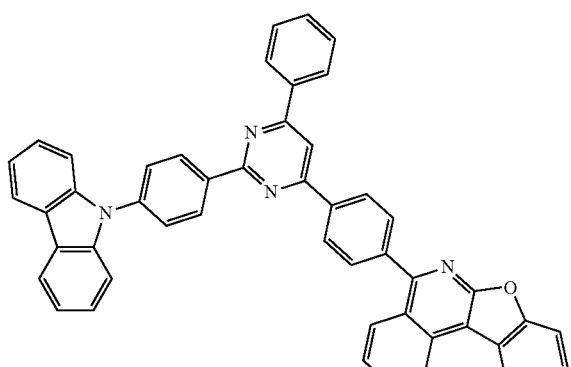
836
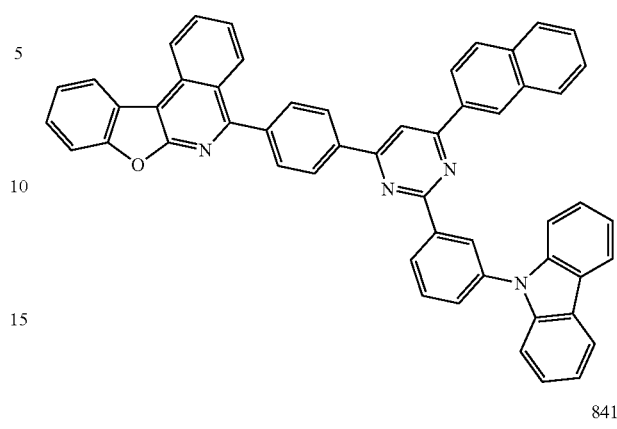
840
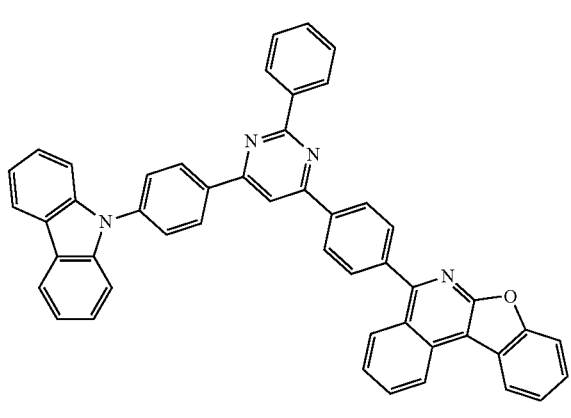
837
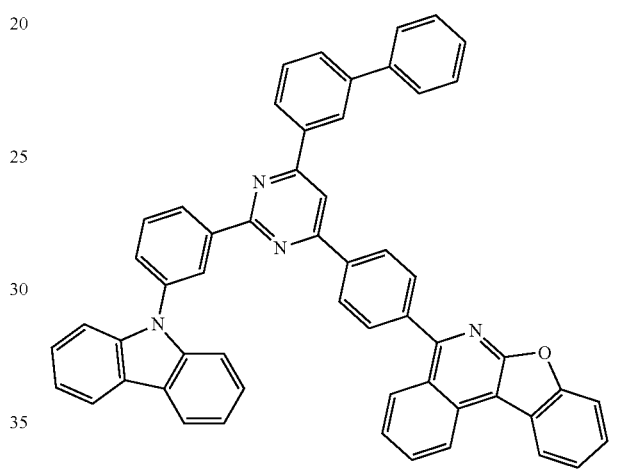
841
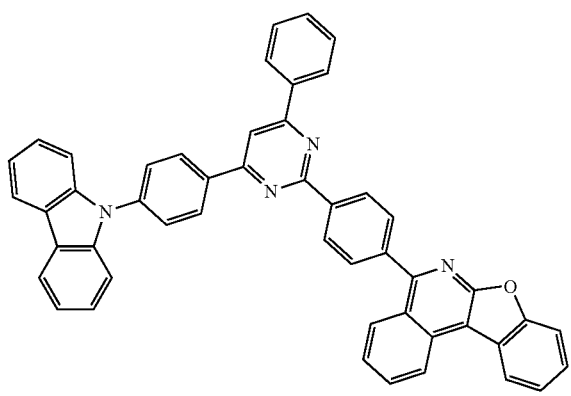
838
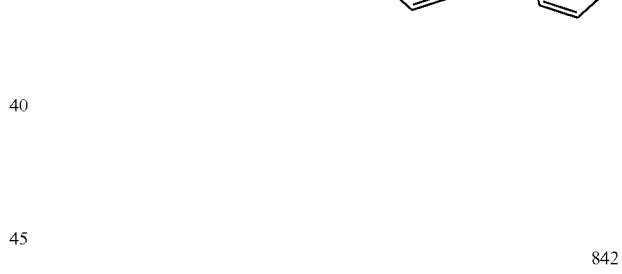
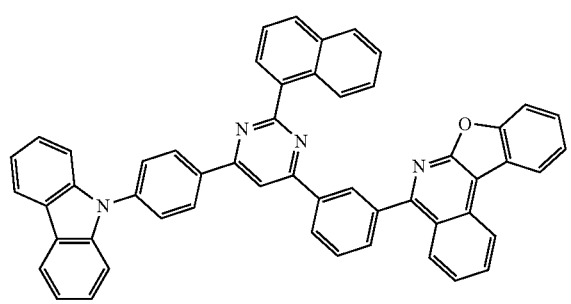
389
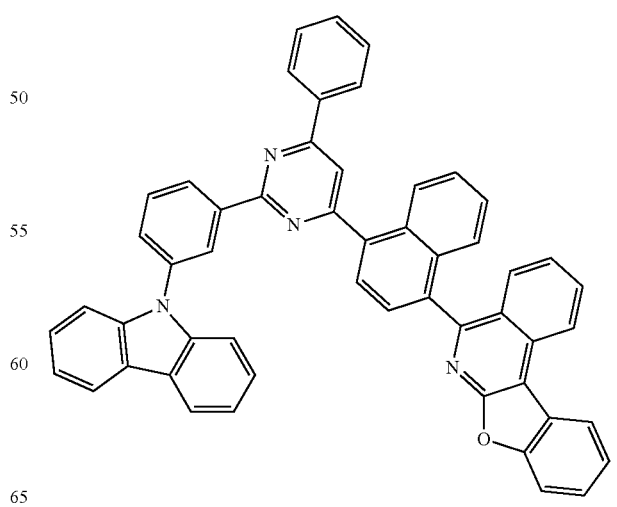
842

843
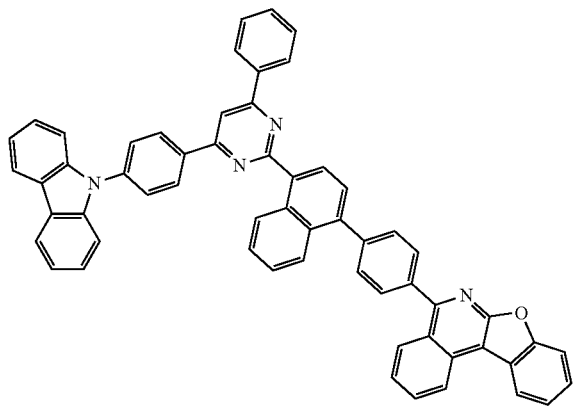
844
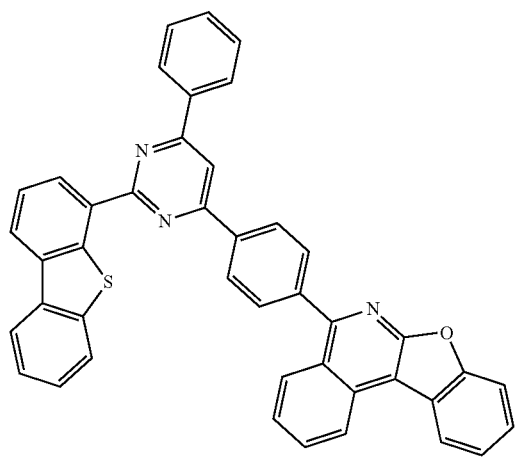
845
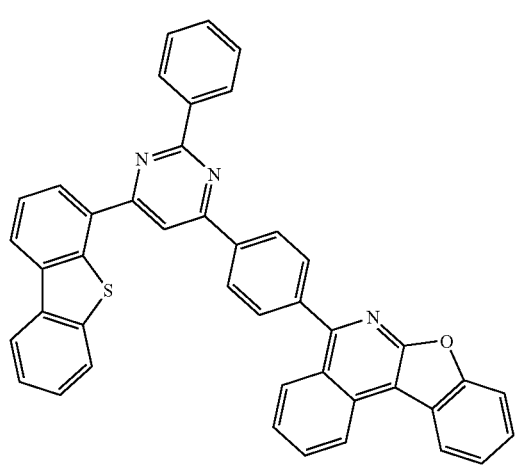
846
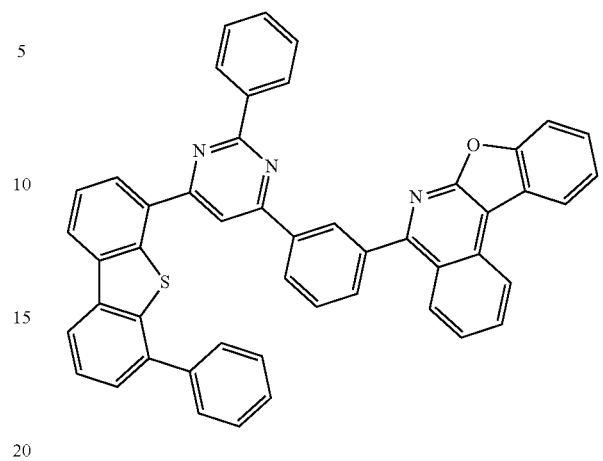
847
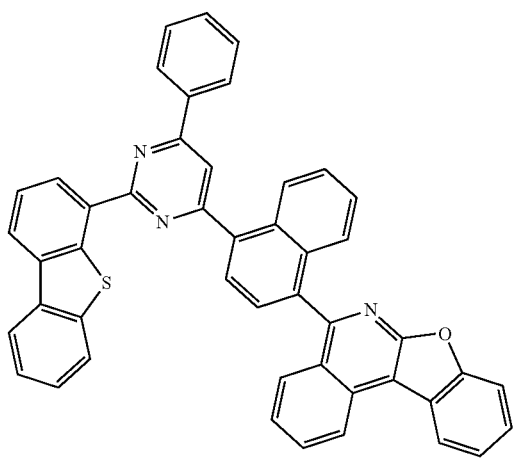
848
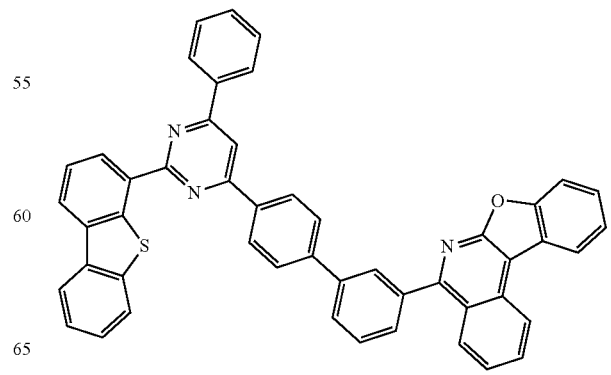

849
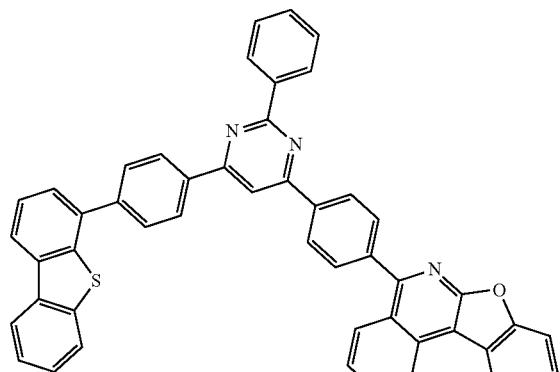
850
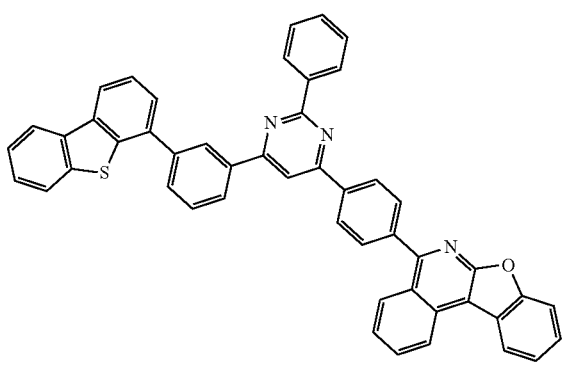
851
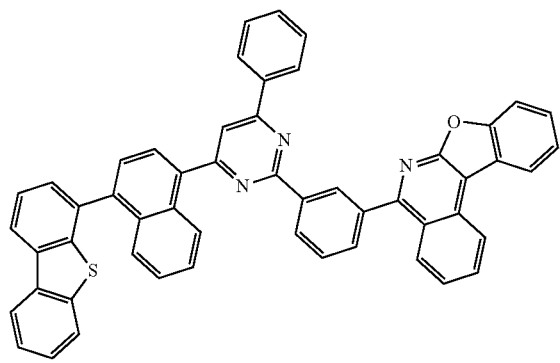
852
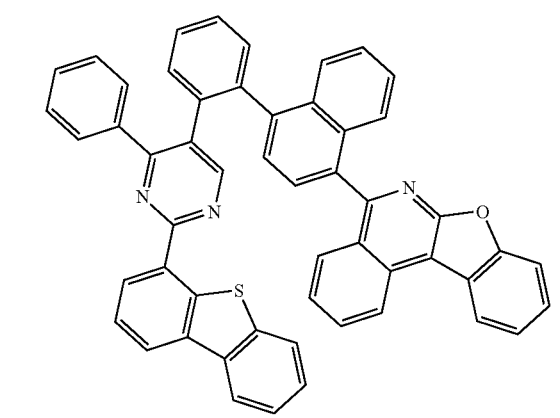
853
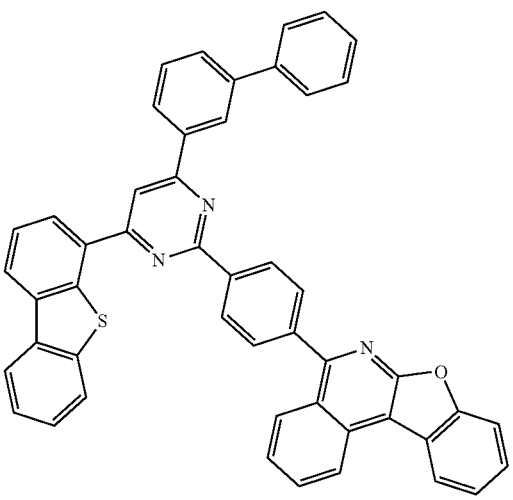
854
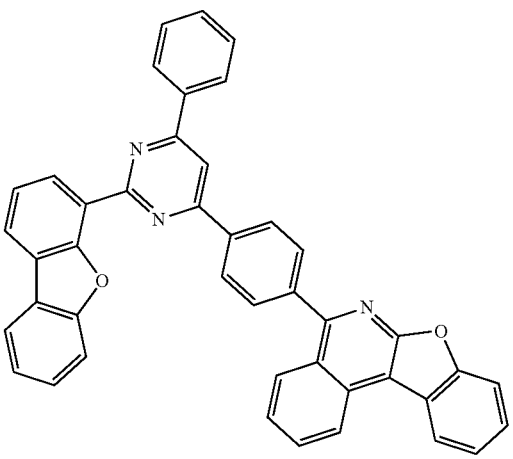
855
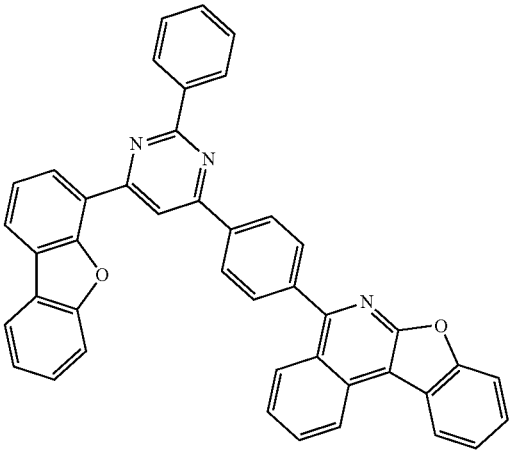

-continued
856
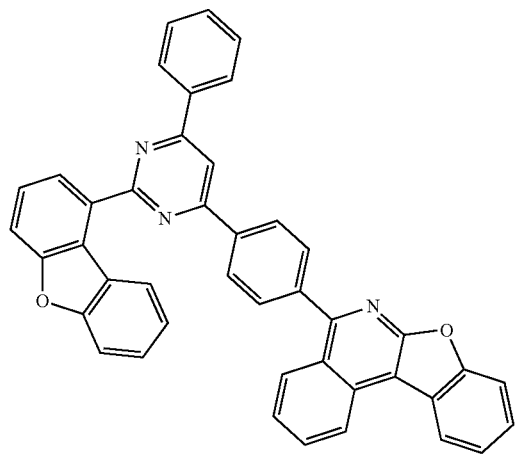
857
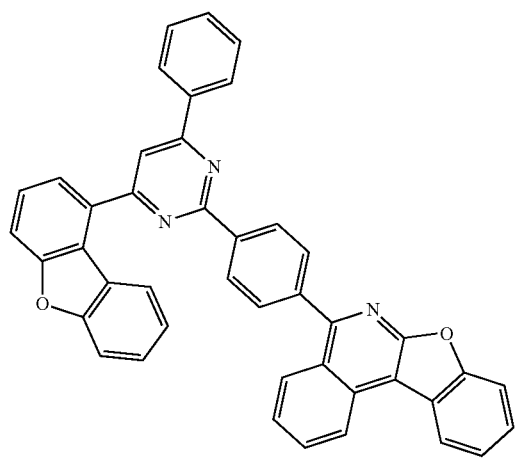
858
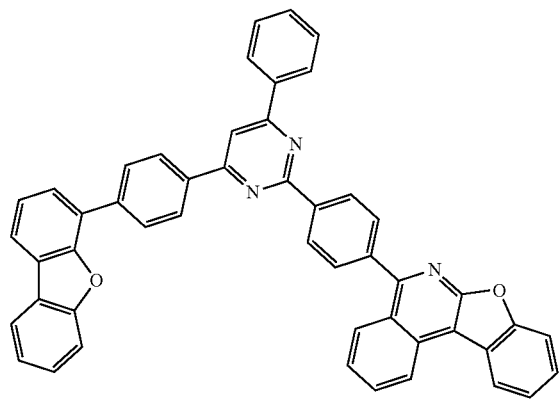
-continued
859
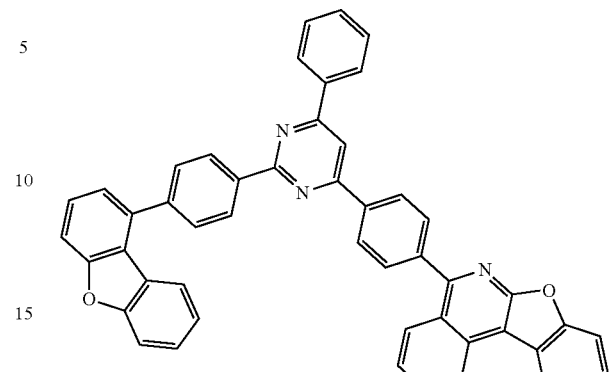
860
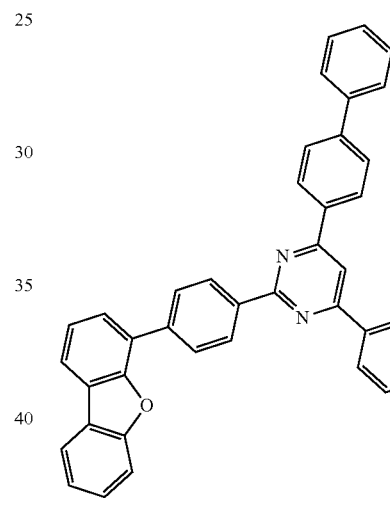
861
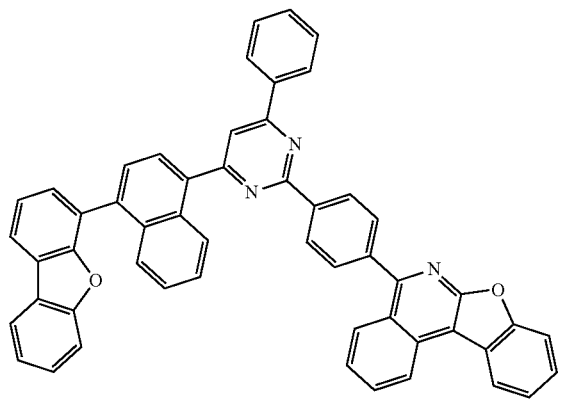

303
-continued
862
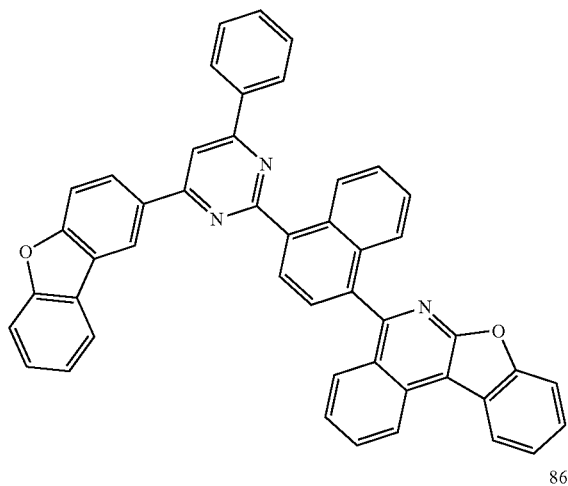
863
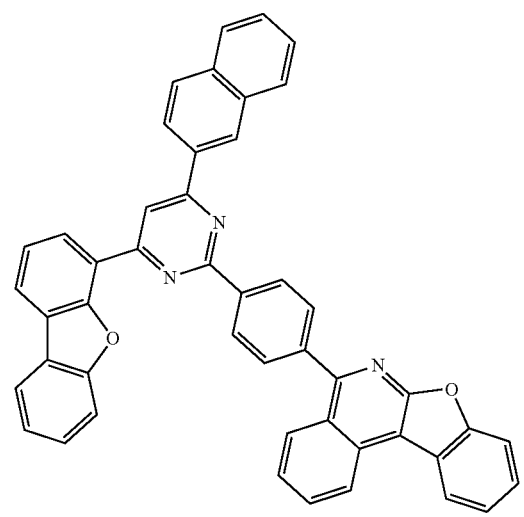
864
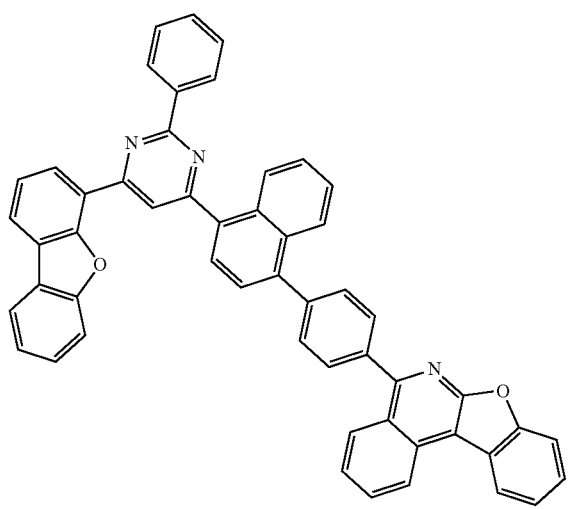
304
-continued
865
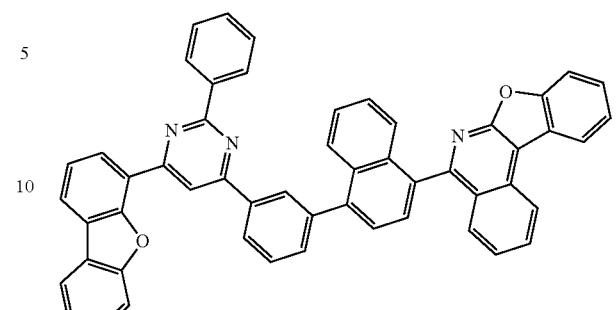
866
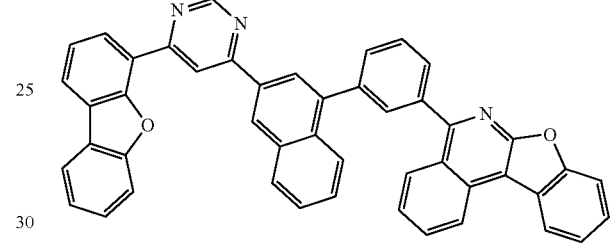
867
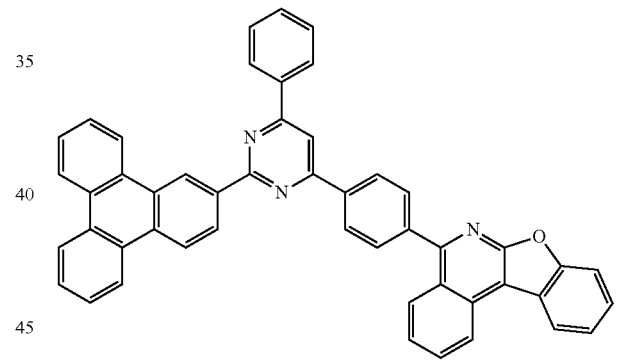
868
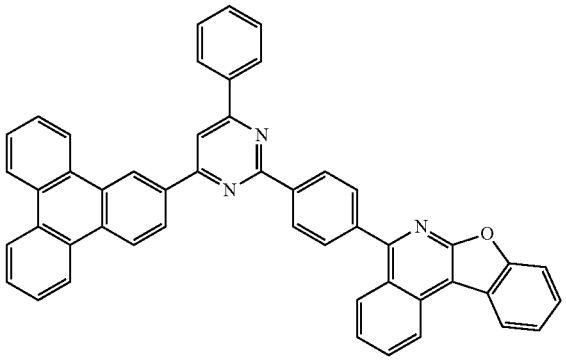

305
-continued
869
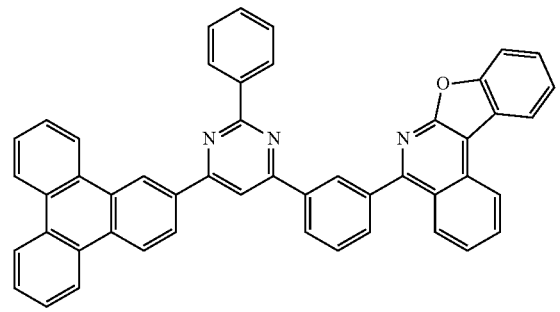
870
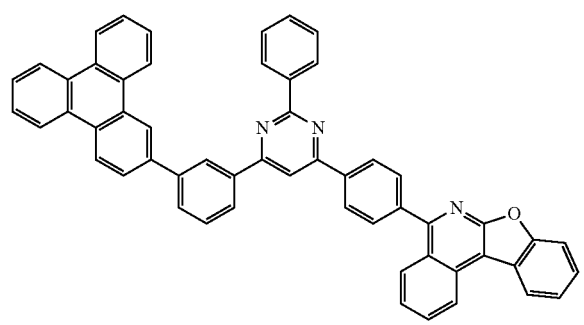
871
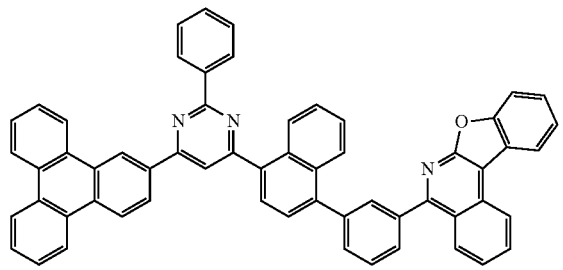
872
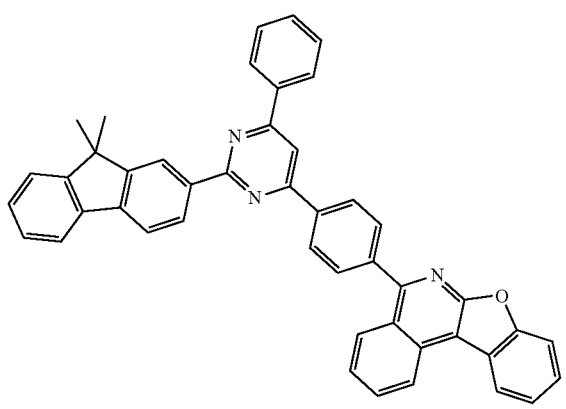
306
-continued
873
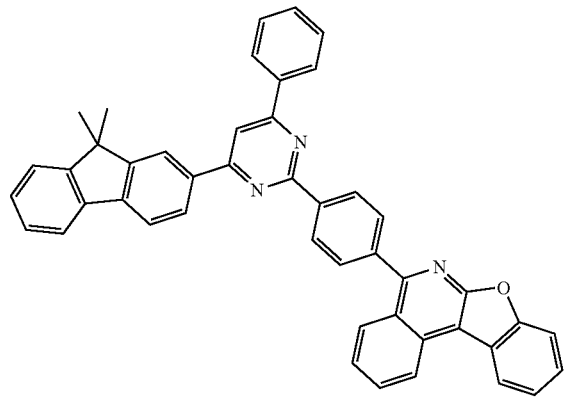
874
875
876
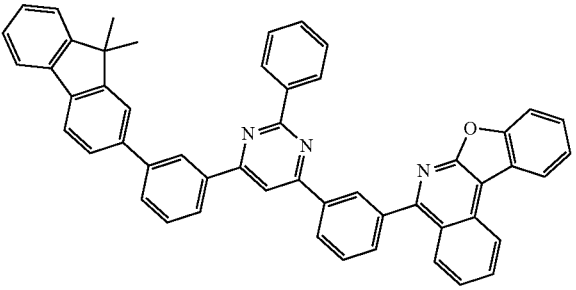

307
-continued
877
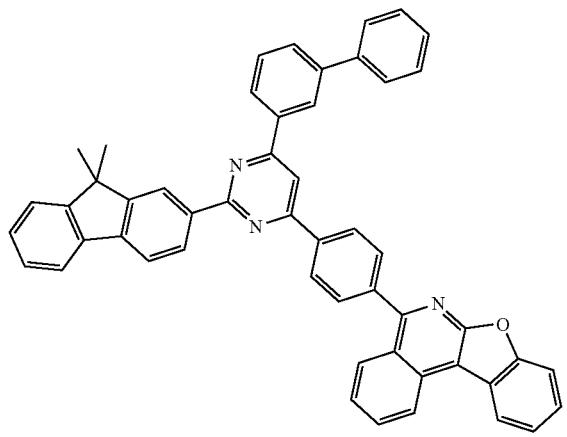
878
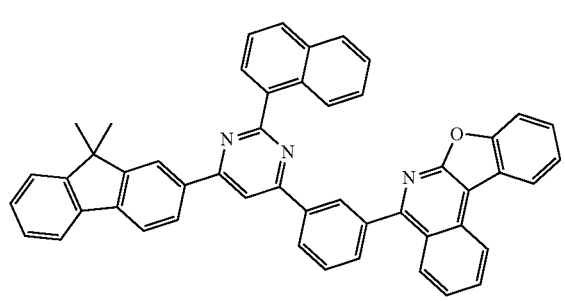
879
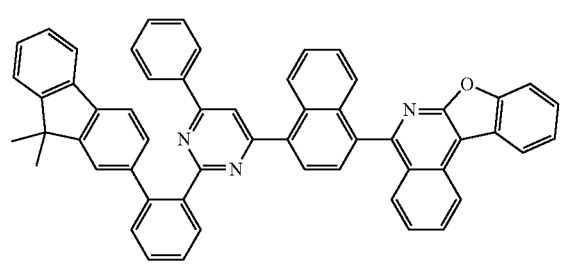
880
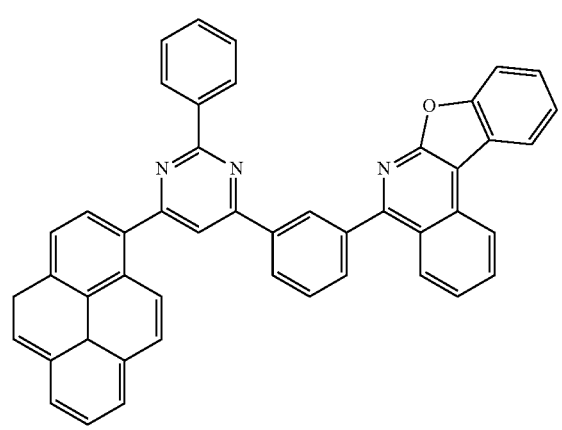
308
-continued
881
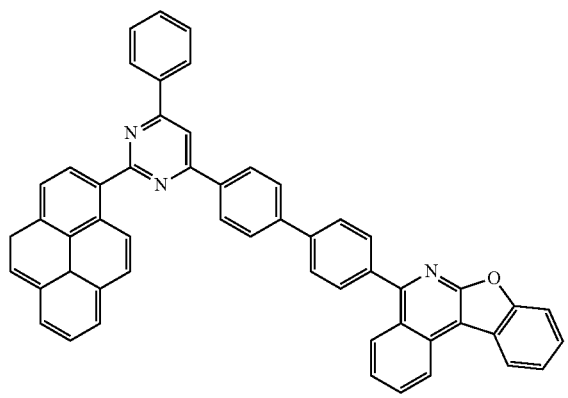
882
883
884
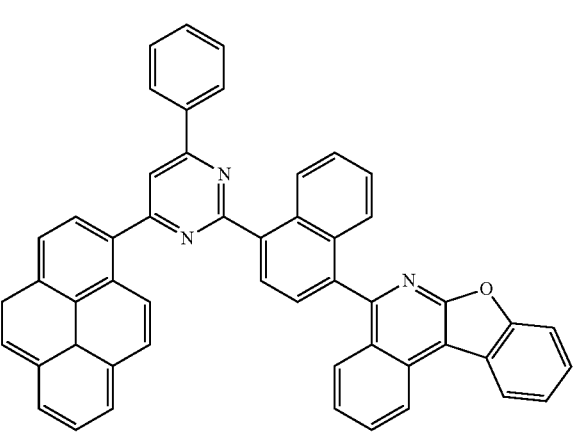

885
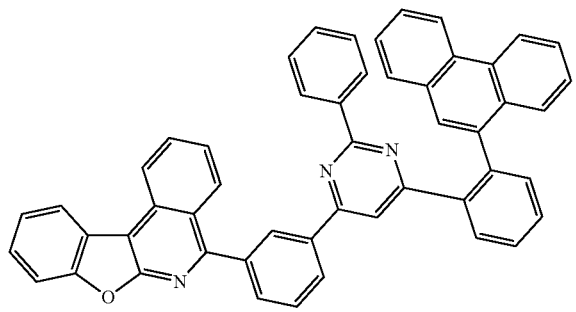
886
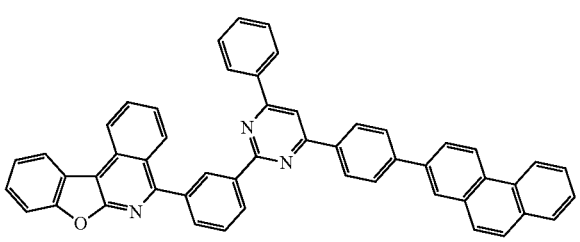
887
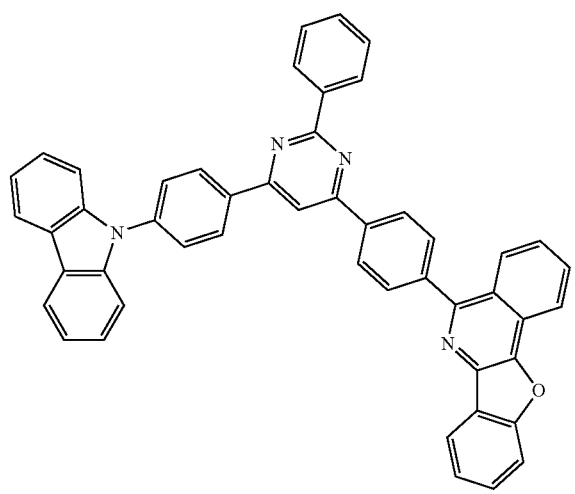
888
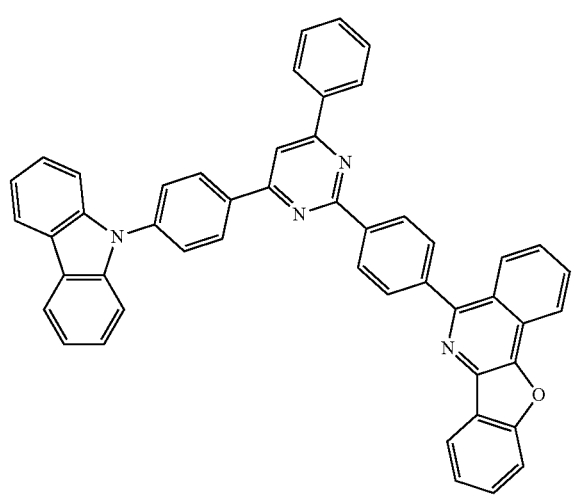
889
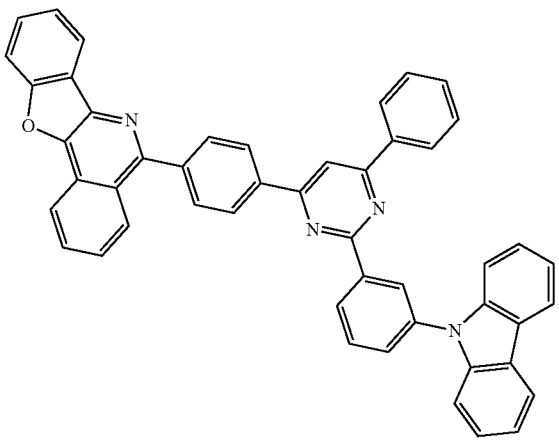
890
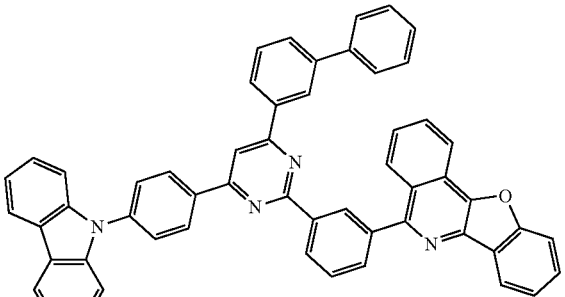
891
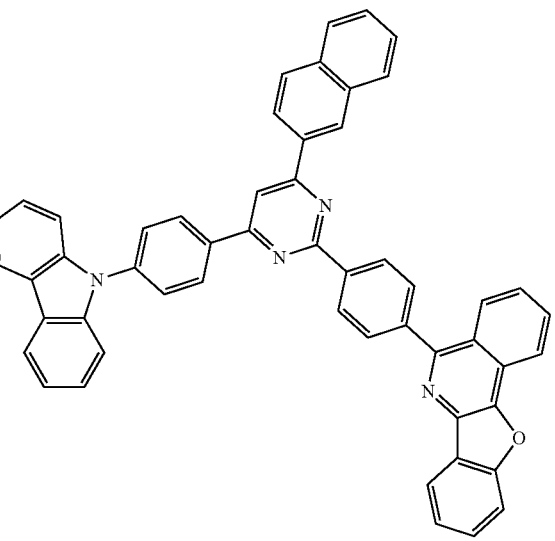

311
-continued
892
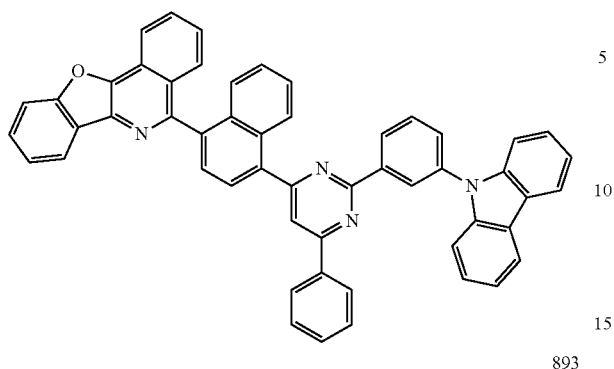
893
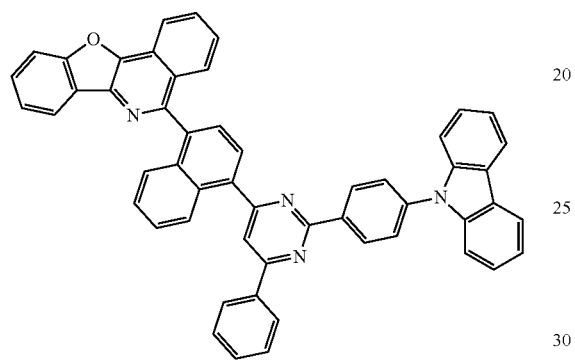
894
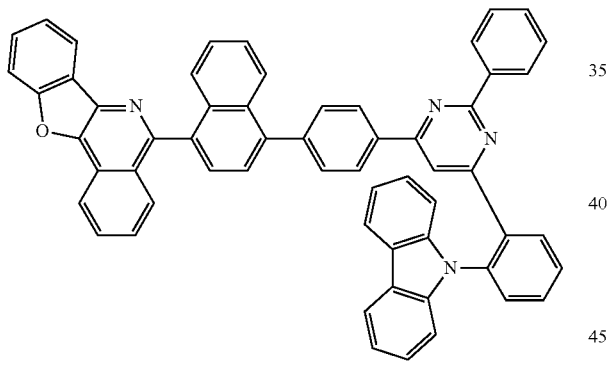
895
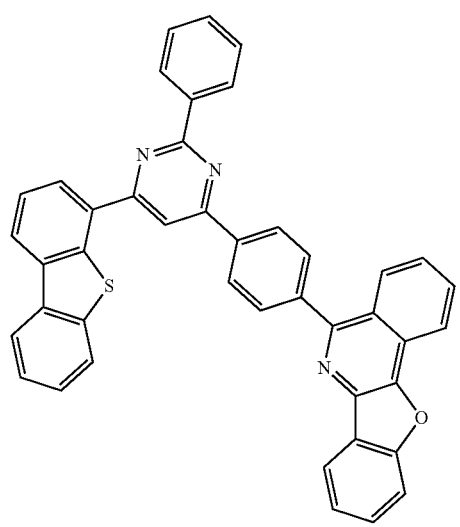
312
-continued
896
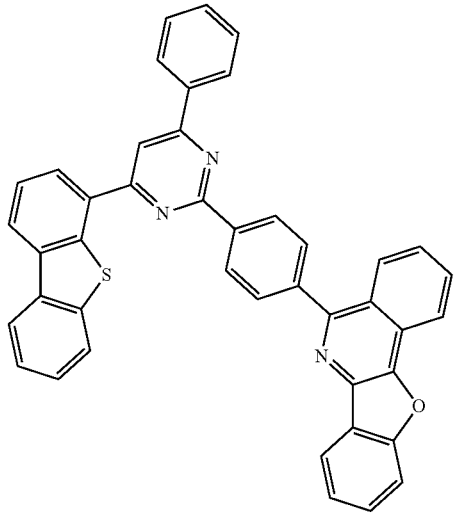
897
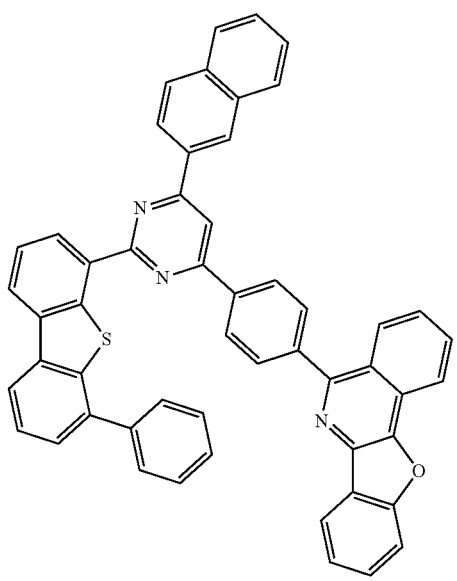
898

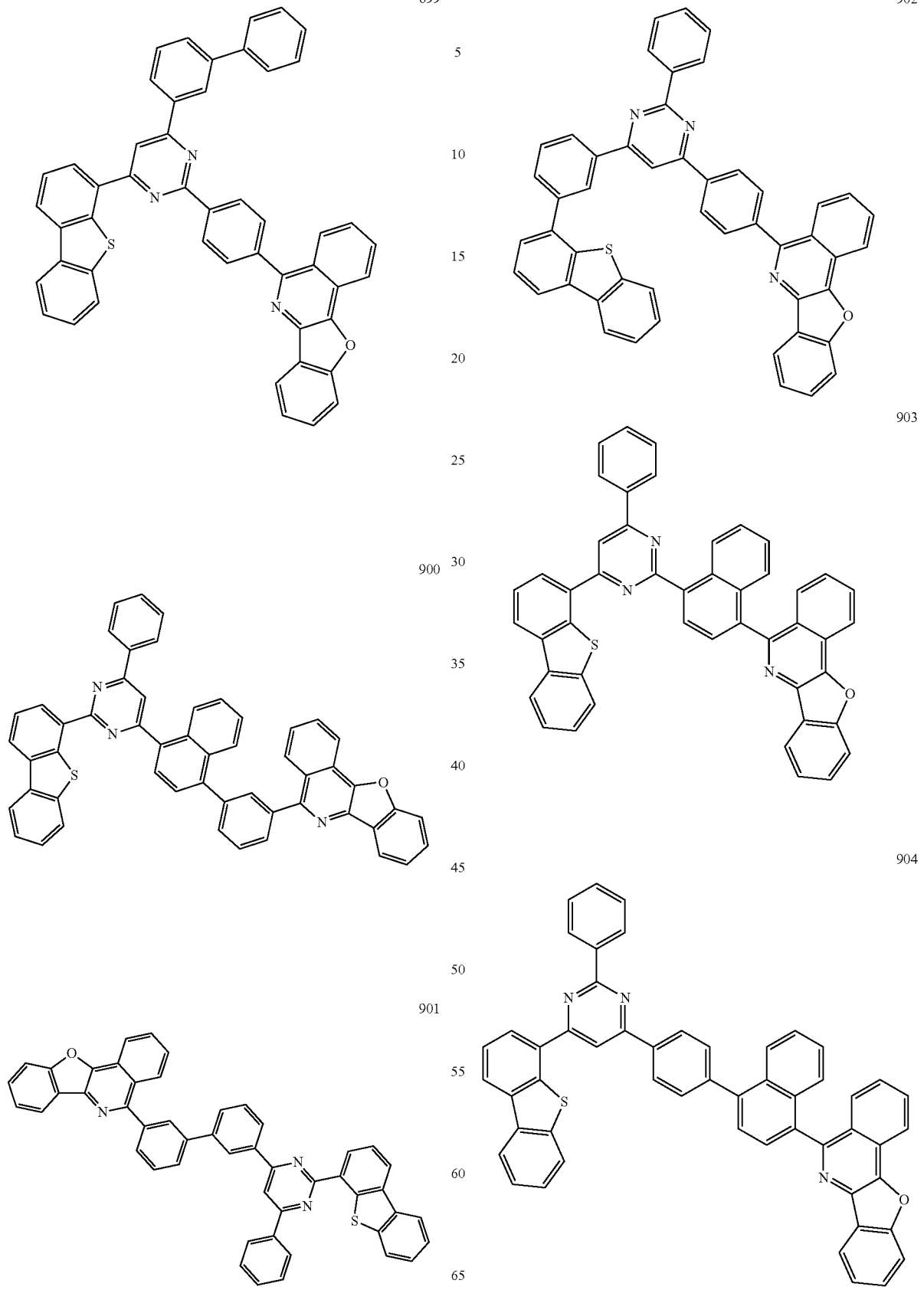

315
-continued
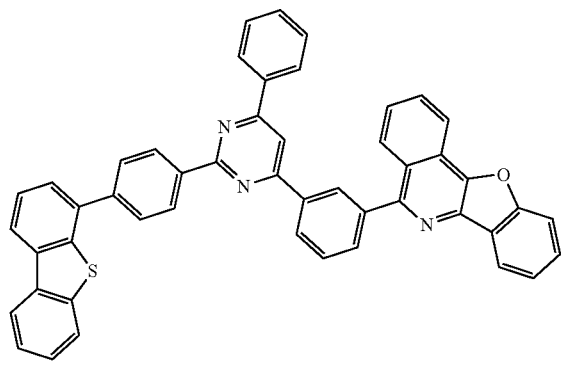
905
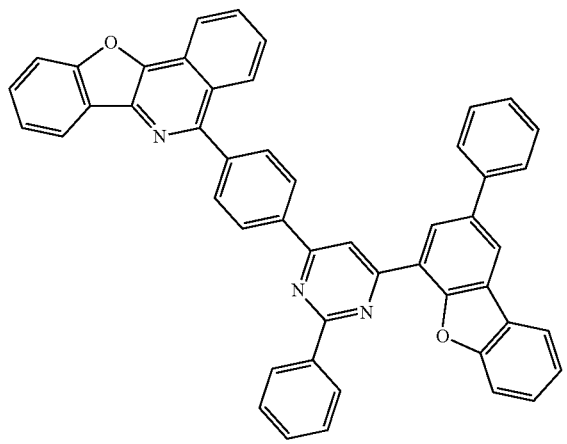
906
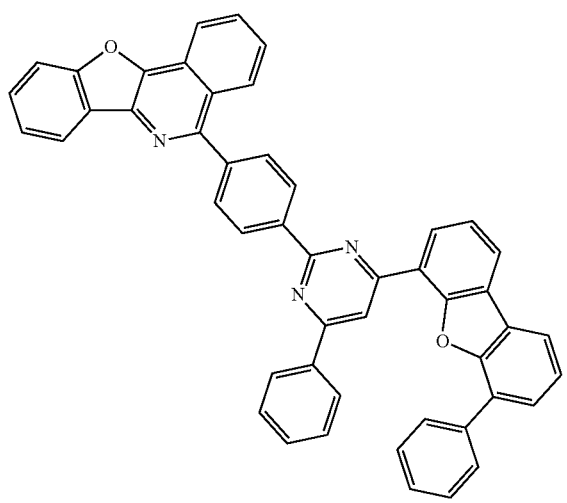
907
316
-continued
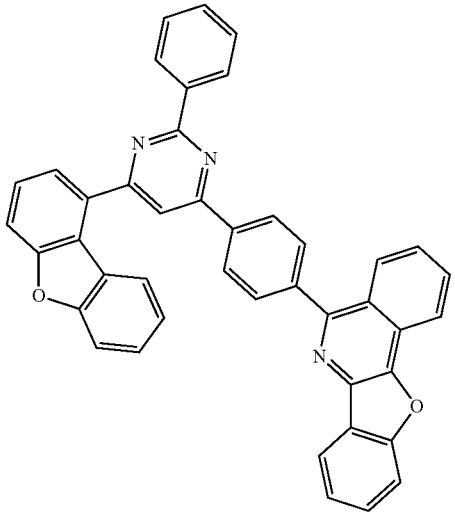
908
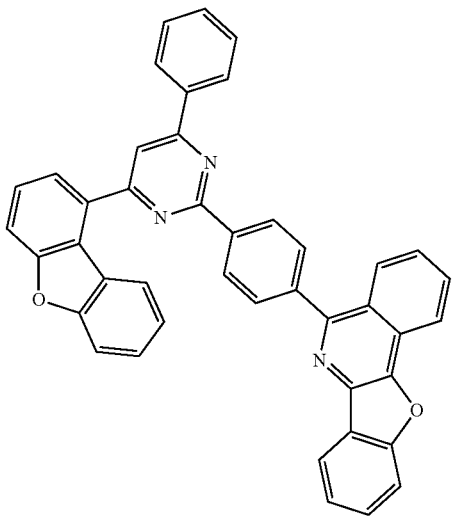
909
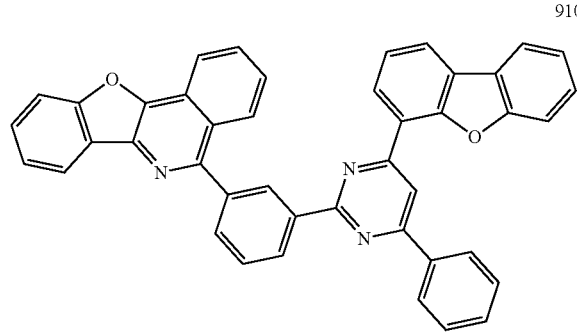
910

911
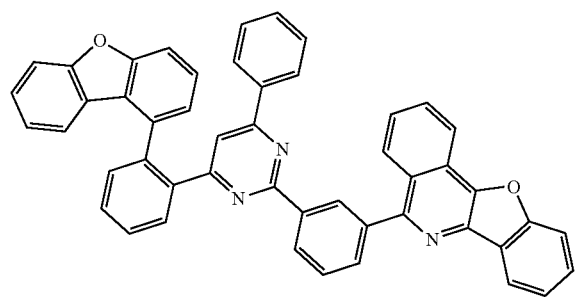
912
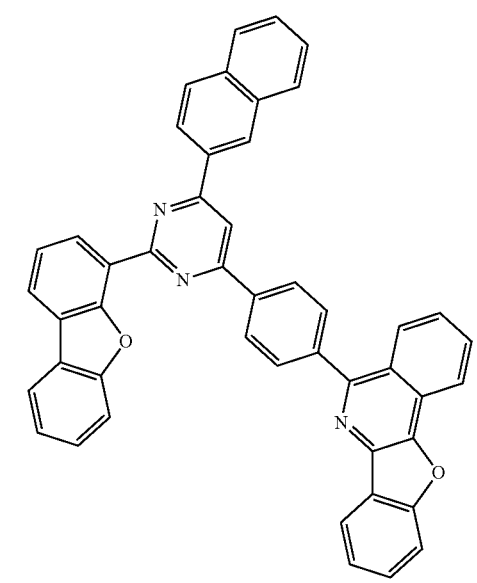
913
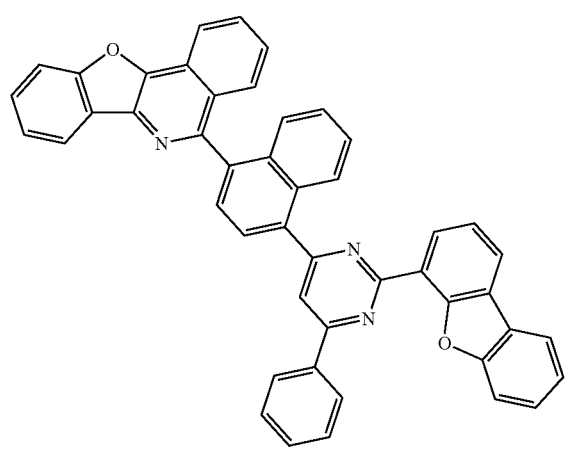
914
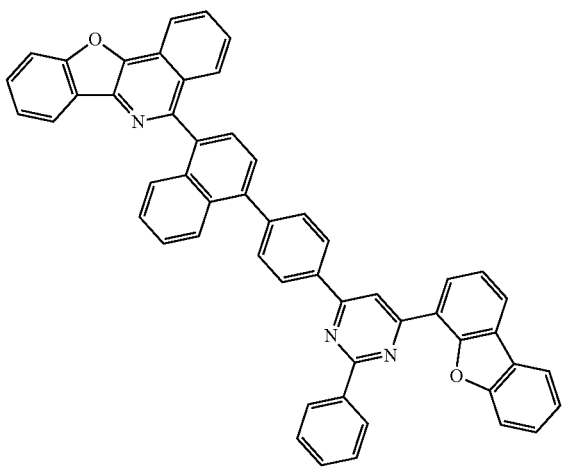
915
916
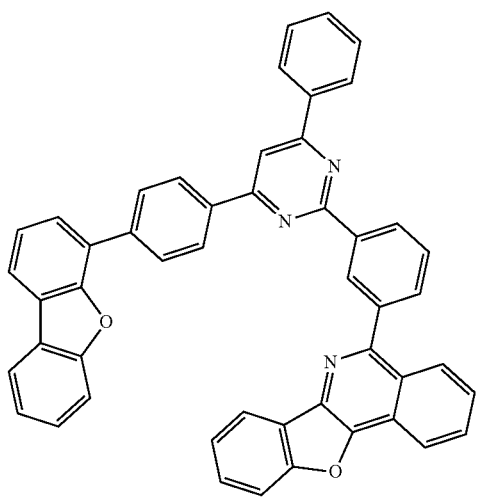

917
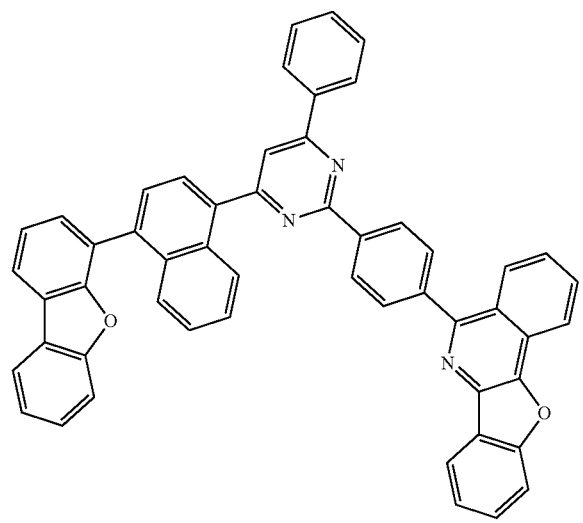
918
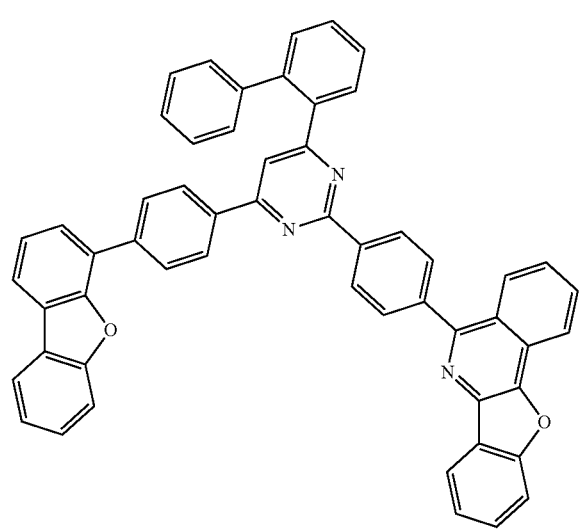
919
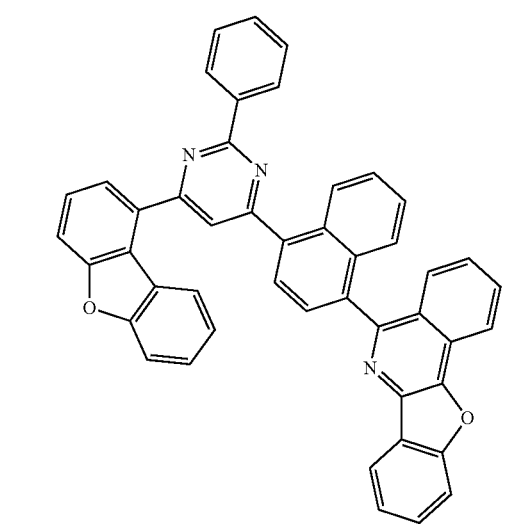
920
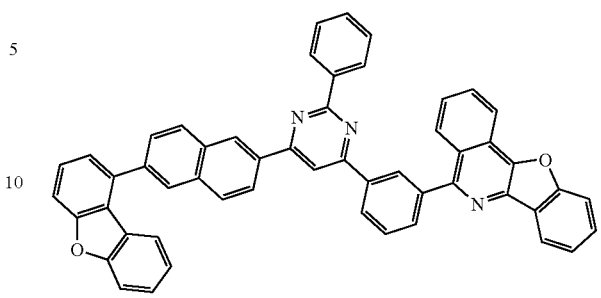
921
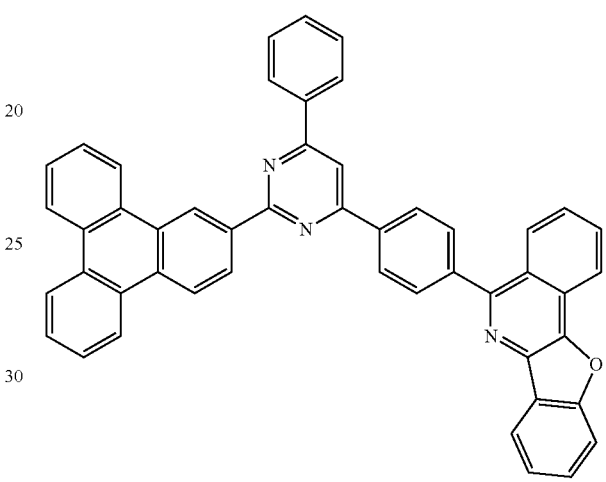
922
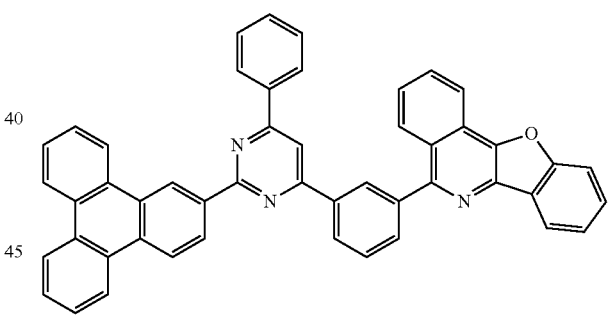
923
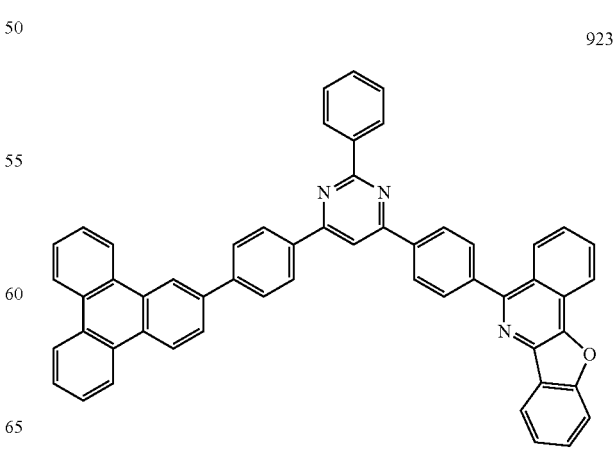

321
-continued
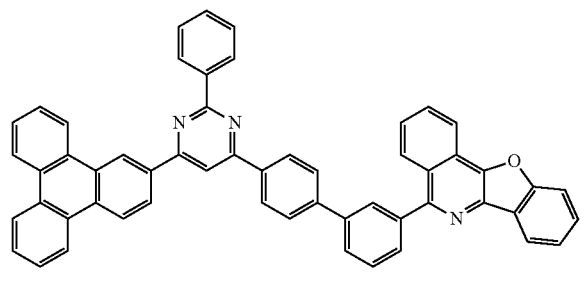
322
-continued
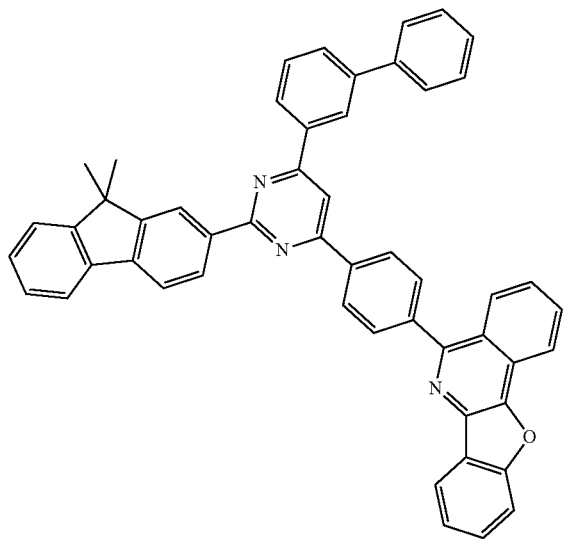
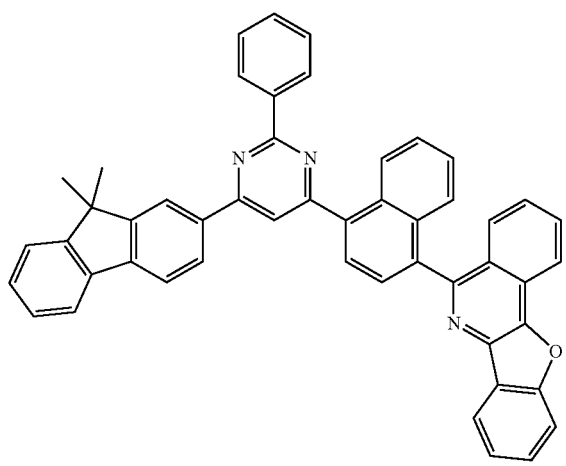
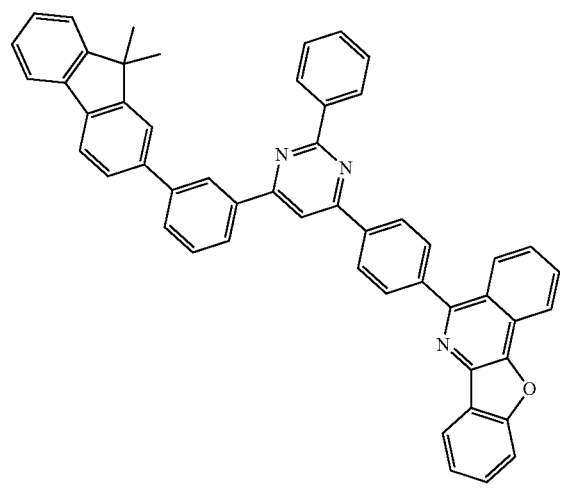

323
-continued
931
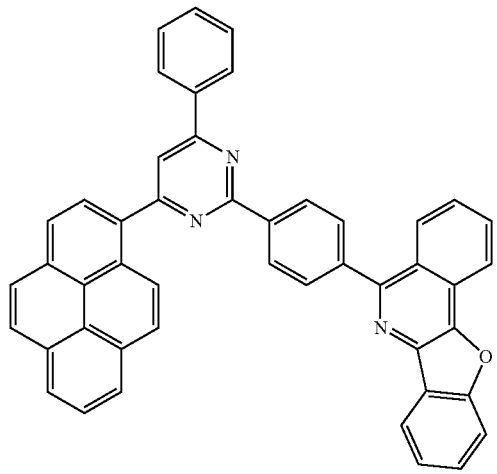
932
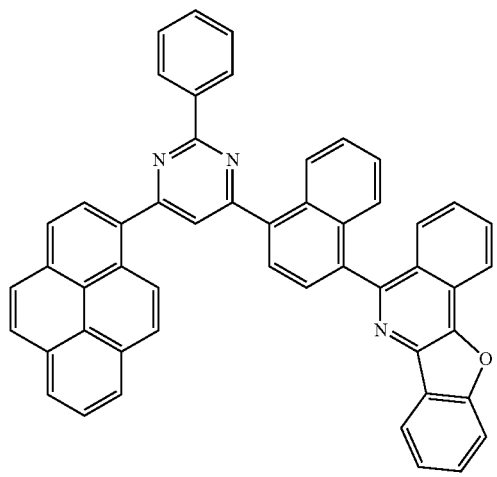
933
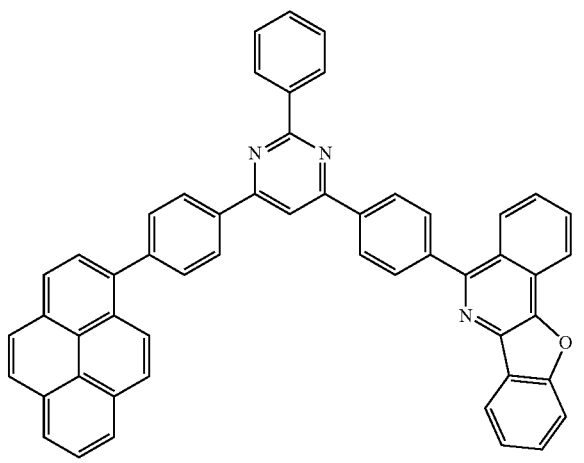
324
-continued
934
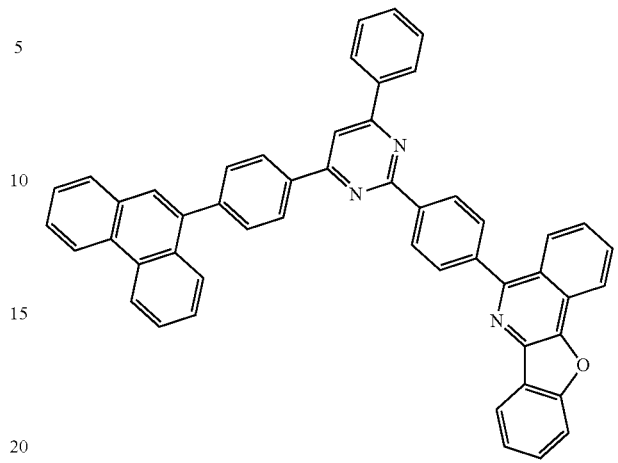
935
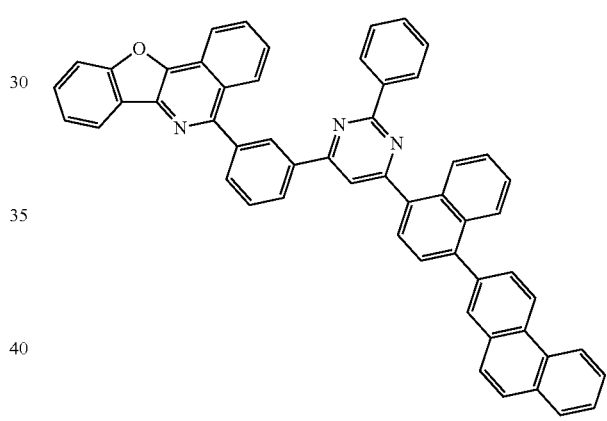
936
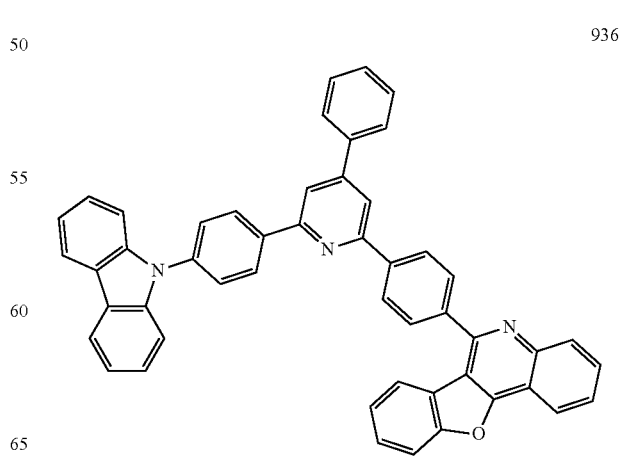

325
-continued
937
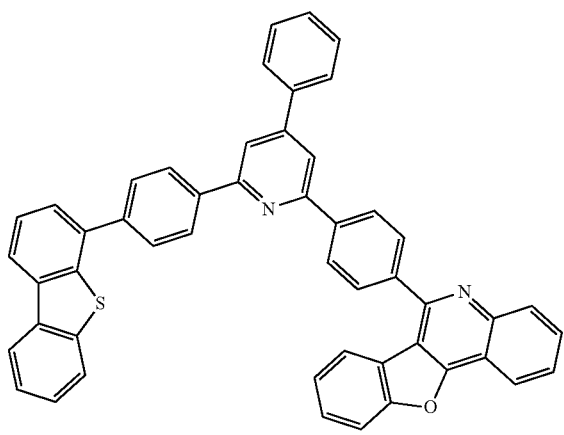
938
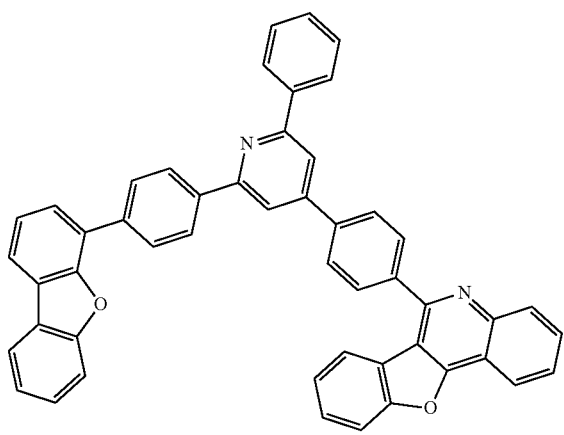
939
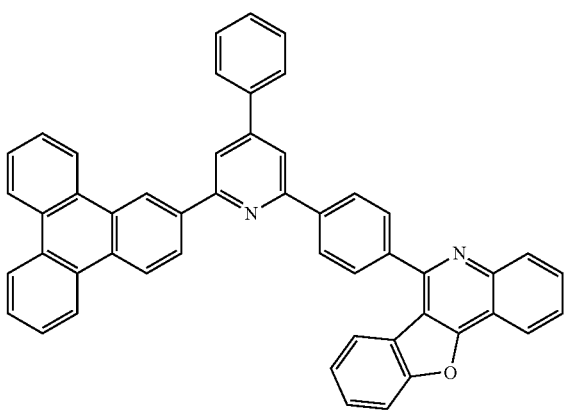
326
-continued
940
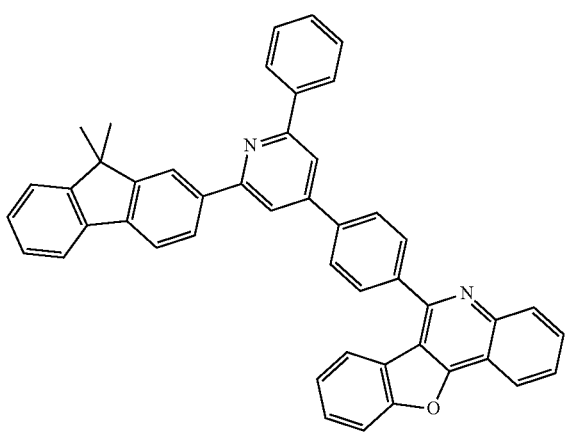
941
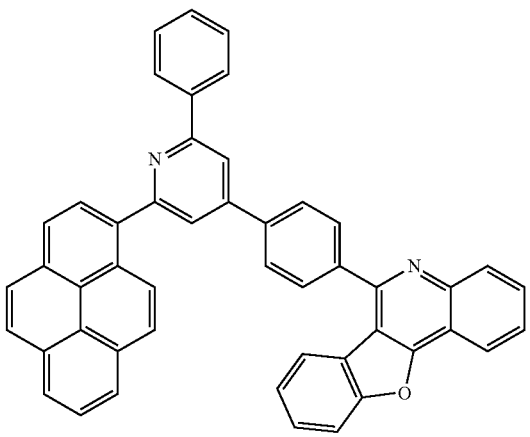
942
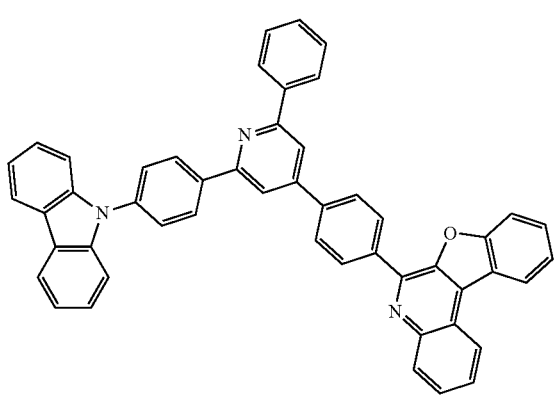

943
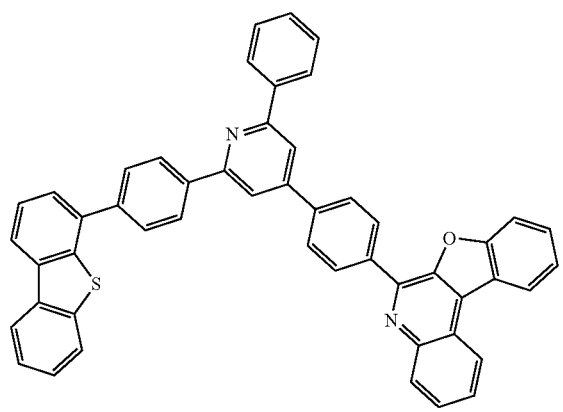
944
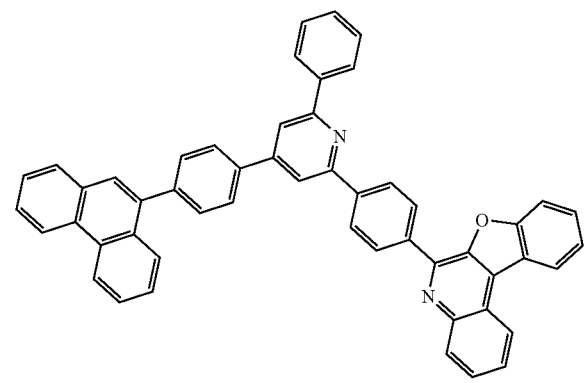
946
945
947
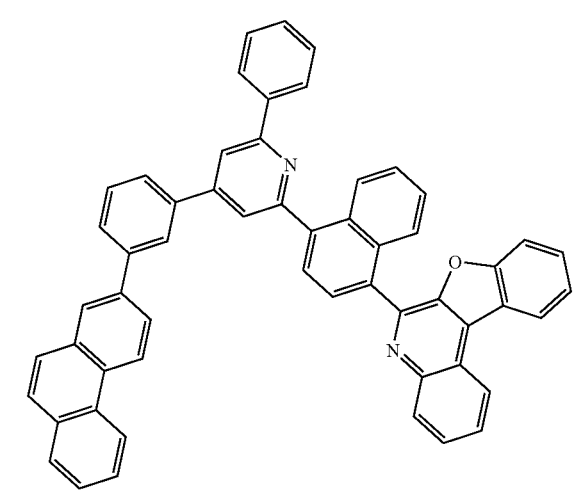
948
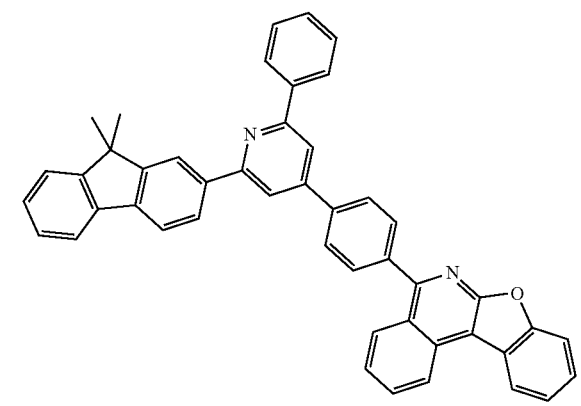

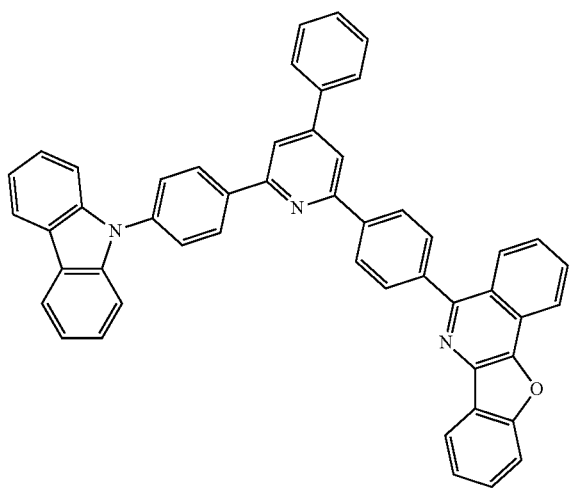
949
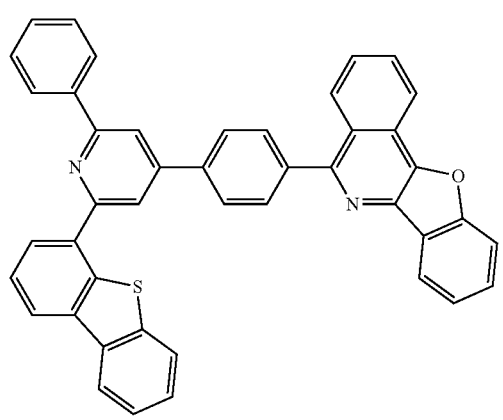
950
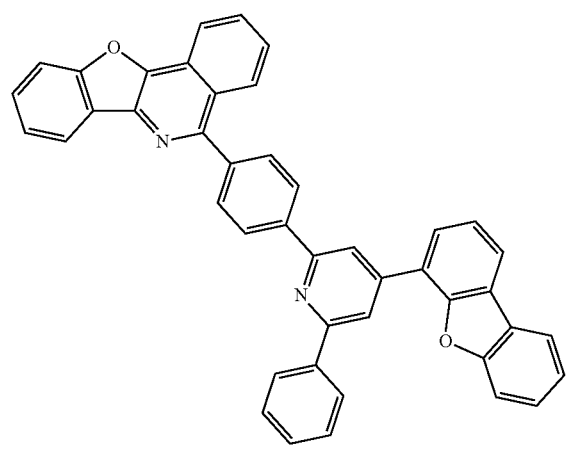
951
In addition, the compound represented by Chemical Formula 1 may be any one of compounds of the following Group III.
[Group III]
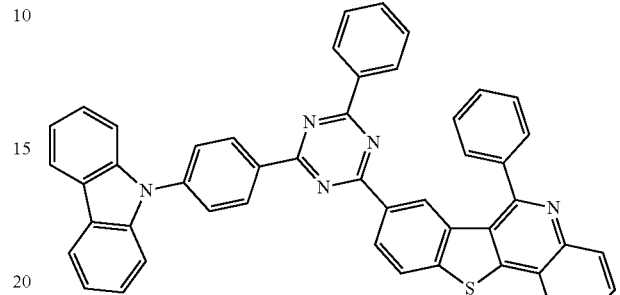
952
953
954
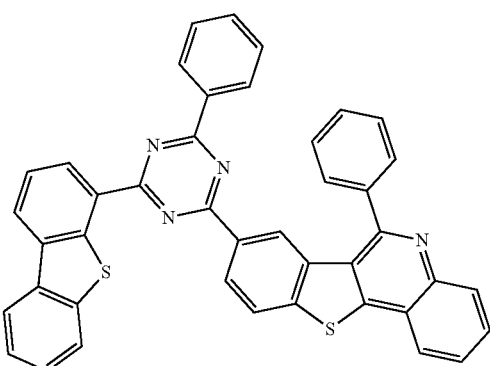
955

956
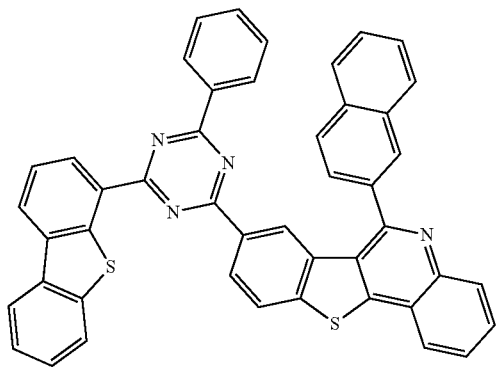
957
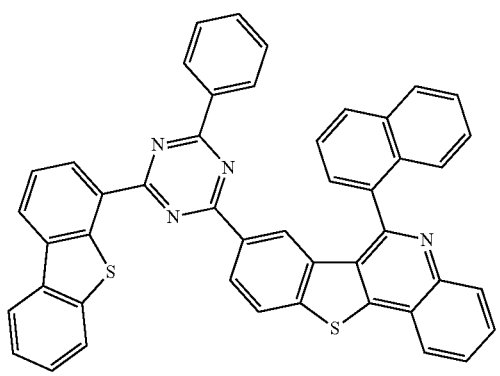
958
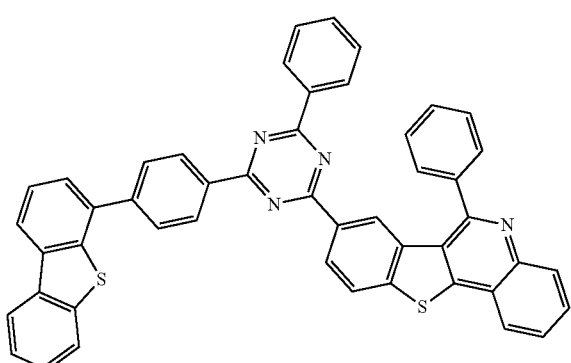
959
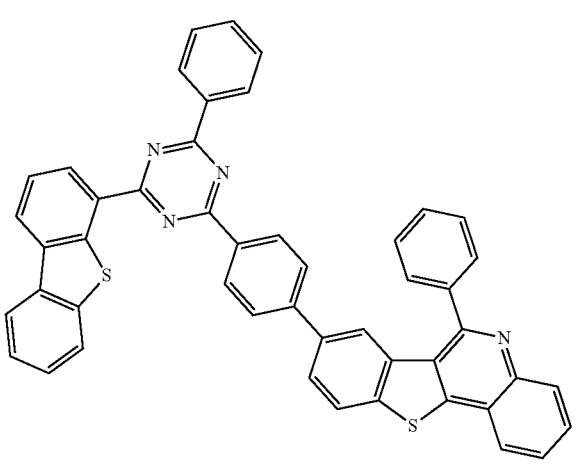
960
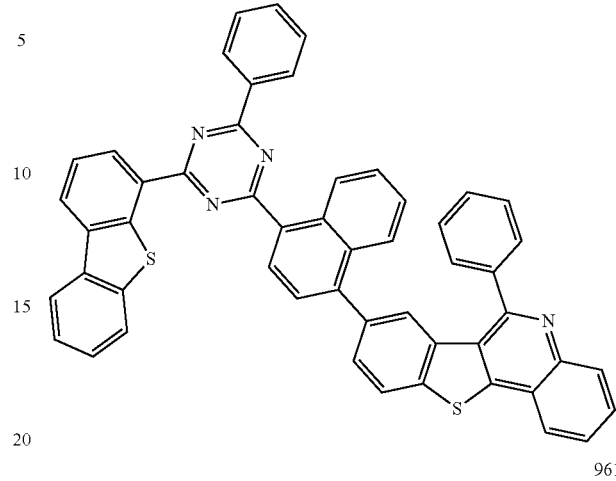
961
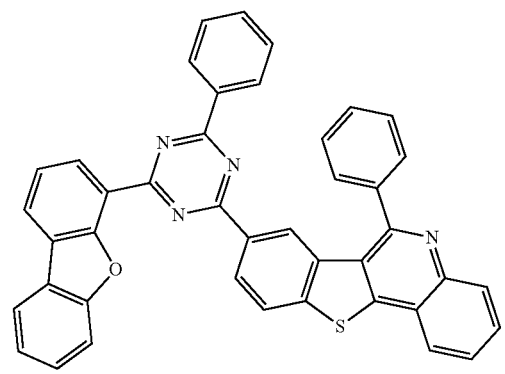
962
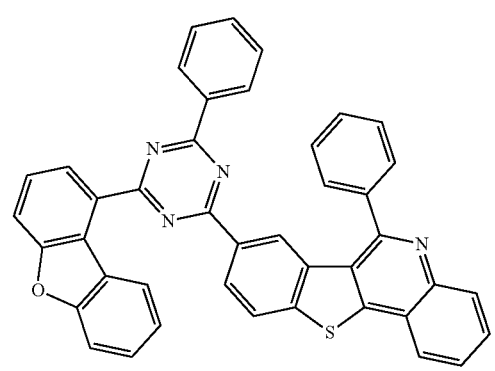
963
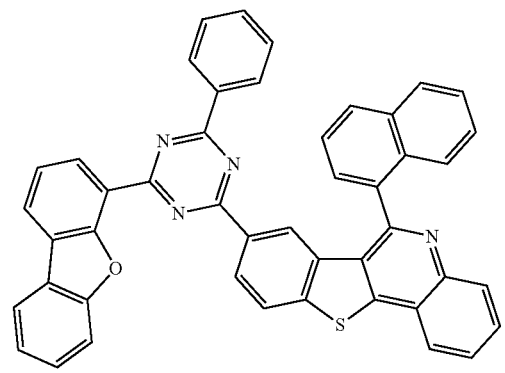

964
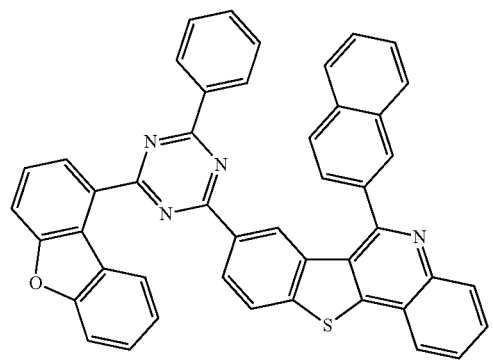
967
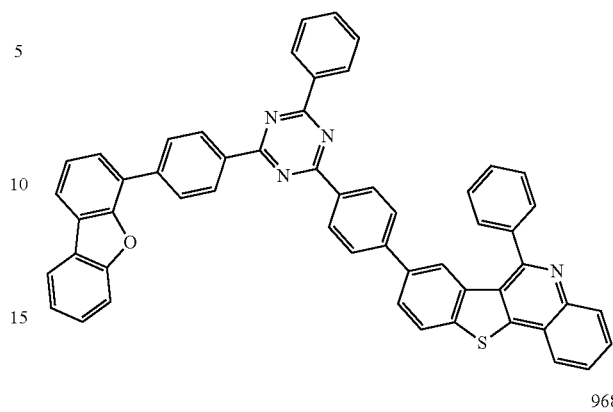
965
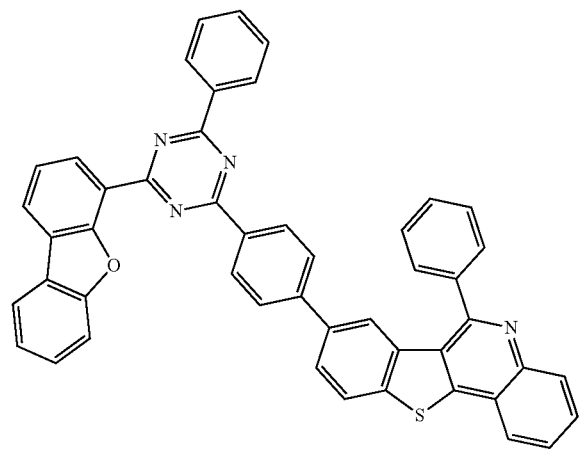
968
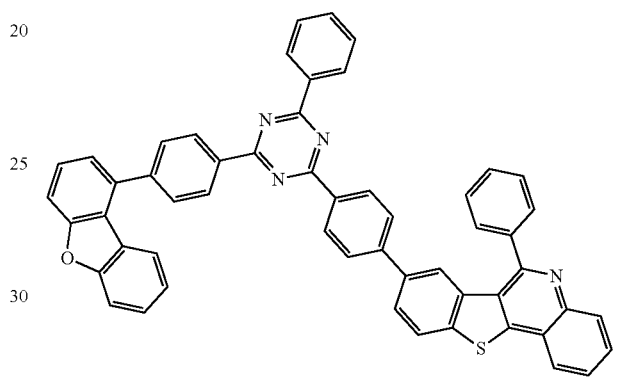
969
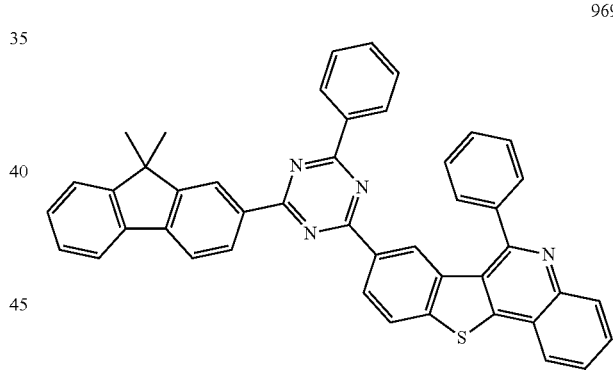
966
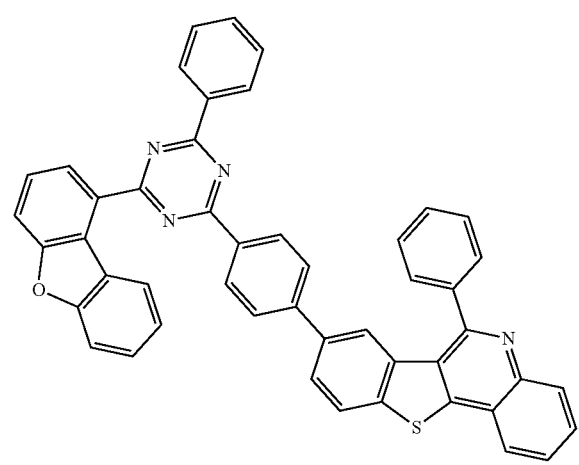
970
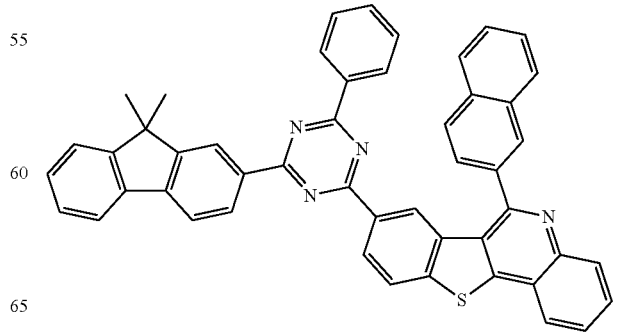

335
-continued
971
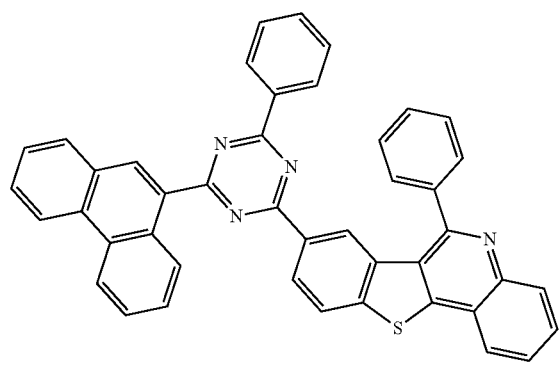
972
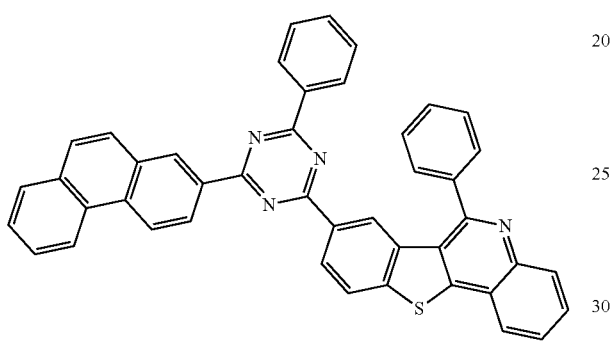
973
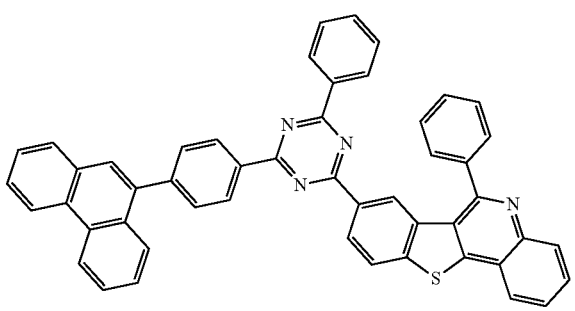
974
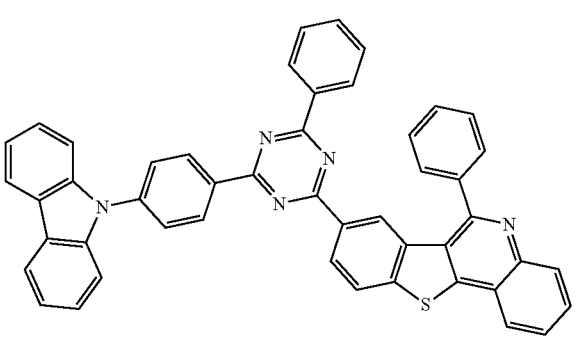
336
-continued
975
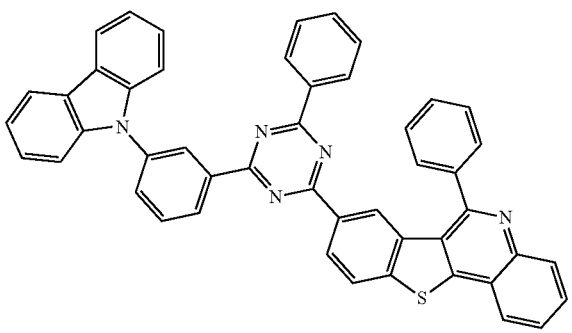
976
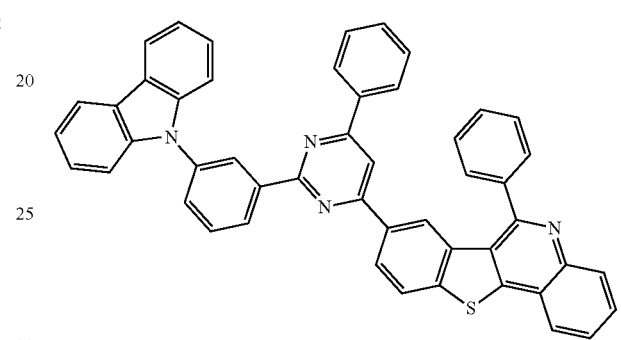
977
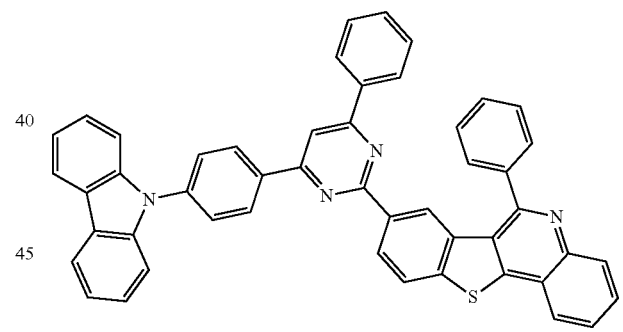
978
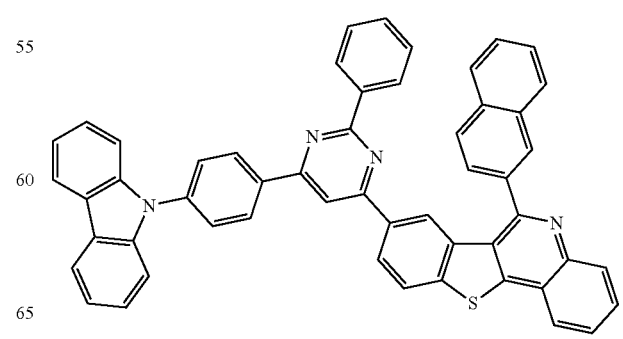

979
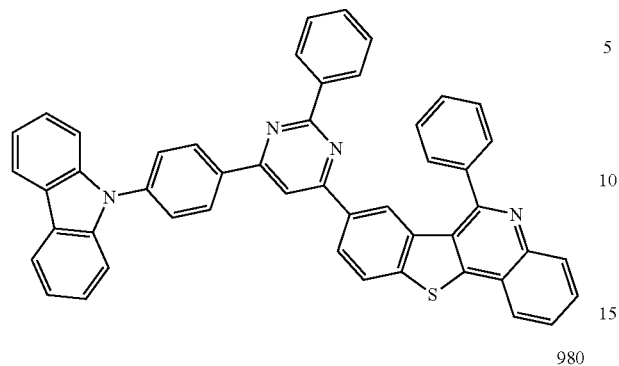
980
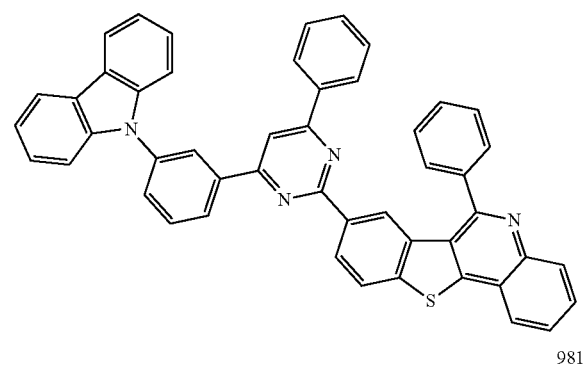
981
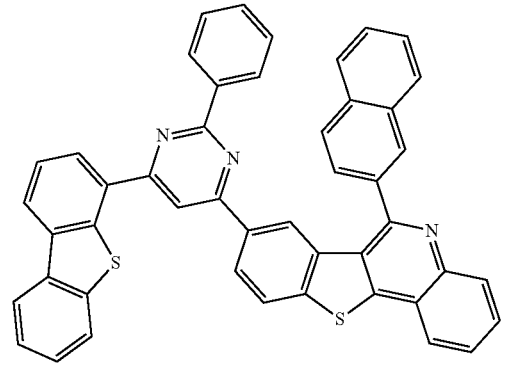
982
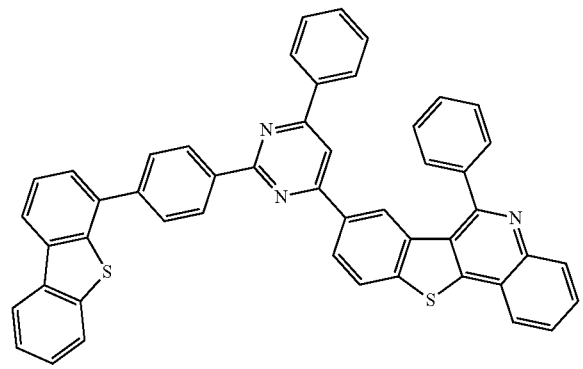
983
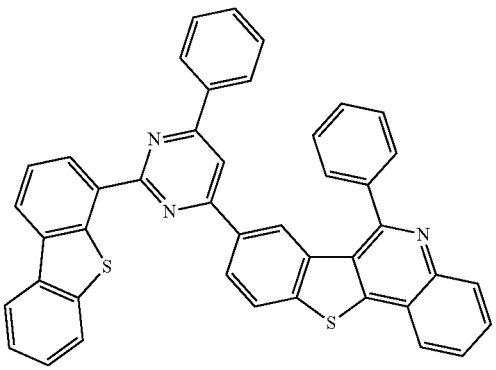
984
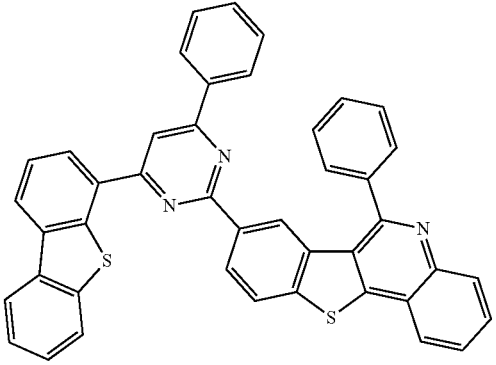
985
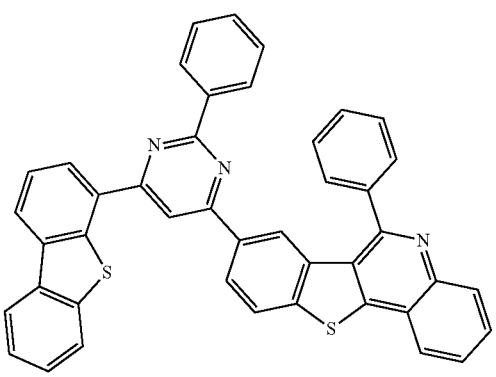
986
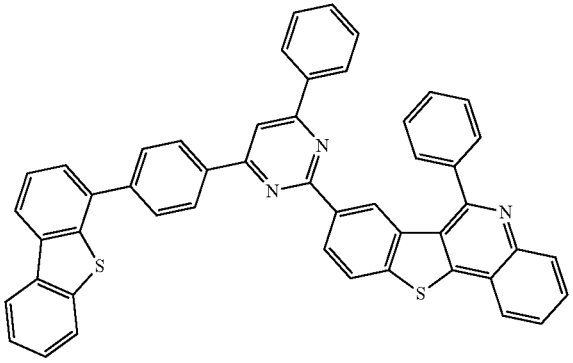

987
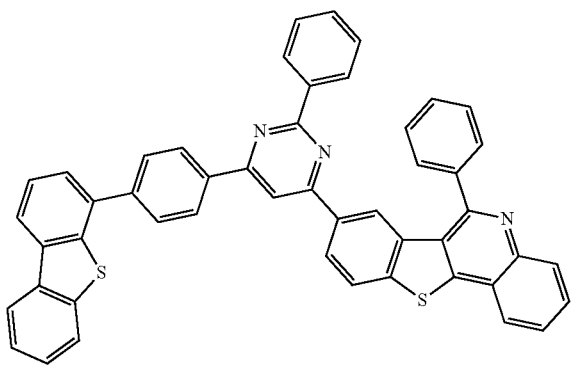
988
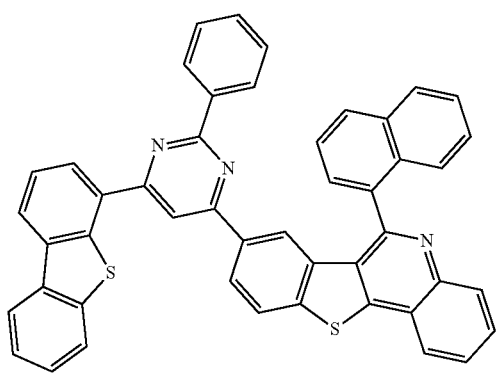
989
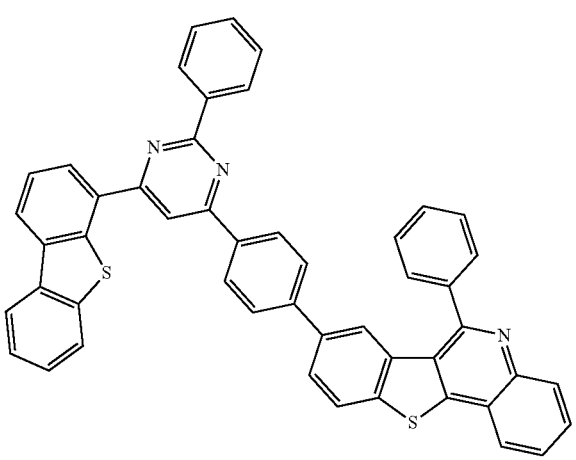
990
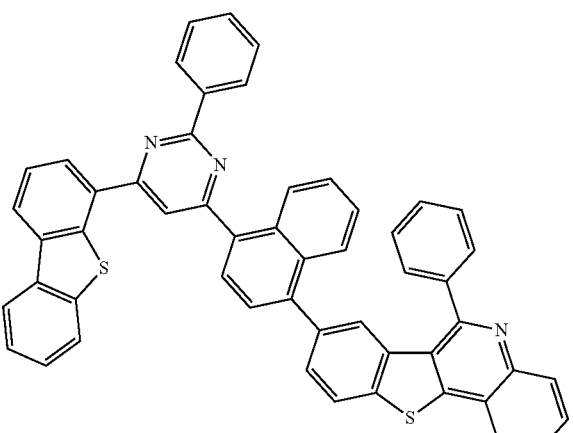
991
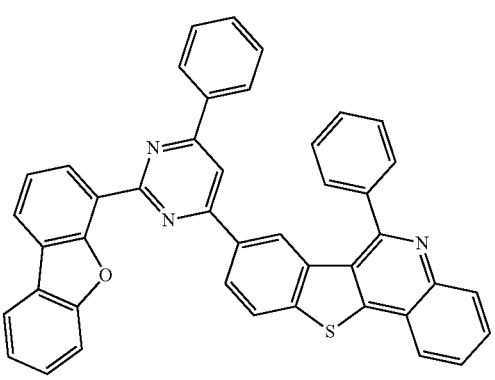
992
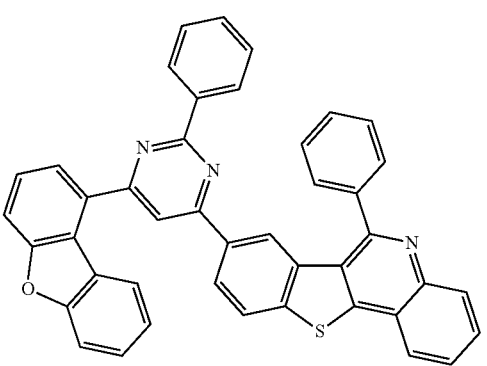
993
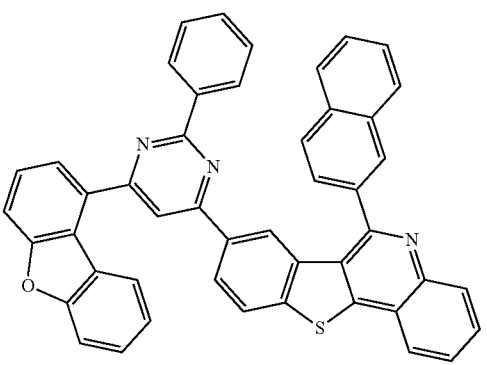

341
-continued
994
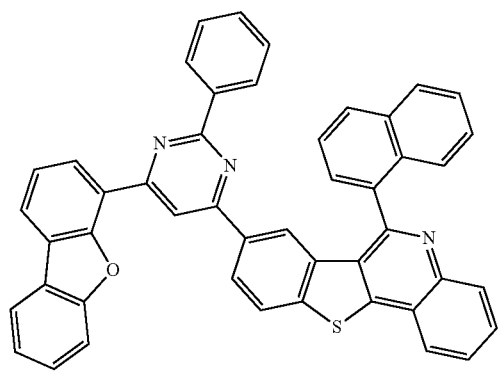
995
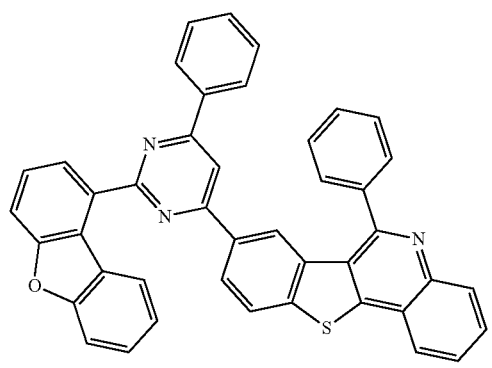
996
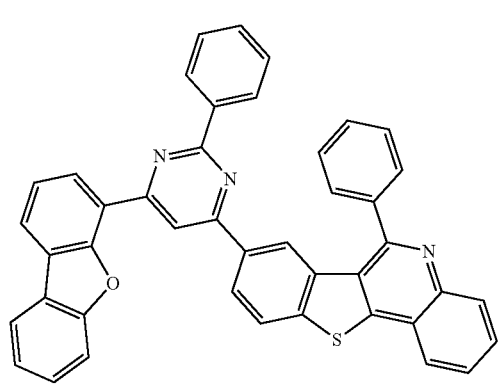
997
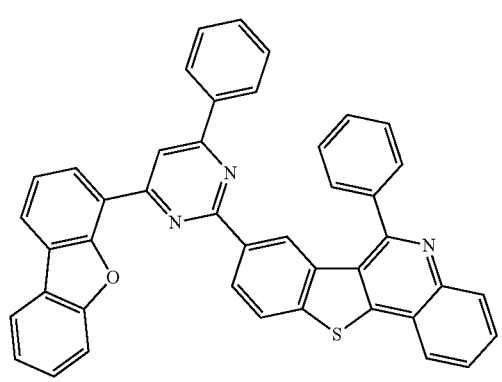
342
-continued
998
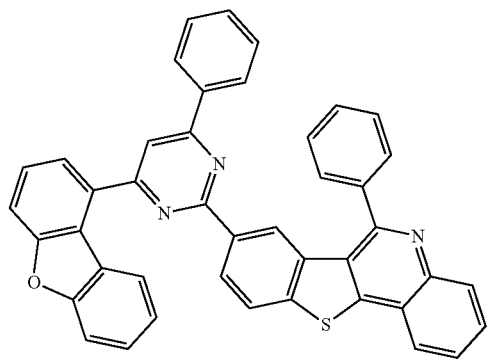
999
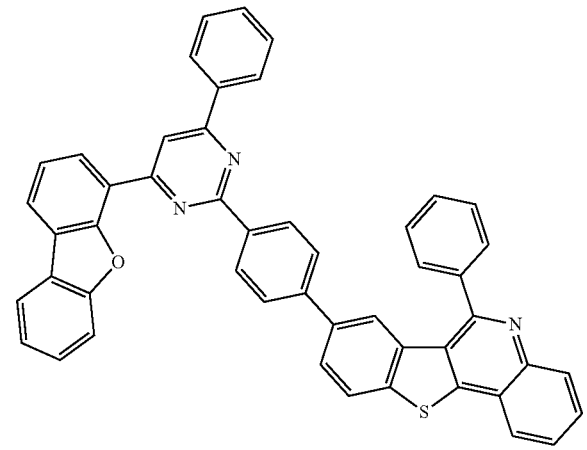
1000
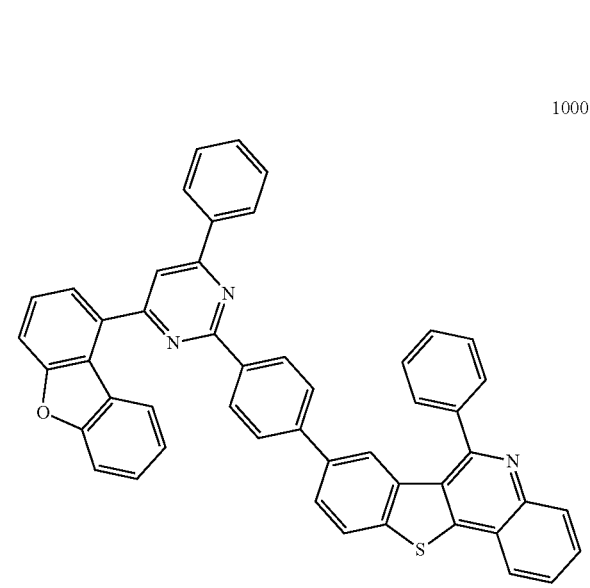

1001
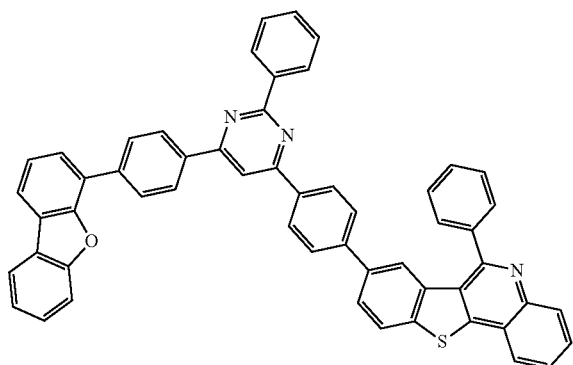
1002
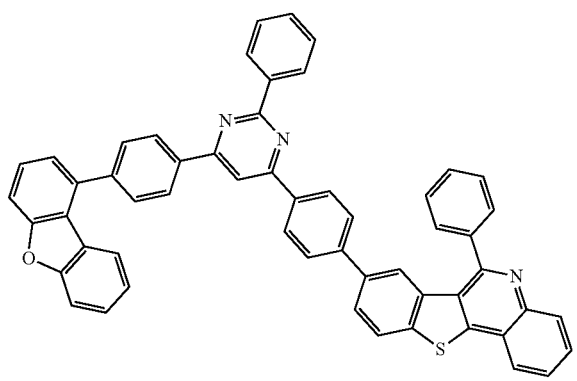
10003
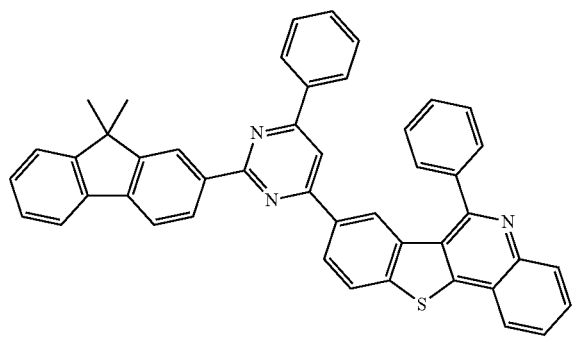
1004
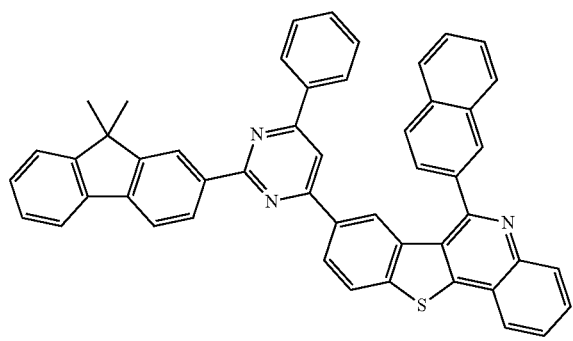
1005
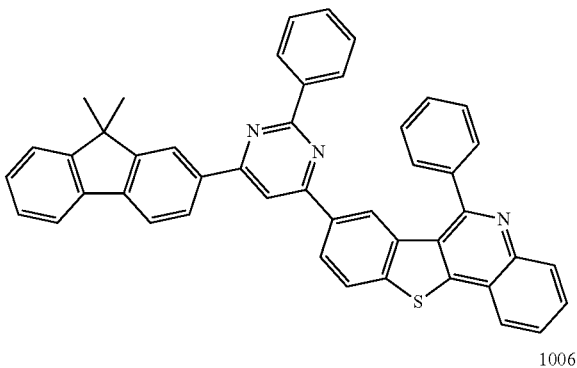
1006
1007
1008
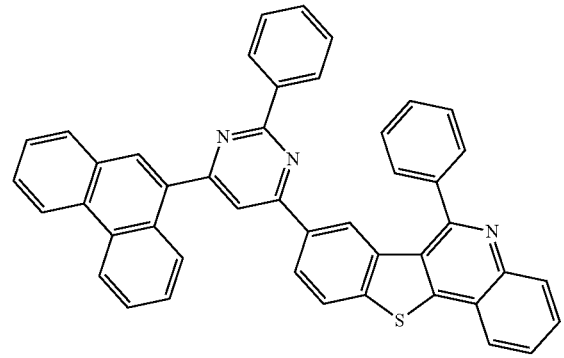

1009
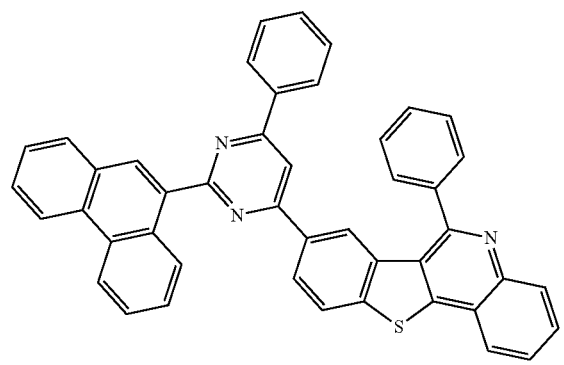
1010
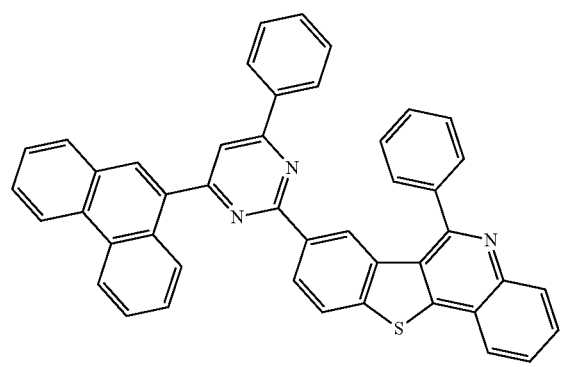
1011
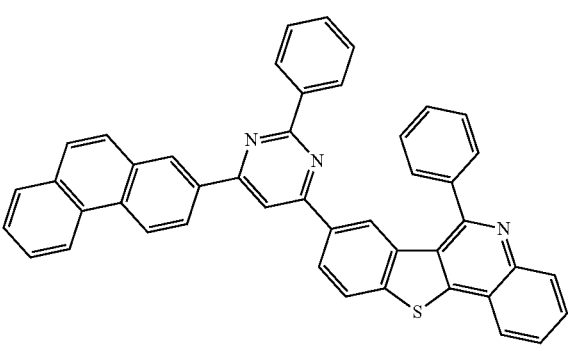
1012
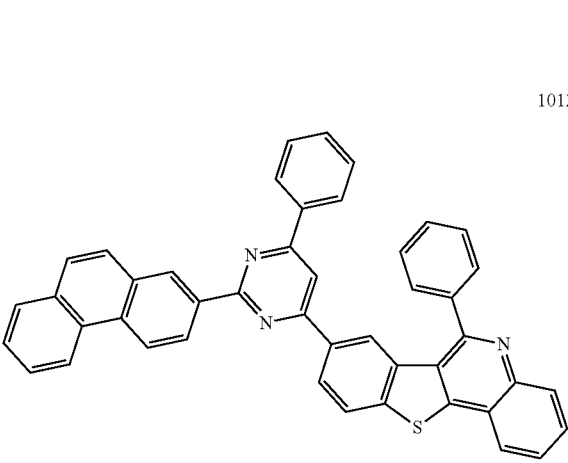
1013
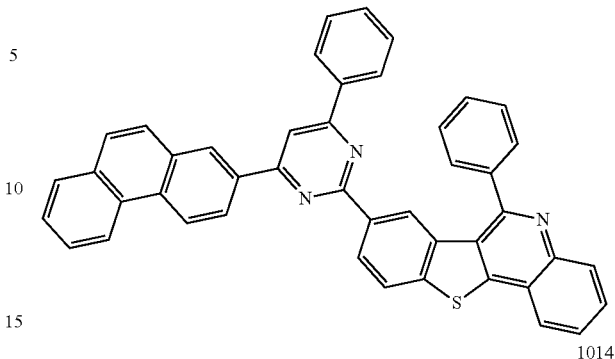
1014
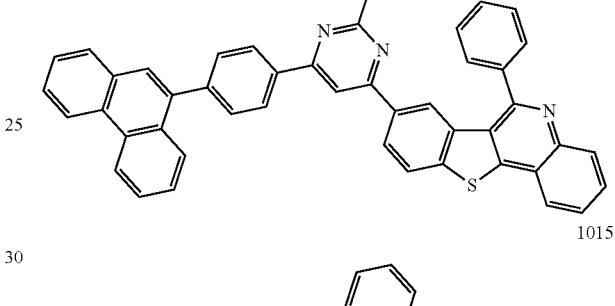
1015
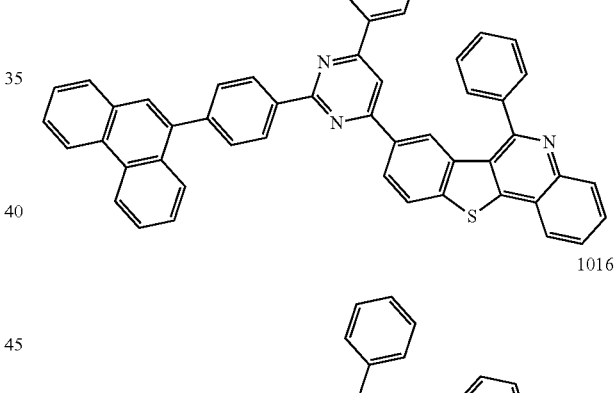
1016
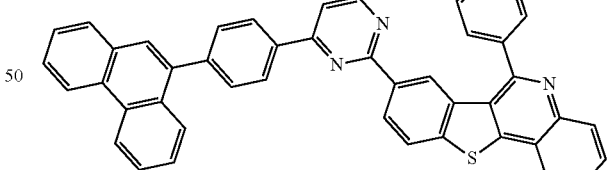
1017
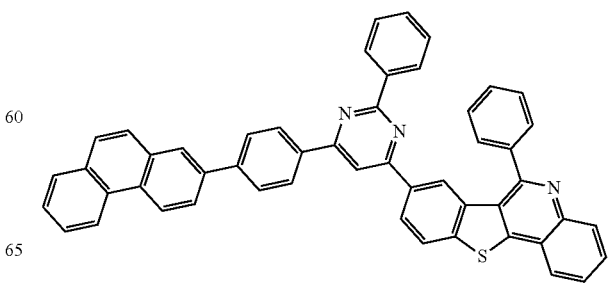

-continued
1018
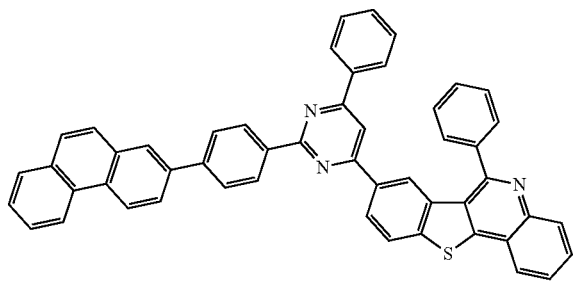
1019
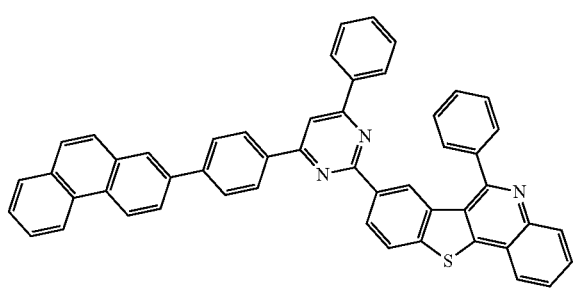
1020
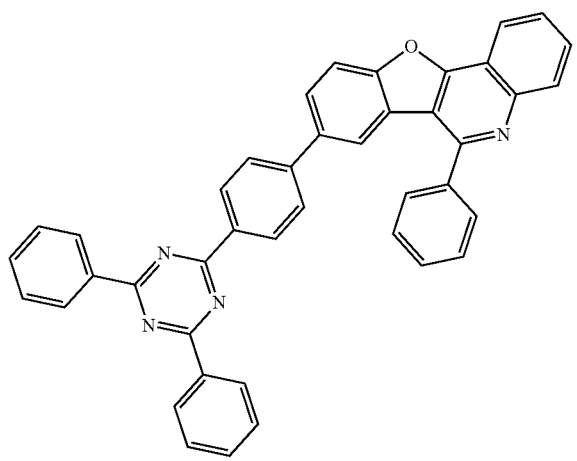
1021
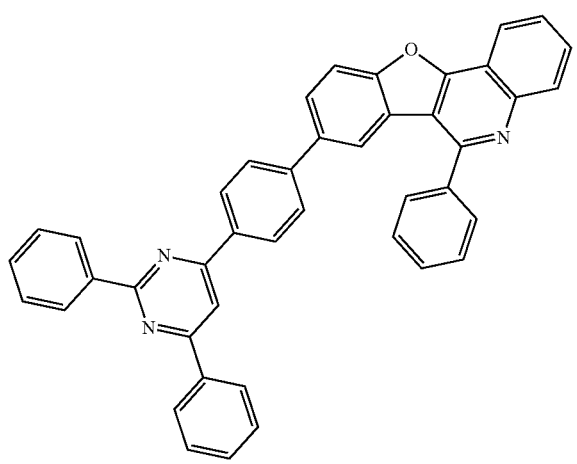
-continued
1022
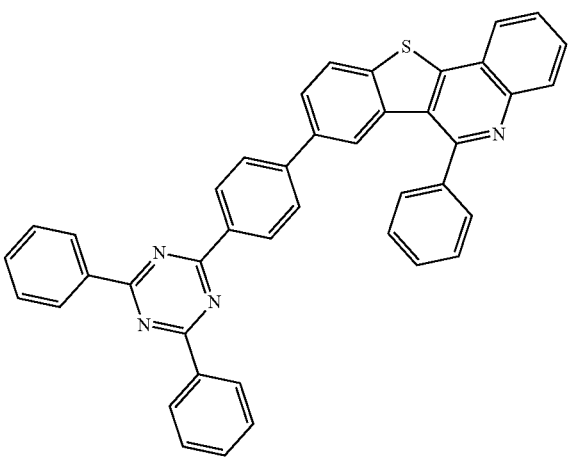
1023
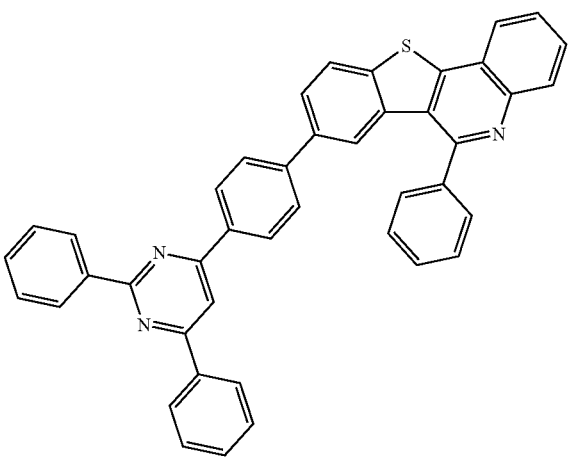
1024
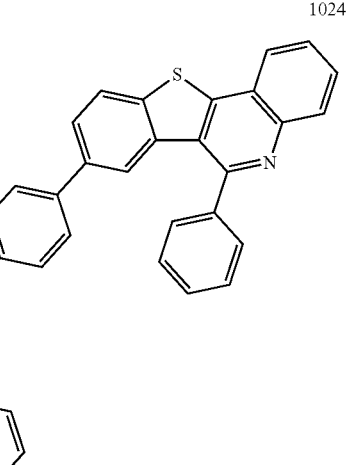

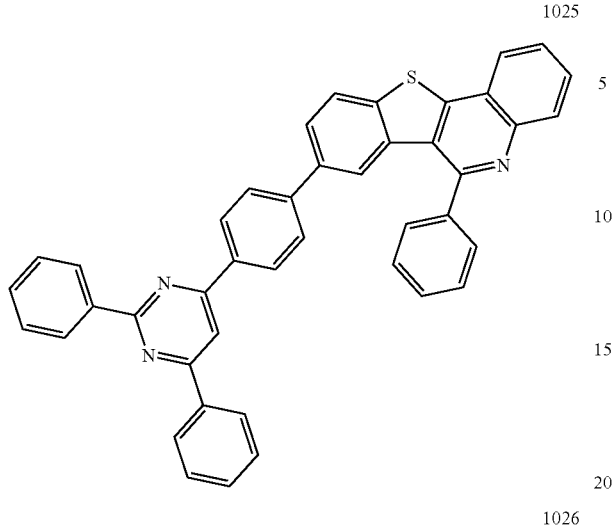
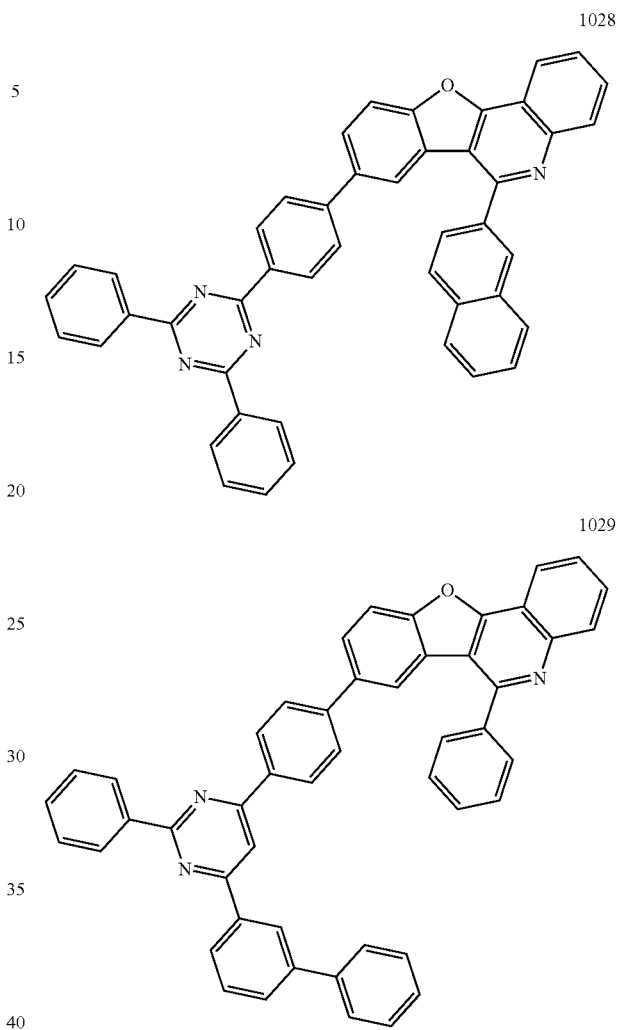
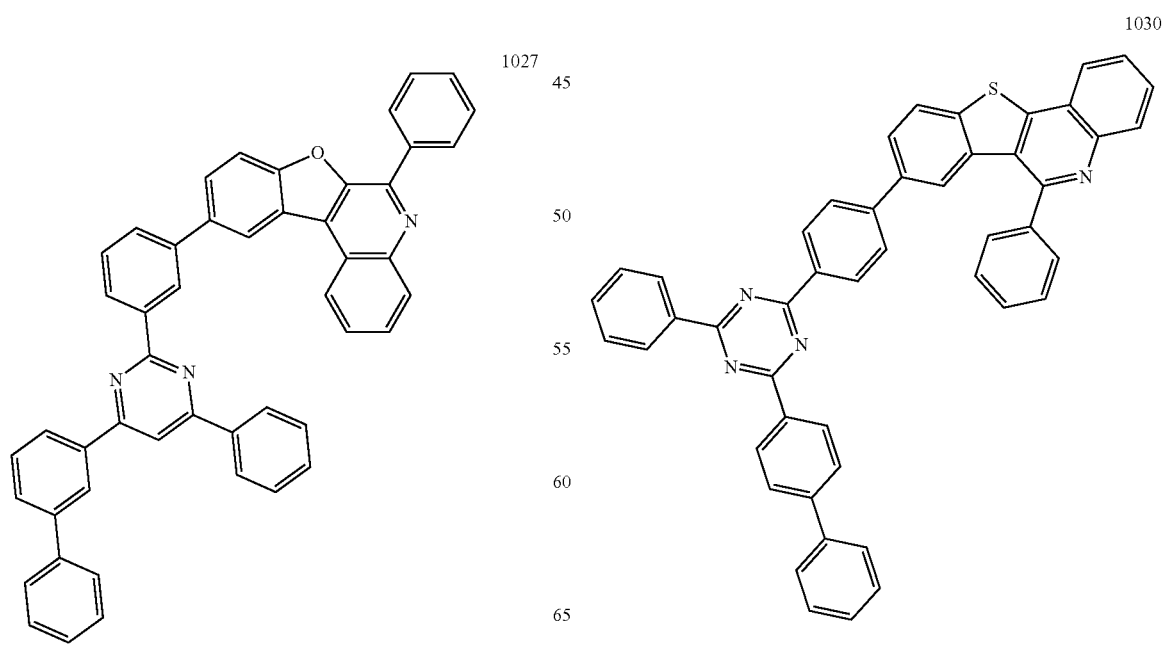

1031
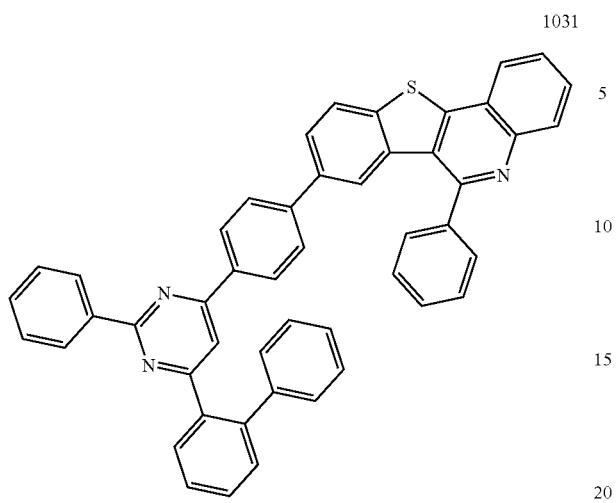
1032
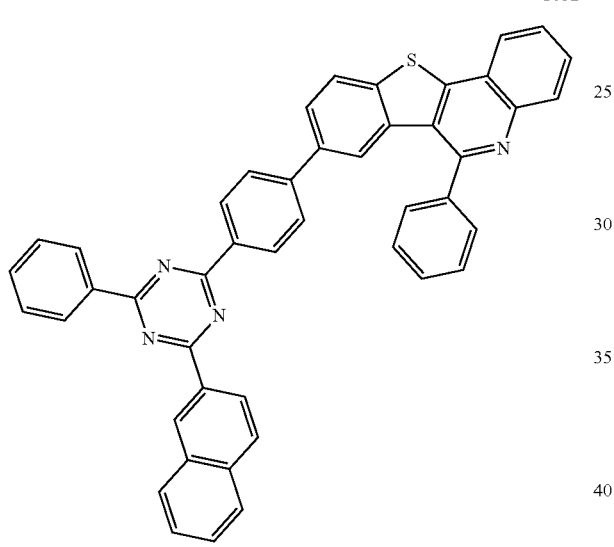
1033
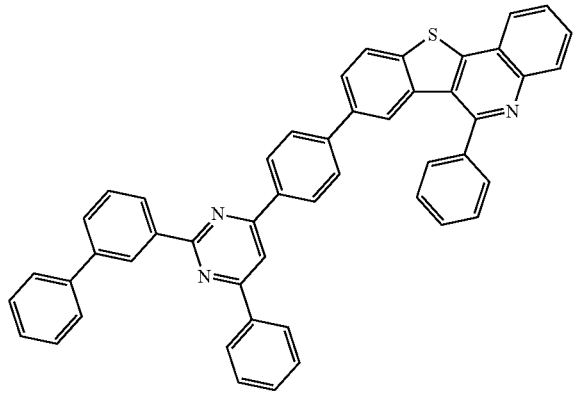
1034
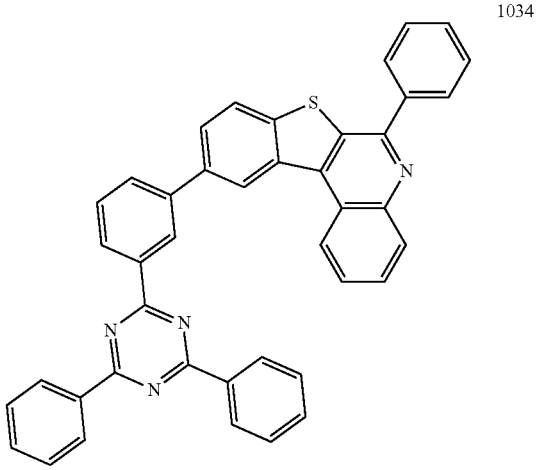
1035
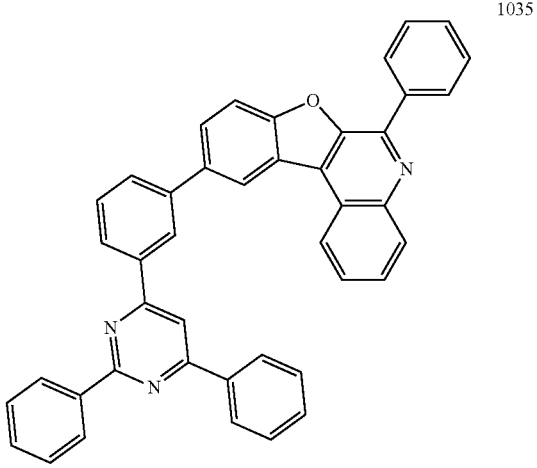
1036
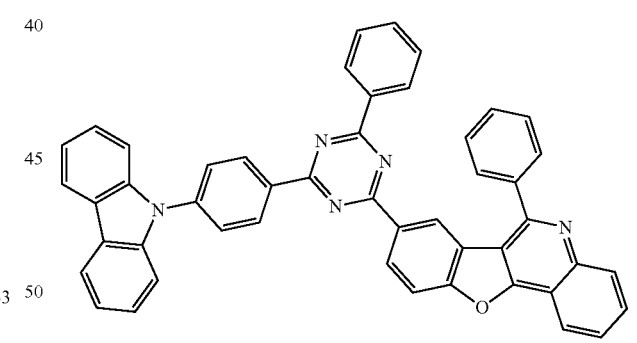
1037
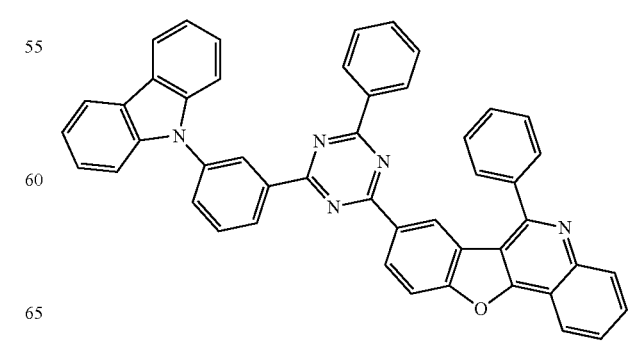

1038
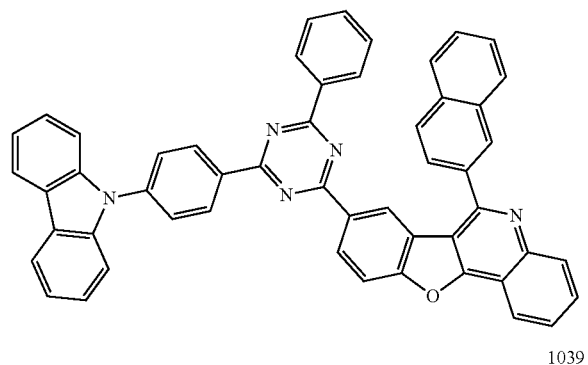
1039
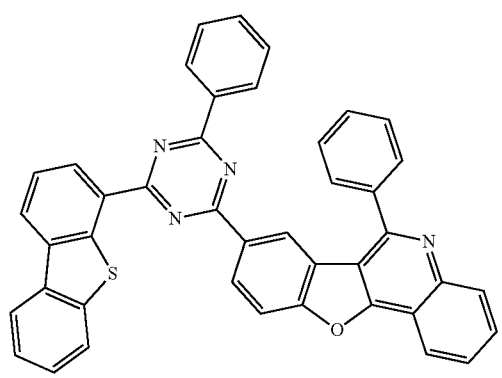
1040
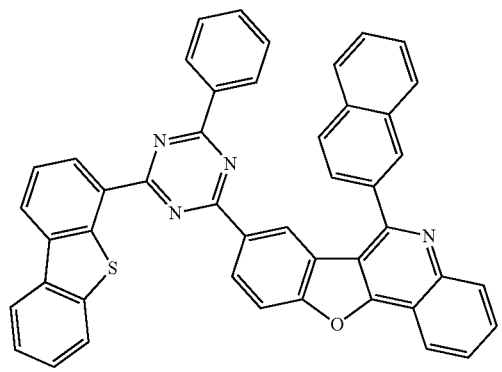
1041
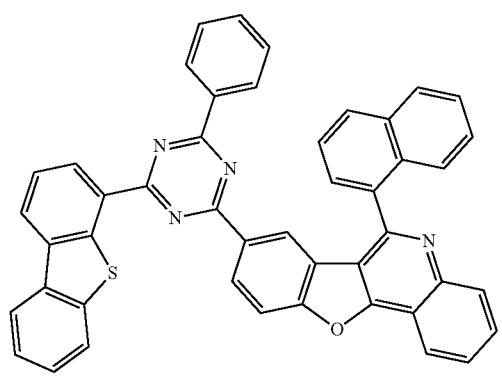
1042
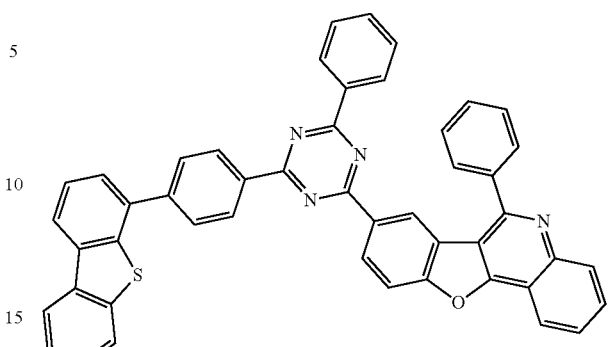
1043
1044
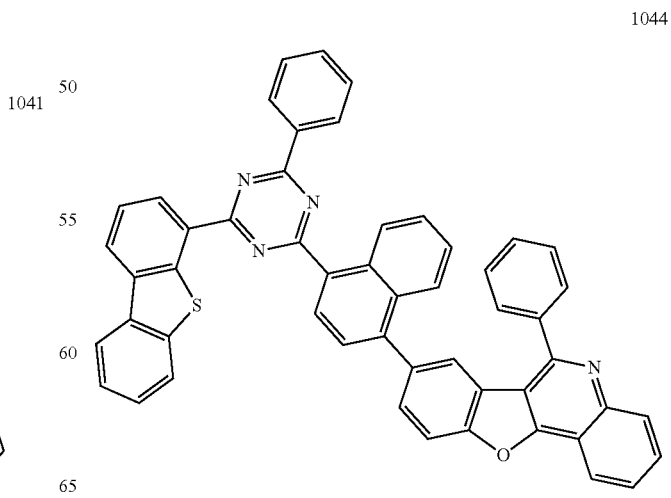

355
-continued
1045
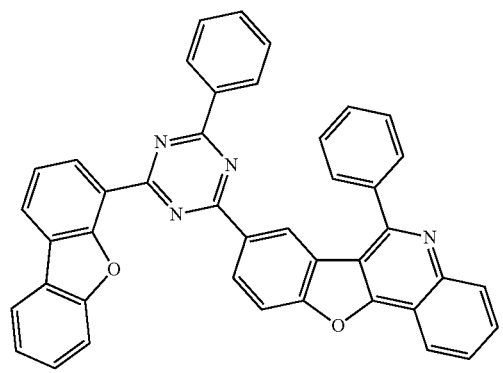
1046
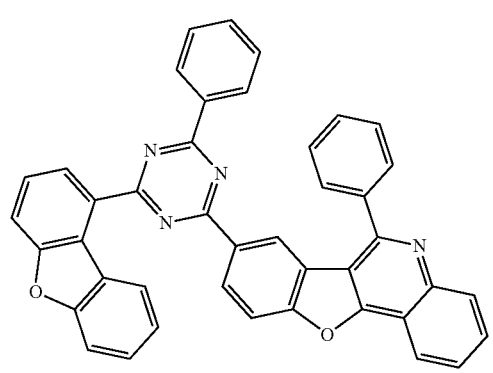
1047
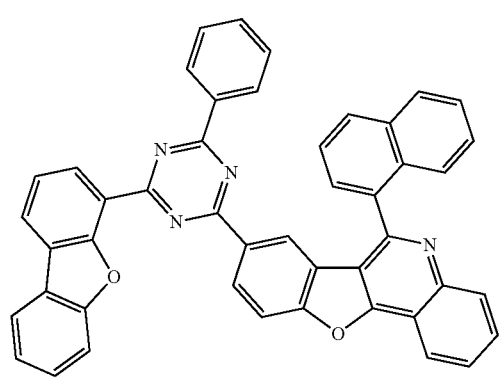
1048
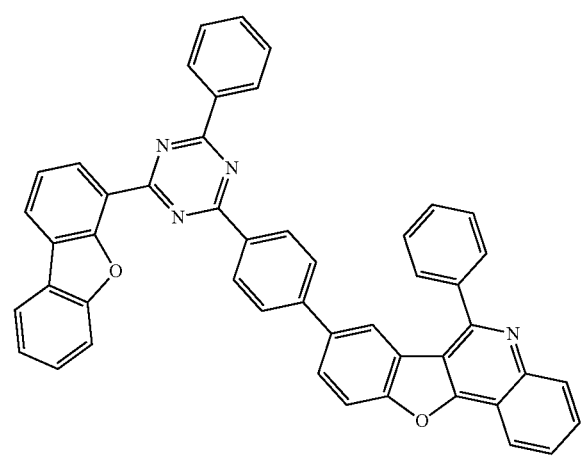
356
-continued
1049
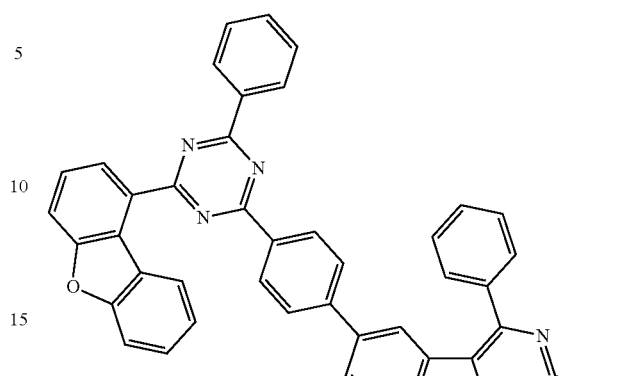
1050
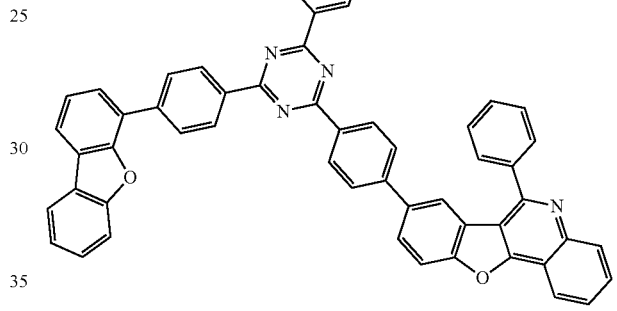
1051
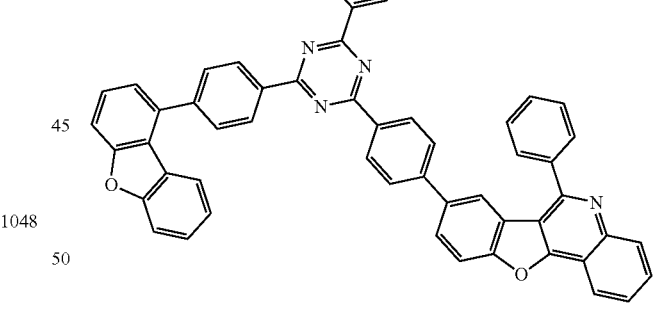
1052
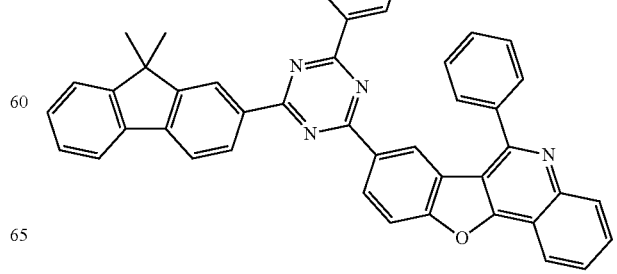

1053
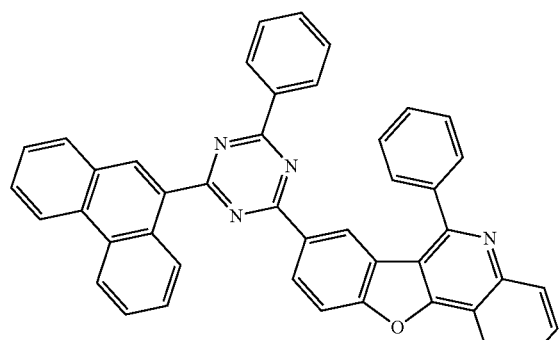
1054
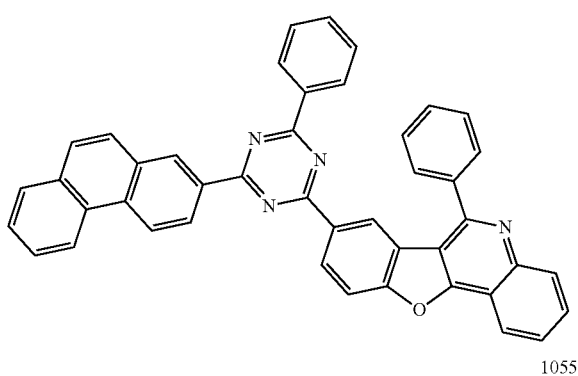
1055
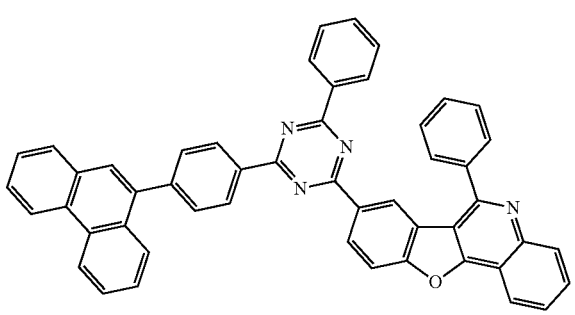
1056
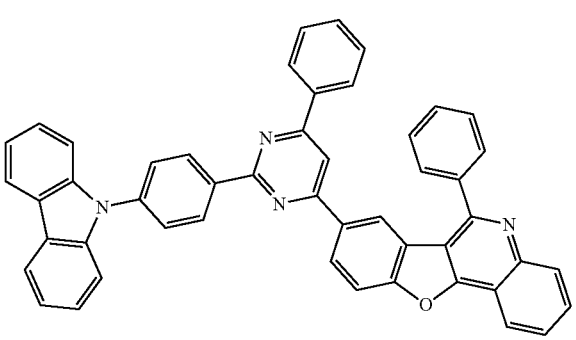
1057
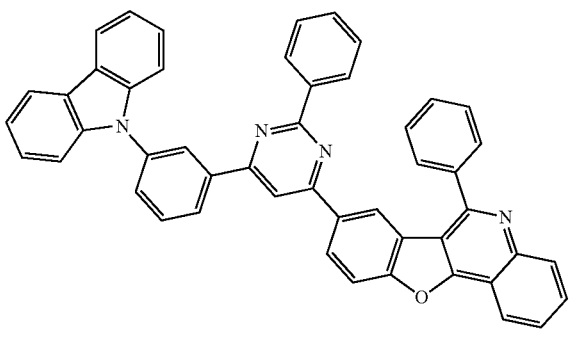
1058
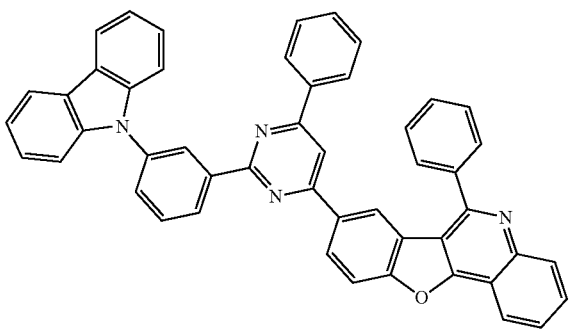
1059
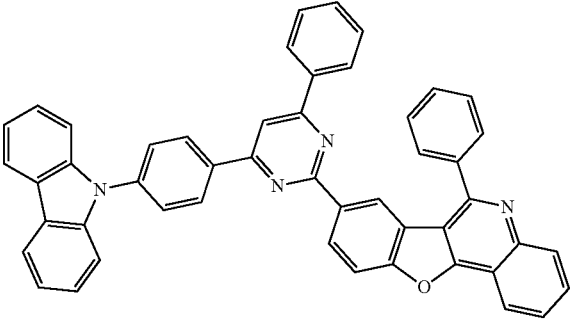
1060
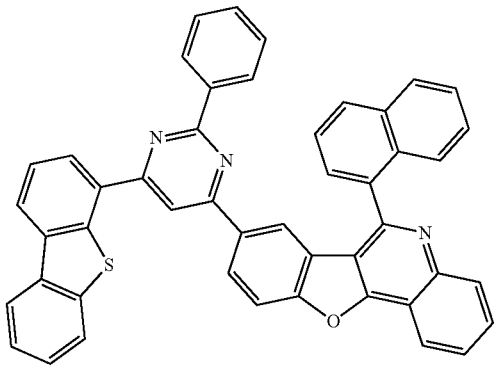

1061
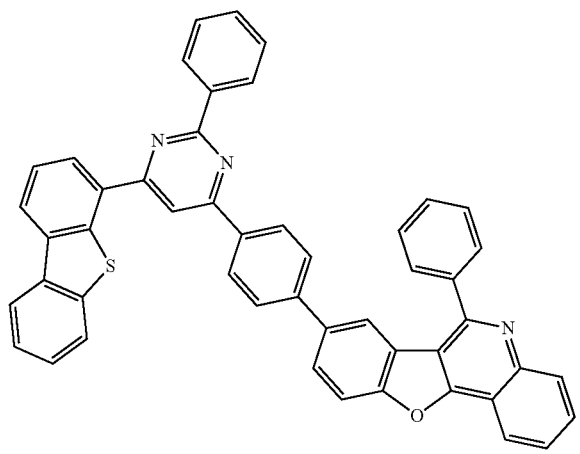
1062
1063
1064
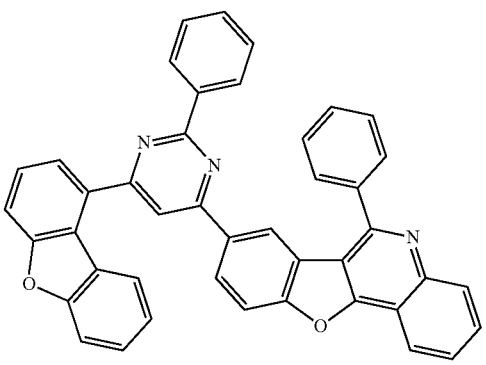
1065
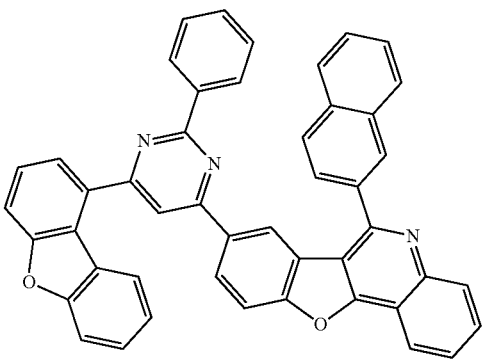
1066
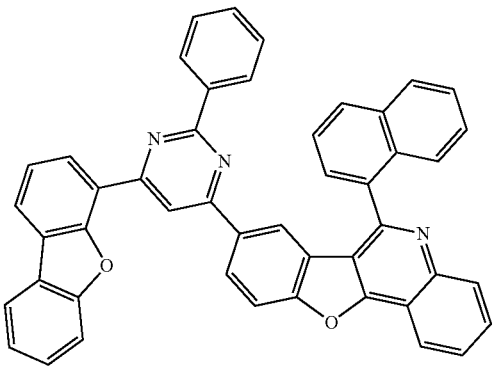
1067
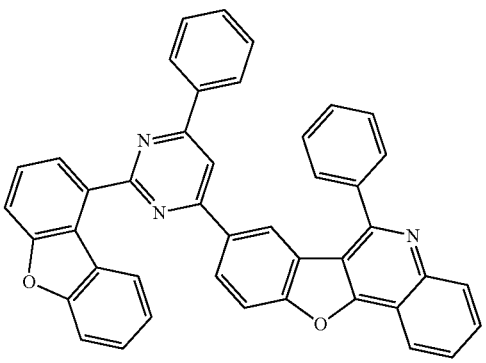

1068
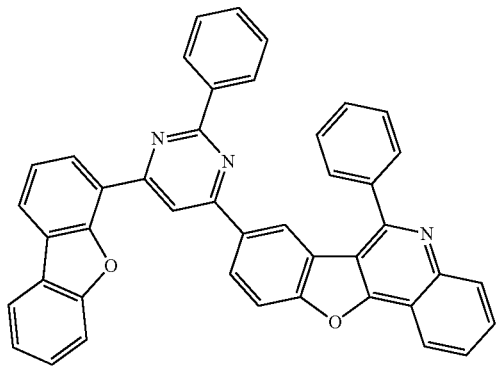
1069
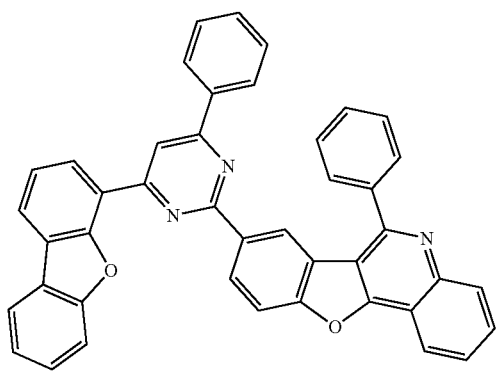
1070
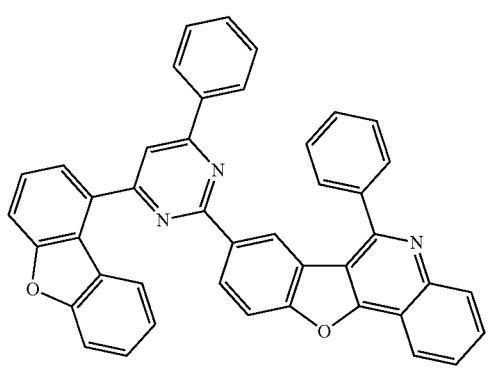
1071
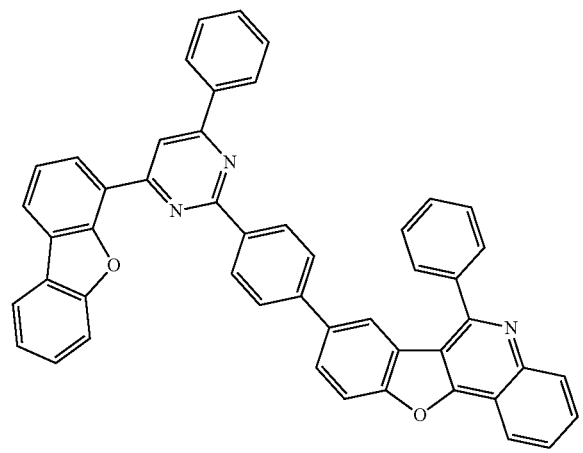
1072
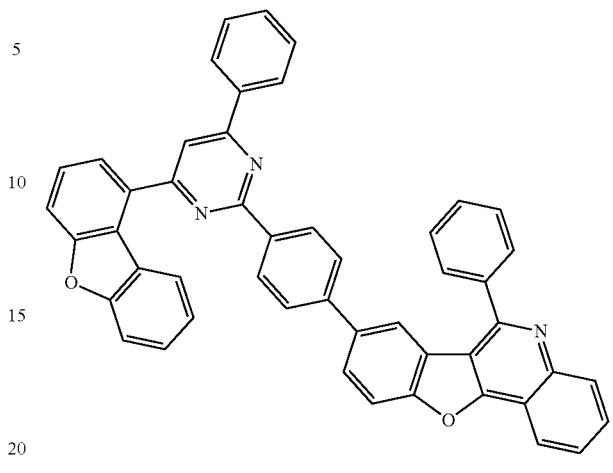
1073
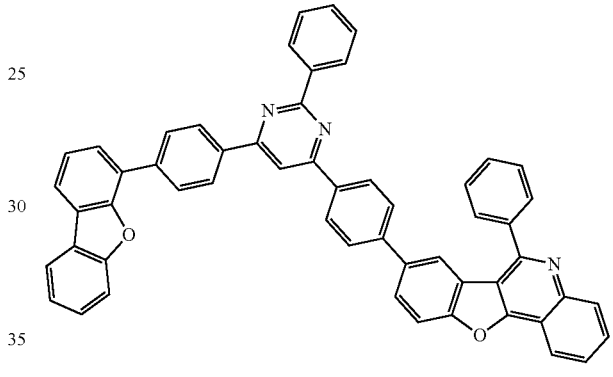
1074
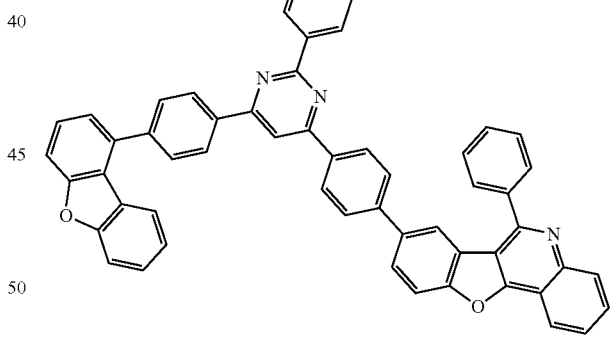
1075
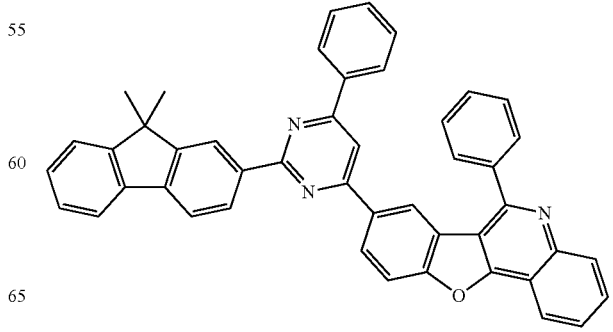

1076
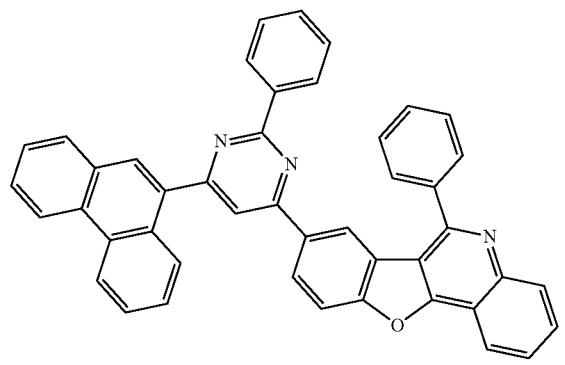
1077

1078
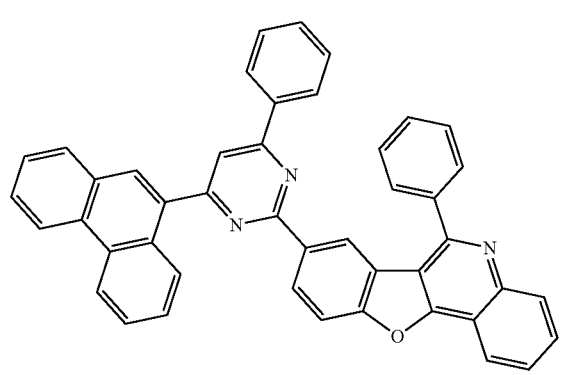
1079
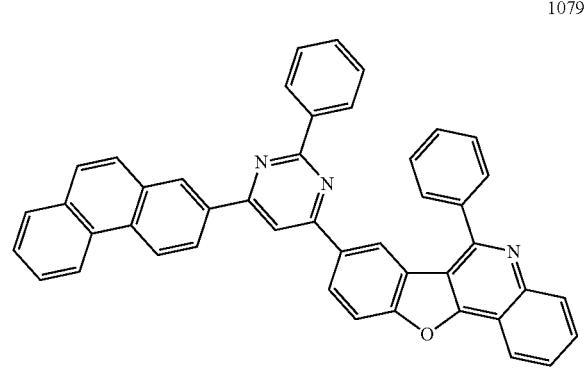
1080
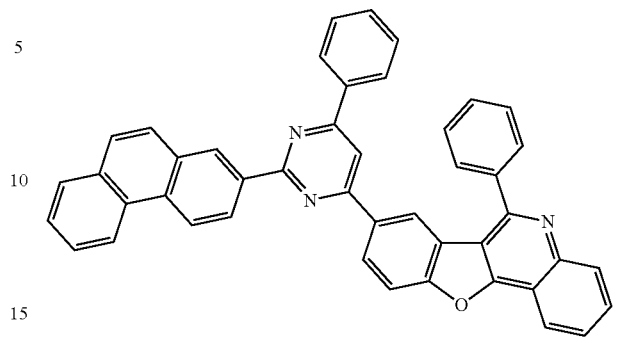
1081
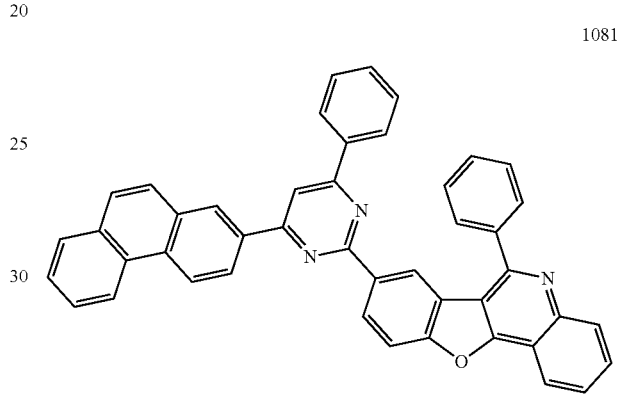
1082
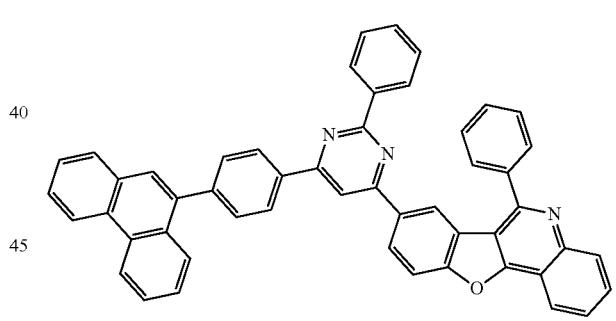
1083
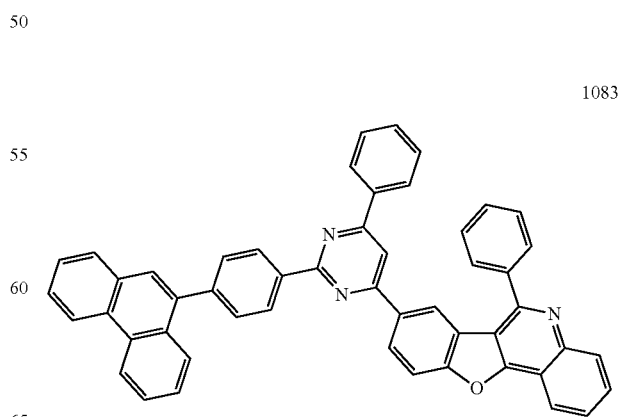

1084
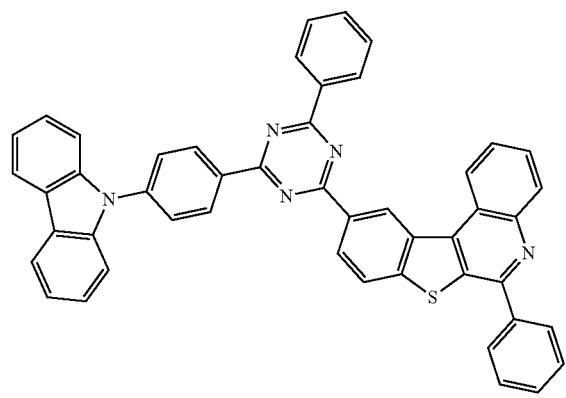
1085
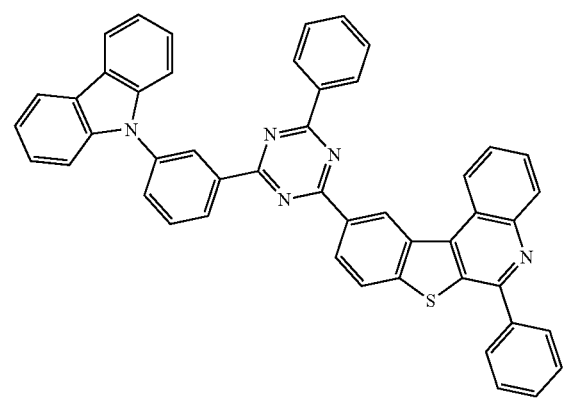
1086
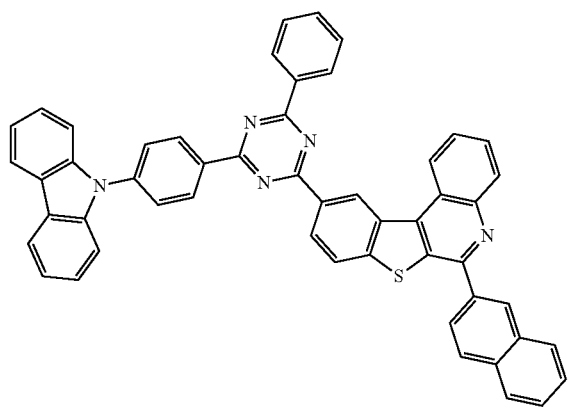
1087
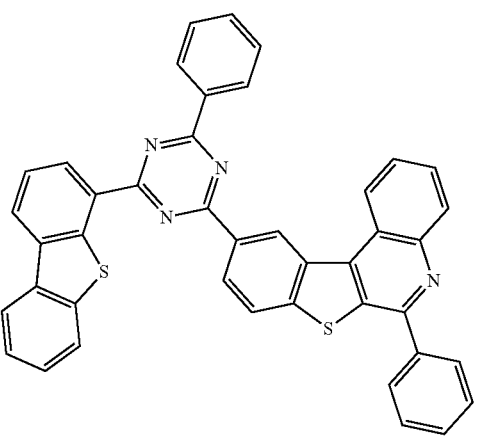
1088
1089
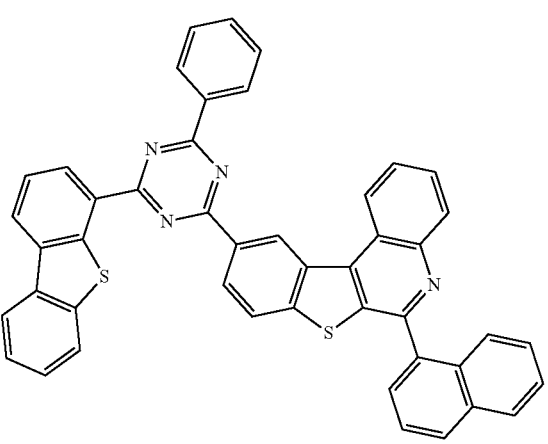

1090
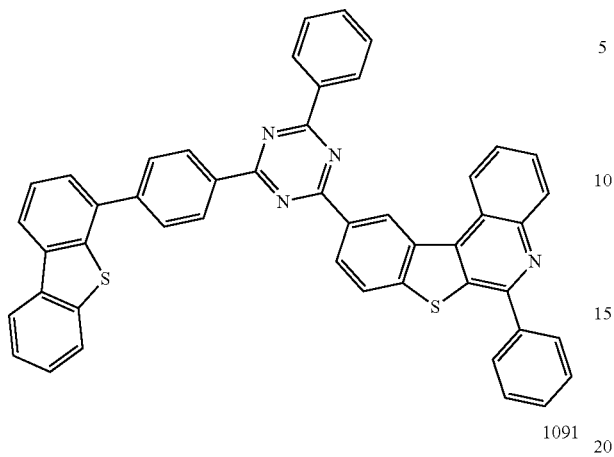
1091
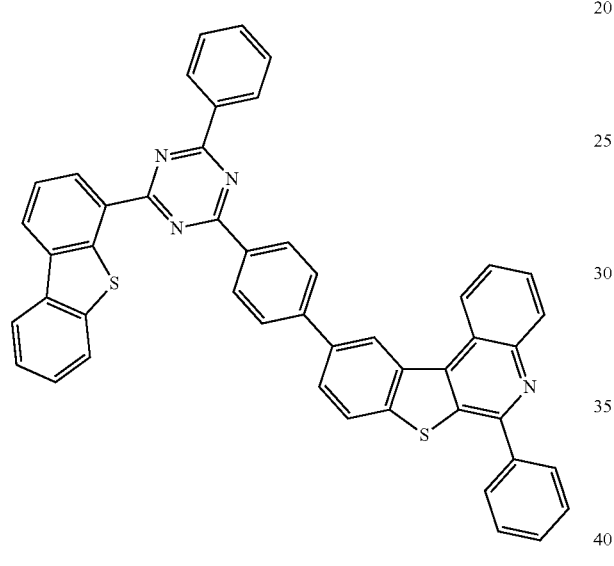
1092
1093
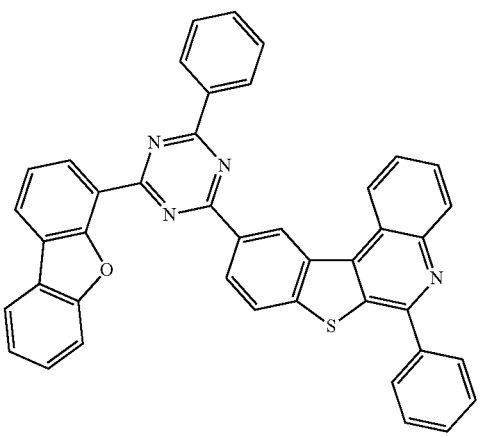
1094
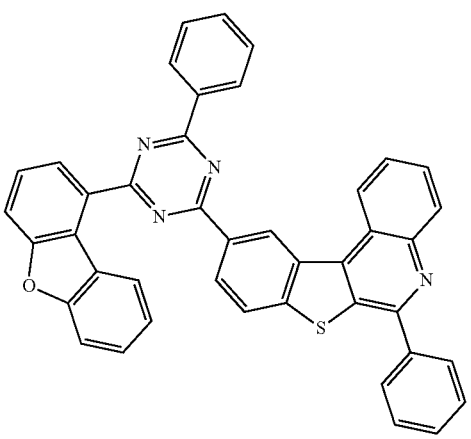
1095
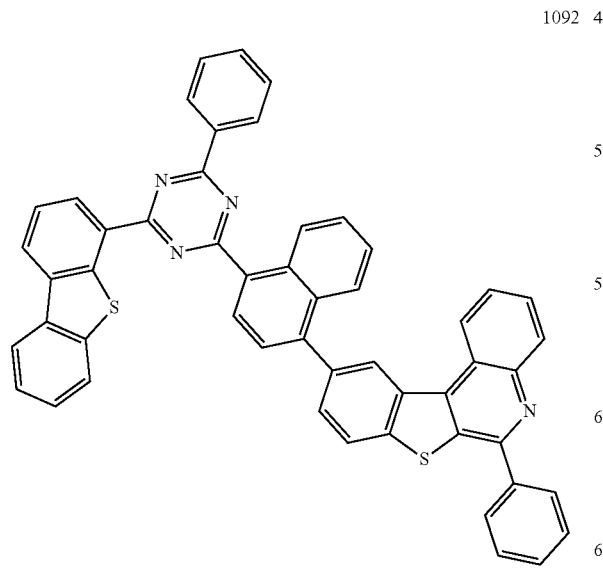
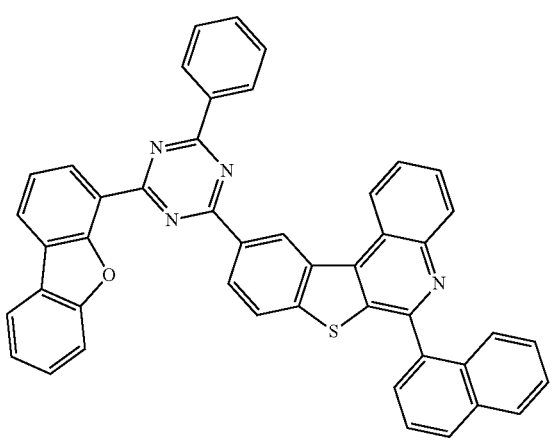

369
-continued
1096
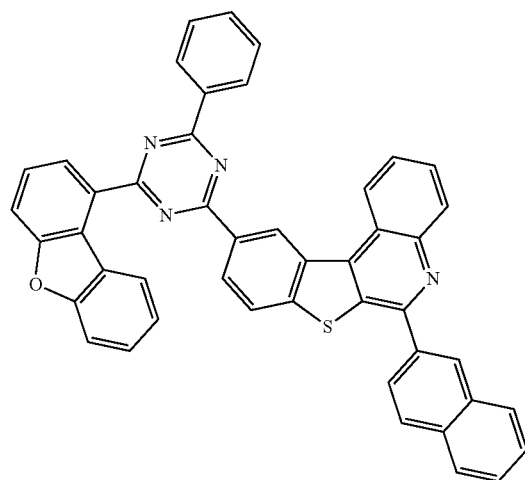
1097
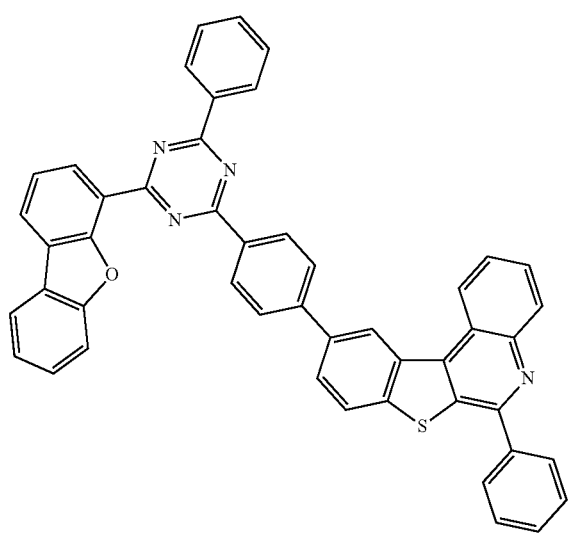
1098
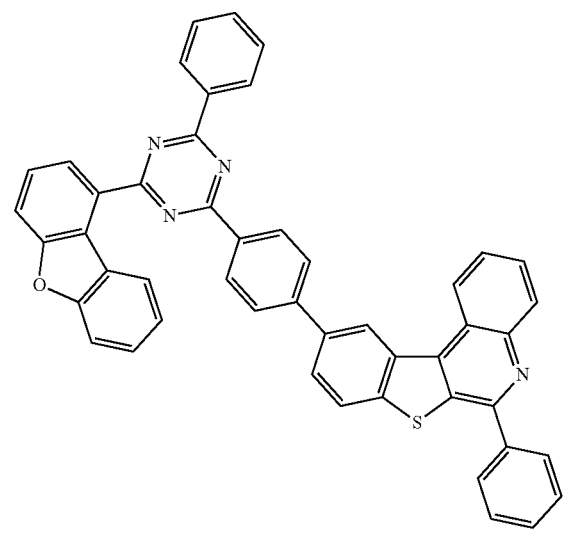
370
-continued
1099
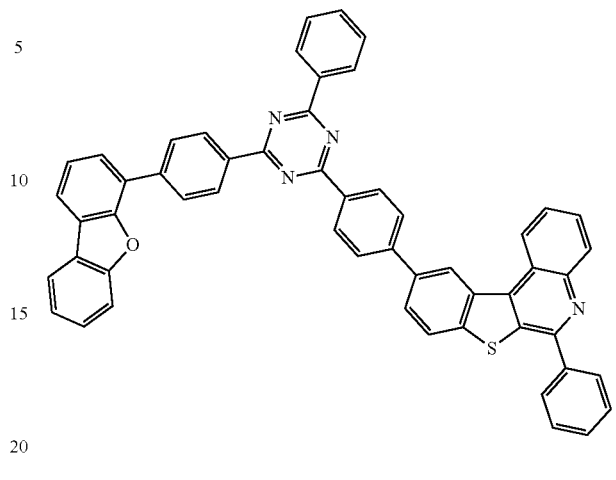
1100
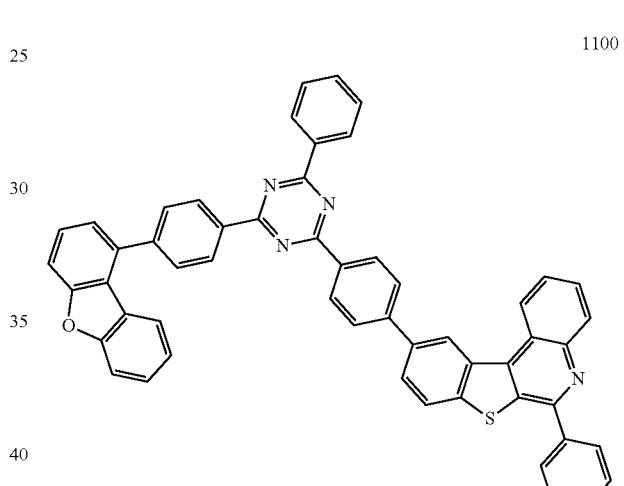
1101
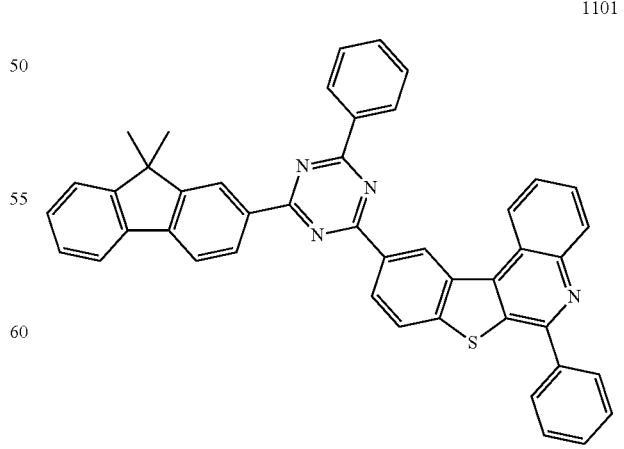

1102
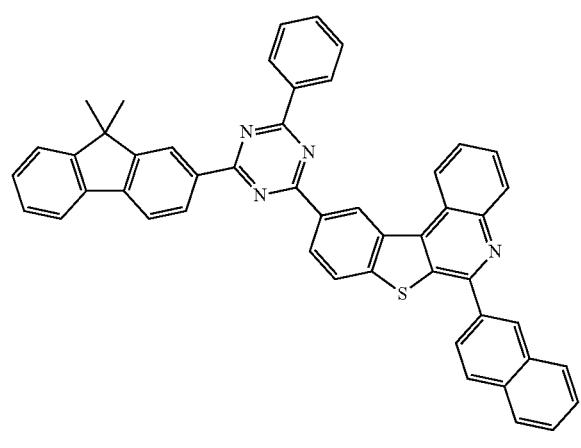
1103
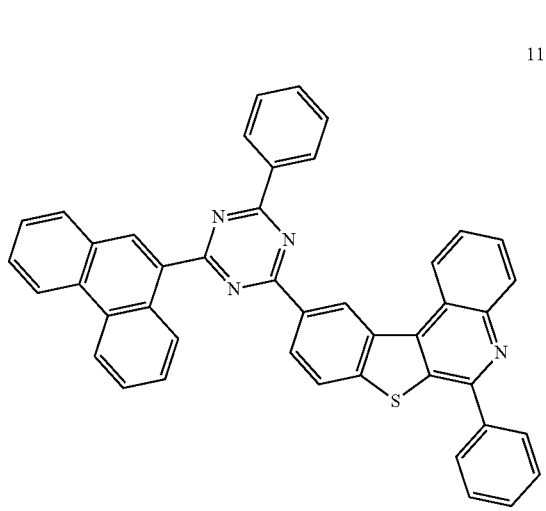
1104
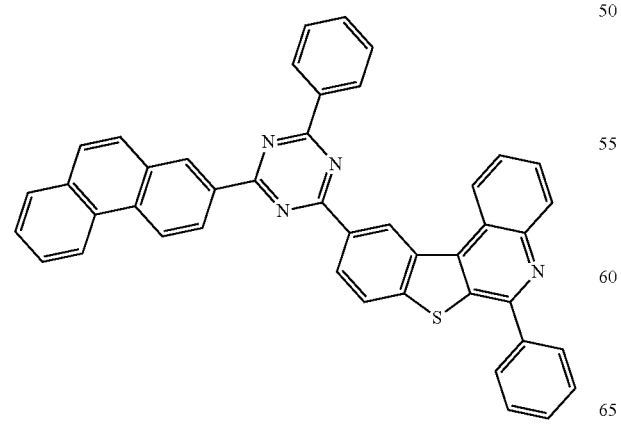
1105
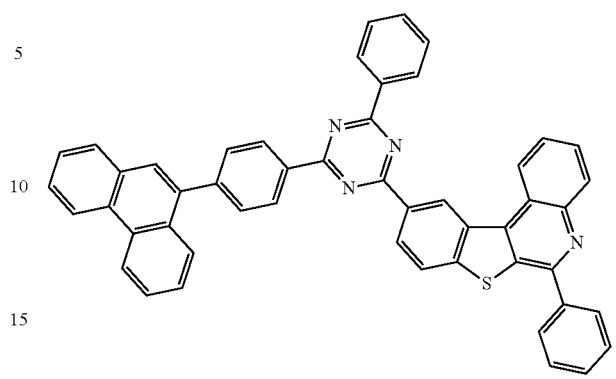
1106
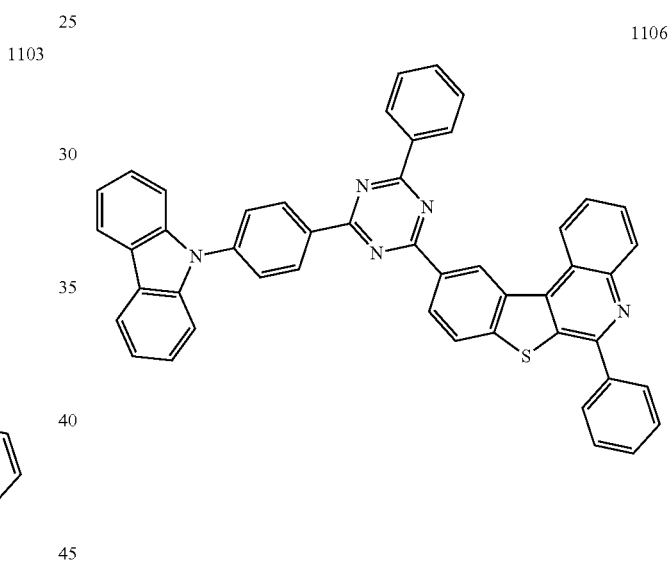
1107
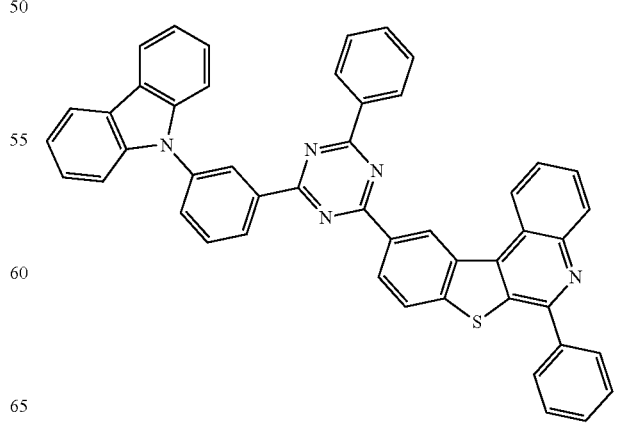

1108
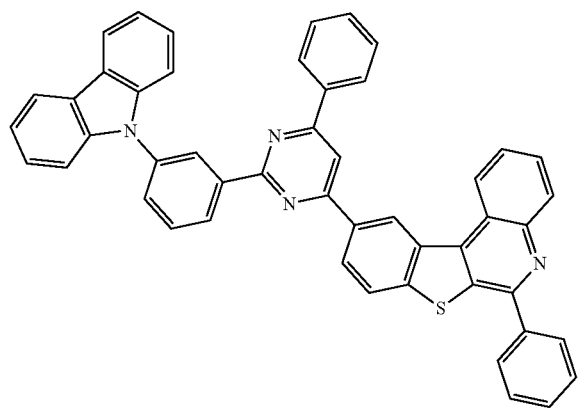
1109
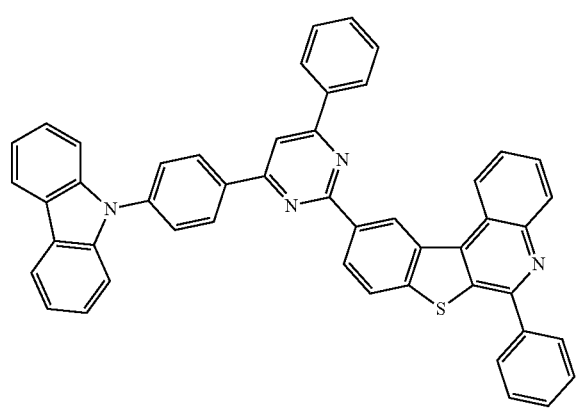
1110
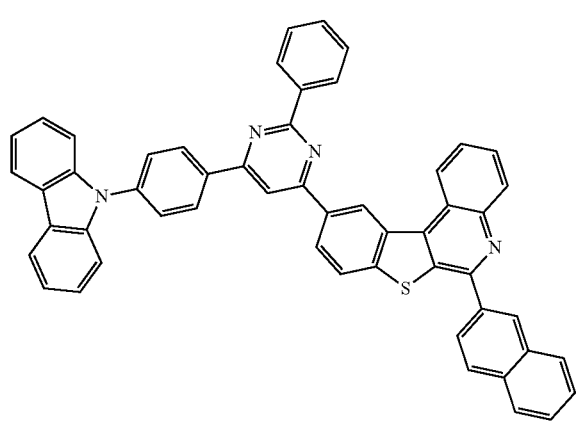
1111
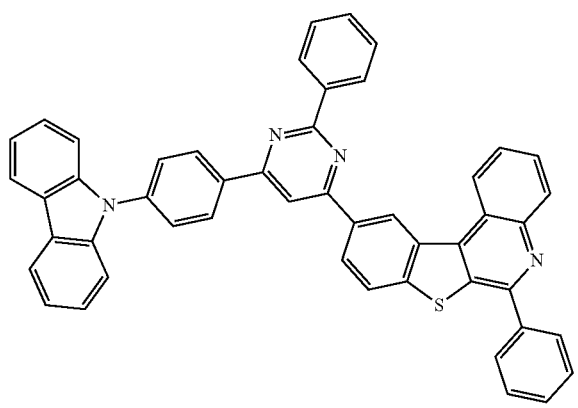
1112
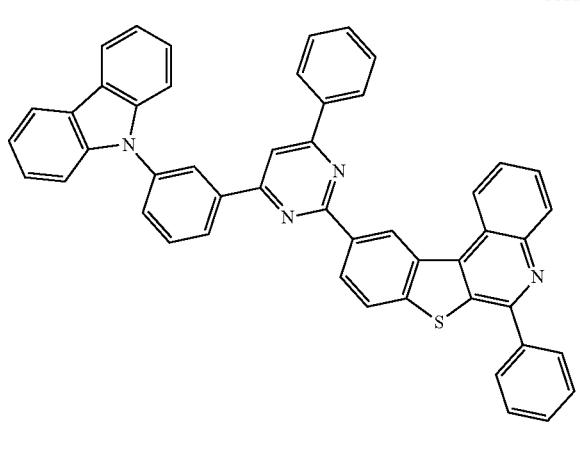
1113
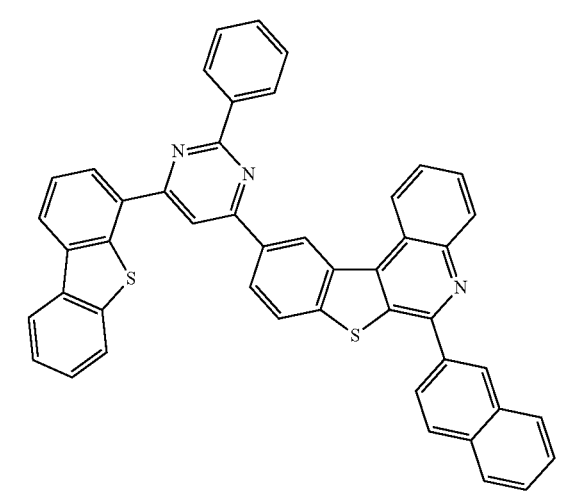

1114
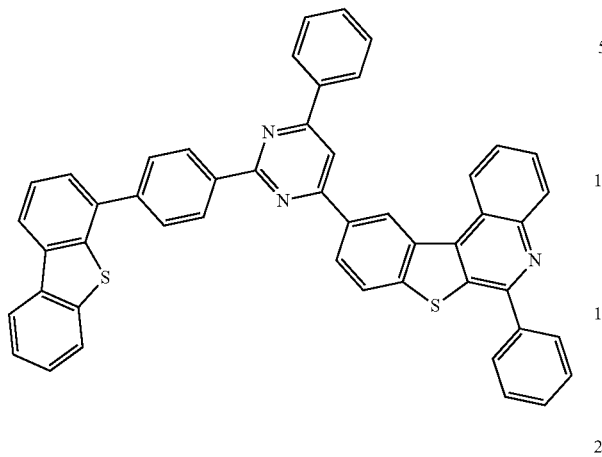
1115
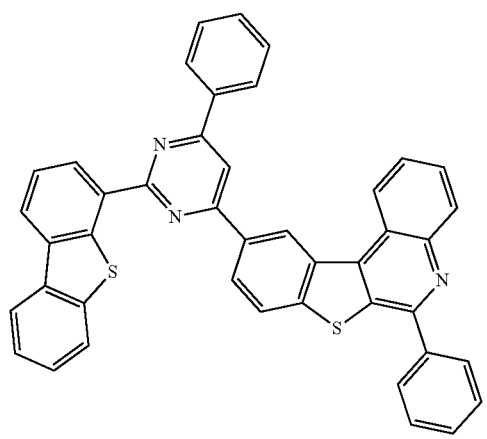
1116
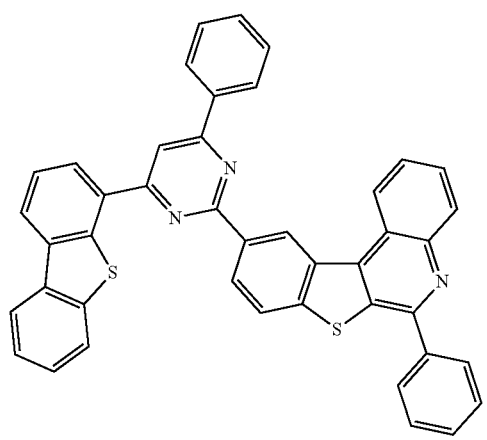
1117
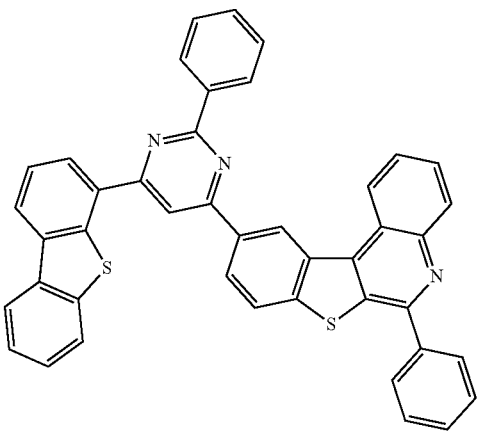
1118
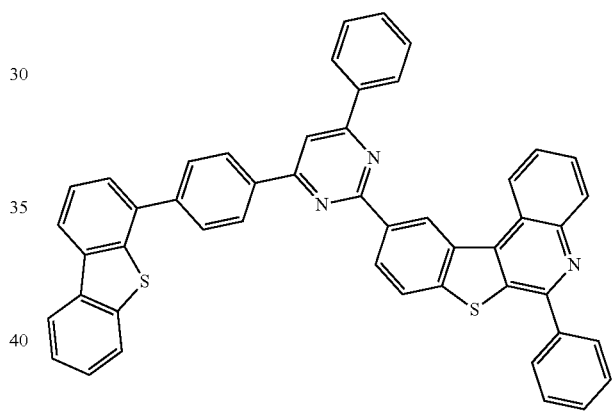
1119
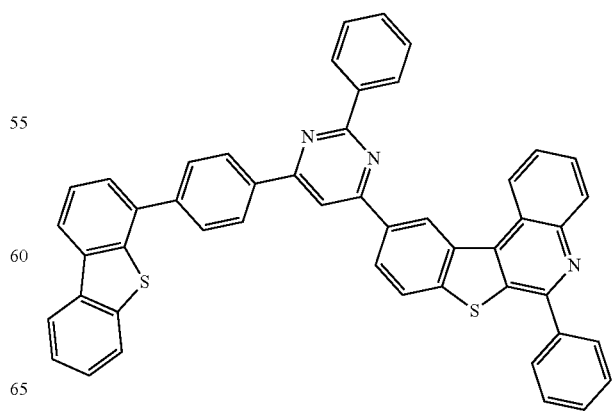

377
-continued
1120
1121
1122
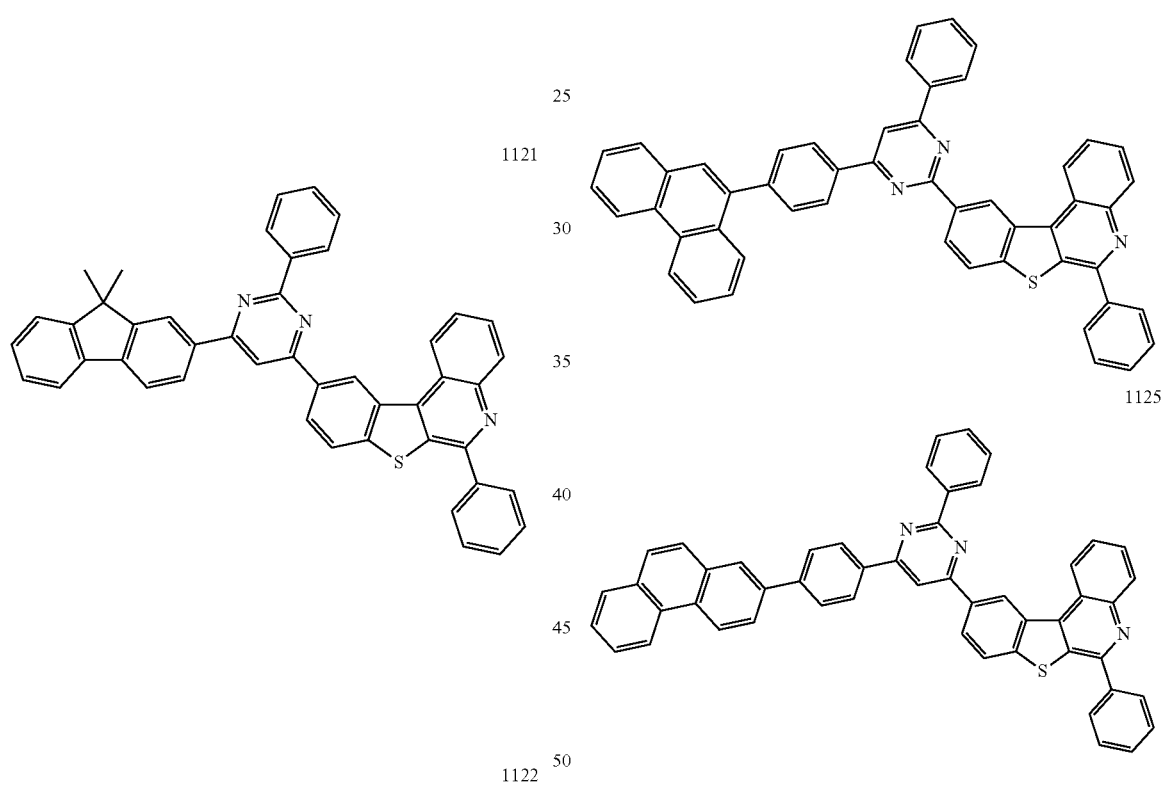
378
-continued
1123
1124
1125
1126
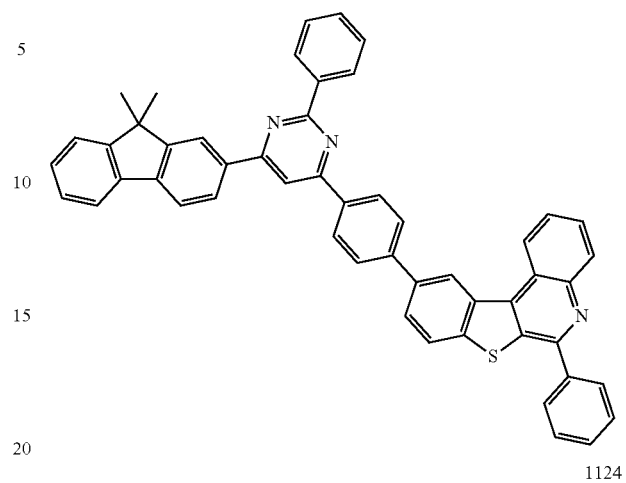
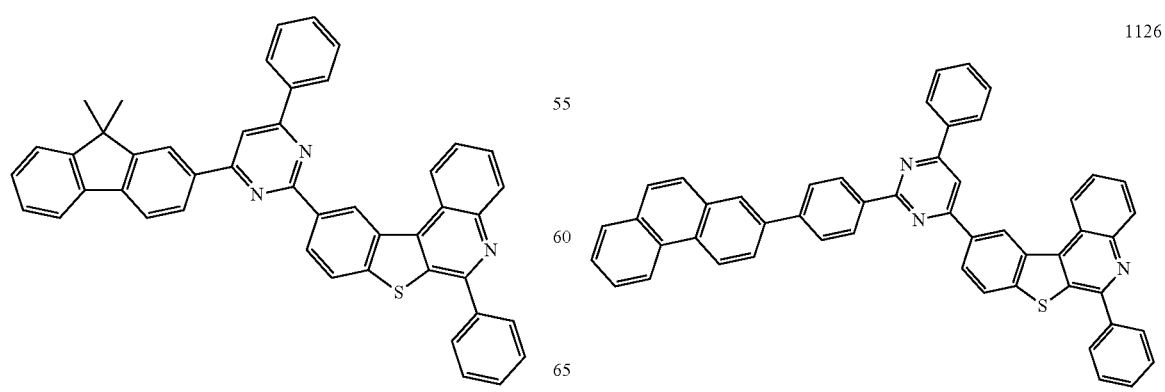

1127
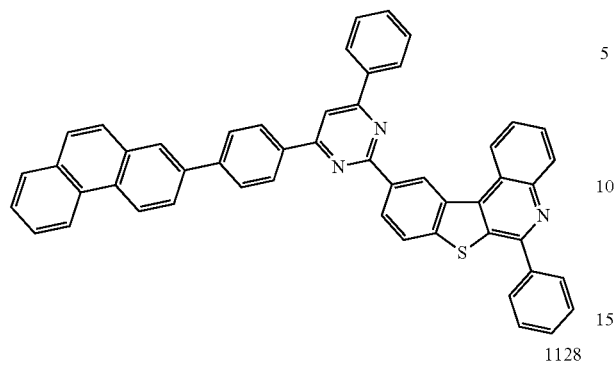
1128
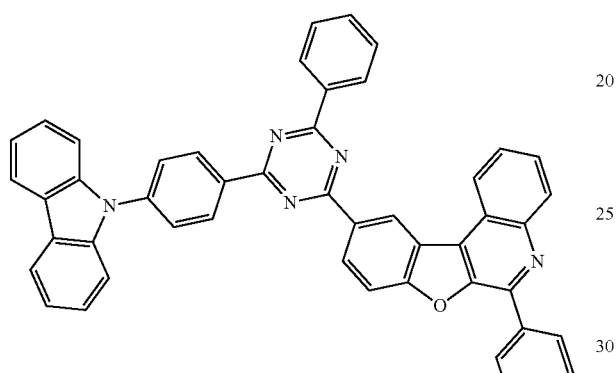
1129
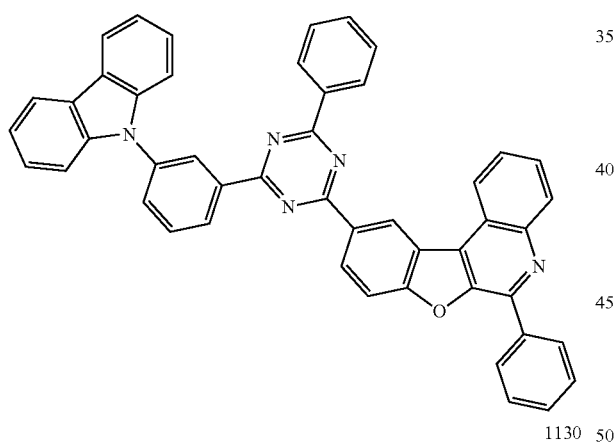
1130
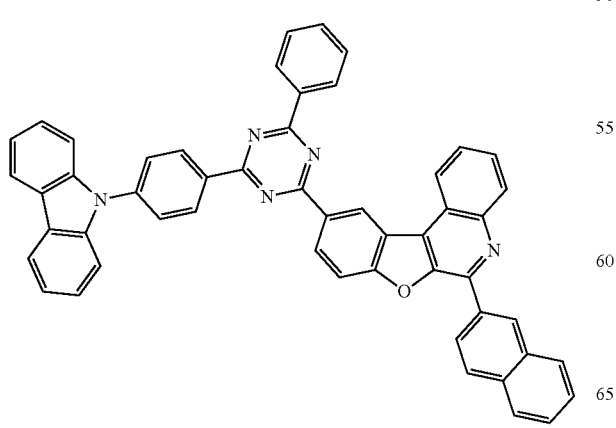
1131
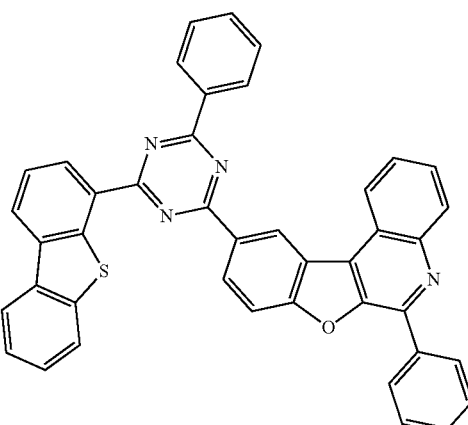
1132
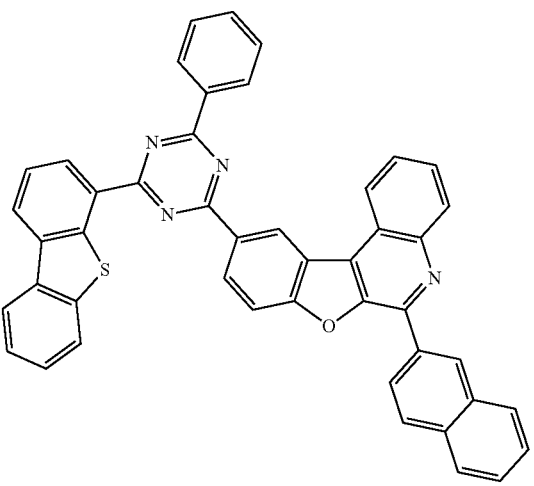
1133
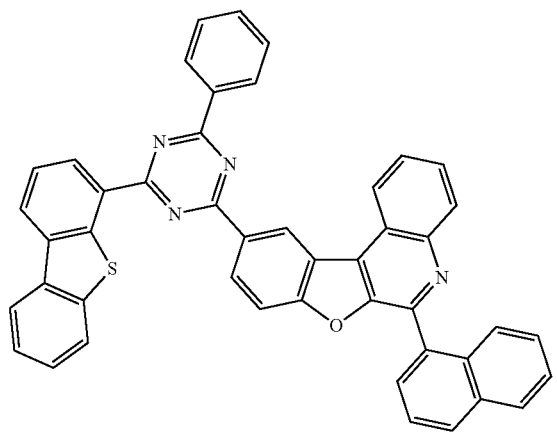

-continued
1134
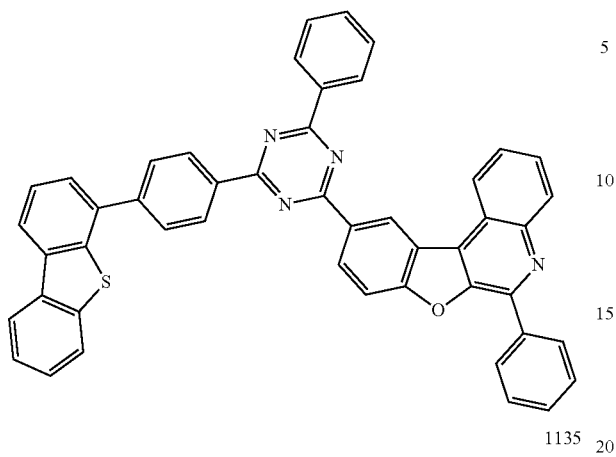
1135
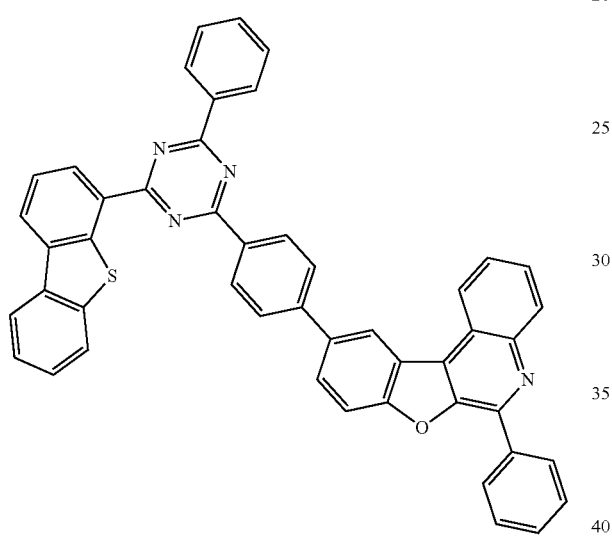
1136
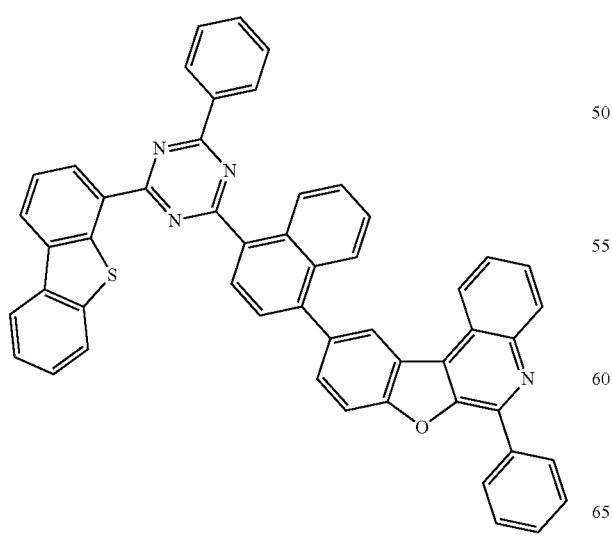
-continued
1137
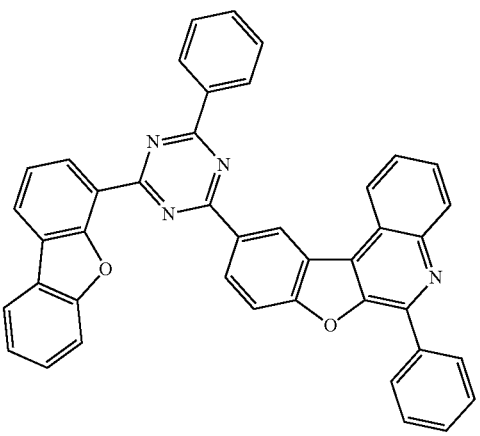
1138
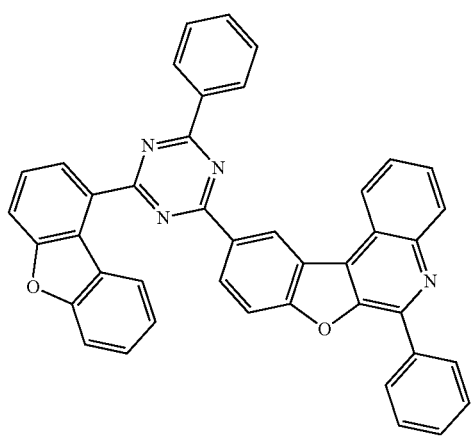
1139
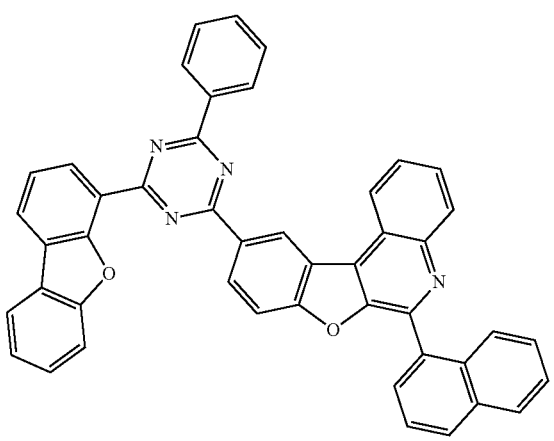

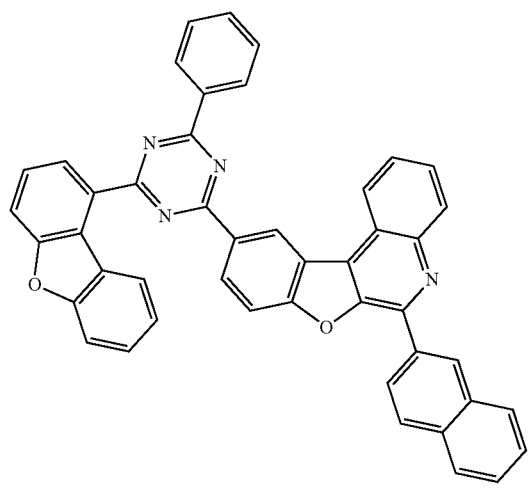
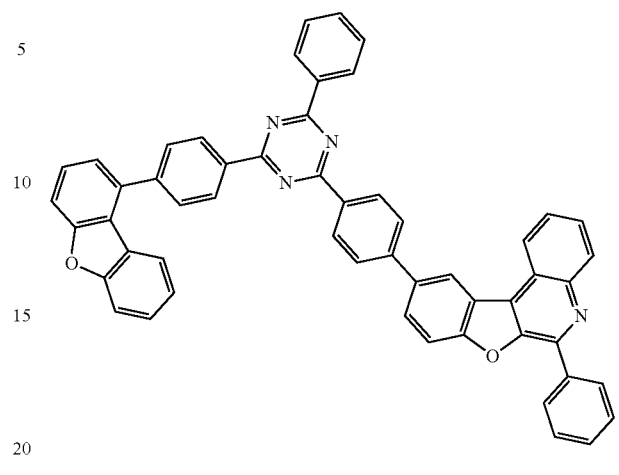
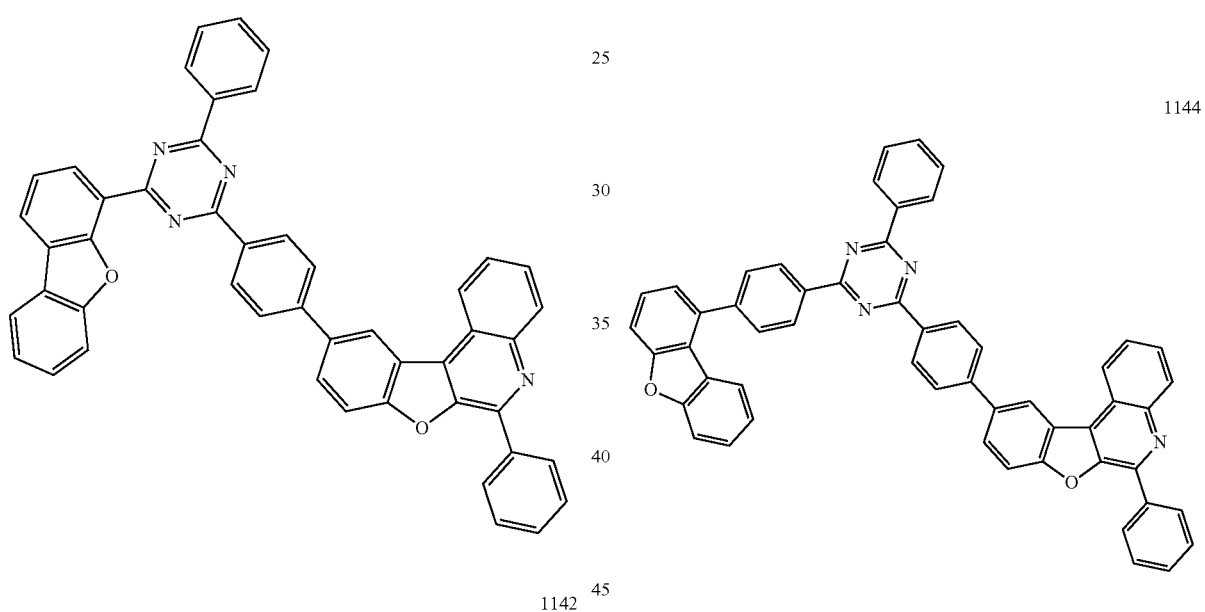
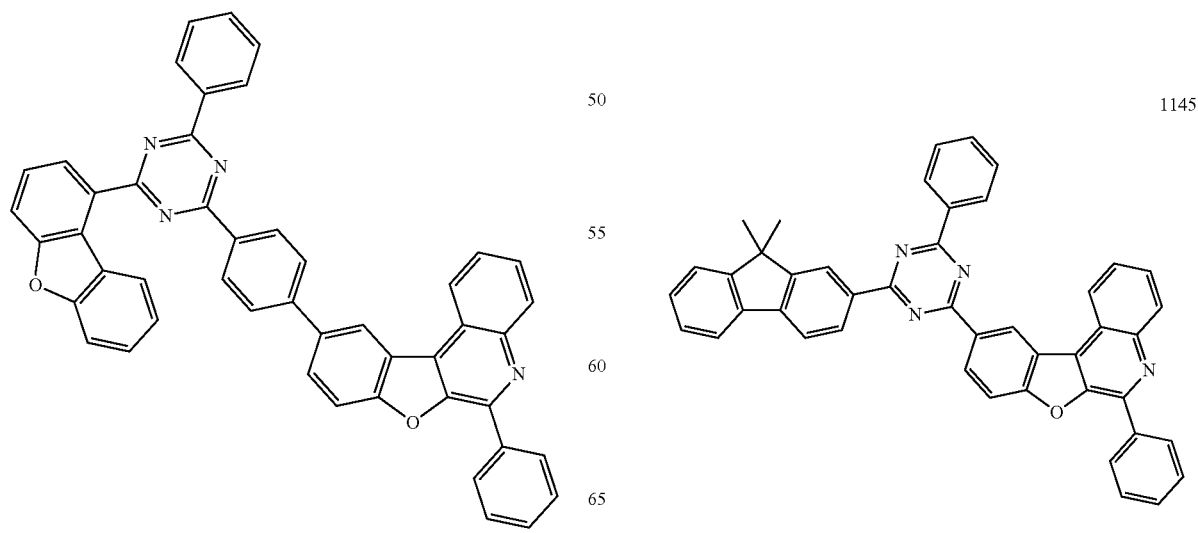

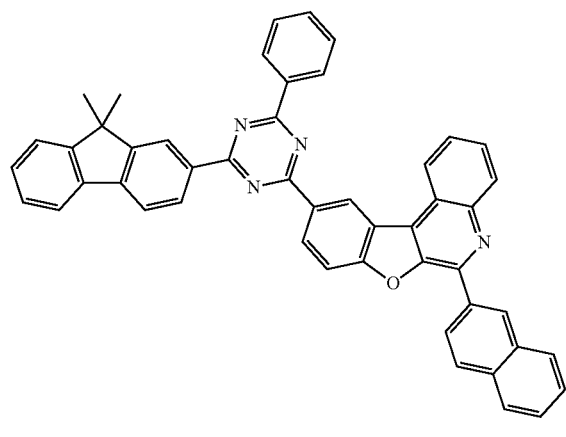
1146
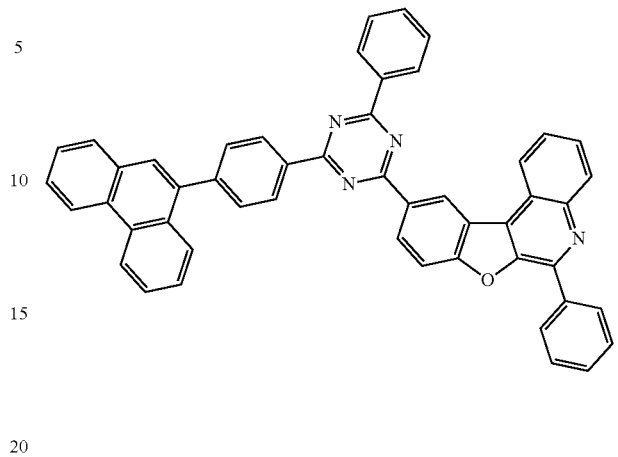
1149
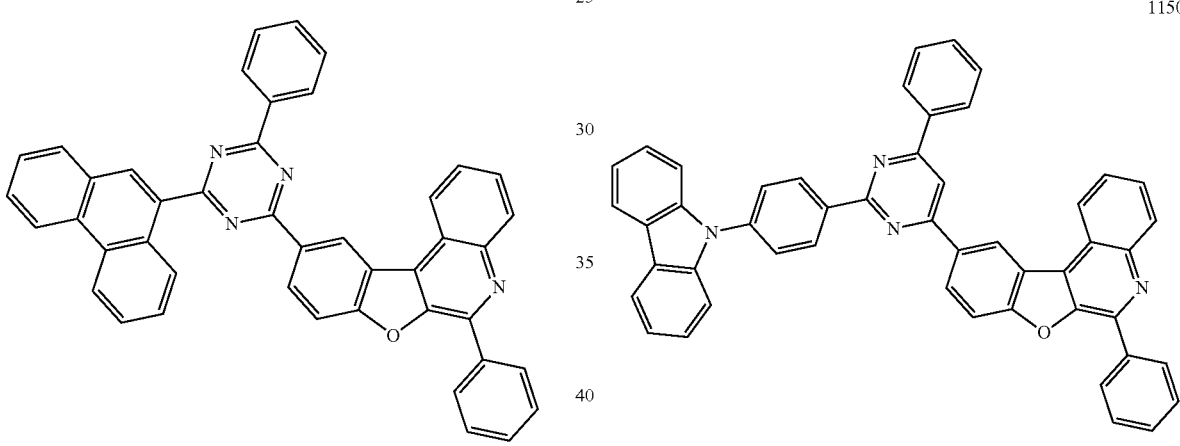
1147
1150
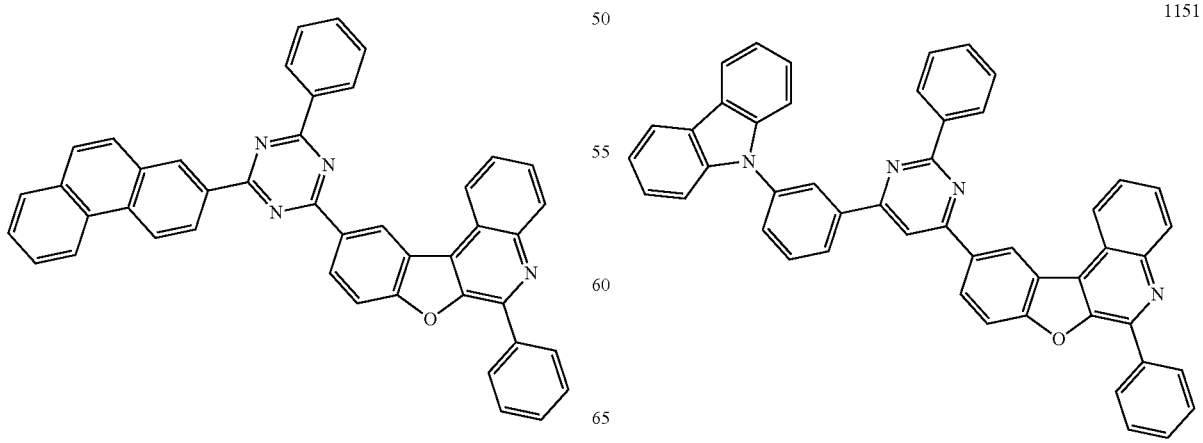
1148
1151

1152
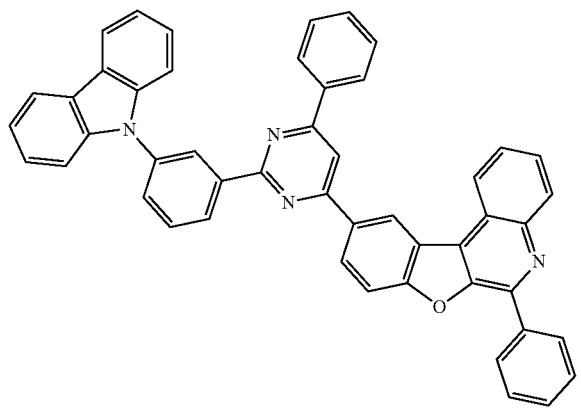
1153
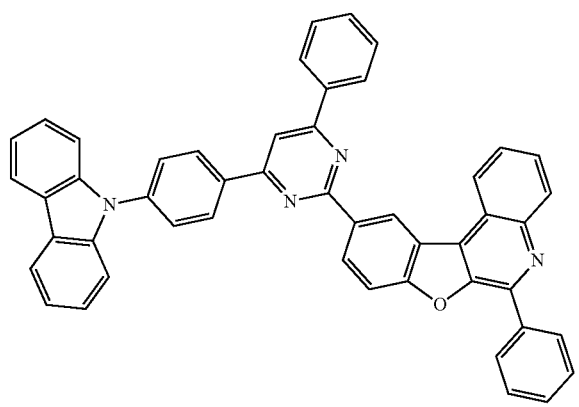
1154
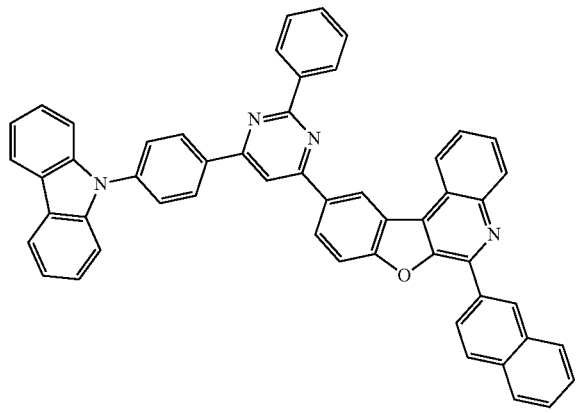
1155
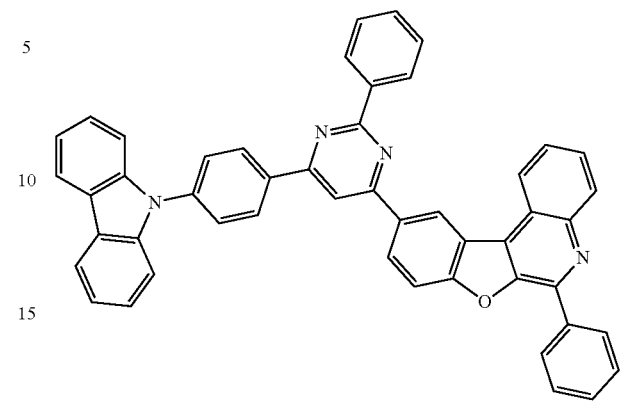
1156
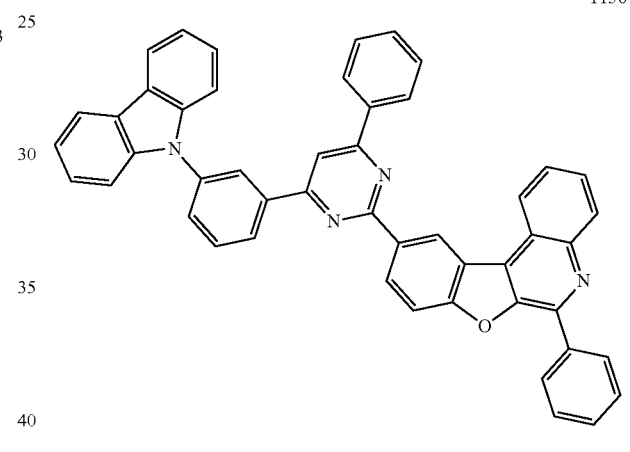
1157
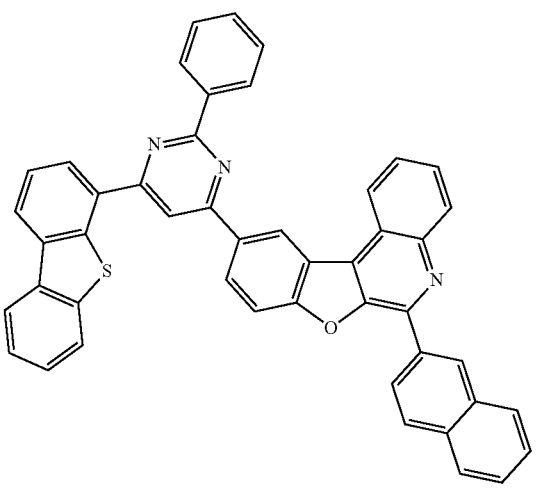

1158
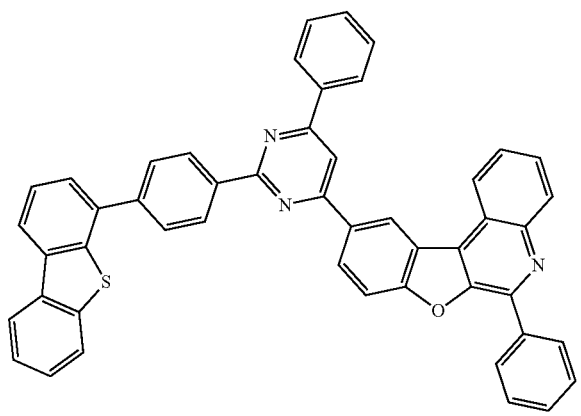
1159
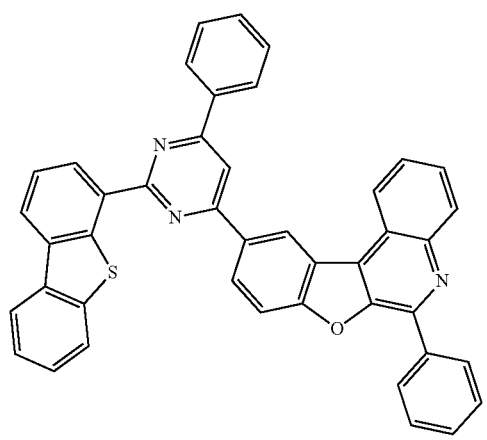
1160
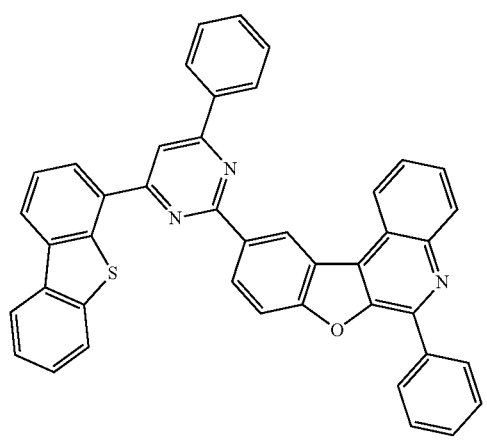
1161
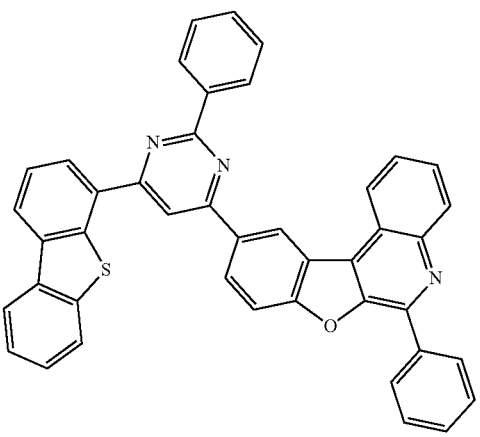
1162
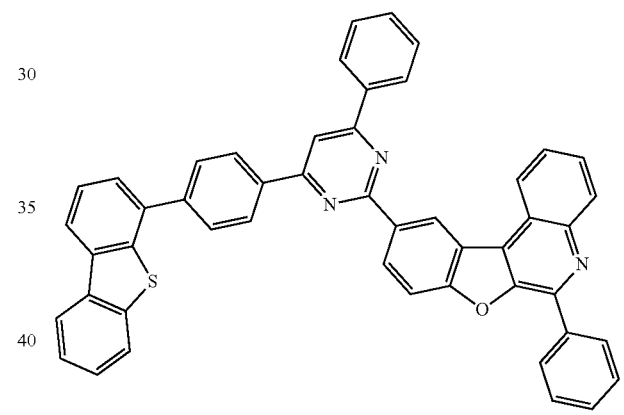
1163
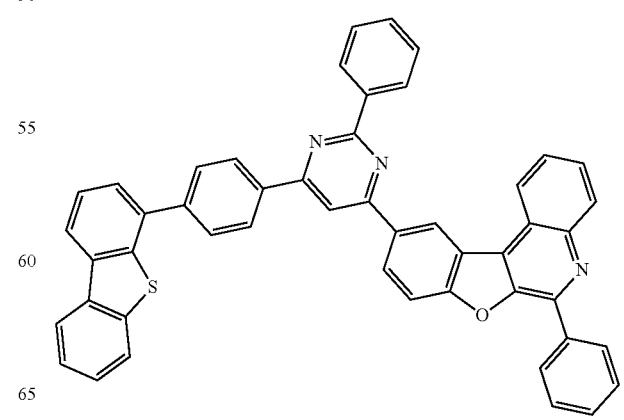

1164
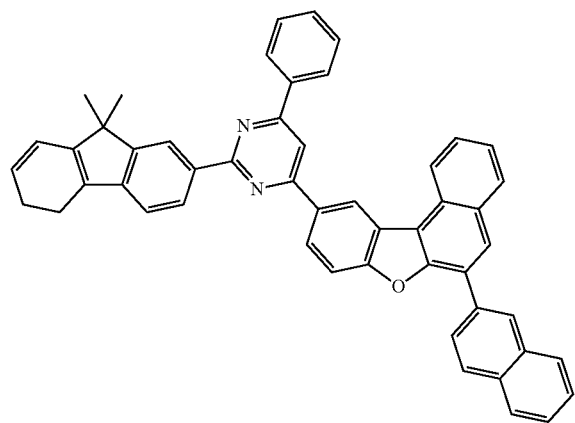
1165
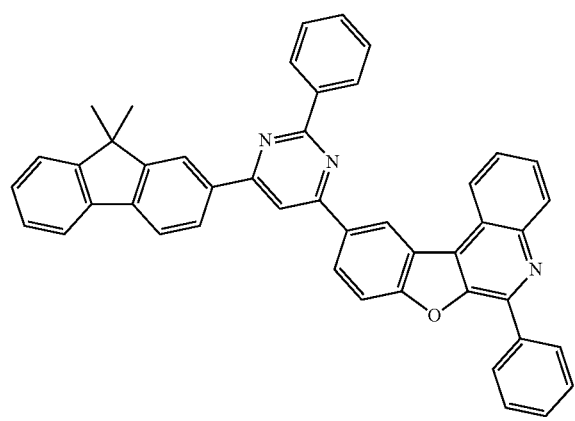
1166
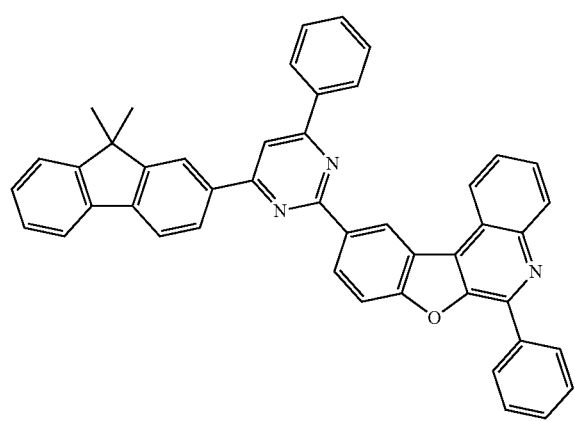
1167
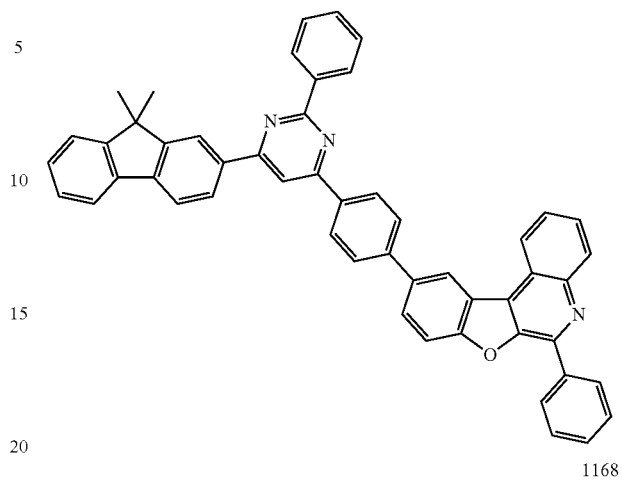
1168
1169
1170
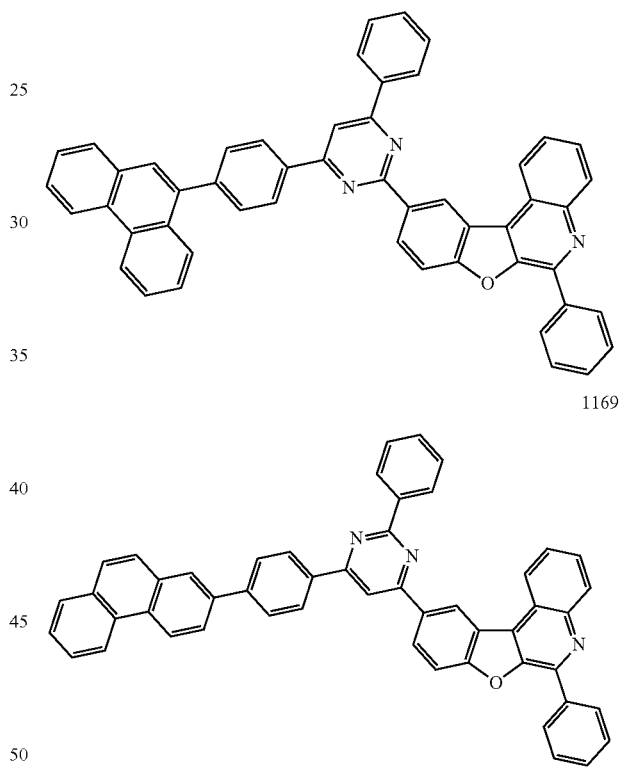
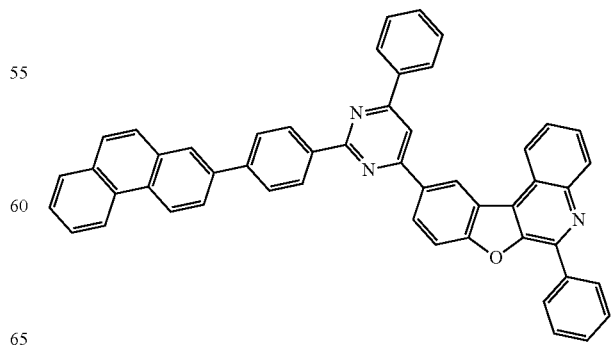

-continued

1171

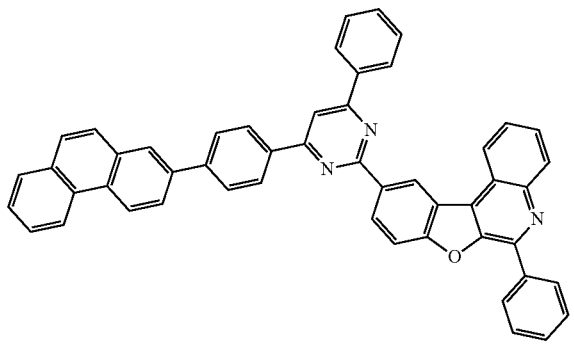

The compound or the composition described above may be for an organic optoelectronic diode, and the compound for an organic optoelectronic diode or the composition for an organic optoelectronic diode may be formed using a dry film-forming method such as chemical vapor deposition.

Hereinafter, an organic optoelectronic diode using the compound for an organic optoelectronic diode or the composition for an organic optoelectronic diode described above will be described.

The organic optoelectronic diode is not particularly limited as long as it is a device capable of interconverting electrical energy and light energy, and examples thereof may comprise an organic photoelectric diode, an organic light emitting diode, an organic solar cell, an organic photo conductor drum and the like.

Another embodiment of the present application provides an organic light emitting diode comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

Specific details on the heterocyclic compound represented by Chemical Formula 1 are the same as the descriptions provided above.

In one embodiment of the present application, the organic light emitting diode may be a blue organic light emitting diode, and the heterocyclic compound according to Chemical Formula 1 may be used as a material of the blue organic light emitting diode.

In one embodiment of the present application, the organic light emitting diode may be a green organic light emitting diode, and the heterocyclic compound according to Chemical Formula 1 may be used as a material of the green organic light emitting diode.

In one embodiment of the present application, the organic light emitting diode may be a red organic light emitting diode, and the heterocyclic compound according to Chemical Formula 1 may be used as a material of the red organic light emitting diode.

The organic light emitting diode of the present disclosure may be manufactured using common organic light emitting diode manufacturing methods and materials except that one or more organic material layers are formed using the heterocyclic compound described above.

The heterocyclic compound may be formed into an organic material layer using a solution coating method as well as a vacuum deposition method when manufacturing the organic light emitting diode. Herein, the solution coating method means spin coating, dip coating, inkjet printing, screen printing, a spray method, roll coating and the like, but is not limited thereto.

Herein, another example of the organic light emitting diode, one example of the organic optoelectronic diode, will be described with reference to accompanying drawings.

FIGS. 1 to 3 illustrate a lamination order of electrodes and organic material layers of an organic light emitting diode according to one embodiment of the present application. However, the scope of the present application is not limited to these diagrams, and structures of organic optoelectronic diodes known in the art may also be used in the present application.

FIG. 1 illustrates an organic light emitting diode in which an anode (200), an organic material layer (300) and a cathode (400) are consecutively laminated on a substrate (100). However, the structure is not limited to such a structure, and as illustrated in FIG. 2, an organic light emitting diode in which a cathode, an organic material layer and an anode are consecutively laminated on a substrate may also be obtained.

FIG. 3 illustrates a case of the organic material layer being a multilayer. The organic light emitting diode according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, layers other than the light emitting layer may not be included, and other necessary functional layers may be further included.

In the organic light emitting diode, the compound represented by Chemical Formula 1 may be used as a material of an electron transfer layer, a hole transfer layer, a hole blocking layer, a light emitting layer or the like. More specifically, the compound represented by Chemical Formula 1 may be used as a material of an electron transfer layer or a hole blocking layer in the organic light emitting diode.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri

[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used and low molecular or high molecular materials may also be used.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among N-type host materials or P-type host materials may be selected, and used as a host material of a light emitting layer.

Examples of the hole blocking material may comprise a triazole derivative, bathocuproine or a mixed ligand complex of aluminum (BAlq), however, the present application is not limited thereto, and the compound of one embodiment of the present disclosure may also be used.

The electron transfer material may be the compound of one embodiment of the present disclosure.

As examples of the electron injection material, LiF is typically used in the art, however, the present application is not limited thereto.

The organic light emitting diode according to one embodiment of the present application may be a top-emission type, a bottom-emission type or a dual-emission type depending on the materials used.

Hereinafter, the embodiments described above will be described in more detail through examples. However, the following examples are for illustrative purposes only and do not limit the scope of a right.

(Preparation of Compound for Organic Optoelectronic Diode)

The following preparation examples use the following General Formula 1 to General Formula 4.

[General Formula 1]

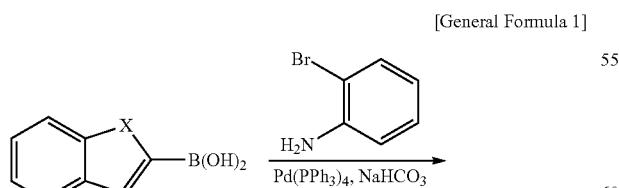

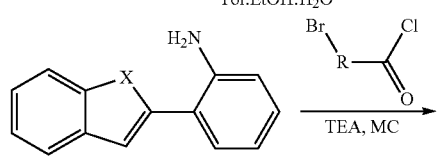

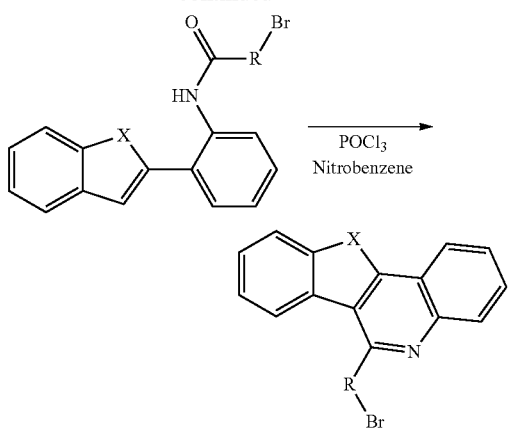

[General Formula 2]

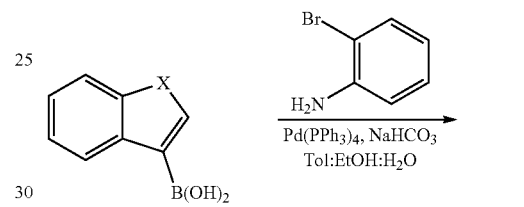

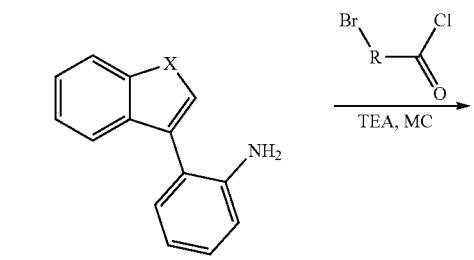

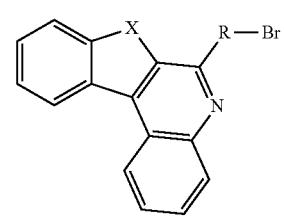

[General Formula 3]

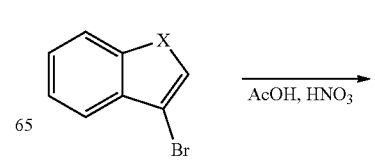

-continued
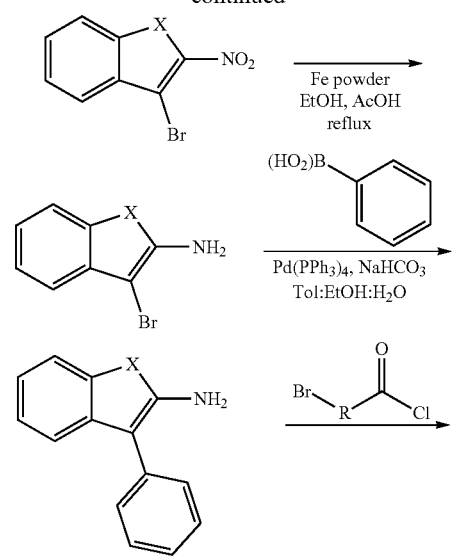
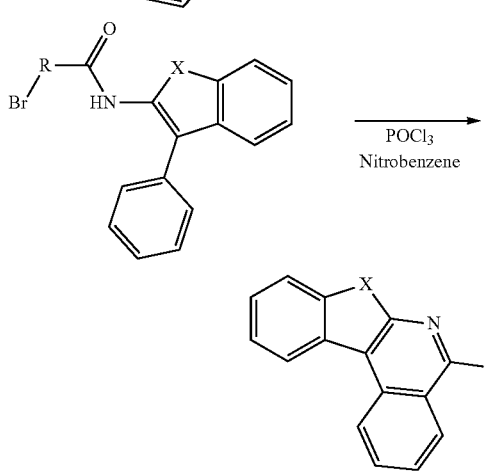
[General Formula 4]
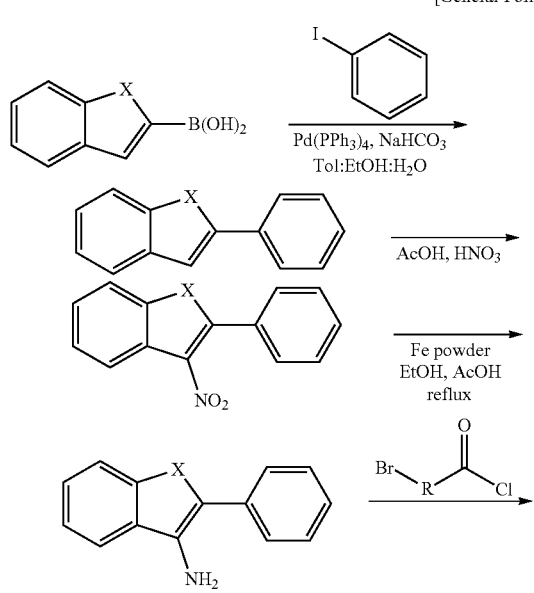
-continued
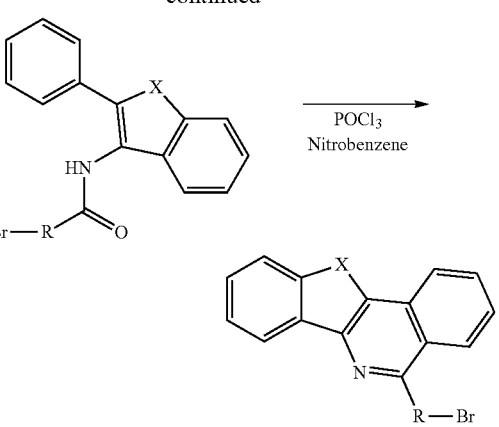
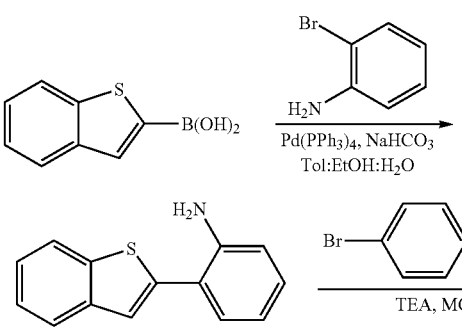
Specific preparation examples are as follows.
[Preparation Example 1-1] Preparation of Compound 1
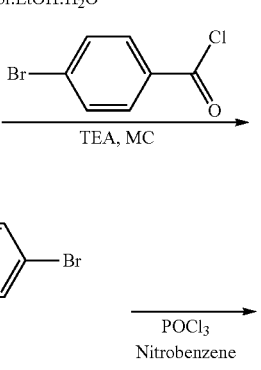
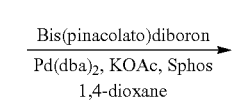

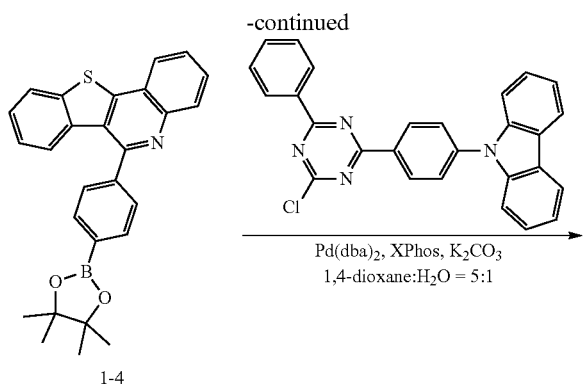

1-4

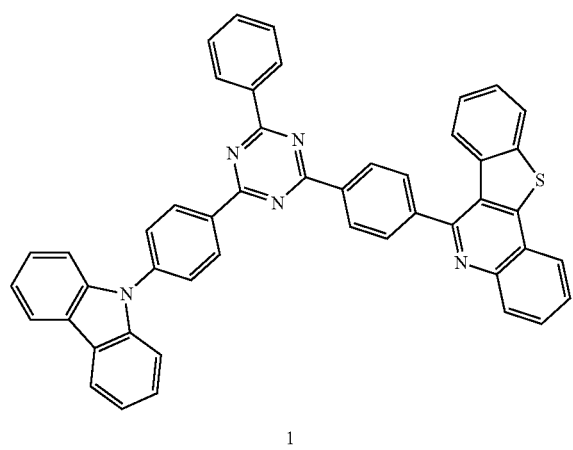

1

1) Preparation of Compound 1-1

After dissolving benzo[b]thiophen-2-ylboronic acid (100 g, 0.561 mol) and 2-bromoaniline (86.7 g, 0.504 mol) in toluene, EtOH and H₂O (1000 mL:200 mL:200 mL), Pd(PPh₃)₄ (32.4 g, 0.028 mol) and NaHCO₃ (141.3 g, 1.68 mol) were introduced thereto, and the result was stirred for 3 hours at 100° C. After the reaction was completed, the reaction solution was extracted by introducing MC and distilled water thereto. After that, the result was dried with anhydrous MgSO₄, and the solvent was removed using a rotary evaporator to obtain liquid-type Compound 1-1 (93 g, 74%).

2) Preparation of Compound 1-2

Compound 1-1 (93 g, 0.412 mol) and triethylamine (86 mL, 0.618 mol) were introduced to and dissolved in MC (1200 mL). 4-Bromobenzoyl chloride (135.6 g, 0.618 mol) dissolved in MC (300 mL) was slowly added dropwise to the mixture at 0° C. After the reaction was completed, white solids present in the reaction solution were filtered and washed with hexane. The result was dried to obtain solid-type Compound 1-2 (134 g, 83%).

3) Preparation of Compound 1-3

After dissolving Compound 1-2 (134 g, 0.329 mol) in nitrobenzene (1500 mL), POCl₃ (46 mL, 0.495 mol) was slowly added dropwise thereto. The result was reacted for 15 hours at 140° C. After the reaction was completed, a solution obtained by dissolving NaHCO₃ in distilled water was slowly introduced to the reaction solution, and the result was stirred. Solids produced after that were filtered and collected. The collected solids were recrystallized with MC and MeOH to obtain solid-type Compound 1-3 (65 g, 51%).

4) Preparation of Compound 1-4

After dissolving Compound 1-3 (10 g, 0.025 mol), bis(pinacolato)diboron (9.7 g, 0.038 mol), KOAc (7.3 g, 0.075 mol) and PdCl₂(dppf) (0.9 g, 0.0012 mol) in 1,4-dioxane (200 mL), the result was reacted for 5 hours at 90° C. After the reaction was completed, the reaction solution was extracted by introducing MC and distilled water thereto. After that, the result was dried with anhydrous MgSO₄, and progressed with column chromatography using MC and hexane as a developing solvent to obtain Compound 1-4 (7.6 g, 70%).

5) Preparation of Compound 1

After dissolving Compound 1-4 (7.6 g, 0.017 mol) and 9-(4-(4-chloro-6-phenyl-1,3,5-triazin-2-yl)phenyl)-9H-carbazole (7.3 g, 0.017 mol) in 1,4-dioxane:H₂O (100 mL:20 mL), Pd₂(dba)₃ (1.5 g, 0.0017 mol), XPhos (1.6 g, 0.0034 mol) and K₂CO₃ (7.0 g, 0.051 mol) were introduced thereto, and the result was stirred for 5 hours at 100° C. After the reaction was completed, solids produced in the reaction solution were washed with 1,4-dioxane and H₂O. After that, only the solids were purified using a recrystallization method in DCB to obtain Compound 1 (7.2 g, 60%).

Preparation Example 1-2

Target compounds were synthesized in the same manner as in Preparation Example 1-1 using Intermediate A instead of 9-(4-(4-chloro-6-phenyl-1,3,5-triazin-2-yl)phenyl)-9H-carbazole.

TABLE 1

| Compound No. | Intermediate A | Target Compound | Yield |
|---|---|---|---|
| 17 | (structure) | (structure) | 61% |

TABLE 1-continued

| Compound No. | Intermediate A | Target Compound | Yield |
|---|---|---|---|
| 21 | | | 63% |
| 29 | | | 60% |
| 40 | | | 61% |
| 42 | | | 54% |

TABLE 1-continued

| Compound No. | Intermediate A | Target Compound | Yield |
|---|---|---|---|
| 50 | | | 61% |
| 52 | | | 60% |
| 55 | | | 62% |
| 60 | | | 63% |

TABLE 1-continued

| Compound No. | Intermediate A | Target Compound | Yield |
|---|---|---|---|
| 62 | | | 64% |
| 250 | | | 61% |
| 264 | | | 60% |
| 266 | | | 60% |

TABLE 1-continued

| Compound No. | Intermediate A | Target Compound | Yield |
|---|---|---|---|
| 270 | | | 61% |
| 283 | | | 62% |
| 285 | | | 61% |
| 290 | | | 60% |

TABLE 1-continued

| Compound No. | Intermediate A | Target Compound | Yield |
|---|---|---|---|
| 296 | | | 60% |
| 299 | | | 61% |
| 462 | | | 60% |
| 465 | | | 61% |

Preparation Example 1-3

Target compounds were synthesized in the same manner as in Preparation Example 1-1 using 3-bromobenzoyl chloride instead of 4-bromobenzoyl chloride, and using Intermediate B instead of 9-(4-(4-chloro-6-phenyl-1,3,5-triazin-2-yl)phenyl)-9H-carbazole.

TABLE 2

| Compound No. | Intermediate B | Target Compound | Yield |
|---|---|---|---|
| 11 | | | 62% |
| 16 | | | 65% |
| 20 | | | 65% |
| 65 | | | 62% |

TABLE 2-continued

| Compound No. | Intermediate B | Target Compound | Yield |
|---|---|---|---|
| 254 | | | 51% |
| 259 | | | 60% |
| 275 | | | 61% |
| 297 | | | 60% |

Preparation Example 1-4
Target compounds were synthesized in the same manner as in Preparation Example 1-1 using 4-bromo-1-naphthoyl chloride instead of 4-bromobenzoyl chloride, and using Intermediate C instead of 9-(4-(4-chloro-6-phenyl-1,3,5-triazin-2-yl)phenyl)-9H-carbazole.
TABLE 3
| Compound No. | Intermediate C | Target Compound | Yield |
|---|---|---|---|
| 13 | 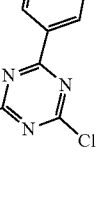 | 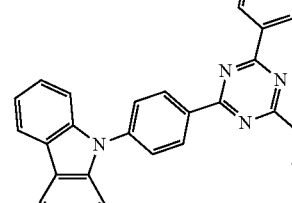 | 53% |
| 24 |  | 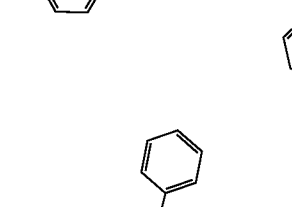 | 55% |
| 38 | 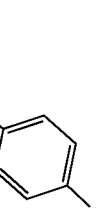 | 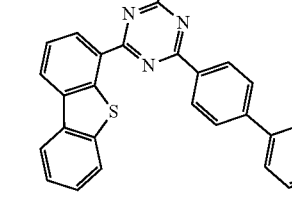 | 53% |

TABLE 3-continued

| Compound No. | Intermediate C | Target Compound | Yield |
|---|---|---|---|
| 44 | | | 53% |
| 265 | | | 55% |
| 282 | | | 52% |
| 288 | | | 52% |

[Preparation Example 2-1] Preparation of Compound 71

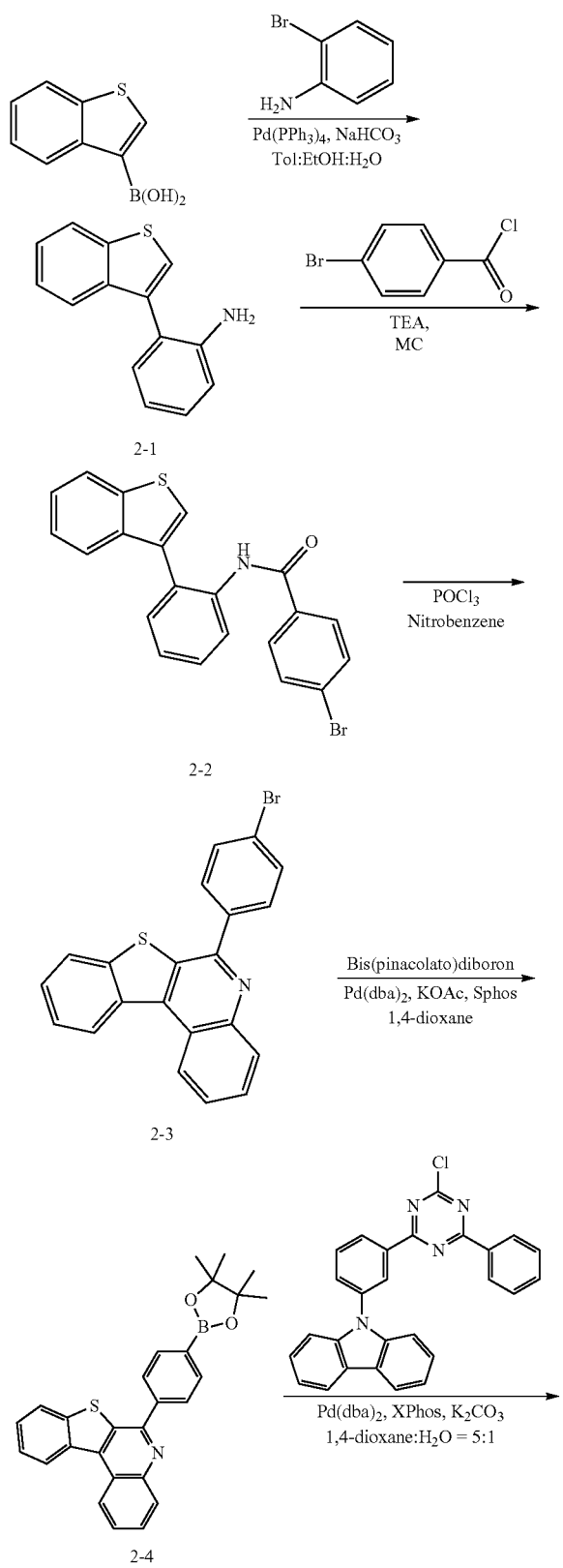

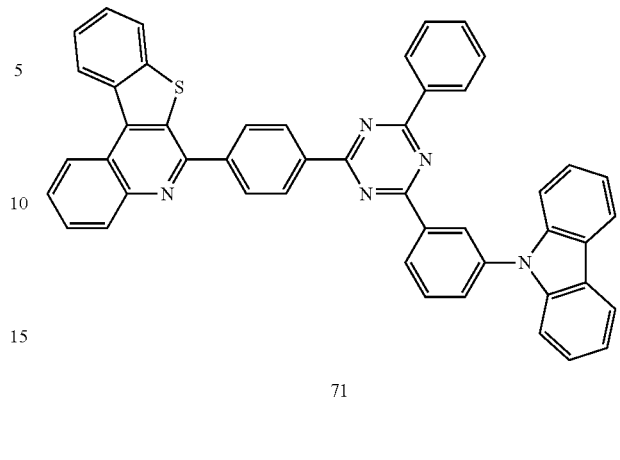

71

1) Preparation of Compound 2-1

After dissolving benzo[b]thiophen-3-ylboronic acid (100 g, 0.561 mol) and 2-bromoaniline (86.7 g, 0.504 mol) in toluene, EtOH and H$_2$O (1000 mL:200 mL:200 mL), Pd(PPh$_3$)$_4$ (32.4 g, 0.028 mol) and NaHCO$_3$ (141.3 g, 1.68 mol) were introduced thereto, and the result was stirred for 3 hours at 100° C. After the reaction was completed, the reaction solution was extracted by introducing MC and distilled water thereto. After that, the result was dried with anhydrous MgSO$_4$, and the solvent was removed using a rotary evaporator to obtain liquid-type Compound 2-1 (93 g, 74%).

2) Preparation of Compound 2-2

Compound 2-1 (93 g, 0.412 mol) and triethylamine (86 mL, 0.618 mol) were introduced to and dissolved in MC (1200 mL). 4-Bromobenzoyl chloride (135.6 g, 0.618 mol) dissolved in MC (300 mL) was slowly added dropwise to the mixture at 0° C. After the reaction was completed, white solids present in the reaction solution were filtered and washed with hexane. The result was dried to obtain solid-type Compound 2-2 (134 g, 83%).

3) Preparation of Compound 2-3

After dissolving Compound 2-2 (134 g, 0.329 mol) in nitrobenzene (1500 mL), POCl$_3$ (46 mL, 0.495 mol) was slowly added dropwise thereto. The result was reacted for 15 hours at 140° C. After the reaction was completed, a solution obtained by dissolving NaHCO$_3$ in distilled water was slowly introduced to the reaction solution, and the result was stirred. Solids produced after that were filtered and collected. The collected solids were recrystallized with MC and MeOH to obtain solid-type Compound 2-3 (65 g, 51%).

4) Preparation of Compound 2-4

After dissolving Compound 2-3 (10 g, 0.025 mol), bis(pinacolato)diboron (9.7 g, 0.038 mol), KOAc (7.3 g, 0.075 mol) and PdCl$_2$(dppf) (0.9 g, 0.0012 mol) in 1,4-dioxane (200 mL), the result was reacted for 5 hours at 90° C. After the reaction was completed, the reaction solution was extracted by introducing MC and distilled water thereto. After that, the result was dried with anhydrous MgSO$_4$, and progressed with column chromatography using MC and hexane as a developing solvent to obtain Compound 2-4 (7.6 g, 70%).

5) Preparation of Compound 71

After dissolving Compound 2-4 (7.6 g, 0.017 mol) and 9-(3-(4-chloro-6-phenyl-1,3,5-triazin-2-yl)phenyl)-9H-carbazole (7.3 g, 0.017 mol) in 1,4-dioxane:H$_2$O (100 mL:20 mL), Pd$_2$(dba)$_3$ (1.5 g, 0.0017 mol), XPhos (1.6 g, 0.0034 mol) and K$_2$CO$_3$ (7.0 g, 0.051 mol) were introduced thereto, and the result was stirred for 5 hours at 100° C. After the reaction was completed, solids produced in the reaction solution were washed with 1,4-dioxane and H$_2$O. After that, only the solids were purified using a recrystallization method in DCB to obtain Compound 71 (7.2 g, 60%).

Preparation Example 2-2

Target compounds were synthesized in the same manner as in Preparation Example 2-1 using Intermediate D instead of 9-(3-(4-chloro-6-phenyl-1,3,5-triazin-2-yl)phenyl)-9H-carbazole.

TABLE 4

| Compound No. | Intermediate D | Target Compound | Yield |
|---|---|---|---|
| 72 | | | 60% |
| 78 | | | 61% |
| 80 | | | 62% |

TABLE 4-continued

| Compound No. | Intermediate D | Target Compound | Yield |
|---|---|---|---|
| 87 | | | 63% |
| 98 | | | 62% |
| 106 | | | 61% |
| 116 | | | 61% |

TABLE 4-continued

| Compound No. | Intermediate D | Target Compound | Yield |
|---|---|---|---|
| 122 | | | 61% |
| 125 | | | 60% |
| 303 | | | 61% |

TABLE 4-continued

| Compound No. | Intermediate D | Target Compound | Yield |
|---|---|---|---|
| 310 | | | 62% |
| 316 | | | 61% |
| 318 | | | 60% |
| 324 | | | 61% |

TABLE 4-continued

| Compound No. | Intermediate D | Target Compound | Yield |
|---|---|---|---|
| 326 | | | 60% |
| 332 | | | 60% |
| 341 | | | 60% |
| 348 | | | 60% |

TABLE 4-continued
| Compound No. | Intermediate D | Target Compound | Yield |
|---|---|---|---|
| 350 | 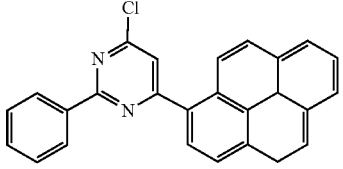 [SMILES: Clc1cc(-c2ccc3c4c2C=CC2=CC=CC(=CC3)C24)nc(-c2ccccc2)n1] | 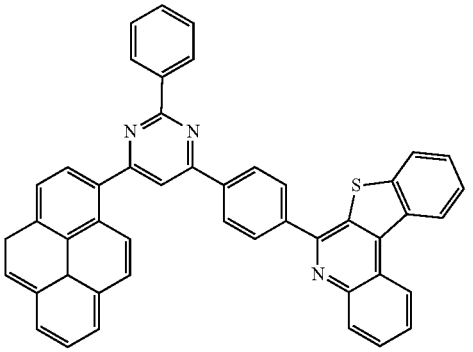 [SMILES: C1=CC2=CCc3ccc(-c4cc(-c5ccc(-c6nc7ccccc7c7c6sc6ccccc67)cc5)nc(-c5ccccc5)n4)c4c3C2C(=C1)C=C4] | 61% |
| 359 | 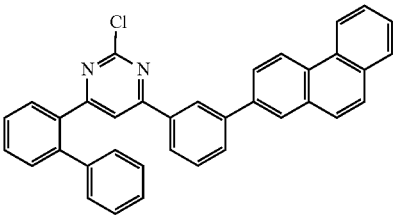 [SMILES: Clc1nc(-c2cccc(-c3ccc4c(ccc5ccccc54)c3)c2)cc(-c2ccccc2-c2ccccc2)n1] | 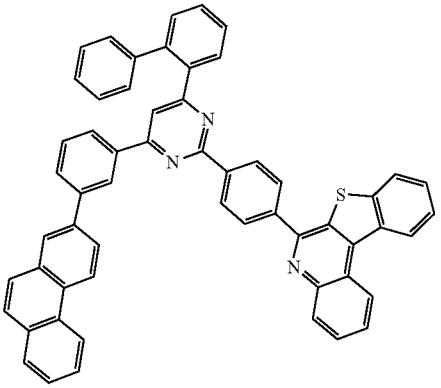 [SMILES: c1ccc(-c2ccccc2-c2cc(-c3cccc(-c4ccc5c(ccc6ccccc65)c4)c3)nc(-c3ccc(-c4nc5ccccc5c5c4sc4ccccc45)cc3)n2)cc1] | 62% |
| 467 | 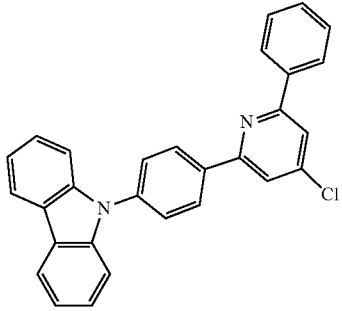 [SMILES: Clc1cc(-c2ccccc2)nc(-c2ccc(-n3c4ccccc4c4ccccc43)cc2)c1] | 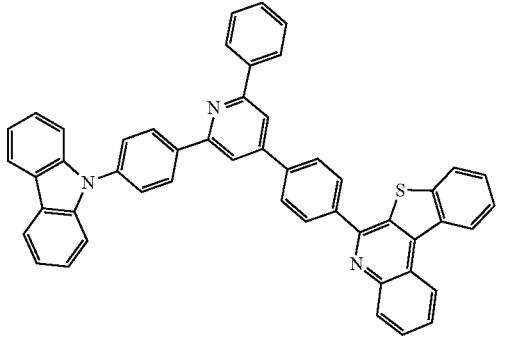 [SMILES: c1ccc(-c2cc(-c3ccc(-c4nc5ccccc5c5c4sc4ccccc45)cc3)cc(-c3ccc(-n4c5ccccc5c5ccccc54)cc3)n2)cc1] | 60% |

Preparation Example 2-3

Target compounds were synthesized in the same manner as in Preparation Example 2-1 using 3-bromobenzoyl chloride instead of 4-bromobenzoyl chloride, and using Intermediate E instead of 9-(3-(4-chloro-6-phenyl-1,3,5-triazin-2-yl)phenyl)-9H-carbazole.

TABLE 5

| Compound No. | Intermediate E | Target Compound | Yield |
| --- | --- | --- | --- |
| 82 | | | 62% |
| 93 | | | 61% |
| 100 | | | 62% |
| 315 | | | 59% |

TABLE 5-continued

| Compound No. | Intermediate E | Target Compound | Yield |
|---|---|---|---|
| 331 | | | 61% |
| 336 | | | 61% |

Preparation Example 2-4

Target compounds were synthesized in the same manner as in Preparation Example 2-2 using 4-bromo-1-naphthoyl chloride instead of 4-bromobenzoyl chloride, and using Intermediate F instead of 9-(3-(4-chloro-6-phenyl-1,3,5-triazin-2-yl)phenyl)-9H-carbazole.

TABLE 6

| Compound No. | Intermediate F | Target Compound | Yield |
|---|---|---|---|
| 75 | | | 53% |

TABLE 6-continued

| Compound No. | Intermediate F | Target Compound | Yield |
| --- | --- | --- | --- |
| 84 | | | 60% |
| 114 | | | 54% |
| 305 | | | 53% |
| 307 | | | 53% |

TABLE 6-continued
| Compound No. | Intermediate F | Target Compound | Yield |
|---|---|---|---|
| 330 | | | 51% |
| 471 | | | 59% |
[Preparation Example 3-1] Preparation of Compound 130
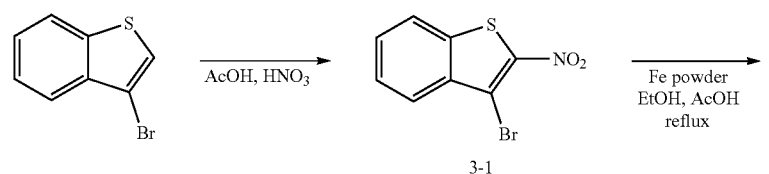
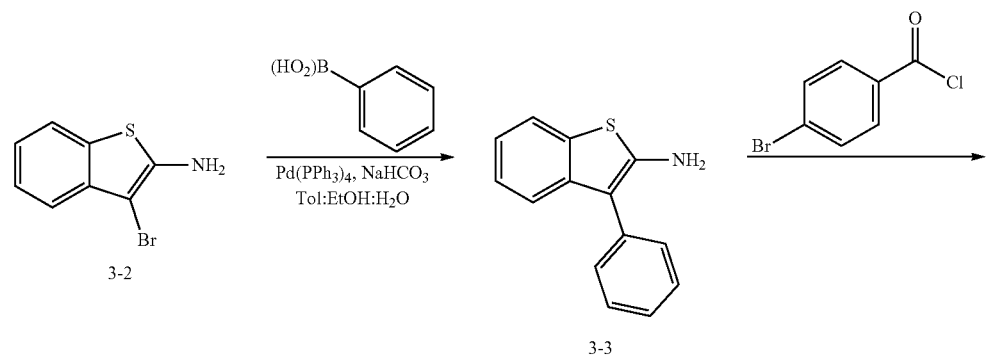

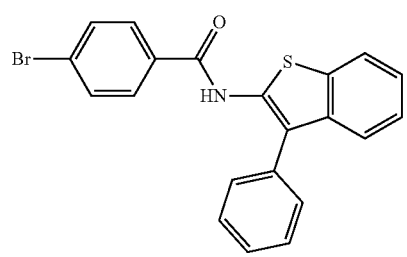

3-4

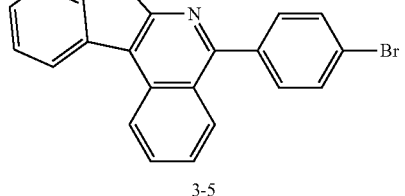

3-5

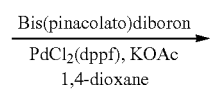

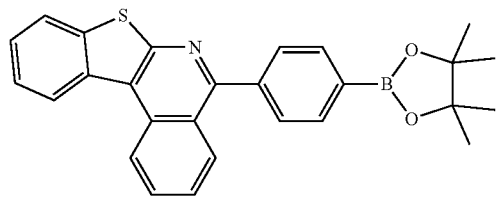

3-6

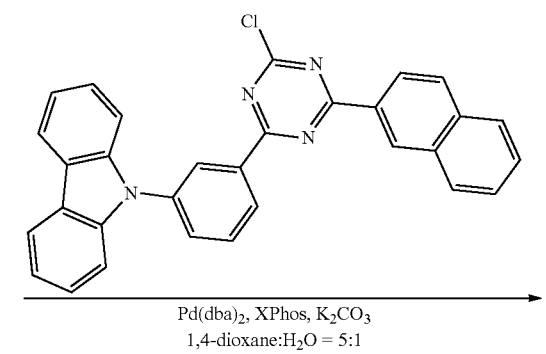

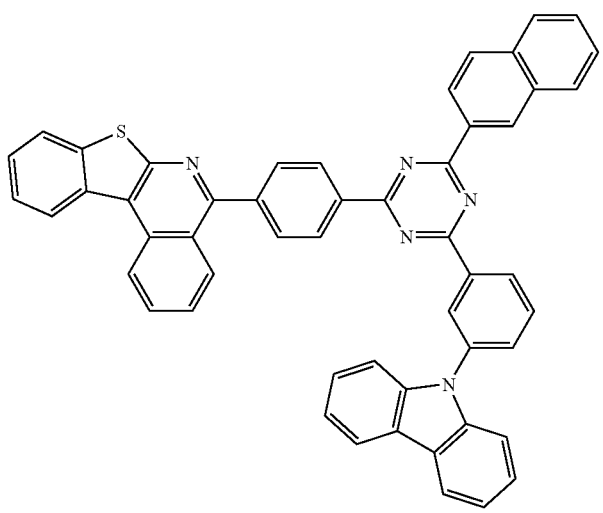

130

1) Preparation of Compound 3-1

3-Bromobenzo[b]thiophene (100 g, 0.469 mol) and acetic acid (1500 mL) were introduced and stirred for 10 minutes at room temperature, and a mixture of acetic acid (1500 mL) and $HNO_3$ (200 mL) was slowly added dropwise thereto. After the reaction was completed in 1 hour, the result was cooled to room temperature, and extracted with distilled water and MC. After drying the organic layer with $MgSO_4$, the solvent was removed using a rotary evaporator, and the result was purified by column chromatography using MC and hexane as a developing solvent to obtain Compound 3-1 (90 g, 77%).

2) Preparation of Compound 3-2

Compound 3-1 (90 g, 0.087 mol), ethanol (3000 mL) and Fe powder (60 g, 0.108 mol) were introduced, and stirred for 10 minutes at room temperature. Acetic acid (300 mL) was slowly added dropwise thereto, and the result was refluxed for 1 hour at 60° C. After the reaction was completed, the result was cooled to room temperature, $H_2O$ was added thereto, and produced solids were filtered and then washed with $H_2O$ and hexane to obtain Compound 3-2 (70 g, 99%).

3) Preparation of Compound 3-3

Compound 3-2 (70 g, 0.306 mol), phenylboronic acid (40 g, 0.336 mol), $Pd(PPh_3)_4$ (17 g, 0.0153 mol) and $Na_2CO_3$ (65 g, 0.609 mol) were refluxed for 1 hour at 120° C. together with toluene (700 mL), ethanol (140 mL) and $H_2O$ (140 mL). After the reaction was completed, the result was cooled to room temperature, and extracted with distilled water and EA. After drying the organic layer with $MgSO_4$, the solvent was removed using a rotary evaporator, and the result was washed with EA and hexane to obtain Compound 3-3 (63 g, 90%).

4) Preparation of Compound 3-4

Compound 3-3 (90 g, 0.399 mol) was dissolved in MC, and stirred for 15 minutes at room temperature together with TEA (56 mL, 0.399 mol). After that, the temperature was maintained at 0° C., and 4-bromobenzoyl chloride (87 g, 0.399 mol) was slowly added thereto. White solids produced after 1 hour were filtered and washed with EA and hexane to obtain Compound 3-4 (150 g, 90%).

5) Preparation of Compound 3-5

Compound 3-4 (150 g, 0.3674 mol), $POCl_3$ (51 mL, 0.551 mol) and nitrobenzene (1500 mL) were introduced, and stirred for 1 hour. The result was reacted for 15 hours at 140° C. After the reaction was completed, a solution obtained by dissolving $NaHCO_3$ in distilled water was slowly introduced to the reaction solution, and the result was stirred. Solids produced after that were filtered and collected. The collected solids were washed with methanol and hexane to obtain Compound 3-5 (110 g, 77%).

6) Preparation of Compound 3-6

After dissolving Compound 3-5 (50 g, 0.128 mol), bis(pinacolato)diboron (48.7 g, 0.192 mol), KOAc (37 g, 0.384 mol) and $PdCl_2$(dppf) (4.6 g, 0.0064 mol) in 1,4-dioxane (1000 mL), the result was reacted for 5 hours at 90° C. After the reaction was completed, the reaction solution was extracted by introducing MC and distilled water thereto. After that, the result was dried with anhydrous $MgSO_4$, and progressed with column chromatography using MC and hexane as a developing solvent to obtain Compound 3-6 (39 g, 70%).

7) Preparation of Compound 130

After dissolving Compound 3-6 (7 g, 0.016 mol) and 9-(3-(4-chloro-6-(naphthalen-2-yl)-1,3,5-triazin-2-yl)phenyl)-9H-carbazole (7.7 g, 0.016 mol) in 1,4-dioxane:$H_2O$ (100 mL:20 mL), $Pd_2$(dba)$_3$ (1.4 g, 0.0016 mol), XPhos (1.5 g, 0.0032 mol) and $K_2CO_3$ (6.6 g, 0.048 mol) were introduced thereto, and the result was stirred for 5 hours at 100° C. After the reaction was completed, solids produced in the reaction solution were washed with 1,4-dioxane and $H_2O$. After that, only the solids were purified using a recrystallization method in DCB to obtain Compound 130 (7.2 g, 60%).

Preparation Example 3-2

Target compounds were synthesized in the same manner as in Preparation Example 3-1 using Intermediate G instead of 9-(3-(4-chloro-6-(naphthalen-2-yl)-1,3,5-triazin-2-yl)phenyl)-9H-carbazole.

TABLE 7

| Compound No. | Intermediate G | Target Compound | Yield |
|---|---|---|---|
| 127 | [structure] | [structure] | 61% |
| 140 | [structure] | [structure] | 61% |

TABLE 7-continued

| Compound No. | Intermediate G | Target Compound | Yield |
|---|---|---|---|
| 150 | | | 62% |
| 152 | | | 60% |
| 166 | | | 61% |
| 362 | | | 60% |

TABLE 7-continued

| Compound No. | Intermediate G | Target Compound | Yield |
| --- | --- | --- | --- |
| 364 | | | 60% |
| 373 | | | 60% |
| 382 | | | 63% |
| 385 | | | 63% |

TABLE 7-continued

| Compound No. | Intermediate G | Target Compound | Yield |
|---|---|---|---|
| 391 | 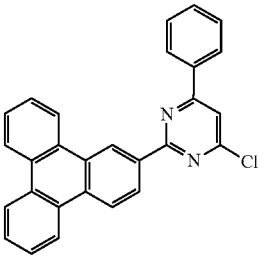 [SMILES: Clc1cc(-c2ccccc2)nc(-c2ccc3c4ccccc4c4ccccc4c3c2)n1] | 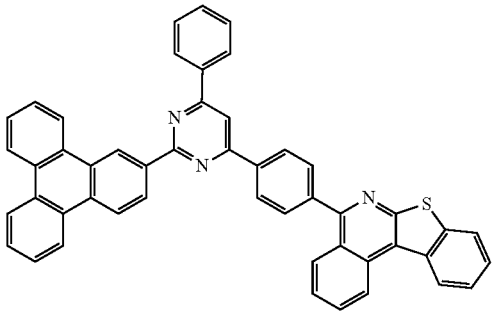 [SMILES: c1ccc(-c2cc(-c3ccc(-c4nc5sc6ccccc6c5c5ccccc45)cc3)nc(-c3ccc4c5ccccc5c5ccccc5c4c3)n2)cc1] | 59% |
| 396 | 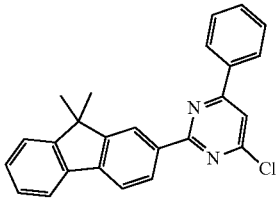 [SMILES: CC1(C)c2ccccc2-c2ccc(-c3nc(Cl)cc(-c4ccccc4)n3)cc21] | 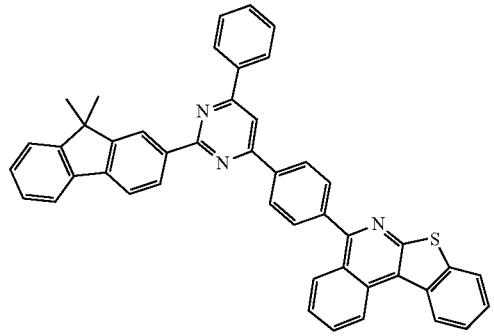 [SMILES: CC1(C)c2ccccc2-c2ccc(-c3nc(-c4ccccc4)cc(-c4ccc(-c5nc6sc7ccccc7c6c6ccccc56)cc4)n3)cc21] | 61% |

Preparation Example 3-3

Target compounds were synthesized in the same manner as in Preparation Example 3-1 using 3-bromobenzoyl chloride instead of 4-bromobenzoyl chloride, and using Intermediate H instead of 9-(3-(4-chloro-6-(naphthalen-2-yl)-1,3,5-triazin-2-yl)phenyl)-9H-carbazole.

TABLE 8

| Compound No. | Intermediate H | Target Compound | Yield |
|---|---|---|---|
| 137 | 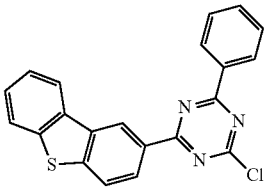 [SMILES: Clc1nc(-c2ccccc2)nc(-c2ccc3sc4ccccc4c3c2)n1] | 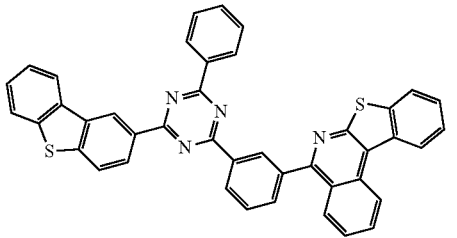 [SMILES: c1ccc(-c2nc(-c3cccc(-c4nc5sc6ccccc6c5c5ccccc45)c3)nc(-c3ccc4sc5ccccc5c4c3)n2)cc1] | 62% |

TABLE 8-continued
| Compound No. | Intermediate H | Target Compound | Yield |
|---|---|---|---|
| 141 | 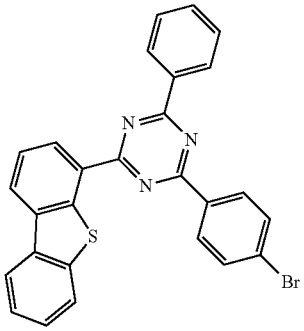 [SMILES: Brc1ccc(-c2nc(-c3ccccc3)nc(-c3cccc4c3sc3ccccc34)n2)cc1] | 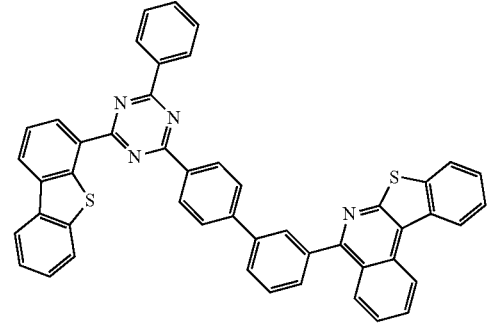 [SMILES: c1ccc(-c2nc(-c3ccc(-c4cccc(-c5nc6sc7ccccc7c6c6ccccc56)c4)cc3)nc(-c3cccc4c3sc3ccccc34)n2)cc1] | 59% |
| 146 | 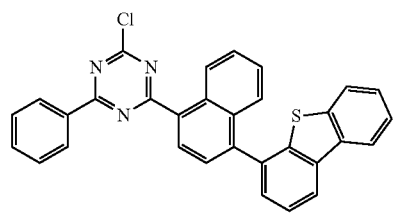 [SMILES: Clc1nc(-c2ccccc2)nc(-c2ccc(-c3cccc4c3sc3ccccc34)c3ccccc23)n1] | 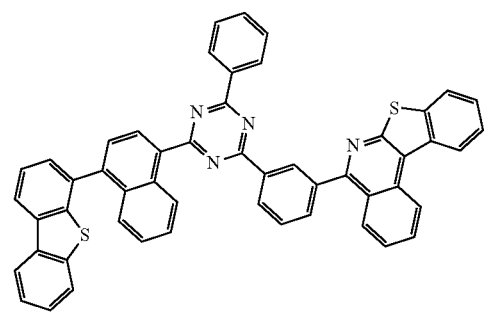 [SMILES: c1ccc(-c2nc(-c3cccc(-c4nc5sc6ccccc6c5c5ccccc45)c3)nc(-c3ccc(-c4cccc5c4sc4ccccc45)c4ccccc34)n2)cc1] | 58% |
| 165 | 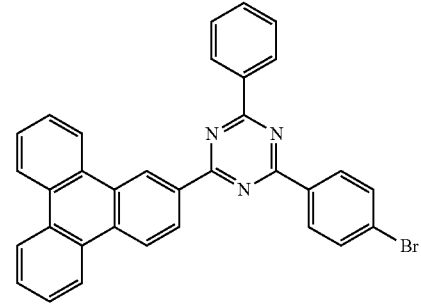 [SMILES: Brc1ccc(-c2nc(-c3ccccc3)nc(-c3ccc4c5ccccc5c5ccccc5c4c3)n2)cc1] | 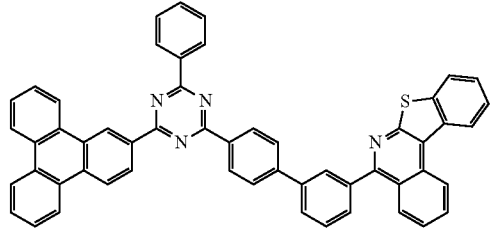 [SMILES: c1ccc(-c2nc(-c3ccc(-c4cccc(-c5nc6sc7ccccc7c6c6ccccc56)c4)cc3)nc(-c3ccc4c5ccccc5c5ccccc5c4c3)n2)cc1] | 59% |
| 169 | 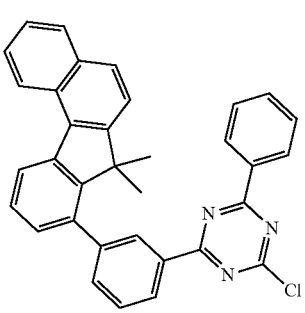 [SMILES: CC1(C)c2ccc3ccccc3c2-c2cccc(-c3cccc(-c4nc(Cl)nc(-c5ccccc5)n4)c3)c21] | 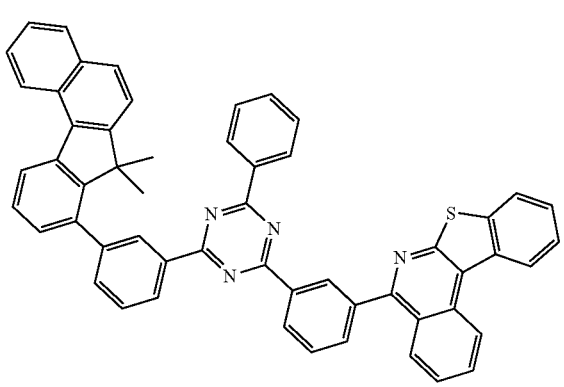 [SMILES: CC1(C)c2ccc3ccccc3c2-c2cccc(-c3cccc(-c4nc(-c5ccccc5)nc(-c5cccc(-c6nc7sc8ccccc8c7c7ccccc67)c5)n4)c3)c21] | 54% |

TABLE 8-continued

| Compound No. | Intermediate H | Target Compound | Yield |
|---|---|---|---|
| 179 | | | 54% |
| 363 | | | 60% |
| 370 | | | 62% |
| 375 | | | 62% |

TABLE 8-continued

| Compound No. | Intermediate H | Target Compound | Yield |
|---|---|---|---|
| 393 | | | 61% |

Preparation Example 3-4

Target compounds were synthesized in the same manner as in Preparation Example 3-1 using 4-bromo-1-naphthoyl chloride instead of 4-bromobenzoyl chloride, and using Intermediate I instead of 9-(3-(4-chloro-6-(naphthalen-2-yl)-1,3,5-triazin-2-yl)phenyl)-9H-carbazole.

TABLE 9

| Compound No. | Intermediate I | Target Compound | Yield |
|---|---|---|---|
| 135 | | | 53% |
| 144 | | | 60% |

TABLE 9-continued

| Compound No. | Intermediate I | Target Compound | Yield |
|---|---|---|---|
| 155 | | | 61% |
| 366 | | | 61% |
| 371 | | | 61% |

TABLE 9-continued
| Compound No. | Intermediate I | Target Compound | Yield |
|---|---|---|---|
| 386 | | | 62% |
| 408 | | | 59% |
[Preparation Example 4-1] Preparation of Compound 190
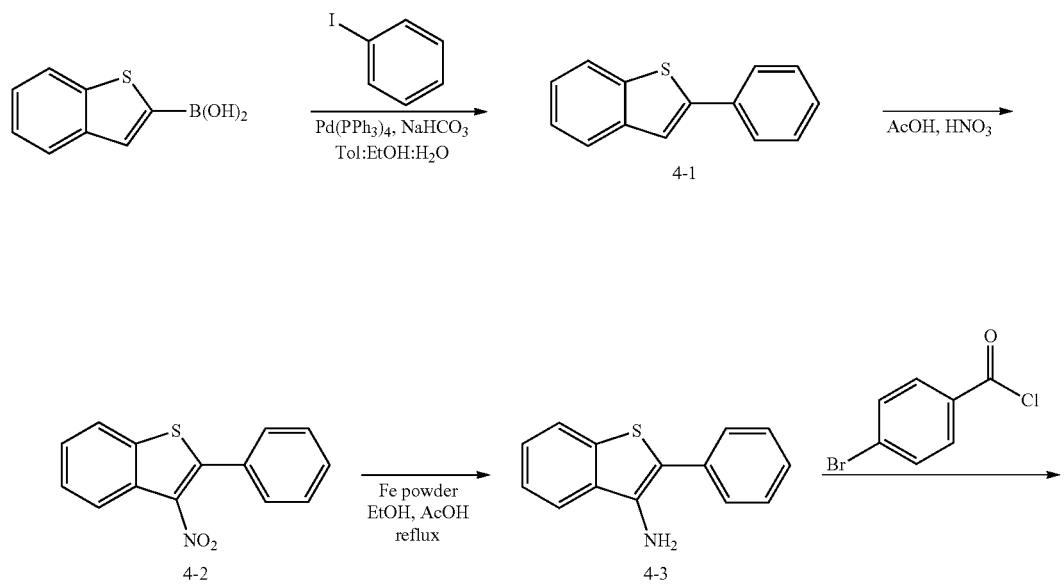

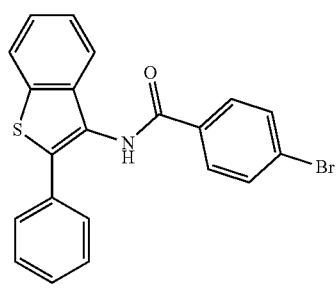

4-4

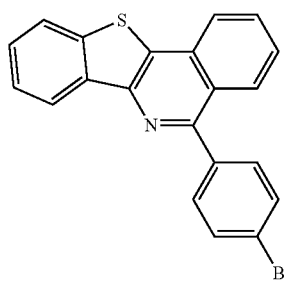

4-5

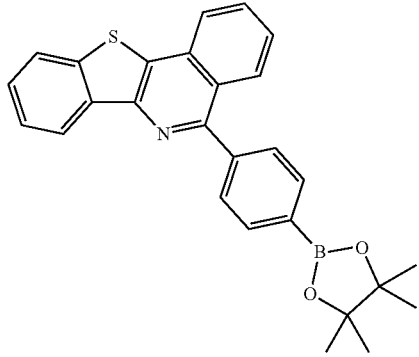

4-6

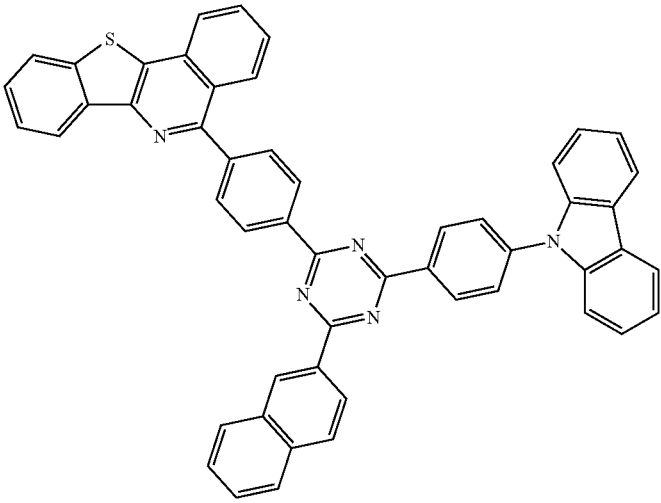

190

1) Preparation of Compound 4-1

Benzo[b]thiophen-2-ylboronic acid (50 g, 0.280 mol), iodobenzene (57 g, 0.280 mol), Pd(PPh$_3$)$_4$ (16.2 g, 0.014 mol) and Na$_2$CO$_3$ (89.6 g, 0.84 mol) were refluxed for 1 hour at 120° C. together with toluene (1000 mL), ethanol (200 mL) and H$_2$O (200 mL). After the reaction was completed, the result was cooled to room temperature, and extracted with distilled water and EA. After drying the organic layer with MgSO$_4$, the solvent was removed using a rotary evaporator to obtain Compound 4-1 (53 g, 90%).

2) Preparation of Compound 4-2

Compound 4-1 (50 g, 0.237 mol) and acetic acid (700 mL) were introduced and stirred for 10 minutes at room temperature, and a mixture of acetic acid (700 mL) and HNO$_3$ (100 mL) was slowly added dropwise thereto. After the reaction was completed in 1 hour, the result was cooled to room temperature and extracted with distilled water and MC. After drying the organic layer with MgSO$_4$, the solvent was removed using a rotary evaporator, and the result was purified by column chromatography using MC and hexane as a developing solvent to obtain Compound 4-2 (46 g, 77%).

3) Preparation of Compound 4-3

Compound 4-2 (46 g, 0.182 mol), ethanol (1000 mL) and Fe powder (30 g, 0.546 mol) were introduced, and stirred for 10 minutes at room temperature. Acetic acid (130 mL) was slowly added dropwise thereto, and the result was refluxed for 1 hour at 60° C. After the reaction was completed, the result was cooled to room temperature, $H_2O$ was added thereto, and produced solids were filtered and then washed with $H_2O$ and hexane to obtain Compound 4-3 (40 g, 99%).

4) Preparation of Compound 4-4

Compound 4-3 (40 g, 0.177 mol) was dissolved in MC, and stirred for 15 minutes at room temperature together with TEA (25 mL, 0.177 mol). After that, the temperature was maintained at 0° C., and 4-bromobenzoyl chloride (77 g, 0.354 mol) was slowly added thereto. White solids produced after 1 hour were filtered and washed with EA and hexane to obtain Compound 4-4 (57 g, 80%).

5) Preparation of Compound 4-5

Compound 4-4 (57 g, 0.139 mol), $POCl_3$ (19.5 mL, 0.208 mol) and nitrobenzene (500 mL) were introduced, and reacted for 15 hours at 140° C. After the reaction was completed, a solution obtained by dissolving $NaHCO_3$ in distilled water was slowly introduced to the reaction solution, and the result was stirred. Solids produced after that were filtered and collected. The collected solids were washed with methanol and hexane to obtain Compound 4-5 (40 g, 74%).

6) Preparation of Compound 4-6

After dissolving Compound 4-5 (40 g, 0.102 mol), bis(pinacolato)diboron (39 g, 0.153 mol), KOAc (30 g, 0.306 mol) and $PdCl_2(dppf)$ (3.7 g, 0.0051 mol) in 1,4-dioxane (1000 mL), the result was reacted for 5 hours at 90° C. After the reaction was completed, the reaction solution was extracted by introducing MC and distilled water thereto. After that, the result was dried with anhydrous $MgSO_4$, and progressed with column chromatography using MC and hexane as a developing solvent to obtain Compound 4-6 (31 g, 70%).

7) Preparation of Compound 190

After dissolving Compound 4-6 (7 g, 0.016 mol) and 9-(4-(4-chloro-6-(naphthalen-2-yl)-1,3,5-triazin-2-yl)phenyl)-9H-carbazole (7.7 g, 0.016 mol) in 1,4-dioxane:$H_2O$ (100 mL:20 mL), $Pd_2(dba)_3$ (1.4 g, 0.0016 mol), XPhos (1.5 g, 0.0032 mol) and $K_2CO_3$ (6.6 g, 0.048 mol) were introduced thereto, and the result was stirred for 5 hours at 100° C. After the reaction was completed, solids produced in the reaction solution were washed with 1,4-dioxane and $H_2O$. After that, only the solids were purified using a recrystallization method in DCB to obtain Compound 190 (7.2 g, 60%).

Preparation Example 4-2

Target compounds were synthesized in the same manner as in Preparation Example 4-1 using Intermediate J instead of 9-(4-(4-chloro-6-(naphthalen-2-yl)-1,3,5-triazin-2-yl)phenyl)-9H-carbazole.

TABLE 10

| Compound No. | Intermediate J | Target Compound | Yield |
|---|---|---|---|
| 199 | [naphthalenyl-triazinyl-chloro with dibenzothiophene structure] | [naphthalenyl-triazinyl structure with dibenzothiophene and phenyl-benzothienoisoquinoline] | 64% |

TABLE 10-continued

| Compound No. | Intermediate J | Target Compound | Yield |
|---|---|---|---|
| 220 | | | 63% |
| 231 | | | 60% |
| 234 | | | 60% |

TABLE 10-continued

| Compound No. | Intermediate J | Target Compound | Yield |
|---|---|---|---|
| 242 | | | 61% |
| 419 | | | 63% |
| 431 | | | 60% |

TABLE 10-continued

| Compound No. | Intermediate J | Target Compound | Yield |
|---|---|---|---|
| 432 | | | 60% |
| 441 | | | 61% |
| 445 | | | 64% |

TABLE 10-continued

| Compound No. | Intermediate J | Target Compound | Yield |
|---|---|---|---|
| 450 | | | 63% |
| 452 | | | 60% |
| 460 | | | 61% |

TABLE 10-continued

| Compound No. | Intermediate J | Target Compound | Yield |
|---|---|---|---|
| 476 | (structure) | (structure) | 61% |

Preparation Example 4-3

Target compounds were synthesized in the same manner as in Preparation Example 4-1 using 3-bromobenzoyl chloride instead of 4-bromobenzoyl chloride, and using Intermediate K instead of 9-(4-(4-chloro-6-(naphthalen-2-yl)-1,3,5-triazin-2-yl)phenyl)-9H-carbazole.

TABLE 11

| Compound No. | Intermediate K | Target Compound | Yield |
|---|---|---|---|
| 198 | (structure) | (structure) | 64% |
| 203 | (structure) | (structure) | 63% |

TABLE 11-continued

| Compound No. | Intermediate K | Target Compound | Yield |
|---|---|---|---|
| 209 | | | 60% |
| 226 | | | 60% |
| 247 | | | 63% |

TABLE 11-continued

| Compound No. | Intermediate K | Target Compound | Yield |
|---|---|---|---|
| 422 | | | 60% |
| 424 | | | 60% |

Preparation Example 4-4

Target compounds were synthesized in the same manner as in Preparation Example 4-1 using 2-bromobenzoyl chloride instead of 4-bromobenzoyl chloride, and using Intermediate L instead of 9-(4-(4-chloro-6-(naphthalen-2-yl)-1,3,5-triazin-2-yl)phenyl)-9H-carbazole.

TABLE 12

| Compound No. | Intermediate L | Target Compound | Yield |
|---|---|---|---|
| 196 | | | 57% |

Preparation Example 4-5

Target compounds were synthesized in the same manner as in Preparation Example 4-1 using 4-bromo-1-naphthoyl chloride instead of 4-bromobenzoyl chloride, and using Intermediate M instead of 9-(4-(4-chloro-6-(naphthalen-2-yl)-1,3,5-triazin-2-yl)phenyl)-9H-carbazole.

TABLE 13

| Compound No. | Intermediate M | Target Compound | Yield |
|---|---|---|---|
| 219 | | | 53% |
| 416 | | | 64% |
| 443 | | | 60% |

TABLE 13-continued
| Compound No. | Intermediate M | Target Compound | Yield |
|---|---|---|---|
| 456 | 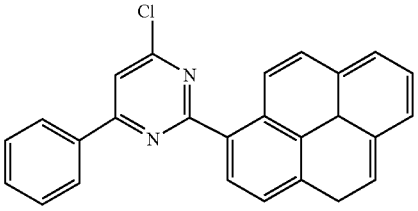 [SMILES: Clc1cc(-c2ccccc2)nc(-c2ccc3c4c2C=CC2=CC=CC(=CC3)C24)n1] | 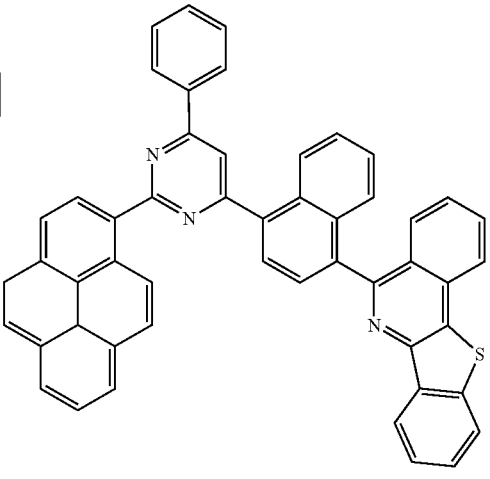 [SMILES: C1=CC2=CCc3ccc(-c4nc(-c5ccccc5)cc(-c5ccc(-c6nc7c8ccccc8sc7c7ccccc67)c6ccccc56)n4)c4c3C2C(=C1)C=C4] | 60% |
[Preparation Example 5-1] Preparation of Compound 480
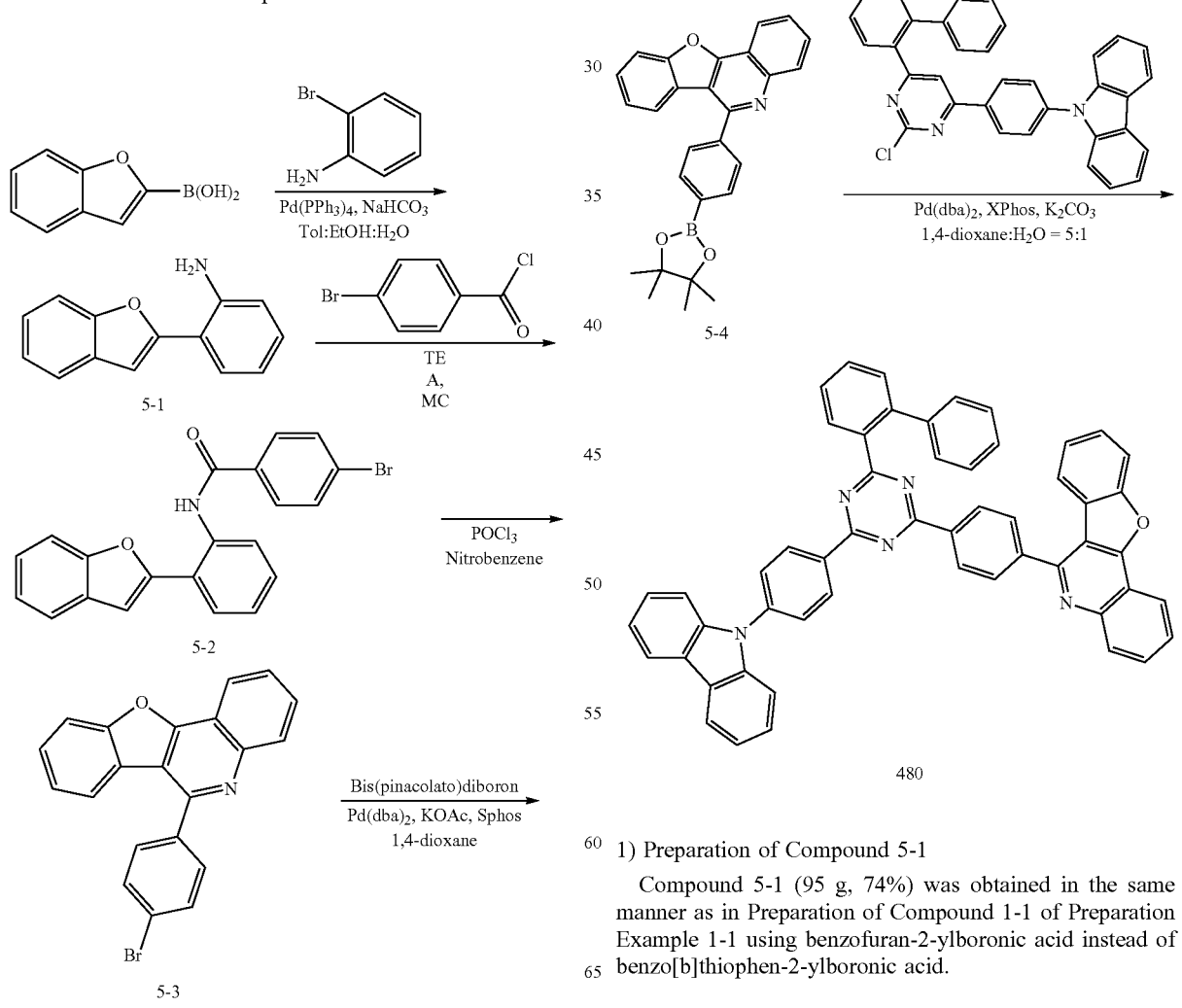
1) Preparation of Compound 5-1
Compound 5-1 (95 g, 74%) was obtained in the same manner as in Preparation of Compound 1-1 of Preparation Example 1-1 using benzofuran-2-ylboronic acid instead of benzo[b]thiophen-2-ylboronic acid.

2) Preparation of Compound 5-2

Compound 5-2 (126 g, 80%) was obtained in the same manner as in Preparation of Compound 1-2 of Preparation Example 1-1 using Compound 5-1 instead of Compound 1-1.

3) Preparation of Compound 5-3

Compound 5-3 (60 g, 50%) was obtained in the same manner as in Preparation of Compound 1-3 of Preparation Example 1-1 using Compound 5-2 instead of Compound 1-2.

4) Preparation of Compound 5-4

Compound 5-4 (7.8 g, 70%) was obtained in the same manner as in Preparation of Compound 1-4 of Preparation Example 1-1 using Compound 5-3 instead of Compound 1-3.

5) Preparation of Compound 480

Compound 480 (5.8 g, 60%) was obtained in the same manner as in Preparation of Compound 1 of Preparation Example 1-1 using Compound 5-3 instead of Compound 1-4, and using 9-(4-(4-([1,1'-biphenyl]-2-yl)-6-chloro-1,3,5-triazin-2-yl)phenyl)-9H-carbazole instead of 9-(4-(4-chloro-6-phenyl-1,3,5-triazin-2-yl)phenyl)-9H-carbazole.

Preparation Example 5-2

Target compounds were synthesized in the same manner as in Preparation Example 5-1 using Intermediate N instead of 9-(4-(4-([1,1'-biphenyl]-2-yl)-6-chloro-1,3,5-triazin-2-yl)phenyl)-9H-carbazole.

TABLE 14

| Compound No. | Intermediate N | Target Compound | Yield |
| --- | --- | --- | --- |
| 479 | | | 64% |
| 486 | | | 60% |
| 493 | | | 61% |

TABLE 14-continued

| Compound No. | Intermediate N | Target Compound | Yield |
|---|---|---|---|
| 498 | | | 64% |
| 502 | | | 63% |
| 508 | | | 60% |
| 511 | | | 60% |

TABLE 14-continued

| Compound No. | Intermediate N | Target Compound | Yield |
|---|---|---|---|
| 540 | | | 63% |
| 725 | | | 60% |
| 727 | | | 60% |
| 736 | | | 63% |

TABLE 14-continued

| Compound No. | Intermediate N | Target Compound | Yield |
|---|---|---|---|
| 740 | | | 60% |
| 742 | | | 60% |
| 748 | | | 61% |

TABLE 14-continued

| Compound No. | Intermediate N | Target Compound | Yield |
|---|---|---|---|
| 750 | | | 64% |
| 754 | | | 63% |
| 763 | | | 60% |
| 768 | | | 64% |

TABLE 14-continued

| Compound No. | Intermediate N | Target Compound | Yield |
|---|---|---|---|
| 774 | | | 63% |
| 936 | | | 60% |
| 938 | | | 61% |

Preparation Example 5-3

Target compounds were synthesized in the same manner as in Preparation Example 5-1 using 3-bromobenzoyl chloride instead of 4-bromobenzoyl chloride, and using Intermediate O instead of 9-(4-(4-([1,1'-biphenyl]-2-yl)-6-chloro-1,3,5-triazin-2-yl)phenyl)-9H-carbazole.

TABLE 15

| Compound No. | Intermediate O | Target Compound | Yield |
|---|---|---|---|
| 488 | | | 64% |
| 517 | | | 60% |
| 519 | | | 60% |
| 524 | | | 61% |

TABLE 15-continued

| Compound No. | Intermediate O | Target Compound | Yield |
|---|---|---|---|
| 537 | | | 64% |
| 737 | | | 60% |
| 751 | | | 61% |
| 753 | | | 64% |

TABLE 15-continued

| Compound No. | Intermediate O | Target Compound | Yield |
|---|---|---|---|
| 757 | | | 63% |

Preparation Example 5-4

Target compounds were synthesized in the same manner as in Preparation Example 5-1 using 4-bromo-1-naphthoyl chloride instead of 4-bromobenzoyl chloride, and using Intermediate P instead of 9-(4-(4-([1,1'-biphenyl]-2-yl)-6-chloro-1,3,5-triazin-2-yl)phenyl)-9H-carbazole.

TABLE 16

| Compound No. | Intermediate P | Target Compound | Yield |
|---|---|---|---|
| 499 | | | 51% |
| 506 | | | 50% |

TABLE 16-continued

| Compound No. | Intermediate P | Target Compound | Yield |
|---|---|---|---|
| 527 | | | 53% |
| 731 | | | 51% |
| 641 | | | 50% |
| 736 | | | 54% |

TABLE 16-continued
| Compound No. | Intermediate P | Target Compound | Yield |
|---|---|---|---|
| 765 | | | 51% |
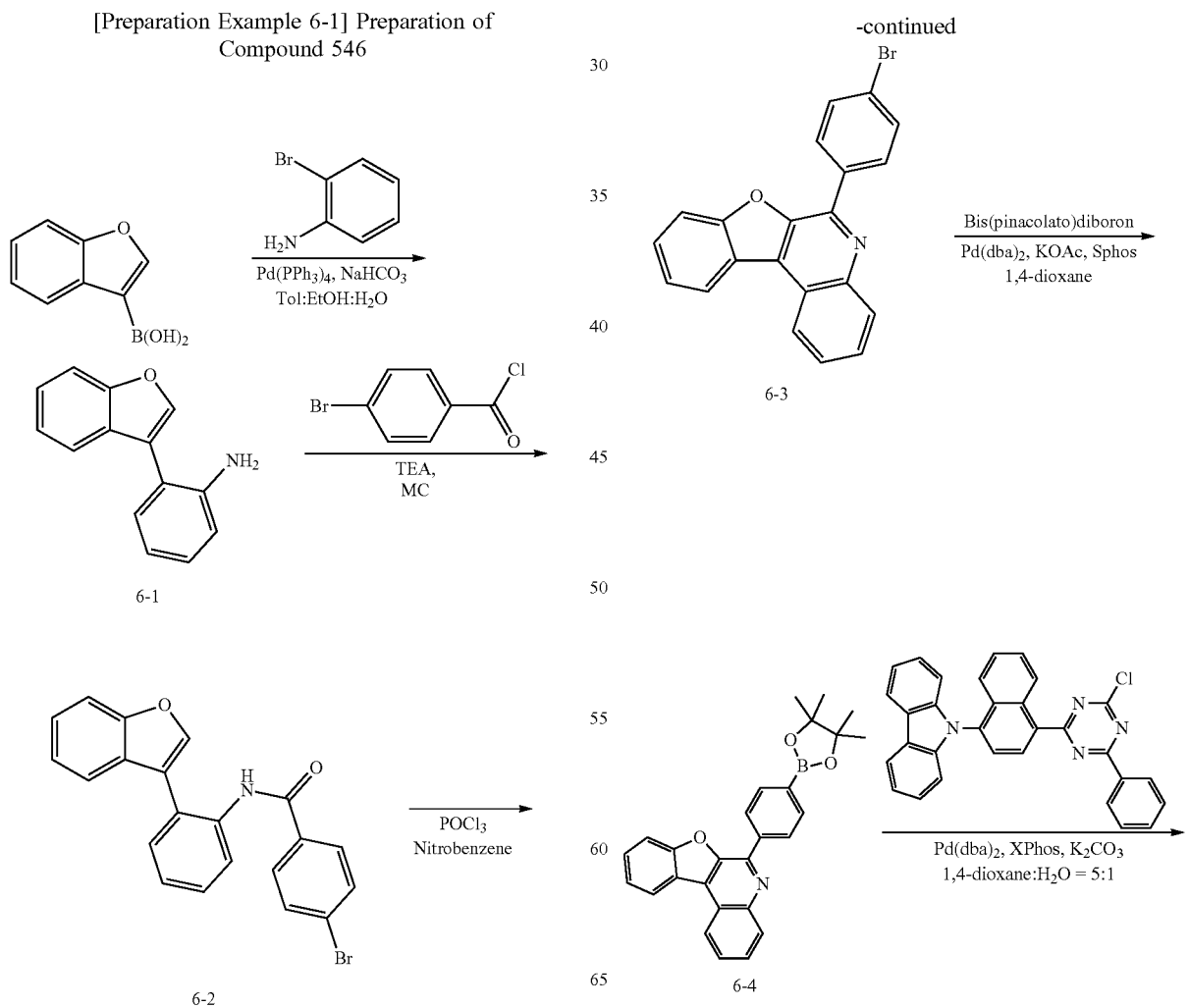
[Preparation Example 6-1] Preparation of Compound 546

505
-continued

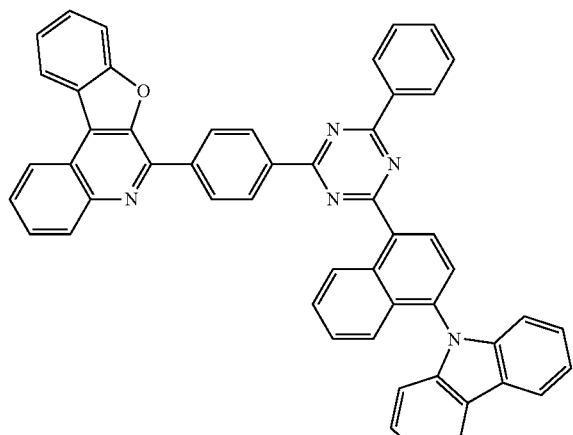

546

1) Preparation of Compound 6-1

Compound 6-1 (90 g, 70%) was obtained in the same manner as in Preparation of Compound 2-1 of Preparation Example 2-1 using benzofuran-3-ylboronic acid instead of benzo[b]thiophen-3-ylboronic acid.

506

2) Preparation of Compound 6-2

Compound 6-2 (134 g, 80%) was obtained in the same manner as in Preparation of Compound 2-2 of Preparation Example 2-1 using Compound 6-1 instead of Compound 2-1.

3) Preparation of Compound 6-3

Compound 6-3 (63 g, 50%) was obtained in the same manner as in Preparation of Compound 2-3 of Preparation Example 2-1 using Compound 6-2 instead of Compound 2-2.

4) Preparation of Compound 6-4

Compound 6-4 (49 g, 70%) was obtained in the same manner as in Preparation of Compound 2-4 of Preparation Example 2-1 using Compound 6-3 instead of Compound 2-3.

5) Preparation of Compound 546

Compound 546 (7.3 g, 60%) was obtained in the same manner as in Preparation of Compound 71 of Preparation Example 2-1 using Compound 6-4 instead of Compound 2-4, and using 9-(4-(4-chloro-6-phenyl-1,3,5-triazin-2-yl) naphthalen-1-yl)-9H-carbazole instead of 9-(3-(4-chloro-6-phenyl-1,3,5-triazin-2-yl)phenyl)-9H-carbazole.

Preparation Example 6-2

Target compounds were synthesized in the same manner as in Preparation Example 6-1 using Intermediate Q instead of 9-(4-(4-chloro-6-phenyl-1,3,5-triazin-2-yl)naphthalen-1-yl)-9H-carbazole.

TABLE 17

| Compound No. | Intermediate Q | Target Compound | Yield |
|---|---|---|---|
| 557 | | | 60% |
| 559 | | | 60% |

TABLE 17-continued

| Compound No. | Intermediate Q | Target Compound | Yield |
| --- | --- | --- | --- |
| 563 | | | 61% |
| 567 | | | 64% |
| 578 | | | 60% |
| 585 | | | 60% |

TABLE 17-continued

| Compound No. | Intermediate Q | Target Compound | Yield |
|---|---|---|---|
| 591 | | | 61% |
| 593 | | | 64% |
| 597 | | | 60% |

TABLE 17-continued

| Compound No. | Intermediate Q | Target Compound | Yield |
| --- | --- | --- | --- |
| 598 | | | 60% |
| 777 | | | 64% |
| 778 | | | 63% |
| 780 | | | 60% |

TABLE 17-continued

| Compound No. | Intermediate Q | Target Compound | Yield |
|---|---|---|---|
| 786 | | | 64% |
| 789 | | | 63% |
| 798 | | | 60% |

TABLE 17-continued
| Compound No. | Intermediate Q | Target Compound | Yield |
|---|---|---|---|
| 803 | 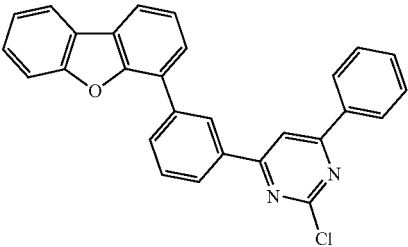 [SMILES: Clc1nc(-c2ccccc2)cc(-c2cccc(-c3cccc4c3oc3ccccc34)c2)n1] | 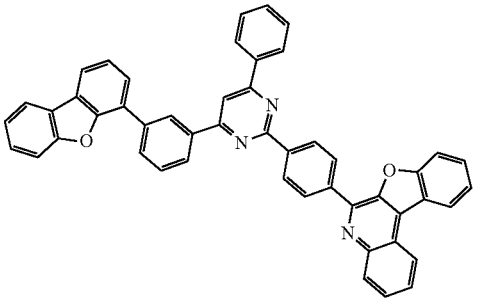 [SMILES: c1ccc(-c2cc(-c3cccc(-c4cccc5c4oc4ccccc45)c3)nc(-c3ccc(-c4nc5ccccc5c5c4oc4ccccc45)cc3)n2)cc1] | 60% |
| 816 | 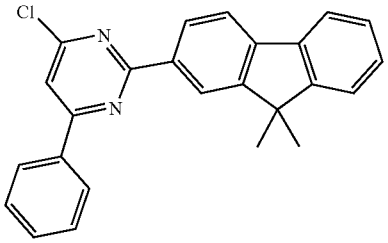 [SMILES: CC1(C)c2ccccc2-c2ccc(-c3nc(Cl)cc(-c4ccccc4)n3)cc21] | 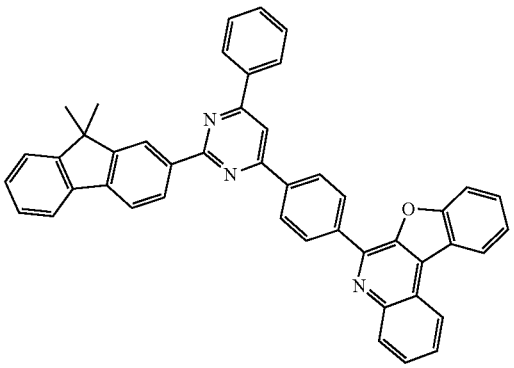 [SMILES: CC1(C)c2ccccc2-c2ccc(-c3nc(-c4ccccc4)cc(-c4ccc(-c5nc6ccccc6c6c5oc5ccccc56)cc4)n3)cc21] | 60% |
| 824 | 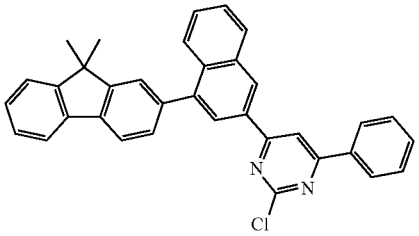 [SMILES: CC1(C)c2ccccc2-c2ccc(-c3cc(-c4cc(-c5ccccc5)nc(Cl)n4)cc4ccccc34)cc21] | 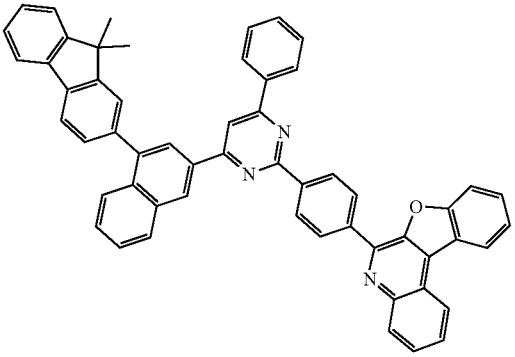 [SMILES: CC1(C)c2ccccc2-c2ccc(-c3cc(-c4cc(-c5ccccc5)nc(-c5ccc(-c6nc7ccccc7c7c6oc6ccccc67)cc5)n4)cc4ccccc34)cc21] | 60% |
| 830 | 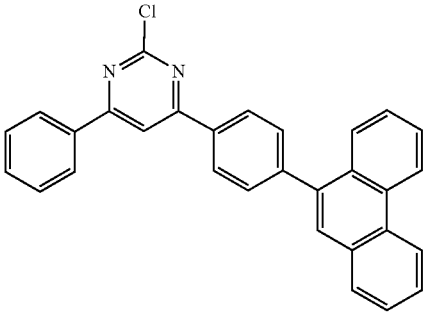 [SMILES: Clc1nc(-c2ccccc2)cc(-c2ccc(-c3cc4ccccc4c4ccccc34)cc2)n1] | 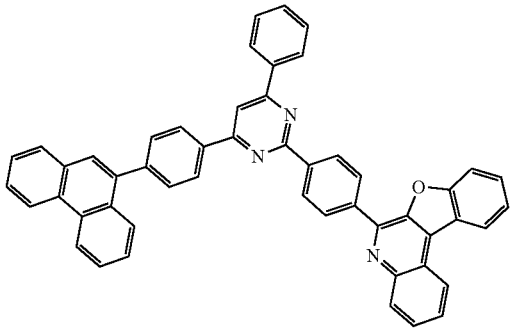 [SMILES: c1ccc(-c2cc(-c3ccc(-c4cc5ccccc5c5ccccc45)cc3)nc(-c3ccc(-c4nc5ccccc5c5c4oc4ccccc45)cc3)n2)cc1] | 61% |

TABLE 17-continued

| Compound No. | Intermediate Q | Target Compound | Yield |
|---|---|---|---|
| 943 | | | 60% |

Preparation Example 6-3

Target compounds were synthesized in the same manner as in Preparation Example 6-1 using 3-bromobenzoyl chloride instead of 4-bromobenzoyl chloride, and using Intermediate R instead of 9-(4-(4-chloro-6-phenyl-1,3,5-triazin-2-yl)naphthalen-1-yl)-9H-carbazole.

TABLE 18

| Compound No. | Intermediate R | Target Compound | Yield |
|---|---|---|---|
| 553 | | | 64% |
| 562 | | | 63% |

TABLE 18-continued

| Compound No. | Intermediate R | Target Compound | Yield |
|---|---|---|---|
| 576 | | | 60% |
| 579 | | | 64% |
| 588 | | | 60% |
| 784 | | | 60% |

TABLE 18-continued

| Compound No. | Intermediate R | Target Compound | Yield |
|---|---|---|---|
| 788 | | | 64% |
| 796 | | | 60% |
| 818 | | | 61% |

Preparation Example 6-4

Target compounds were synthesized in the same manner as in Preparation Example 6-1 using 4-bromo-1-naphthoyl chloride instead of 4-bromobenzoyl chloride, and using Intermediate S instead of 9-(4-(4-chloro-6-phenyl-1,3,5-triazin-2-yl)naphthalen-1-yl)-9H-carbazole.

TABLE 19

| Compound No. | Intermediate S | Target Compound | Yield |
|---|---|---|---|
| 550 | | | 63% |

TABLE 19-continued

| Compound No. | Intermediate S | Target Compound | Yield |
| --- | --- | --- | --- |
| 573 | | | 64% |
| 587 | | | 63% |
| 782 | | | 60% |
| 811 | | | 64% |

TABLE 19-continued
| Compound No. | Intermediate S | Target Compound | Yield |
|---|---|---|---|
| 820 | 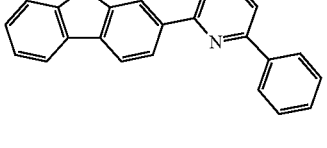 | 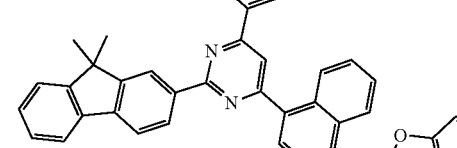 | 63% |
| 829 | 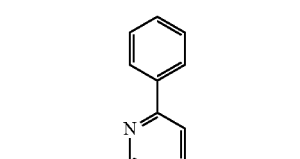 | 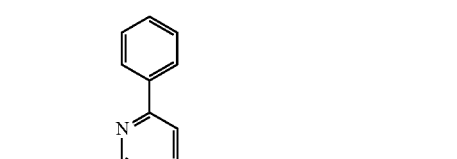 | 60% |
| 833 |  |  | 60% |

[Preparation Example 7-1] Preparation of Compound 609
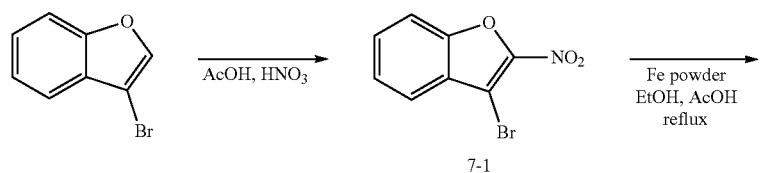
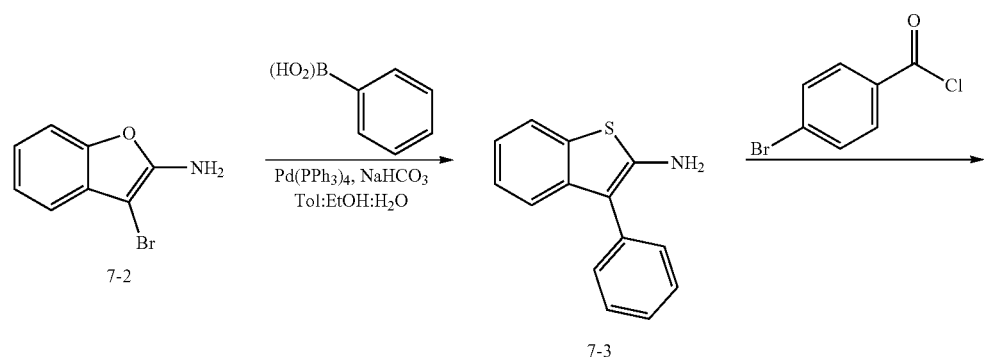
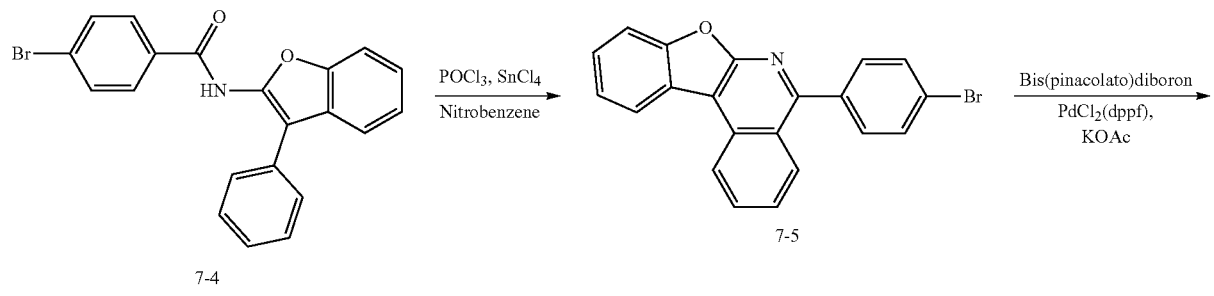

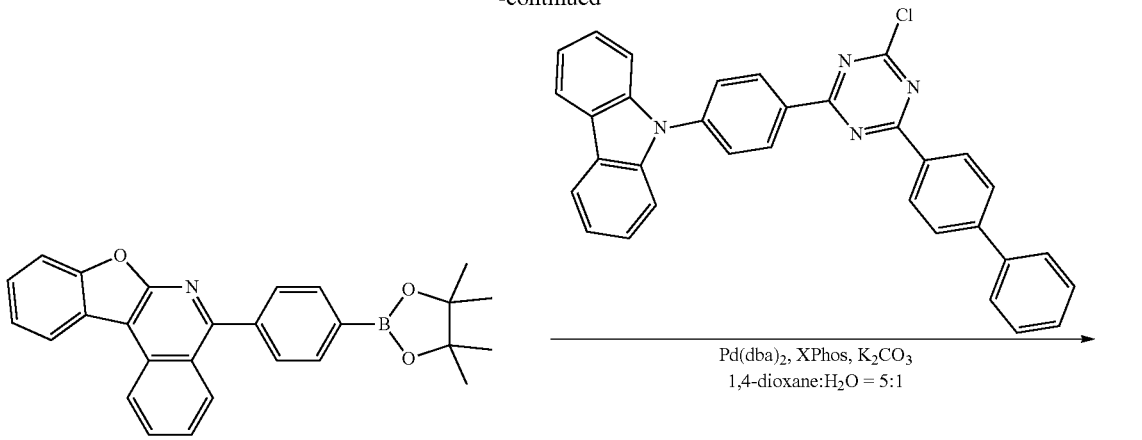

7-6

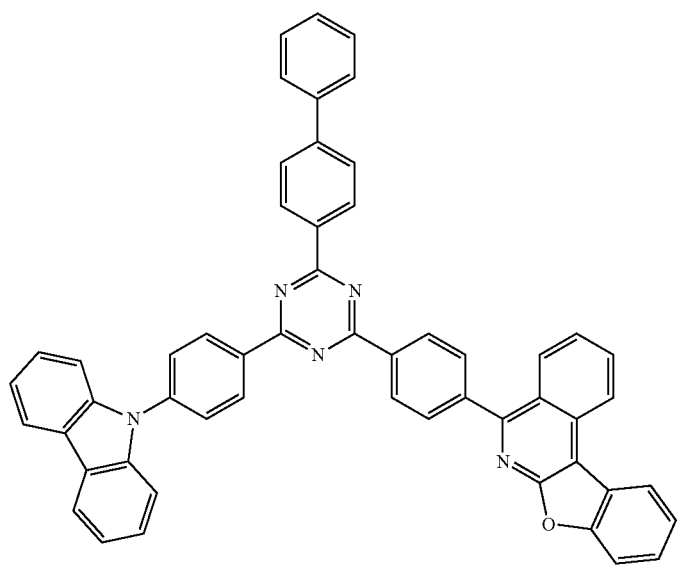

609

1) Preparation of Compound 7-1

Compound 7-1 (92 g, 75%) was obtained in the same manner as in Preparation of Compound 3-1 of Preparation Example 3-1 using 3-bromobenzofuran instead of 3-bromobenzo[b]thiophene.

2) Preparation of Compound 7-2

Compound 7-2 (89 g, 97%) was obtained in the same manner as in Preparation of Compound 3-2 of Preparation Example 3-1 using Compound 7-1 instead of Compound 3-1.

3) Preparation of Compound 7-3

Compound 7-3 (79, 90%) was obtained in the same manner as in Preparation of Compound 3-3 of Preparation Example 3-1 using Compound 7-2 instead of Compound 3-2.

4) Preparation of Compound 7-4

Compound 7-4 (133 g, 90%) was obtained in the same manner as in Preparation of Compound 3-4 of Preparation Example 3-1 using Compound 7-3 instead of Compound 3-3.

5) Preparation of Compound 7-5

Compound 7-5 (121 g, 70%) was obtained in the same manner as in Preparation of Compound 3-5 of Preparation Example 3-1 using Compound 7-4 instead of Compound 3-4.

6) Preparation of Compound 7-6

Compound 7-6 (41 g, 68%) was obtained in the same manner as in Preparation of Compound 3-6 of Preparation Example 3-1 using Compound 7-5 instead of Compound 3-5.

7) Preparation of Compound 609

Compound 609 (7.4 g, 0.58%) was obtained in the same manner as in Preparation of Compound 130 of Preparation Example 3-1 using Compound 7-6 instead of Compound 3-6, and using 9-(4-(4-([1,1'-biphenyl]-4-yl)-6-chloro-1,3,5-triazin-2-yl)phenyl)-9H-carbazole instead of 9-(3-(4-chloro-6-(naphthalen-2-yl)-1,3,5-triazin-2-yl)phenyl)-9H-carbazole.

Preparation Example 7-2

Target compounds were synthesized in the same manner as in Preparation Example 7-1 using Intermediate T instead of 9-(4-(4-([1,1'-biphenyl]-4-yl)-6-chloro-1,3,5-triazin-2-yl)phenyl)-9H-carbazole.

TABLE 20

| Compound No. | Intermediate T | Target Compound | Yield |
|---|---|---|---|
| 605 | | | 64% |
| 616 | | | 60% |
| 618 | | | 60% |
| 626 | | | 61% |

TABLE 20-continued

| Compound No. | Intermediate T | Target Compound | Yield |
|---|---|---|---|
| 638 | | | 63% |
| 650 | | | 60% |
| 661 | | | 60% |
| 836 | | | 64% |

TABLE 20-continued

| Compound No. | Intermediate T | Target Compound | Yield |
|---|---|---|---|
| 837 | | | 63% |
| 844 | | | 64% |
| 854 | | | 60% |
| 856 | | | 64% |

TABLE 20-continued
| Compound No. | Intermediate T | Target Compound | Yield |
|---|---|---|---|
| 864 | 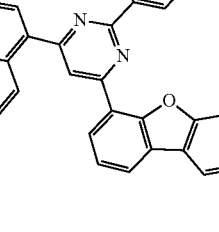 | 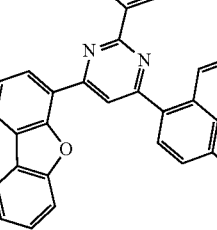 | 60% |
| 867 | 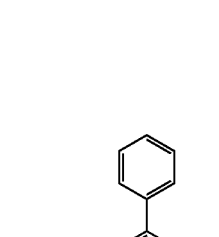 | 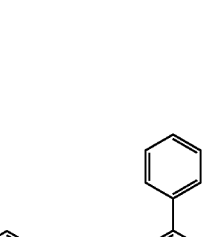 | 60% |
| 882 | 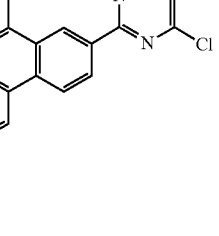 | 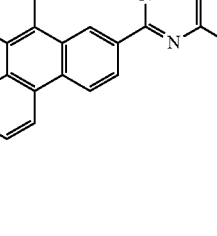 | 61% |
| 948 | 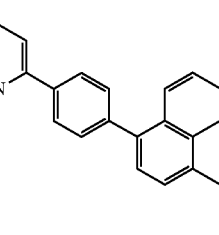 | 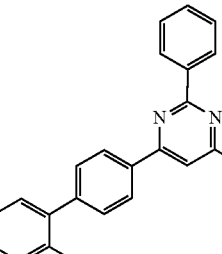 | 60% |

Preparation Example 7-3
Target compounds were synthesized in the same manner as in Preparation Example 7-1 using 3-bromobenzoyl chloride instead of 4-bromobenzoyl chloride, and using Intermediate U instead of 9-(4-(4-([1,1'-biphenyl]-4-yl)-6-chloro-1,3,5-triazin-2-yl)phenyl)-9H-carbazole.
TABLE 21
| Compound No. | Intermediate U | Target Compound | Yield |
|---|---|---|---|
| 604 | 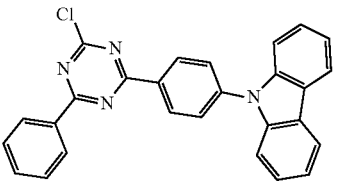 [SMILES: Clc1nc(-c2ccccc2)nc(-c2ccc(-n3c4ccccc4c4ccccc43)cc2)n1] | 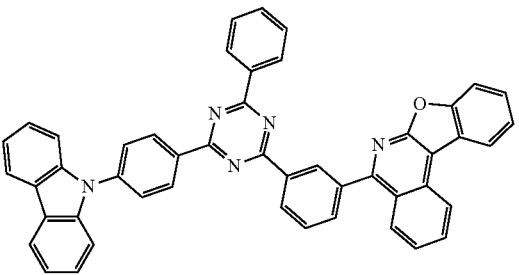 [SMILES: c1ccc(-c2nc(-c3ccc(-n4c5ccccc5c5ccccc54)cc3)nc(-c3cccc(-c4nc5oc6ccccc6c5c5ccccc45)c3)n2)cc1] | 64% |
| 613 | 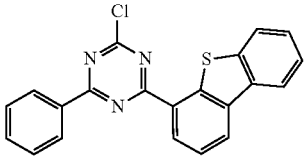 [SMILES: Clc1nc(-c2ccccc2)nc(-c2cccc3c2sc2ccccc23)n1] | 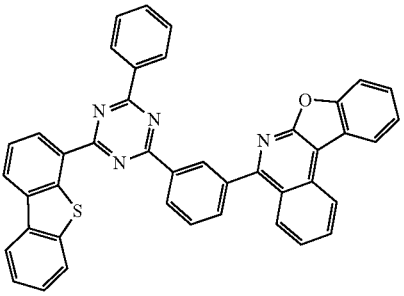 [SMILES: c1ccc(-c2nc(-c3cccc(-c4nc5oc6ccccc6c5c5ccccc45)c3)nc(-c3cccc4c3sc3ccccc34)n2)cc1] | 63% |
| 617 | 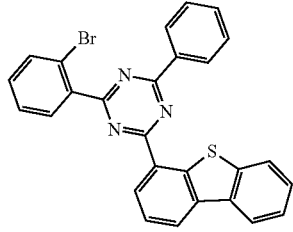 [SMILES: Brc1ccccc1-c1nc(-c2ccccc2)nc(-c2cccc3c2sc2ccccc23)n1] | 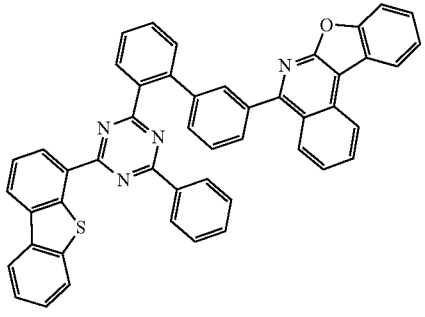 [SMILES: c1ccc(-c2nc(-c3ccccc3-c3cccc(-c4nc5oc6ccccc6c5c5ccccc45)c3)nc(-c3cccc4c3sc3ccccc34)n2)cc1] | 60% |
| 641 | 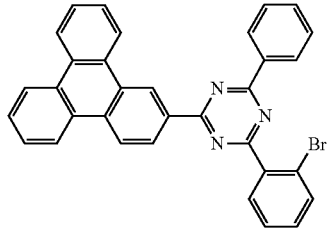 [SMILES: Brc1ccccc1-c1nc(-c2ccccc2)nc(-c2ccc3c4ccccc4c4ccccc4c3c2)n1] | 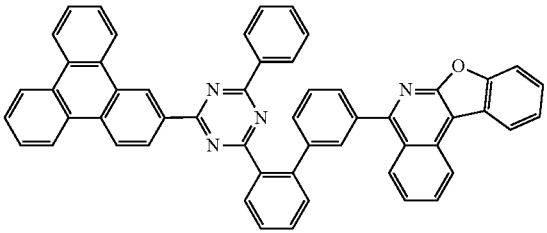 [SMILES: c1ccc(-c2nc(-c3ccc4c5ccccc5c5ccccc5c4c3)nc(-c3ccccc3-c3cccc(-c4nc5oc6ccccc6c5c5ccccc45)c3)n2)cc1] | 64% |
| 645 | 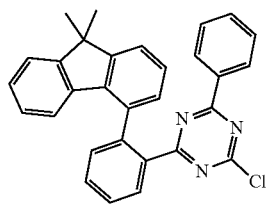 [SMILES: CC1(C)c2ccccc2-c2c(-c3ccccc3-c3nc(Cl)nc(-c4ccccc4)n3)cccc21] | 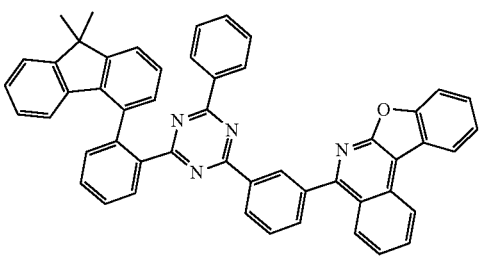 [SMILES: CC1(C)c2ccccc2-c2c(-c3ccccc3-c3nc(-c4ccccc4)nc(-c4cccc(-c5nc6oc7ccccc7c6c6ccccc56)c4)n3)cccc21] | 63% |

TABLE 21-continued

| Compound No. | Intermediate U | Target Compound | Yield |
|---|---|---|---|
| 663 | | | 60% |
| 839 | | | 64% |
| 846 | | | 63% |
| 848 | | | 60% |
| 866 | | | 60% |

TABLE 21-continued

| Compound No. | Intermediate U | Target Compound | Yield |
|---|---|---|---|
| 874 | | | 61% |
| 876 | | | 64% |
| 880 | | | 63% |
| 885 | | | 60% |
| 886 | | | 60% |

Preparation Example 7-4

Target compounds were synthesized in the same manner as in Preparation Example 7-1 using 4-bromo-1-naphthoyl chloride instead of 4-bromobenzoyl chloride, and using Intermediate V instead of 9-(4-(4-([1,1'-biphenyl]-4-yl)-6-chloro-1,3,5-triazin-2-yl)phenyl)-9H-carbazole.

TABLE 22

| Compound No. | Intermediate V | Target Compound | Yield |
|---|---|---|---|
| 608 | | | 64% |
| 621 | | | 63% |
| 632 | | | 60% |

TABLE 22-continued

| Compound No. | Intermediate V | Target Compound | Yield |
| --- | --- | --- | --- |
| 653 | | | 61% |
| 852 | | | 60% |
| 865 | | | 60% |
| 879 | | | 61% |

[Preparation Example 8-1] Preparation of Compound 664
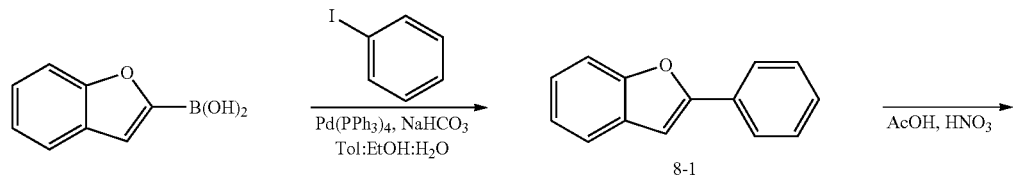
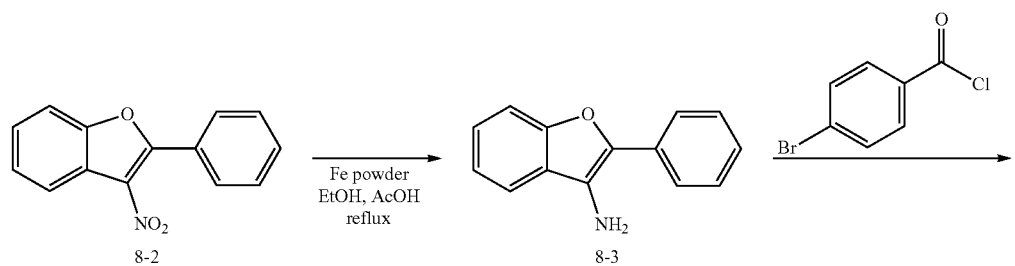
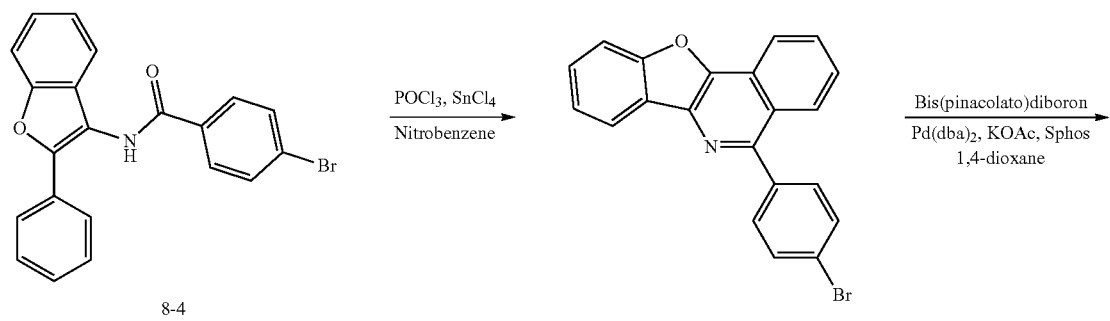

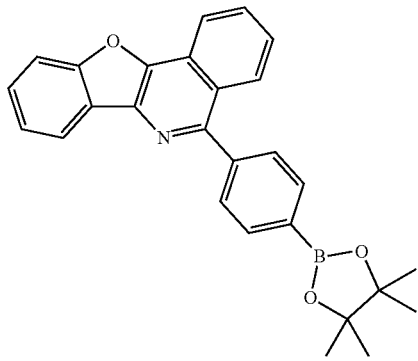

8-6

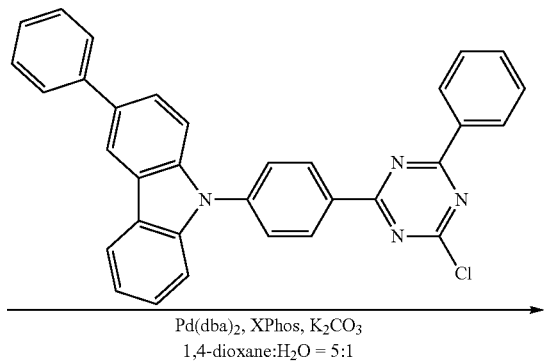

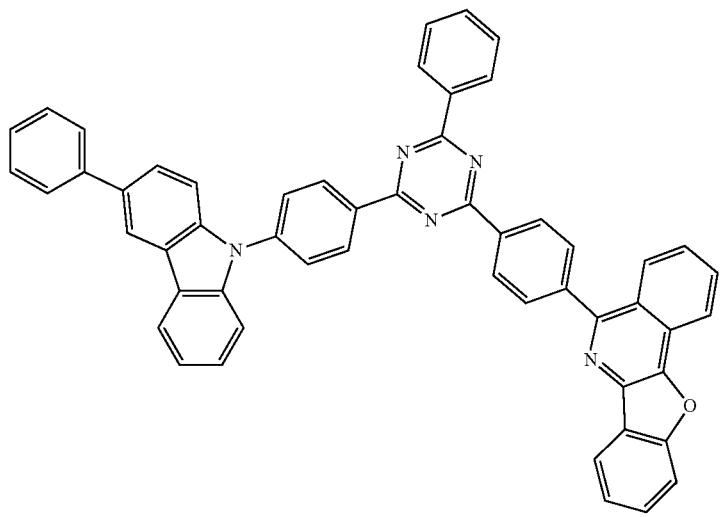

664

1) Preparation of Compound 8-1

Compound 8-1 (54 g, 91%) was obtained in the same manner as in Preparation of Compound 4-1 of Preparation Example 4-1 using benzofuran-2-ylboronic acid instead of benzo[b]thiophen-2-ylboronic acid.

2) Preparation of Compound 8-2

Compound 8-2 (50 g, 72%) was obtained in the same manner as in Preparation of Compound 4-2 of Preparation Example 4-1 using Compound 8-1 instead of Compound 4-1.

3) Preparation of Compound 8-3

Compound 8-3 (42 g, 97%) was obtained in the same manner as in Preparation of Compound 4-3 of Preparation Example 4-1 using Compound 8-2 instead of Compound 4-2.

4) Preparation of Compound 8-4

Compound 8-4 (63 g, 80%) was obtained in the same manner as in Preparation of Compound 4-4 of Preparation Example 4-1 using Compound 8-3 instead of Compound 4-3.

5) Preparation of Compound 8-5

Compound 8-5 (46 g, 76%) was obtained in the same manner as in Preparation of Compound 4-5 of Preparation Example 4-1 using Compound 8-4 instead of Compound 4-4.

6) Preparation of Compound 8-6

Compound 8-6 (36 g, 70%) was obtained in the same manner as in Preparation of Compound 4-6 of Preparation Example 4-1 using Compound 8-5 instead of Compound 4-5.

7) Preparation of Compound 664

Compound 664 (9 g, 62%) was obtained in the same manner as in Preparation of Compound 210 of Preparation Example 4-1 using Compound 8-6 instead of Compound 4-6, and using 9-(4-(4-chloro-6-phenyl-1,3,5-triazin-2-yl)phenyl)-3-phenyl-9H-carbazole instead of 9-(4-(4-chloro-6-(naphthalen-2-yl)-1,3,5-triazin-2-yl)phenyl)-9H-carbazole.

Preparation Example 8-2

Target compounds were synthesized in the same manner as in Preparation Example 8-1 using Intermediate W instead of 9-(4-(4-chloro-6-phenyl-1,3,5-triazin-2-yl)phenyl)-3-phenyl-9H-carbazole.

TABLE 23

| Compound No. | Intermediate W | Target Compound | Yield |
|---|---|---|---|
| 666 | | | 64% |
| 668 | | | 63% |
| 681 | | | 60% |
| 696 | | | 63% |

TABLE 23-continued

| Compound No. | Intermediate W | Target Compound | Yield |
|---|---|---|---|
| 703 | | | 60% |
| 712 | | | 61% |
| 722 | | | 64% |
| 888 | | | 63% |

TABLE 23-continued

| Compound No. | Intermediate W | Target Compound | Yield |
| --- | --- | --- | --- |
| 889 | | | 60% |
| 897 | | | 61% |
| 902 | | | 64% |
| 906 | | | 63% |

TABLE 23-continued

| Compound No. | Intermediate W | Target Compound | Yield |
|---|---|---|---|
| 907 | | | 60% |
| 917 | | | 61% |
| 930 | | | 60% |
| 931 | | | 60% |

Preparation Example 8-3

Target compounds were synthesized in the same manner as in Preparation Example 8-1 using 3-bromobenzoyl chloride instead of 4-bromobenzoyl chloride, and using Intermediate X instead of 9-(4-(4-chloro-6-phenyl-1,3,5-triazin-2-yl)phenyl)-3-phenyl-9H-carbazole.

TABLE 24

| Compound No. | Intermediate X | Target Compound | Yield |
|---|---|---|---|
| 667 | | | 64% |
| 674 | | | 63% |
| 680 | | | 60% |
| 687 | | | 64% |

TABLE 24-continued
| Compound No. | Intermediate X | Target Compound | Yield |
|---|---|---|---|
| 691 | 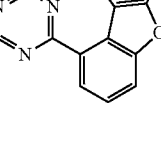 | 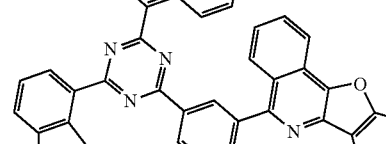 | 63% |
| 700 | 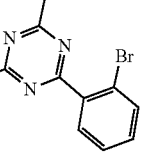 | 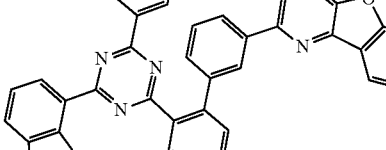 | 60% |
| 724 | 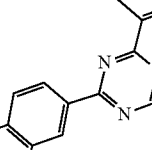 | 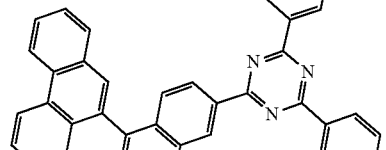 | 61% |
| 898 |  |  | 63% |

TABLE 24-continued

| Compound No. | Intermediate X | Target Compound | Yield |
| --- | --- | --- | --- |
| 905 | | | 60% |
| 916 | | | 60% |
| 920 | | | 60% |
| 935 | | | 60% |

TABLE 24-continued

| Compound No. | Intermediate X | Target Compound | Yield |
|---|---|---|---|
| 949 | | | 60% |

Preparation Example 8-4

Target compounds were synthesized in the same manner as in Preparation Example 8-1 using 4-bromo-1-naphthoyl chloride instead of 4-bromobenzoyl chloride, and using Intermediate Y instead of 9-(4-(4-chloro-6-phenyl-1,3,5-triazin-2-yl)phenyl)-3-phenyl-9H-carbazole.

TABLE 25

| Compound No. | Intermediate Y | Target Compound | Yield |
|---|---|---|---|
| 671 | | | 63% |
| 682 | | | 60% |

TABLE 25-continued

| Compound No. | Intermediate Y | Target Compound | Yield |
|---|---|---|---|
| 699 | | | 64% |
| 721 | | | 63% |
| 894 | | | 60% |
| 903 | | | 61% |

TABLE 25-continued
| Compound No. | Intermediate Y | Target Compound | Yield |
|---|---|---|---|
| 913 | 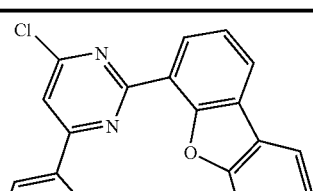 | 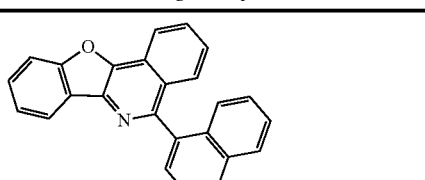 | 60% |
[Preparation Example 9-1] Preparation of Compound 935
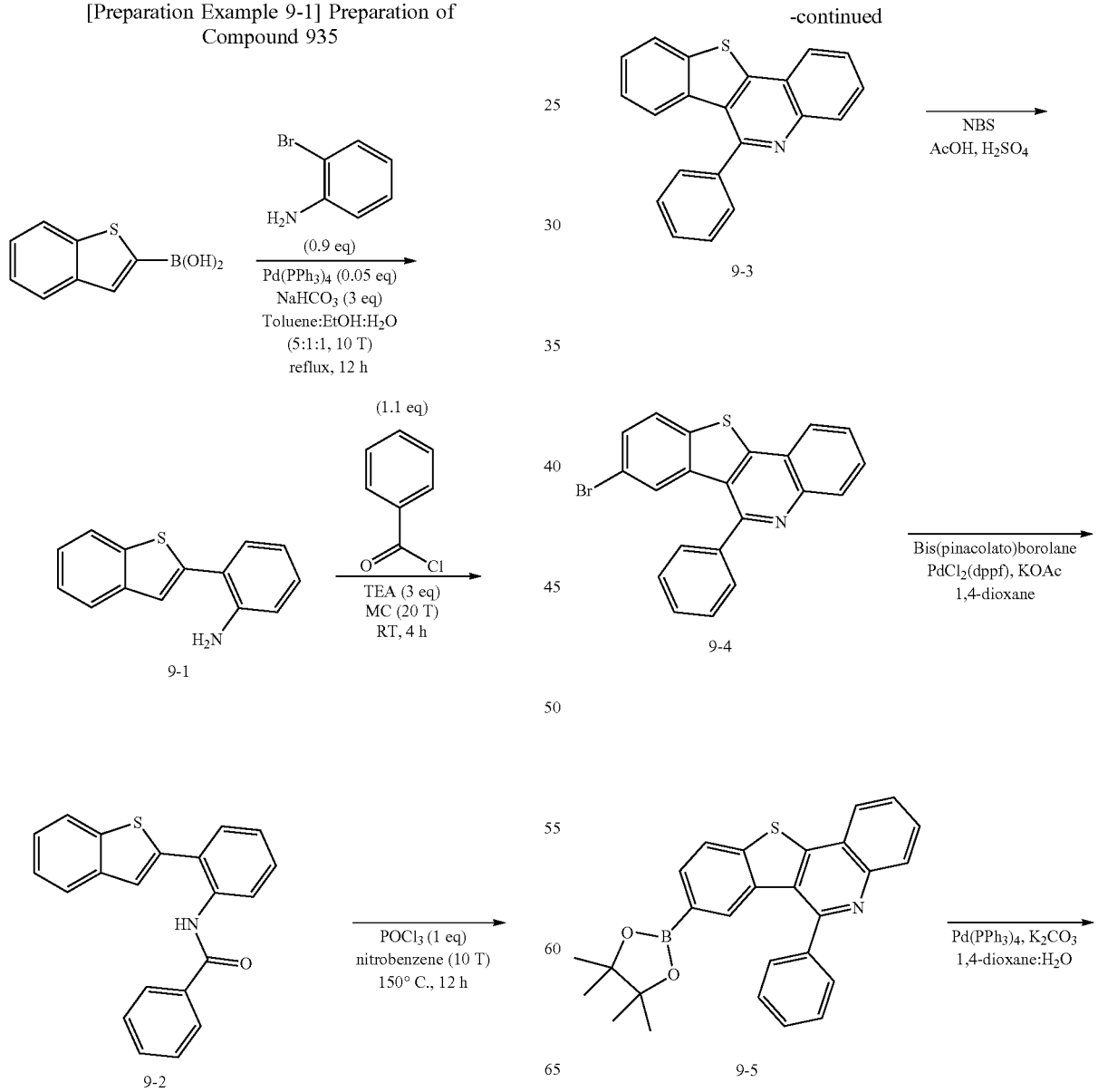

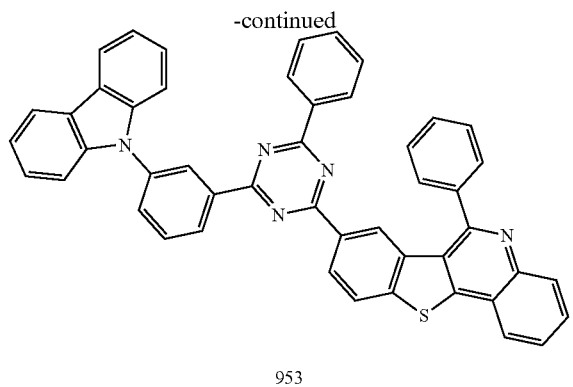

953

1) Preparation of Compound 9-1

After dissolving benzo[b]thiophen-2-ylboronic acid (100 g, 0.561 mol) and 2-bromoaniline (86.7 g, 0.504 mol) in toluene, EtOH and $H_2O$ (1000 mL:200 mL:200 mL), $Pd(PPh_3)_4$ (32.4 g, 0.028 mol) and $NaHCO_3$ (141.3 g, 1.68 mol) were introduced thereto, and the result was stirred for 3 hours at 100° C. After the reaction was completed, the reaction solution was extracted by introducing MC and distilled water thereto. After that, the result was dried with anhydrous $MgSO_4$, and the solvent was removed using a rotary evaporator to obtain liquid-type Compound 9-1 (93 g, 74%).

2) Preparation of Compound 9-2

Compound 9-1 (93 g, 0.412 mol) and triethylamine (86 mL, 0.618 mol) were introduced to and dissolved in MC (1200 mL). Benzoyl chloride (135.6 g, 0.618 mol) dissolved in MC (300 mL) was slowly added dropwise to the mixture at 0° C. After the reaction was completed, white solids present in the reaction solution were filtered and washed with hexane. The result was dried to obtain solid-type Compound 9-2 (134 g, 83%).

3) Preparation of Compound 9-3

After dissolving Compound 9-2 (134 g, 0.329 mol) in nitrobenzene (1500 mL), $POCl_3$ (46 mL, 0.495 mol) was slowly added dropwise thereto. The result was reacted for 15 hours at 140° C. After the reaction was completed, a solution obtained by dissolving $NaHCO_3$ in distilled water was slowly introduced to the reaction solution, and the result was stirred. Solids produced after that were filtered and collected. The collected solids were recrystallized with MC and MeOH to obtain solid-type Compound 9-3 (65 g, 51%).

4) Preparation of Compound 9-4

Compound 9-3 (10 g, 0.0352 mol, 1 eq.), NBS (7.5 g, 0.0423 mol, 1.2 eq.) and acetic acid (AcOH) (200 ml, 20 T) were introduced, and stirred for 20 minutes. $H_2SO_4$ (100 ml, 10 T) was slowly introduced thereto. The result was stirred for 1 hour at room temperature, and water (150 ml) was introduced thereto to terminate the reaction. The result was extracted with MC, silica filtered to remove impurities, and then stirred with MeOH. Produced solids were filtered to obtain Compound 9-4 (10.6 g, 81%).

5) Preparation of Compound 9-5

After dissolving Compound 9-4 (38 g, 0.102 mol), bis(pinacolato)diboron (39 g, 0.153 mol), KOAc (30 g, 0.306 mol) and $PdCl_2(dppf)$ (3.7 g, 0.0051 mol) in 1,4-dioxane (1000 mL), the result was reacted for 5 hours at 90° C. After the reaction was completed, the reaction solution was extracted by introducing MC and distilled water thereto. After that, the result was dried with anhydrous $MgSO_4$, and the solids were filtered to obtain Compound 9-5 (28 g, 67%).

6) Preparation of Compound 935

After dissolving Compound 9-5 (6.7 g, 0.016 mol) and 9-(3-(4-chloro-6-phenyl-1,3,5-triazin-2-yl)phenyl)-9H-carbazole (6.8 g, 0.016 mol) in 1,4-dioxane:$H_2O$ (100 mL:20 mL), $Pd_2(dba)_3$ (1.4 g, 0.0016 mol), XPhos (1.5 g, 0.0032 mol) and $K_2CO_3$ (6.6 g, 0.048 mol) were introduced thereto, and the result was stirred for 5 hours at 100° C. After the reaction was completed, solids produced in the reaction solution were washed with 1,4-dioxane and $H_2O$. After that, only the solids were purified using a recrystallization method in DCB to obtain Compound 935 (7.2 g, 64%).

Preparation Example 9-2

Target compounds were synthesized in the same manner as in Preparation Example 9-1 using Intermediate Z instead of 9-(3-(4-chloro-6-phenyl-1,3,5-triazin-2-yl)phenyl)-9H-carbazole.

TABLE 26

| Compound No. | Intermediate Z | Target Compound | Yield |
|---|---|---|---|
| 956 | | | 63% |

TABLE 26-continued
| Compound No. | Intermediate Z | Target Compound | Yield |
|---|---|---|---|
| 960 | 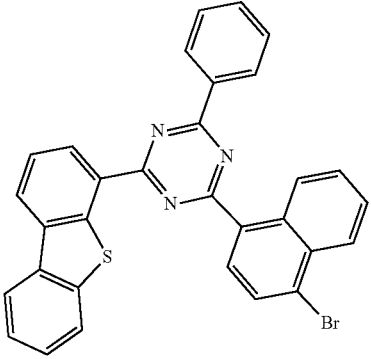 [SMILES: Brc1ccc(-c2nc(-c3ccccc3)nc(-c3cccc4c3sc3ccccc34)n2)c2ccccc12] | 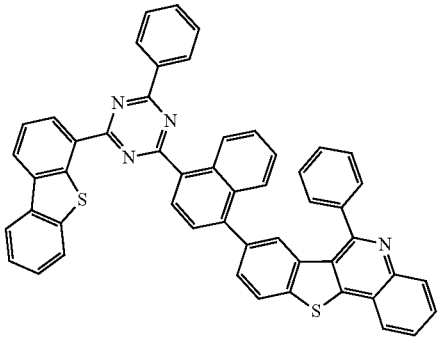 [SMILES: c1ccc(-c2nc(-c3ccc(-c4ccc5sc6c7ccccc7nc(-c7ccccc7)c6c5c4)c4ccccc34)nc(-c3cccc4c3sc3ccccc34)n2)cc1] | 61% |
| 962 | 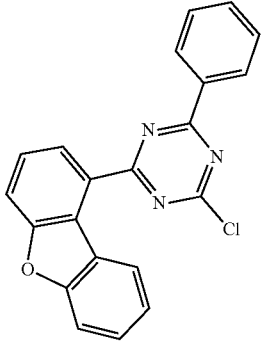 [SMILES: Clc1nc(-c2ccccc2)nc(-c2cccc3oc4ccccc4c23)n1] | 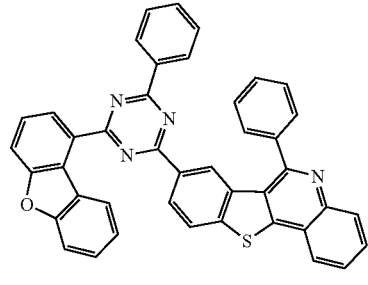 [SMILES: c1ccc(-c2nc(-c3ccc4sc5c6ccccc6nc(-c6ccccc6)c5c4c3)nc(-c3cccc4oc5ccccc5c34)n2)cc1] | 68% |
| 966 | 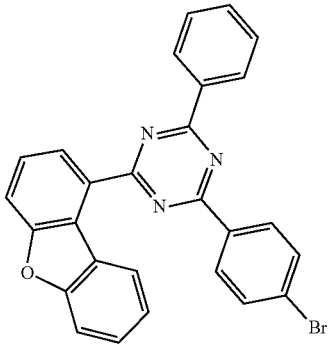 [SMILES: Brc1ccc(-c2nc(-c3ccccc3)nc(-c3cccc4oc5ccccc5c34)n2)cc1] | 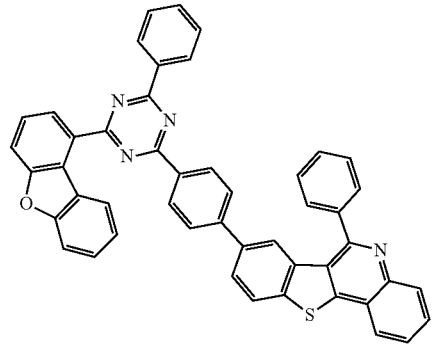 [SMILES: c1ccc(-c2nc(-c3ccc(-c4ccc5sc6c7ccccc7nc(-c7ccccc7)c6c5c4)cc3)nc(-c3cccc4oc5ccccc5c34)n2)cc1] | 62% |
| 969 | 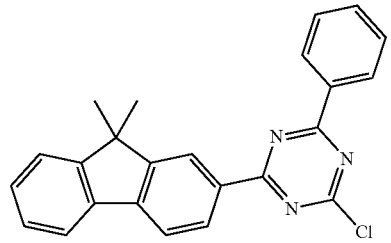 [SMILES: CC1(C)c2ccccc2-c2ccc(-c3nc(Cl)nc(-c4ccccc4)n3)cc21] | 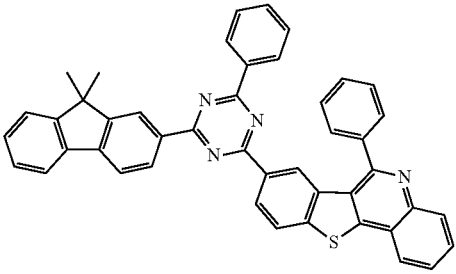 [SMILES: CC1(C)c2ccccc2-c2ccc(-c3nc(-c4ccccc4)nc(-c4ccc5sc6c7ccccc7nc(-c7ccccc7)c6c5c4)n3)cc21] | 61% |

TABLE 26-continued
| Compound No. | Intermediate Z | Target Compound | Yield |
|---|---|---|---|
| 973 | 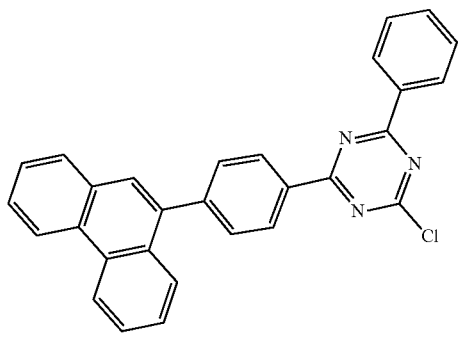 [SMILES: Clc1nc(-c2ccccc2)nc(-c2ccc(-c3cc4ccccc4c4ccccc34)cc2)n1] | 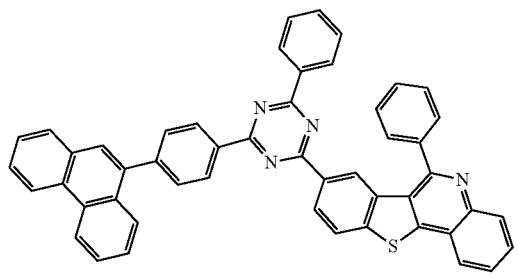 [SMILES: c1ccc(-c2nc(-c3ccc(-c4cc5ccccc5c5ccccc45)cc3)nc(-c3ccc4sc5c6ccccc6nc(-c6ccccc6)c5c4c3)n2)cc1] | 61% |
| 975 | 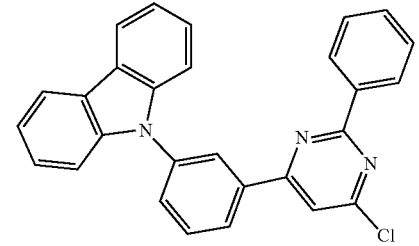 [SMILES: Clc1cc(-c2cccc(-n3c4ccccc4c4ccccc43)c2)nc(-c2ccccc2)n1] | 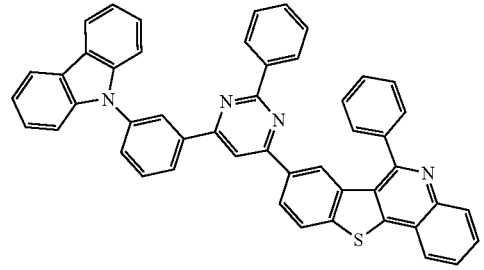 [SMILES: c1ccc(-c2nc(-c3cccc(-n4c5ccccc5c5ccccc54)c3)cc(-c3ccc4sc5c6ccccc6nc(-c6ccccc6)c5c4c3)n2)cc1] | 68% |
| 981 | 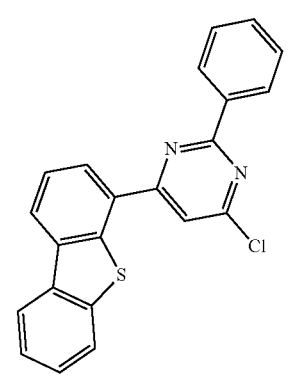 [SMILES: Clc1cc(-c2cccc3c2sc2ccccc23)nc(-c2ccccc2)n1] | 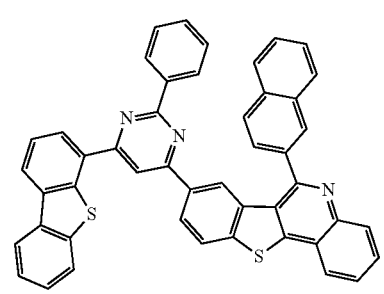 [SMILES: c1ccc(-c2nc(-c3ccc4sc5c6ccccc6nc(-c6ccc7ccccc7c6)c5c4c3)cc(-c3cccc4c3sc3ccccc34)n2)cc1] | 68% |
| 984 | 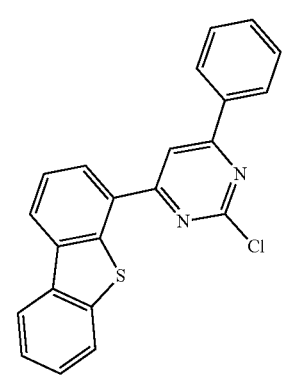 [SMILES: Clc1nc(-c2ccccc2)cc(-c2cccc3c2sc2ccccc23)n1] | 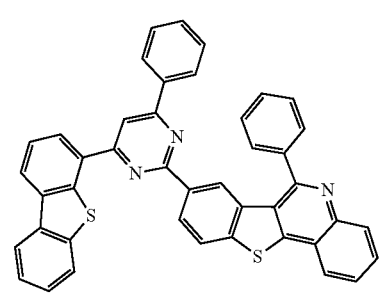 [SMILES: c1ccc(-c2cc(-c3cccc4c3sc3ccccc34)nc(-c3ccc4sc5c6ccccc6nc(-c6ccccc6)c5c4c3)n2)cc1] | 68% |

TABLE 26-continued
| Compound No. | Intermediate Z | Target Compound | Yield |
|---|---|---|---|
| 986 | 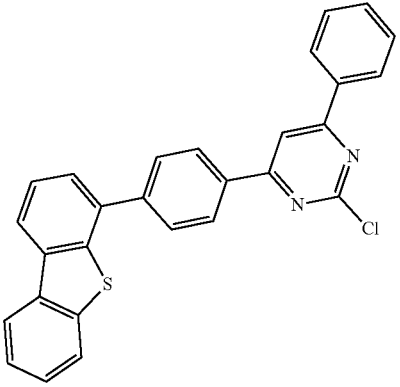 [SMILES: Clc1nc(-c2ccccc2)cc(-c2ccc(-c3cccc4c3sc3ccccc34)cc2)n1] | 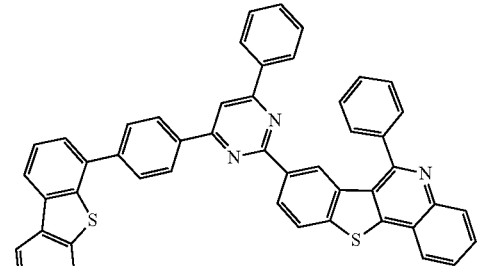 | 62% |
| 989 | 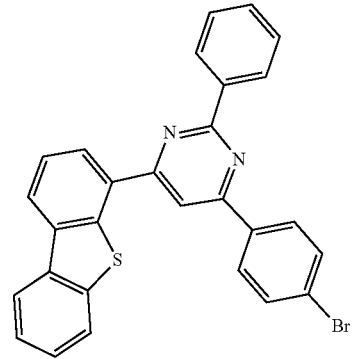 [SMILES: Brc1ccc(-c2cc(-c3cccc4c3sc3ccccc34)nc(-c3ccccc3)n2)cc1] | 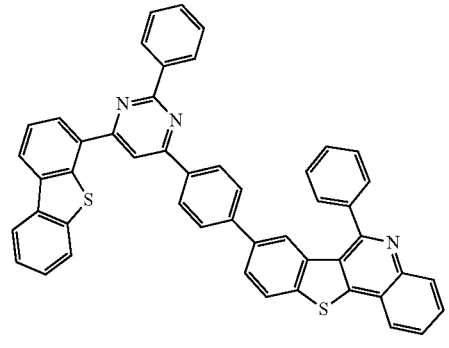 [SMILES: c1ccc(-c2nc(-c3ccc(-c4ccc5sc6c7ccccc7nc(-c7ccccc7)c6c5c4)cc3)cc(-c3cccc4c3sc3ccccc34)n2)cc1] | 62% |
| 991 | 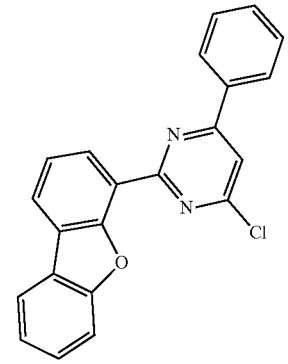 [SMILES: Clc1cc(-c2ccccc2)nc(-c2cccc3c2oc2ccccc23)n1] | 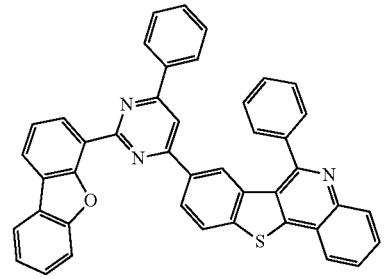 [SMILES: c1ccc(-c2cc(-c3ccc4sc5c6ccccc6nc(-c6ccccc6)c5c4c3)nc(-c3cccc4c3oc3ccccc34)n2)cc1] | 67% |
| 996 | 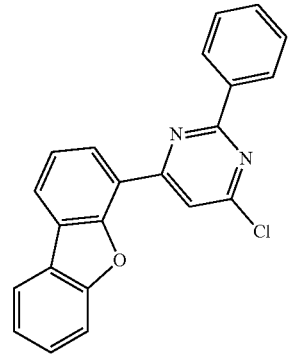 [SMILES: Clc1cc(-c2cccc3c2oc2ccccc23)nc(-c2ccccc2)n1] | 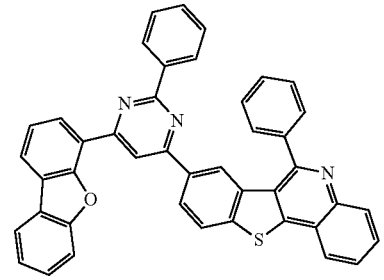 [SMILES: c1ccc(-c2nc(-c3ccc4sc5c6ccccc6nc(-c6ccccc6)c5c4c3)cc(-c3cccc4c3oc3ccccc34)n2)cc1] | 60% |

TABLE 26-continued
| Compound No. | Intermediate Z | Target Compound | Yield |
|---|---|---|---|
| 1003 | 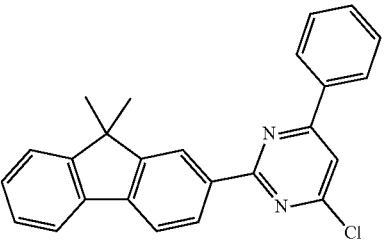 [SMILES: CC1(C)c2ccccc2-c2ccc(-c3nc(Cl)cc(-c4ccccc4)n3)cc21] | 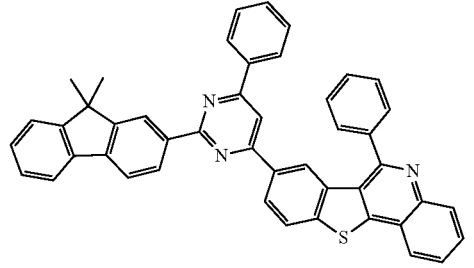 [SMILES: CC1(C)c2ccccc2-c2ccc(-c3nc(-c4ccccc4)cc(-c4ccc5sc6c7ccccc7nc(-c7ccccc7)c6c5c4)n3)cc21] | 63% |
| 1007 | 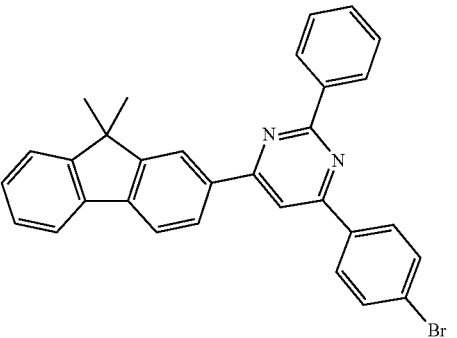 [SMILES: CC1(C)c2ccccc2-c2ccc(-c3cc(-c4ccc(Br)cc4)nc(-c4ccccc4)n3)cc21] | 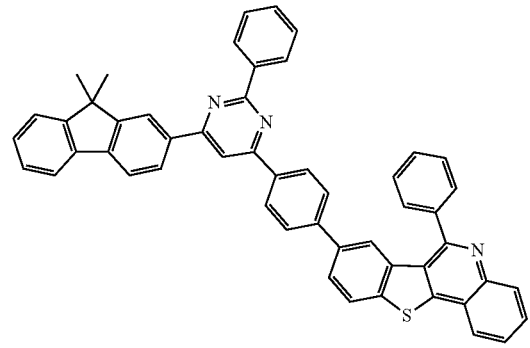 [SMILES: CC1(C)c2ccccc2-c2ccc(-c3cc(-c4ccc(-c5ccc6sc7c8ccccc8nc(-c8ccccc8)c7c6c5)cc4)nc(-c4ccccc4)n3)cc21] | 60% |
| 1013 | 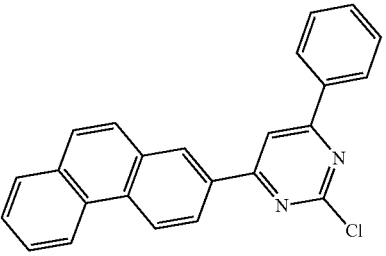 [SMILES: Clc1nc(-c2ccccc2)cc(-c2ccc3c(ccc4ccccc43)c2)n1] | 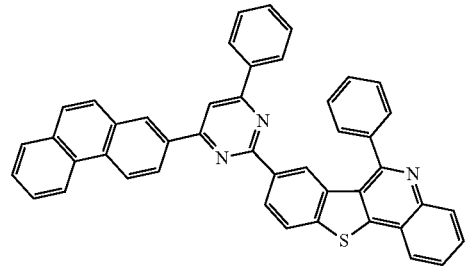 [SMILES: c1ccc(-c2cc(-c3ccc4c(ccc5ccccc54)c3)nc(-c3ccc4sc5c6ccccc6nc(-c6ccccc6)c5c4c3)n2)cc1] | 62% |
| 1014 | 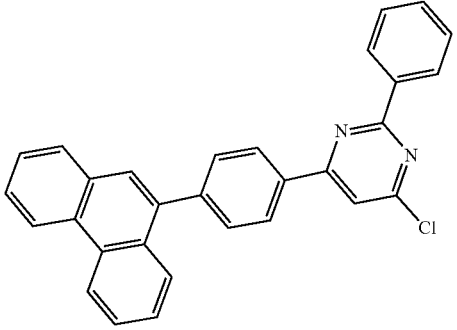 [SMILES: Clc1cc(-c2ccc(-c3cc4ccccc4c4ccccc34)cc2)nc(-c2ccccc2)n1] | 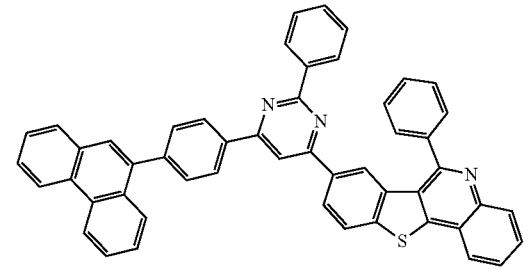 [SMILES: c1ccc(-c2nc(-c3ccc(-c4cc5ccccc5c5ccccc45)cc3)cc(-c3ccc4sc5c6ccccc6nc(-c6ccccc6)c5c4c3)n2)cc1] | 62% |

TABLE 26-continued
| Compound No. | Intermediate Z | Target Compound | Yield |
|---|---|---|---|
| 1030 | 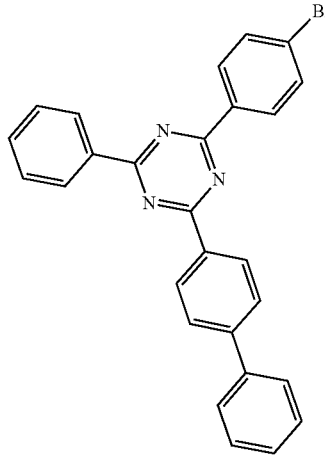 | 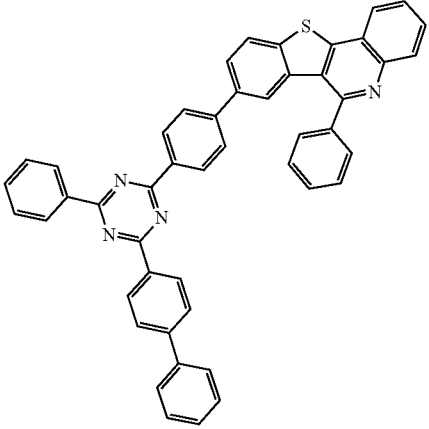 [SMILES: c1ccc(-c2ccc(-c3nc(-c4ccccc4)nc(-c4ccc(-c5ccc6sc7c8ccccc8nc(-c8ccccc8)c7c6c5)cc4)n3)cc2)cc1] | 61% |
| 1031 | 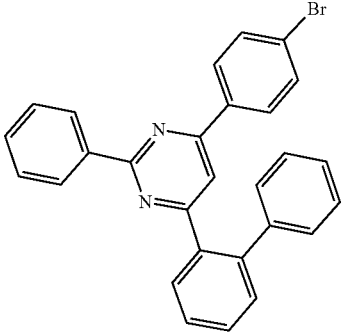 [SMILES: Brc1ccc(-c2cc(-c3ccccc3-c3ccccc3)nc(-c3ccccc3)n2)cc1] | 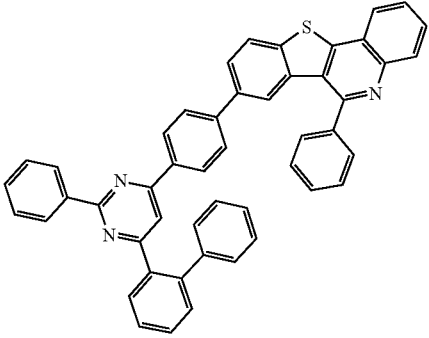 [SMILES: c1ccc(-c2nc(-c3ccc(-c4ccc5sc6c7ccccc7nc(-c7ccccc7)c6c5c4)cc3)cc(-c3ccccc3-c3ccccc3)n2)cc1] | 61% |
| 1033 | 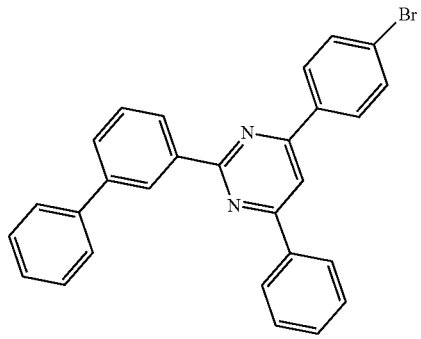 [SMILES: Brc1ccc(-c2cc(-c3ccccc3)nc(-c3cccc(-c4ccccc4)c3)n2)cc1] | 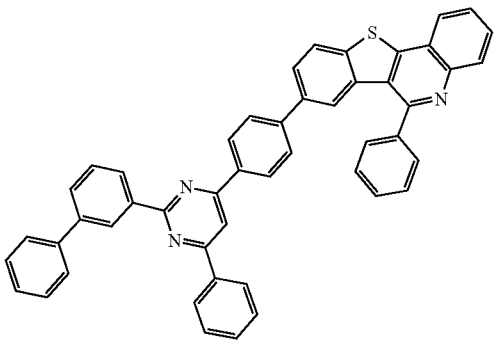 [SMILES: c1ccc(-c2cccc(-c3nc(-c4ccccc4)cc(-c4ccc(-c5ccc6sc7c8ccccc8nc(-c8ccccc8)c7c6c5)cc4)n3)c2)cc1] | 61% |

[Preparation Example 10-1] Preparation of Compound 1046

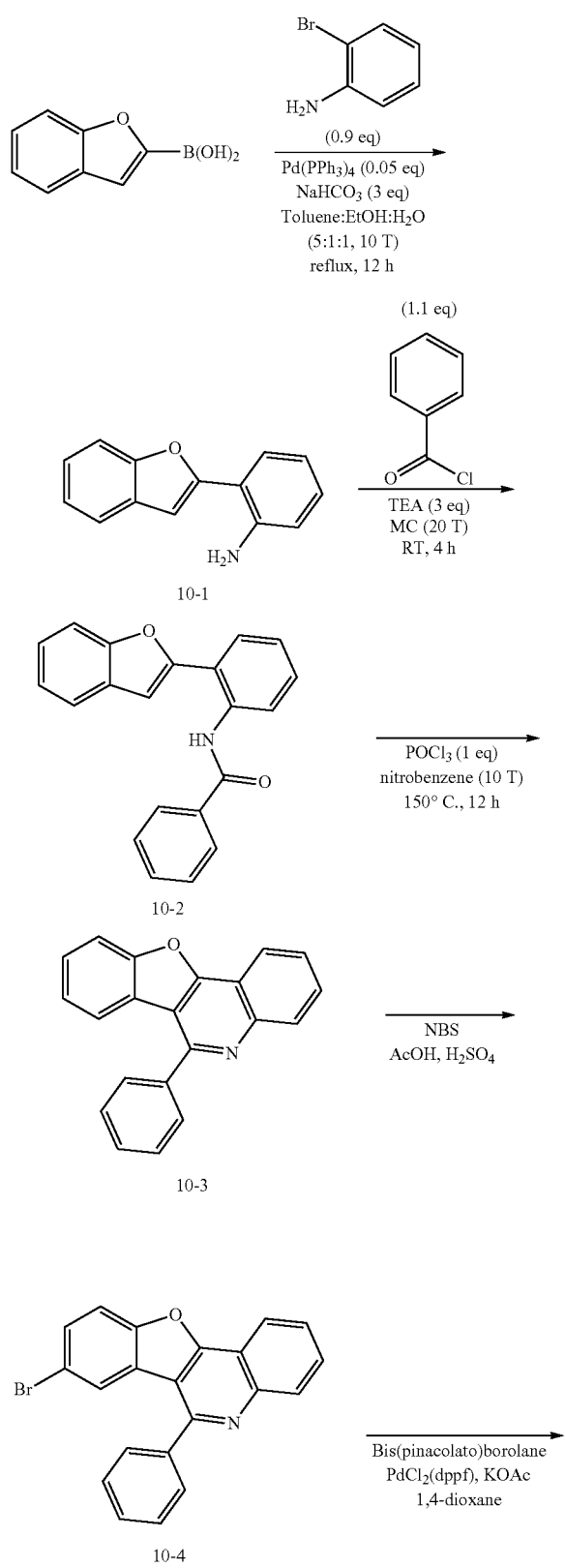

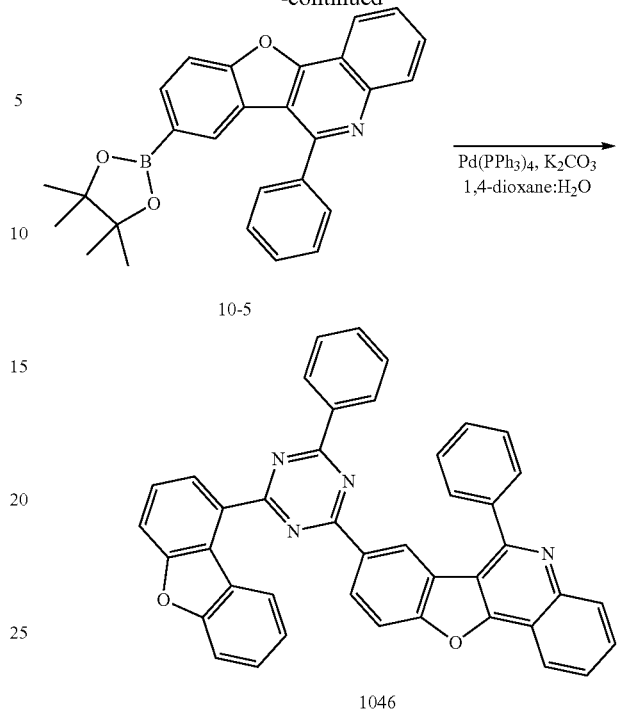

1) Preparation of Compound 10-1
Compound 10-1 (54 g, 91%) was obtained in the same manner as in Preparation of Compound 9-1 of Preparation Example 9-1 using benzofuran-2-ylboronic acid instead of benzo[b]thiophen-2-ylboronic acid.

2) Preparation of Compound 10-2
Compound 10-2 (50 g, 72%) was obtained in the same manner as in Preparation of Compound 9-2 of Preparation Example 9-1 using Compound 10-1 instead of Compound 9-1.

3) Preparation of Compound 10-3
Compound 10-3 (42 g, 97%) was obtained in the same manner as in Preparation of Compound 9-3 of Preparation Example 9-1 using Compound 10-2 instead of Compound 9-2.

4) Preparation of Compound 10-4
Compound 10-4 (63 g, 80%) was obtained in the same manner as in Preparation of Compound 9-4 of Preparation Example 9-1 using Compound 10-3 instead of Compound 9-3.

5) Preparation of Compound 10-5
Compound 10-5 (46 g, 76%) was obtained in the same manner as in Preparation of Compound 9-5 of Preparation Example 9-1 using Compound 10-4 instead of Compound 9-4.

6) Preparation of Compound 1046
Compound 1046 (7 g, 65%) was obtained in the same manner as in Preparation of Compound 935 of Preparation Example 9-1 using Compound 10-5 instead of Compound 9-5, and using 2-chloro-4-(dibenzo[b,d]furan-1-yl)-6-phenyl-1,3,5-triazine instead of 9-(3-(4-chloro-6-phenyl-1,3,5-triazin-2-yl)phenyl)-9H-carbazole.

Preparation Example 10-2

Target compounds were synthesized in the same manner as in Preparation Example 10-1 using Intermediate a instead of 2-chloro-4-(dibenzo[b,d]furan-1-yl)-6-phenyl-1,3,5-triazine.

TABLE 27

| Compound No. | Intermediate a | Target Compound | Yield |
| --- | --- | --- | --- |
| 1020 | | | 63% |
| 1021 | | | 62% |
| 1034 | | | 61% |
| 1035 | | | 67% |

TABLE 27-continued

| Compound No. | Intermediate a | Target Compound | Yield |
|---|---|---|---|
| 1036 | | | 61% |
| 1039 | | | 62% |
| 1041 | | | 61% |
| 1042 | | | 62% |

TABLE 27-continued

| Compound No. | Intermediate a | Target Compound | Yield |
|---|---|---|---|
| 1044 | | | 60% |
| 1049 | | | 62% |
| 1052 | | | 60% |
| 1053 | | | 65% |

TABLE 27-continued

| Compound No. | Intermediate a | Target Compound | Yield |
| --- | --- | --- | --- |
| 1057 | | | 65% |
| 1058 | | | 60% |
| 1061 | | | 60% |
| 1065 | | | 63% |

TABLE 27-continued

| Compound No. | Intermediate a | Target Compound | Yield |
| --- | --- | --- | --- |
| 1072 | | | 65% |
| 1073 | | | 65% |
| 1078 | | | 61% |
| 1082 | | | 64% |

[Preparation Example 11-1] Preparation of Compound 1084

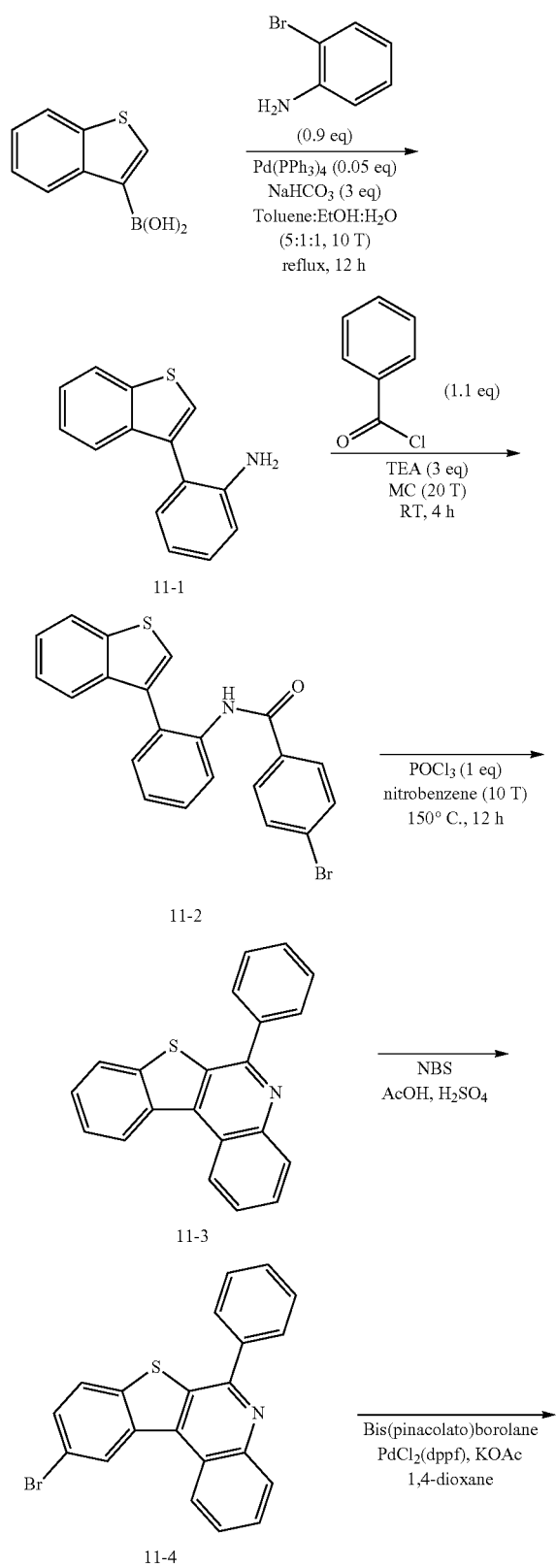

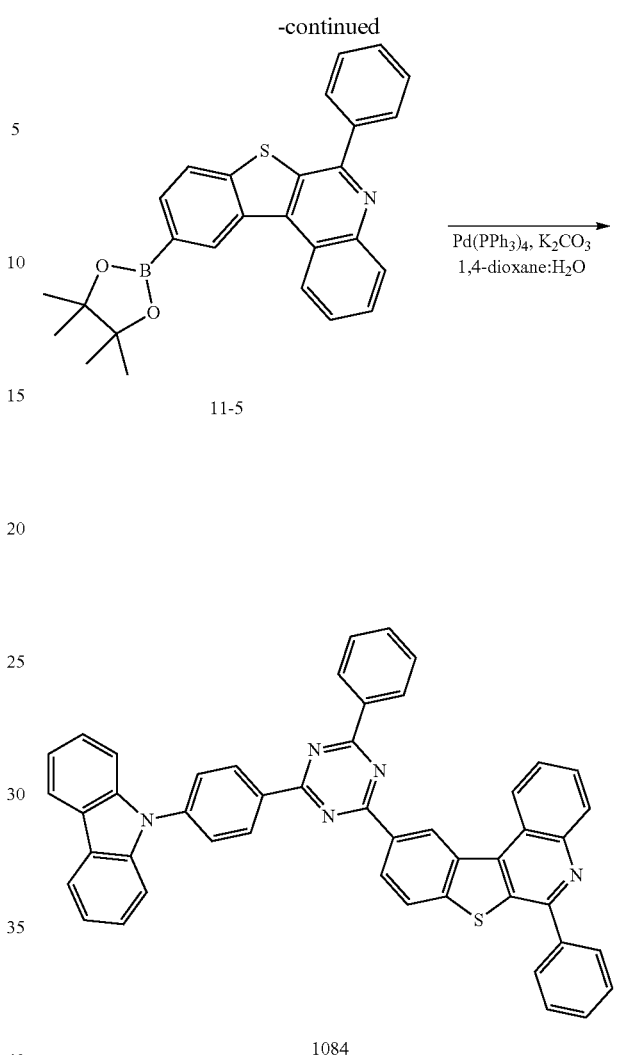

1) Preparation of Compound 11-1

After dissolving benzo[b]thiophen-3-ylboronic acid (100 g, 0.561 mol) and 2-bromoaniline (86.7 g, 0.504 mol) in toluene, EtOH and H₂O (1000 mL:200 mL:200 mL), Pd(PPh₃)₄ (32.4 g, 0.028 mol) and NaHCO₃ (141.3 g, 1.68 mol) were introduced thereto, and the result was stirred for 3 hours at 100° C. After the reaction was completed, the reaction solution was extracted by introducing MC and distilled water thereto. After that, the result was dried with anhydrous MgSO₄, and the solvent was removed using a rotary evaporator to obtain liquid-type Compound 11-1 (93 g, 74%).

2) Preparation of Compound 11-2

Compound 11-1 (93 g, 0.412 mol) and triethylamine (86 mL, 0.618 mol) were introduced to and dissolved in MC (1200 mL). Benzoyl chloride (135.6 g, 0.618 mol) dissolved in MC (300 mL) was slowly added dropwise to the mixture at 0° C. After the reaction was completed, white solids present in the reaction solution were filtered and washed with hexane. The result was dried to obtain solid-type Compound 11-2 (134 g, 83%).

3) Preparation of Compound 11-3

After dissolving Compound 11-2 (134 g, 0.329 mol) in nitrobenzene (1500 mL), POCl₃ (46 mL, 0.495 mol) was slowly added dropwise thereto. The result was reacted for 15 hours at 140° C. After the reaction was completed, a solution obtained by dissolving NaHCO₃ in distilled water was slowly introduced to the reaction solution, and the result was stirred. Solids produced after that were filtered and collected. The collected solids were recrystallized with MC and MeOH to obtain solid-type Compound 11-3 (65 g, 51%).

4) Preparation of Compound 11-4

Compound 11-3 (10 g, 0.0352 mol, 1 eq.), NBS (7.5 g, 0.0423 mol, 1.2 eq.) and AcOH (200 ml, 20 T) were introduced, and stirred for 20 minutes. H₂SO₄ (100 ml, 10 T) was slowly introduced thereto. The result was stirred for 1 hour at room temperature, and water (150 ml) was introduced thereto to terminate the reaction. The result was extracted with MC, silica filtered to remove impurities, and then stirred with MeOH. Produced solids were filtered to obtain Compound 11-4 (10.6 g, 81%).

5) Preparation of Compound 11-5

After dissolving Compound 11-4 (38 g, 0.102 mol), bis(pinacolato)diboron (39 g, 0.153 mol), KOAc (30 g, 0.306 mol) and PdCl₂(dppf) (3.7 g, 0.0051 mol) in 1,4-dioxane (1000 mL), the result was reacted for 5 hours at 90° C. After the reaction was completed, the reaction solution was extracted by introducing MC and distilled water thereto. After that, the result was dried with anhydrous MgSO₄, and the solids were filtered to obtain Compound 11-5 (28 g, 67%).

6) Preparation of Compound 1084

After dissolving Compound 11-5 (6.7 g, 0.016 mol) and 9-(4-(4-chloro-6-phenyl-1,3,5-triazin-2-yl)phenyl)-9H-carbazole (6.8 g, 0.016 mol) in 1,4-dioxane:H₂O (100 mL:20 mL), Pd₂(dba)₃ (1.4 g, 0.0016 mol), XPhos (1.5 g, 0.0032 mol) and K₂CO₃ (6.6 g, 0.048 mol) were introduced thereto, and the result was stirred for 5 hours at 100° C. After the reaction was completed, solids produced in the reaction solution were washed with 1,4-dioxane and H₂O. After that, only the solids were purified using a recrystallization method in DCB to obtain Compound 1084 (7.2 g, 64%).

Preparation Example 11-2

Target compounds were synthesized in the same manner as in Preparation Example 11-1 using Intermediate b instead of 9-(4-(4-chloro-6-phenyl-1,3,5-triazin-2-yl)phenyl)-9H-carbazole.

TABLE 28

| Compound No. | Intermediate b | Target Compound | Yield |
|---|---|---|---|
| 1026 | [structure] | [structure] | 60% |
| 1090 | [structure] | [structure] | 63% |

TABLE 28-continued

| Compound No. | Intermediate b | Target Compound | Yield |
|---|---|---|---|
| 1091 | | | 61% |
| 1093 | | | 66% |
| 1098 | | | 63% |
| 1102 | | | 64% |

TABLE 28-continued

| Compound No. | Intermediate b | Target Compound | Yield |
| --- | --- | --- | --- |
| 1103 | | | 66% |
| 1105 | | | 65% |
| 1109 | | | 63% |
| 1111 | | | 61% |

TABLE 28-continued

| Compound No. | Intermediate b | Target Compound | Yield |
|---|---|---|---|
| 1114 | | | 66% |
| 1119 | | | 63% |
| 1121 | | | 60% |
| 1124 | | | 61% |

[Preparation Example 12-1] Preparation of Compound 1129

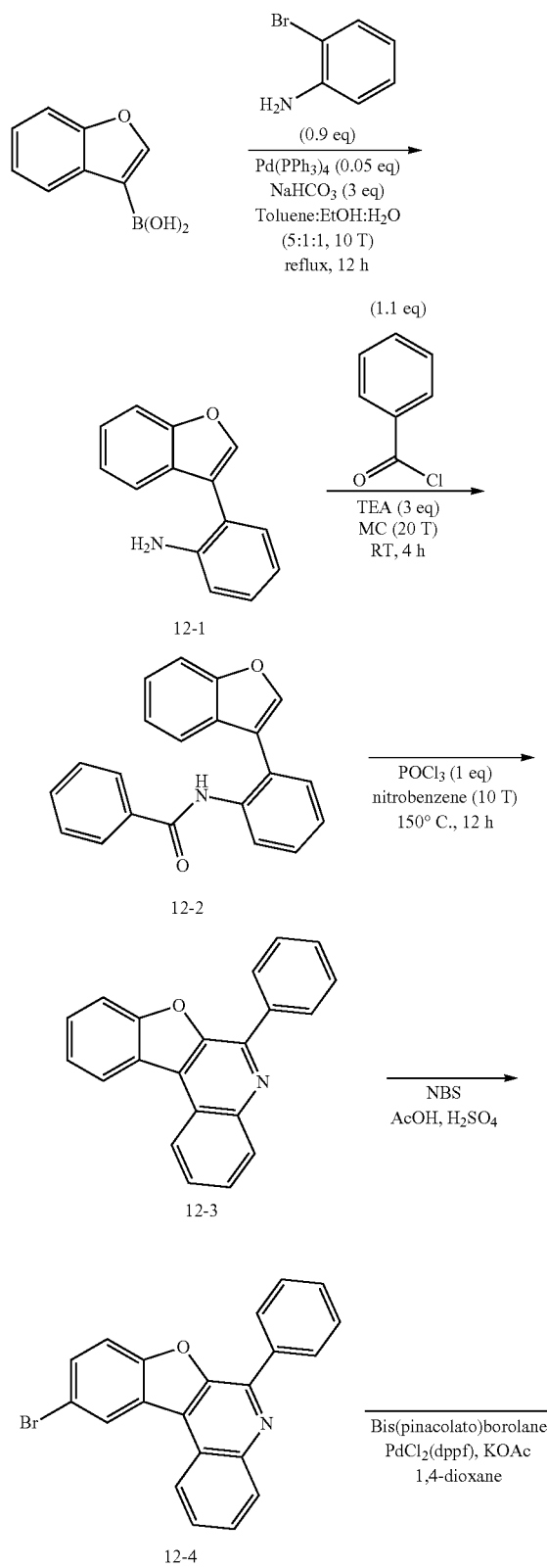

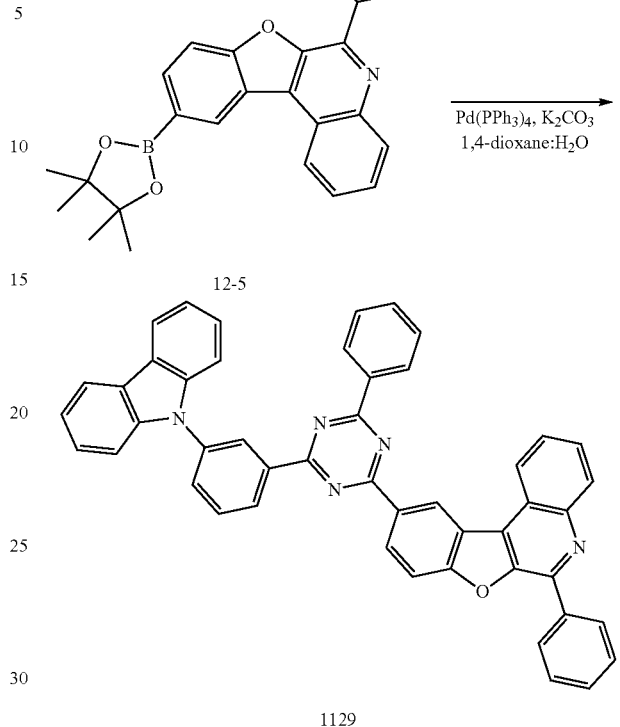

1) Preparation of Compound 12-1

Compound 12-1 (54 g, 91%) was obtained in the same manner as in Preparation of Compound 10-1 of Preparation Example 10-1 using benzofuran-3-ylboronic acid instead of benzofuran-2-ylboronic acid.

2) Preparation of Compound 12-2

Compound 12-2 (50 g, 72%) was obtained in the same manner as in Preparation of Compound 10-2 of Preparation Example 10-1 using Compound 12-1 instead of Compound 10-1.

3) Preparation of Compound 12-3

Compound 12-3 (42 g, 97%) was obtained in the same manner as in Preparation of Compound 10-3 of Preparation Example 10-1 using Compound 12-2 instead of Compound 10-2.

4) Preparation of Compound 12-4

Compound 12-4 (63 g, 80%) was obtained in the same manner as in Preparation of Compound 10-4 of Preparation Example 10-1 using Compound 12-3 instead of Compound 10-3.

5) Preparation of Compound 12-5

Compound 12-5 (46 g, 76%) was obtained in the same manner as in Preparation of Compound 10-5 of Preparation Example 10-1 using Compound 12-4 instead of Compound 10-4.

6) Preparation of Compound 1129

Compound 1129 (7 g, 65%) was obtained in the same manner as in Preparation of Compound 1046 of Preparation Example 10-1 using Compound 12-5 instead of Compound 10-4, and using 9-(3-(4-chloro-6-phenyl-1,3,5-triazin-2-yl)phenyl)-9H-carbazole instead of 2-chloro-4-(dibenzo[b,d]furan-1-yl)-6-phenyl-1,3,5-triazine.

Preparation Example 12-2

Target compounds were synthesized in the same manner as in Preparation Example 10-1 using Intermediate c instead of 9-(3-(4-chloro-6-phenyl-1,3,5-triazin-2-yl)phenyl)-9H-carbazole.

TABLE 29

| Compound No. | Intermediate c | Target Compound | Yield |
|---|---|---|---|
| 1027 | | | 66% |
| 1135 | | | 65% |
| 1138 | | | 63% |

TABLE 29-continued

| Compound No. | Intermediate c | Target Compound | Yield |
|---|---|---|---|
| 1142 | | | 61% |
| 1143 | | | 66% |
| 1146 | | | 65% |
| 1147 | | | 63% |

TABLE 29-continued
| Compound No. | Intermediate c | Target Compound | Yield |
|---|---|---|---|
| 1150 | 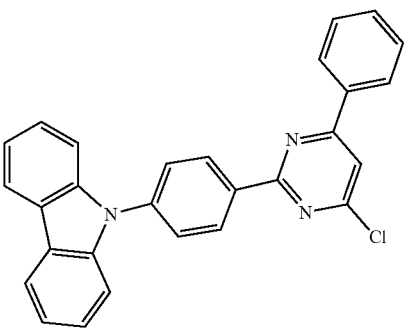 | 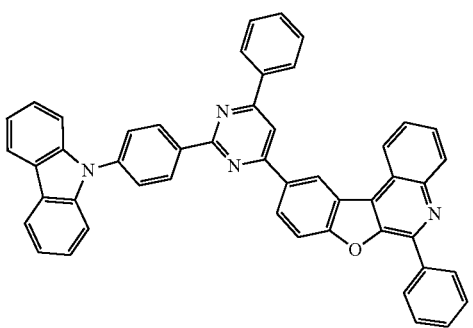 | 61% |
| 1151 | 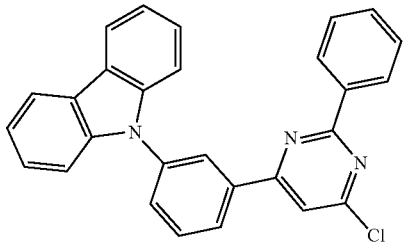 | 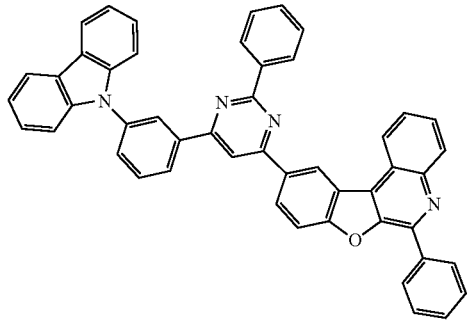 | 66% |
| 1157 | 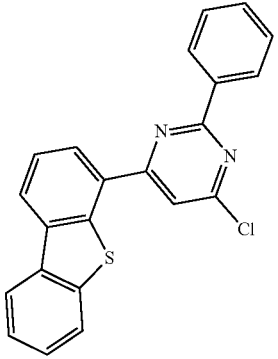 | 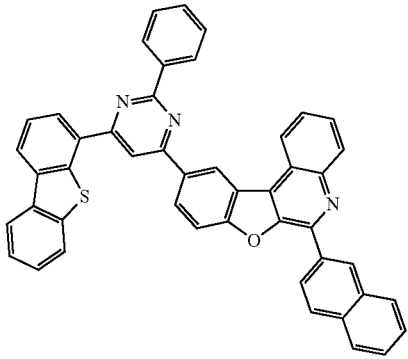 | 65% |
| 1162 | 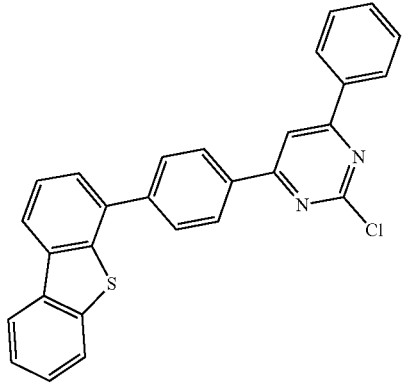 | 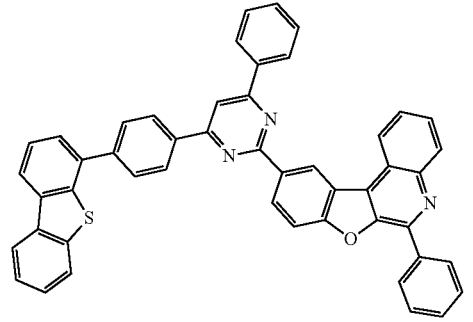 | 63% |

TABLE 29-continued

| Compound No. | Intermediate c | Target Compound | Yield |
|---|---|---|---|
| 1165 | | | 60% |
| 1166 | | | 64% |
| 1169 | | | 64% |

The prepared compounds were identified from Mass and NMR results.

TABLE 30

| Compound | $^1$H NMR (CDCl$_3$, 300 Mz) |
|---|---|
| 1 | δ = 8.69(2H, 2d), 8.55(1H, d), 8.45(1H, d), 8.36(2H, d), 8.20(1H, d), 7.96~85(10H, m), 7.70(1H, t), 7.58~7.49 (7H, m), 7.35(1H, t), 7.20~7.16(2H, m) |
| 11 | δ = 8.55(1H, d), 8.45(1H, d), 8.36~8.33(4H, m), 8.24~8.19(4H, m), 7.96~7.84(6H, m), 7.73~7.49(12H, m), 7.35(1H, t), 7.25~7.16(4H, m) |
| 13 | δ = 8.97(2H, d), 8.68(1H, d), 8.55(1H, d), 8.45(1H, d), 8.36(2H, d), 8.29(1H, d), 8.20(1H, d), 7.94~7.85(8H, m), 7.70(1H, t), 7.59~7.49(9H, m), 7.35(1H, t), 7.20(1H, t), 7.16(1H, t) |
| 16 | δ = 8.55(1H, d), 8.45~8.33(6H, m), 8.20(1H, d), 7.94~7.85(5H, m), 7.73~7.70(3H, m), 7.56~7.49(7H, m) |
| 17 | δ = 8.69(2H, d), 8.55(1H, d), 8.45(2H, d), 8.36(2H, d), 8.20(1H, d), 7.96~7.85(9H, m), 7.70(2H, m), 7.56~7.49(7H, m), 7.25(2H, d) |
| 20 | δ = 8.55(1H, d), 8.45~8.33(6H, m), 8.20(1H, d), 7.96~7.85(7H, m), 7.73~7.70(3H, m), 7.61~7.49(8H, m), 7.25(2H, d) |
| 21 | δ = 8.69(2H, d), 8.45~8.36(5H, m), 8.20(1H, d), 8.03~7.85(9H, m), 7.70~7.49(11H, m) |
| 24 | δ = 9.02(1H, d), 8.95(1H, d), 8.55(1H, d), 8.45~8.36(5H, m), 8.20(1H, d), 7.96~7.85(8H, m), 7.70(2H, t), 7.56~7.46(9H, m), 7.25(2H, d) |

TABLE 30-continued

| Compound | ¹H NMR (CDCl₃, 300 Mz) |
|---|---|
| 29 | δ = 8.69(2H, d), 8.45(1H, d), 8.36(2H, d), 8.20(1H, d), 7.96~7.79(9H, m), 7.70(1H, t), 7.56~7.31(8H, m) |
| 38 | δ = 9.02(1H, d), 8.95(1H, d), 8.45(2H, d), 8.36(2H, d), 8.20(1H, d), 8.08(1H, d), 7.96~7.85(8H, m), 7.70(1H, t), 7.54~7.25(13H, m) |
| 40 | δ = 8.69(2H, d), 8.45~8.36(4H, m), 8.20(1H, d), 8.08(1H, d), 7.94~7.85(8H, m), 7.73~7.70(2H, m), 7.56~7.49(8H, m), 7.39~7.31(2H, m) |
| 42 | δ = 9.60(1H, d), 9.27(1H, s), 8.69(2H, d), 8.45(1H, d), 8.36~8.30(4H, m), 8.20~8.15(2H, m), 7.96~7.85(5H, m), 7.70~7.49(12H, m) |
| 44 | δ = 9.60(1H, d), 9.27(1H, s), 8.97(2H, d), 8.68(1H, d), 8.45(1H, d), 8.36~8.29(5H, m), 8.20~8.15(2H, m), 7.94~7.85(3H, m), 7.70~7.49(14H, m) |
| 50 | δ = 9.09(1H, s), 8.69(2H, d), 8.49~8.45(2H, m), 8.20~8.16(2H, m), 8.08~7.85(9H, m), 7.70~7.49(8H, m), 7.38(1H, t), 7.28(1H, t), 1.69(6H, s) |
| 52 | δ = 8.69(2H, d), 8.45(1H, d), 8.36(2H, d), 8.20(1H, d), 8.09(1H, d), 7.96~7.70(11H, m), 7.56~7.49(6H, m), 7.38(1H, t), 7.28~7.25(3H, m), 1.69(6H, s) |
| 55 | δ = 8.69(2H, d), 8.52~8.45(2H, d), 8.36~8.31(3H, m), 8.20~7.85(12H, m), 7.70(2H, m), 7.56~7.49(5H, m) |
| 60 | δ = 9.08(1H, d), 8.84(1H, d), 8.69(2H, d), 8.45(1H, d), 8.36(2H, d), 8.20(1H, d), 8.17(1H, d), 8.05(1H, s), 7.96~7.85(6H, m), 7.70~7.49(10H, m) |
| 62 | δ = 9.08(1H, d), 8.84(1H, d), 8.69(2H, d), 8.45(2H, d), 8.36(2H, d), 8.27(1H, d), 8.20(1H, d), 8.05(1H, s), 7.96~7.85(8H, m), 7.70~7.49(10H, m), 7.25(2H, d) |
| 65 | δ = 9.11(1H, d), 8.70(1H, d), 8.45~8.36(9H, m), 8.20(1H, d), 7.94~7.85(6H, m), 7.70~7.49(12H, m) |
| 71 | δ = 8.69(2H, d), 8.55(1H, d), 8.45(1H, d), 8.36(2H, d), 8.24~8.19(4H, m), 7.96~7.85(6H, m), 7.70~7.49(10H, m), 7.35(1H, t), 7.16(1H, t) |
| 72 | δ = 9.09(1H, s), 8.69(2H, d), 8.55~8.45(3H, m), 8.24~7.85(13H, m), 7.70~7.49(9H, m), 7.35(1H, t), 7.20~7.16(2H, m) |
| 75 | δ = 9.02(1H, d), 8.95(1H, d), 8.55(1H, d), 8.45(2H, d), 8.36(2H, m), 8.24~8.19(4H, m), 7.96~7.84(7H, m), 7.70~7.46(12H, m), 7.35(1H, t), 7.25~7.16(4H, m) |
| 78 | δ = 8.69(2H, d), 8.55(1H, d), 8.45~8.38(3H, m), 8.20(1H, d), 7.96~7.85(8H, m), 7.75~7.70(5H, m), 7.61~7.41(8H, m) |
| 80 | δ = 8.97(1H, d), 8.69(2H, d), 8.45(2H, d), 8.25~8.10(5H, m), 8.00~7.85(9H, m), 7.77(1H, t), 7.59~7.49(6H, m) |
| 82 | δ = 8.55(1H, d), 8.45~8.33(6H, m), 8.20(1H, d), 7.96~7.85(7H, m), 7.73~7.70(3H, m), 7.61~7.49(8H, m), 7.25(2H, d) |
| 84 | δ = 8.97(2H, d), 8.68(1H, d), 8.55(1H, d), 8.45~8.29(5H, m), 8.20(1H, d), 7.94~7.85(5H, m), 7.70(2H, m), 7.59~7.49(9H, m) |
| 87 | δ = 8.69(2H, d), 8.45(1H, d), 8.36(2H, d), 8.20(1H, d), 8.03~7.76(10H, m), 7.56~7.31(8H, m) |
| 93 | δ = 8.45~8.33(6H, m), 8.20(1H, d), 8.08~7.85(8H, m), 7.73~7.70(2H, m), 7.54~7.46(7H, m), 7.39~7.25(4H, m) |
| 98 | δ = 9.02(1H, d), 8.95(1H, d), 8.69(2H, d), 8.45(1H, d), 8.36(2H, d), 8.20(1H, d), 8.08~8.06(2H, d), 7.98~7.84(6H, m), 7.70(1H, t), 7.51~7.25(13H, m) |
| 100 | δ = 8.45~8.33(6H, m), 8.20(1H, d), 8.08(1H, d), 7.98~7.85(6H, m), 7.73~7.49(12H, m), 7.39~7.31(2H, m) |
| 106 | δ = 9.60(1H, d), 9.27(1H, s), 9.09(1H, s), 8.69(2H, d), 8.49(1H, d), 8.45(1H, d), 8.33~8.30(2H, m), 8.20~7.85(10H, m), 7.70~7.49(11H, m) |
| 114 | δ = 9.02(1H, d), 8.95(1H, d), 8.45(2H, d), 8.36(2H, d), 8.20(1H, d), 8.09(1H, d), 7.94~7.89(10H, m), 7.56~7.38(9H, m), 7.28~7.25(3H, m), 1.69(6H, s) |
| 116 | δ = 8.69(2H, d), 8.45~8.36(4H, m), 8.20(1H, d), 8.00~7.85(8H, m), 7.73~7.49(11H, m), 7.38(1H, t), 7.28(1H, t), 1.69(6H, s) |
| 122 | δ = 9.11(1H, d), 8.70~8.69(3H, m), 8.46~8.36(6H, m), 8.20(1H, d), 7.96~7.85(8H, m), 7.75~7.49(11H, m) |
| 125 | δ = 9.09(1H, s), 9.09(1H, d), 8.84(1H, d), 8.69(2H, d), 8.49~8.45(2H, m), 8.27~7.85(14H, m), 7.70~7.49(9H, m), 7.25(2H, d) |
| 127 | δ = 8.69(2H, d), 8.55(1H, d), 8.45(1H, d), 8.36(2H, d), 8.19(1H, d), 7.96~7.88(10H, m), 7.58~7.49(9H, m), 7.35(1H, t), 7.20~7.16(2H, m) |
| 130 | δ = 9.09(1H, s), 8.69(2H, d), 8.55~8.45(3H, m), 8.24~7.88(12H, m), 7.68~7.49(10H, m), 7.35(1H, t), 7.20~7.16(2H, m) |
| 135 | δ = 9.02(1H, d), 8.95(1H, d), 8.55(1H, d), 8.45(2H, d), 8.36(2H, d), 8.19(1H, d), 7.97~7.88(11H, m), 7.58~7.49(11H, m), 7.35(1H, t), 7.25~7.16(4H, m) |
| 137 | δ = 8.45~8.33(7H, m), 8.12(1H, s), 7.99~7.88(6H, m), 7.73(1H, t), 7.56~7.49(9H, m) |
| 140 | δ = 8.69(2H, d), 8.55(1H, d), 8.45(2H, d), 8.36(2H, d), 7.96~7.85(9H, m), 7.70(1H, t), 7.46~7.49(9H, m), 7.25(2H, d) |
| 141 | δ = 8.55(1H, d), 8.45(2H, d), 8.36~8.33(4H, m), 7.96~7.88(7H, m), 7.73~7.70(2H, m), 7.56~7.49(10H, m), 7.25(2H, d) |
| 144 | δ = 8.97(2H, d), 8.68(1H, d), 8.55(1H, d), 8.45~8.29(5H, m), 7.97~7.88(5H, m), 7.70(1H, t), 7.59~7.49(11H, m) |

TABLE 30-continued

| Compound | ¹H NMR (CDCl₃, 300 Mz) |
|---|---|
| 146 | δ = 9.02(1H, d), 8.95(1H, d), 8.55(1H, d), 8.45~8.32(8H, m), 8.06(1H, d), 7.93~7.84(5H, m), 7.73~7.70(2H, m), 7.56~7.46(11H, m) |
| 150 | δ = 8.97(1H, d), 8.69(2H, d), 8.45(1H, d), 8.25(1H, t), 8.15~8.10(2H, m), 8.00~7.82(8H, m), 7.69(1H, d), 7.57~7.31(10H, m) |
| 152 | δ = 8.69(2H, d), 8.45(1H, d), 8.36(2H, d), 7.98~7.82(9H, m), 7.69(1H, t), 7.57~7.49(9H, m), 7.39~7.25(4H, m) |
| 155 | δ = 8.97(2H, d), 8.68(1H, d), 8.45(1H, d), 8.36~8.29(3H, 22), 8.08(1H, d), 7.97~7.88(5H, m), 7.59~7.31(13H, m) |
| 165 | δ = 9.60(1H, d), 9.27(1H, s), 8.45(1H, d), 8.36~8.30(6H, m), 8.15(1H, d), 7.96~7.88(5H, m), 7.73~7.49(15H, m), 7.25(2H, d) |
| 166 | δ = 8.69(2H, d), 8.45(1H, d), 8.36(2H, d), 8.09(1H, d), 7.96~7.89(7H, m), 7.78(1H, d), 7.55~7.49(8H, m), 7.38(1H, t), 7.28(1H, t), 1.69(6H, s) |
| 169 | δ = 8.85(1H, d), 8.45~8.33(8H, m), 8.08(1H, d), 7.97~7.88(5H, m), 7.78~7.73(4H, m), 7.61~7.40(9H, m), 7.29(1H, t), 7.09(1H, d), 1.75(6H, s) |
| 179 | δ = 8.52~8.31(8H, m), 8.15~7.88(10H, m), 7.73~7.70(3H, m), 7.61~7.49(9H, m) |
| 190 | δ = 9.09(1H, s), 8.69(2H, d), 8.55~8.49(2H, d), 8.19~8.16(2H, m), 8.08~7.91(13H, m), 7.61~7.35(9H, m), 7.20~7.16(2H, m) |
| 196 | δ = 8.55(1H, d), 8.36~8.35(3H, m), 8.19(1H, d), 8.05(1H, d), 7.96~7.88(11H, m), 7.60~7.35(12H, m), 7.25~7.16(4H, m) |
| 198 | δ = 8.55(1H, d), 8.45~8.33(6H, m), 8.05(1H, d), 7.97~7.88(5H, m), 7.73~7.70(2H, m), 7.56~7.42(9H, m) |
| 199 | δ = 9.09(1H, s), 8.69(2H, d), 8.55~8.45(3H, m), 8.16~7.88(11H, m), 7.70~7.42(9H, m) |
| 203 | δ = 8.45(1H, d), 8.36~8.33(4H, m), 8.24~8.20(2H, d), 8.05~7.88(8H, m), 7.73(1H, t), 7.61~7.42(10H, m), 7.25(2H, d) |
| 209 | δ = 9.02(1H, d), 8.95(1H, d), 8.55(1H, d), 8.45~8.32(7H, m), 8.05(2H, d), 7.97~7.84(5H, m), 7.73~7.70(2H, m), 7.56~7.42(11H, m) |
| 219 | δ = 8.97(2H, d), 8.68(1H, d), 8.36~8.29(3H, m), 8.08~7.88(7H, m), 7.59~7.31(13H, m) |
| 220 | δ = 8.69(2H, d), 8.36(2H, d), 8.05~7.88(11H, m), 7.55~7.25(13H, m) |
| 226 | δ = 9.07(1H, s), 8.50(1H, d), 8.36~8.33(5H, m), 8.14(1H, d), 8.05~7.82(7H, m), 7.73~7.69(2H, m), 7.57~7.31(13H, m) |
| 231 | δ = 8.69(2H, d), 8.36(2H, d), 8.05(1H, d), 7.96~7.88(6H, m), 7.78(1H, d), 7.65(1H, d), 7.55~7.38(10H, m), 7.28(1H, t), 1.69(6H, s) |
| 234 | δ = 8.69(2H, d), 8.38(1H, d), 8.09~8.05(2H, d), 7.97~7.88(8H, m), 7.78~7.73(4H, m), 7.61~7.38(10H, m), 7.28(1H, t), 1.69(6H, s) |
| 242 | δ = 8.69(2H, d), 8.52(1H, d), 8.36~8.31(3H, m), 8.15~7.88(14H, m), 7.70(1H, d), 7.55~7.42(7H, m), 7.25(2H, d) |
| 247 | δ = 8.98(1H, d), 8.41~8.23(8H, m), 8.08~7.88(8H, m), 7.75~7.42(11H, m), 7.25(2H, d) |
| 254 | δ = 8.55(1H, d), 8.45(1H, d), 8.35~8.19(10H, m), 7.93~7.49(19H, m), 7.35(1H, t), 7.20~7.16(2H, m) |
| 259 | δ = 8.55(1H, d), 8.45(2H, d), 8.35~8.33(4H, m), 8.23(1H, s), 8.20(1H, d), 7.94~7.85(6H, m), 7.73~7.70(3H, m), 7.56~7.49(7H, m) |
| 264 | δ = 8.69(2H, d), 8.55(1H, d), 8.45(2H, d), 8.32~8.30(3H, m), 8.23~8.20(2H, d), 7.96~7.85(8H, m), 7.70(2H, t), 7.56~7.49(7H, m), 7.25(2H, d) |
| 265 | δ = 8.97(2H, d), 8.68(1H, d), 8.55(1H, d), 8.45(2H, d), 8.29~8.20(3H, m), 7.94~7.85(7H, m), 7.70(2H, t), 7.59~7.49(9H, m) |
| 266 | δ = 9.02(1H, d), 8.95(1H, d), 8.69(2H, d), 8.55(1H, d), 8.45(2H, d), 8.35~8.30(5H, m), 8.23~8.20(2H, m), 8.06(1H, d), 7.94~7.85(5H, m), 7.70(2H, t), 7.56~7.46(9H, m) |
| 270 | δ = 8.69(2H, d), 8.45(2H, d), 8.23(1H, s), 8.20(1H, d), 8.08~7.85(11H, m), 7.70~7.49(8H, m), 7.39~7.31(2H, m) |
| 275 | δ = 8.45(1H, d), 8.33(2H, d), 8.23(1H, s), 8.20(1H, d), 8.08~7.85(11H, m), 7.73~7.70(2H, m), 7.56~7.49(7H, m), 7.39~7.25(4H, m) |
| 282 | δ = 9.60(1H, d), 9.27(1H, s), 8.97(2H, d), 8.68(1H, d), 8.45(1H, d), 8.35~8.20(8H, m), 7.94~7.85(3H, m), 7.70~7.49(14H, m) |
| 283 | δ = 8.69(2H, d), 8.45(1H, d), 8.35~8.30(4H, m), 8.23~8.18(3H, m), 7.94~7.85(4H, m), 7.74~7.68(3H, m), 7.56~7.49(6H, m), 7.38(1H, t), 7.28(1H, t), 1.69(6H, s) |
| 285 | δ = 8.69(2H, d), 8.45(1H, d), 8.23(1H, s), 8.20(1H, d), 8.09(1H, d), 7.96~7.70(11H, m), 7.56~7.49(6H, m), 7.38(1H, t), 7.28(1H, t), 1.69(6H, s) |
| 288 | δ = 8.97(2H, d), 8.68(1H, d), 8.45(1H, d), 8.29(1H, d), 8.23(1H, s), 8.20(1H, d), 8.09(1H, d), 7.94~7.70(9H, m), 7.59~7.49(8H, m), 8.38(1H, t), 8.28(1H, t), 1.69(6H, s) |
| 290 | δ = 8.69(2H, d), 8.45(1H, d), 8.35~8.30(4H, m), 8.23(1H, s), 8.20(1H, d), 8.09(1H, d), 7.94~7.70(10H, m), 7.61~7.49(7H, m), 7.38(1H, t), 7.28(1H, t), 1.69(6H, s) |
| 296 | δ = 9.08(1H, d), 8.84(1H, d), 8.69(2H, d), 8.45(1H, d), 8.23(1H, s), 8.20~8.17(2H, m), 8.05(1H, s), 7.96~7.85(8H, m), 7.70~7.49(10H, m) |
| 297 | δ = 9.11(1H, d), 8.70(1H, d), 8.46~8.33(4H, m), 8.23~8.20(3H, m), 7.94~7.85(7H, m), 7.75~7.49(10H, m) |

TABLE 30-continued

| Compound | ¹H NMR (CDCl₃, 300 Mz) |
|---|---|
| 299 | δ = 9.08(1H, d), 8.84(1H, d), 8.69(2H, d), 8.45(1H, d), 8.30~8.20(5H, m), 8.05(1H, s), 7.96~7.85(8H, m), 7.75~7.41(14H, m), 7.25(2H, d) |
| 303 | δ = 8.69(2H, d), 8.55(1H, d), 8.46(2H, d), 8.30~8.19(7H, m), 8.06~7.85(8H, m), 7.70~7.49(9H, m), 7.35(1H, t), 7.20~7.16(2H, m) |
| 305 | δ = 9.02(1H, d), 8.95(1H, d), 8.55(1H, d), 8.45(2H, d), 8.35~8.19(8H, m), 7.94~7.80(6H, m), 7.70~7.46(12H, m), 7.35(1H, t), 7.25~7.16(4H, m) |
| 307 | δ = 8.97(2H, d), 8.68(1H, d), 8.55(1H, d), 8.45(1H, d), 8.29~8.19(6H, m), 7.95~7.85(6H, m), 7.70~7.49(12H, m), 7.35(1H, t), 7.20~7.16(2H, m) |
| 310 | δ = 8.69(2H, d), 8.55(1H, d), 8.45(2H, d), 8.30(2H, d), 8.23(1H, s), 8.20(1H, d), 7.94~7.85(7H, m), 7.70(2H, m), 7.56~7.49(7H, m) |
| 315 | δ = 8.55(1H, d), 8.45(2H, d), 8.33~8.30(4H, m), 8.23(1H, s), 8.20(1H, d), 7.94~7.85(9H, m), 7.73~7.70(3H, m), 7.61~7.49(8H, m) |
| 316 | δ = 8.69(2H, d), 8.45(2H, d), 8.35~8.30(4H, m), 8.23(1H, s), 8.20(1H, d), 8.12(2H, d), 7.99~7.85(7H, m), 7.73~7.70(2H, m), 7.61~7.49(8H, m) |
| 318 | δ = 8.69(2H, d), 8.55(1H, d), 8.45(2H, d), 8.32~8.30(3H, m), 8.23(1H, s), 8.20(1H, d), 7.96~7.70(12H, m), 7.60~7.41(9H, m), 7.25(2H, d) |
| 324 | δ = 8.69(2H, d), 8.45(1H, d), 8.30(2H, d), 8.23(1H, s), 8.20(1H, d), 8.08(1H, d), 7.98~7.85(11H, m), 7.70(1H, t), 7.54~7.31(9H, m) |
| 326 | δ = 8.69(2H, d), 8.45(1H, d), 8.30(2H, d), 8.23(1H, s), 8.20(1H, d), 7.98~7.85(9H, m), 7.70~7.69(2H, m), 7.57~7.25(11H, m) |
| 330 | δ = 9.02(1H, d), 8.95(1H, d), 8.45(2H, m), 8.35(2H, d), 8.23(1H, s), 8.20(1H, d), 8.08(1H, d), 7.98~7.84(7H, m), 7.74~7.70(3H, m), 7.61~7.31(12H, m) |
| 331 | δ = 8.45(1H, d), 8.35~8.33(4H, m), 8.23(1H, s), 8.20(1H, d), 8.08(1H, d), 7.98~7.85(6H, m), 7.74~7.49(13H, m), 7.39~7.31(2H, m) |
| 332 | δ = 9.60(1H, d), 9.27(1H, s), 8.69(2H, d), 8.45(1H, d), 8.35~8.15(9H, m), 7.94~7.85(3H, m), 7.70~7.49(12H, m) |
| 336 | δ = 9.60(1H, d), 8.27(1H, s), 8.45(1H, d), 8.33~8.30(4H, m), 8.23(1H, s), 8.20~8.15(2H, m), 7.94~7.85(6H, m), 7.73~7.49(13H, m) |
| 341 | δ = 8.69(2H, d), 8.45(1H, d), 8.35~8.30(5H, m), 8.23(1H, s), 8.22~8.20(2H, m), 8.10~8.06(2H, m), 7.94~7.46(12H, m), 7.34(1H, d) |
| 348 | δ = 8.69(2H, d), 8.45(1H, d), 8.23(1H, s), 8.20(1H, d), 8.09(1H, d), 7.96~7.70(14H, m), 7.61~7.49(7H, m), 7.38(1H, t), 7.28(1H, t), 1.69(6H, s) |
| 350 | δ = 8.69(2H, d), 8.52~8.45(2H, m), 8.35~8.08(12H, m), 7.94~7.85(4H, m), 7.70(2H, m), 7.56~7.49(5H, m) |
| 359 | δ = 9.11(1H, d), 8.70~8.69(3H, m), 8.46~8.43(3H, m), 8.23(1H, s), 8.20(1H, d), 7.96~7.41(26H, m) |
| 362 | δ = 8.69(2H, d), 8.55(1H, d), 8.45(1H, d), 8.23(1H, s), 8.19(1H, d), 7.97~7.88(12H, m), 7.58~7.49(9H, m), 7.35(1H, t), 7.20~7.16(1H, m) |
| 363 | δ = 8.55(1H, d), 8.45(1H, d), 8.35~8.33(4H, m), 8.23(1H, s), 8.19(1H, d), 7.94~7.88(9H, m), 7.73(1H, t), 7.58~7.49(9H, m), 7.35(1H, t), 8.20~7.16(2H, m) |
| 364 | δ = 8.69(2H, d), 8.55(1H, d), 8.46(2H, d), 8.30~8.19(6H, m), 8.06~7.88(8H, m), 7.68~7.49(10H, m), 7.35(1H, t), 7.20~7.16(2H, m) |
| 366 | δ = 8.97(2H, d), 8.68(1H, d), 8.55(1H, d), 8.45(1H, d), 8.29~8.19(5H, m), 7.94~7.88(6H, m), 7.68~7.49(13H, m), 7.35(1H, t), 7.20~7.16(2H, m) |
| 370 | δ = 8.55(1H, d), 8.45(2H, d), 8.35~8.33(4H, m), 8.23(1H, s), 7.94~7.88(6H, m), 7.73~7.70(2H, m), 7.56~7.49(9H, m) |
| 371 | δ = 8.97(2H, d), 8.68(1H, d), 8.55(1H, d), 8.45(1H, d), 8.29(1H, d), 8.23(1H, s), 7.97~7.88(7H, m), 7.70(1H, t), 7.59~7.49(11H, m) |
| 373 | δ = 8.69(2H, d), 8.55(1H, d), 8.45(2H, d), 8.35~8.23(8H, m), 7.97~7.88(4H, m), 7.70(1H, t), 7.58~7.49(9H, m), 7.25(2H, d) |
| 375 | δ = 9.02(1H, d), 8.95(1H, d), 8.45~8.33(5H, m), 8.24~8.17(4H, m), 8.06(1H, d), 7.94~7.84(7H, m), 7.73(1H, t), 7.56~7.46(11H, m) |
| 382 | δ = 8.69(2H, d), 8.45(1H, d), 8.30(2H, d), 8.23(1H, s), 8.08~7.88(10H, m), 7.56~7.25(13H, m) |
| 385 | δ = 9.02(1H, d), 8.95(1H, d), 8.69(2H, d), 8.45(1H, d), 8.23(1H, s), 8.08~7.88(12H, m), 7.55~7.31(13H, m) |
| 386 | δ = 8.97(2H, d), 8.68(1H, d), 8.45(1H, d), 8.29(1H, d), 8.23(1H, s), 8.03~7.76(9H, m), 7.59~7.31(12H, m) |
| 391 | δ = 9.60(1H, d), 9.27(1H, s), 8.69(2H, d), 8.45(1H, d), 8.33~8.23(5H, m), 8.15(1H, d), 7.97~7.88(5H, m), 7.70~7.49(13H, m) |
| 393 | δ = 9.60(1H, d), 9.27(1H, s), 8.45(1H, d), 8.35~8.33(6H, m), 8.23(1H, s), 8.15(1H, d), 7.94~7.88(4H, m), 7.73~7.49(14H, m) |
| 396 | δ = 8.69(2H, d), 8.45(1H, d), 8.30(2H, d), 8.23(1H, s), 8.09(1H, d), 7.97~7.88(7H, m), 7.78(1H, t), 7.56~7.49(8H, m), 7.38(1H, t), 7.28(1H, t), 1.69(6H, s) |
| 408 | δ = 8.97(2H, d), 8.68(1H, d), 8.52(1H, d), 8.45(1H, d), 8.31~8.23(3H, m), 8.15~7.88(11H, m), 7.70(1H, d), 7.59~7.49(9H, m) |
| 416 | δ = 8.97(2H, d), 8.68(1H, d), 8.55(1H, d), 8.29~8.19(5H, m), 8.05~7.88(7H, m), 7.68~7.35(14H, m), 7.20~7.16(2H, m) |
| 419 | δ = 8.69(2H, d), 8.55(1H, d), 8.45(1H, d), 8.35~8.30(4H, m), 8.05(1H, d), 7.97~7.88(5H, m), 7.70(1H, t), 7.56~7.42(9H, m) |
| 422 | δ = 8.45(1H, d), 8.33(2H, s), 8.23(1H, s), 8.05~7.88(10H, m), 7.73~7.68(2H, m), 7.56~7.42(9H, m) |
| 424 | δ = 8.55(1H, d), 8.45(1H, d), 8.33~8.30(4H, m), 8.23(1H, s), 8.05~7.85(10H, m), 7.73~7.70(2H, m), 7.61~7.42(10H, m) |

TABLE 30-continued

| Compound | ¹H NMR (CDCl₃, 300 Mz) |
|---|---|
| 431 | δ = 8.69(2H, d), 8.30(2H, d), 8.23(1H, s), 8.08~7.88(9H, m), 7.55~7.31(11H, m) |
| 432 | δ = 8.69(2H, d), 8.35~8.23(5H, m), 8.05~7.82(6H, m), 7.69(1H, d), 7.57~7.42(11H, m) |
| 441 | δ = 8.95(1H, d), 8.69(2H, d), 8.23(1H, s), 8.20(1H, d), 8.12(1H, s), 8.05~7.71(13H, m), 7.55~7.31(12H, m) |
| 443 | δ = 8.97(2H, d), 8.68(1H, d), 8.35~8.23(4H, m), 8.05~7.82(6H, m), 7.69(1H, d), 7.59~7.31(13H, m) |
| 445 | δ = 9.60(1H, d), 9.27(1H, s), 8.69(2H, d), 8.33~8.23(5H, m), 8.15(1H, d), 8.05~7.88(6H, m), 7.70~7.42(13H, m) |
| 450 | δ = 8.93(1H, d), 8.69(2H, d), 8.35~8.23(6H, m), 8.05~7.88(6H, m), 7.74(1H, d), 7.57~7.38(11H, m), 1.75(6H, s) |
| 452 | δ = 8.69(2H, d), 8.30(2H, d), 8.23(1H, s), 8.09~8.05(2H, m), 7.97~7.88(7H, m), 7.78~7.73(4H, m), 7.61~7.38(10H, m), 7.28(1H, t), 1.69(6H, s) |
| 456 | δ = 8.97(2H, d), 8.68(1H, d), 8.52(1H, d), 8.31~8.23(3H, m), 8.08~7.88(12H, m), 7.70(1H, d), 7.59~7.42(9H, m) |
| 460 | δ = 9.08(1H, d), 9.02(1H, d), 8.95(1H, d), 8.84~8.79(2H, m), 8.69(2H, d), 8.23(1H, s), 8.06~7.88(12H, m), 7.70~7.42(13H, m) |
| 462 | δ = 8.69(6H, m), 8.55(1H, d), 8.45(2H, d), 8.32(1H, d), 8.20(3H, m), 7.94~7.85(4H, m), 7.75~7.70(4H, m), 7.56~7.41(7H, m), 7.25(2H, d) |
| 465 | δ = 8.69(2H, d), 8.45(1H, d), 8.29~8.28(3H, m), 8.20~8.17(4H, m), 8.09(1H, d), 7.94~7.85(6H, m), 7.70(1H, t), 7.56~7.49(6H, m), 7.38(1H, t), 7.28(1H, t), 1.69(6H, s) |
| 467 | δ = 8.69(2H, d), 8.55(1H, d), 8.45(1H, d), 8.30~8.19(8H, m), 7.94~7.85(8H, m), 7.70(1H, t), 7.58~7.49(7H, m), 7.35(1H, t), 7.20~7.16(2H, m) |
| 471 | δ = 9.11(1H, d), 8.97(2H, d), 8.70~8.68(3H, m), 8.46~8.43(3H+21 m), 8.29~8.20(5H, m), 7.94~7.85(6H, m), 7.73~7.49(14H, m) |
| 476 | δ = 8.69(4H, d), 8.29(2H, d), 8.20(2H, s), 8.08~7.88(7H, m), 7.55~7.31(11H, m) |
| 479 | δ = 8.97(1H, d), 8.69(2H, d), 8.55(1H, d), 8.25~8.10(5H, m), 8.00~7.85(10H, m), 7.70(1H, t), 7.59~7.50(5H, m), 7.39~7.31(3H, m), 7.20~7.16(2H, m) |
| 480 | δ = 8.69(2H, d), 8.55(1H, d), 8.19(1H, d), 7.96~7.85(14H, m), 7.70(1H, t), 7.60~7.31(11H, m), 7.20~7.16(2H, m) |
| 486 | δ = 8.69(2H, d), 8.55(1H, d), 8.38~8.36(3H, m), 8.24~8.19(4H, m), 7.98~7.85(7H, m), 7.73~7.50(11H, m), 7.39~7.31(3H, m), 7.20~7.16(2H, m) |
| 488 | δ = 8.55(1H, d), 8.38~8.33(5H, m), 8.20(1H, d), 7.94~7.85(9H, m), 7.73~7.70(3H, m), 7.61~7.50(8H, m), 7.39~7.31(3H, m), 7.20~7.16(2H, m) |
| 493 | δ = 9.02(1H, d), 8.95(1H, d), 8.69(2H, d), 8.55(1H, d), 8.45(1H, d), 8.36(2H, d), 8.20(1H, d), 8.06(1H, d), 7.98~7.84(6H, m), 7.70(2H, m), 7.56~7.25(12H, m) |
| 498 | δ = 8.69(2H, d), 8.55(1H, d), 8.45(1H, d), 8.36~8.32(3H, m), 8.20(1H, d), 7.96~7.85(8H, m), 7.70(2H, t), 7.56~7.49(6H, m), 7.39~7.25(4H, m) |
| 499 | δ = 8.97(2H, d), 8.68(1H, d), 8.55(1H, d), 8.45(1H, d), 8.36~8.29(3H, m), 8.20(1H, d), 7.98~7.85(5H, m), 7.70(2H, t), 7.56~7.31(10H, m) |
| 502 | δ = 8.69(2H, d), 8.36(2H, d), 8.20(1H, d), 8.08(1H, d), 7.98~7.85(7H, m), 7.70(1H, t), 7.54~7.50(6H, m), 7.39~7.31(4H, m) |
| 506 | δ = 8.97(2H, d), 8.68(1H, d), 8.36~8.29(3H, m), 8.20(1H, d), 7.98~7.82(5H, m), 7.70~7.69(2H, m), 7.59~7.50(8H, m), 7.39~7.31(4H, m) |
| 508 | δ = 8.69(2H, d), 8.36(2H, d), 8.20(1H, d), 8.08~7.94(9H, m), 7.85(1H, t), 7.70(1H, t), 7.54~7.70(6H, m), 7.39~7.25(6H, m) |
| 511 | δ = 9.02(1H, d), 8.95(1H, d), 8.69(2H, d), 8.36(2H, d), 8.20(1H, d), 8.08~7.94(8H, m), 7.84(2H, m), 7.70(1H, t), 7.54~7.31(12H, m) |
| 517 | δ = 8.36~8.33(4H, m), 8.20(1H, d), 8.08(1H, d), 7.98~7.85(7H, m), 7.73~7.70(2H, m), 7.61~7.50(7H, m), 7.39~7.25(6H, m) |
| 519 | δ = 9.60(1H, d), 9.27(1H, s), 8.36~8.30(7H, m), 8.20~8.15(2H, d), 7.98~7.94(2H, m), 7.85(1H, t), 7.73~7.64(6H, m), 7.54~7.50(6H, m), 7.39~7.31(2H, m) |
| 524 | δ = 8.36~8.33(5H, m), 8.20(1H, d), 8.09(1H, d), 7.98~7.70(8H, m), 7.55~7.50(5H, m), 7.39~7.28(4H, m), 1.69 (6H, s) |
| 527 | δ = 9.02(1H, d), 8.95(1H, d), 8.45(1H, d), 8.36(2H, d), 8.20(1H, d), 8.09(1H, d), 7.98~7.78(10H, m), 7.55~7.25(13H, m), 1.69(6H, s) |
| 537 | δ = 9.11(1H, d), 8.70(1H, d), 8.46(1H, s), 8.38~8.33(4H, m), 8.21~8.20(2H, m), 7.98~7.85(6H, m), 7.73~7.31(15H, m) |
| 540 | δ = 9.08(1H, d), 8.84(1H, d), 8.69(2H, d), 8.36~8.20(5H, m), 8.05~7.85(8H, m), 7.73~7.50(11H, m), 7.39~7.31(2H, m) |
| 546 | δ = 8.97(1H, d), 8.69(2H, d), 8.55(1H, d), 8.36(2H, d), 8.24~8.12(4H, m), 7.96~7.79(7H, m), 7.70(1H, t), 7.59~7.50(8H, m), 7.39~7.31(3H, m), 7.20~7.16(2H, m) |
| 550 | δ = 8.97(2H, d), 8.68(1H, d), 8.55(1H, d), 8.36~8.19(7H, m), 7.98~7.85(4H, m), 7.70~7.50(11H, m), 7.39~7.31(3H, m), 7.20~7.16(2H, m) |
| 553 | δ = 8.55(1H, d), 8.45~8.33(6H, m), 8.20(1H, d), 7.98~7.85(5H, m), 7.73~7.70(3H, m), 7.56~7.31(8H, m) |

TABLE 30-continued

| Compound | ¹H NMR (CDCl₃, 300 Mz) |
|---|---|
| 557 | δ = 8.69(2H, d), 8.55(1H, d), 8.45(1H, d), 8.36(2H, d), 8.20(1H, d), 7.96~7.85(9H, m), 7.70(2H, t), 7.56~7.25(10H, m) |
| 559 | δ = 8.69(2H, d), 8.55(1H, d), 8.45(1H, d), 8.36~8.32(3H, m), 8.20(1H, d), 7.98~7.85(8H, m), 7.70(2H, m), 7.56~7.49(6H, m), 7.39~7.25(4H, m) |
| 562 | δ = 9.02(1H, d), 8.95(1H, d), 8.55(1H, d), 8.45~8.31(7H, m), 8.20(1H, d), 8.06(1H, d), 7.98~7.84(5H, m), 7.73~7.70(3H, m), 7.56~7.31(10H, m) |
| 563 | δ = 8.69(2H, d), 8.36(2H, d), 8.20(1H, d), 8.08(1H, d), .7.98~7.85(7H, m), 7.70(1H, t), 7.54~7.50(6H, m), 7.39~7.31(4H, m) |
| 567 | δ = 8.69(2H, d), 8.36(2H, d), 8.20(1H, d), 7.98~7.94(7H, m), 7.82(1H, d), 7.70~7.69(2H, m), 7.57~7.50(6H, m), 7.39~7.25(6H, m) |
| 573 | δ = 9.02(1H, d), 8.95(1H, d), 8.45(1H, d), 8.36(2H, d), 8.20(1H, d), 8.03~7.76(11H, m), 7.54~7.25(13H, m) |
| 576 | δ = 8.36~8.33(4H, m), 8.20(1H, d), 8.08(1H, d), 7.98~7.85(7H, m), 7.70~7.50(11H, m), 7.39~7.31(4H, m) |
| 578 | δ = 9.60(1H, d), 8.27(1H, s), 8.69(2H, d), 8.36~8.33(5H, m), 8.20(1H, d), 7.98~7.85(7H, m), 7.70~7.50(13H, m), 7.39~7.31(2H, m) |
| 579 | δ = 9.60(1H, d), 9.27(1H, s), 8.36~8.30(6H, m), 8.20~8.15(2H, m), 7.98~7.85(5H, m), 7.73~7.50(13H, m), 7.39~7.25(4H, m) |
| 585 | δ = 8.69(2H, d), 8.36(2H, d), 8.20(1H, d), 8.09(1H, d), 7.98~7.78(9H, m), 7.55~7.50(5H, m), 7.39~7.28(4H, m), 1.69(6H, s) |
| 587 | δ = 8.97(2H, d), 8.69(1H, d), 8.36~8.29(3H, m), 8.20(1H, d), 8.00~7.85(5H, m), 7.70~7.68(2H, m), 7.59~7.50(8H, m), 7.39~7.28(4H, m), 1.69(6H, s) |
| 588 | δ = 9.03(1H, d), 8.36~8.33(4H, m), 8.20~8.09(4H, m), 7.98~7.50(17H, m), 7.39~7.21(4H, m), 1.69(6H, s) |
| 591 | δ = 8.69(2H, d), 8.50(1H, d), 8.36~8.20(5H, m), 8.09~7.78(13H, m), 7.55~7.50(5H, m), 7.39~7.28(4H, m), 1.69(6H, s) |
| 593 | δ = 8.95(1H, d), 8.69(2H, d), 8.52~8.50(2H, m), 8.38~8.31(2H, m), 8.20~7.52(22H, m), 7.39~7.31(3H, m) |
| 597 | δ = 9.08(1H, d), 9.02(1H, d), 8.95(1H, d), 8.84(1H, d), 8.79(1H, d), 8.69(2H, d), 8.36(2H, d), 8.20(1H, d), 8.06~7.84(9H, m), 7.70~7.31(13H, m) |
| 598 | δ = 9.11(1H, d), 9.03(1H, d), 8.70~8.69(3H, m), 8.46~8.36(4H, m), 8.20~8.13(3H, m), 7.96~7.54(18H, m), 7.39~7.31(2H, m) |
| 604 | δ = 8.55(1H, d), 8.38~8.33(5H, m), 8.19(1H, d), 7.98~7.88(7H, m), 773(1H, t), 7.59~7.50(8H, m), 7.39~7.31(3H, m), 7.20~7.16(2H, m) |
| 605 | δ = 8.69(2H, d), 8.55(1H, d), 8.36(2H, d), 8.24~8.21(2H, m), 7.98~7.88(8H, m), 7.75~7.31(17H, m), 7.16(1H, t) |
| 608 | δ = 8.97(2H, d), 8.68(1H, d), 8.55(1H, d), 8.36~8.19(6H, m), 7.98~7.88(4H, m), 7.69~7.50(19H, m), 7.39~7.31(3H, m), 7.20~7.16(2H, m) |
| 609 | δ = 8.69(2H, d), 8.55(1H, d), 8.19(1H, d), 7.98~7.88(12H, m), 7.75(2H, d), 7.59~7.16(15H, m) |
| 613 | δ = 8.55(1H, d), 8.45~8.33(6H, m), 7.98~7.88(5H, m), 7.73~7.70(2H, m), 7.59~7.31(10H, m) |
| 616 | δ = 9.05(1H, d), 8.91(1H, d), 8.69(2H, d), 8.55~8.45(3H, m), 8.36(2H, d), 7.98~7.88(7H, m), 7.77~7.70(2H, m), 7.59~7.25(12H, m) |
| 617 | δ = 8.55(1H, d), 8.45(1H, d), 8.36~8.33(4H, m), 7.98~7.88(7H, m), 7.70~7.31(15H, m) |
| 618 | δ = 8.69(2H, d), 8.45(1H, d), 8.36(2H, d), 8.36~8.17(3H, m), 7.98~7.88(8H, m), 7.60~7.49(10H, m), 7.39~7.31(2H, m) |
| 621 | δ = 9.02(1H, d), 8.95(1H, d), 8.45~8.36(4H, m), 8.12(1H, s), 7.99~7.84(9H, m), 7.59~7.25(14H, m) |
| 626 | δ = 8.69(2H, d), 8.38(1H, d), 8.09~7.82(11H, m), 7.73~7.54(11H, m), 7.39~7.31(5H, m) |
| 632 | δ = 8.97(2H, d), 8.68(1H, d), 8.36~8.29(3H, dd), 7.98~7.82(5H, m), 7.69(1H, d), 7.59~7.50(10H, m), 7.39~7.31(4H, m) |
| 638 | δ = 9.60(1H, d), 9.27(1H, s), 8.69(2H, d), 8.36~8.30(4H, m), 8.15(1H, d), 7.98~7.88(5H, m), 7.70~7.50(12H, m), 7.35~7.31(2H, m) |
| 641 | δ = 9.60(1H, d), 9.27(1H, s), 8.36~8.30(6H, m), 8.15(1H, d), 7.98~7.96(5H, m), 7.70~7.50(16H, m), 7.39~7.31(2H, m) |
| 645 | δ = 8.38~8.33(5H, m), 7.98~7.88(6H, m), 7.73~7.28(17H, m), 1.69(6H, s) |
| 650 | δ = 9.03(1H, d), 8.69(2H, d), 8.36(2H, d), 8.14~8.13(2H, m), 7.98~7.78(8H, m), 7.65~7.28(15H, m), 1.69(6H, s) |
| 653 | δ = 8.97(2H, d), 8.68(1H, d), 8.38~8.29(6H, m), 8.19(2H, d), 8.08~7.88(9H, m), 7.73(1H, t), 7.61~7.50(9H, m), 7.39~7.31(2H, m) |
| 661 | δ = 9.02~8.95(3H, m), 8.69(2H, d), 8.41~8.23(5H, m), 8.08~7.90(9H, m), 7.68~7.31(13H, m) |
| 663 | δ = 9.27(1H, s), 9.08(1H, d), 8.52(1H, d), 8.38~8.27(6H, m), 8.15(1H, d), 8.05~31(20H, m) |
| 664 | δ = 8.69(2H, d), 8.55(1H, d), 8.36(2H, d), 7.99~7.88(11H, m), 7.77~7.65(5H, m), 7.55~7.35(10H, m), 7.22~7.16(2H, m) |
| 666 | δ = 9.09(1H, s), 8.69(2H, d), 8.55(1H, d), 8.49(1H, d), 8.19~8.16(2H, m), 8.08~7.88(11H, m), 7.70~7.50(8H, m), 7.36~7.35(2H, m), 7.22~7.16(3H, m) |
| 667 | δ = 8.55(1H, d), 8.38~8.33(3H, m), 8.19(1H, d), 7.96~7.88(9H, m), 7.79~7.35(16H, m), 7.22~7.16(3H, m) |

TABLE 30-continued

| Compound | ¹H NMR (CDCl₃, 300 Mz) |
|---|---|
| 668 | δ = 8.69(2H, d), 8.55~8.54(2H, m), 8.36(2H, d), 8.24~8.21(2H, d), 7.99~7.88(6H, m), 7.70~7.54(13H, m), 7.36~7.35(2H, m), 7.20~7.16(2H, m) |
| 671 | δ = 9.02(1H, t), 8.95(1H, d), 8.55~8.45(3H, m), 8.36(2H, d), 8.12~8.11(2H, d), 7.97~7.84(10H, m), 7.72~7.65(4H, m), 7.57~7.46(8H, m), 7.36~7.35(2H, m), 7.25~7.16(4H, m) |
| 674 | δ = 8.45~8.33(6H, m), 8.03~7.88(5H, m), 7.73~7.49(11H, m), 7.36(1H, t), 7.22(1H, t) |
| 680 | δ = 8.55(1H, d), 8.45~8.33(6H, m), 7.97~7.88(5H, m), 7.73~7.49(14H, m), 7.36(1H, t), 7.22(1H, t) |
| 681 | δ = 8.69(2H, d), 8.55(1H, d), 8.45(1H, d), 8.36~8.32(3H, m), 7.96~7.88(7H, m), 7.70~7.65(3H, m), 7.56~7.49(7H, m), 7.36(1H, t), 7.25~7.22(3H, m) |
| 682 | δ = 8.97(2H, d), 8.68(1H, d), 8.55~8.54(2H, m), 8.36~8.29(3H, m), 7.99~7.50(18H, m), 7.36(1H, t), 7.22(1H, t) |
| 687 | δ = 8.38~8.33(5H, m), 8.16~8.08(3H, m), 7.97(1H, d), 7.88~7.84(3H, m), 7.73~7.65(5H, m), 7.55~7.48(7H, m), 7.36(1H, t), 7.22(1H, t) |
| 691 | δ = 8.97(1H, d), 8.38~8.25(4H, m), 8.15~8.10(2H, m), 8.00~7.82(5H, m), 7.73~7.52(10H, m), 7.39~7.22(4H, m) |
| 696 | δ = 8.69(2H, d), 8.36(2H, d), 8.08(1H, d), 7.98~7.88(6H, m), 7.70~7.50(11H, m), 7.39~7.22(6H, m) |
| 699 | δ = 8.95(2H, d), 8.45~8.36(4H, m), 8.08(1H, d), 7.98~7.84(6H, m), 7.73~7.22(1~7H, m) |
| 700 | δ = 8.36~8.33(4H, m), 8.08(1H, d), 7.98~7.88(6H, m), 7.70~7.50(13H, m), 7.39~7.22(4H, m) |
| 703 | δ = 9.60(1H, d), 9.27(1H, s), 8.69(2H, d), 8.36~8.30(4H, m), 8.15(1H, d), 7.96~7.88(4H, m), 7.70~7.50(13H, m), 7.36(1H, t), 7.22(1H, t) |
| 712 | δ = 8.69(2H, d), 8.38~8.36(3H, m), 8.09(1H, d), 7.96~7.88(7H, m), 7.73~7.50(11H, m), 7.38~7.22(4H, m) |
| 721 | δ = 9.02(2H, d), 8.95(2H, d), 8.52~8.45(2H, m), 8.36~8.31(3H, m), 8.15~7.88(11H, m), 7.70~7.65(3H, m), 7.55~7.36(10H, m), 7.22(1H, t) |
| 722 | δ = 9.08(1H, d), 8.84(1H, d), 8.69(2H, d), 8.36(2H, d), 8.27(1H, d), 8.05(1H, s), 7.97~7.88(7H, m), 7.70~7.50(11H, m), 7.36(1H, t), 7.25~7.22(3H, m) |
| 724 | δ = 9.08(1H, d), 8.84~8.79(2H, m), 8.50(1H, d), 8.36~8.23(7H, m), 8.09~7.88(6H, m), 7.77~7.50(13H, m), 7.36(1H, t), 7.22(1H, t) |
| 725 | δ = 8.69(2H, d), 8.55(1H, d), 8.35~8.30(4H, m), 8.23(1H, s), 8.20(1H, d), 7.98~7.85(8H, m), 7.70(1H, t), 7.58~7.50(6H, m), 7.39~7.31(3H, m), 7.20~7.16(2H, m) |
| 727 | δ = 8.69(2H, d), 8.55(1H, d), 8.30(2H, d), 8.23(1H, s), 8.19(1H, d), 7.98~7.80(9H, m), 7.70(1H, t), 7.58~7.31(10H, m), 7.20~7.16(2H, m) |
| 731 | δ = 8.97(2H, d), 8.68(1H, d), 8.55(1H, d), 8.29(1H, d), 8.23(1H, s), 8.20~2.19(2H, m), 7.98~7.85(10H, m), 7.70(1H, t), 7.59~7.49(8H, m), 7.39~7.31(2H, m), 7.20~7.16(2H, m) |
| 736 | δ = 8.69(2H, d), 8.55(1H, d), 8.45(1H, d), 8.35~8.30(4H, m), 8.23(1H, s), 8.20(1H, d), 7.98~7.85(9H, m), 7.70(2H, m), 7.56~7.50(6H, m), 7.39~7.31(2H, m) |
| 737 | δ = 8.55(1H, d), 8.45(1H, d), 8.35~8.33(4H, m), 8.23(1H, s), 8.20(1H, d), 7.96~7.85(7H, m), 7.73~7.31(14H, m) |
| 740 | δ = 8.69(2H, d), 8.55(1H, d), 8.45(1H, d), 8.32~8.30(3H, m), 8.23(1H, s), 8.20(1H, d), 7.98~7.85(8H, m), 7.70(2H, m), 7.56~7.25(10H, m) |
| 742 | δ = 8.71~8.69(3H, m), 8.55~8.45(3H, m), 8.35~8.09(9H, m), 7.98~7.85(4H, m), 7.70~7.31(12H, m) |
| 748 | δ = 8.69(2H, d), 8.35~7.20(6H, m), 7.98~7.94(3H, m), 7.85~7.82(2H, m), 7.70~7.69(2H, m), 7.57~7.50(6H, m), 7.39~7.31(4H, m) |
| 750 | δ = 8.97(1H, d), 8.69(2H, d), 8.30~8.10(7H, m), 8.00~7.82(6H, m), 7.70~7,69(2H, m), 7.59~7.52(5H, m), 7.39~7.31(4H, m) |
| 751 | δ = 8.38~8.20(7H, m), 8.08~7.85(8H, m), 7.73~7.70(2H, m), 7.55~7.31(12H, m) |
| 753 | δ = 8.33(2H, d), 8.23(1H, s), 8.20(1H, d), 8.02~7.85(11H, m), 7.75~7.70(5H, m), 7.61~7.25(13H, m) |
| 754 | δ = 9.60(1H, d), 9.27(1H, s), 8.69(2H, d), 8.33~8.30(2H, m), 8.23(1H, s), 820~8.15(2H, d), 7.98~7.85(7H, m), 7.70~7.31(13H, m) |
| 757 | δ = 9.60(1H, d), 9.27(1H, s), 8.35~8.30(6H, m), 8.23(1H, s), 8.20~8.15(2H, d), 7.98~7.85(4H, m), 7.73~7.64(6H, m), 7.54~7.50(6H, m), 7.39~7.31(2H, m) |
| 763 | δ = 9.02(1H, d), 8.95(1H, d), 8.69(2H, d), 8.35(2H, d) 8.30(2H, d), 8.23(1H, s), 8.20(1H, d), 8.09~8.06(2H, m), 7.98~7.70(8H, m), 7.54~7.28(11H, m), 1.69(6H, s) |
| 764 | δ = 8.97(2H, d), 8.68(1H, d), 8.29(1H, d), 8.23(1H, s), 8.20(1H, d), 8.09(1H, d), 7.98~7.70(9H, m), 7.59~7.49(7H, m), 7.39~7.28(4H, m), 1.69(6H, s) |
| 765 | δ = 9.03(1H, d), 8.97(2H, d), 8.68(1H, d), 8.35~8.09(8H, m), 7.98~7.70(8H, m), 7.60~7.50(9H, m), 7.39~7.28(4H, m), 1.69(6H, s) |
| 768 | δ = 8.69(2H, d), 8.52(1H, d), 8.31(1H, d), 8.23~7.85(15H, m), 7.70(2H, m), 7.55~7.49(4H, m), 7.39~7.31(2H, m) |
| 774 | δ = 9.08(1H, d), 9.02(1H, d), 8.95(1H, d), 8.84~8.79(2H, m), 8.69(2H, d), 8.30~8.20(4H, m), 8.06~7.84(9H, m), 7.70~7.31(13H, m) |

TABLE 30-continued

| Compound | ¹H NMR (CDCl₃, 300 Mz) |
|---|---|
| 777 | δ = 8.69(2H, d), 8.55(1H, d), 8.35~8.11(11H, m), 7.98~7.70(6H, m), 7.60~7.50(7H, m), 7.39~7.31(3H, m), 7.20~7.16(2H, m) |
| 778 | δ = 8.69(2H, d), 8.55(1H, d), 8.23(1H, s), 8.20~8.19(2H, m), 7.98~7.85(11H, m), 7.70(1H, t), 7.58~7.49(6H, m), 7.39~7.31(3H, m), 7.20~7.16(2H, m) |
| 780 | δ = 8.69(2H, d), 8.55(1H, d), 8.30~8.20(6H, m), 7.98~7.31(24H, m), 7.16(1H, t) |
| 782 | δ = 8.97(2H, d), 8.68(1H, d), 8.55(1H, d), 8.29~8.19(4H, m), 7.98~7.85(10H, m), 7.70(1H, t), 7.59~7.49(8H, m), 7.39~7.31(3H, m), 7.20~7.16(2H, m) |
| 784 | δ = 8.60(1H, s), 8.55(1H, d), 8.33(2H, d), 8.23(1H, s), 8.20~8.19(2H, d), 8.11(1H, d), 8.03~7.85(9H, m), 7.73~7.49(10H, m), 7.39~7.31(3H, m), 7.20~7.16(2H, m) |
| 786 | δ = 8.69(2H, d), 8.45(1H, d), 8.30(2H, d), 8.23(1H, s), 8.20(1H, d), 8.12(1H, s), 7.99~7.85(8H, m), 7.70(1H, t), 7.56~7.31(8H, m) |
| 788 | δ = 8.55(1H, d), 8.45(1H, d), 8.35~8.33(4H, m), 8.23(1H, s), 8.20(1H, d), 7.98~7.85(6H, m), 7.73~7.70(3H, m), 7.56~7.31(8H, m) |
| 789 | δ = 9.09(1H, s), 8.69(2H, d), 8.55~8.45(3H, m), 8.30~7.85(12H, m), 7.70~7.31(9H, m) |
| 796 | δ = 9.02(1H, d), 8.95(1H, d), 8.55(1H, d), 8.45~8.32(5H, m), 8.23(1H, s), 8.20(1H, d), 8.06~7.85(8H, m), 7.73~7.70(3H, m), 7.56~7.31(10H, m) |
| 798 | δ = 8.69(2H, d), 8.23(1H, s), 8.20(1H, d), 8.08(1H, d), 7.98~7.85(8H, m), 7.74~7.70(2H, m), 7.55~7.31(10H, m) |
| 803 | δ = 8.69(2H, d), 8.23(1H, s), 8.20(1H, d), 8.08~7.85(12H, m), 7.73~7.70(2H, m), 7.61~7.49(7H, m), 7.39~7.31(4H, m) |
| 811 | δ = 9.27(1H, s), 8.97(2H, d), 8.68(1H, d), 8.33~8.15(6H, m), 7.98~7.85(5H, m), 7.70~7.31(15H, m) |
| 816 | δ = 8.69(2H, d), 8.30(2H, d), 8.23(1H, s), 8.20(1H, d), 8.09(1H, d), 7.98~7.70(9H, m), 7.55~7.49(5H, m), 7.39~7.29(4H, m), 1.69(6H, s) |
| 818 | δ = 8.38~8.33(3H, m), 8.23(1H, s), 8.20(1H, d), 8.09(1H, d), 7.98~7.70(10H, m), 7.55~7.49(5H, m), 7.39~7.28(4H, m), 1.69(6H, s) |
| 820 | δ = 8.97(2H, d), 8.68(1H, d), 8.29(1H, d), 8.23(1H, s), 8.20(1H, d), 8.09(1H, d), 7.98~7.70(9H, m), 7.59~7.49(7H, m), 7.39~7.28(4H+21m), 1.69(6H, s) |
| 824 | δ = 8.95(1H, d), 8.69(2H, d), 8.23(1H, s), 8.20(2H, d), 8.12(1H, s), 8.09(1H, d), 7.98~7.71(12H, m), 7.55~7.28(11H, m), 1.69(6H, s) |
| 829 | δ = 9.02(1H, d), 8.96(1H, d), 8.52~8.45(2H, m), 8.31~7.84(17H, m), 7.70(2H, m), 7.55~7.25(10H, m) |
| 830 | δ = 9.08(1H, d), 8.84(1H, d), 8.69(2H, d), 8.30~8.20(5H, m), 8.05~7.85(9H, m), 7.70~7.25(13H, m) |
| 833 | δ = 9.11(1H, d), 8.97(2H, d), 8.70~8.68(2H, m), 8.46~8.20(7H, m), 7.98~7.85(7H, m), 7.75~7.50(12H, m), 7.39~7.31(2H, m) |
| 836 | δ = 8.69(2H, d), 8.55(1H, d), 8.30(2H, d), 8.23(1H, s), 8.19(1H, d), 7.98~7.88(10H, m), 7.59~7.49(8H, m), 7.39~7.31(3H, m), 7.20~7.16(2H, m) |
| 837 | δ = 8.69(2H, d), 8.55(1H, d), 8.35~8.30(4H, m), 8.23(1H, s), 8.19(1H, d), 7.98~7.88(8H, m), 7.59~7.50(8H, m), 7.39~7.31(3H+21m), 7.20~7.16(2H, m) |
| 839 | δ = 8.97(1H, d), 8.55(1H, d), 8.33(2H, m), 8.25~8.10(5H, m), 8.00~7.88(10H, m), 7.73(1H, t), 7.59~7.50(7H, m), 7.39~7.31(3H, m), 7.20~7.16(2H, m) |
| 844 | δ = 8.69(2H, d), 8.55(1H, d), 8.45(1H, d), 8.30(2H, d), 8.23(1H, s), 7.98~7.88(7H, m), 7.70(1H, t), 7.59~7.31(10H, m) |
| 846 | δ = 8.55(2H, d), 8.35~8.32(5H, m), 8.23(1H, s), 7.98~7.88(5H, m), 7.73~7.70(2H, m), 7.59~7.31(13H, m) |
| 848 | δ = 8.55(1H, d), 8.45(1H, d), 8.33~8.30(4H, m), 8.23(1H, s), 7.98~7.85(9H, m), 7.73~7.70(2H, m), 7.59~7.31(11H, m) |
| 852 | δ = 9.11(1H, s), 9.02(1H, d), 8.95(1H, d), 8.55(1H, d), 8.45(2H, d), 7.98~7.80(10H, m), 7.70~7.31(15H, m) |
| 854 | δ = 8.69(2H, d), 8.30(2H, d), 8.23(1H, s), 8.08(1H, d), 7.98~7.88(7H, m), 7.59~7.31(12H, m) |
| 856 | δ = 8.69(2H, d), 8.30(2H, d), 8.23(1H, s), 7.98~7.82(7H, m), 7.69(1H, d), 7.59~7.31(12H, m) |
| 864 | δ = 9.02(1H, d), 8.95(1H, d), 8.69(2H, d), 8.35(2H, d), 8.23(1H, s), 8.08~7.97(5H, m), 7.888~7.84(2H, m), 7.74(1H, d), 7.59~7.25(16H, m) |
| 865 | δ = 9.02(1H, d), 8.95(1H, d), 8.45(1H, d), 8.35(2H, d), 8.23(1H, s), 8.08(1H, d), 7.98~7.84(7H, m), 7.74~7.73(2H, m), 7.61~7.31(15H, m) |
| 866 | δ = 8.95(1H, d), 8.35~8.33(4H, m), 8.23(1H, s), 8.20(1H, d), 8.12~8.08(2H, m), 7.98~7.97(3H, m), 7.88(1H, d), 7.74~7.71(3H, m), 7.61~7.50(10H, m), 7.39~7.31(5H, m) |
| 867 | δ = 9.60(1H, d), 9.27(1H, s), 8.69(2H, d), 8.33~8.23(5H, m), 8.15(1H, d), 7.98~7.88(5H, m), 7.70~7.31(14H, m) |
| 874 | δ = 8.46(1H, s), 8.33(2H, d), 8.23(1H, s), 8.09~7.88(11H, m), 7.78~7.73(2H, m), 7.61~7.54(6H, m), 7.39~7.28(4H, m), 1.69(6H, s) |
| 876 | δ = 8.35(2H, d), 8.33(2H, m), 8.23(1H, s), 8.09(1H, d), 7.98~7.88(8H, m), 7.78~7.73(3H, m), 7.61~7.50(8H, m), 7.39~7.28(4H, m), 1.69(6H, s) |

TABLE 30-continued

| Compound | ¹H NMR (CDCl₃, 300 Mz) |
|---|---|
| 879 | δ = 8.97(2H, d), 8.68(1H, d), 8.29(1H, d), 8.23(1H, s), 8.09(1H, d), 7.98~7.88(9H, m), 7.18(1H, d), 7.60~7.49(11H, m), 7.39~7.28(4H, m), 1.69(6H, s) |
| 880 | δ = 8.52(1H, d), 8.35~8.31(5H, m), 8.23(1H, s), 8.15~7.88(10H, m), 7.73~7.70(2H, m), 7.59~7.50(6H, m), 7.39~7.31(2H, m) |
| 882 | δ = 8.69(2H, d), 8.52(1H, d), 8.35~8.23(8H, m), 8.15~7.88(9H, m), 7.70(1H, d), 7.59~7.50(6H, m), 7.39~7.25(4H, m) |
| 885 | δ = 9.08(1H, d), 8.84~8.79(2H, d), 8.35~8.33(4H, m), 8.23(1H, s), 8.05~7.88(8H, m), 7.73~7.50(13H, m), 7.39~7.31(2H, m) |
| 886 | δ = 9.11(1H, d), 8.70(1H, d), 8.46~8.23(8H, m), 7.98~7.88(9H, m), 7.75~7.31(12H, m) |
| 888 | 8.69(2H, d), 8.55(1H, d), 8.23(1H, s), 8.19(1H, d), 7.97~7.88(11H, m), 7.70~7.49(9H, m), 7.35(2H, m), 7.22~7.16(3H, m) |
| 889 | δ = 8.69(2H, d), 8.55(1H, d), 8.30~8.19(6H, m), 7.97~7.88(5H, m), 7.70~7.49(11H, m), 7.36~7.35(2H, m), 7.22~7.16(3H, m) |
| 894 | δ = 9.02(1H, d), 8.95(1H, d), 8.55(1H, d), 8.45(1H, d), 8.35~8.30(4H, m), 8.23(1H, s), 8.19(1H, d), 7.97~7.80(7H, m), 7.65~7.35(14H, m), 7.25~7.16(5H, m) |
| 897 | δ = 8.69(2H, d), 8.55(2H, d), 8.46(1H, s), 8.32~8.23(5H, m), 8.06~7.88(6H, m), 7.70~7.36(14H, m), 7.22(1H, t) |
| 898 | δ = 8.55(1H, d), 8.45(1H, d), 8.33(2H, d), 8.23(1H, s), 7.97~7.88(7H, m), 7.73~7.49(11H, m), 7.36(1H, t), 7.22(1H, t) |
| 902 | δ = 8.69(2H, d), 8.55(1H, d), 8.45(1H, d), 8.35~8.23(6H, m), 7.97~7.88(5H, m), 7.70~7.49(12H, m), 7.36(1H, t), 7.22(1H, t) |
| 903 | δ = 8.97(2H, d), 8.68(1H, d), 8.55(1H, d), 8.45(1H, d), 8.29(1H, d), 8.23(1H, s), 7.97~7.88(6H, m), 7.70~7.49(12H, m), 7.36(1H, t), 7.22(1H, t) |
| 905 | δ = 8.55(1H, d), 8.45(1H, d), 8.33~8.32(3H, m), 8.23(1H, s), 7.97~7.88(8H, m), 7.73~7.65(4H, m), 7.56~7.49(7H, m), 7.36(1H, t), 7.25~7.22(3H, m) |
| 906 | δ = 8.69(2H, d), 8.35~8.30(4H, m), 7.98~7.87(5H, m), 7.75~7.65(4H, m), 7.55~7.22(13H, m) |
| 907 | δ = 8.69(2H, d), 8.30(2H, d), 8.23(1H, s), 8.08~7.88(8H, m), 7.70~7.65(2H, m), 7.56~7.36(13H, m), 7.22(1H, t) |
| 913 | δ = 8.97(2H, d), 8.68(1H, d), 8.29(1H, d), 8.23(1H, s), 8.08(1H, d), 7.98~7.88(6H, m), 7.70~7.22(15H, m) |
| 916 | δ = 8.38~8.30(5H, m), 8.23(1H, s), 8.08~7.88(7H, m), 7.73~7.65(3H, m), 7.55~7.49(7H, m), 7.36~7.22(6H, m) |
| 917 | δ = 9.02(1H, d), 8.95(1H, d), 8.69(2H, d), 8.23(1H, s), 8.08~7.88(11H, m), 7.70~7.65(2H, m), 7.55~7.22(13H, m) |
| 920 | δ = 8.52(1H, s), 8.35~8.33(4H, m), 8.23(1H, s), 8.00~7.82(8H, m), 7.73~7.50(12H, m), 7.39~7.22(5H, m) |
| 930 | δ = 8.69(2H, d), 8.35~8.30(4H, m), 8.23(1H, s), 8.09(1H, d), 7.97~7.88(5H, m), 7.78~7.50(11H, m), 7.38~7.21(4H, m), 1.69(6H, s) |
| 931 | δ = 8.69(2H, d), 8.52(1H, d), 8.31(1H, d), 8.23(1H, s), 8.15~7.88(12H, m), 7.70~7.65(3H, m), 7.55~7.49(5H, m), 7.36(1H, t), 7.22(1H, t) |
| 935 | δ = 9.11(1H, d), 9.02(1H, d), 8.95(1H, d), 8.70(1H, d), 8.46~7.33(6H, m), 8.23(1H, s), 8.06(1H, d), 7.94~7.84(6H, m), 7.75~7.36(14H, m), 7.22(1H, t) |
| 936 | δ = 8.69(4H, m), 8.55(1H, d), 8.30(2H, d), 8.20~8.19(4H, m), 7.98~7.85(6H, m), 7.75~7.70(3H, m), 7.58~7.31(9H, m), 7.20~7.16(2H, m) |
| 938 | δ = 8.69(4H, m), 8.29(2H, d), 8.20(3H, m), 8.08~7.85(8H, m), 7.70(1H, t), 7.55~7.25(12H, m) |
| 943 | δ = 8.69(4H, m), 8.55(1H, d), 8.45(1H, d), 8.32~8.20(6H, m), 7.98~7.85(6H, m), 7.70(2H, t), 7.55~7.25(10H, m) |
| 948 | δ = 8.69(2H, d), 8.29~8.28(3H, m), 8.20~8.17(3H, m), 8.09(1H, d), 7.98~7.85(6H, m), 7.59~7.49(7H, m), 7.39~7.28(4H, m), 1.69(6H, s) |
| 949 | δ = 8.69(4H, m), 8.55(1H, d), 8.30(2H, d), 8.20~8.19(3H, m), 7.97~7.88(5H, m), 7.75~7.35(13H, m), 7.22~7.16(3H, m) |
| 953 | δ = 8.55(1H, d), 8.36(2H, d), 8.24~8.12(7H, m), 7.99~7.85(5H, m), 7.70~7.49(11H, m), 7.35(1H, t), 7.20~7.16(2H, m) |
| 956 | δ = 8.88(1H, s), 8.55(1H, d), 8.45~8.36(3H, m), 8.20(1H, d), 8.06~7.85(10H, m), 7.70~7.49(9H, m) |
| 960 | δ = 9.02(2H, d), 8.95(2H, d), 8.55(1H, d), 8.45(1H, d), 8.36(2H, m), 8.20~7.85(12H, m), 7.70~7.49(12H, m) |
| 962 | δ = 8.36(2H, d), 8.20(3H, m), 8.12(1H, s), 7.99~7.82(6H, m), 7.70~7.39(12H, m) |
| 966 | δ = 8.36(2H, d), 8.20~8.12(5H, m), 7.99~7.94(5H, m), 7.85~7.82(2H, m), 7.70~7.39(14H, m) |
| 969 | δ = 8.36(2H, d), 8.19(3H, m), 8.12(1H, s), 8.09(1H, s), 7.99~7.65(10H, m), 7.55~7.49(5H, m), 7.38(1H, t), 7.28(1H, t), 1.69(6H, s) |
| 973 | 9.08(1H, d), 8.84(1H, d), 8.36~8.12(7H, m), 8.05~7.85(8H, m), 7.70~7,63(7H, m), 7.50~7.49(3H, m), 7.25(2H, d) |
| 975 | 8.55(1H, d), 8.35(2H, m), 8.23~8.12(7H, m), 7.99~7.80(6H, m), 7.70~7.50(11H, m), 7.35(1H, t), 7.20~7.16(2H, m) |
| 981 | 8.85(1H, s), 8.55(1H, d), 8.45~8.35(4H, m), 8.23(1H, s), 8.20(1H, d), 8.12~7.85(10H, m), 7.70~7.49(9H, m) |

TABLE 30-continued

| Compound | $^1$H NMR (CDCl$_3$, 300 Mz) |
|---|---|
| 984 | 8.55(1H, d), 8.45(1H, d), 8.23~8.12(5H, m), 7.99~7.85(8H, m), 7.70~7.49(10H, m) |
| 986 | 8.55(1H, d), 8.45(1H, d), 8.32~8.12(8H, m), 7.99~7.85(7H, m), 7.70~7.49(10H, m), 7.25(2H, d) |
| 989 | 8.55(1H, d), 8.45(1H, d), 8.35~8.12(10H, m), 7.99~7.85(7H, m), 7.70~7.49(10H, m) |
| 991 | 8.23~8.08(6H, m), 7.99~7.85(8H, m), 7.70~7.31(11H, m) |
| 996 | 8.35(2H, d), 8.23~8.08(6H, m), 7.99~7.85(5H, m), 7.74~7.65(4H, m), 7.54~7.49(6H, m), 7.39~7.31(2H, m) |
| 1003 | 8.23~8.19(4H, m), 8.12~8.09(2H, m), 7.99~7.65(12H, m), 7.55~7.49(5H, m), 7.38(1H, t), 7.28(1H, t) |
| 1007 | 8.35~8.30(4H, m), 8.23(1H, s), 8.20~8.09(6H, m), 7.99~7.65(11H, m), 7.55~7.49(5H, m), 7.38(1H, t), 7.28(1H, t), 1.69(6H, s) |
| 1013 | 9.11(1H, d), 8.70(1H, d), 8.46(1H, s), 8.23~8.12(6H, m), 7.99~7.85(8H, m), 7.75~7.49(10H, m) |
| 1014 | 9.08(1H, d), 8.84(1H, d), 8.35~8.12(10H, m), 8.05~7.85(6H, m), 7.70~7.63(7H, m), 7.50~7.49(4H, m), 7.25(2H, d) |
| 1020 | 8.36(4H, m), 8.20~8.19(3H, m), 7.96~7.79(7H, m), 7.70~7.65(3H, m), 7.50~7.49(7H, m), 7.25(2H, d) |
| 1021 | 8.35~8.30(4H, m), 8.23(1H, s), 8.20~8.19(3H, m), 7.94~7.79(9H, m), 7.70~7.49(10H, m) |
| 1026 | 8.38~8.36(3H, m), 8.23~8.20(3H, m), 8.12(2H, m), 7.99~7.94(5H, m), 7.85(1H, t), 7.75~7.70(4H, m), 7.61~7.41(10H, m), 7.24(2H, m) |
| 1027 | 8.38(1H, d), 8.23~8.20(4H, m), 7.94~7.70(15H, m), 7.61~7.41(11H, m) |
| 1030 | 8.36(2H, d), 8.20~8.12(5H, m), 7.99~7.94(6H, m), 7.85(1H, t), 7.75~7.65(5H, m), 7.50~7.41(7H, m), 7.25(4H, m) |
| 1031 | 8.35~8.12(10H, m), 7.99~7.41(21H, m) |
| 1033 | 8.38~8.12(9H, m), 7.99~7.85(8H, m), 7.75~7.49(14H, m) |
| 1034 | 8.38~8.36(5H, m), 8.23~8.20(3H, m), 8.12(2H, m), 7.99~7.94(3H, m), 7.85(1H, t), 7.73~7.70(2H, m), 7.61~7.49(10H, m) |
| 1035 | 8.35(2H, d), 8.23~8.20(4H, m), 7.94~7.73(11H, m), 7.61~7.4910H, m) |
| 1036 | 8.55(1H, d), 8.36(2H, d), 8.20~8.19(4H, m), 7.94~7.83(10H, m), 7.70~7.50(9H, m), 7.35(1H, t), 7.20~7.16(2H, m) |
| 1039 | 8.55(1H, d), 8.45(1H, d), 8.36(2H, d), 8.20~8.19(3H, m), 7.94~7.79(7H, m), 7.70~7.49(10H, m) |
| 1041 | 8.97(1H, d), 8.55~8.45(3H, m), 8.36(2H, m), 8.25~8.15(3H, m), 8.00~7.79(8H, m), 7.70(2H, t), 7.59~7.49(7H, m) |
| 1042 | 8.55(1H, d), 8.45(1H, d), 8.36~8.32(3H, m), 8.20~8.19(3H, m), 7.96~7.79(8H, m), 7.70~7.49(10H, m), 7.25(2H, d) |
| 1044 | 9.02(1H, d), 8.95(1H, d), 8.55(1H, d), 8.45(1H, d), 8.36(2H, d), 8.20(3H, m), 8.06(1H, d), 7.94~7.79(8H, m), 7.70~7.49(12H, m) |
| 1046 | 8.36(2H, d), 8.20~8.19(3H, m), 7.98~7.79(7H, m), 7.70~7.39(12H, m) |
| 1049 | 8.36(2H, d), 8.20~8.19(3H, m), 7.98~7.82(9H, m), 7.70~7.39(14H, m) |
| 1052 | 8.36(2H, d), 8.20~8.19(3H, m), 8.09(1H, d), 7.90~7.65(11H, m), 7.55~7.49(5H, m), 7.38(1H, t), 7.28(1H, t), 1.69(6H, s) |
| 1053 | 9.08(1H, d), 8.84(1H, d), 8.36(2H, d), 8.20~8.17(4H, m), 8.05(1H, s), 7.90~7.62(13H, m), 7.50~7.49(4H, m) |
| 1057 | 8.55(1H, d), 8.35(2H, d), 8.23(1H, s), 8.20~8.19(4H, m), 7.94~7.79(7H, m), 7.70~7.49(11H, m), 7.35(1H, t), 7.20~7.16(2H, m) |
| 1058 | 8.55(1H, d), 8.24~8.19(7H, m), 7.94~7.79(8H, m), 7.70~7.49(11H, m), 7.35(1H, t), 7.20~7.16(2H, m) |
| 1061 | 8.55(1H, d), 8.45(1H, d), 8.35~8.30(4H, m), 8.23(1H, s), 8.20~8.19(3H, m), 7.94~7.79(9H, m), 7.70~7.49(10H, m) |
| 1065 | 8.85(1H, s), 8.37~8.35(3H, m), 8.23(1H, s), 8.20(1H, d), 8.06~7.50(20H, m), 7.39~7.31(2H, m) |
| 1072 | 8.23(1H, s), 8.20~8.19(3H, m), 7.98~7.82(11H, m), 7.70~7.31(14H, m) |
| 1073 | 8.35~8.19(10H, m), 8.08~7.79(10H, m), 7.70~7.65(3H, m), 7.54~7.49(6H, m), 7.39~7.25(4H, m) |
| 1078 | 9.08(1H, d), 8.84(1H, d), 8.23~8.17(5H, m), 8.05(1H, s), 7.94~7.49(19H, m) |
| 1082 | 9.08(1H, d), 8.84(1H, d), 8.35~8.19(9H, m), 8.05(1H, s), 7.90~7.63(13H, m), 7.50~7.49(4H, m), 7.25(2H, d) |
| 1084 | 8.55(1H, d), 8.36(2H, d), 8.23~8.19(4H, m), 8.12(1H, s), 7.99~7.85(9H, m), 7.70(1H, t), 7.58~7.49(8H, m), 7.35(1H, t), 7.20~7.16(2H, m) |
| 1090 | 8.55(1H, d), 8.45(1H, d), 8.36~8.32(3H, m), 8.23~8.20(3H, m), 8.12(1H, s), 7.99~7.85(7H, m), 7.70(2H, m), 7.56~7.49(8H, m), 7.25(2H, m) |
| 1091 | 8.55(1H, d), 8.45(1H, d), 8.36(2H, m), 8.23~8.20(3H, m), 8.12(2H, m), 7.99~7.85(7H, m), 7.70(2H, m), 7.56~7.49(8H, m), 7.25(2H, m) |
| 1093 | 8.36(2H, d), 8.23~8.20(3H, m), 8.12(1H, s), 8.08(1H, d), 7.99~7.85(6H, m), 7.70(1H, t), 7.54~7.39(8H, m), 7.39~7.31(2H, m) |
| 1098 | 8.36(2H, m), 8.23~8.20(3H, m), 8.12(2H, m), 7.99~7.94(5H, m), 7.85~7.82(2H, m), 7.70~7.69(2H, m), 7.57~7.49(8H, m), 7.39~7.25(4H, m) |
| 1102 | 8.85(1H, s), 8.37~8.36(3H, m), 8.20(1H, d), 8.12~7.50(19H, m), 7.38(1H, t), 7.28(1H, t), 1.69(6H, s) |
| 1103 | 9.08(1H, d), 8.84(1H, d), 8.36(2H, d), 8.23~8.12(5H, m), 8.05~7.85(6H, m), 7.70~7.49(11H, m) |
| 1105 | 9.08(1H, d), 8.84(1H, d), 8.36(2H, d), 8.27~8.20(4H, m), 8.12(1H, s), 8.05~7.85(8H, m), 7.70~7.49(11H, m), 7.25(2H, m) |

TABLE 30-continued

| Compound | ¹H NMR (CDCl₃, 300 Mz) |
|---|---|
| 1109 | 8.55(1H, d), 8.23~8.19(5H, m), 8.12(1H, s), 7.99~7.85(11H, m), 7.70(1H, t), 7.58~7.49(8H, m), 7.35(1H, t), 7.20~7.16(2H, m) |
| 1111 | 8.55(1H, d), 8.35(2H, m), 8.23~8.19(5H, m), 8.12(1H, s), 7.99~7.85(9H, m), 7.70(1H, t), 7.58~7.49(8H, m), 7.35(1H, t), 7.20~7.16(2H, m) |
| 1114 | 8.55(1H, d), 8.45(1H, d), 8.32(1H, d), 8.23(3H, m), 8.20(1H, d), 8.12(1H, s), 7.99~7.85(9H, m), 7.70(2H, m), 7.55~7.49(6H, m), 7.25(2H, m) |
| 1119 | 8.55(1H, d), 8.45(1H, d), 8.35~8.20(9H, m), 8.12(1H, s), 7.99~7.85(5H, m), 7.70(2H, m), 7.56~7.49(8H, m), 7.25(2H, m) |
| 1121 | 8.35(2H, d), 8.23~8.20(4H, m), 8.12~8.09(2H, m), 7.99~7.70(8H, m), 7.55~7.49(7H, m), 7.38(1H, t), 7.28(1H, t), 1.69(6H, s) |
| 1124 | 9.08(1H, d), 8.84(1H, d), 8.30~8.20(7H, m), 8.12(1H, s), 8.05~7.85(8H, m), 7.70~7.49(11H, m), 7.25(2H, d) |
| 1129 | 8.55(1H, d), 8.36(2H, d), 8.23~8.19(6H, m), 7.94~7.83(6H, m), 7.70~7.49(11H, m), 7.35(1H, t), 7.20~7.16(2H, m) |
| 1135 | 8.55(1H, d), 8.45(1H, d), 8.36(2H, m), 8.23~8.20(3H, m), 7.96~7.79(9H, m), 7.70(2H, m), 7.56~7.49(8H, m), 7.25(2H, d) |
| 1138 | 8.36(2H, d), 8.23~8.20(3H, m), 7.98~7.79(7H, m), 7.70~7.69(2H, m), 7.57~7.49(8H, m), 7.39~7.31(2H, m) |
| 1142 | 8.36(2H, d), 8.23~8.20(3H, m), 7.98~7.79(9H, m), 7.70~7.69(2H, m), 7.57~7.49(8H, m), 7.39~7.25(4H, m) |
| 1143 | 8.36(2H, d), 8.23~8.20(3H, m), 8.08~7.79(12H, m), 7.70(1H, t), 7.54~7.49(8H, m), 7.39~7.25(6H, m) |
| 1146 | 8.85(1H, s), 8.36(3H, m), 8.20(1H, d), 8.09~7.50(19H, m), 7.38(1H, t), 7.28(1H, t), 1.69(6H, s) |
| 1147 | 9.08(1H, d), 8.84(1H, d), 8.36(2H, d), 8.23~8.17(4H, m), 8.05(1H, s), 7.94~7.49(17H, m) |
| 1150 | 8.55(1H, d), 8.23~8.19(5H, m), 7.94~7.83(12H, m), 7.70(1H, t), 7.58~7.49(8H, m), 7.35(1H, t), 7.20~7.16(2H, m) |
| 1151 | 8.55(1H, d), 8.35(2H, m), 8.23~8.19(6H, m), 7.94~7.79(7H, m), 7.70~7.49(11H, m), 7.35(1H, t), 7.20~7.16(2H, m) |
| 1157 | 8.85(1H, s), 8.55(1H, d), 8.45~8.35(4H, m), 8.23~8.20(2H, m), 8.06~7.49(19H, m) |
| 1162 | 8.55(1H, d), 8.45(1H, d), 8.32~8.20(7H, m), 7.94~7.79(8H, m), 7.70(2H, m), 7.56~7.49(8H, m), 7.25(2H, d) |
| 1165 | 8.35(2H, d), 8.23~8.20(4H, m), 8.09(1H, d), 7.90~7.70(9H, m), 7.55~7.49(7H, m), 7.38(1H, t), 7.28(1H, t) 1.69(6H, s) |
| 1166 | 8.23~8.20(4H, m), 8.09(1H, d), 7.94~7.70(11H, m), 7.55~7.49(7H, m), 7.38(1H, t), 7.28(1H, t), 1.69(6H, s) |
| 1169 | 9.11(1H, d), 8.70(1H, d), 8.46~8.20(10H, m), 7.92~7.49(19H, m) |

TABLE 31

| Compound | FD-MS | Compound | FD-MS |
|---|---|---|---|
| 1 | m/z = 629.71 (C43H27N5O = 629.22) | 519 | m/z = 676.76 (C48H28N4O = 676.23) |
| 11 | m/z = 707.84 (C48H29N5S = 707.21) | 524 | m/z = 642.75 (C45H30N4O = 642.24) |
| 13 | m/z = 783.94 (C54H33N5S = 783.25) | 527 | m/z = 768.90 (C55H36N4O = 768.29) |
| 16 | m/z = 757.90 (C52H31N5S = 757.23) | 537 | m/z = 702.80 (C50H30N4O = 702.24) |
| 17 | m/z = 648.80 (C42H24N4S2 = 648.14) | 540 | m/z = 702.80 (C50H30N4O = 702.24) |
| 20 | m/z = 724.89 (C48H28N4S2 = 724.18) | 546 | m/z = 741.84 (C52H31N5O = 741.25) |
| 21 | m/z = 724.89 (C48H28N4S2 = 724.18) | 550 | m/z = 741.84 (C52H31N5O = 741.25) |
| 24 | m/z = 774.95 (C52H30N4S2 = 774.19) | 553 | m/z = 632.73 (C42H24N4OS = 632.17) |
| 29 | m/z = 632.73 (C42H24N4OS = 632.17) | 557 | m/z = 696.82 (C47H28N4OS = 696.20) |
| 38 | m/z = 758.89 (C52H30N4OS = 758.21) | 559 | m/z = 708.83 (C48H28N4OS = 708.20) |
| 40 | m/z = 708.83 (C48H28N4OS = 708.20) | 562 | m/z = 758.89 (C52H30N4OS = 758.21) |
| 42 | m/z = 692.83 (C48H28N4S = 692.20) | 563 | m/z = 616.67 (C42H24N4O2 = 616.19) |
| 44 | m/z = 742.89 (C52H30N4S = 742.22) | 567 | m/z = 692.76 (C48H28N4O2 = 692.22) |
| 50 | m/z = 708.87 (C49H32N4S = 708.23) | 573 | m/z = 741.84 (C52H31N5O = 741.25) |
| 52 | m/z = 734.91 (C51H34N4S = 734.25) | 576 | m/z = 692.76 (C48H28N4O2 = 692.22) |
| 55 | m/z = 666.79 (C46H26N4S = 666.19) | 579 | m/z = 752.86 (C54H32N4O = 752.26) |
| 60 | m/z = 642.77 (C44H26N4S = 642.19) | 578 | m/z = 752.86 (C54H32N4O = 752.26) |
| 62 | m/z = 718.87 (C50H30N4S = 718.22) | 585 | m/z = 642.75 (C45H30N4O = 642.24) |
| 65 | m/z = 718.87 (C50H30N4S = 718.22) | 589 | m/z = 692.80 (C49H32N4O = 692.26) |
| 71 | m/z = 707.84 (C48H29N5S = 707.21) | 588 | m/z = 768.90 (C55H36N4O = 768.29) |
| 72 | m/z = 757.90 (C52H31N5S = 757.23) | 591 | m/z = 768.90 (C55H36N4O = 768.29) |
| 75 | m/z = 834.00 (C58H35N5S = 833.26) | 593 | m/z = 776.88 (C56H32N4O = 776.26) |
| 78 | m/z = 724.89 (C48H28N4S2 = 724.18) | 597 | m/z = 752.86 (C54H32N4O = 752.26) |
| 80 | m/z = 698.86 (C46H26N4S2 = 698.16) | 598 | m/z = 752.86 (C54H32N4O = 752.26) |
| 82 | m/z = 724.89 (C48H28N4S2 = 724.18) | 604 | m/z = 691.78 (C48H29N5O = 691.24) |
| 84 | m/z = 698.86 (C46H26N4S2 = 698.16) | 605 | m/z = 767.87 (C54H33N5O = 767.27) |
| 87 | m/z = 632.73 (C42H24N4OS = 632.17) | 608 | m/z = 741.84 (C52H31N5O = 741.25) |
| 93 | m/z = 708.83 (C48H28N4OS = 708.20) | 609 | m/z = 767.87 (C54H33N5O = 767.27) |
| 98 | m/z = 758.89 (C52H30N4OS = 758.21) | 613 | m/z = 632.73 (C42H24N4OS = 632.17) |

TABLE 31-continued

| Compound | FD-MS | Compound | FD-MS |
|---|---|---|---|
| 100 | m/z = 708.83 (C48H28N4OS = 708.20) | 616 | m/z = 758.89 (C52H30N4OS = 758.21) |
| 106 | m/z = 742.89 (C52H30N4S = 742.22) | 617 | m/z = 708.83 (C48H28N4OS = 708.20) |
| 116 | m/z = 734.91 (C51H34N4S = 734.25) | 618 | m/z = 708.83 (C48H28N4OS = 708.20) |
| 122 | m/z = 718.87 (C50H30N4S = 718.22) | 621 | m/z = 758.89 (C52H30N4OS = 758.21) |
| 125 | m/z = 768.92 (C54H32N4S = 768.23) | 626 | m/z = 742.82 (C52H30N4O2 = 742.24) |
| 127 | m/z = 707.84 (C48H29N5S = 707.21) | 632 | m/z = 666.72 (C46H26N4O2 = 666.21) |
| 130 | m/z = 757.90 (C52H31N5S = 757.23) | 638 | m/z = 676.76 (C48H28N4O = 676.23) |
| 135 | m/z = 834.00 (C58H35N5S = 833.26) | 641 | m/z = 752.86 (C54H32N4O = 752.26) |
| 137 | m/z = 648.80 (C42H24N4S2 = 648.14) | 645 | m/z = 718.84 (C51H34N4O = 718.27) |
| 140 | m/z = 724.89 (C48H28N4S2 = 724.18) | 650 | m/z = 768.90 (C55H36N4O = 768.29) |
| 141 | m/z = 724.89 (C48H28N4S2 = 724.18) | 653 | m/z = 776.88 (C56H32N4O = 776.26) |
| 144 | m/z = 698.86 (C46H26N4S2 = 698.16) | 661 | m/z = 752.86 (C54H32N4O = 752.26) |
| 146 | m/z = 774.95 (C52H30N4S2 = 774.19) | 663 | m/z = 702.80 (C50H30N4O = 702.24) |
| 155 | m/z = 682.79 (C46H26N4OS = 682.18) | 664 | m/z = 767.87 (C54H33N5O = 767.27) |
| 150 | m/z = 682.79 (C46H26N4OS = 682.18) | 666 | m/z = 741.84 (C52H31N5O = 741.25) |
| 152 | m/z = 708.83 (C48H28N4OS = 708.20) | 667 | m/z = 767.87 (C54H33N5O = 767.27) |
| 165 | m/z = 768.92 (C54H32N4S = 768.23) | 668 | m/z = 741.84 (C52H31N5O = 741.25) |
| 166 | m/z = 658.81 (C45H30N4S = 658.22) | 671 | m/z = 867.99 (C62H37N5O = 867.30) |
| 169 | m/z = 784.97 (C55H36N4S = 784.27) | 674 | m/z = 632.73 (C42H24N4OS = 632.17) |
| 190 | m/z = 757.23 (C52H31N5S = 757.90) | 680 | m/z = 708.83 (C48H28N4OS = 708.20) |
| 196 | m/z = 783.94 (C54H33N5S = 783.25) | 681 | m/z = 708.83 (C48H28N4OS = 708.20) |
| 198 | m/z = 648.80 (C42H24N4S2 = 648.14) | 682 | m/z = 732.85 (C50H28N4OS = 732.20) |
| 199 | m/z = 698.86 (C46H26N4S2 = 698.16) | 687 | m/z = 666.72 (C46H26N4O2 = 666.21) |
| 203 | m/z = 724.89 (C48H28N4S2 = 724.18) | 691 | m/z = 666.72 (C46H26N4O2 = 666.21) |
| 209 | m/z = 774.95 (C52H30N4S2 = 774.19) | 696 | m/z = 692.76 (C48H28N4O2 = 692.22) |
| 219 | m/z = 682.79 (C46H26N4OS = 682.18) | 699 | m/z = 742.82 (C52H30N4O2 = 742.24) |
| 220 | m/z = 708.83 (C48H28N4OS = 708.20) | 700 | m/z = 692.76 (C48H28N4O2 = 692.22) |
| 226 | m/z = 758.89 (C52H30N4OS = 758.21) | 703 | m/z = 676.76 (C48H28N4O = 676.23) |
| 231 | m/z = 658.81 (C45H30N4S = 658.22) | 712 | m/z = 718.84 (C51H34N4O = 718.27) |
| 234 | m/z = 734.91 (C51H34N4S = 734.25) | 721 | m/z = 826.95 (C60H34N4O = 826.27) |
| 242 | m/z = 742.90 (C52H30N4S = 742.21) | 722 | m/z = 702.80 (C50H30N4O = 702.24) |
| 247 | m/z = 744.23 (C50H30N4S = 744.23) | 724 | m/z = 752.86 (C54H32N4O = 752.26) |
| 250 | m/z = 706.85 (C49H30N4S = 706.22) | 725 | m/z = 690.79 (C49H30N4O = 690.24) |
| 254 | m/z = 782.95 (C55H34N4S = 782.25) | 727 | m/z = 690.79 (C49H30N4O = 690.24) |
| 259 | m/z = 647.81 (C43H25N3S2 = 647.15) | 731 | m/z = 707.84 (C49H29N3OS = 707.20) |
| 264 | m/z = 723.90 (C49H29N3S2 = 723.18) | 736 | m/z = 740.85 (C53H32N4O = 740.26) |
| 265 | m/z = 697.87 (C47H27N3S2 = 697.16) | 737 | m/z = 707.84 (C49H29N3OS = 707.20) |
| 266 | m/z = 773.96 (C53H31N3S2 = 773.20) | 740 | m/z = 707.84 (C49H29N3OS = 707.20) |
| 270 | m/z = 681.80 (C47H27N3OS = 681.19) | 742 | m/z = 757.90 (C53H31N3OS = 757.22) |
| 275 | m/z = 707.84 (C49H29N3OS = 707.20) | 748 | m/z = 615.68 (C43H25N3O2 = 615.19) |
| 282 | m/z = 741.90 (C53H31N3S = 741.22) | 750 | m/z = 665.74 (C47H27N3O2 = 665.21) |
| 283 | m/z = 657.82 (C46H31N3S = 657.22) | 751 | m/z = 691.77 (C49H29N3O2 = 691.23) |
| 285 | m/z = 657.82 (C46H31N3S = 657.22) | 753 | m/z = 767.87 (C55H33N3O2 = 767.22) |
| 288 | m/z = 707.88 (C50H33N3S = 707.24) | 754 | m/z = 675.77 (C49H29N3O = 675.23) |
| 290 | m/z = 733.92 (C52H35N3S = 733.26) | 757 | m/z = 675.77 (C49H29N3O = 675.23) |
| 296 | m/z = 641.78 (C45H27N3S = 641.19) | 763 | m/z = 767.91 (C56H37N3O = 767.29) |
| 297 | m/z = 641.78 (C45H27N3S = 641.19) | 764 | m/z = 691.82 (C50H33N3O = 691.26) |
| 299 | m/z = 793.97 (C57H35N3S = 793.26) | 765 | m/z = 817.97 (C60H39N3O = 817.31) |
| 303 | m/z = 756.91 (C53H32N4S = 756.23) | 768 | m/z = 649.75 (C47H27N3O = 649.21) |
| 305 | m/z = 833.01 (C59H36N4S = 832.27) | 774 | m/z = 751.87 (C55H33N3O = 751.26) |
| 307 | m/z = 756.91 (C53H32N4S = 756.23) | 777 | m/z = 740.85 (C53H32N4O = 740.26) |
| 310 | m/z = 647.81 (C43H25N3S2 = 647.15) | 778 | m/z = 690.79 (C49H30N4O = 690.24) |
| 315 | m/z = 723.90 (C49H29N3S2 = 723.18) | 780 | m/z = 766.88 (C55H34N4O = 766.27) |
| 316 | m/z = 723.90 (C49H29N3S2 = 723.18) | 782 | m/z = 725.85 (C53H31N3O = 725.24) |
| 318 | m/z = 800.00 (C55H33N3S2 = 799.21) | 784 | m/z = 740.85 (C53H32N4O = 740.26) |
| 324 | m/z = 707.84 (C49H29N3OS = 707.20) | 786 | m/z = 631.74 (C43H25N3OS = 631.17) |
| 326 | m/z = 707.84 (C49H29N3OS = 707.20) | 788 | m/z = 631.74 (C43H25N3OS = 631.17) |
| 330 | m/z = 757.90 (C53H31N3OS = 757.22) | 789 | m/z = 681.80 (C47H27N3OS = 681.19) |
| 331 | m/z = 707.84 (C49H29N3OS = 707.20) | 796 | m/z = 757.90 (C53H31N3OS = 757.22) |
| 332 | m/z = 691.84 (C49H29N3S = 691.21) | 798 | m/z = 615.68 (C43H25N3O2 = 615.19) |
| 336 | m/z = 691.84 (C49H29N3S = 691.21) | 803 | m/z = 691.77 (C49H29N3O2 = 691.23) |
| 341 | m/z = 707.88 (C50H33N3S = 707.24) | 811 | m/z = 725.83 (C53H31N3O = 725.25) |
| 348 | m/z = 733.92 (C52H35N3S = 733.26) | 816 | m/z = 641.76 (C46H31N3O = 641.25) |
| 350 | m/z = 665.80 (C47H27N3S = 665.19) | 818 | m/z = 641.76 (C46H31N3O = 641.25) |
| 359 | m/z = 793.97 (C57H35N3S = 793.26) | 820 | m/z = 691.82 (C50H33N3O = 691.26) |
| 362 | m/z = 706.85 (C49H30N4S = 706.22) | 824 | m/z = 767.91 (C56H37N3O = 767.29) |
| 363 | m/z = 706.85 (C49H30N4S = 706.22) | 829 | m/z = 775.89 (C57H33N3O = 775.26) |
| 364 | m/z = 756.91 (C53H32N4S = 756.23) | 830 | m/z = 701.81 (C51H31N3O = 701.25) |
| 366 | m/z = 756.91 (C53H32N4S = 756.23) | 833 | m/z = 751.87 (C55H33N3O = 751.26) |
| 370 | m/z = 647.81 (C43H25N3S2 = 647.15) | 836 | m/z = 690.79 (C49H30N4O = 690.24) |
| 371 | m/z = 697.87 (C47H27N3S2 = 697.16) | 837 | m/z = 690.79 (C49H30N4O = 690.24) |
| 373 | m/z = 723.90 (C49H29N3S2 = 723.18) | 839 | m/z = 740.85 (C53H32N4O = 740.26) |
| 375 | m/z = 773.96 (C53H31N3S2 = 773.20) | 844 | m/z = 631.74 (C43H25N3OS = 631.17) |
| 382 | m/z = 707.84 (C49H29N3OS = 707.20) | 846 | m/z = 707.84 (C49H29N3OS = 707.20) |
| 385 | m/z = 757.90 (C53H31N3OS = 757.22) | 848 | m/z = 707.84 (C49H29N3OS = 707.20) |
| 386 | m/z = 681.80 (C47H27N3OS = 681.19) | 852 | m/z = 757.90 (C53H31N3OS = 757.22) |
| 391 | m/z = 691.84 (C49H29N3S = 691.21) | 854 | m/z = 615.68 (C43H25N3O2 = 615.19) |

TABLE 31-continued

| Compound | FD-MS | Compound | FD-MS |
| --- | --- | --- | --- |
| 393 | m/z = 691.84 (C49H29N3S = 691.21) | 856 | m/z = 615.68 (C43H25N3O2 = 615.19) |
| 396 | m/z = 657.82 (C46H31N3S = 657.22) | 864 | m/z = 741.83 (C53H31N3O2 = 741.24) |
| 408 | m/z = 715.86 (C51H29N3S = 715.21) | 865 | m/z = 741.83 (C53H31N3O2 = 741.24) |
| 416 | m/z = 756.91 (C53H32N4S = 756.23) | 867 | m/z = 675.77 (C49H29N3O = 675.23) |
| 419 | m/z = 647.81 (C43H25N3S2 = 647.15) | 874 | m/z = 691.82 (C50H33N3O = 691.26) |
| 422 | m/z = 647.81 (C43H25N3S2 = 647.15) | 876 | m/z = 717.85 (C52H35N3O = 717.28) |
| 424 | m/z = 723.90 (C49H29N3S2 = 723.18) | 879 | m/z = 767.91 (C56H37N3O = 767.29) |
| 431 | m/z = 631.74 (C43H25N3OS = 631.17) | 880 | m/z = 649.74 (C47H27N3O = 649.22) |
| 432 | m/z = 631.74 (C43H25N3OS = 631.17) | 882 | m/z = 727.85 (C53H33N3O = 727.26) |
| 441 | m/z = 757.90 (C53H31N3OS = 757.22) | 885 | m/z = 701.81 (C51H31N3O = 701.25) |
| 443 | m/z = 681.80 (C47H27N3OS = 681.19) | 886 | m/z = 701.81 (C51H31N3O = 701.25) |
| 445 | m/z = 691.84 (C49H29N3S = 691.21) | 888 | m/z = 690.79 (C49H30N4O = 690.24) |
| 450 | m/z = 707.88 (C50H33N3S = 707.24) | 889 | m/z = 690.79 (C49H30N4O = 690.24) |
| 452 | m/z = 733.92 (C52H35N3S = 733.26) | 894 | m/z = 816.94 (C59H36N4O = 816.29) |
| 456 | m/z = 715.86 (C51H29N3S = 715.21) | 897 | m/z = 757.90 (C53H31N3OS = 757.22) |
| 460 | m/z = 767.94 (C55H33N3S = 767.24) | 898 | m/z = 631.74 (C43H25N3OS = 631.17) |
| 462 | m/z = 722.92 (C50H30N2S2 = 722.19) | 902 | m/z = 707.84 (C49H29N3OS = 707.20) |
| 465 | m/z = 656.84 (C47H32N2S = 656.23) | 903 | m/z = 681.80 (C47H27N3OS = 681.19) |
| 467 | m/z = 705.87 (C50H31N3S = 705.22) | 905 | m/z = 707.84 (C49H29N3OS = 707.20) |
| 471 | m/z = 766.95 (C56H34N2S = 766.24) | 906 | m/z = 691.77 (C49H29N3O2 = 691.23) |
| 476 | m/z = 630.76 (C44H26N2OS = 630.18) | 907 | m/z = 691.77 (C49H29N3O2 = 691.23) |
| 479 | m/z = 741.84 (C52H31N5O = 741.25) | 913 | m/z = 665.74 (C47H27N3O2 = 665.21) |
| 480 | m/z = 767.87 (C54H33N5O = 767.27) | 916 | m/z = 691.77 (C49H29N3O2 = 691.23) |
| 486 | m/z = 767.87 (C54H33N5O = 767.27) | 917 | m/z = 741.83 (C53H31N3O2 = 741.24) |
| 488 | m/z = 767.87 (C54H33N5O = 767.27) | 920 | m/z = 741.83 (C53H31N3O2 = 741.24) |
| 493 | m/z = 758.89 (C52H30N4OS = 758.21) | 930 | m/z = 717.85 (C52H35N3O = 717.28) |
| 498 | m/z = 708.83 (C48H28N4OS = 708.20) | 931 | m/z = 649.74 (C47H27N3O = 649.22) |
| 499 | m/z = 682.79 (C46H26N4OS = 682.18) | 935 | m/z = 751.87 (C55H33N3O = 751.26) |
| 502 | m/z = 616.67 (C42H24N4O2 = 616.19) | 936 | m/z = 689.80 (C50H31N3O = 689.25) |
| 506 | m/z = 692.76 (C48H28N4O2 = 692.22) | 938 | m/z = 690.79 (C50H30N2O2 = 690.23) |
| 508 | m/z = 742.82 (C52H30N4O2 = 742.24) | 943 | m/z = 706.85 (C50H30N2OS = 706.21) |
| 511 | m/z = 742.82 (C52H30N4O2 = 742.24) | 948 | m/z = 640.77 (C47H32N2O = 640.25) |
| 517 | m/z = 692.76 (C48H28N4O2 = 692.22) | 949 | m/z = 689.80 (C50H31N3O = 689.25) |
| 953 | m/z = 707.85 (C48H29N5S = 707.21) | 956 | m/z = 698.16 (C46H26N4S2 = 698.16) |
| 960 | m/z = 774.96 (C52H30N4S2 = 774.19) | 962 | m/z = 632.74 (C42H24N4OS = 632.16) |
| 966 | m/z = 708.83 (C48H28N4OS = 708.19) | 969 | m/z = 658.82 (C45H30N4S = 658.21) |
| 973 | m/z = 718.87 (C50H30N4S = 718.21) | 975 | m/z = 706.86 (C49H30N4S = 706.21) |
| 981 | m/z = 697.87 (C47H27N3S2 = 697.16) | 984 | m/z = 647.81 (C43H25N3S2 = 647.14) |
| 986 | m/z = 723.91 (C49H29N3S2 = 723.18) | 989 | m/z = 723.91 (C49H29N3S2 = 723.18) |
| 991 | m/z = 631.75 (C43H25N3OS = 631.17) | 996 | m/z = 631.75 (C43H25N3OS = 631.17) |
| 1003 | m/z = 657.83 (C46H31N3S = 657.22) | 1007 | m/z = 733.93 (C52H35N3S = 733.25) |
| 1013 | m/z = 641.79 (C45H27N3S = 641.19) | 1014 | m/z = 717.89 (C51H31N3S = 717.22) |
| 1020 | m/z = 602.69 (C42H26N4O = 602.21) | 1021 | m/z = 601.70 (C43H27N3O = 601.21) |
| 1026 | m/z = 694.85 (C48H30N4S = 694.21) | 1027 | m/z = 677.80 (C49H31N3O = 677.24) |
| 1030 | m/z = 694.85 (C48H30N4S = 694.21) | 1031 | m/z = 693.86 (C49H31N3S = 693.22) |
| 1033 | m/z = 693.86 (C49H31N3S = 693.22) | 1034 | m/z = 618.75 (C42H26N4S = 618.18) |
| 1035 | m/z = 601.70 (C43H27N3O = 601.21) | 1036 | m/z = 691.79 (C48H29N5O = 691.23) |
| 1039 | m/z = 632.74 (C42H24N4OS = 632.16) | 1041 | m/z = 682.80 (C46H26N4OS = 682.18) |
| 1042 | m/z = 708.83 (C48H28N4OS = 708.19) | 1044 | m/z = 758.89 (C52H30N4OS = 758.21) |
| 1046 | m/z = 616.68 (C42H24N4O2 = 616.19) | 1049 | m/z = 692.77 (C48H28N4O2 = 692.22) |
| 1052 | m/z = 642.76 (C45H30N4O = 642.24) | 1053 | m/z = 626.71 (C44H26N4O = 626.21) |
| 1057 | m/z = 690.80 (C49H30N4O = 690.24) | 1058 | m/z = 690.80 (C49H30N4O = 690.24) |
| 1061 | m/z = 707.85 (C49H29N3OS = 707.20) | 1065 | m/z = 665.75 (C47H27N3O2 = 665.21) |
| 1072 | m/z = 691.79 (C49H29N3O2 = 691.22) | 1073 | m/z = 767.88 (C55H33N3O2 = 767.25) |
| 1078 | m/z = 625.73 (C45H27N3O = 625.21) | 1082 | m/z = 701.82 (C51H31N3O = 701.24) |
| 1084 | m/z = 707.85 (C48H29N5S = 707.21) | 1090 | m/z = 724.90 (C48H28N4S2 = 724.17) |
| 1091 | m/z7 = 24.90 (C48H28N4S2 = 724.17) | 1093 | m/z = 632.74 (C42H24N4OS = 632.16) |
| 1098 | m/z = 708.83 (C48H28N4OS = 708.19) | 1102 | m/z = 708.88 (C49H32N4S = 708.23) |
| 1103 | m/z = 642.78 (C44H26N4S = 642.18) | 1105 | m/z = 718.87 (C50H30N4S = 718.21) |
| 1109 | m/z = 706.86 (C49H30N4S = 706.21) | 1111 | m/z = 706.86 (C49H30N4S = 706.21) |
| 1119 | m/z = 723.91 (C49H29N3S2 = 723.18) | 1121 | m/z = 657.83 (C46H31N3S = 657.22) |
| 1124 | m/z = 717.89 (C51H31N3S = 717.22) | 1129 | m/z = 691.79 (C48H29N5O = 691.23) |
| 1135 | m/z = 708.83 (C48H28N4OS = 708.19) | 1138 | m/z = 616.68 (C42H24N4O2 = 616.19) |
| 1142 | m/z = 692.77 (C48H28N4O2 = 692.22) | 1143 | m/z = 768.87 (C54H32N4O2 = 768.25) |
| 1146 | m/z = 692.82 (C49H32N4O = 692.25) | 1147 | m/z = 626.71 (C44H26N4O = 626.21) |
| 1150 | m/z = 690.80 (C49H30N4O = 690.24) | 1151 | m/z = 690.80 (C49H30N4O = 690.24) |
| 1157 | m/z = 681.81 (C47H27N3OS = 681.18) | 1162 | m/z = 707.85 (C49H29N3OS = 707.20) |
| 1165 | m/z = 641.77 (C46H31N3O = 641.24) | 1166 | m/z = 641.77 (C46H31N3O = 641.24) |
| 1169 | m/z = 701.82 (C51H31N3O = 701.24) | | |

[Experimental Example 1] (Manufacture of Organic Light Emitting Diode-Electron Transfer Layer)

Comparative Example 1

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, the ITO substrate was installed in a substrate folder of a vacuum deposition apparatus, and the following 4,4',4"-tris(N,N-(2-naphthyl)-phenylamino)triphenylamine (2-TNATA) was introduced to a cell in the vacuum deposition apparatus.

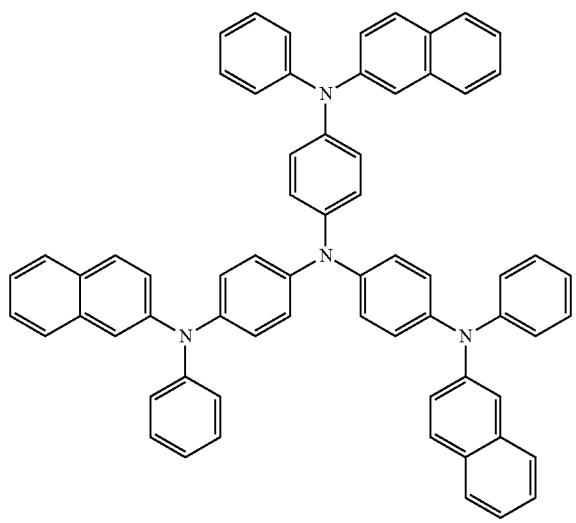

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

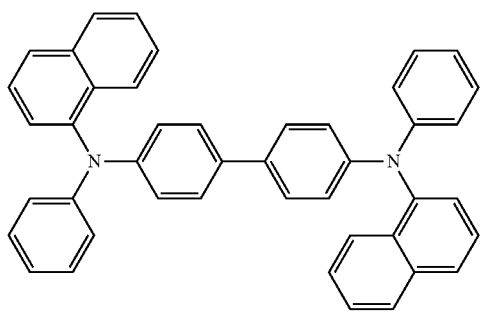

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

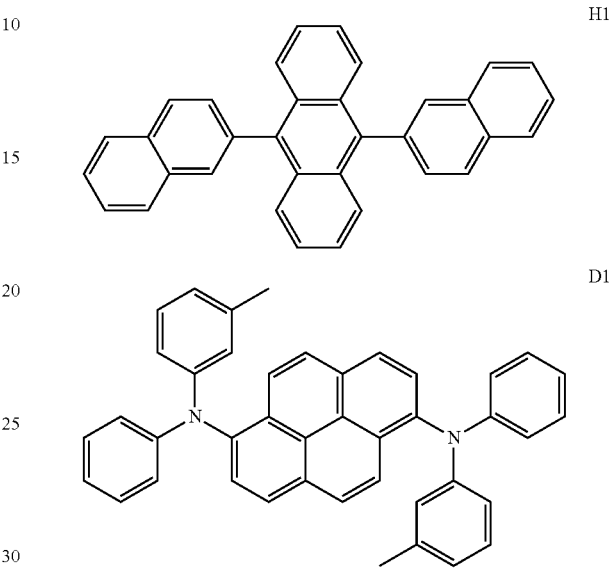

Subsequently, as an electron transfer layer, a compound of the following structural formula E1 was deposited to a thickness of 300 Å.

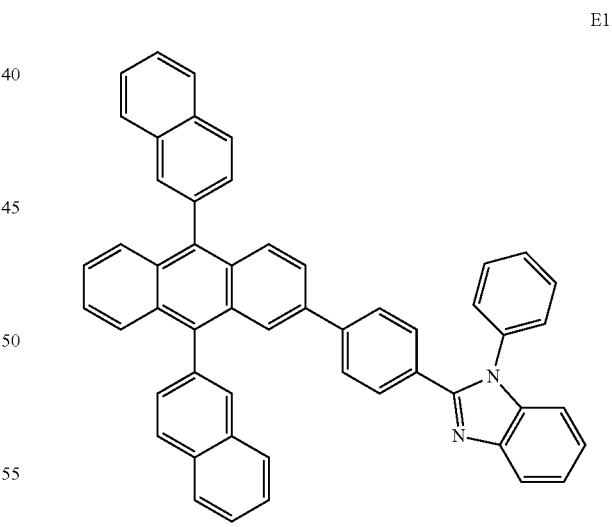

As an electron injection layer, lithium fluoride (LiF) was deposited to a thickness of 10 Å, and an Al cathode was deposited to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Comparative Example 2 and Comparative Example 3

Organic electroluminescent diodes were manufactured in the same manner as in Comparative Example 1 except that Compound A and Compound B were used instead of E1 used when forming the electron transfer layer.

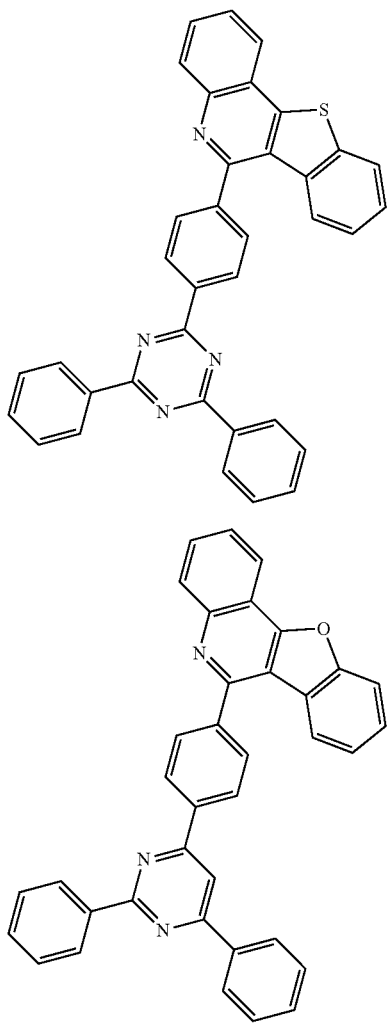

Examples 1 to 226

Organic electroluminescent diodes were manufactured in the same manner as in Comparative Example 1 except that compounds presented in Table 32 were used instead of E1 when forming the electron transfer layer.

Evaluation: Driving Voltage, Light Emission Efficiency, Color Coordinate (CIE) and Lifetime of Organic Electroluminescent Diode Results of measuring driving voltage, light emission efficiency, color coordinate (CIE) and lifetime of the blue organic light emitting diode manufactured according to the present disclosure are as shown in Table 32.

Electroluminescent (EL) properties were measured using M7000 manufactured by McScience Inc., and with the measurement results, $T_{95}$ was measured when standard luminance was 3,500 cd/m$^2$ using a lifetime measurement system (M6000) manufactured by McScience Inc. Results of measuring driving voltage, light emission efficiency, color coordinate (CIE) and lifetime of the blue organic electroluminescent diode manufactured according to the present disclosure are as shown in Table 32.

TABLE 32

| | Compound | Driving Voltage (V) | Light Emission Efficiency (cd/A) | CIE (x, y) | Lifetime (T95) |
|---|---|---|---|---|---|
| Comparative Example 1 | E1 | 5.70 | 6.00 | (0.134, 0.102) | 20 |
| Comparative Example 2 | A | 6.10 | 4.57 | (0.134, 0.098) | 18 |
| Comparative Example 3 | B | 6.06 | 4.68 | (0.134, 0.098) | 19 |
| Example 1 | 1 | 5.42 | 6.22 | (0.134, 0.101) | 42 |
| Example 2 | 11 | 5.44 | 6.22 | (0.134, 0.102) | 34 |
| Example 3 | 13 | 5.62 | 5.95 | (0.134, 0.103) | 37 |
| Example 4 | 16 | 5.01 | 6.10 | (0.134, 0.100) | 32 |
| Example 5 | 17 | 5.62 | 6.38 | (0.134, 0.100) | 35 |
| Example 6 | 20 | 5.32 | 6.20 | (0.134, 0.102) | 39 |
| Example 7 | 24 | 5.45 | 6.11 | (0.134, 0.103) | 30 |
| Example 8 | 29 | 5.44 | 6.34 | (0.134, 0.102) | 36 |
| Example 9 | 38 | 5.62 | 6.20 | (0.134, 0.101) | 39 |
| Example 10 | 40 | 5.40 | 6.12 | (0.134, 0.103) | 40 |
| Example 11 | 42 | 5.61 | 6.01 | (0.134, 0.102) | 35 |
| Example 12 | 52 | 5.45 | 6.22 | (0.134, 0.101) | 37 |
| Example 13 | 55 | 4.98 | 5.99 | (0.134, 0.101) | 38 |
| Example 14 | 60 | 5.21 | 6.23 | (0.134, 0.100) | 45 |
| Example 15 | 62 | 5.05 | 6.12 | (0.134, 0.100) | 38 |
| Example 16 | 65 | 5.21 | 6.01 | (0.134, 0.101) | 35 |
| Example 17 | 71 | 5.31 | 5.78 | (0.134, 0.100) | 37 |
| Example 18 | 78 | 5.62 | 5.41 | (0.134, 0.100) | 30 |
| Example 19 | 80 | 5.44 | 6.13 | (0.134, 0.102) | 32 |
| Example 20 | 82 | 5.38 | 6.38 | (0.134, 0.101) | 39 |
| Example 21 | 84 | 5.38 | 6.20 | (0.134, 0.103) | 31 |
| Example 22 | 87 | 5.39 | 6.02 | (0.134, 0.102) | 39 |
| Example 23 | 93 | 5.31 | 5.87 | (0.134, 0.100) | 35 |
| Example 24 | 100 | 5.15 | 5.87 | (0.134, 0.102) | 33 |
| Example 25 | 114 | 5.21 | 5.90 | (0.134, 0.101) | 32 |
| Example 26 | 116 | 5.01 | 6.21 | (0.134, 0.101) | 39 |
| Example 27 | 125 | 5.62 | 5.90 | (0.134, 0.100) | 34 |
| Example 28 | 127 | 5.39 | 5.95 | (0.134, 0.101) | 34 |
| Example 29 | 130 | 5.40 | 5.85 | (0.134, 0.101) | 34 |
| Example 30 | 137 | 5.38 | 6.38 | (0.134, 0.101) | 39 |
| Example 31 | 140 | 5.38 | 6.04 | (0.134, 0.103) | 35 |
| Example 32 | 141 | 5.21 | 6.42 | (0.134, 0.102) | 40 |
| Example 33 | 144 | 5.01 | 6.01 | (0.134, 0.101) | 35 |
| Example 34 | 152 | 4.91 | 6.00 | (0.134, 0.102) | 35 |
| Example 35 | 155 | 5.21 | 6.12 | (0.134, 0.101) | 37 |
| Example 36 | 165 | 5.38 | 6.03 | (0.134, 0.101) | 35 |
| Example 37 | 166 | 5.00 | 6.10 | (0.134, 0.102) | 36 |
| Example 38 | 190 | 5.39 | 6.04 | (0.134, 0.102) | 32 |
| Example 39 | 198 | 5.33 | 6.21 | (0.134, 0.101) | 35 |
| Example 40 | 199 | 5.41 | 6.04 | (0.134, 0.102) | 34 |
| Example 41 | 203 | 5.01 | 5.99 | (0.134, 0.101) | 37 |
| Example 42 | 219 | 4.98 | 6.03 | (0.134, 0.101) | 34 |
| Example 43 | 220 | 5.21 | 6.07 | (0.134, 0.102) | 38 |
| Example 44 | 234 | 5.39 | 5.95 | (0.134, 0.101) | 34 |
| Example 45 | 254 | 5.12 | 6.41 | (0.134, 0.102) | 44 |
| Example 46 | 259 | 4.98 | 6.34 | (0.134, 0.100) | 41 |
| Example 47 | 264 | 5.12 | 6.51 | (0.134, 0.100) | 44 |
| Example 48 | 265 | 5.21 | 6.22 | (0.134, 0.102) | 37 |
| Example 49 | 266 | 5.23 | 6.22 | (0.134, 0.100) | 38 |
| Example 50 | 270 | 5.11 | 6.21 | (0.134, 0.100) | 35 |
| Example 51 | 275 | 5.62 | 5.98 | (0.134, 0.100) | 39 |
| Example 52 | 285 | 4.75 | 5.78 | (0.134, 0.102) | 38 |
| Example 53 | 288 | 4.72 | 5.88 | (0.134, 0.102) | 38 |
| Example 54 | 290 | 4.91 | 5.98 | (0.134, 0.100) | 47 |
| Example 55 | 296 | 5.01 | 6.02 | (0.134, 0.100) | 45 |
| Example 56 | 297 | 5.00 | 6.61 | (0.134, 0.101) | 44 |
| Example 57 | 305 | 5.62 | 5.98 | (0.134, 0.100) | 34 |
| Example 58 | 307 | 5.31 | 6.53 | (0.134, 0.102) | 35 |
| Example 59 | 310 | 5.31 | 6.55 | (0.134, 0.102) | 38 |
| Example 60 | 315 | 5.21 | 6.40 | (0.134, 0.101) | 41 |

TABLE 32-continued

| | Compound | Driving Voltage (V) | Light Emission Efficiency (cd/A) | CIE (x, y) | Lifetime (T95) |
|---|---|---|---|---|---|
| Example 61 | 316 | 5.44 | 6.04 | (0.134, 0.100) | 32 |
| Example 62 | 326 | 5.21 | 6.11 | (0.134, 0.100) | 47 |
| Example 63 | 330 | 4.96 | 6.88 | (0.134, 0.100) | 30 |
| Example 64 | 331 | 4.95 | 6.95 | (0.134, 0.100) | 31 |
| Example 65 | 332 | 5.24 | 6.01 | (0.134, 0.100) | 35 |
| Example 66 | 336 | 5.62 | 5.98 | (0.134, 0.100) | 30 |
| Example 67 | 348 | 4.98 | 6.21 | (0.134, 0.102) | 46 |
| Example 68 | 350 | 5.40 | 6.12 | (0.134, 0.101) | 29 |
| Example 69 | 362 | 5.27 | 6.33 | (0.134, 0.101) | 43 |
| Example 70 | 363 | 5.01 | 6.20 | (0.134, 0.102) | 44 |
| Example 71 | 366 | 5.39 | 6.88 | (0.134, 0.100) | 30 |
| Example 72 | 370 | 5.21 | 6.21 | (0.134, 0.100) | 30 |
| Example 73 | 371 | 5.02 | 6.11 | (0.134, 0.101) | 38 |
| Example 74 | 373 | 5.15 | 6.11 | (0.134, 0.100) | 40 |
| Example 75 | 382 | 4.82 | 6.00 | (0.134, 0.102) | 40 |
| Example 76 | 391 | 5.21 | 6.53 | (0.134, 0.102) | 33 |
| Example 77 | 393 | 5.40 | 6.12 | (0.134, 0.101) | 31 |
| Example 78 | 396 | 4.98 | 6.22 | (0.134, 0.102) | 43 |
| Example 79 | 408 | 5.51 | 6.21 | (0.134, 0.102) | 39 |
| Example 80 | 416 | 5.01 | 6.11 | (0.134, 0.100) | 46 |
| Example 81 | 419 | 5.44 | 6.13 | (0.134, 0.102) | 32 |
| Example 82 | 422 | 5.42 | 6.02 | (0.134, 0.100) | 33 |
| Example 83 | 431 | 5.28 | 6.11 | (0.134, 0.102) | 38 |
| Example 84 | 432 | 5.30 | 6.01 | (0.134, 0.102) | 31 |
| Example 85 | 443 | 5.31 | 6.04 | (0.134, 0.102) | 32 |
| Example 86 | 445 | 4.63 | 6.11 | (0.134, 0.102) | 34 |
| Example 87 | 460 | 4.91 | 6.12 | (0.134, 0.100) | 33 |
| Example 88 | 462 | 4.99 | 6.01 | (0.134, 0.100) | 31 |
| Example 89 | 467 | 4.98 | 6.01 | (0.134, 0.100) | 33 |
| Example 90 | 480 | 5.62 | 5.98 | (0.134, 0.100) | 33 |
| Example 91 | 486 | 5.43 | 6.03 | (0.134, 0.102) | 35 |
| Example 92 | 498 | 4.88 | 6.01 | (0.134, 0.102) | 42 |
| Example 93 | 499 | 5.40 | 6.12 | (0.134, 0.101) | 39 |
| Example 94 | 502 | 5.01 | 6.04 | (0.134, 0.100) | 37 |
| Example 95 | 506 | 5.39 | 6.01 | (0.134, 0.101) | 32 |
| Example 96 | 508 | 4.89 | 6.24 | (0.134, 0.102) | 38 |
| Example 97 | 517 | 4.91 | 6.82 | (0.134, 0.100) | 30 |
| Example 98 | 519 | 5.19 | 5.71 | (0.134, 0.102) | 32 |
| Example 99 | 524 | 5.33 | 6.78 | (0.134, 0.100) | 31 |
| Example 100 | 546 | 4.90 | 5.71 | (0.134, 0.100) | 31 |
| Example 101 | 550 | 4.98 | 6.03 | (0.134, 0.100) | 37 |
| Example 102 | 553 | 5.32 | 5.98 | (0.134, 0.100) | 33 |
| Example 103 | 557 | 5.02 | 6.11 | (0.134, 0.100) | 37 |
| Example 104 | 559 | 5.05 | 6.09 | (0.134, 0.100) | 40 |
| Example 105 | 562 | 5.42 | 6.11 | (0.134, 0.101) | 33 |
| Example 106 | 563 | 4.85 | 6.01 | (0.134, 0.102) | 38 |
| Example 107 | 567 | 4.80 | 6.14 | (0.134, 0.100) | 39 |
| Example 108 | 573 | 4.98 | 6.22 | (0.134, 0.100) | 32 |
| Example 109 | 576 | 5.03 | 5.98 | (0.134, 0.100) | 33 |
| Example 110 | 585 | 5.25 | 6.02 | (0.134, 0.101) | 35 |
| Example 111 | 588 | 5.25 | 5.70 | (0.134, 0.101) | 32 |
| Example 112 | 604 | 4.74 | 5.83 | (0.134, 0.102) | 35 |
| Example 113 | 605 | 5.42 | 6.13 | (0.134, 0.101) | 35 |
| Example 114 | 608 | 4.74 | 5.83 | (0.134, 0.102) | 35 |
| Example 115 | 609 | 5.31 | 6.10 | (0.134, 0.101) | 36 |
| Example 116 | 613 | 5.44 | 5.89 | (0.134, 0.100) | 41 |
| Example 117 | 617 | 5.36 | 6.01 | (0.134, 0.101) | 37 |
| Example 118 | 618 | 5.21 | 6.11 | (0.134, 0.100) | 37 |
| Example 119 | 621 | 5.11 | 6.21 | (0.134, 0.100) | 36 |
| Example 120 | 626 | 5.26 | 6.07 | (0.134, 0.100) | 34 |
| Example 121 | 632 | 5.34 | 6.11 | (0.134, 0.101) | 38 |
| Example 122 | 641 | 4.86 | 5.93 | (0.134, 0.102) | 32 |
| Example 123 | 653 | 5.21 | 6.11 | (0.134, 0.102) | 34 |
| Example 124 | 661 | 5.31 | 5.88 | (0.134, 0.100) | 32 |
| Example 125 | 664 | 5.31 | 6.01 | (0.134, 0.100) | 35 |
| Example 126 | 671 | 5.22 | 6.04 | (0.134, 0.100) | 35 |
| Example 127 | 674 | 5.13 | 6.24 | (0.134, 0.102) | 41 |
| Example 128 | 680 | 5.31 | 6.21 | (0.134, 0.102) | 37 |
| Example 129 | 681 | 4.72 | 5.91 | (0.134, 0.100) | 38 |
| Example 130 | 682 | 4.79 | 6.55 | (0.134, 0.102) | 31 |
| Example 131 | 699 | 4.88 | 6.13 | (0.134, 0.101) | 31 |
| Example 132 | 700 | 5.12 | 5.89 | (0.134, 0.100) | 34 |
| Example 133 | 703 | 5.31 | 6.01 | (0.134, 0.101) | 35 |
| Example 134 | 712 | 5.11 | 6.21 | (0.134, 0.100) | 39 |
| Example 135 | 721 | 5.45 | 6.21 | (0.134, 0.101) | 37 |
| Example 136 | 722 | 5.44 | 6.22 | (0.134, 0.102) | 34 |
| Example 137 | 725 | 4.99 | 6.21 | (0.134, 0.103) | 46 |
| Example 138 | 731 | 4.98 | 6.44 | (0.134, 0.100) | 32 |
| Example 139 | 736 | 5.62 | 6.38 | (0.134, 0.100) | 35 |
| Example 140 | 737 | 5.45 | 5.87 | (0.134, 0.102) | 32 |
| Example 141 | 740 | 5.45 | 6.06 | (0.134, 0.103) | 41 |
| Example 142 | 748 | 5.01 | 6.43 | (0.134, 0.100) | 42 |
| Example 143 | 751 | 5.21 | 6.20 | (0.134, 0.101) | 48 |
| Example 144 | 754 | 5.40 | 5.88 | (0.134, 0.103) | 35 |
| Example 145 | 757 | 5.60 | 5.92 | (0.134, 0.102) | 35 |
| Example 146 | 764 | 5.45 | 6.22 | (0.134, 0.101) | 37 |
| Example 147 | 768 | 5.40 | 5.88 | (0.134, 0.103) | 34 |
| Example 148 | 774 | 5.21 | 6.21 | (0.134, 0.100) | 45 |
| Example 149 | 778 | 4.81 | 6.01 | (0.134, 0.100) | 46 |
| Example 150 | 780 | 5.33 | 6.21 | (0.134, 0.101) | 35 |
| Example 151 | 782 | 5.05 | 6.31 | (0.134, 0.100) | 44 |
| Example 152 | 786 | 5.03 | 6.11 | (0.134, 0.100) | 44 |
| Example 153 | 788 | 5.01 | 6.08 | (0.134, 0.100) | 40 |
| Example 154 | 789 | 5.38 | 6.38 | (0.134, 0.101) | 35 |
| Example 155 | 796 | 5.38 | 6.20 | (0.134, 0.103) | 34 |
| Example 156 | 798 | 4.80 | 6.01 | (0.134, 0.102) | 39 |
| Example 157 | 803 | 5.38 | 6.14 | (0.134, 0.100) | 42 |
| Example 158 | 811 | 5.62 | 5.98 | (0.134, 0.100) | 33 |
| Example 159 | 816 | 5.21 | 6.21 | (0.134, 0.101) | 44 |
| Example 160 | 818 | 5.39 | 6.01 | (0.134, 0.101) | 32 |
| Example 161 | 820 | 5.21 | 6.51 | (0.134, 0.100) | 40 |
| Example 162 | 829 | 5.39 | 6.01 | (0.134, 0.101) | 36 |
| Example 163 | 830 | 5.01 | 6.21 | (0.134, 0.100) | 47 |
| Example 164 | 836 | 4.98 | 6.22 | (0.134, 0.100) | 42 |
| Example 165 | 837 | 5.02 | 6.21 | (0.134, 0.101) | 43 |
| Example 166 | 839 | 4.71 | 5.45 | (0.134, 0.102) | 35 |
| Example 167 | 844 | 4.72 | 5.98 | (0.134, 0.102) | 40 |
| Example 168 | 848 | 4.74 | 6.50 | (0.134, 0.102) | 45 |
| Example 169 | 854 | 4.82 | 6.31 | (0.134, 0.102) | 44 |
| Example 170 | 856 | 4.83 | 6.29 | (0.134, 0.102) | 45 |
| Example 171 | 864 | 5.21 | 5.99 | (0.134, 0.100) | 33 |
| Example 172 | 865 | 5.44 | 5.89 | (0.134, 0.100) | 34 |
| Example 173 | 867 | 5.50 | 6.12 | (0.134, 0.103) | 37 |
| Example 174 | 874 | 5.60 | 6.21 | (0.134, 0.102) | 40 |
| Example 175 | 876 | 4.82 | 6.33 | (0.134, 0.102) | 45 |
| Example 176 | 880 | 5.21 | 6.13 | (0.134, 0.101) | 33 |
| Example 177 | 882 | 5.62 | 6.20 | (0.134, 0.100) | 34 |
| Example 178 | 886 | 5.11 | 6.12 | (0.134, 0.100) | 33 |
| Example 179 | 888 | 4.91 | 6.21 | (0.134, 0.101) | 46 |
| Example 180 | 889 | 4.93 | 6.21 | (0.134, 0.101) | 45 |
| Example 181 | 894 | 5.62 | 5.95 | (0.134, 0.100) | 33 |
| Example 182 | 898 | 5.13 | 6.21 | (0.134, 0.102) | 41 |
| Example 183 | 902 | 5.32 | 6.38 | (0.134, 0.101) | 43 |
| Example 184 | 903 | 5.25 | 6.20 | (0.134, 0.103) | 37 |
| Example 185 | 905 | 5.07 | 6.33 | (0.134, 0.102) | 44 |
| Example 186 | 906 | 4.77 | 6.21 | (0.134, 0.101) | 33 |
| Example 187 | 907 | 4.91 | 6.22 | (0.134, 0.102) | 33 |
| Example 188 | 913 | 4.91 | 6.12 | (0.134, 0.101) | 31 |
| Example 189 | 916 | 4.88 | 6.04 | (0.134, 0.101) | 33 |
| Example 190 | 917 | 4.68 | 5.88 | (0.134, 0.100) | 32 |
| Example 191 | 930 | 4.77 | 5.91 | (0.134, 0.100) | 39 |
| Example 192 | 931 | 4.98 | 5.93 | (0.134, 0.100) | 35 |
| Example 193 | 953 | 4.91 | 6.21 | (0.134, 0.100) | 46 |
| Example 194 | 960 | 5.12 | 6.21 | (0.134, 0.101) | 38 |
| Example 195 | 966 | 4.93 | 6.21 | (0.134, 0.101) | 45 |
| Example 196 | 969 | 5.62 | 5.95 | (0.134, 0.100) | 33 |
| Example 197 | 975 | 4.92 | 6.21 | (0.134, 0.102) | 41 |
| Example 198 | 984 | 5.32 | 6.38 | (0.134, 0.101) | 32 |
| Example 199 | 989 | 5.11 | 6.20 | (0.134, 0.103) | 37 |
| Example 200 | 996 | 5.07 | 6.33 | (0.134, 0.102) | 32 |
| Example 201 | 1003 | 5.32 | 6.21 | (0.134, 0.101) | 33 |
| Example 202 | 1007 | 5.11 | 6.31 | (0.134, 0.102) | 35 |
| Example 203 | 1013 | 4.91 | 6.12 | (0.134, 0.101) | 45 |
| Example 204 | 1020 | 4.88 | 6.04 | (0.134, 0.101) | 39 |

TABLE 32-continued

| Compound | Driving Voltage (V) | Light Emission Efficiency (cd/A) | CIE (x, y) | Lifetime (T95) |
|---|---|---|---|---|
| Example 205 | 1021 | 4.68 | 5.88 | (0.134, 0.100) | 41 |
| Example 206 | 1026 | 4.77 | 5.91 | (0.134, 0.100) | 39 |
| Example 207 | 1030 | 5.20 | 5.93 | (0.134, 0.100) | 40 |
| Example 208 | 1031 | 5.21 | 5.91 | (0.134, 0.101) | 39 |
| Example 209 | 1033 | 5.20 | 5.91 | (0.134, 0.101) | 40 |
| Example 210 | 1034 | 4.66 | 6.21 | (0.134, 0.100) | 33 |
| Example 211 | 1035 | 4.71 | 6.01 | (0.134, 0.101) | 36 |
| Example 212 | 1036 | 5.01 | 6.21 | (0.134, 0.100) | 42 |
| Example 213 | 1042 | 4.98 | 6.22 | (0.134, 0.100) | 42 |
| Example 214 | 1058 | 5.02 | 6.21 | (0.134, 0.101) | 47 |
| Example 215 | 1061 | 4.81 | 6.11 | (0.134, 0.101) | 40 |
| Example 216 | 1084 | 5.11 | 5.98 | (0.134, 0.102) | 43 |
| Example 217 | 1093 | 4.74 | 5.21 | (0.134, 0.102) | 35 |
| Example 218 | 1098 | 5.21 | 6.31 | (0.134, 0.102) | 44 |
| Example 219 | 1111 | 5.15 | 6.01 | (0.134, 0.102) | 46 |
| Example 220 | 1135 | 4.71 | 5.45 | (0.134, 0.102) | 38 |
| Example 221 | 1143 | 4.72 | 5.98 | (0.134, 0.102) | 40 |
| Example 222 | 1147 | 4.71 | 5.45 | (0.134, 0.102) | 35 |
| Example 223 | 1150 | 4.72 | 6.01 | (0.134, 0.102) | 43 |
| Example 224 | 1151 | 4.84 | 6.21 | (0.134, 0.102) | 43 |
| Example 225 | 1162 | 4.82 | 6.31 | (0.134, 0.102) | 44 |
| Example 226 | 1165 | 5.11 | 5.89 | (0.134, 0.102) | 39 |

As seen from the results of Table 32, the organic light emitting diode using the electron transfer layer material of the blue organic light emitting diode of the present disclosure had lower driving voltage and improved light emission efficiency and lifetime compared to Comparative Example 1.

In addition, light emission efficiency and lifetime were significantly improved when using Compounds 254, 259, 264, 290, 296, 297, 326, 348, 315, 362, 363, 416, 725, 748, 740, 751, 778, 803, 836, 837, 888, 889 and 905 compared to Comparative Example 2 and Comparative Example 3.

[Experimental Example 2] (Manufacture of Organic Light Emitting Diode-Hole Blocking Layer)

Comparative Example 4

A transparent ITO electrode thin film obtained from glass for an OLED (manufactured by Samsung-Corning Co., Ltd.) was ultrasonic cleaned using trichloroethylene, acetone, ethanol and distilled water consecutively for 5 minutes each, stored in isopropanol, and used.

Next, the ITO substrate was installed in a substrate folder of a vacuum deposition apparatus, and the following 4,4', 4"-tris(N,N-(2-naphthyl)-phenylamino)triphenylamine (2-TNATA) was introduced to a cell in the vacuum deposition apparatus.

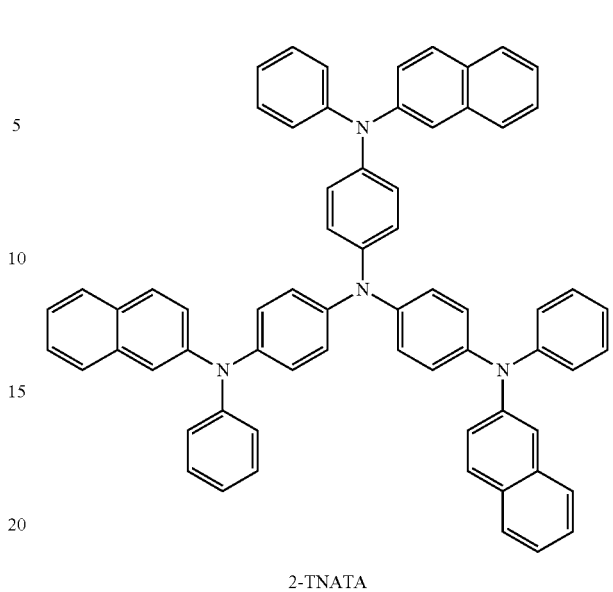

2-TNATA

Subsequently, the chamber was evacuated until the degree of vacuum therein reached $10^{-6}$ torr, and then 2-TNATA was evaporated by applying a current to the cell to deposit a hole injection layer having a thickness of 600 Å on the ITO substrate.

To another cell in the vacuum deposition apparatus, the following N,N'-bis(α-naphthyl)-N,N'-diphenyl-4,4'-diamine (NPB) was introduced, and evaporated by applying a current to the cell to deposit a hole transfer layer having a thickness of 300 Å on the hole injection layer.

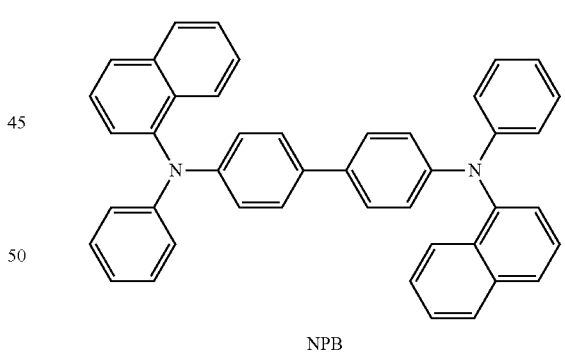

NPB

After forming the hole injection layer and the hole transfer layer as above, a blue light emitting material having a structure as below was deposited thereon as a light emitting layer. Specifically, in one side cell in the vacuum deposition apparatus, H1, a blue light emitting host material, was vacuum deposited to a thickness of 200 Å, and D1, a blue light emitting dopant material, was vacuum deposited thereon by 5% with respect to the host material.

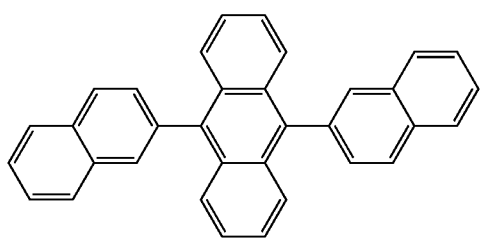

H1

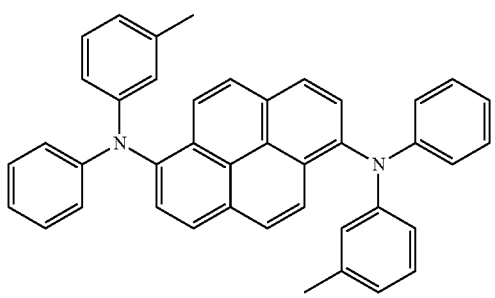

D1

Subsequently, as an electron transfer layer, a compound of the following structural formula E1 was deposited to a thickness of 300 Å.

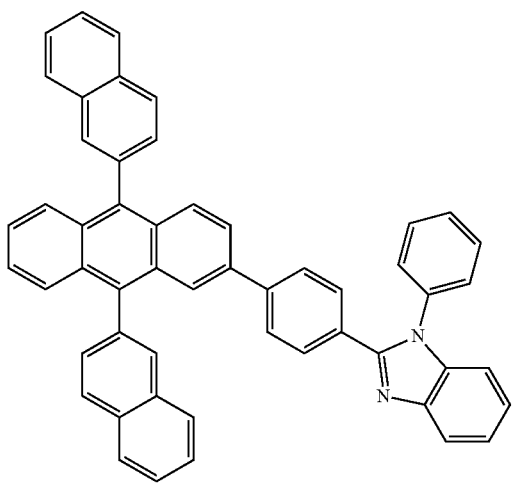

E1

As an electron injection layer, lithium fluoride (LiF) was deposited to a thickness of 10 Å, and an Al cathode was deposited to a thickness of 1,000 Å, and as a result, an OLED was manufactured.

Meanwhile, all the organic compounds required to manufacture the OLED were vacuum sublimation purified under $10^{-6}$ torr to $10^{-8}$ torr by each material to be used in the OLED manufacture.

Comparative Example 5 and Comparative Example 6

In Comparative Example 5, an organic electroluminescent diode was manufactured in the same manner as in Comparative Example 4 except that E1 was formed to a thickness of 250 Å as the electron transfer layer, and on the electron transfer layer, a hole blocking layer having a thickness of 50 Å was formed using Compound C.

In addition, in Comparative Example 6, an organic electroluminescent diode was manufactured in the same manner as in Comparative Example 4 except that E1 was formed to a thickness of 250 Å as the electron transfer layer, and on the electron transfer layer, a hole blocking layer having a thickness of 50 Å was formed using Compound D.

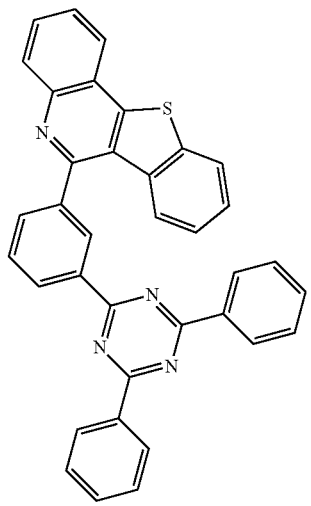

C

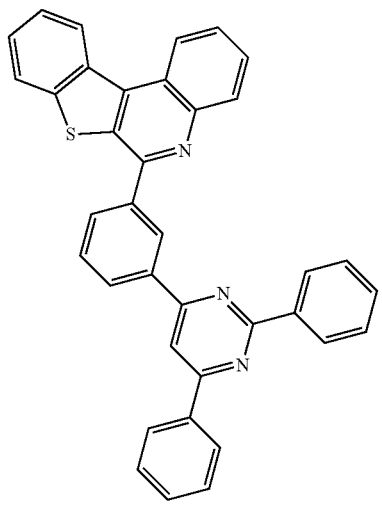

D

Examples 227 to 271

Organic electroluminescent diodes were manufactured in the same manner as in Comparative Example 4 except that E1 was formed to a thickness of 250 Å as the electron transfer layer, and on the electron transfer layer, a hole blocking layer having a thickness of 50 Å was formed using compounds presented in the following Table 33.

Results of measuring driving voltage, light emission efficiency, color coordinate (CIE) and lifetime of the blue organic light emitting diode manufactured according to the present disclosure are as shown in Table 33.

TABLE 33

| Compound | Driving Voltage (V) | Light Emission Efficiency (cd/A) | CIE (x, y) | Lifetime (T95) |
| --- | --- | --- | --- | --- |
| Comparative Example 4 | — | 5.51 | 5.94 | (0.134, 0.100) | 31 |
| Comparative Example 5 | C | 6.25 | 4.62 | (0.134, 0.101) | 18 |
| Comparative Example 6 | D | 6.27 | 4.80 | (0.134, 0.101) | 20 |
| Example 227 | 1 | 5.14 | 6.32 | (0.134, 0.102) | 35 |
| Example 228 | 11 | 5.34 | 6.22 | (0.134, 0.101) | 36 |
| Example 229 | 16 | 5.24 | 6.30 | (0.134, 0.102) | 35 |
| Example 230 | 17 | 5.42 | 6.21 | (0.134, 0.101) | 36 |
| Example 231 | 60 | 5.33 | 6.01 | (0.134, 0.102) | 39 |
| Example 232 | 71 | 5.36 | 6.04 | (0.134, 0.102) | 37 |
| Example 233 | 93 | 5.35 | 6.11 | (0.134, 0.102) | 36 |
| Example 234 | 127 | 5.33 | 6.12 | (0.134, 0.102) | 36 |
| Example 235 | 166 | 5.36 | 6.05 | (0.134, 0.102) | 37 |
| Example 236 | 203 | 5.32 | 5.88 | (0.134, 0.102) | 34 |
| Example 237 | 234 | 5.22 | 5.91 | (0.134, 0.102) | 33 |
| Example 238 | 254 | 4.90 | 6.04 | (0.134, 0.102) | 45 |
| Example 239 | 264 | 4.98 | 6.11 | (0.134, 0.101) | 41 |
| Example 240 | 297 | 5.21 | 6.35 | (0.134, 0.102) | 44 |
| Example 241 | 326 | 5.32 | 6.55 | (0.134, 0.102) | 40 |
| Example 242 | 362 | 5.21 | 6.41 | (0.134, 0.101) | 43 |
| Example 243 | 396 | 5.21 | 6.44 | (0.134, 0.102) | 44 |
| Example 244 | 550 | 5.14 | 6.01 | (0.134, 0.101) | 34 |
| Example 245 | 585 | 5.18 | 6.11 | (0.134, 0.102) | 36 |
| Example 246 | 681 | 5.21 | 6.51 | (0.134, 0.101) | 45 |
| Example 247 | 725 | 5.11 | 6.44 | (0.134, 0.101) | 40 |
| Example 248 | 782 | 5.01 | 6.03 | (0.134, 0.102) | 42 |
| Example 249 | 816 | 5.05 | 6.01 | (0.134, 0.102) | 41 |
| Example 250 | 867 | 4.89 | 5.99 | (0.134, 0.102) | 41 |
| Example 251 | 902 | 4.90 | 5.91 | (0.134, 0.102) | 42 |
| Example 252 | 1027 | 4.99 | 5.81 | (0.134, 0.102) | 39 |
| Example 253 | 1039 | 4.88 | 5.71 | (0.134, 0.101) | 36 |
| Example 254 | 1041 | 4.91 | 5.61 | (0.134, 0.102) | 32 |
| Example 255 | 1044 | 5.42 | 6.21 | (0.134, 0.101) | 36 |
| Example 256 | 1053 | 4.98 | 5.81 | (0.134, 0.101) | 33 |
| Example 257 | 1057 | 5.36 | 6.21 | (0.134, 0.102) | 41 |
| Example 258 | 1063 | 4.88 | 5.70 | (0.134, 0.102) | 33 |
| Example 259 | 1078 | 4.91 | 5.81 | (0.134, 0.101) | 36 |
| Example 260 | 1082 | 5.36 | 6.05 | (0.134, 0.102) | 37 |
| Example 261 | 1090 | 5.32 | 5.88 | (0.134, 0.102) | 38 |
| Example 262 | 1093 | 4.81 | 5.51 | (0.134, 0.102) | 33 |
| Example 263 | 1102 | 5.21 | 6.04 | (0.134, 0.102) | 38 |
| Example 264 | 1103 | 4.78 | 5.41 | (0.134, 0.101) | 33 |
| Example 265 | 1111 | 5.24 | 6.30 | (0.134, 0.102) | 35 |
| Example 266 | 1119 | 5.42 | 6.21 | (0.134, 0.101) | 36 |
| Example 267 | 1124 | 5.33 | 6.01 | (0.134, 0.102) | 39 |
| Example 268 | 1151 | 5.36 | 6.04 | (0.134, 0.102) | 37 |
| Example 269 | 1157 | 4.98 | 5.71 | (0.134, 0.102) | 33 |
| Example 270 | 1166 | 4.71 | 5.88 | (0.134, 0.102) | 34 |
| Example 271 | 1169 | 5.36 | 6.05 | (0.134, 0.102) | 37 |

As seen from the results of Table 33, the organic light emitting diode using the hole blocking layer material of the blue organic light emitting diode of the present disclosure had lower driving voltage and significantly improved light emission efficiency and lifetime compared to Comparative Example 4. In addition, light emission efficiency and lifetime were significantly improved compared to Comparative Example 5 and Comparative Example 6. Such results are due to the fact that the organic light emitting diode using the hole blocking layer material of the blue organic light emitting diode is a bipolar type having both a p-type and an n-type, and hole leakage may be prevented, and excitons may be effectively locked in the light emitting layer.

Hereinbefore, preferred examples of the present disclosure have been described in detail, however, the scope of a right of the present disclosure is not limited thereto, and various modifications and improvements made by those skilled in the art using the basic concept of the present disclosure defined in the attached claims also fall within the scope of a right of the present disclosure.

The invention claimed is:

1. A compound represented by the following Chemical Formula 1:

[Chemical Formula 1]

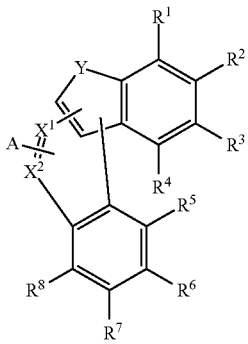

wherein, in Chemical Formula 1, at least one of $X^1$ and $X^2$ is —N—, and the other one is —CA-;

Y is —S— or —O—;

$R^5$ to $R^8$ are each independently hydrogen, or deuterium,

A and $R^1$ to $R^4$ are each independently hydrogen, deuterium, a cyano group, a substituted or unsubstituted C1 to C60 alkyl group, or a substituted or unsubstituted C6 to C60 aryl group; and any one of A and $R^1$ to $R^4$ is represented by the following Chemical Formula 2,

[Chemical Formula 2]

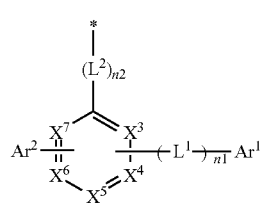

in Chemical Formula 2, $Ar^1$ and $Ar^2$ are each independently a substituted or unsubstituted C6 to C60 aryl group, or a substituted or unsubstituted C2 to C60 heteroaryl group;

at least one of X³ to X⁷ is —N—, one of X³ to X⁷ is —C((L¹)$_{n1}$—Ar¹)—, one of X³ to X⁷ is —C(Ar²)—, and the rest are one of —N—, —CH— or —CR—;

L¹ and L² are each independently a single bond, a substituted or unsubstituted C6 to C60 arylene group, or a substituted or unsubstituted C2 to C60 heteroarylene group;

n1 and n2 are each independently one of integers of 0 to 2;

R is deuterium, —CN, a substituted or unsubstituted C1 to C60 linear or branched alkyl group, a substituted or unsubstituted C6 to C60 monocyclic or polycyclic aryl group, or a substituted or unsubstituted C2 to C60 monocyclic or polycyclic heteroaryl group;

when any one of R¹ to R⁴ of Chemical Formula 1 is represented by Chemical Formula 2, A is a substituted or unsubstituted C6 to C60 aryl group, when A of Chemical Formula 1 is represented by Chemical Formula 2, at least any one of Ar¹ and Ar² of Chemical Formula 2 is a substituted or unsubstituted C2 to C60 heteroaryl group, or a substituted or unsubstituted C10 to C60 fused cyclic aryl group; and

* is a bonding position.

2. The compound of claim 1, which is represented by the following Chemical Formula 4:

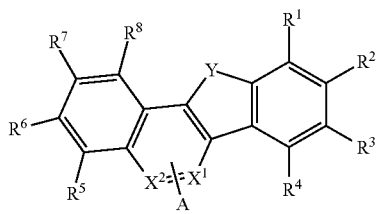

[Chemical Formula 4]

wherein, in Chemical Formula 4,
each substituent has the same definition as in Chemical Formula 1.

3. The compound of claim 1, which is represented by the following Chemical Formula 5:

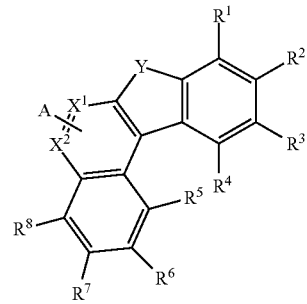

[Chemical Formula 5]

wherein, in Chemical Formula 5,
each substituent has the same definition as in Chemical Formula 1.

4. The compound of claim 1, wherein Ar¹ is a substituent having hole properties.

5. The compound of claim 1, wherein Ar¹ is,
(1) a substituted or unsubstituted carbazolyl group;
(2) a substituted or unsubstituted dibenzofuranyl group;
(3) a substituted or unsubstituted dibenzothiophenyl group;
(4) a substituted or unsubstituted 9,9-dialkylfluorenyl group or 9,9-diarylfluorenyl group, the alkyl group of the dialkyl is a substituted or unsubstituted C1 to C60 alkyl group, and the aryl group of the diaryl group is a substituted or unsubstituted C6 to C60 aryl group; or
(5) a substituted or unsubstituted 9,9-dimethylfluorenyl group.

6. The compound of claim 1, wherein Ar¹ is,
(1) a substituted or unsubstituted anthracenyl group;
(2) a substituted or unsubstituted phenanthryl group;
(3) a substituted or unsubstituted pyrenyl group;
(4) a substituted or unsubstituted triphenylenyl group;
(5) a substituted or unsubstituted terphenyl group; or
(6) a substituted or unsubstituted quaterphenyl group.

7. The compound of claim 1, wherein the compound represented by Chemical Formula 1 is any one of compounds of the following Group I:

[Group I]

1

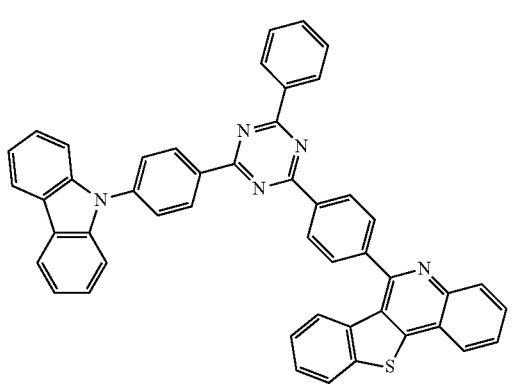

2

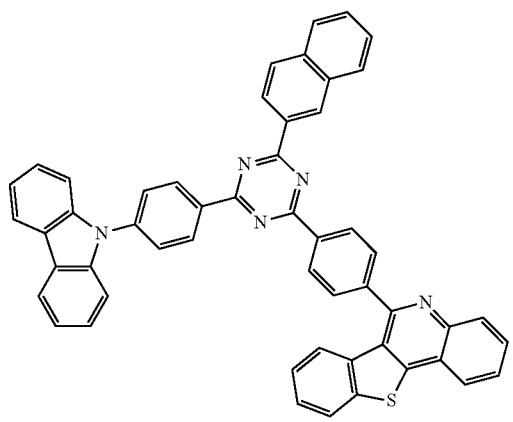

655 656
3  4
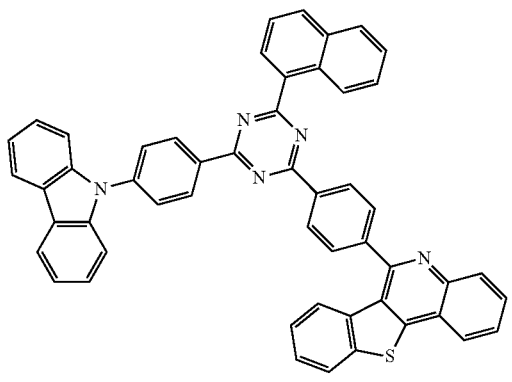 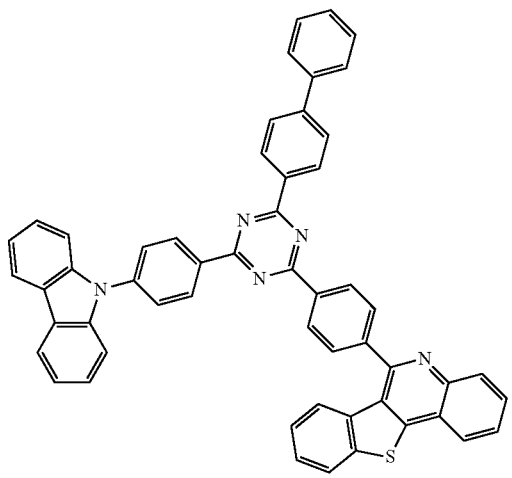
5  6
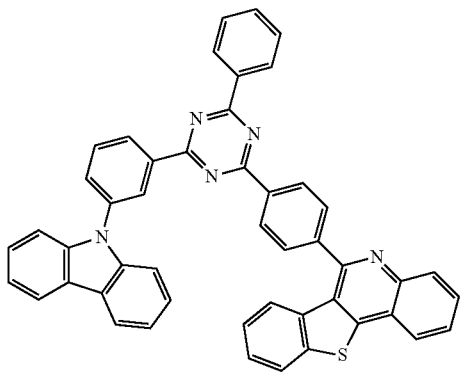 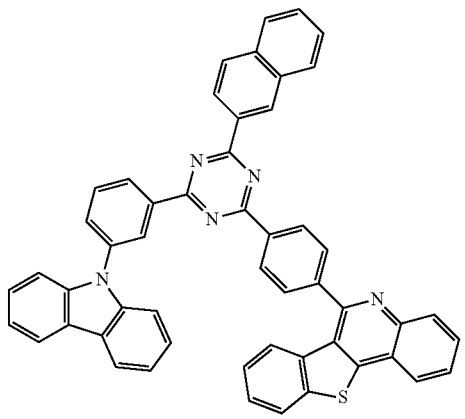
7  8
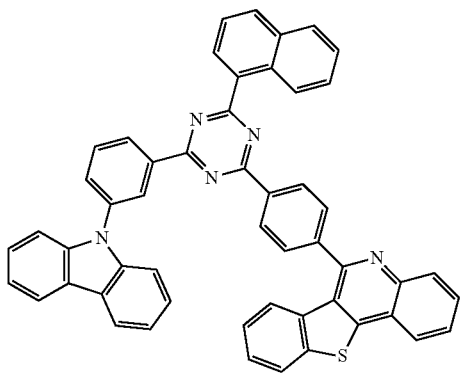 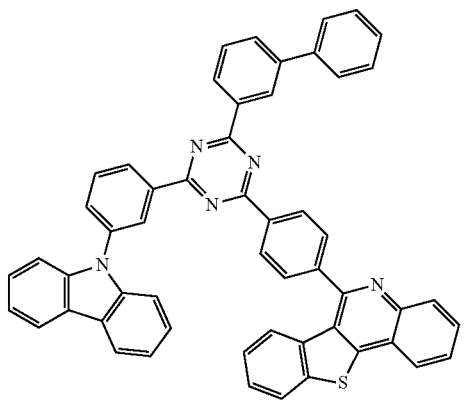

-continued
9
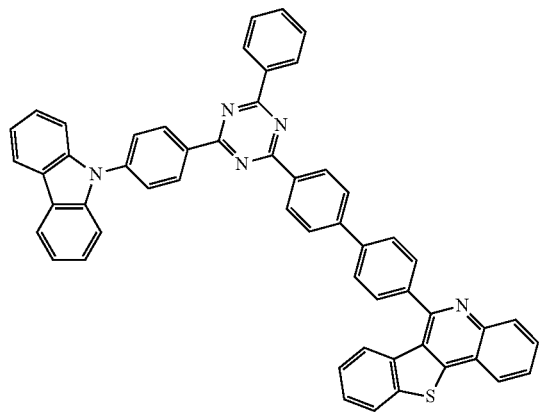
10
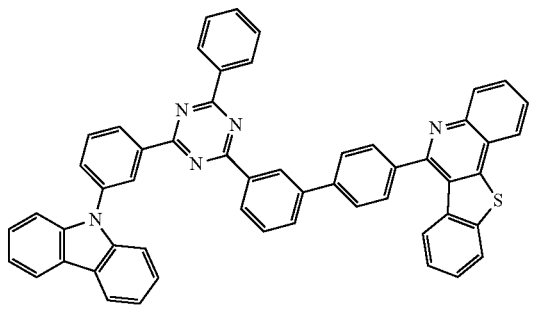
11
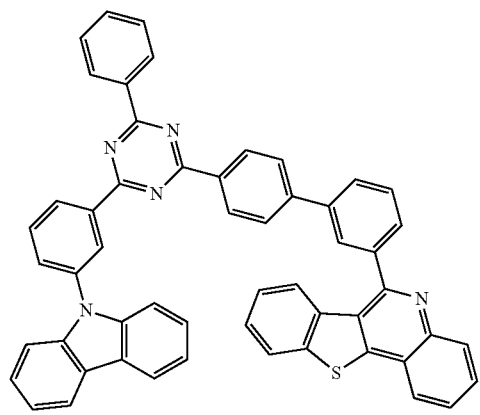
12
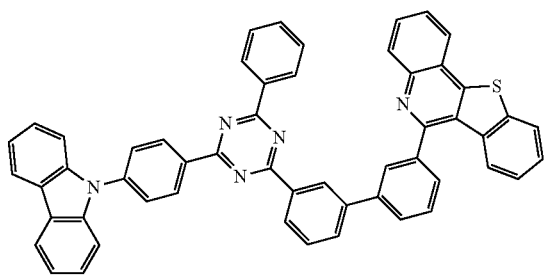
13
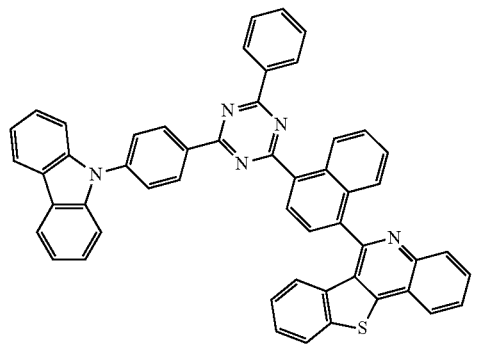
14
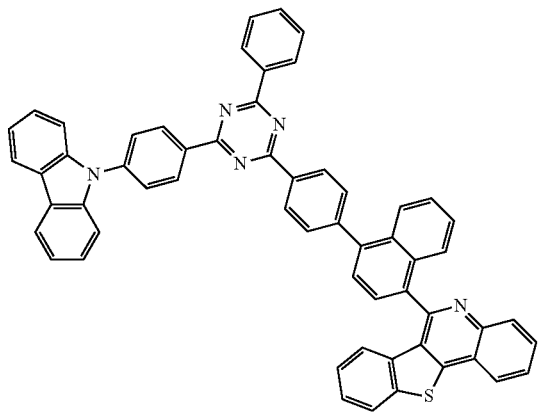

-continued
15
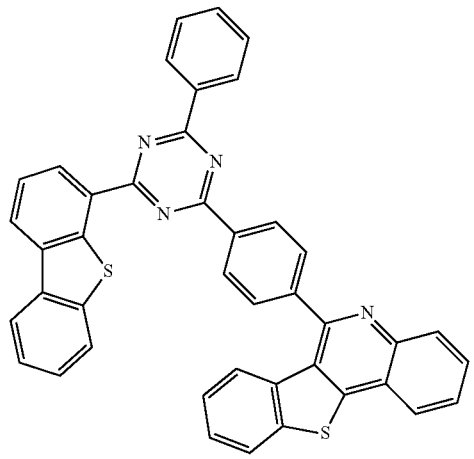
16
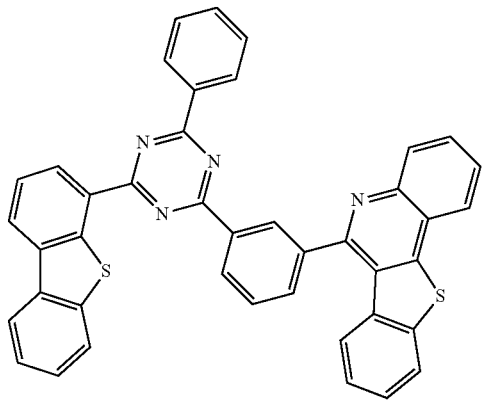
17
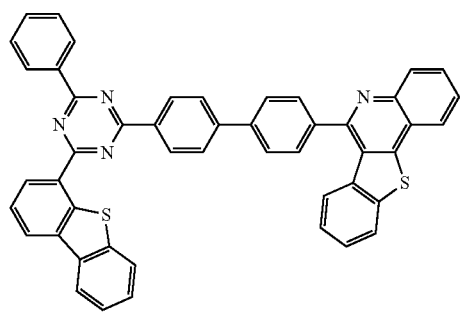
18
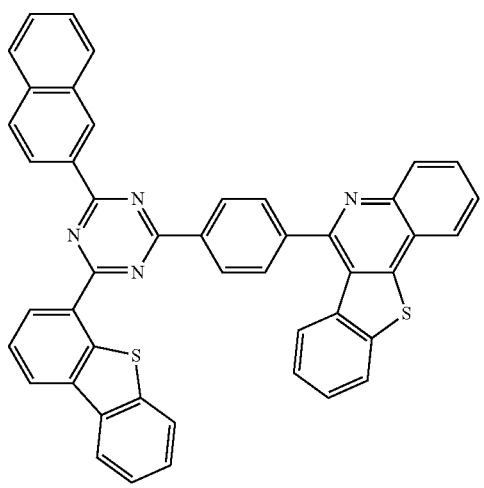
19
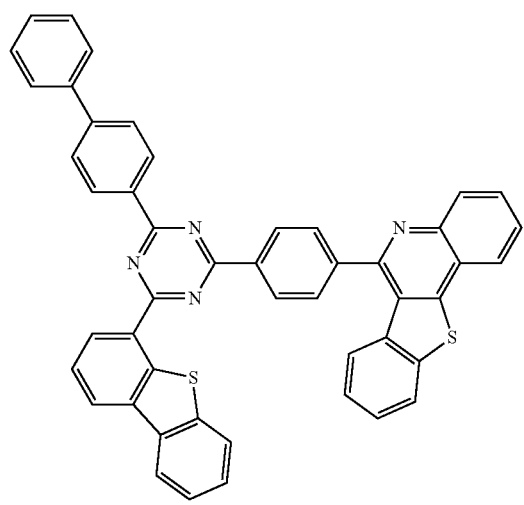
20
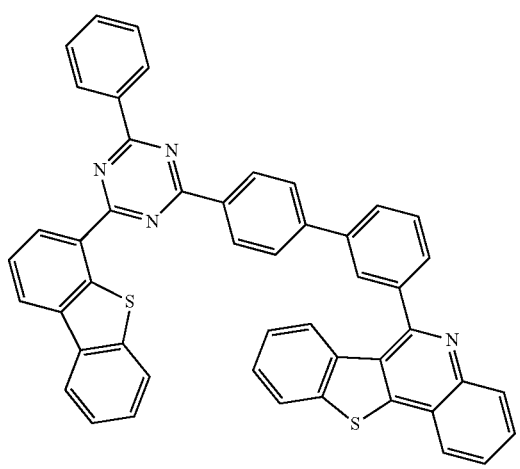

-continued
21
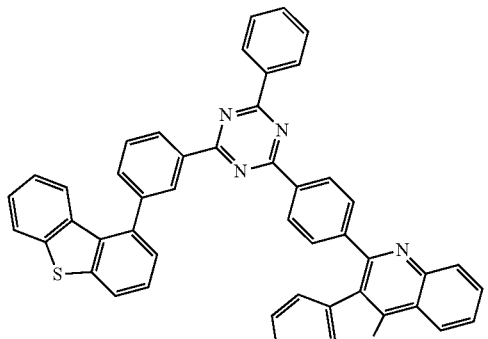
22
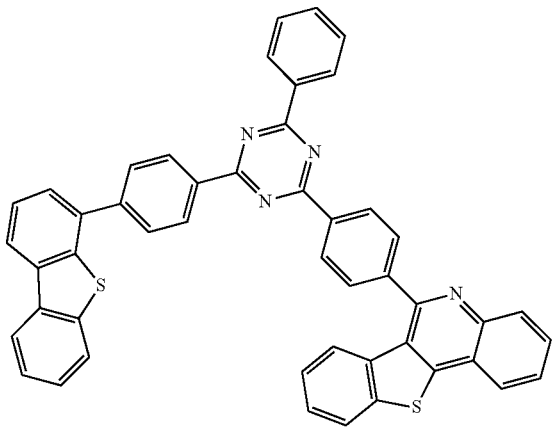
23
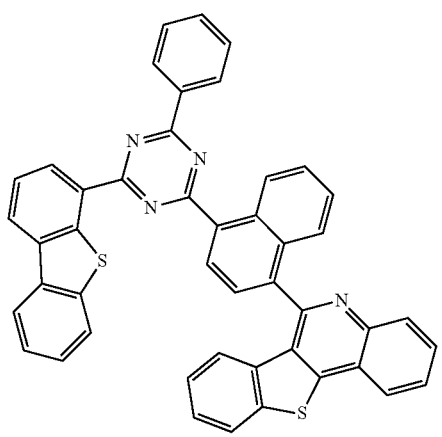
24
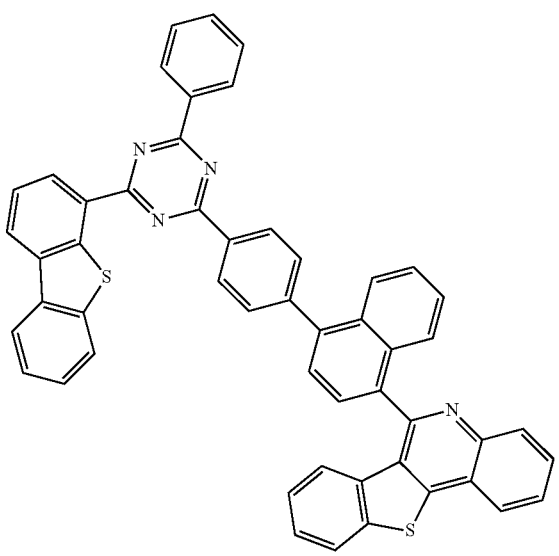
25
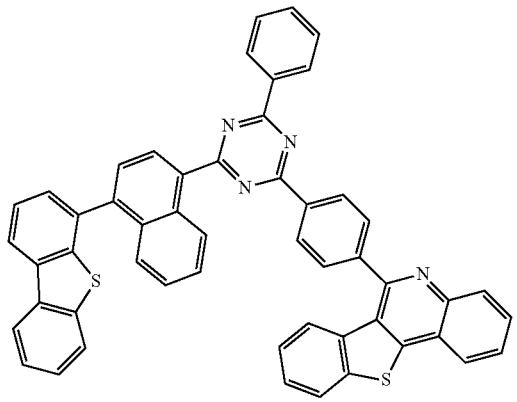
26
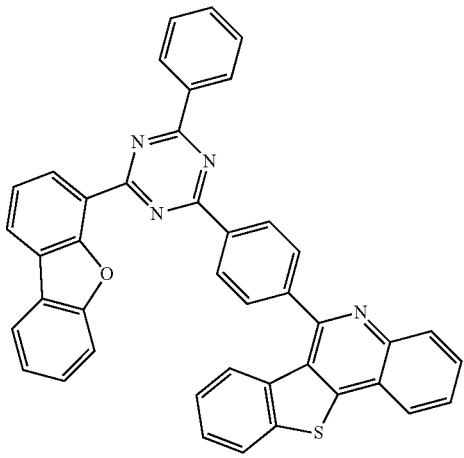

-continued
27
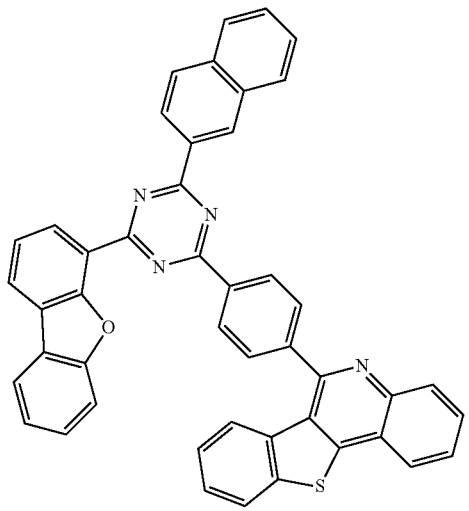
28
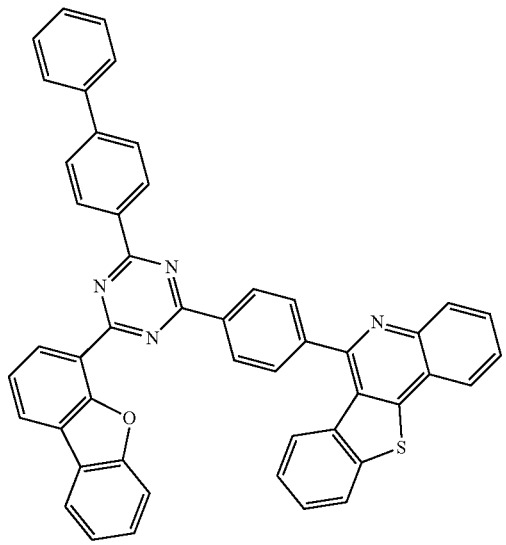
29
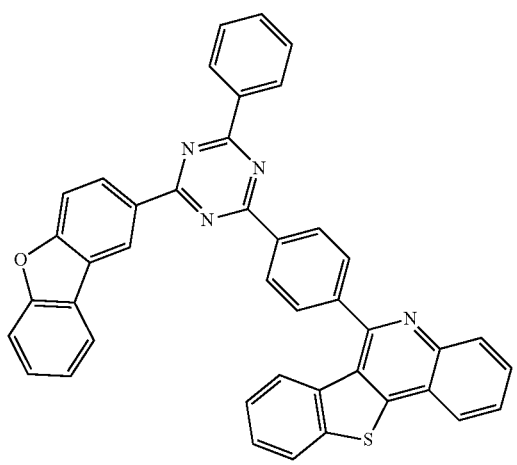
30
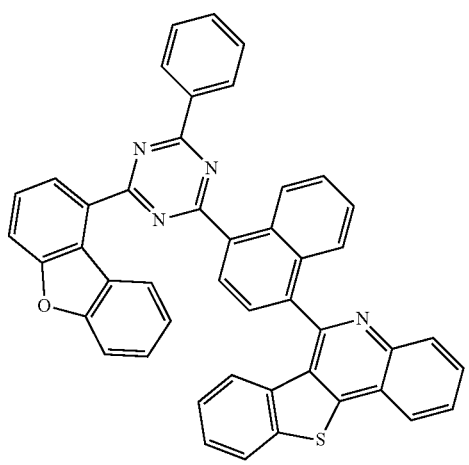
31
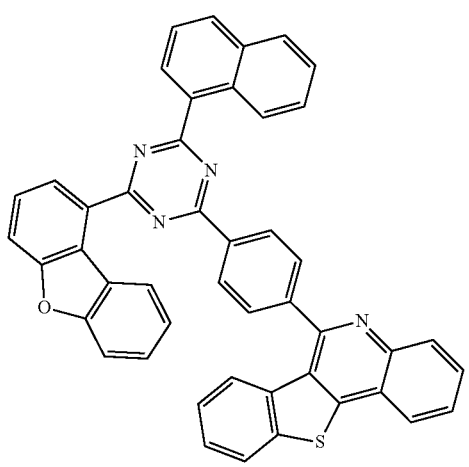
32
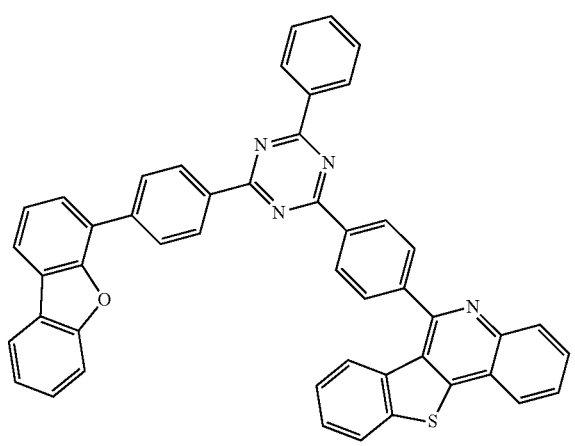

-continued
665
33
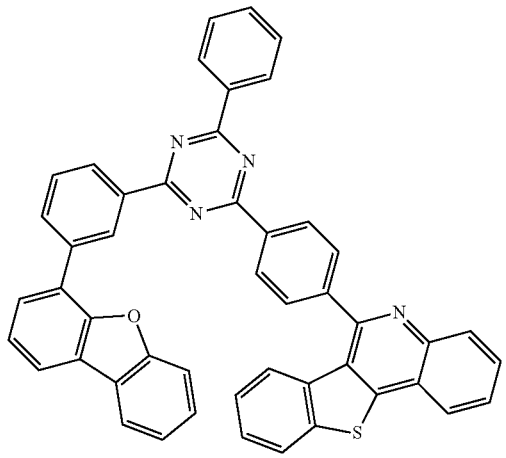
34
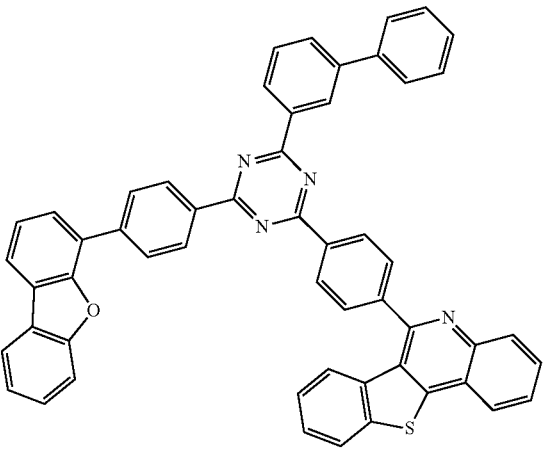
35
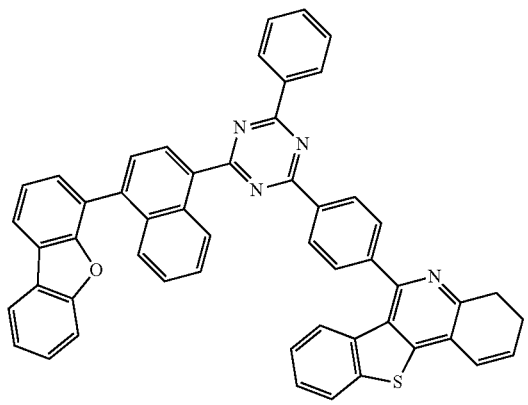
36
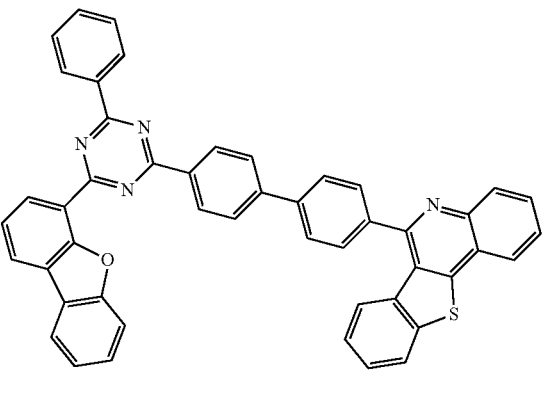
37
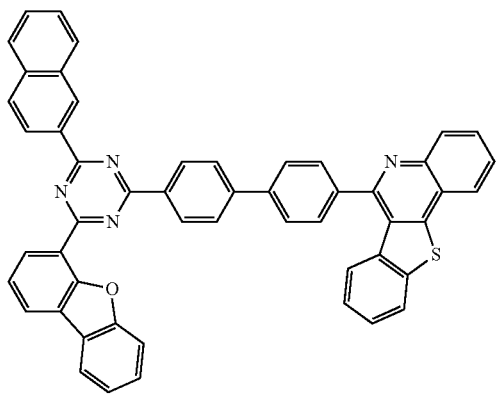
38
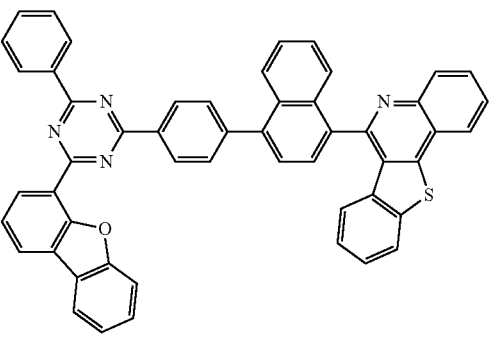
39
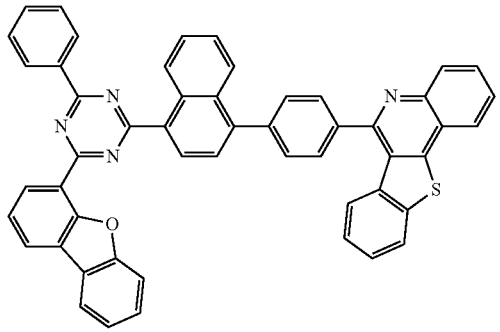
40
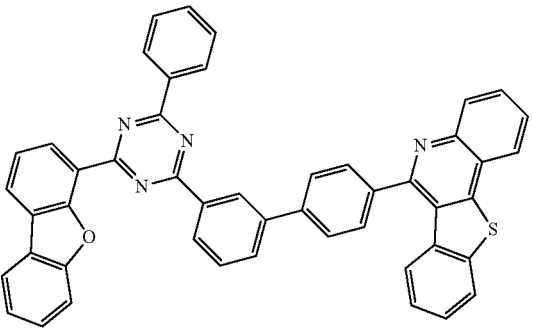

-continued
41
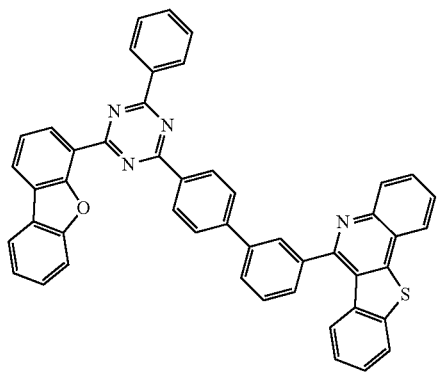
42
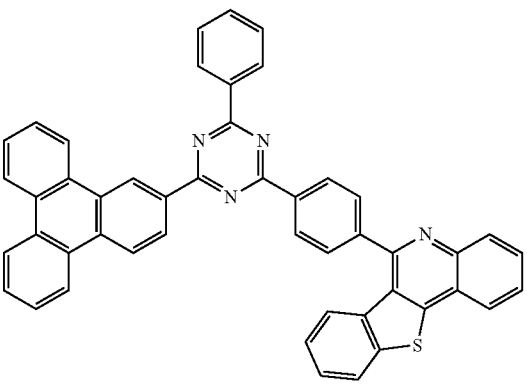
43
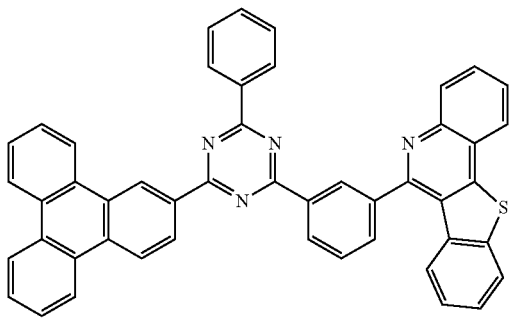
44
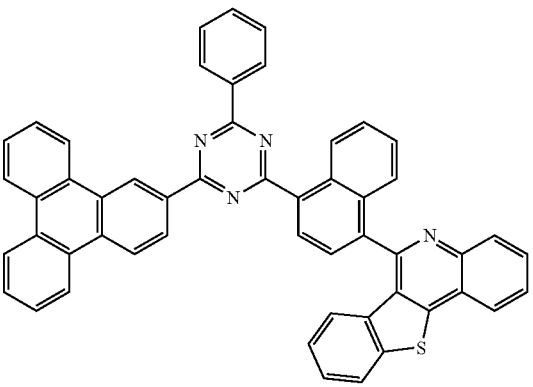
45
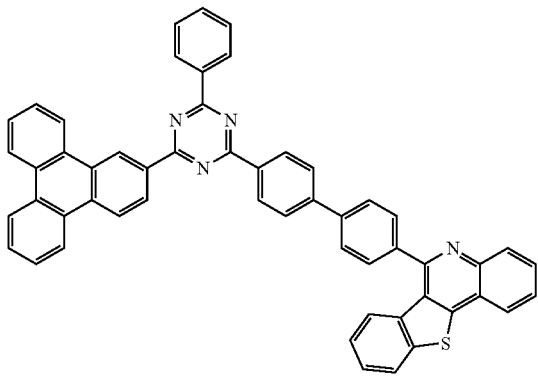
46
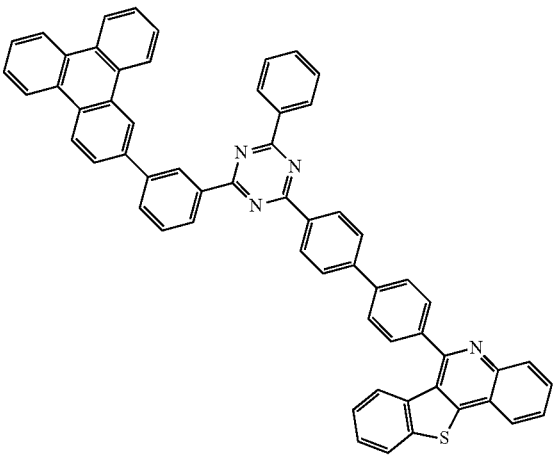
47
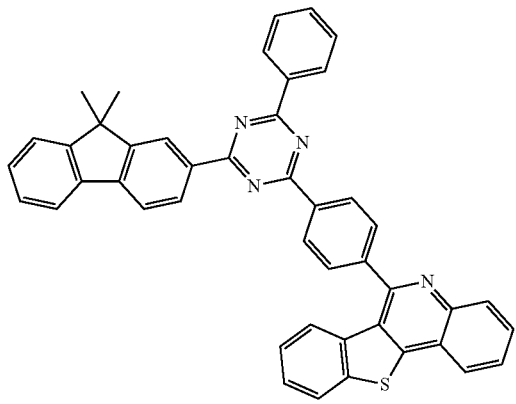
48
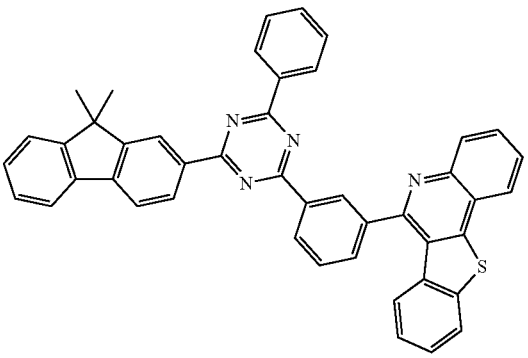

-continued
49
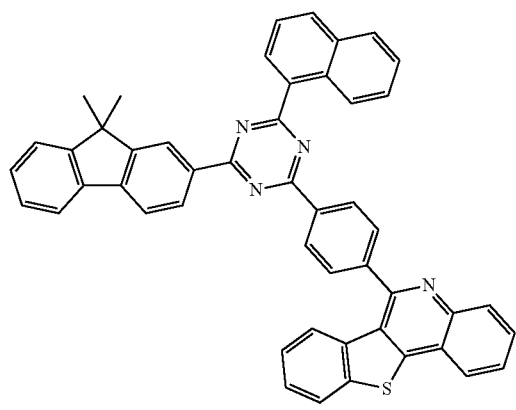
50
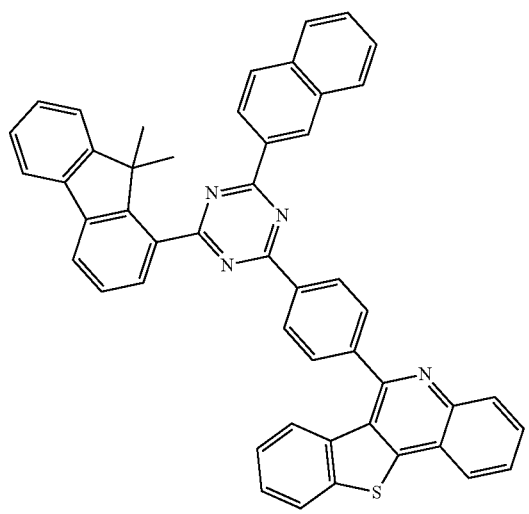
51
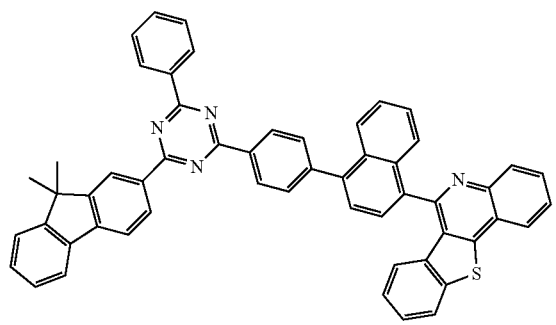
52
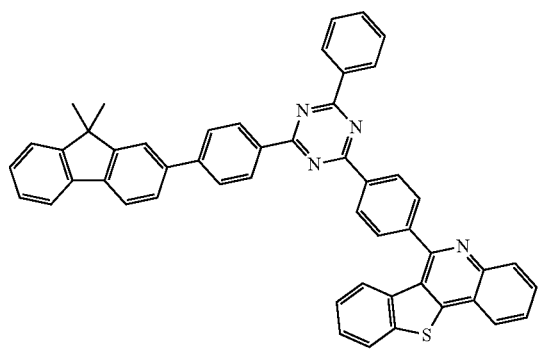
53
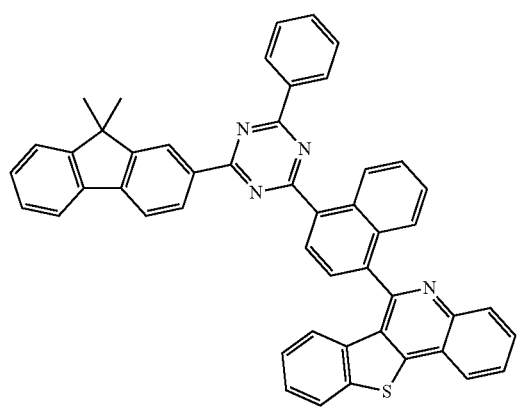
54
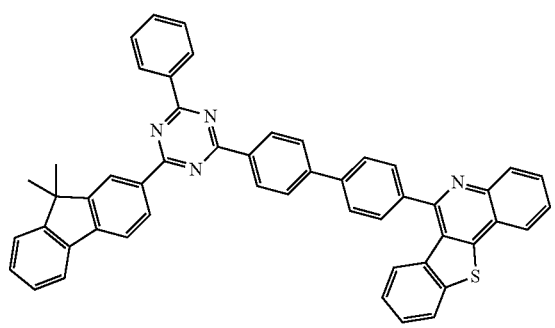

55
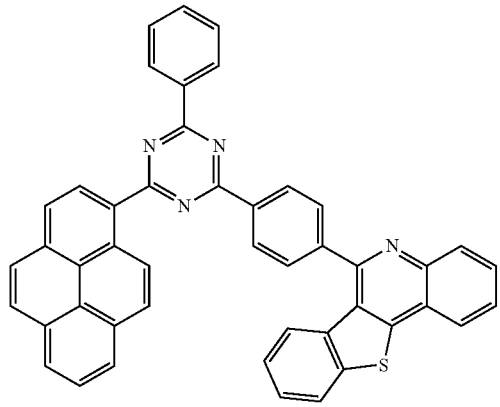
56
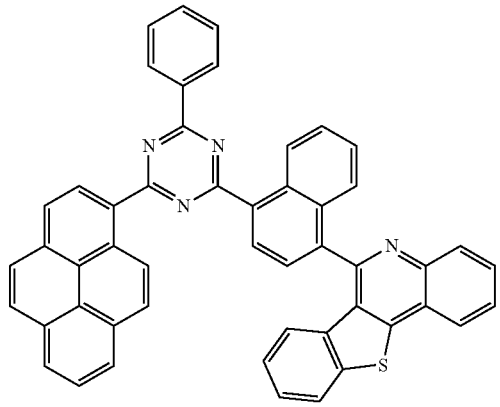
57
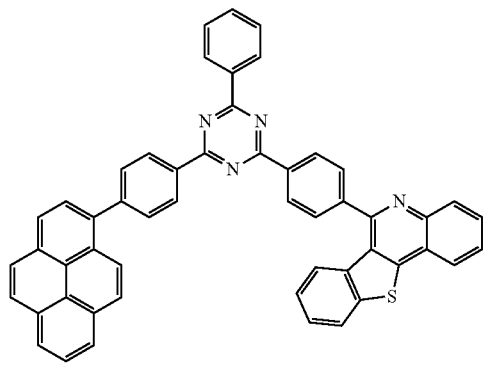
58
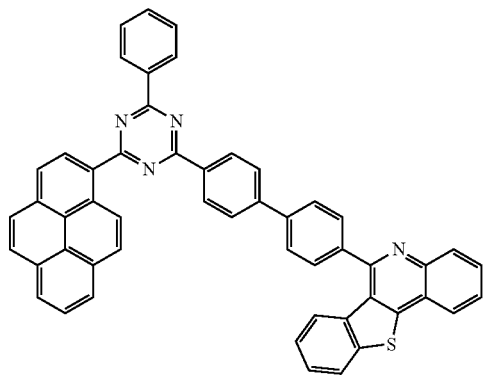
59
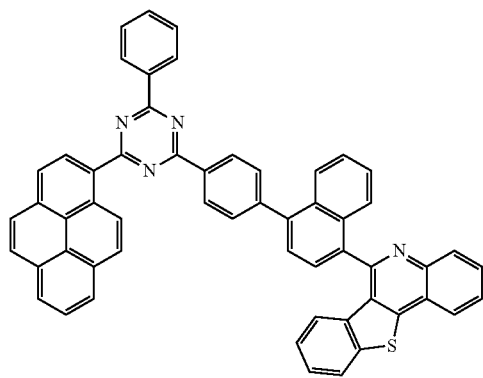
60
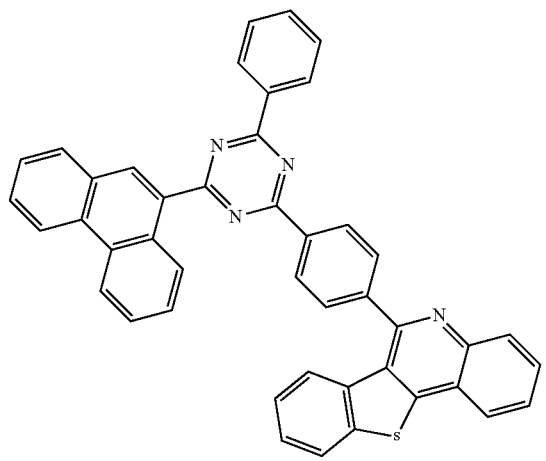
61
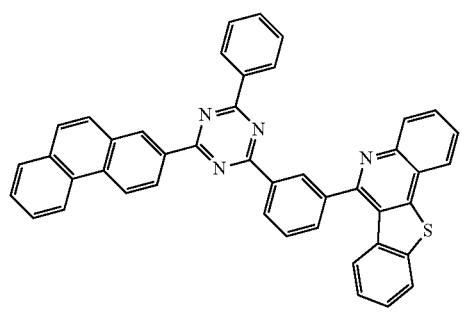
62
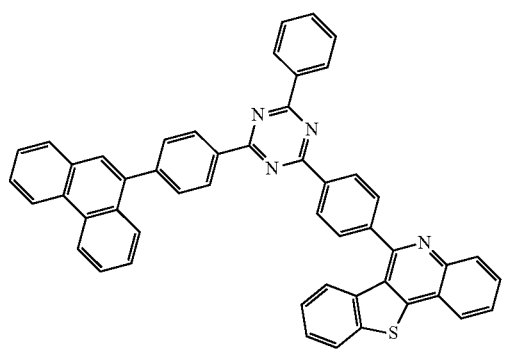

63
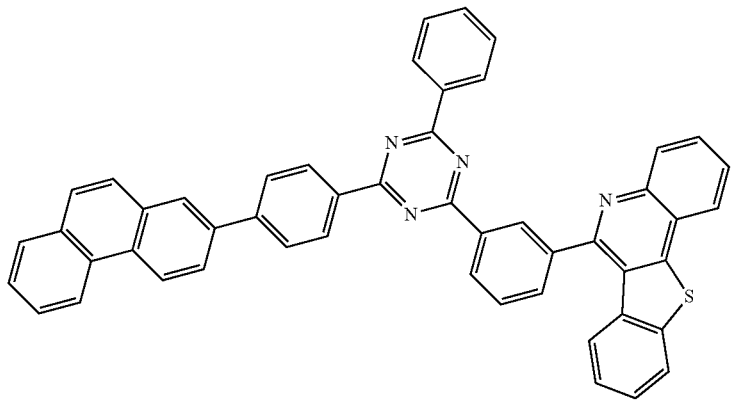
64
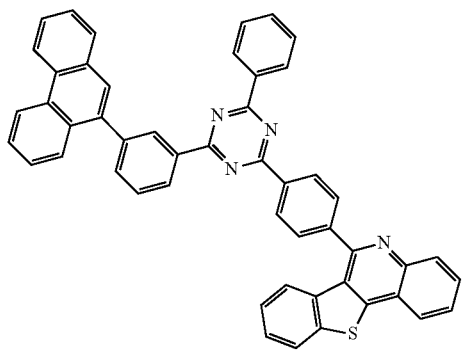
65
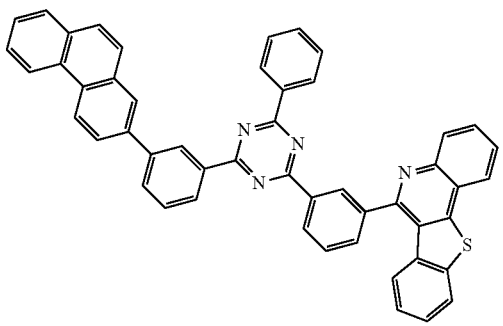
66
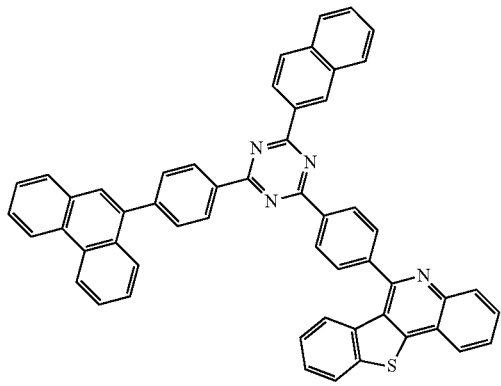
67
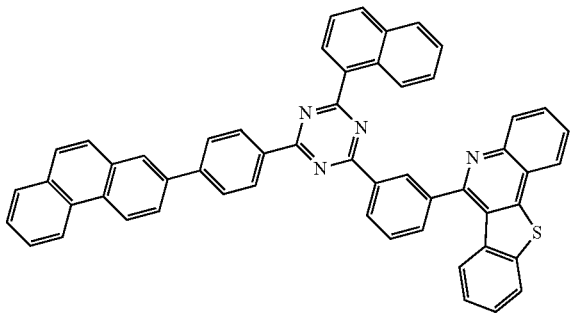
68
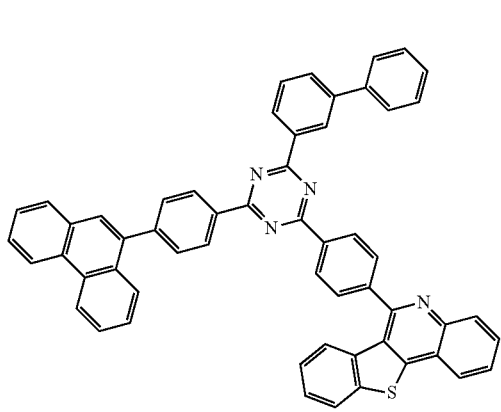
69
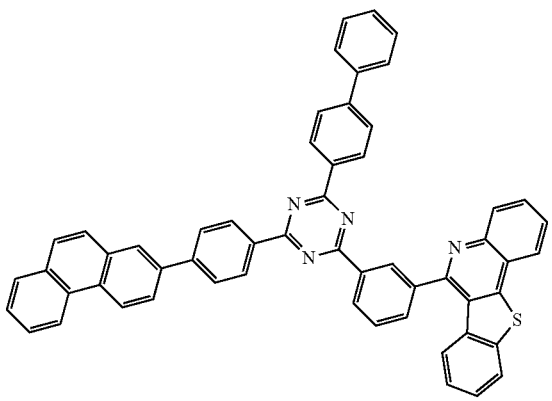

-continued
70
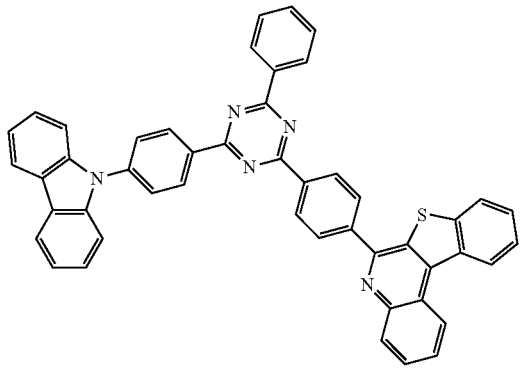
71
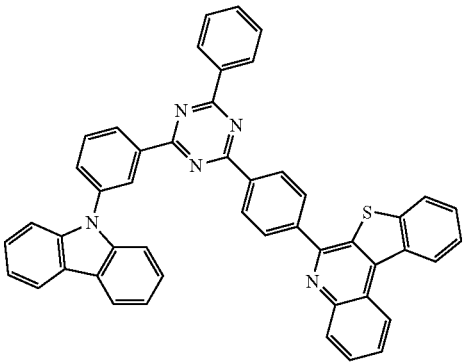
72
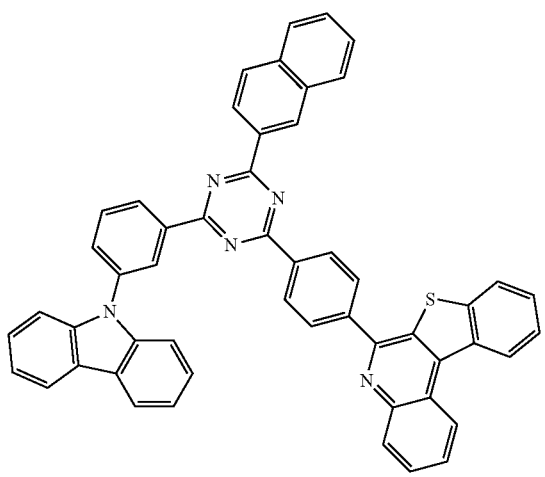
73
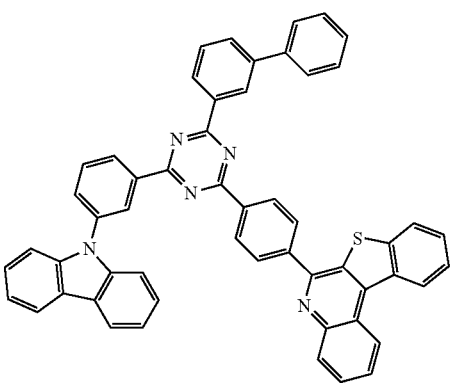
74
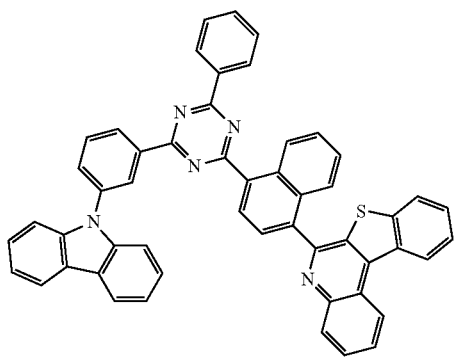
75
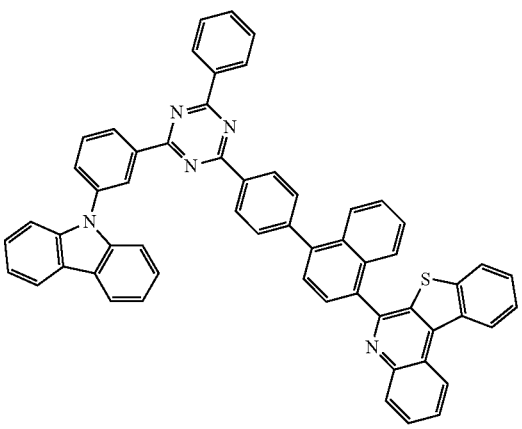

-continued
76
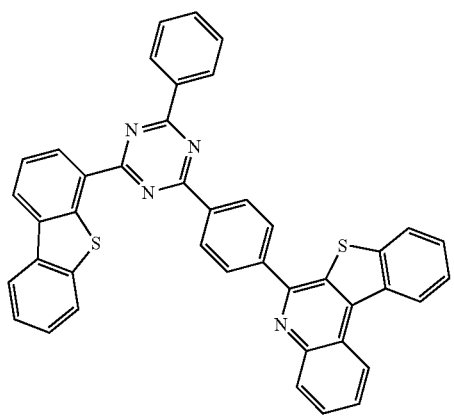
77
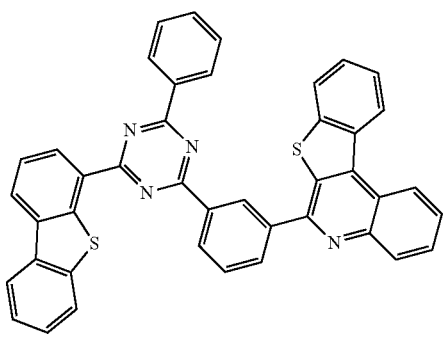
78
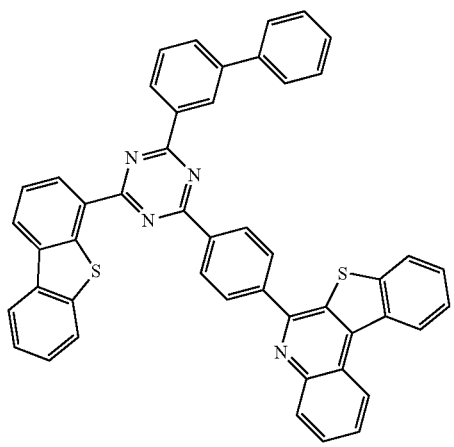
79
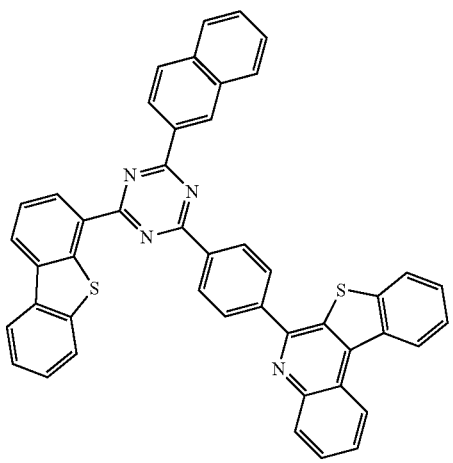
80
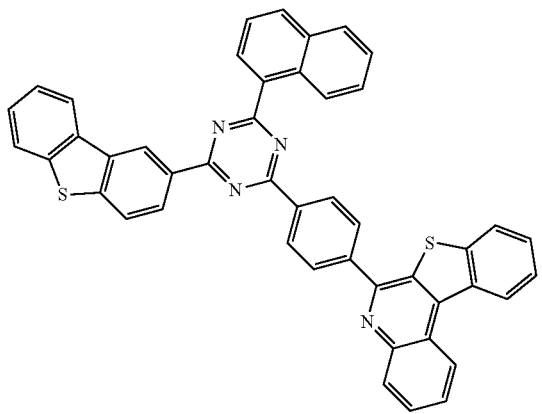
81
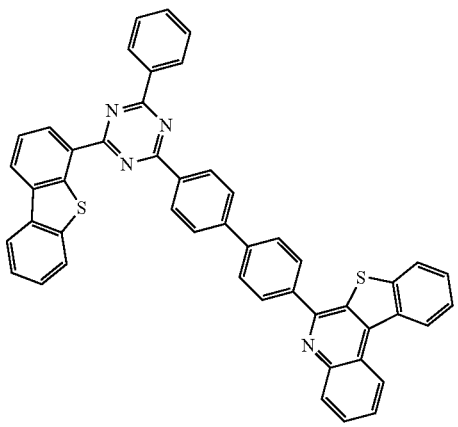

-continued
82
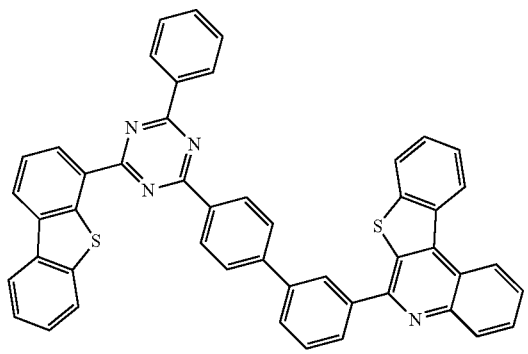
83
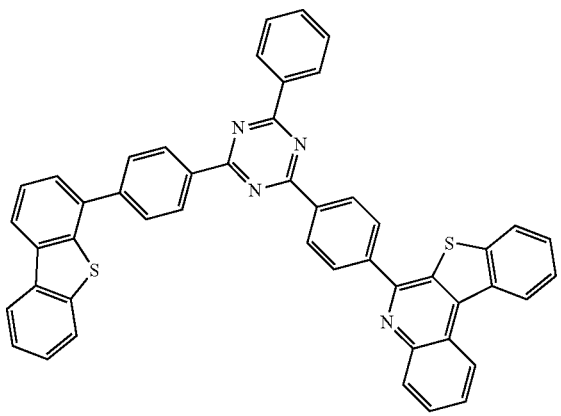
84
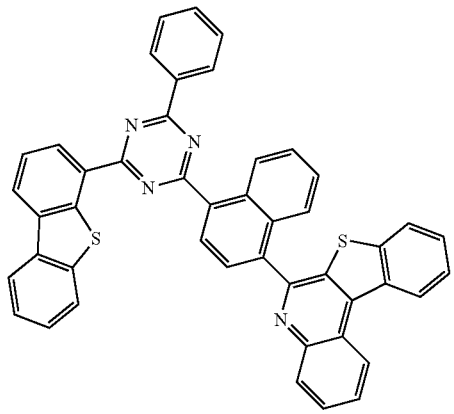
85
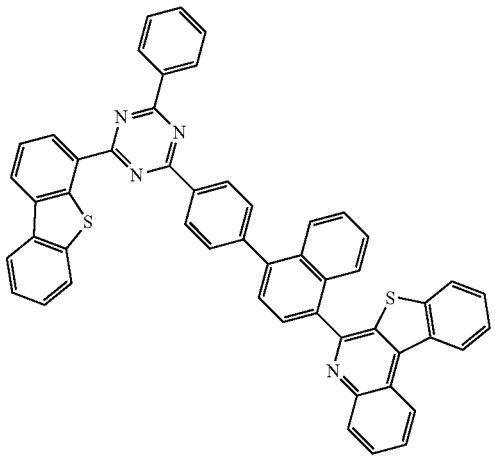
86
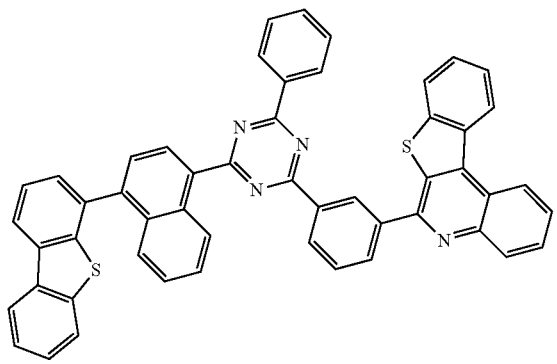
87
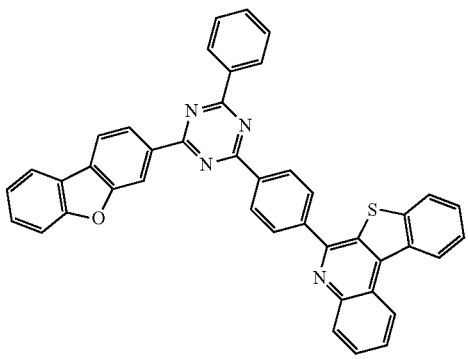

-continued
88
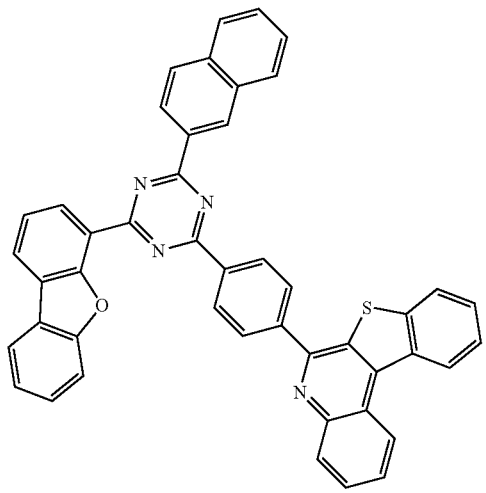
89
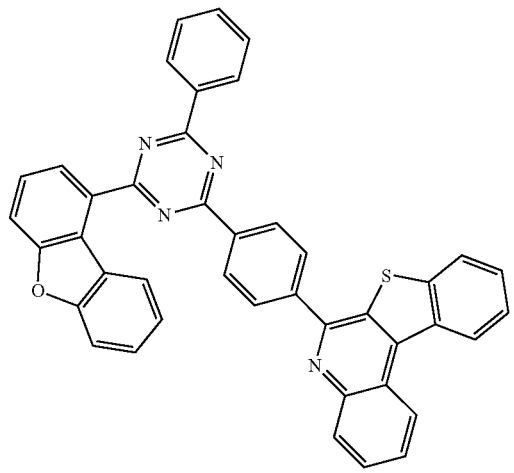
90
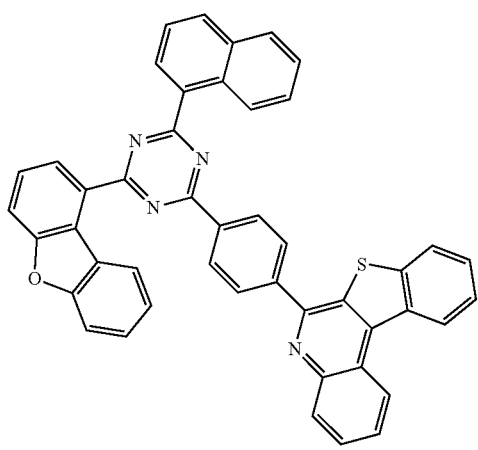
91
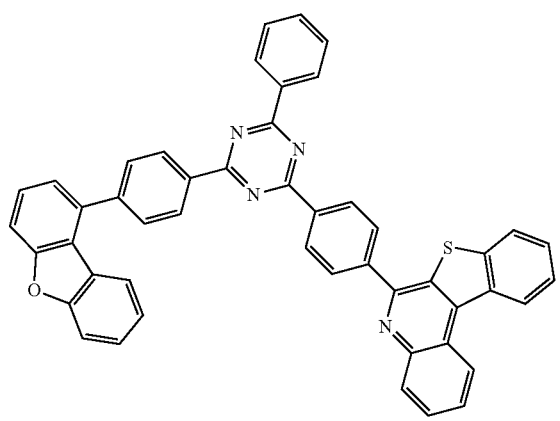
92
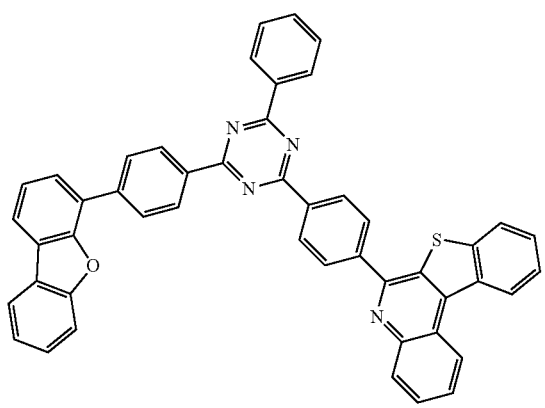
93
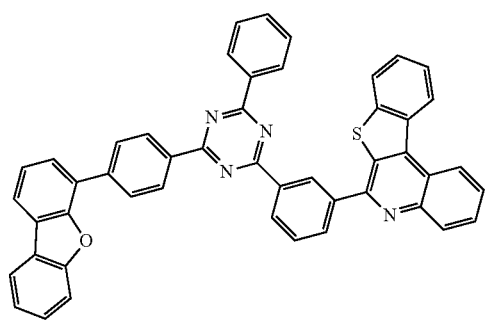

94
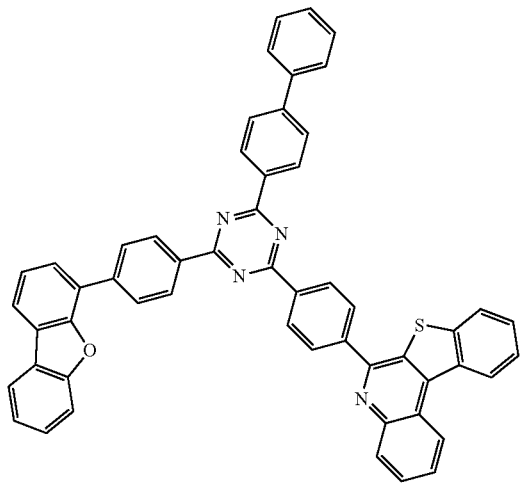
95
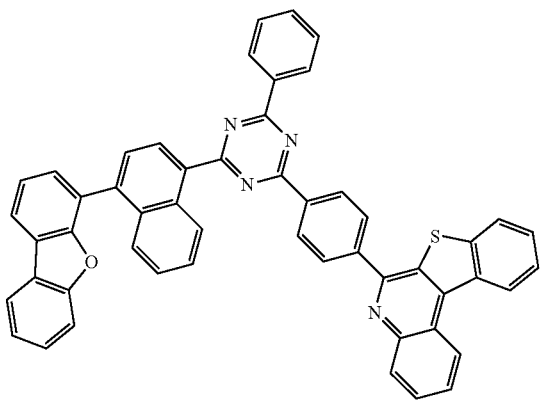
96
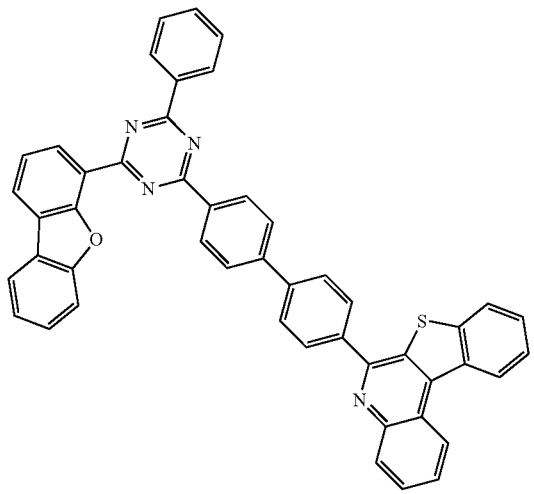
97
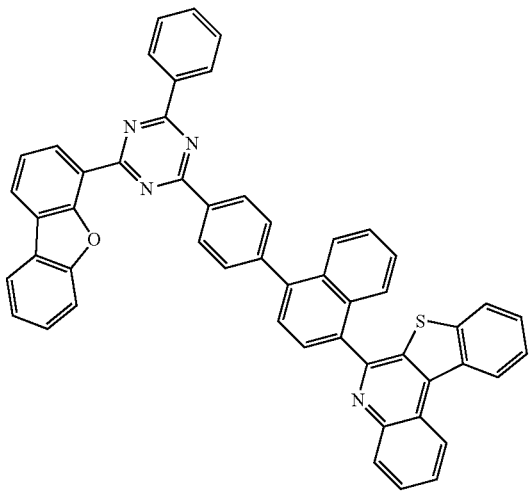
98
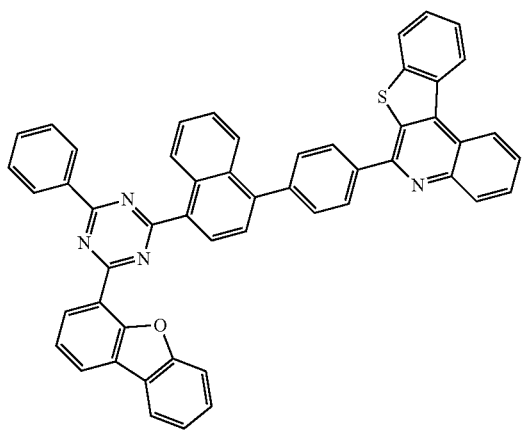
99
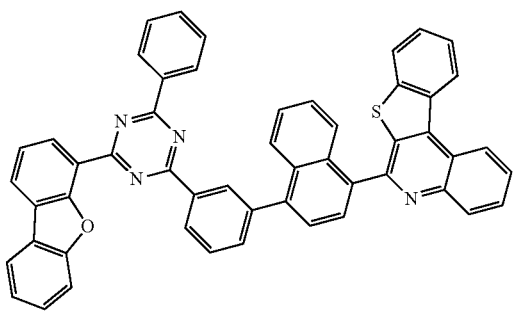

100
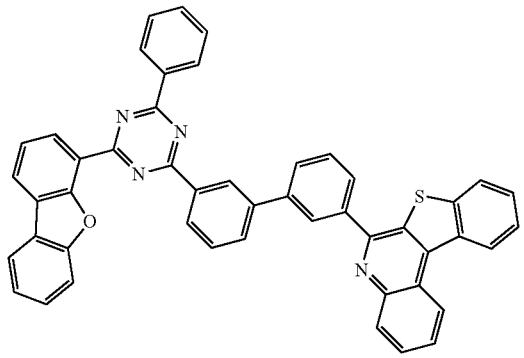
101
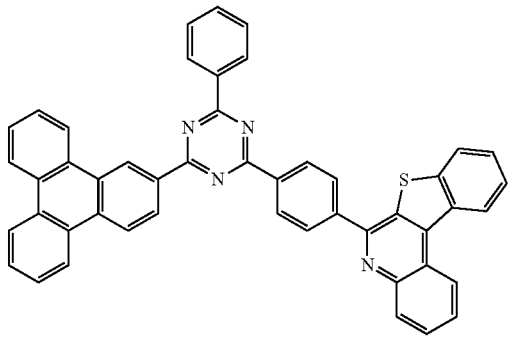
102
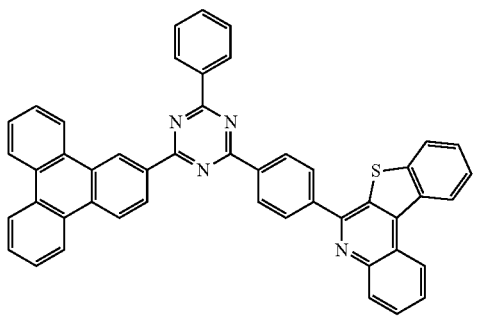
103
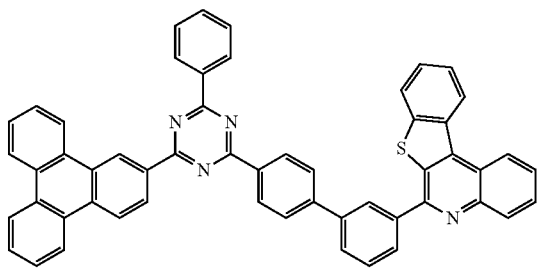
104
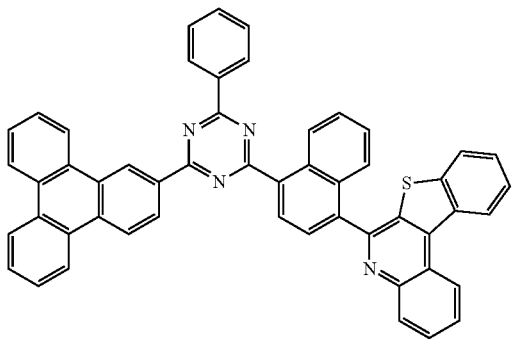
105
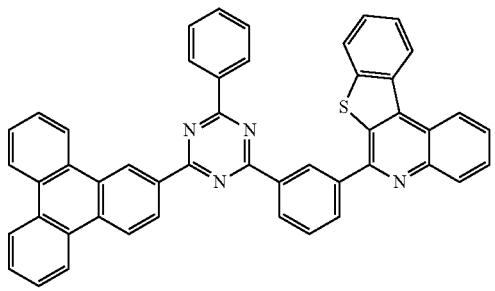
106
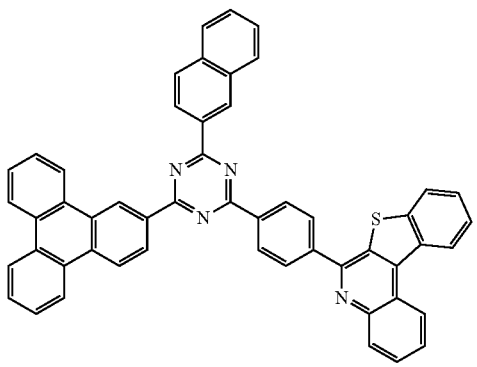
107
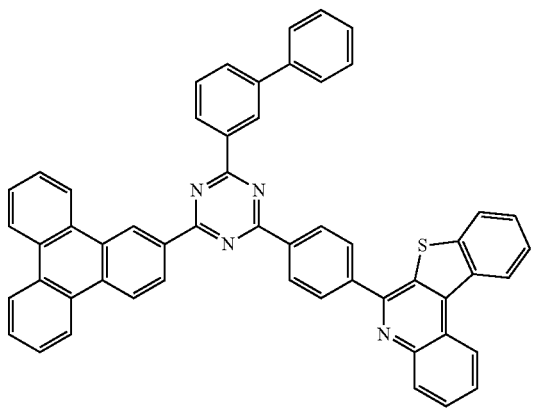

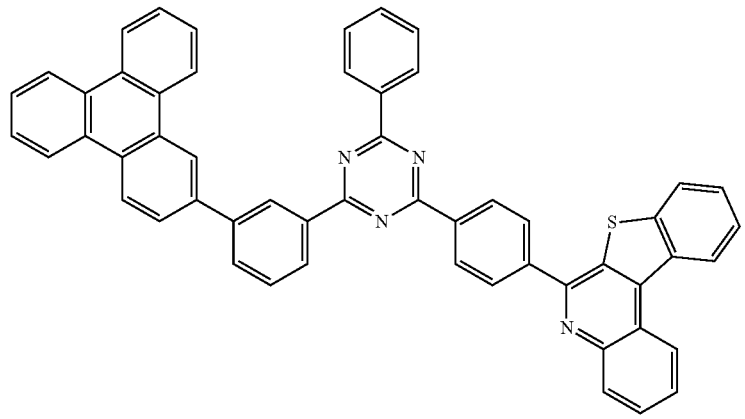
108
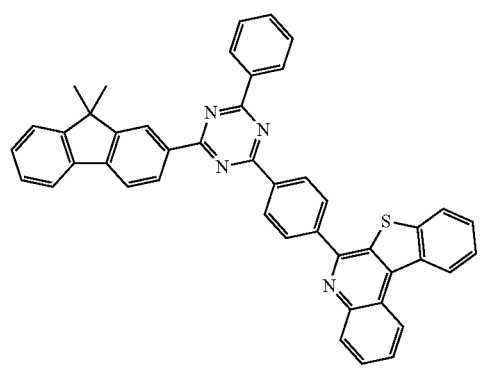
109
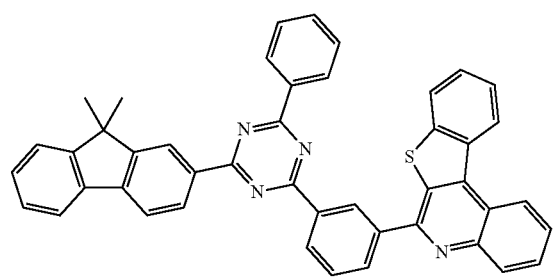
110
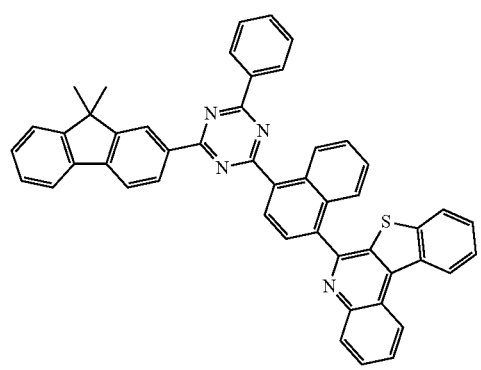
111
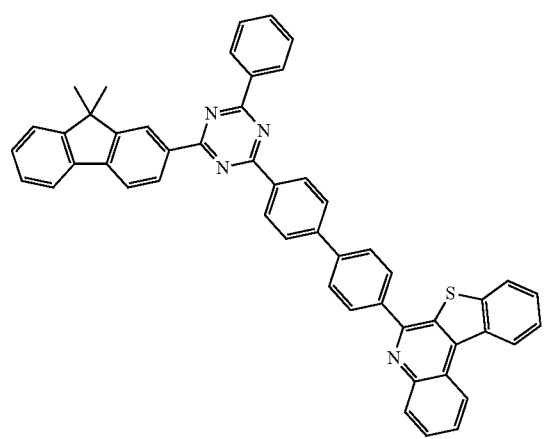
112

113
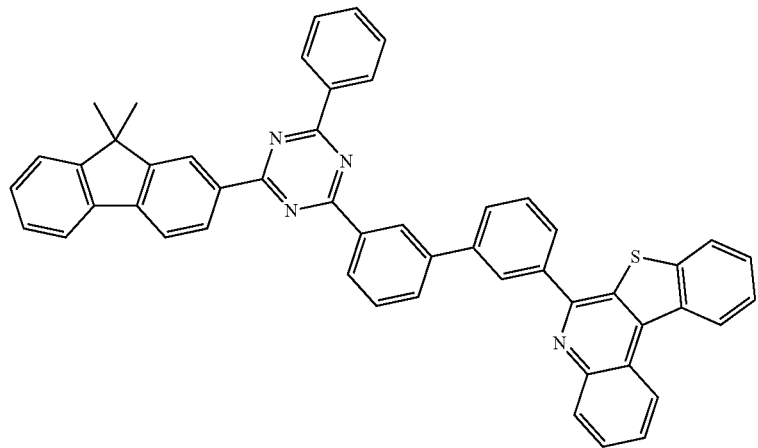
114
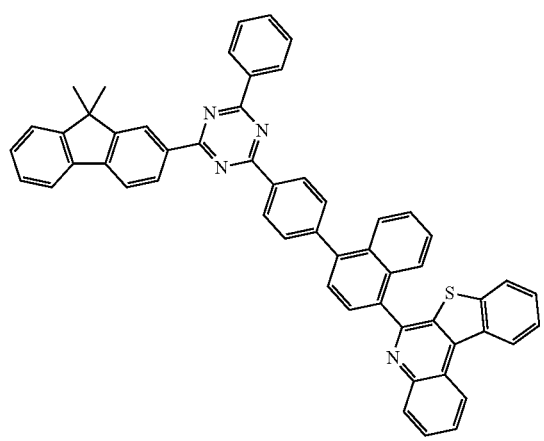
115
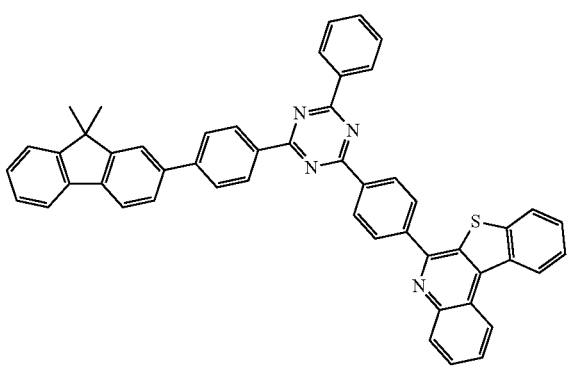
116
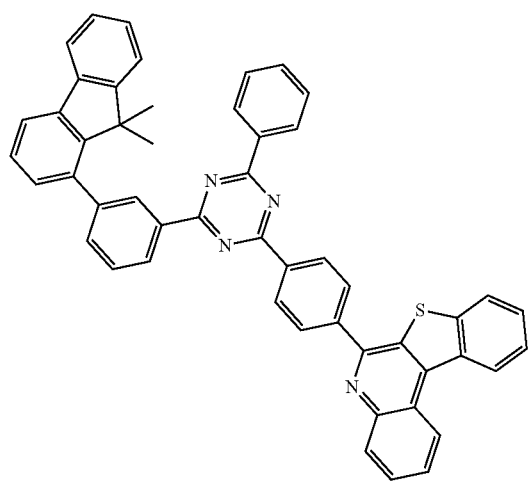
117
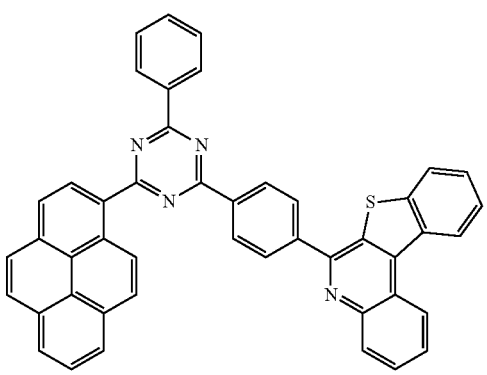

-continued
118
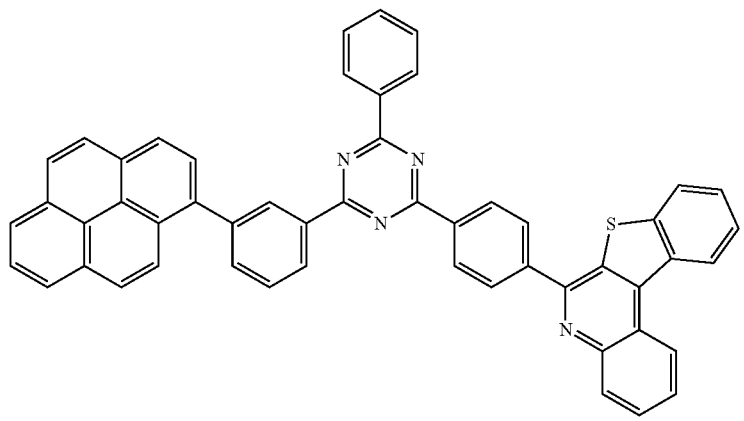
119 120
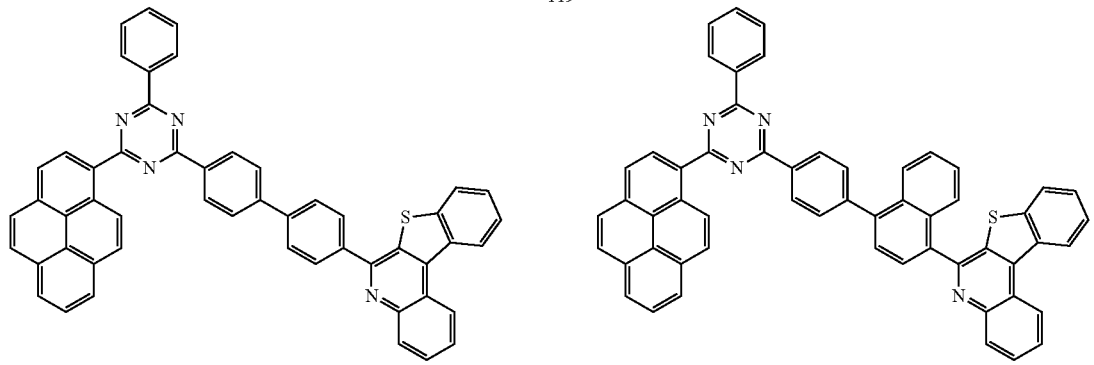
121 122
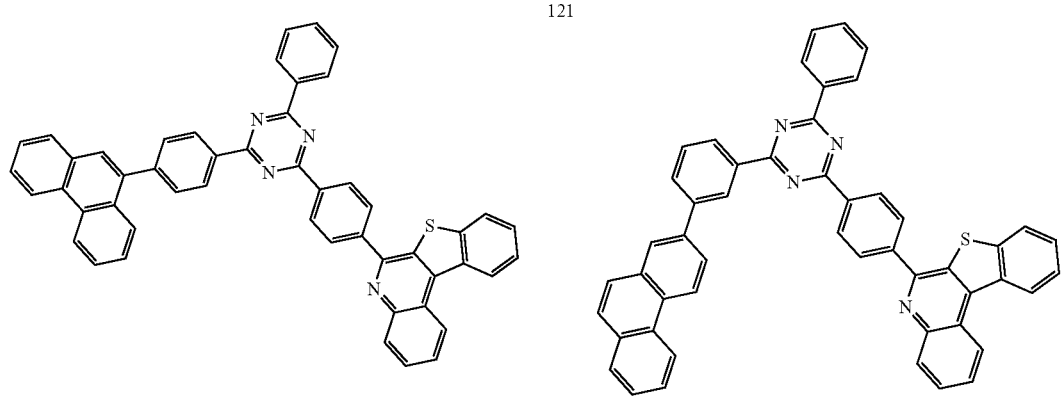
123 124
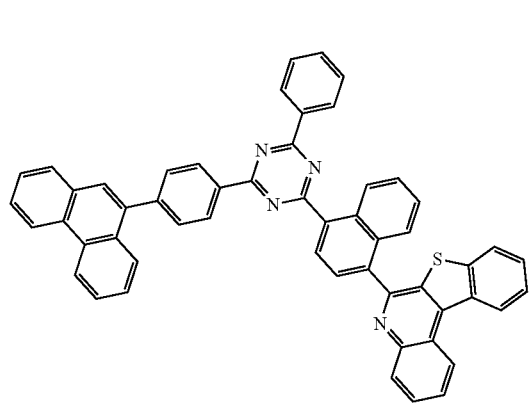 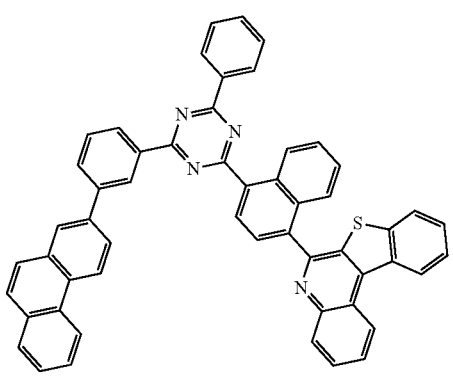

-continued
125
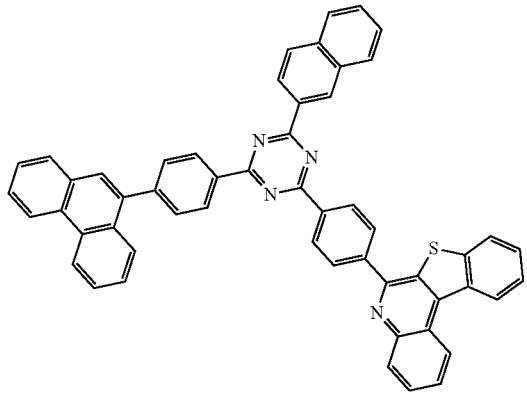
126
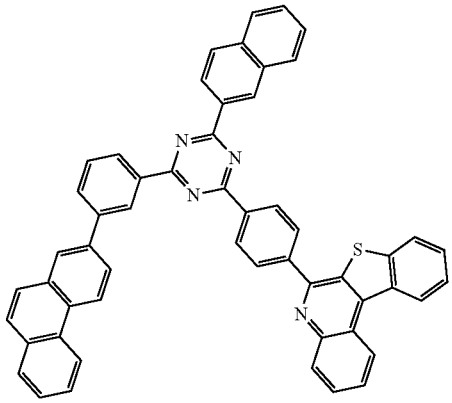
127
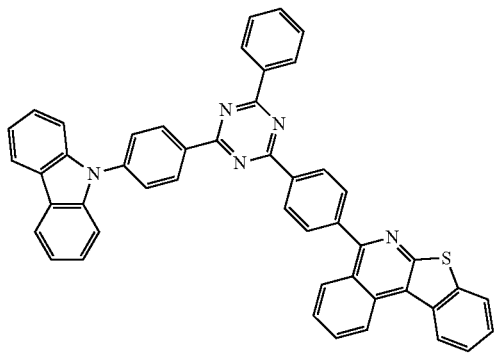
128
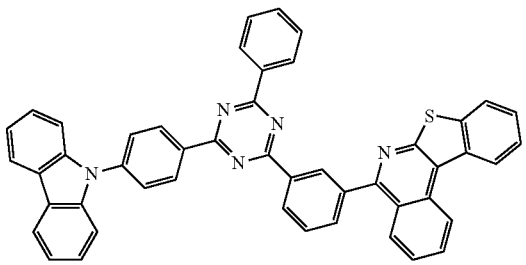
129
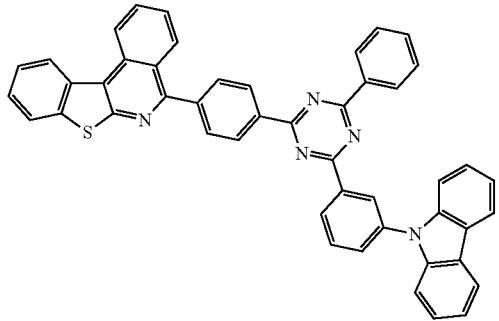
130
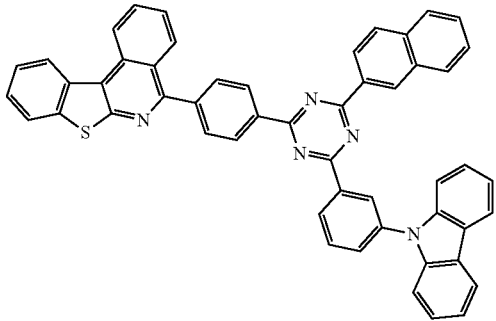
131
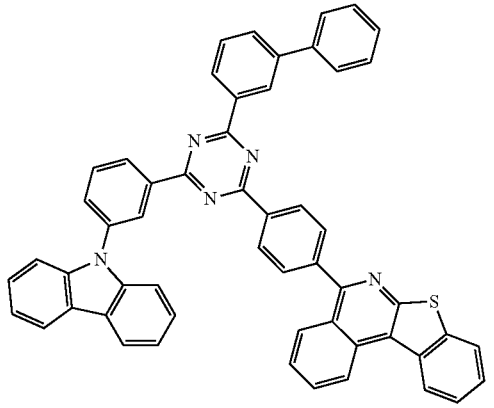
132
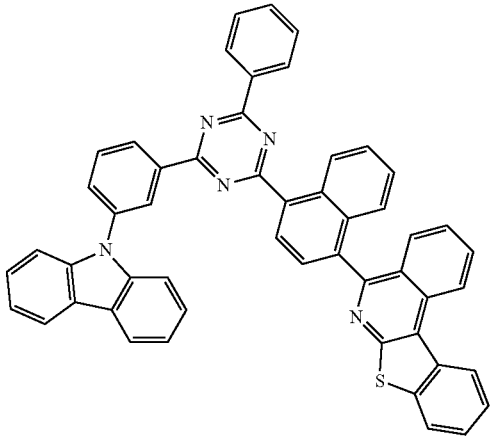

-continued
133
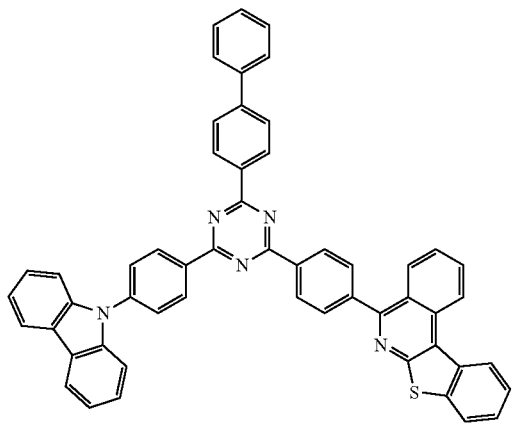
134
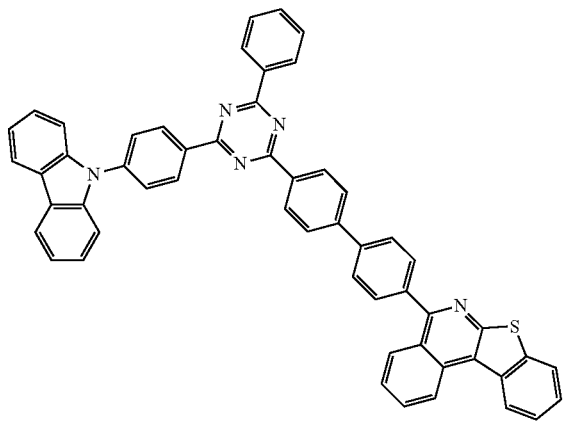
135
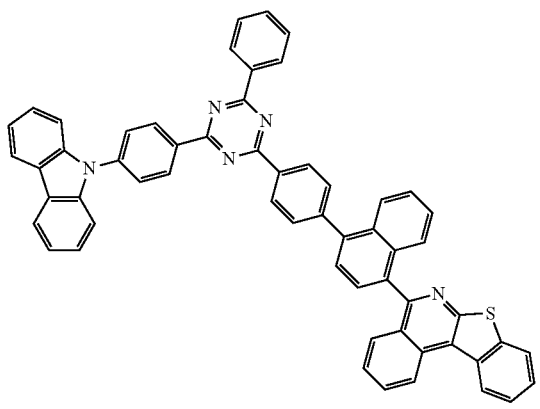
136
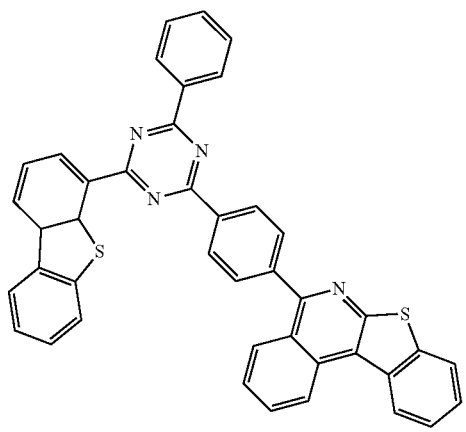
137
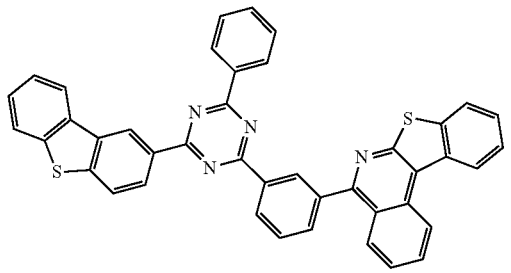
138
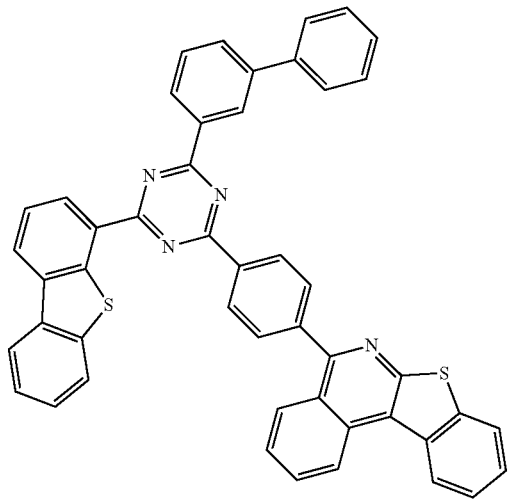

-continued
139
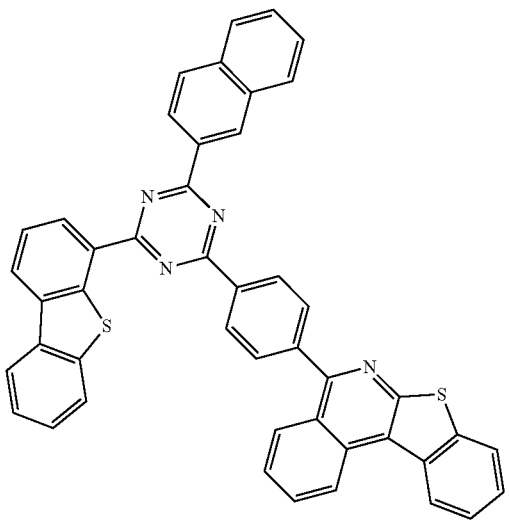
140
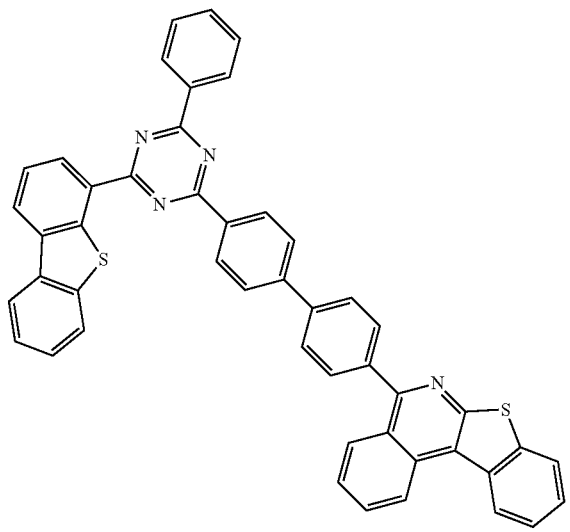
141
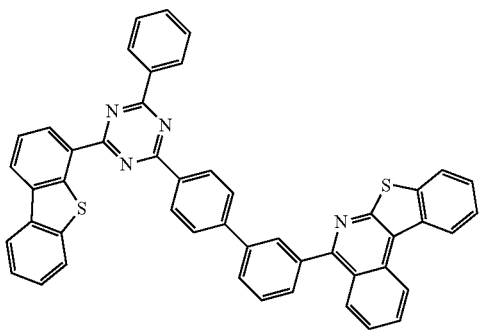
142
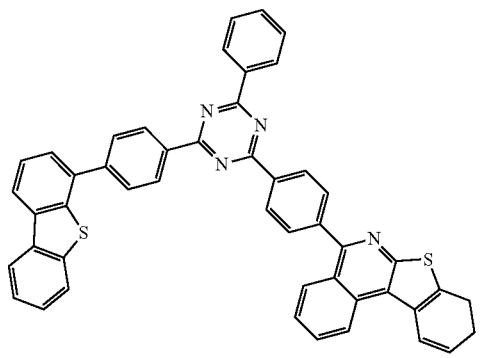
143
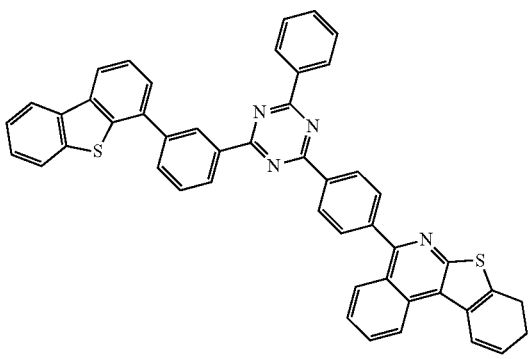
144
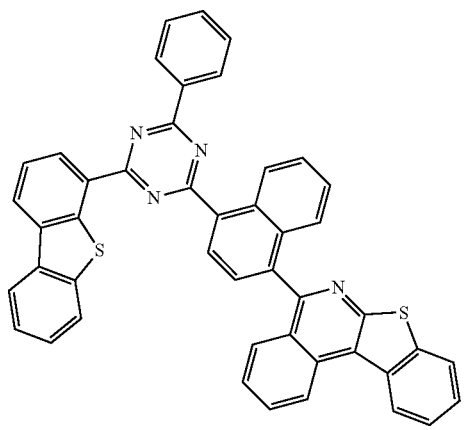

-continued
145
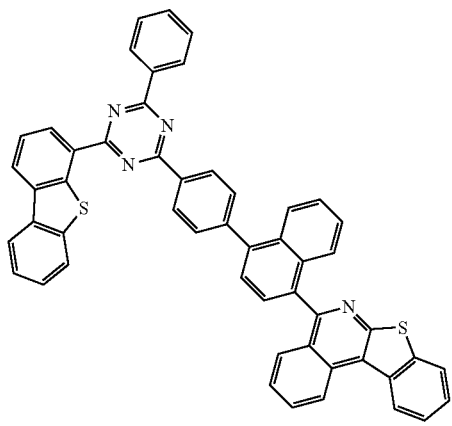
146
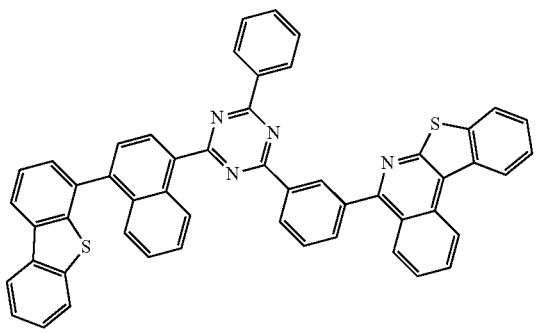
147
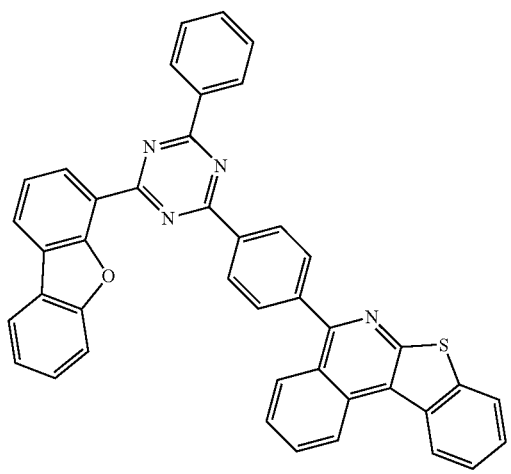
148
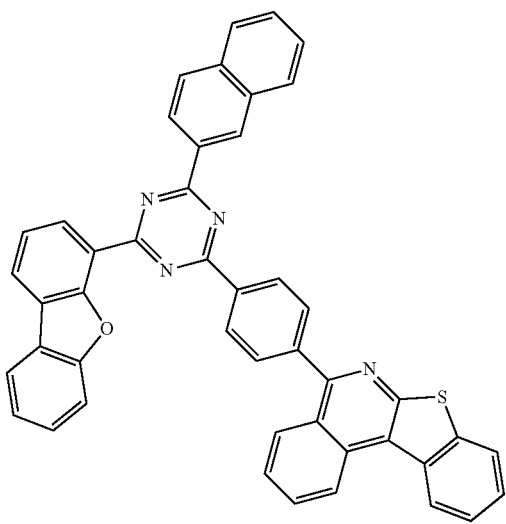
149
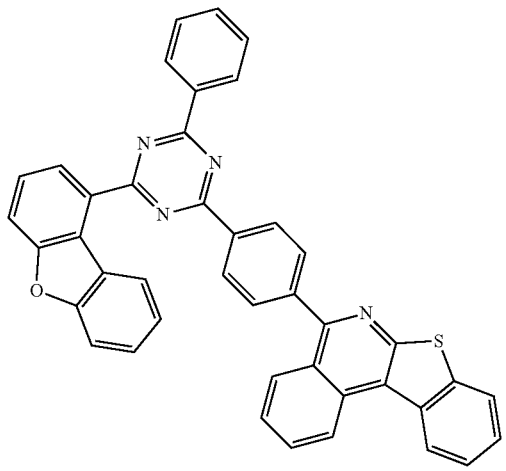
150
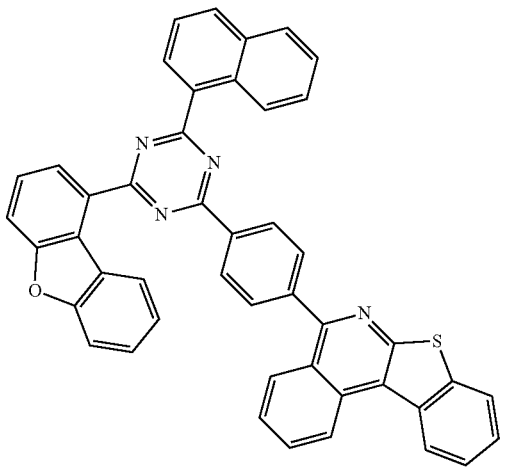

151
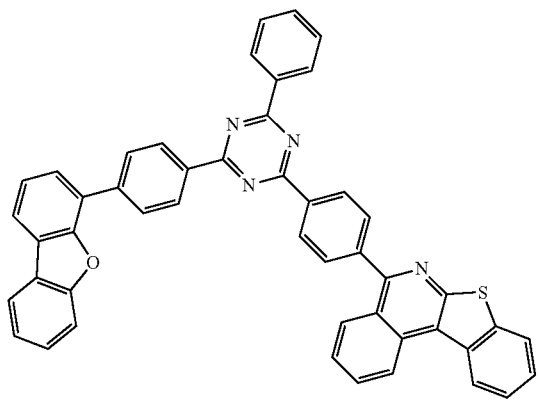
152
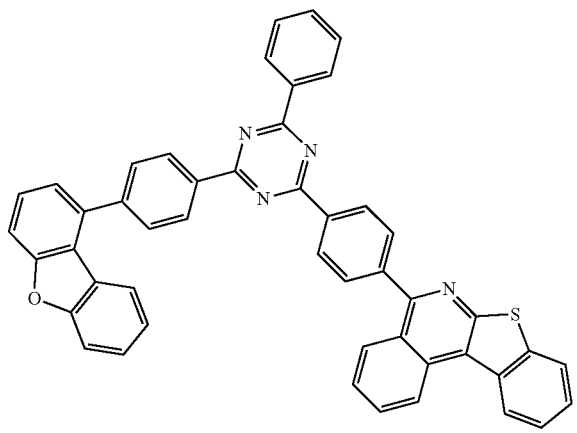
153
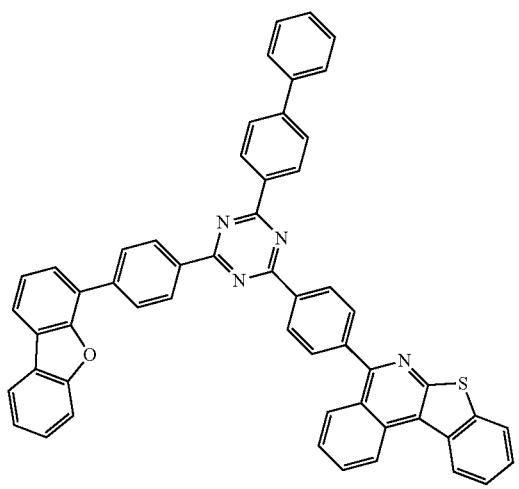
154
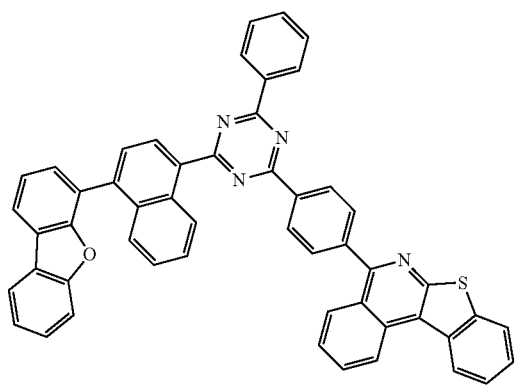
155
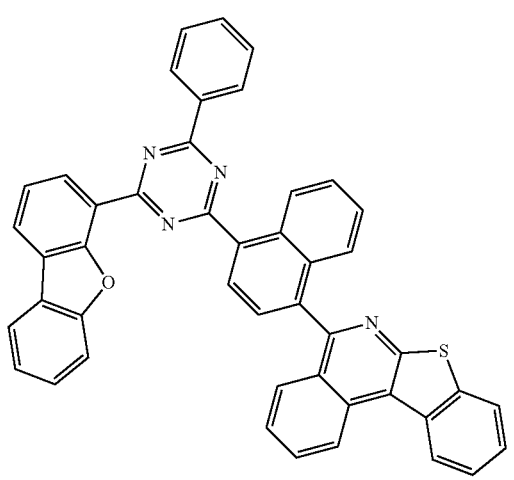
156
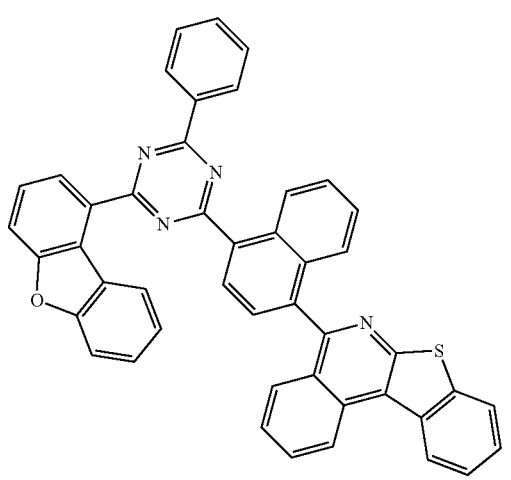

-continued
157
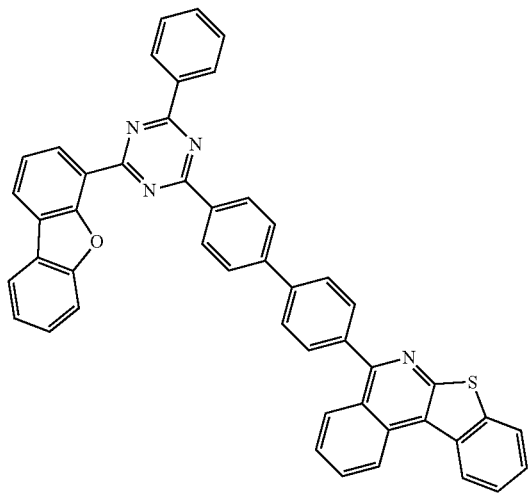
158
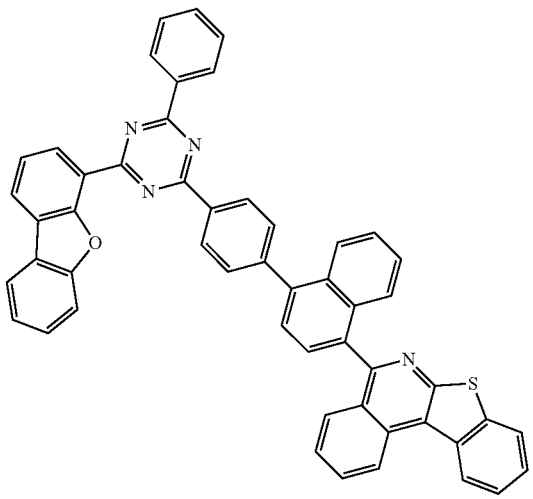
159
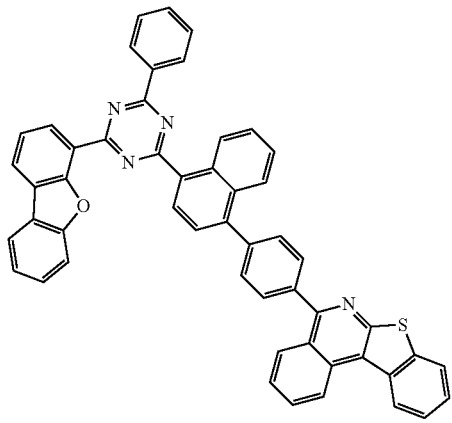
160
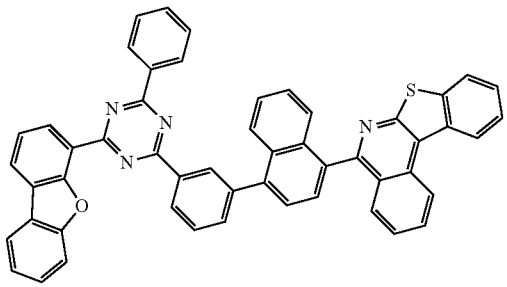
161
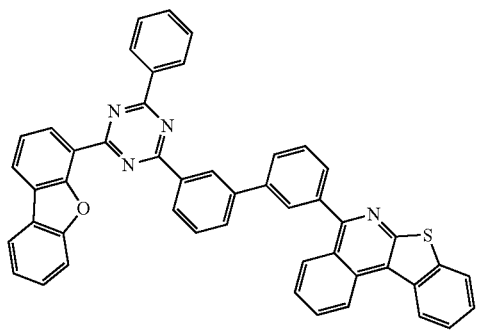
162
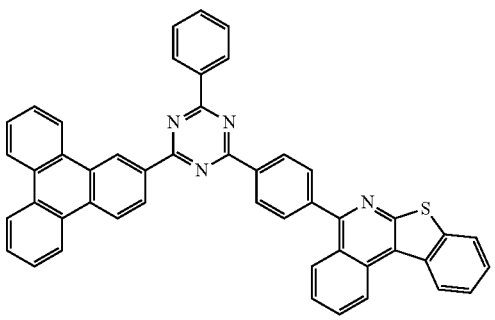
163
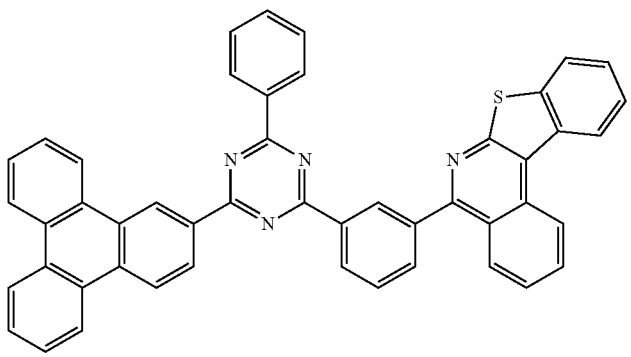

-continued
164
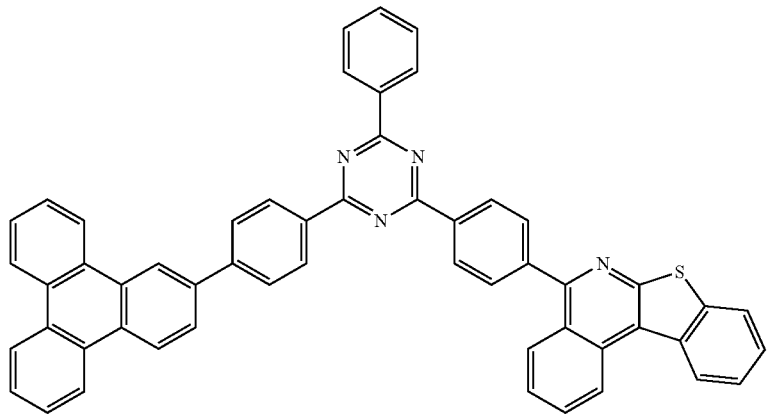
165
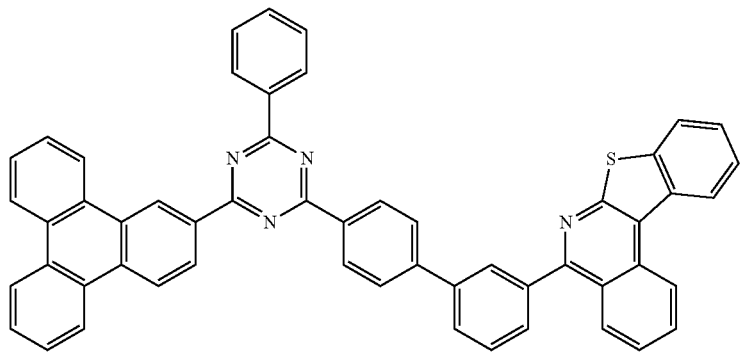
166
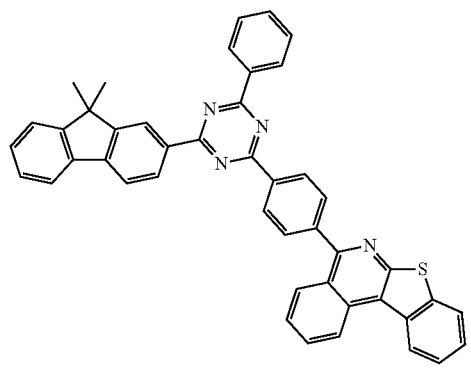
167
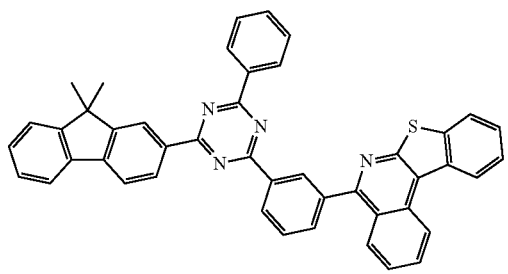
168
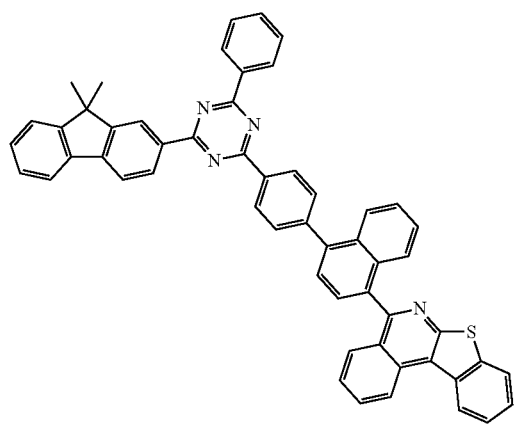
169
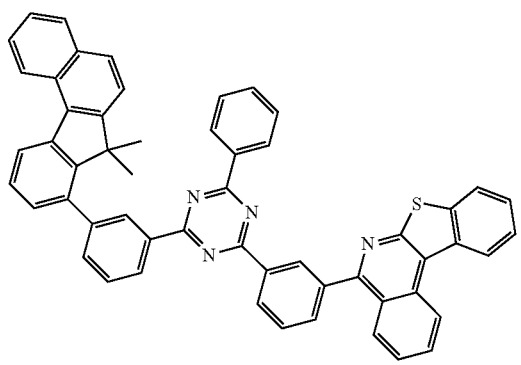

-continued
170
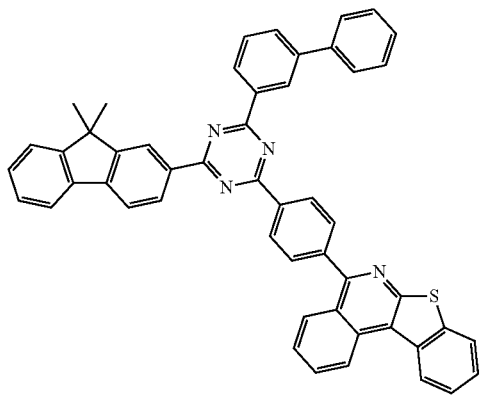
171
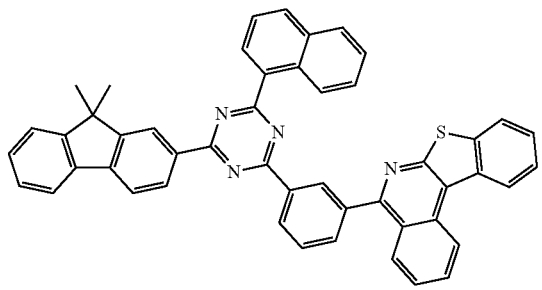
172
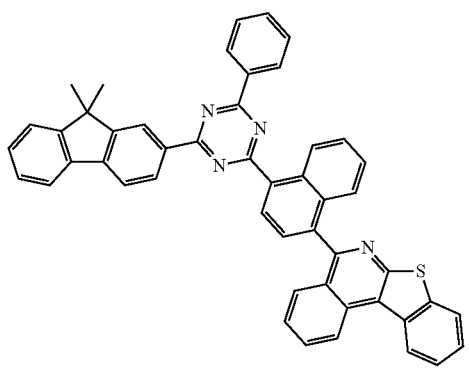
173
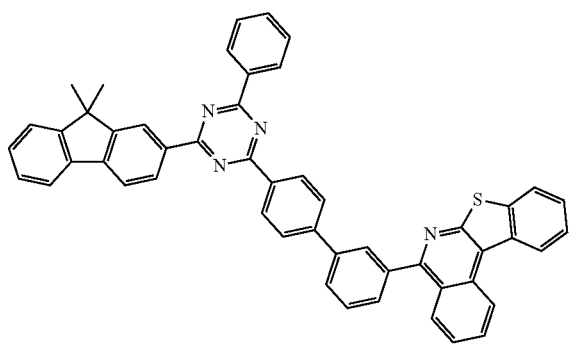
174
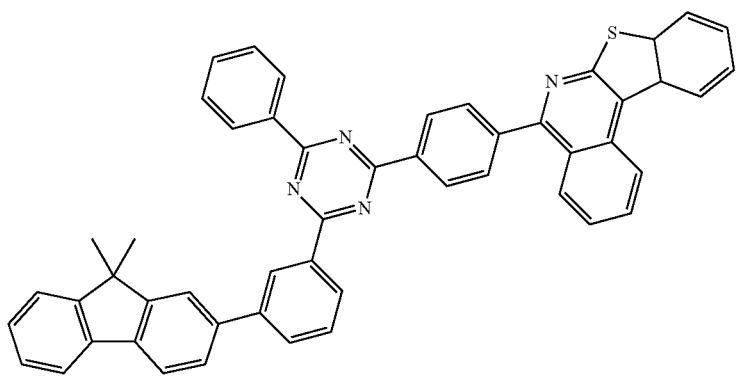
175
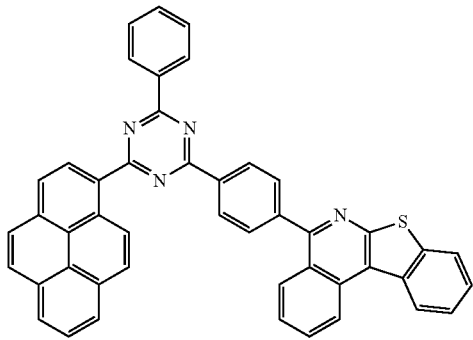
176
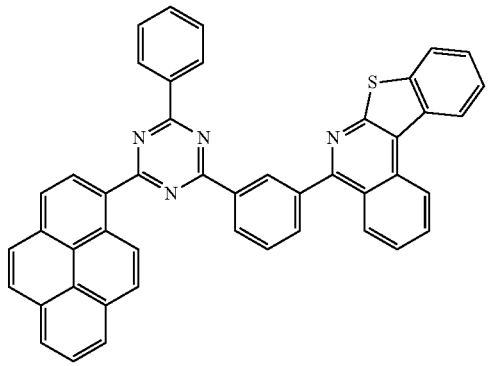

177
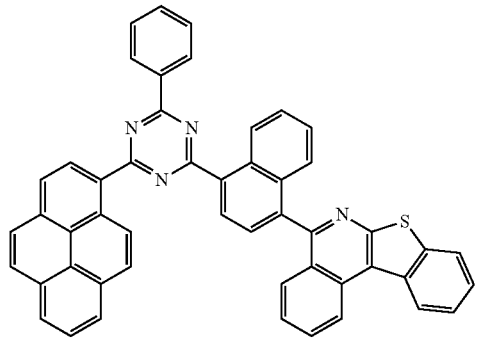
178
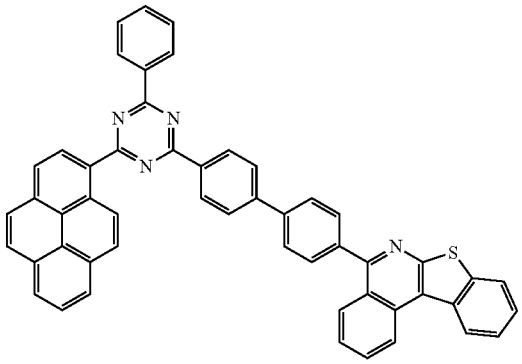
179
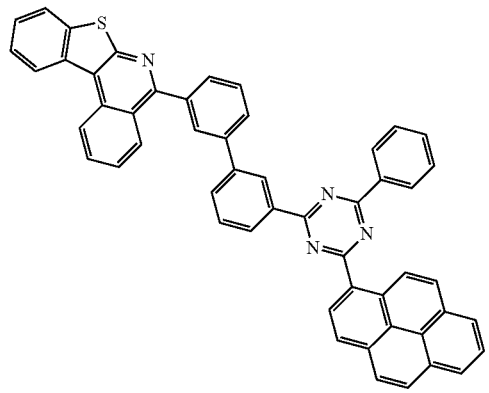
180
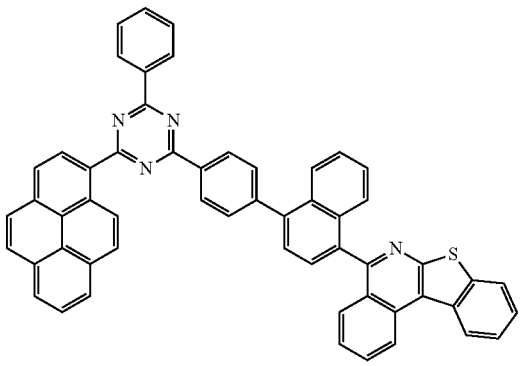
181
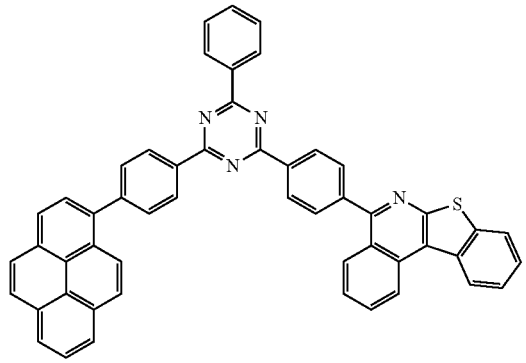
182
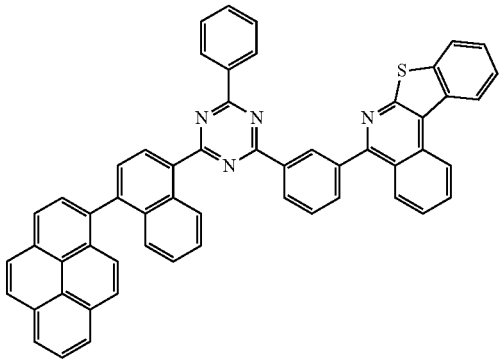
183
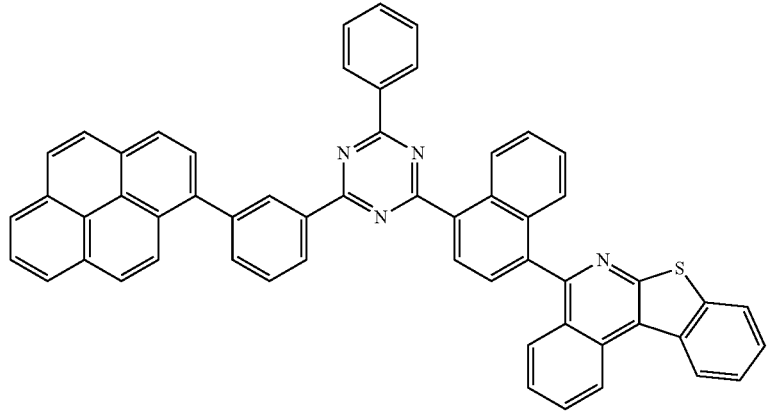

-continued
184
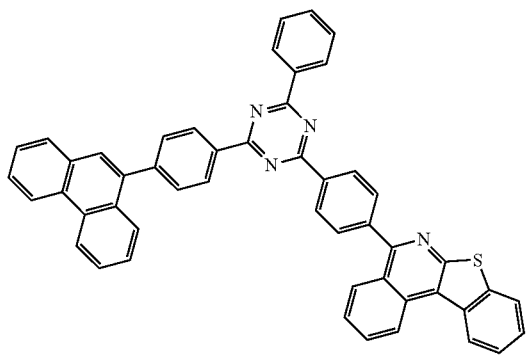
185
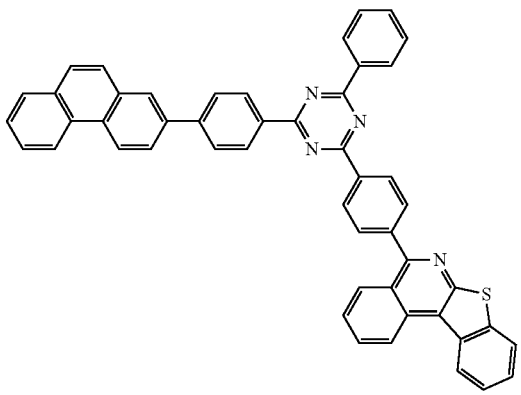
186
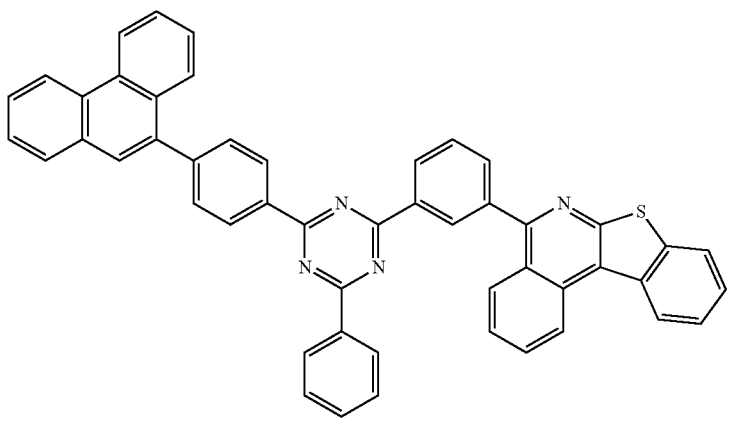
187
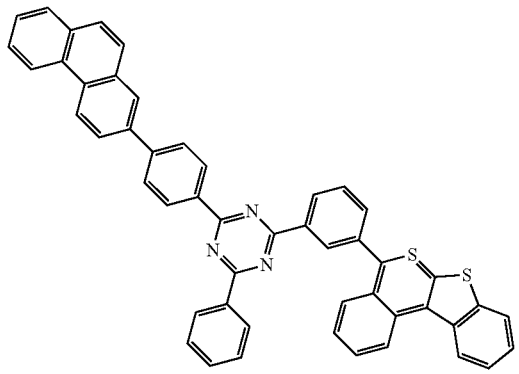
188
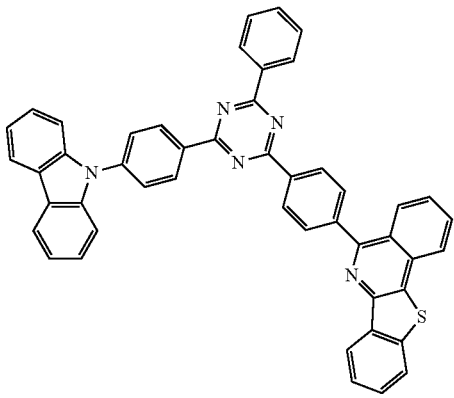
189
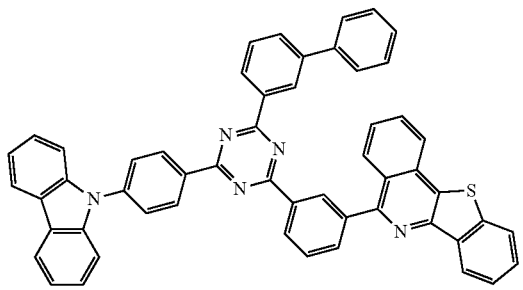
190
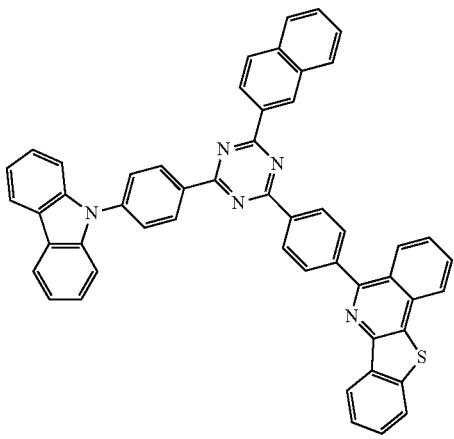

713
-continued
191
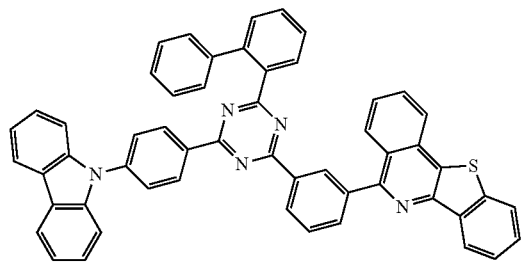
192
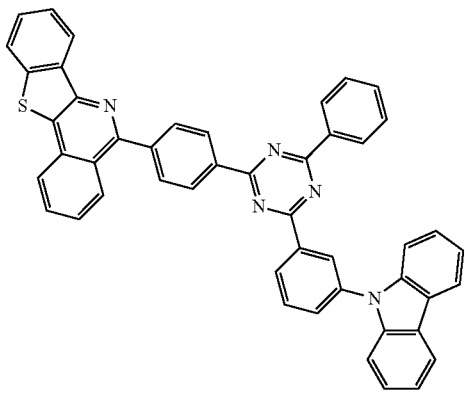
193
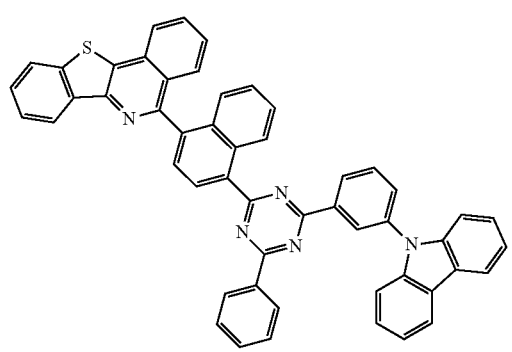
194
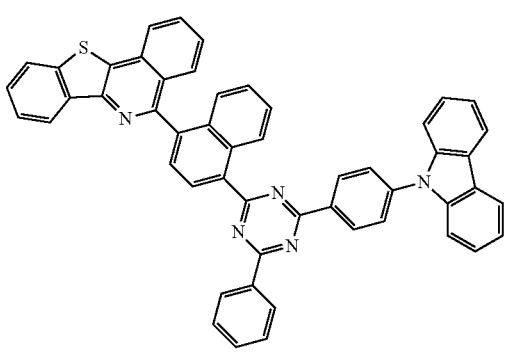
195
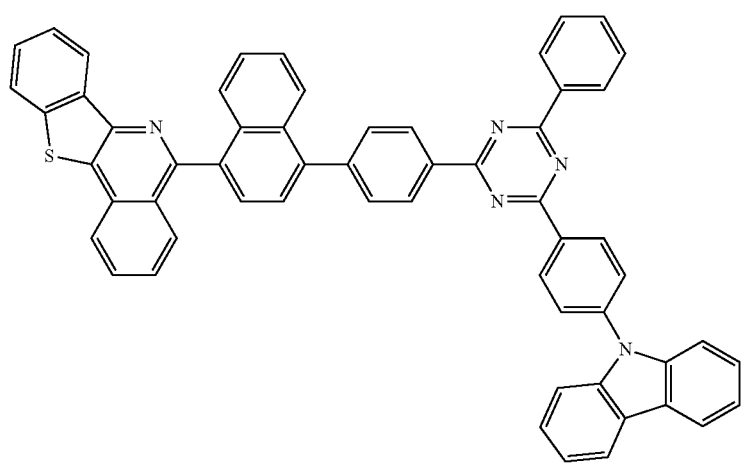

196
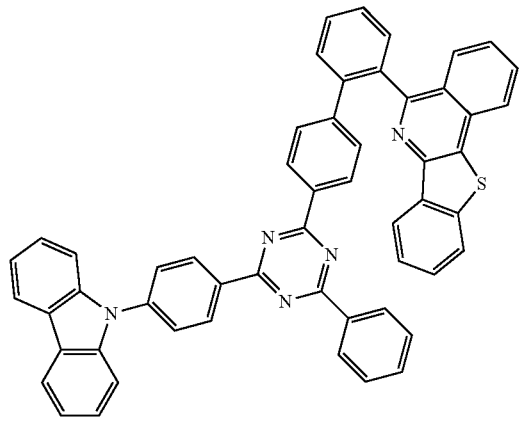
197
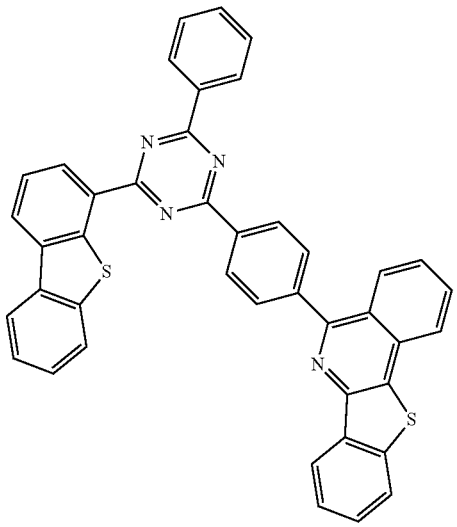
198
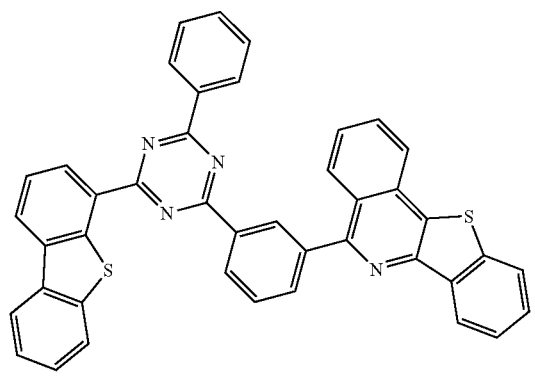
199
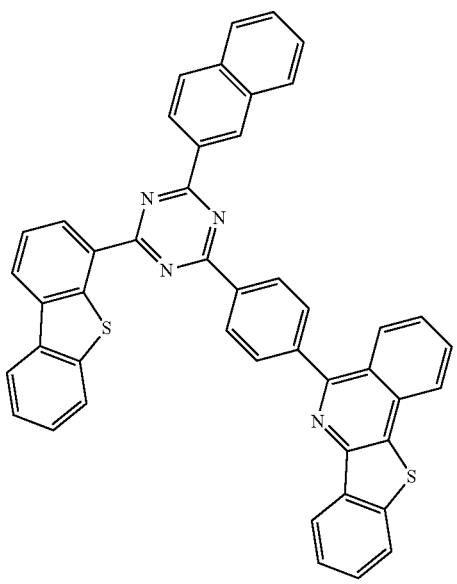

200
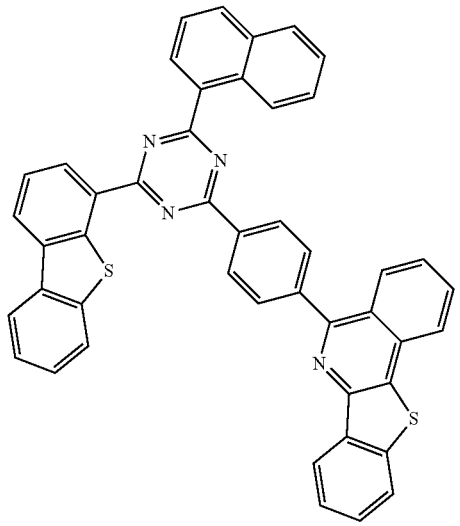
201
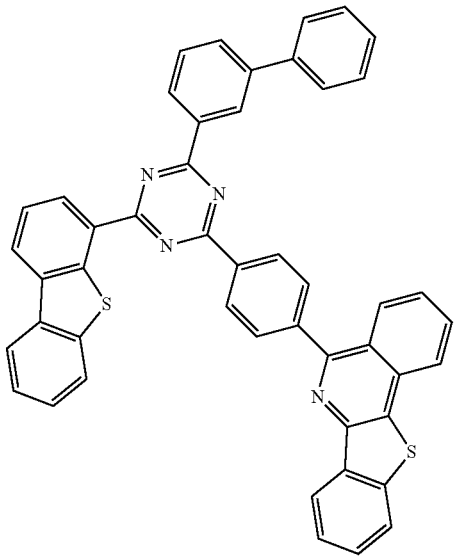
202
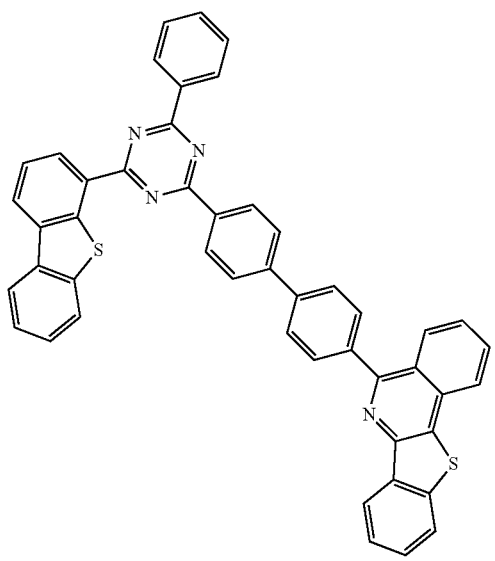
203
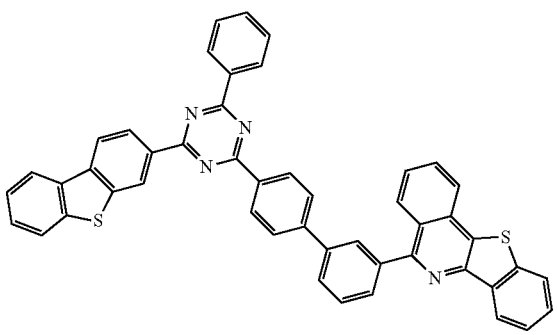
204
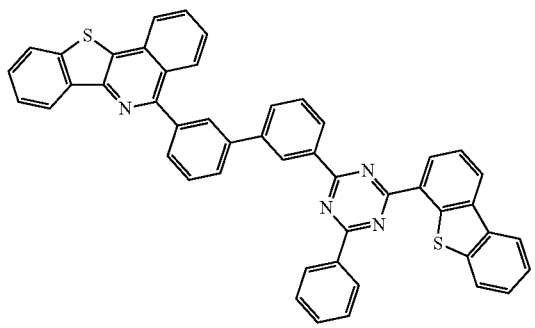
205
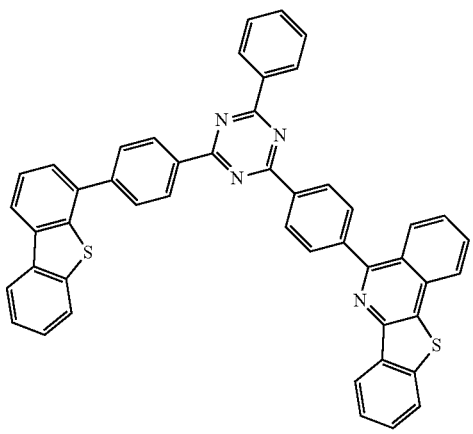

-continued
206
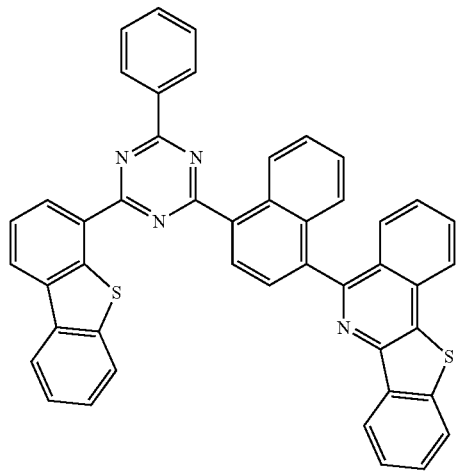
207
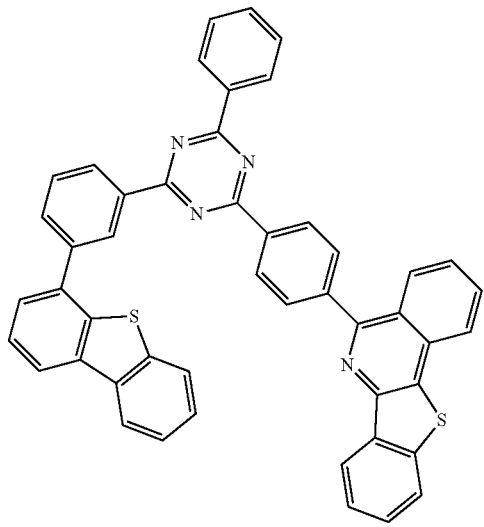
208
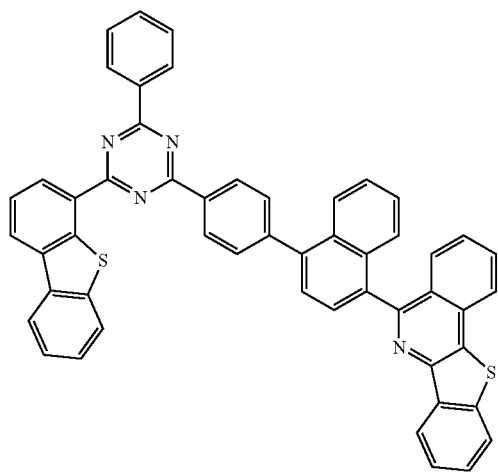
209
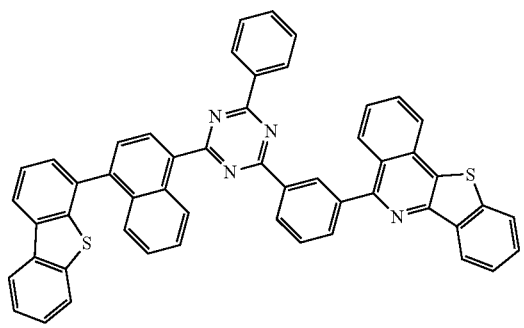
219
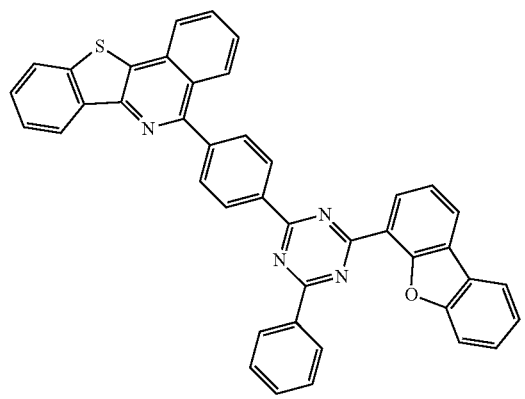
211
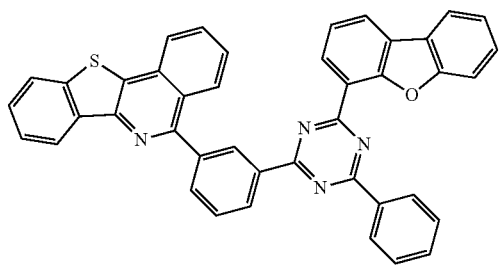

212
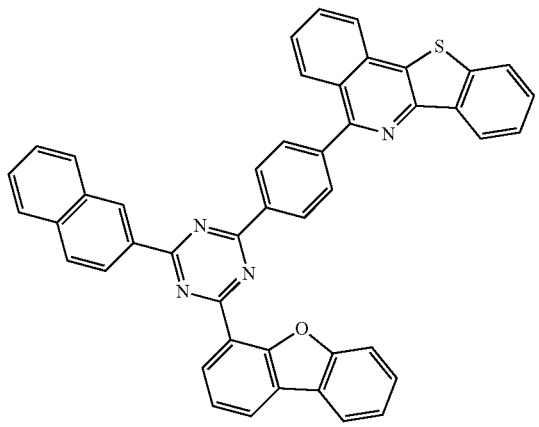
213
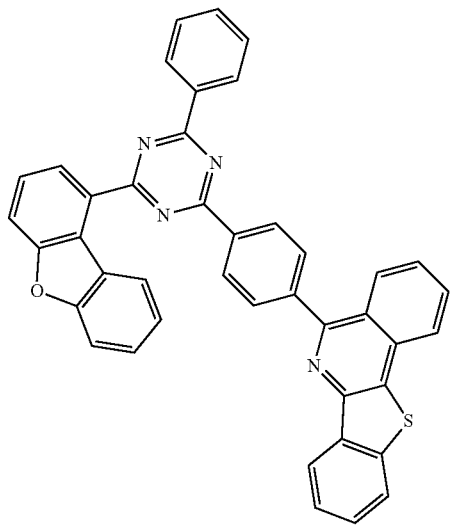
214
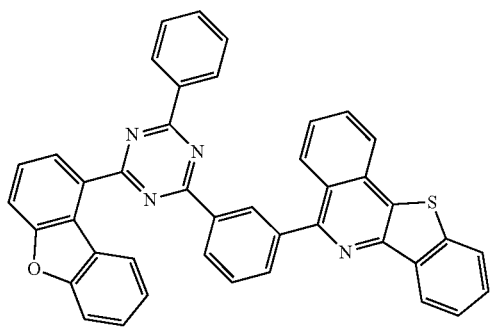
215
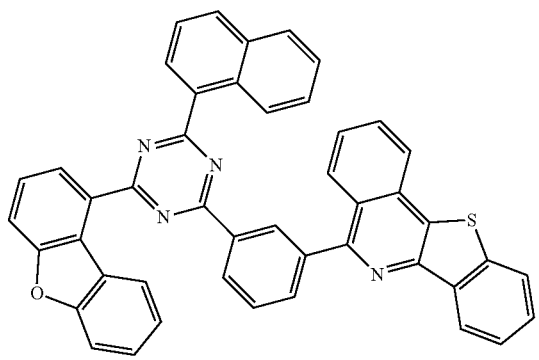
216
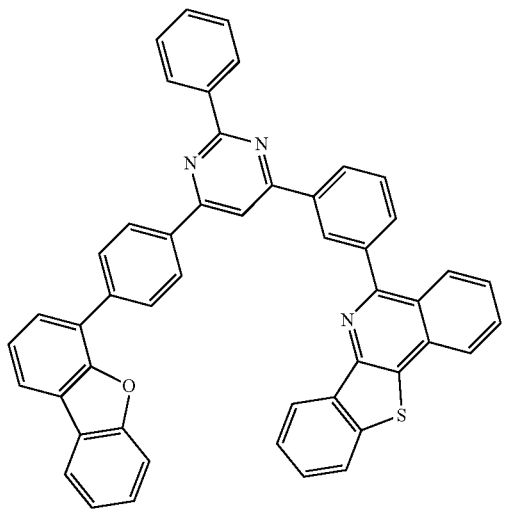
217
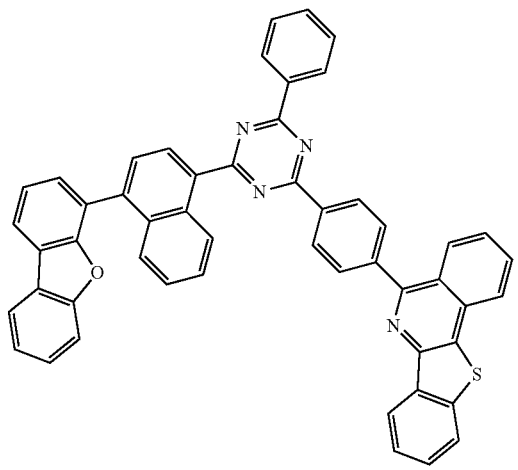

723
724
-continued
218 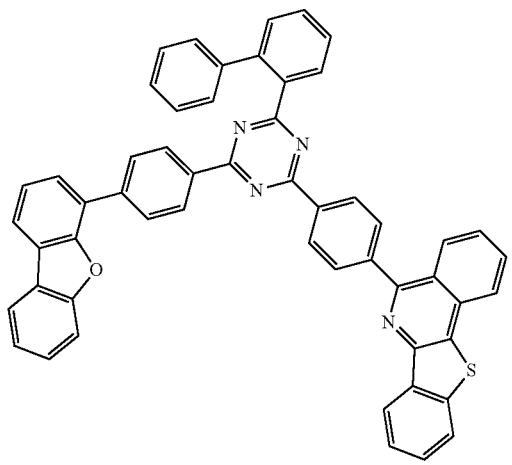
219 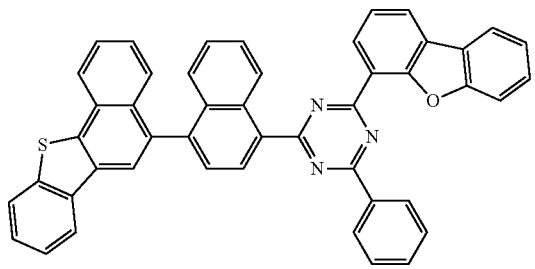
220 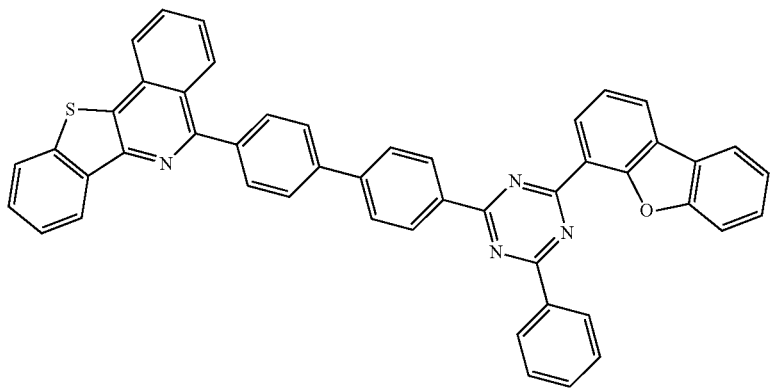
221 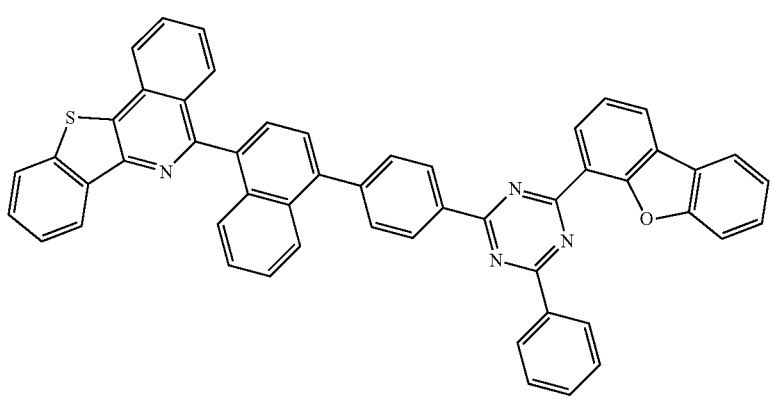

-continued
222
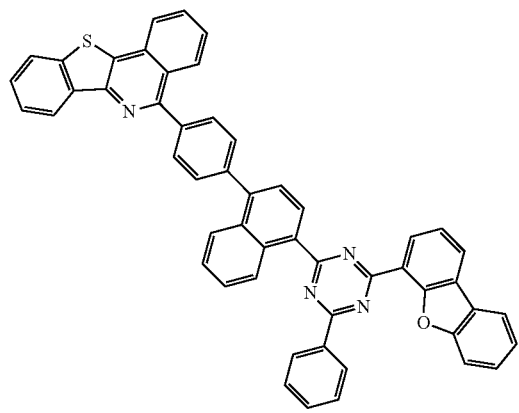
223
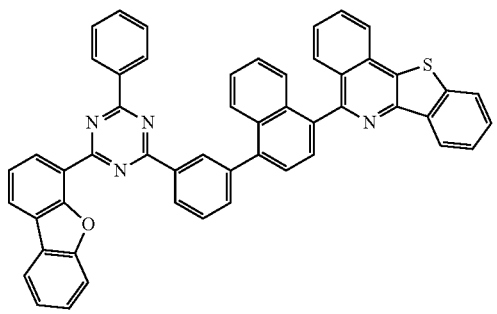
224
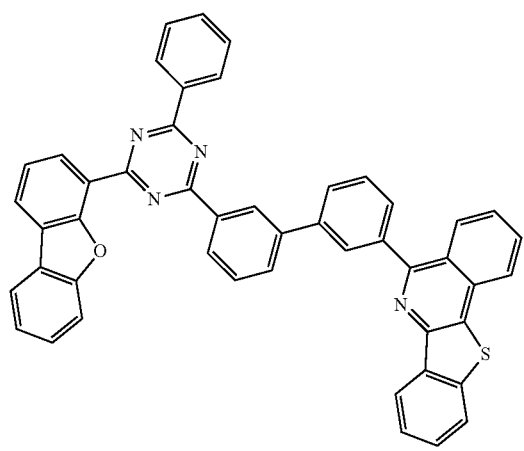
225
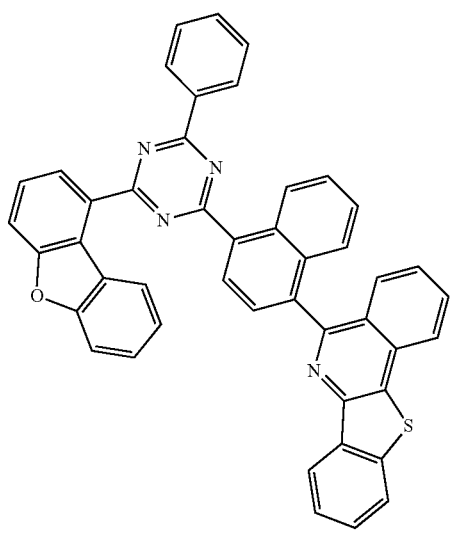
226
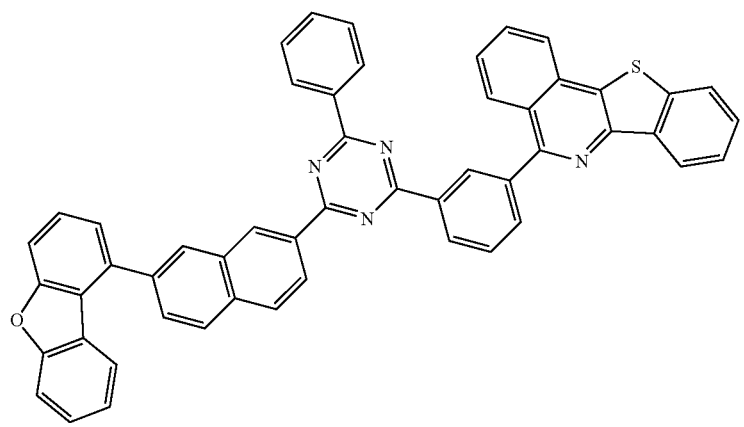

227
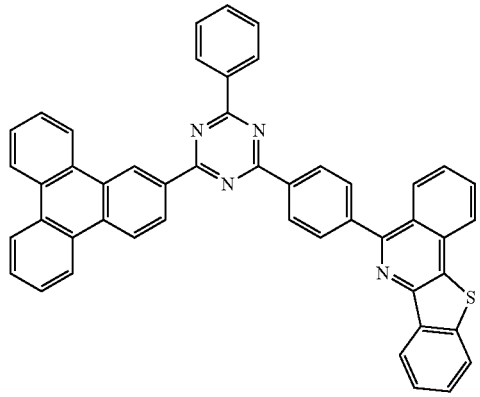
228
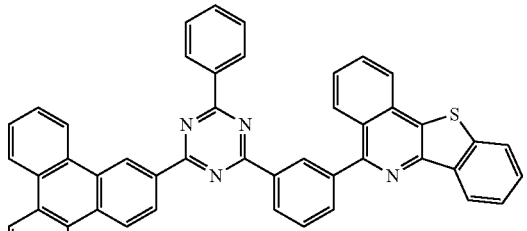
229
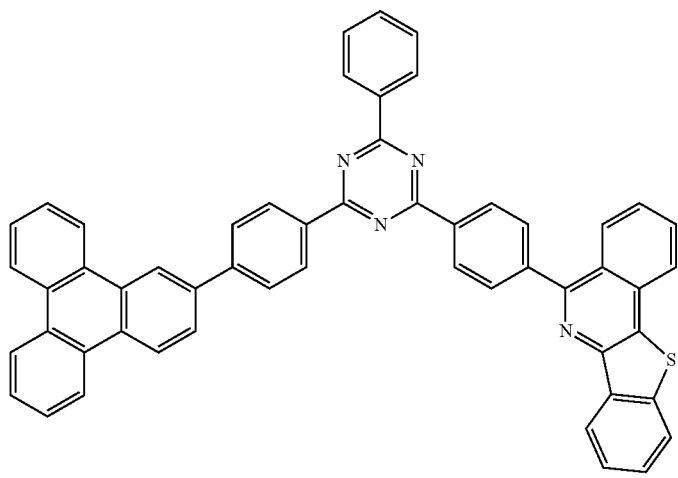
230
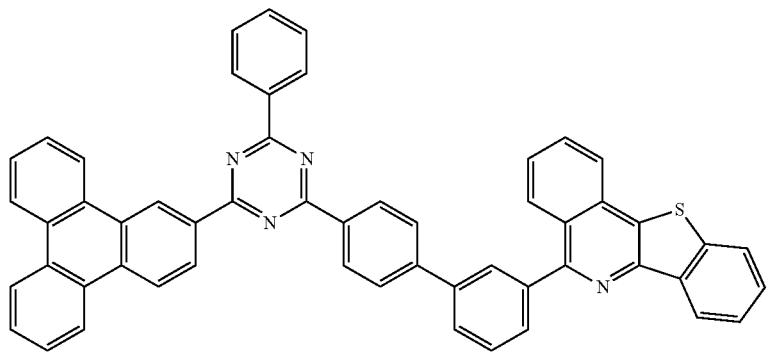

-continued
231
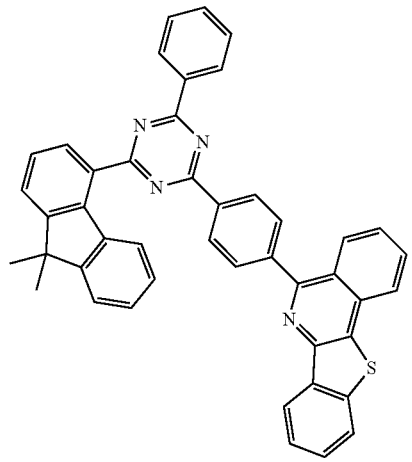
232
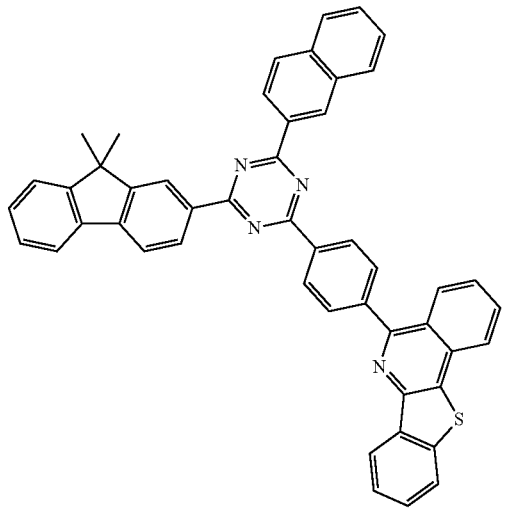
233
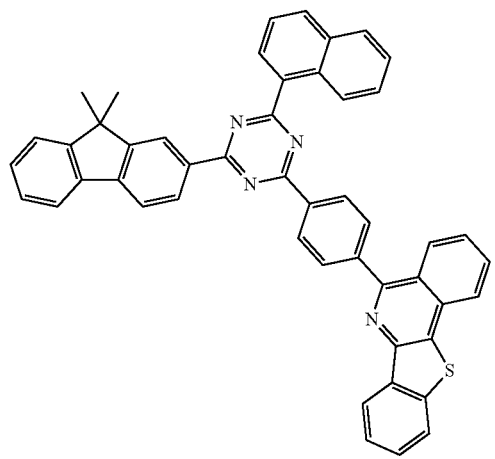
234
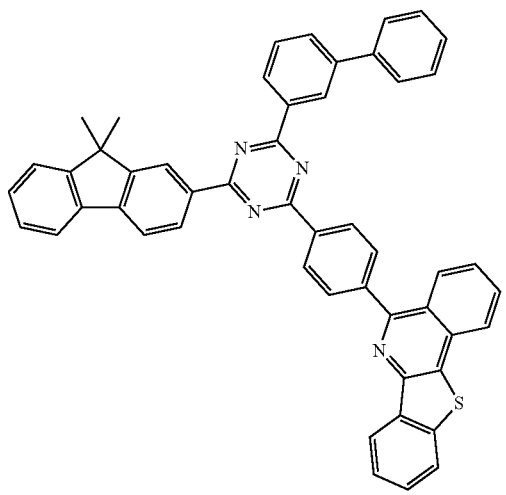
235
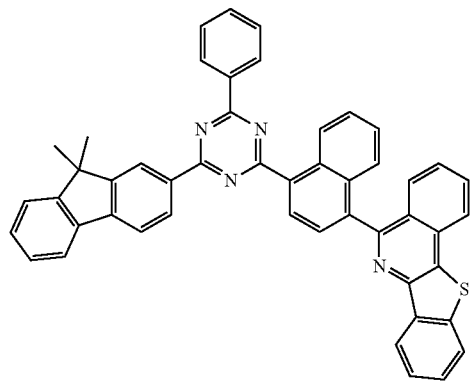
236
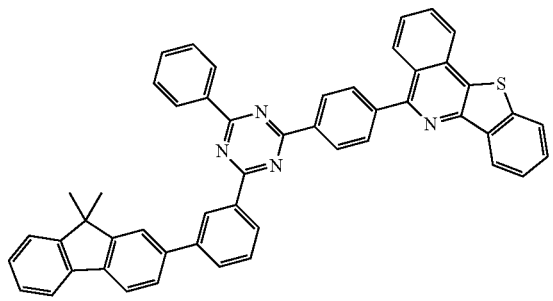

237
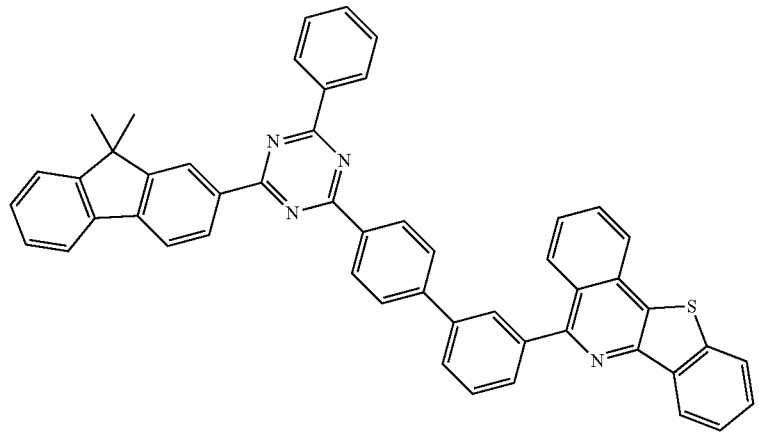
238
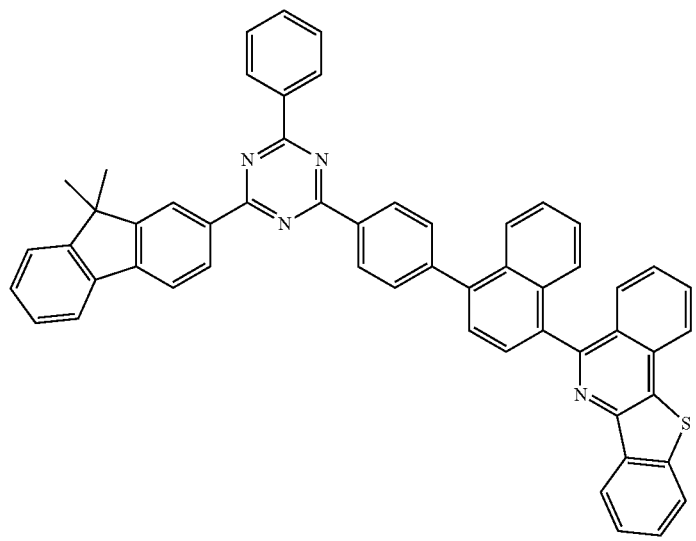
239
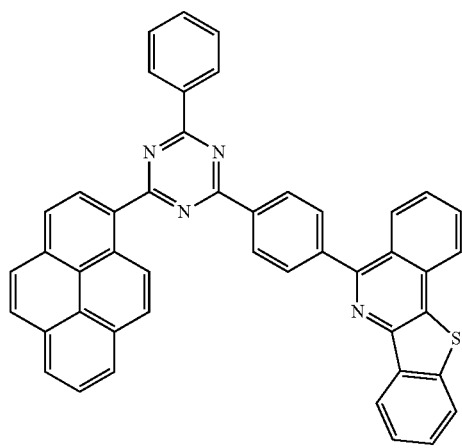
240
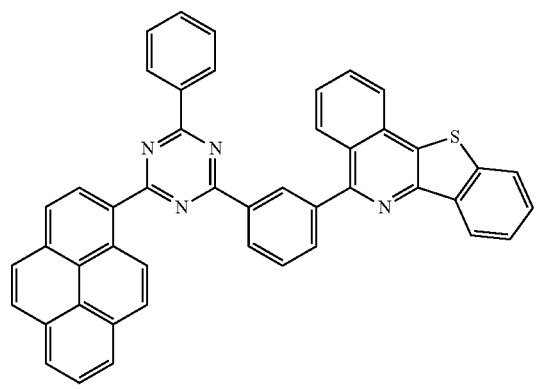

-continued
241
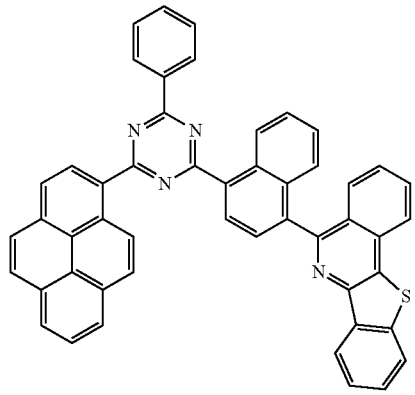
242
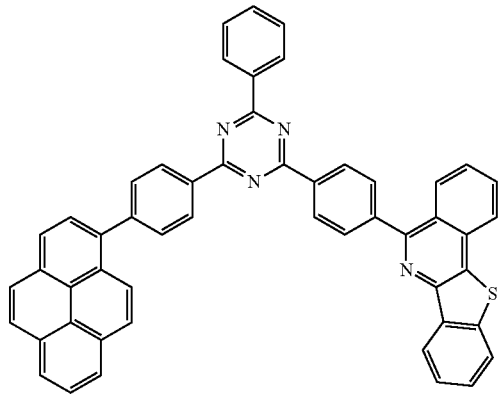
243
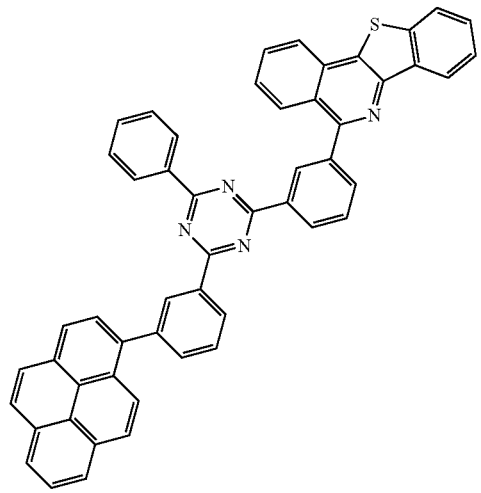
244
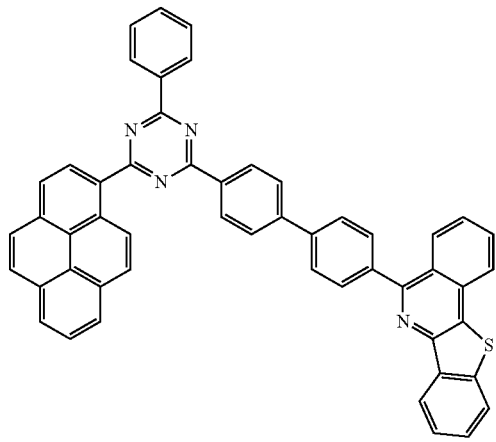
245
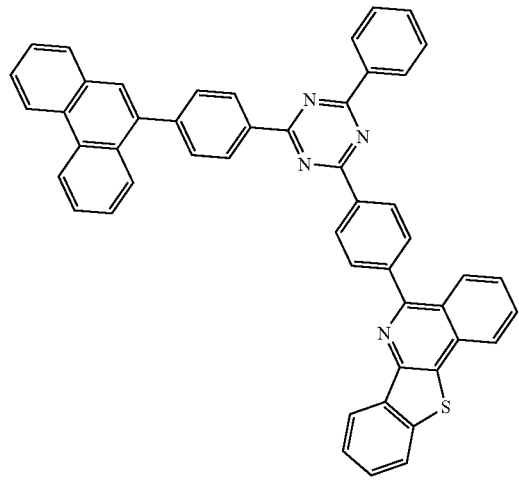
246
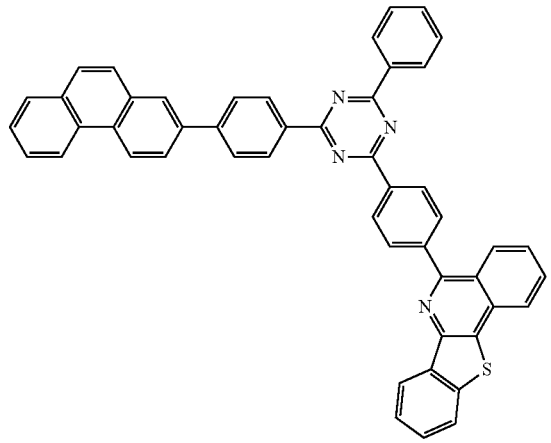

-continued
247
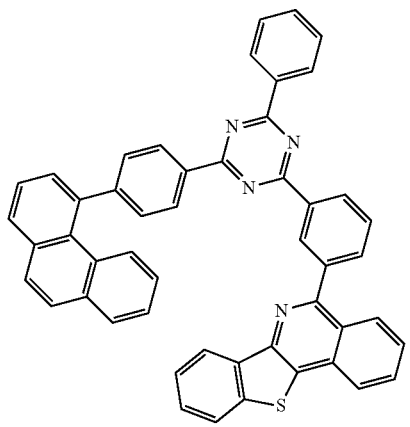
248
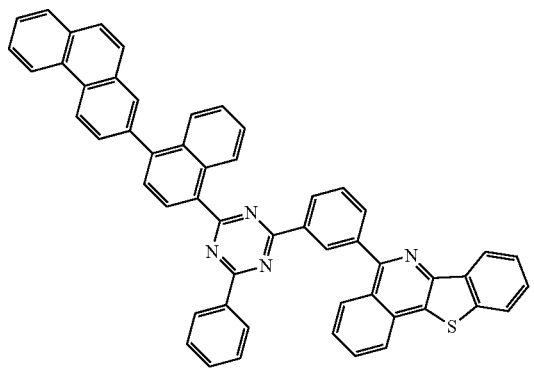
249
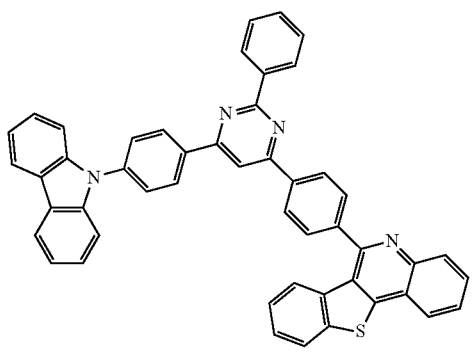
250
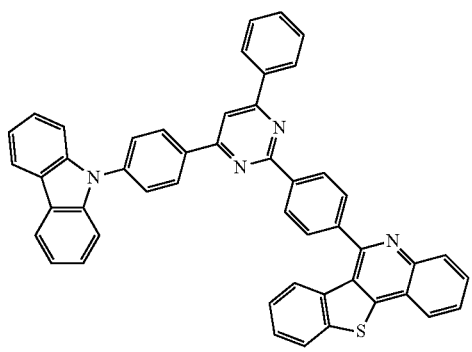
251
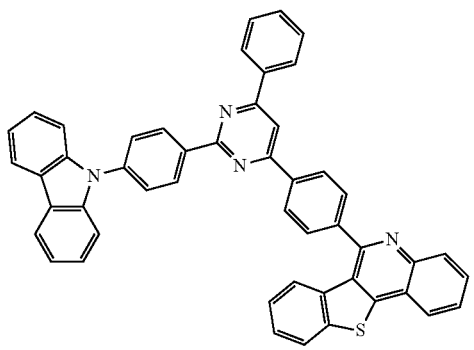
252
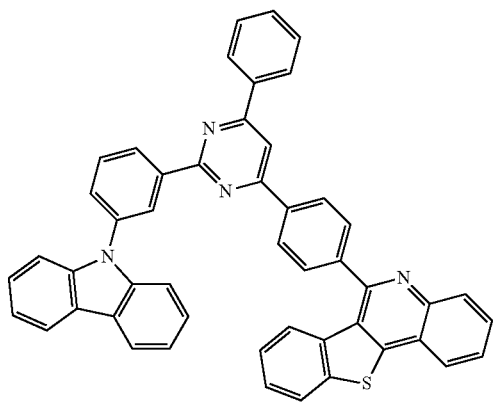
253
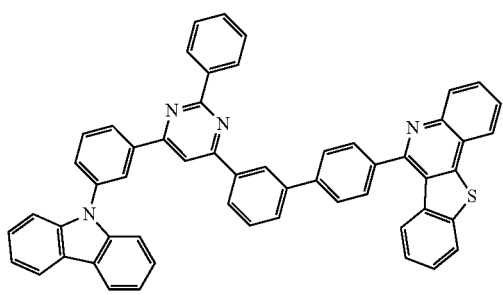
254
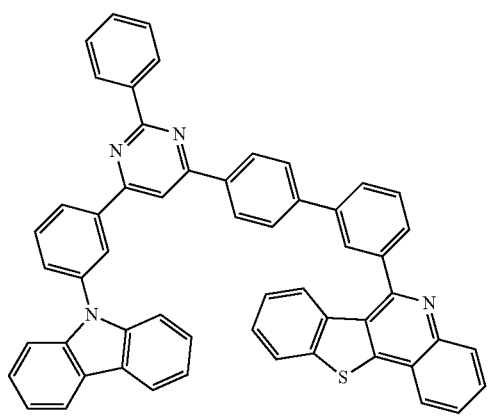

255
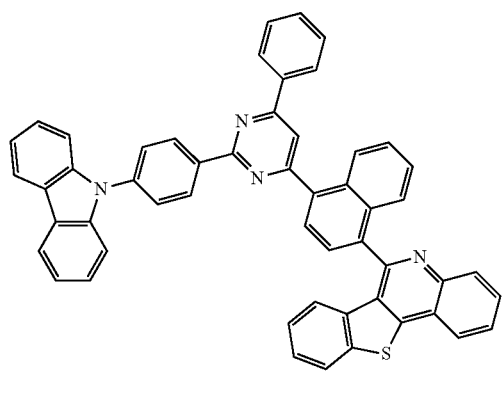
256
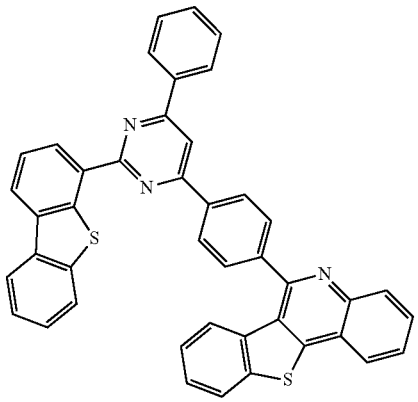
257
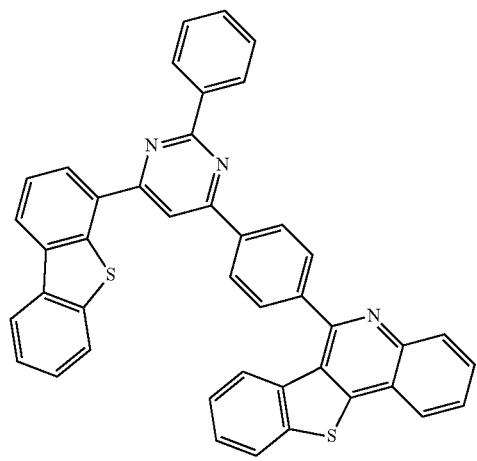
258
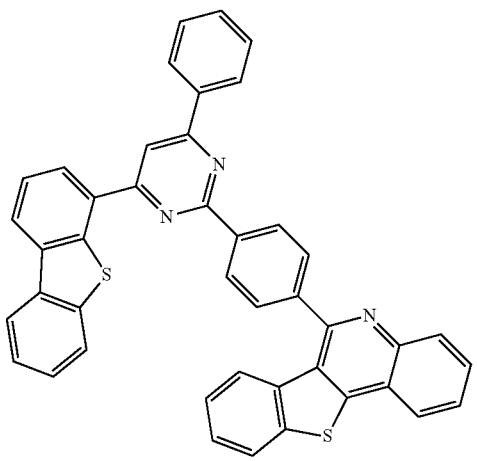
259
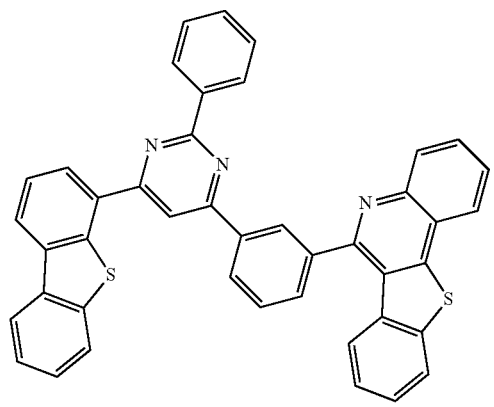
260
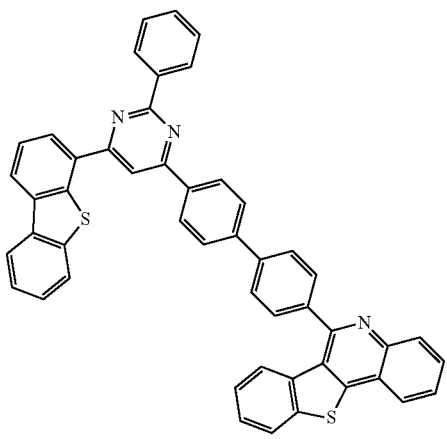

-continued
261
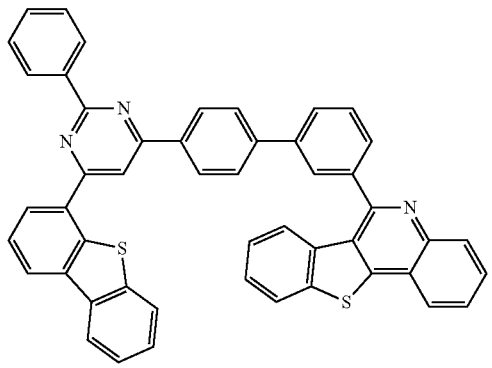
262
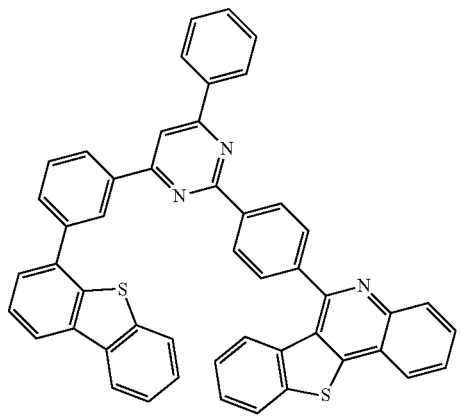
263
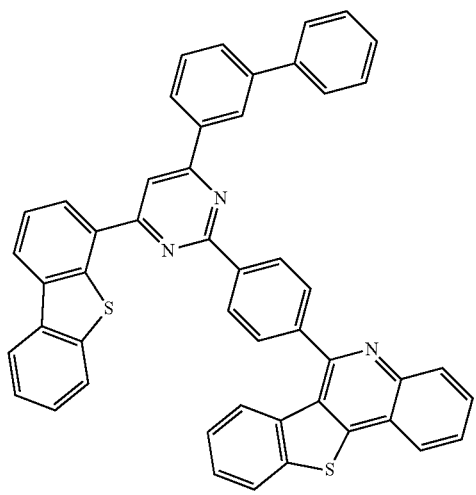
264
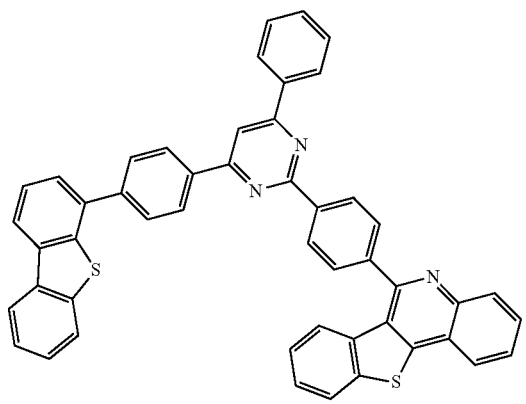
264
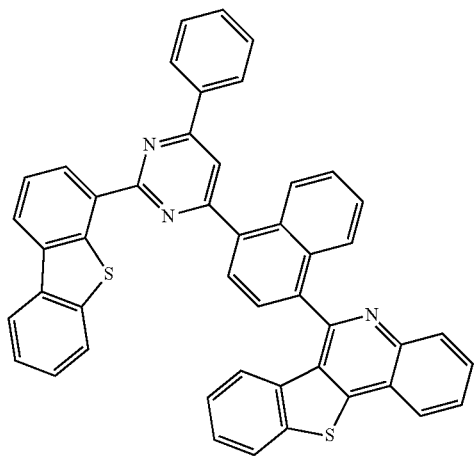
266
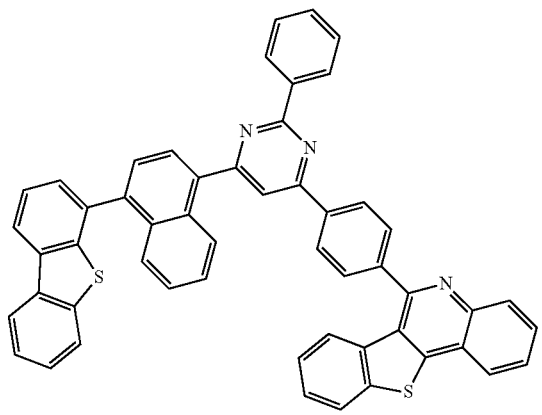

267
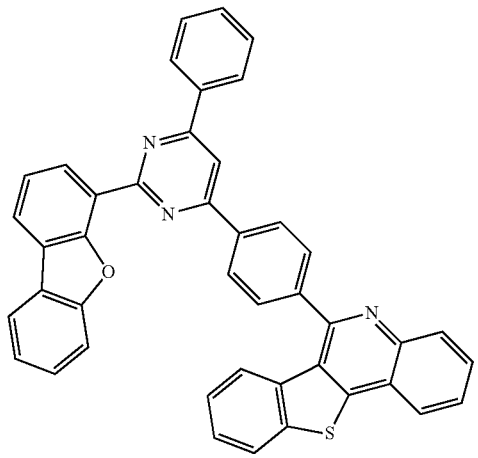
268
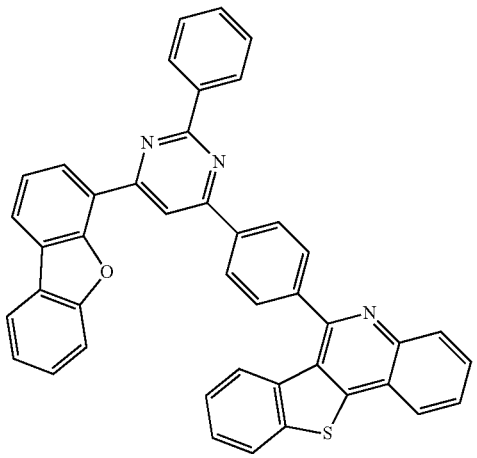
289
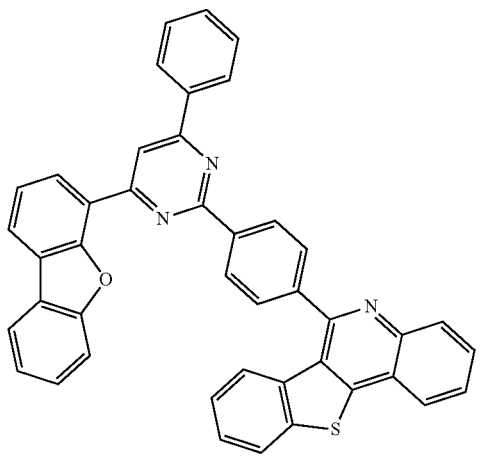
290
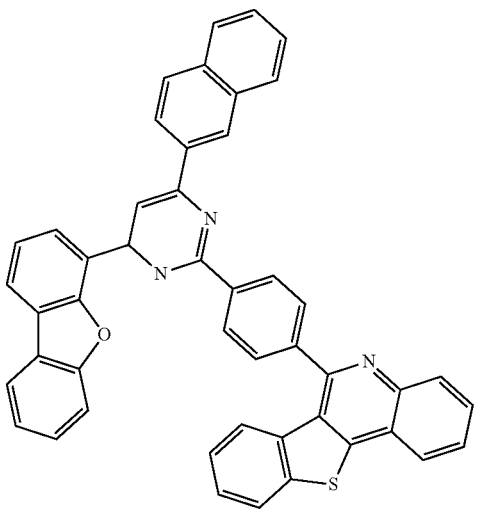

291
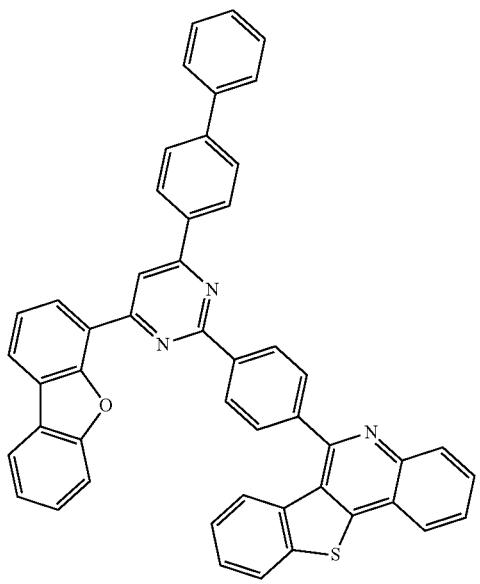
292
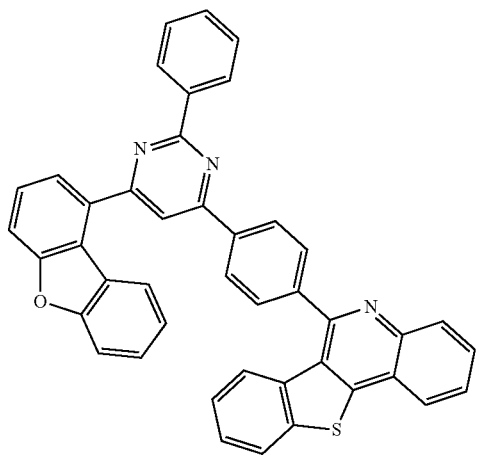
293
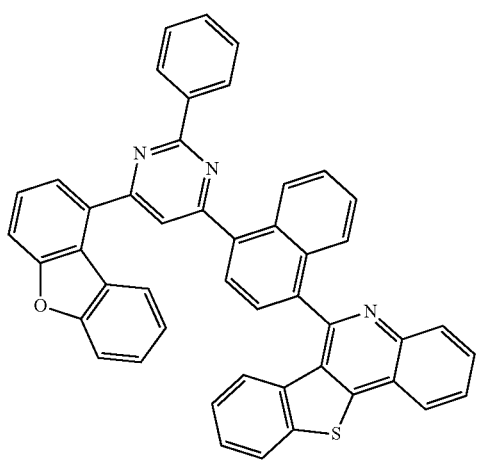
294
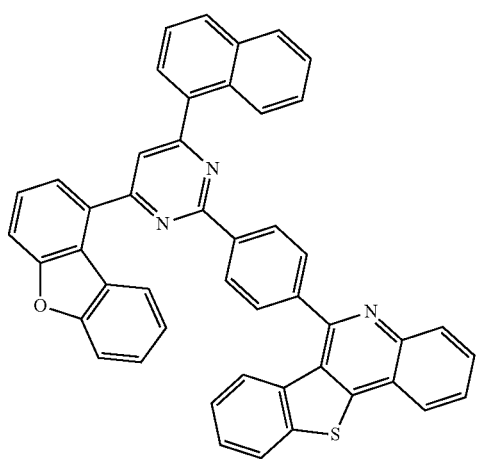
275
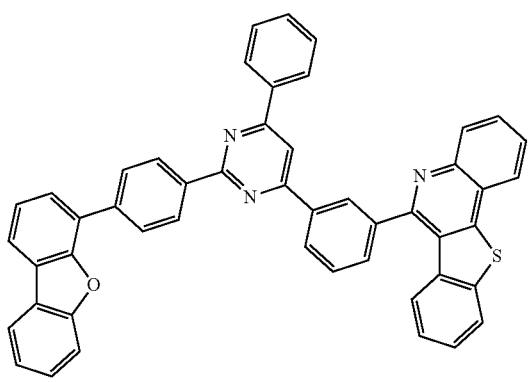
276
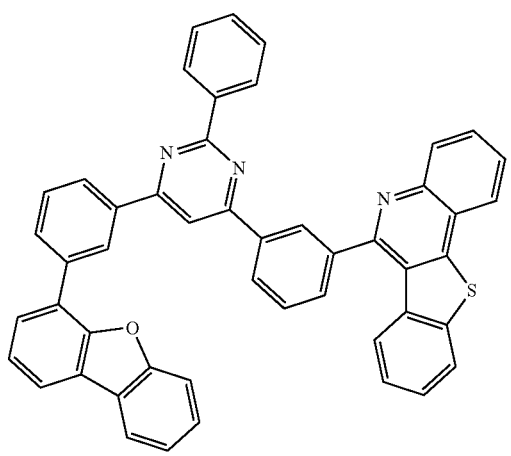

-continued
277
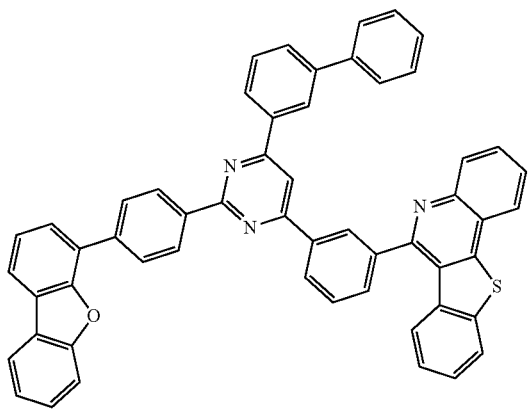
278
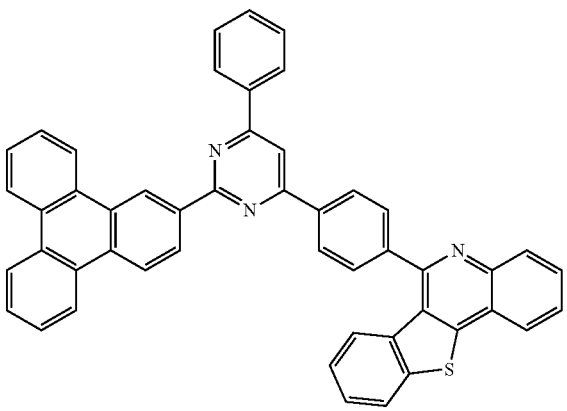
279
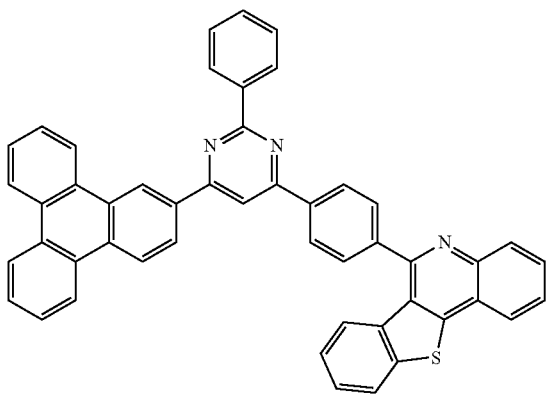
280
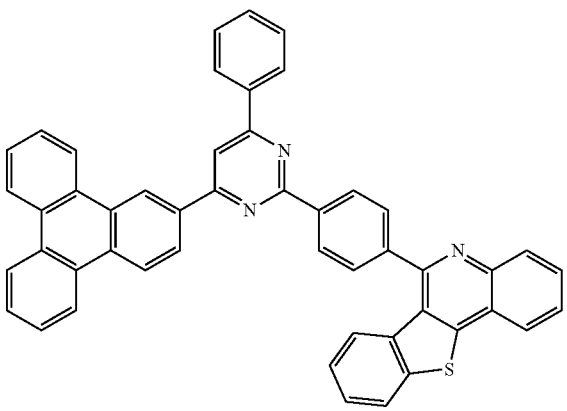
281
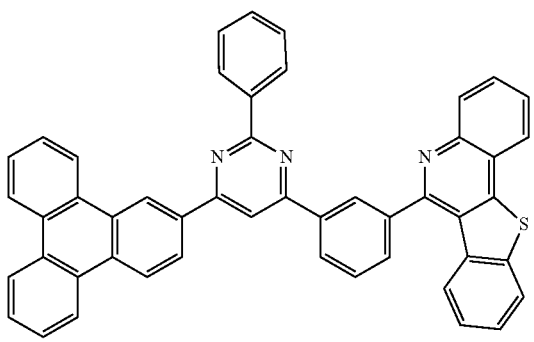
282
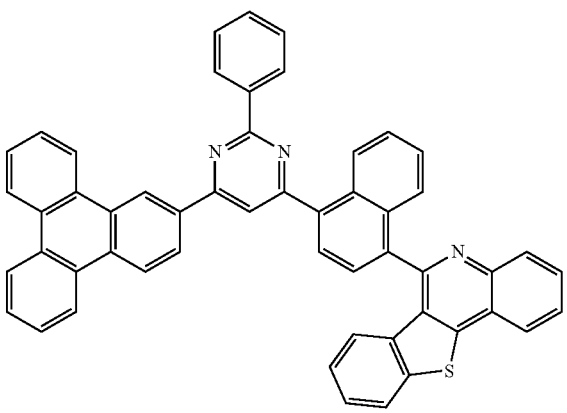

-continued
283
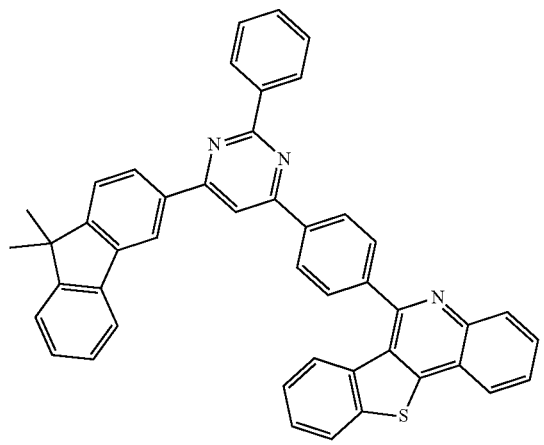
284
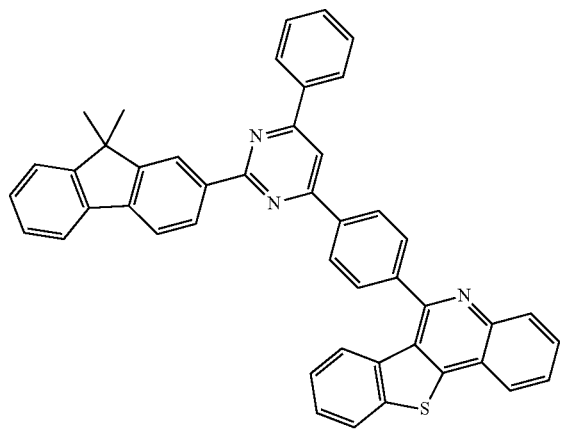
285
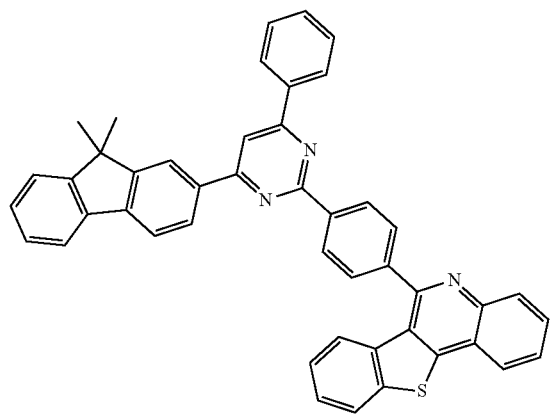
286
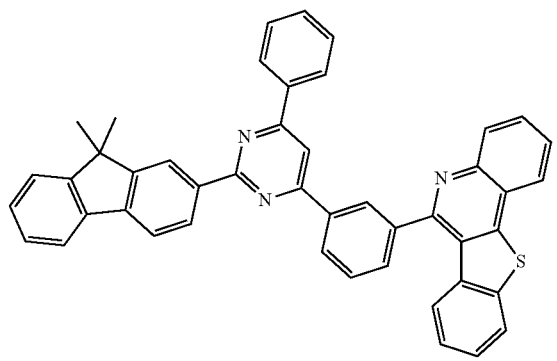
287
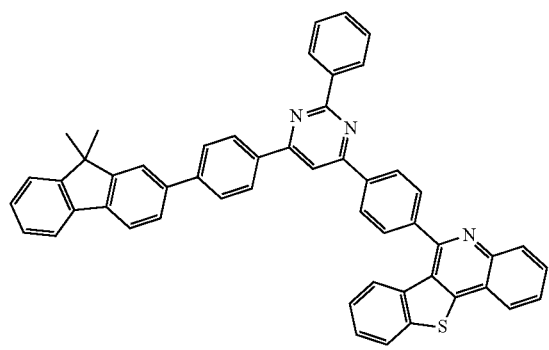
288
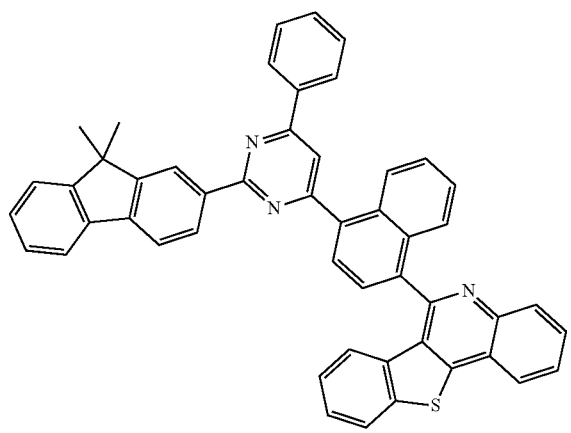

-continued
289
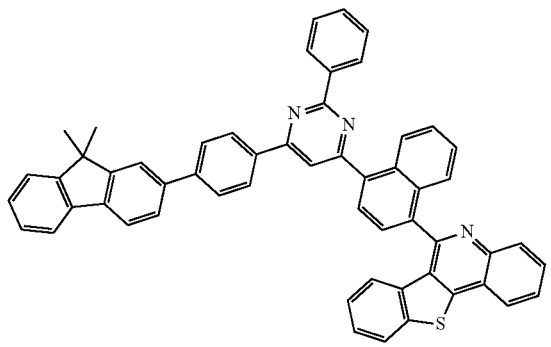
290
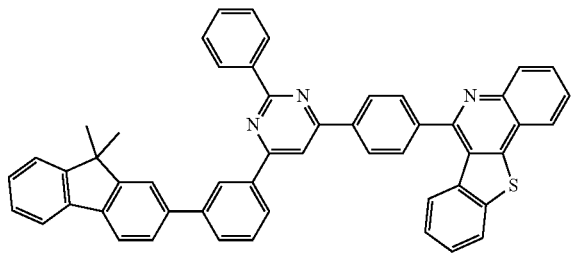
291
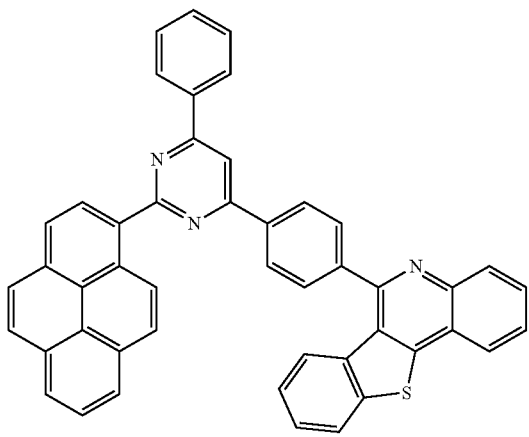
292
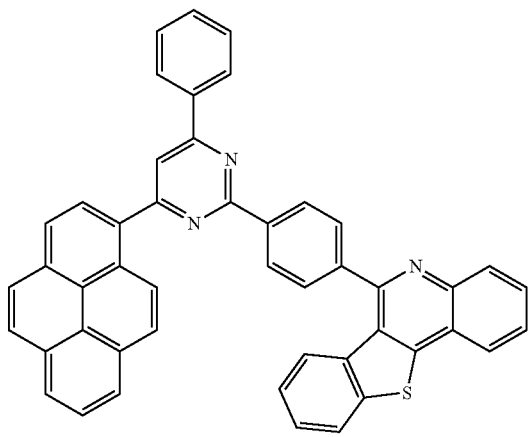
293
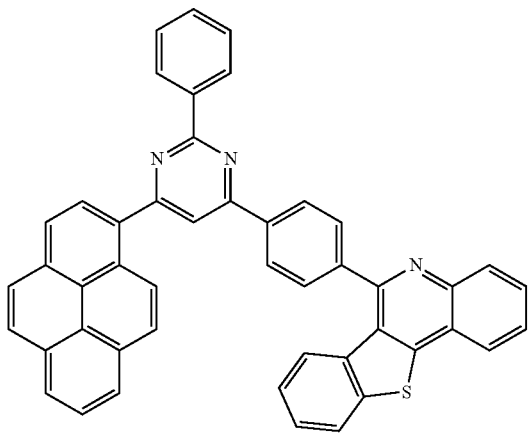
294
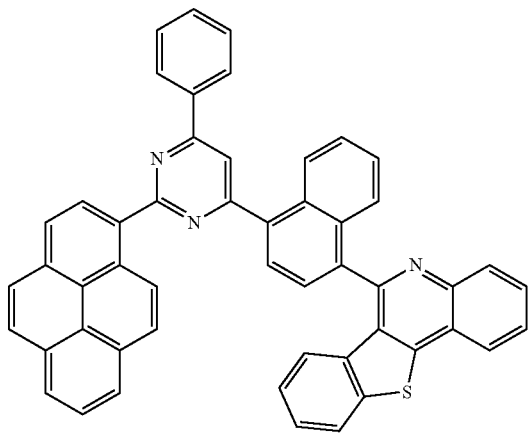

-continued
295
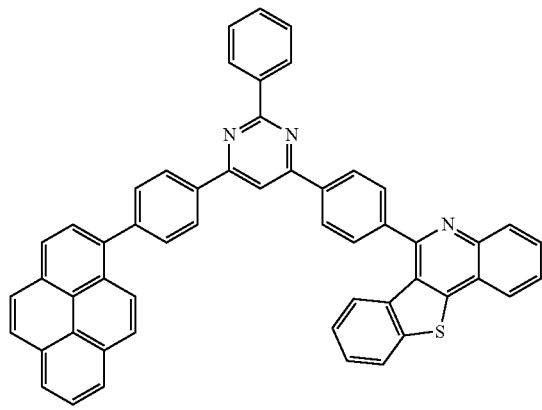
296
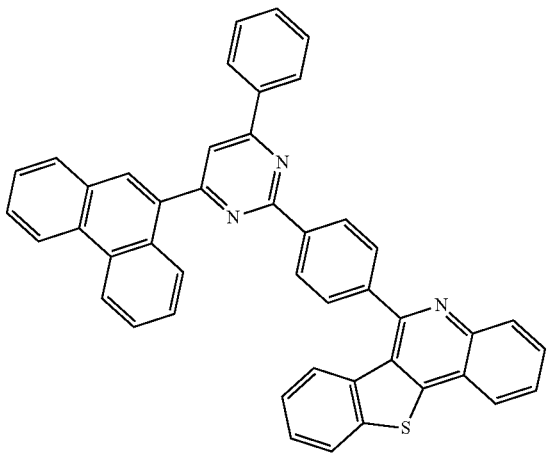
297
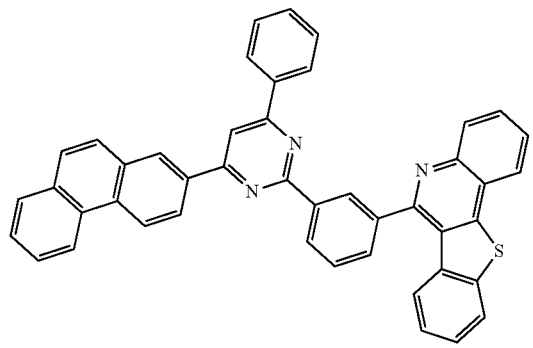
298
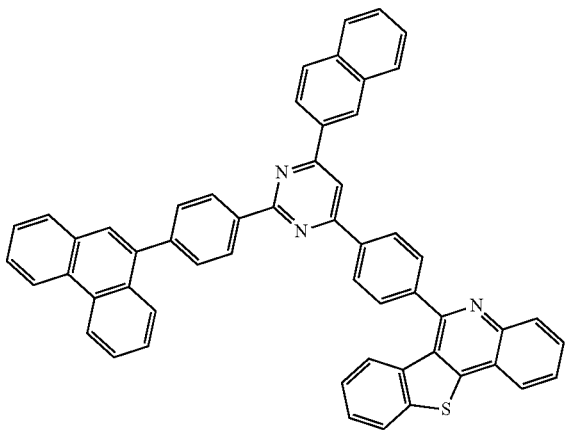
299
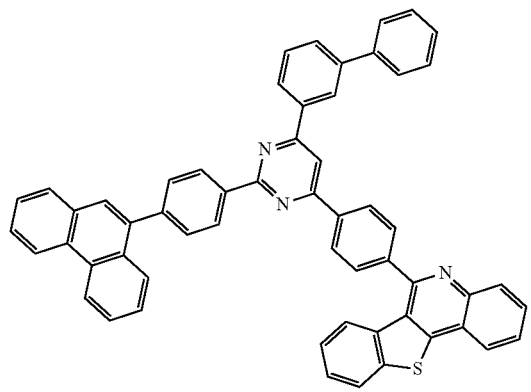
300
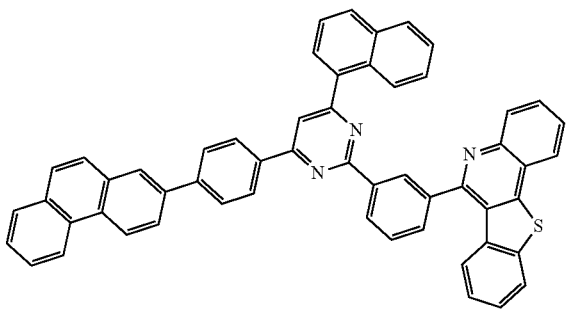

-continued
301
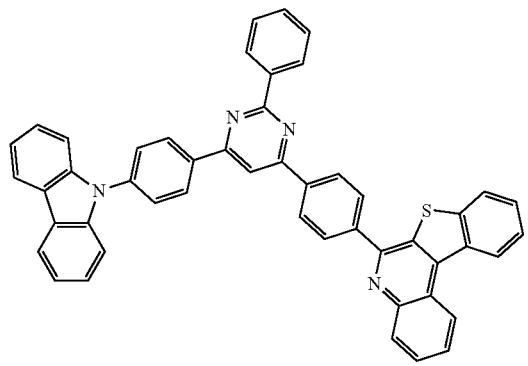
302
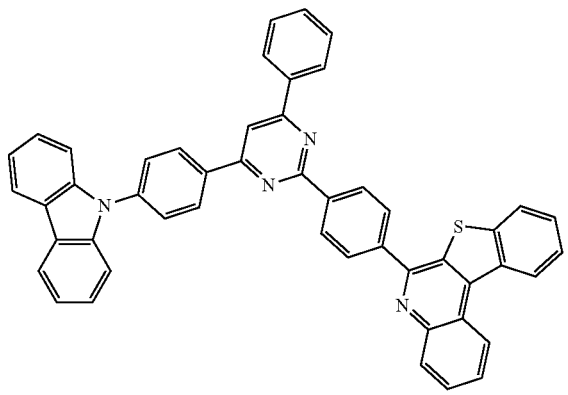
303
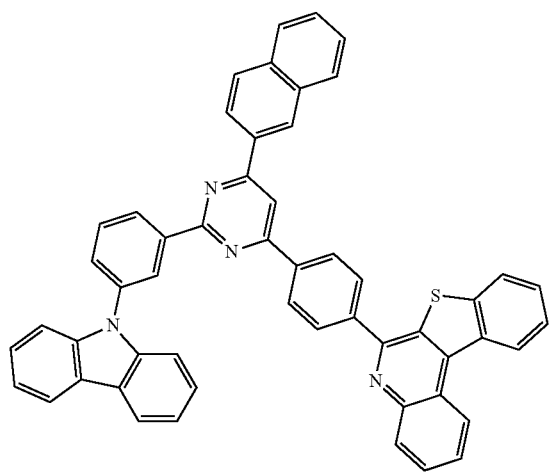
304
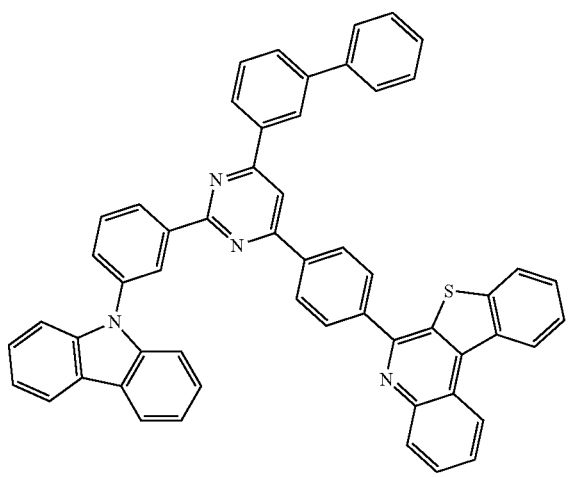
305
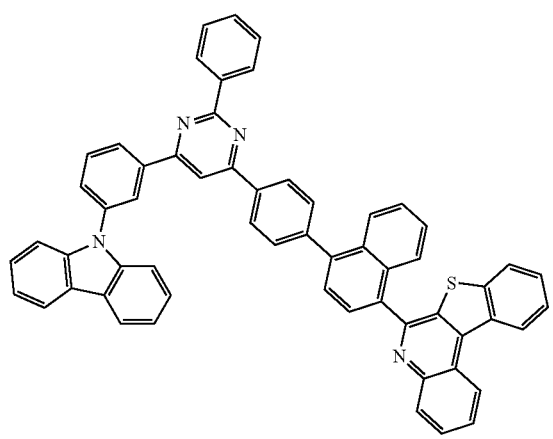
306
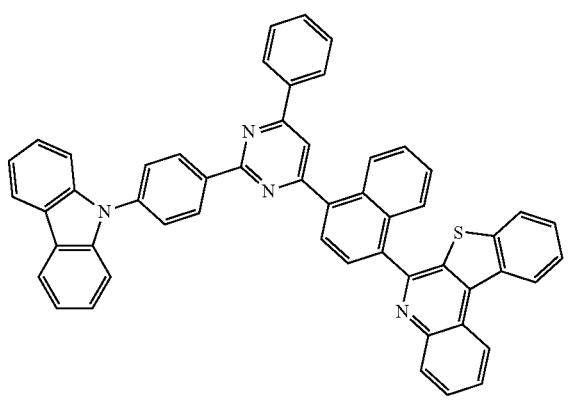

-continued
307
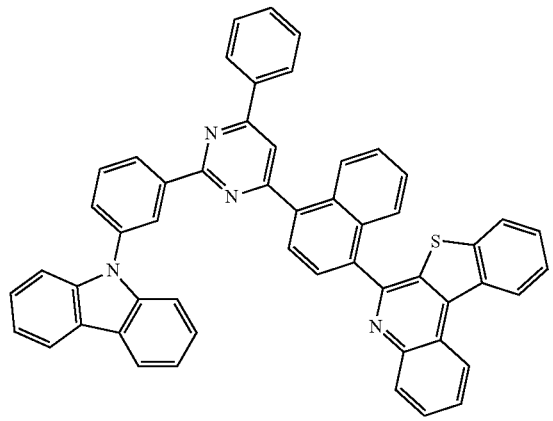
308
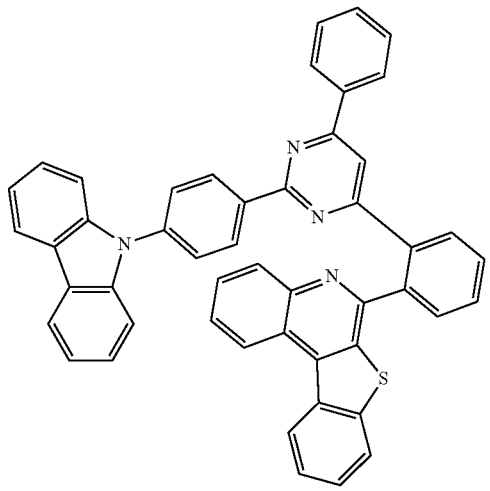
309
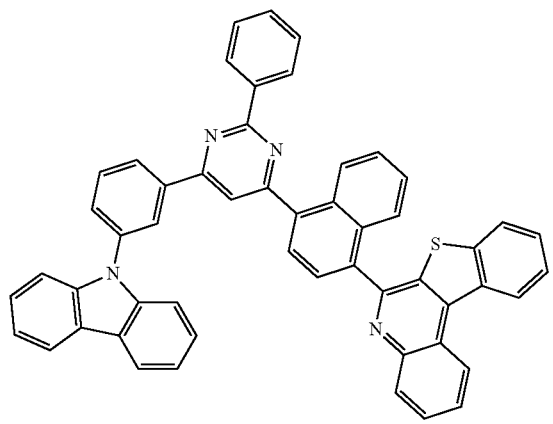
310
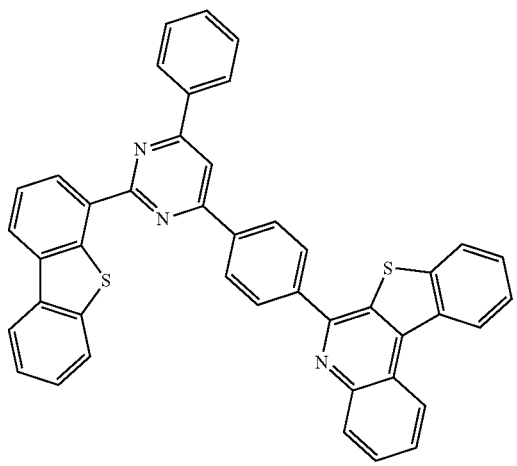
311
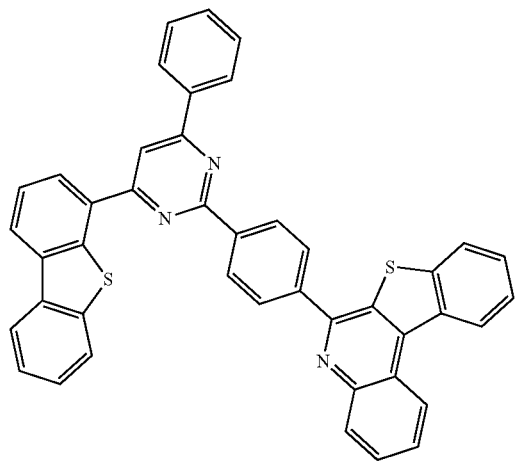
312
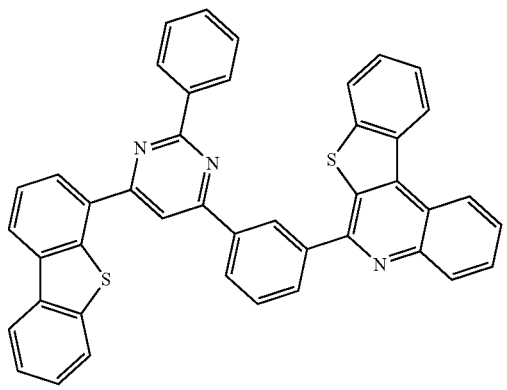

317
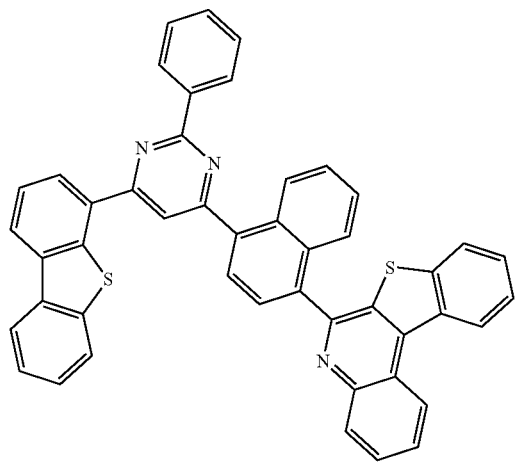
318
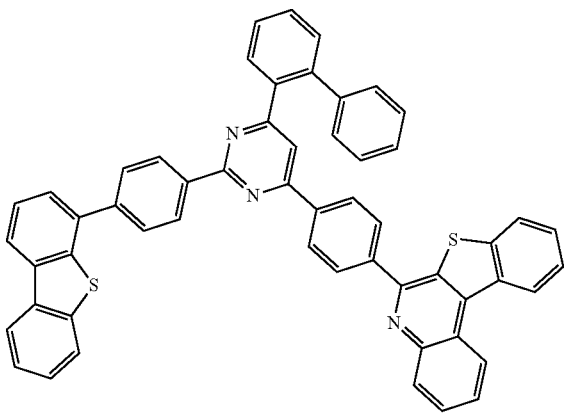
319
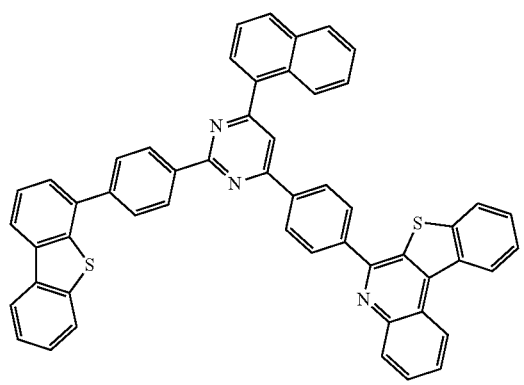
320
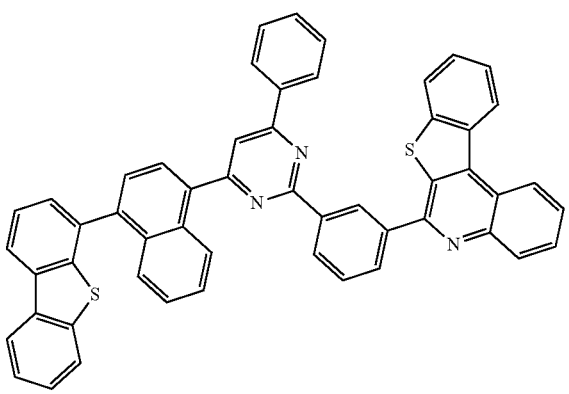
321
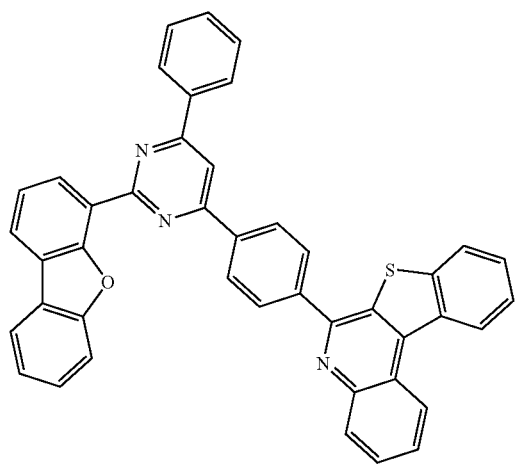
322
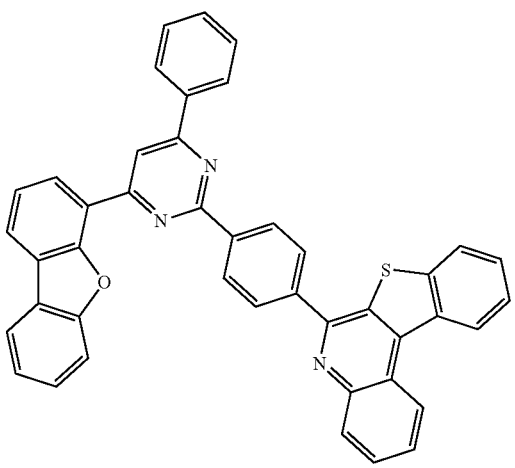

-continued
323
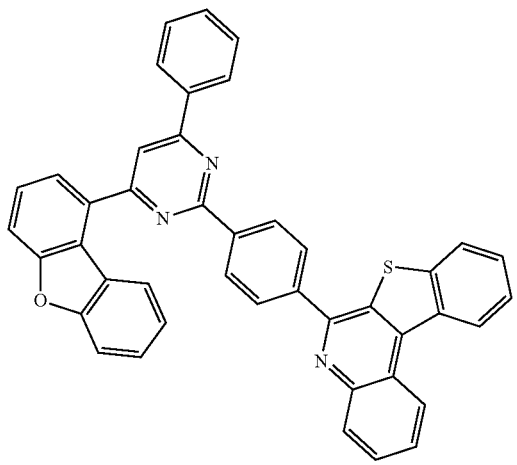
324
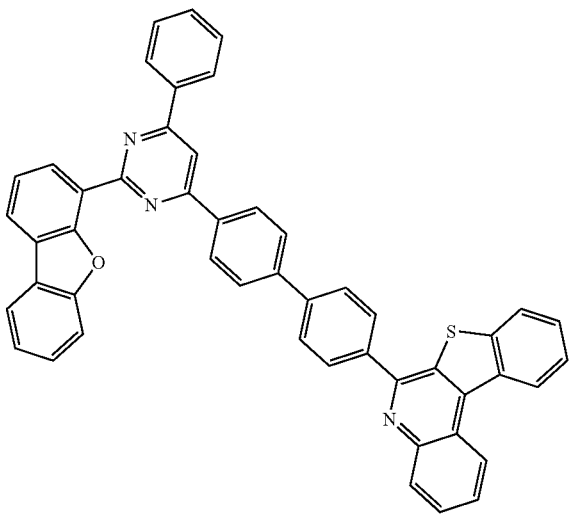
325
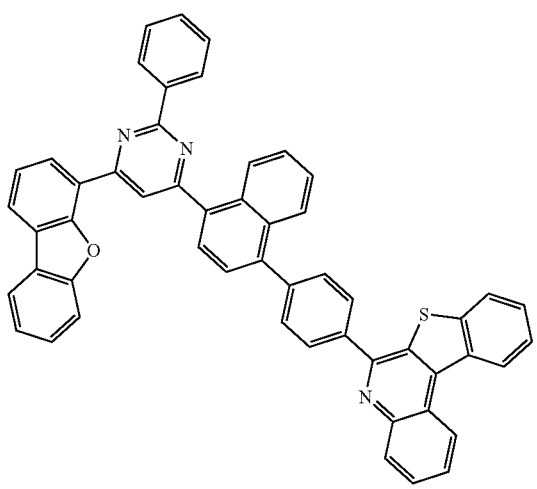
326
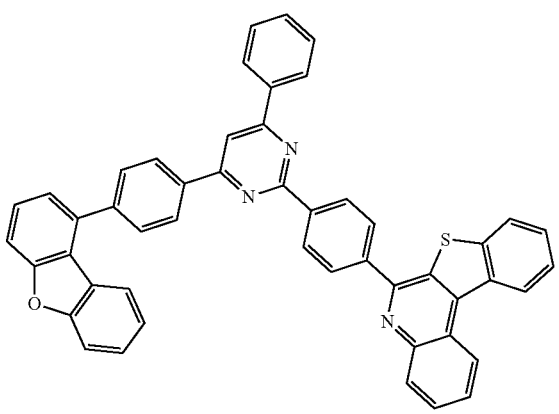
327
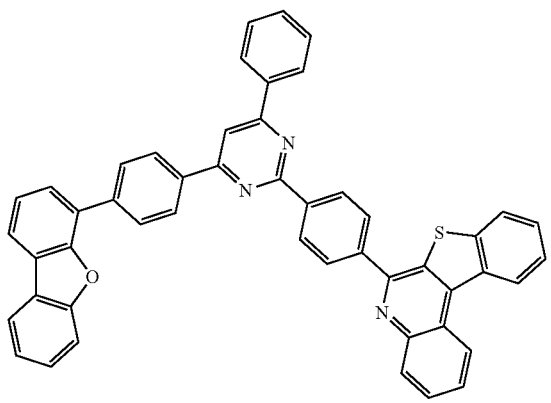
328
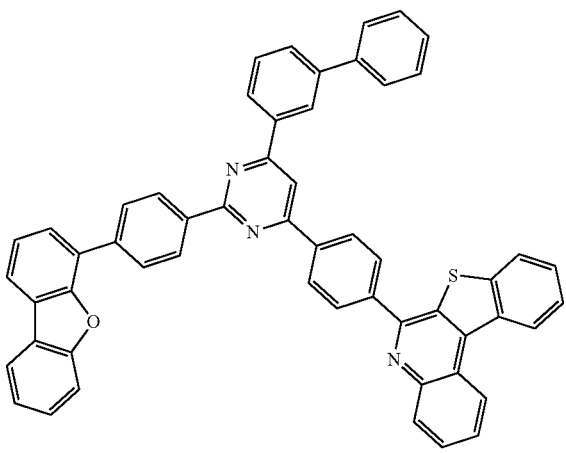

329
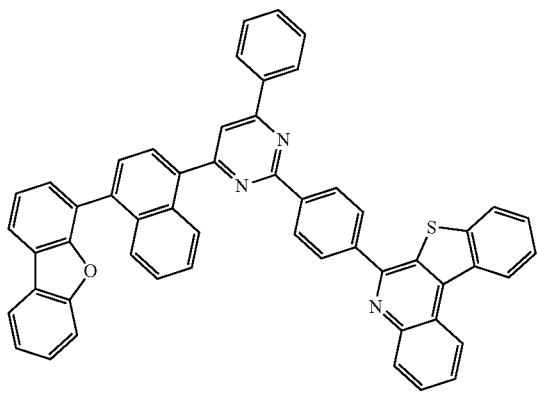
330
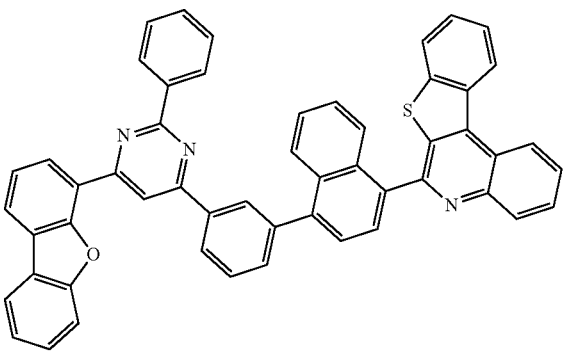
331
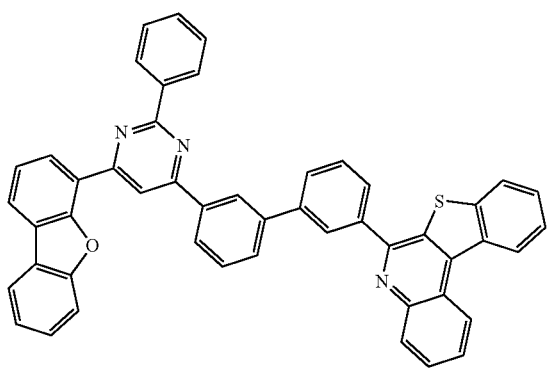
332
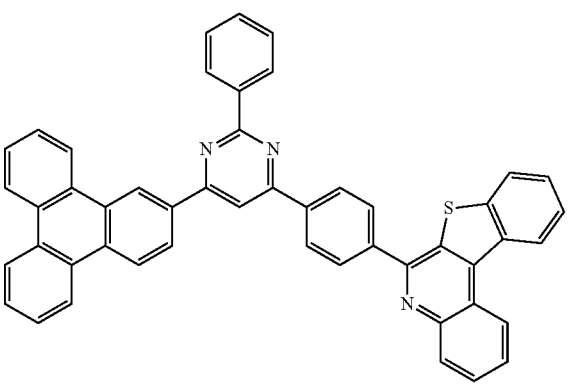
333
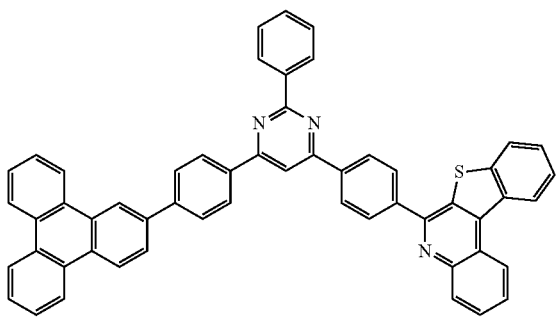
334
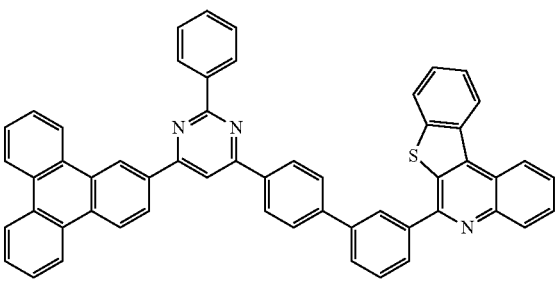
335
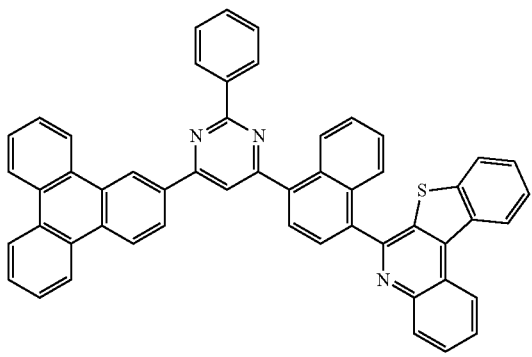
336
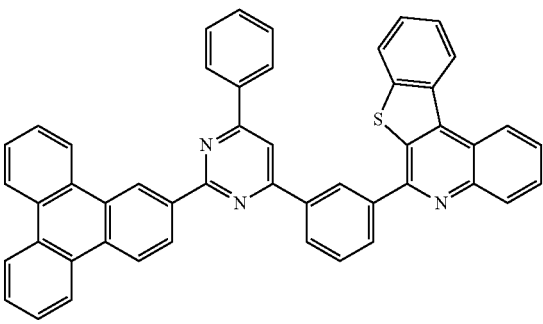

337
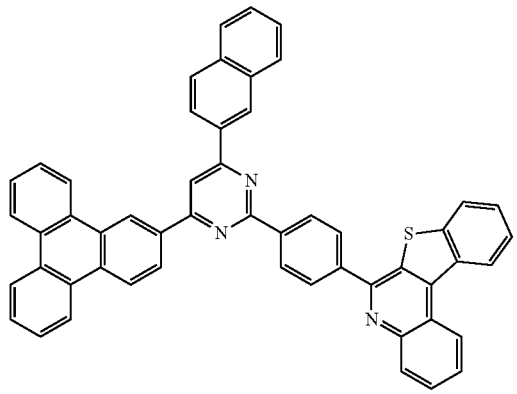
338
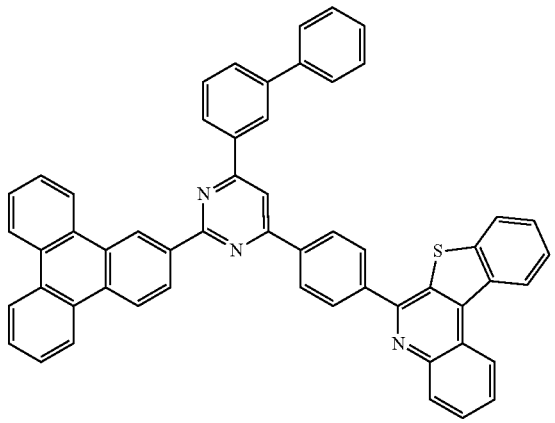
339
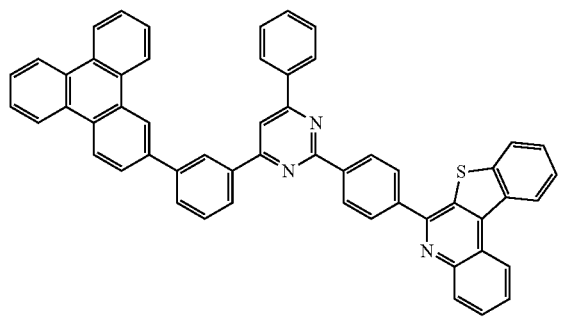
340
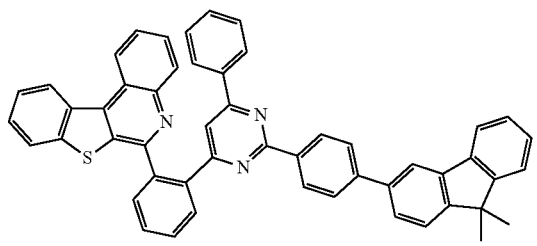
341
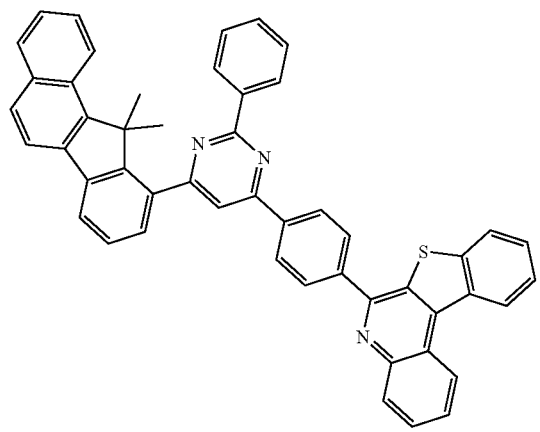
342
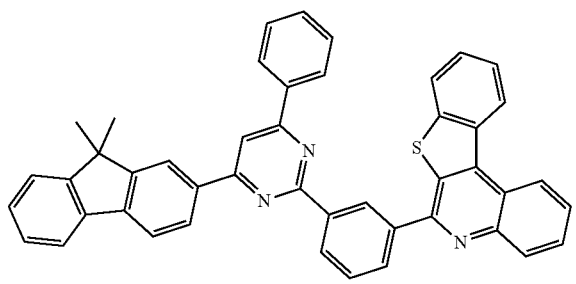
343
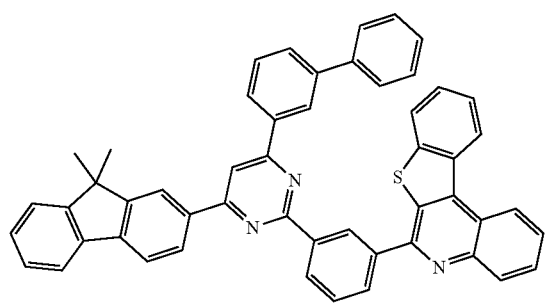
344
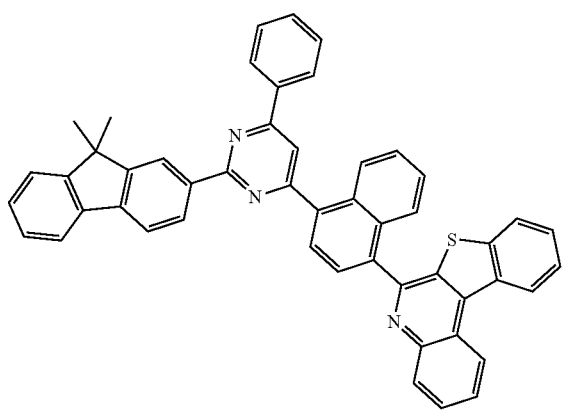

-continued
345
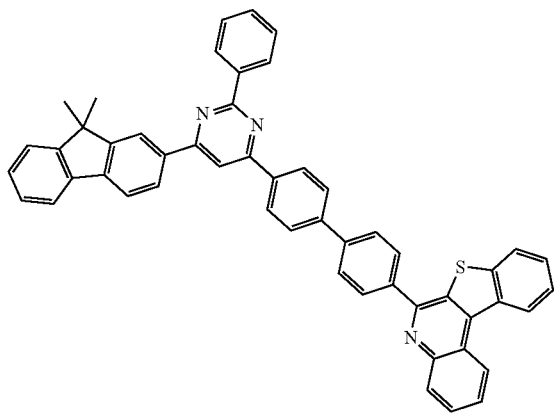
346
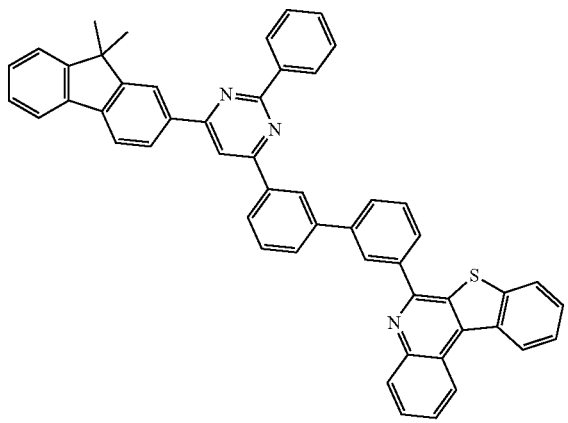
347
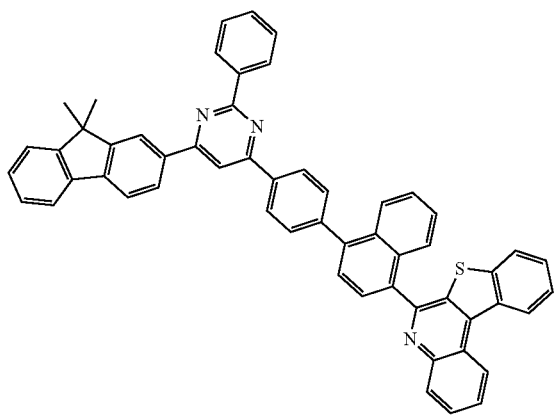
348
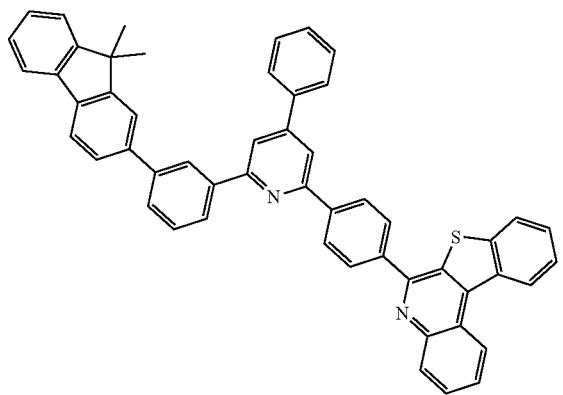
349
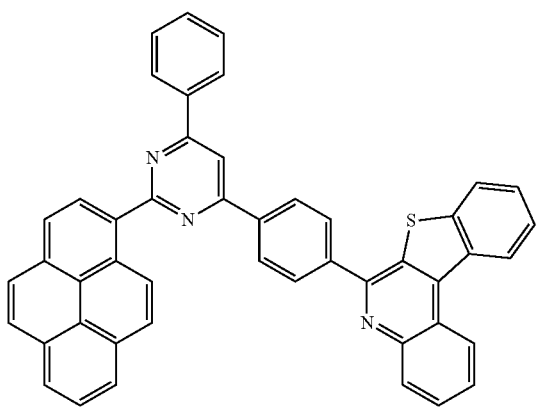
350
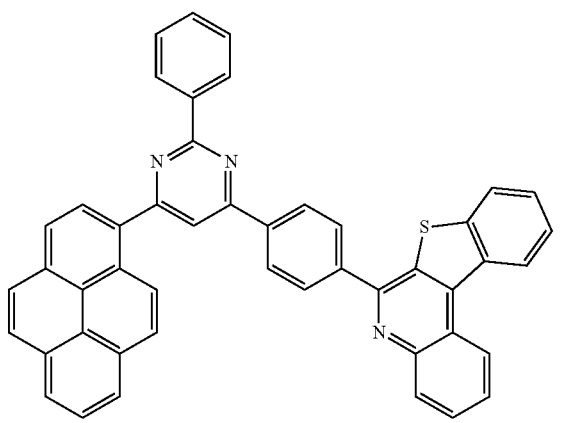

351
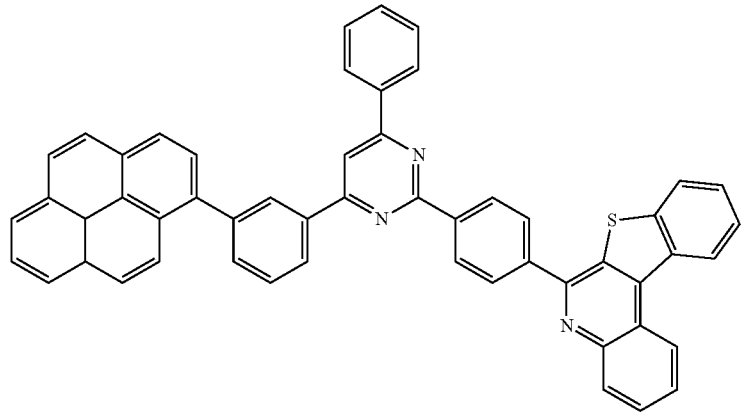
352
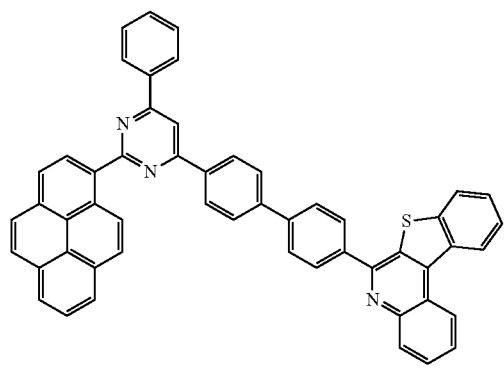
353
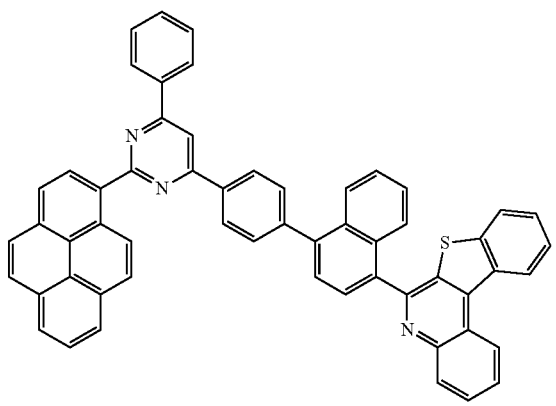
354
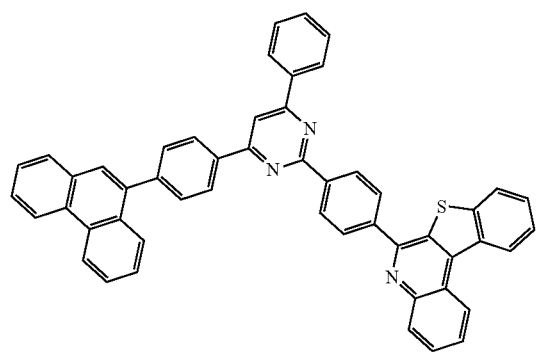
355
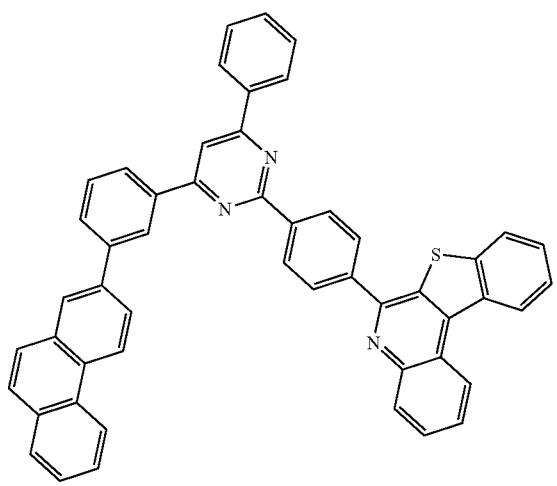

-continued
356
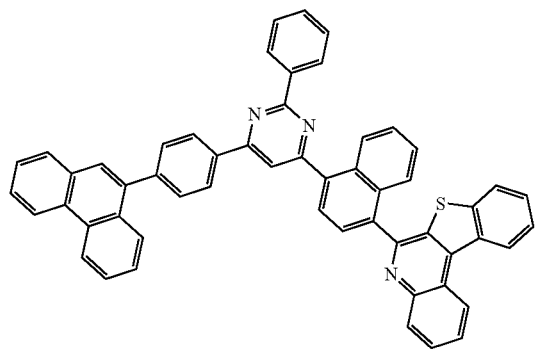
357
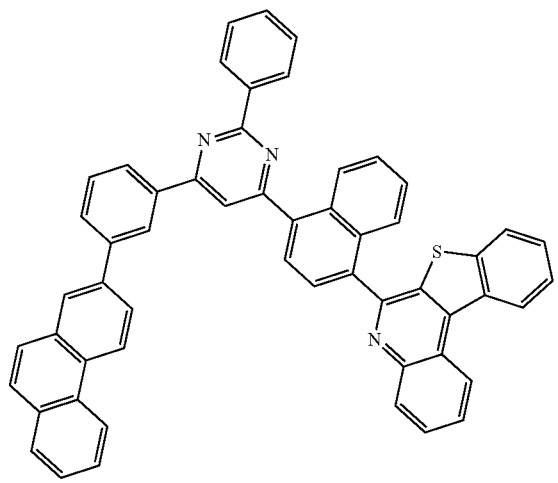
358
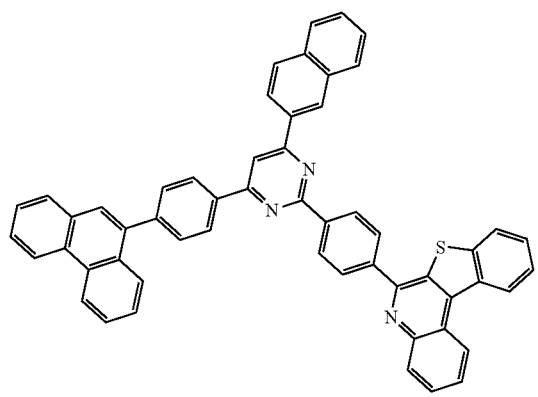
359
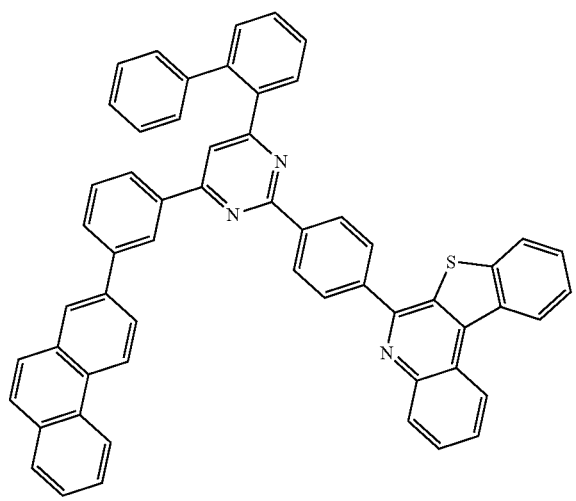
360
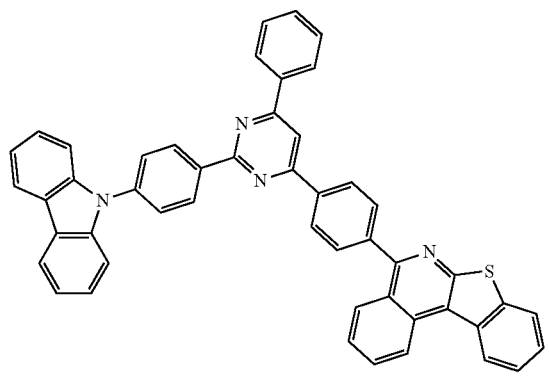
361
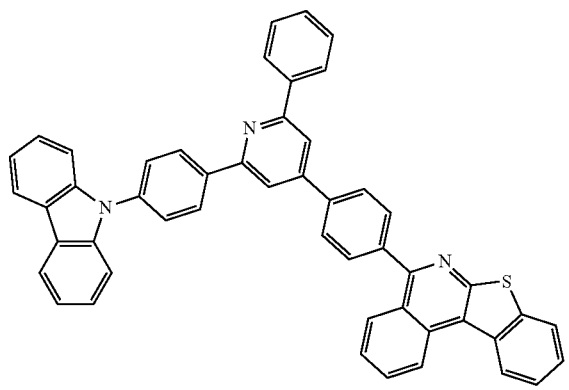

-continued
362
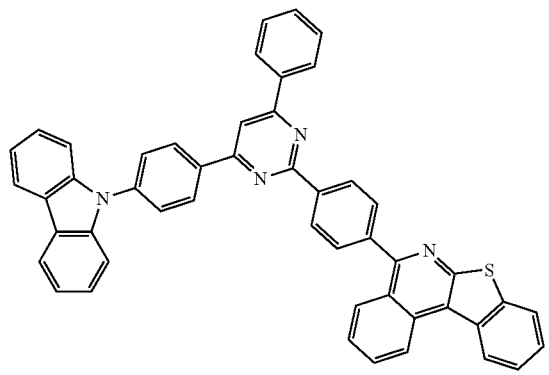
363
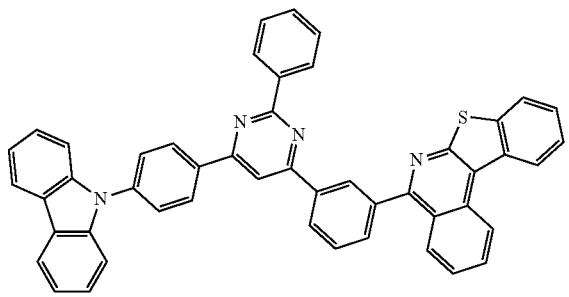
364
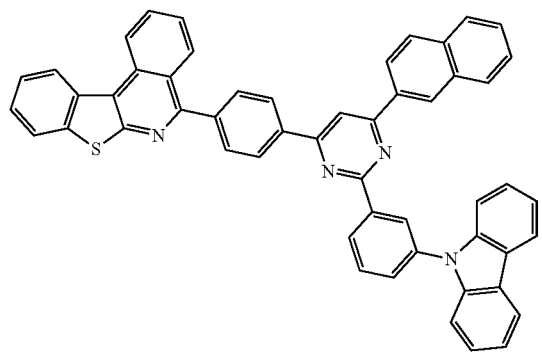
365
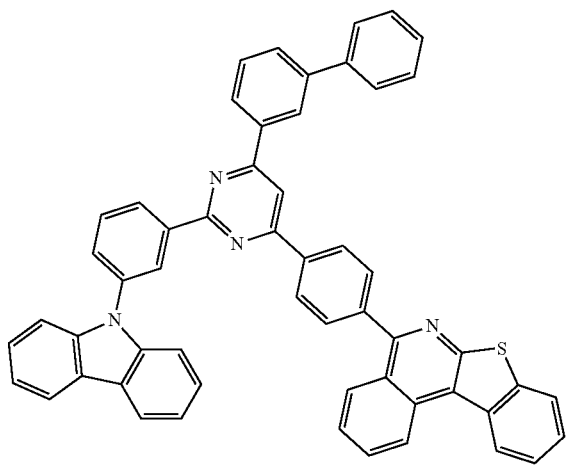
366
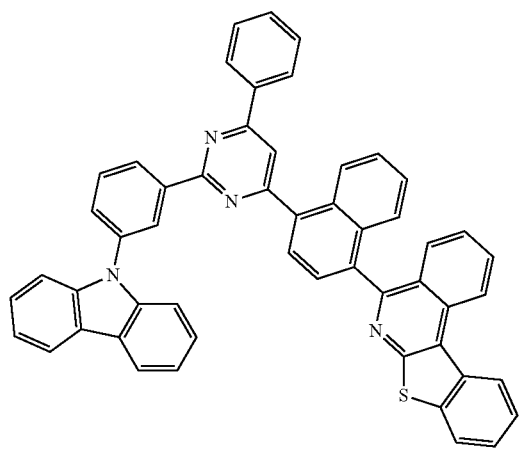
367
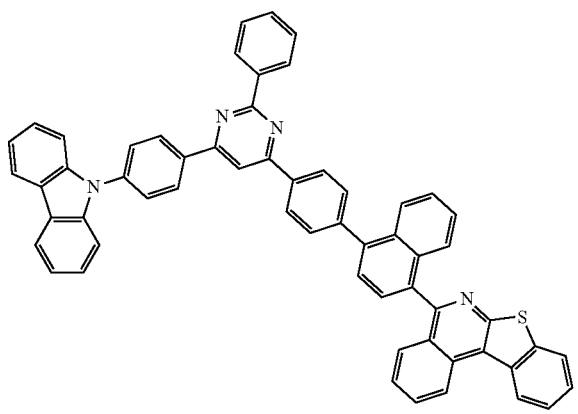

-continued
368
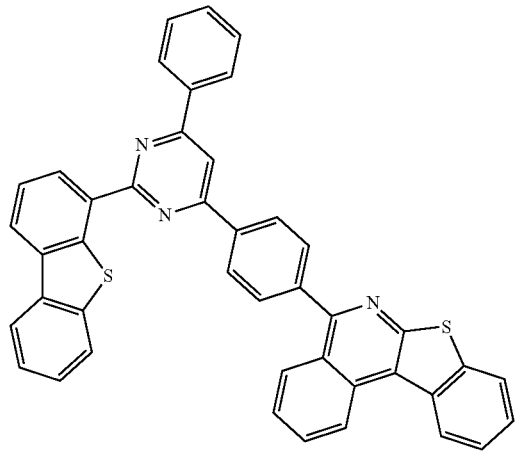
369
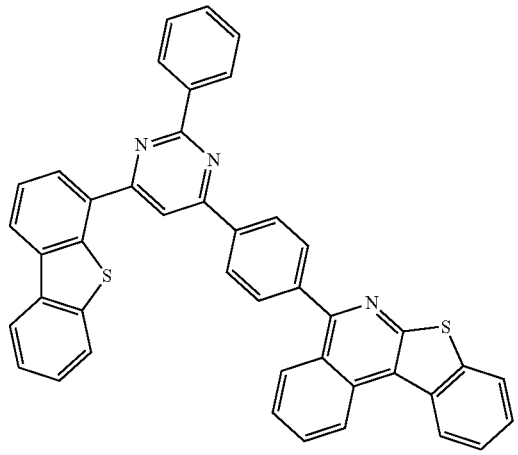
370
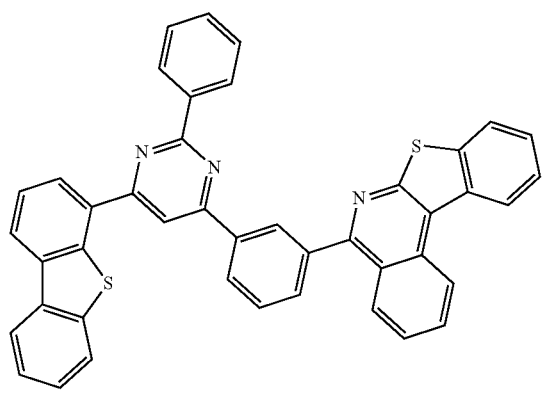
371
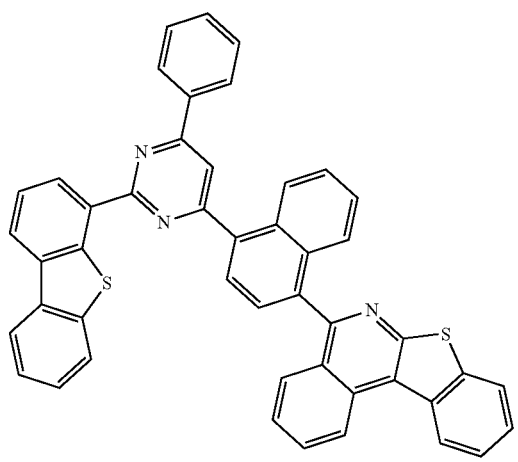
372
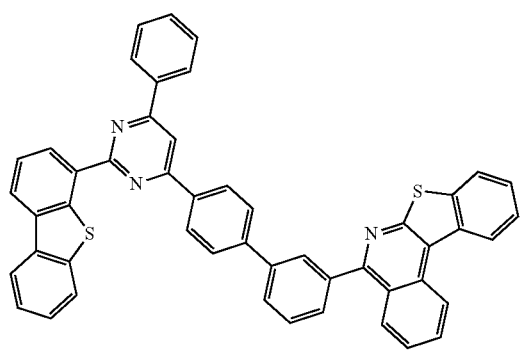
373
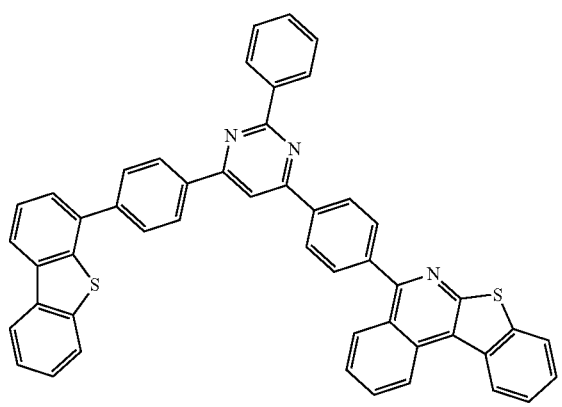

274
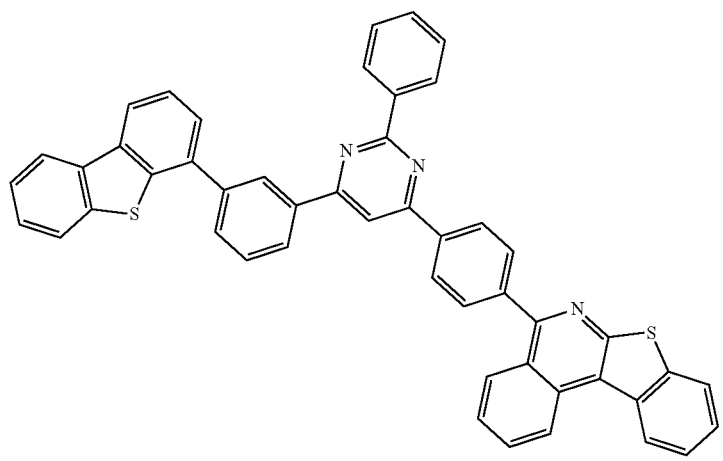
275
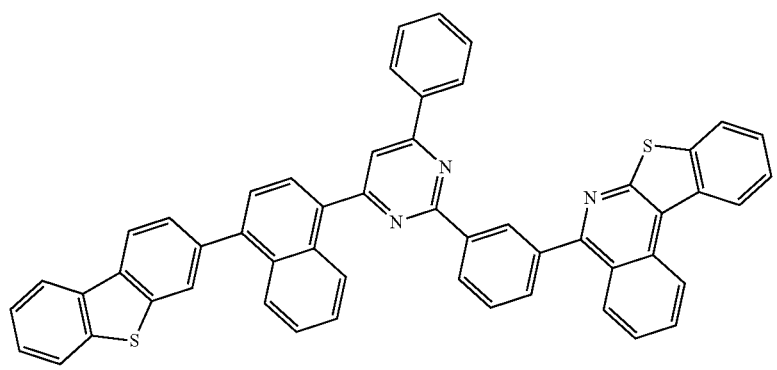
276
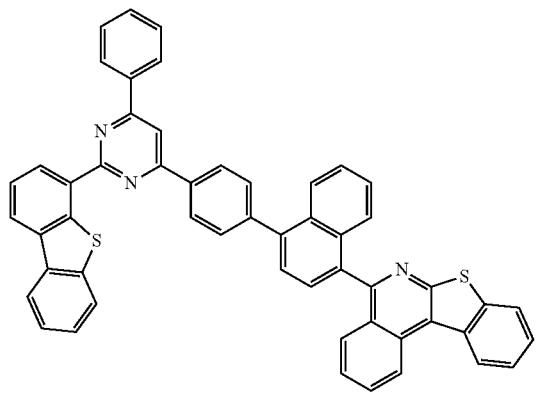
277
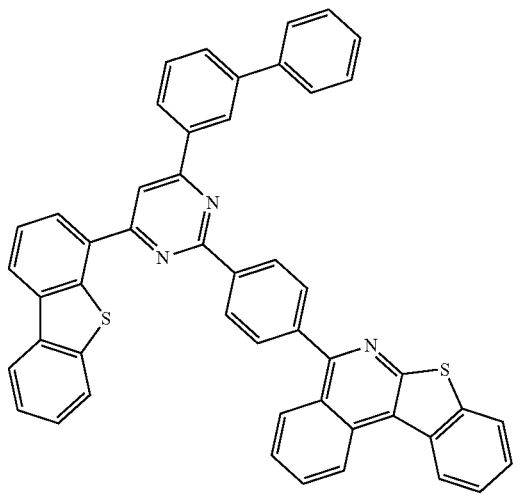

-continued
278
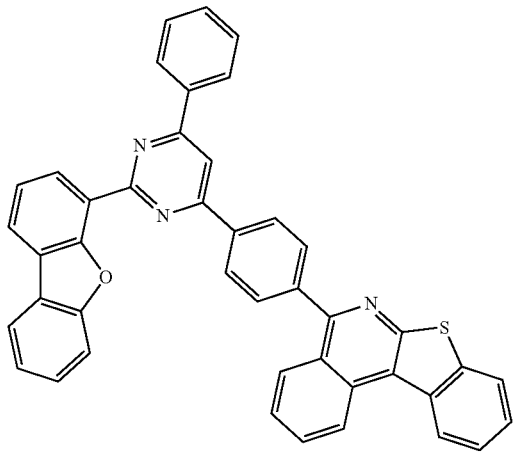
279
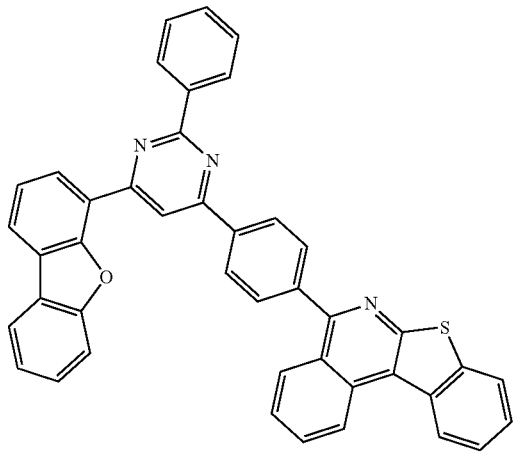
380
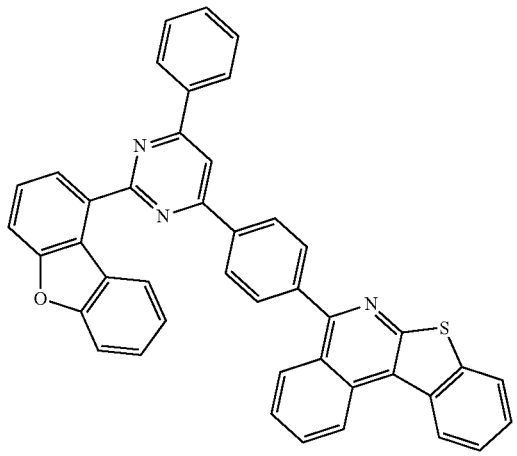
381
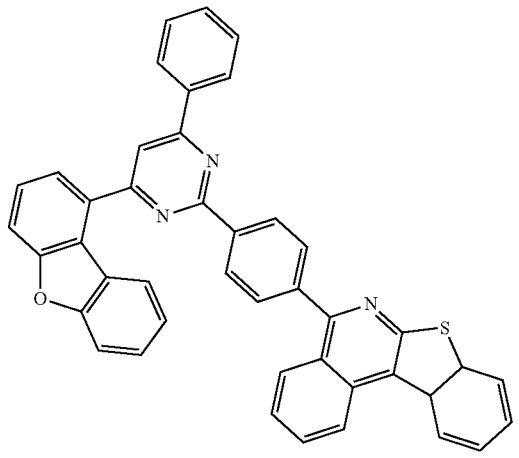
382
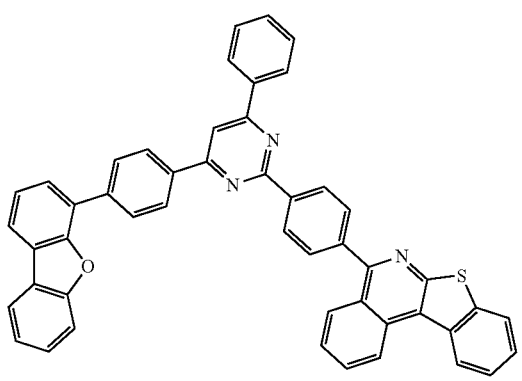
383
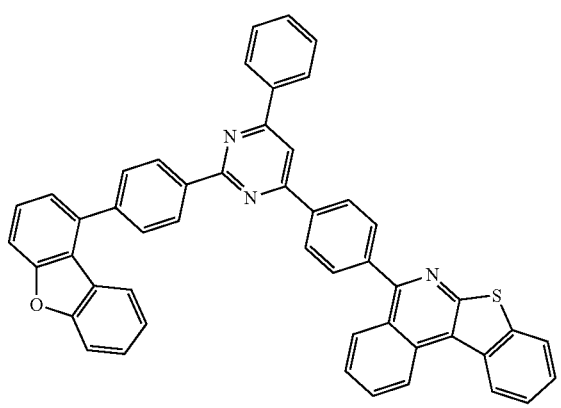

-continued
384
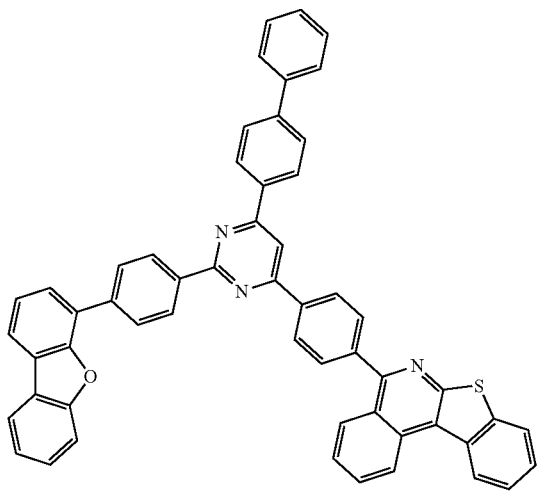
385
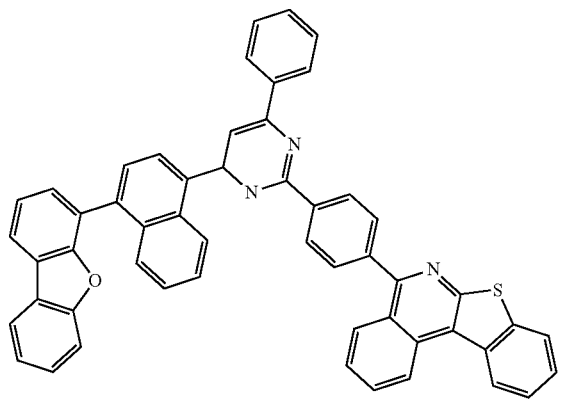
386
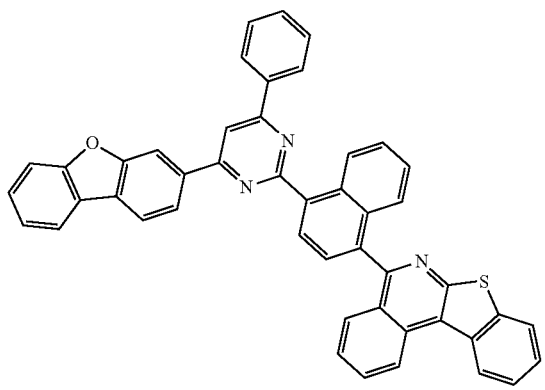
387
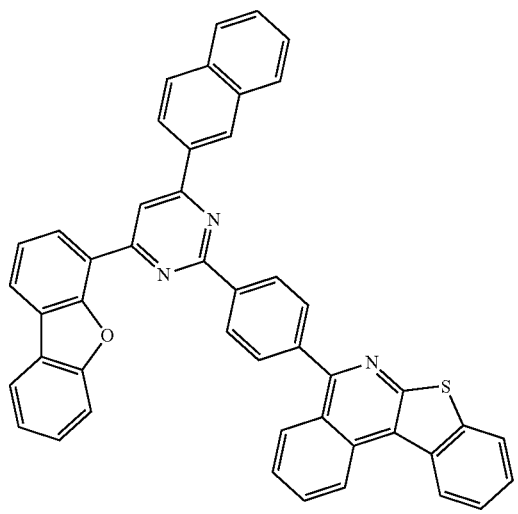
388
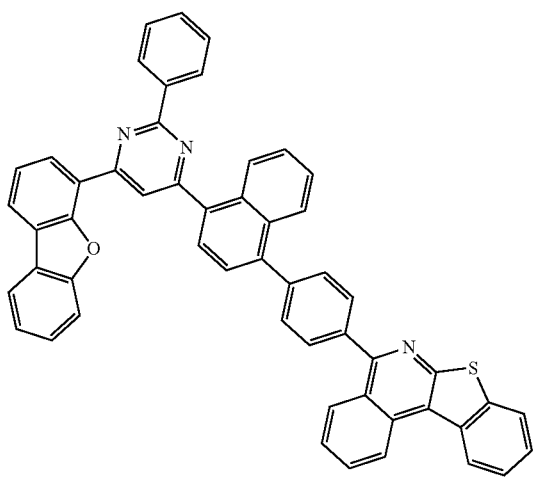
389
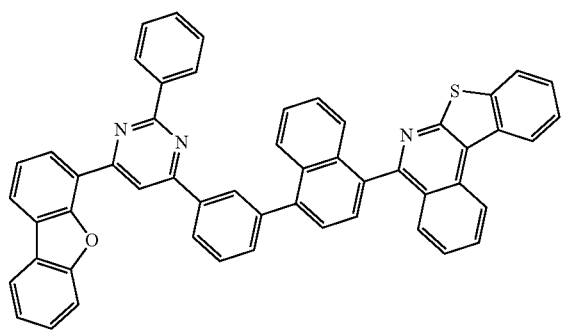

-continued
390
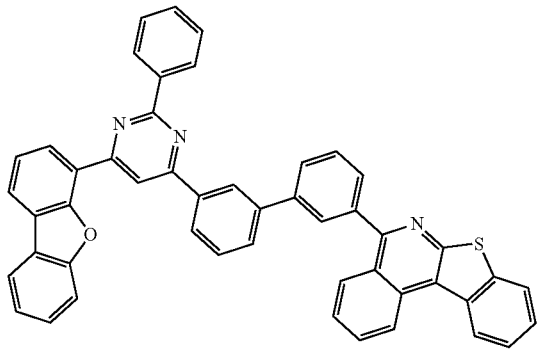
391
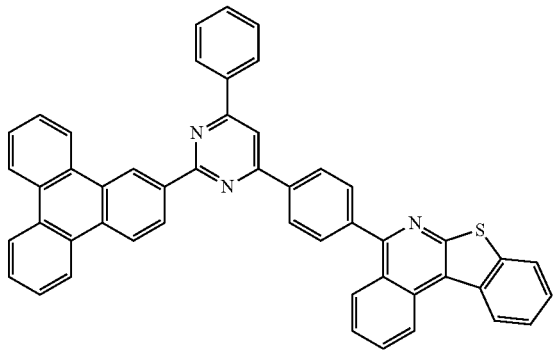
392
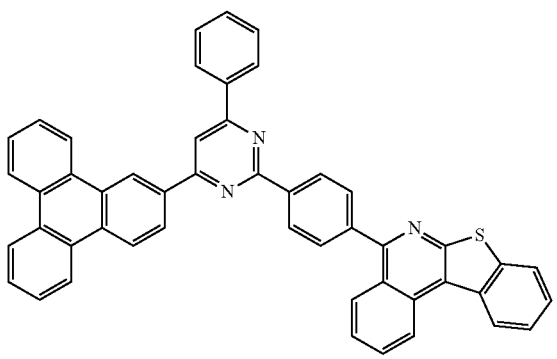
393
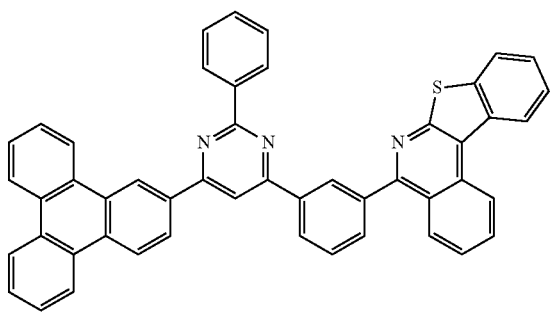
394
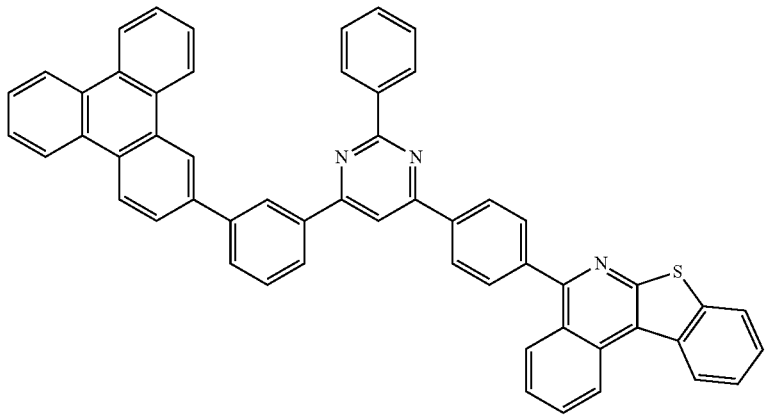
395
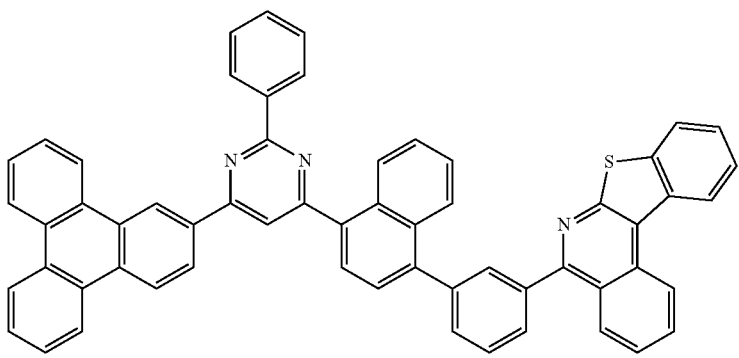

396
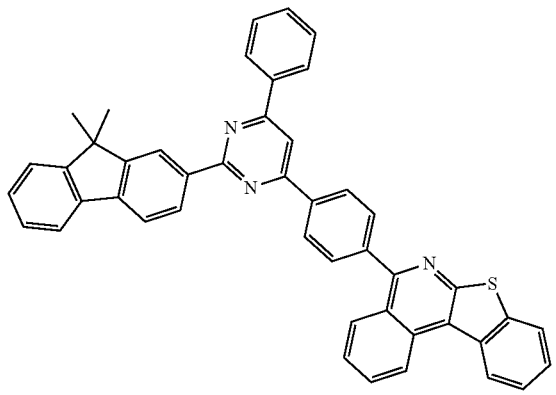
397
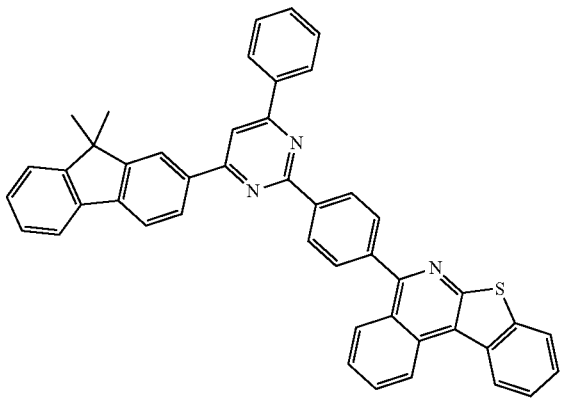
398
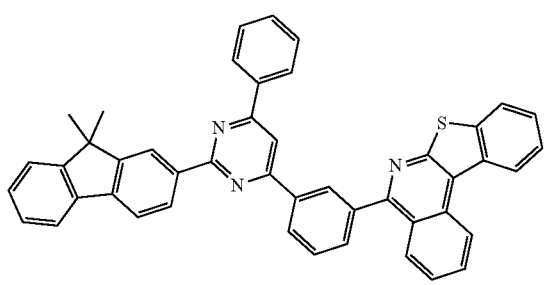
399
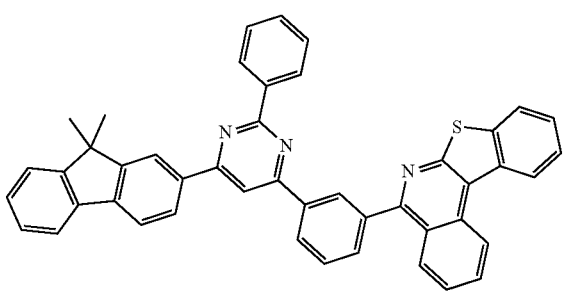
400
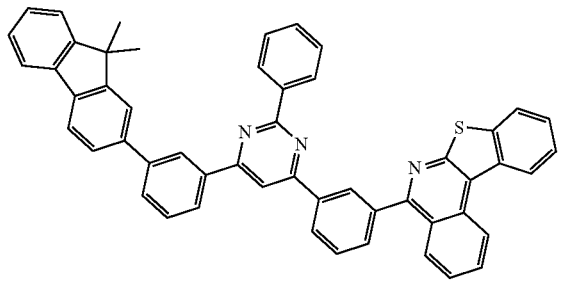
401
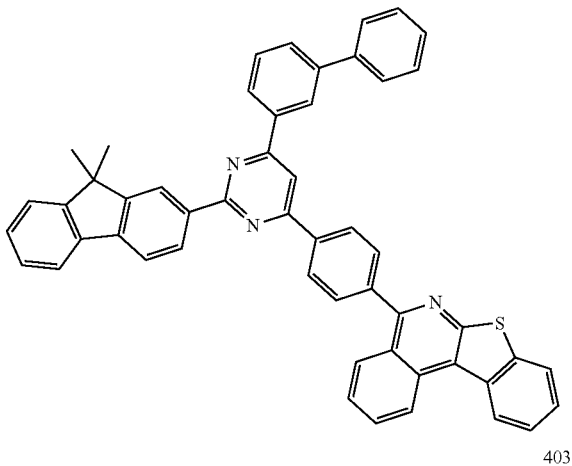
402
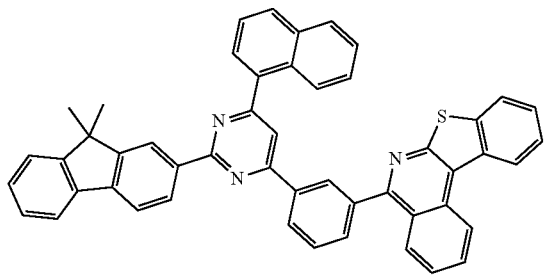
403
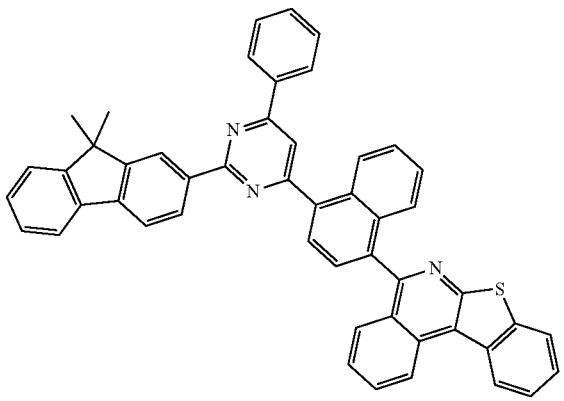

404
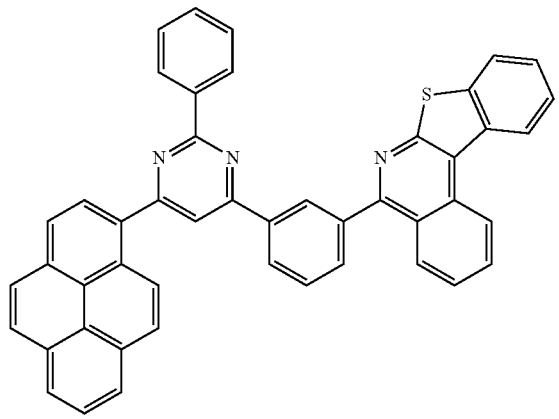
405
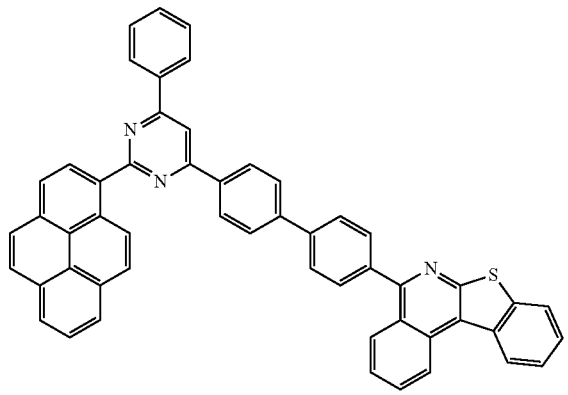
406
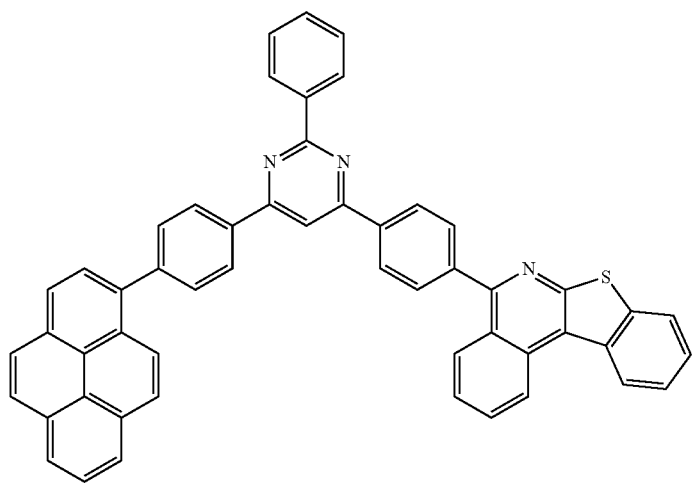
407
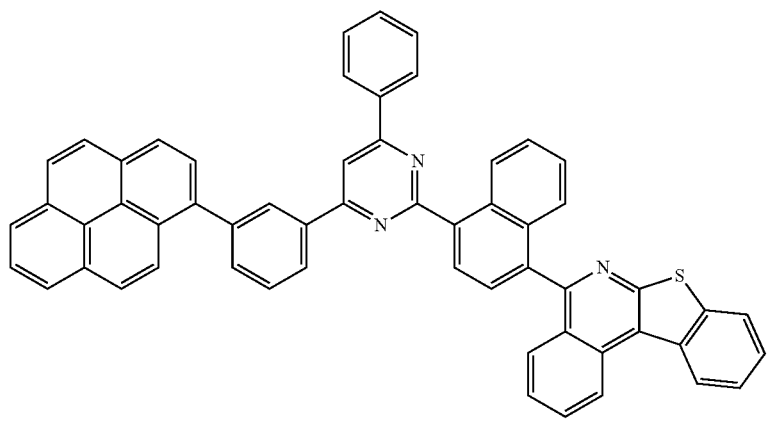

408
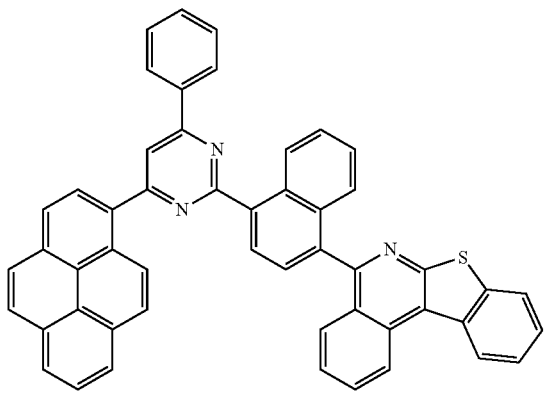
409
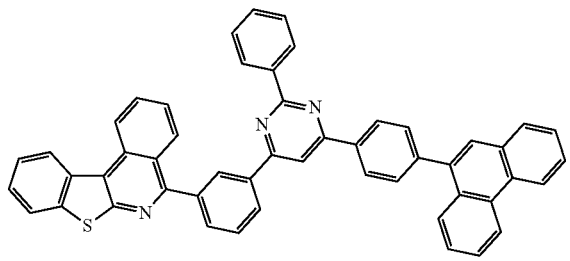
410
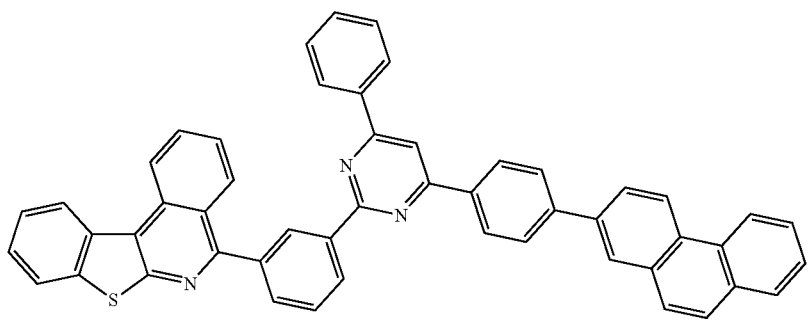
411
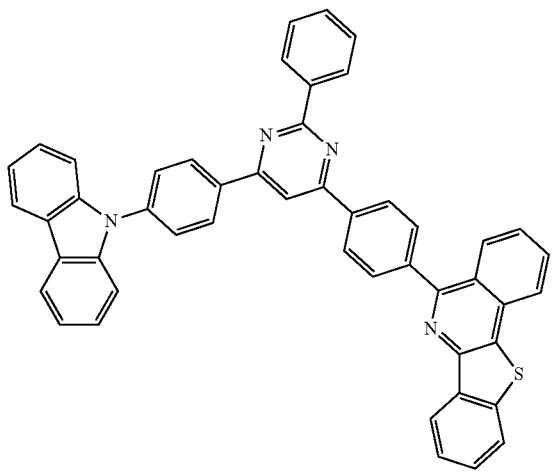
412
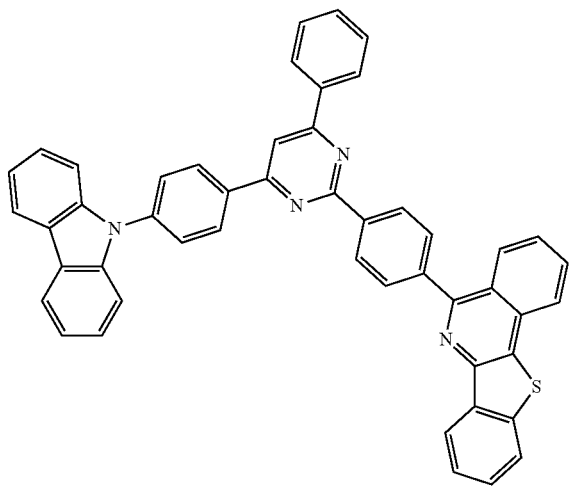

-continued
413
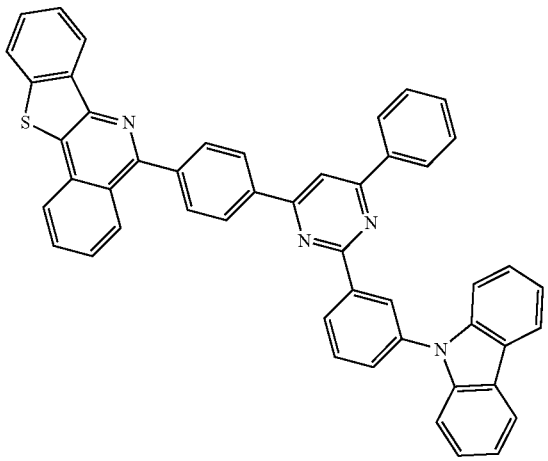
414
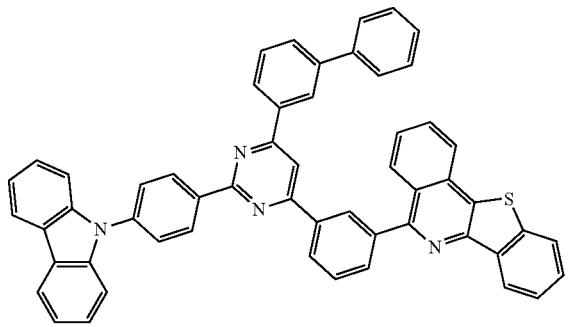
415
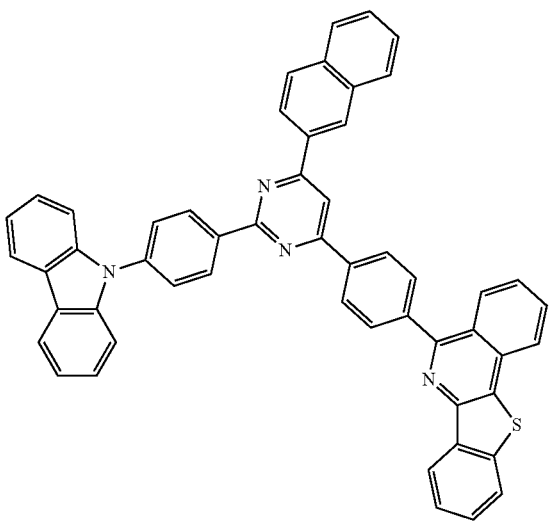
416
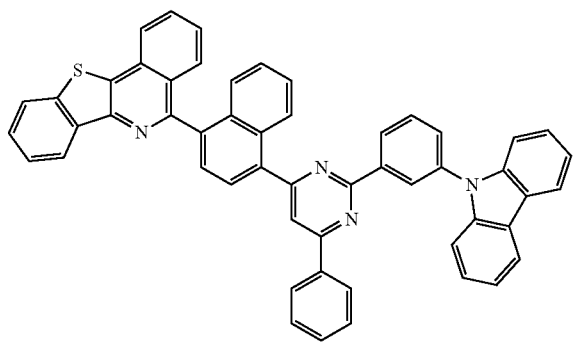
417
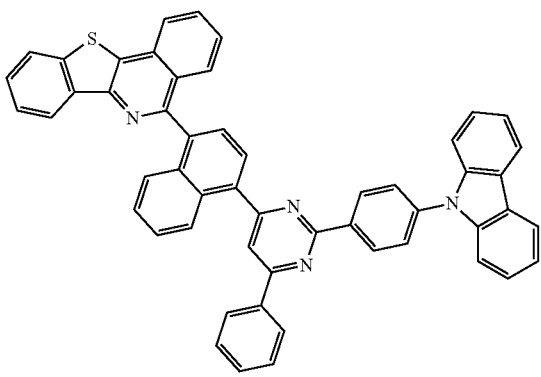
418
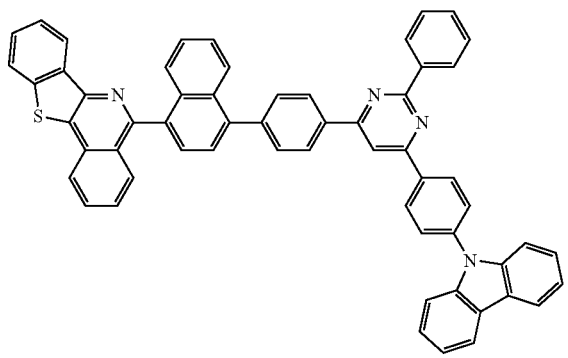

-continued
419 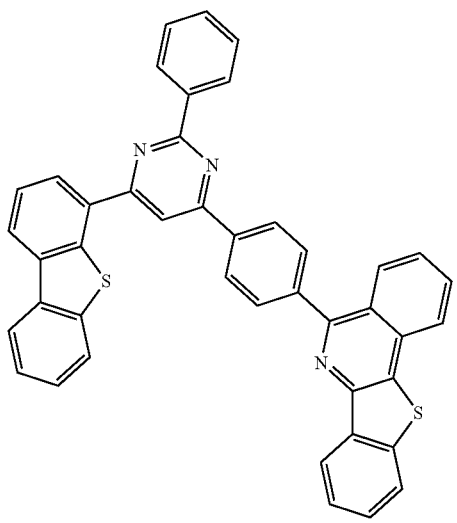
420 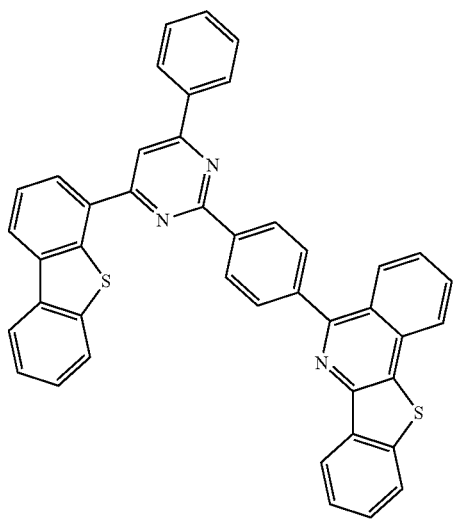
421 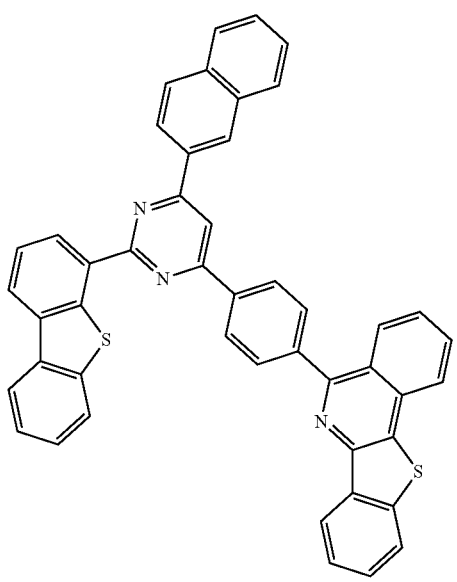
422 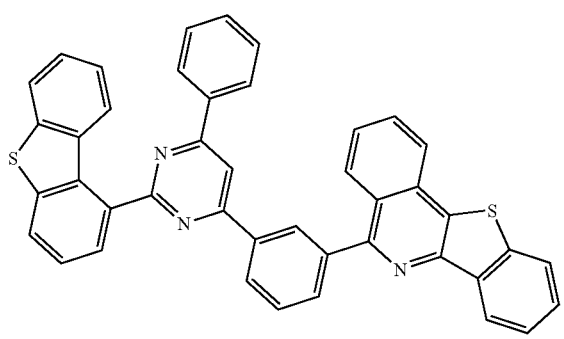

-continued
423
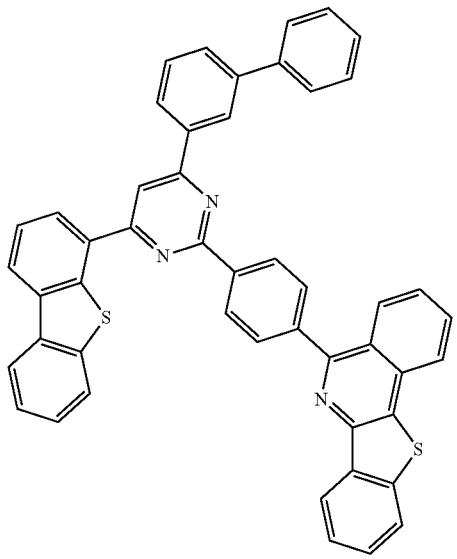
424
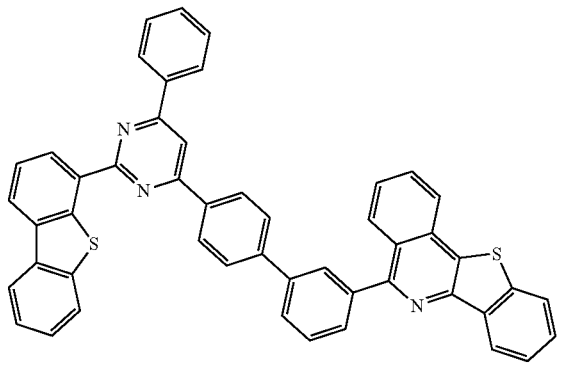
425
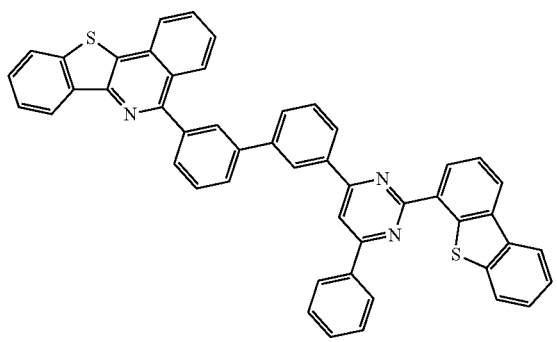
426
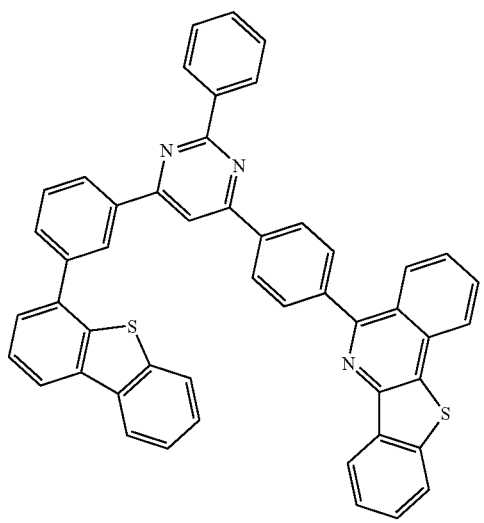
427
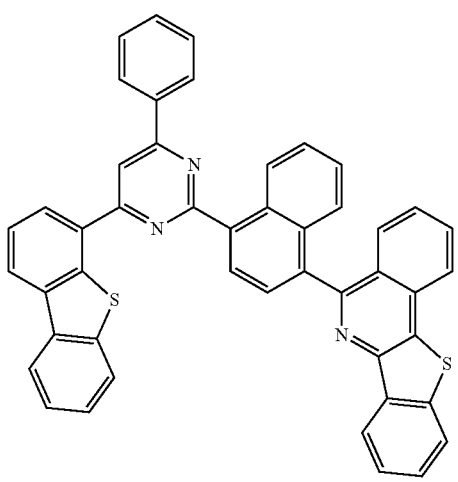
428
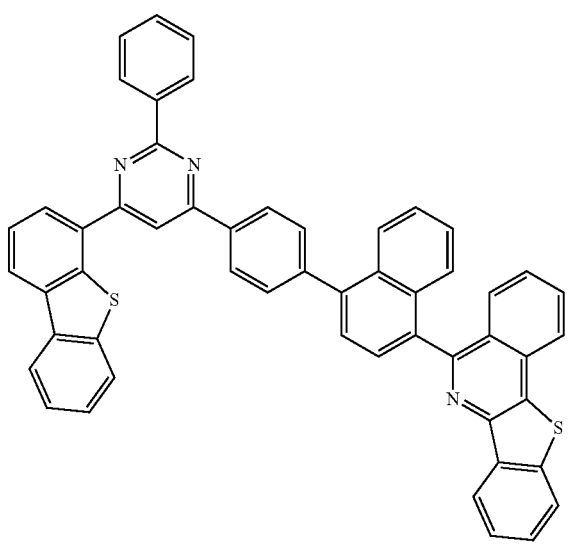

429
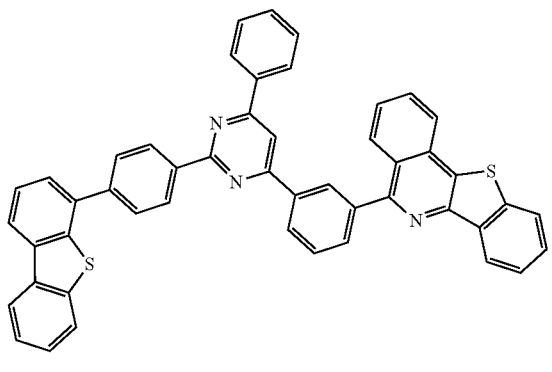
430
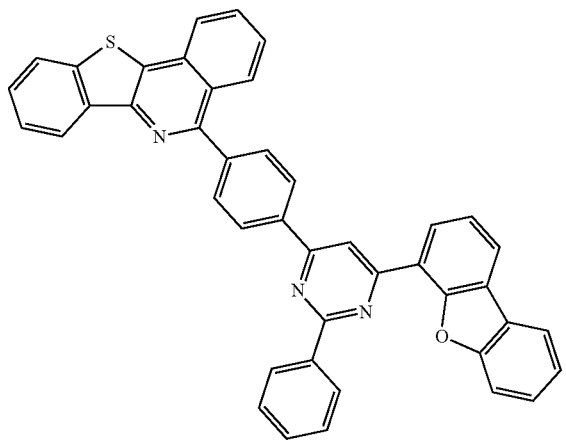
431
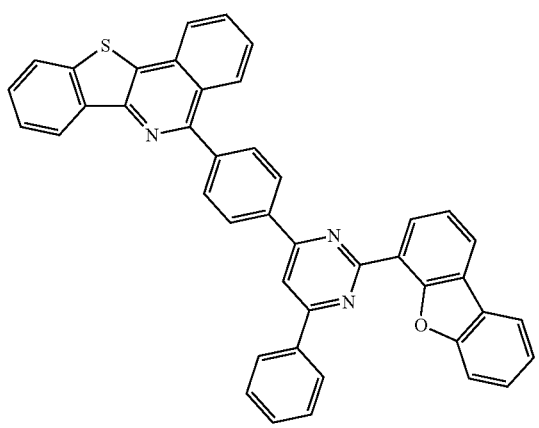
432
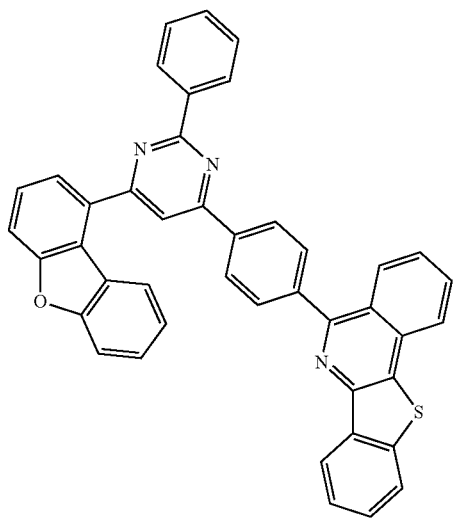
433
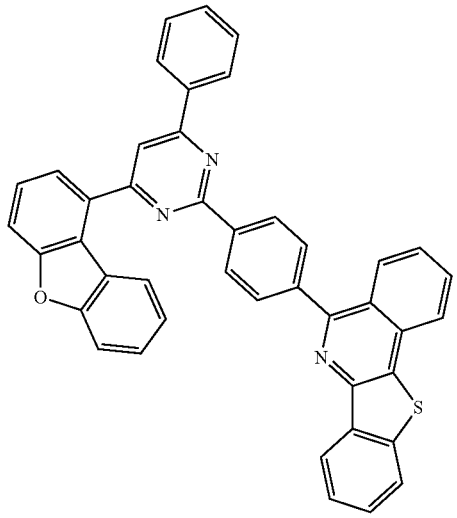
434
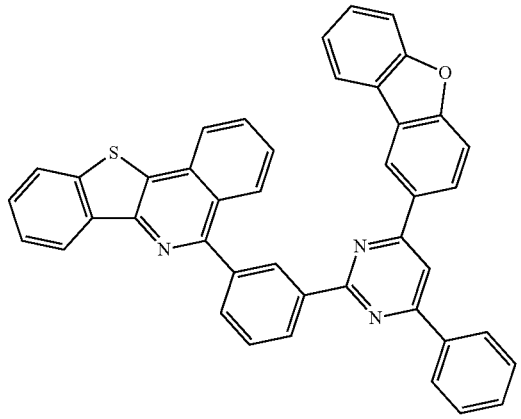

435
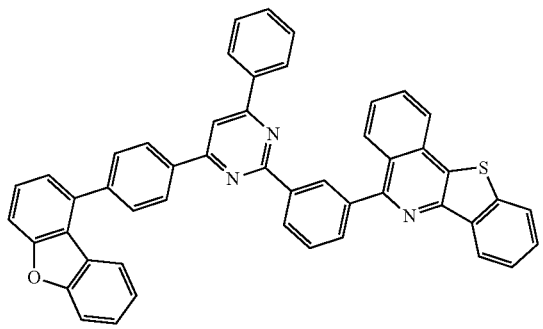
436
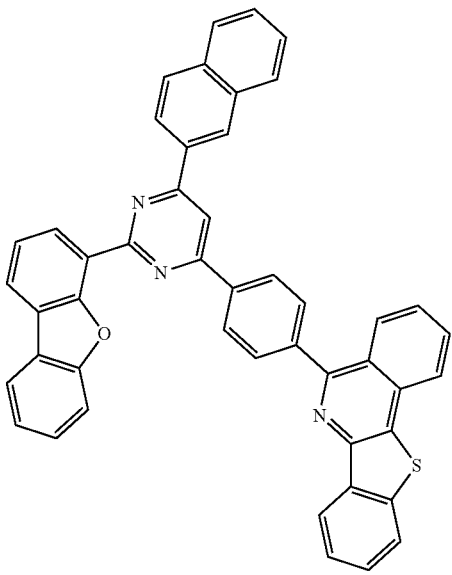
437
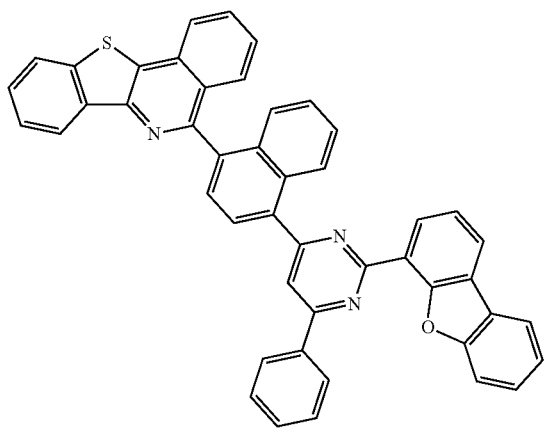
438
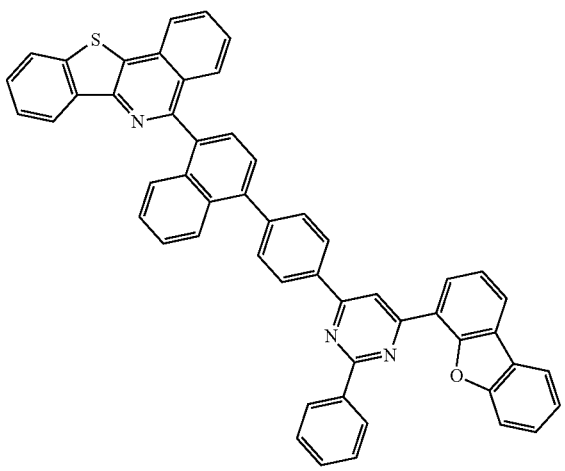
439
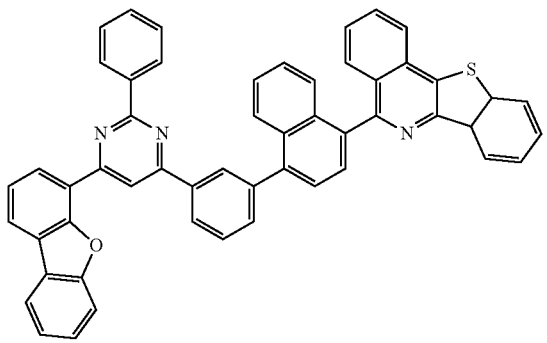
440
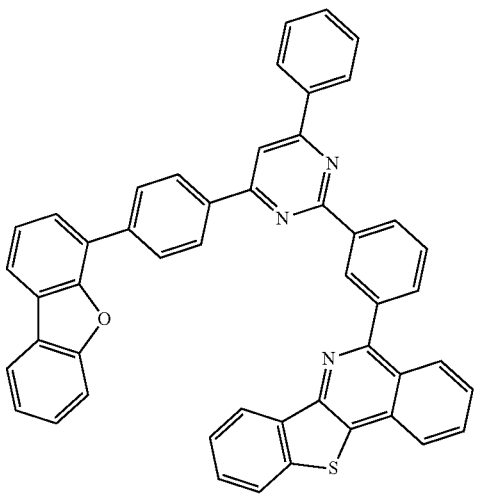

441
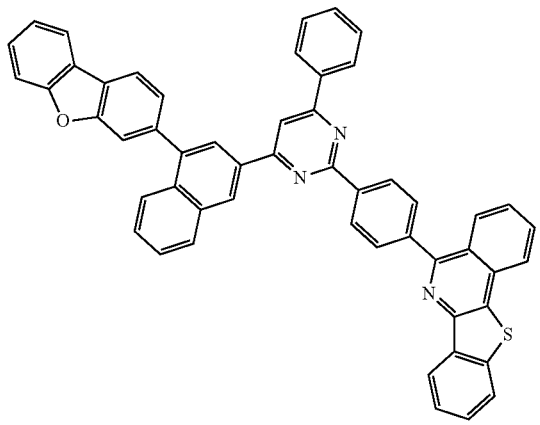
442
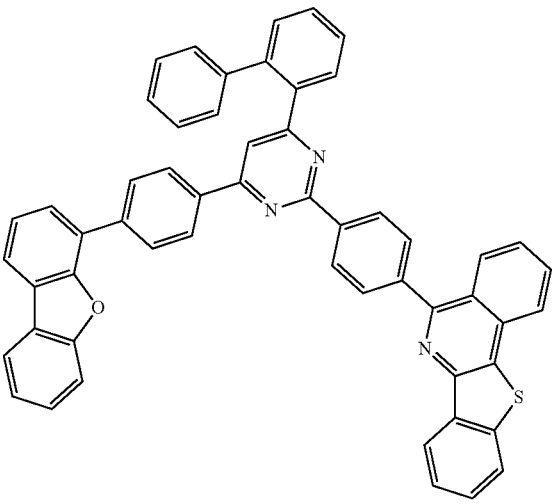
443
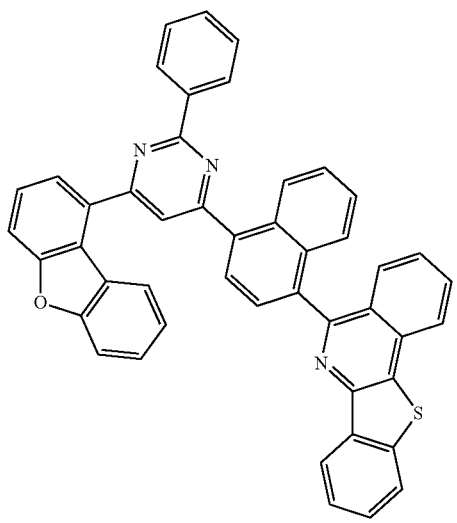
444
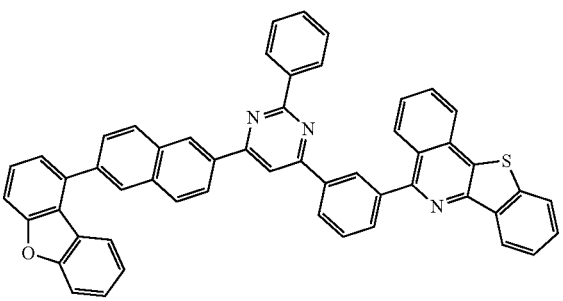
445
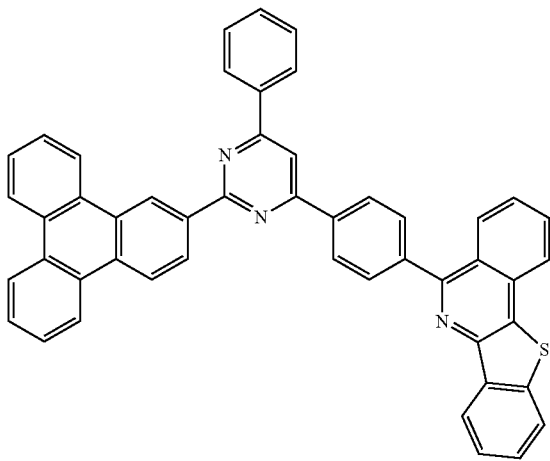
446
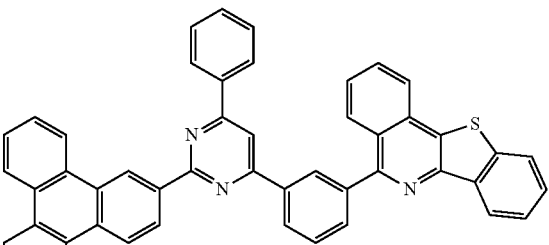

447
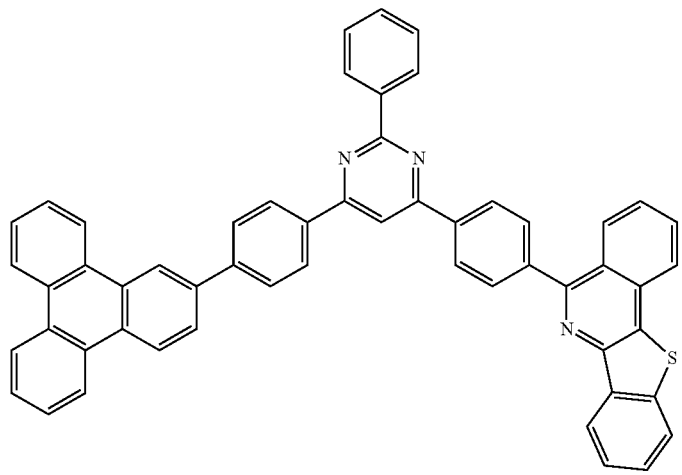
448
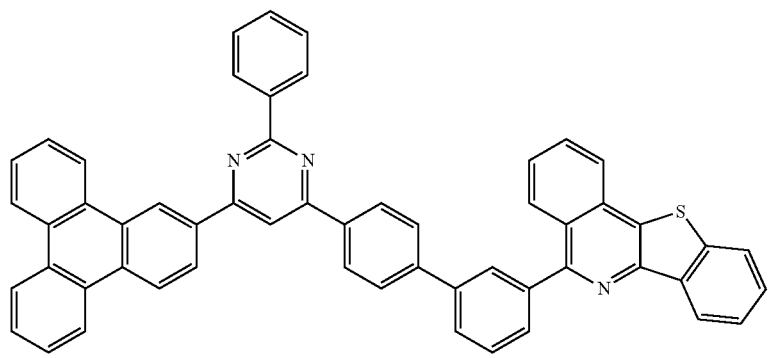
449
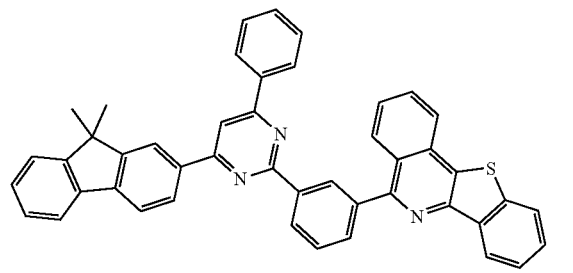
450
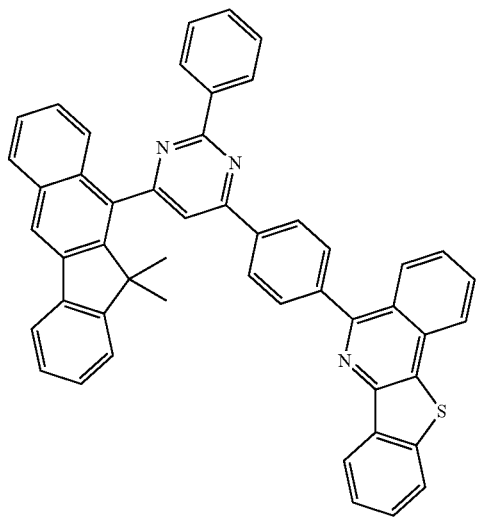

-continued
451
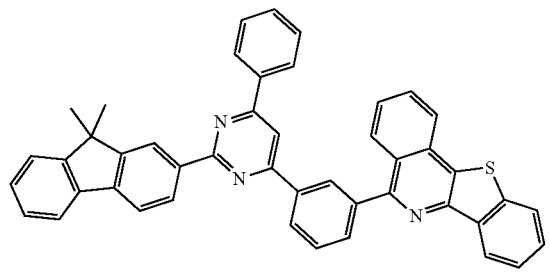
452
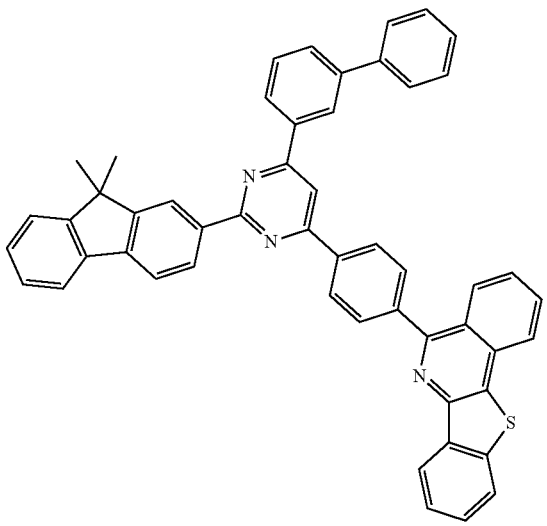
453
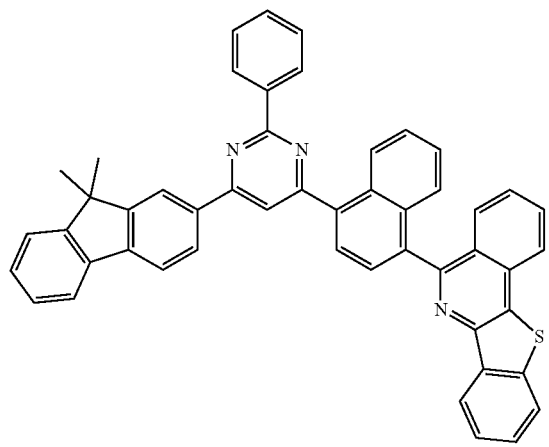
454
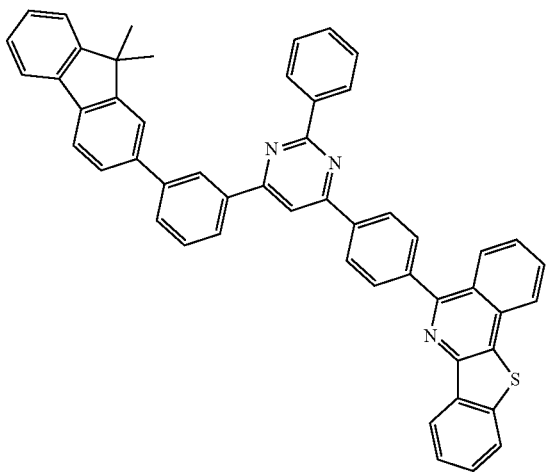
455
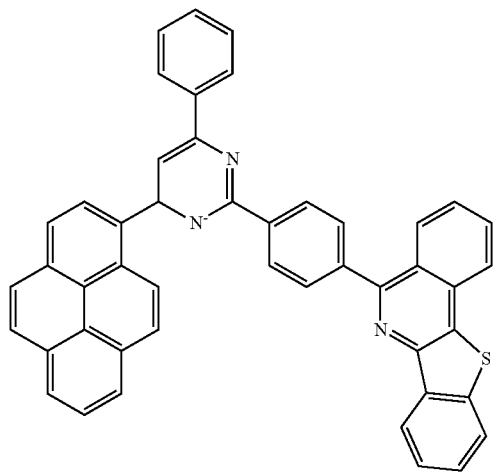
456
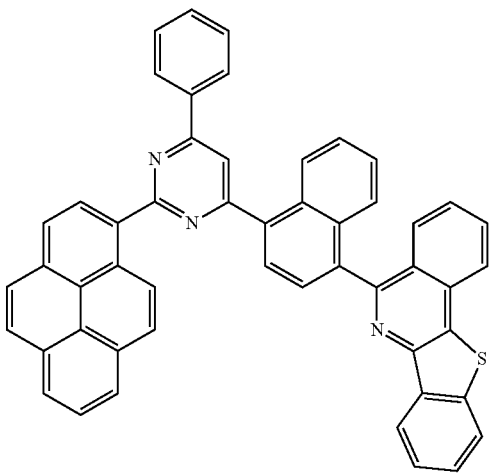

-continued
457
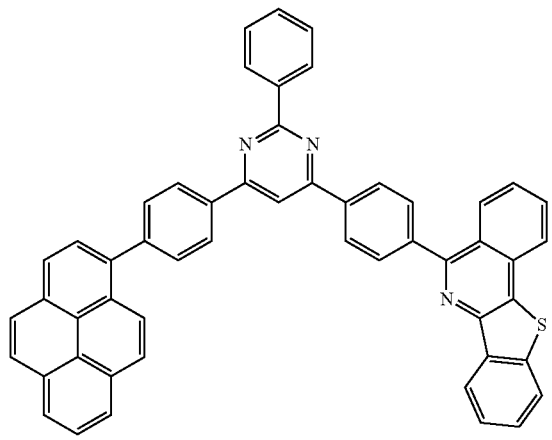
458
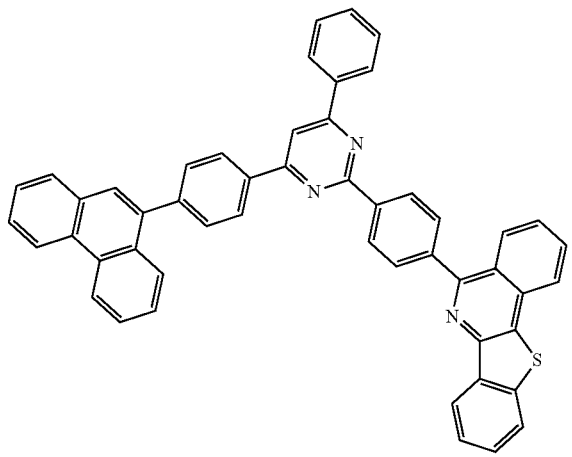
459
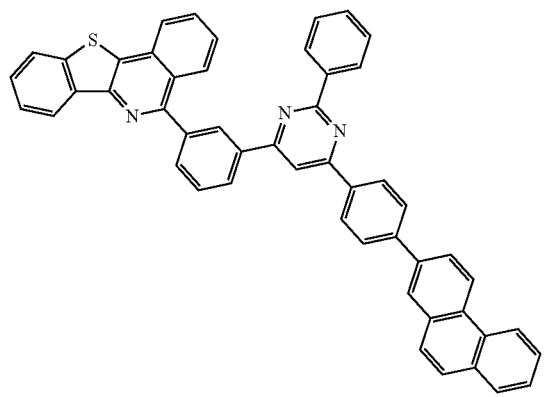
460
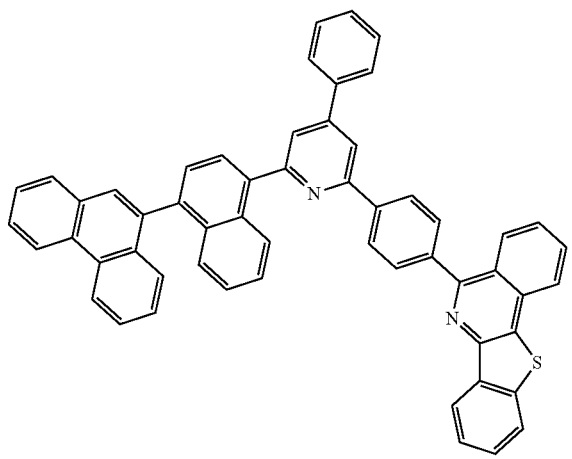
461
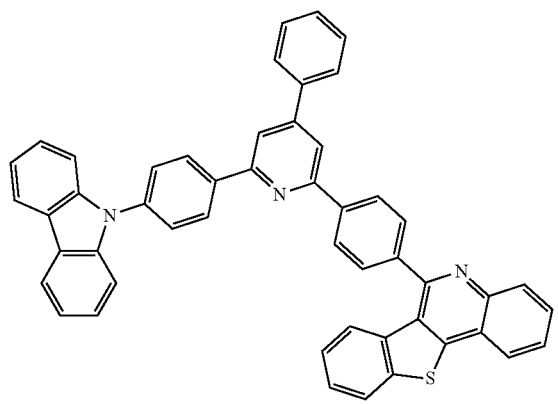
462
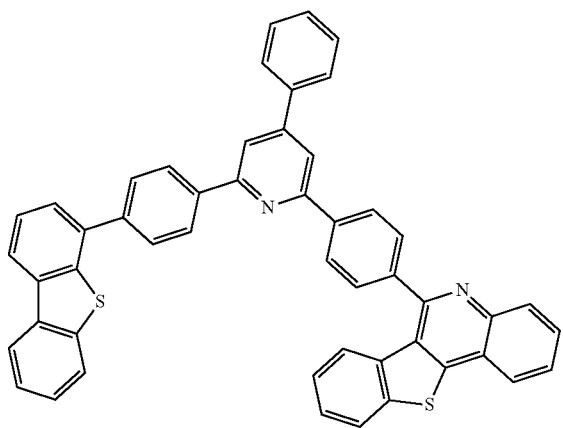

-continued
463
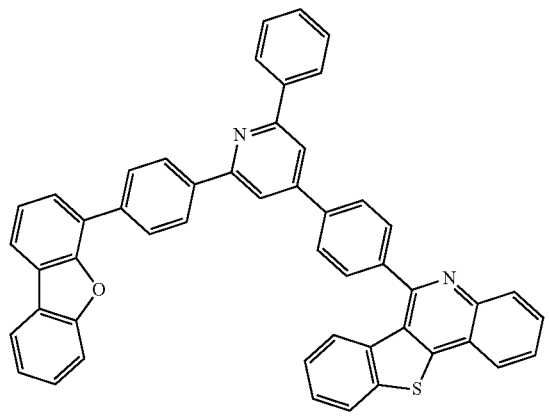
464
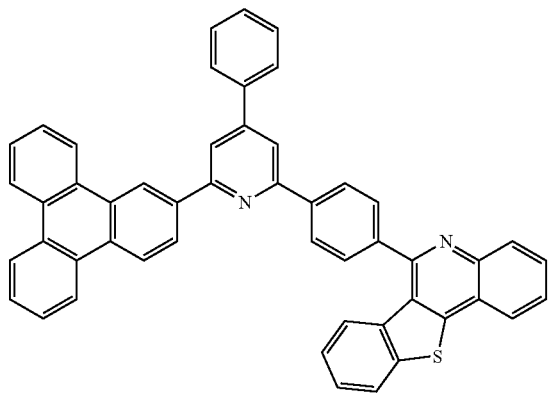
465
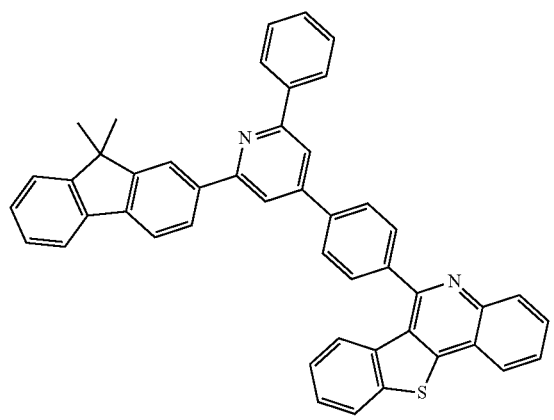
466
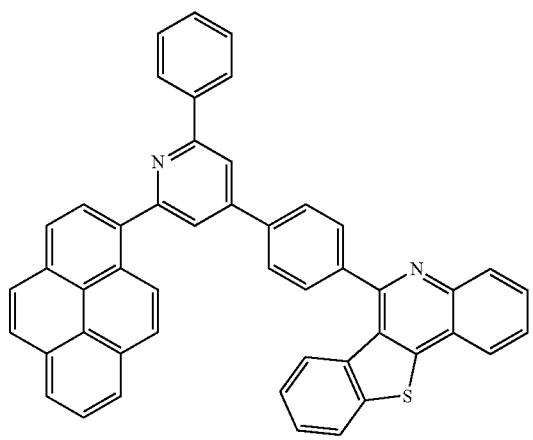
467
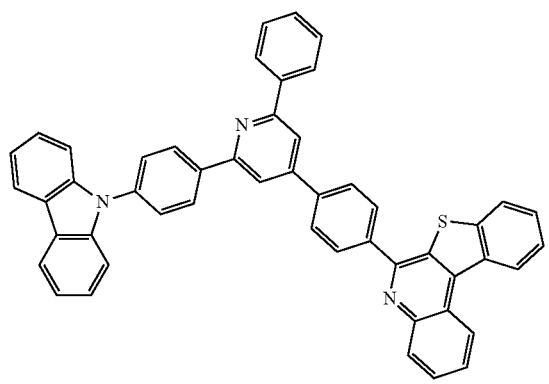
468
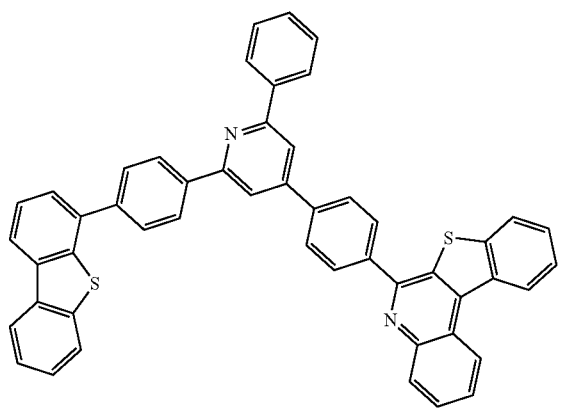

469
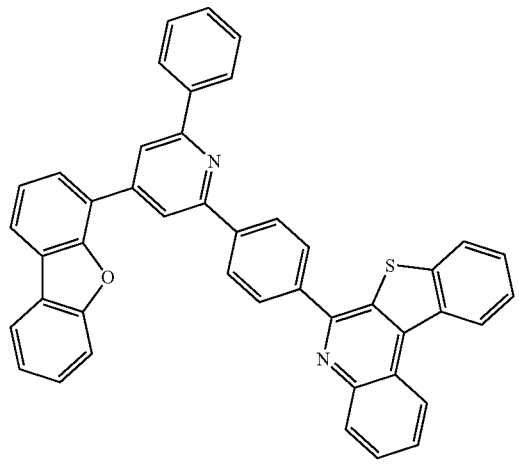
470
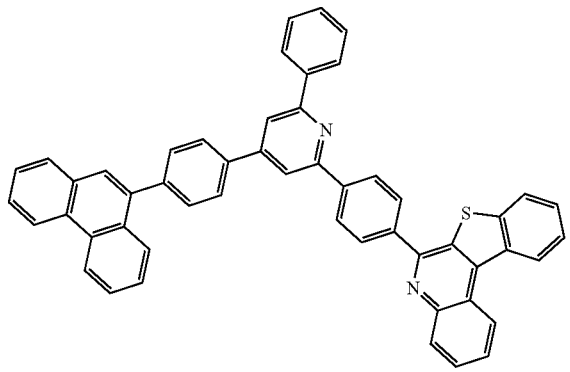
471
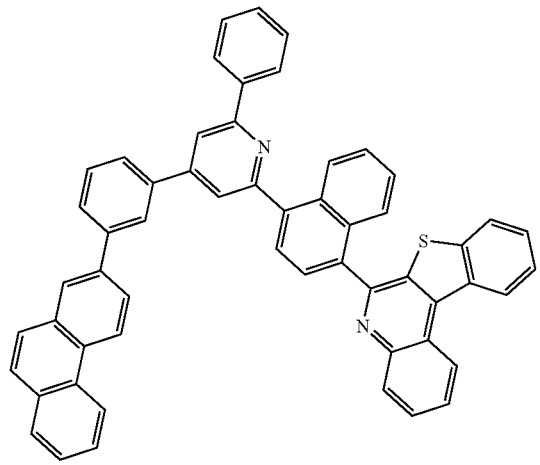
472
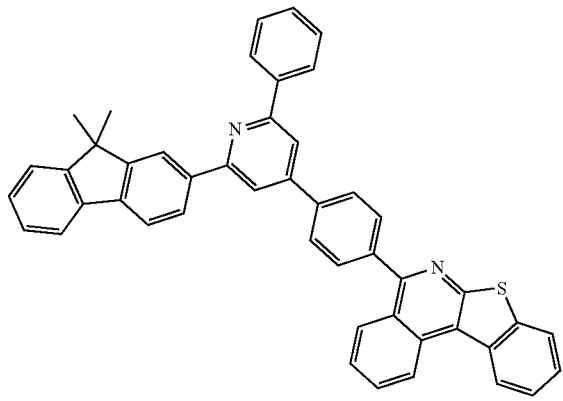
473
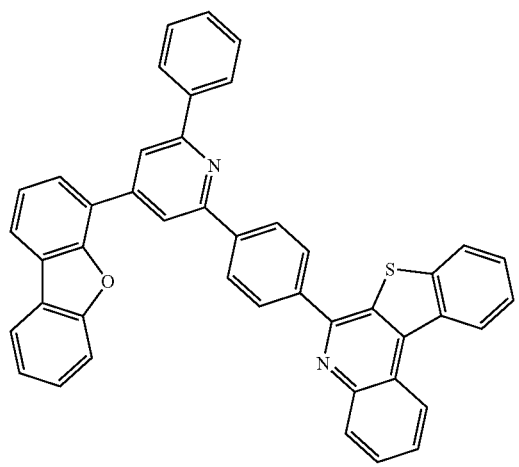
474
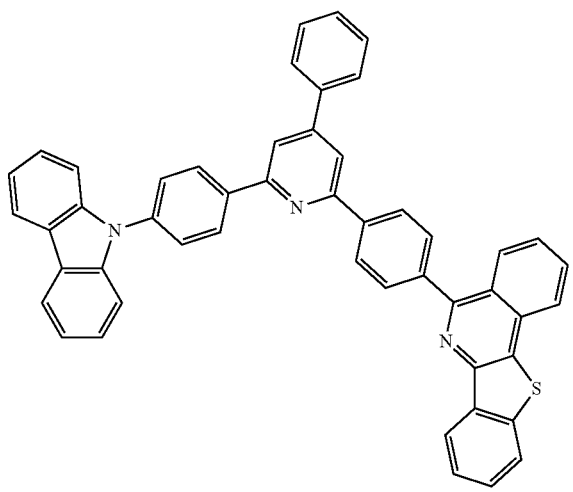

475
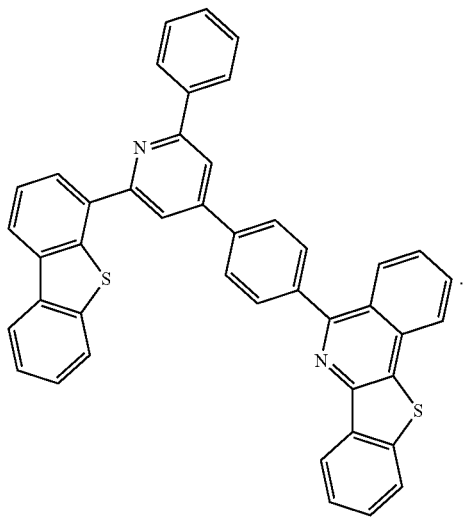
8. The compound of claim 1, wherein the compound represented by Chemical Formula 1 is any one of compounds of the following Group II:
[Group II]
476
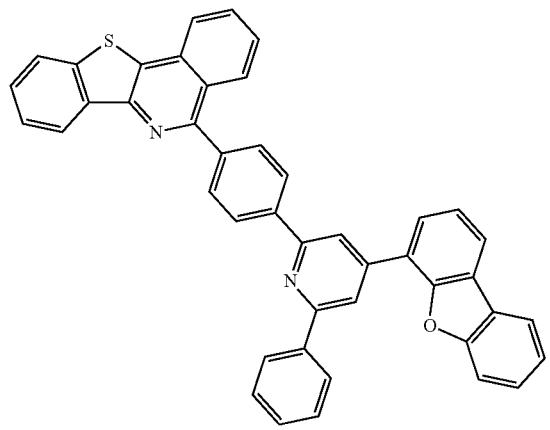
477
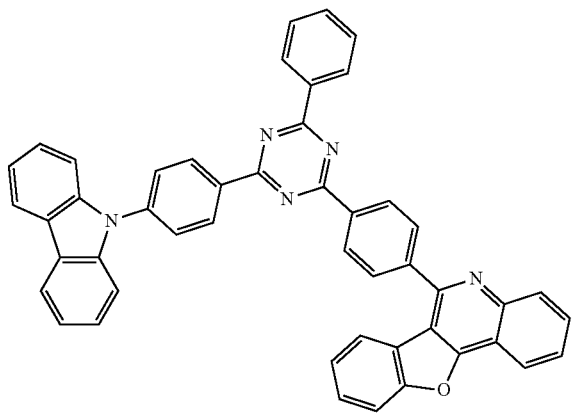
478
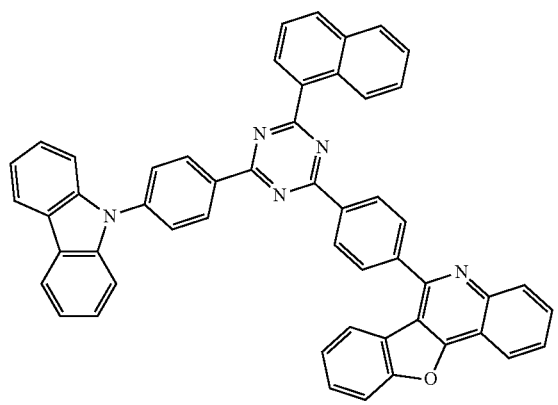
479
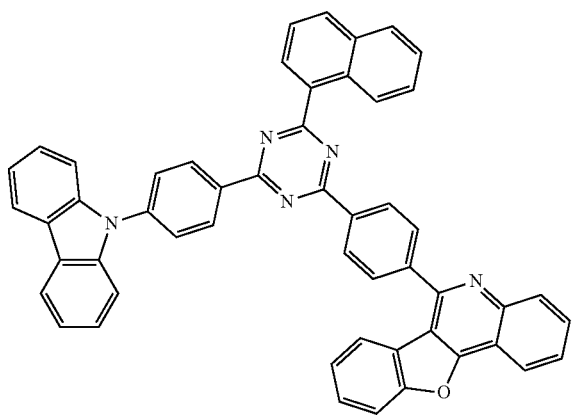

813 814
-continued
480
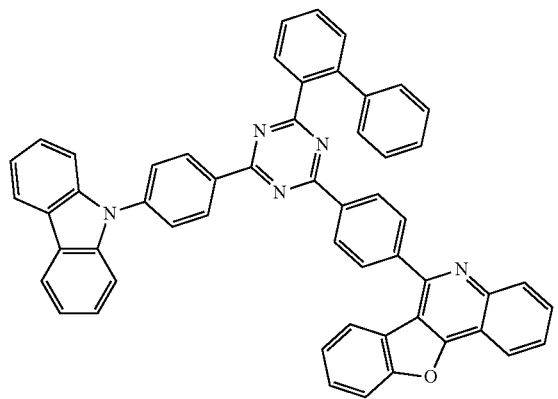
481
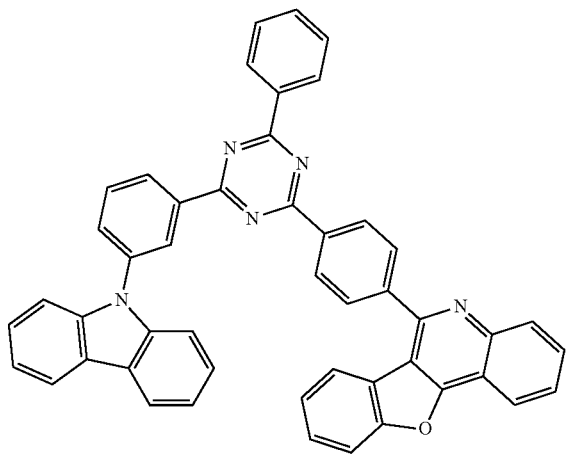
482
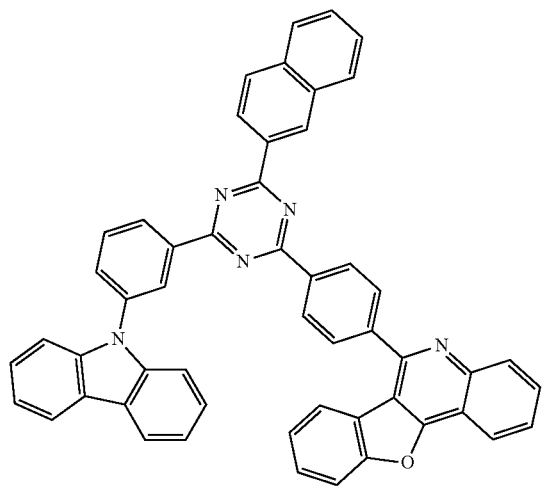
483
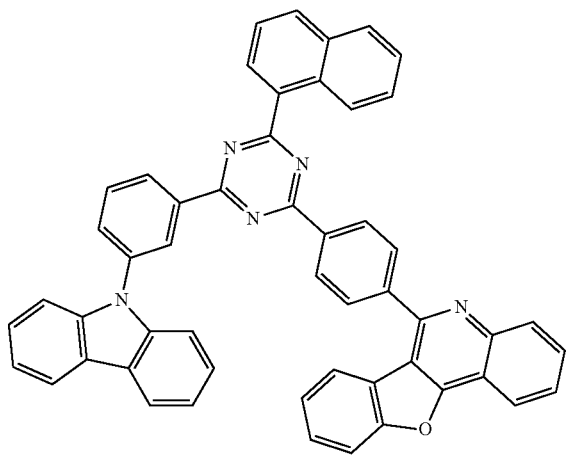
484
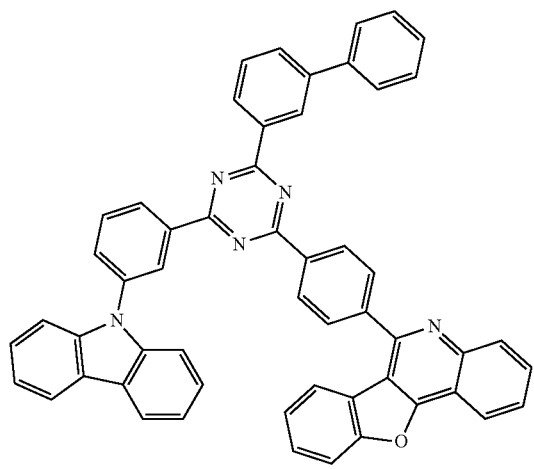
485
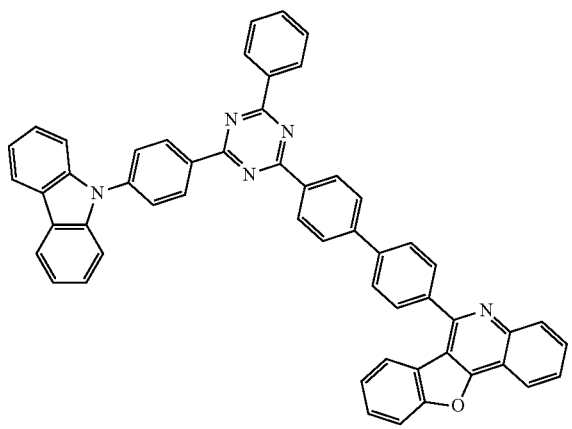

486
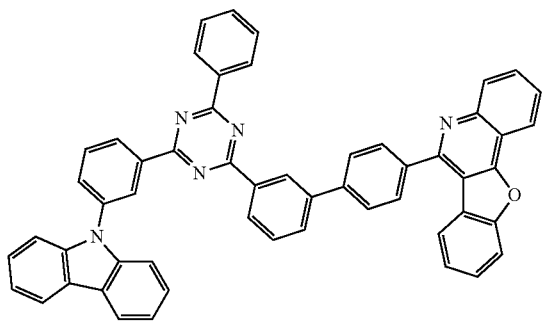
487
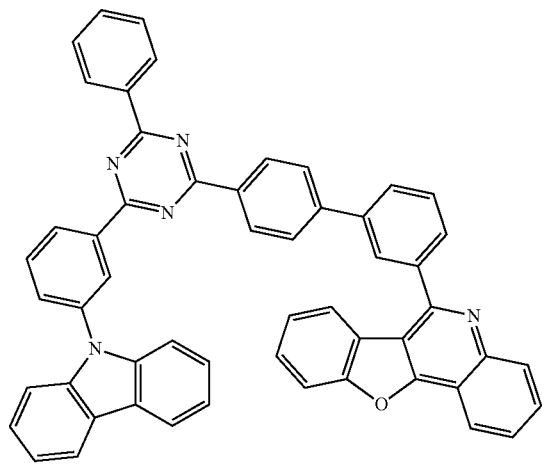
488
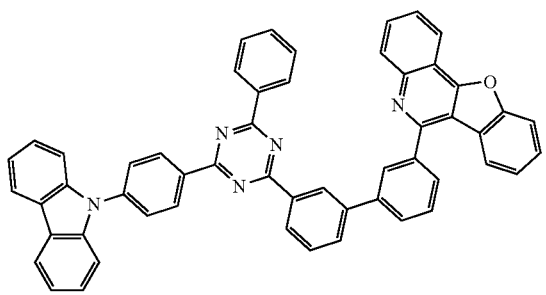
489
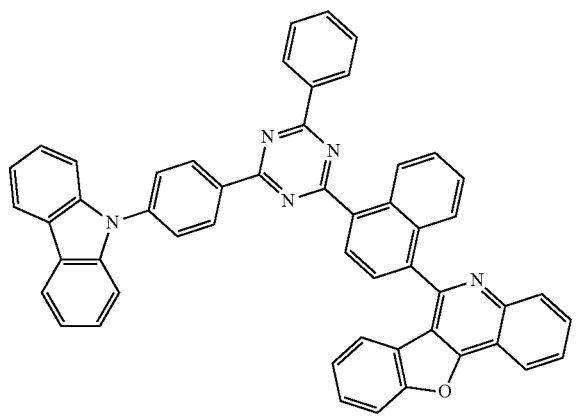
490
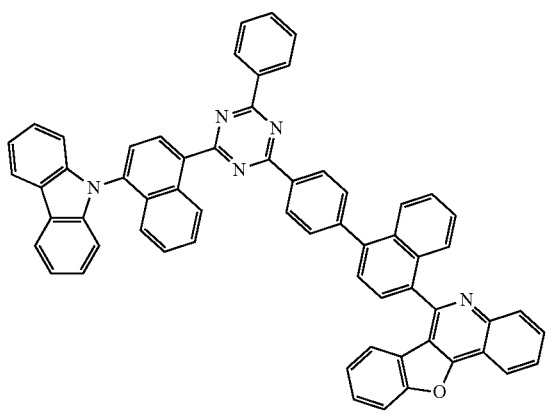
491
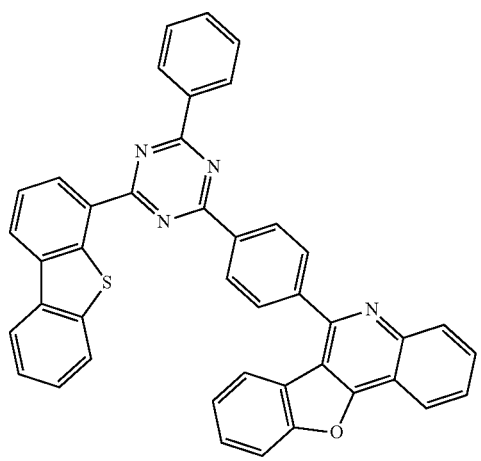

-continued
492
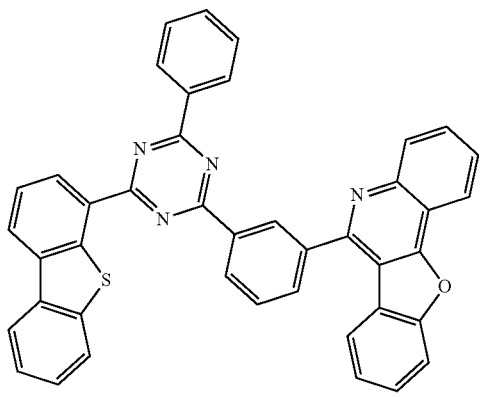
493
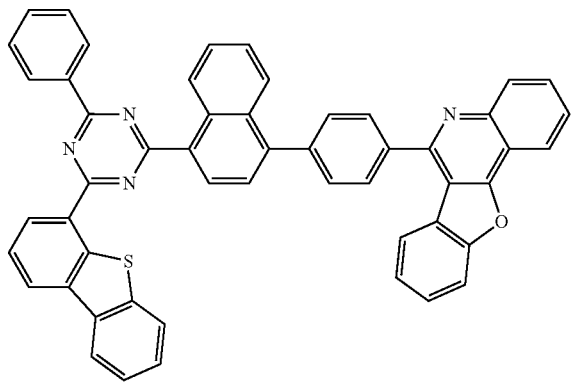
494
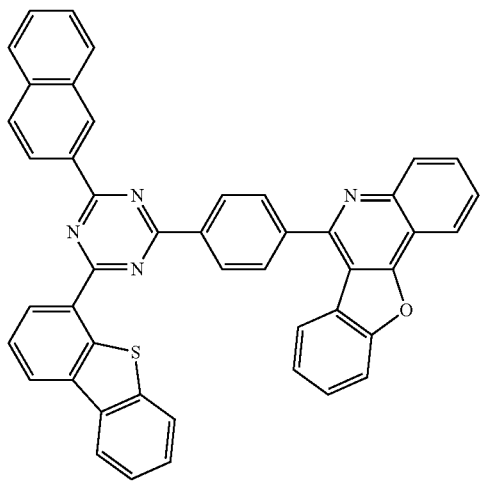
495
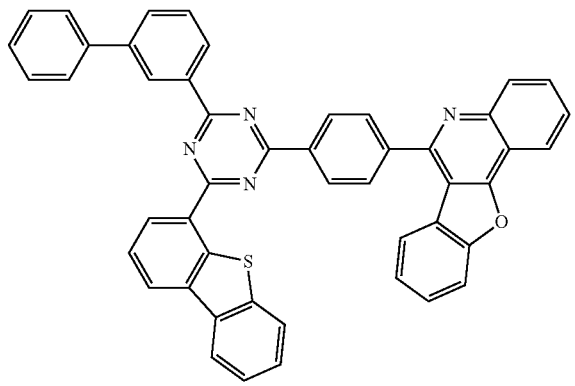
496
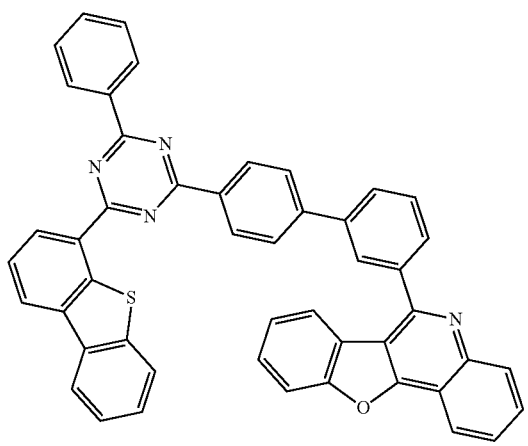
497
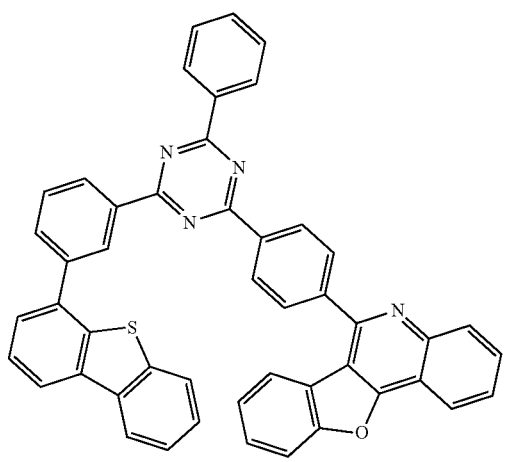

-continued
498
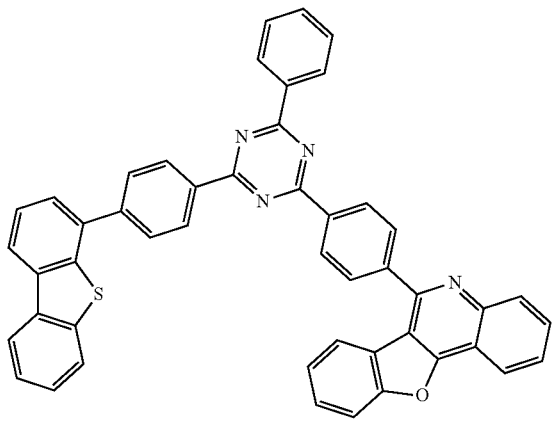
499
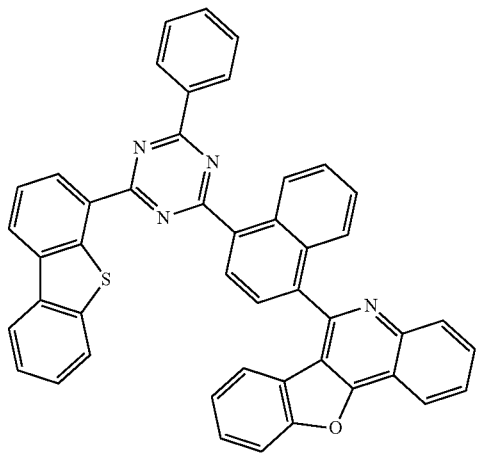
500
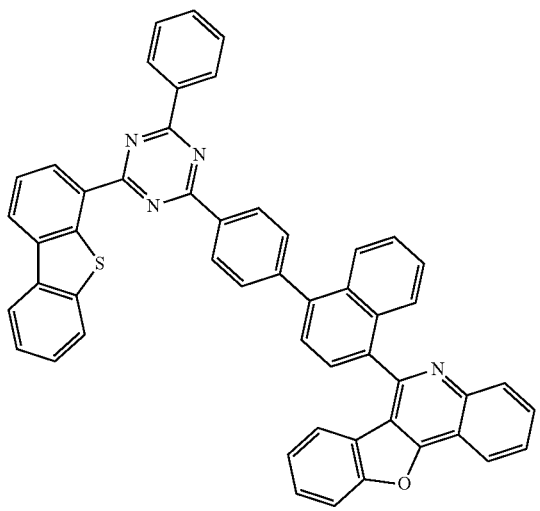
501
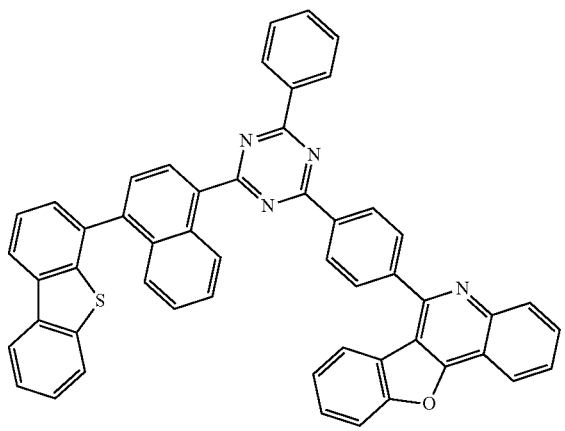
502
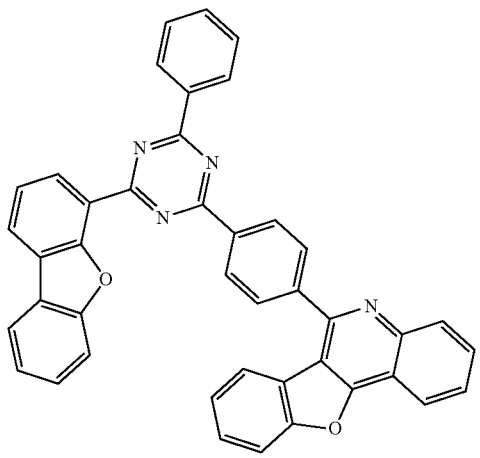
503
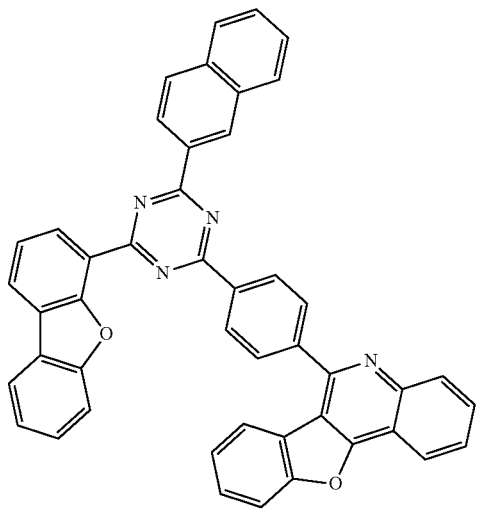

-continued
504
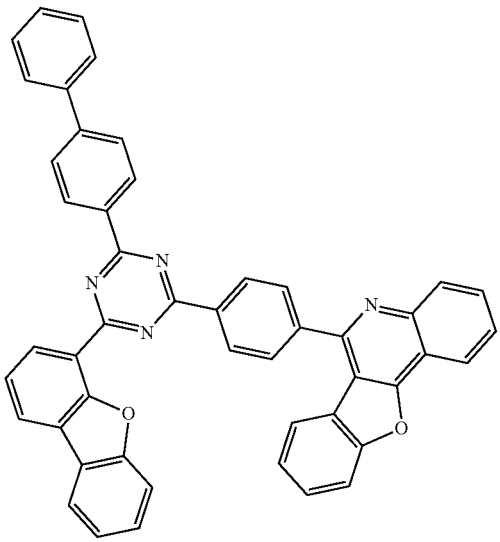
505
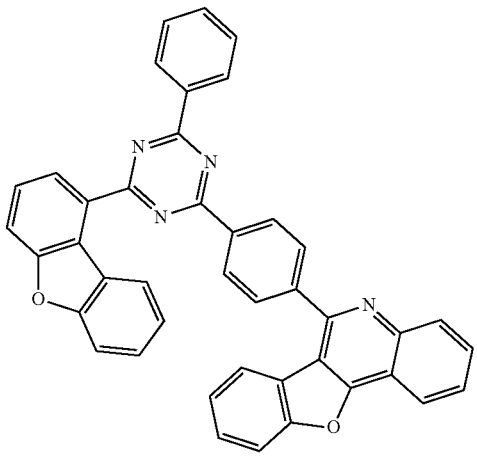
506
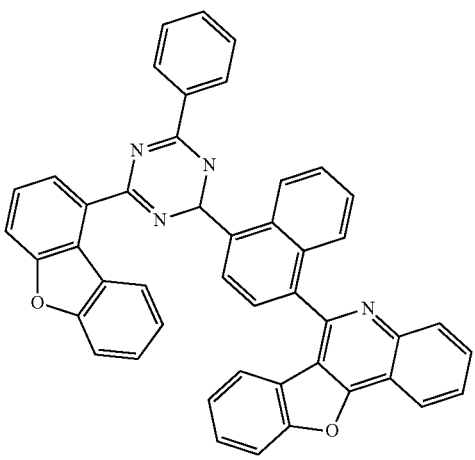
507
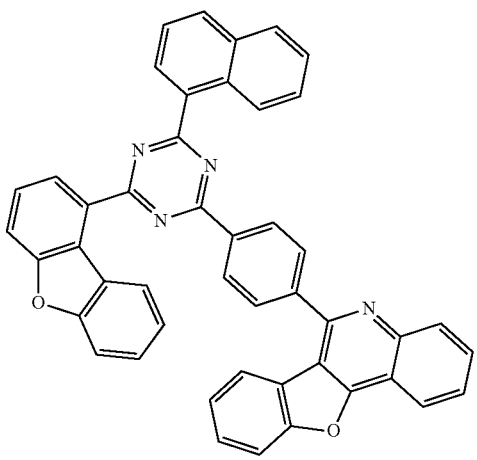
508
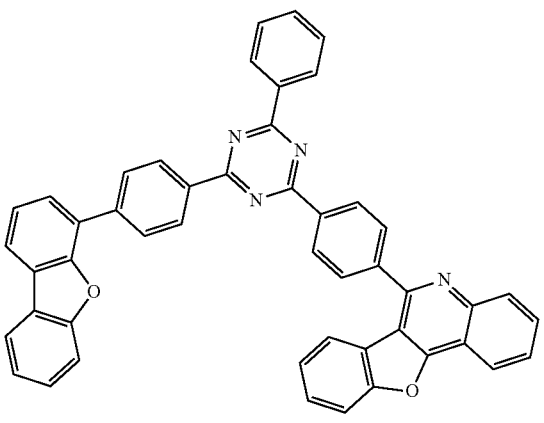
509
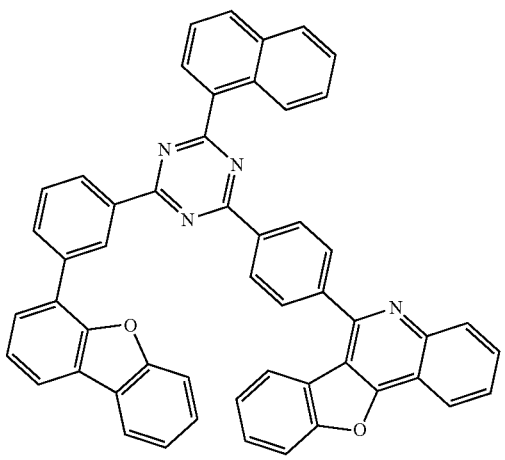

-continued
823
510
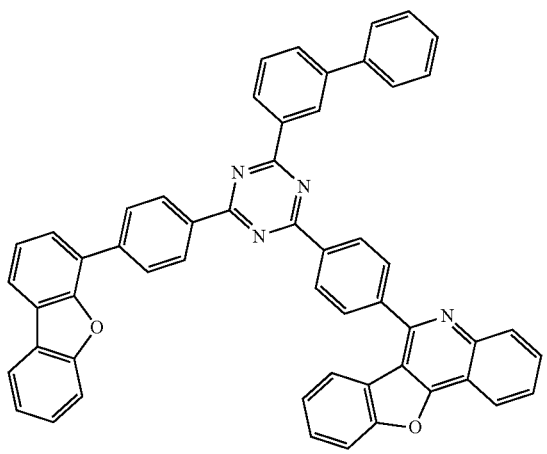
824
511
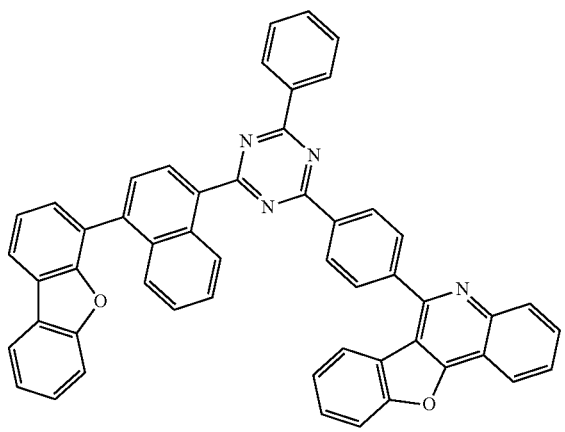
512
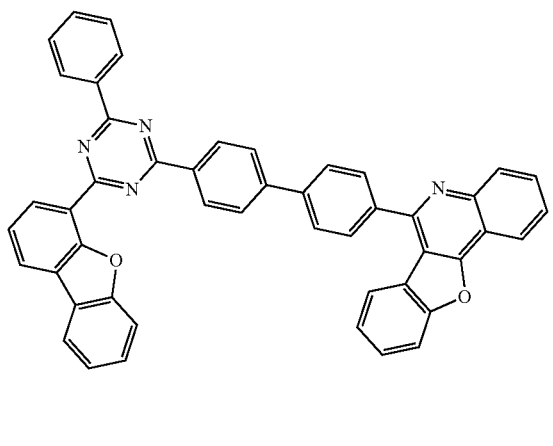
513
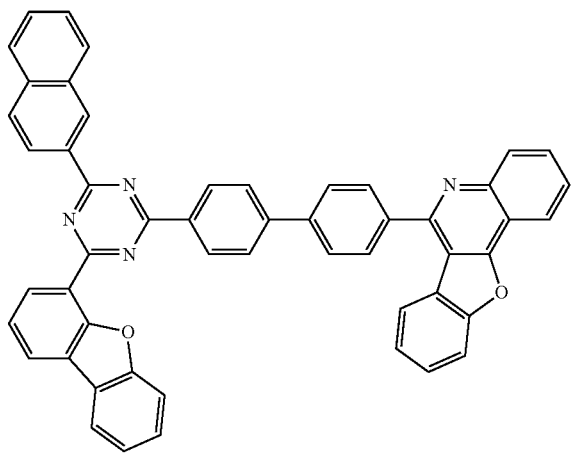
514
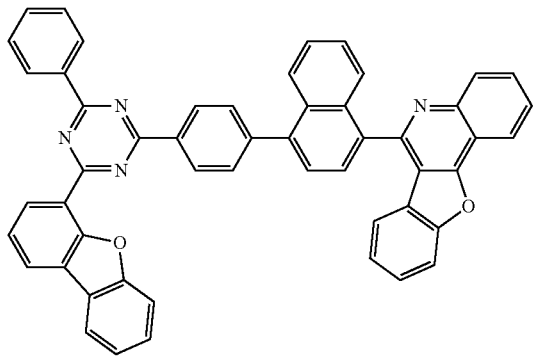
515
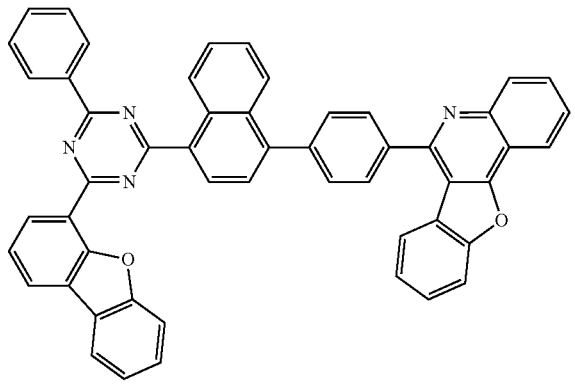

-continued
516
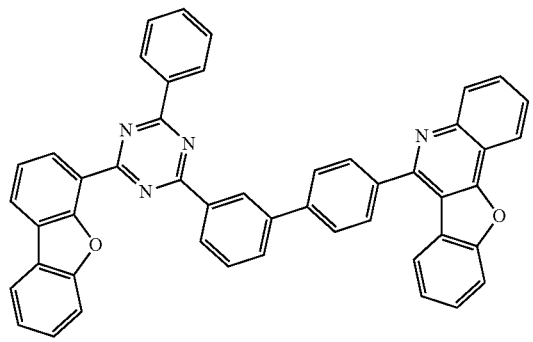
517
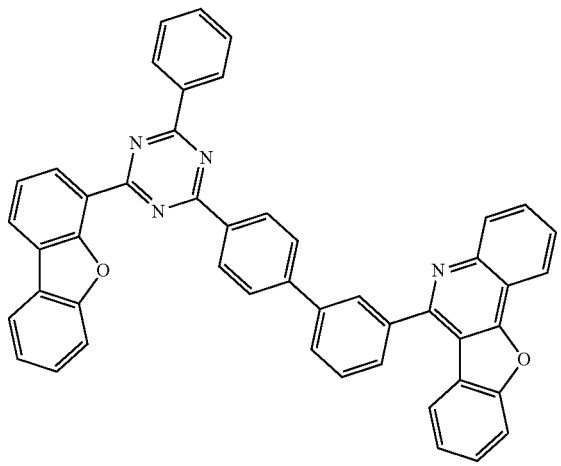
518
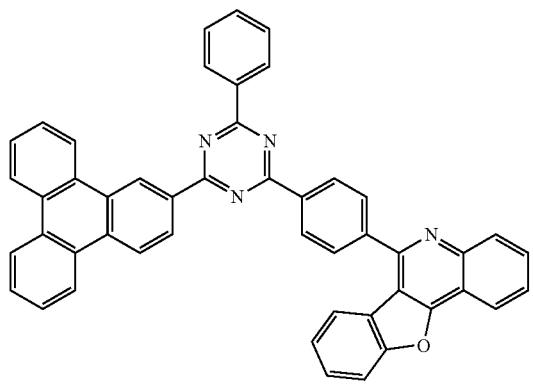
519
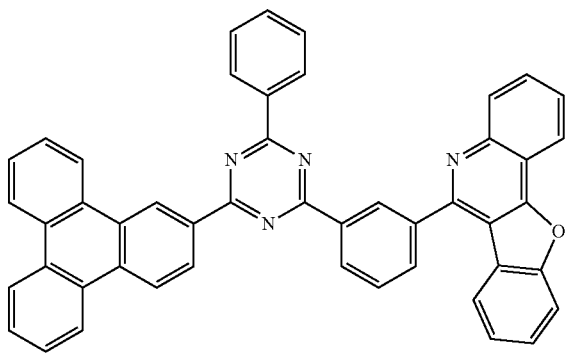
520
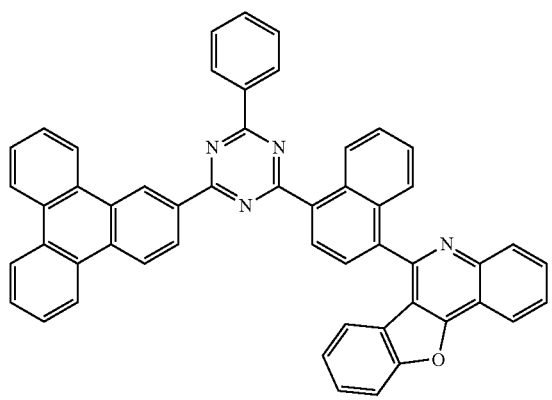
521
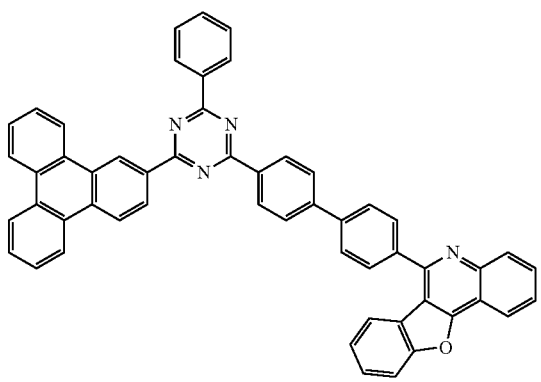

522
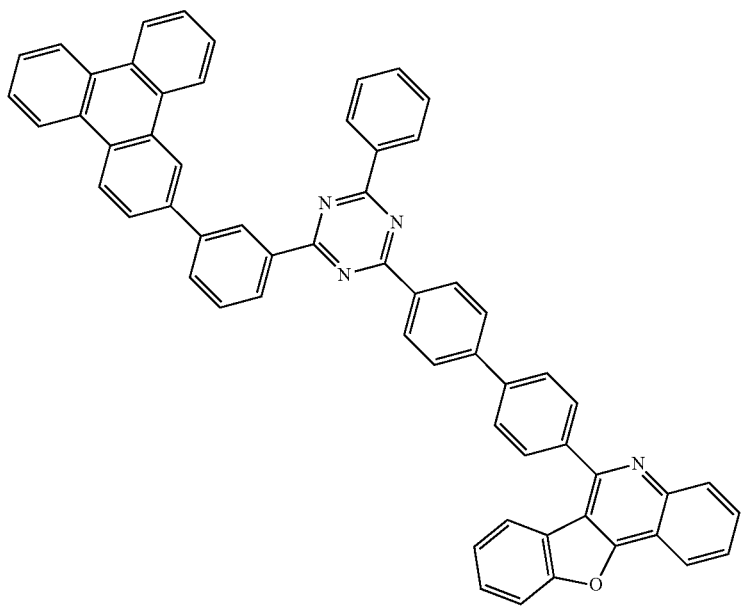
523 524
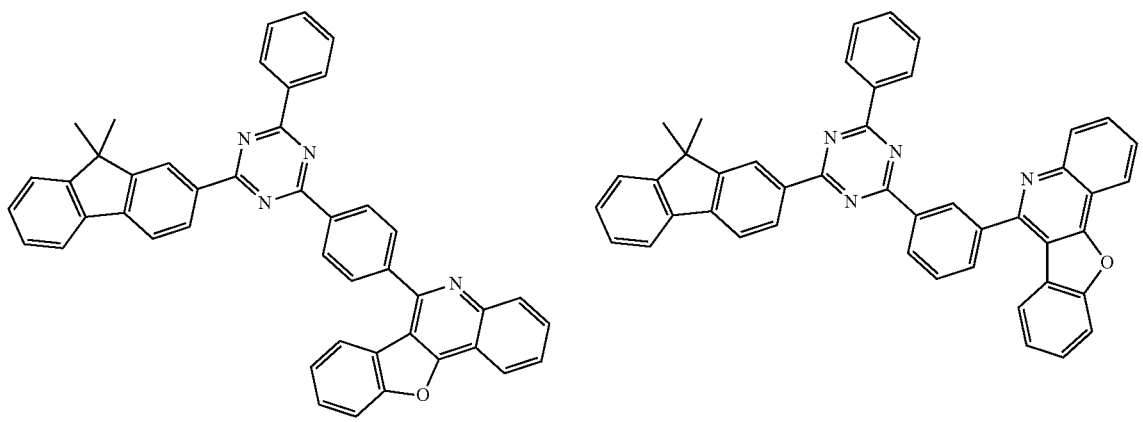
525 526
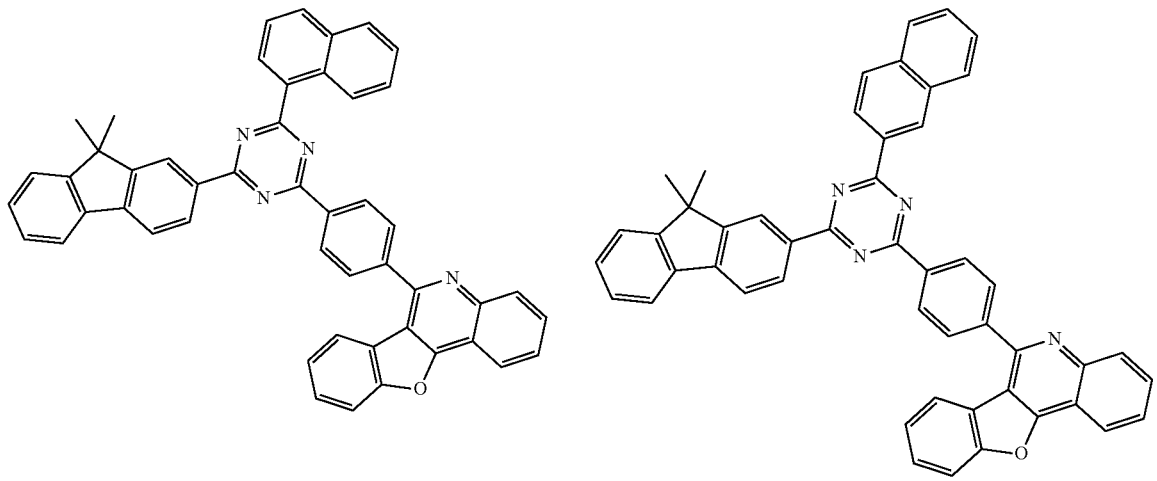

527
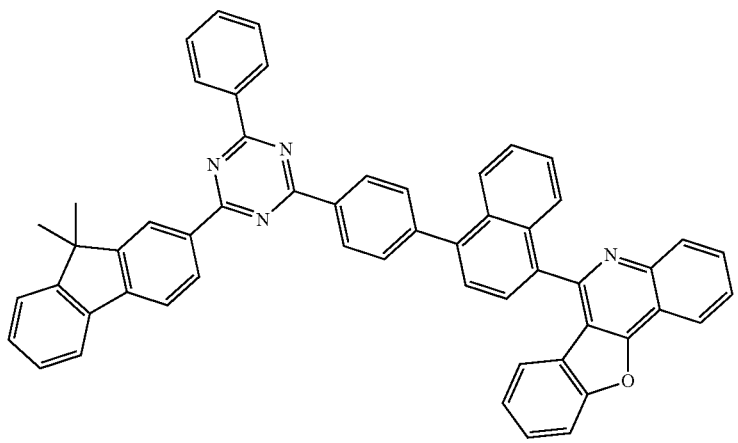
528
529
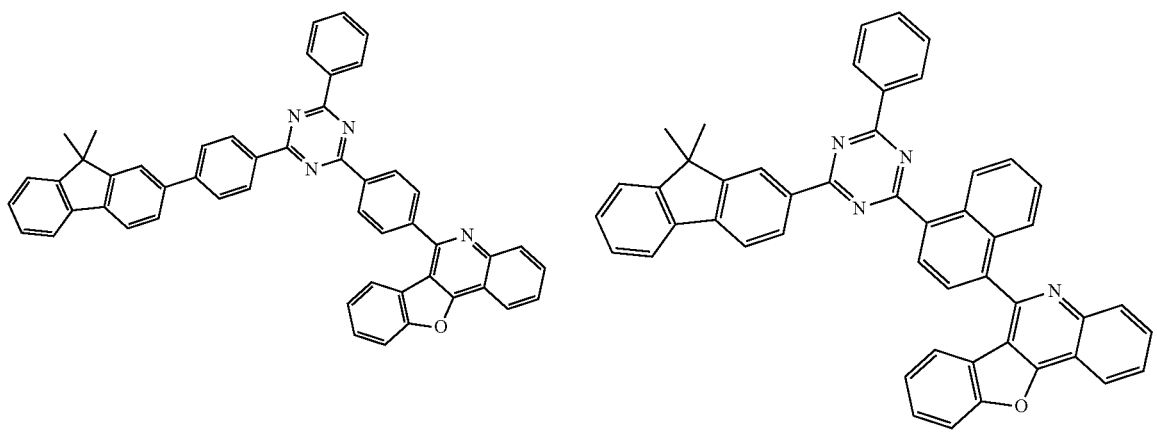
530
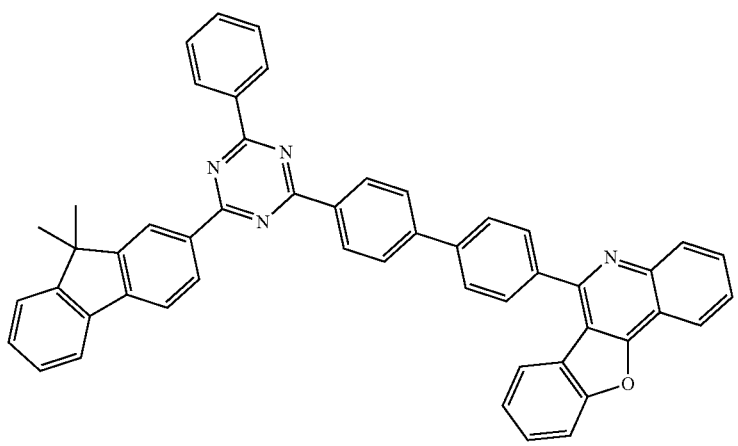

-continued
531
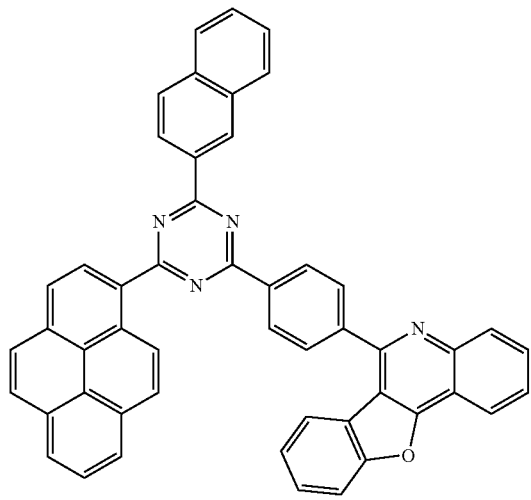
532
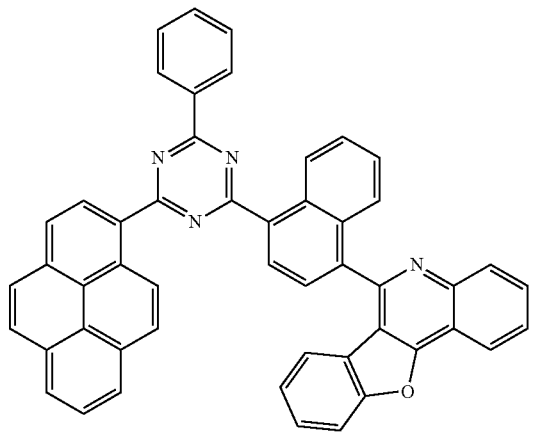
533
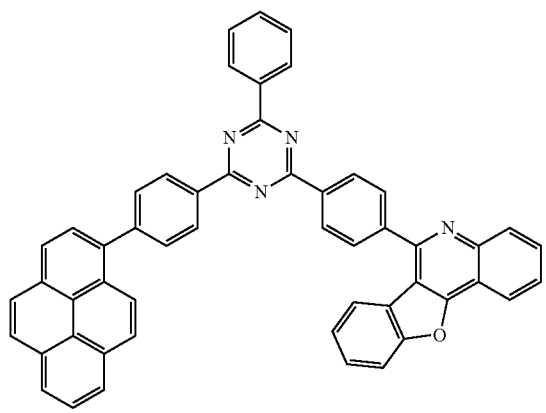
534
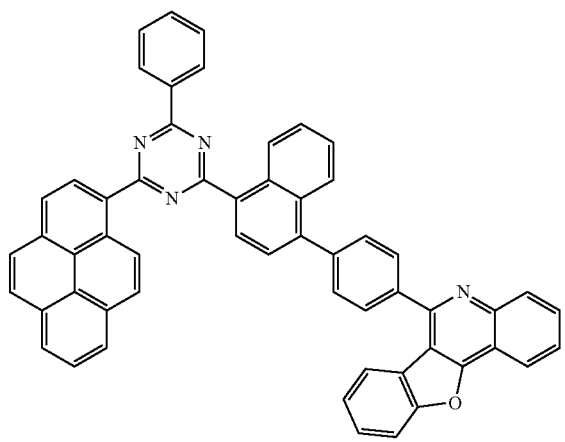
535
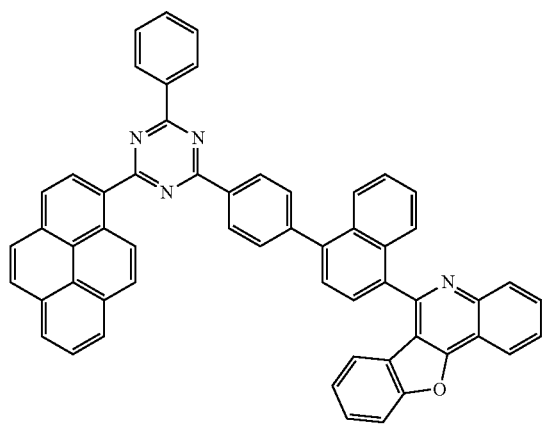
536
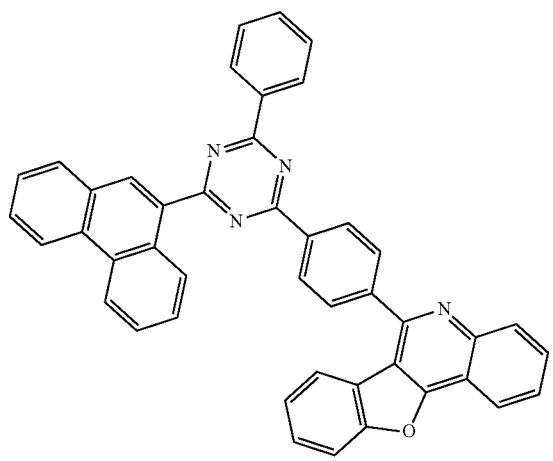

537
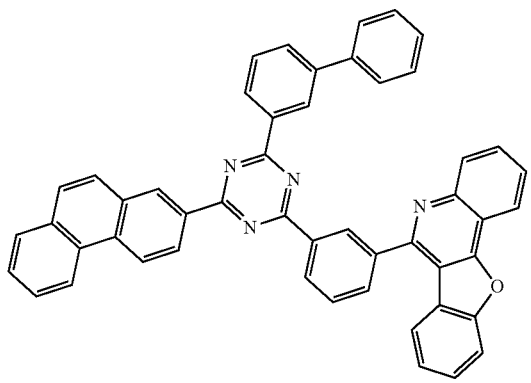
538
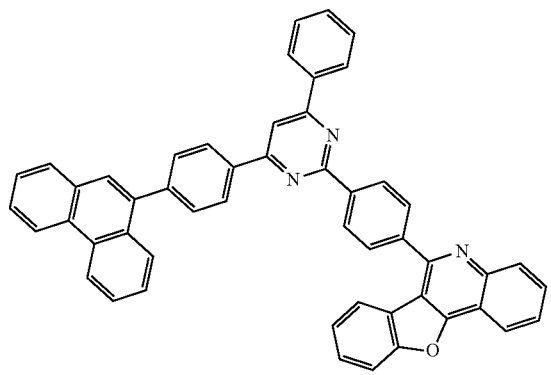
539
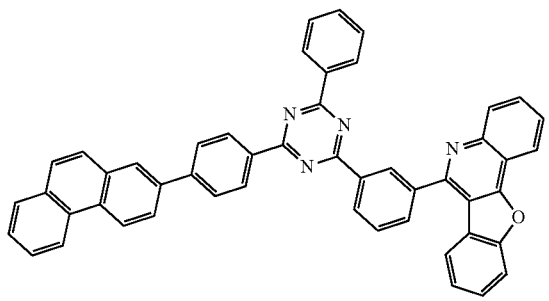
540
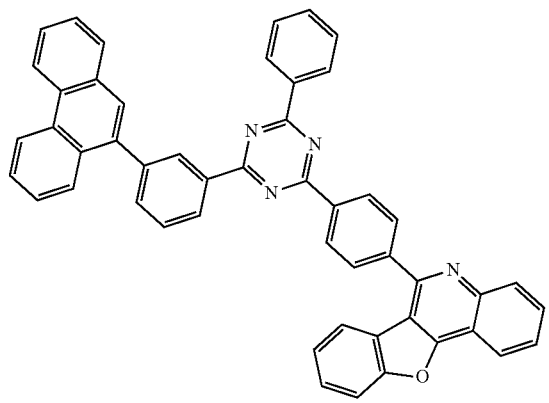
541
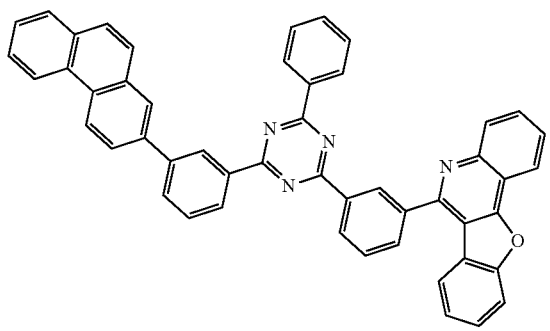
542
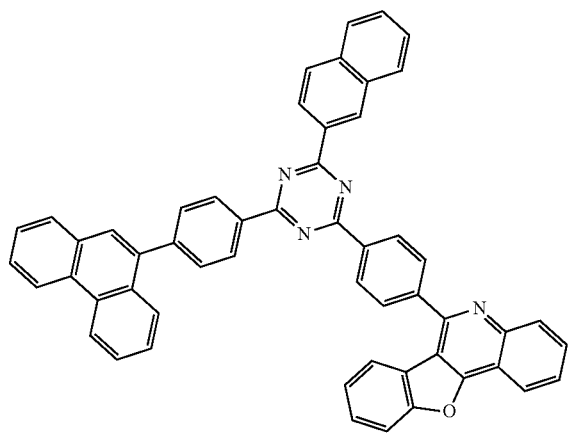

-continued
543
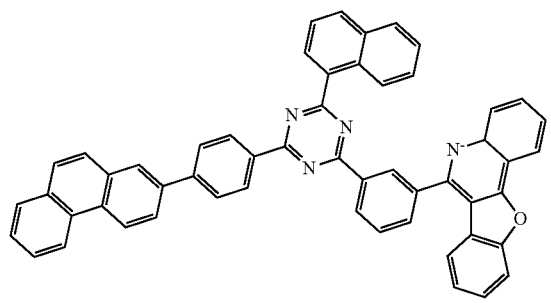
544
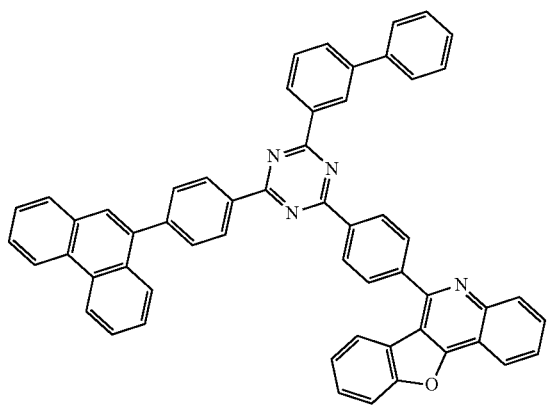
545
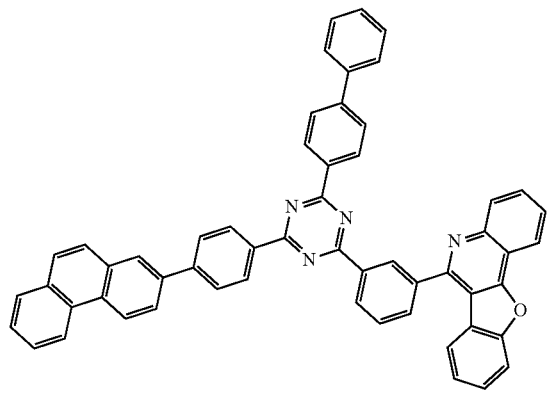
546
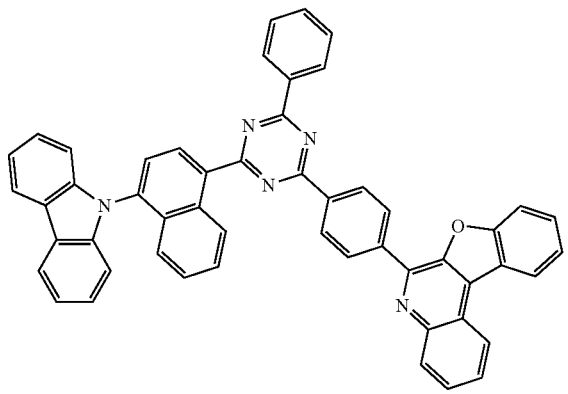
547
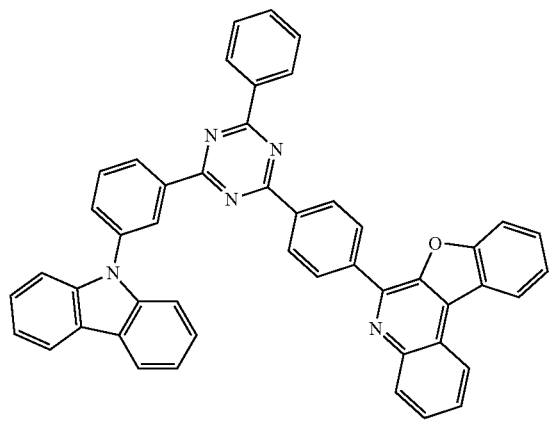
548
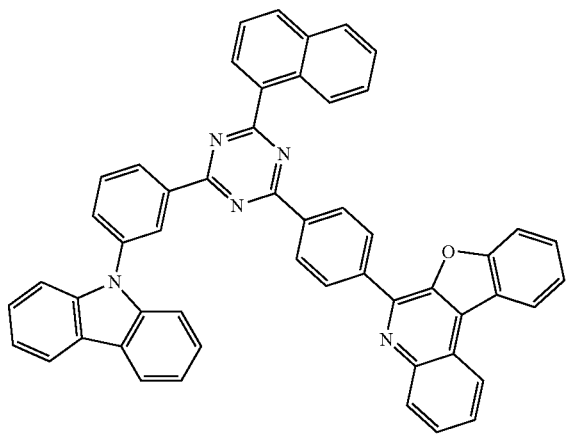

-continued
549
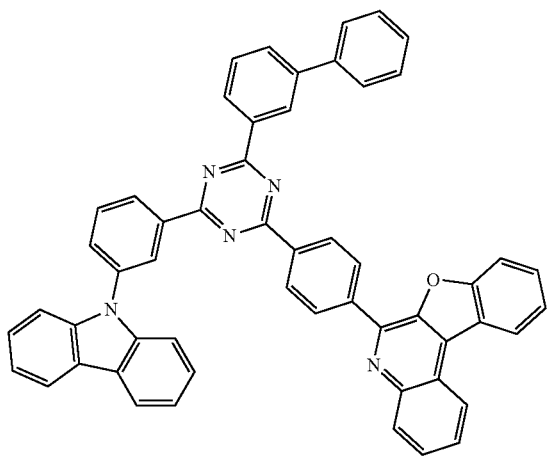
550
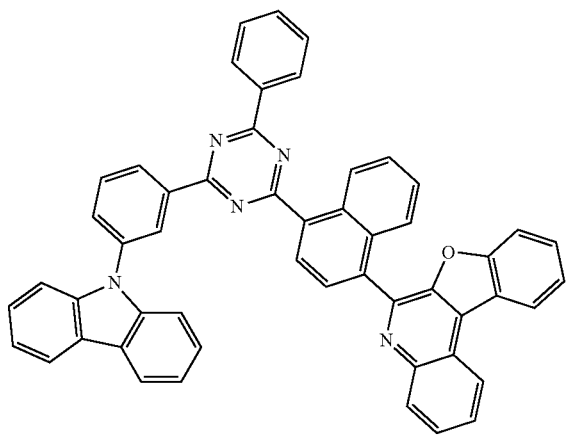
551
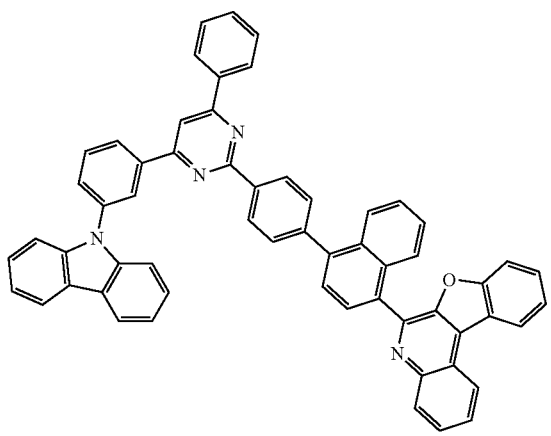
552
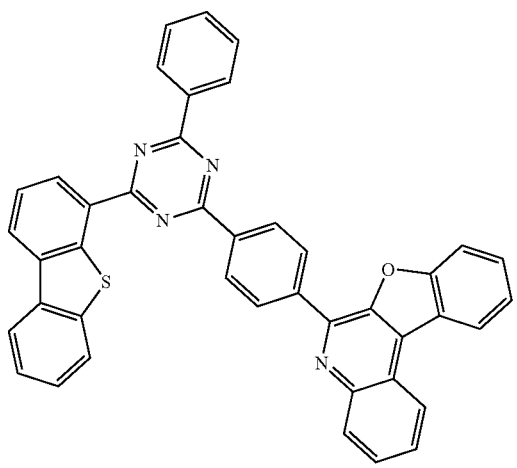
553
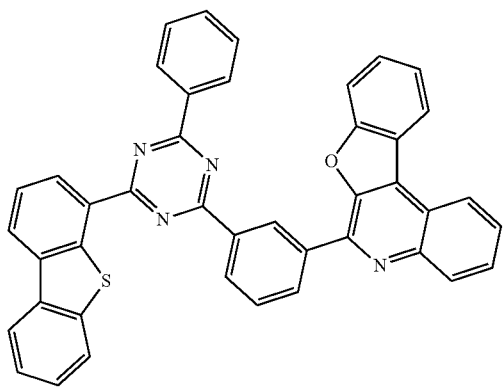
554
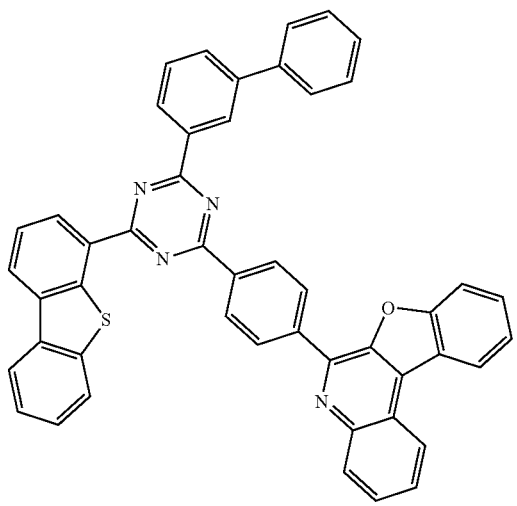

-continued
555
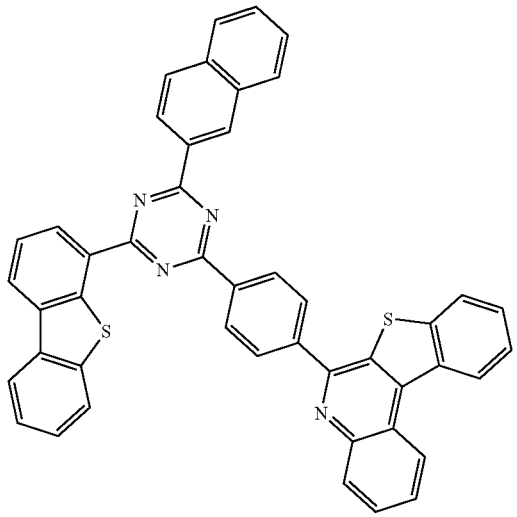
556
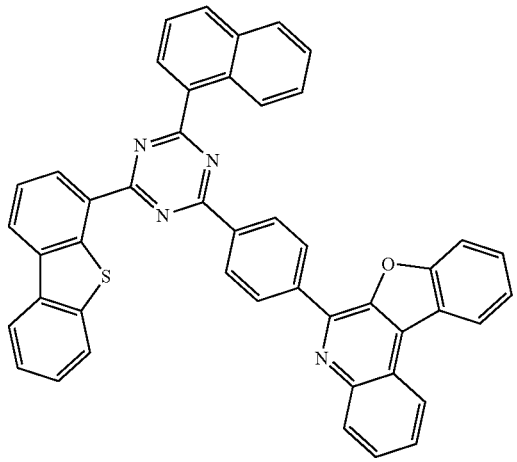
557
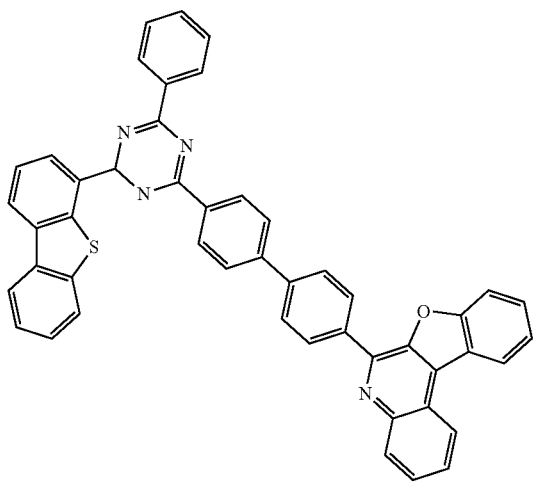
558
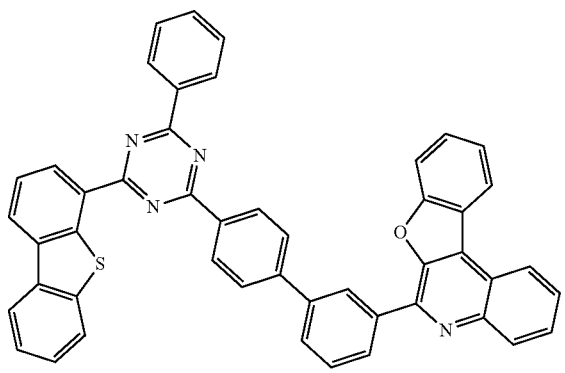
559
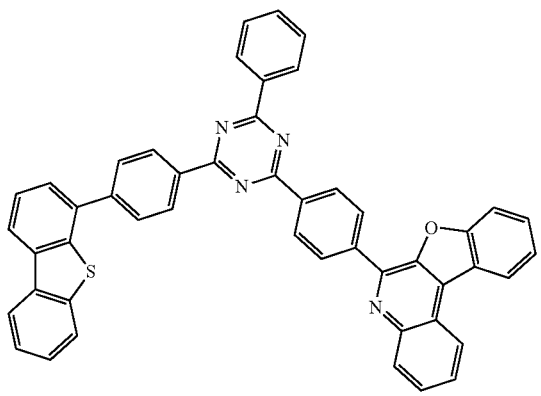
560
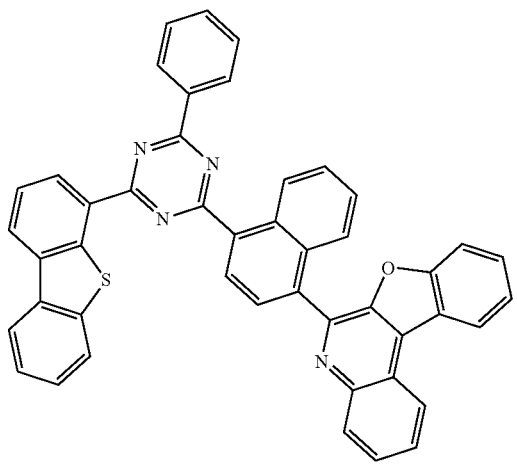

-continued
561
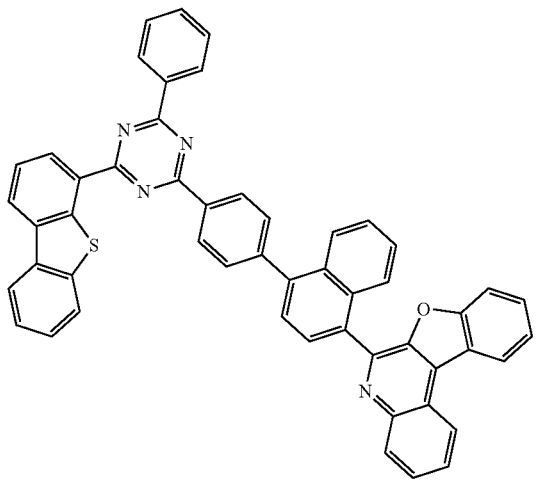
562
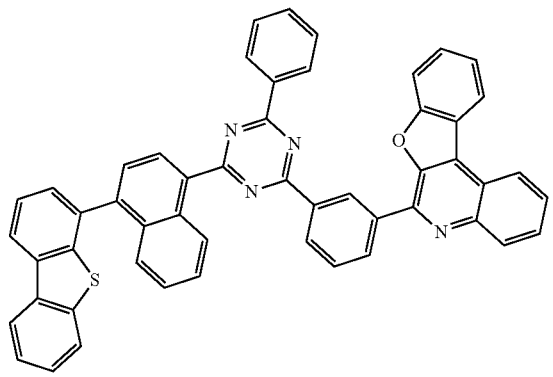
563
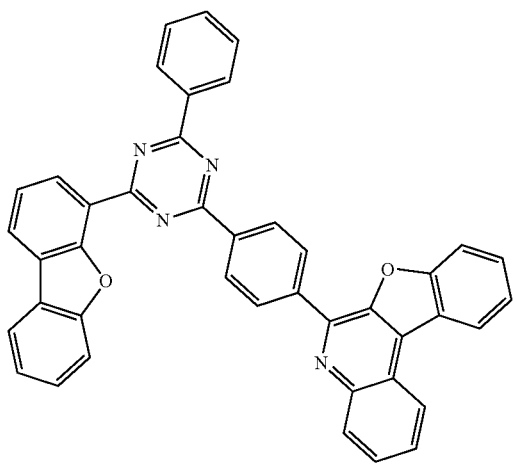
564
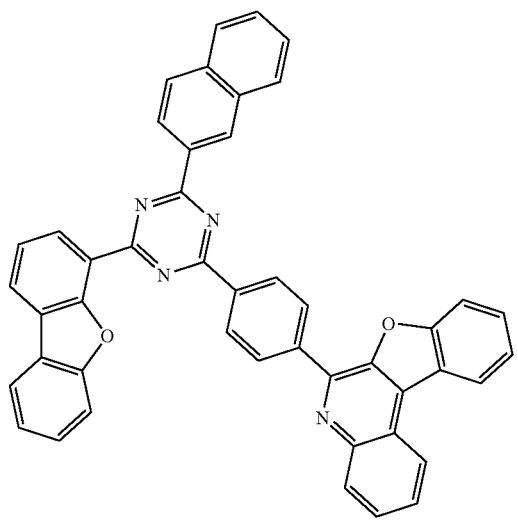
565
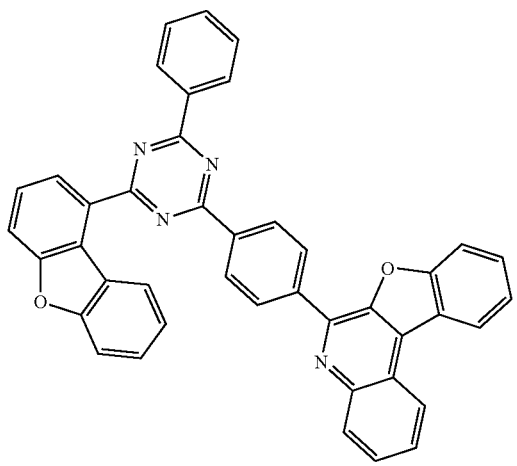
566
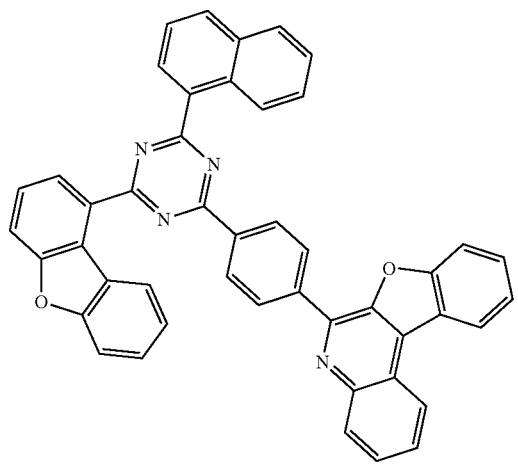

-continued
567
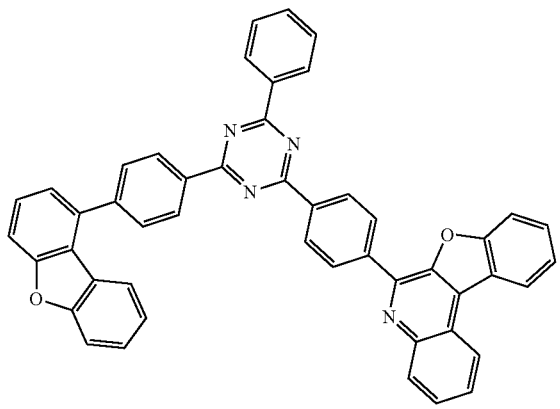
568
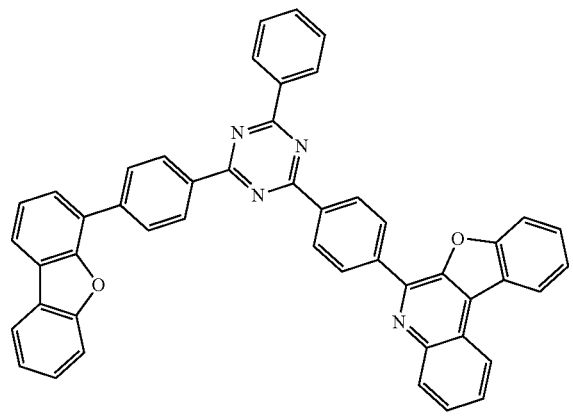
569
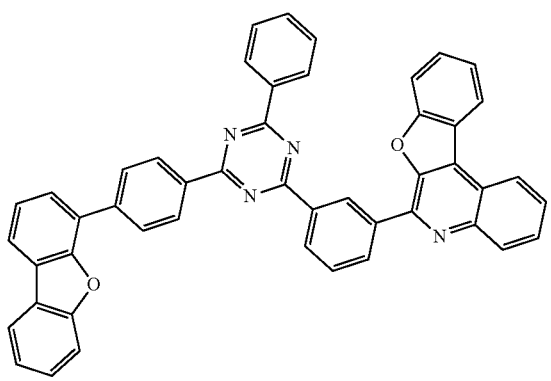
570
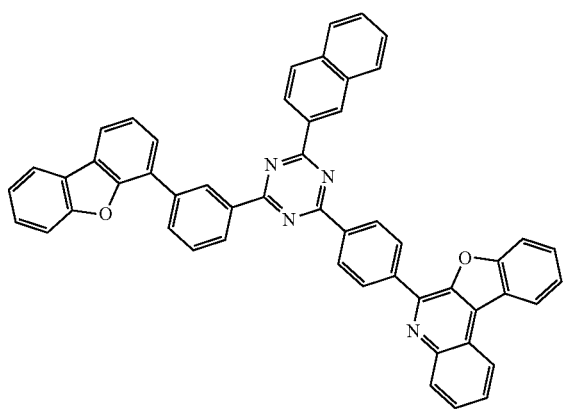
571
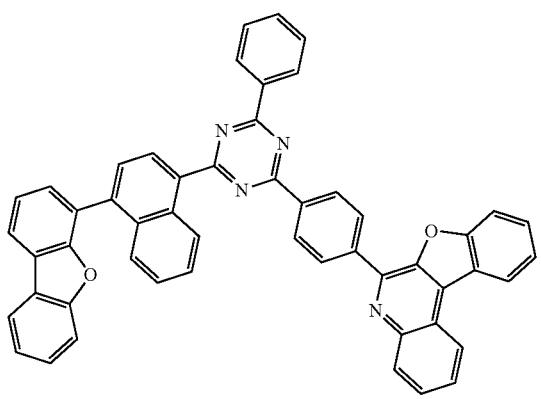
572
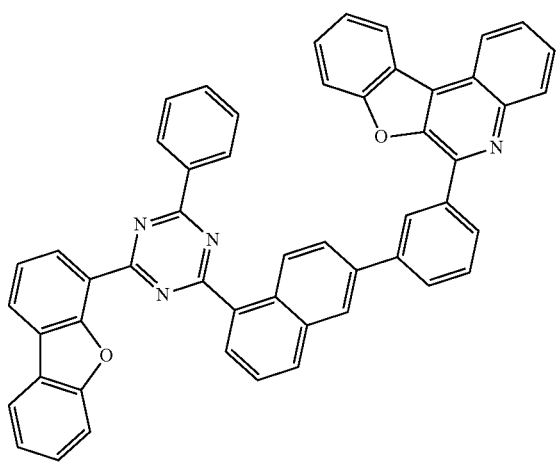

573
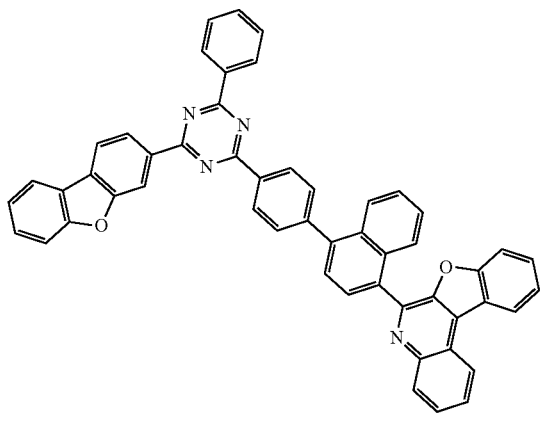
574
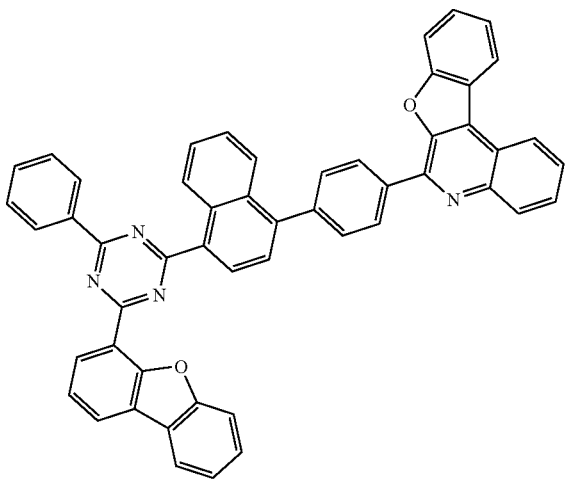
575
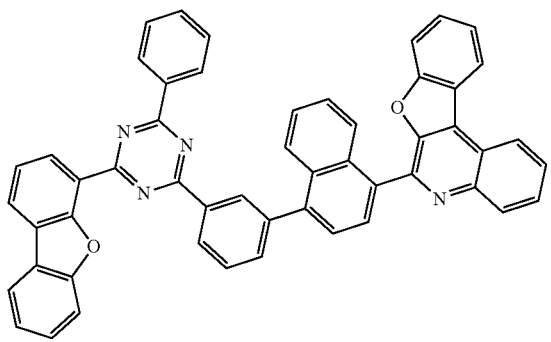
576
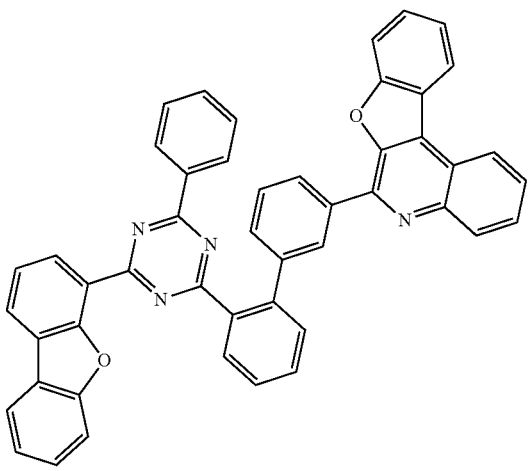
577
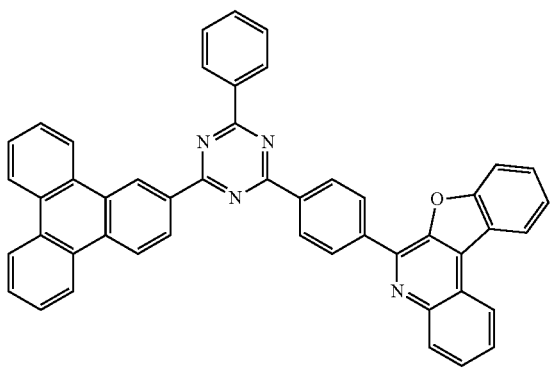
578
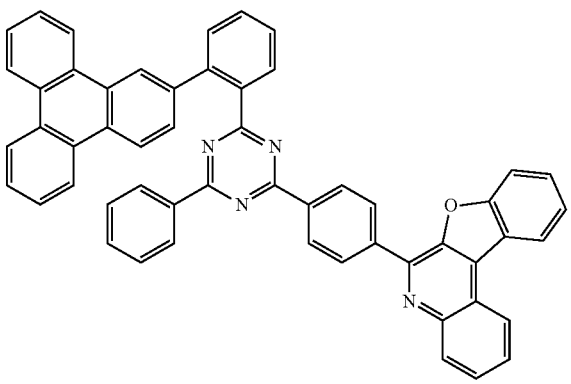

-continued
579
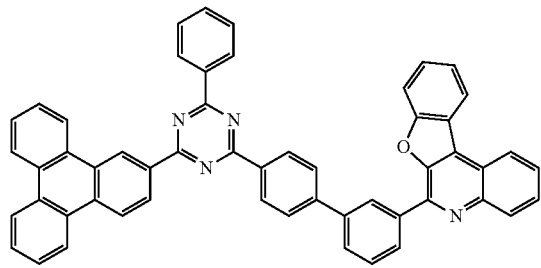
580
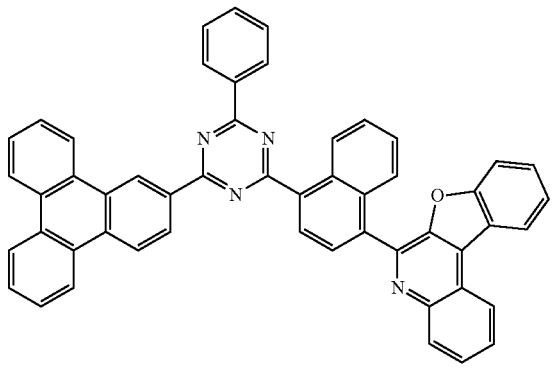
581
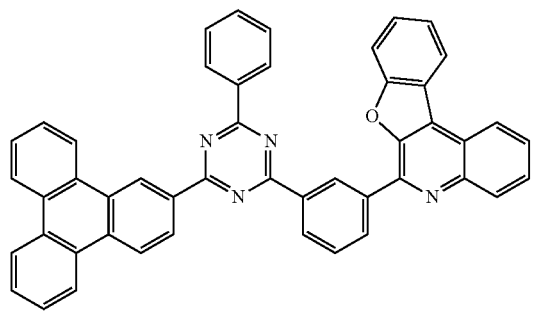
582
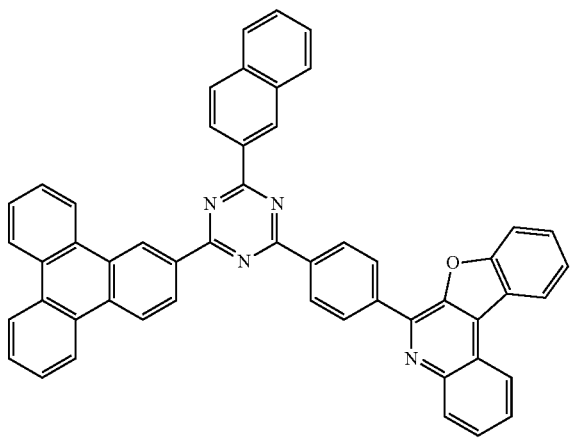
583
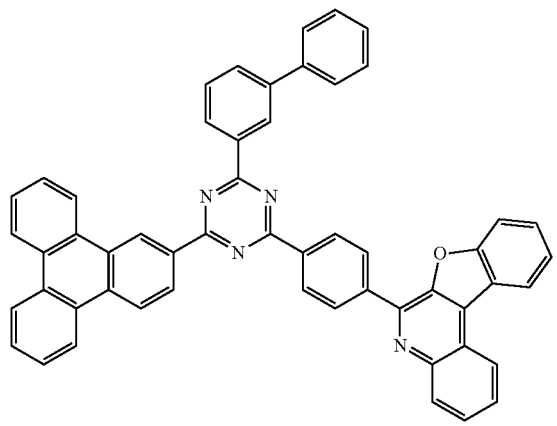
584
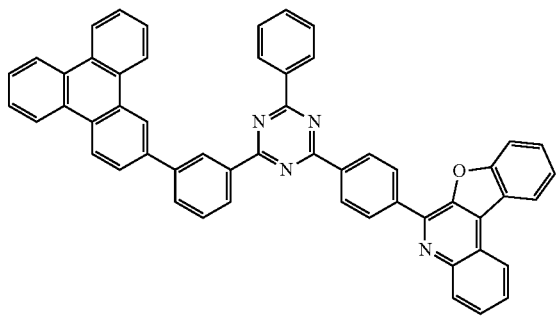

-continued
585
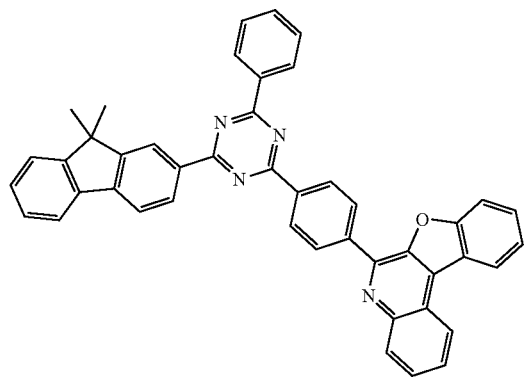
586
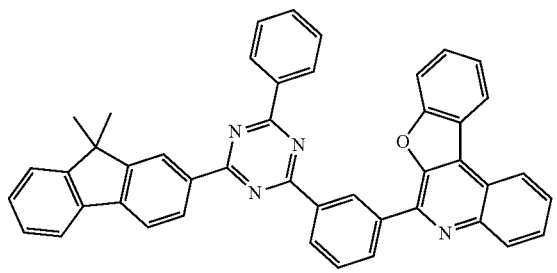
587
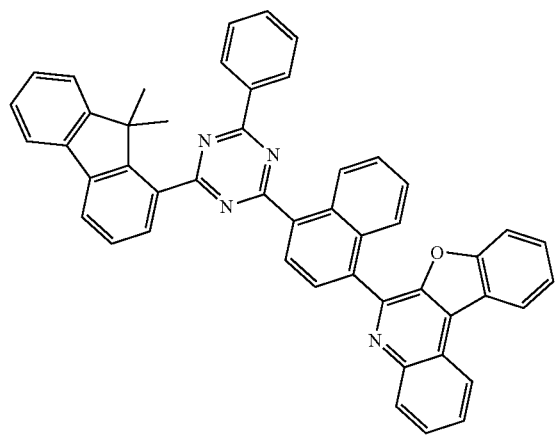
588
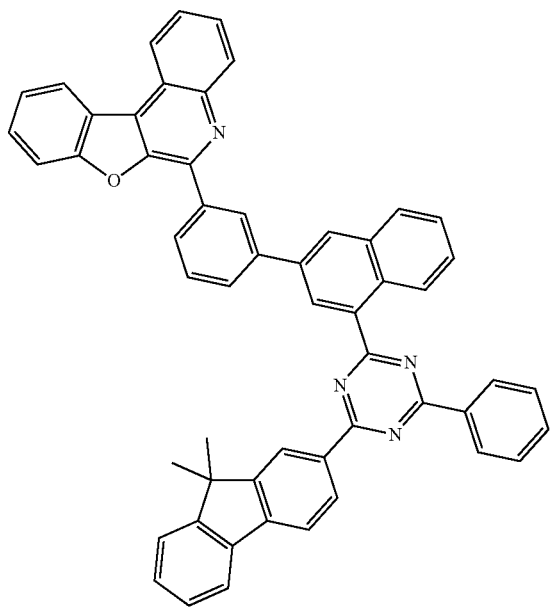
589
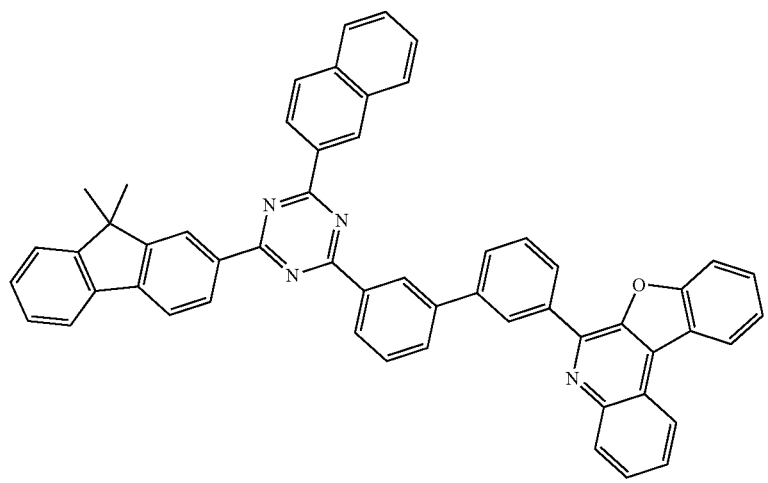

590
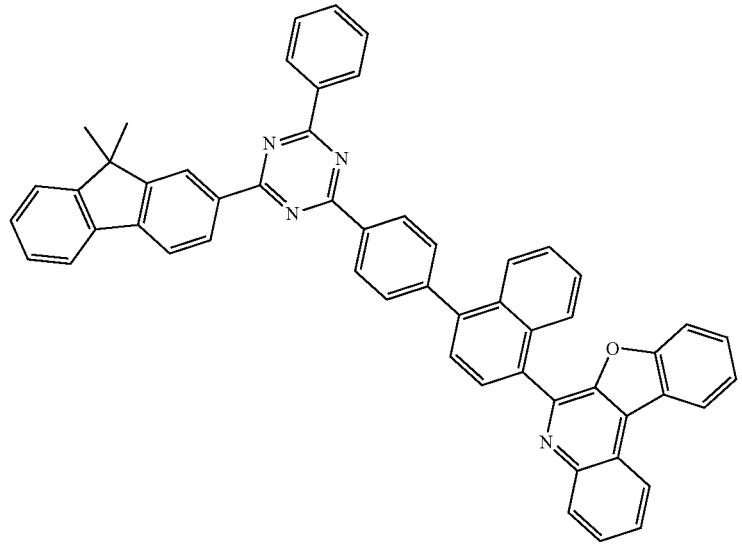
591
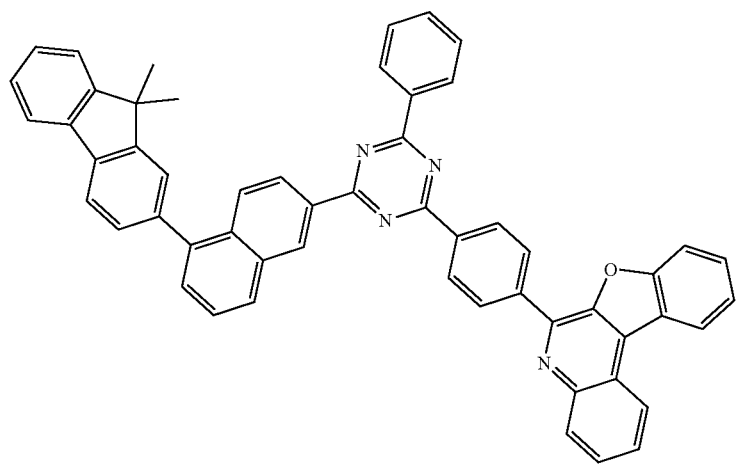
592
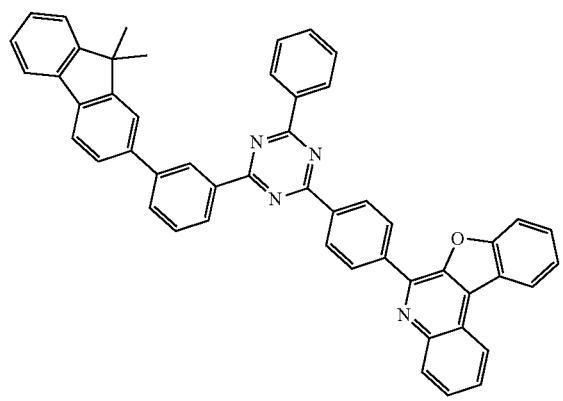
593
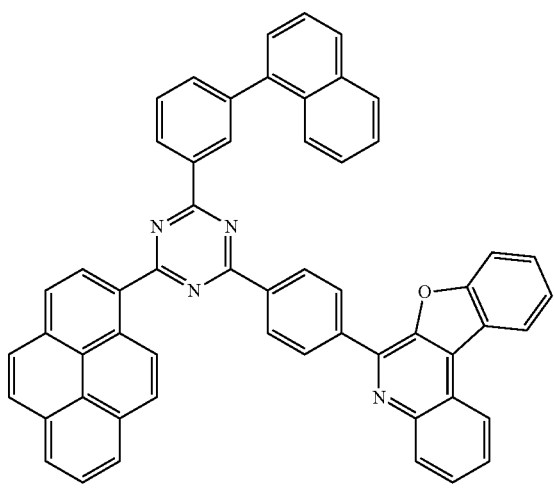

-continued
594
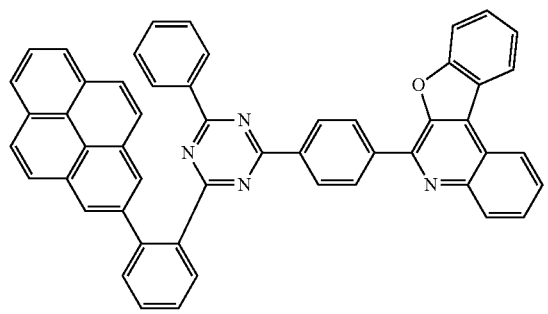
595
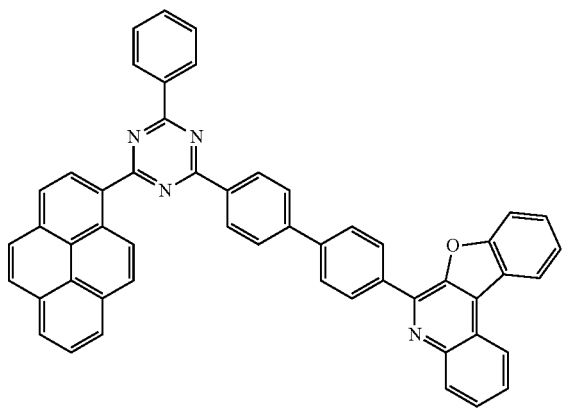
596
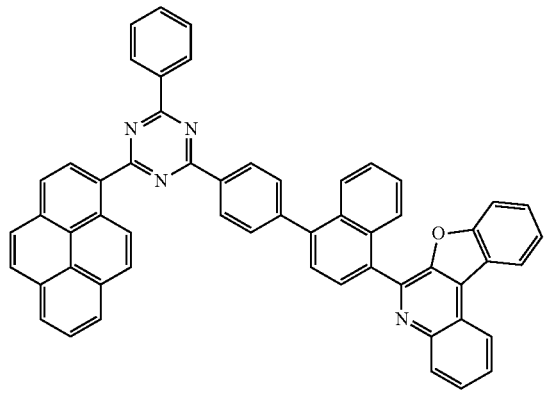
597
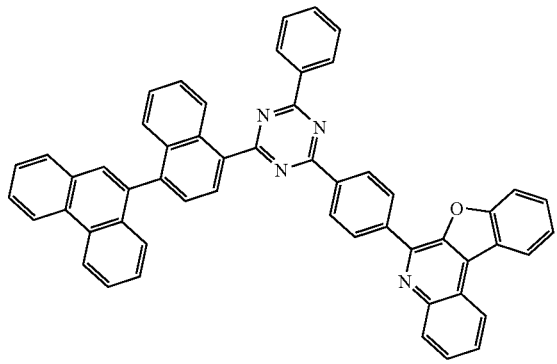
598
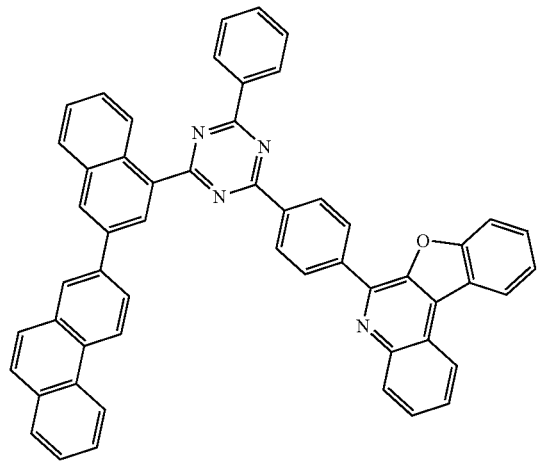
599
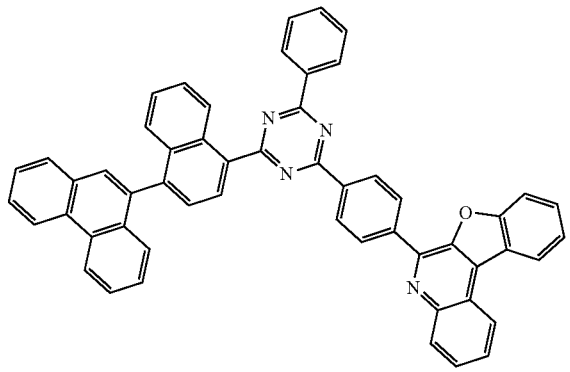

-continued
600
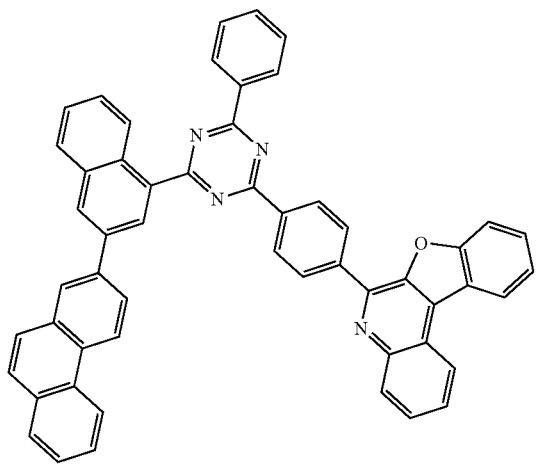
601
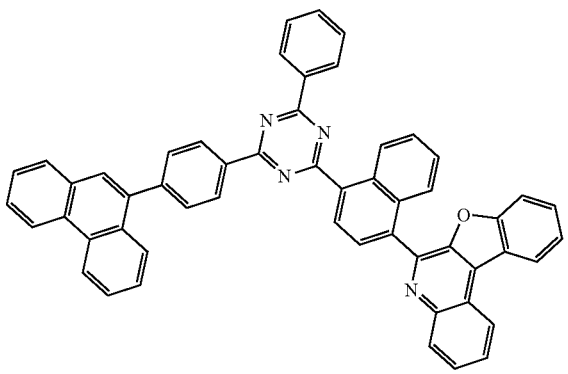
602
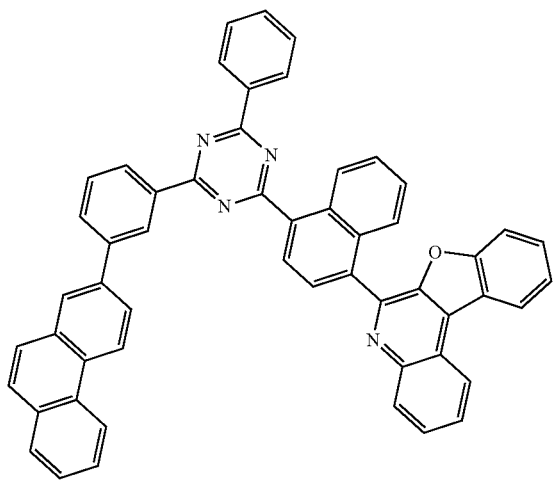
603
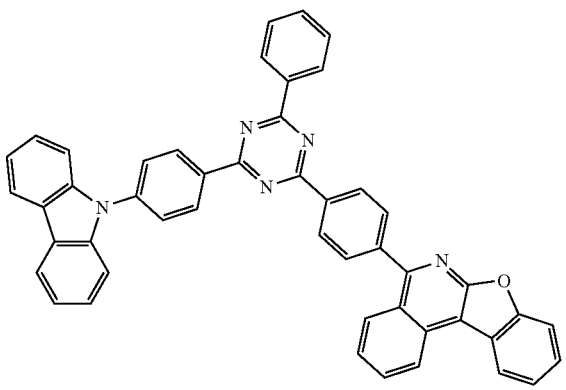
604
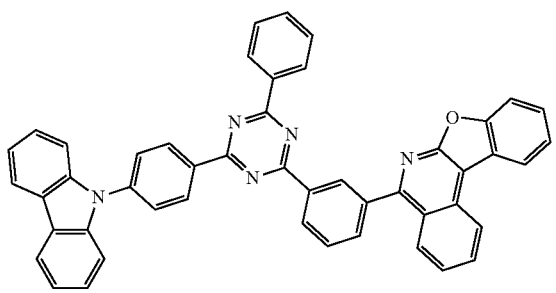
605
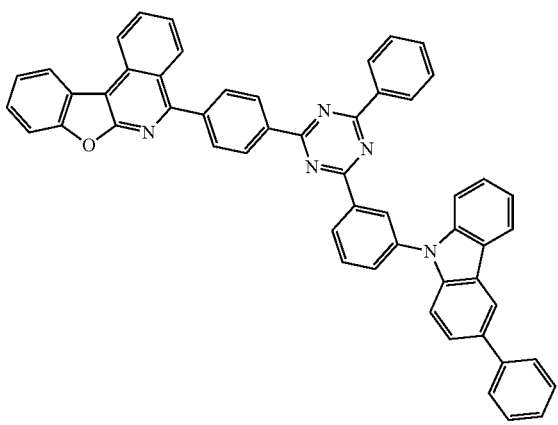

-continued
606
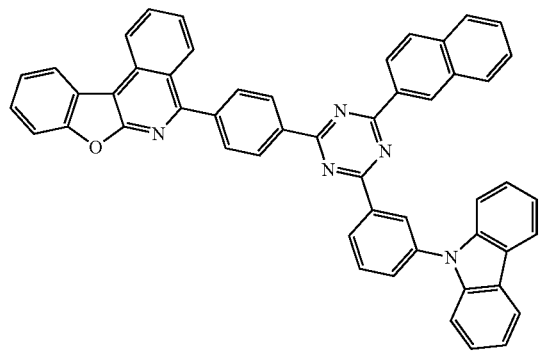
607
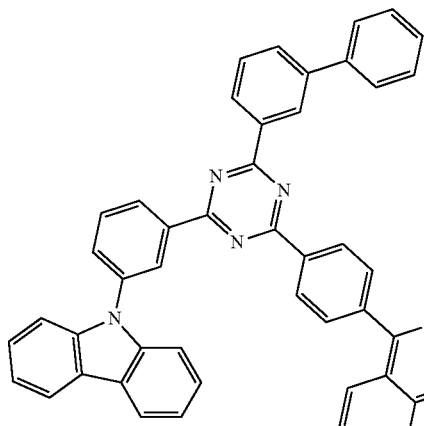
608
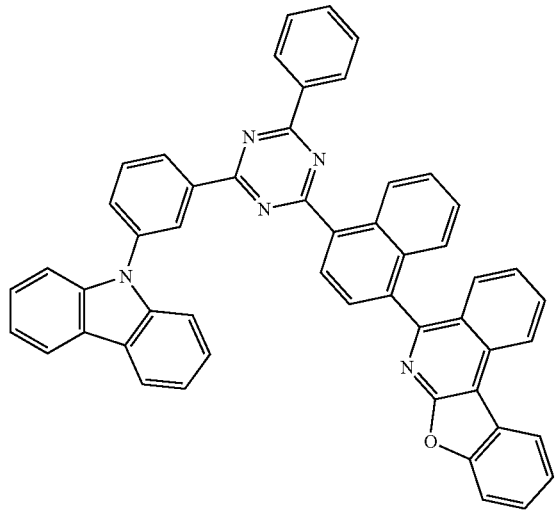
609
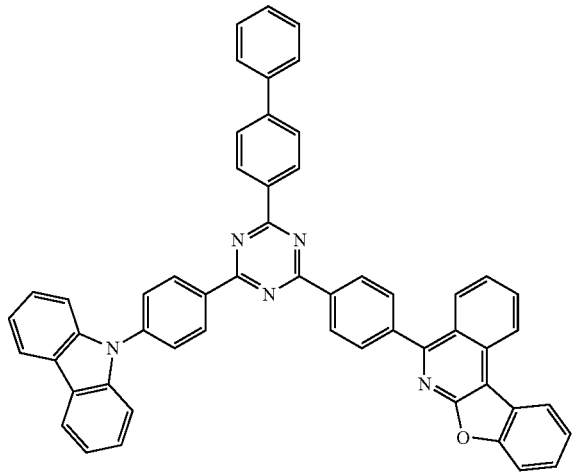
610
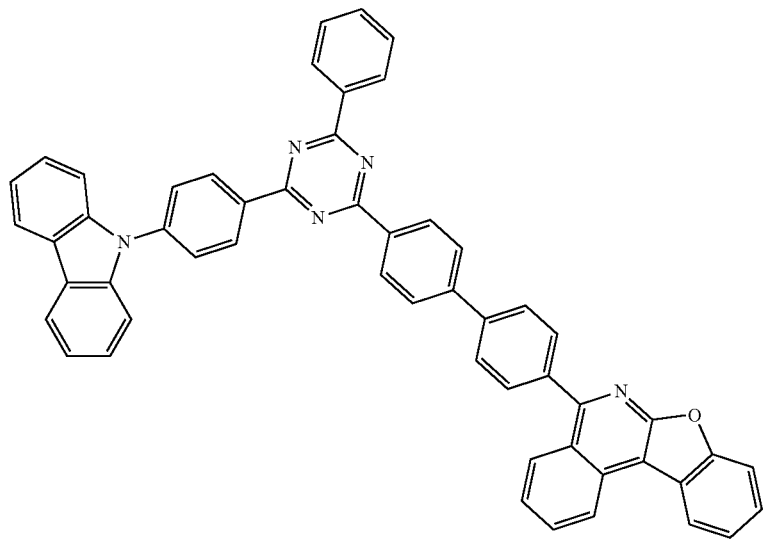

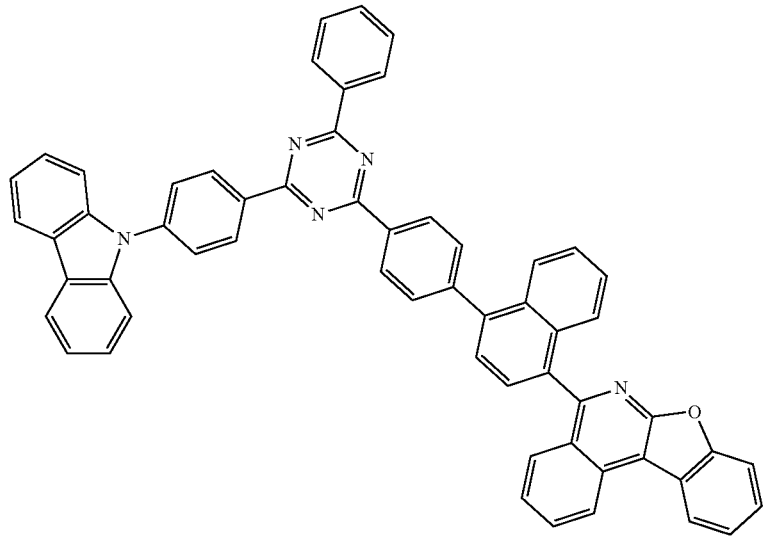
611
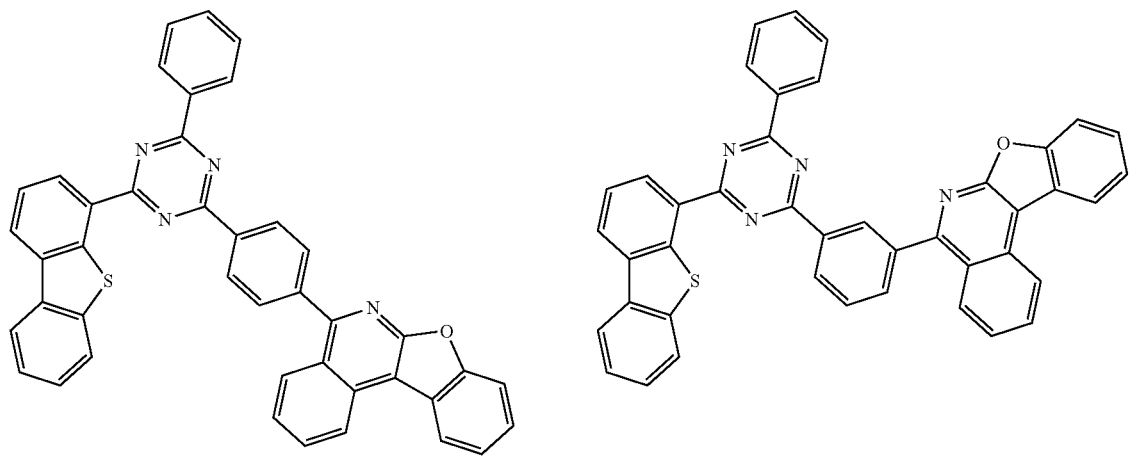
612
613
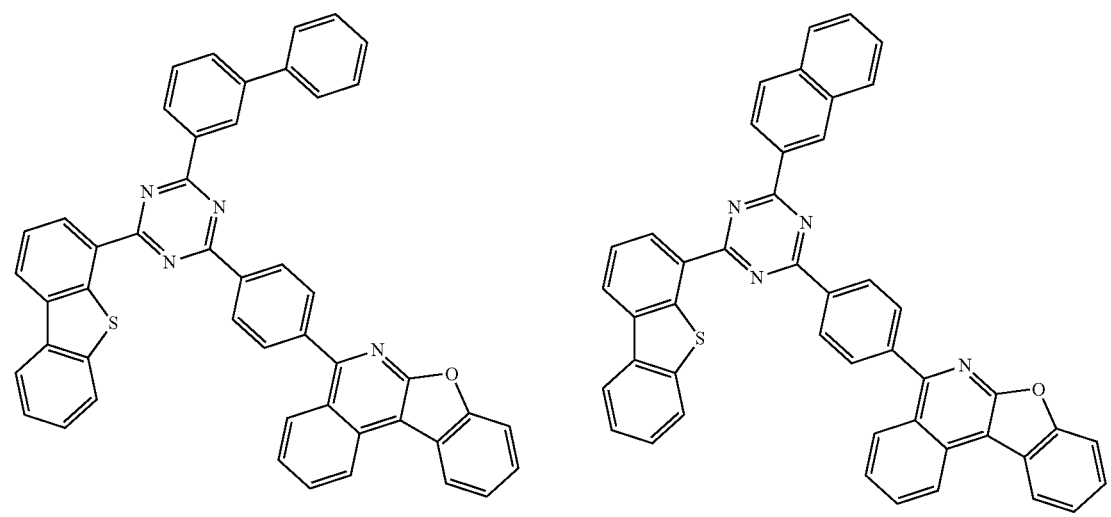
615

-continued
616
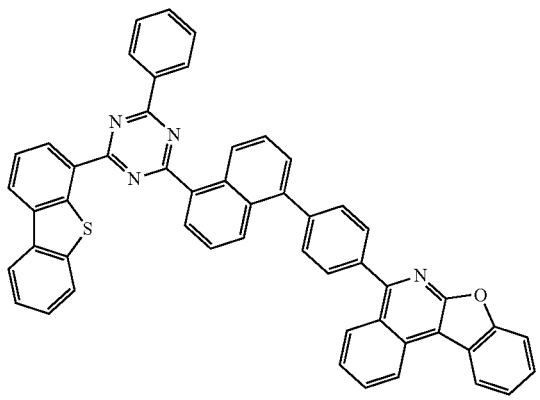
617
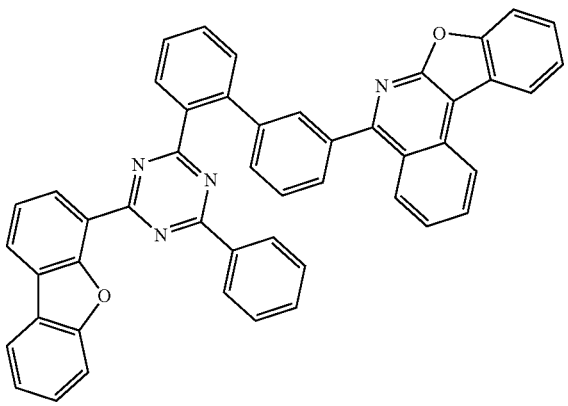
618
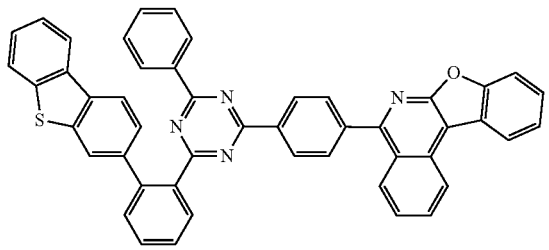
619
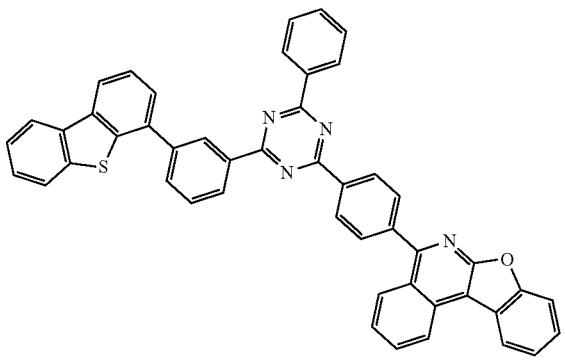
620
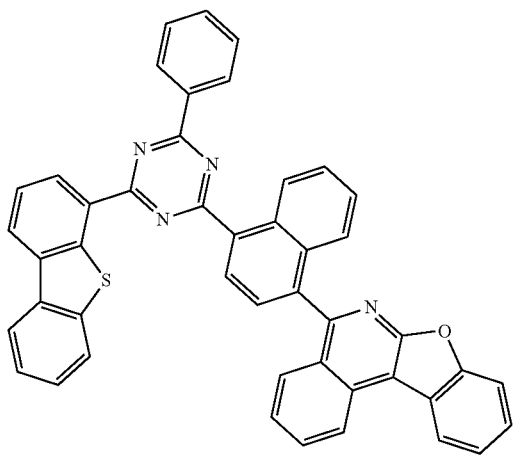
621
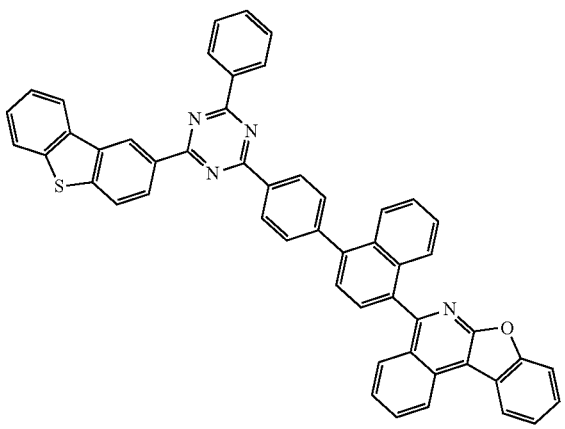

622
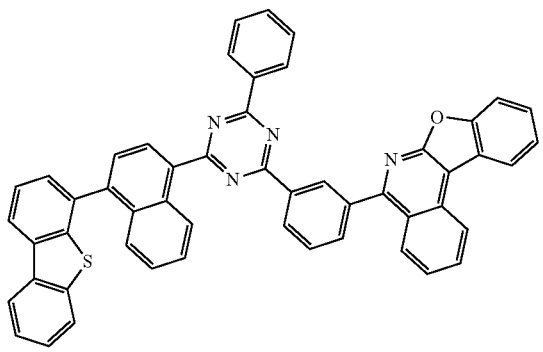
623
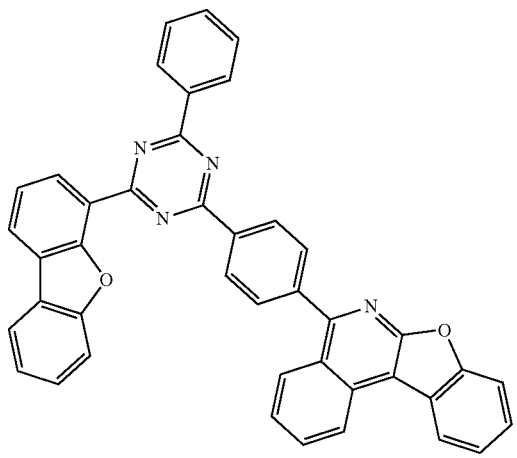
624
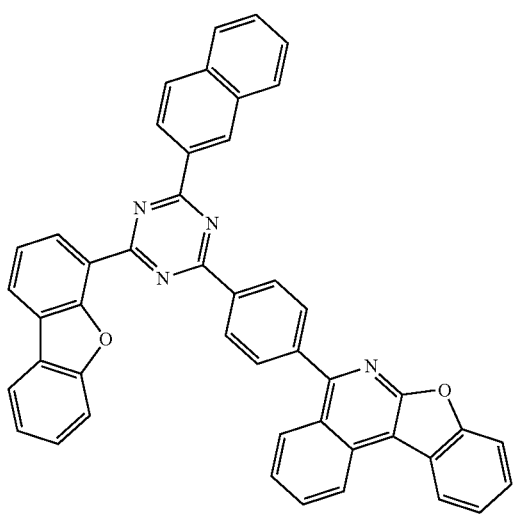
625
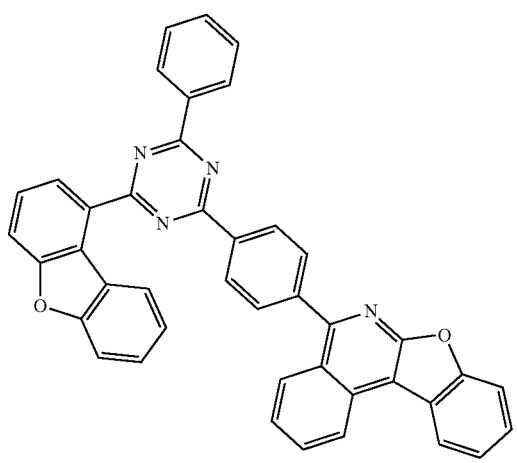
626
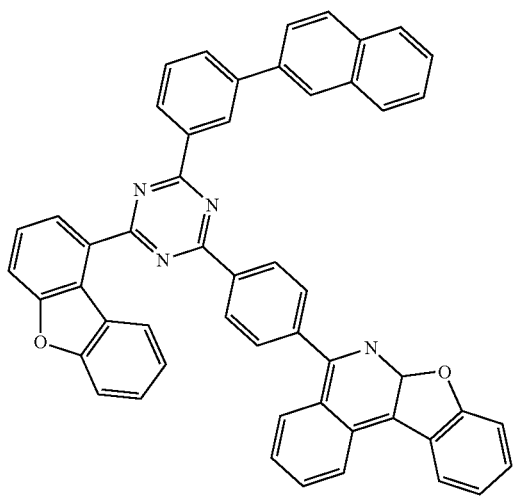
627
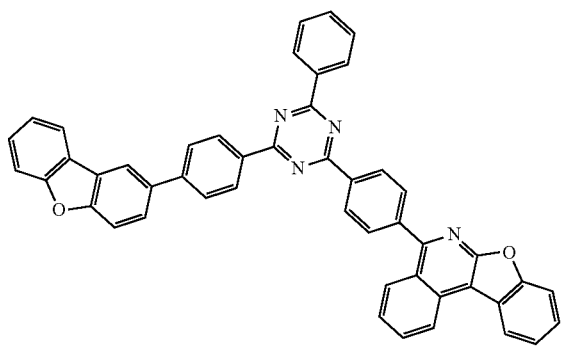

865 866
-continued
628
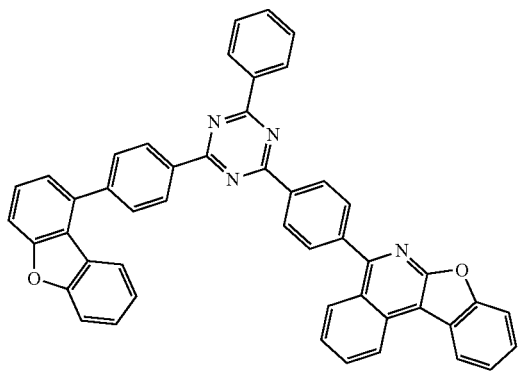
629
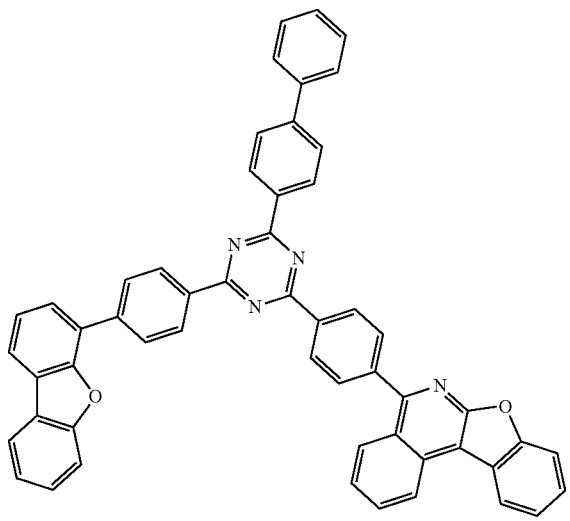
630
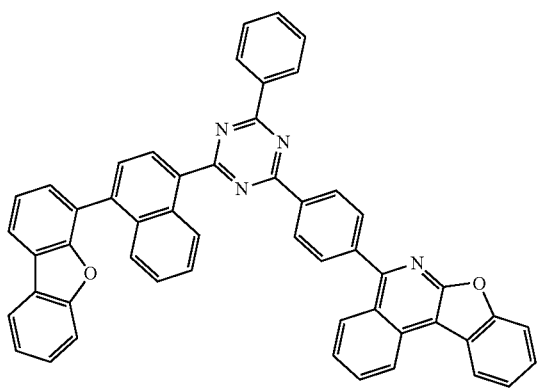
631
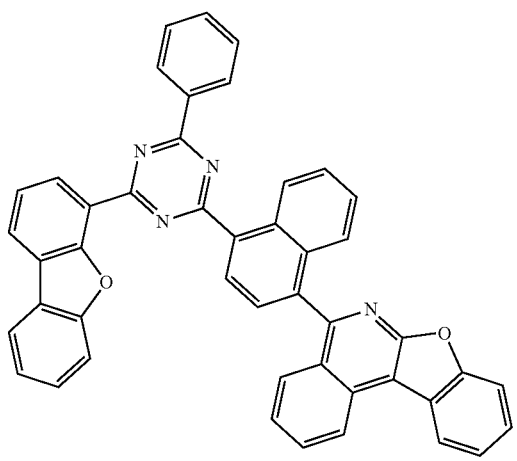
632
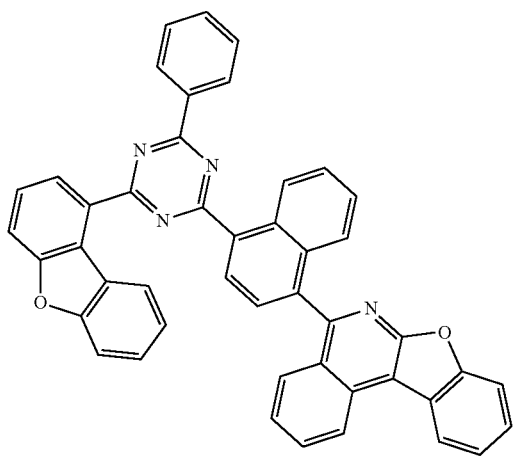
633
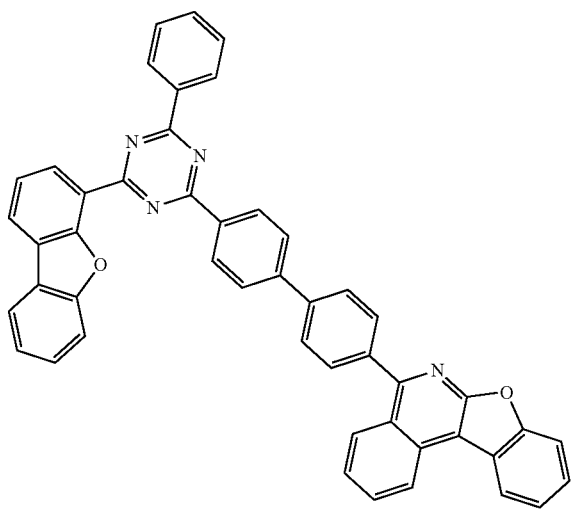

-continued
634
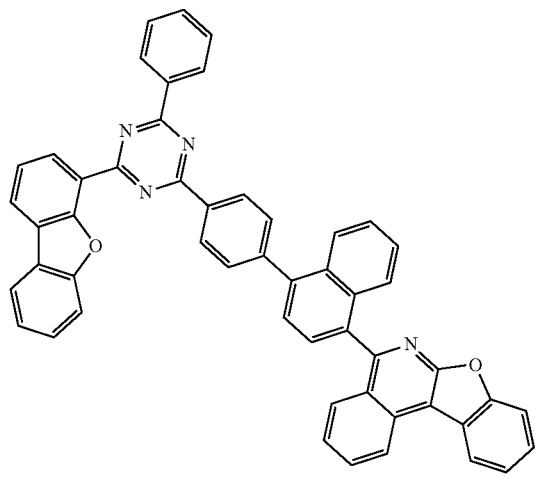
635
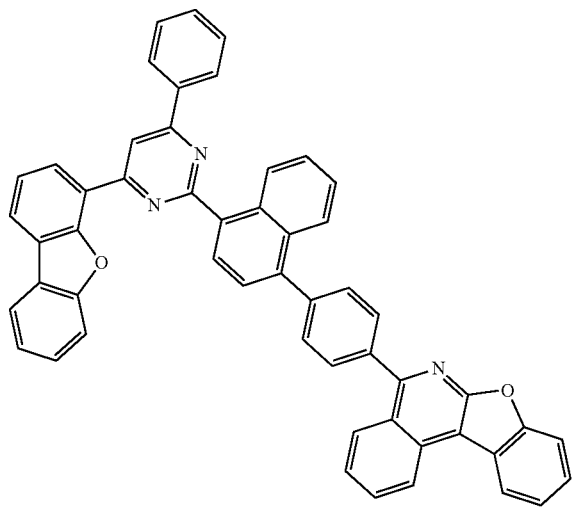
636
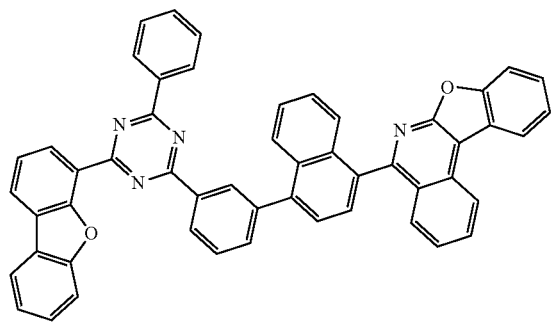
637
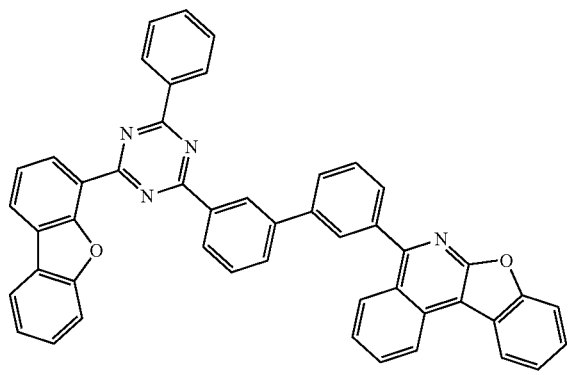
638
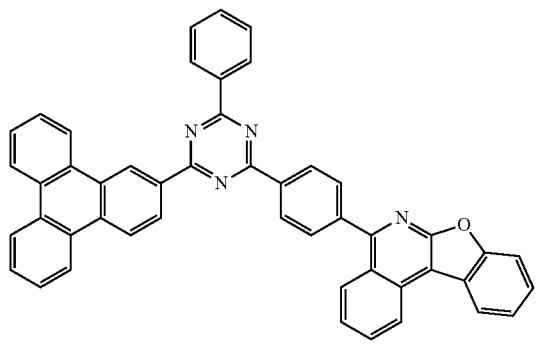
639
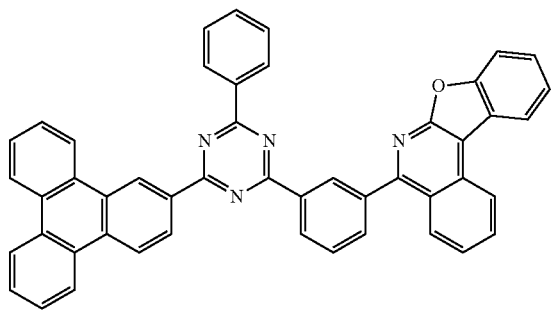

-continued
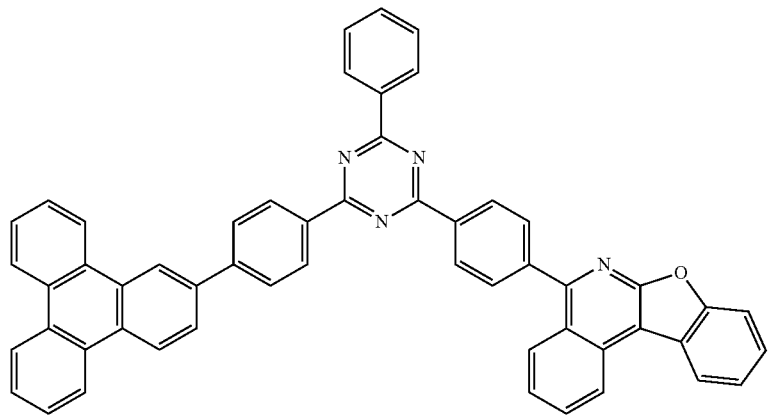
640
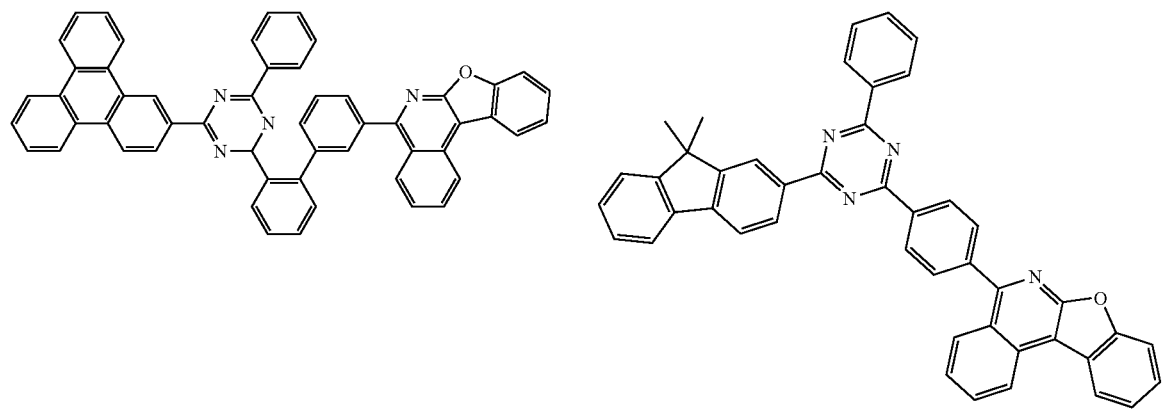
641 642
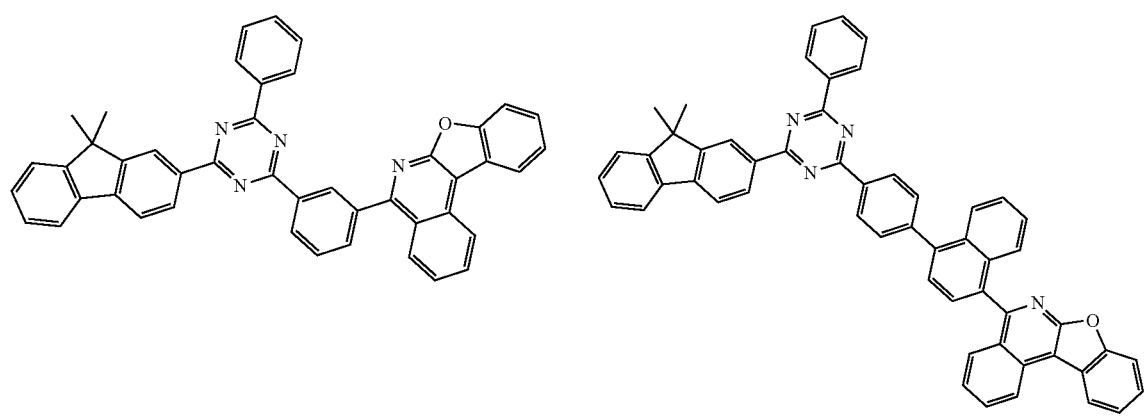
643 644

645
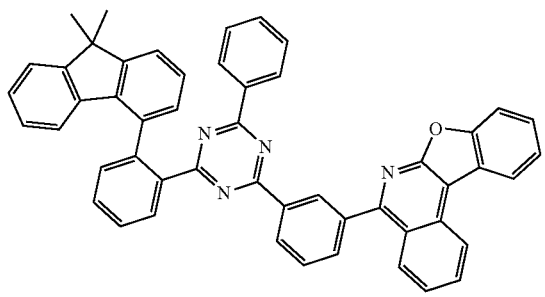
646
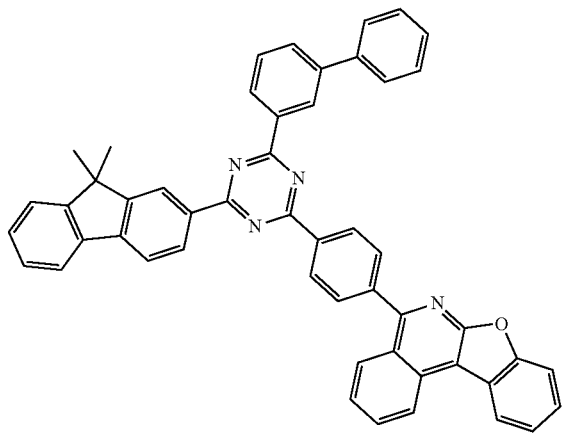
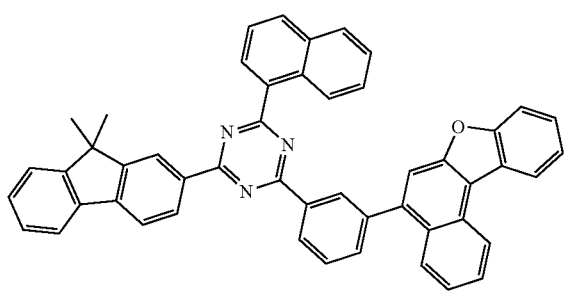
648
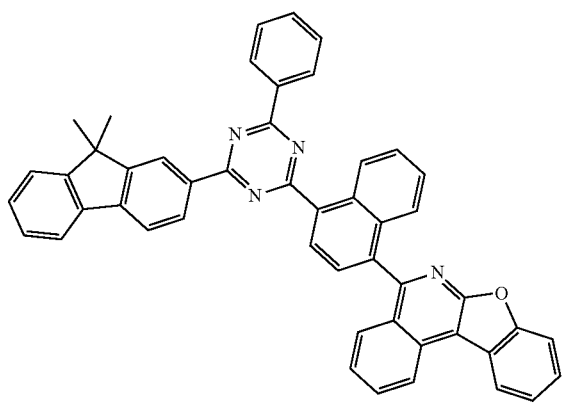
649
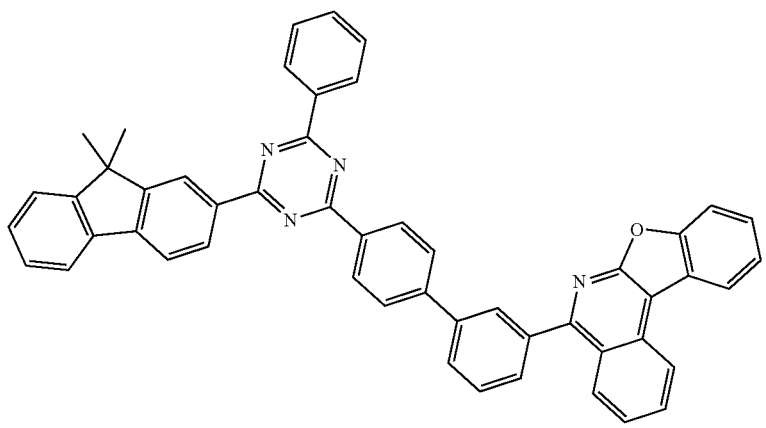

-continued
650
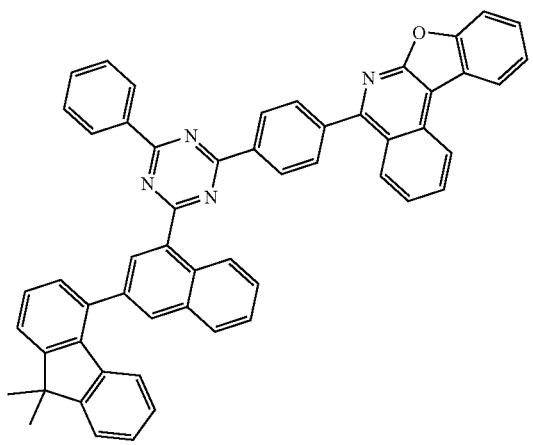
651
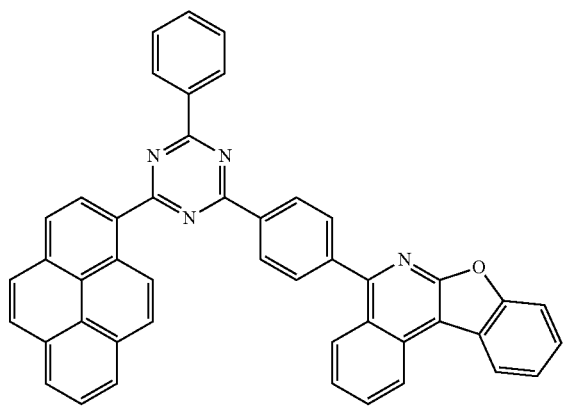
652
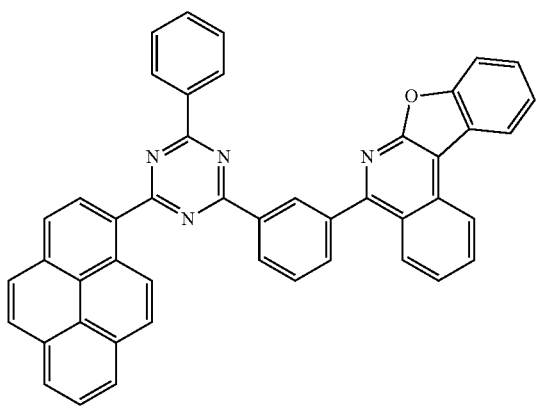
653
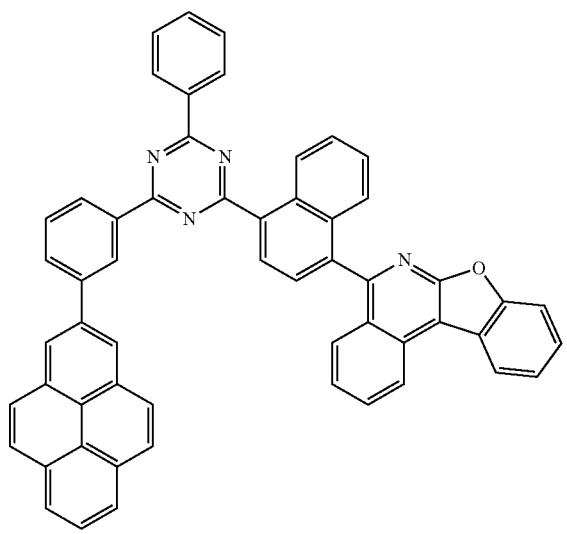
654
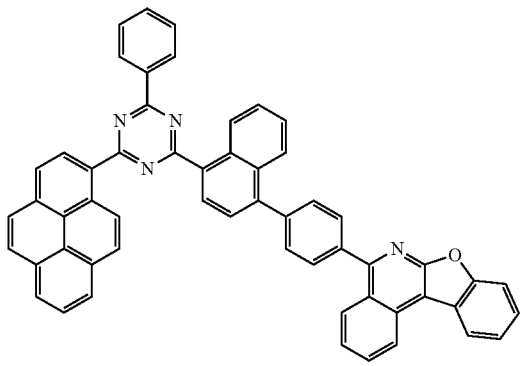
655
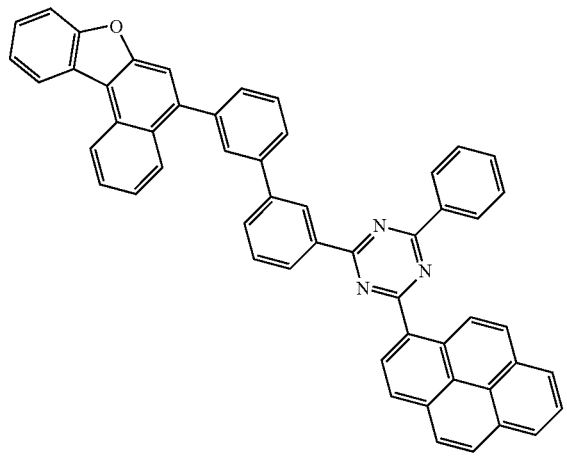

656
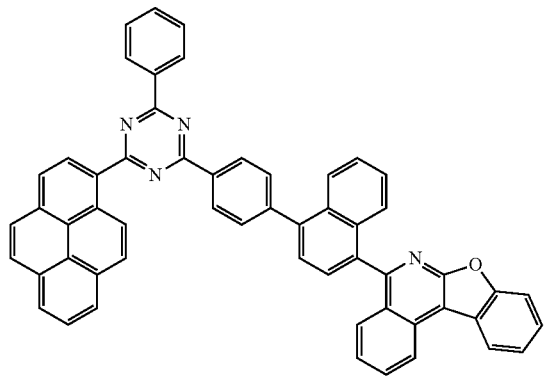
657
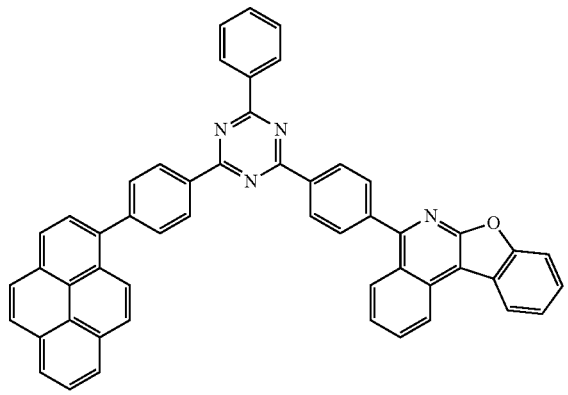
658
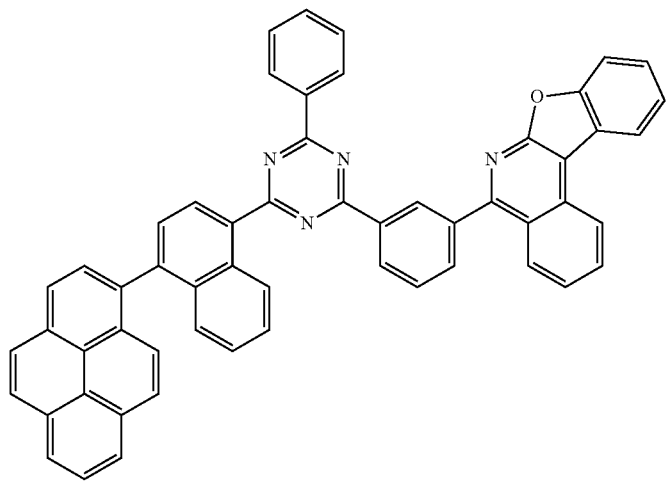
659
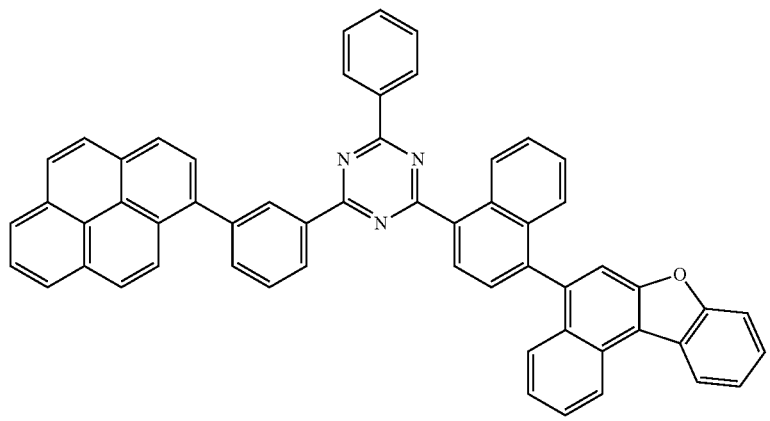

-continued
660
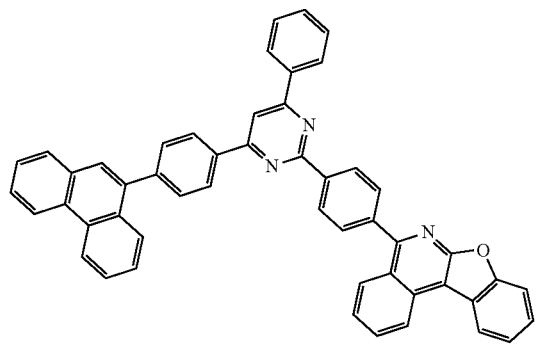
661
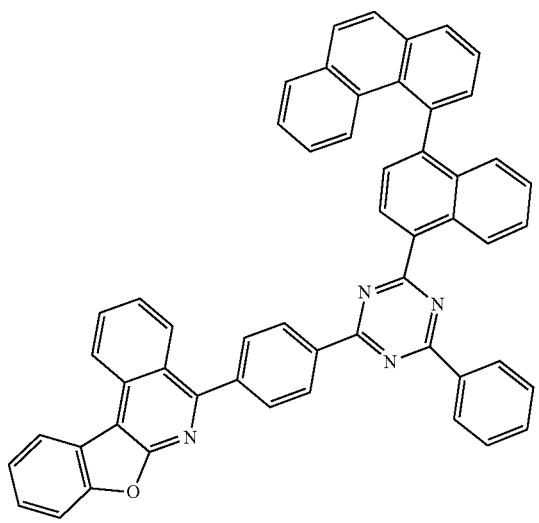
662
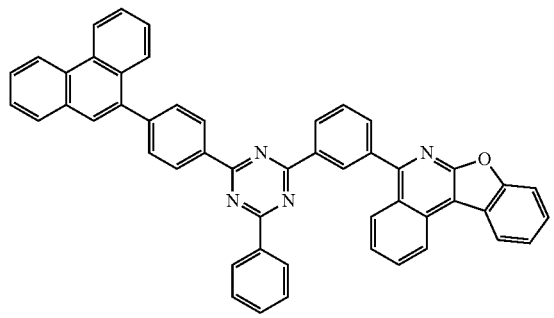
663
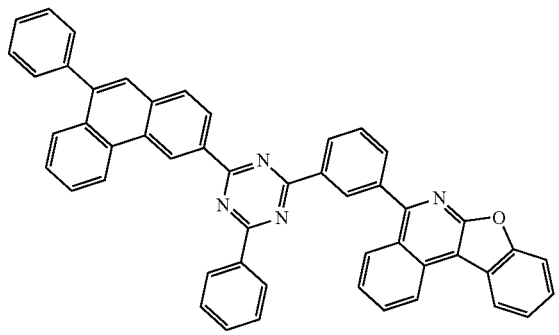
664
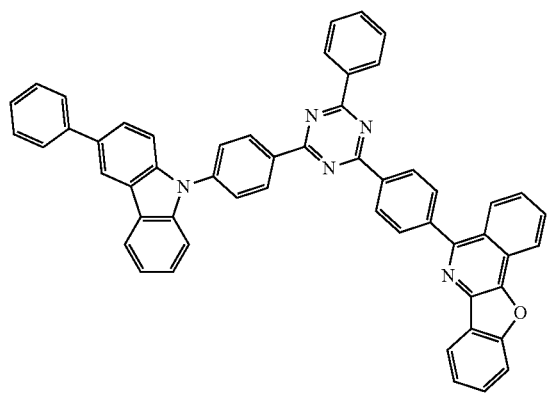
665
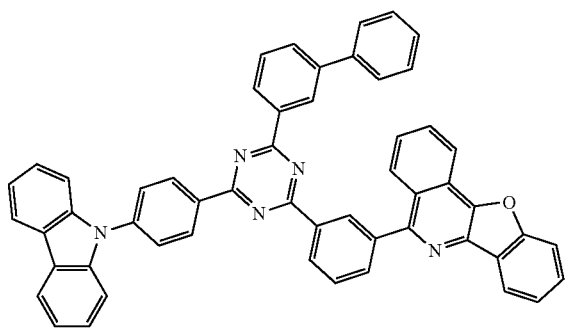

-continued
666
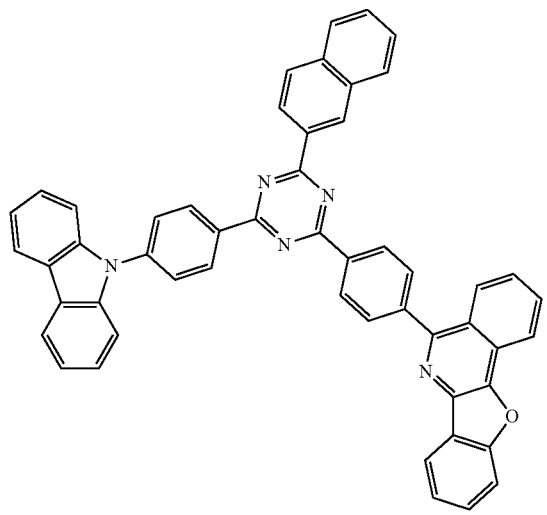
667
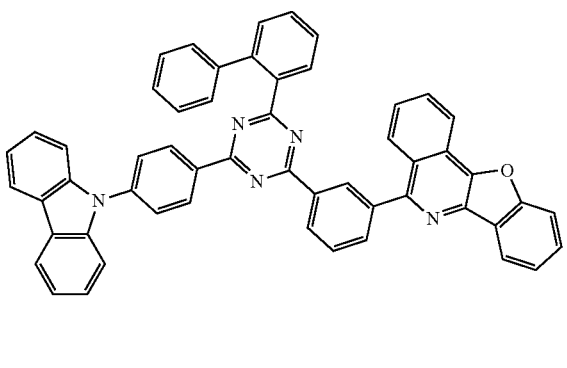
668
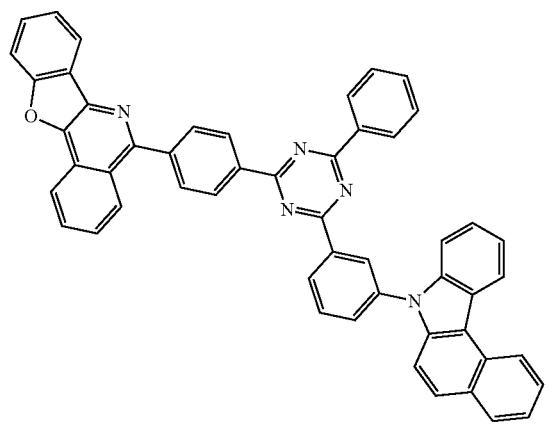
669
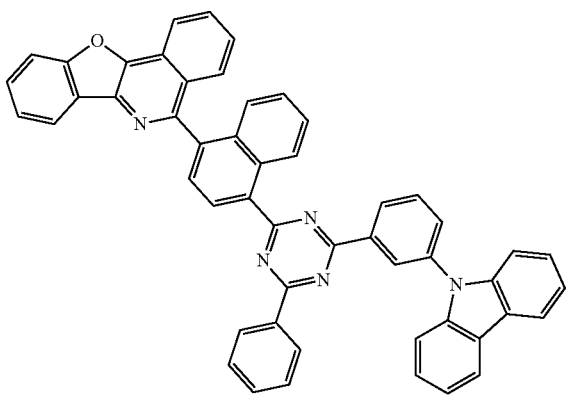
670
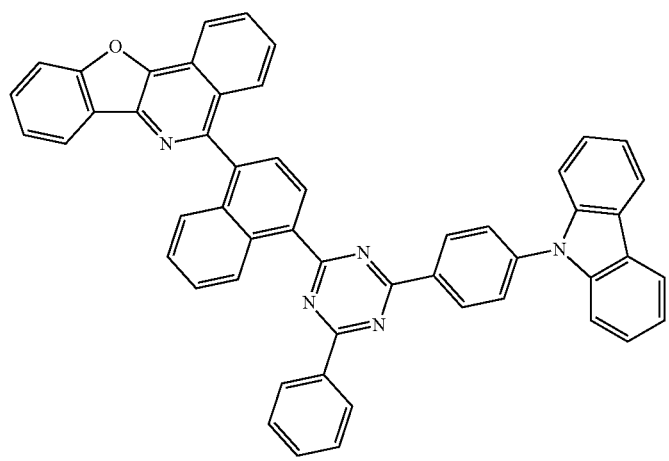

-continued
881
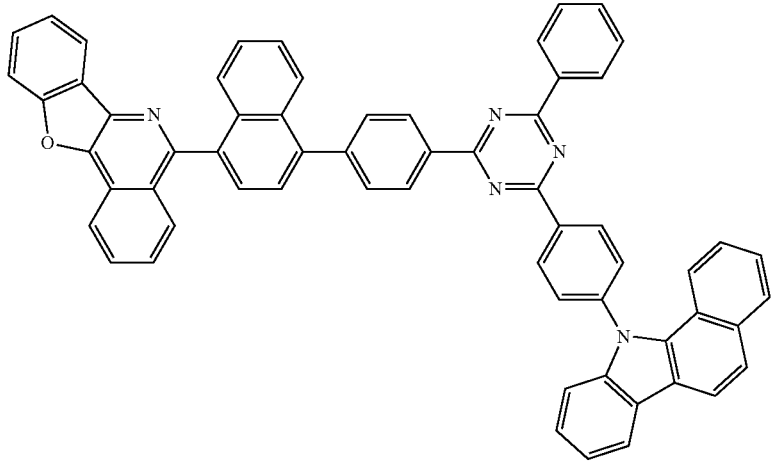
671
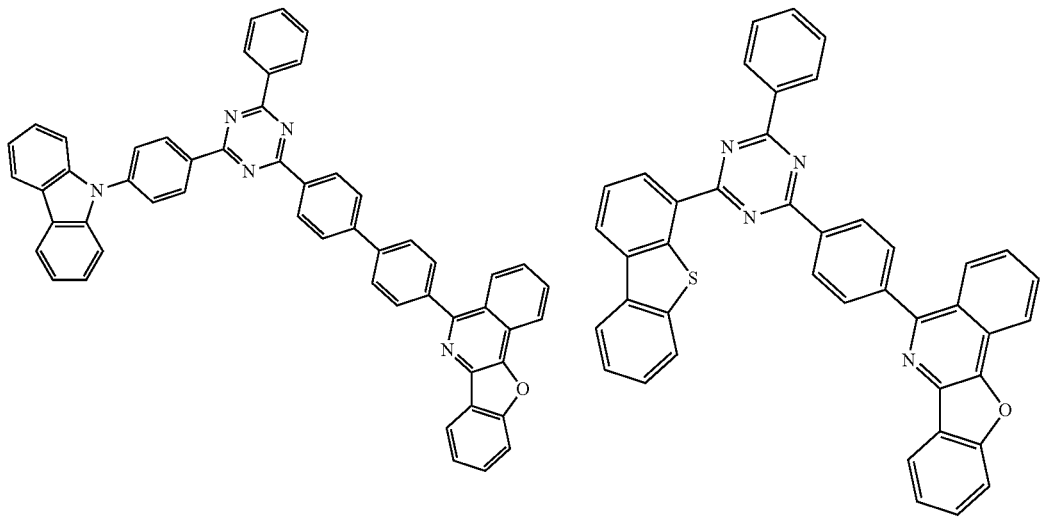
672
673
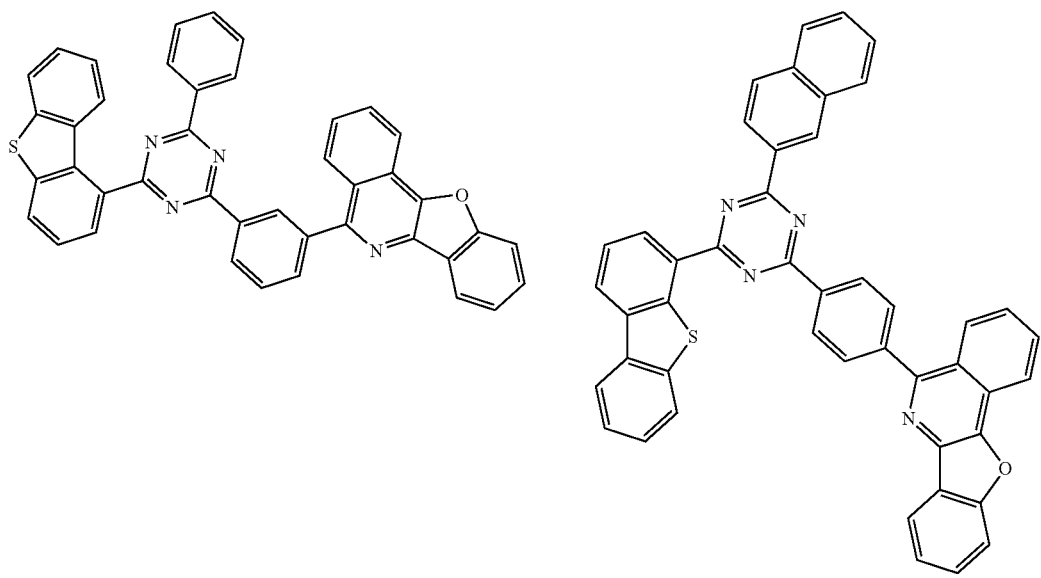
674
685

-continued
883
676
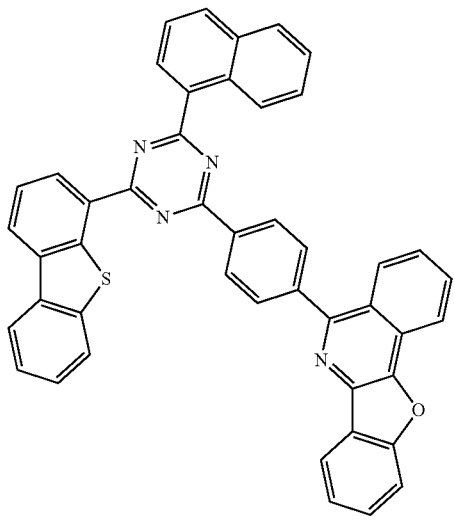
678
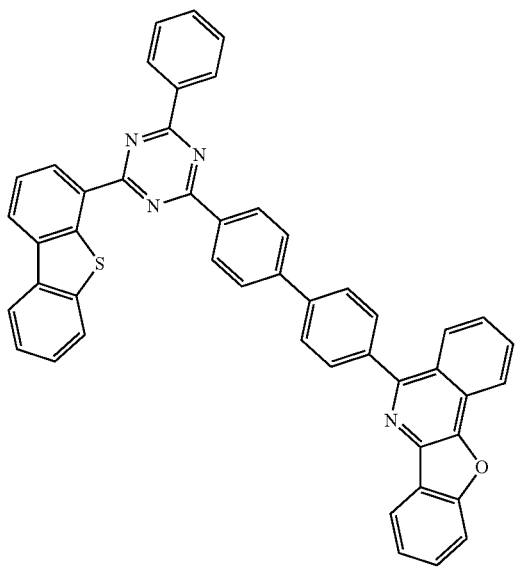
680
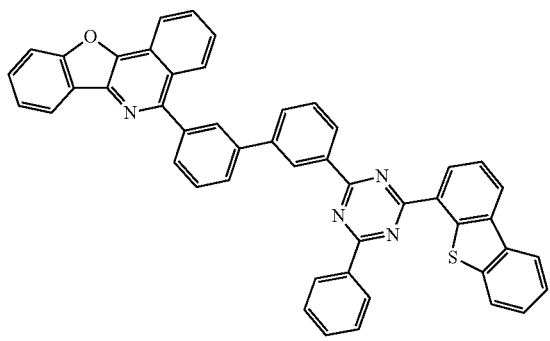
884
677
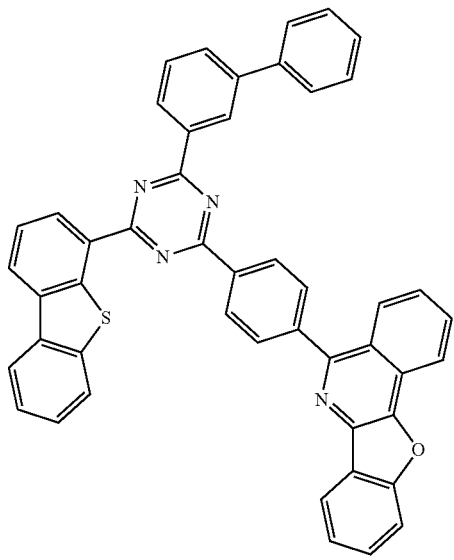
679
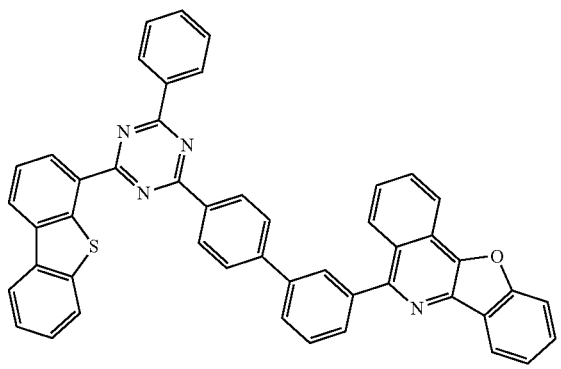
681
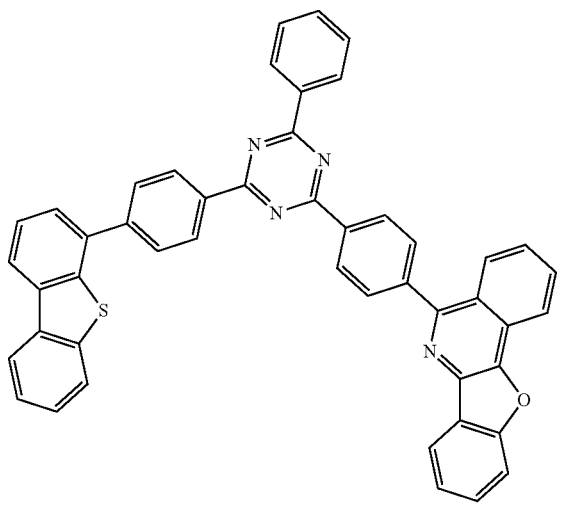

885
886
-continued
682
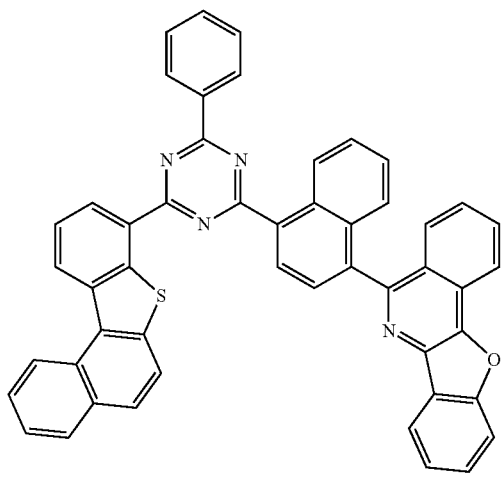
683
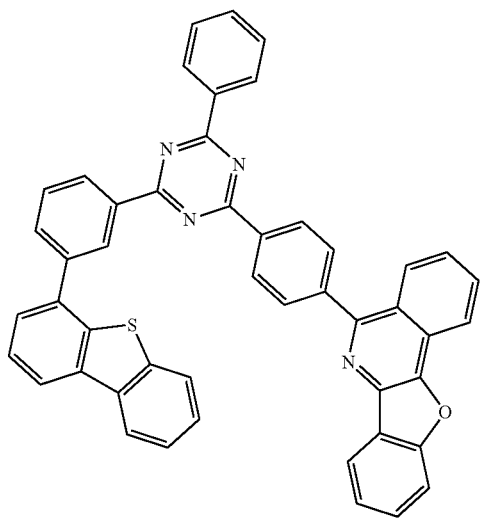
684
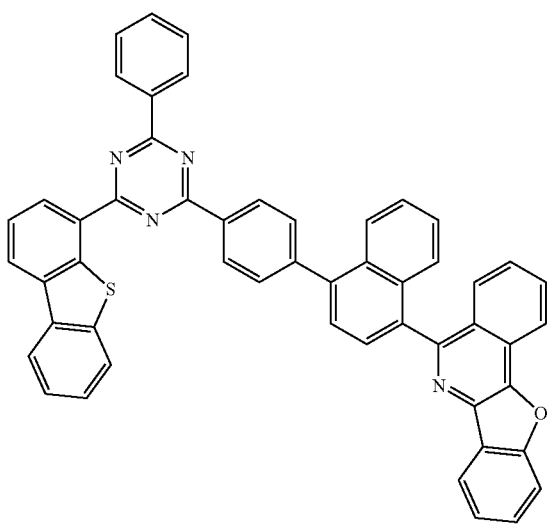
685
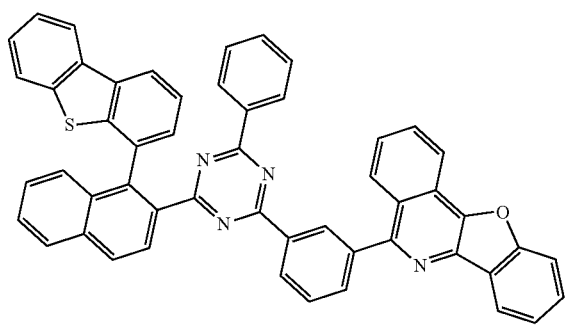
686
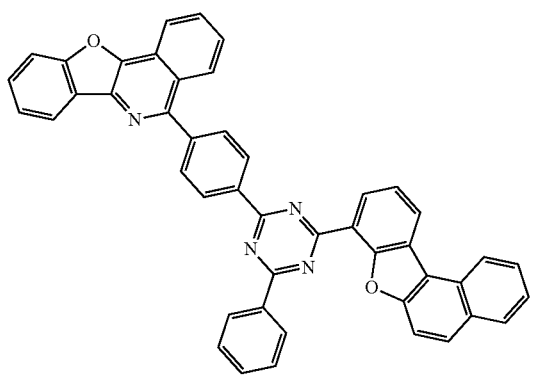
687
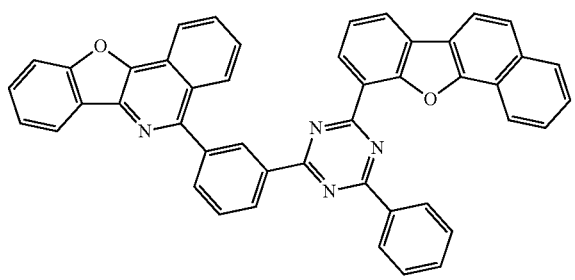

-continued
688
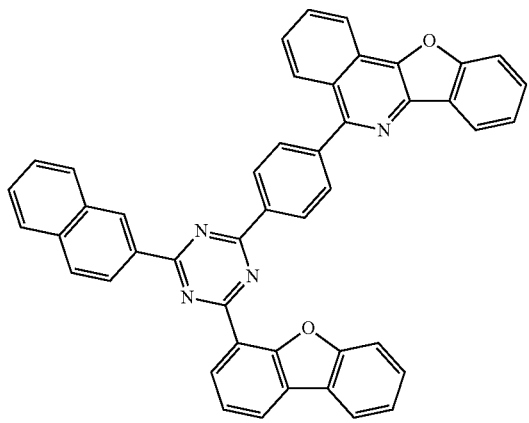
689
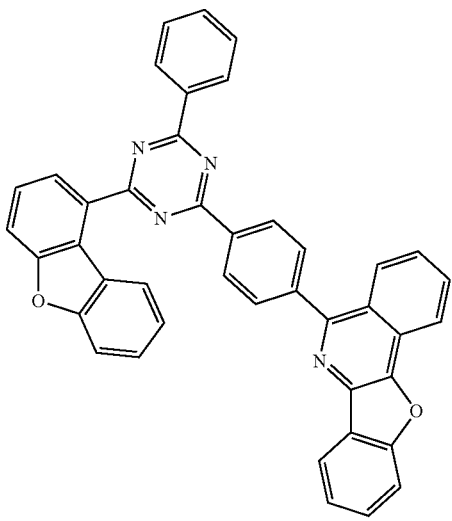
690
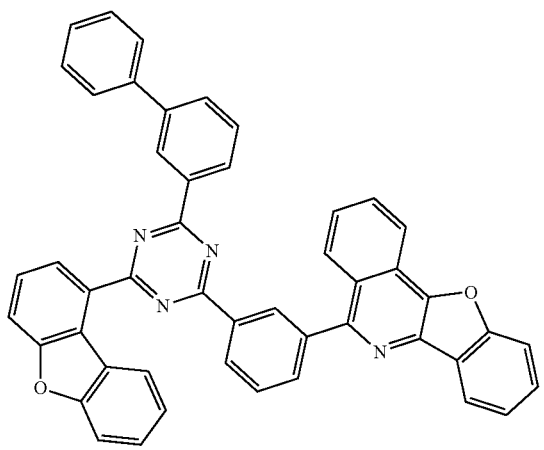
691
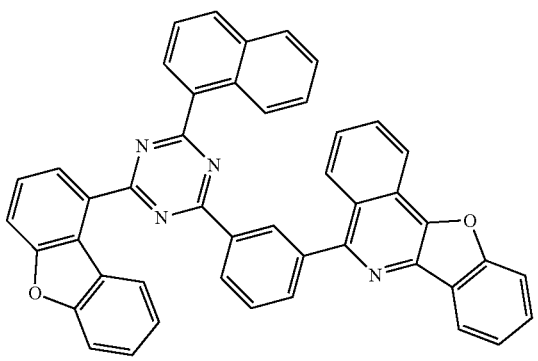
692
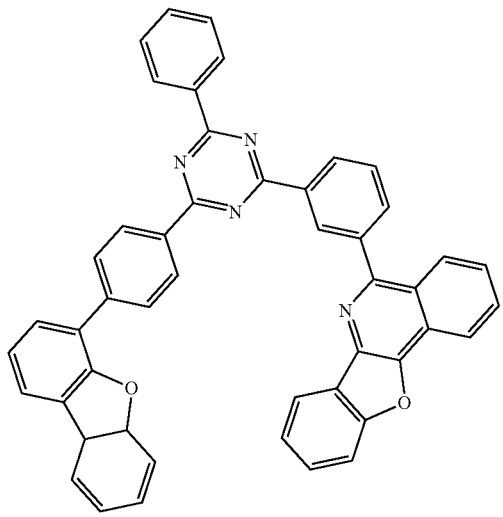
693
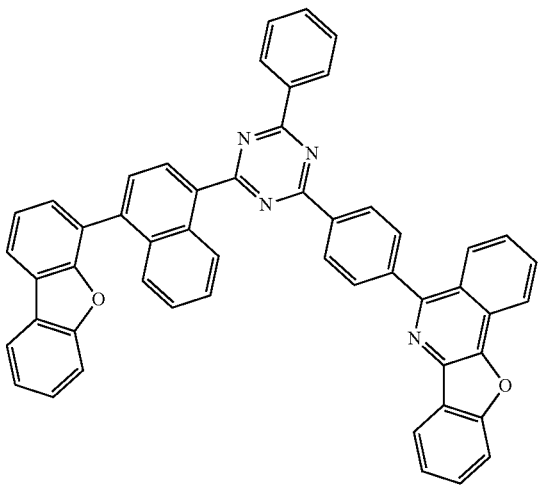

-continued
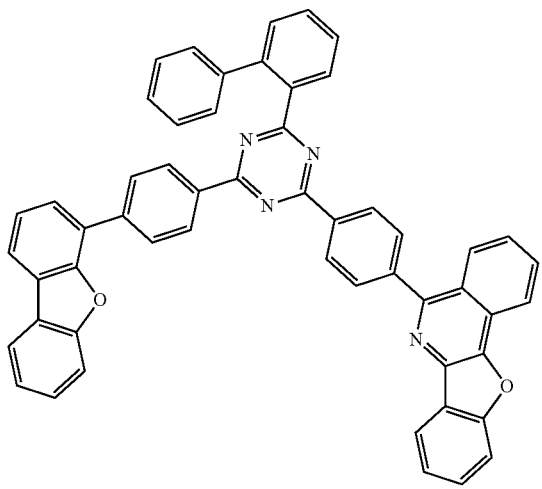
694
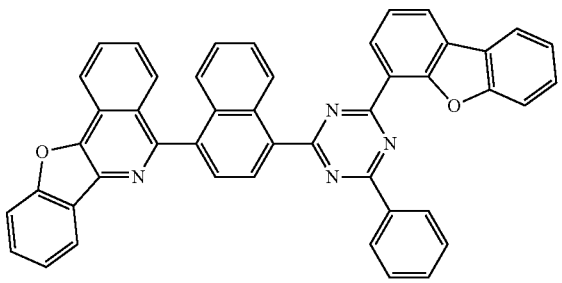
695
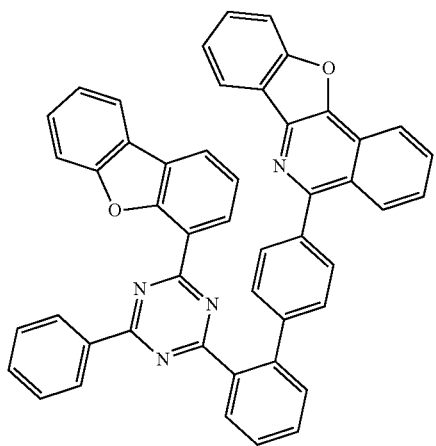
696
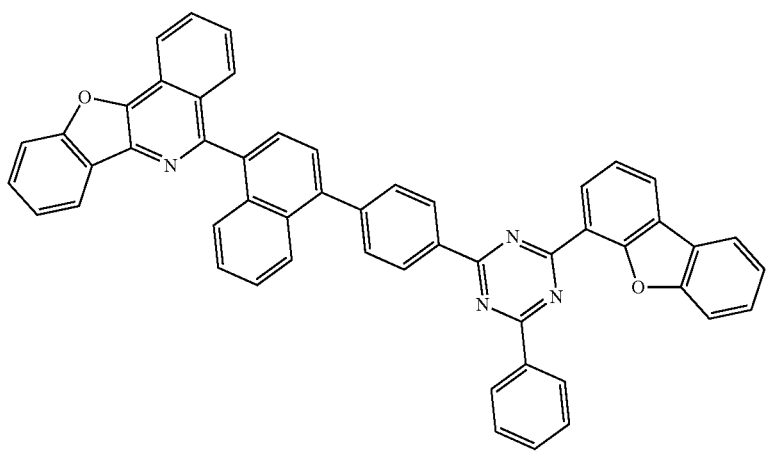
697

698
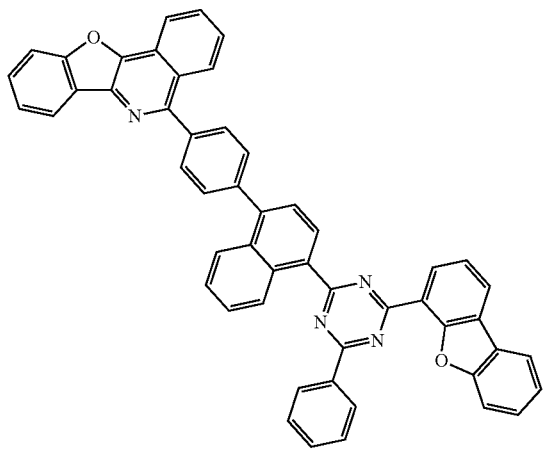
699
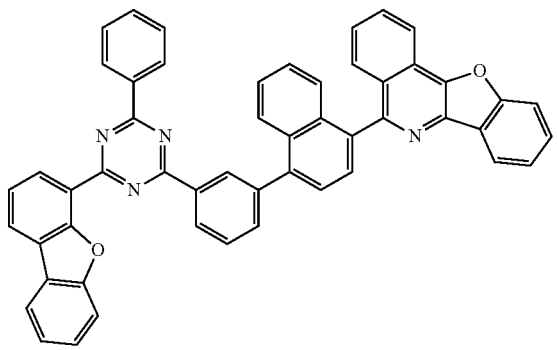
700
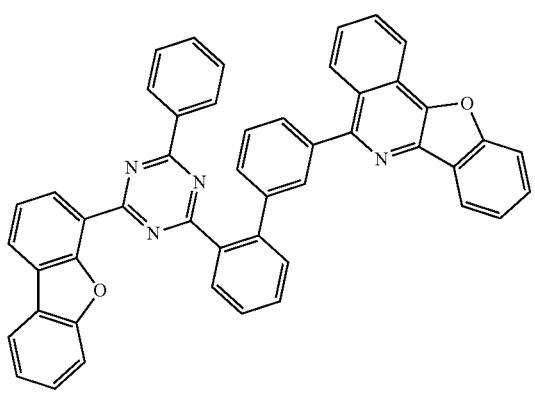
701
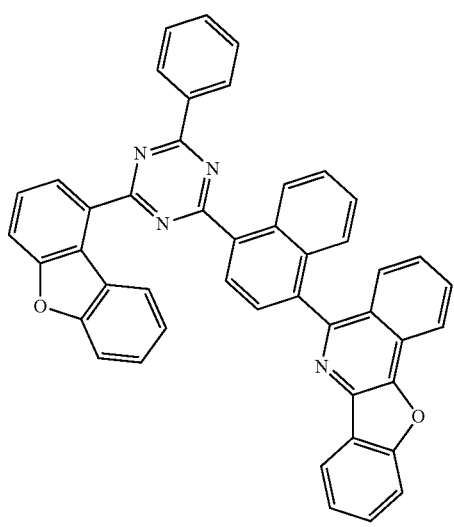
702
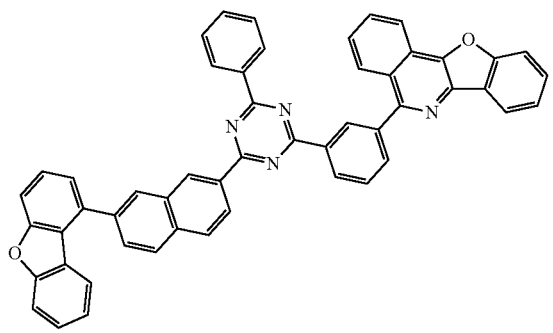
703
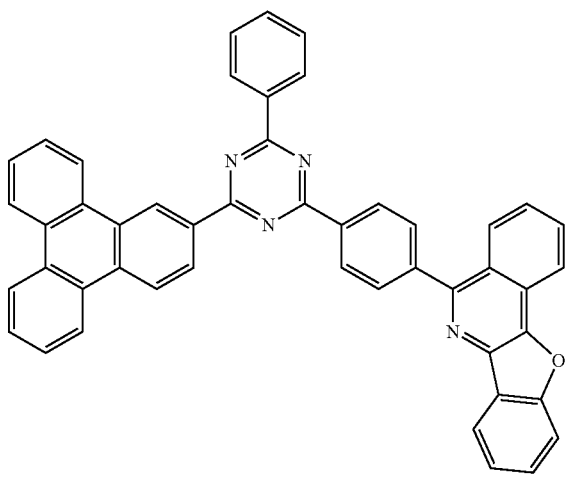

893 894
-continued
704 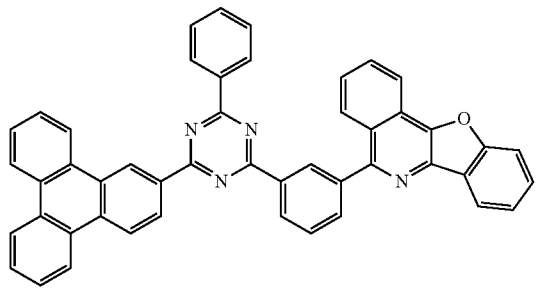
705 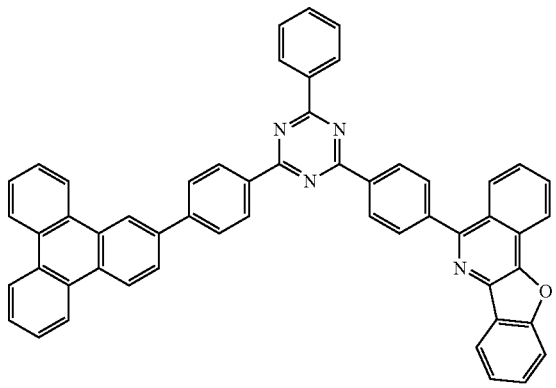
706 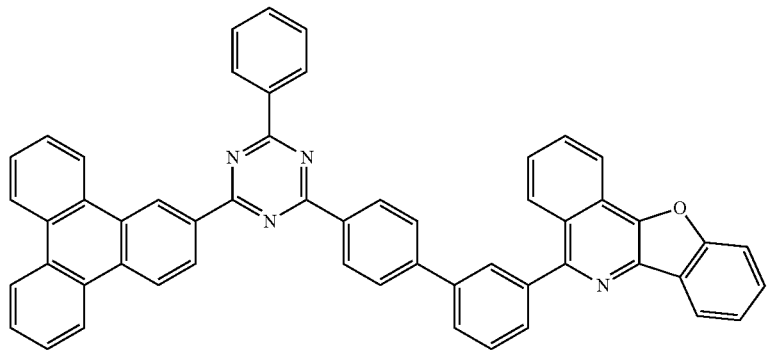
707 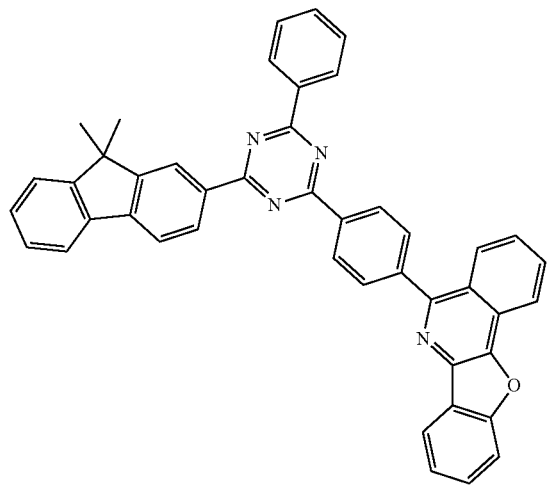
708 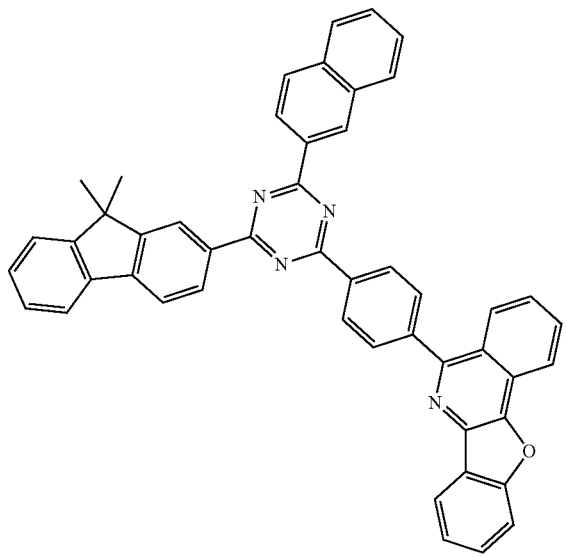

-continued
709
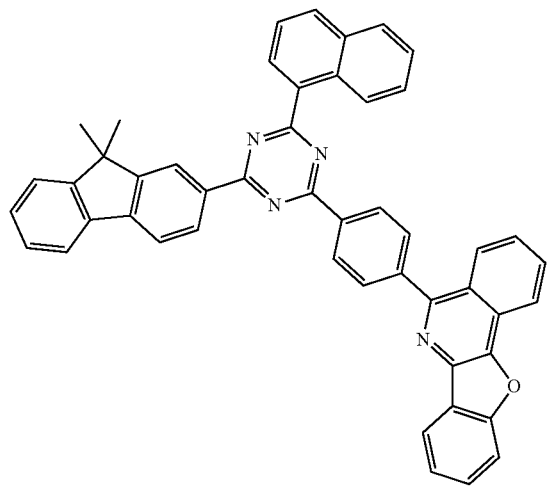
710
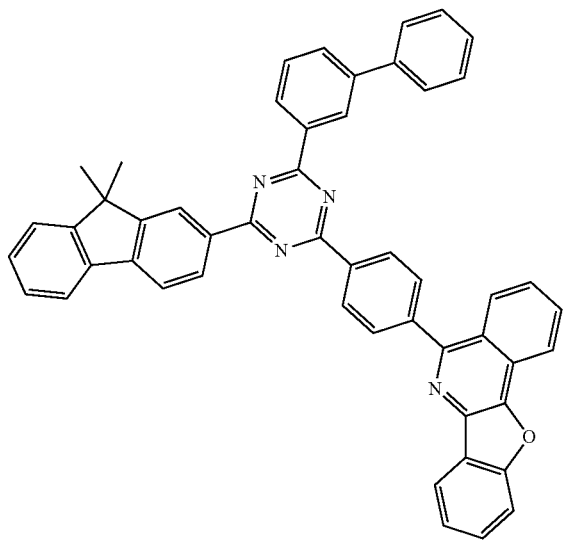
711
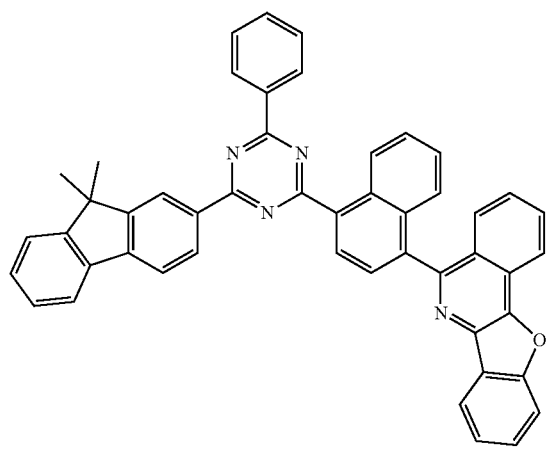
712
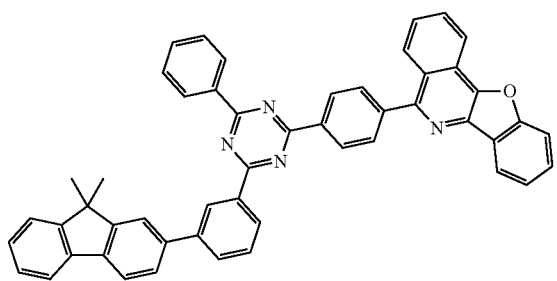
713
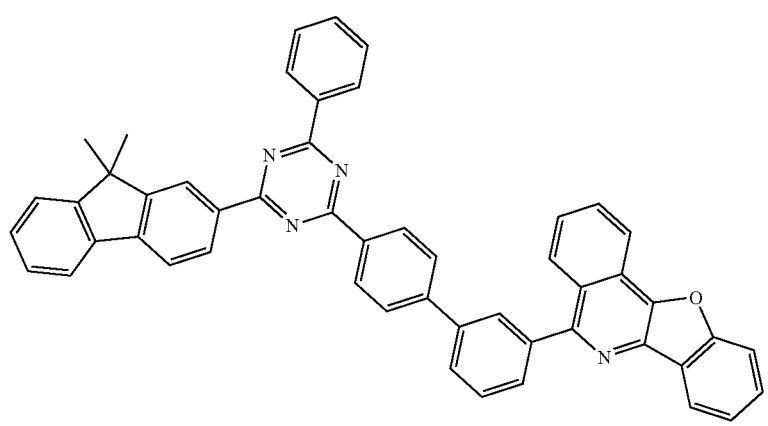

-continued
714
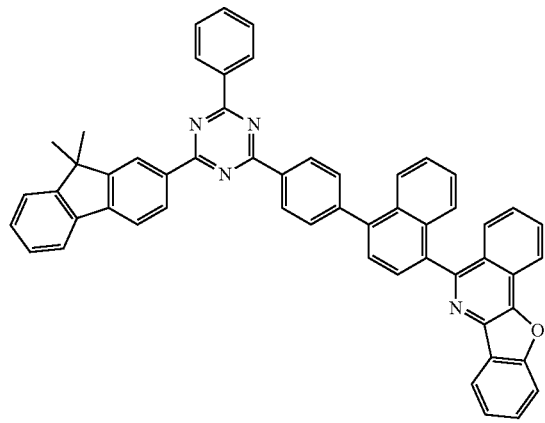
715
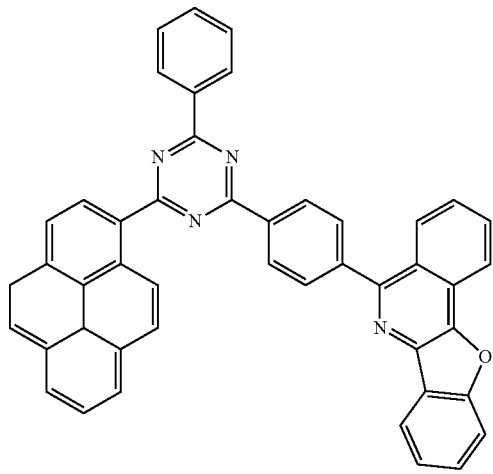
716
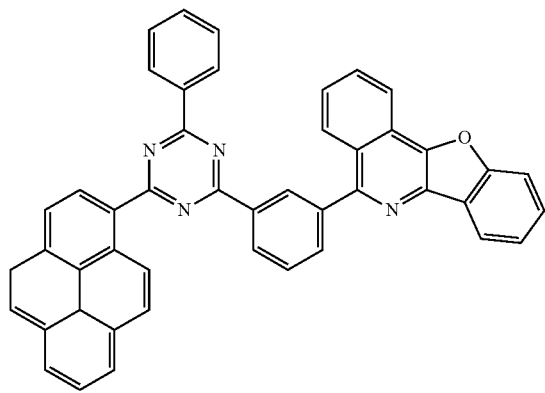
717
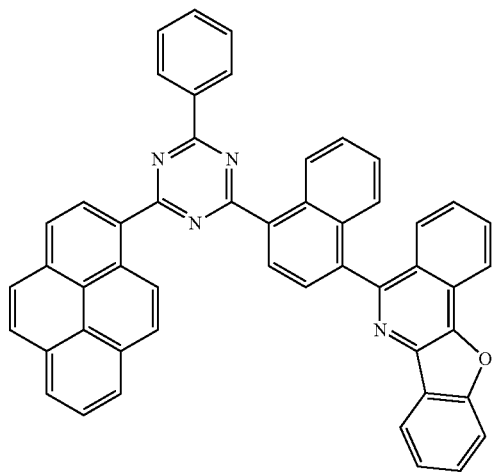
718
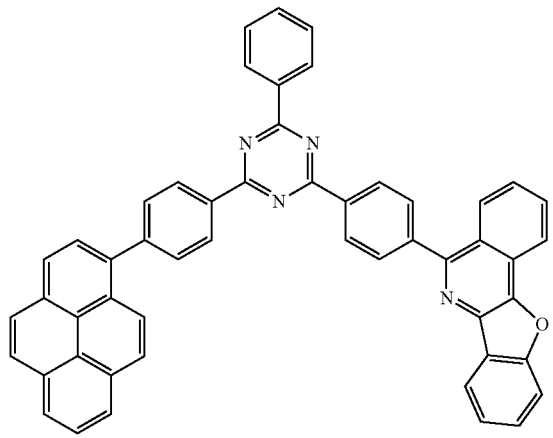
719
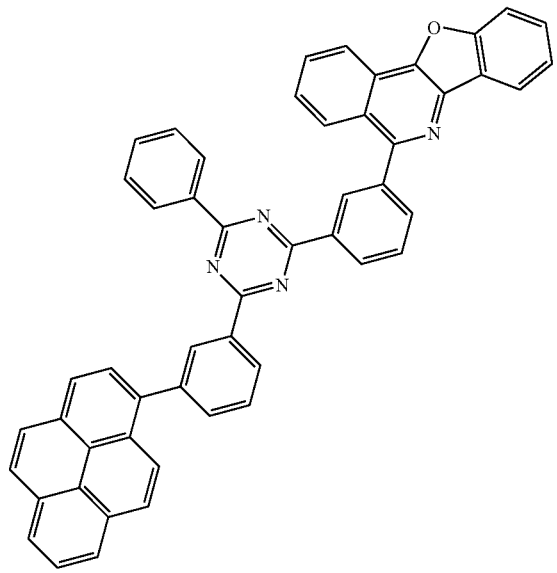

-continued
720
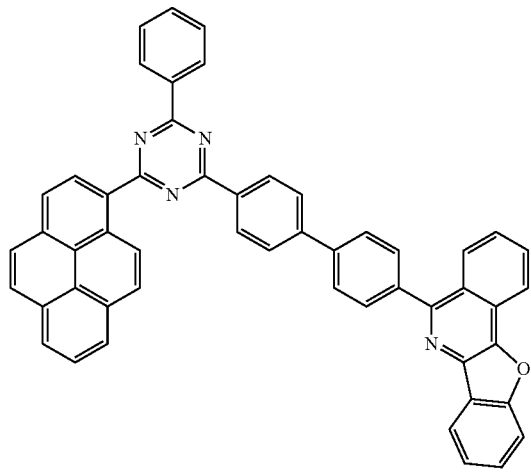
721
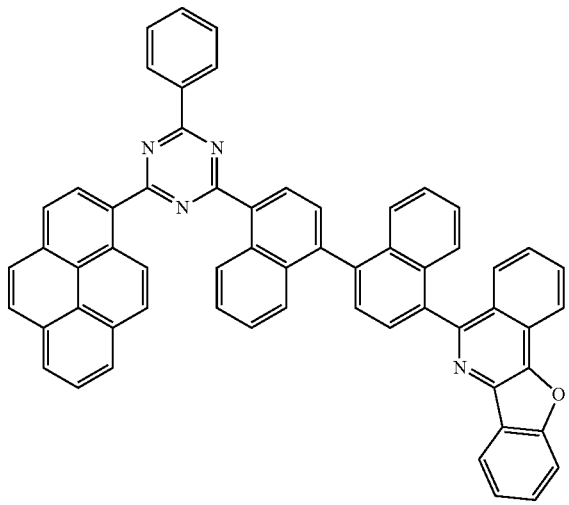
722
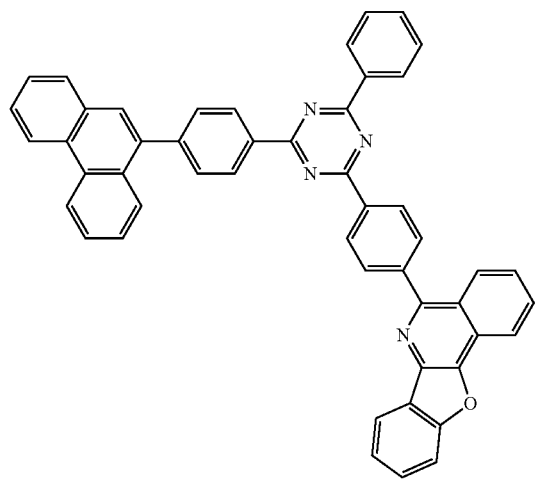
723
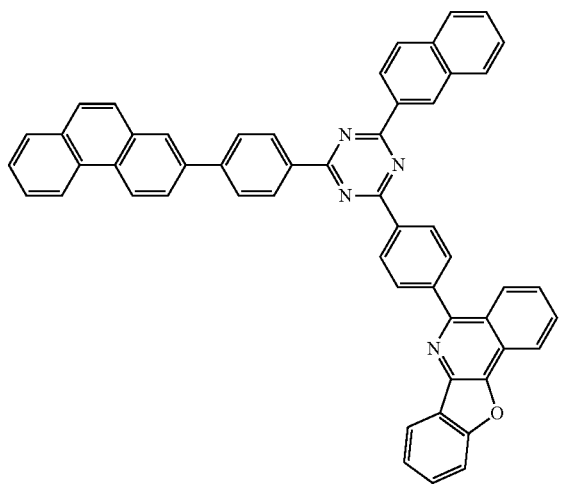
724
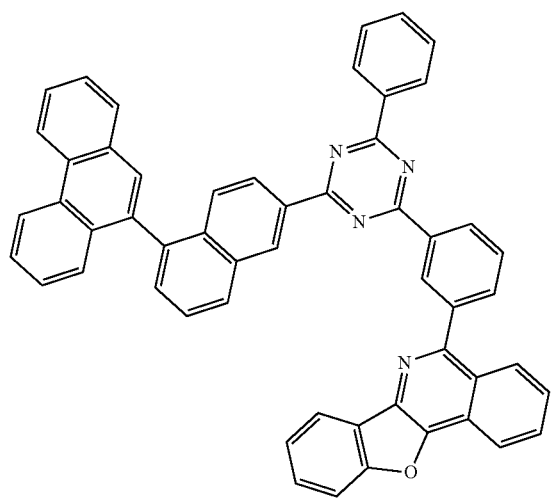

901
725
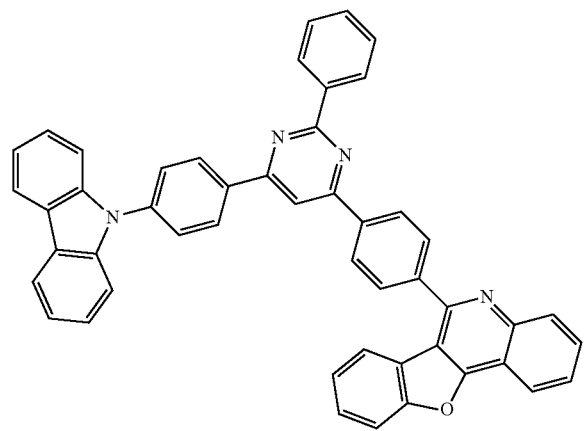
726
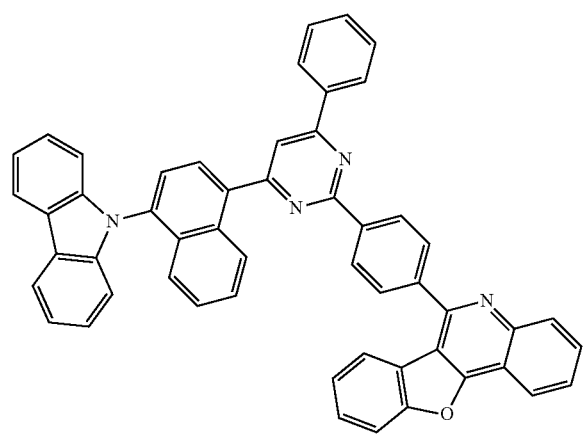
727
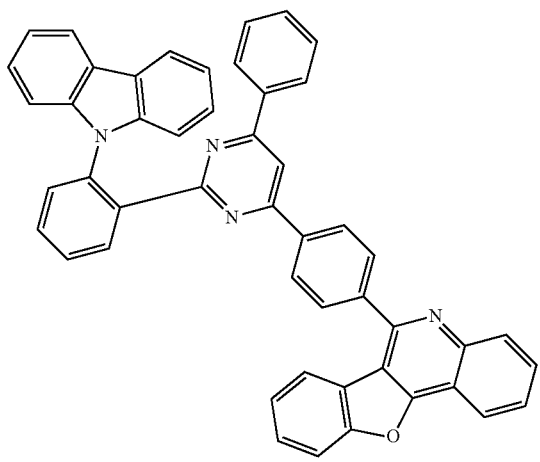
902
-continued
278
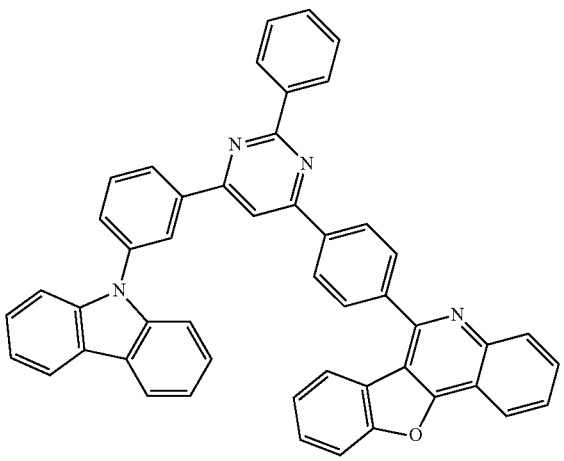
729
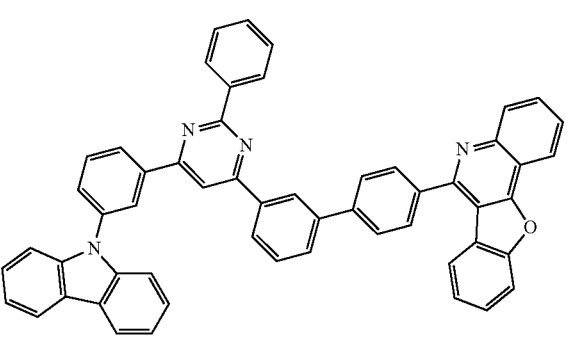
730
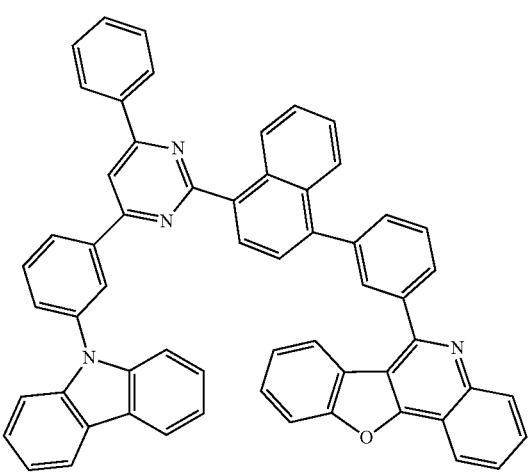

903
-continued
731
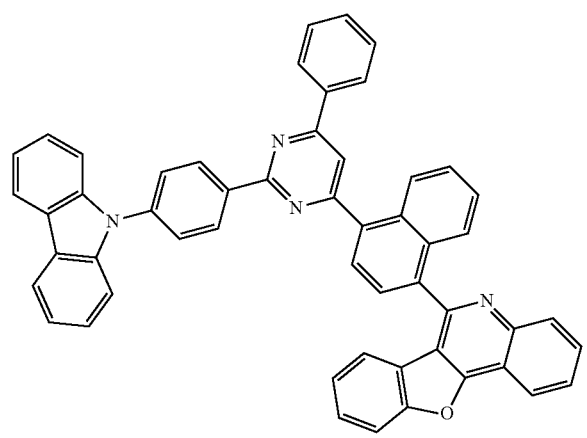
732
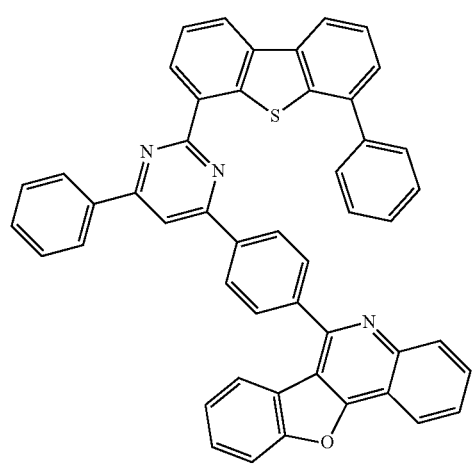
733
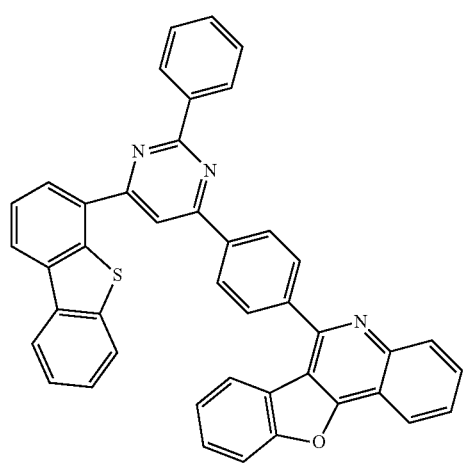
904
-continued
734
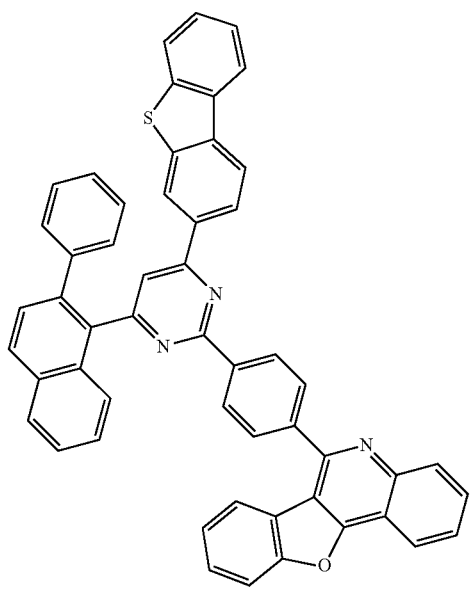
735
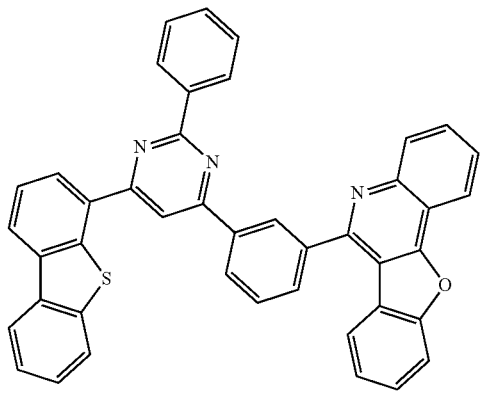
736
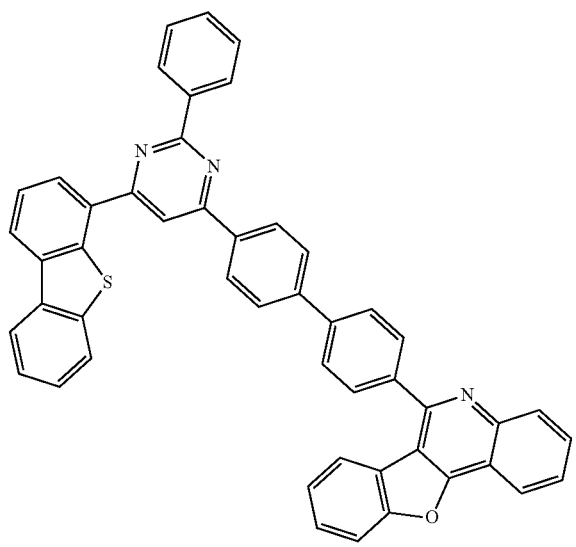

-continued
737
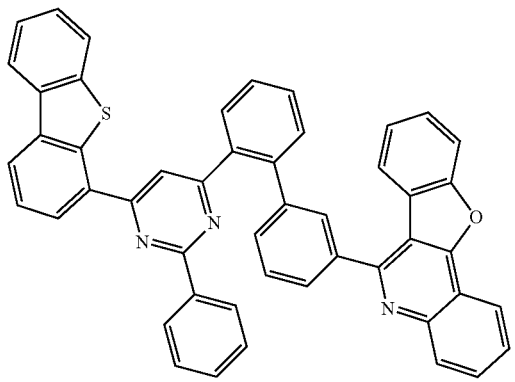
738
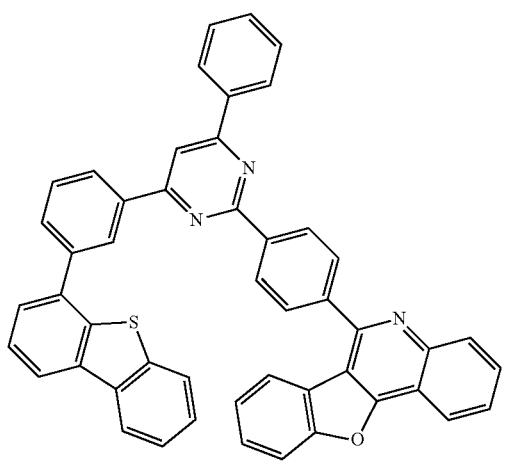
739
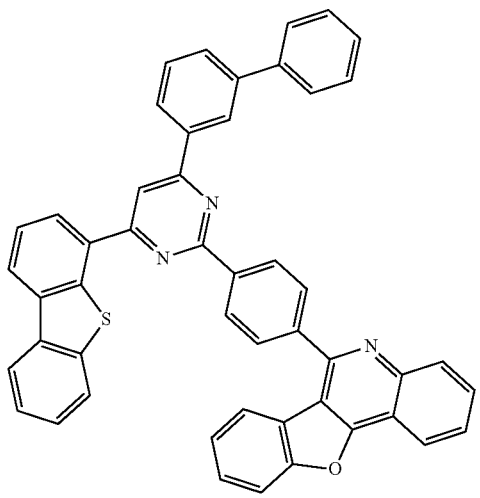
-continued
740
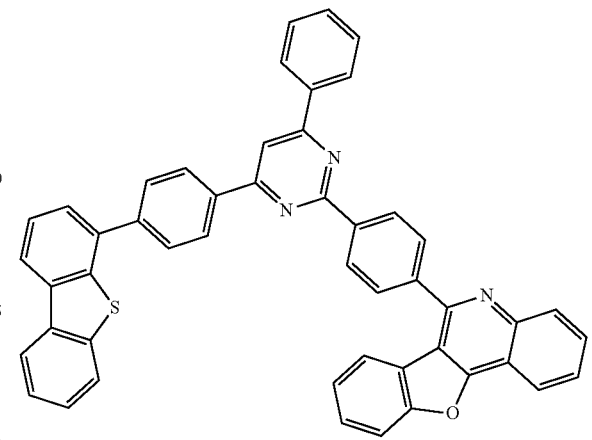
741
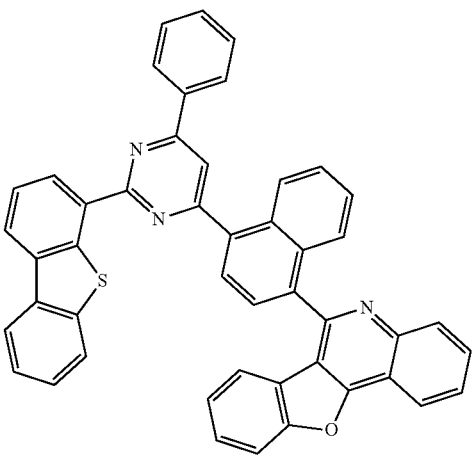
742
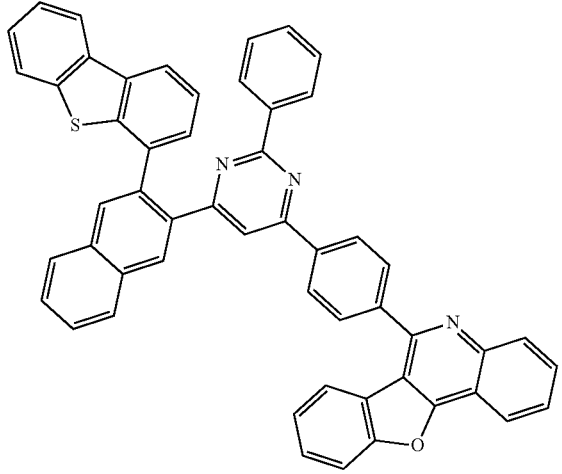

743
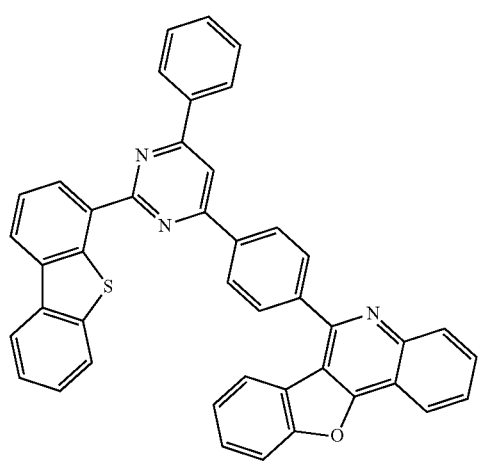
744
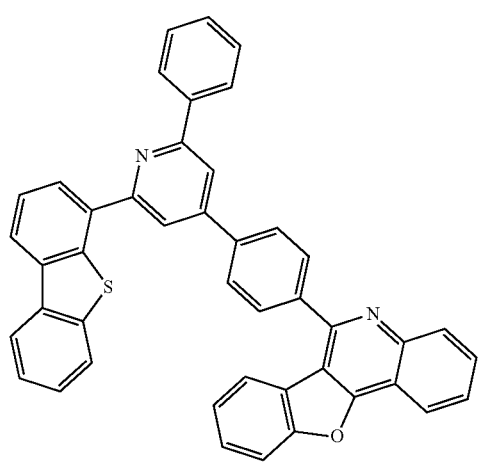
745
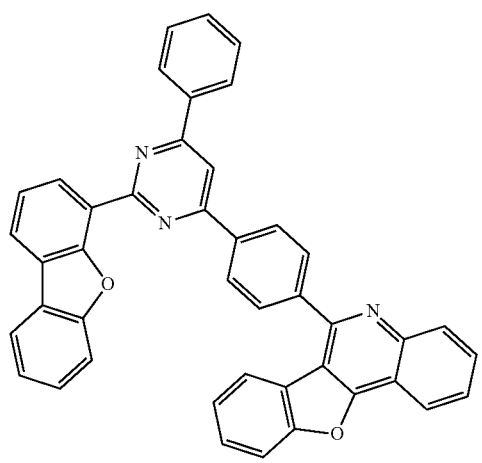
746
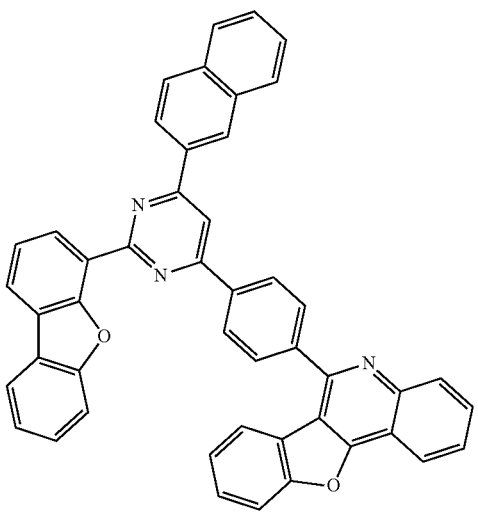
747
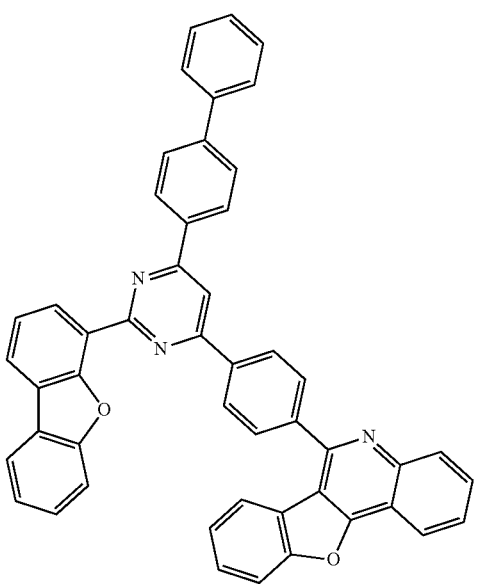
748
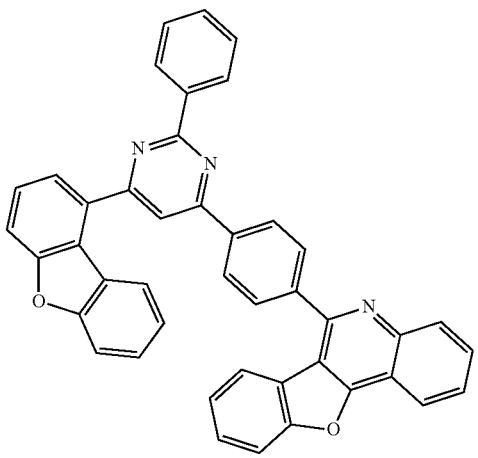

909
-continued
749
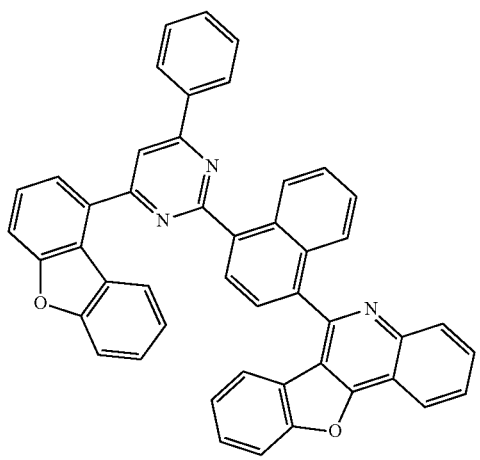
750
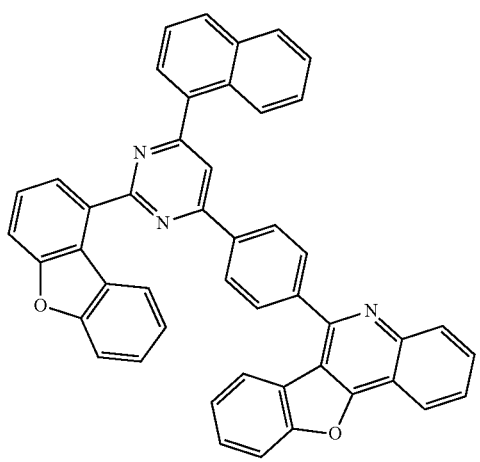
751
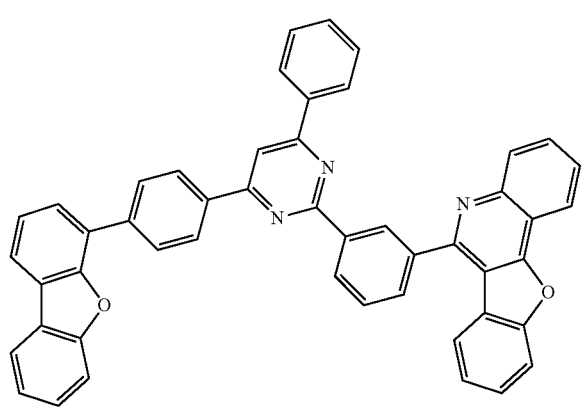
910
-continued
752
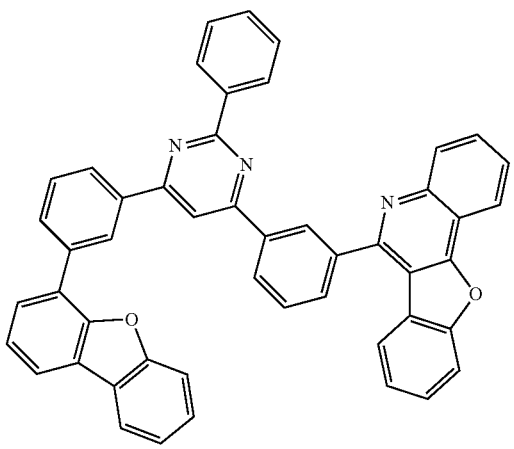
753
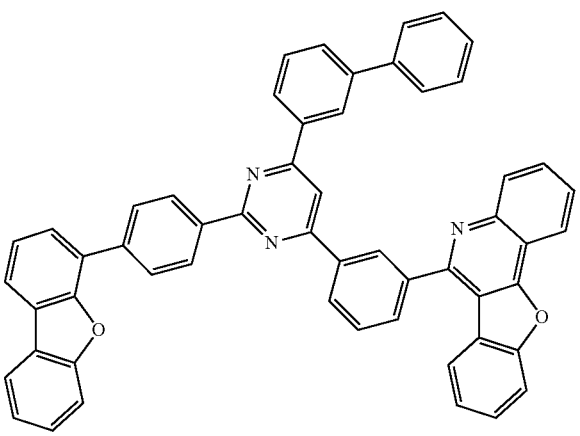
754
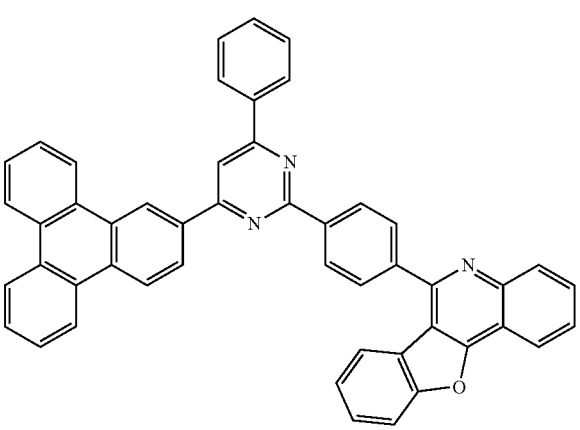

911
-continued
755
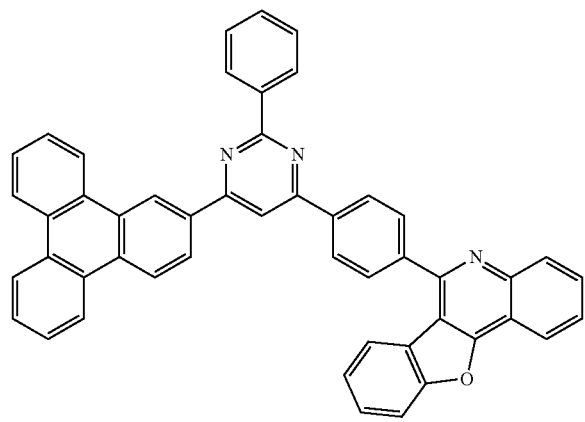
756
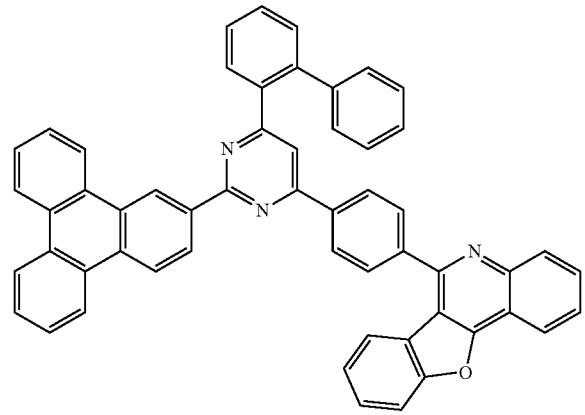
757
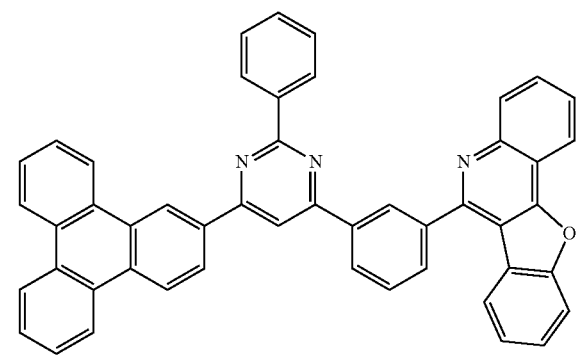
912
-continued
758
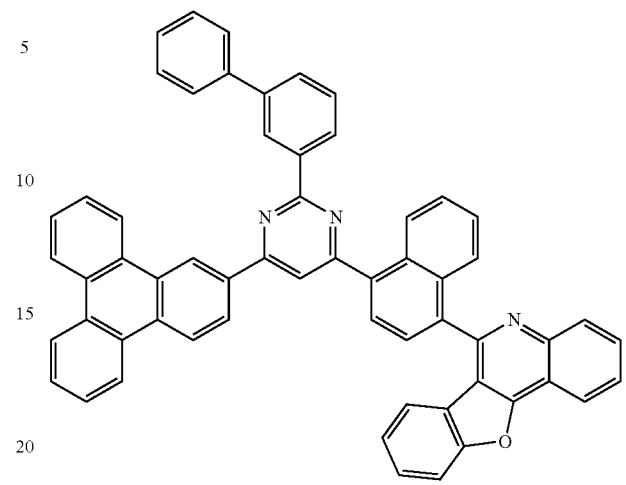
759
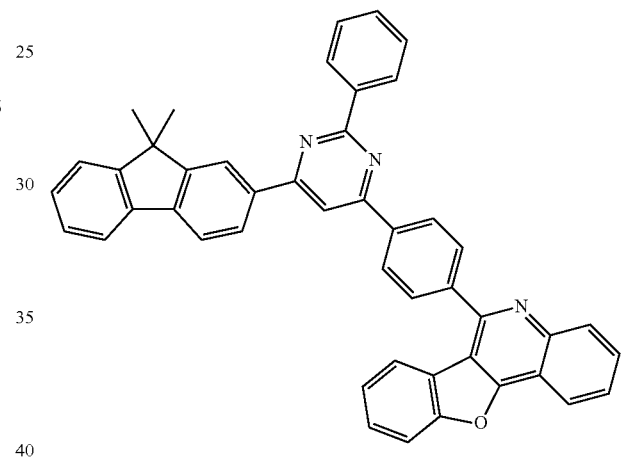
760
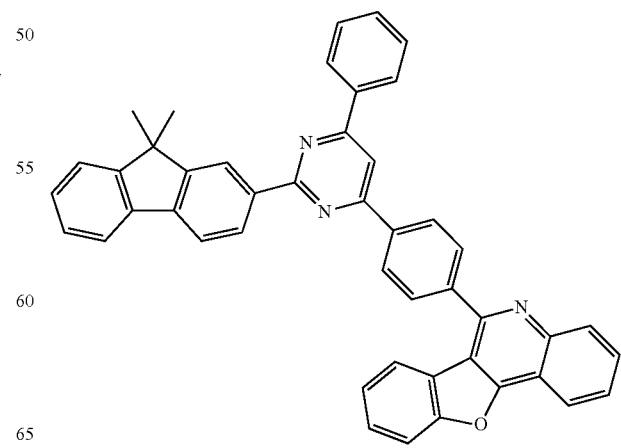

761
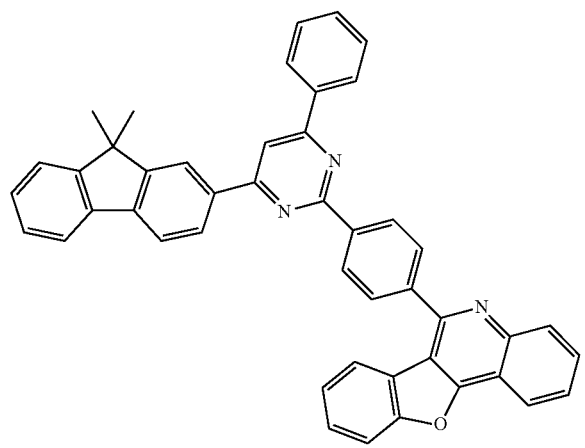
762
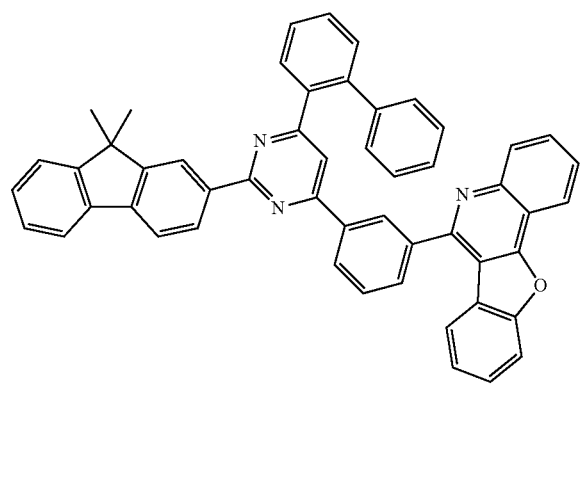
763
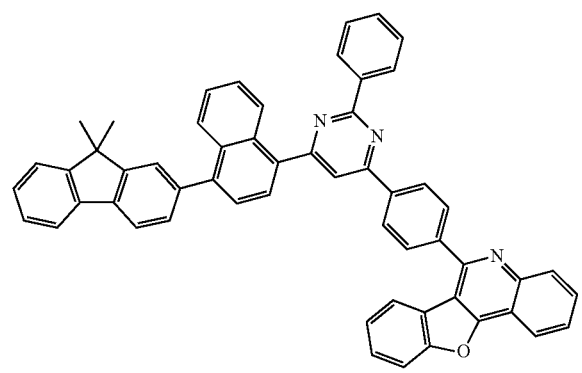
764
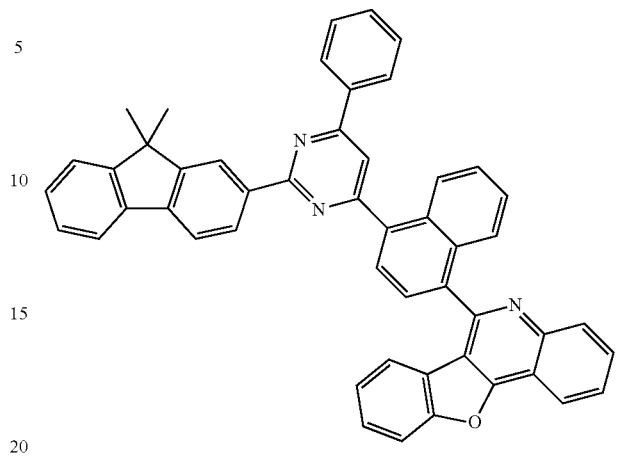
765
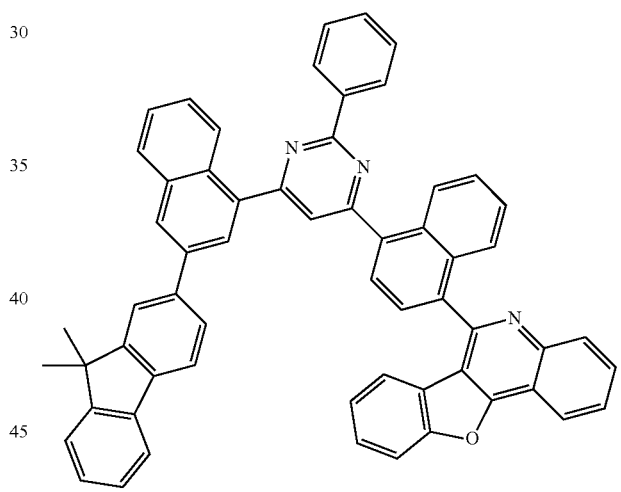
766
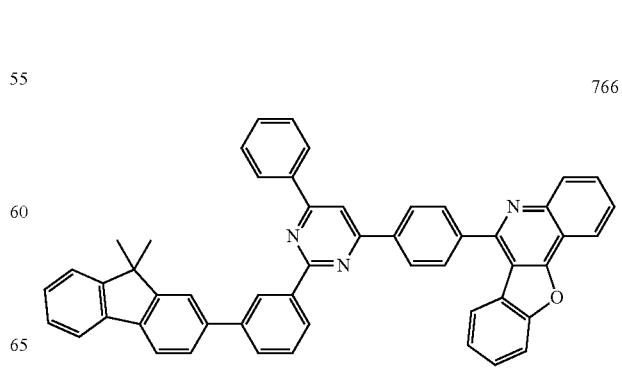

915-continued
767
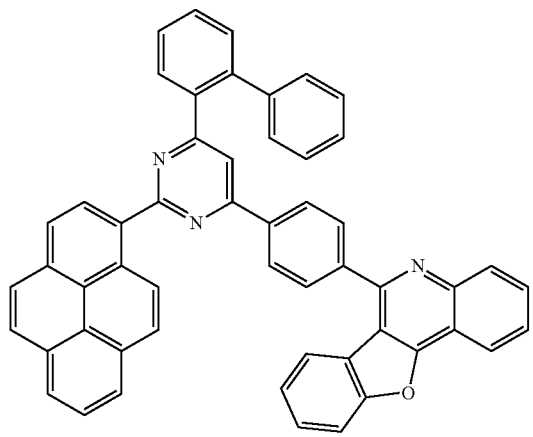
768
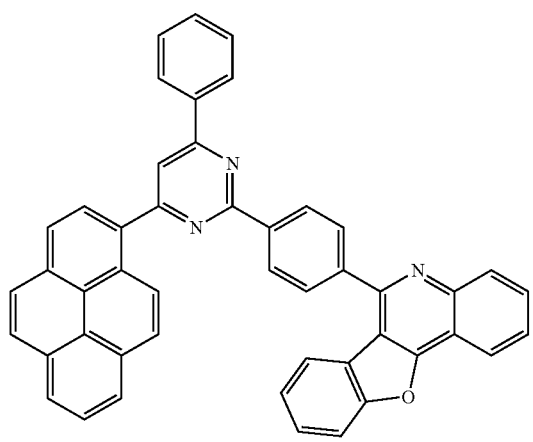
769
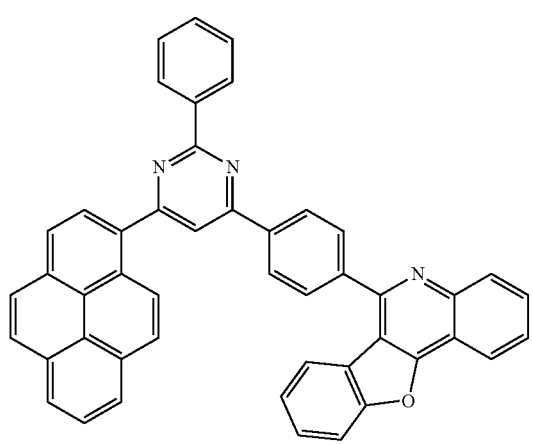
916-continued
770
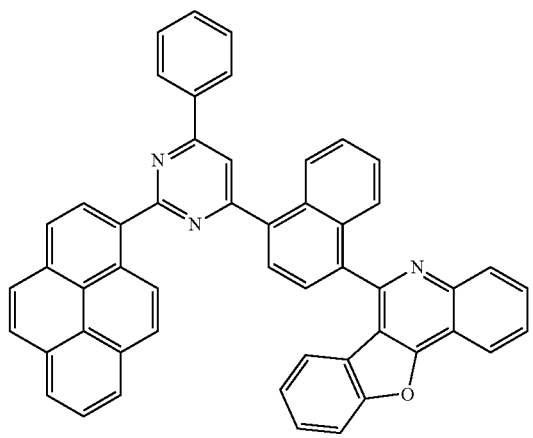
771
772
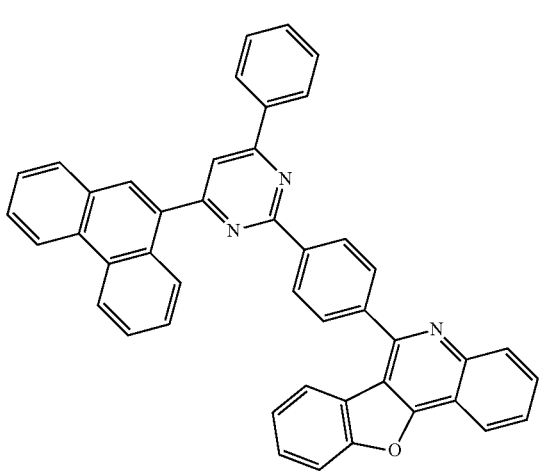

917
-continued
773
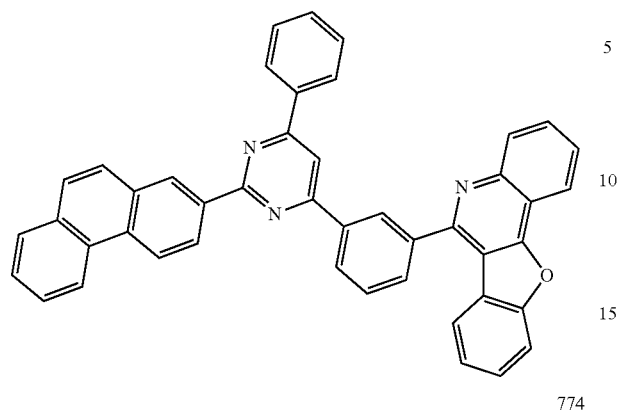
774
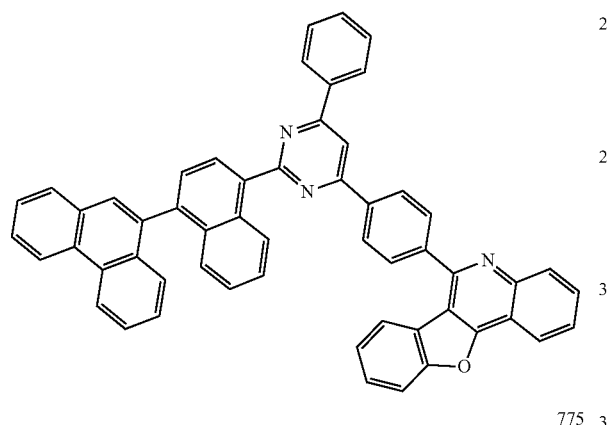
775
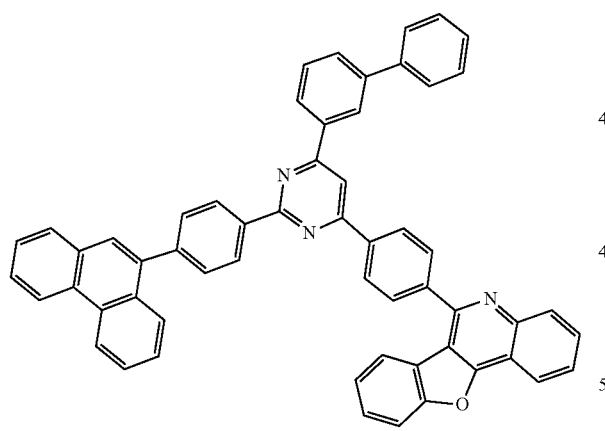
776
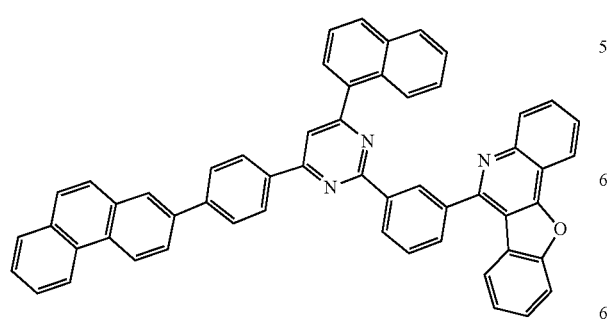
918
-continued
777
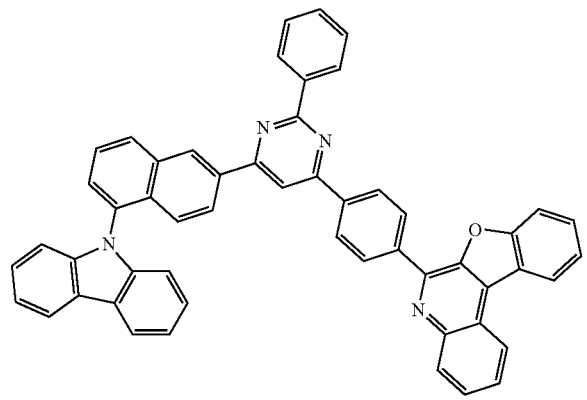
778
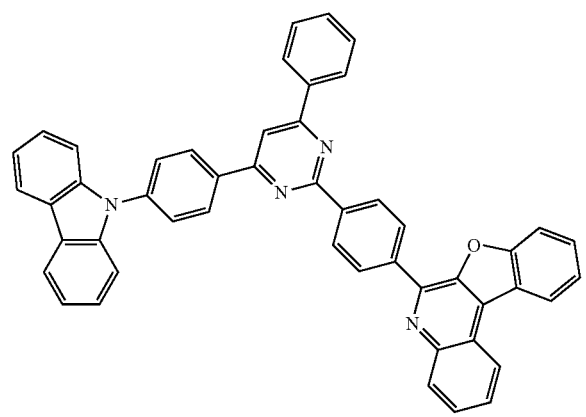
779
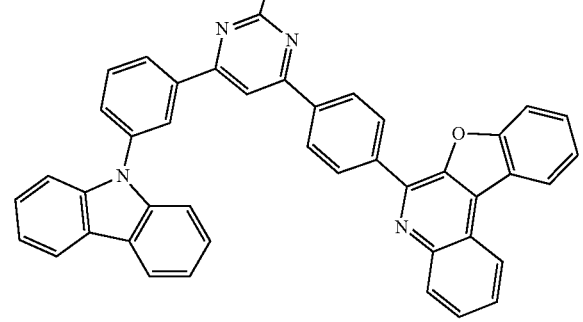

919
-continued
780
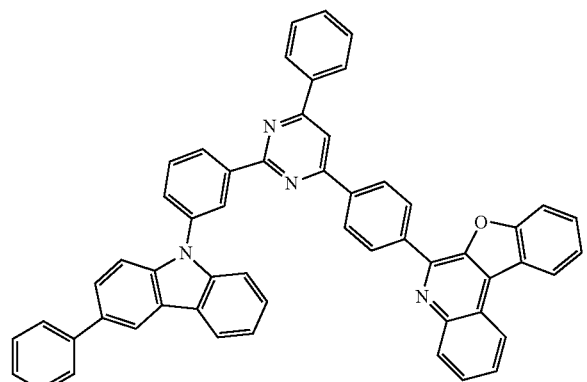
781
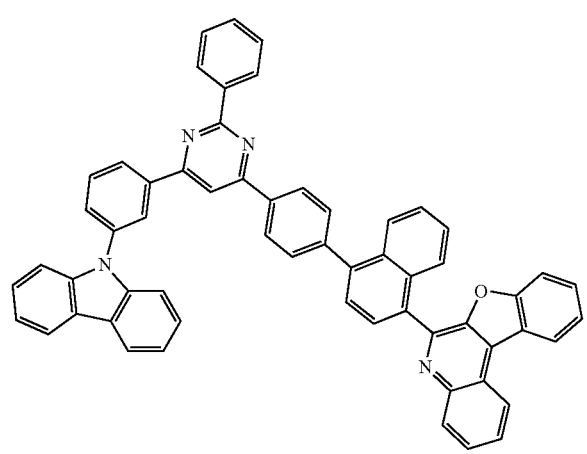
782
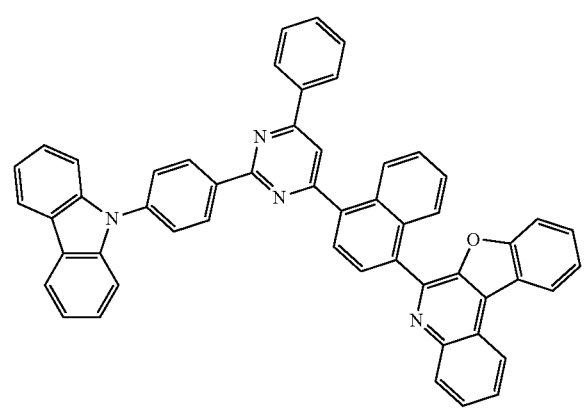
920
-continued
783
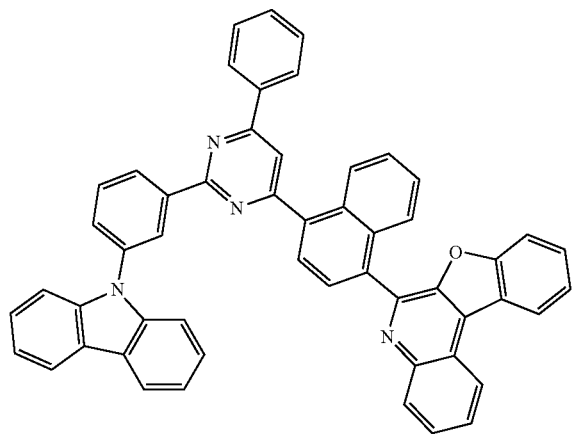
784
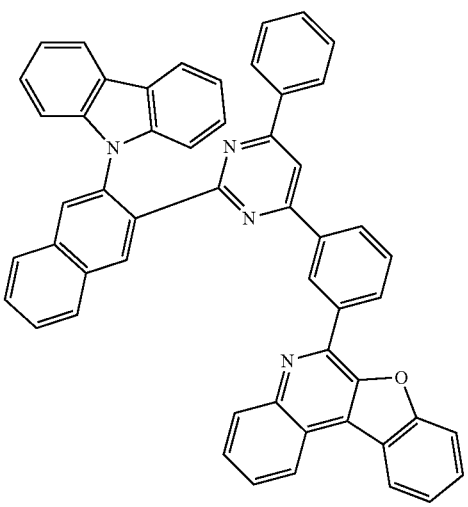
785
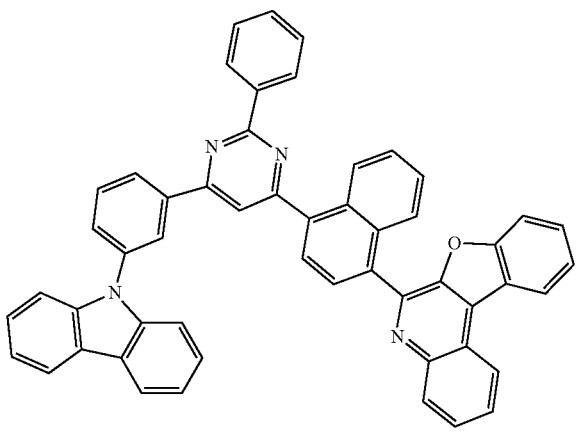

921
-continued
786
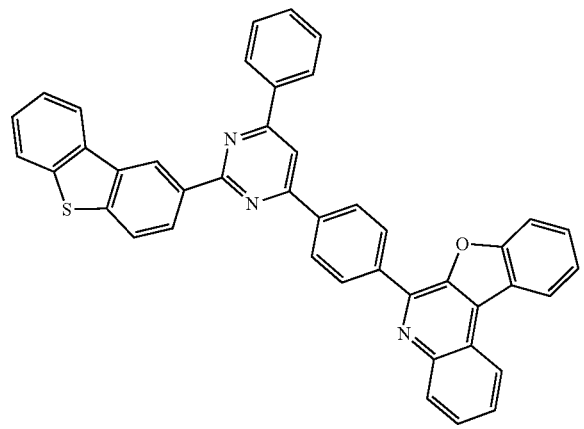
787
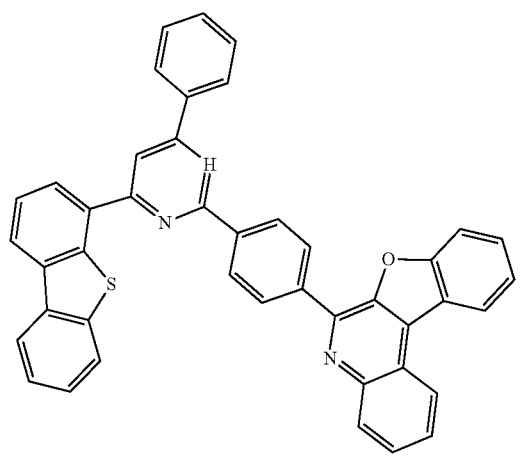
788
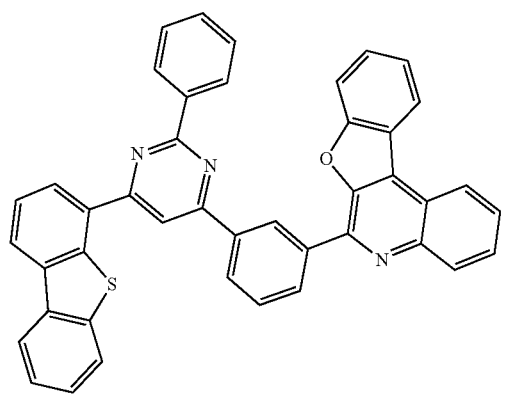
922
-continued
789
790
791
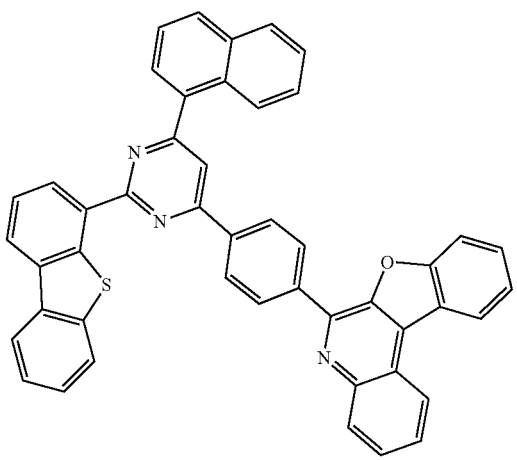
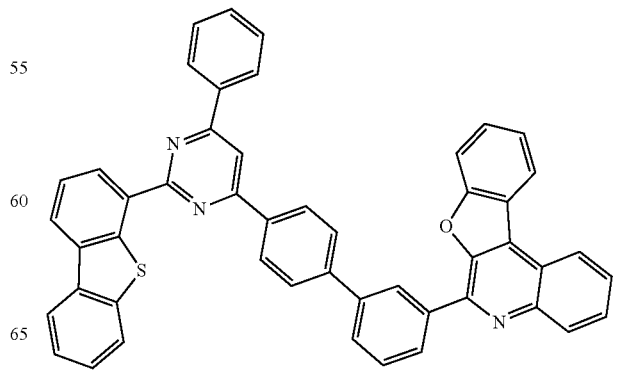

923
-continued
792
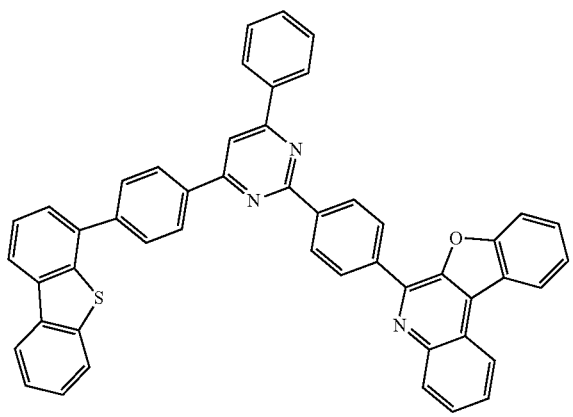
793
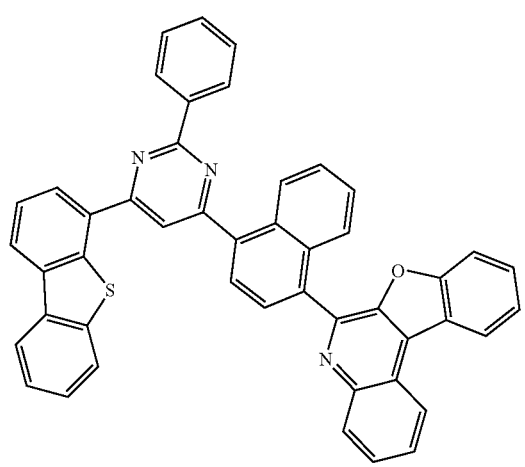
794
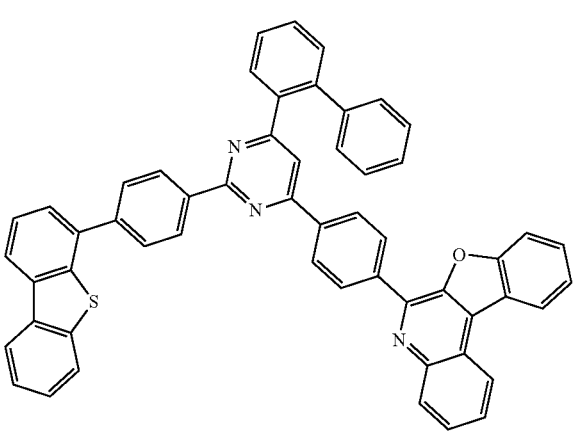
924
-continued
795
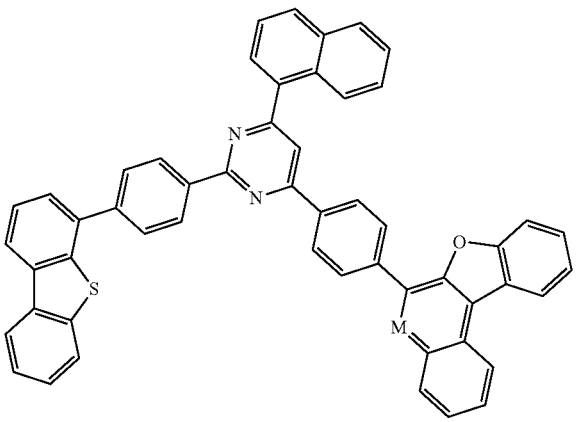
796
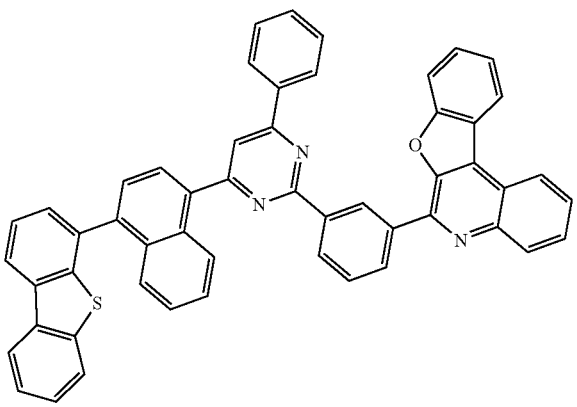
797
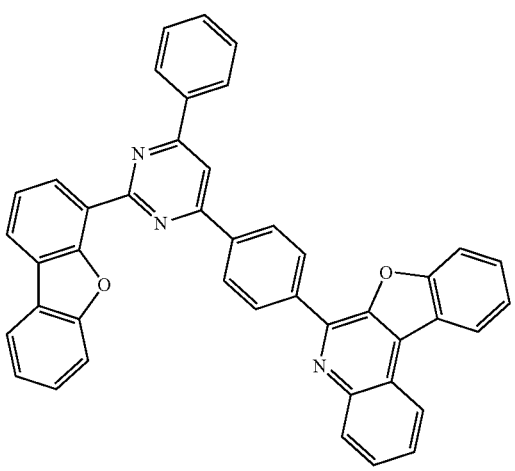

925
-continued
926
-continued
798
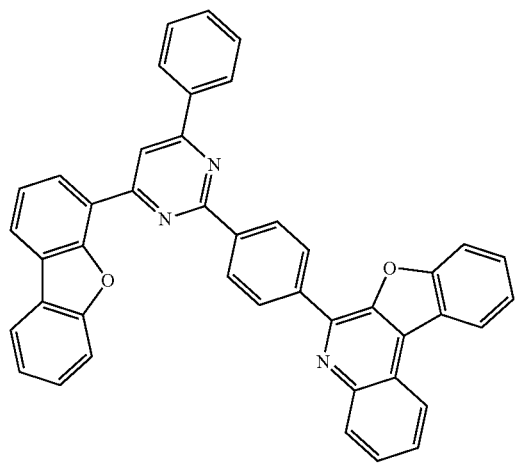
801
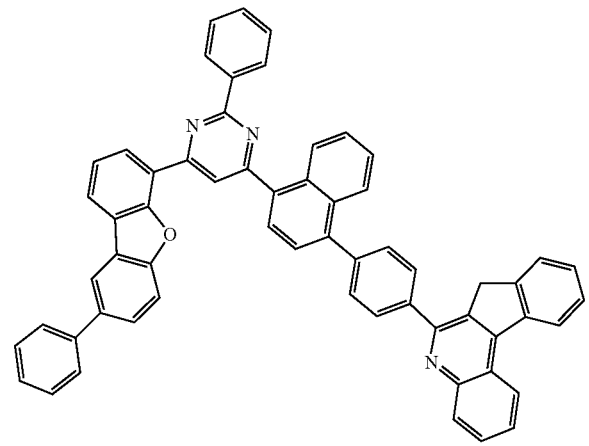
799
800
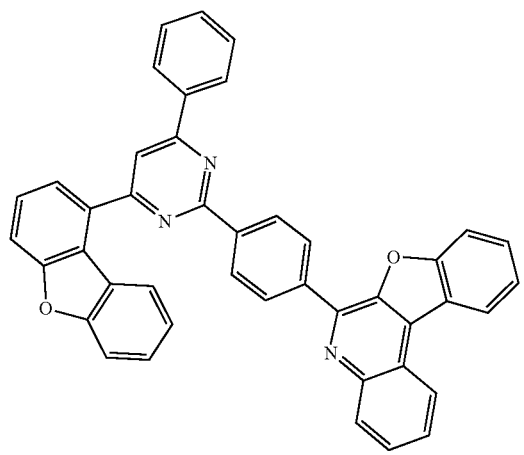
802
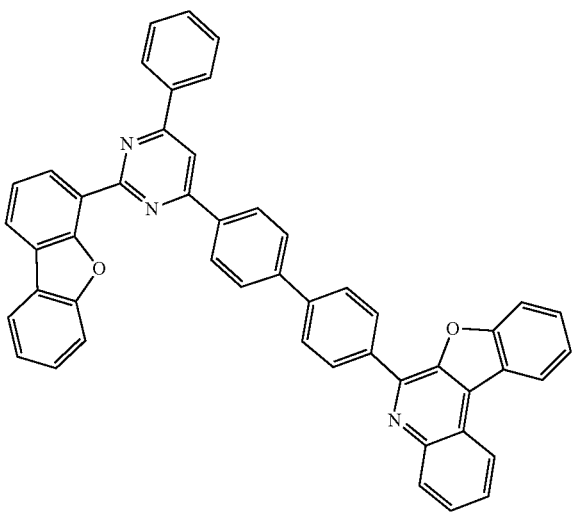
803
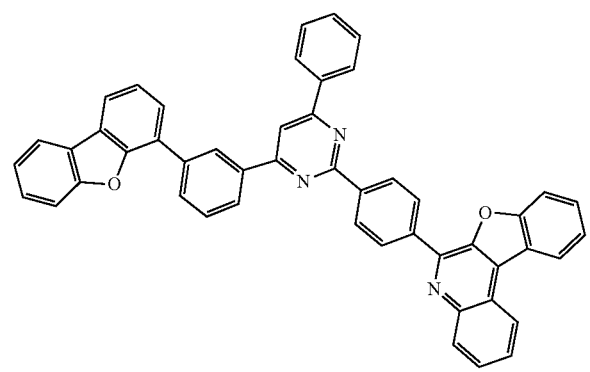

804
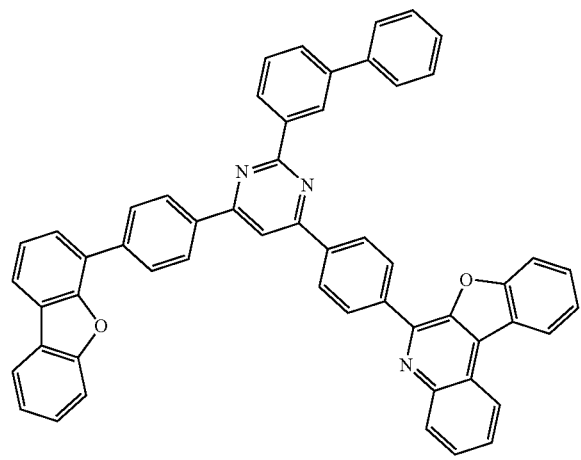
805
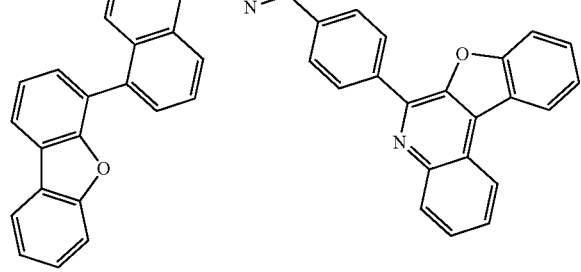
806
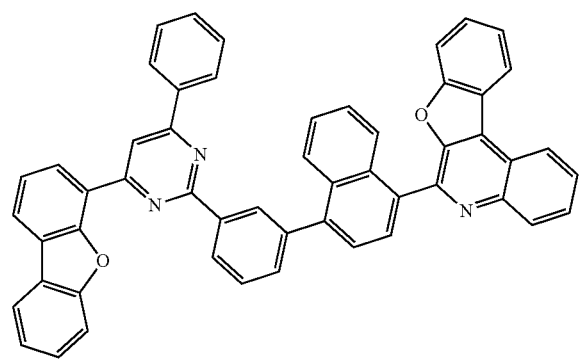
807
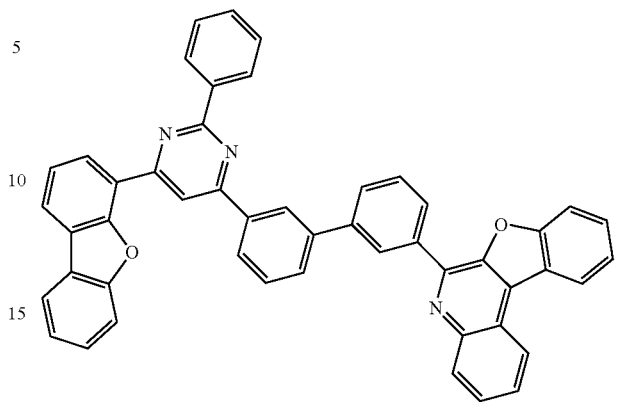
808
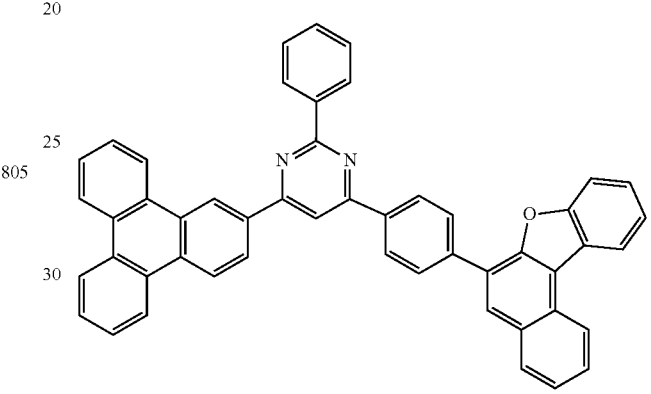
809
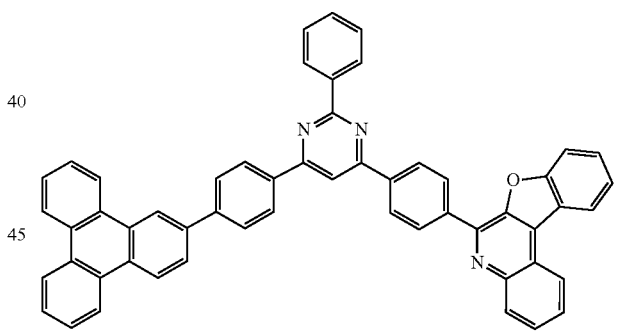
810
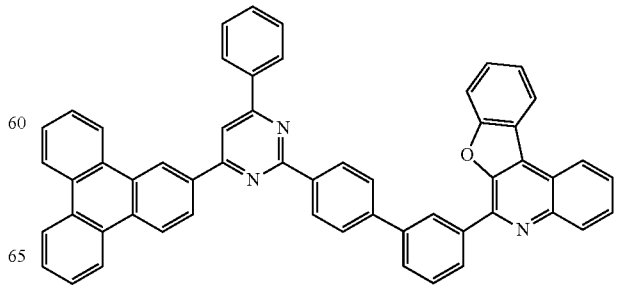

929
-continued
811
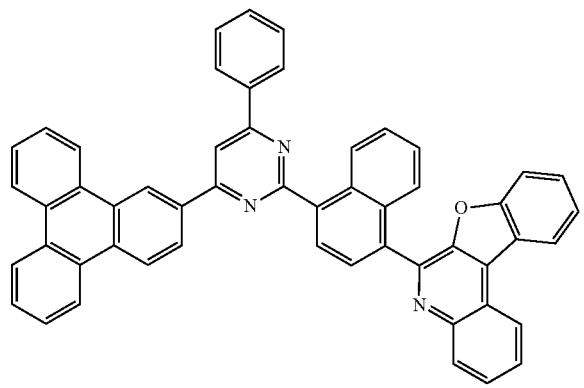
812
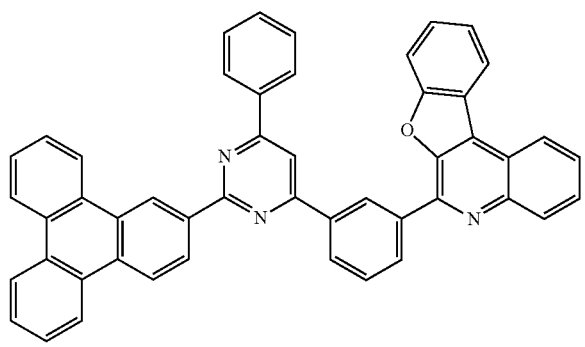
813
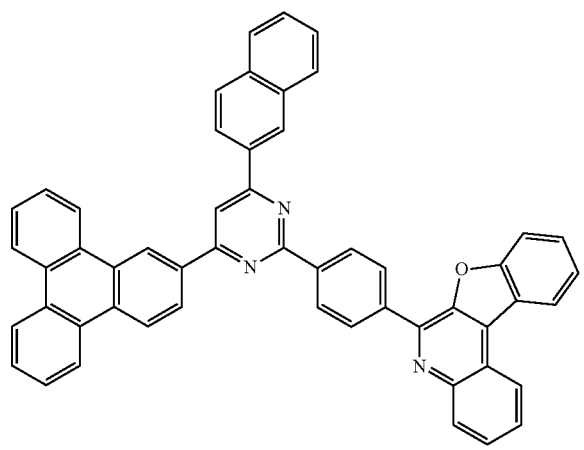
930
-continued
814
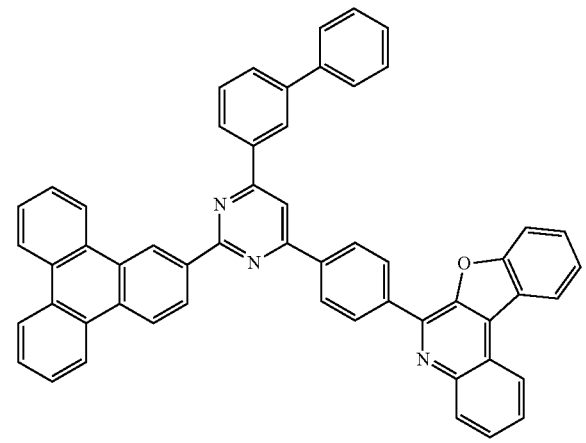
815
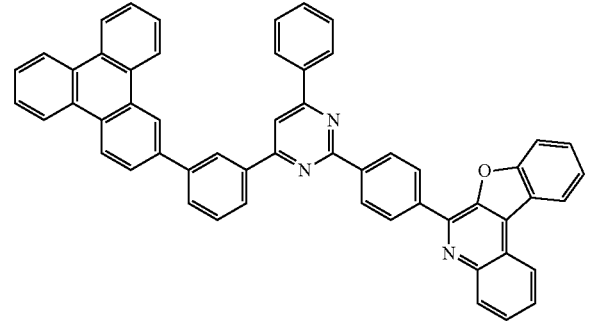
816
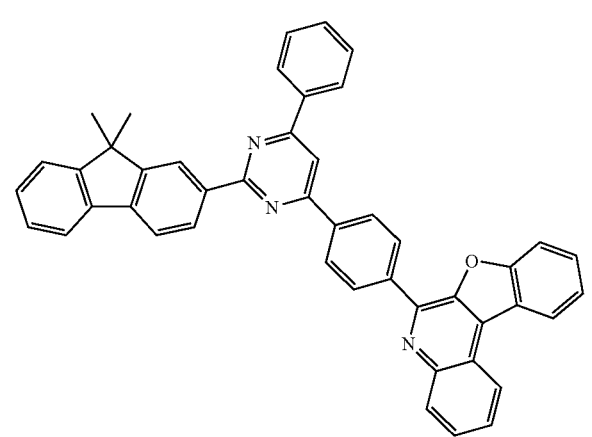

931
-continued
817
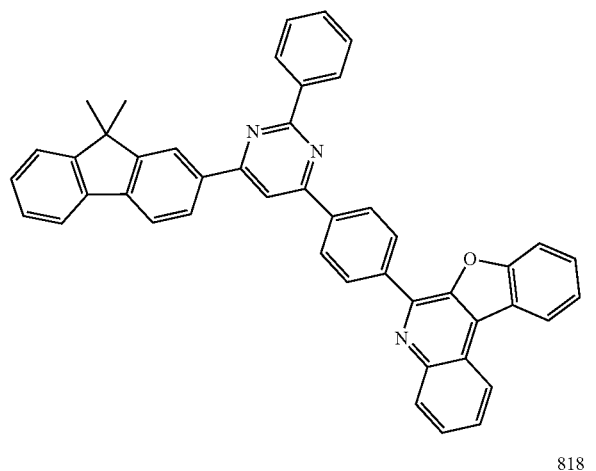
818
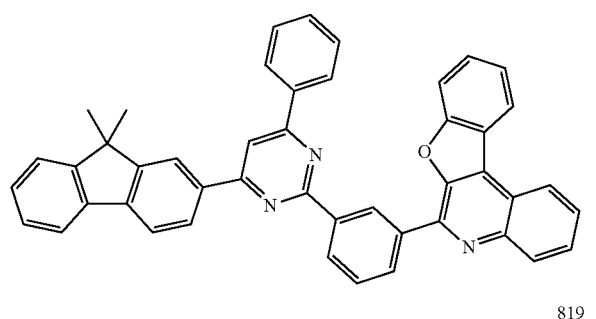
819
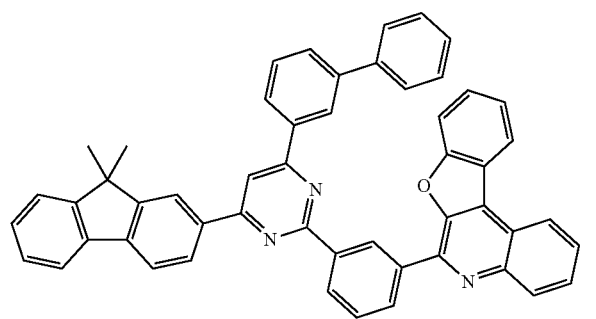
820
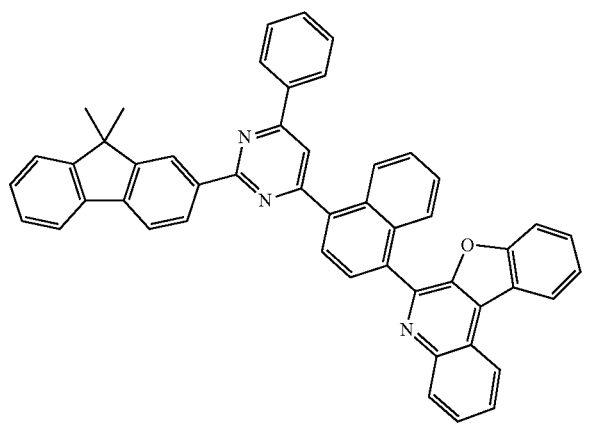
932
-continued
821
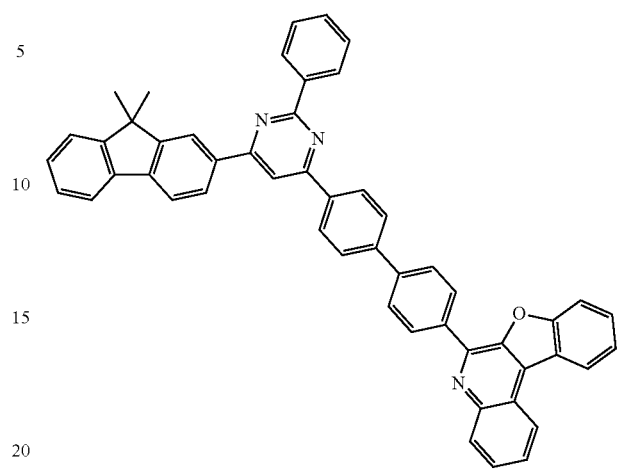
822
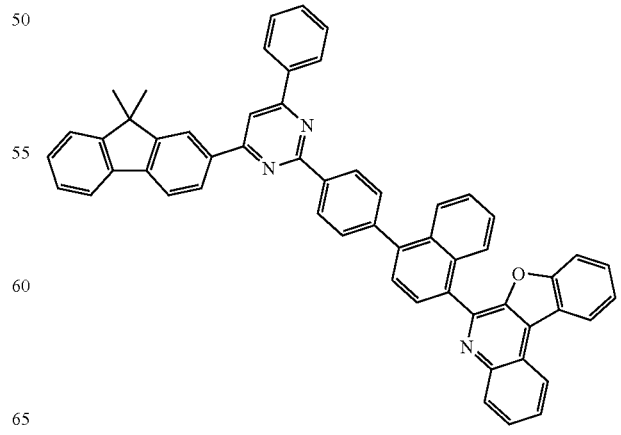
823

933
-continued
824
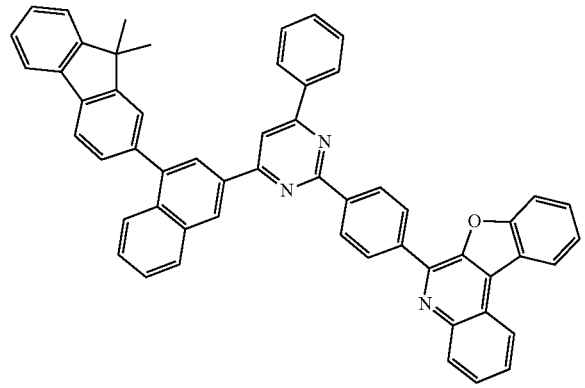
825
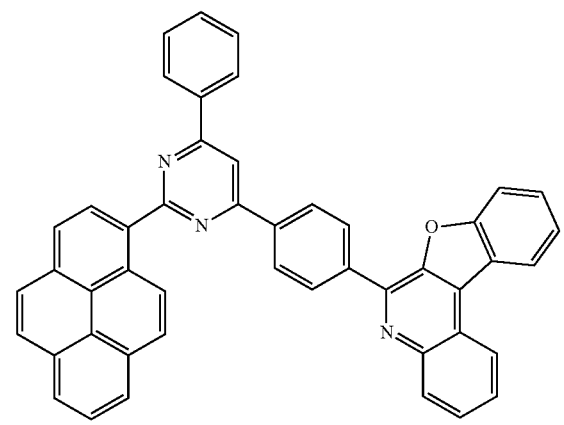
826
827
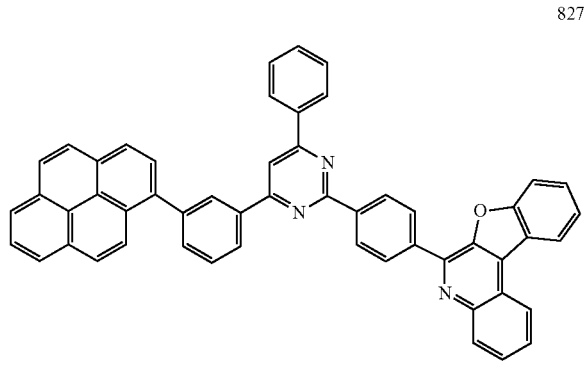
934
-continued
828
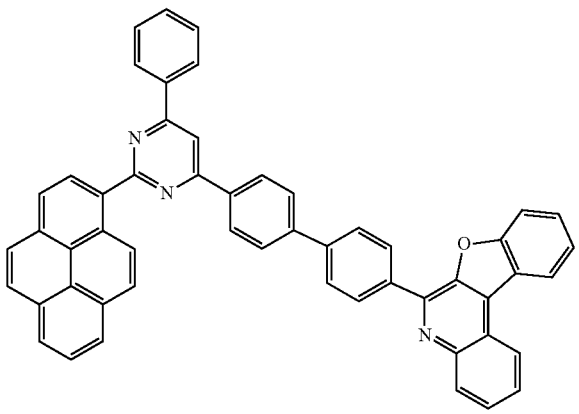
829
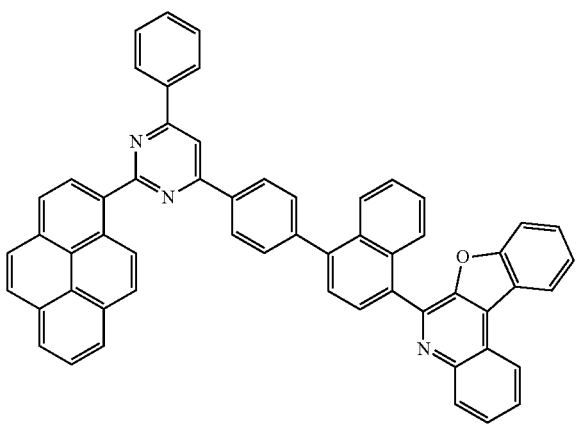
830
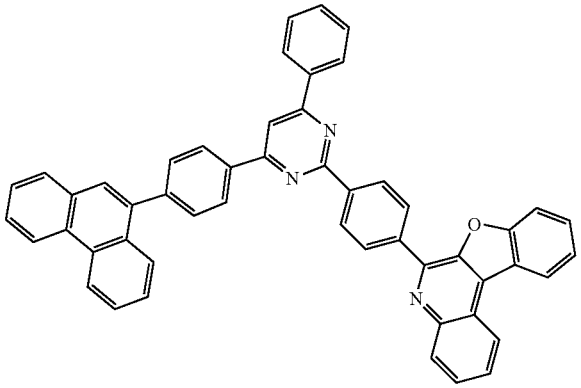

935 -continued

831

832

833

936 -continued

834

835

836

-continued
837
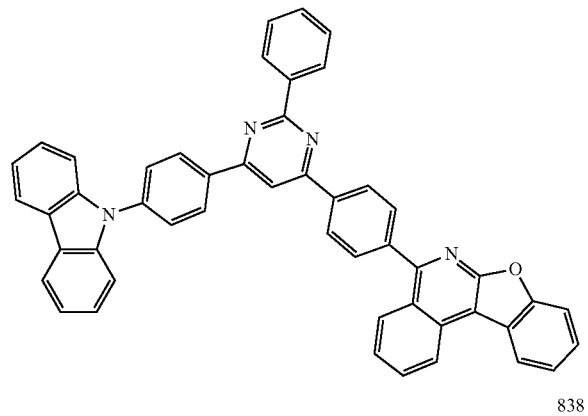
838
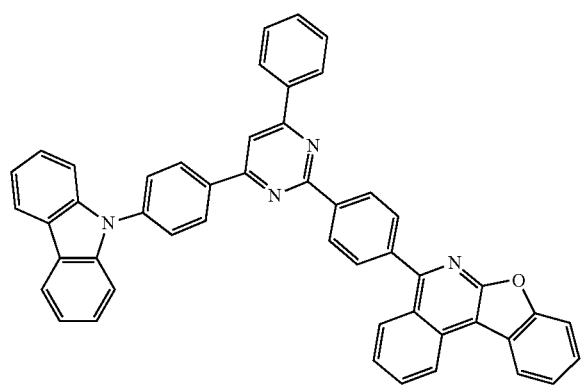
839
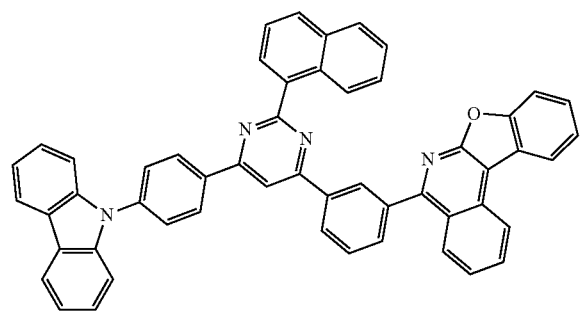
840
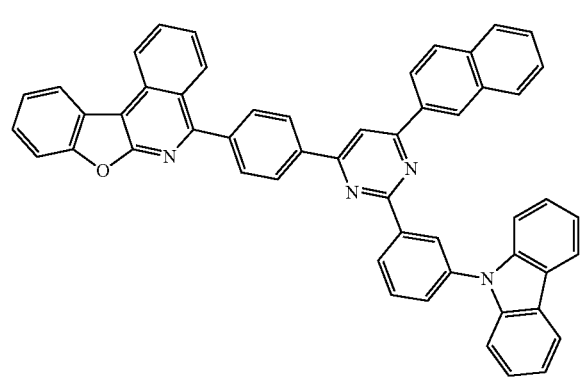
-continued
841
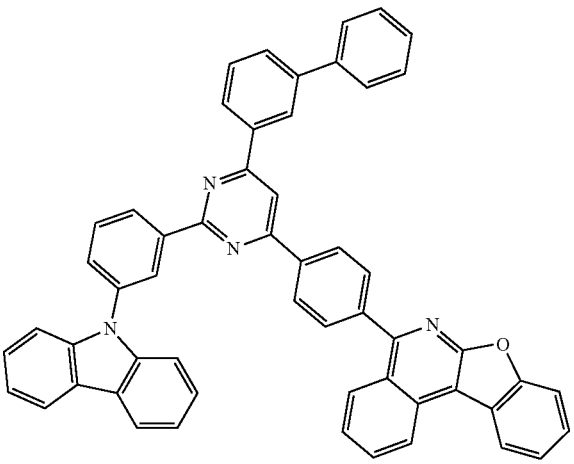
842
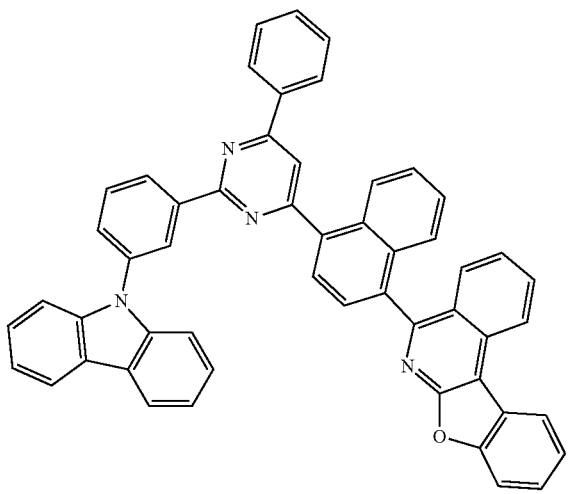
843
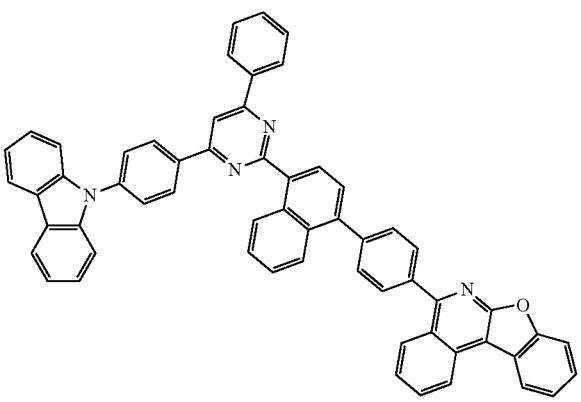

939
-continued
844
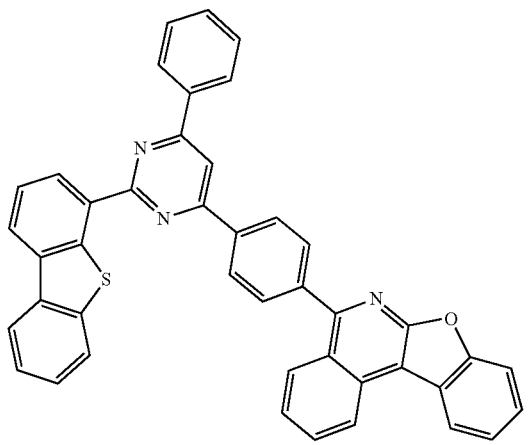
845
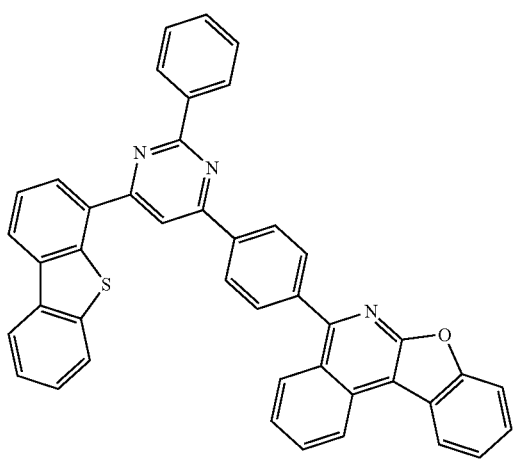
846
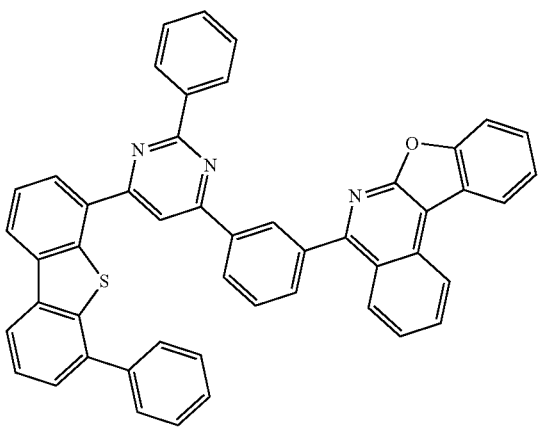
940
-continued
847
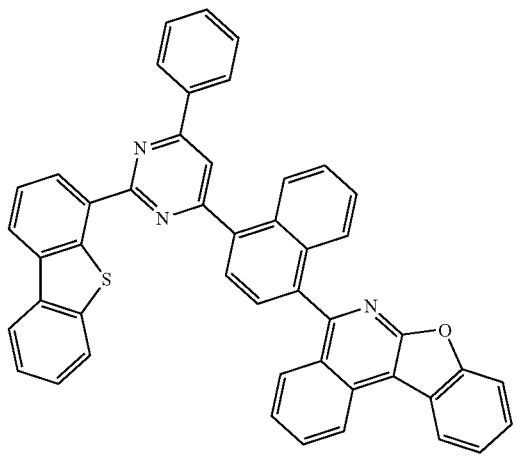
848
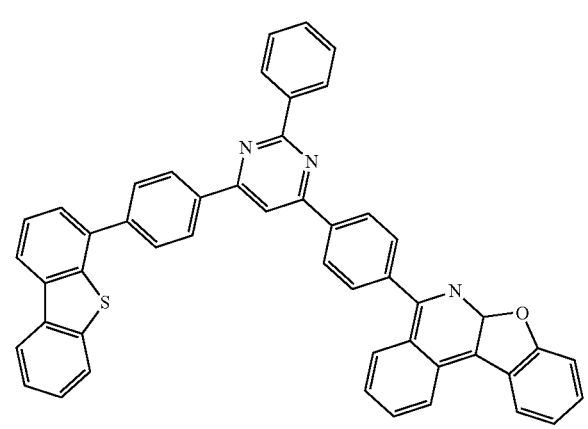
849

941
-continued
850
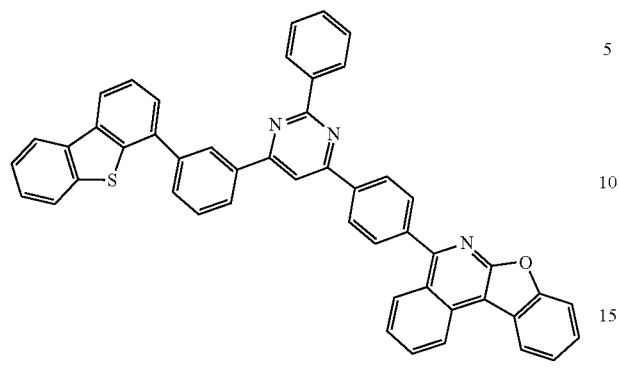
851
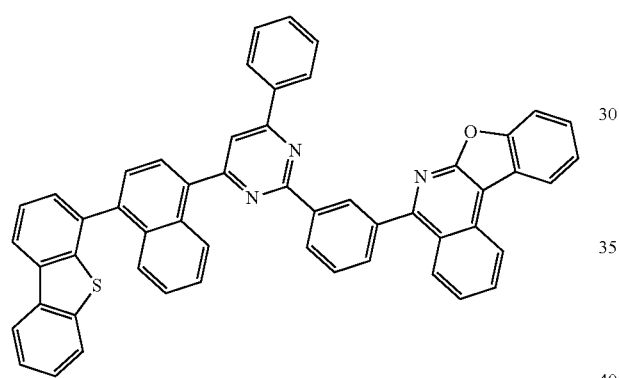
852
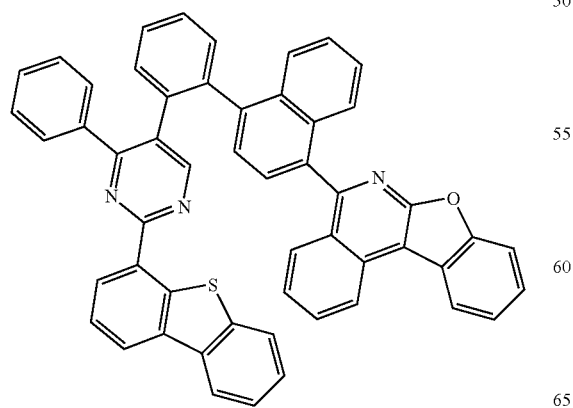
942
-continued
853
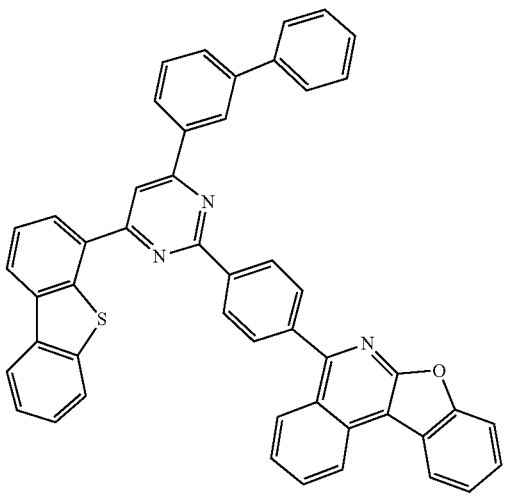
854
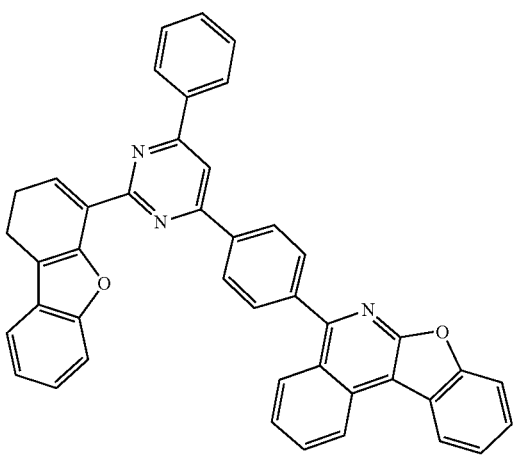
855
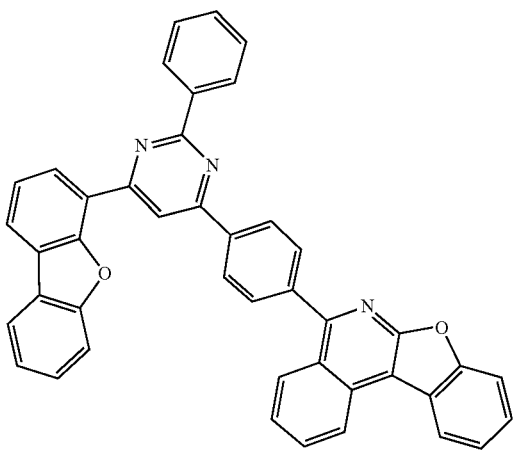

856
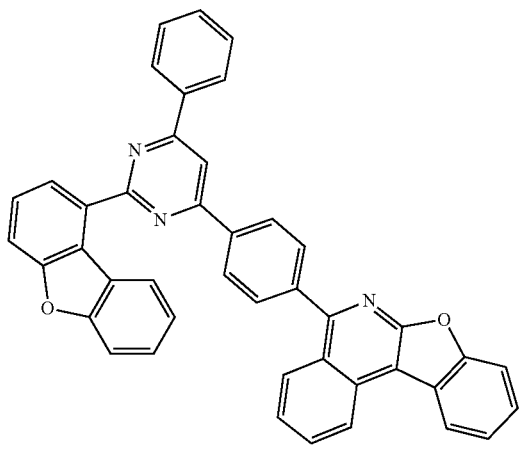
857
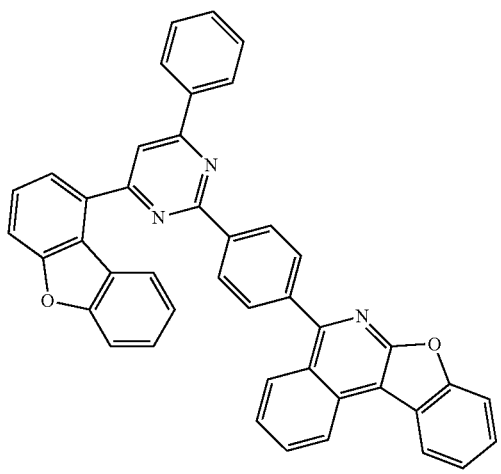
858
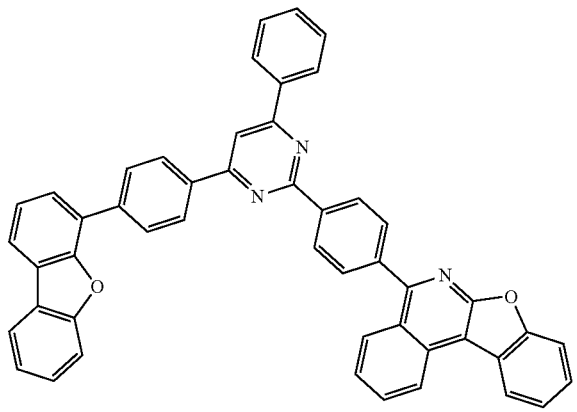
859
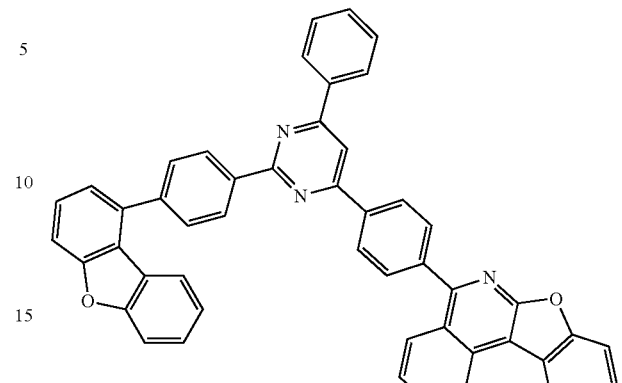
860
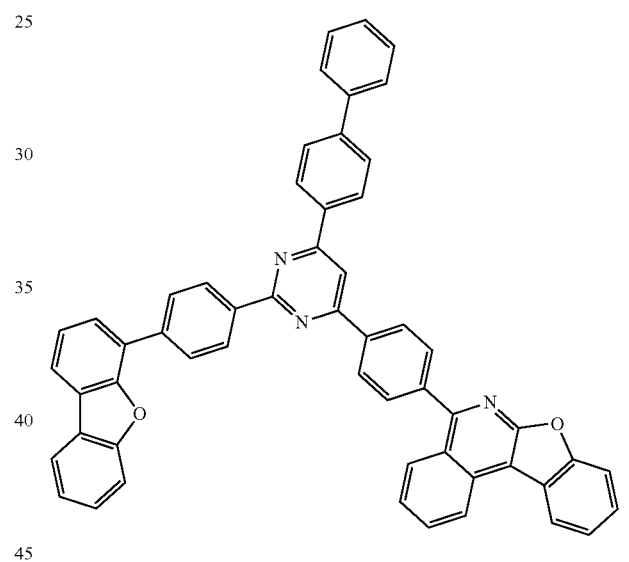
861
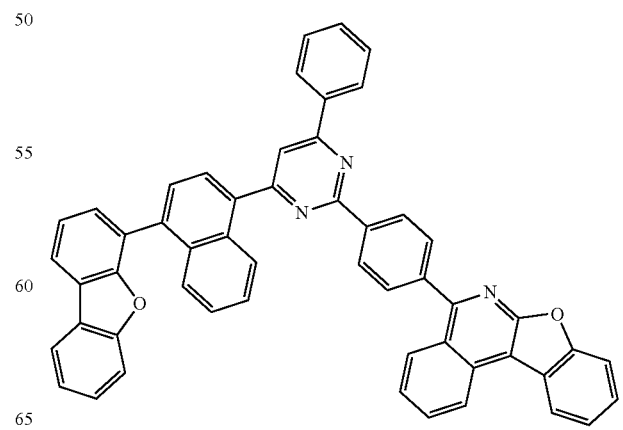

945
-continued
862
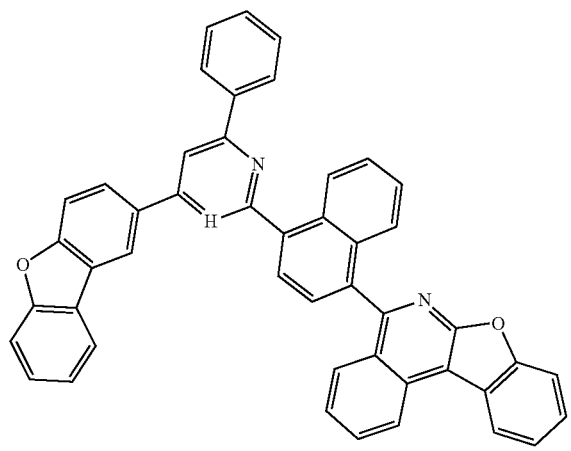
863
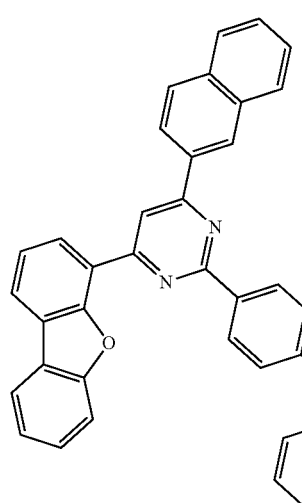
864
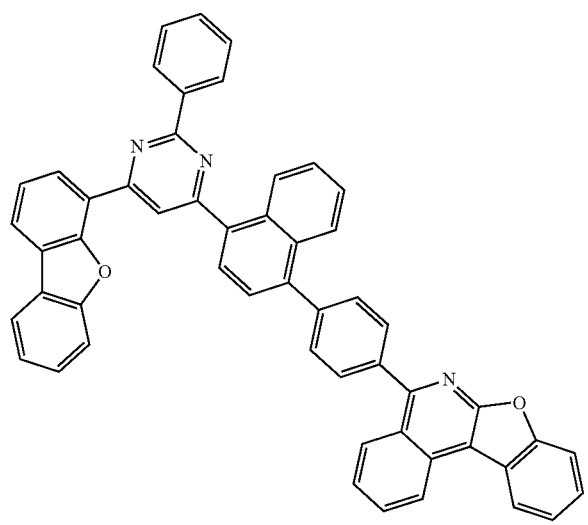
946
-continued
865
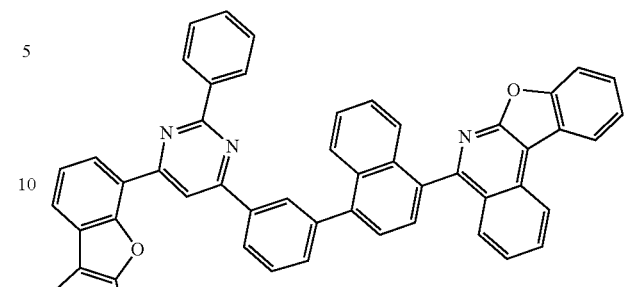
866
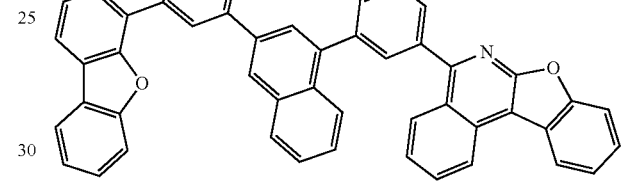
867
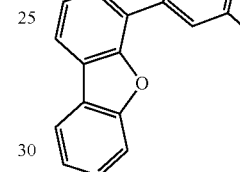
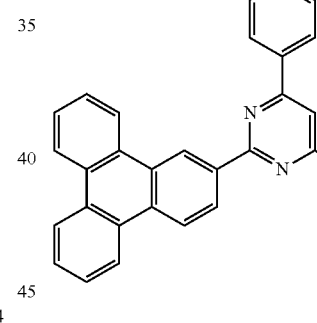
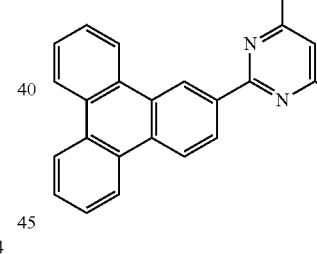
868
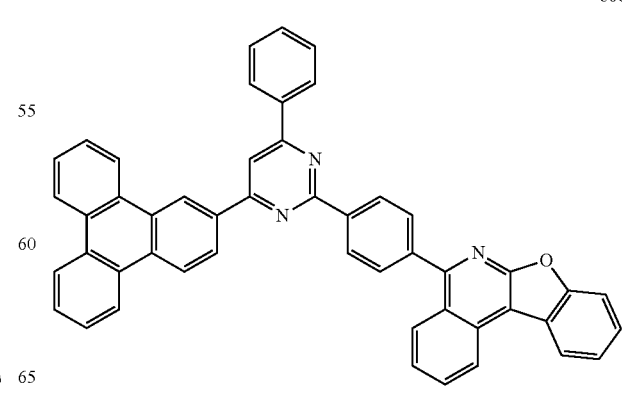
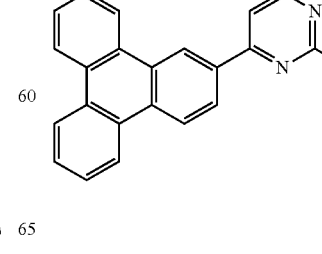
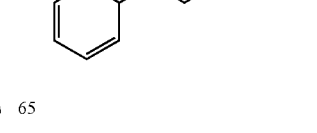

947
-continued
869
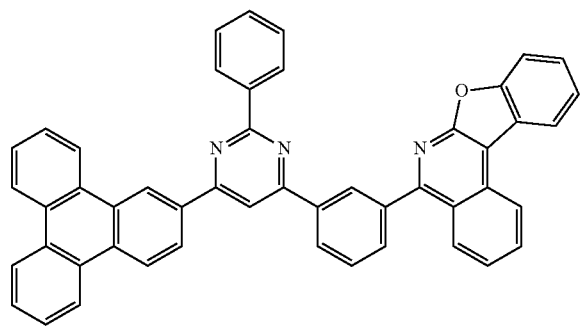
870
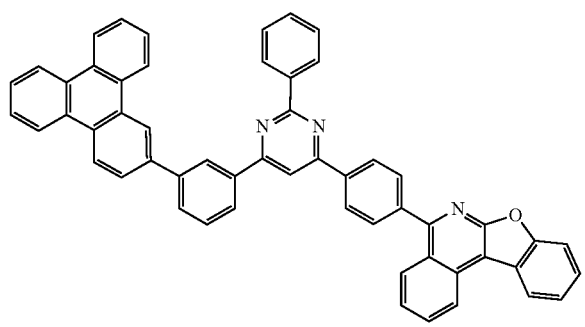
871
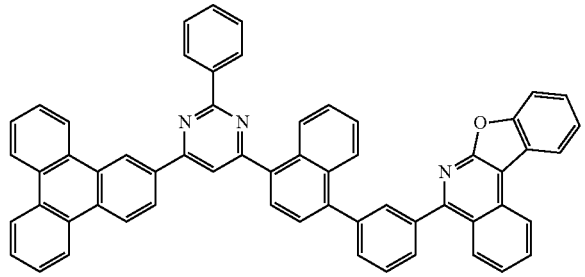
872
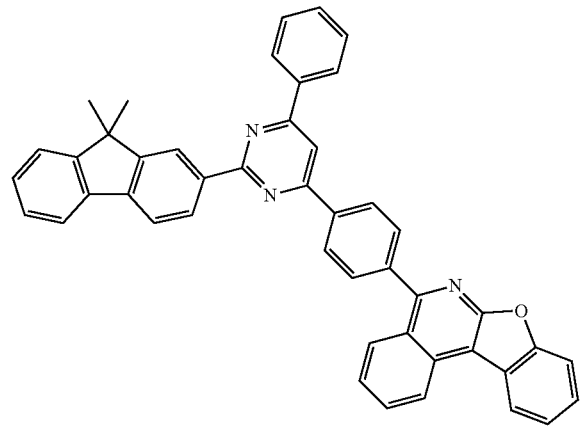
948
-continued
873
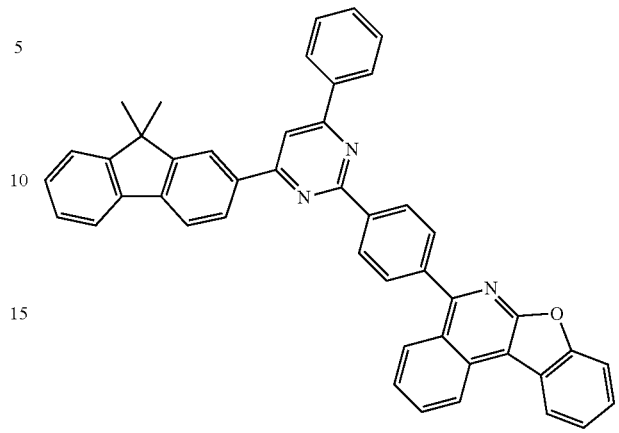
874
875
876
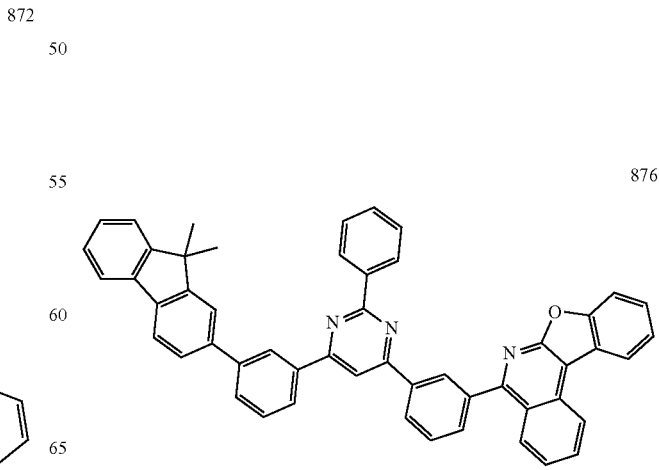

877
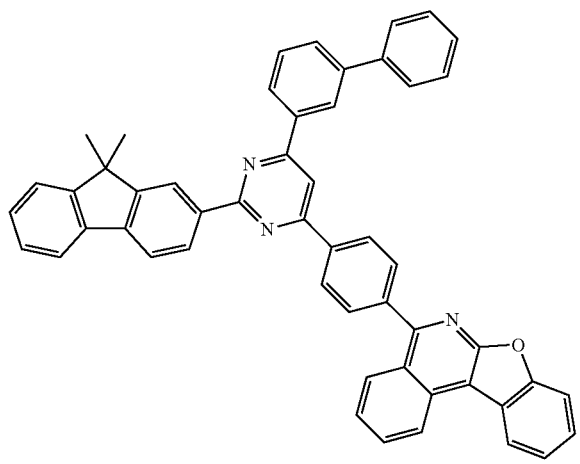
878
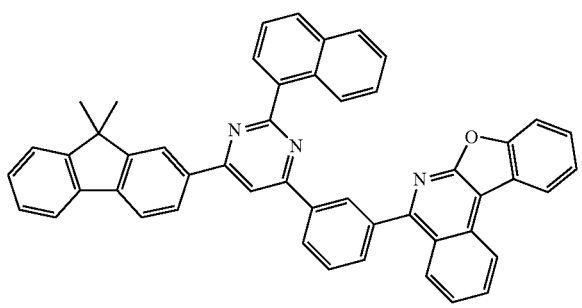
879
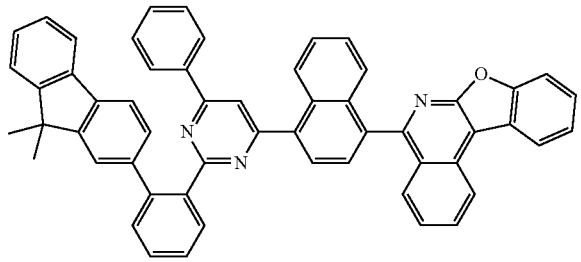
880
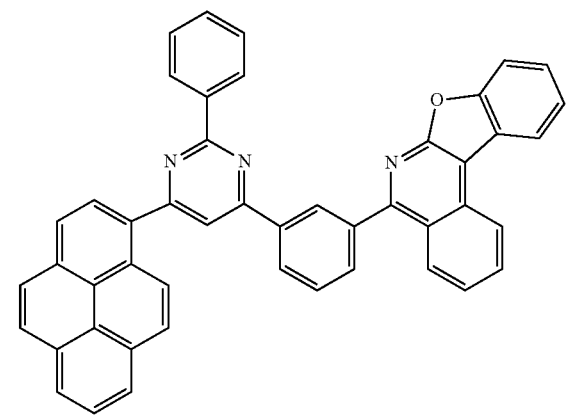
881
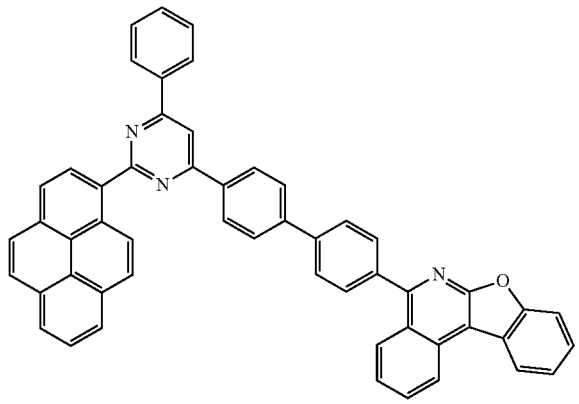
882
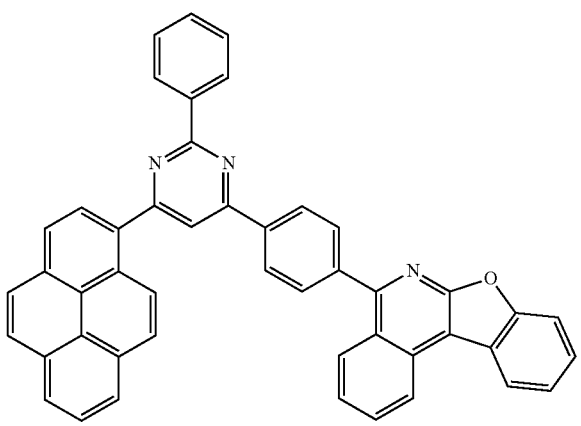
883
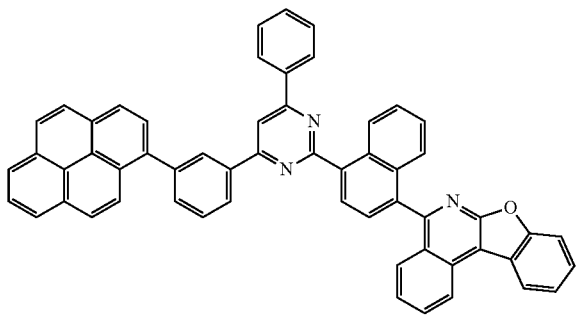
884
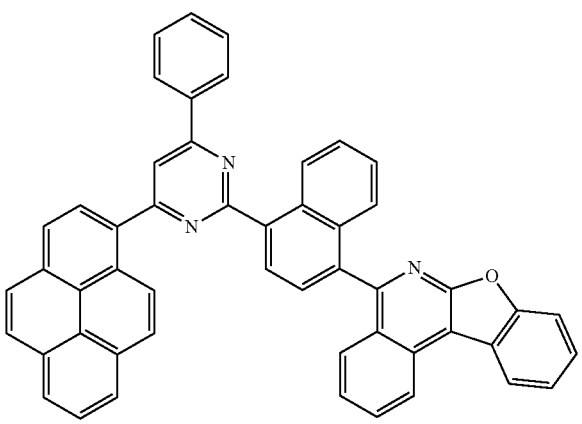

951
-continued
885
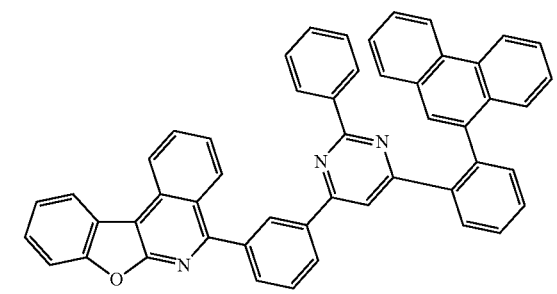
886
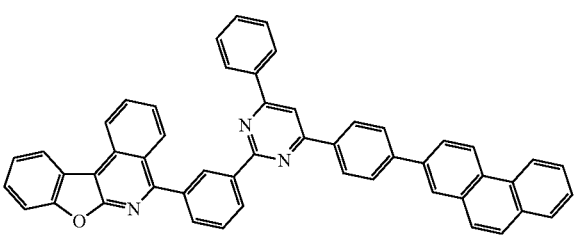
887
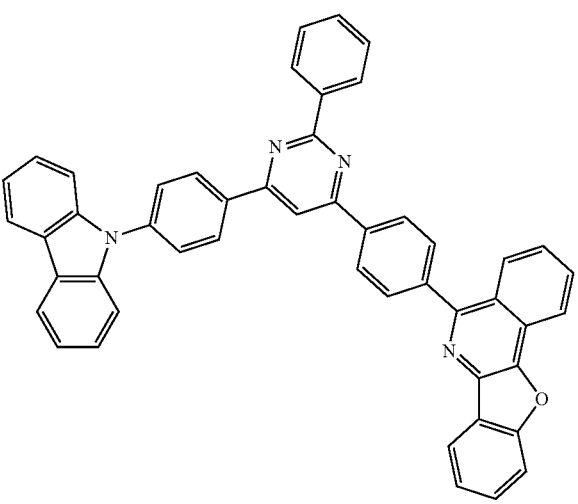
888
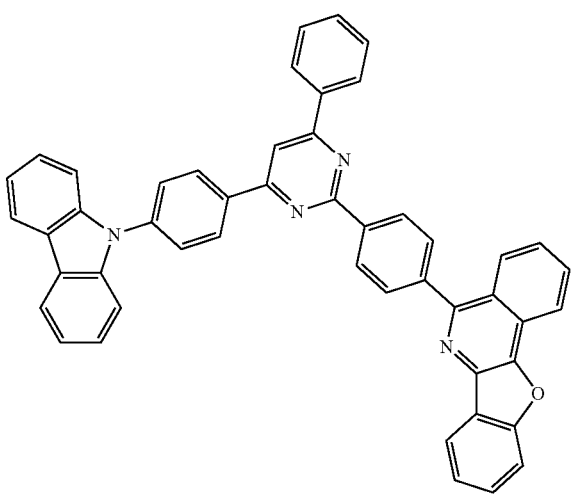
952
-continued
889
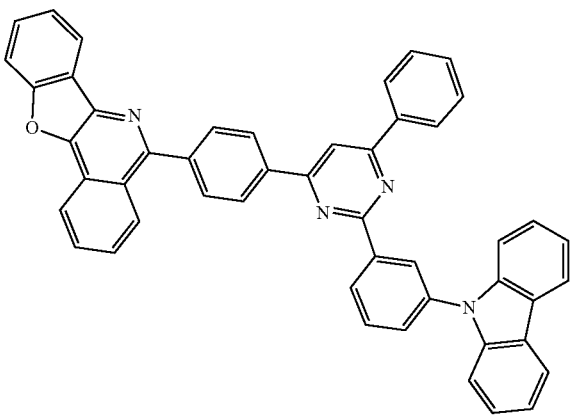
890
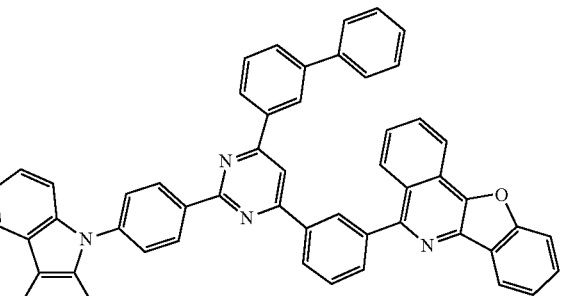
891
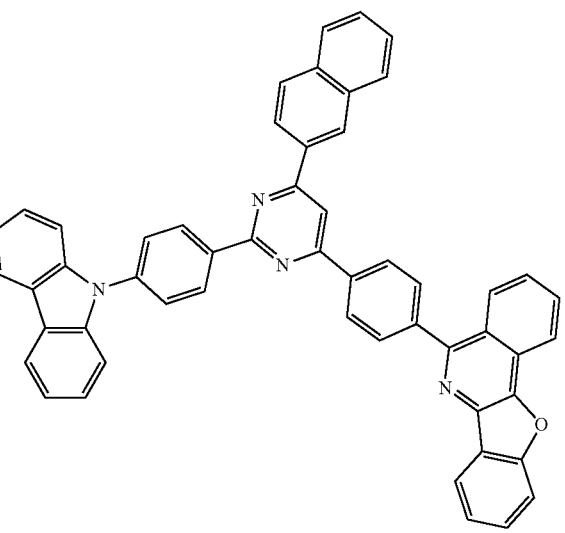

892
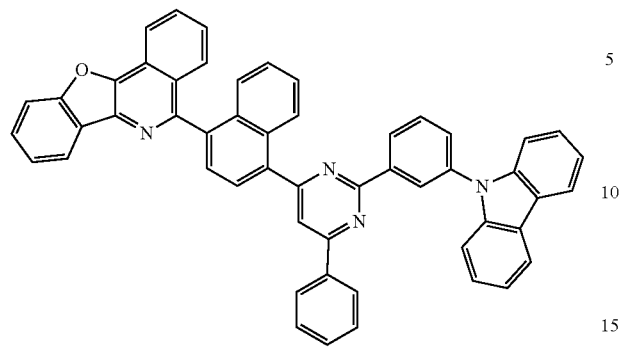
893
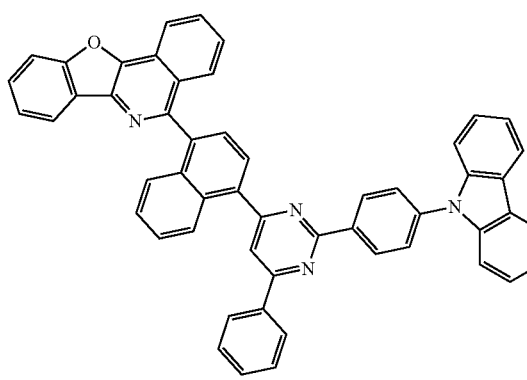
894
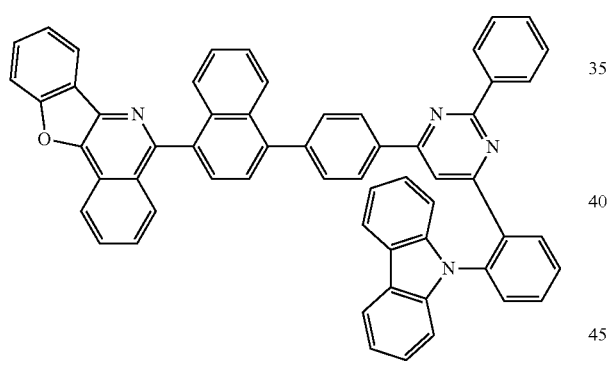
895
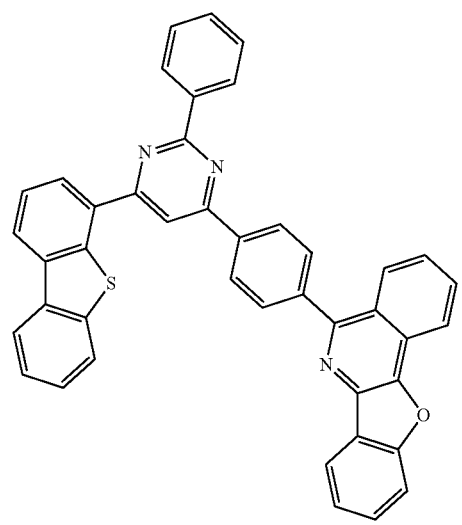
896
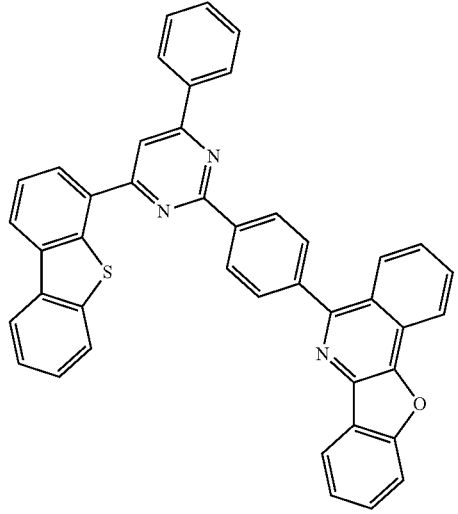
897
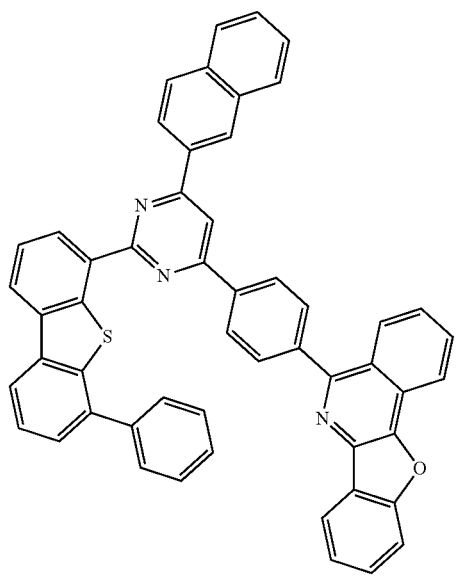
898
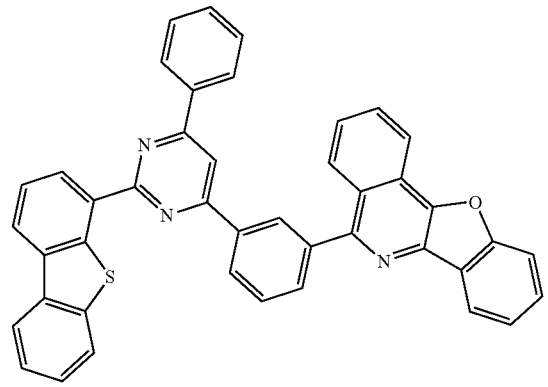

955
-continued
899
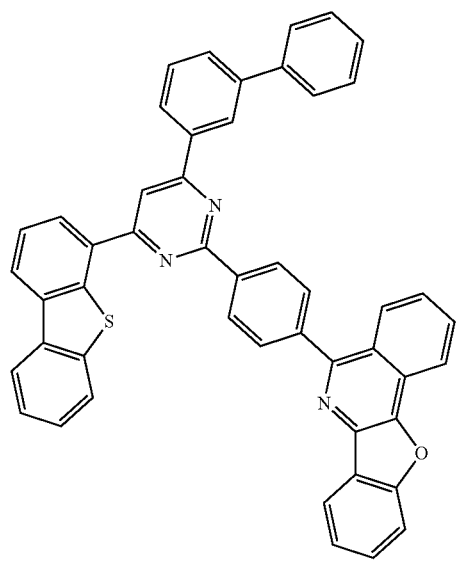
900
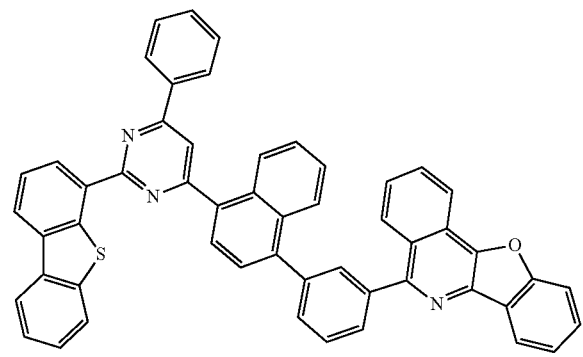
901
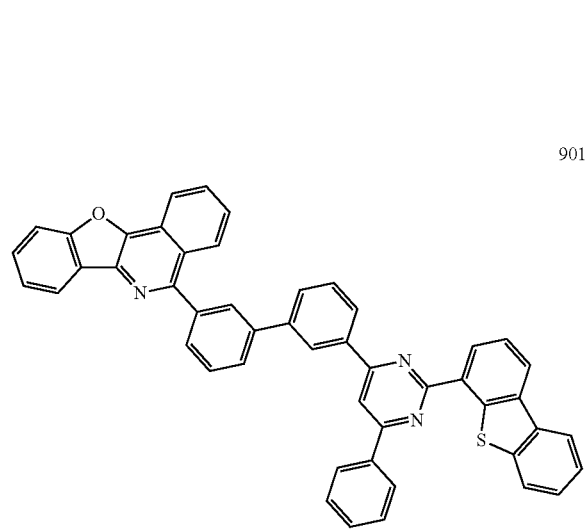
956
-continued
902
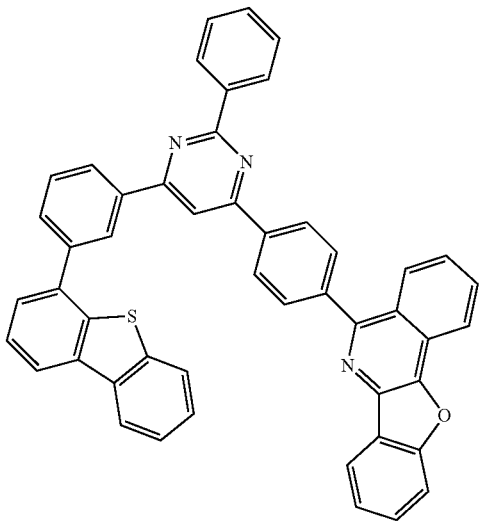
903
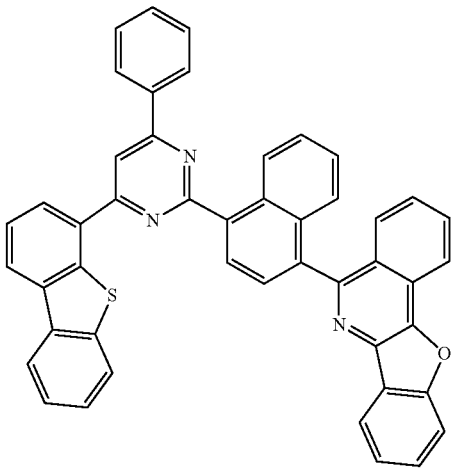
904
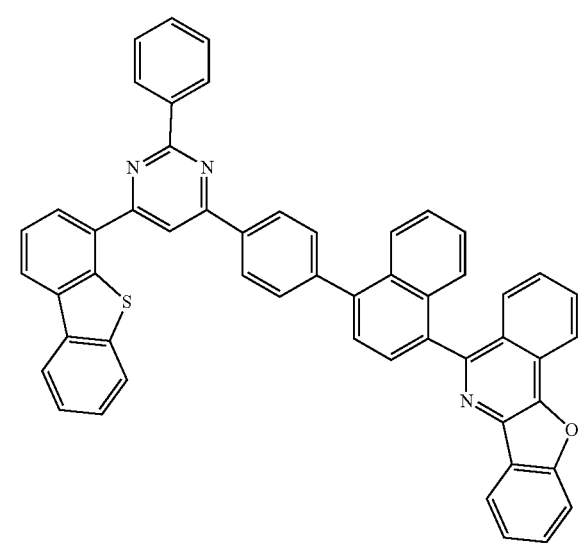

-continued
905
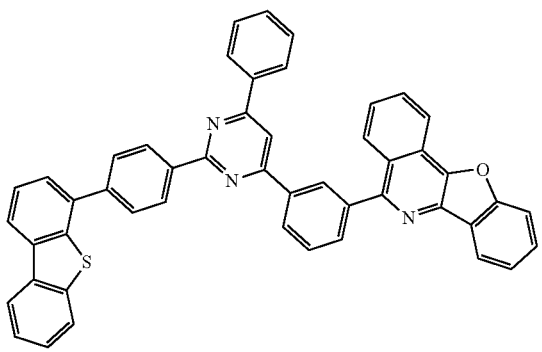
906
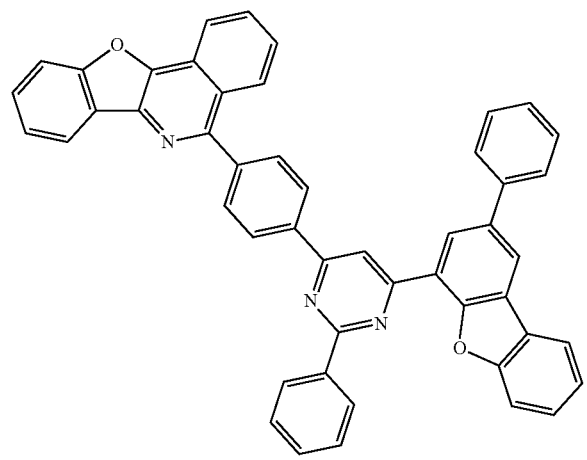
907
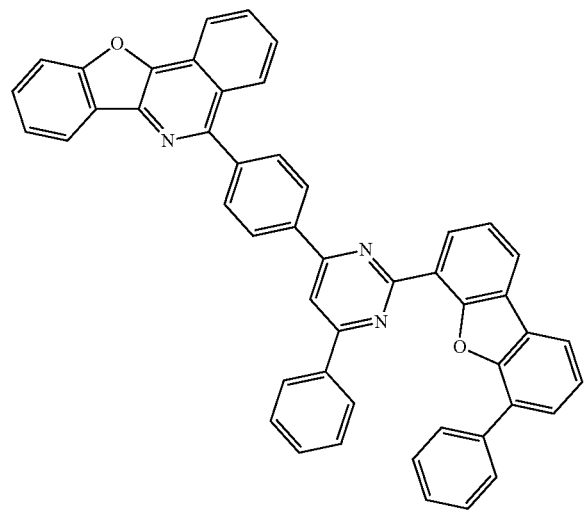
-continued
908
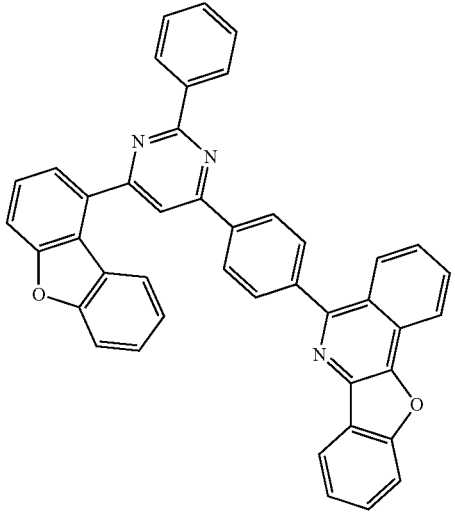
909
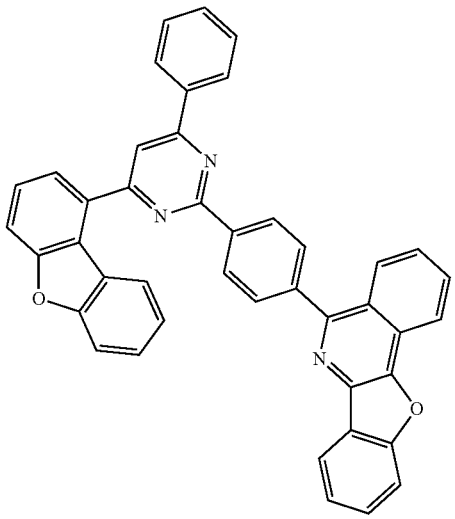
910
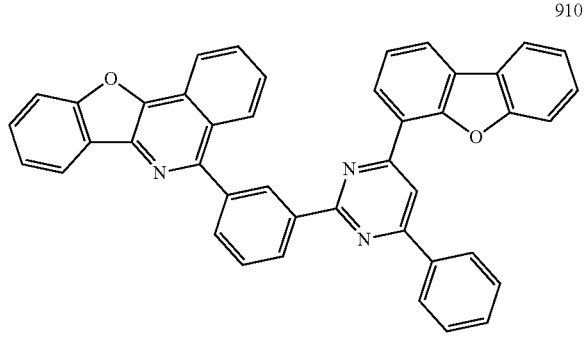

959
-continued
960
-continued
911
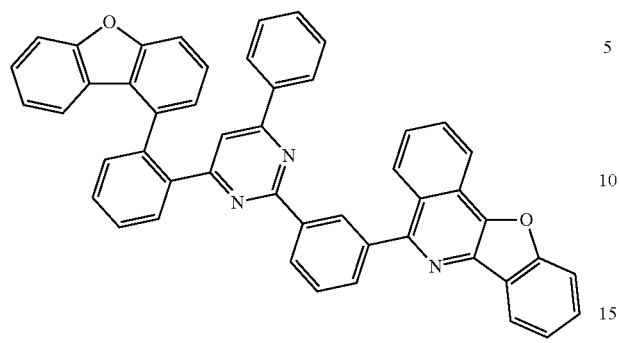
914
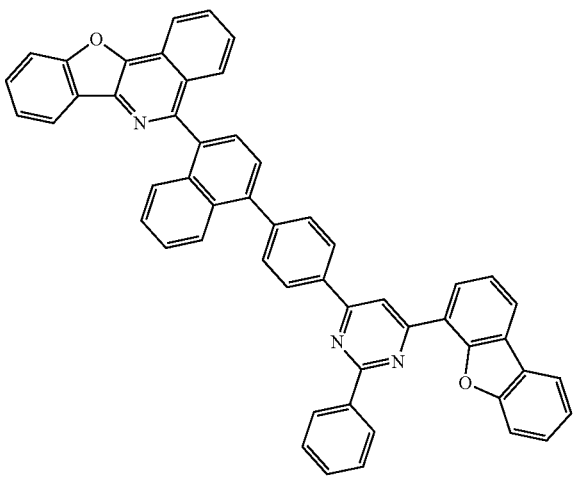
912
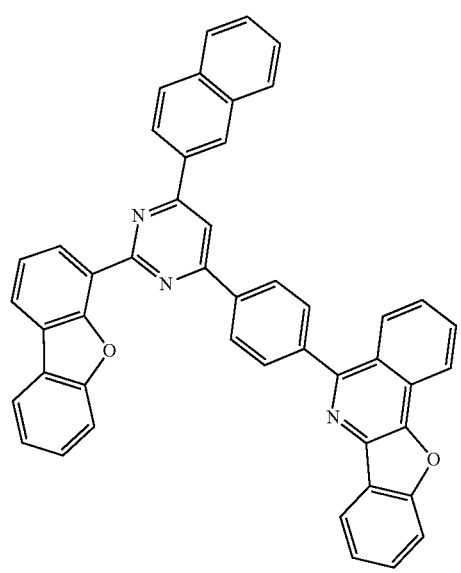
915
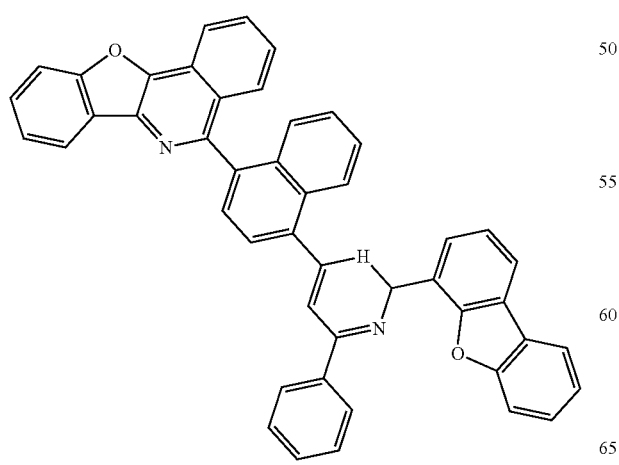
913
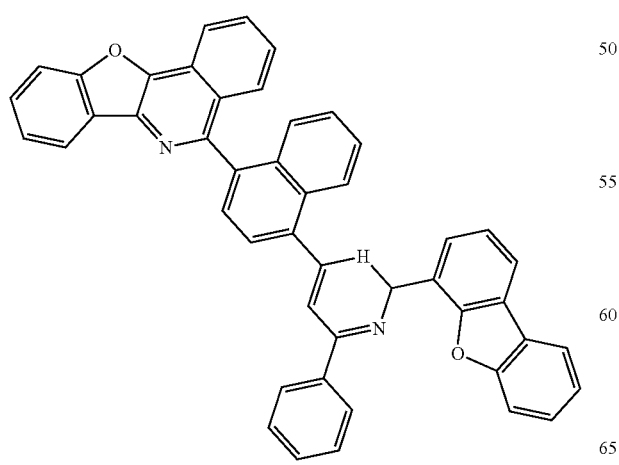
916
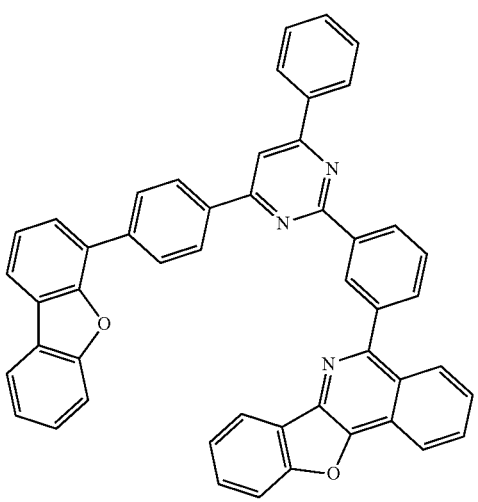

917
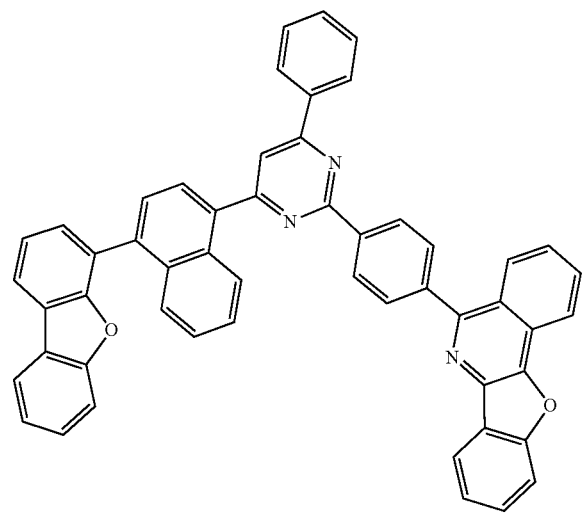
918
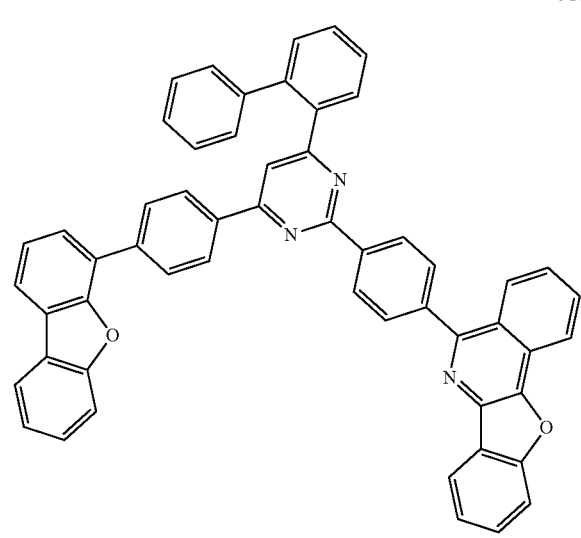
919
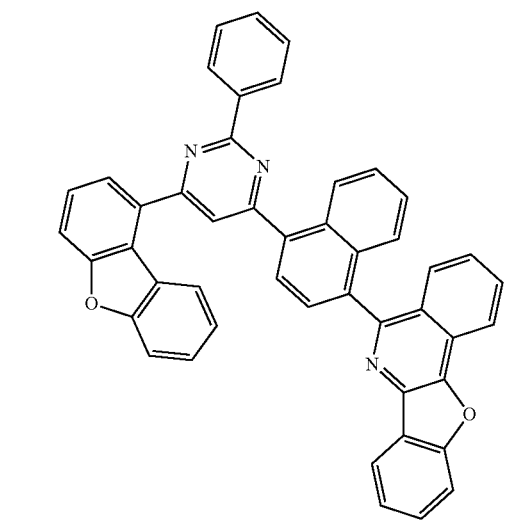
920
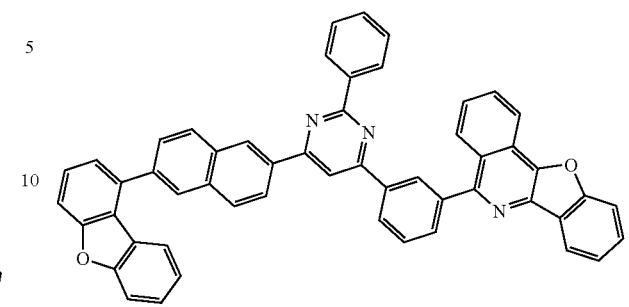
921
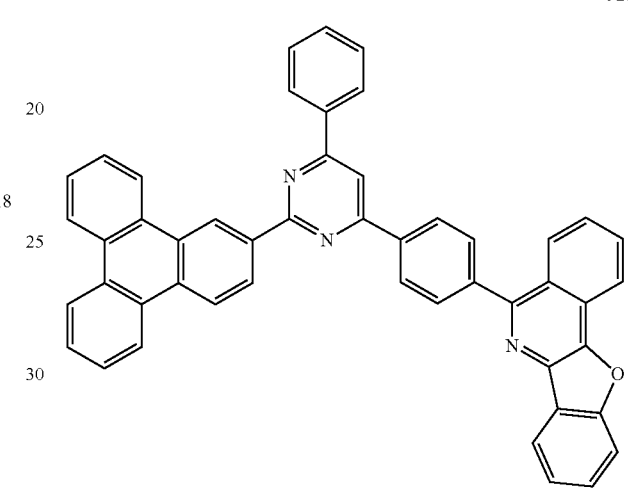
922
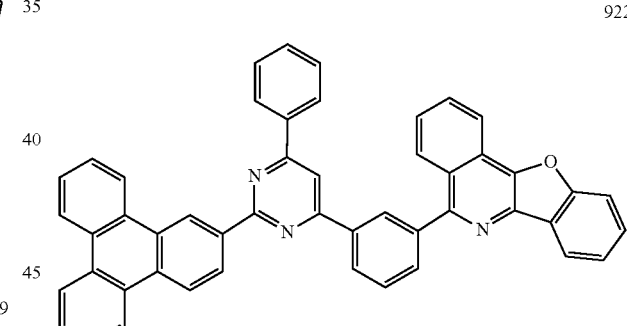
923
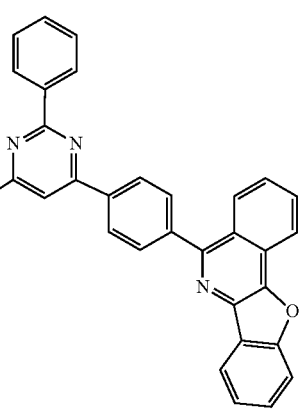

963
-continued
924
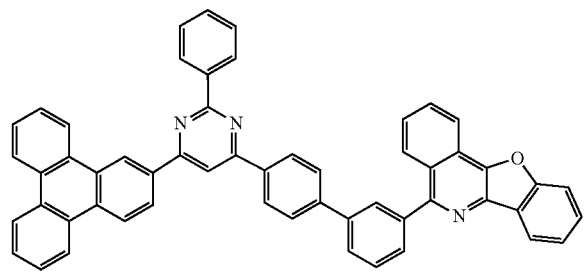
925
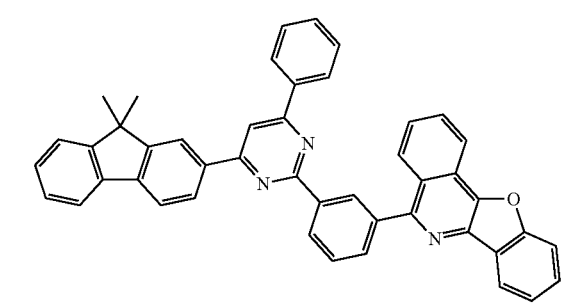
926
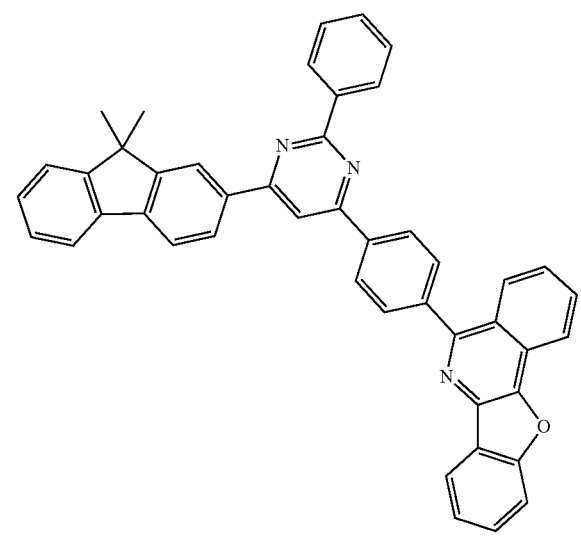
927
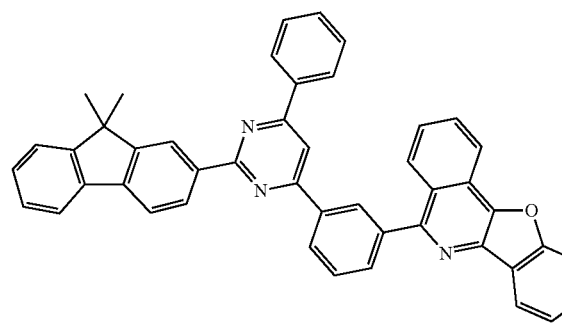
964
-continued
928
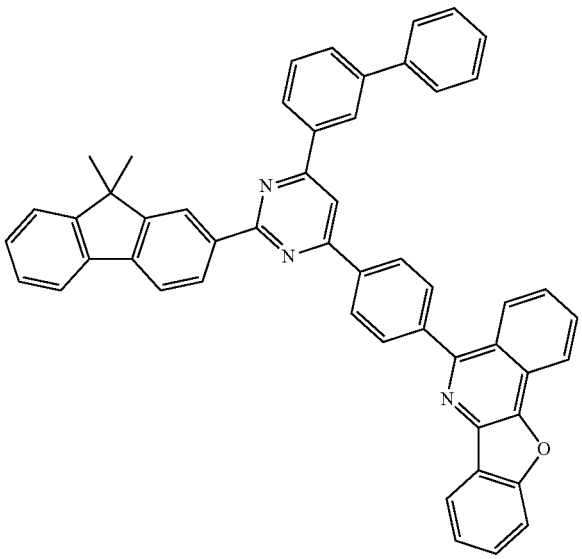
929
930

965
-continued
931
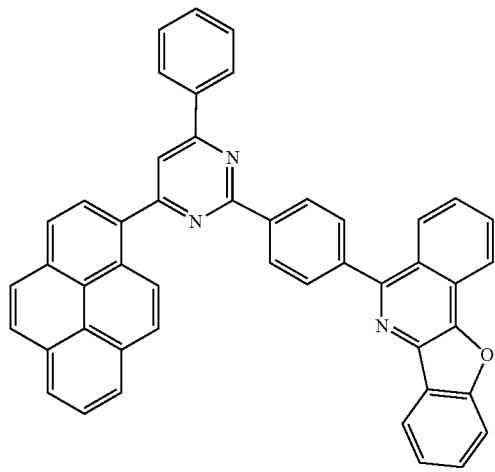
932
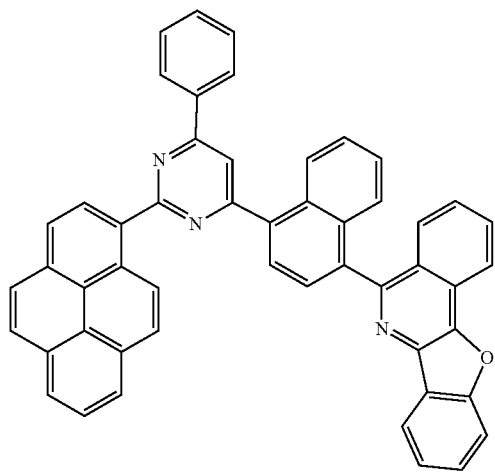
933
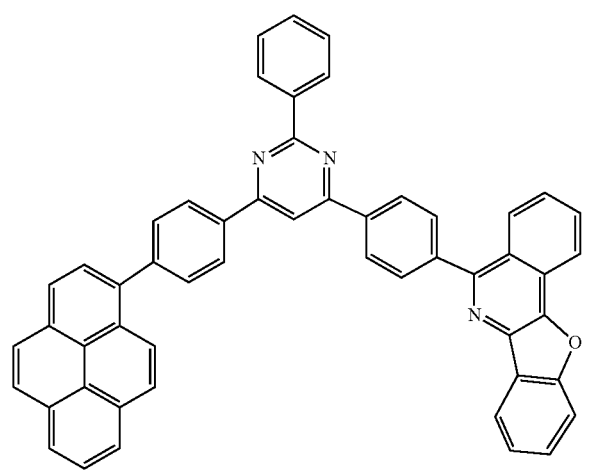
966
-continued
934
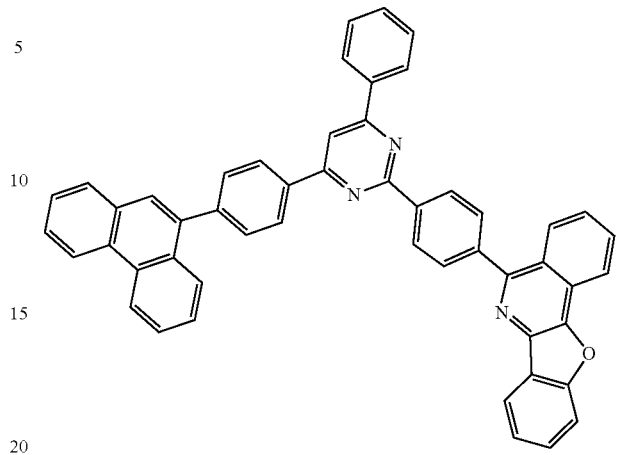
935
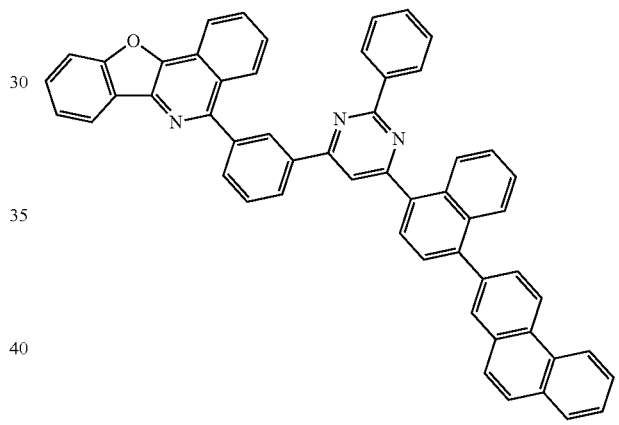
936
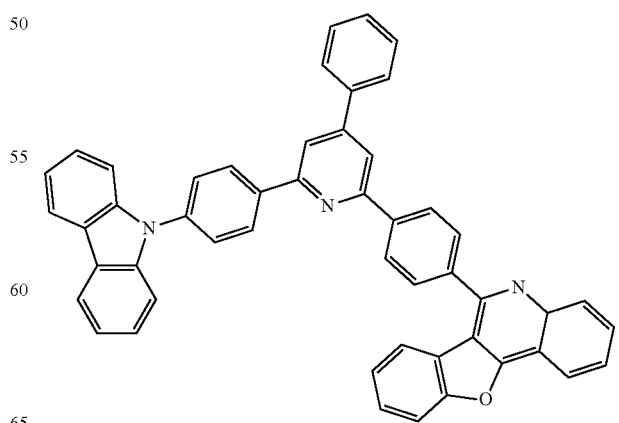

937
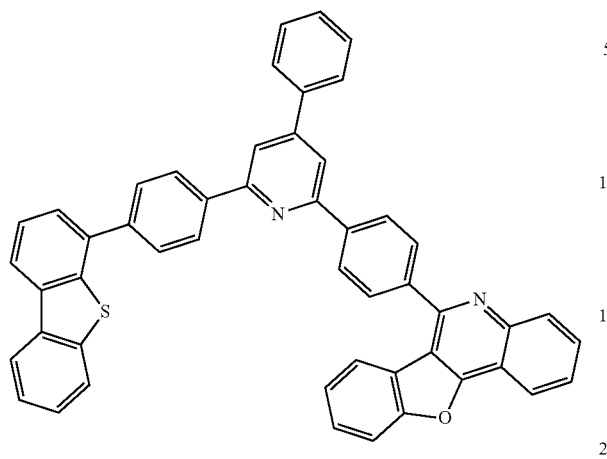
938
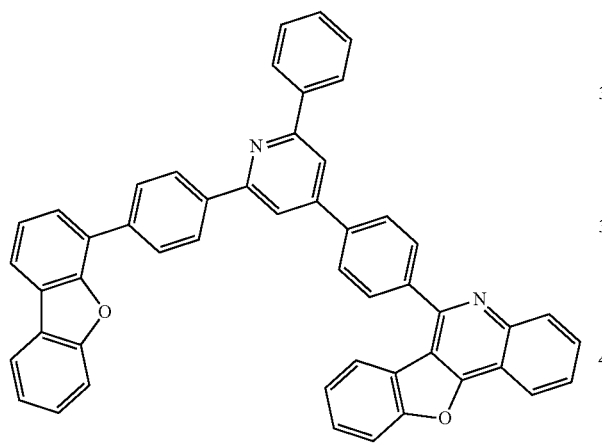
939
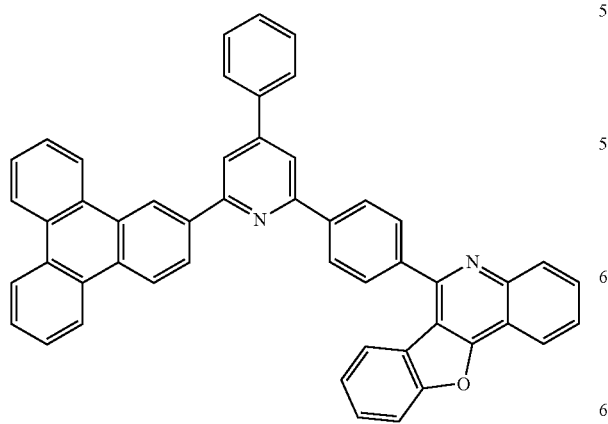
940
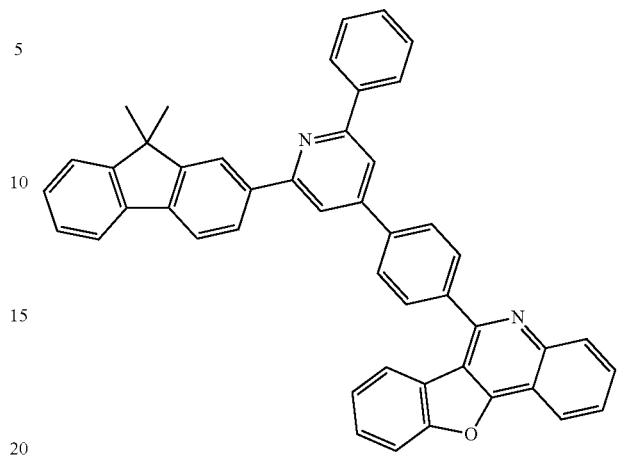
941
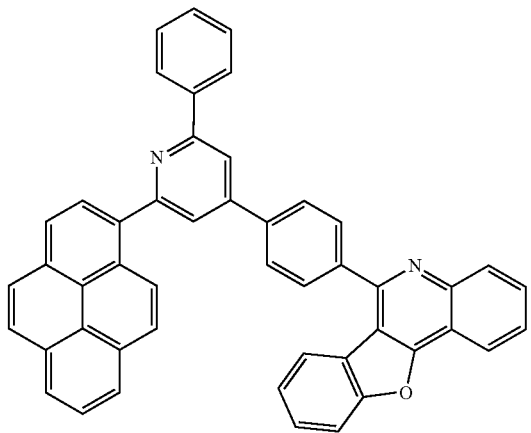
942
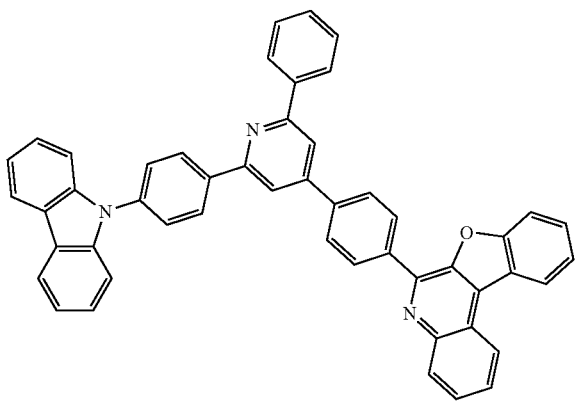

969 -continued
943
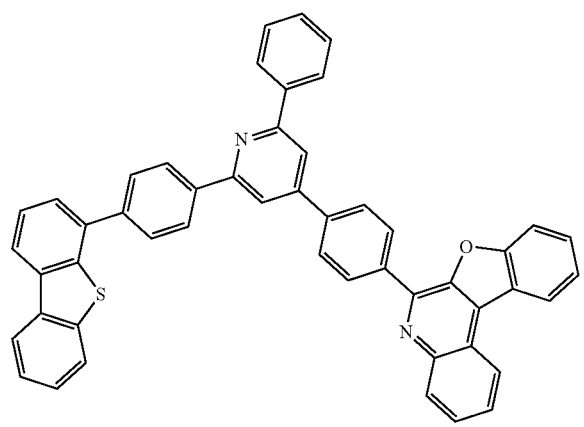
944
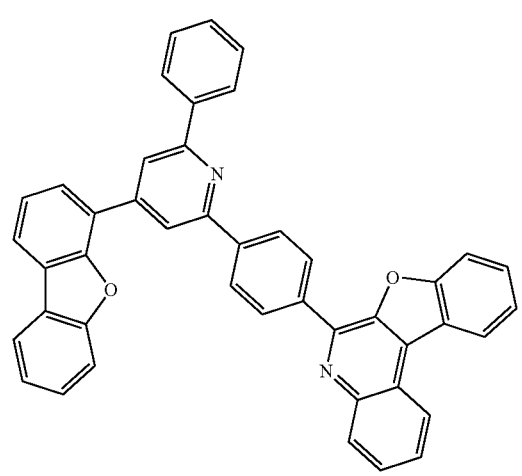
945
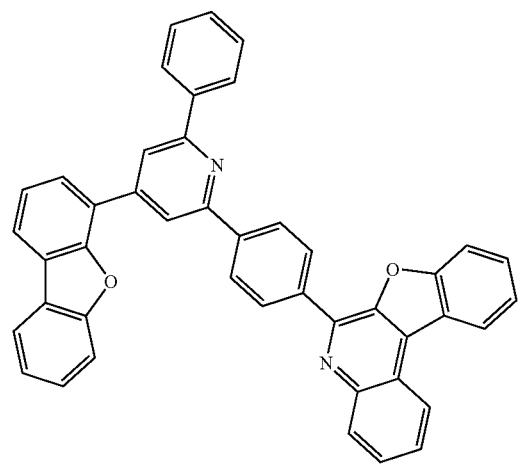
970 -continued
946
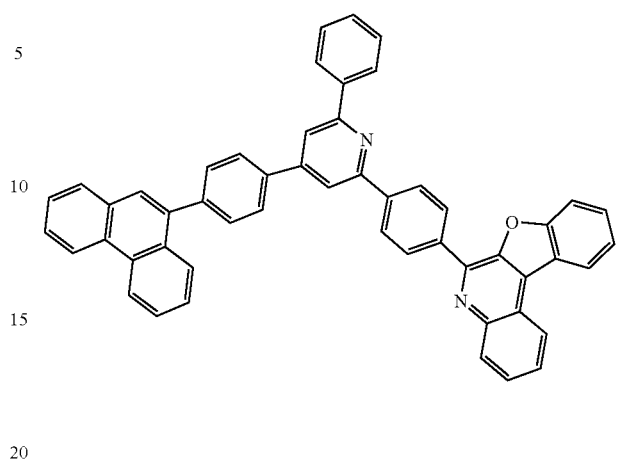
947
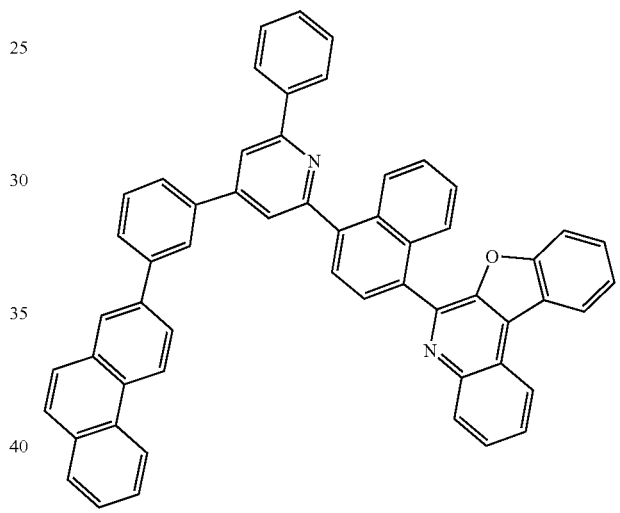
948
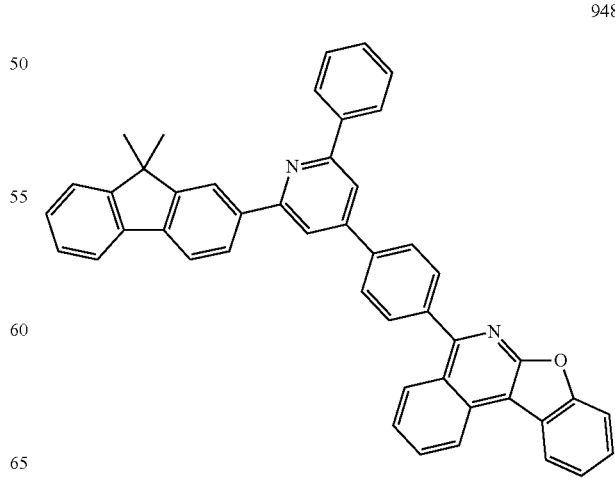

-continued
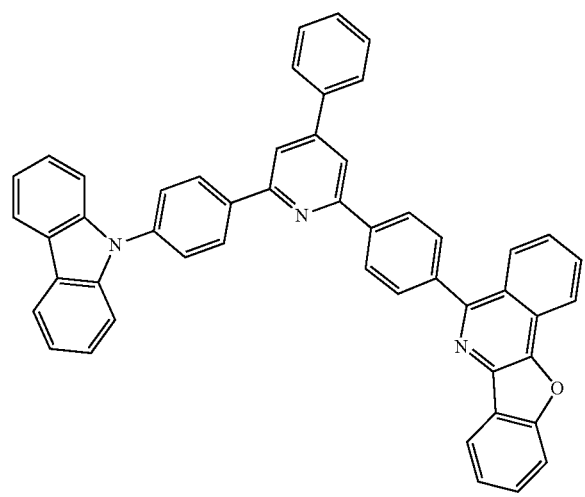
949
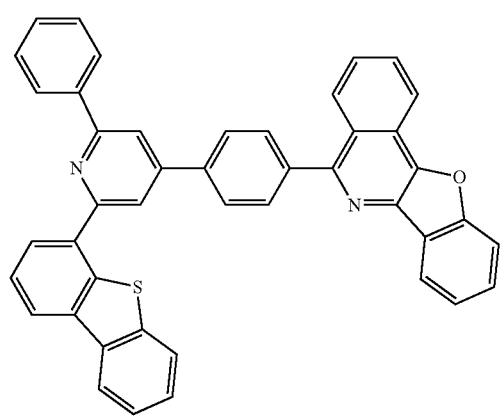
950
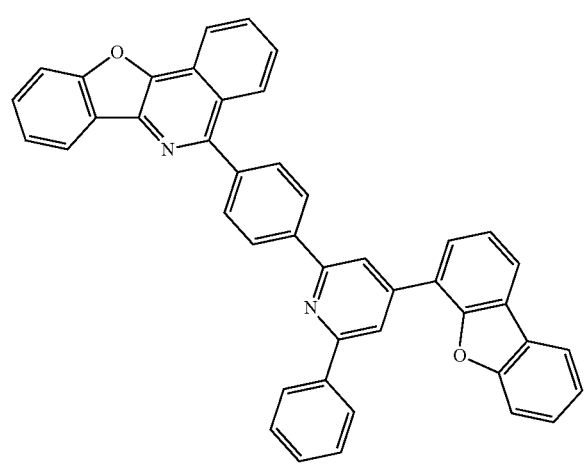
951
9. The compound of claim 1, wherein the compound represented by Chemical Formula 1 is any one of compounds of the following Group III:
[Group III]
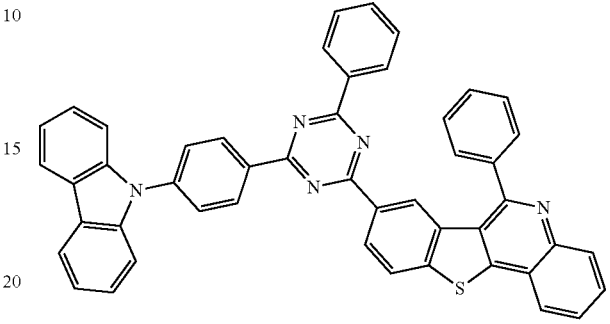
952
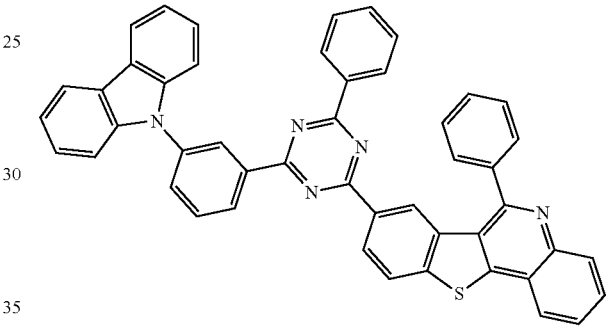
953
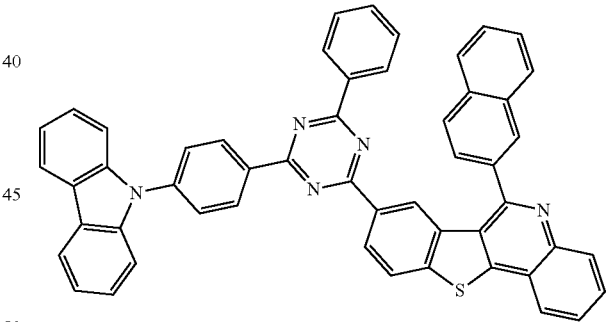
954
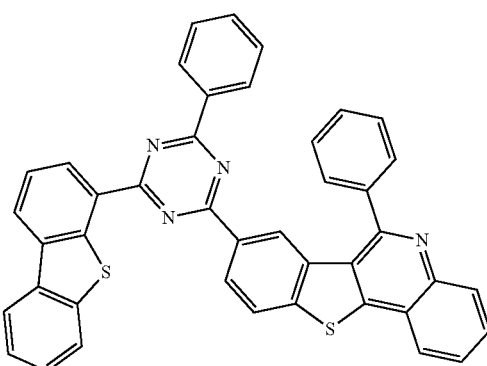
955

956
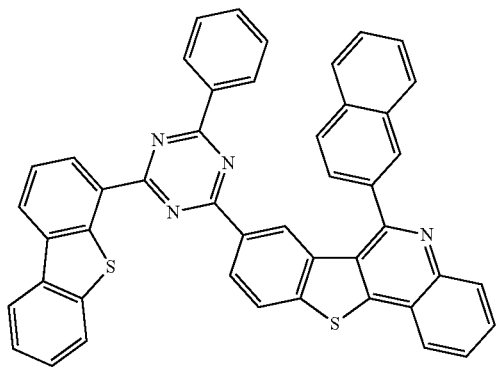
957
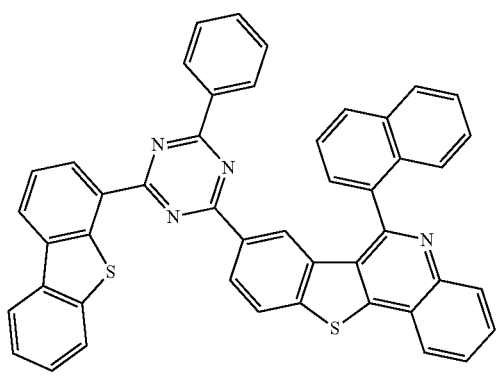
958
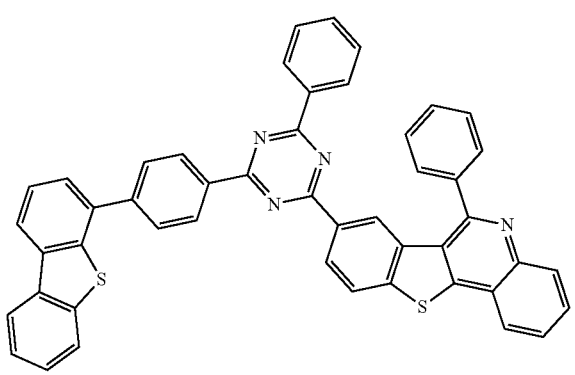
959
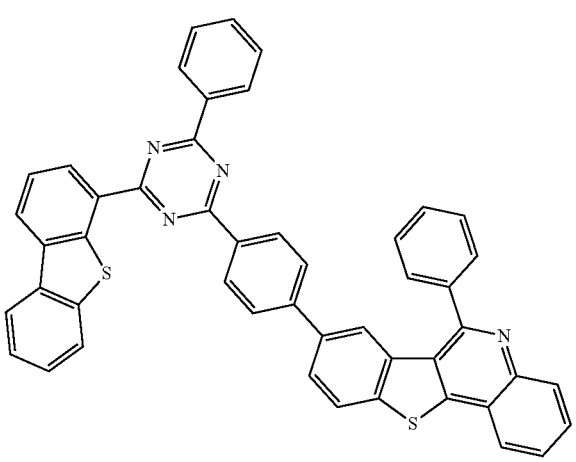
960
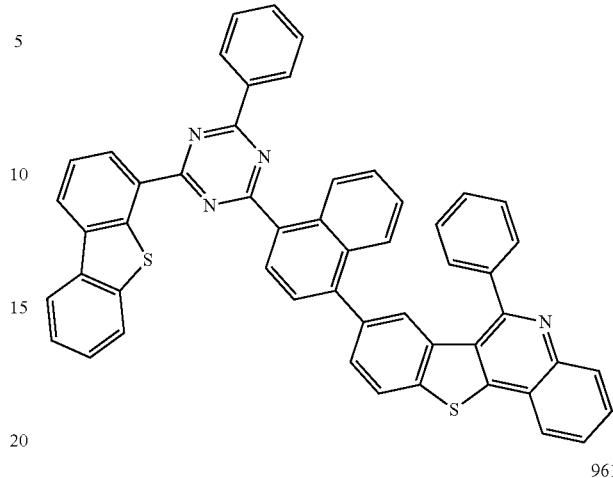
961
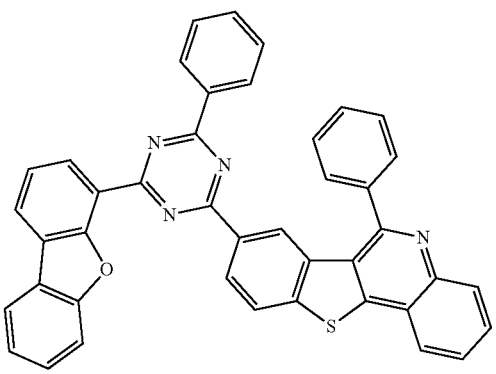
962
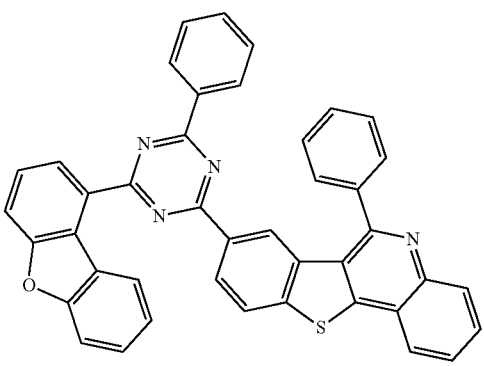
963
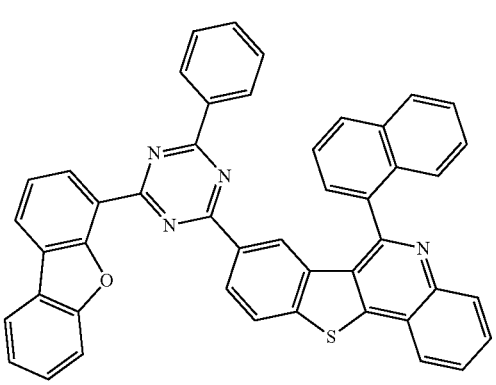

-continued
964
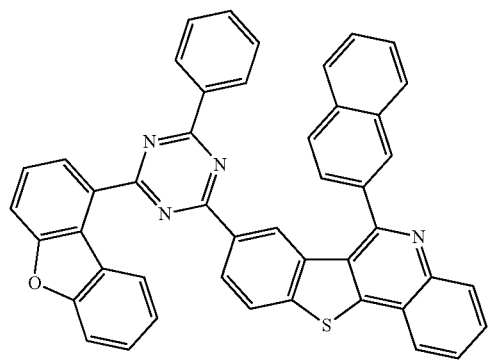
965
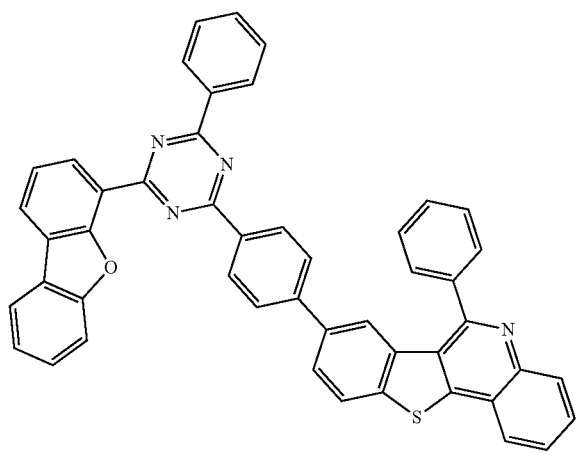
966
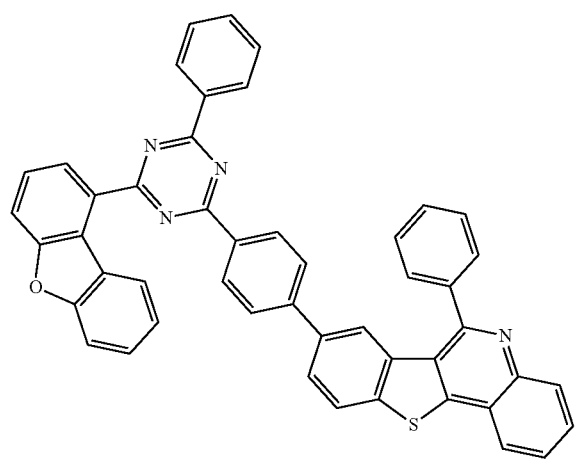
-continued
967
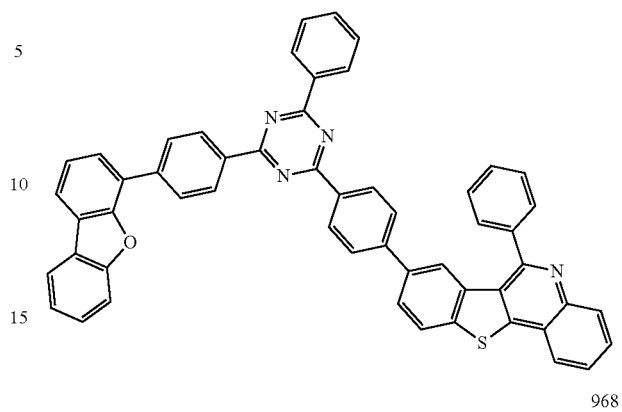
968
969
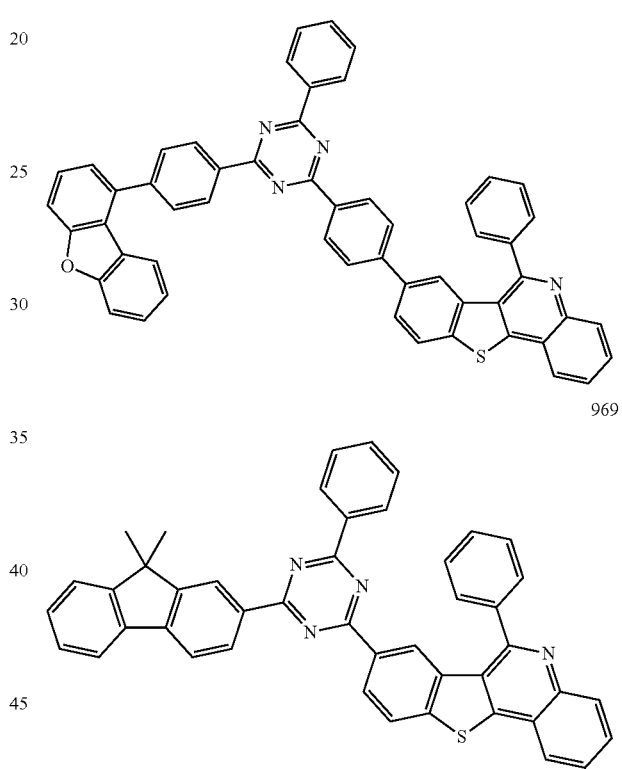
970
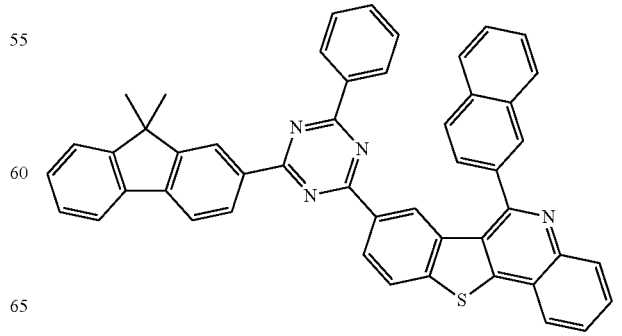

-continued
971
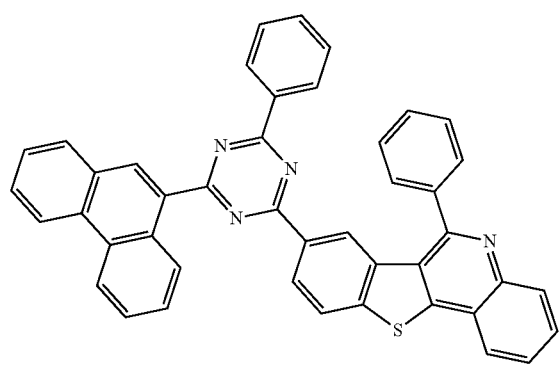
972
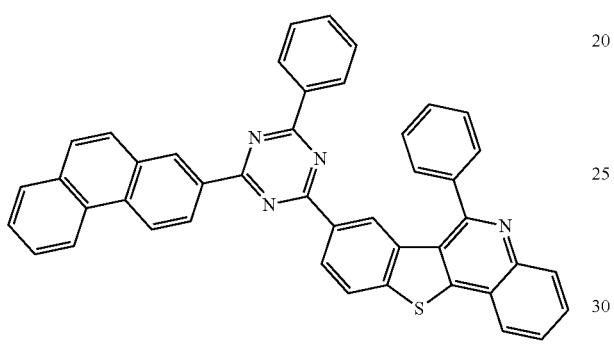
973
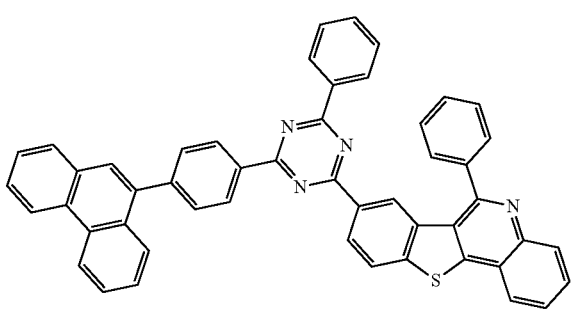
974
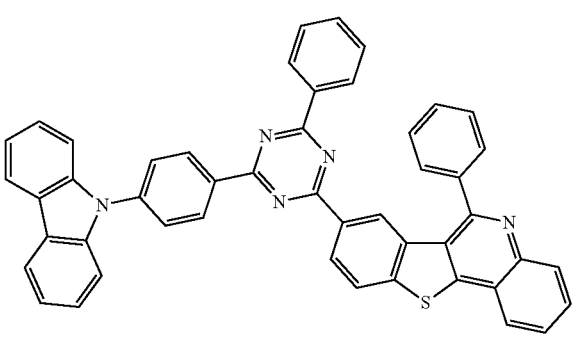 [SMILES: c1ccc(-c2nc(-c3ccc(-n4c5ccccc5c5ccccc54)cc3)nc(-c3ccc4oc5c6ccccc6nc(-c6ccccc6)c5c4c3)n2)cc1]
-continued
975
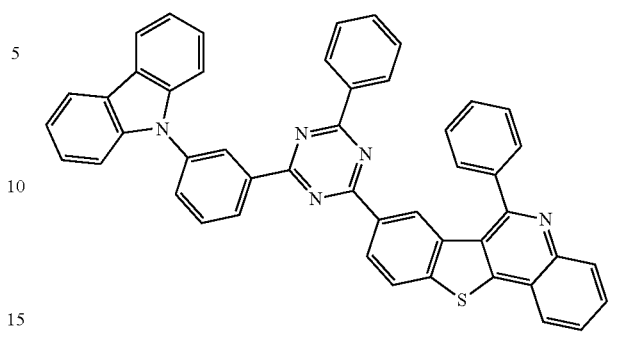
976
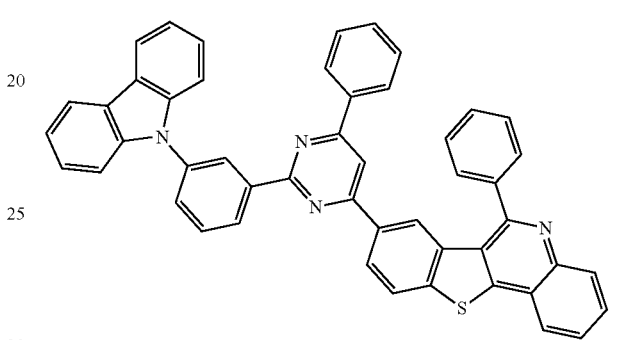
977
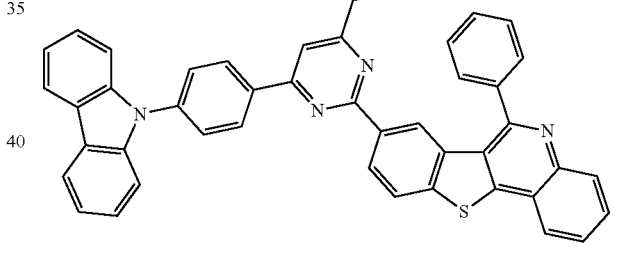
978
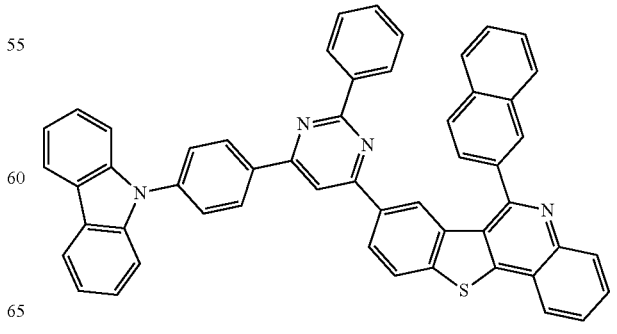

-continued
979
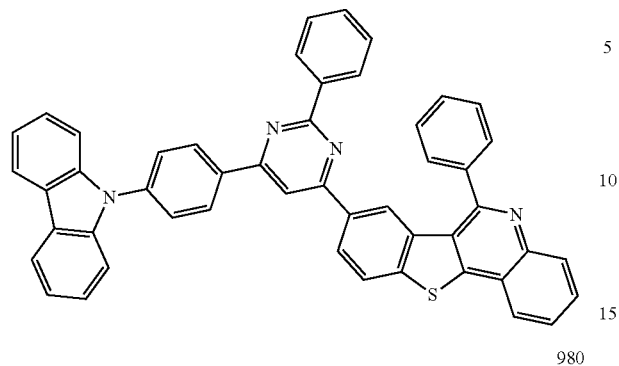
980
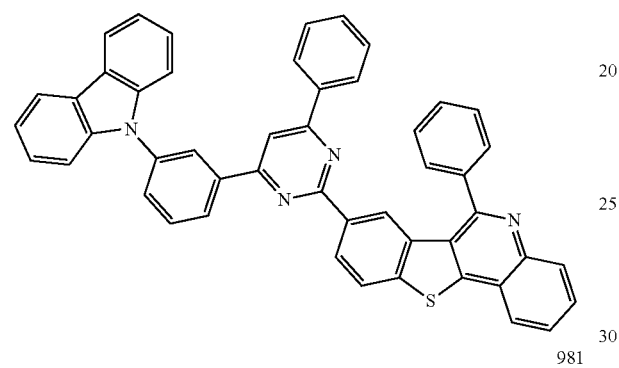
981
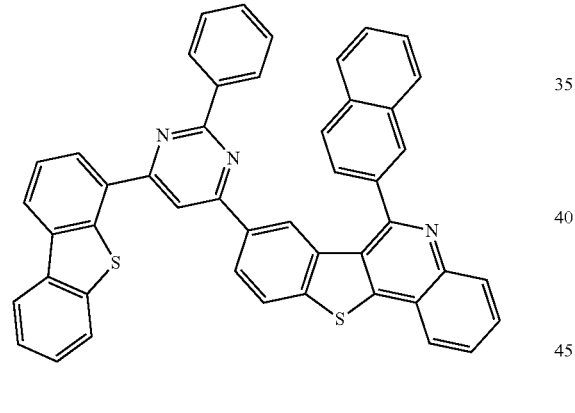
982
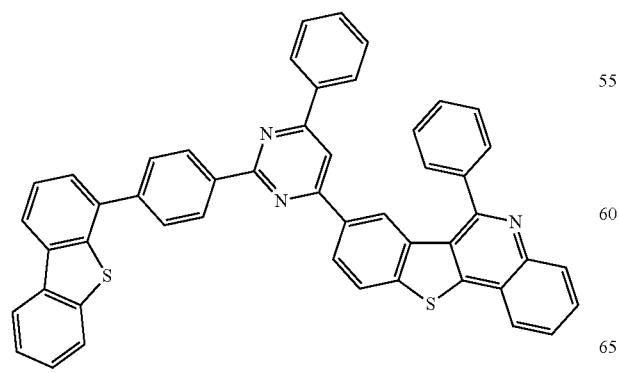
-continued
983
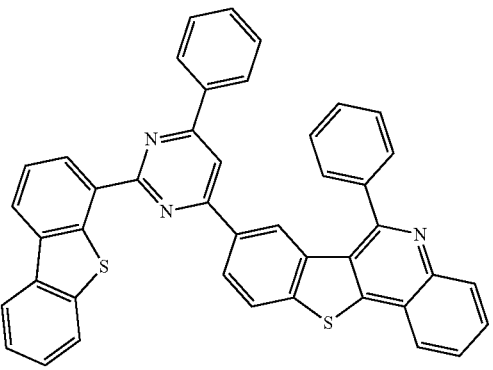
984
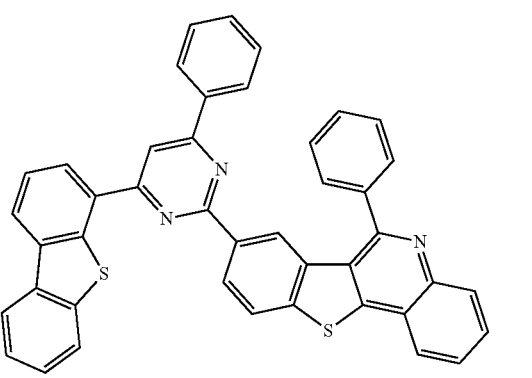
985
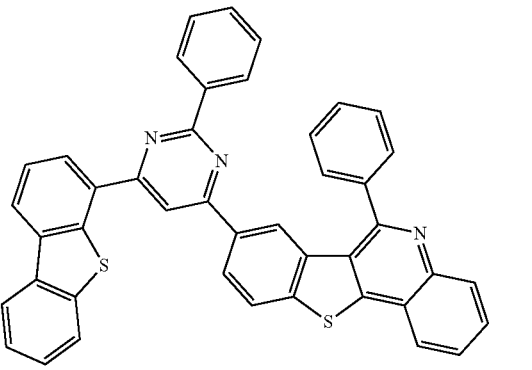
986
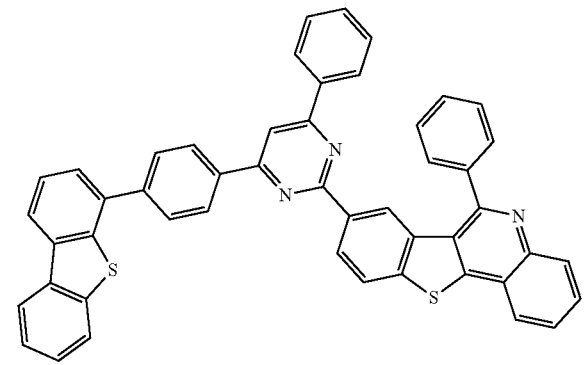

-continued
987
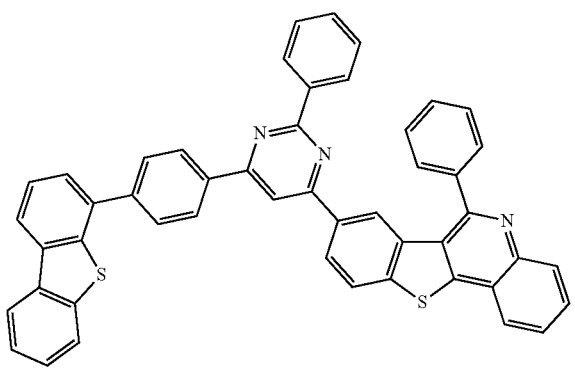
988
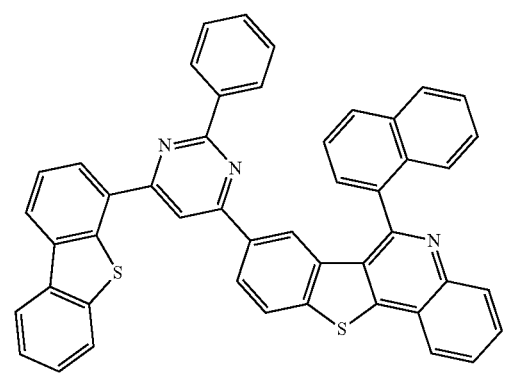
989
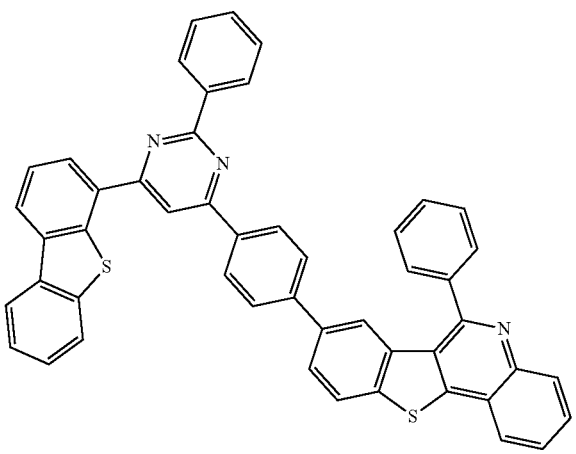
-continued
990
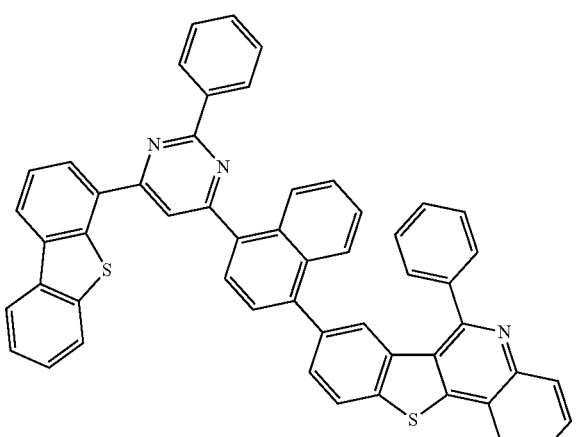
991
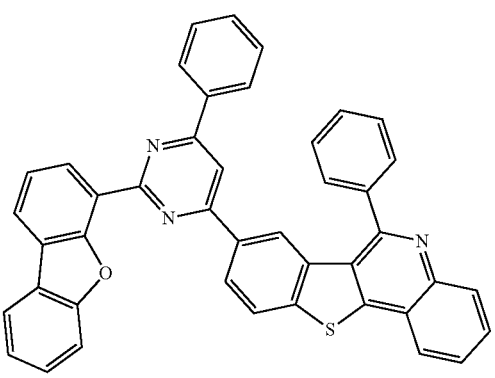
992
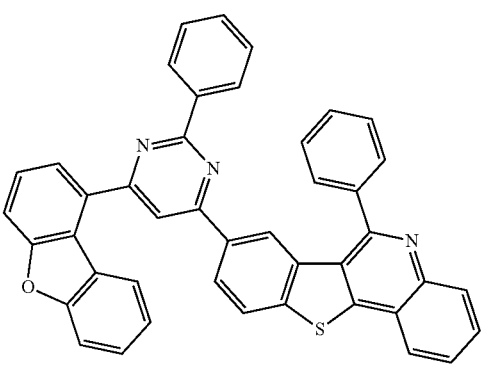
993
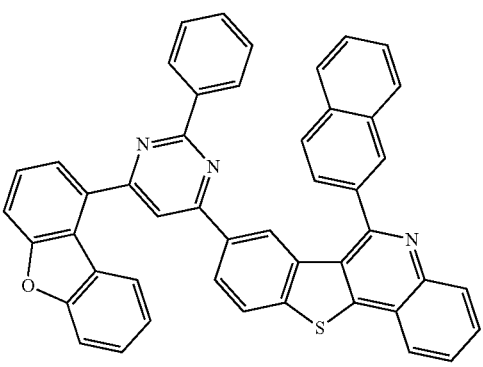

983
-continued
994
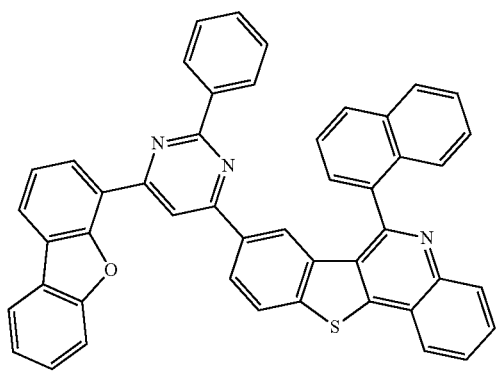
995
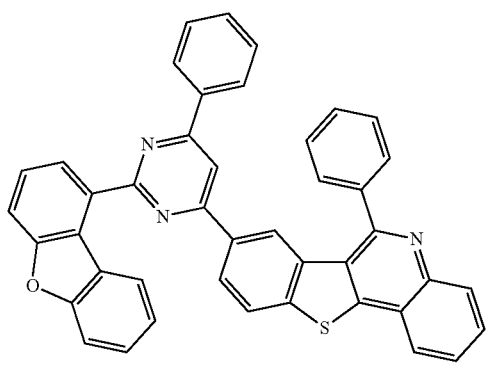
996
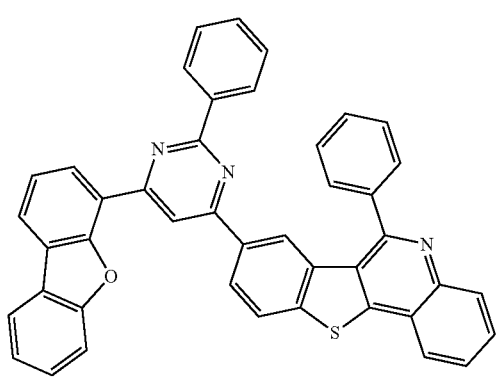 [SMILES: c1ccc(-c2nc(-c3ccc4oc5c6ccccc6nc(-c6ccccc6)c5c4c3)nc(-c3cccc4c3sc3ccccc34)n2)cc1]
997
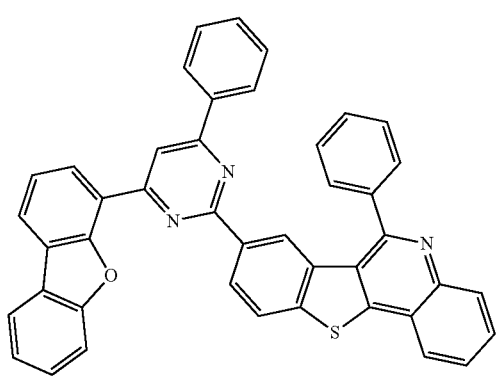
984
-continued
998
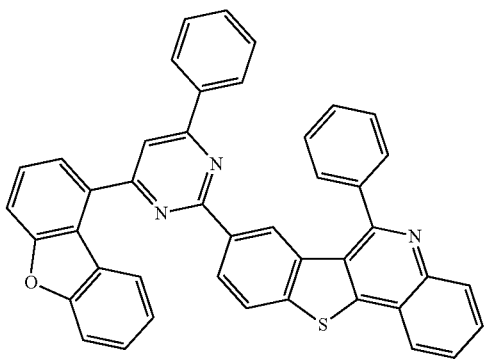
999
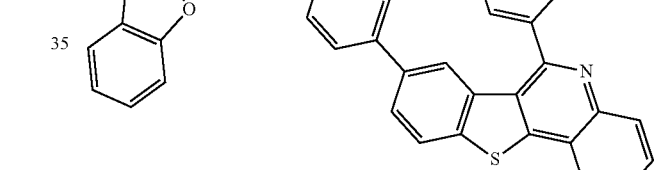
1000
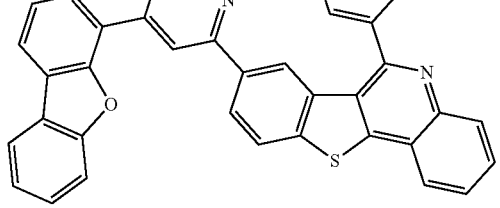

985
-continued
1001
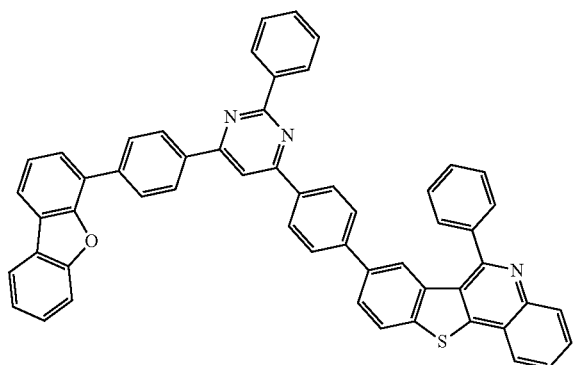
1002
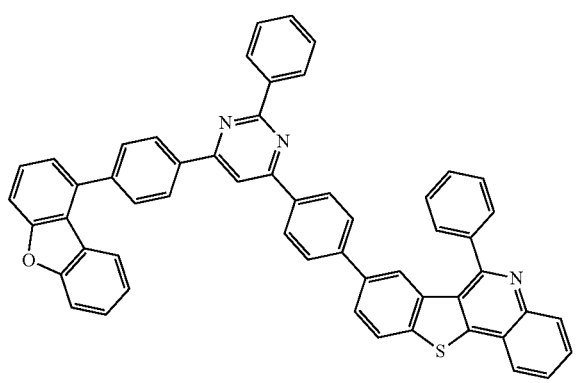
10003
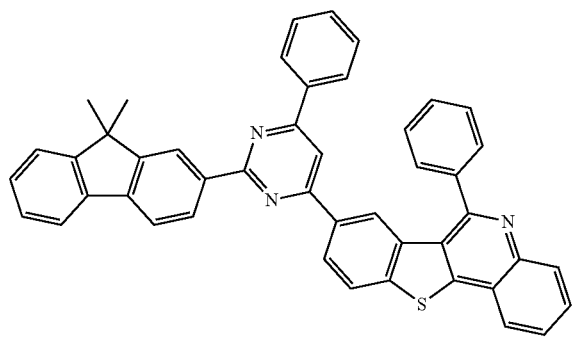
1004
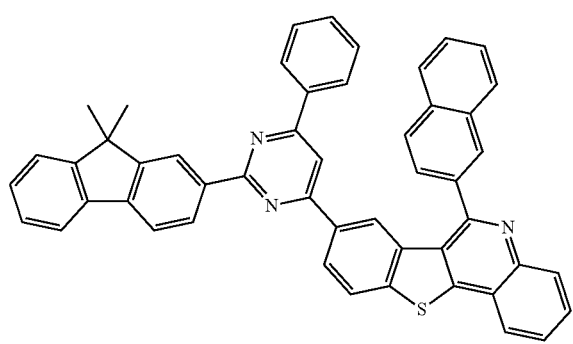
986
-continued
1005
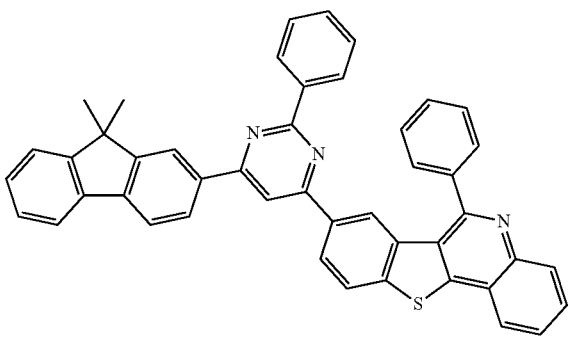
1006
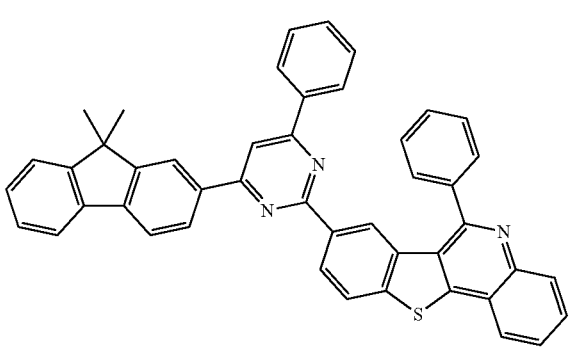
1007
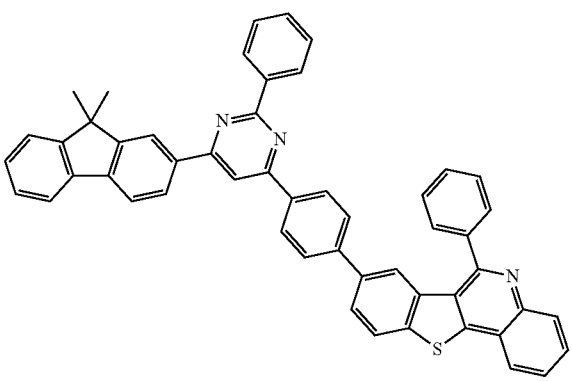
1008
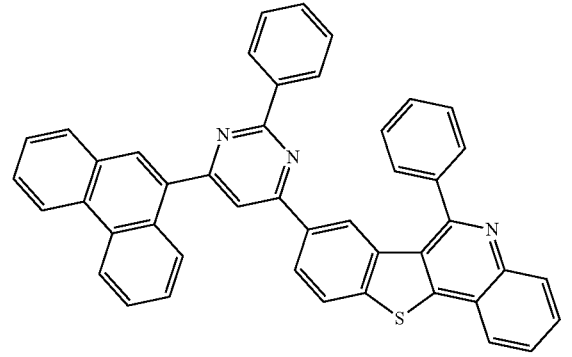 [SMILES: c1ccc(-c2nc(-c3ccc4oc5c6ccccc6nc(-c6ccccc6)c5c4c3)nc(-c3cc4ccccc4c4ccccc34)n2)cc1]

1009
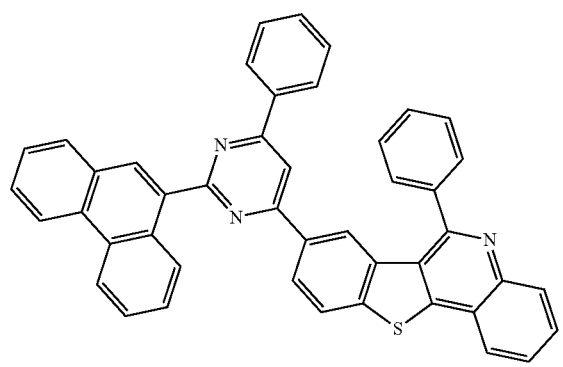
1010
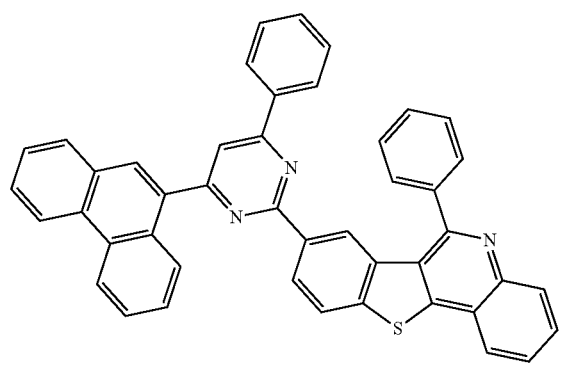
1011
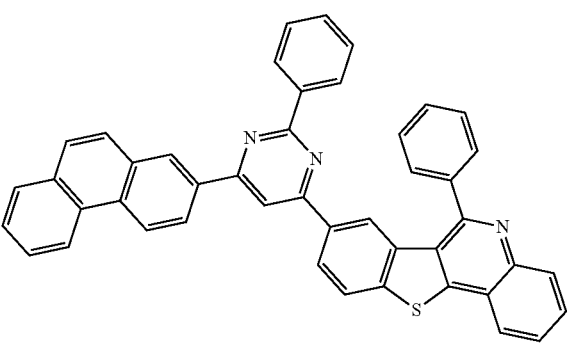
1012
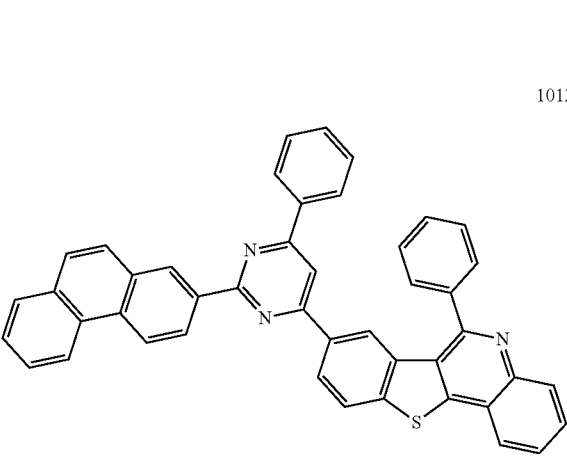
1013
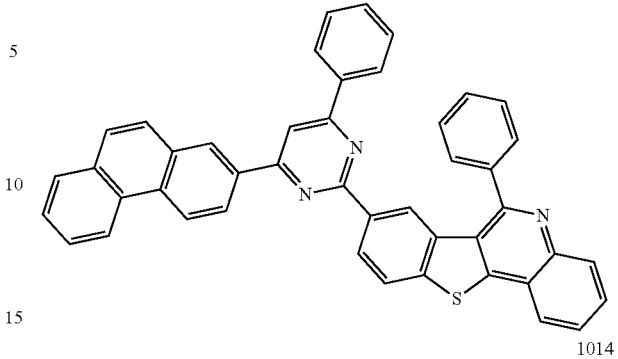
1014
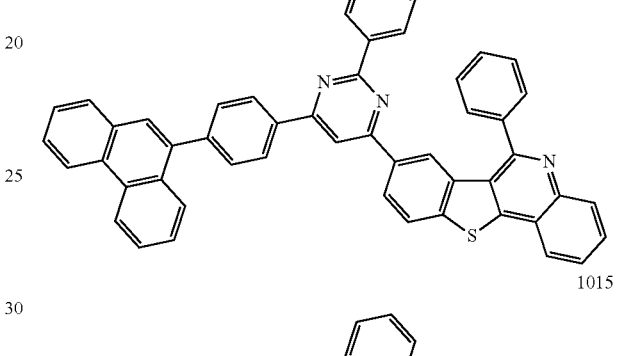
1015
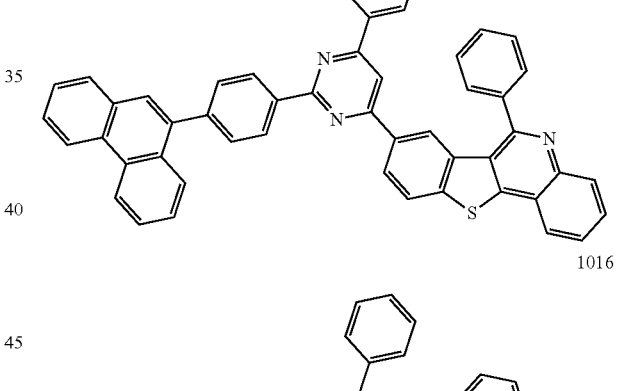
1016
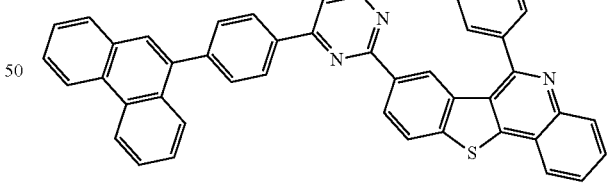
1017
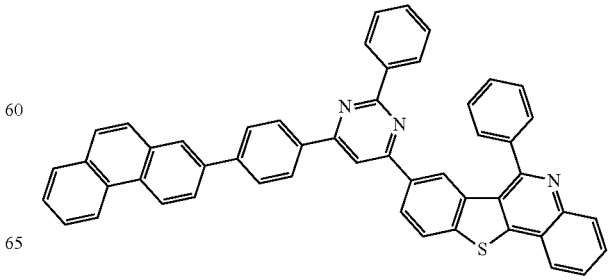

989
-continued
1018
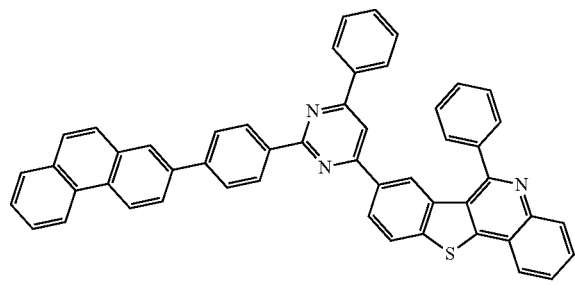
1019
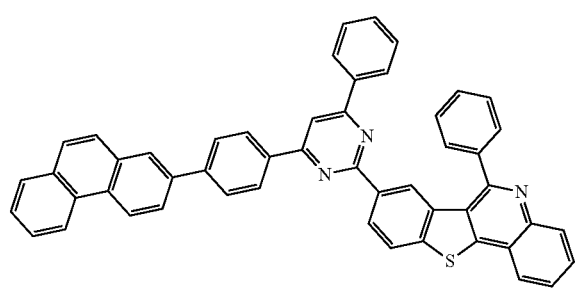
1020
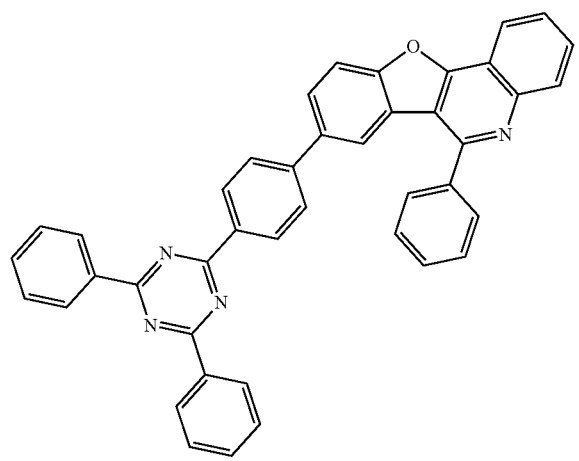
1021
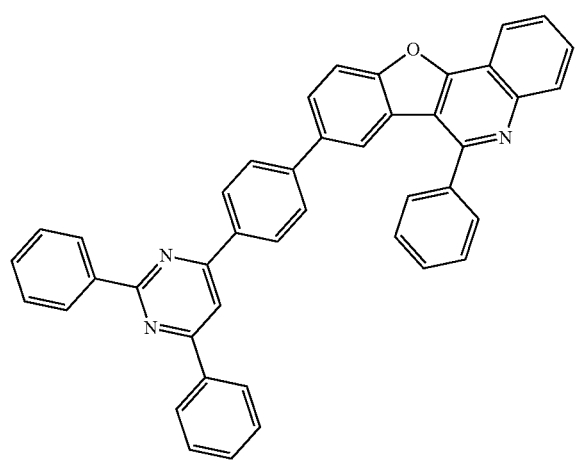
990
-continued
1022
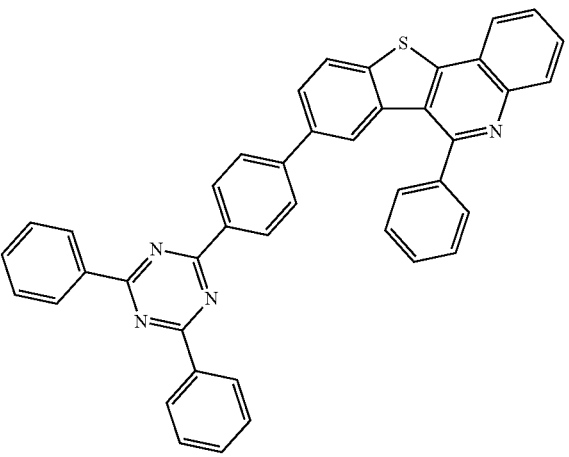
1023
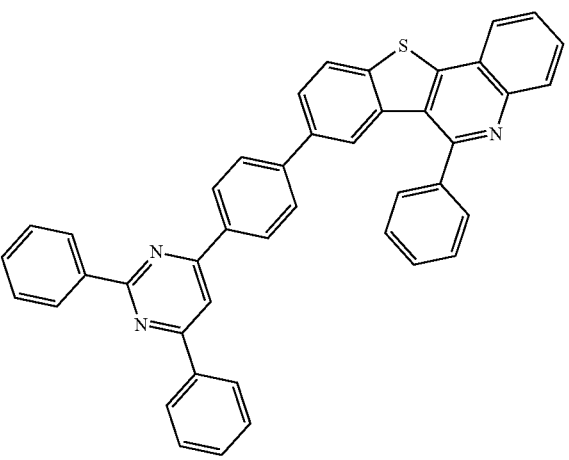
1024
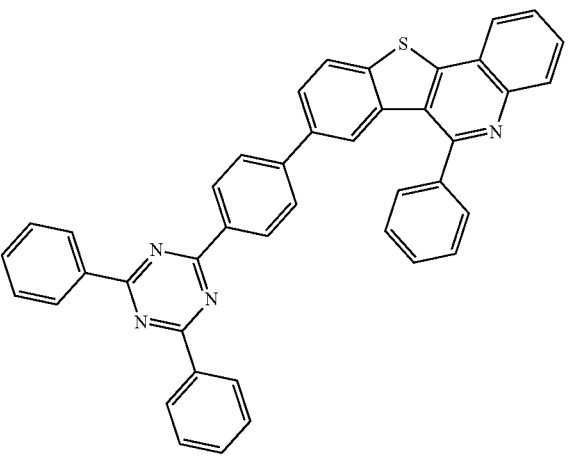

1025
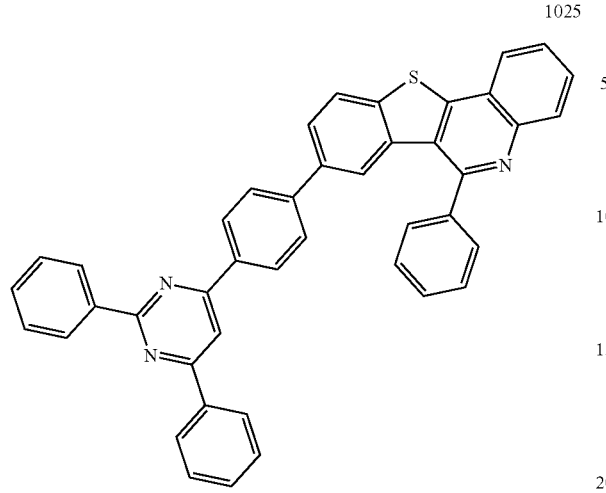
1026
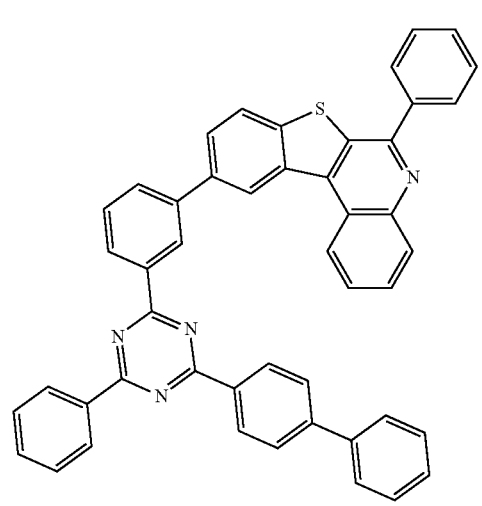
1027
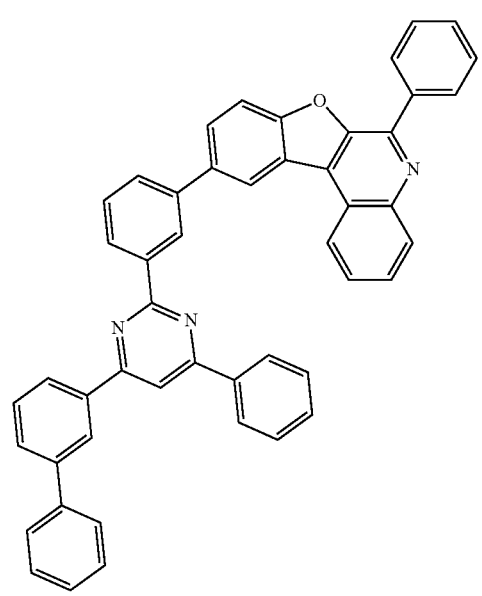
1028
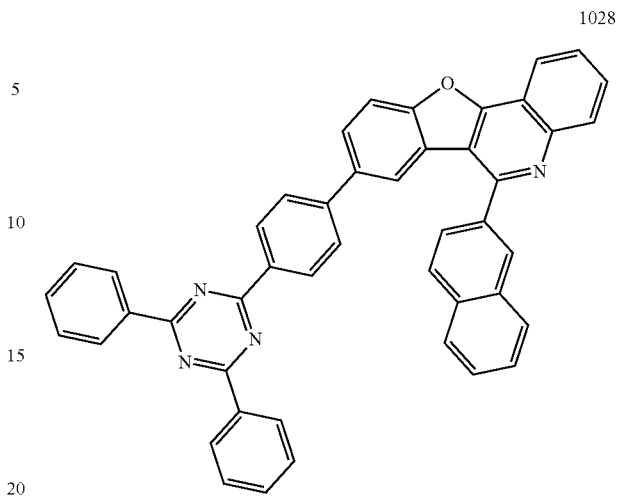
1029
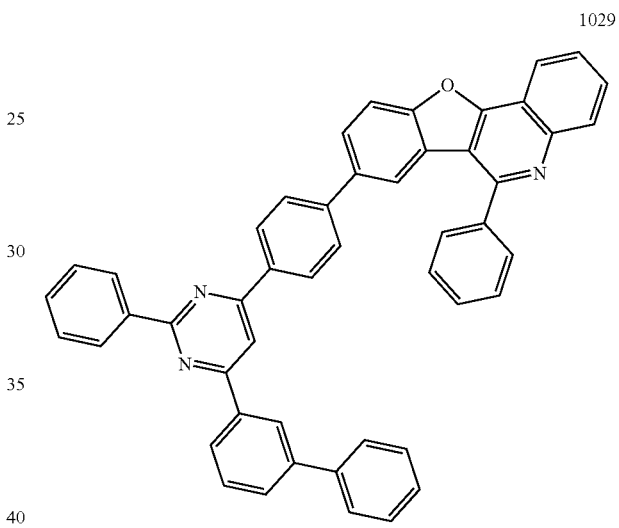
1030
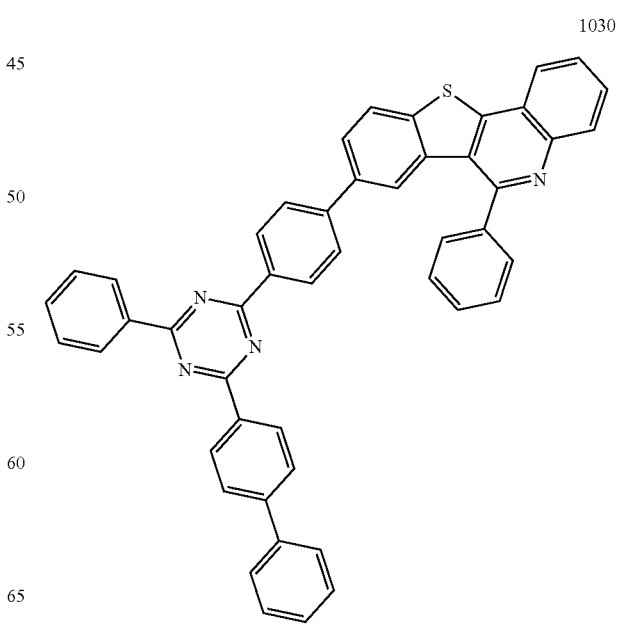

1031
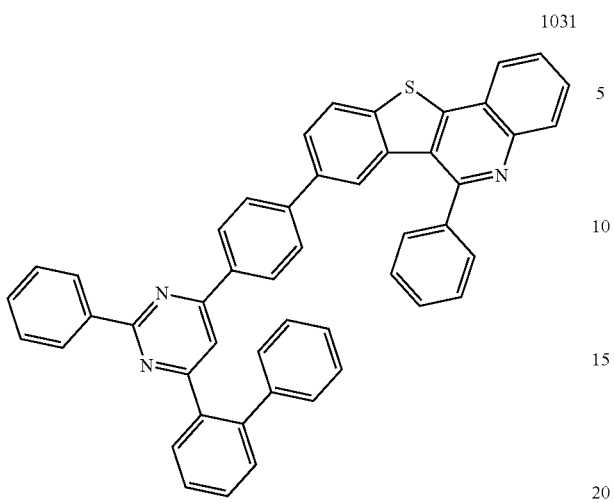
1032
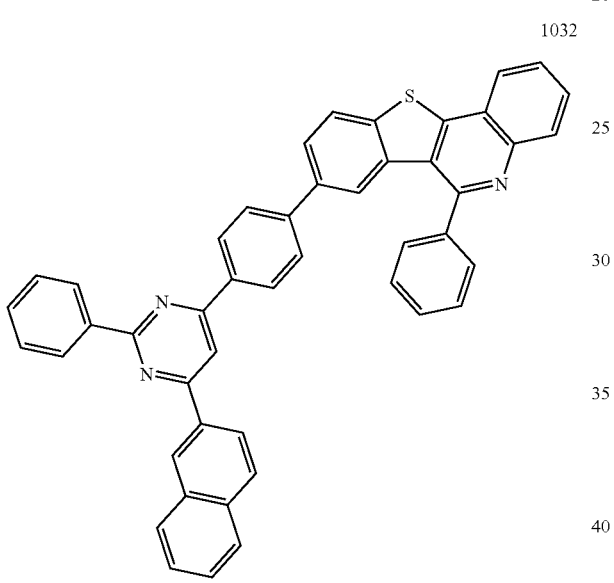
1033
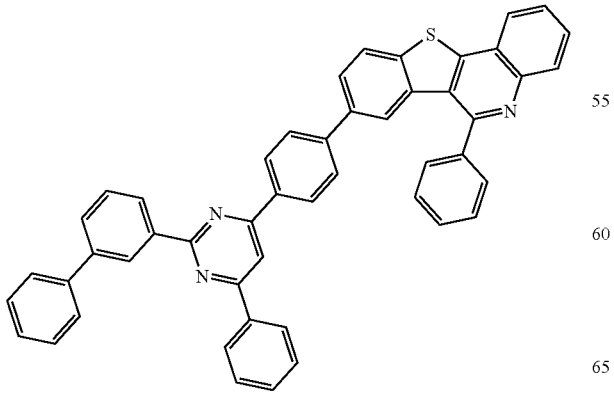
1034
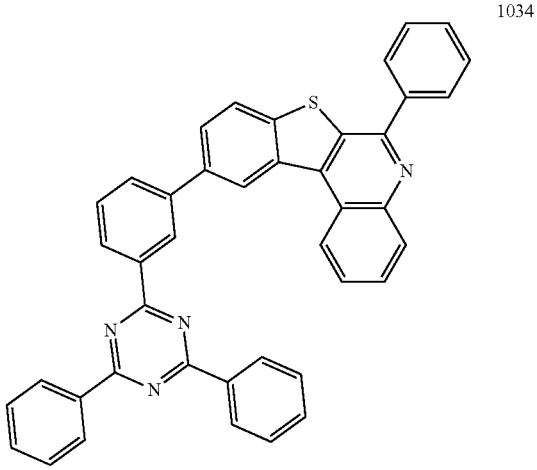
1035
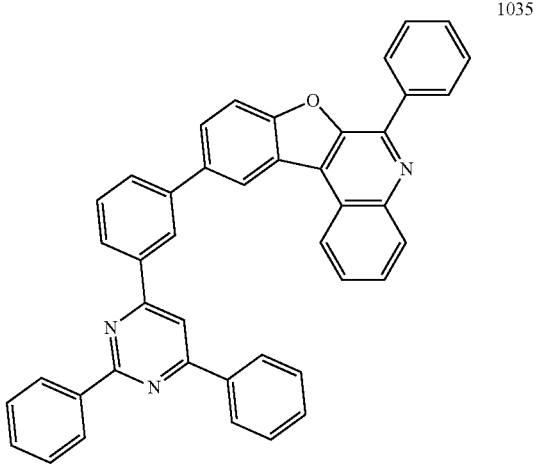
1036
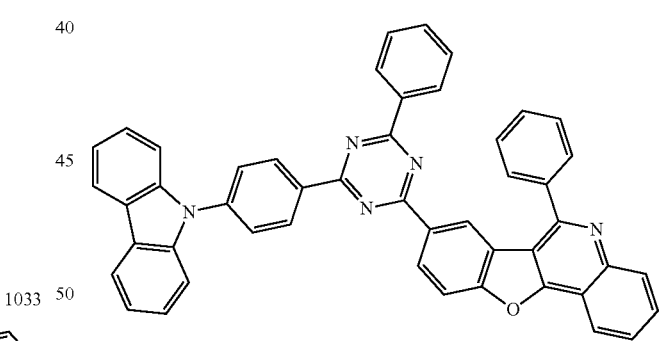
1037
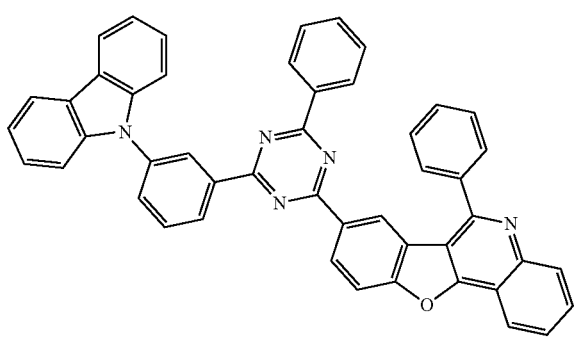

995
-continued
1038
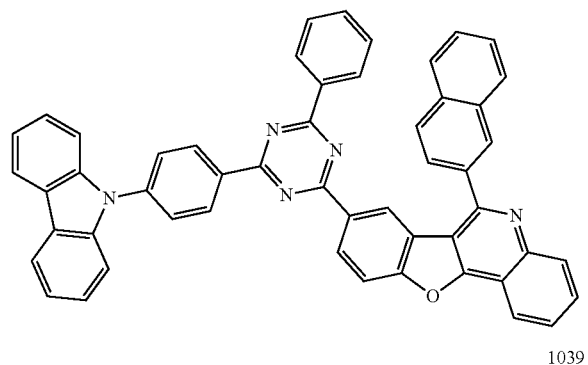
1039
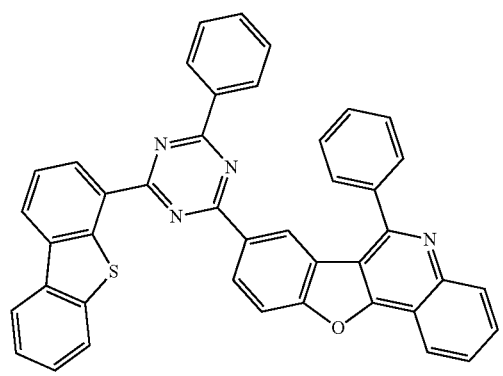
1040
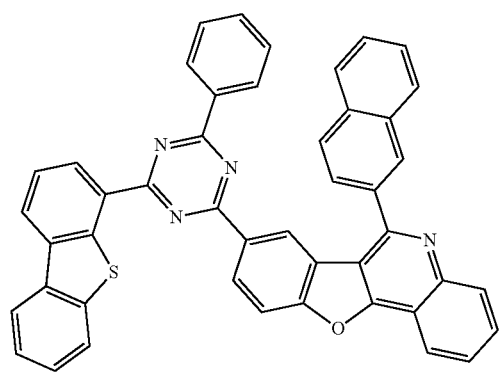
1041
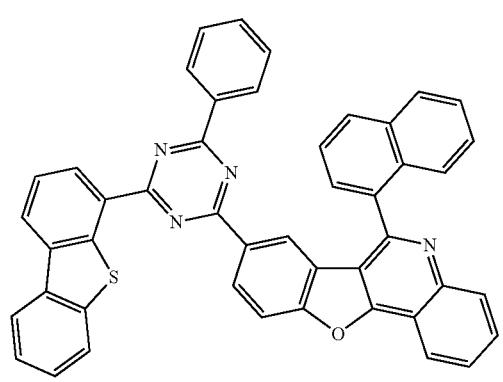
996
-continued
1042
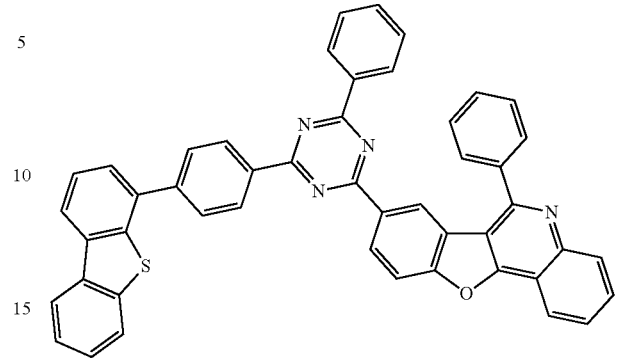
1043
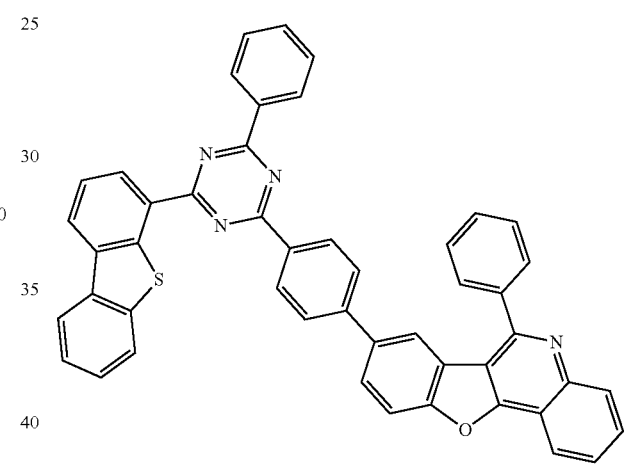
1044
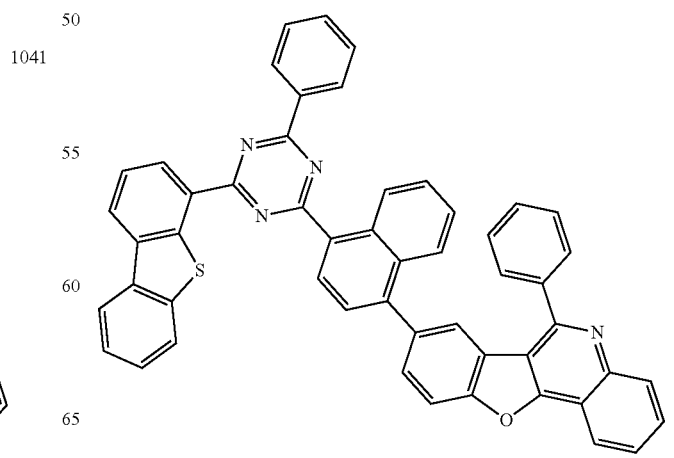

1045
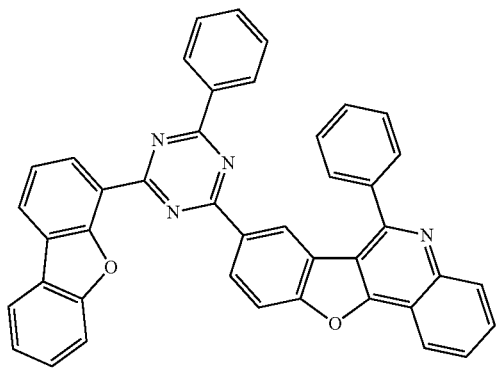
1046
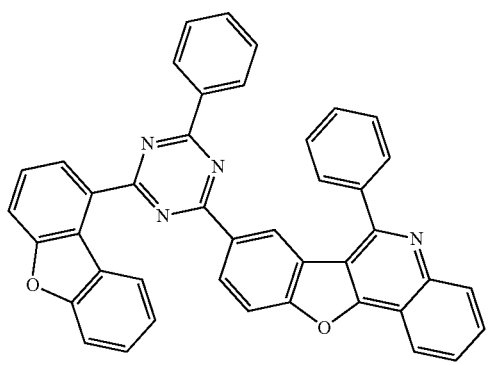
1047
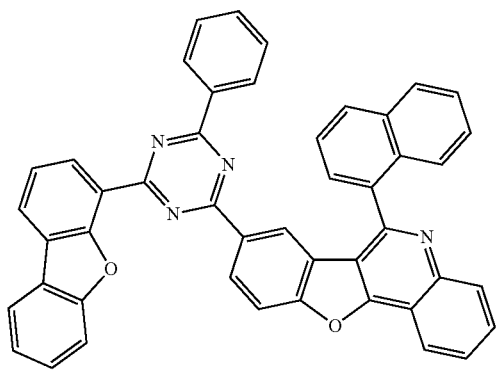
1048
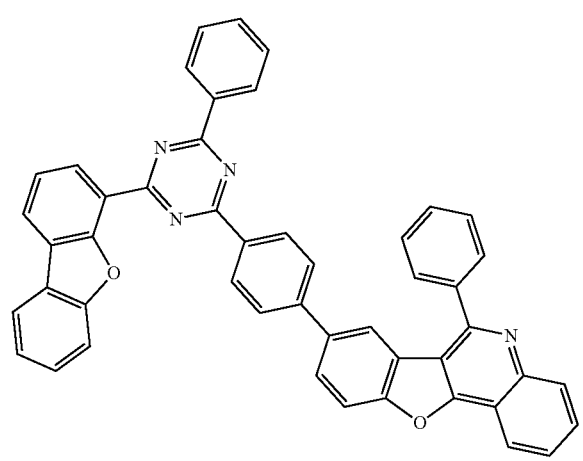
1049
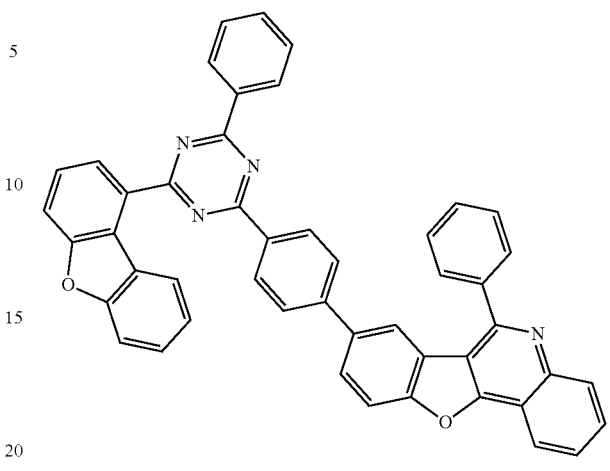
1050
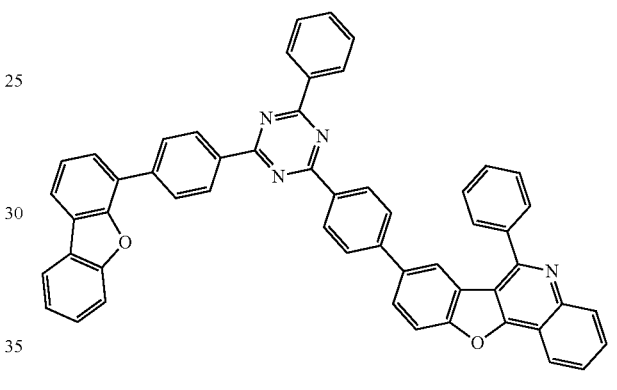
1051
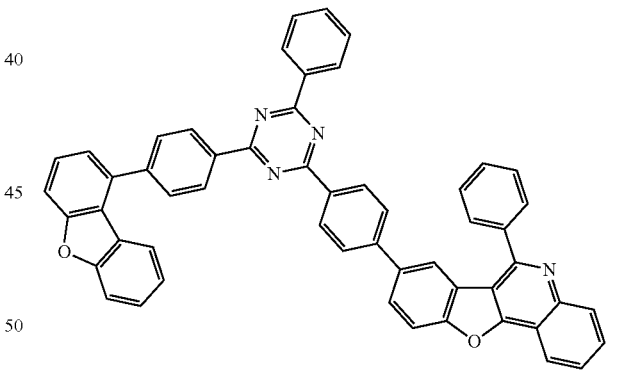
1052
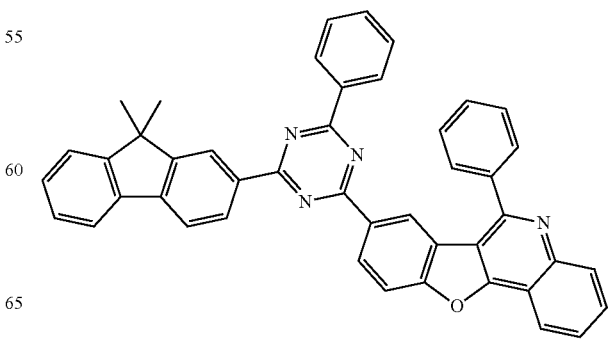

| 1053 | 1057 |
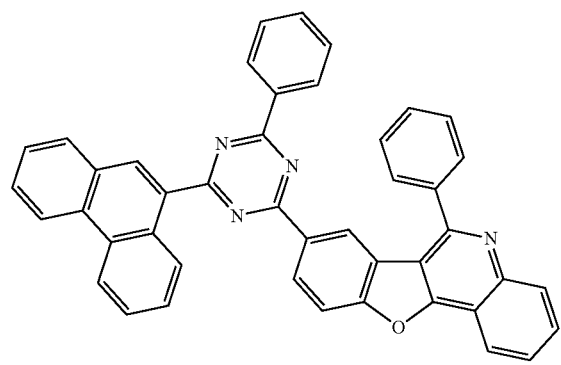
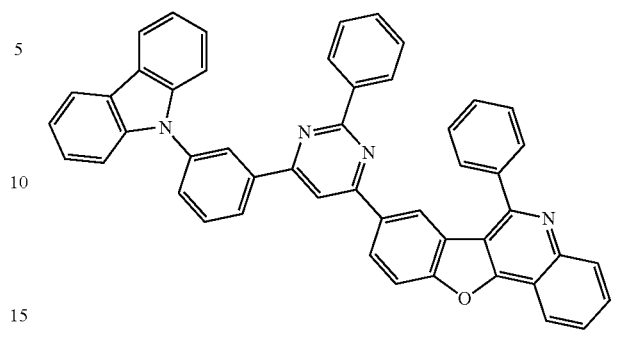
1054
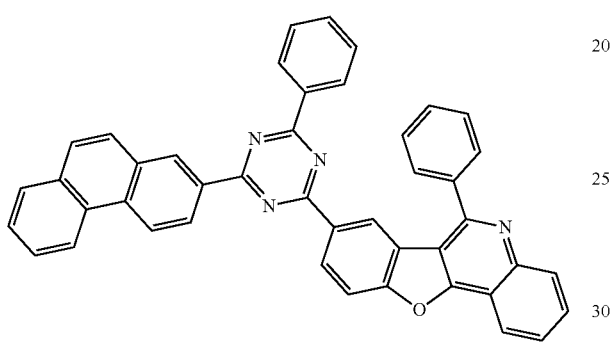
1058
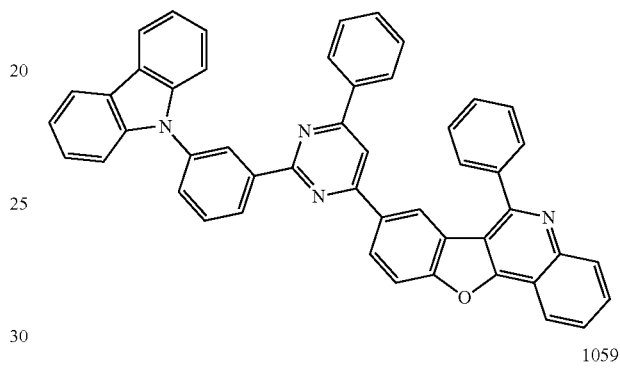
1055
1059
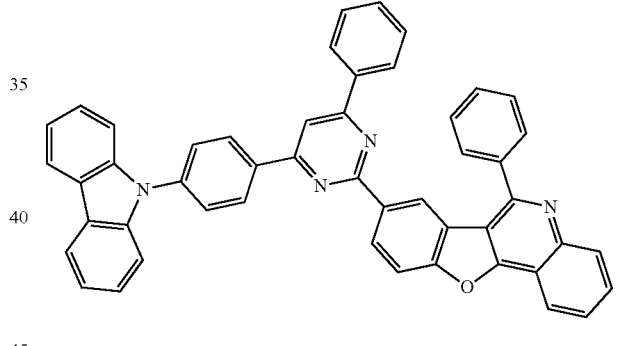
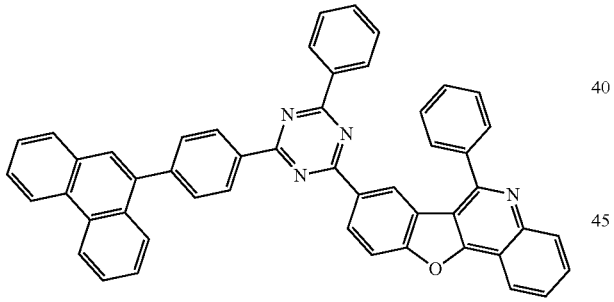
1056
1060
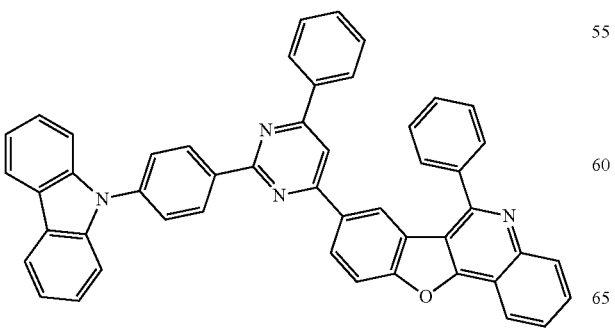
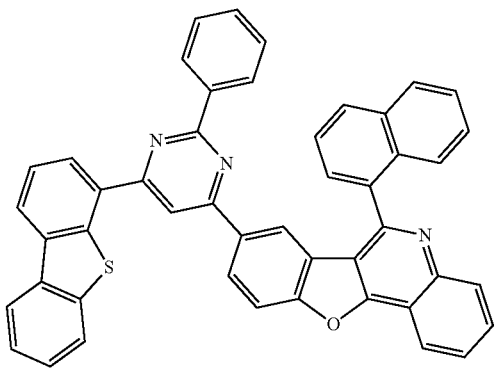

1001
-continued
1061
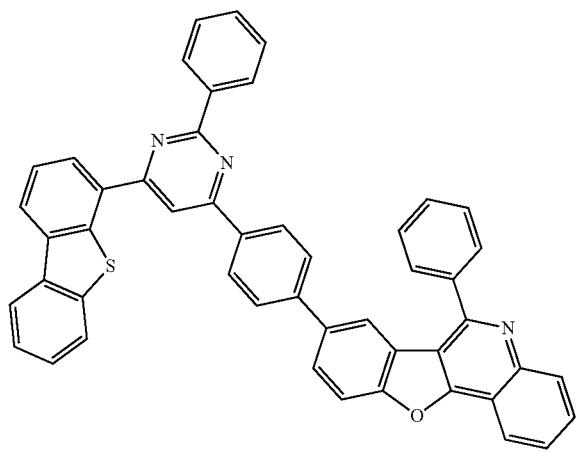
1062
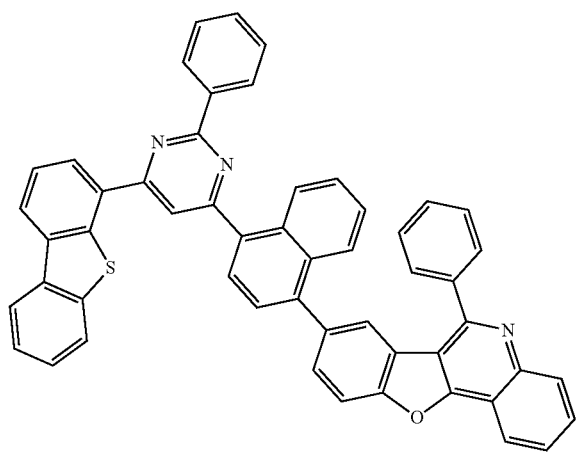
1063
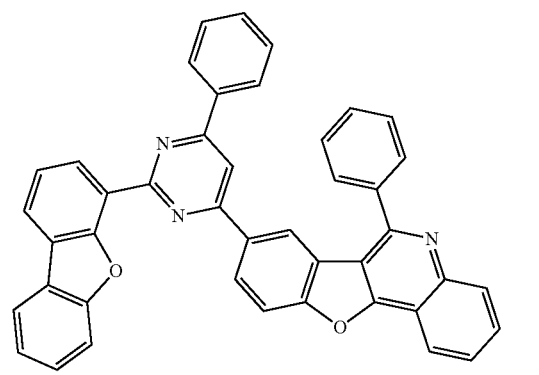
1002
-continued
1064
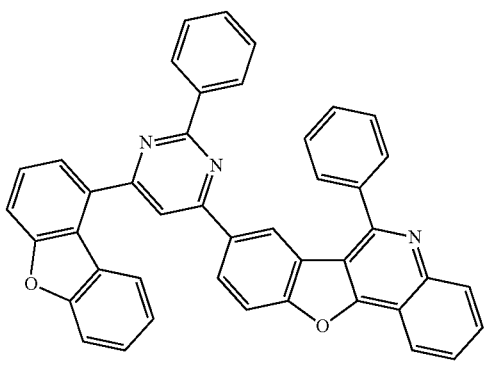
1065
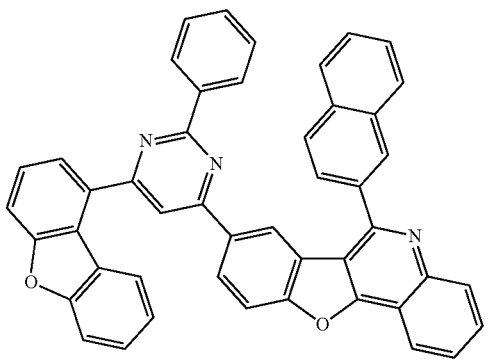 [SMILES: c1ccc(-c2nc(-c3ccc4oc5c6ccccc6nc(-c6ccc7ccccc7c6)c5c4c3)cc(-c3cccc4oc5ccccc5c34)n2)cc1]
1066
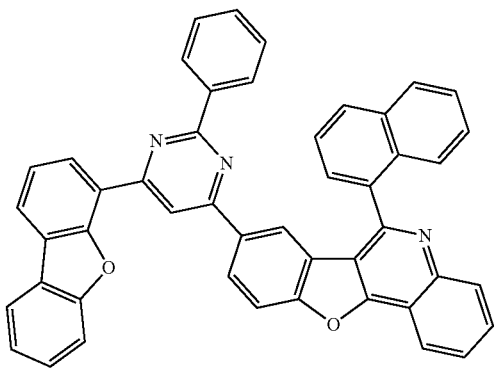
1067
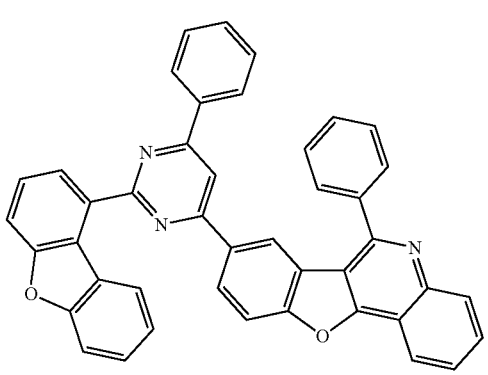

1003
-continued
1068
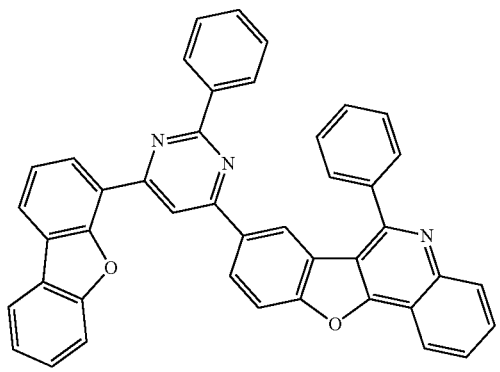
1069
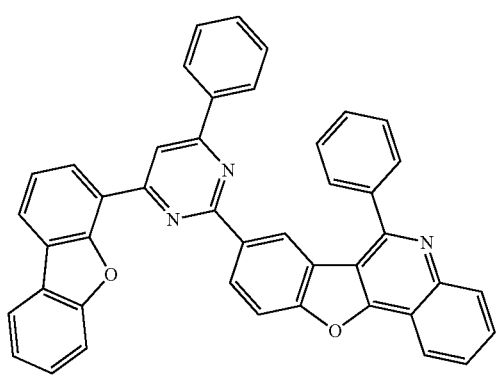
1070
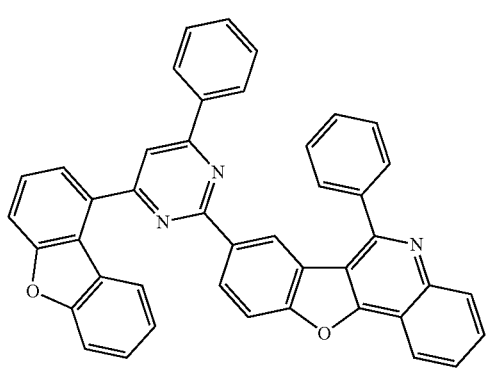
1071
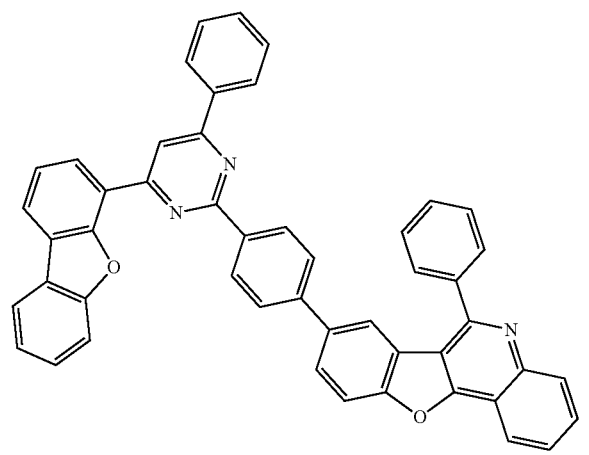
1004
-continued
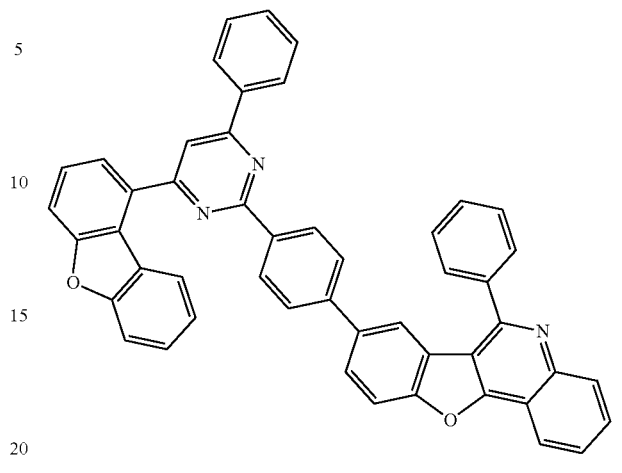
1072
1073
1074
1075

1076
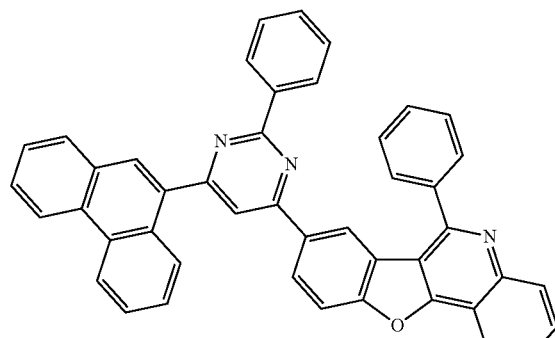
1077
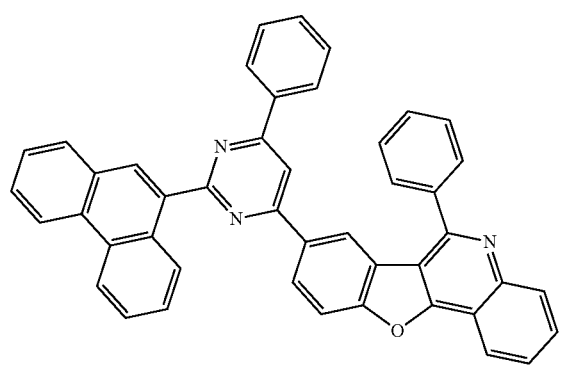
1078
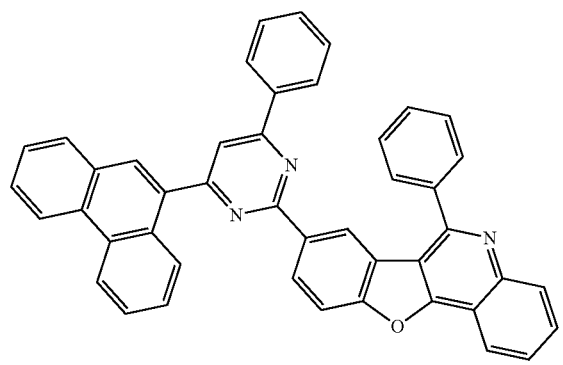 [SMILES: c1ccc(-c2cc(-c3cc4ccccc4c4ccccc34)nc(-c3ccc4oc5c6ccccc6nc(-c6ccccc6)c5c4c3)n2)cc1]
1079
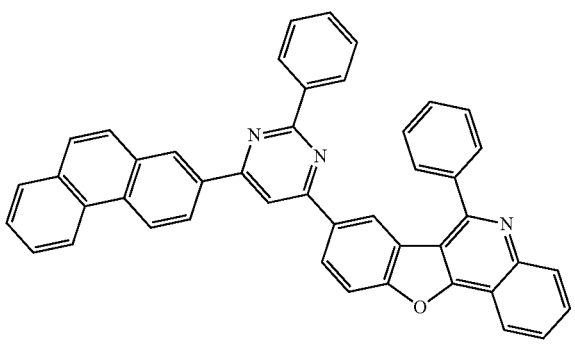
1080
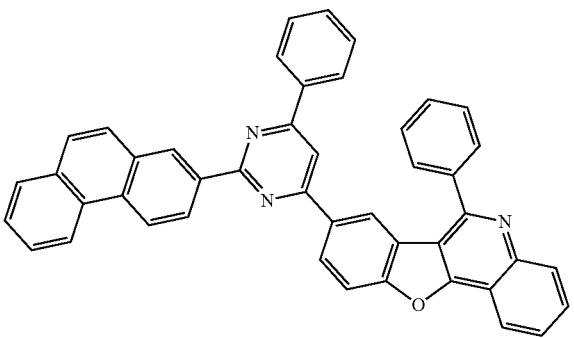
1081
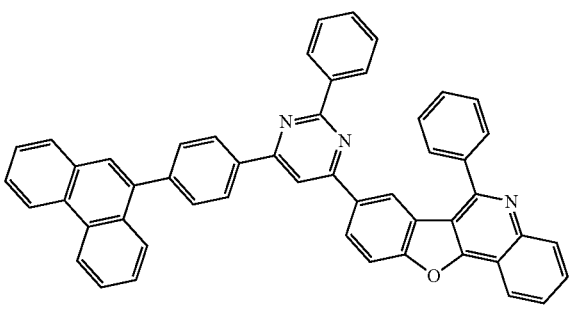
1082
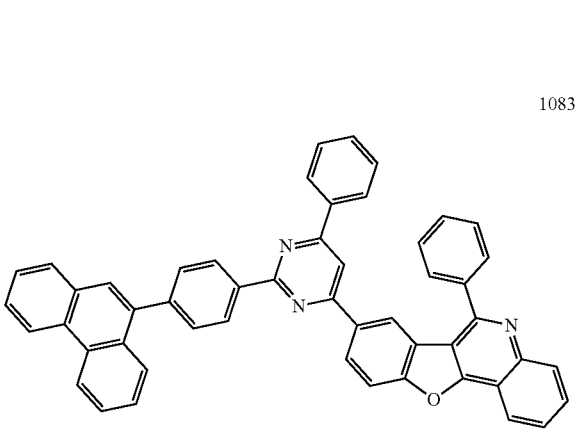
1083

1007
-continued
1084
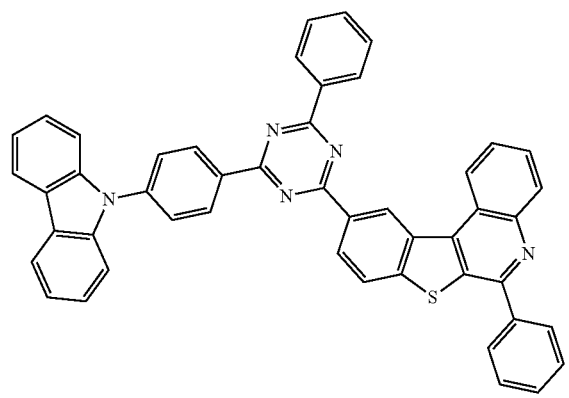
1085
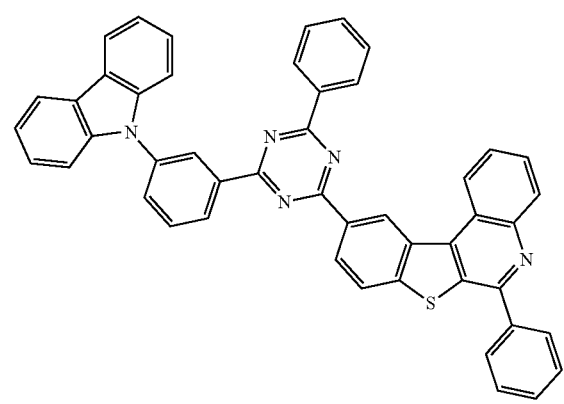
1086
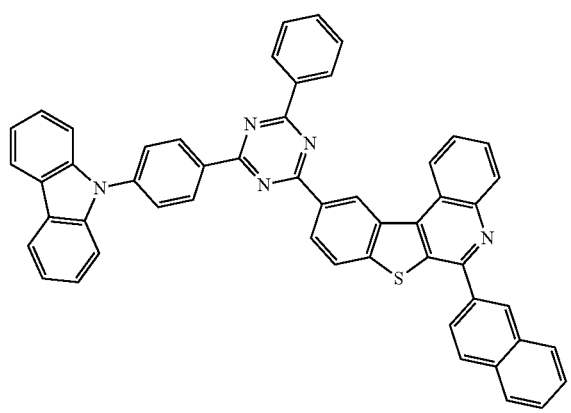
1008
-continued
1087
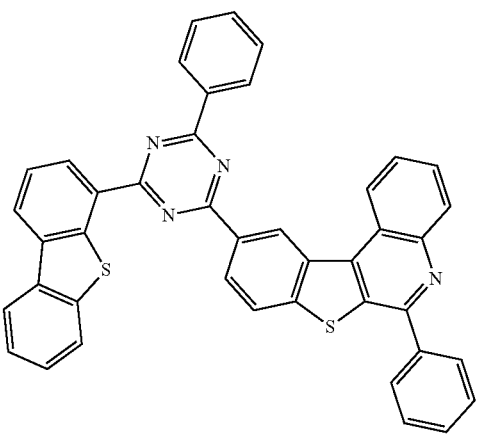
1088
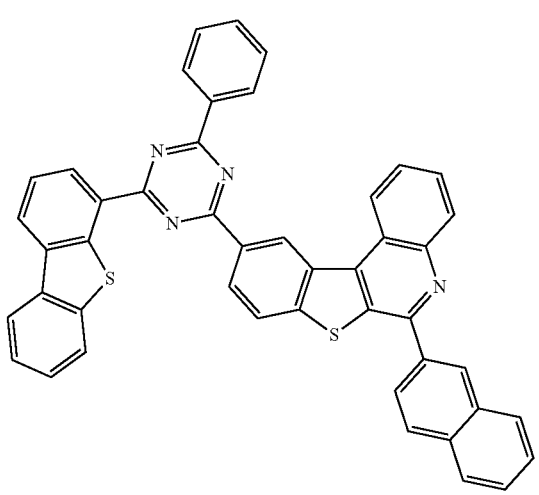
1089
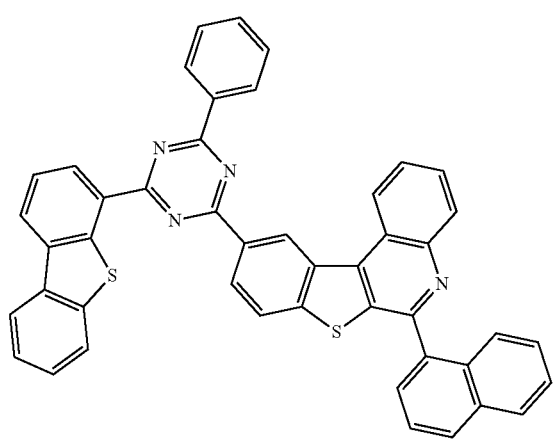

1009
-continued
1090
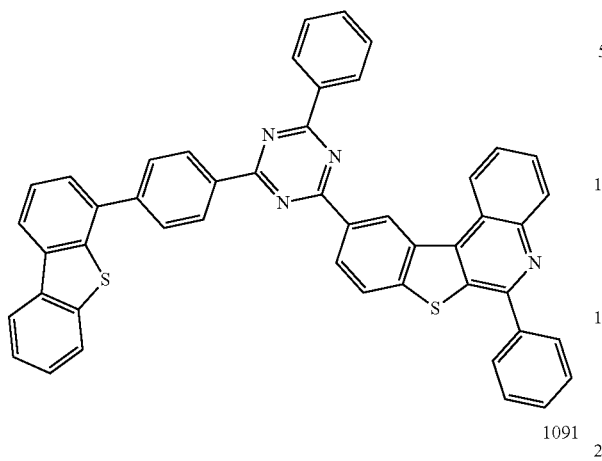
1091
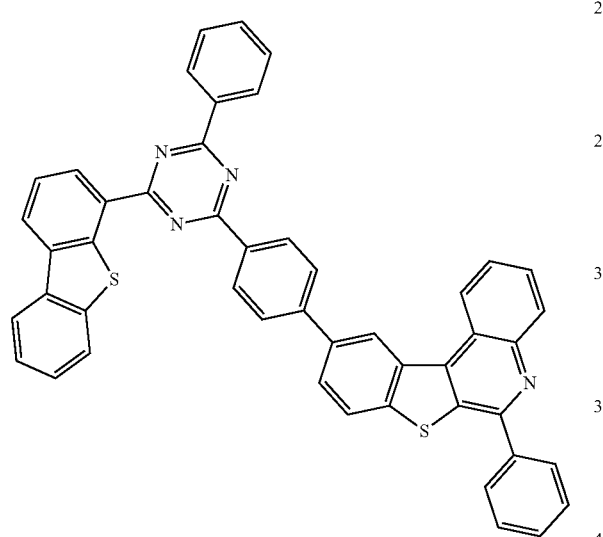
1092
1010
-continued
1093
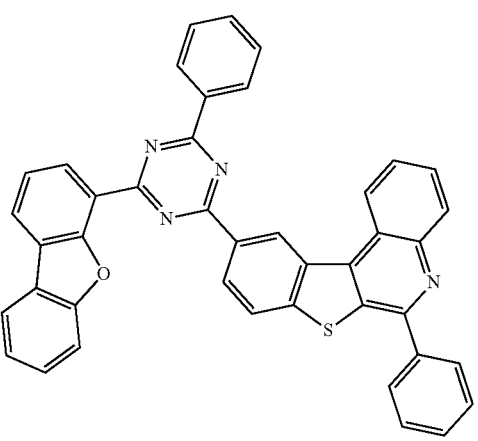
1094
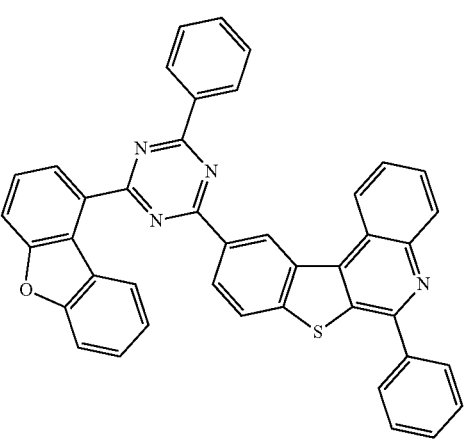
1095
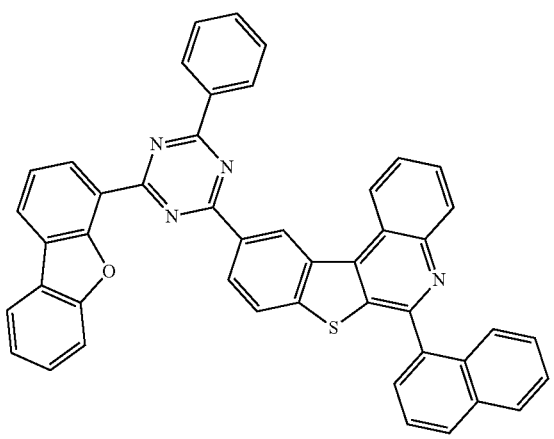
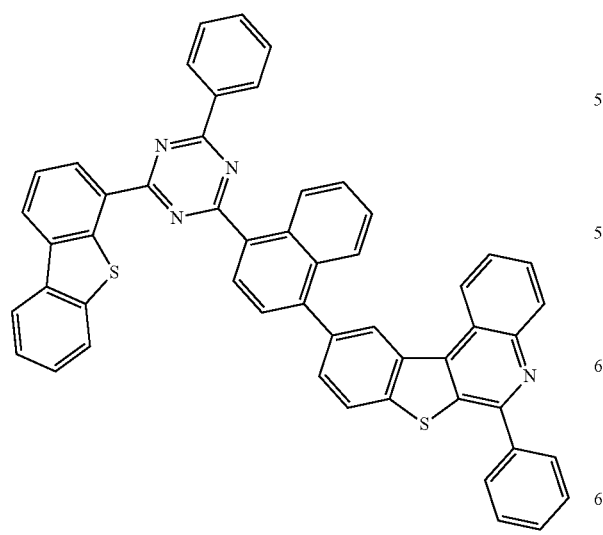

1011
-continued
1012
-continued
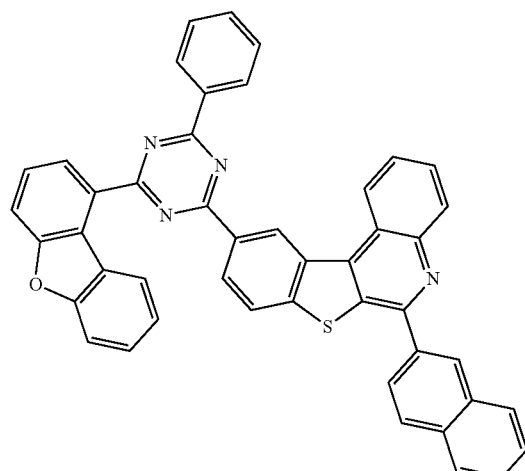
1096
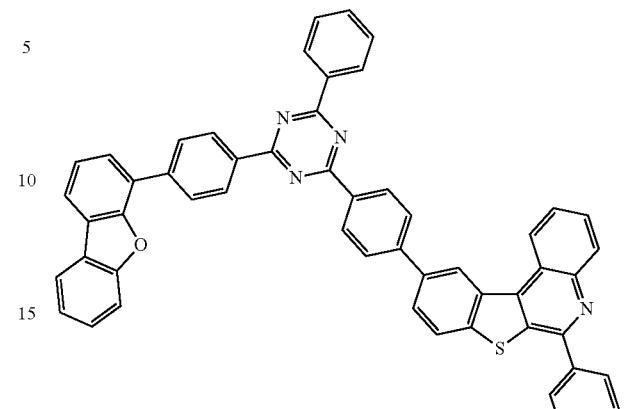
1099
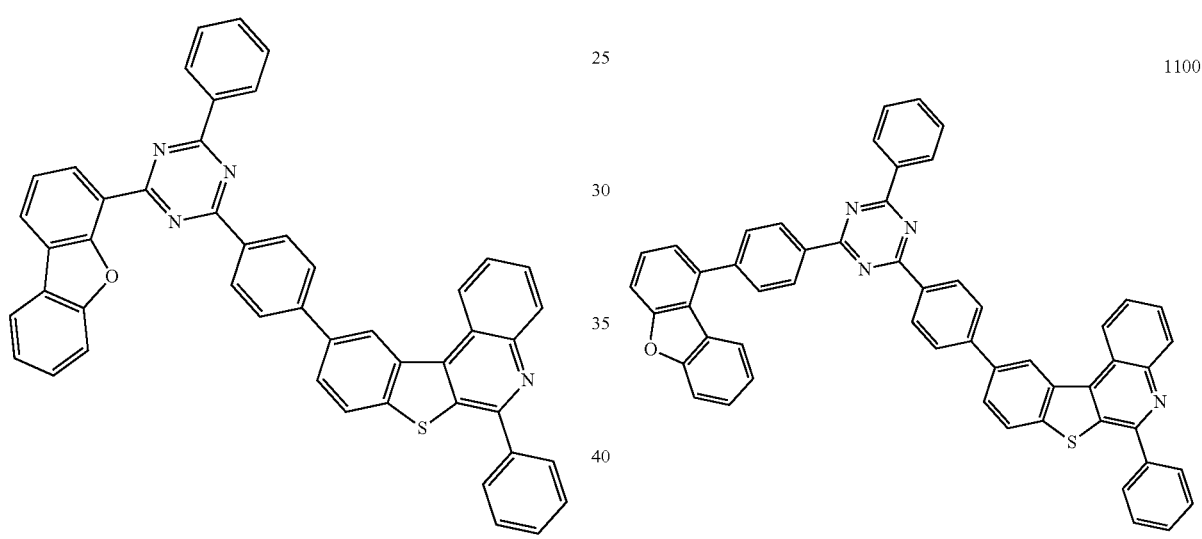
1097
1100
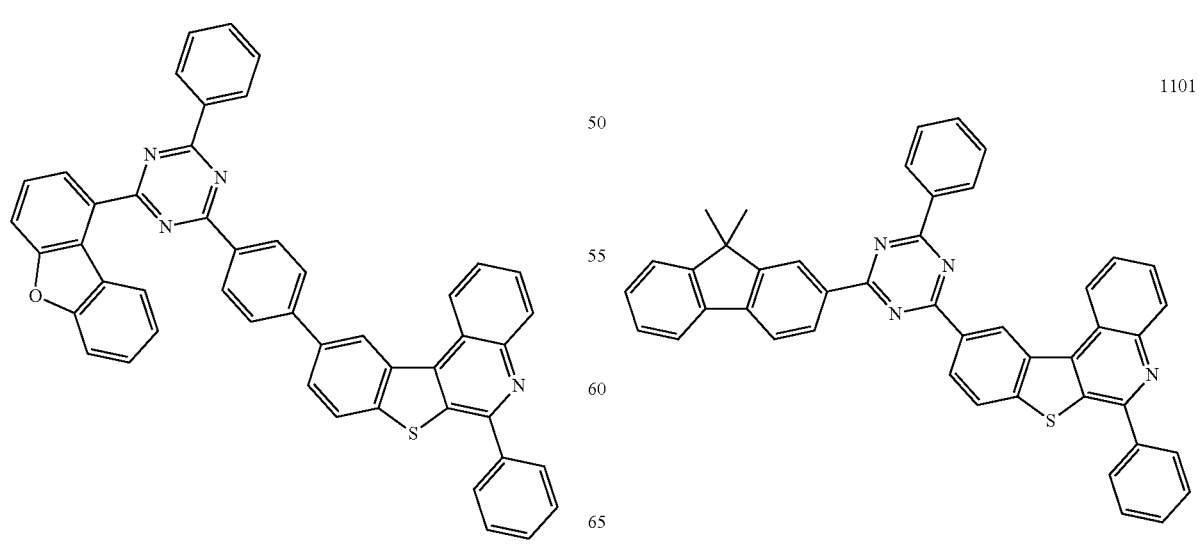
1098
1101

1013
-continued
1102
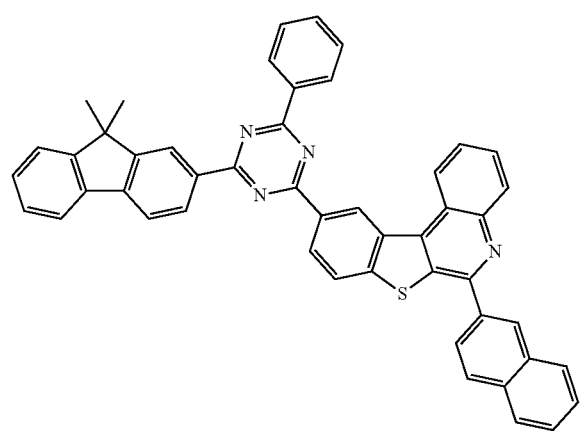
1103
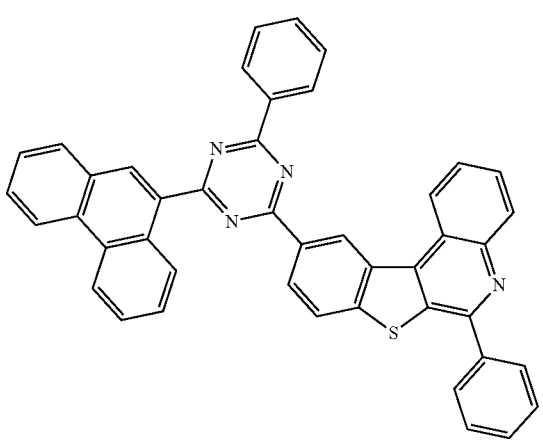 [SMILES: c1ccc(-c2nc(-c3ccc4sc5c(-c6ccccc6)nc6ccccc6c5c4c3)nc(-c3cc4ccccc4c4ccccc34)n2)cc1]
1104
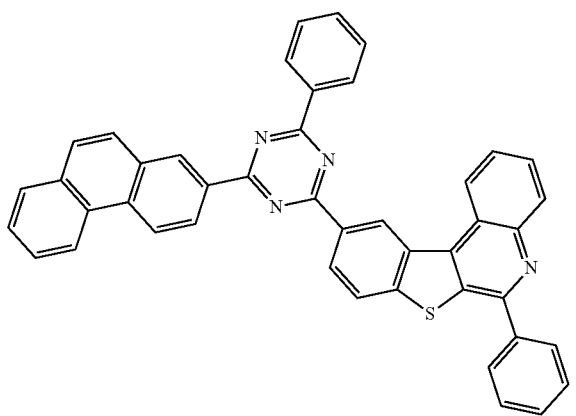
1014
-continued
1105
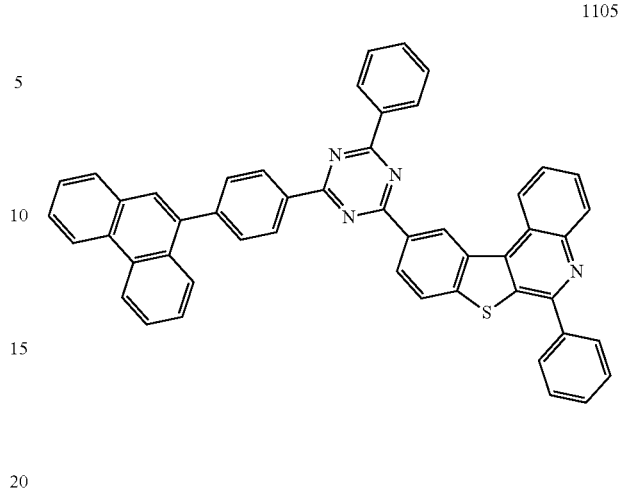
1106
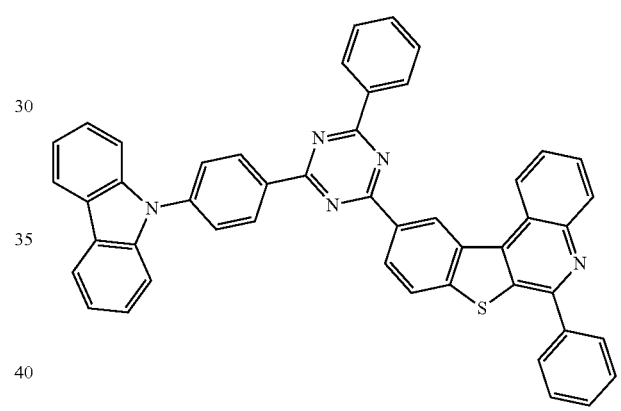
1107
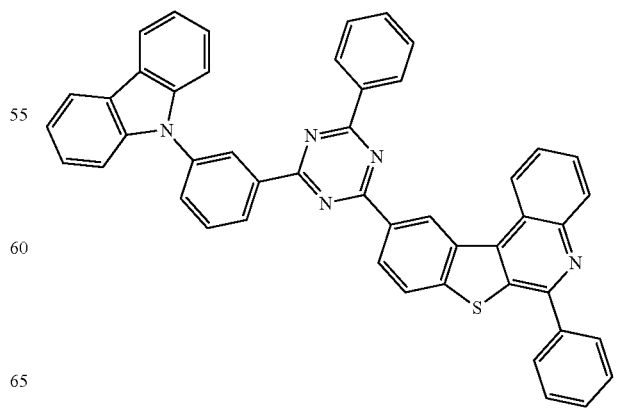

-continued
1108
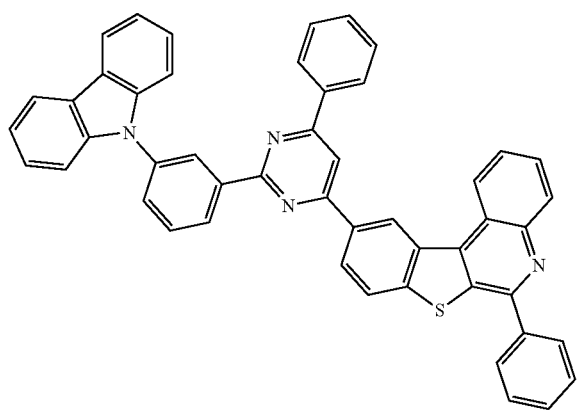
1109
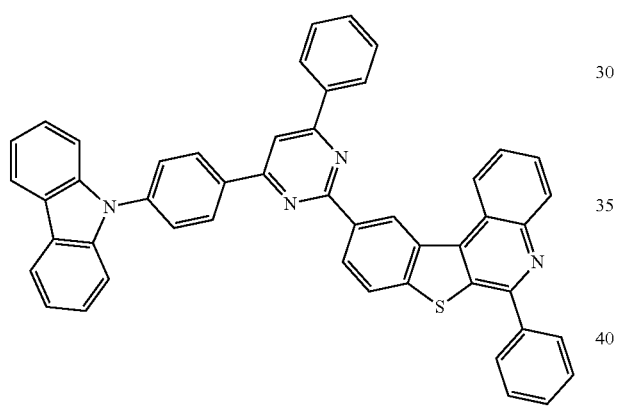
1110
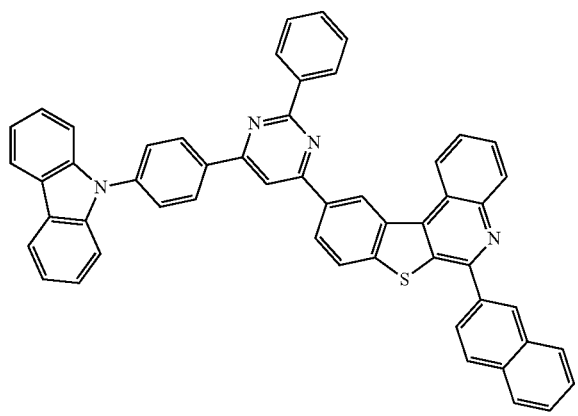
-continued
1111
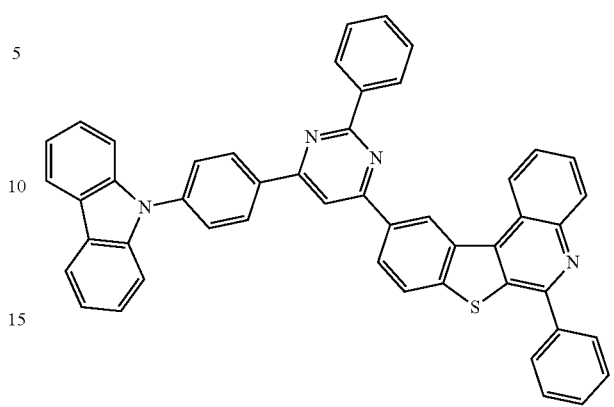
1112
1113
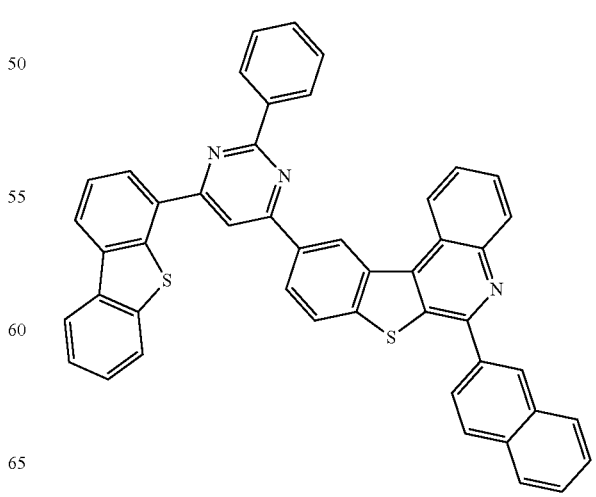

-continued
1114
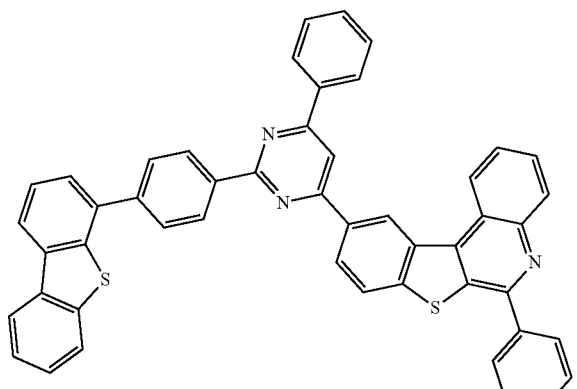
1115
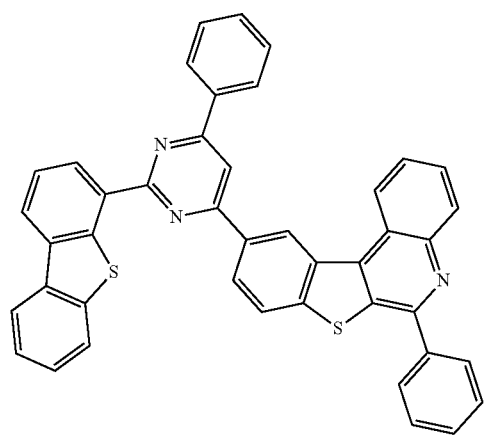
1116
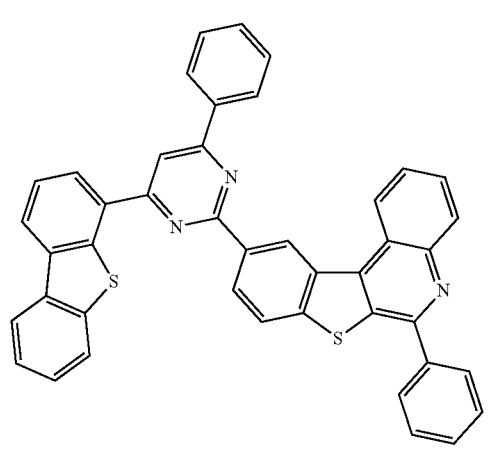
-continued
1117
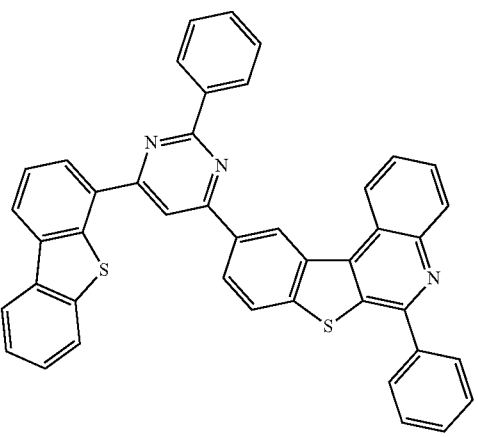
1118
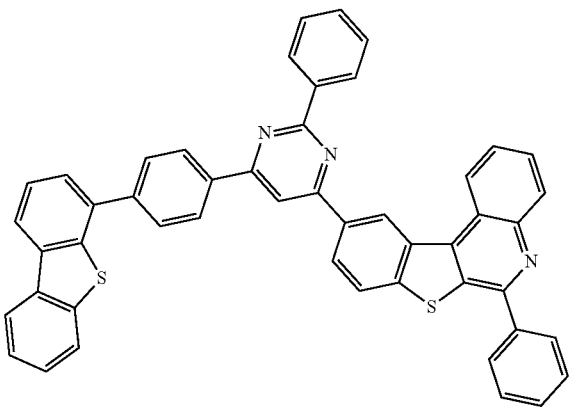 [SMILES: c1ccc(-c2cc(-c3ccc4sc5c(-c6ccccc6)nc6ccccc6c5c4c3)nc(-c3ccc(-c4cccc5c4sc4ccccc45)cc3)n2)cc1]
1119

1019
-continued
1120
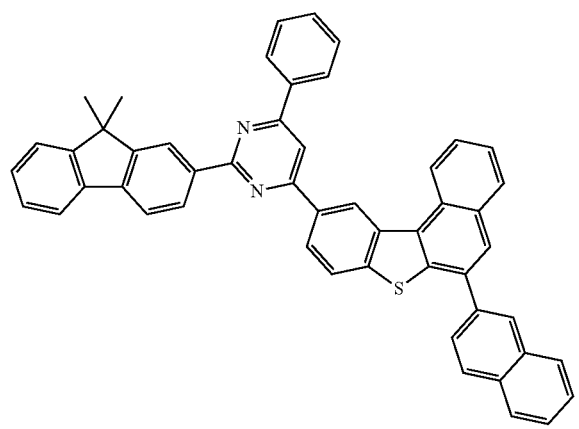
1121
1122
1020
-continued
1123
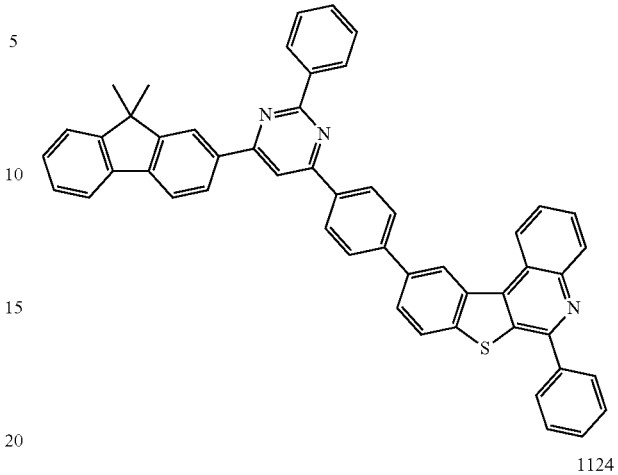
1124
1125
1126
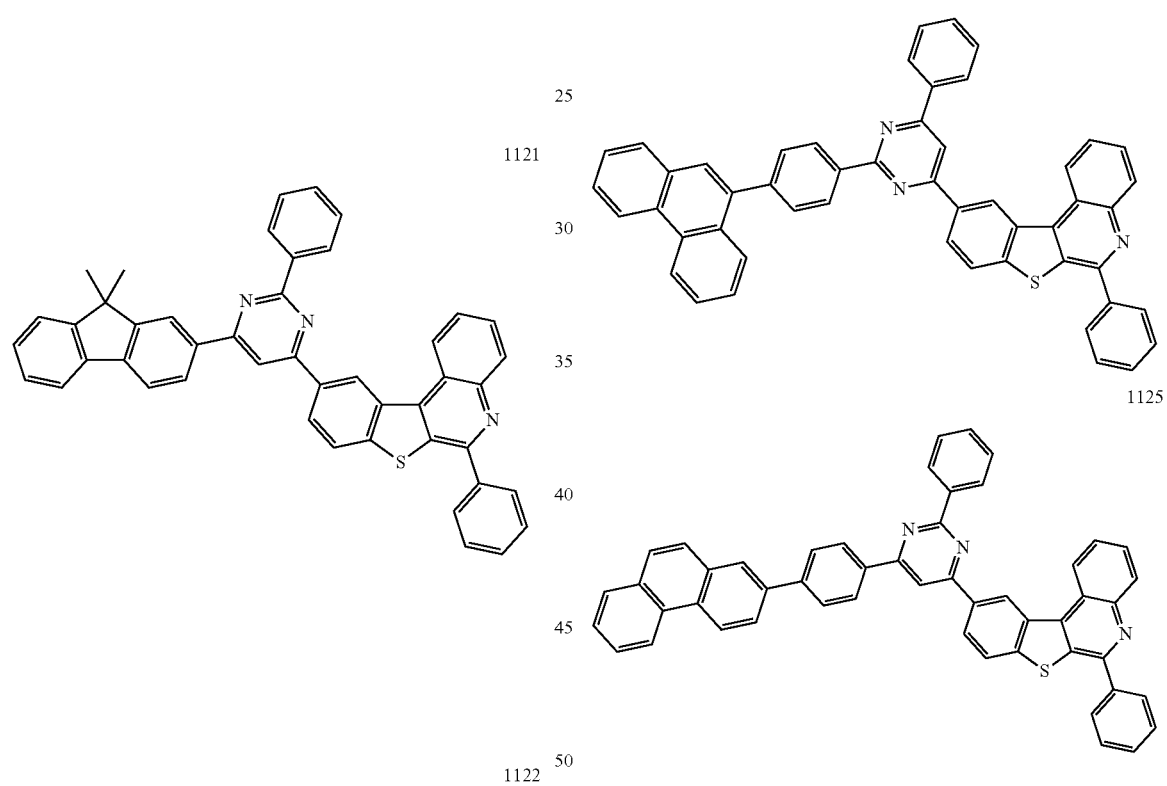
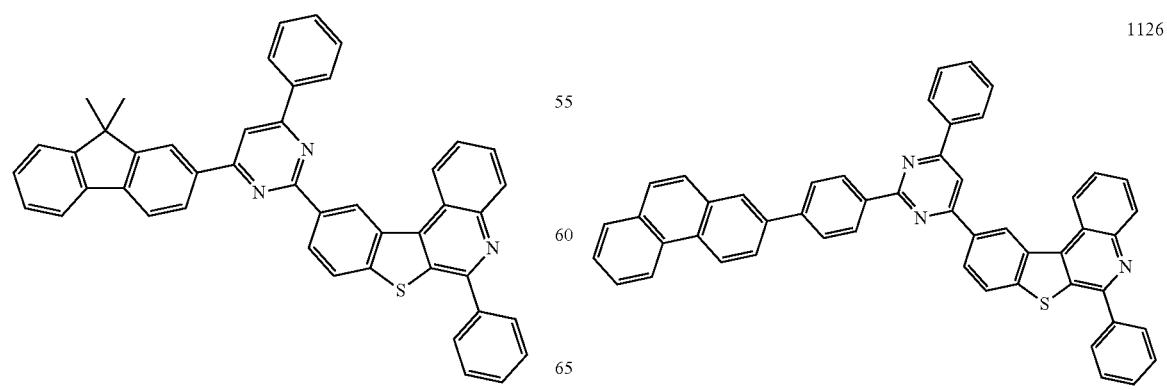

1127
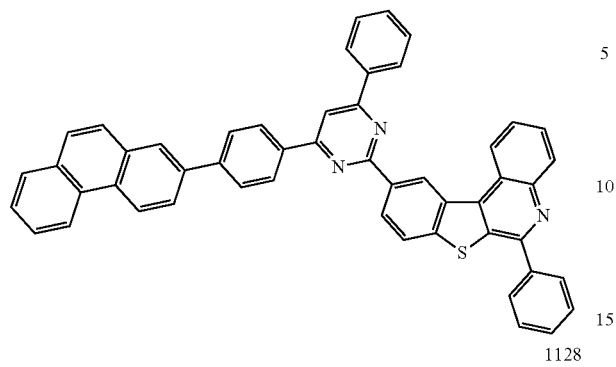
1128
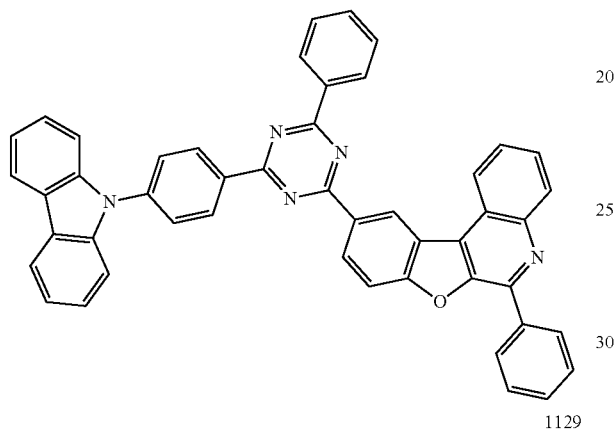
1129
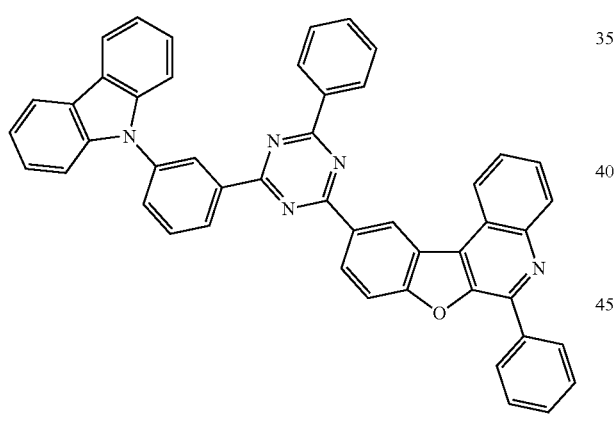
1130
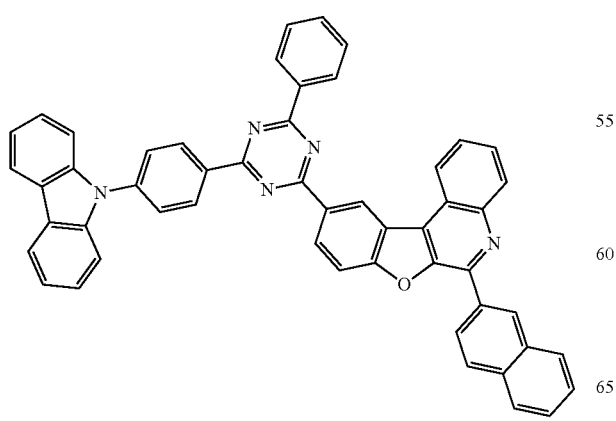
1131
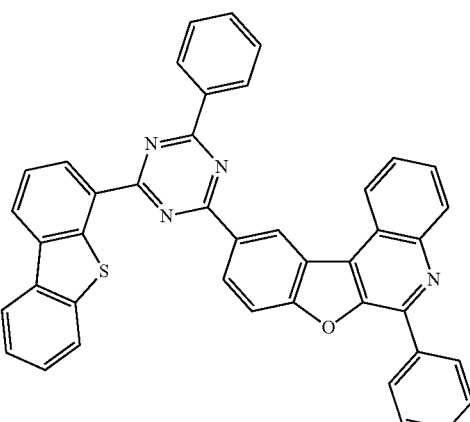
1132
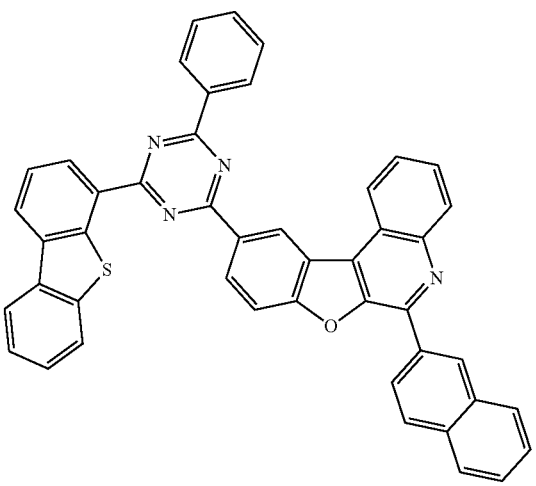
1133

1134
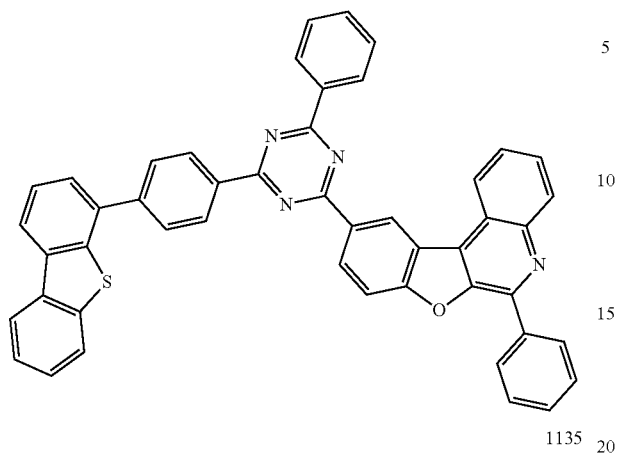
1135
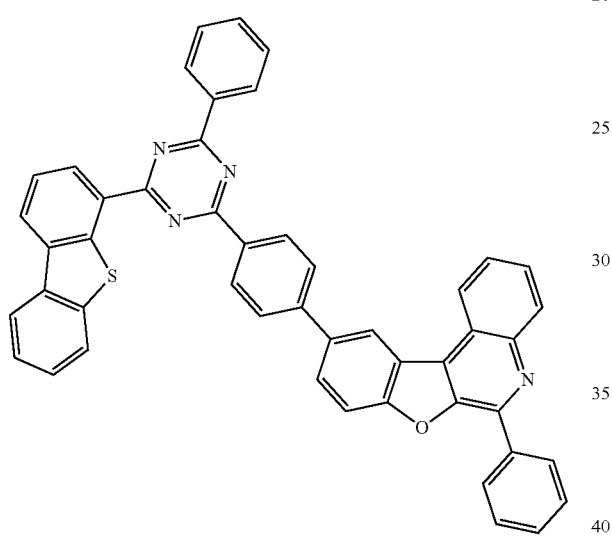
1136
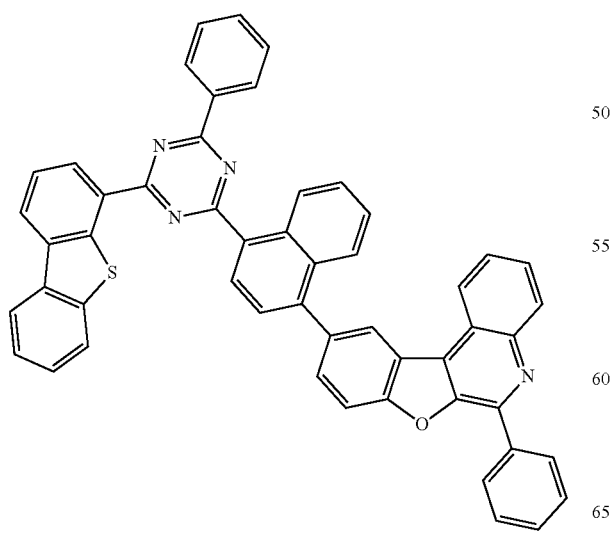
1137
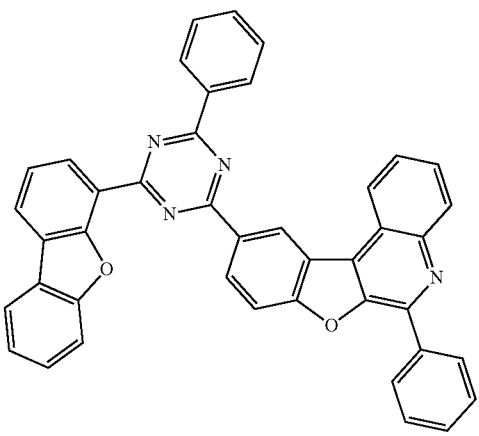
1138
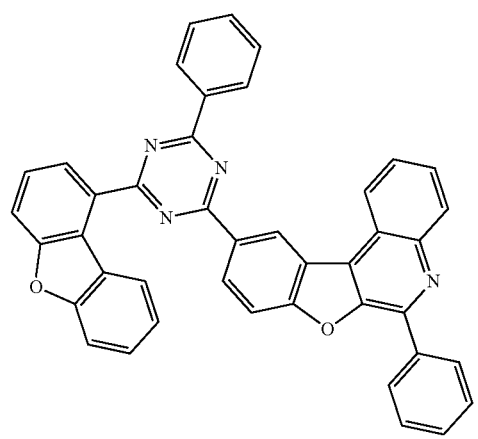 [SMILES: c1ccc(-c2nc(-c3ccc4oc5c(-c6ccccc6)nc6ccccc6c5c4c3)nc(-c3cccc4oc5ccccc5c34)n2)cc1]
1139
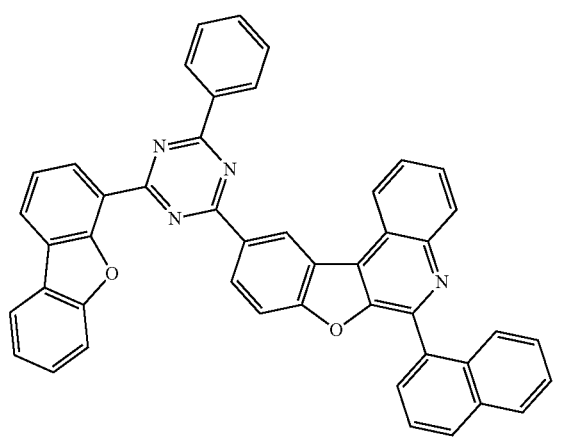

1025
-continued
1140
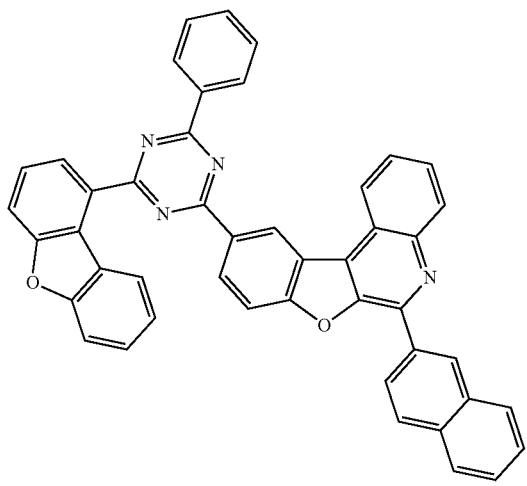
1141
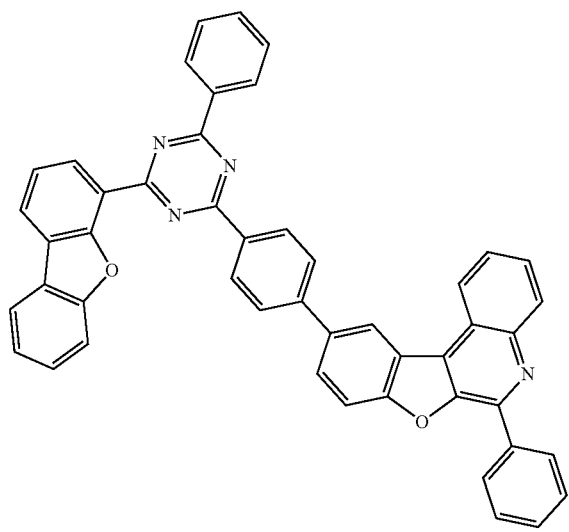
1142
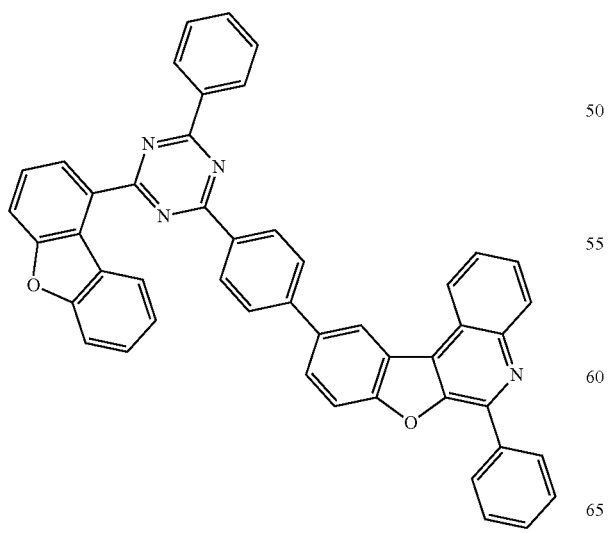
1026
-continued
1143
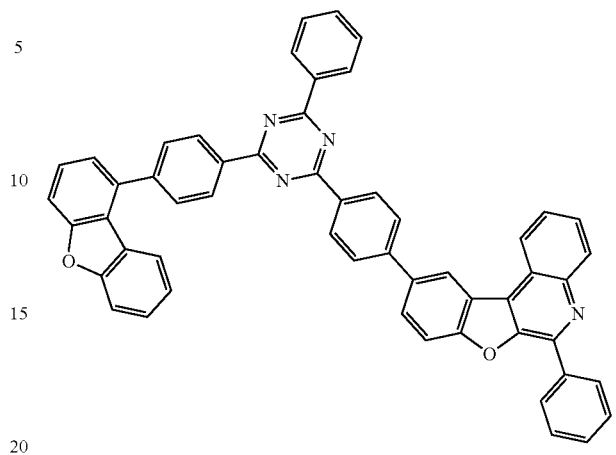
1144
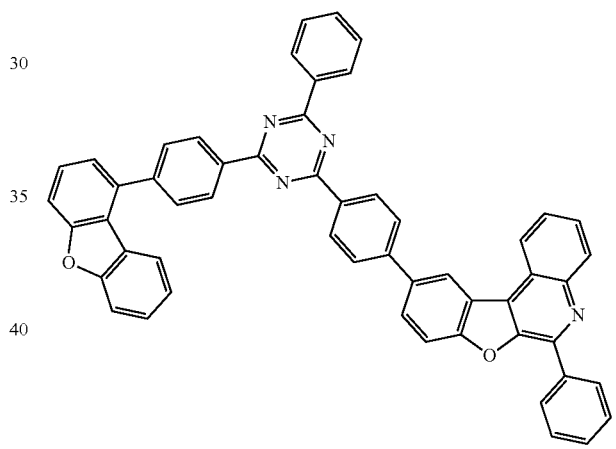
1145
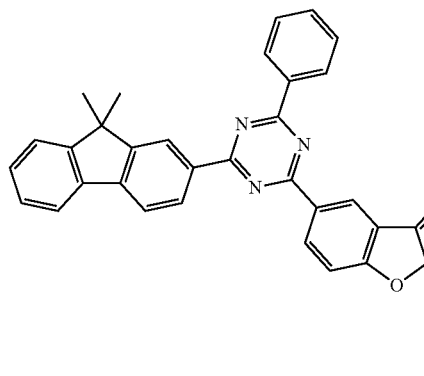

1146
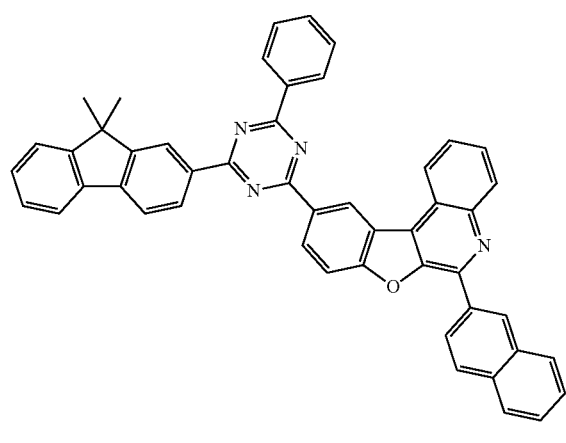
1147
1148
1149
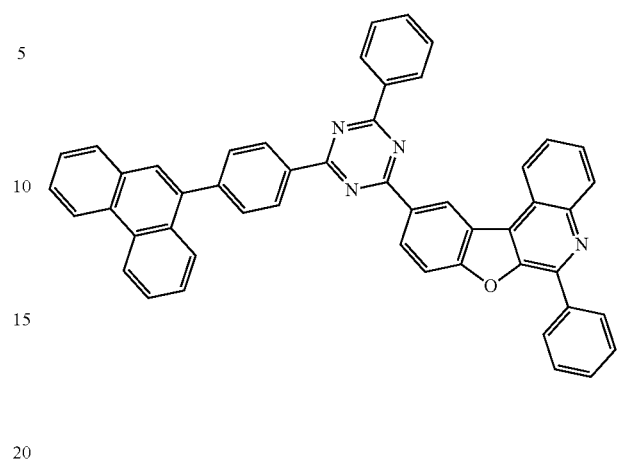
1150
1151

1029
-continued
1152
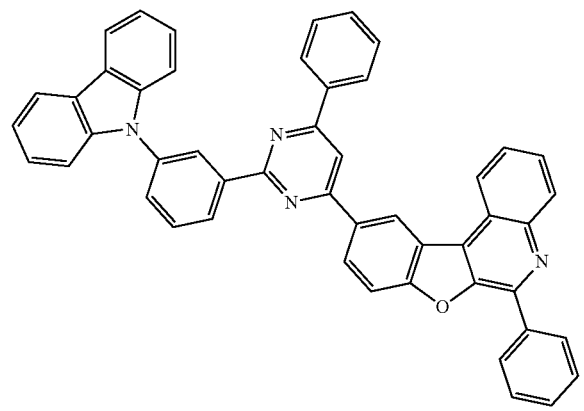
1153
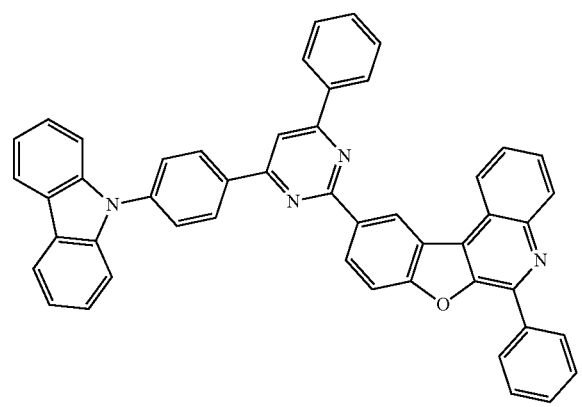
1154
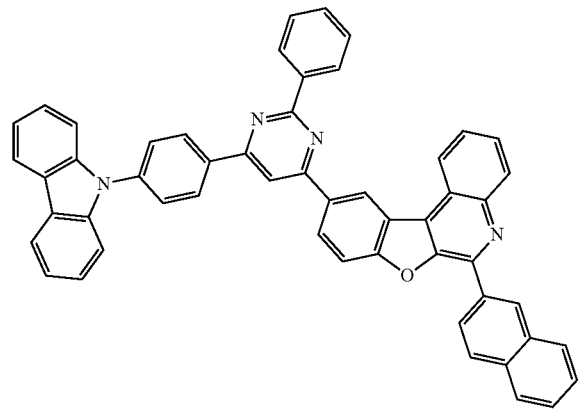
1030
-continued
1155
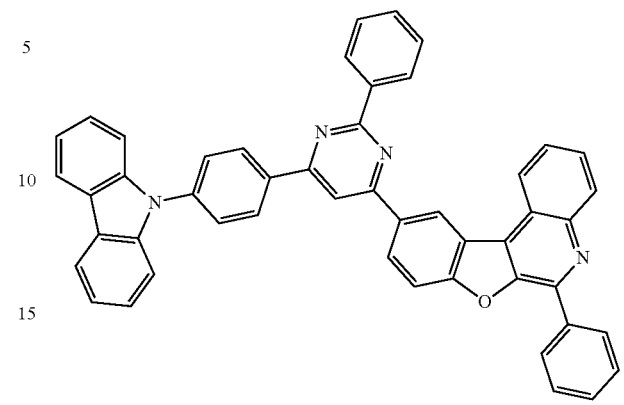
1156
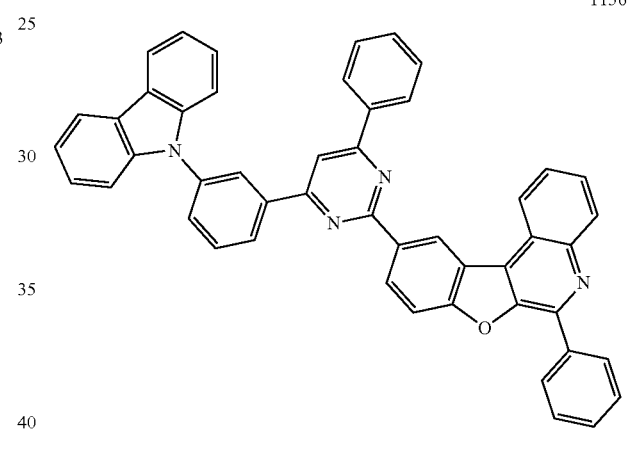
1157
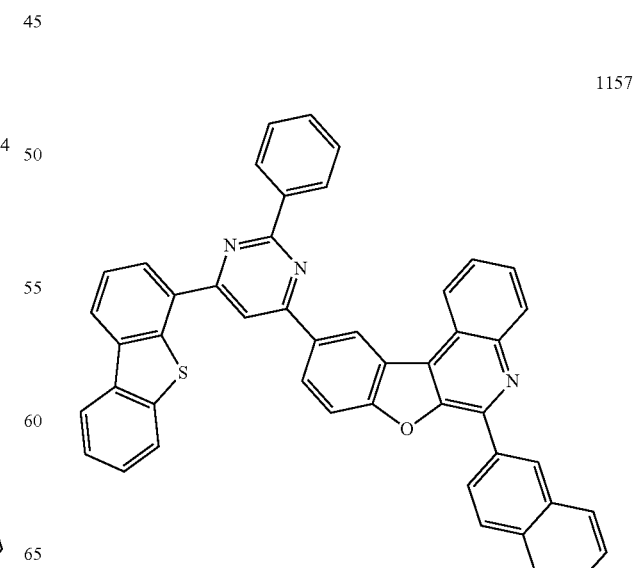

1158
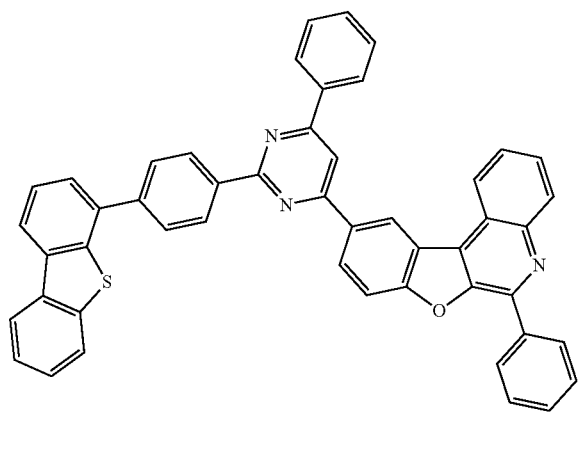
1159
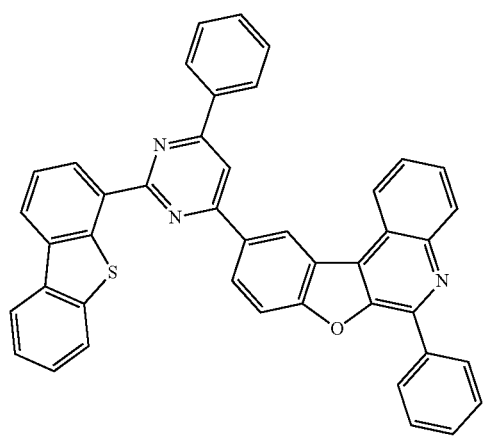
1160
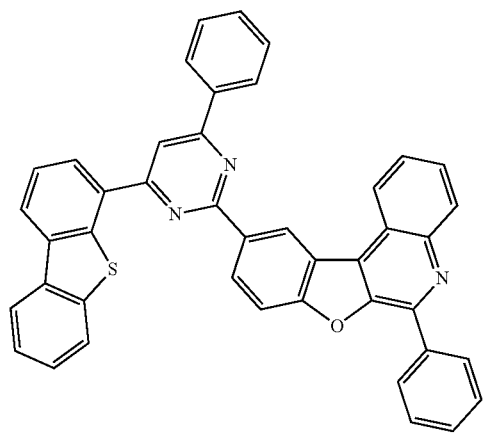
1161
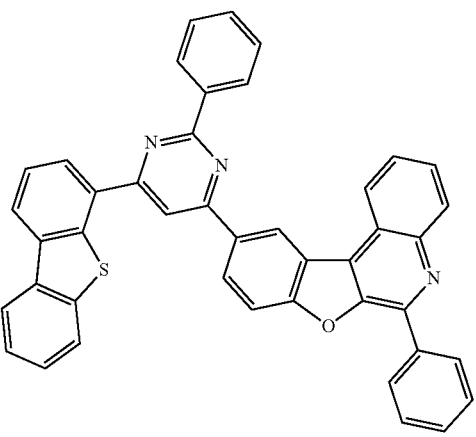
1162
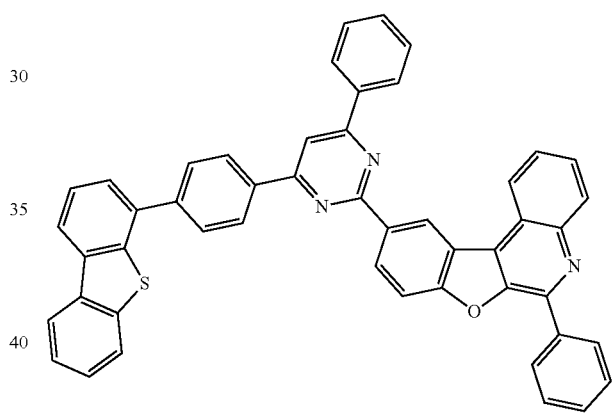
1163
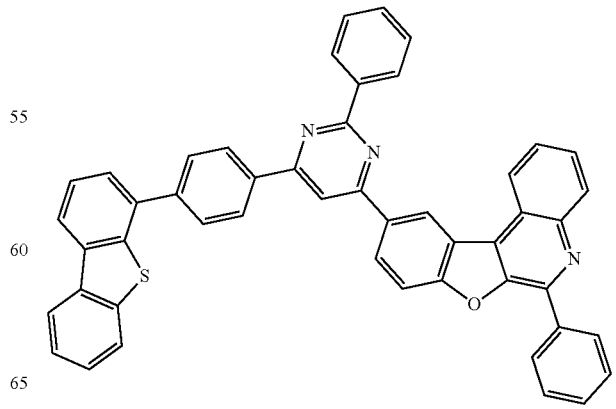

1033 -continued
1164
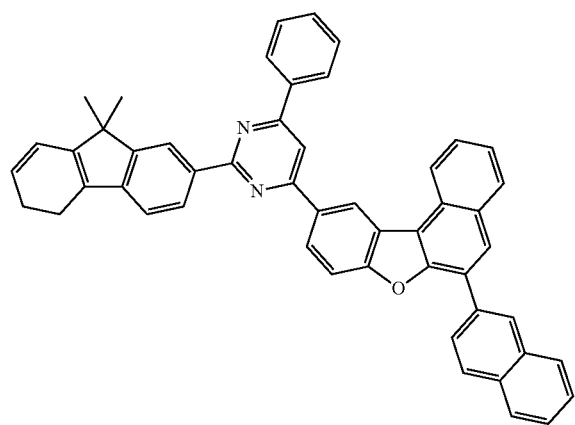
1165
1034 -continued
1167
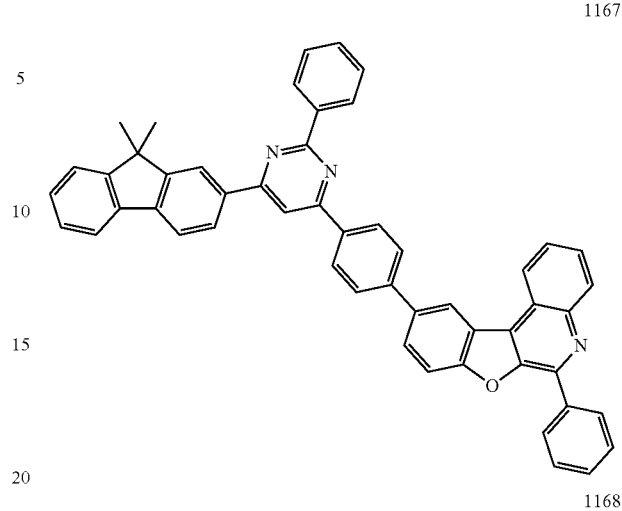
1168
1169
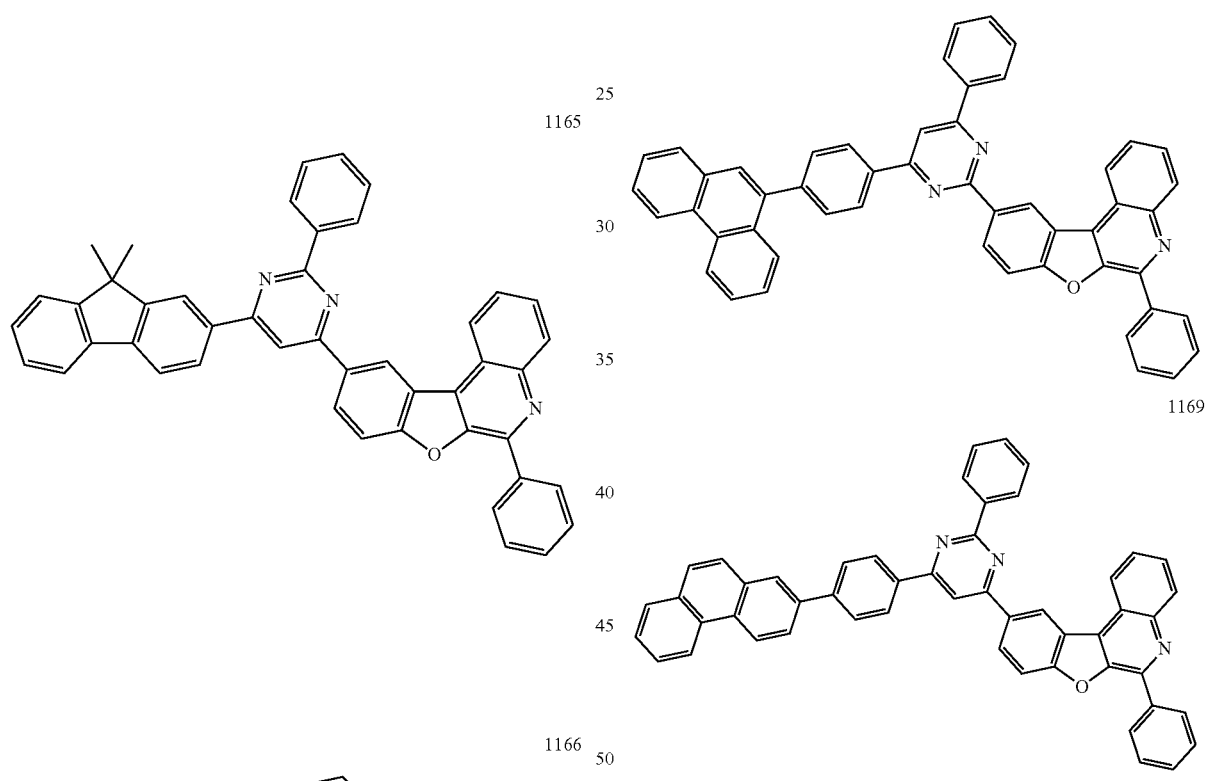
1166
1170
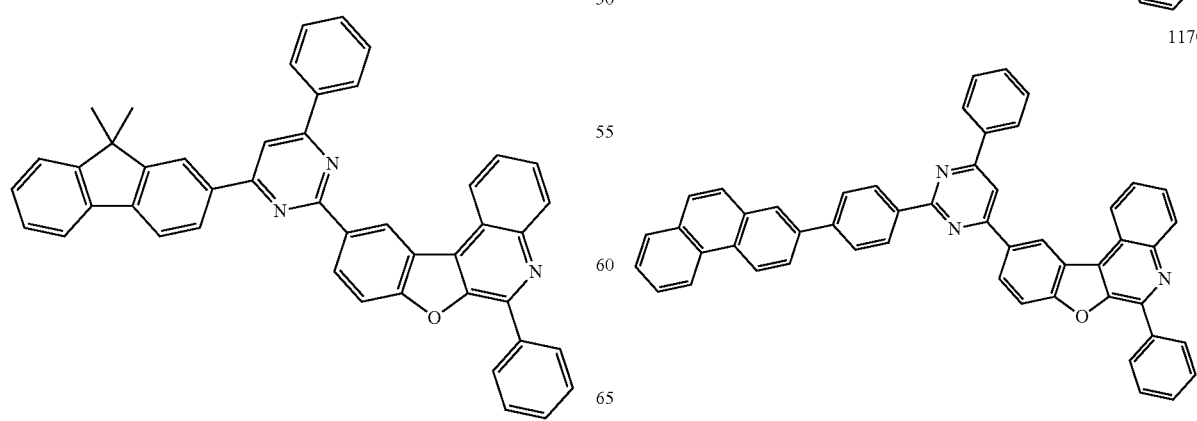

1171

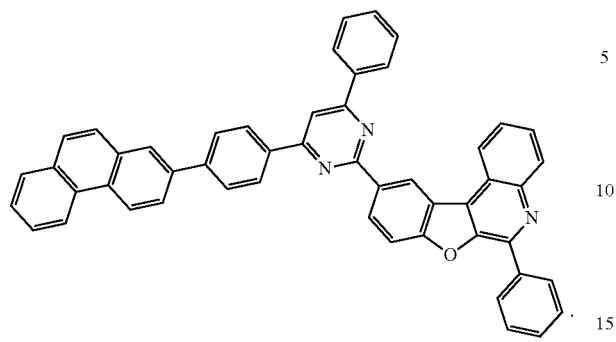

10. An organic optoelectronic diode comprising:
an anode and a cathode facing each other; and
at least one organic layer disposed between the anode and the cathode,
wherein the organic layer comprises the compound of claim 1.

11. The organic optoelectronic diode of claim 10, wherein the organic layer comprises an electron transfer layer, and the electron transfer layer comprises the compound.

12. The organic optoelectronic diode of claim 10, wherein the organic layer comprises a hole blocking layer, and the hole blocking layer comprises the compound.

13. A display device comprising the organic optoelectronic diode of claim 10.

* * * * *